US012521455B2

(12) United States Patent
Liu et al.

(10) Patent No.: US 12,521,455 B2
(45) Date of Patent: Jan. 13, 2026

(54) KISSPEPTIN RECEPTOR (KISS1R) TARGETED THERAPEUTICS AND USES THEREOF

(71) Applicant: Radionetics Oncology, Inc., San Diego, CA (US)

(72) Inventors: Junjie Liu, San Diego, CA (US); Yunfei Zhu, San Diego, CA (US); Yifeng Xiong, San Diego, CA (US); Jian Zhao, San Diego, CA (US)

(73) Assignee: Radionetics Oncology, Inc., San Diego, CA (US)

( * ) Notice: Subject to any disclaimer, the term of this patent is extended or adjusted under 35 U.S.C. 154(b) by 0 days.

(21) Appl. No.: 19/172,351

(22) Filed: Apr. 7, 2025

(65) Prior Publication Data

US 2025/0312499 A1 Oct. 9, 2025

Related U.S. Application Data

(60) Provisional application No. 63/683,591, filed on Aug. 15, 2024, provisional application No. 63/631,177, filed on Apr. 8, 2024.

(51) Int. Cl.
*A61K 51/08* (2006.01)

(52) U.S. Cl.
CPC ........ *A61K 51/088* (2013.01); *A61K 2121/00* (2013.01)

(58) Field of Classification Search
CPC ...... A61K 51/00; A61K 51/08; A61K 51/088; A61K 2121/00
See application file for complete search history.

(56) References Cited

U.S. PATENT DOCUMENTS

| | | | | |
|---|---|---|---|---|
| 6,800,611 | B2 | 10/2004 | Fujii et al. | |
| 8,361,968 | B2 | 1/2013 | Kitada et al. | |
| 8,404,643 | B2 | 3/2013 | Asami et al. | |
| 8,716,228 | B2 | 5/2014 | Eisenbach-Schwartz et al. | |
| 8,778,871 | B2 | 7/2014 | Kitada et al. | |
| 9,035,023 | B2 * | 5/2015 | Maecke | A61P 35/00 530/328 |
| 9,884,891 | B2 | 2/2018 | Beltramo et al. | |
| 2011/0118172 | A1 | 5/2011 | Asami et al. | |
| 2015/0361138 | A1 | 12/2015 | Beltramo et al. | |

FOREIGN PATENT DOCUMENTS

| | | | | |
|---|---|---|---|---|
| JP | 2004217651 | A | 8/2004 | |
| WO | WO-2007072997 | A1 | 6/2007 | |
| WO | WO-2008050897 | A1 | 5/2008 | |
| WO | WO-2010076896 | A1 | 7/2010 | |
| WO | WO-2014118318 | A1 | 8/2014 | |
| WO | WO-2023072971 | A2 * | 5/2023 | A61K 51/088 |
| WO | WO-2024206577 | A1 | 10/2024 | |

OTHER PUBLICATIONS

Scarso et al., Proceedings of the National Academy of Sciences of the United States of America, vol. 99, No. 8, pp. 5144-5149 (Year: 2002).*

Amblard, M. et al. Methods and protocols of modern solid phase Peptide synthesis. Molecular Biotechnology 33(3):239-254 (2006).

Asami, T. et al. Design, synthesis, and biological evaluation of novel investigational nonapeptide KISS1R agonists with testosterone-suppressive activity. Journal of Medicinal Chemistry 56(21):8298-8307 (2013).

Asami, Taiji et al. Serum stability of selected decapeptide agonists of KISS1R using pseudopeptides. Bioorganic & medicinal chemistry letters 22:6391-6396 (2012).

Behrendt, R. et al. Advances in Fmoc solid-phase peptide synthesis. Peptide science 22:04-27 (2016).

Beltramo, M. et al. Rational design of triazololipopeptides analogs of kisspeptin inducing a long-lasting increase of gonadotropins. Journal of Medicinal Chemistry 58(8):3459-3470 (2015).

Berge, Stephen M. et al. Pharmaceutical Salts. Journal of Pharmaceutical Sciences 66(1):1-19 (1977).

Bundgaard, Hans. Chapter 5: Design and Application of Prodrugs. In: Textbook of Drug Design and Development :113-191 (1991).

Bundgaard, Hans. Means to Enhance Penetration: Prodrugs as a Means to Improve the Delivery of Peptide Drugs. Advanced Drug Delivery Review 8(1):1-38 (1992).

Curtis, A. E. et al. A kisspeptin-10 analog with greater in vivo bioactivity than kisspeptin-10. American Journal of Physiology-Endocrinology and Metabolism 298(2):E296-E303 (2010).

Decourt, C. et al. A synthetic kisspeptin analog that triggers ovulation and advances puberty. Scientific Reports 6(26908):01-10 (2016).

Findeisen, M. et al. RFamide peptides: structure, function, mechanisms and pharmaceutical potential. Pharmaceuticals 4(9):1248-1280 (2011).

Guillier, F et al. Linkers and cleavage strategies in solid-phase organic synthesis and combinatorial chemistry. Chemical reviews 100(6):2091-158 (2000).

Hasegawa, Koki et al. Kiss1R Identification and Biodistribution Analysis Employing a Western Ligand Blot and Ligand-Derivative Stain with a FITC-Kisspeptin Derivative. ChemMedChem 15(18):1699-1705 (2020) (includes Corrigendum) .

Hasegawa, Koki. et al. P329—Synthesis of 67Ga—labeled Kisspeptin10 and in vivo evaluation for medullary thyroid carcinoma imaging. Journal of Labelled Compounds and Radiopharmaceuticals 60(Suppl 1):S501 (2017).

Kleynhans, Janke et al. P-171—Radiolabelling of DOTA-Kisspeptin with gallium-68 and lutetium-177. Nuclear Medicine and Biology 108-109:S143 (2022).

Krchnak, V. et al. Solid phase heterocyclic chemistry. Chemical reviews 102(1):61-92 (2002).

(Continued)

*Primary Examiner* — D. L. Jones

(74) *Attorney, Agent, or Firm* — WILSON SONSINI GOODRICH & ROSATI

(57) ABSTRACT

Described herein are radiotherapeutics that target tumor cells expressing the Kisspeptin receptor (KISS1R) and their use in the treatment and/or diagnosis of cancer.

30 Claims, 6 Drawing Sheets

Specification includes a Sequence Listing.

(56) References Cited

OTHER PUBLICATIONS

Mead, Emma J. et al. Kisspeptins Are Novel Potent Vasoconstrictors in Humans, with a Discrete Localization of Their Receptor, G Protein-Coupled Receptor 54, to Atherosclerosis-Prone Vessels. Endocrinology 148(1):140-147 (2007).
Merrifield, B., Solid Phase Synthesis. Science 232(4748):341-347 (1986).
Moriya, Yuu et al. Investigation of disposition for TAK-448, a synthetic peptide of kisspeptin analog, in rats and dogs using the radiolabeled TAK-448 suitable for pharmacokinetic study. Xenobiotica 49(7):833-839 (2019).
Niida, A. et al. Design and synthesis of downsized metastin (45-54) analogs with maintenance of high GPR54 activity. Bioorganic & Medicinal Chemistry Letters 16(1):134-137 (2006).
Palomo, J. M. et al. Solid-phase peptide synthesis: An overview focused on the preparation of biologically relevant peptides. RSC Adv 4 (62):32658-32672 (2014).
PCT/US2024/021888 International Search Report and Written Opinion dated Jul. 3, 2024.
Price, Eric W, and Chris Orvig. Matching Chelators to Radiometals for Radiopharmaceuticals. Chemical Society Reviews 43(1):260-290 (2014). Published Online Oct. 30, 2013.
Suhadolnik, R. J. et al. Nucleoside antibiotics. I. Biochemical tools for studying the structural requirements for interaction at the catalytic and regulatory sites of ribonucleotide reductase from Lactobacillus leichmannii. J Biol Chem 243(12):3552-3559 (1968).
Widder, Kenneth J. et al. Method in Enzymology. Academic Press 112:309-396 (1985).
PCT/US2025/023506 International Search Report and Written Opinion dated Jun. 27, 2025.

* cited by examiner

KISSPEPTIN RECEPTOR (KISS1R) TARGETED THERAPEUTICS AND USES THEREOF

CROSS-REFERENCE TO RELATED APPLICATIONS

This application claims the benefit of U.S. Provisional Patent Application No. 63/631,177, filed Apr. 8, 2024, and U.S. Provisional Patent Application No. 63/683,591, filed Aug. 15, 2024, which are incorporated herein by reference in their entireties.

FIELD OF THE INVENTION

Described herein are radiotherapeutics that target tumor cells expressing Kisspeptin receptor (KISS1R) and methods of using such radiotherapeutics as cancer therapeutics, diagnostics, or both.

SEQUENCE LISTING

The instant application contains a Sequence Listing which has been submitted electronically in XML format and is hereby incorporated by reference in its entirety. Said XML copy, created on Mar. 31, 2025, is named 63172-710_201_SL.xml and is 1,990,980 bytes in size.

BACKGROUND OF THE INVENTION

Neoplasms are abnormal growth of cells and cause enormous medical burdens, including morbidity and mortality, in humans. Neoplasms include benign or noncancerous neoplasms which do not display malignant features and are generally unlikely to become dangerous (e.g., adenomas). Malignant neoplasms display features such as genetic mutations, loss of normal function, rapid division, and ability metastasize (invade) to other tissues; and neoplasms of uncertain or unknown behavior. Malignant neoplasms (i.e., cancerous solid tumors) are the leading cause of death in industrialized countries. Noncancerous neoplasms including benign adenomas can also cause significant morbidity and mortality. Although standard treatments can achieve significant effects in tumor growth inhibition and even tumor elimination, the applied drugs exhibit only minor selectivity for the malignant tissue over healthy tissue and their severe side effects limit their efficacy and use. Specific targeting of neoplastic cells without affecting healthy tissue is a major desire for effective solid tumor therapy.

G protein-coupled receptors (GPCRs) are an important class of cell surface receptors that are frequently overexpressed in tumor cells and considered promising targets for selective tumor therapy. KISS1R, also referred as GPR54, is a GPCR overexpressed in several cancers, including, but not limited to, breast cancer, renal cell carcinoma, and lung cancer. Additionally, the kisspeptin/KISS1R signaling pathway is responsible for secretion of gonadotropin-releasing hormone (GnRH), an important modulator of the reproductive system. GnRH receptors are expressed in various tumor cells such as melanoma, prostate and endometrial carcinomas, leiomyomas, leiomyosarcomas, breast cancer, choriocarcinoma, epithelial and stromal tumors of the ovary. As such, targeted delivery of radionuclides to tumors with KISS1R-targeting conjugates offers a novel approach to treat and diagnose various cancers

SUMMARY OF THE INVENTION

Described herein are radiopharmaceuticals for use in the diagnosis and/or treatment of tumors. The present disclosure provides an alternative and improved method for the treatment of tumors by targeting tumors that overexpress the Kisspeptin receptor (KISS1R). In some embodiments, the radiopharmaceuticals disclosed herein are useful in the treatment of tumors that overexpress KISS1R. In some other embodiments, the radiopharmaceuticals disclosed herein are useful in the identification of tissues or organs in a subject comprising tumors overexpressing KISS1R. The radiopharmaceuticals disclosed herein are also useful in vivo imaging of a subject for the presence of and distribution of tumors that overexpress KISS1R in the subject.

In one aspect, described herein is a compound of Formula (I), or a pharmaceutically acceptable salt thereof:

Formula (I)

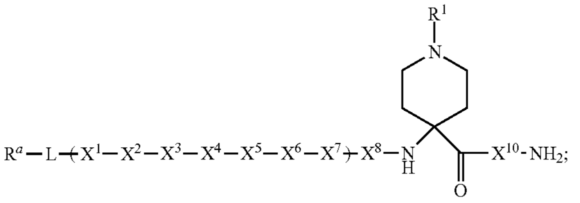

wherein:

$R^a$ is a chelating moiety or a radionuclide complex thereof;

L is an optional linker that is attached to any one of $X^1$, $X^2$, $X^3$, $X^4$, $X^5$, $X^6$, or $X^7$;

or L is attached to $X^8$ if $X^1$, $X^2$, $X^3$, $X^4$, $X^5$, $X^6$, and $X^7$ are absent; and $R^1$ is H,

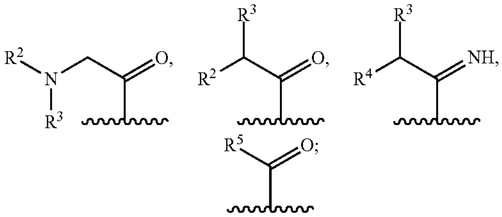

or $R^2$ is $C_1$-$C_6$ alkyl, substituted or unsubstituted heteroalkyl, —$(CHR^6)_n$-heterocycloalkyl, —$(CHR^6)_n$-aryl, —$(CHR^6)_n$-heteroaryl, —C(═O)—$(CHR^6)_n$-aryl, or —C(═O)NH—$(CHR^6)_n$-aryl; wherein $C_1$-$C_6$ alkyl is optionally substituted with $R^7$, and wherein the heterocycloalkyl, aryl, or heteroaryl are each independently optionally substituted with $R^7$, $R^8$, $R^9$, $R^{10}$, and $R^{11}$;

$R^3$ is H or $C_1$-$C_4$ alkyl;

$R^4$ is H, $C_1$-$C_4$ alkyl, or $R^2$;

$R^5$ is substituted or unsubstituted alkyl, substituted or unsubstituted heteroalkyl, or —$(CHR^6)_n$-aryl; wherein aryl is optionally substituted with $R^7$, $R^8$, $R^9$, $R^{10}$, and $R^{11}$;

each $R^6$ is independently H, F, —$CH_3$, —$NH_2$, or —OH;

$R^7$, $R^8$, $R^9$, $R^{10}$, and $R^{11}$ are each independently selected from H, F, Cl, Br, I, —OH, —O—$C_1$-$C_4$ alkyl, —$NH_2$, —$NHC_1$-$C_4$ alkyl, —N($C_1$-$C_4$ alkyl)$_2$, —CN, —$CO_2H$, —$CO_2C_1$-$C_4$ alkyl, —$C_1$-$C_6$ alkyl, —$C_1$-$C_6$ fluroroalkyl or —$C_3$-$C_6$ cycloalkyl;

n is 0, 1, 2, 3, 4, 5, or 6;

$X^1$ is absent, tyrosine (Tyr), glycine (Gly), sarcosine (Sar), alanine (Ala), aspartic acid (Asp), lysine (Lys), phenylalanine (Phe), 3-(3-pyridyl)alanine (3-Pal), threonine (Thr), methionine (Met), 4-iodophenylalanine (Phe(4-I)), N6-(4-(p-tolyl)butanoyl)-lysine, N6-(4-(4-iodophenyl)butanoyl)-lysine, or γ-glutamic acid (γ-Glu);

$X^2$ is absent, asparagine (Asn), glutamine (Gln), aspartic acid (Asp), glutamic acid (Glu), serine (Ser), histidine (His), alanine (Ala), sarcosine (Sar), tyrosine (Tyr), Proline (Pro), hydroxyproline (Hyp), azetidine-2-carboxylic acid (Aze), 2,3,4,5-tetrahydroisoquinoline-3-carboxylic acid (Tic), phenylalanine (Phe), 3-(2-pyridyl)alanine (2-Pal), 3-(3-pyridyl)alanine (3-Pal), or 3-(4-pyridyl)alanine (4-Pal);

$X^3$ is absent, tryptophan (Trp), serine (Ser), leucine (Leu), isoleucine (Ile), phenylalanine (Phe), 4-iodophenylalanine (Phe(4-I)), 3-(2-pyridyl)alanine (2-Pal), 3-(3-pyridyl)alanine (3-Pal), 3-(4-pyridyl)alanine (4-Pal), 2-amino-3-(naphthalen-2-yl)propanoic acid (H-2-NAL-OH), lysine (Lys), asparagine (Asn), glutamine (Gln), aspartic acid (Asp), glutamic acid (Glu), arginine (Arg), methyl arginine (Arg(Me)), norarginine (AGBA), methyl norarginine (AGBA(Me)), hormoarginine (HArg), methyl homoarginine (HArg(Me)), citrulline (Cit), methyl citrulline (Cit(Me)), canavanine, methyl-canavanine, glycine (Gly), alanine (Ala), sarcosine (Sar), tyrosine (Tyr), cyclohexylalanine (Ch a), 3-(1-naphthyl)alanine (α-Nal), 3-(2-naphthyl)alanine (β-Nal), threonine (Thr), proline (Pro), hydroxyproline (Hyp), tetrahydroisoquinoline-3-carboxylic acid (Tic), O-phospho-serine (SOP), 2-amino-4-(2H-tetrazol-5-yl)butanoic acid, β-glutamic acid, 8-aminoquinoline-3-carboxylic acid, biphenylalanine (Bip), 4-benzoylphenylalanine (Bpa), or 3-(9-anthryl)-alanine (H-Ala(9-Anth)-OH or AAP);

$X^4$ is absent, asparagine (Asn), glutamine (Gln), aspartic acid (Asp), glutamic acid (Glu), tryptophan (Trp), glycine (Gly), tyrosine (Tyr), alanine (Ala), sarcosine (Sar), or arginine (Arg);

$X^5$ is absent, serine (Ser), threonine (Thr), lysine (Lys), asparagine (Asn), glutamine (Gln), aspartic acid (Asp), glutamic acid (Glu), glycine (Gly), alanine (Ala), or sarcosine (Sar);

$X^6$ is absent, phenylalanine (Phe), alpha-methylphenylalanine (α-Me-Phe), N-methylphenylalanine (N-Me-Phe), 2-fluorophenylalanine (2-F-Phe), 3-fluorophenylalanine (3-F-Phe), 4-fluorophenylalanine (4-F-Phe), 4-iodophenylalanine (Phe(4-I)), 2-amino-2-indancarboxylic acid (Aic), biphenylalanine (Bip), β-(2-thienyl)-Ala, tryptophan (Trp), 2-aminotetralin-2-carboxylic acid (Atc), 3-(2-thienyl)-alanine, 3-(4-pyridyl) alanine (4-Pal), cyclohexylalanine (Cha), or tyrosine (Tyr);

$X^7$ is absent, glycine (Gly), aza-glycine (aza-Gly), alanine (Ala), N-methylglycine (Sar), or 1-aminocyclopropane-1-carboxylic acid (ACC);

$X^8$ is leucine (Leu), norvaline (Nva), valine (Val), isoleucine (lie), homoalanine (HAla), tryptophan (Trp), phenylalanine (Phe), or phenylglycine (Phg), or —$X^7$—$X^8$— is

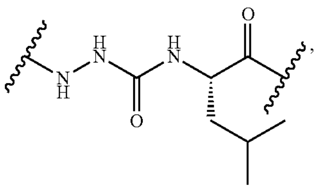

-continued

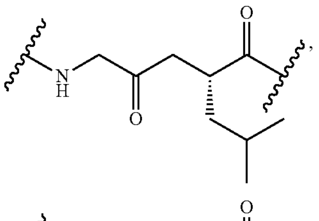

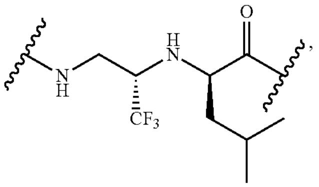

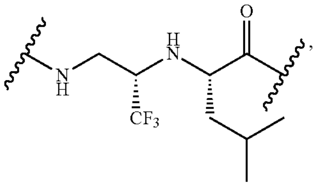

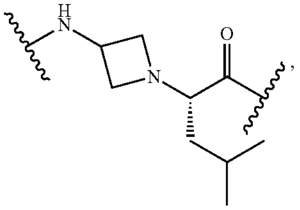

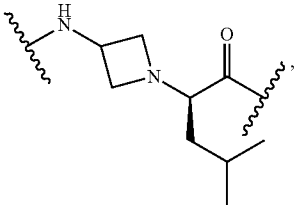

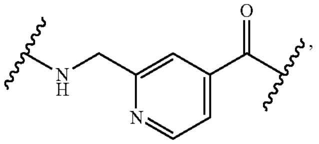

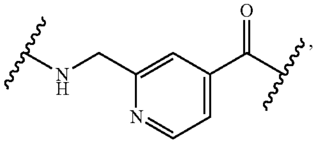

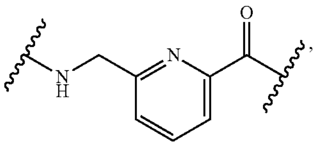

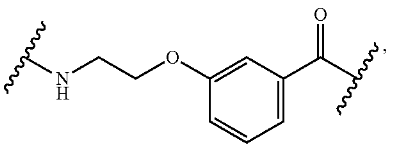

-continued
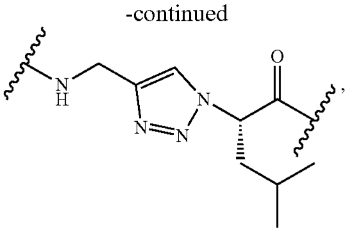,
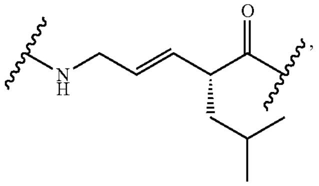,
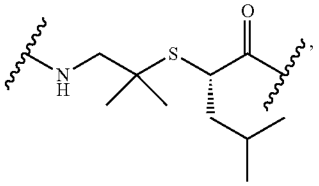,
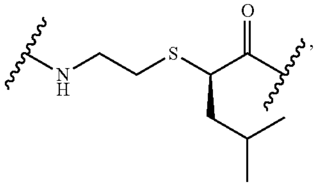,
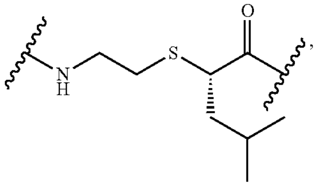,
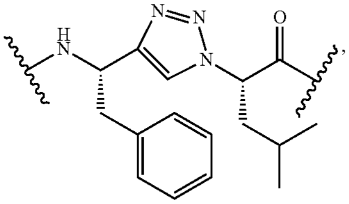,
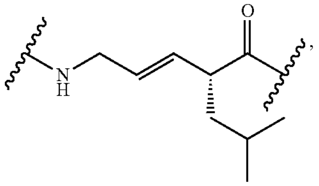,
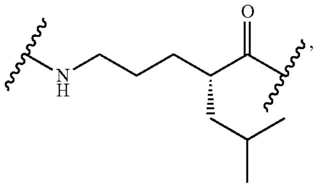,
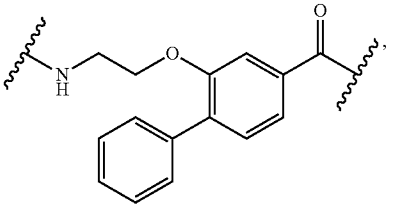,
-continued
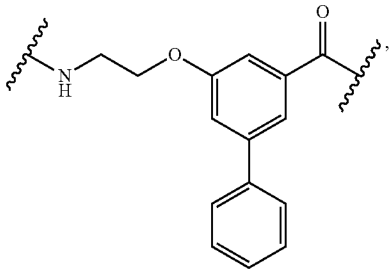,
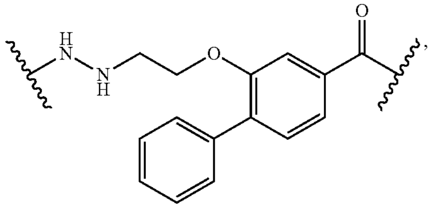,
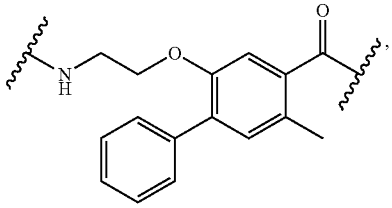,
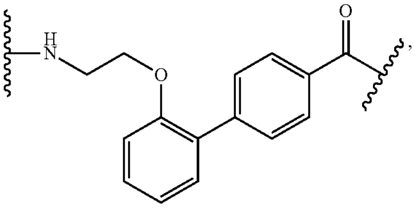, or
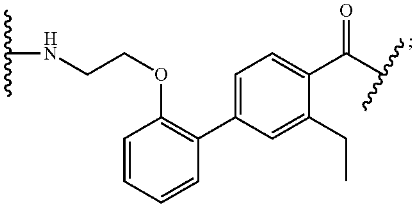;
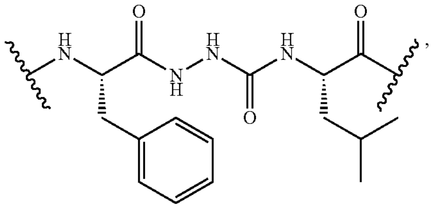,
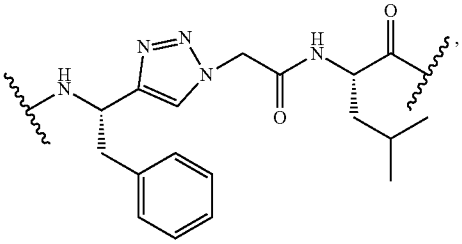, -continued

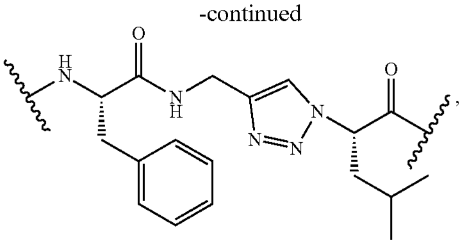

, or

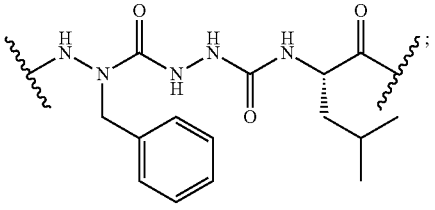

;

or $—X^6—X^7—X^8—$ is

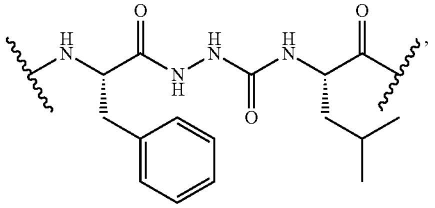

,

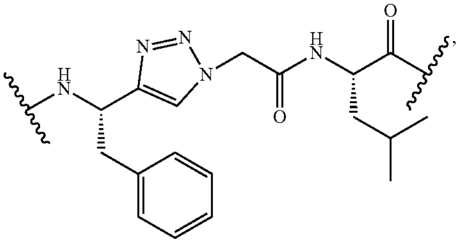

,

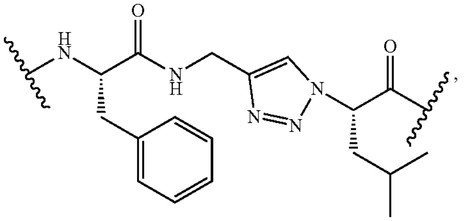

, or

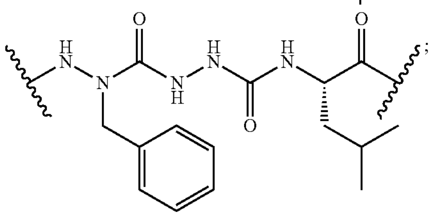

;

$X^{10}$ is tryptophan (Trp), 1-methyltryptophan (1MT), tyrosine (Tyr), phenylalanine (Phe), 4-cyano phenylalanine (Phe(4-CN)), 3-(4-pyridyl)alanine (4-Pal), leucine (Leu), phenylglycine (Phg), cyclohexylalanine (Cha), 3-(1-naphthyl)alanine (α-Nal), 3-(2-naphthyl)-alanine (β-Nal), histidine (His), or 3-nitro-tyrosine (Tyr(3-$NO_2$));

wherein the N-terminal amino acid or the compound of Formula (I) is optionally substituted with $—C(=O)—C_1$-$C_{20}$ alkyl, $—C(=O)—(CH_2CH_2O)_y—CH_2CH_2—R^{15}$, $—C_1$-$C_{20}$alkyl, N-hexadecanoyl-Glu, $—C_4$-$C_{20}$ polyethylene glycol, a saccharide, $—R^{16}$, $—C(=O)—(CH_2CH_2O)_x—CH_3$, $—C(=O)—(CH_2CH_2O)_x—H$, $—C(=O)—CH_2CH_2—CH(COOH)—R^{15}$, $—C(=O)—(CH_2)_2R^{19}$, or $—C(=O)CH_2NHCH_2R^{19}$;

$R^{15}$ is selected from $—OR^{16}$, $—N(R^{16})_2$, $—C(=O)OR^{16}$, or $—C(=O)N(R^{16})_2$;

each $R^{16}$ is independently H, $—C_1$-$C_6$ alkyl, $—C(=O)—(CH_2)_vR^{19}$, $—C(=O)CH_2NHCH_2R^{19}$, or a saccharide or derivative thereof;

$R^{19}$ is 4-iodophenylene, 4-methylphenylene, or 3-fluoro-4-methylphenylene;

y is 0, 1, 2, 3, 4, 5, 6, 7, 8, 9, or 10; x is an integer from 1 and 25; and v is 1, 2, 3, or 4;

wherein any free —NH— of a peptide bond is optionally independently substituted with $—CH_3$ or $—CH_2CH_3$; and wherein any alpha position of an amino acid is optionally independently substituted with $—CH_3$ or $—CH_2CH_3$.

In some embodiments, $R^a$ is a chelating moiety independently selected from the group consisting of:

(CM-1)

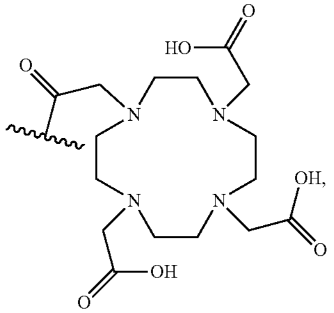

(CM-2)

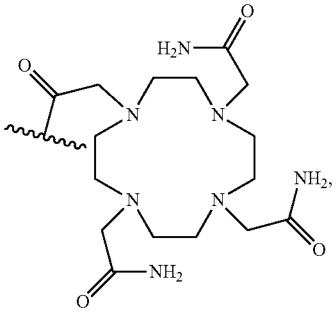

(CM-3)

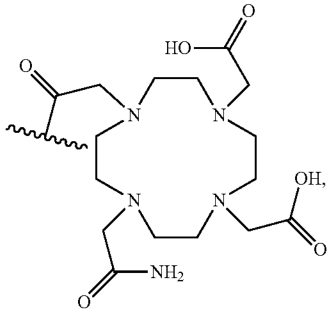

-continued (CM-4)

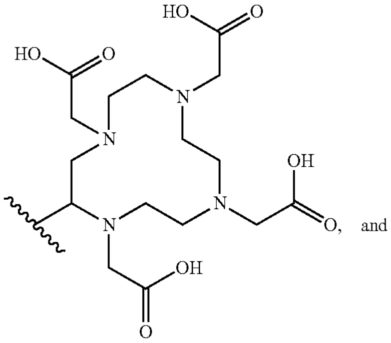

, and (CM-5)

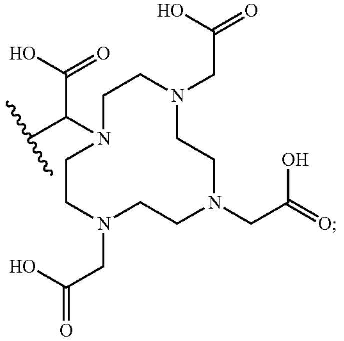

;

or a radionuclide complex thereof.

In some embodiments, -L- is absent, $*\text{-}L^1$, $*—NR^{17}\text{-}L^1\text{-}$, $*—NR^{17}\text{-}L^5\text{-}L^1\text{-}$, $*—NR^{17}\text{-}L^5\text{-}C(=O)\text{-}L^1\text{-}$, $*—NR^{17}\text{-}L^5\text{-}NR^{17}—C(=O)\text{-}L^1\text{-}$, $*\text{-}L^5\text{-}C(=O)\text{-}L^1\text{-}$, $*\text{-}L^5\text{-}L^1\text{-}$, $*—NR^{17}\text{-}L^5\text{-}NR^{17}\text{-}L^1\text{-}$, L, $*—NR^{17}\text{-}L^5\text{-}C(=O)NR^{17}\text{-}L^1\text{-}$, $*\text{-}(L^3)\text{-}_w$, $*—NR^{17}\text{-}L^5\text{-}C(=O)\text{-}L^3\text{-}NR^{17}\text{-}L^5\text{-}C(=O)—$, or $*\text{-}(L^3)_w\text{-}NR^{17}\text{-}L^5\text{-}C(=O)\text{-}L^1\text{-}$; wherein * denotes the attachment point to $R^a$;

$L^5$ is substituted or unsubstituted $C_1$-$C_6$ alkylene;

or $L^5$ and $R^{17}$ are taken together with the N atom to which they are attached to form N-heterocycloalkyl;

$R^{17}$ is selected from hydrogen, $C_1$-$C_6$ alkyl, $C_1$-$C_6$ alkyl-$CO_2H$, $—(CH_2CH_2O)_zCH_2CH_2—CO_2H$;

$L^1$ is absent, $\text{-}L^2\text{-}$, $\text{-}L^2\text{-}(L^3)_w\text{-}$, $\text{-}(L^3)_w\text{-}L^2\text{-}$, or $\text{-}L^2\text{-}(L^3)_w\text{-}L^2\text{-}(L^3)_w$;

each $L^2$ is independently absent, $—C_0$-$C_6$ alkylene-(substituted or unsubstituted arylene)-$C_0$-$C_6$ alkylene-C(=O)—, $—C_0$-$C_6$ alkylene-(substituted or unsubstituted arylene)-$C_0$-$C_6$ alkylene-OC(=O)—, $—C_0$-$C_6$ alkylene-(substituted or unsubstituted cyclohexylene)-$C_0$-$C_6$ alkylene-C(=O)—, $—C_0$-$C_6$ alkylene-(substituted or unsubstituted heterocycloalkylene)-$C_0$-$C_6$ alkylene-C(=O)—, $—C_0$-$C_6$alkylene-(substituted or unsubstituted heteroarylene)-$C_0$-$C_6$ alkylene-C(=O)—, $—C_0$-$C_6$ alkylene-(substituted or unsubstituted heteroarylene)-$C_0$-$C_6$ alkylene-OC(=O)—, $—C_4$-$C_{20}$ polyethylene glycol, $C_4$-$C_{20}$ polyethylene glycol-C(=O)—, substituted or unsubstituted $—C_1$-$C_{20}$ alkylene, substituted or unsubstituted $C_1$-$C_{20}$ alkylene-C(=O)—, substituted or unsubstituted 2 to 20 membered heteroalkylene, $—(CH_2CH_2O)_z—CH_2—$, $—(CH_2CH_2O)_z—CH_2CH_2—$, $—(CH_2CH_2O)_z—CH_2—C(=O)—$; or $—(CH_2CH_2O)—CH_2CH_2—C(=O)—$;

each z is independently 1, 2, 3, 4, 5, or 6;

each $L^3$ is independently selected from natural or unnatural amino acids, wherein any free amine of an amino acid or peptide bond is optionally independently substituted with $L^4$, and wherein when two or more amino acids are present then the N atom of the amide linking the amino acids is optionally substituted with $—CH_3$;

each $L^4$ is independently selected from $—C_1$-$C_6$ alkyl, $—C(=O)—C_1$-$C_6$ alkyl-C(=O)—, $—C(=O)—NH—C_1$-$C_6$ alkyl-C(=O)—, $—C(=O)—C_1$-$C_6$ alkyl-(substituted or unsubstituted heteroaryl)-$C_1$-$C_6$ alkyl-C(=O)—, $—C_1$-$C_6$ alkyl-C(=O)—, $—C(=O)—C_1$-$C_6$ alkyl-(substituted or unsubstituted aryl)-, and $—C_1$-$C_6$ alkyl-(substituted or unsubstituted aryl)-C(=O)—; wherein if $L^4$ is present then: $L^4$ is attached to the any one of $X^1$, $X^2$, $X^3$, $X^4$, $X^5$, $X^6$, or $X^7$, or $L^4$ is attached to $X^8$ if $X^1$, $X^2$, $X^3$, $X^4$, $X^5$, $X^6$ and $X^7$ are absent, and each w is independently 1, 2, 3, 4, 5, or 6.

In some embodiments, the radionuclide of the radionuclide complex is: an Auger electron-emitting radionuclide; or an α-emitting radionuclide; or a β-emitting radionuclide; or a γ-emitting radionuclide.

Also described herein is a pharmaceutical composition comprising a compound described herein (e.g., a compound of Formula (I), or a pharmaceutically acceptable salt thereof, and at least one pharmaceutically acceptable excipient. In some embodiments, the pharmaceutical composition is formulated for administration to a mammal by intravenous administration or subcutaneous administration. In some embodiments, the pharmaceutical composition is formulated for administration to a mammal by intravenous administration.

In another aspect, described herein is a method for the treatment of cancer comprising administering to a mammal with cancer an effective amount of a compound described herein (e.g., a compound of Formula (I)), or a pharmaceutically acceptable salt thereof, or an effective amount of pharmaceutical composition comprising a compound described herein (e.g., a compound of Formula (I)), or a pharmaceutically acceptable salt thereof. In some embodiments, the cancer comprises tumors and the tumors overexpress the Kisspeptin receptor (KISS1R). In some embodiments, the cancer is glioma, thyroid cancer, lung cancer, colorectal cancer, stomach cancer, liver cancer, pancreatic cancer, renal cancer, prostate cancer, testis cancer, breast cancer, cervical cancer, endometrial cancer, ovarian cancer or melanoma. In some embodiments, the cancer is breast cancer. In some embodiments, the cancer is renal cancer. In some embodiments, the cancer is lung cancer.

In another aspect, described herein is a method for treating tumors in a mammal with a radionuclide comprising administering to the mammal a compound described herein (e.g., a compound of Formula (I)), or a pharmaceutically acceptable salt thereof, or a pharmaceutical composition comprising a compound described herein (e.g., a compound of Formula (I)), or a pharmaceutically acceptable salt thereof. In some embodiments, the mammal has been diagnosed with breast cancer. In some embodiments, the mammal has been diagnosed with renal cancer. In some embodiments, the mammal has been diagnosed with lung cancer.

In another aspect, described herein is a method of targeting delivery of a radionuclide to tumors in a mammal comprising administering to a mammal with tumors a compound described herein (e.g., a compound of Formula (I)), or a pharmaceutically acceptable salt thereof, or a pharmaceutical composition comprising a compound described herein (e.g., a compound of Formula (I)), or a pharmaceutically acceptable salt thereof; wherein the tumors overexpress the Kisspeptin receptor (KISS1R).

In another aspect, described herein is a method for identifying tissues or organs in a mammal with tumors expressing the Kisspeptin receptor (KISS1R) comprising administering to the mammal a compound described herein (e.g., a compound of Formula (I)), or a pharmaceutically acceptable salt thereof, or a pharmaceutical composition comprising a compound described herein (e.g., a compound of Formula (I)), or a pharmaceutically acceptable salt thereof; and performing positron emission tomography (PET) analysis, single-photon emission computerized tomography (SPECT), or magnetic resonance imaging (MIR); wherein $R^a$ is a chelating moiety-diagnostic radionuclide complex.

In yet another aspect, described herein is a method for the in vivo imaging of tissues or organs in mammal with tumors expressing the Kisspeptin receptor (KISS1R) comprising administering to the mammal a compound described herein (e.g., a compound of Formula (I)), or a pharmaceutically acceptable salt thereof, or a pharmaceutical composition comprising a compound described herein (e.g., a compound of Formula (I)), or a pharmaceutically acceptable salt thereof; and performing positron emission tomography (PET) analysis, single-photon emission computerized tomography (SPECT), or magnetic resonance imaging (MRI); wherein $R^a$ is a chelating moiety-diagnostic radionuclide complex.

In any of the embodiments disclosed herein, the mammal is a human.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Figure 1:
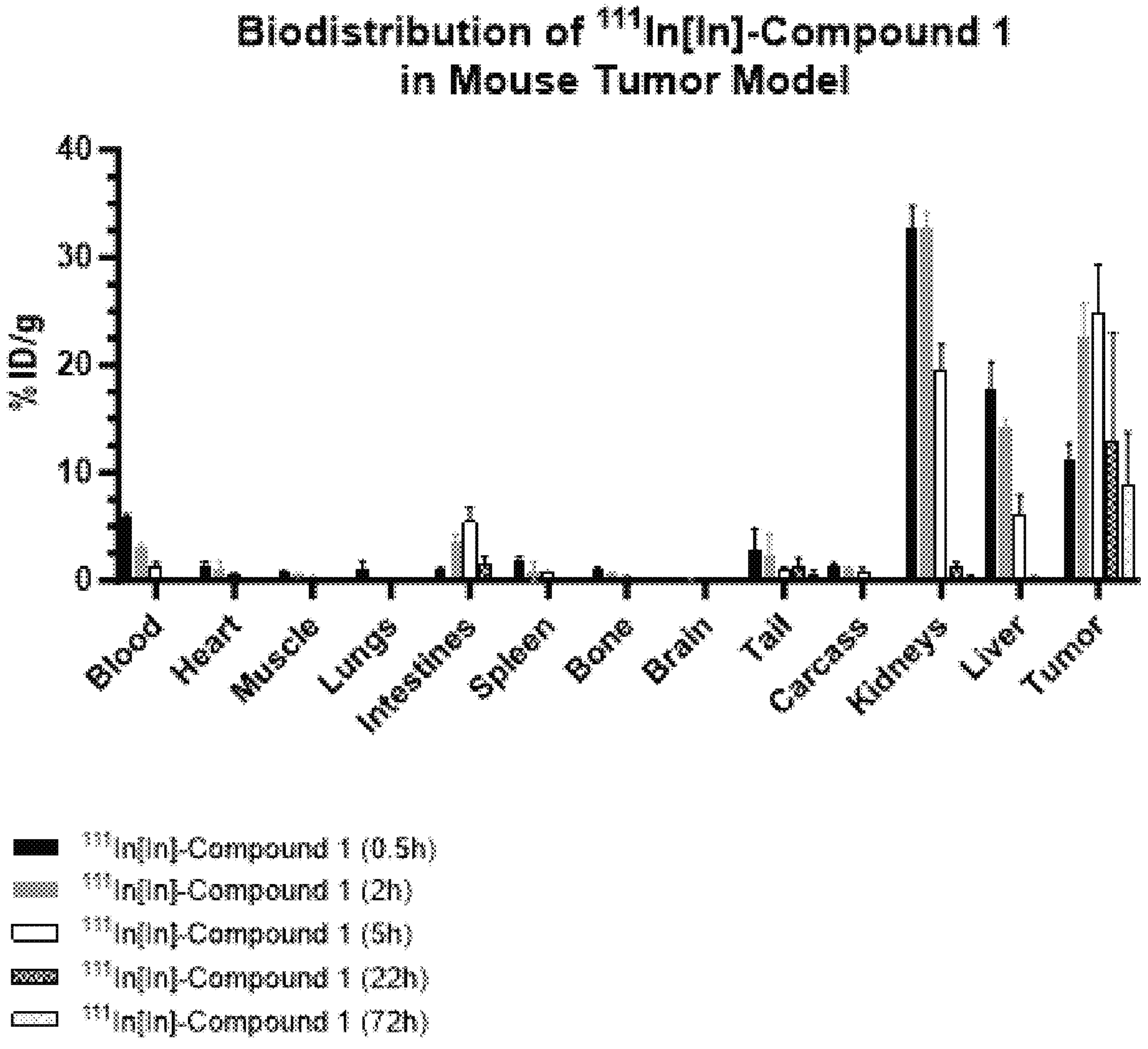
FIG. 1 depicts biodistribution of $^{111}$In[In]-Compound 1 in tumor bearing Swiss nude mice. Timepoints are 0.5, 2.0, 5.0, 24 and 72 h post IV treatment. Activity is measured as percentage of injected dose per gram of tissue (% ID/g).
Figure 2:
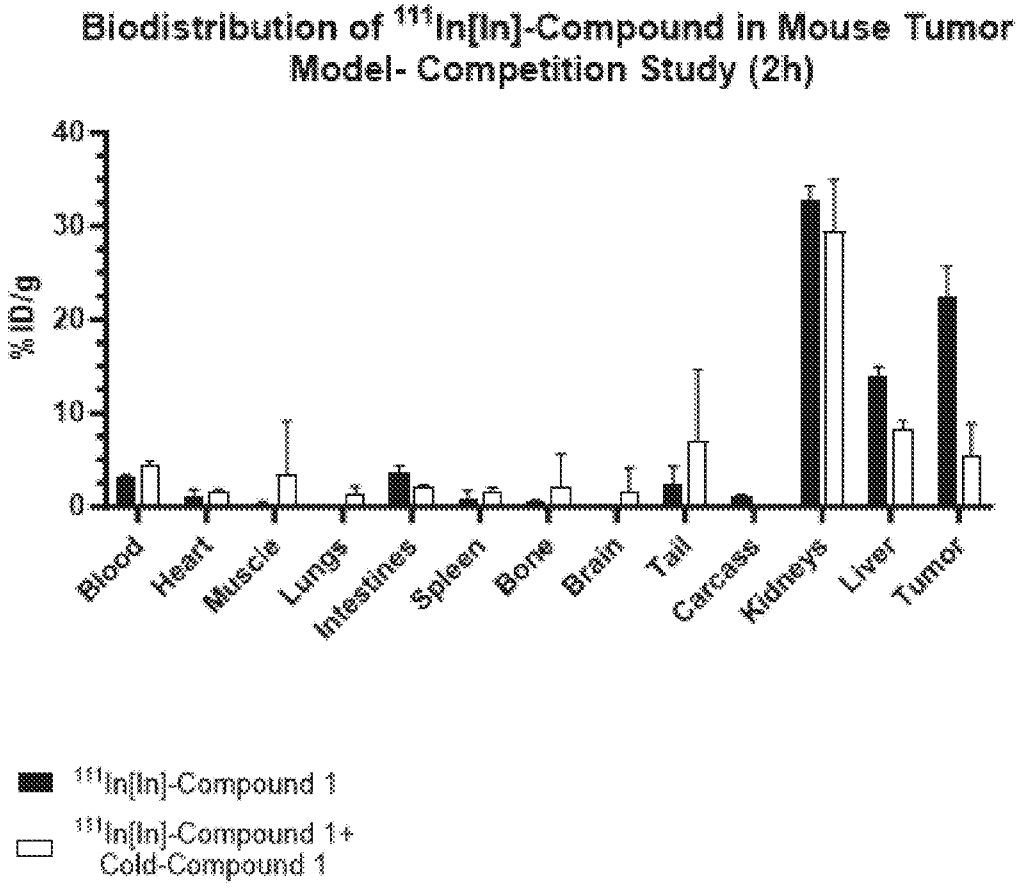
FIG. 2 depicts competition study of $^{111}$In[In]-Compound 1 co-administered with excessive unlabeled Compound 1 (1:100 ratio respectively) in tumor bearing Swiss nude mice. Timepoint is 2 h. Activity is measured as percentage of injected dose per gram of tissue (% ID/g).
Figure 3:
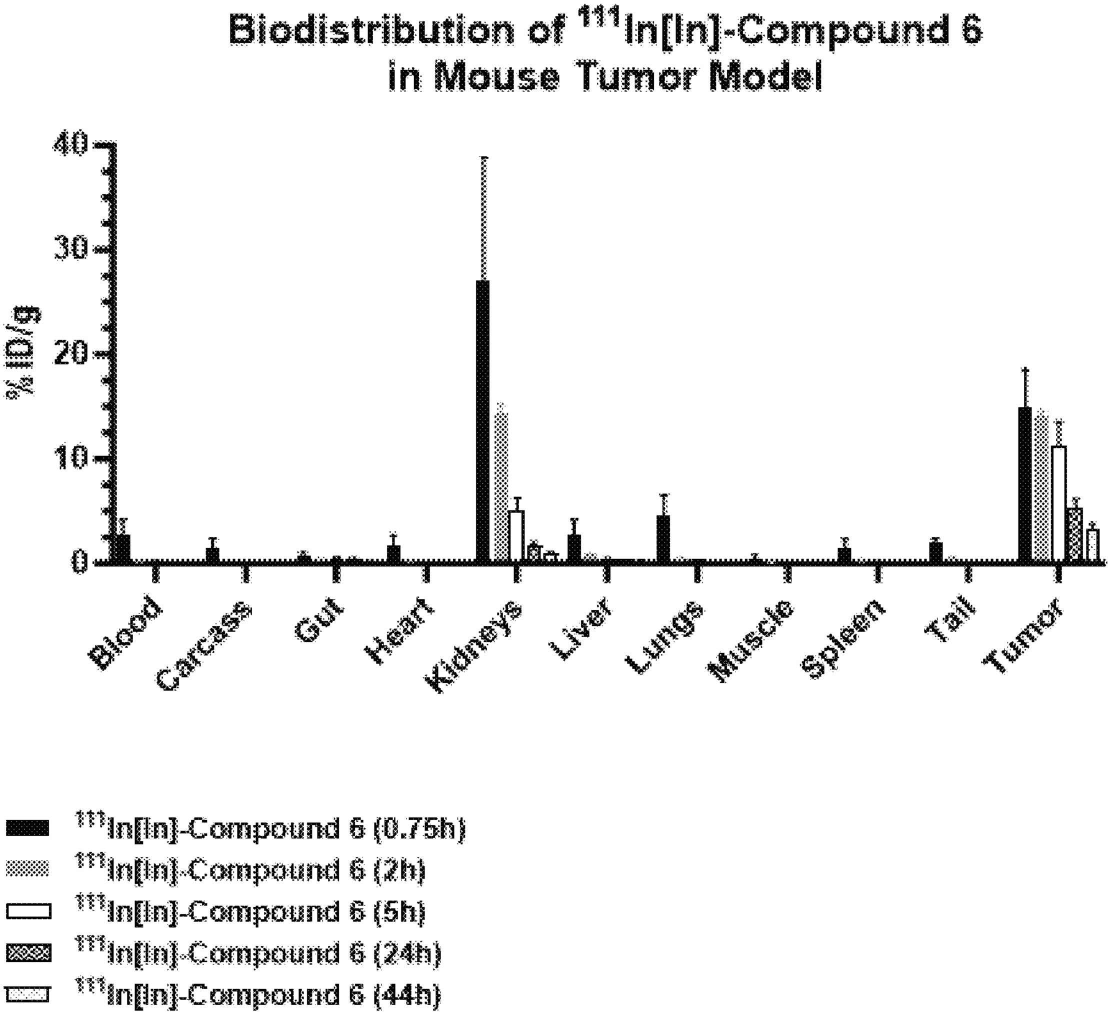
FIG. 3 depicts biodistribution of $^{111}$In[In]-Compound 6 in tumor bearing Swiss nude mice. Timepoints are 0.75, 2.0, 5.0, 24 and 44 h post IV treatment. Activity is measured as percentage of injected dose per gram of tissue (% ID/g).
Figure 4:
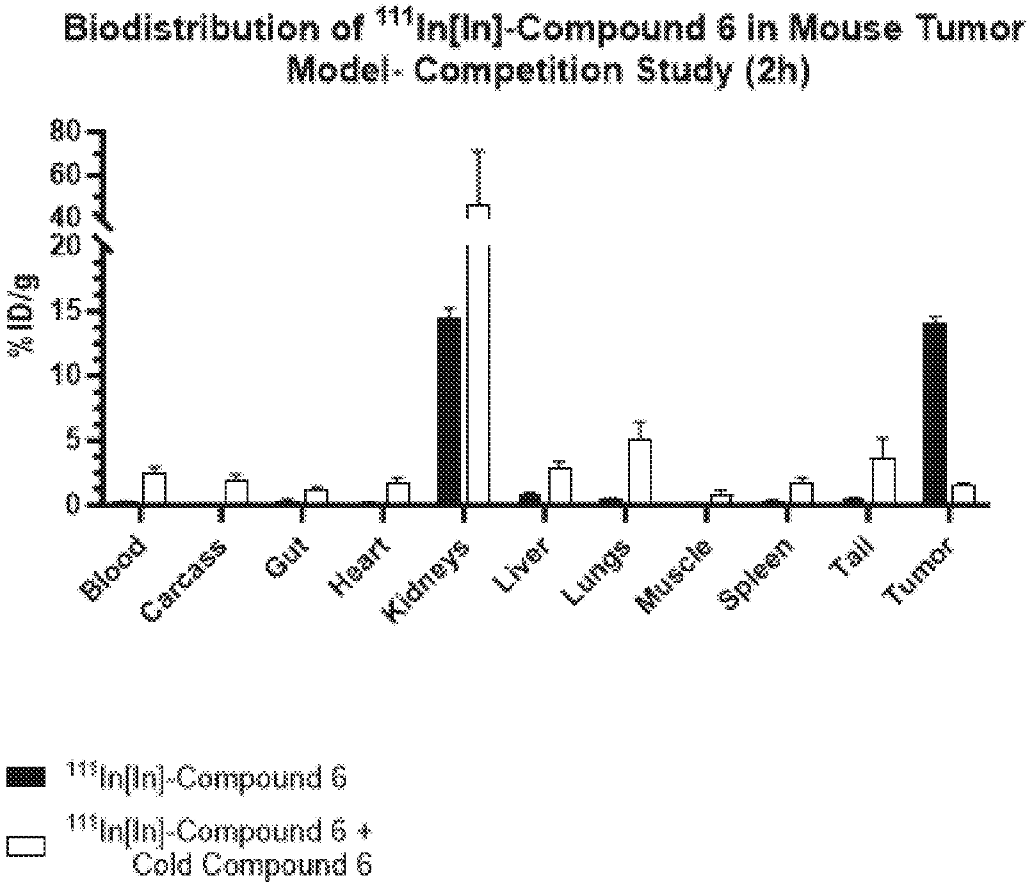
FIG. 4 depicts competition study of $^{111}$In[In]-Compound 6 co-administered with excessive unlabeled Compound 6 (1:100 ratio respectively) in tumor bearing Swiss nude mice. Timepoint is 2 h. Activity is measured as percentage of injected dose per gram of tissue (% ID/g).
Figure 5:
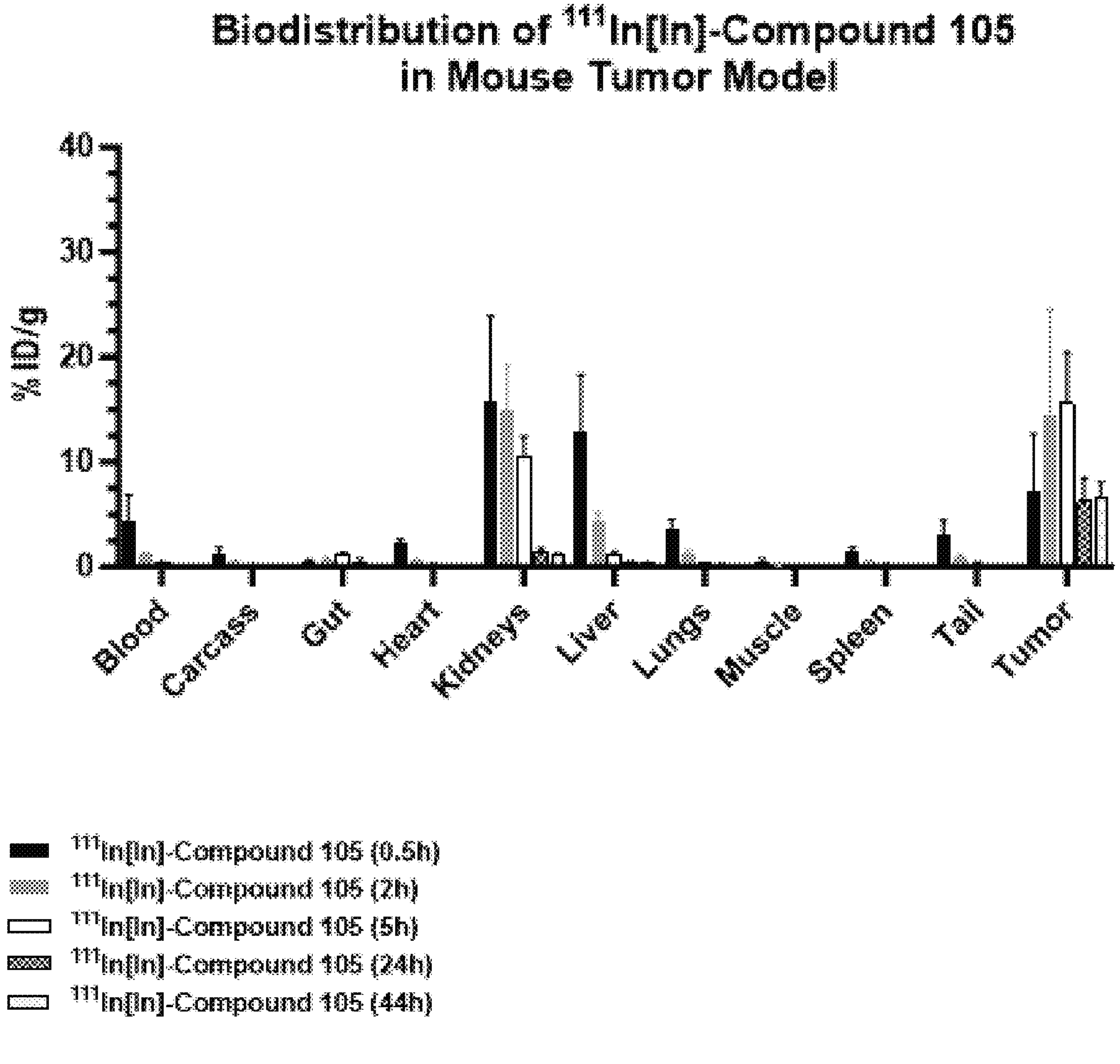
FIG. 5 depicts biodistribution of $^{111}$In[In]-Compound 105 in tumor bearing Swiss nude mice. Timepoints are 0.5, 2.0, 5.0, 24 and 44 h post IV treatment. Activity is measured as percentage of injected dose per gram of tissue (% ID/g).
Figure 6:
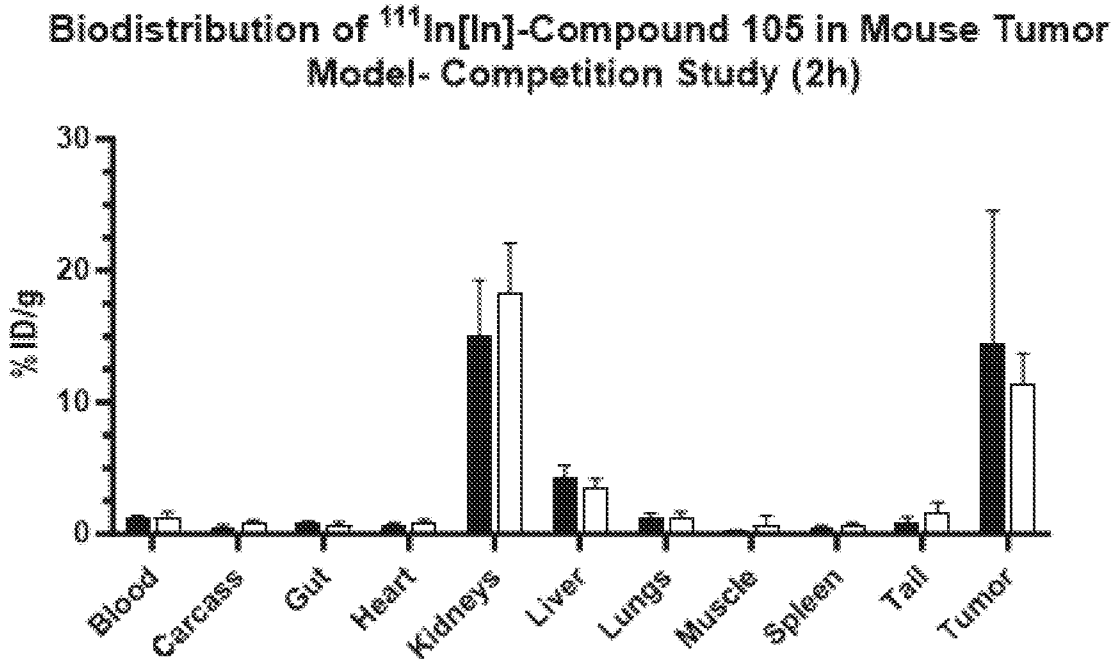
FIG. 6 depicts competition study of $^{111}$In[In]-Compound 1 co-administered with excessive unlabeled Compound 1 (1:100 ratio respectively) in tumor bearing Swiss nude mice. Timepoints is 2 h. Activity is measured as percentage of injected dose per gram of tissue (% ID/g).

Cancer, a disease in which some cells undergo a genetic change in the control of their growth and replication that results in uncontrolled growth and spreading, is one of the leading causes of death worldwide. General types of cancers include solid tumors (cancers that typically originate in organs), carcinomas (cancers that originate in skin or tissues that line organs), sarcomas (cancers of connective tissues such as bones), leukemias cancers of bone marrow), and lymphomas and myelomas (cancers of the immune system). Neoplasms are abnormal growth of cells that result in solid tumors which may be benign (i.e. do not display malignant features and are generally unlikely to become dangerous such as adenomas), malignant (i.e. display features such as genetic mutations, loss of normal function, rapid division, and ability metastasize (invade) to other tissues), and of uncertain or unknown behavior. State-of-the-art treatment of neoplasms is accomplished by a combination of surgical procedures, chemotherapy, and radiation therapy. Surgical procedures can be curative under some conditions, but often require multiple interventions and are often done in combination with radiation and chemotherapy. Chemotherapy proves to be a potent weapon in the fight against cancer in many cases. Chemotherapy is typically performed by systemic administration of potent cytotoxic drugs, but these compounds often lack tumor selectivity and therefore also kill healthy cells in the body. The resulting non-specific toxicity is the cause of severe side effects of chemotherapy which occur because chemotherapy does not target the cancerous cells specifically over other cells. Radiotherapy is the use of high-energy radiation to kill cells. The source of radiation may be external-beam radiation (applied using an external source), internal radiation (placement of a radioactive material near the target cells), or radiotherapy from the systemic administration of a radioactive material. Like chemotherapy, many radiation therapy options also lack tumor cell identification properties needed to achieve the ultimate goal of targeted tumor therapy with drug molecules or radionuclides.

Described herein are radiopharmaceuticals that selectively deliver radionuclides to malignant cells that overexpress KISS1R for use in cancer detection, image guided cancer surgery, and selective tumor killing.

The Kisspeptin Receptor (KISS1R)

Kisspeptin (KP) is a peptide hormone cleaved from a 145 amino acid precursor protein (KiSS1) encoded by the KiSS1 gene. Kisspeptin is made up of 54 amino acids that can be proteolytically processed into shorter peptides with a common C-terminal decapeptide sequence: Tyr-Asn-Trp-Asn-Ser-Phe-Gly-Leu-Arg-Phe-$NH_2$ (SEQ ID NO: 828). This sequence strongly binds to a G-protein coupled receptor GPR54, also known as Kisspeptin receptor (KISS1R). The KP/KISS1R signaling system has been shown to exhibit dual roles in cancer; that is, the KiSS1 gene has been reported as a metastasis promoter and suppressor, depending on the type of cancer.

Kisspeptin and its receptor are expressed in several tissues, including the brain, pancreas, placenta, and testis. KISS1R is a G-protein coupled seven transmembrane receptor. Binding of kisspeptin to KISS1R activates G-protein Gq/11 and phospholipase C to hydrolyze phosphatidylinositol-4,5-bisphosphate (PIP2) into inositol 1,4,5-triphosphate (IP3) and diacylglycerol (DAG). IP3 activates intracellular calcium release and DAG activates the mitogen-activated protein kinase (MAPK) pathway. There are several downstream effects of these signals, including effects on hormone secretion, metastasis, migration, angiogenesis, and proliferation.

The KP/KISS1R signaling system has been suggested to promote metastasis in breast cancer and liver cancer, and suppress metastasis in bladder cancer, ovarian cancer, colorectal cancer, pancreatic cancer, prostate cancer, lung cancer, and thyroid cancer. The KP/KISS1R signaling system has also been described as an important modulator of gonadotropin-releasing hormone (GnRH), a key regulator of the human reproductive system. Peptide analogs of kisspeptin have been shown to interrupt kisspeptin signaling and suppress the pulsatile secretion of GnRH, showing promise for treating hormone-dependence diseases such as prostate cancer. These peptide analogs show evidence of higher metabolic stability than native kisspeptins and also display good KISS1R agonist activity. Radiopharmaceuticals targeting KISS1R are important for the development of new cancer therapies.

Breast Cancer

Breast cancer is a type of cancer that starts in the breast. It can start in one or both breasts, in various parts of the breast. There are many types of breast cancer, and a breast cancer's type is determined by the specific cells in the breast that become cancer.

Breast Cancer Types

Most breast cancers are carcinomas, which are tumors that start in the epithelial cells that line organs and tissues throughout the body. When carcinomas form in the breast, they are usually a more specific type called adenocarcinoma, which starts in cells in the ducts (the milk ducts) or the lobules (glands in the breast that make milk).

The type of breast cancer can also refer to whether the cancer has spread or not. In situ breast cancer (ductal carcinoma in situ or DCIS) is a pre-cancer that starts in a milk duct and has not grown into the rest of the breast tissue. The term invasive (or infiltrating) breast cancer is used to describe any type of breast cancer that has spread (invaded) into the surrounding breast tissue.

Breast Cancer Staging

The staging system most often used for breast cancer is the American Joint Committee on Cancer (AJCC) TNM system. The most recent AJCC system, effective January 2018, has both clinical and pathologic staging systems for breast cancer:

The pathologic stage (also called the surgical stage) is determined by examining tissue removed during an operation.

Sometimes, if surgery is not possible right away or at all, the cancer will be given a clinical stage instead. This is based on the results of a physical exam, biopsy, and imaging tests. The clinical stage is used to help plan treatment. Sometimes, though, the cancer has spread further than the clinical stage estimates, and may not predict the patient's outlook as accurately as a pathologic stage.

In both staging systems, 7 key pieces of information are used:

i. The extent (size) of the tumor (T);
ii. The spread to nearby lymph nodes (N);
iii. The spread (metastasis) to distant sites (M);
iv. Estrogen Receptor (ER) status;
v. Progesterone Receptor (PR) status;
vi. HER2 status; and
vii. Grade of the cancer (G).

In addition, Oncotype Dx® Recurrence Score results may also be considered in the stage in certain situations. Once all of these factors have been determined, this information is combined in a process called stage grouping to assign an overall stage.

Breast Cancer Treatment

Tumors can form in the breasts. The types of treatment used to treat breast tumors include: surgery, radiation therapy, chemotherapy, hormone therapy, targeted drug therapy and immunotherapy.

There are two main types of surgery to remove breast cancer: breast-conserving surgery and mastectomy. Breast-conserving surgery is surgery to remove the cancer as well as some surrounding normal tissue. Only the part of the breast containing the cancer is removed. How much breast is removed depends on where and how big the tumor is, as well as other factors. This surgery is also called a lumpectomy, quadrantectomy, partial mastectomy, or segmental mastectomy. Mastectomy is a surgery in which the entire breast is removed, including all of the breast tissue and sometimes other nearby tissues. There are several different types of mastectomies. Some women may also have both breasts removed in a double mastectomy. Sometimes surgery is done to remove the nearby lymph nodes and other tissue where the cancer has spread.

Radiation therapy uses high-energy x-rays or other types of radiation to kill cancer cells or keep them from growing. There are two types of radiation therapy: external radiation therapy uses a machine outside the body to send radiation toward the area of the body with cancer; internal radiation therapy uses a radioactive substance sealed in needles, seeds, wires, or catheters that are placed directly into or near the cancer. Additionally, targeted radiopharmaceuticals can provide targeted radiation to the site of the tumor. Chemotherapy is a cancer treatment that uses drugs to stop the growth of cancer cells, either by killing the cells or by stopping them from dividing.

Thus, a need exists for treatment options for breast tumors. Described herein are radiopharmaceuticals that target delivery of radionuclides to breast tumors, which overexpress the KISS1R. Targeted therapies usually cause less harm to normal cells than chemotherapy or radiation therapy do.

Solid Tumors: Benign and/or Malignant Neoplasms (Cancer)

In one aspect, the KISS1R-targeted radiopharmaceuticals described herein are used to treat benign and/or malignant neoplasms (solid tumors), wherein the neoplasm comprises cells that overexpress KISS1R on the cell surface.

The term "neoplasm" as used herein, refers to an abnormal growth of cells that may proliferate in an uncontrolled way and may have the ability to metastasize (spread).

Neoplasms include solid tumors, adenomas, carcinomas, sarcomas, leukemias and lymphomas, at any stage of the disease with or without metastases.

A solid tumor is an abnormal mass of tissue that usually does not contain cysts or liquid areas. Solid tumors may be benign (not cancer), or malignant (cancer). Different types of solid tumors are named for the type of cells that form them. Examples of solid tumors are sarcomas, carcinomas, and lymphomas. Leukemias (cancers of the blood) generally do not form solid tumors.

Solid tumors are cancers that typically originate in organs, such as the bladder, bowel, brain, breast, endometrium, heart, kidney, lung, liver, uterus, ovaries, pancreas or other endocrine organs (thyroid), and prostate.

In some embodiments, the KISS1R-targeted radiopharmaceuticals described herein are used to treat an adenoma. An adenoma is a tumor that is not cancer. It starts in gland-like cells of the epithelial tissue (thin layer of tissue that covers organs, glands, and other structures within the body). An adenoma can grow from many glandular organs, including the adrenal glands, pituitary gland, thyroid, prostate, and others Even though benign, they have the potential to cause serious health complications by compressing other structures (mass effect) and by producing large amounts of hormones in an unregulated, non-feedback-dependent manner (causing paraneoplastic syndromes). Overtime adenomas may transform to become malignant, at which point they are called adenocarcinomas.

Adenomas may be found in the colon (e.g. adenomatous polyps, which have a tendency to become malignant and to lead to colon cancer), kidneys (e.g. renal adenomas may be precursor lesions to renal carcinomas), adrenal glands (e.g. adrenal adenomas; some secrete hormones such as cortisol, causing Cushing's syndrome, aldosterone causing Conn's syndrome, or androgens causing hyperandrogenism), thyroid (e.g. thyroid adenoma), pituitary (e.g. pituitary adenomas, such as prolactinoma, Cushing's disease and acromegaly), parathyroid (e.g. an adenoma of a parathyroid gland may secrete inappropriately high amounts of parathyroid hormone and thereby cause primary hyperparathyroidism), liver (e.g. hepatocellular adenoma), breast (e.g. fibroadenomas), appendix (e.g. cystadenoma), bronchial (e.g. bronchial adenomas may cause carcinoid syndrome, a type of paraneoplastic syndrome), prostate (e.g. prostate adenoma), sebaceous gland (e.g. sebaceous adenoma), and salivary glands.

Metastasis is the spread of malignant cells to new areas of the body, often by way of the lymph system or bloodstream. A metastatic tumor is one that has spread from the primary site of origin, or where it started, into different areas of the body. Metastatic tumors comprise malignant cells that may express cell surface KISS1R.

Tumors formed from cells that have spread are called secondary tumors. Tumors may have spread to areas near the primary site, called regional metastasis, or to parts of the body that are farther away, called distant metastasis.

In some embodiments, the tumor to be treated comprises tumor cells expressing KISS1R, wherein the tumor is a primary or metastatic tumor. In some embodiments, the tumor to be treated comprises tumor cells expressing KISS1R, wherein the tumor is a primary or metastatic tumor of breast origin. In some embodiments, the tumor to be treated comprises tumor cells expressing KISS1R, wherein the tumor is a primary or metastatic tumor of endometrial origin. In some embodiments, the tumor to be treated comprises tumor cells expressing KISS1R, wherein the tumor is a primary or metastatic tumor of ovarian origin. In some embodiments, the tumor to be treated comprises tumor cells expressing KISS1R, wherein the tumor is a primary or metastatic tumor of prostate origin. In some embodiments, the tumor to be treated comprises tumor cells expressing KISS1R, wherein the tumor is a primary or metastatic tumor of renal origin. In some embodiments, the tumor to be treated comprises tumor cells expressing KISS1R, wherein the tumor is a primary or metastatic tumor of lung origin.

In some embodiments, the KISS1R-targeted radiopharmaceuticals described herein are used to treat a carcinoma. Carcinomas include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelial carcinoma, and nasopharyngeal carcinoma, etc. In some embodiments, the KISS1R-targeted radiopharmaceuticals described herein are used to treat breast carcinoma. In some embodiments, the KISS1R-targeted radiopharmaceuticals described herein are used to treat renal cell carcinoma. In some embodiments, the KISS1R-targeted radiopharmaceuticals described herein are used to treat lung carcinoma.

In some embodiments, the KISS1R-targeted radiopharmaceuticals described herein are used to treat a sarcoma. Sarcomas include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Solid tumors include, but are not limited to, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma. Benign solid tumors include adenomas.

Primary and metastatic tumors include, e.g., lung cancer (including, but not limited to, lung adenocarcinoma, squamous cell carcinoma, large cell carcinoma, bronchioloalveolar carcinoma, non-small-cell carcinoma, small cell carcinoma, mesothelioma); breast cancer (including, but not limited to, ductal carcinoma, lobular carcinoma, inflammatory breast cancer, clear cell carcinoma, mucinous carcinoma); colorectal cancer (including, but not limited to, colon cancer, rectal cancer); anal cancer; pancreatic cancer (including, but not limited to, pancreatic adenocarcinoma, islet cell carcinoma, neuroendocrine tumors); prostate cancer; ovarian carcinoma (including, but not limited to, ovarian epithelial carcinoma or surface epithelial-stromal tumor including serous tumor, endometrioid tumor and mucinous cystadenocarcinoma, sex-cord-stromal tumor); liver and bile duct carcinoma (including, but not limited to, hepatocellular carcinoma, cholangiocarcinoma, hemangioma); esophageal carcinoma (including, but not limited to, esophageal adenocarcinoma and squamous cell carcinoma); non-Hodgkin's lymphoma; bladder carcinoma; carcinoma of the uterus (including, but not limited to, endometrial adenocarcinoma, uterine papillary serous carcinoma, uterine clear-cell carcinoma, uterine sarcomas and leiomyosarcomas, mixed mullerian tumors); glioma, glioblastoma, medulloblastoma, and other tumors of the brain; kidney cancers (including, but not limited to, renal cell carcinoma, clear cell carcinoma, Wilm's tumor); cancer of the head and neck (including, but not limited to, squamous cell carcinomas); cancer of the stomach (including, but not limited to, stomach adenocarcinoma, gastrointestinal stromal tumor); multiple myeloma; testicular cancer; germ cell tumor; neuroendocrine tumor;

cervical cancer; carcinoids of the gastrointestinal tract, breast, and other organs; and signet ring cell carcinoma.

Representative Kisspeptin Receptor (KISS1R) Targeting Conjugates

In some embodiments, the KISS1R-targeted radiopharmaceuticals described herein have an affinity to KISS1R that is at least 10-fold, at least 50-fold, at least 100-fold, at least 200-fold, at least 500-fold, or at least 1000-fold greater than the affinity for other non-target receptors.

In some embodiments, the KISS1R-targeted radiopharmaceuticals described herein preferentially accumulate in tumor tissues that express the targeted KISS1R. In some embodiments, the KISS1R-targeted radiopharmaceuticals described herein preferentially accumulate in tissues or organs comprising tumor cells that express KISS1R as compared to tissues or organ(s) lacking tumor cells that express KISS1R. In some embodiments, the KISS1R-targeted radiopharmaceuticals described herein preferentially accumulate at least 1-fold, at least 2-fold, at least 3-fold, at least 4-fold, at least 5-fold, or greater than 5-fold more in tissues or organ(s) comprising tumor cells that express KISS1R as compared to tissues or organs lacking tumor cells that express KISS1R. It is understood that the compound may accumulate in certain tissues and organs involved in the metabolism and or excretion of therapeutics, including but not limited to the kidneys and liver.

In one aspect, described herein is a compound of Formula (I), or a pharmaceutically acceptable salt thereof:

Formula (I)

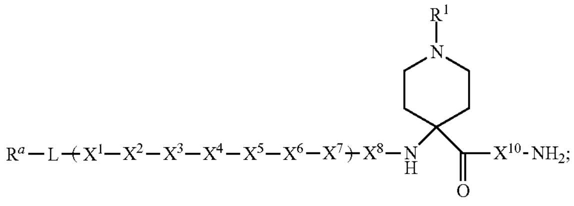

wherein:

$R^a$ is a chelating moiety or a radionuclide complex thereof;

L is an optional linker that is attached to any one of $X^1$, $X^2$, $X^3$, $X^4$, $X^5$, $X^6$, or $X^7$;

or L is attached to $X^8$ if $X^1$, $X^2$, $X^3$, $X^4$, $X^4$, $X^6$, and $X^7$ are absent;

$R^1$ is H,

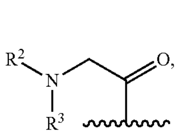 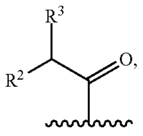 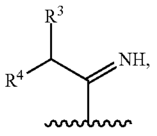 or

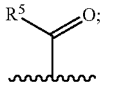

$R^2$ is $C_1$-$C_6$ alkyl, substituted or unsubstituted heteroalkyl, —$(CHR^6)_n$-heterocycloalkyl, —$(CHR^6)_n$-aryl, —$(CHR^6)_n$-heteroaryl, —C(═O)—$(CHR^6)_n$-aryl, or —C(═O)NH—$(CHR^6)_n$-aryl; wherein $C_1$-$C_6$ alkyl is optionally substituted with $R^7$, and wherein the heterocycloalkyl, aryl, or heteroaryl are each independently optionally substituted with $R^7$, $R^8$, $R^9$, $R^{10}$, and $R^3$ is H or $C_1$-$C_4$ alkyl;

$R^4$ is H, $C_1$-$C_4$ alkyl, or $R^2$;

$R^5$ is substituted or unsubstituted alkyl, substituted or unsubstituted heteroalkyl, or —$(CHR^6)_n$-aryl; wherein aryl is optionally substituted with $R^7$, $R^8$, $R^9$, $R^{10}$, and $R^{11}$;

each $R^6$ is independently H, F, —$CH_3$, —$NH_2$, or —OH;

$R^7$, $R^8$, $R^9$, $R^{10}$, and $R^{11}$ are each independently selected from H, F, Cl, Br, I, —OH, —O—$C_1$-$C_4$ alkyl, —$NH_2$, —$NHC_1$-$C_4$ alkyl, —N($C_1$-$C_4$ alkyl)$_2$, —CN, —$CO_2$, —$CO_2C_1$-$C_4$ alkyl, —$C_1$-$C_6$ alkyl, —$C_1$-$C_6$ fluroroalkyl or —$C_3$-$C_6$ cycloalkyl;

n is 0, 1, 2, 3, 4, 5, or 6;

$X^1$ is absent, tyrosine (Tyr), glycine (Gly), sarcosine (Sar), alanine (Ala), aspartic acid (Asp), lysine (Lys), phenylalanine (Phe), or D-3-(3-pyridyl)alanine (D-3-Pal), threonine (Thr), methionine (Met), 4-iodophenylalanine (Phe(4-I)), N6-(4-(p-tolyl)butanoyl)-lysine, or N6-(4-(4-iodophenyl)butanoyl)-lysine, or γ-glutamic acid (γ-Glu);

$X^2$ is absent, asparagine (Asn), glutamine (Gln), aspartic acid (Asp), glutamic acid (Glu), serine (Ser), histidine (His), alanine (Ala), sarcosine (Sar), tyrosine (Tyr), proline (Pro), hydroxyproline (Hyp), azetidine-2-carboxylic acid (Aze), 2,3,4,5-tetrahydroisoquinoline-3-carboxylic acid (Tic), phenylalanine (Phe), 3-(2-pyridyl)alanine (2-Pal), 3-(3-pyridyl)alanine (3-Pal), or 3-(4-pyridylalanine (4-Pal);

$X^3$ is absent, tryptophan (Trp), serine (Ser), leucine (Leu), isoleucine (Ile), phenylalanine (Phe), 4-iodophenylalanine (Phe(4-4)), 3-(2-pyridyl)alanine (2-Pal), 3-(3-pyridyl)alanine (3-Pal), 3-(4-pyridyl)alanine (4-Pal), 2-amino-3-(naphthalen-2-yl)propanoic acid (1H-2-NAL-OH), lysine (Lys), asparagine (Asn), glutamine (Gln), aspartic acid (Asp), glutamic acid (Glu), arginine (Arg), methyl arginine (Arg(Me)), norarginine (AGBA), methyl norarginine (AGBA(Me)), homoarginine (HArg), methyl homoarginine (HArg(Me)), citrulline (Cit), methyl citrulline (Cit(Me)), canavanine, methyl-canavanine, glycine (Gly), alanine (Ala), sarcosine (Sar), tyrosine (Tyr), cyclohexylalanine (Cha), 3-(1-naphthyl)alanine (α-Nal), 3-(2-naphthyl)alanine (β-Nal), threonine (Thr), proline (Pro), hydroxyproline (Hyp), tetrahydroisoquinoline-3-carboxylic acid (Tic), O-phospho-serine (SOP), 2-amino-4-(2H-tetrazol-5-yl) butanoic acid, β-glutamic acid, 8-aminoquinoline-3-carboxylic acid, biphenylalanine (Bip), 4-benzoylphenylalanine (Bpa), or 3-(9-anthryl)-alanine (H-Ala(9-Anth)-OH or AAP);

$X^4$ is absent, asparagine (Asn), glutamine (Gln), aspartic acid (Asp), glutamic acid (Glu), tryptophan (Trp), glycine (Gly), tyrosine (Tyr), alanine (Ala), sarcosine (Sar), or arginine (Arg);

$X^5$ is absent, serine Ser), threonine (Thr), lysine (Lys), asparagine (Asn), glutamine (Gln), aspartic acid (Asp), glutamic acid (Glu), glycine (Gly), alanine (Ala), or sarcosine (Sar);

$X^6$ is absent, phenylalanine (Phe), alpha-methylphenylalanine (α-Me-Phe), N-methylphenylalanine (N-Me-Phe), 2-fluorophenylalanine (2-F-Phe), 3-fluorophenylalanine (3-F-Phe), 4-fluorophenylalanine (4-F-Phe), 4-iodophenylalanine (Phe(4-I)), 2-amino-2-indancarboxylic acid (Aic), biphenylalanine (Bip), (β-(2-thienyl)-Ala), tryptophan (Trp), 2-aminotetralin-2-carboxylic acid (Atc), 3-(2-thienyl)-alanine, 3-(4-pyridyl) alanine (4-Pal), cyclohexylalanine (Cha), or tyrosine (Tyr);

$X^7$ is absent, glycine (Gly), aza-glycine (aza-Gly), alanine (Ala), N-methylglycine (Sar), or 1-aminocyclopropane-1-carboxylic acid (ACC);

$X^8$ is leucine (Leu), norvaline (Nva) valine (Val) isoleucine (Lie), homoalanine (HAla), tryptophan (Trp), phenylalanine (Phe), or phenylglycine (Phg);

or —$X^7$—$X^8$— is

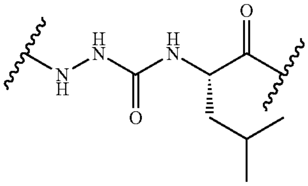
,
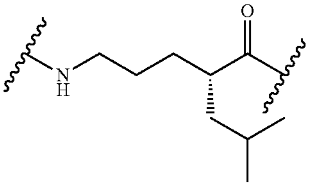
,
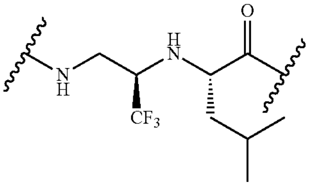
,
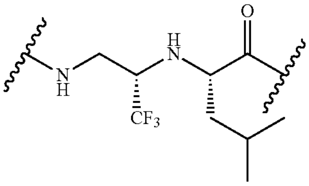
,
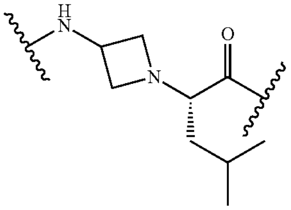
,
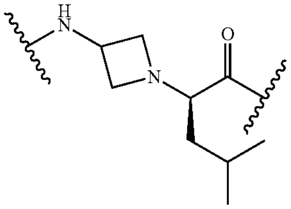
,
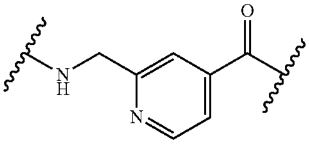
,
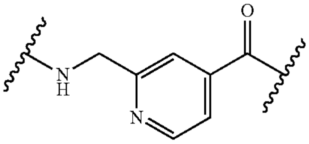
, -continued

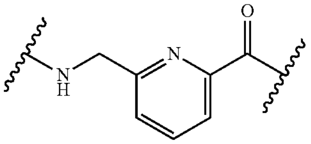
,
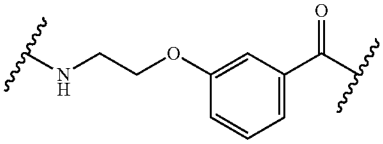
,
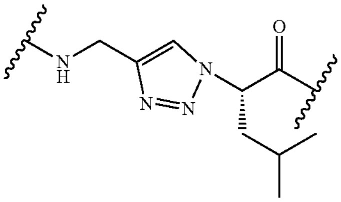
,
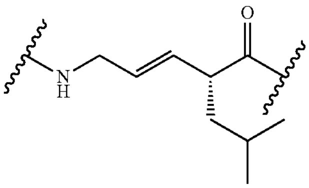
,
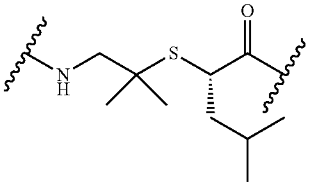
,
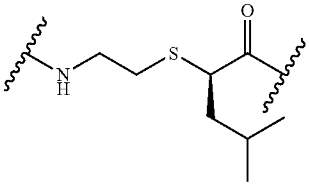
,
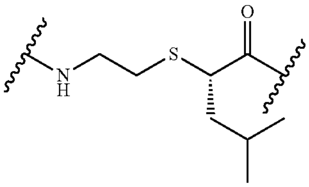
,
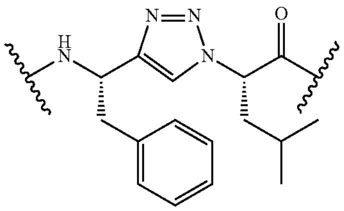
,
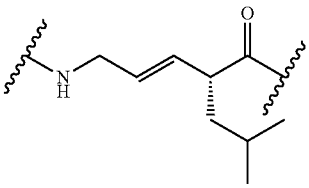
, -continued
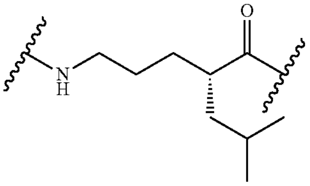
,
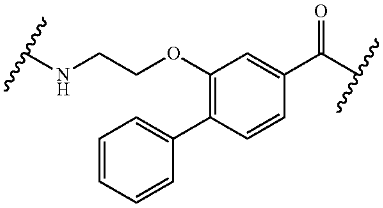
,
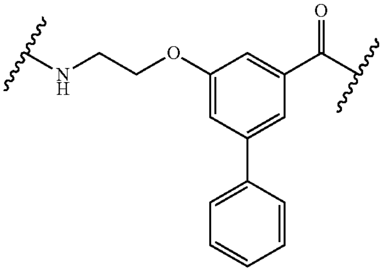
,
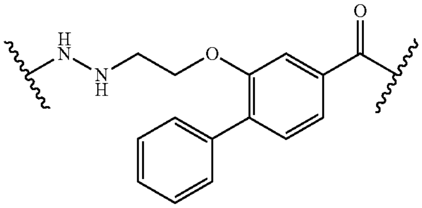
,
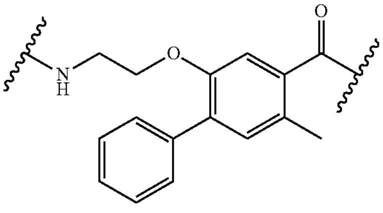
,
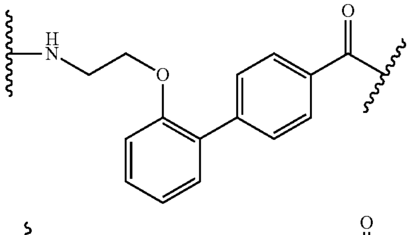
, or
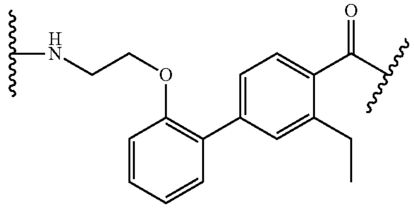
;
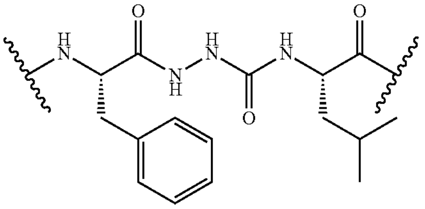
,
-continued
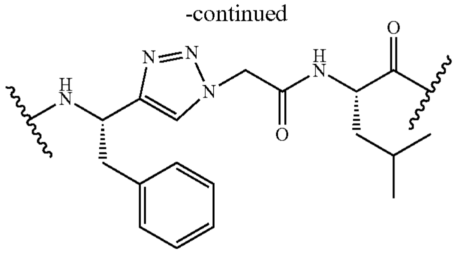
,
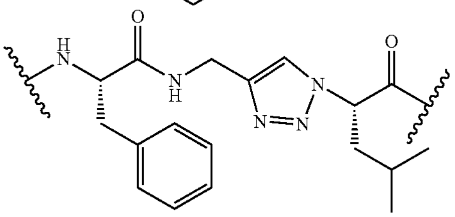
, or
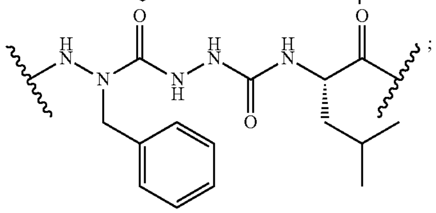
;
or —$X^6$—$X^7$—$X^8$— is
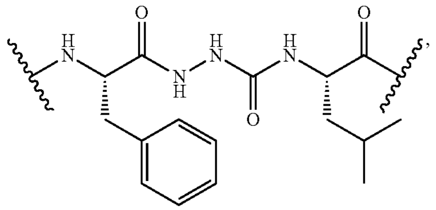
,
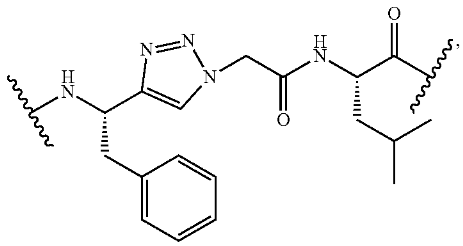
,
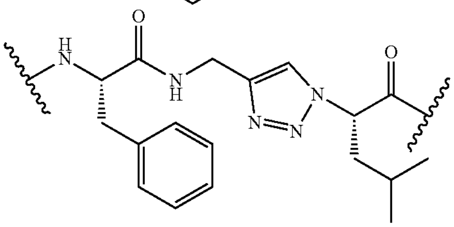
, or
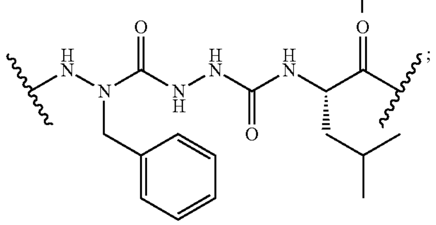
;
$X^{10}$ is tryptophan (Trp), 1-methyltryptophan (1MT), tyrosine (Tyr), phenylalanine (Phe), 4-cyano phenylalanine (Phe(4-CN)), 3-(4-pyridyl)alanine (4-Pal), leucine (Leu), phenylglycine (Phg), cyclohexylalanine (Cha), 3-(1-naphthyl)alanine (α-Nal), 3-(2-naphthyl)-alanine (β-Nal), histidine (His), or 3-nitro-tyrosine (Tyr(3-$NO_2$));

wherein the N-terminal amino acid or the compound of Formula (I) is optionally substituted with —C(=O)—$C_1$-$C_{20}$ alkyl, —C(=O)—$(CH_2CH_2O)_y$—$CH_2CH_2$—$R^{15}$, $C_1$-$C_{20}$ alkyl, N-hexadecanoyl-Glu, $C_4$-$C_{20}$ polyethylene glycol, a saccharide, —$R^{16}$, —C(=O)—$(CH_2CH_2O)_x$—$CH_3$, —C(=O)—$(CH_2CH_2)_x$—H, —C(=O)—$CH_2CH_2CH$(COOH)—$R^{15}$, —C(=O)—$(CH_2)_2R^{19}$, or —C(=O)$CH_2NHCH_2R^{19}$;

$R^{15}$ is selected from —$OR^{16}$, —$N(R^{16})_2$, —C(=O)$OR^{16}$, or —C(=O)$N(R^{16})_2$;

each $R^{16}$ is independently H, —$C_1$-$C_6$ alkyl, —C(=O)—$(CH_2)_vR^{19}$, —C(=O)$CH_2NHCH_2R^{19}$, or a saccharide or derivative thereof:

$R^{19}$ is 4-iodophenylene, 4-methylphenylene, or 3-fluoro-4-methylphenylene;

y is 0, 1, 2, 3, 4, 5, 6, 7, 8, 9, or 10;

x is an integer from 1 and 25; and v is 1, 2, 3, or 4;

wherein any free —NH— of a peptide bond is optionally independently substituted with —$CH_3$ or —$CH_2CH_3$; and wherein any alpha position of an amino acid is optionally independently substituted with —$CH_3$ or —$CH_2CH_3$.

In some embodiments, described herein is a compound of Formula (I), or a pharmaceutically acceptable salt thereof:

Formula (I)

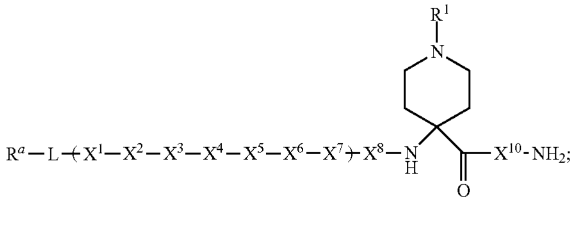

wherein:

$R^a$ is a chelating moiety or a radionuclide complex thereof;

L is an optional linker that is attached to any one of $X^1$, $X^2$, $X^3$, $X^4$, $X^5$, $X^6$, or $X^7$;

or L is attached to $X^8$ if $X^1$, $X^2$, $X^3$, $X^4$, $X^5$, $X^6$, and $X^7$ are absent; and $R^1$ is H,

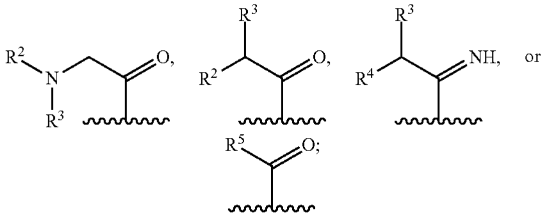

$R^2$ is $C_1$-$C_6$ alkyl, substituted or unsubstituted heteroalkyl, —$(CHR^9)_n$-aryl, —C(=O)—$(CHR^6)_n$-aryl, or —C(=O)NH—$(CHR^6)_n$-aryl; wherein $C_1$-$C_6$ alkyl is optionally substituted with $R^7$, and wherein aryl is optionally substituted with $R^7$, $R^8$, $R^9$, $R^{10}$, and $R^{11}$;

$R^3$ is H or $C_1$-$C_4$ alkyl;

$R^4$ is H, $C_1$-$C_4$ alkyl, or $R^2$;

$R^5$ is substituted or unsubstituted alkyl, substituted or unsubstituted heteroalkyl, or —$(CHR^6)_n$-aryl; wherein aryl is optionally substituted with $R^7$, $R^8$, $R^9$, $R^{10}$, and $R^{11}$;

each $R^6$ is independently H, F, —$CH_3$, —$NH_2$, or —OH;

$R^7$, $R^8$, $R^9$, $R^{10}$, and $R^{11}$ are independently selected from H, F, Cl, Br, I, —OH, —O—$C_1$-$C_4$ alkyl, —$NH_2$, —$NHC_1$-$C_4$ alkyl, —N($C_1$-$C_4$ alkyl$)_2$, —CN, —$CO_2H$, —$CO_2C_1$-$C_4$ alkyl, —$C_1$-$C_6$ alkyl, —$C_1$-$C_6$ fluoroalkyl or —$C_3$-$C_6$ cycloalkyl;

n is 0, 1, 2, 3, 4, 5, or 6;

$X^1$ is absent, tyrosine (Tyr), glycine (Gly), sarcosine (Sar), alanine (Ala), aspartic acid (Asp), lysine (Lys), phenylalanine (Phe), or D-3-(3-pyridyl)alanine (D-3-Pal);

$X^2$ is absent, asparagine (Asn), glutamine (Gln), aspartic acid (Asp), glutamic acid (Glu), serine (Ser), histidine (His), alanine (Ala), sarcosine (Sar), tyrosine (Tyr), Proline (Pro), hydroxyproline (Hyp), azetidine-2-carboxylic acid (Aze), 2,3,4,5-tetrahydroisoquinoline-3-carboxylic acid (Tic), phenylalanine (Phe), 3-(2-pyridyl)alanine (2-Pal), 3-(3-pyridyl)alanine (3-Pal), or 3-(4-pyridyl)alanine (4-Pal);

$X^3$ is absent, tryptophan (Trp), serine (Ser), leucine (Leu), isoleucine (Ile), phenylalanine (Phe), 3-(2-pyridyl)alanine (2-Pal), 3-(3-pyridyl)alanine (3-Pal), 3-(4-pyridyl) alanine (4-Pal), lysine (Lys), asparagine (Asn), glutamine (Gln), aspartic acid (Asp), glutamic acid (Glu), arginine (Arg), methyl arginine (Arg(Me)), norarginine (AGBA), methyl norarginine (AGBA(Me)), homoarginine (HArg), methyl homoarginine (HArg(Me)), citrulline (Cit), methyl citrulline (Cit(Me)), canavanine, methyl-canavanine, glycine (Gly), alanine (Ala), sarcosine (Sar), tyrosine (Tyr), cyclohexylalanine (Cha), 3-(1-naphthyl)alanine (α-Nal), 3-(2-naphthyl)alanine (β-Nal), or threonine (Thr), proline (Pro), hydroxyproline (Hyp), or tetrahydroisoquinoline-3-carboxylic acid (Tic);

$X^4$ is absent, asparagine (Asn), glutamine (Gln), aspartic acid (Asp), glutamic acid (Glu), tryptophan (Trp), glycine (Gly), tyrosine (Tyr), alanine (Ala), or sarcosine (Sar);

$X^5$ is absent, serine (Ser), threonine (Thr), lysine (Lys), asparagine (Asn), glutamine (Gln), aspartic acid (Asp), glutamic acid (Glu), glycine (Gly), alanine (Ala), or sarcosine (Sar);

$X^6$ is absent, phenylalanine (Phe), alpha-methylphenylalanine (α-Me-Phe), N-methylphenylalanine (N-Me-Phe), 2-fluorophenylalanine (2-F-Phe), 3-fluorophenylalanine (3-F-Phe), 4-fluorophenylalanine (4-F-Phe), 2-amino-2-indancarboxylic acid (Aic), biphenylalanine (Bip), tryptophan (Trp), 2-aminotetralin-2-carboxylic acid (Atc);

$X^7$ is absent, glycine (Gly), aza-glycine (aza-Gly), alanine (Ala), N-methylglycine (Sar), or 1-aminocyclopropane-1-carboxylic acid (ACC);

$X^8$ is leucine (Leu), norvaline (Nva), valine (Val), isoleucine (Ile), homoalanine (HAla), tryptophan (Trp), phenylalanine (Phe), or phenylglycine (Phg);

or —$X^7$—$X^8$— is
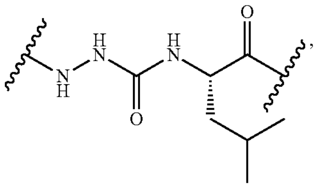
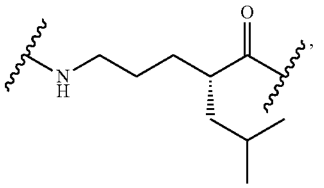
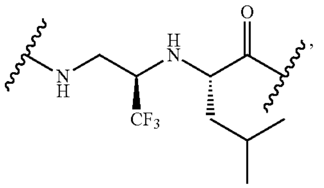
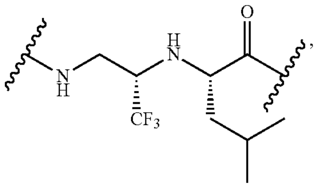
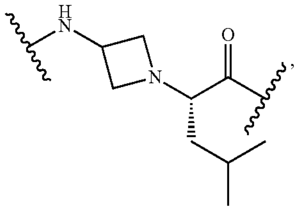
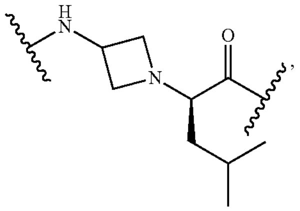
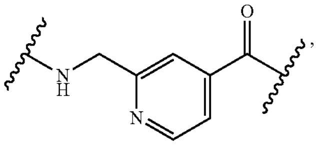
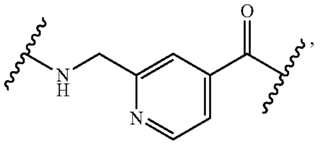
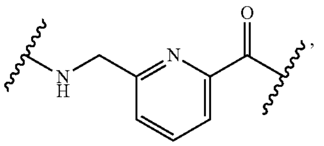
-continued
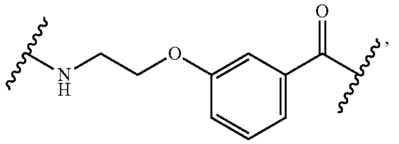
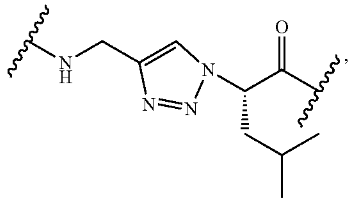
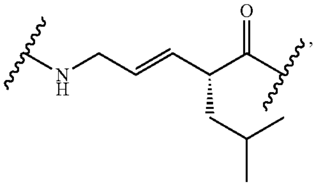
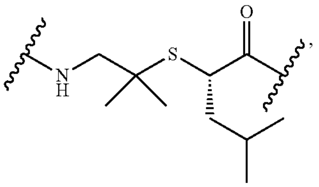
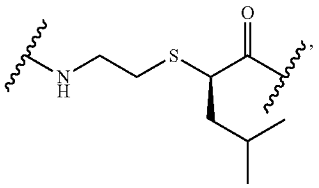
or
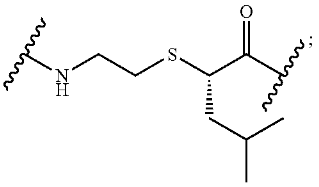
or —$X^6$—$X^7$—$X^8$— is
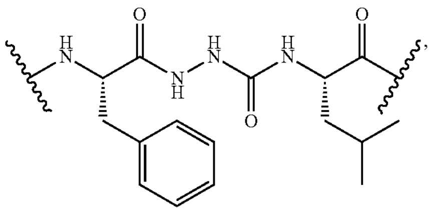
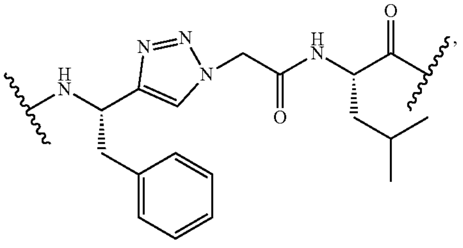
or -continued

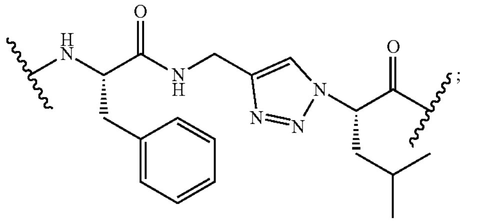

$X^{10}$ is tryptophan (Trp), 1-methyltryptophan (1MT), tyrosine (Tyr), phenylalanine (Phe), 4-cyano phenylalanine (Phe(4-CN)), 3-(4-pyridyl)alanine (4-Pal), leucine (Leu), phenylglycine (Phg), cyclohexylalanine (Cha) 3-(1-naphthyl)alanine (α-Nal), 3-(2-naphthyl)-alanine (r-Nal);

wherein the N-terminal amino acid or the compound of Formula (I) is optionally substituted with —C(═O)—$C_1$-$C_{20}$ alkyl, —C(═O)—$(CH_2CH_2O)_y$—$CH_2CH_2$—$R^{15}$, $C_1$-$C_{20}$alkyl, N-hexadecanoyl-Glu, $C_4$-$C_{20}$ polyethylene glycol, a saccharide $R^{15}$ is selected from —$OR^{16}$, —$N(R^{16})_2$, —C(═O)$OR^{16}$, —C(═O)$N(R^{16})_2$;

each $R^{16}$ is independently H, —$C_1$-$C_6$ alkyl, or a saccharide or derivative thereof;

y is 0, 2, 3, 4, 5, 6, 7, 8, 9, or 10;

wherein any free —NH— of a peptide bond is optionally independently substituted with —$CH_3$ or —$CH_2CH_3$; and wherein any alpha position of an amino acid is optionally independently substituted with —$CH_3$ or —$CH_2CH_3$.

In some embodiments, $X^1$ is absent, tyrosine (Tyr), glycine (Gly), sarcosine (Sar), alanine (Ala), aspartic acid (Asp), lysine (Lys), phenylalanine (Phe), 3-(3-pyridyl)alanine (3-Pal) (3-Pal), threonine (Thr), methionine (Met), 4-iodophenylalanine (Phe(4-I)), N6-(4-(p-tolyl)butanoyl)-lysine, N6-(4-(4-iodophenyl)butanoyl)-lysine, or γ-glutamic acid (γ-Glu);

$X^2$ is absent, asparagine (Asn), glutamine (Gln), aspartic acid (Asp), glutamic acid (Glu), serine (Ser), histidine (His), alanine (Ala), sarcosine (Sar), tyrosine (Tyr), proline (Pro), hydroxyproline (Hyp), azetidine-2-carboxylic acid (Aze), 2,3,4,5-tetrahydroisoquinoline-3-carboxylic acid (Tic), phenylalanine (Phe), 3-(2-pyridyl)alanine (2-Pal), 3-(3-pyridyl)alanine (3-Pal), or 3-(4-pyridyl)alanine (4-Pal);

$X^3$ is absent, tryptophan (Trp), serine (Ser), leucine (Leu), isoleucine (Ile), phenylalanine (Phe), 4-iodophenylalanine (Phe(4-I)), 3-(2-pyridyl)alanine (2-Pal), 3-(3-pyridyl)alanine (3-Pal), 3-(4-pyridyl)alanine (4-Pal), 2-amino-3-(naphthalen-2-yl)propanoic acid (H-2-NAL-OH), lysine (Lys), asparagine (Asn), glutamine (Gln), aspartic acid (Asp), glutamic acid (Gi), arginine (Arg), methyl arginine (Arg(Me)), norarginine (AGBA), methyl norarginine (AGBA(Me)), homoarginine (HArg), methyl homoarginine (HArg(Me)), citrulline (Cit), methyl citrulline (Cit(Me)), canavanine, methyl-canavanine, glycine (Gly), alanine (Ala), sarcosine (Sar), tyrosine (Tyr), cyclohexylalanine (Cha), 3-(1-naphthyl)alanine (α-Nal), 3-(2-naphthyl)alanine (β-Nal), threonine (Thr), proline (Pro), hydroxyproline (Hyp), tetrahydroisoquinoline-3-carboxylic acid (Tic), O-phospho-serine (SOP), 2-amino-4-(2H-tetrazol-5-yl) butanoic acid, β-glutamic acid (bGlu), 8-aminoquinoline-3-carboxylic acid, biphenylalanine (Bip), 4-benzoylphenylalanine (Bpa), or 3-(9-anthryl)-alanine (H-Ala (9-Anth)-OH or AAP);

$X^4$ is absent, asparagine (Asn), glutamine (Gln), aspartic acid (Asp), glutamic acid (Glu), tryptophan (Trp), glycine (Gly), D-alanine (D-Ala), sarcosine (Sar), or arginine (Arg); and $X^5$ is absent, serine (Ser), threonine (Thr), lysine (Lys), asparagine (Asn), glutamine (Gln), aspartic acid (Asp), glutamic acid (Glu), glycine (Gly), alanine (Ala), or sarcosine (Sar).

In some embodiments, $X^1$ is absent, D-tyrosine (D-Tyr), glycine (Gly), sarcosine (Sar), D-alanine (D-Ala), aspartic acid (Asp), lysine (Lys), phenylalanine (Phe), or D-3-(3-pyridyl)alanine (3-Pal) (D-3-Pal);

$X^2$ is absent, D-asparagine (D-Asn), glutamine (Gln), aspartic acid (Asp), glutamic acid (Glu), D-serine (D-Ser), D-histidine (D-His), alanine (Ala), sarcosine (Sar), tyrosine (Tyr), Proline (Pro), hydroxyproline (Hyp), azetidine-2-carboxylic acid (Aze), 2,3,4,5-tetrahydroisoquinoline-3-carboxylic acid (Tic), phenylalanine (Phe), 3-(2-pyridyl)alanine (2-Pal), 3-(3-pyridyl) alanine (3-Pal), or 3-(4-pyridyl)alanine (4-Pal);

$X^3$ is absent, D-tryptophan (D-Trp), serine (Ser), leucine (Leu), isoleucine (Ile), phenylalanine (Phe), D-3-(2-pyridyl)alanine (D-2-Pal), D-3-(3-pyridyl)alanine (D-3-Pal), D-3-(4-pyridyl)alanine (D-4-Pal), D-lysine (D-Lys), asparagine (Asn), glutamine (Gln), D-aspartic acid (D-Asp), D-glutamic acid (D-Glu), arginine (Arg), methyl arginine (Arg(Me)), norarginine (AGBA), methyl norarginine (AGBA(Me)), homoarginine (HArg), methyl homoarginine (HArg(Me)), citrulline (Cit), methyl citrulline (Cit(Me)), canavanine, methyl-canavanine, glycine (Gly), alanine (Ala), sarcosine (Sar), tyrosine (Tyr), cyclohexylalanine (Cha), 3-(1-naphthyl)alanine (α-Nal), 3-(2-naphthyl)alanine (β-Nal), threonine (Thr), proline (Pro), hydroxyproline (Hyp), tetrahydroisoquinoline-3-carboxylic acid (Tic);

$X^4$ is absent, D-asparagine (D-Asn), glutamine (Gln), D-aspartic acid (D-Asp), glutamic acid (Glu), tryptophan (Trp), glycine (Gly), D-alanine (D-Ala), or sarcosine (Sar); and $X^5$ is absent, serine (Ser), threonine (Thr), lysine (Lys), D-asparagine (D-Asn), glutamine (Gln), aspartic acid (Asp), glutamic acid (Glu), glycine (Gly), alanine (Ala), or sarcosine (Sar).

In some embodiments, $X^1$ is absent, tyrosine (Tyr), 3-(3-pyridyl)alanine (3-Pal), or γ-glutamic acid (γ-Glu);

$X^2$ is absent, asparagine (Asn), glutamine (Gln), serine (Ser), histidine (His), or phenylalanine (Phe);

$X^3$ is absent, tryptophan (Trp), isoleucine (Ile), 3-(4-pyridyl)alanine (4-Pal), lysine (Lys), aspartic acid (Asp), glutamic acid (Glu), glycine (Gly), alanine (Ala), cyclohexylalanine (Cha), 3-(2-naphthyl)alanine (β-Nal), hydroxyproline (Hyp), biphenylalanine (Bip), 4-benzoylphenylalanine (Bpa), or 3-(9-anthryl)-alanine (H-Ala(9-Anth)-OH or AAP);

$X^4$ is absent, asparagine (Asn), or glutamine (Gln); and $X^5$ is absent, serine (Ser), threonine (Thr), glycine (Gly), or alanine (Ala).

In some embodiments, $X^1$ is tyrosine (Tyr), 3-(3-pyridyl)alanine (3-Pal), or γ-glutamic acid (γ-Glu);

$X^2$ is absent;

$X^3$ is tryptophan (Trp) isoleucine (Ile), 3-(4-pyridyl)alanine (4-Pal), lysine (Lys), aspartic acid (Asp), glutamic acid (Glu), glycine (Gly), alanine (Ala), cyclohexylalanine (Cha), 3-(2-naphthyl)alanine (β-Nal), hydroxyproline (Hyp), biphenylalanine (Bip), 4-benzoylphenylalanine (Bpa), or 3-(9-anthryl)-alanine (1-Ala(9-Anth)-OH or AAP);

$X^4$ is asparagine (Asn) or glutamine (Gln); and $X^5$ is serine (Ser), threonine (Thr), glycine (Gly), or alanine (Ala).

In some embodiments, $X^1$ is absent, tyrosine (Tyr), or 3-(3-pyridyl)alanine (3-Pal));

$X^2$ is absent, asparagine (Asn), glutamine (Gln), serine (Ser), D-histidine (D-His), or phenylalanine (Phe);

$X^3$ is absent, tryptophan (Trp), isoleucine (Ile), 3-(4-pyridyl)alanine (4-Pal), lysine (Lys), aspartic acid (Asp), glutamic acid (Glu), glycine (Gly), alanine (Ala), cyclohexylalanine (Cha), hydroxyproline (Hyp), biphenylalanine (Bip); 4-benzoylphenylalanine (Bpa), or 3-(9-anthryl)-alanine (AAP);

$X^4$ is absent, asparagine (Asn), or glutamine (Gln); and $X^5$ is absent, serine (Ser), threonine (Thr), glycine (Gly), or alanine (Ala).

In some embodiments, $X^1$ is tyrosine (Tyr), or 3-(3-pyridyl)alanine (3-Pal));

$X^2$ is absent;

$X^3$ is tryptophan (Trp), isoleucine (Ile), 3-(4-pyridyl) alanine (4-Pal), lysine (Lys), aspartic acid (Asp), glutamic acid (Glu), glycine (Gly), alanine (Ala), cyclohexylalanine (Cha), hydroxyproline (Hyp), biphenylalanine (lip); 4-benzoylphenylalanine (Bpa), or 3-(9-anthryl)-alanine (AAP);

$X^4$ is asparagine (Asn), or glutamine (Gln); and $X^5$ is serine (Ser), threonine (Thr), glycine (Gly), or alanine (Ala).

In some embodiments, $X^1$ is not absent; $X^2$ is absent; $X^3$ is not absent; $X^4$ is not absent; and $X^5$ is not absent.

In some embodiments, XV is D-tyrosine (D-Tyr); $X^2$ is absent; $X^3$ is D-tryptophan (D-Trp), biphenylalanine (Bip); 4-benzoylphenylalanine (Bpa), or 3-(9-anthryl)-alanine (AAP); $X^4$ is asparagine (Asn); and $X^5$ is serine (Set) or threonine (Thr).

In some embodiments, $X^1$ is absent, Tyr, Asp, Lys, 3-Pal, Sar, or Phe; and $X^2$ is absent, Asn, Gln, Asp, Glu, Ser, His, Ala, Sar, Pro, Hyp, Aze, Tic, Phe, or 4-Pal.

In some embodiments, $X^1$ is absent, D-Tyr, Asp, Lys, D-3-Pal, Sar, or Phe; and $X^2$ is absent, D-Asn, Gln, Asp, Glu, Ser, His, Ala, Sar, Pro, Hyp, Aze, Tic, Phe, or 4-Pal.

In some embodiments, $X^3$ is absent, Trp, Ser, Ile, Phe, 4-Pal, Lys, Asn, Gln, Asp, Glu, Arg, Arg(Me), AGBA, AGBA(Me), Harg, Harg(Me), Cit, Cit(Me), canavanine, methyl-canavanine, Gly, Ala, Sar, Tyr, Cha, β-Nal, Hyp, Thr, Bip, Bpa, or H-Ala(9-Anth)-OH; $X^4$ is absent, Asn, Gln, Asp, Glu, Trp, Gly, Ala, or Sar; and $X^5$ is absent, Ser, Thr, Asn, Gln, Asp, Glu, Gly, Ala or Sar.

In some embodiments, $X^3$ is absent, Trp, Ser, Ile, Phe, 4-Pal, Lys, Asn, Gln, Asp, Glu, Arg, Arg(Me), AGBA, AGBA(Me), Harg, Harg(Me), Cit, Cit(Me) canavanine, methyl-canavanine, Gly, Ala, Sar, Tyr, Cha, β-Nal, Hyp, Thr, Bip, Bpa, or AAP; $X^4$ is absent, -Asn, Gln, Asp, Glu, Trp, Gly, Ala, or Sar; and $X^5$ is absent, Thr, Ser or Ala.

In some embodiments, $X^1$ is absent, Tyr, Asp, Lys, 3-Pal, Sar, or Phe; $X^2$ is absent, Asn, Gln, Asp, Glu, Ser, His, Ala, Sar, Pro, Hyp, Aze, Tic, Phe, or 4-Pal; $X^3$ is absent, Trp, Ser, Ile, Phe, 4-Pal, Lys, Asn, Gln, Asp, Glu, Arg, Arg(Me), Gly, Ala, Sar, Tyr, Cha, β-Nal, Hyp, Thr, Bip, Bpa, or AAP; $X^4$ is absent, Asn, Gln, Asp, Glu, Trp, Gly, Ala, or Sar; and $X^5$ is absent, Thr, Ser, Gly, or Ala.

In some embodiments, $X^1$ is absent, Tyr, Asp, Lys, 3-Pal, Sar, or Phe. In some embodiments, $X^1$ is absent, D-Tyr, Asp, Lys, D-3-Pal, Sar, or Phe. In some embodiments, $X^1$ is absent, Tyr, or 3-Pal. In some embodiments, $X^1$ is absent. In some embodiments, $X^1$ is Tyr. In some embodiments, $X^1$ is D-Tyr. In some embodiments, $X^1$ is 3-Pal.

In some embodiments, $X^2$ is absent, Asn, Gln, Asp, Glu, Ser, His, Ala, Sar, Pro, Hyp, Aze, Tic, Phe, or 4-Pal. In some embodiments, $X^2$ is absent, D-Asn, Gln, Asp, Glu, Ser, His, Ala, Sar, Pro, Hyp, Aze, Tic, Phe, or 4-Pal. In some embodiments, $X^2$ is absent, D-Asn, Gln, Asp, Glu, Ala, Sar, Pro, Hyp, Aze, Tic, Phe, or 4-Pal. In some embodiments, $X^2$ is absent, Asn, Gln, Ser, or His. In some embodiments, $X^2$ is absent. In some embodiments, $X^2$ is Asn. In some embodiments, $X^2$ is Gln. In some embodiments, $X^2$ is Ser. In some embodiments, $X^2$ is His.

In some embodiments, $X^3$ is absent, Trp, Ser, Ile, Phe, 4-Pal, Lys, Asn, Gln, Asp, Glu, Arg, Arg(Me), AGBA, AGBA(Me), HArg, HArg(Me), Cit, Cit(Me), canavanine, methyl-canavanine, Gly, Ala, Sar, Tyr, Cha, β-Nal, Hyp, Thr, Bip, Bpa, or H-Ala(9-Anth)-OH. In some embodiments, $X^3$ is absent, Trp, Ser, Ile, Phe, 4-Pal, Lys, Asn, Gln, Asp, Glu, Arg, Arg(Me), AGBA, AGBA(Me), HArg, HArg(Me), Cit, Cit(Me), canavanine, methyl-canavanine, Gly, Ala, Sar, Tyr, Cha, β-Nal, Hyp, or Thr. In some embodiments, $X^3$ is $X^3$ is absent, D-Trp, Ser, Ile, Phe, 4-Pal, D-Lys, Asn, Gln, D-Asp, D-Glu, Arg, Arg(Me), AGBA, AGBA(Me), HArg, HArg (Me), Cit, Cit(Me), canavanine, methyl-canavanine, Gly, Ala, Sat, Tyr, Cha, β-Nal, Hyp, or Thr. In some embodiments, $X^3$ is absent, D-Trp, Ser, Ile, Phe, 4-Pal, D-Lys, Asn, Gln, D-Asp, D-Glu, Arg, Arg(Me), Gly, Ala, Sar, Tyr, Cha, β-Nal, Hyp, or Thr. In some embodiments, $X^3$ is absent, Trp, Ile, 4-Pal, Lys, Asp, Glu, Gly, Ala, Cha, β-Nal, Hyp, Bip, Bpa, or AAP. In some embodiments, $X^3$ is absent, Ile, 4-Pal, Lys, Asp, Glu, Gly, Ala, Cha, β-Nal, or Hyp. In some embodiments, $X^3$ is Trp, Bip, Bpa, or AAP. In some embodiments, $X^3$ is absent. In some embodiments, $X^3$ is Trp. In some embodiments, $X^3$ is Ile. In some embodiments, $X^3$ is 4-Pal. In some embodiments, $X^3$ is Lys. In some embodiments, $X^3$ is Asp. In some embodiments, $X^3$ is Glu. In some embodiments, $X^3$ is Gly. In some embodiments, $X^3$ is Ala. In some embodiments, $X^3$ is Cha. In some embodiments, $X^3$ is β-Nal. In some embodiments, $X^3$ is Hyp. In some embodiments, $X^3$ is Bip. In some embodiments, $X^3$ is Bpa. In some embodiments, $X^3$ is AAP In some embodiments, $X^4$ is absent, Asn, Gln, Asp, Glu, Trp, Gly, Ala, or Sar. In some embodiments, $X^4$ is D-Asn, Gln, Asp, Glu, Trp, Gly, Ala, or Sar. In some embodiments, $X^4$ is absent, Asn, or Gln. In some embodiments, $X^4$ is absent. In some embodiments, $X^4$ is Asn. In some embodiments, $X^4$ is Gln.

In some embodiments, $X^5$ is absent, Ser, Thr, Asn, Gln, Asp, Glu, Gly, Ala or Sar. In some embodiments, $X^5$ is absent, Thr, Ser or Ala. In some embodiments, $X^5$ is absent, Ser, Thr, Gly, or Ala. In some embodiments, $X^5$ is absent. In some embodiments, $X^5$ is Ser. In some embodiments, $X^5$ is Thr. In some embodiments, $X^5$ is Gly. In some embodiments, $X^5$ is Ala.

In some embodiments, $X^6$ is Phe, 3-F-Phe, Bip, β-(2-thienyl)-Ala), Cha, or Tyr. In some embodiments, $X^6$ is Phe. In some embodiments, $X^6$ is 3-F-Phe. In some embodiments, $X^6$ is Bip. In some embodiments, $X^6$ is β-(2-thienyl)-Ala. In some embodiments, $X^6$ is Cha. In some embodiments, $X^6$ is Tyr.

In some embodiments, $X^7$ is Gly or azaGly. In some embodiments, $X^7$ is Gly. In some embodiments, $X^7$ is azaGly.

In some embodiments, $X^8$ is Leu or Nva. In some embodiments, $X^8$ is Leu. In some embodiments, $X^8$ is Nva.

In some embodiments, $X^8$ is Leu, Nva, Ile, HAla, or Phe, and $X^{10}$ is Trp, 1MT, Tyr, 4-Pal, Phe(4-CN) or Phe.

In some embodiments, $X^6$ is

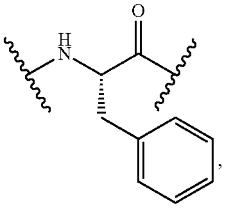,
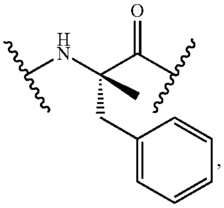,
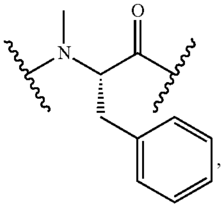,
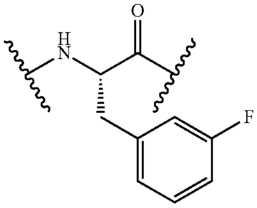,
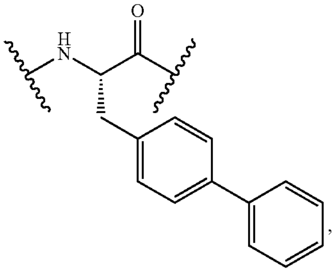, or
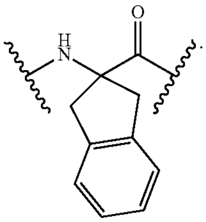.

In some embodiments, $X^6$ is

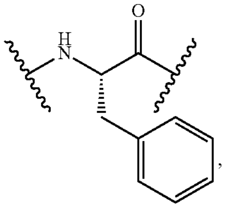,
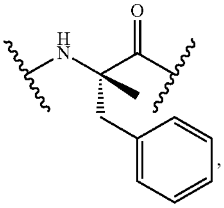,
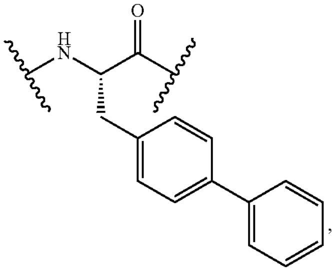, or

-continued

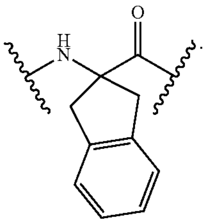.

In some embodiments, $X^7$ is

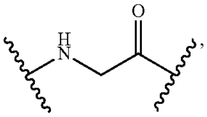,
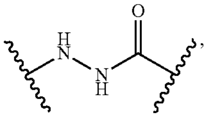,
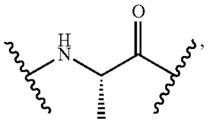,
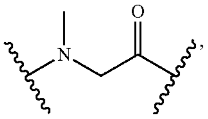, or
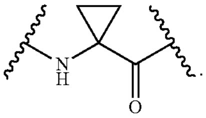.

In some embodiments, $X^7$ is or

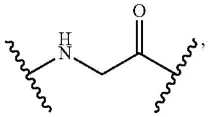,
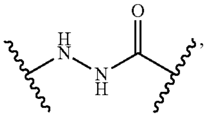, or
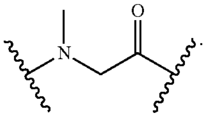.

In some embodiments, $X^8$ is

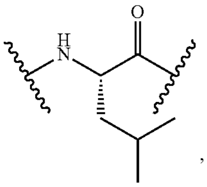,
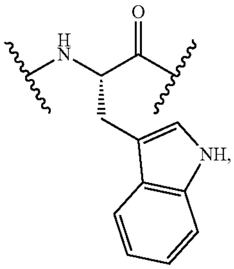
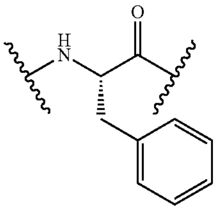, or
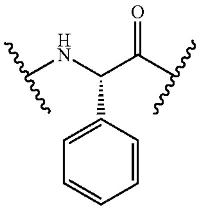,

In some embodiments, $X^8$ is
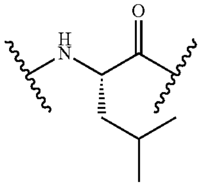
or
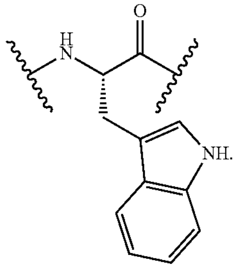
In some embodiments, $X^6$ is
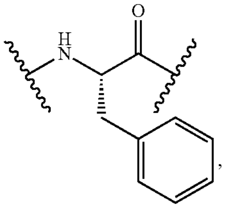
,
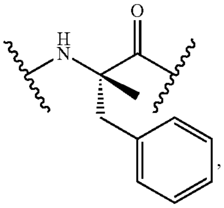
,
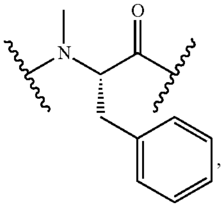
,
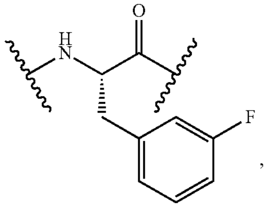
,
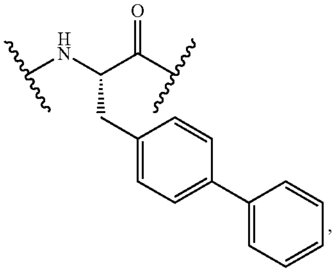
, or
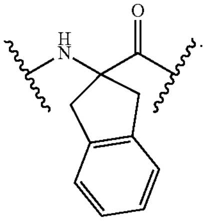
.
$X^7$ is
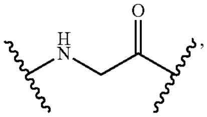
,
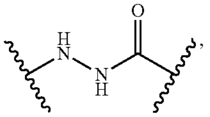
,
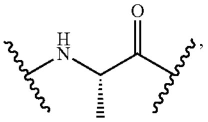
,
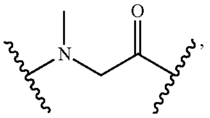
, or
-continued
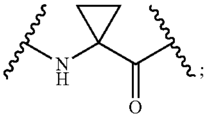
; $X^8$ is
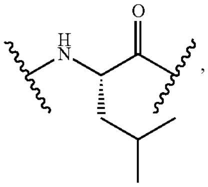
,
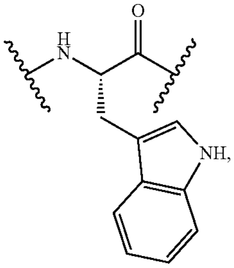
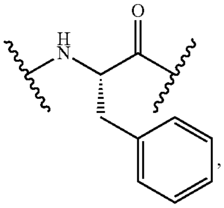
, or
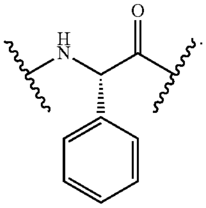
In some embodiments, $X^6$ is
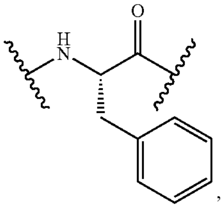
,
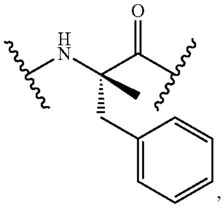
,
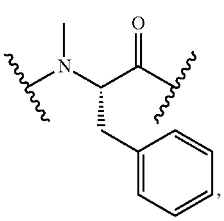
, or
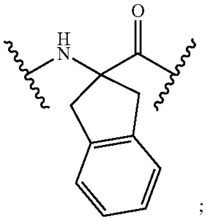
;
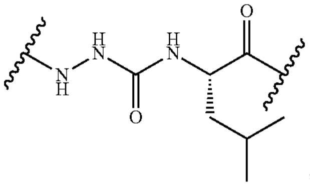
,
$X^7$—$X^8$— is
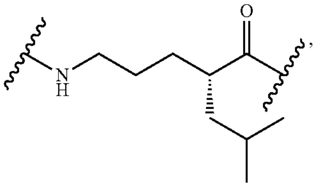
, -continued
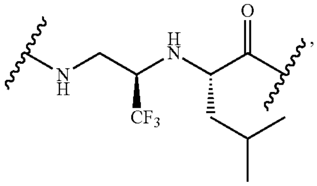
,
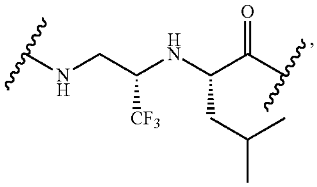
,
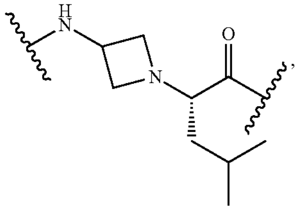
,
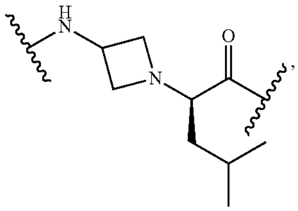
,
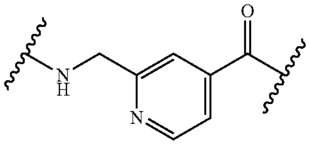
,
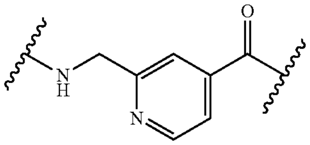
,
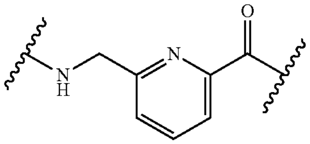
,
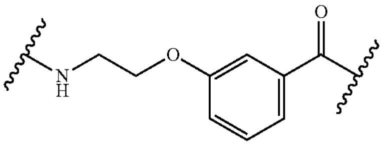
,
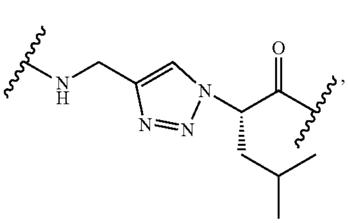
,
-continued
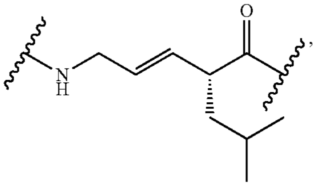
,
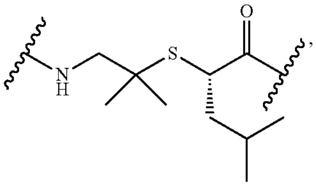
,
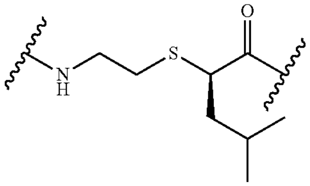
, or
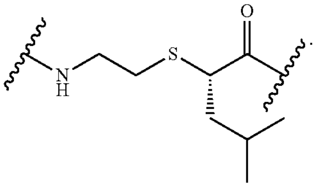
.
In some embodiments, —$X^6$—$X^7$—$X^8$— is
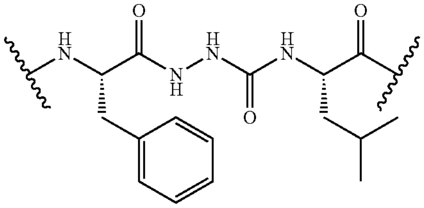
,
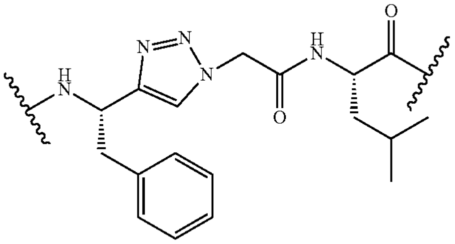
,
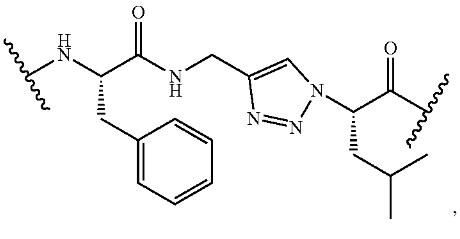
, or -continued

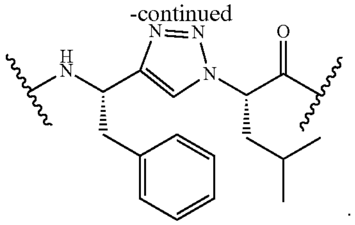

In any embodiment described herein,

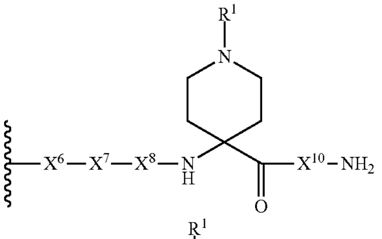

is

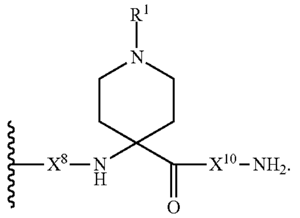

In some embodiments, $X^6$ is absent, $X^7$ is absent, $X^8$ is not absent, and $X^{10}$ is not absent.

In any embodiment described herein,

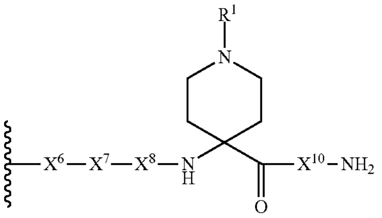

is

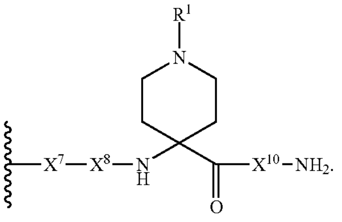

In some embodiments, $X^6$ is absent. $X^7$ is not absent, $X^8$ is not absent, and $X^{10}$ is not absent. In some embodiments, $X^6$ is absent, $X^7$ is not absent, $X^8$ is not absent, and $X^{10}$ is Trp or Tyr. In some embodiments, $X^6$ is absent, $X^7$ is AzaGly, $X^8$ is not absent, and $X^{10}$ is Trp or Tyr. In some embodiments, $X^6$ is absent, $X^7$ is AzaGly, $X^8$ is Leu, and $X^{10}$ is Trp or Tyr.

In some embodiments, $X^6$ is not absent, $X^7$ is not absent, $X^8$ is not absent, and $X^{10}$ is Trp or Tyr. In some embodiments, $X^6$ is AzaGly, $X^7$ is not absent, Xu is not absent, and $X^{10}$ is Trp or Tyr. In some embodiments, $X^6$ is AzaGly, $X^7$ is Leu, $X^8$ is not absent, and $X^{11}$ is Trp or Tyr.

In some embodiments, $X^{10}$ is Trp, 1MT, Tyr, Phe, Phe(4-CN), 4-Pal, Leu, Phg, Cha, α-Nal, or β-Nal. In some embodiments, $X^{10}$ is Trp, 1MT, Tyr, Phe, Phe(4-CN), 4-Pal, or Leu. In some embodiments, $X^{10}$ is Trp, Tyr, Phe, or Phe(4-CN). In some embodiments, $X^{10}$ is 1MT, 4-Pal, or Leu. In some embodiments, $X^{10}$ is Trp. In some embodiments, $X^{10}$ is Tyr. In some embodiments, $X^{10}$ is Phe. In some embodiments, $X^{10}$ is Phe(4-CN). In some embodiments, $X^{10}$ is 1MT. In some embodiments, $X^{10}$ is 4-Pal. In some embodiments, $X^{10}$ is Leu.

In some embodiments, $X^1$ is absent; $X^2$ is absent; $X^3$ is absent; $X^4$ is absent; and $X^5$ is absent; $X^6$ is absent, $X^7$ is absent, $X^8$ is not absent, and $X^{10}$ is not absent.

In some embodiments, $X^1$ is absent; $X^2$ is absent; $X^3$ is absent; $X^4$ is absent; and $X^5$ is absent; $X^6$ is absent, $X^7$ is not absent, $X^8$ is not absent, and $X^{10}$ is not absent.

In some embodiments, $X^1$ is absent; $X^2$ is absent; $X^3$ is absent; $X^4$ is absent; and $X^5$ is absent; $X^6$ is not absent, $X^7$ is not absent, $X^8$ is not absent, and $X^{10}$ is not absent.

In some embodiments, $X^1$ is absent; $X^2$ is absent; $X^3$ is absent; $X^4$ is absent; and $X^5$ is not absent; $X^6$ is not absent, $X^7$ is not absent, $X^8$ is not absent, and $X^{10}$ is not absent.

In some embodiments, $X^1$ is absent; $X^2$ is absent; $X^3$ is absent; $X^4$ is not absent; and $X^5$ is not absent; $X^6$ is not absent, $X^7$ is not absent, $X^8$ is not absent, and $X^{10}$ is not absent.

In some embodiments, $X^1$ is absent; $X^2$ is absent; $X^3$ is not absent; $X^4$ is not absent; and $X^5$ is not absent; $X^6$ is not absent, $X^7$ is not absent, $X^8$ is not absent, and $X^{10}$ is not absent.

In some embodiments, $X^1$ is not absent; $X^2$ is absent; $X^3$ is not absent; $X^4$ is not absent; and $X^5$ is not absent; $X^6$ is not absent, $X^7$ is not absent, $X^8$ is not absent, and $X^{10}$ is not absent.

In some embodiments, $X^1$ is not absent; $X^2$ is absent; $X^3$ is not absent; $X^4$ is not absent; and $X^5$ is not absent; $X^6$ is not absent, $X^7$ is not absent, $X^8$ is not absent, and $X^{10}$ is not absent. In some embodiments, $X^1$ is absent, Tyr, Asp, Lys, 3-Pal, Sar, or Phe; $X^2$ is absent; $X^3$ is absent, Trp, Ile, 4-Pal, Lys, Asp, Glu, Gly, Ala, Cha, β-Nal, Hyp, Bip, Bpa, or AAP; $X^4$ is Asn, or Gln; $X^5$ is Ser, Thr, Gly, or Ala; $X^6$ is Phe, 3-F-Phe, Bip, β-(2-thienyl)-Ala), Cha, or Tyr; $X^7$ is Gly or azaGly; $X^8$ is Leu or Nva; $X^8$ is Leu, Nva, Ile, HAla, or Phe, and $X^{10}$ is Trp, 1MT, Tyr, 4-Pal, Phe(4-CN) or Phe.

In some embodiments, the N-terminal amino acid or the compound of Formula (I) is optionally substituted with $—C(=O)—C_1$-$C_{20}$ alkyl, $—C(=O)—(CH_2CH_2O)_y—CH_2CH_2—R^{15}$, $C_1$-$C_{20}$ alkyl N-hexadecanoyl-Glu, $C_4$-$C_{20}$ polyethylene glycol, a saccharide, $—R^{16}$, $—C(=O)—(CH_2CH_2O)_x—CH_3$, $—C(=O)—(CH_2CH_2O)_x—H$, $—C(=O)—CH_2CH_2CH(COOH)—R^{15}$, $—C(=O)—(CH_2)_2R^{19}$, or $—C(=O)CH_2NHCH_2R^{19}$; $R^{15}$ is selected from $—OR^{16}$, $—N(R^{16})_2$, $—C(=O)OR^{16}$, or $—C(=O)N(R^{16})_2$; each $R^{16}$ is independently H, $—C_1$-$C_6$ alkyl, $—C(=O)—(CH_2)_vR^{19}$, $—C(=O)CH_2NHCH_2R^{19}$, or a saccharide or derivative thereof; $R^{19}$ is 4-iodophenylene, 4-methylphenylene, or 3-fluoro-4-methylphenylene; y is 0, 1, 2, 3, 4, 5, 6, 7, 8, 9, or 10; x is an integer from 1 and 25; and v is 1, 2, 3, or 4.

In some embodiments, the N-terminal amino acid or the compound of Formula (I) is optionally substituted with $—C(=O)—C_1$-$C_{20}$ alkyl. In some embodiments, the N-terminal amino acid or the compound of Formula (I) is optionally substituted with $—C(=O)—(CH_2)_2R^{19}$. In some embodiments, the N-terminal amino acid or the compound of Formula (I) is substituted with $—R^{16}$. In some embodiments, the N-terminal amino acid or the compound of Formula (I) is substituted with $—R^{16}$ and $R^{16}$ is $C(=O)—(CH_2)_vR^{19}$. In some embodiments, the N-terminal amino acid or the compound of Formula (I) is substituted with —C(═O)—$(CH_2CH_2O)_y$—$CH_2CH_2$—$R^{15}$. In some embodiments, the N-terminal amino acid or the compound of Formula (I) is substituted with —C(═O)—$(CH_2CH_2O)_y$—$CH_2CH_2$—$R^{15}$, $R^{15}$ is —$OR^{16}$ or —$N(R^{16})_2$, and each $R^{16}$ is independently H, —$C_1$-$C_6$ alkyl, or —C(═O)—$(CH_2)_vR_{19}$. In some embodiments, y is 2. In some embodiments, v is 2. In some embodiments, $R^{16}$ is H or —$CH_3$. In some embodiments, $R^{19}$ is 4-iodophenylene or 4-methylphenylene.

In some embodiments $R^{15}$ is

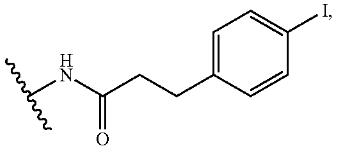

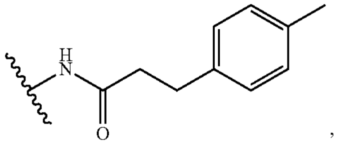

, or

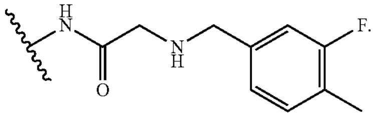

In some embodiments, the N-terminal amino acid or the compound of Formula (I) is substituted with —C(═O)—$(CH_2CH_2O)_y$—$CH_2CH_2$—$R^{15}$ and $R^{15}$ is

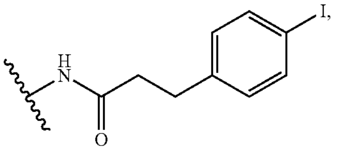

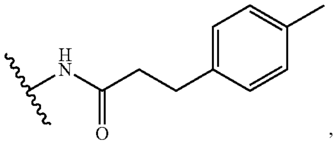

, or

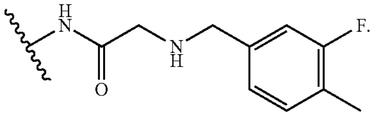

In some embodiments, x is 3 or 9 or 25.

In some embodiments, the N-terminal amino acid or the compound of Formula (I) is optionally substituted with

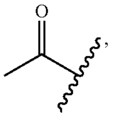

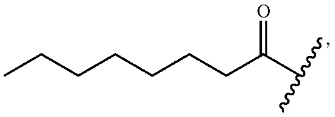

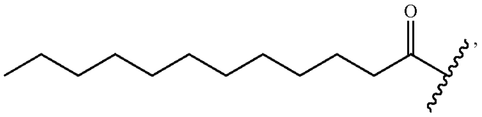

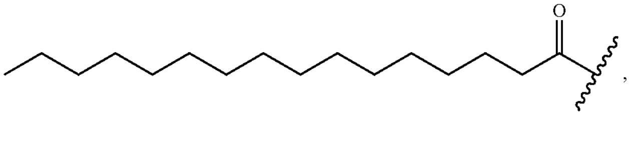

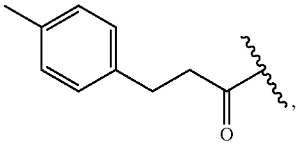

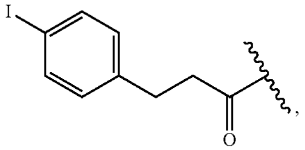

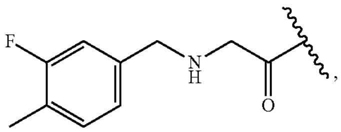

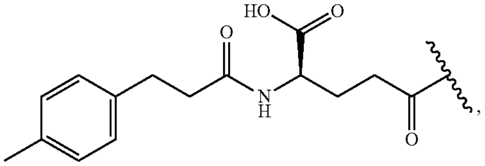

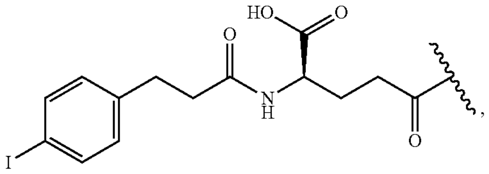

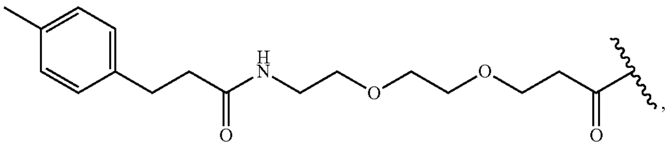

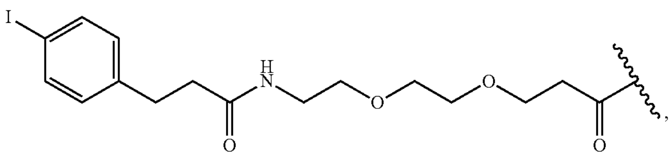

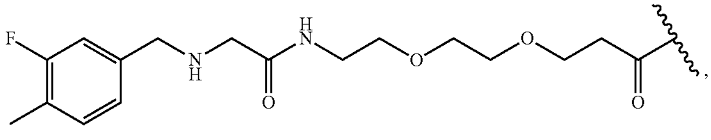

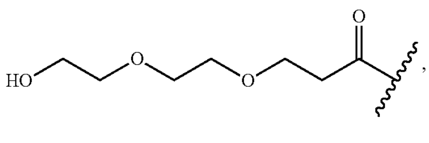

-continued
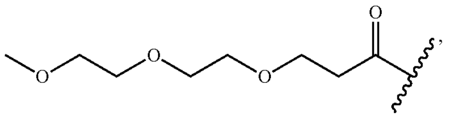
or
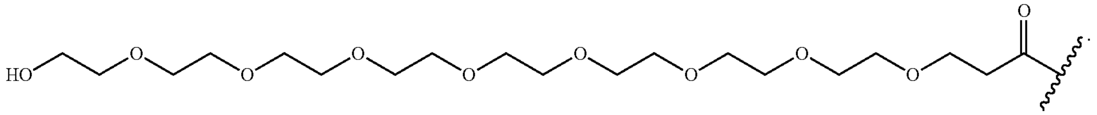
In some embodiments, $R^1$ is
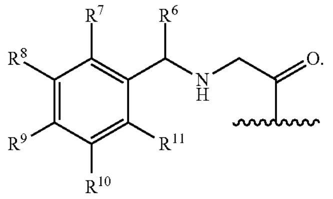
In some embodiments. $R^1$ is
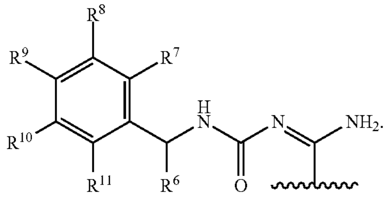
In some embodiments, $R^1$ is
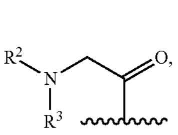
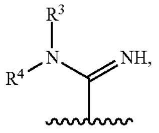
or
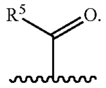
In some embodiments, $R^1$ is
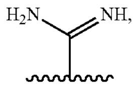
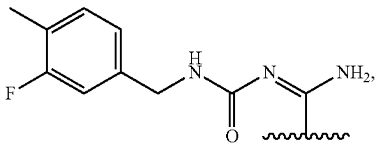
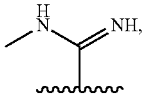
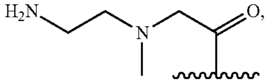
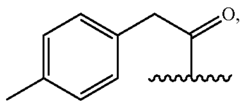
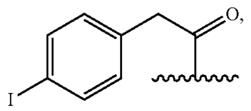
-continued
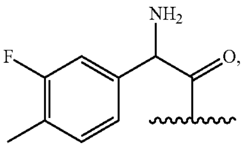
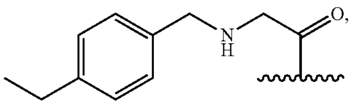
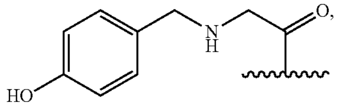
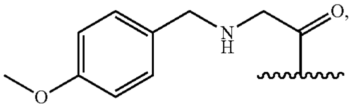
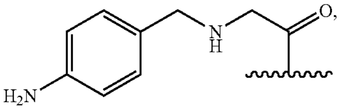
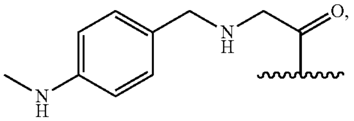
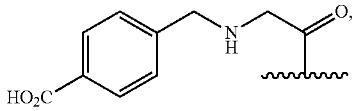
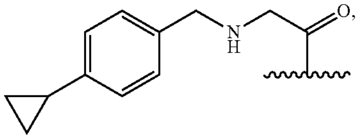
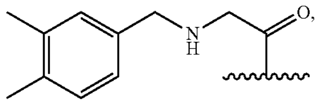
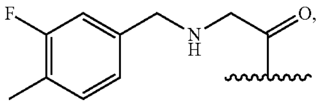
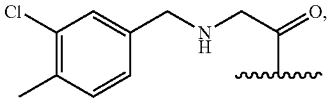
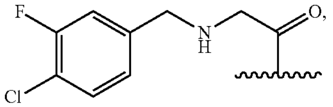

-continued
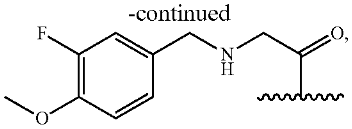
,
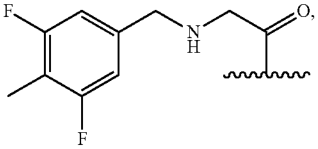
,
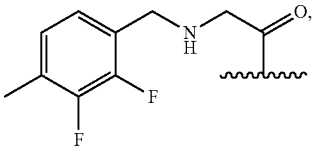
,
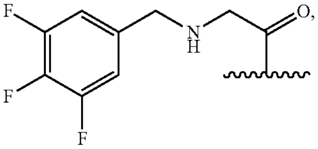
,
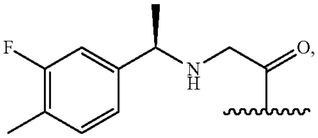
,
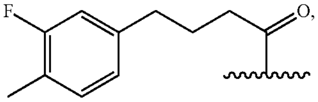
,
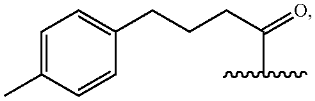
, 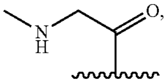
,
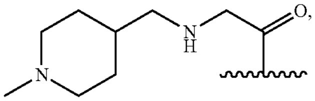
,
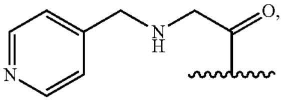
,
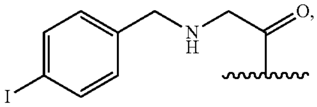
,
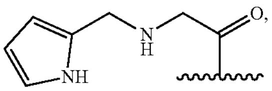
,
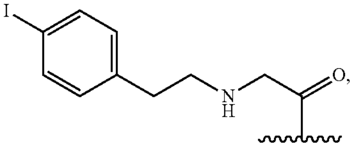
,
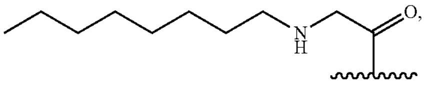
,
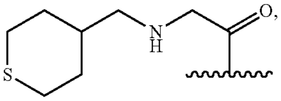
,
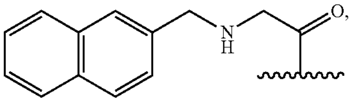
, or
-continued
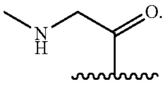
.
In some embodiments, $R^1$ is
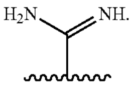
.
In some embodiments, $R^1$ is
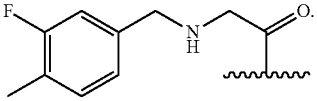 [SMILES: *C(=O)CNCc1ccc(C)c(F)c1]
.
In some embodiments, $R^1$ is
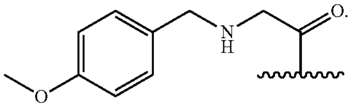 [SMILES: *C(=O)CNCc1ccc(OC)cc1]
.
In some embodiments, $R^1$ is
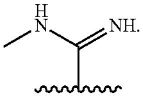 [SMILES: *C(=N)NC]
.
In some embodiments, $R^1$ is
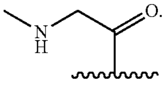 [SMILES: *C(=O)CNC]
.
In some embodiments, $R^2$ is
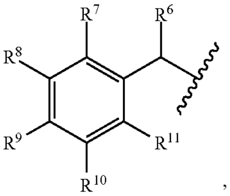
, 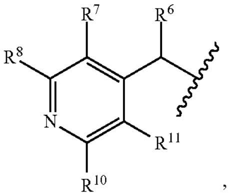
,
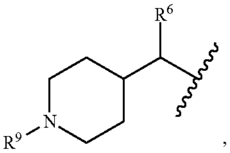
, 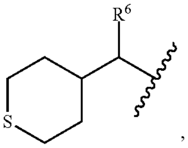
, or -continued

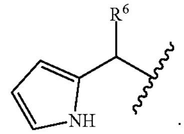

In some embodiments, $R^2$ is

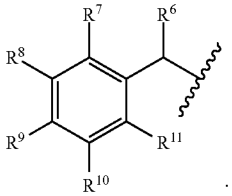

In some embodiments, $R^2$ is $C_1$-$C_6$ alkyl, wherein $C_1$-$C_6$ alkyl is optionally substituted with $R^7$.

In some embodiments, $R^2$ is

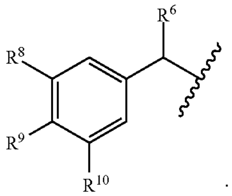

In some embodiments, $R^3$ is H or —$CH_3$, and $R^4$ is H, —$CH_3$, or $R^2$.

In some embodiments, $R^5$ is

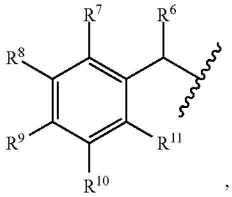

,

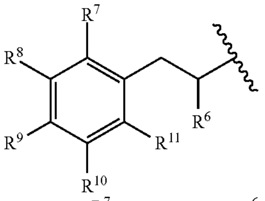

, or

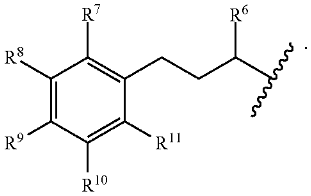

In some embodiments, $R^7$, $R^8$, $R^9$, $R^{10}$, and $R^{11}$ are each independently selected from H, F, Cl, Br, I, —OH, —$OCH_3$, —$OCH_2CH_3$, —$NH_2$—, —$NHCH_3$, —$N(CH_3)_2$, —CN, —$CO_2H$, —$CO_2CH_3$, —$CO_2CH_2CH_3$, —$CH_3$, —$CH_2CH_3$, —$CH(CH_3)_2$, —$(CH_3)_3$, —$CF_3$, —$CH_2F$, —$CH_2F$, or cyclopropyl.

In some embodiments, $R^7$ is H. In some embodiments, $R^8$ is F, Cl, Br, I, —$CH_3$, —$CH_2CH_3$, or —$CF_3$. In some embodiments, $R^9$ is H, F, Cl, Br, I, —OH, —$OCH_3$, —$OCH_2CH_3$, —$NH_2$—, —$NHCH_3$, —$N(CH_3)_2$, —$CO_2H$, —$CO_2CH_3$, —$CO_2CH_2CH_3$, —$CH_3$, —$CH_2CH_3$, —$CH(CH_3)_2$, —$(CH_3)_3$, —$CF_3$, —$CH_2F$, —$CH_2F$, or cyclopropyl. In some embodiments, $R^{10}$ is F, Cl, Br, I, —$CH_3$, —$CH_2CH_3$, or —$CF_3$. In some embodiments, $R^{11}$ is H, F, Cl, Br, or I.

In some embodiments, $R^8$ is F, Cl, Br, or I and $R^9$ is —$CH_3$, —$CH_2CH_3$, or —$CF_3$.

In some embodiments, $R^8$ is H or F and $R^9$ is —$CH_3$, —$OCH_3$.

In some embodiments,

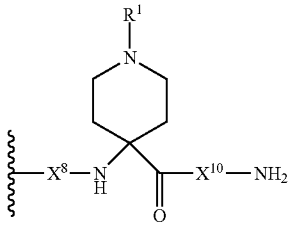

is

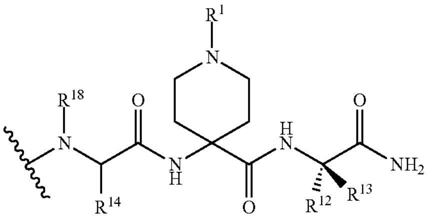

wherein, $R^{18}$ is H or —$CH_3$;

$R^{12}$ is

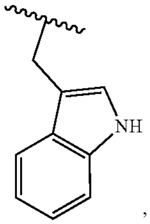

,

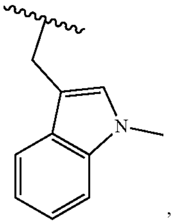

,

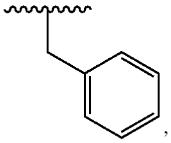

,

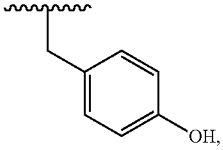

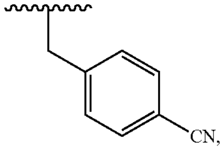

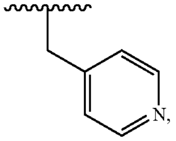

or

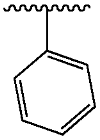

;

$R^{13}$ is H or —$CH_3$; and $R^{14}$ is

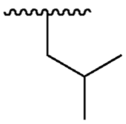

,

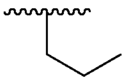

,

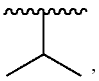

,

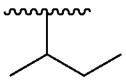

,

-continued
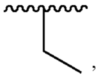, 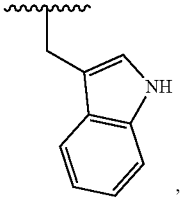, 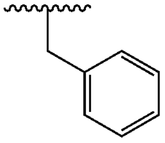, or
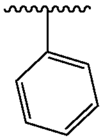.
In some embodiments, $R^{18}$ is H or —$CH_3$, and $R^{12}$ is
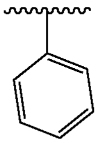.
In some embodiments, $R^{12}$ is
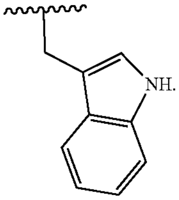 [SMILES: *Cc1c[nH]c2ccccc12]
In some embodiments, $R^{14}$ is
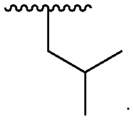 [SMILES: *CC(C)C].
In some embodiments,
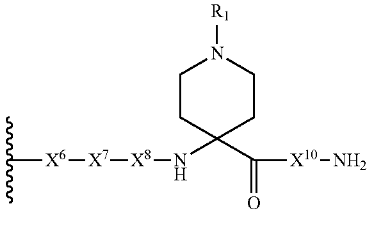 is
-continued
(SEQ ID NO: 159)
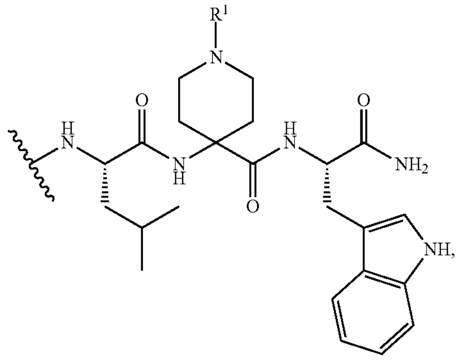
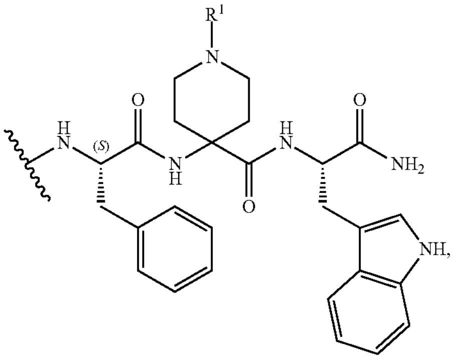
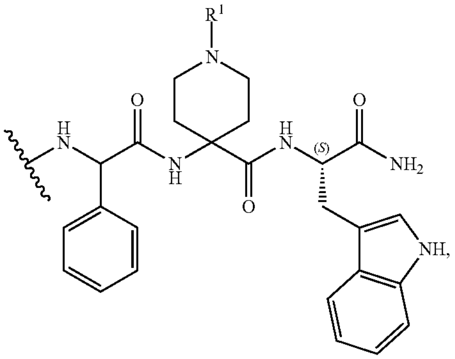
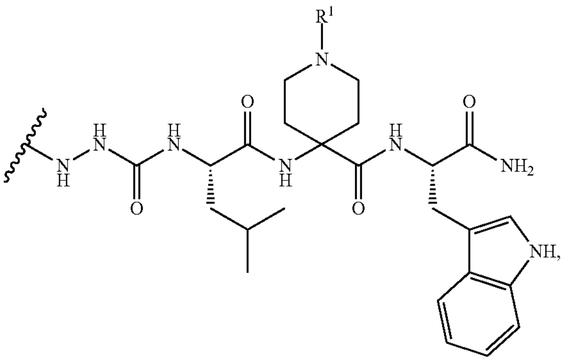

-continued
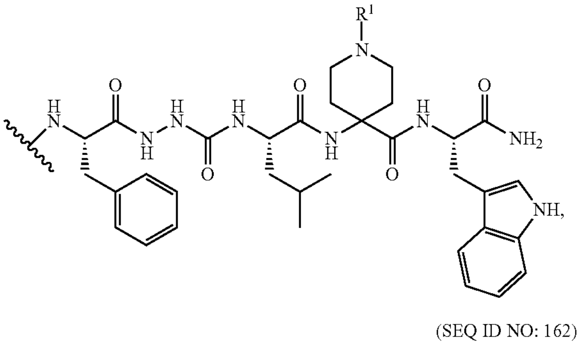
(SEQ ID NO: 162)
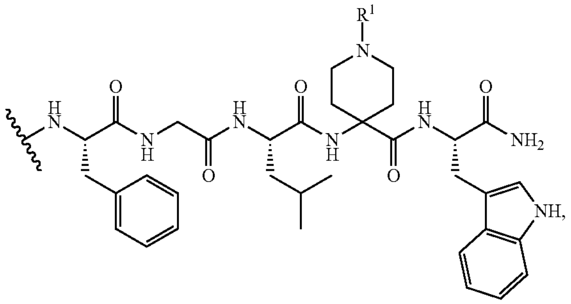
(SEQ ID NO: 164)
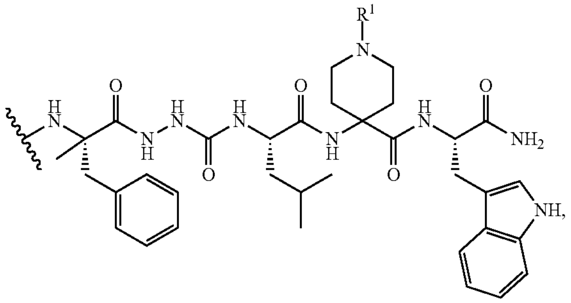
(SEQ ID NO: 161)
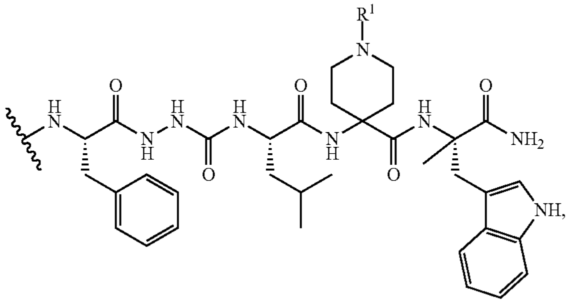
(SEQ ID NO: 166)
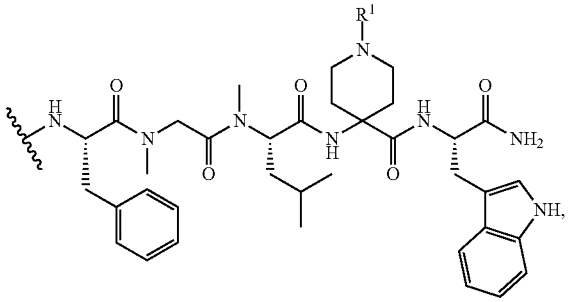
-continued
(SEQ ID NO: 163)
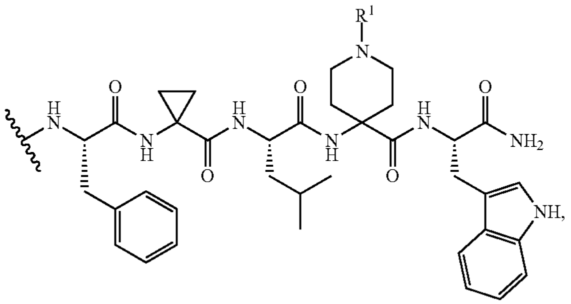
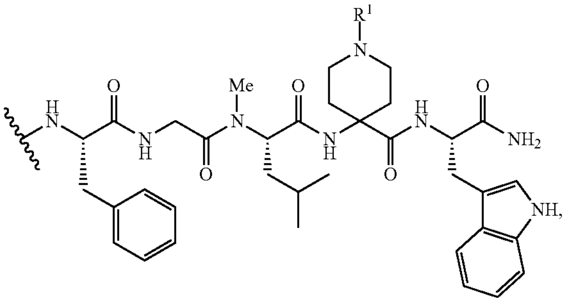
(SEQ ID NO: 165)
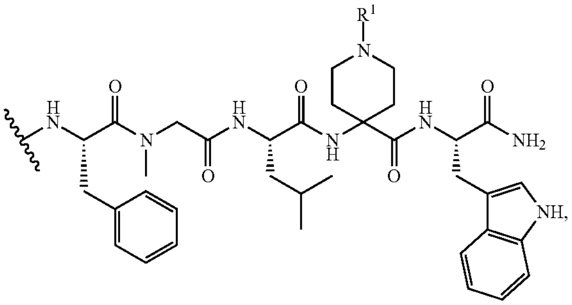
(SEQ ID NO: 166)
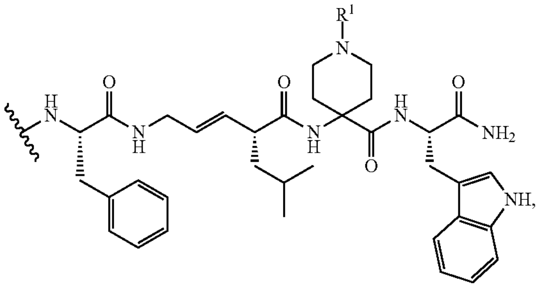
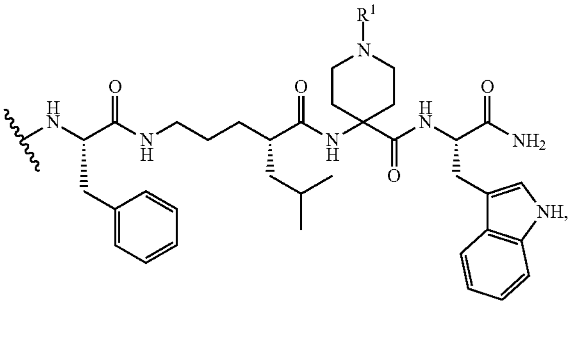

-continued
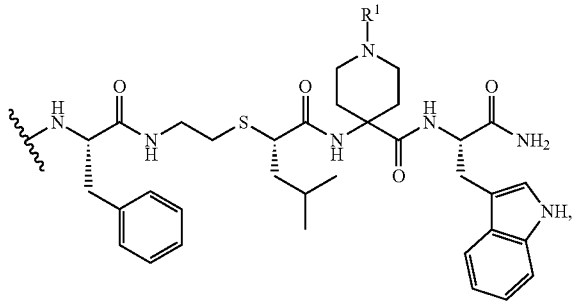
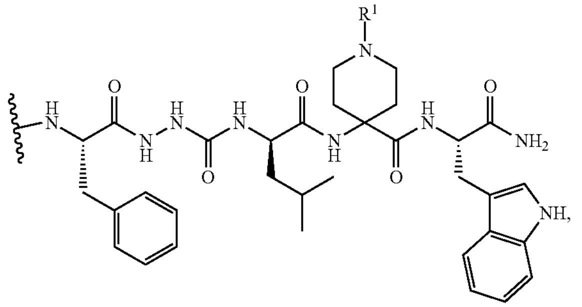
(SEQ ID NO: 197)
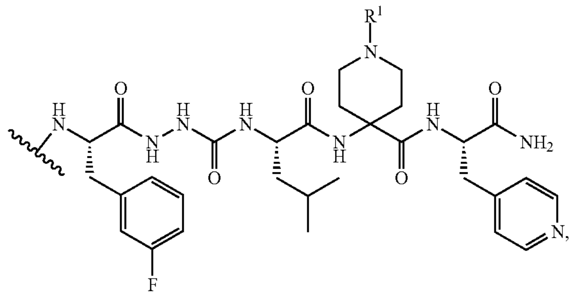
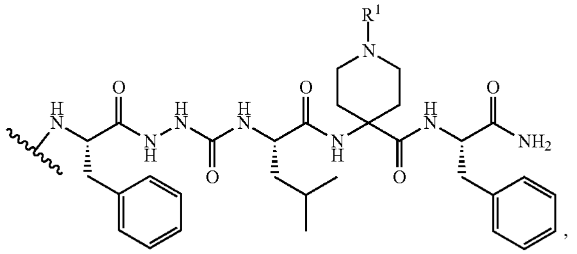
(SEQ ID NO: 774)
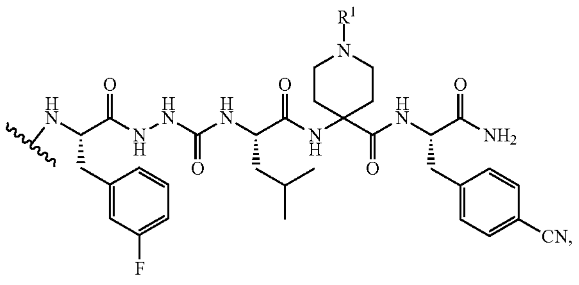
-continued
(SEQ ID NO: 775)
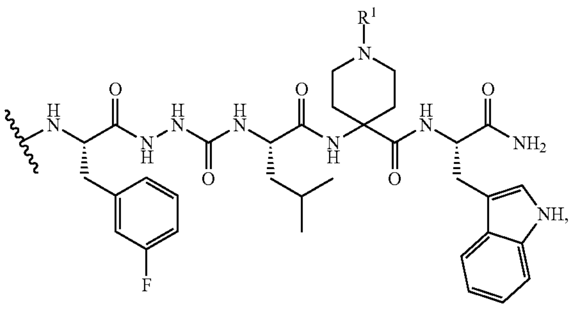
(SEQ ID NO: 160)
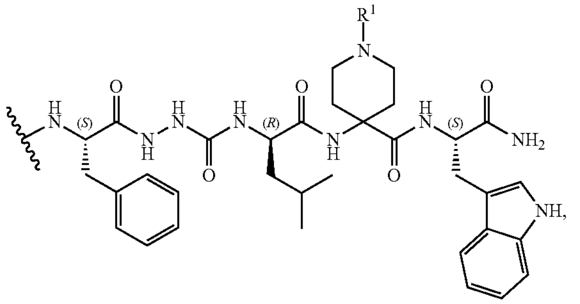
(SEQ ID NO: 206)
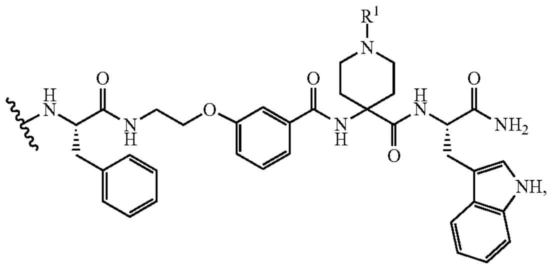
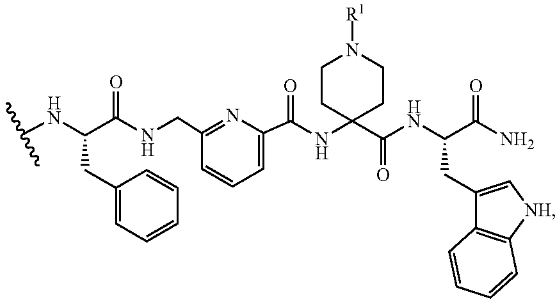
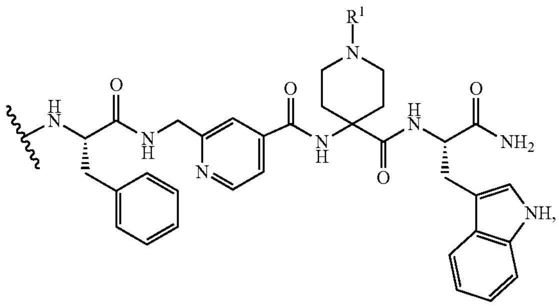

-continued
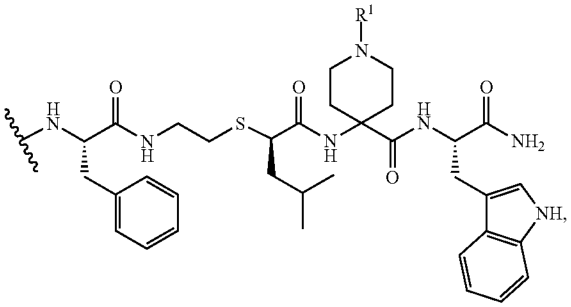
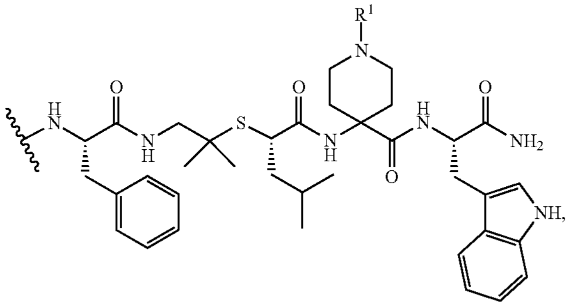
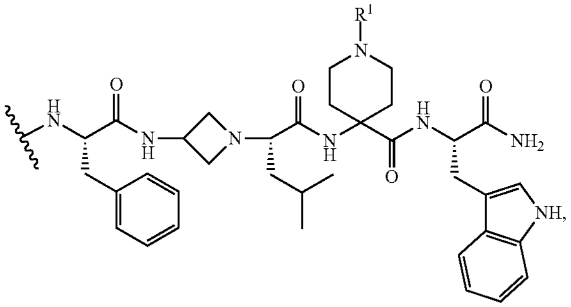
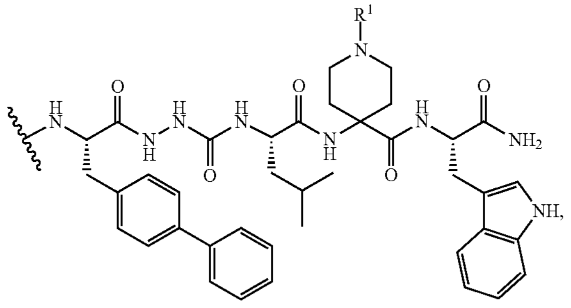
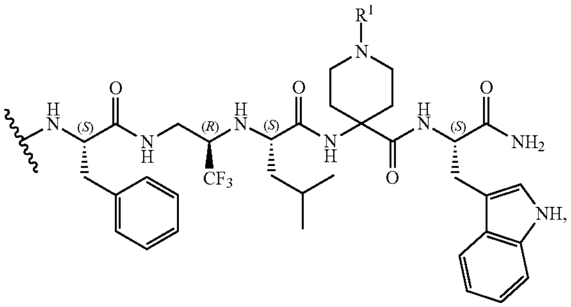
-continued
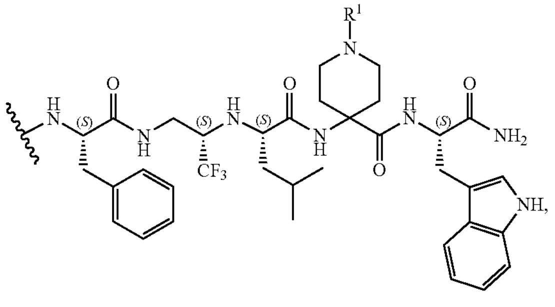
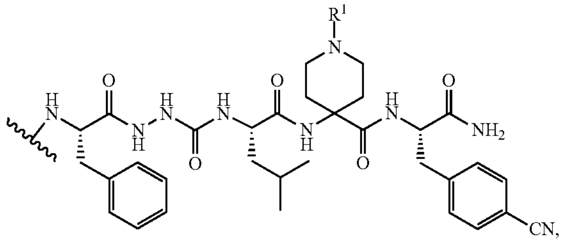
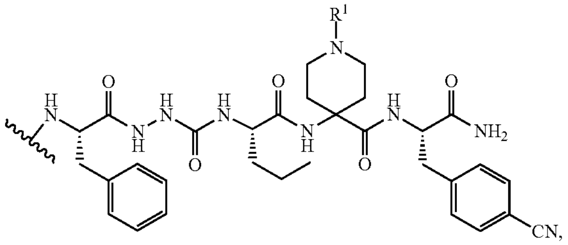
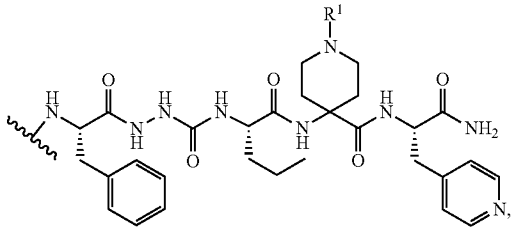
or
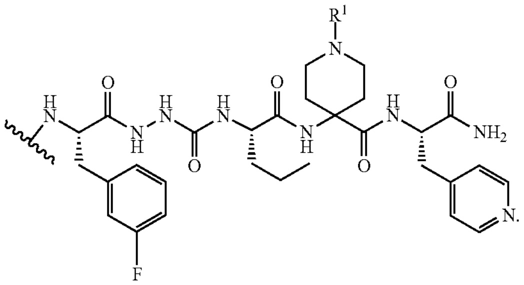
In some embodiments,
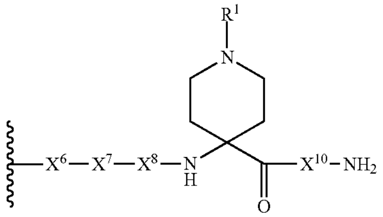
is -continued
(SEQ ID NO: 159)
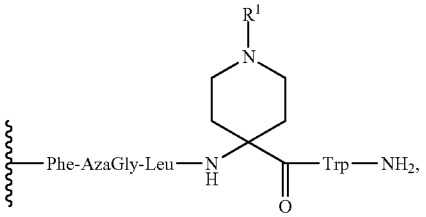
(SEQ ID NO: 160)
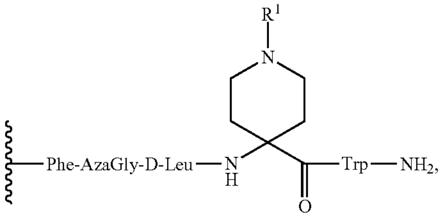
(SEQ ID NO: 161)
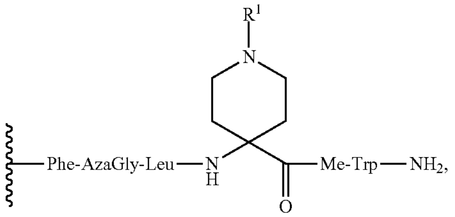
(SEQ ID NO: 162)
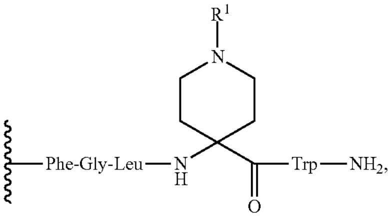
(SEQ ID NO: 163)
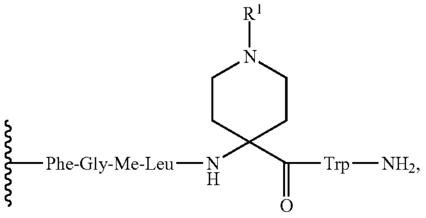
(SEQ ID NO NO: 261)
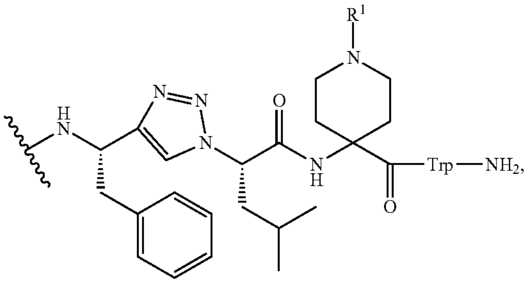
-continued
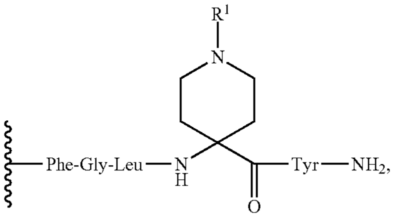
(SEQ ID NO: 165)
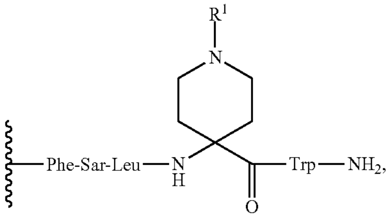
(SEQ ID NO: 166)
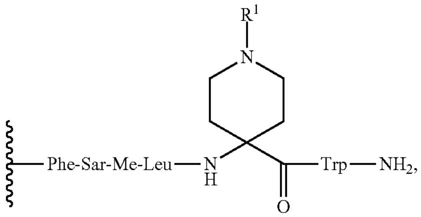
(SEQ ID NO: 775)
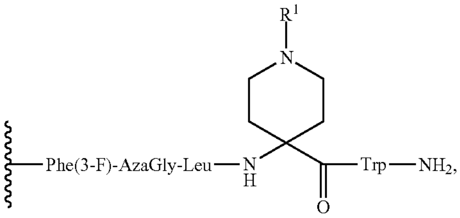
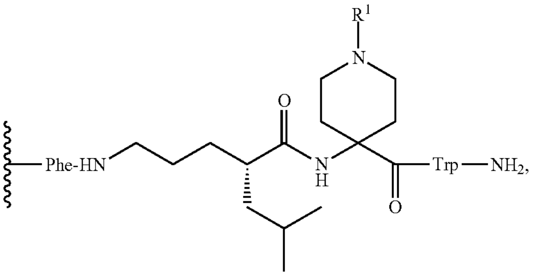
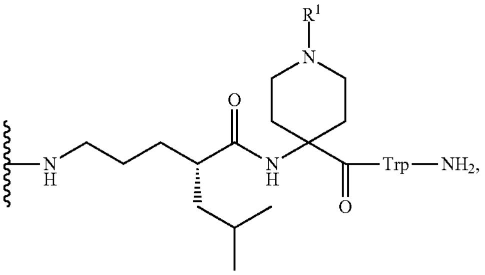

-continued
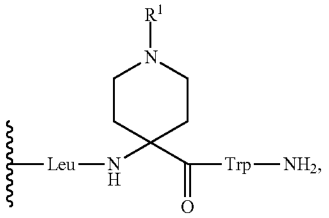
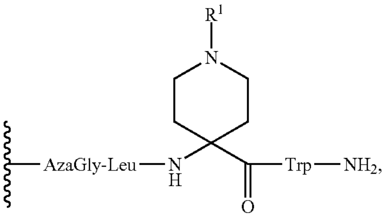
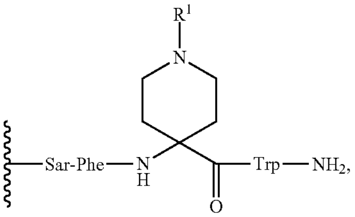
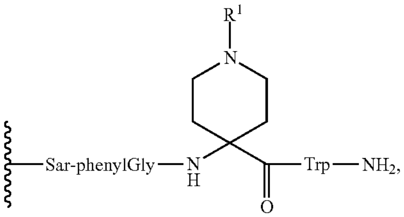
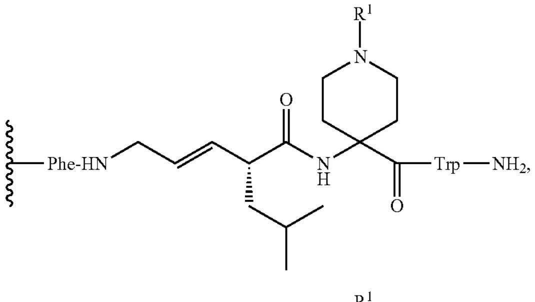
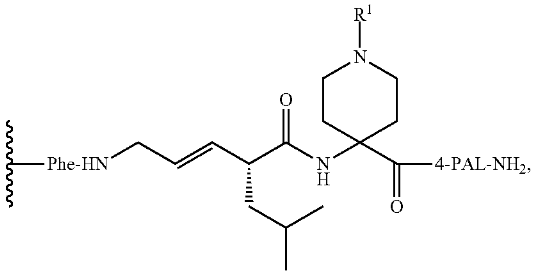
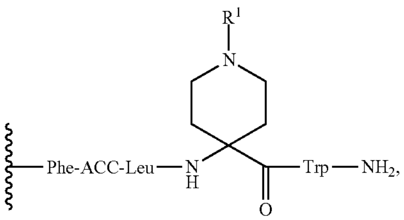
-continued
(SEQ ID NO: 197)
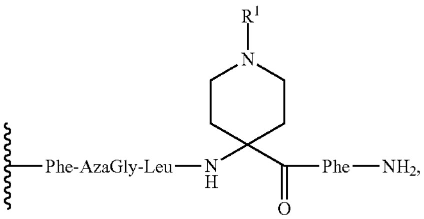
(SEQ ID NO: 206)
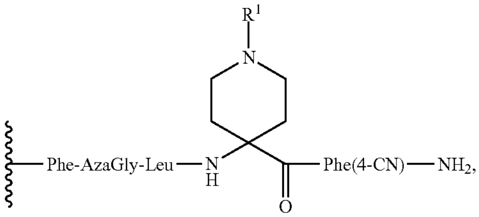
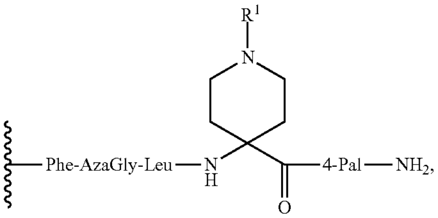
(SEQ ID NO: 786)
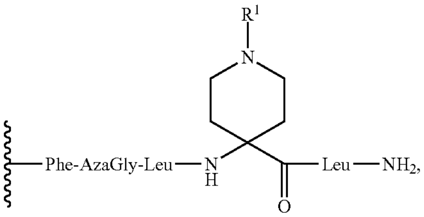
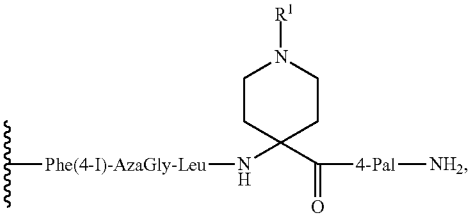
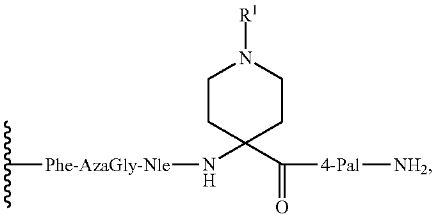
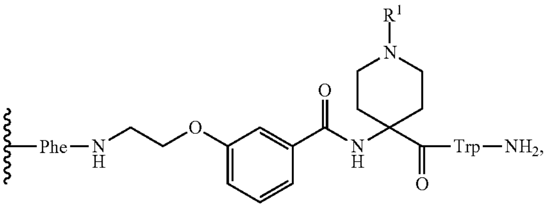

-continued
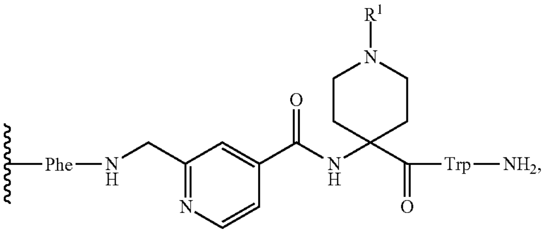
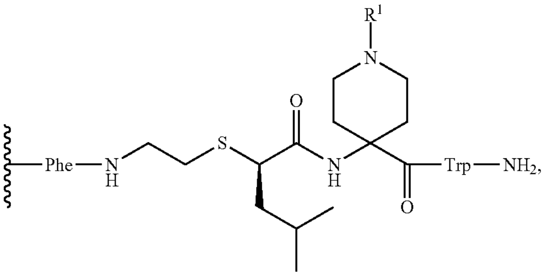
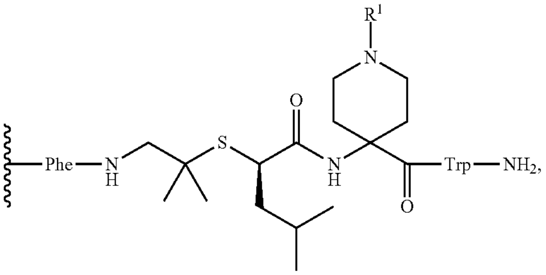
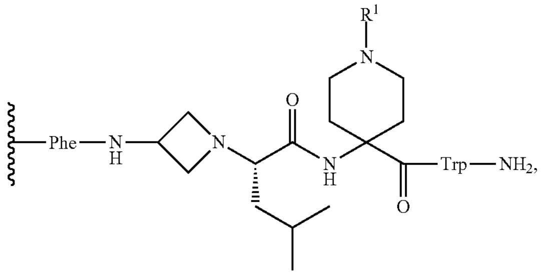
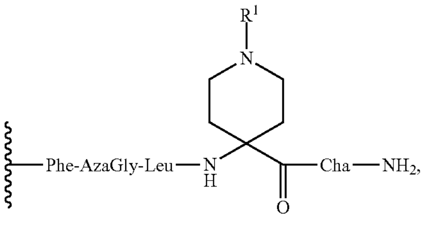
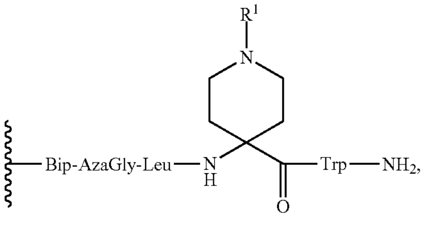
-continued
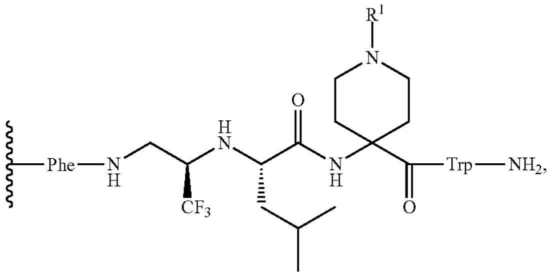
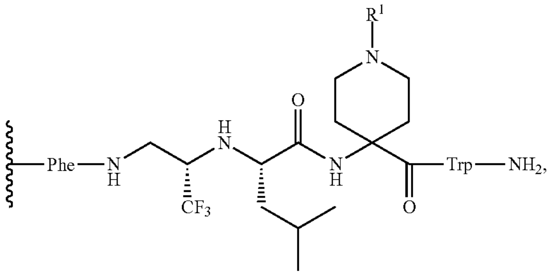
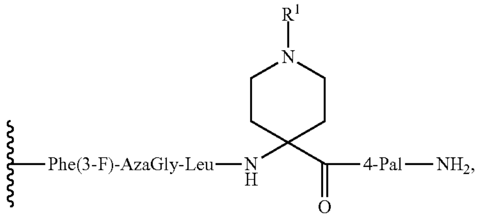
(SEQ ID NO: 262)
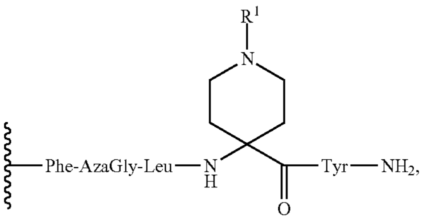
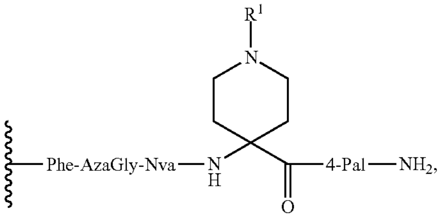
(SEQ ID NO: 790)
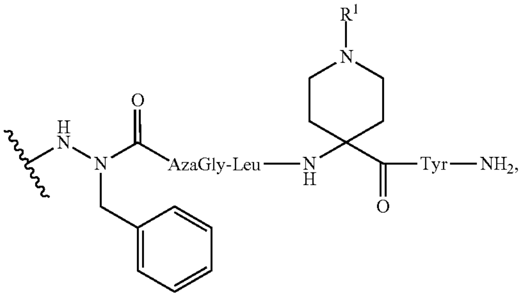

-continued
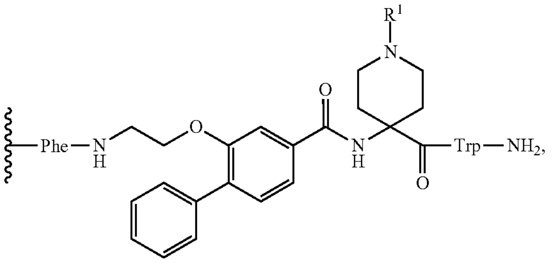
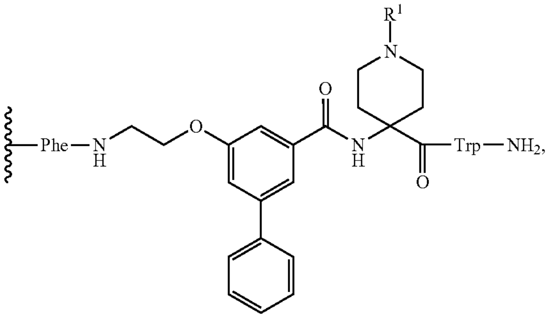
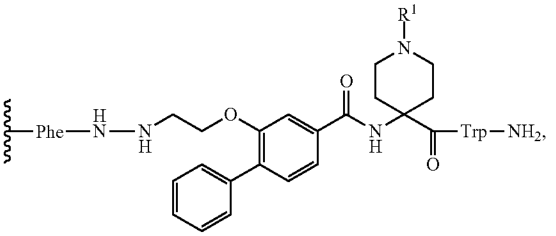
(SEQ ID NO: 792)
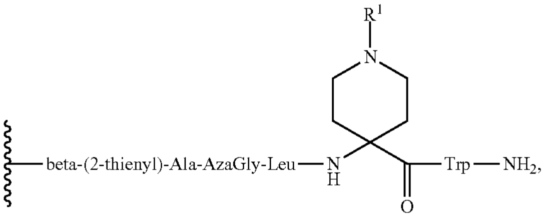
(SEQ ID NO: 277)
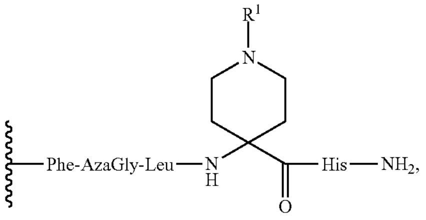
(SEQ ID NO: 793)
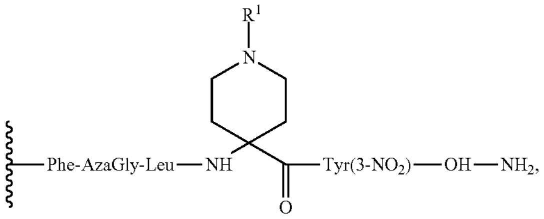
-continued
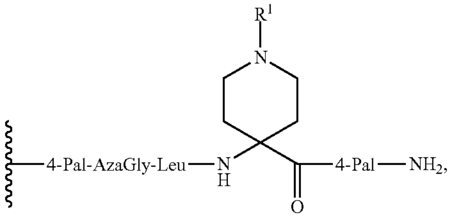
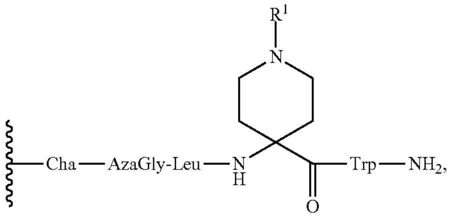
(SEQ ID NO: 192)
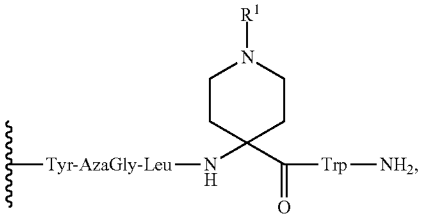
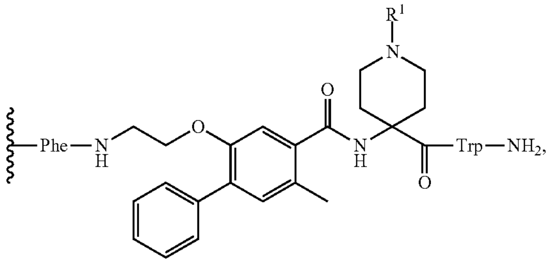
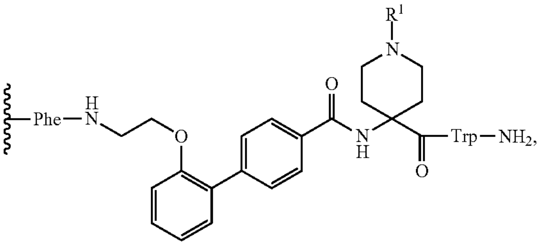
or
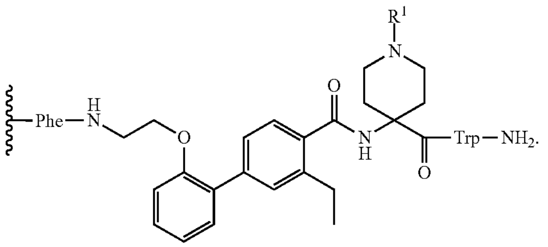

In some embodiments,
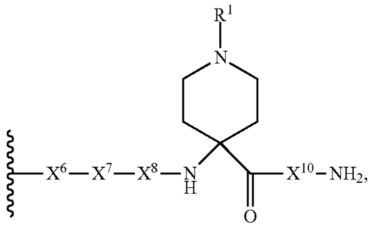
is
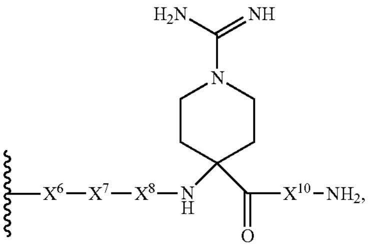
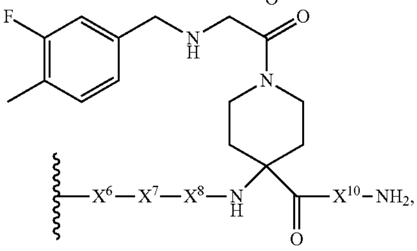
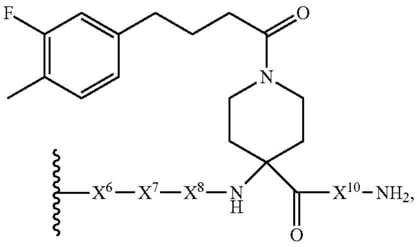
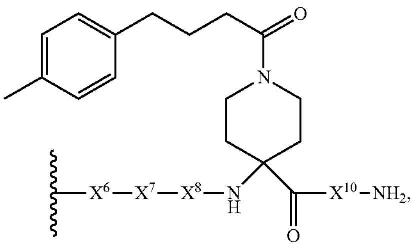
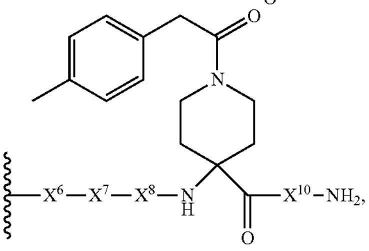
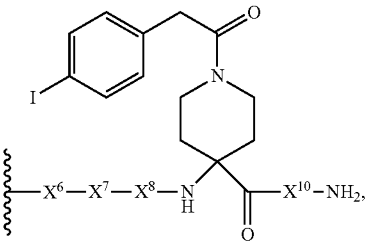
-continued
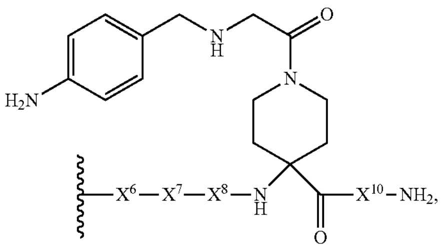
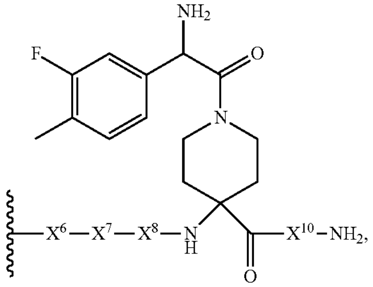
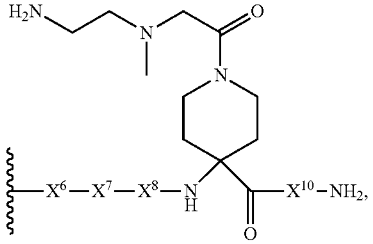
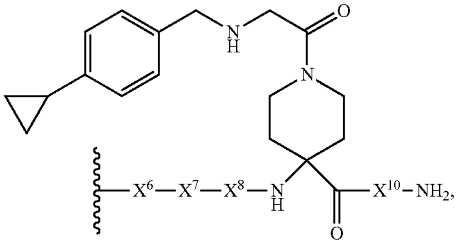
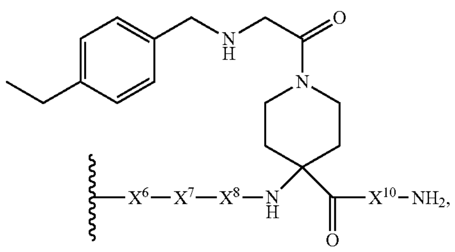
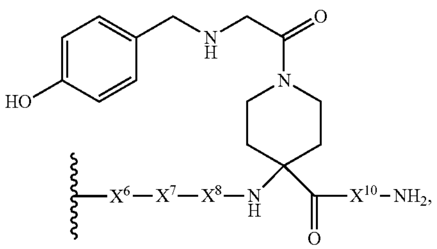

-continued
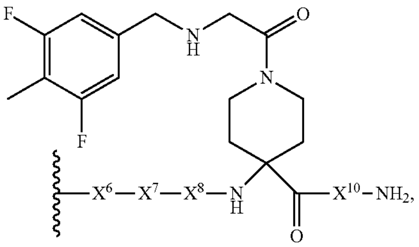
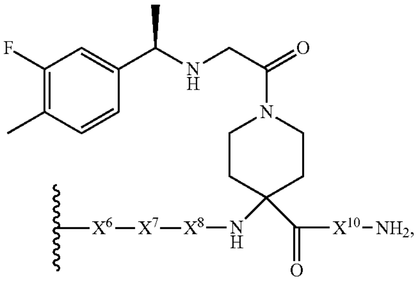
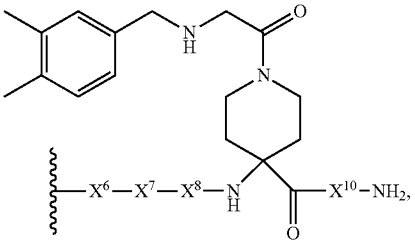
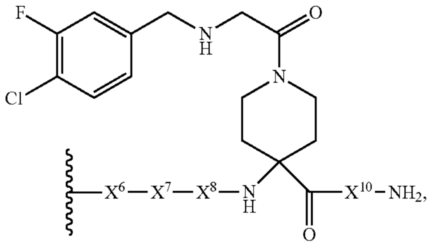
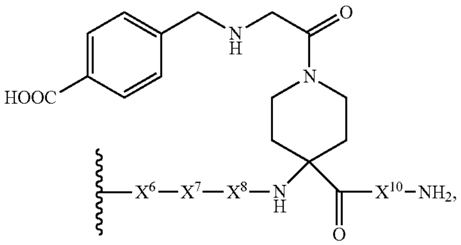
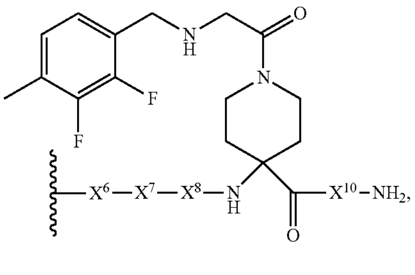
-continued
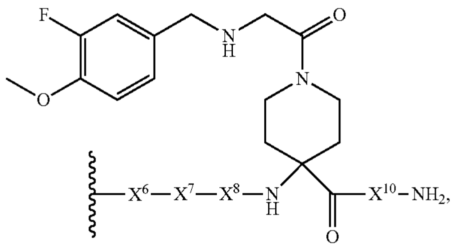
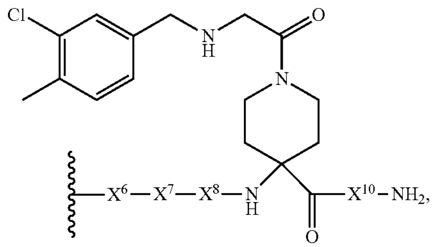
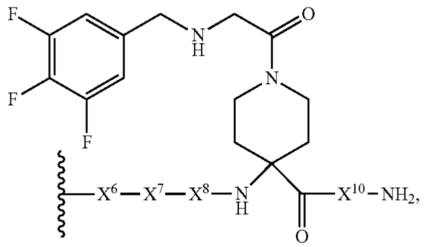
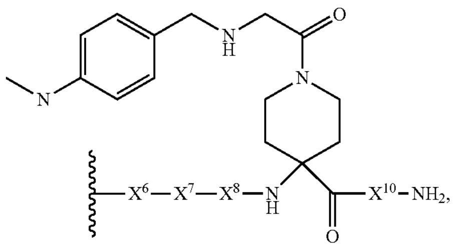
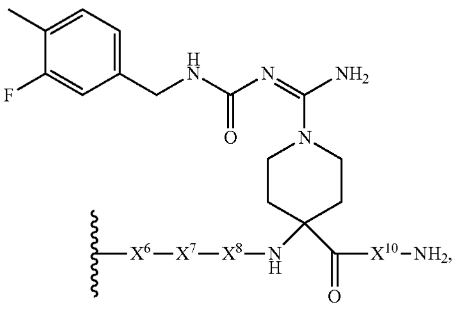
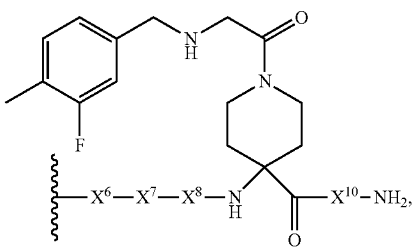

-continued
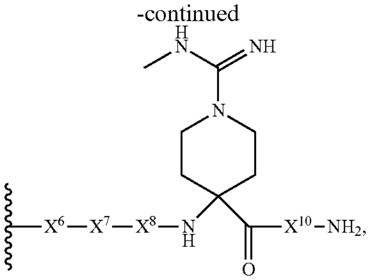
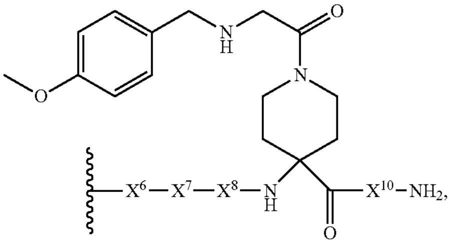
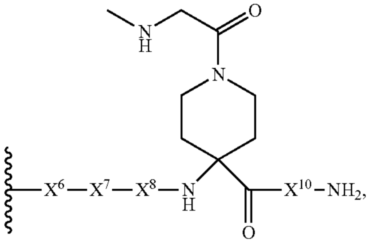
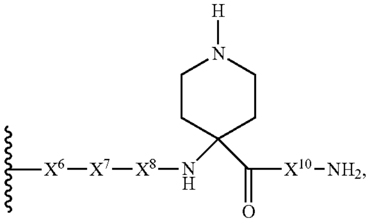
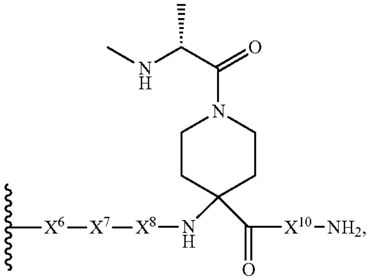
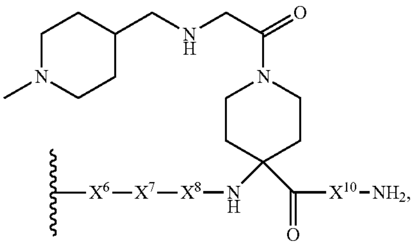
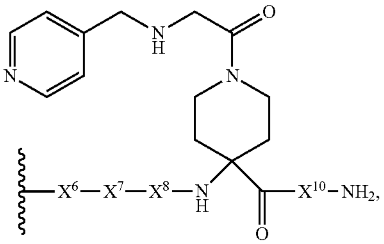
-continued
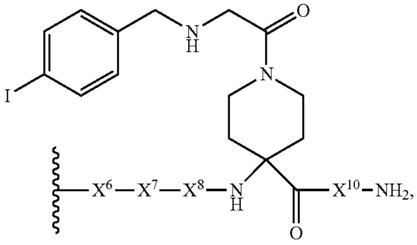
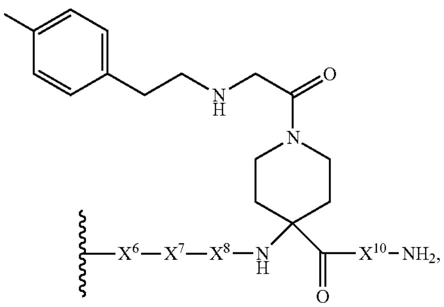
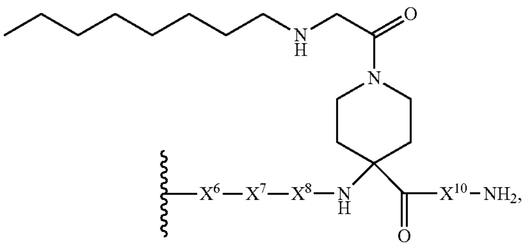
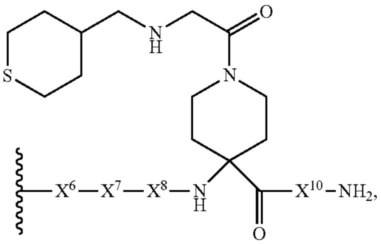
or
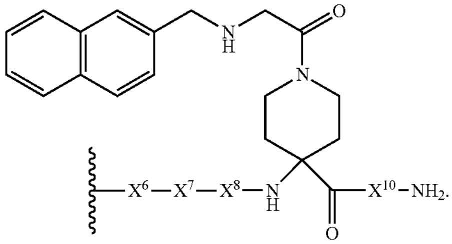
In some embodiments,
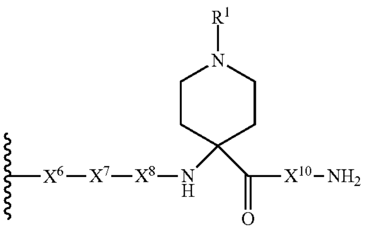
is -continued
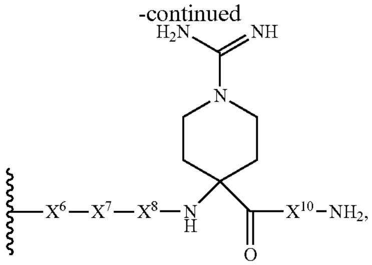
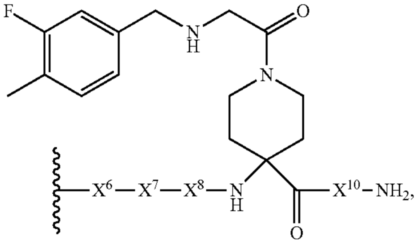
-continued
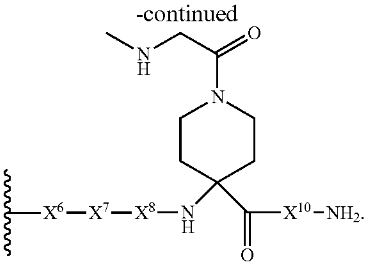
In some embodiments,
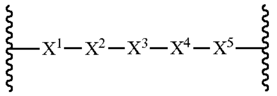
is absent.
(SEQ ID NO: 2)
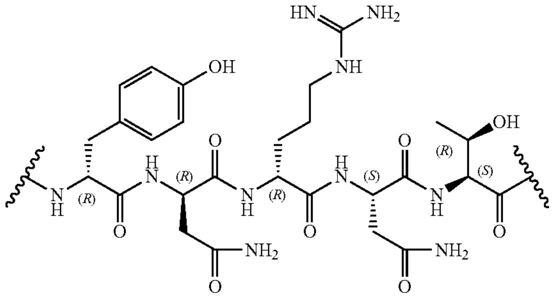
,
(SEQ ID NO: 3)
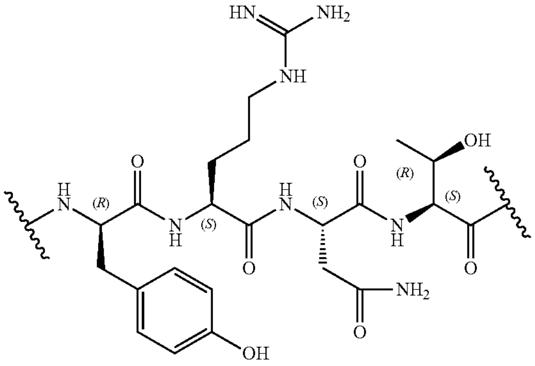
,
(SEQ ID NO: 4)
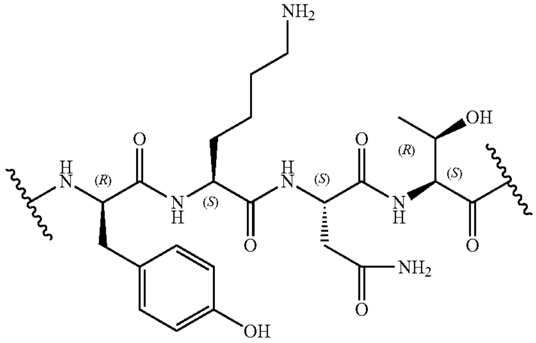
,
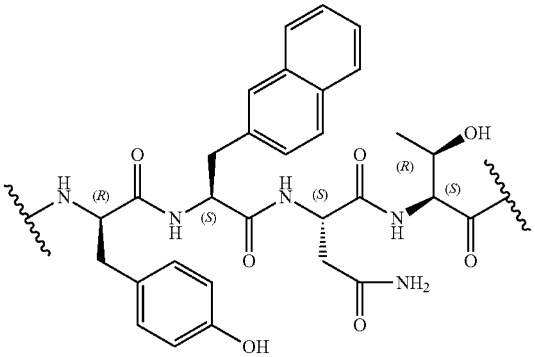
,
(SEQ ID NO: 7)
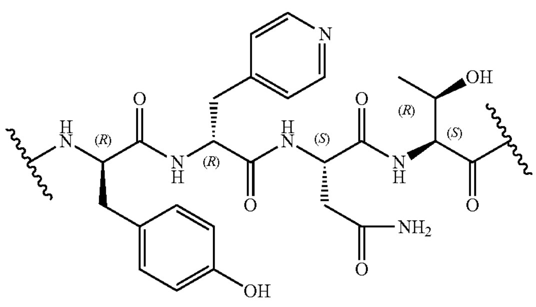
,
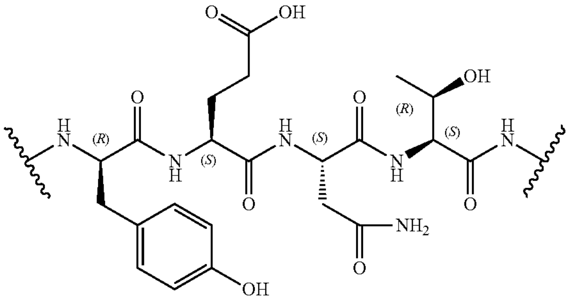
, -continued
(SEQ ID NO: 8)
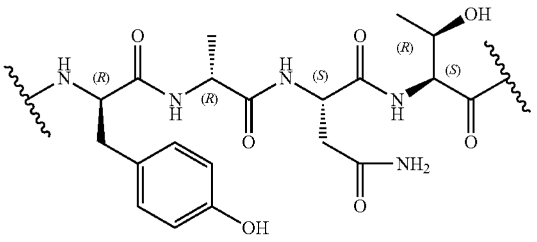
,
(SEQ ID NO: 9)
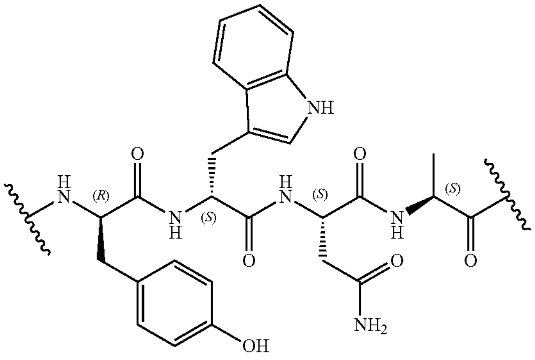
,
(SEQ ID NO: 10)
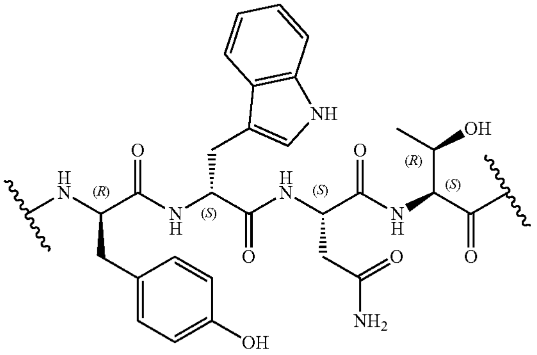
,
(SEQ ID NO: 11)
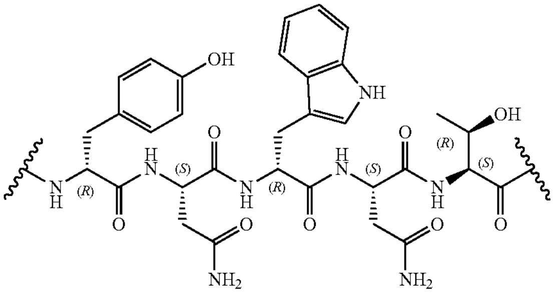
,
(SEQ ID NO: 12)
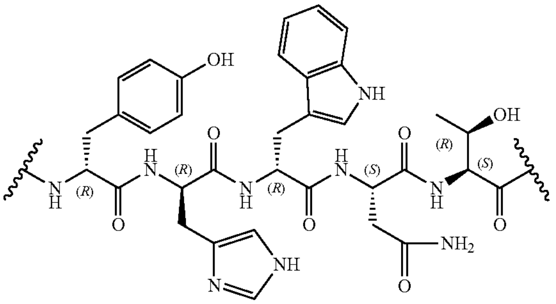
,
(SEQ ID NO: 13)
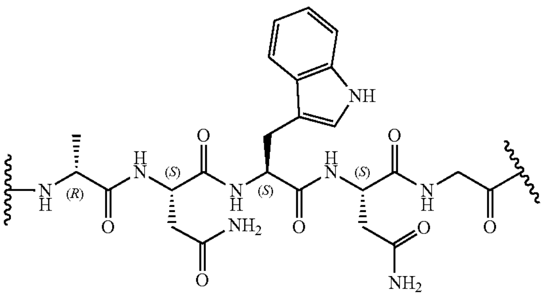
,
(SEQ ID NO: 14)
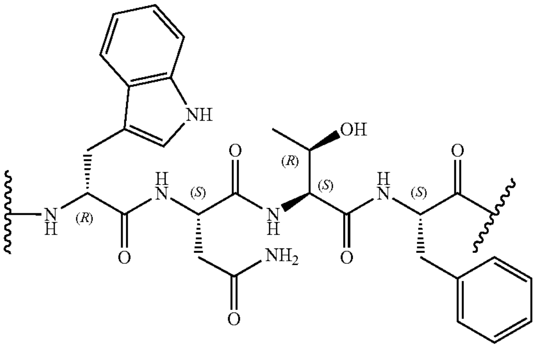
, -continued
(SEQ ID NO: 15)
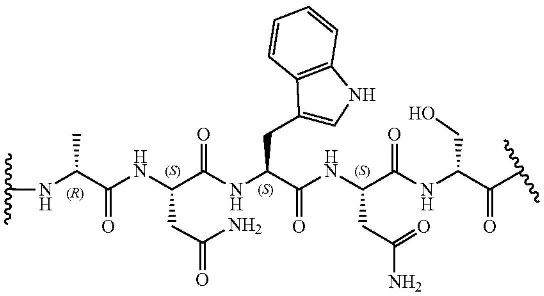,
(SEQ ID NO: 16)
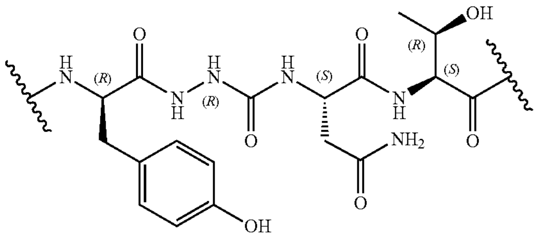,
(SEQ ID NO: 17)
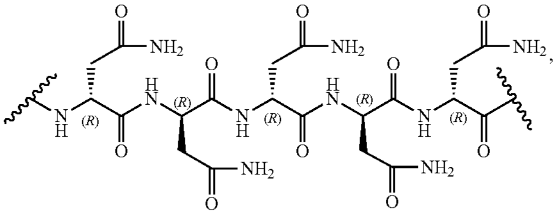,
(SEQ ID NO: 18)
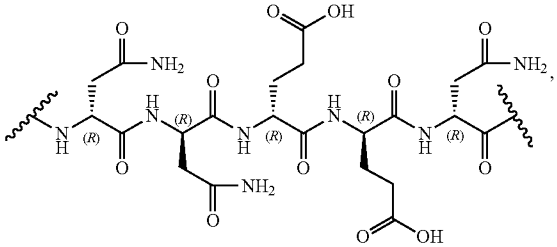,
(SEQ ID NO: 19)
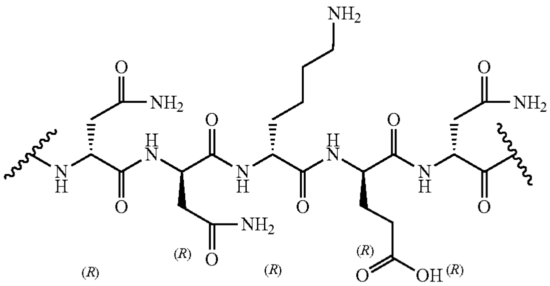,
(SEQ ID NO: 20)
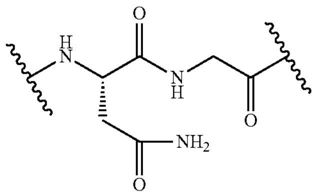,
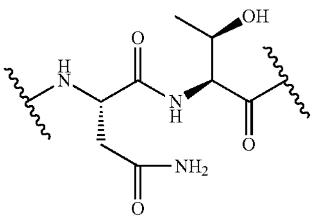,
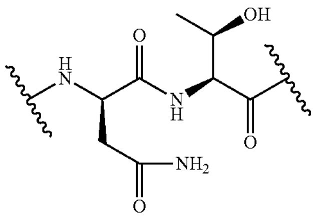,
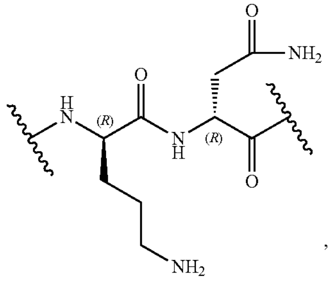,
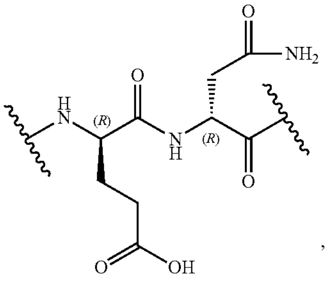,
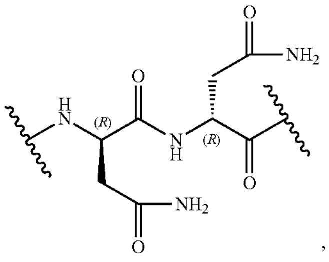, -continued
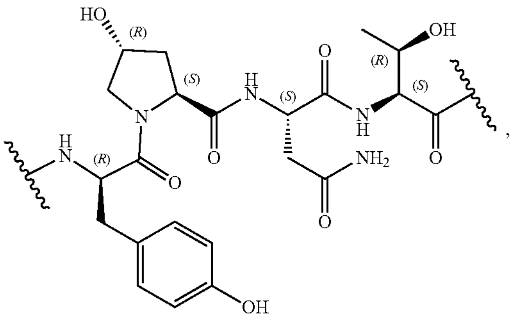
(SEQ ID NO: 21)
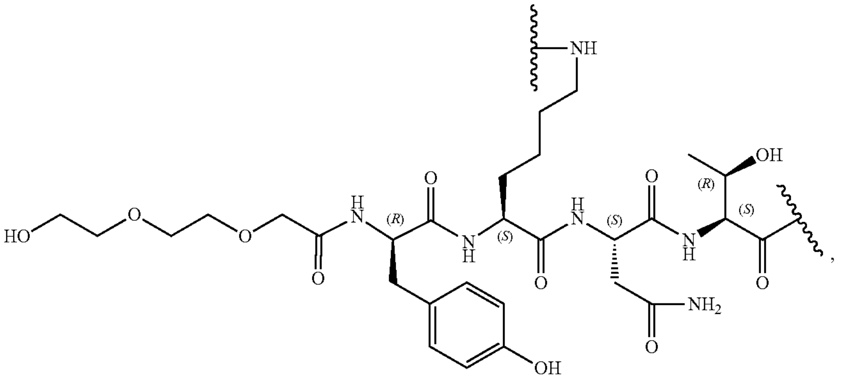
(SEQ ID NO: 22)
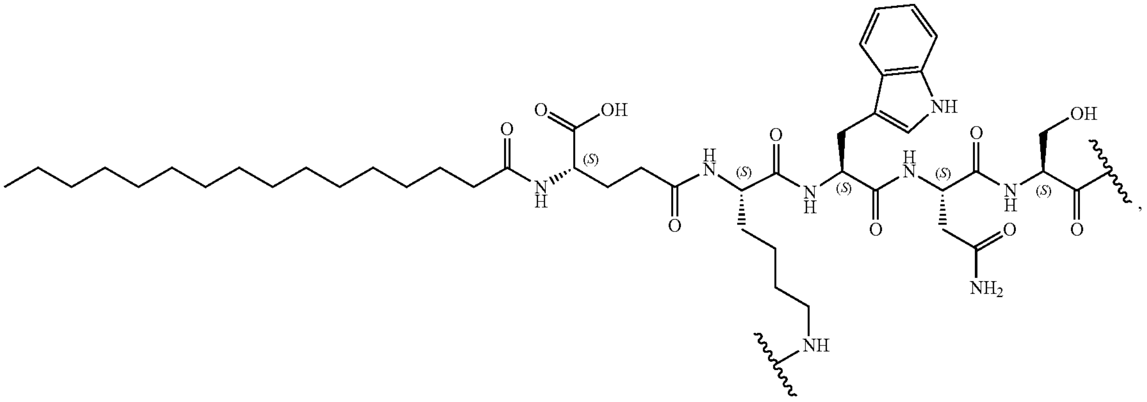
(SEQ ID NO: 23)
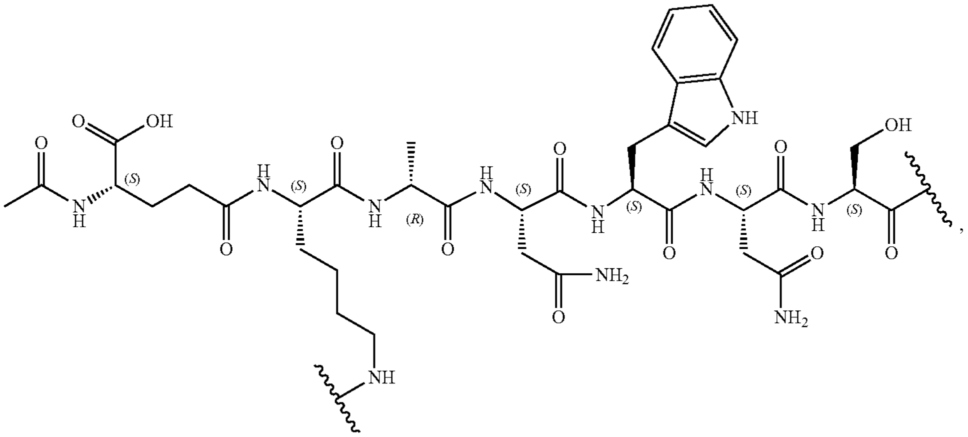

-continued (SEQ ID NO: 24)

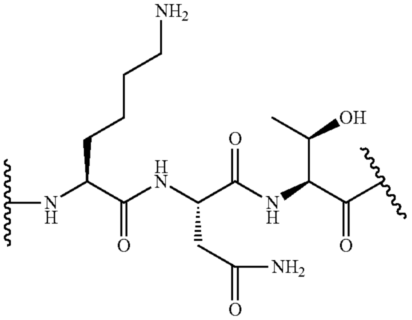

,

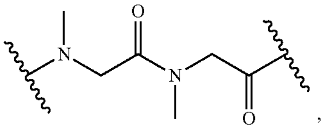

,

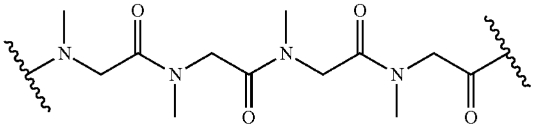

, (SEQ ID NO: 25)

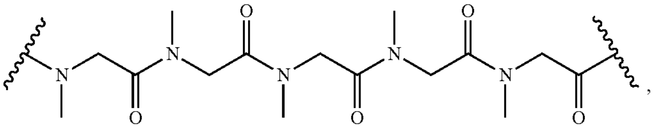

, or (SEQ ID NO: 26)

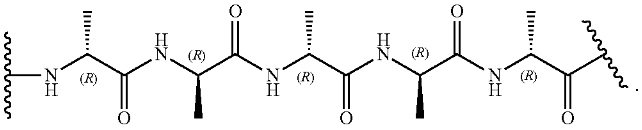

.

In some embodiments,

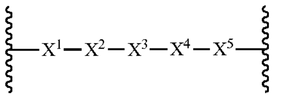

is absent, Asn-, -Lys-, -2-Pal-, -Thr-, -Trp-, -Asn-Asn-, -Asn-Gly-, -Asn-Thr-, -Glu-Asn-, -Glu-Thr-, -Lys-Asn-, -Lys(DOTA)-Asn-, -Lys-Thr-, -Lys(DOTA)-Thr-, -Lys-Glu-, -Lys(DOTA)-Glu-, -Sar-Sar-, -AAP-Asn-Thr-, -Asn-Phe-Thr-, -Glu-Asn-Thr-, -D-Glu-Asn-Thr-, -bGlu-Asn-Thr-, -Gly-Tyr-Ahx-, -Lys-Asn-Thr-, -D-β-Nal-Asn-Thr-, -D-4Pal-Asn-Thr-, -Thr-Asn-Arg-, -Trp-Asn-Thr-, -D-Trp-Asn-Thr-, -D-Tyr-Asn-Thr-, -Lys-Asn-Thr-, -Lys(DOTA)-Asn-Thr-, -Gly-Tyr-β-Nal-Ahx-, -Lys-Trp-Asn-Thr-(SEQ 1) NO: 28), -Phe(4-I)-Trp-Asn-Thr- (SEQ ID NO: 29), -D-Phe (4-I)-D-Trp-Asn-Thr-(SEQ ID NO: 30), -Sar-Sar-Sar-Sar-(SEQ ID NO: 24), D-Trp-Asn-Thr-Phe- (SEQ ID NO: 14), -D-Tyr-AAP-Asn-Thr-, -D-Tyr-Arg-Asn-Thr- (SEQ ID NO: 3), -D-Tyr-D-Ala-Asn-Thr- (SEQ ID NO: 8), -Tyr-AzaGly-Asn-Thr- (SEQ ID NO: 32), -D-Tyr-AzaGly-Asn-Thr- (SEQ ID NO: 16), -D-Tyr-Bip-Asn-Thr-, -D-Tyr-Bpa-Asn-Thr-, -D-Tyr-Glu-Asn-Thr- (SEQ ID NO: 7), -D-Tyr-Hyp-Asn-Thr-, -D-Tyr-D-Hyp-Asn-Thr-, -Tyr-Hyp-Asn-Thr-, -D-Tyr-Lys-Asn-Thr- (SEQ ID NO: 4), -D-Tyr-Lys(DOTA)-Asn-Thr- (SEQ ID NO: 38), HO—$(CH_2CH_2O)_2$—$CH_2C(=O)$-D-Tyr-Lys(DOTA)-Asn-Thr-(SEQ ID NO: 845), -Tyr-D-Lys-Asn-Thr- (SEQ ID NO: 829), -Tyr-D-Lys(DOTA)-Asn-Thr-(SEQ ID NO: 39), -D-Tyr-D-Lys-Asn-Thr- (SEQ ID NO: 830), -D-Tyr-D-Lys(DOTA)-Asn-Thr-(SEQ ID NO: 40), -Tyr-β-Nal-Asn-Thr-, -D-Tyr-r-Nal-Asn-Thr-, -D-Tyr-D-β-Nal-Asn-Thr-, -Tyr-4Pal-Asn-Thr-, -D-Tyr-4Pal-Asn-Thr-, -D-Tyr-D-4Pal-Asn-Thr-, -D-Tyr-Phe(4-I)-Asn-Thr-(SEQ ID NO: 45), -Tyr-Pro-Asn-Thr- (SEQ ID NO: 46), -D-Tyr-Pro-Asn-Thr-(SEQ ID NO: 20), D-Tyr-Trp-Asn-Ala- (SEQ ID NO: 9), -D-Tyr-D-Trp-Asn-Ala-(SEQ ID NO: 47), -D-Tyr-Trp-Asn-Thr- (SEQ ID NO: 10), -D-Tyr-D-Trp-Asn-Thr- (SEQ ID NO: 1), -D-Ala-D-Ala-D-Ala-D-Ala-D-Ala- (SEQ ID NO: 26), D-Ala-Asn-Trp-Asn-Gly- (SEQ ID NO: 13), D-Ala-Asn-Trp-Asn-D-Ser (SEQ ID NO: 15), -D-Asn-D-Asn-D-Asn-D-Asn-D-Asn-(SEQ ID NO: 17), -D-Asn-D-Asn-D-Glu-D-Glu-D-Asn- (SEQ ID NO: 18), -D-Asn-D-Asn-D-Lys-D-Glu-D-Asn-(SEQ ID NO: 19), -γ-D-Glu-D-Tyr-Lys(DOTA)-Asn-Thr- (SEQ ID NO: 48) -Gly-D-Tyr-β-Nal-Asn-Thr- (SEQ ID NO: 49), -Gly-Tyr-D-Trp-Asn-Thr- (SEQ ID NO: 50), -Sar-Sar-Sar-Sar-Sar- (SEQ ID NO: 25), -Tyr-Asn-Trp-Asn-Ser- (SEQ ID NO: 51), -D-Tyr-D-Asn-D-Arg-Asn-Thr-(SEQ ID NO: 2), -D-Tyr-Asn-D-Trp-Asn-Thr (SEQ ID NO: 11), -Tyr-Glu-Asn-Thr-3-F-Phe- (SEQ ID NO: 52), -D-Tyr-D-H-is-D-Trp-Asn-Thr-(SEQ ID NO: 12), -Tyr-Trp-Asn-Thr-3-F-Phe- (SEQ ID NO: 53), -D-Tyr-D-Trp-Asn-Thr-3-F-Phe- (SEQ ID NO: 54), Palmitic Acid-γGlu-Lys(DOTA)-Tyr-Asn-Trp-Asn-Ser-(SEQ ID NO: 846), or Ac-γGlu-Lys(DOTA)-D-Ala-Asn-Trp-Asn-Gly-(SEQ ID NO: 847).

In some embodiments,

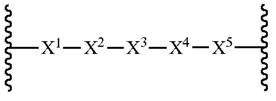

-continued
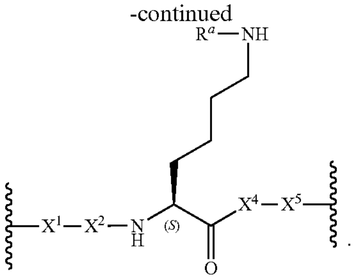
is
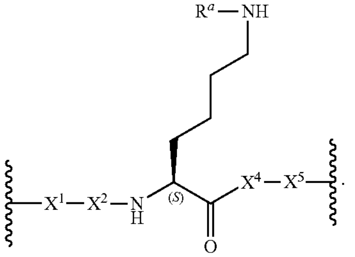
In some embodiments,
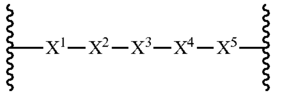
is
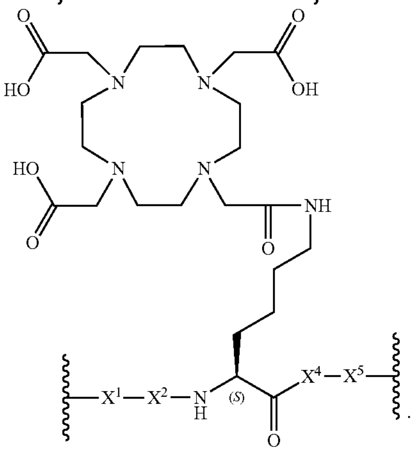
In some embodiments,
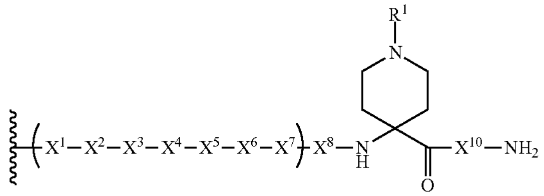
is
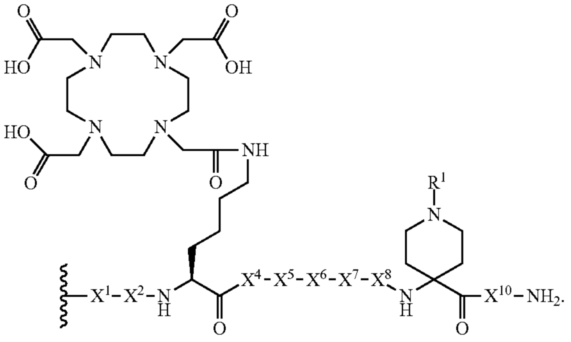
In some embodiments,
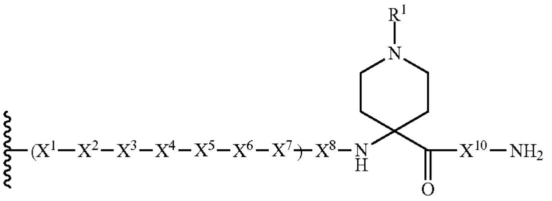
is
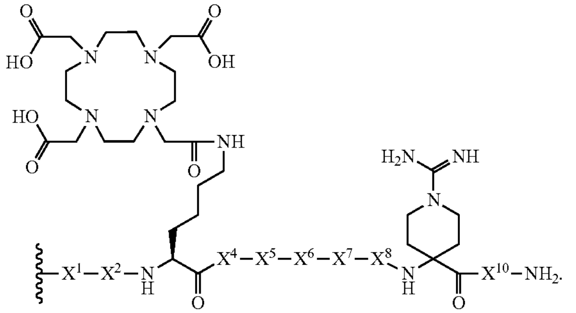
In some embodiments,
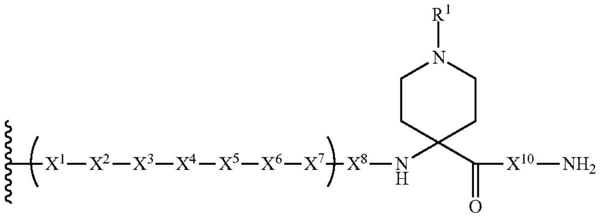
is -continued
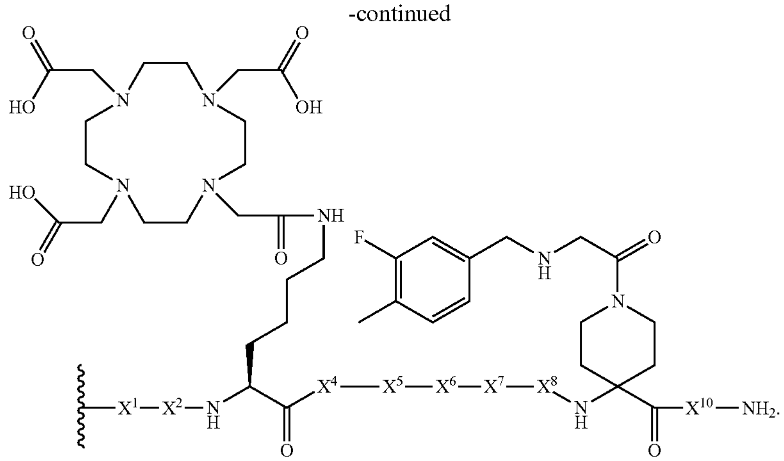
In some embodiments,
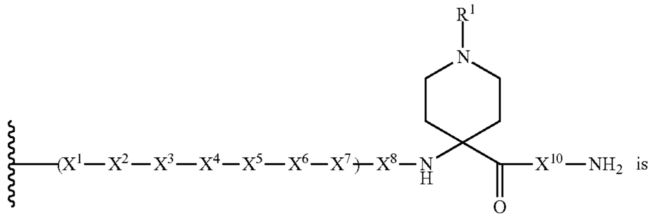
(SEQ ID NO: 55)
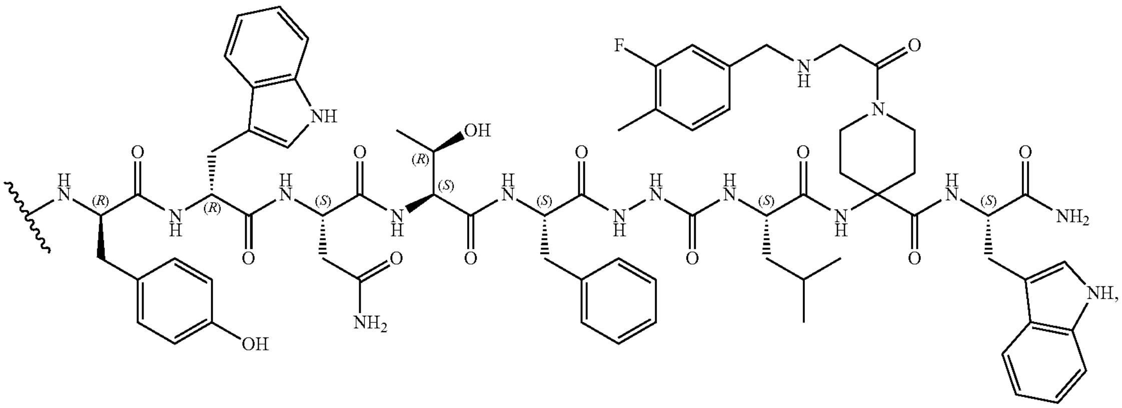
(SEQ ID NO: 56)
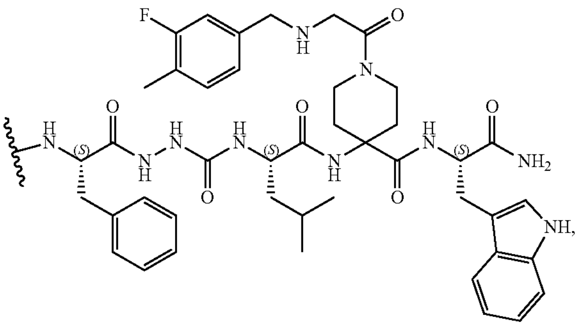
(SEQ ID NO: 57)
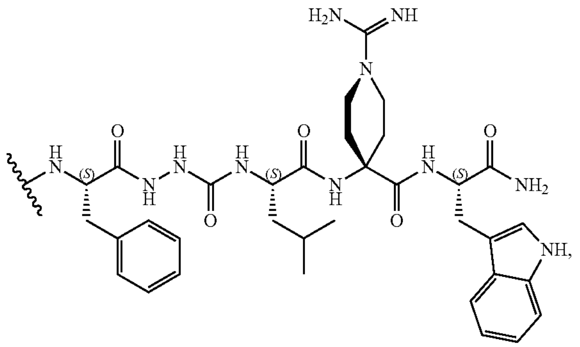

-continued
(SEQ ID NO: 58)
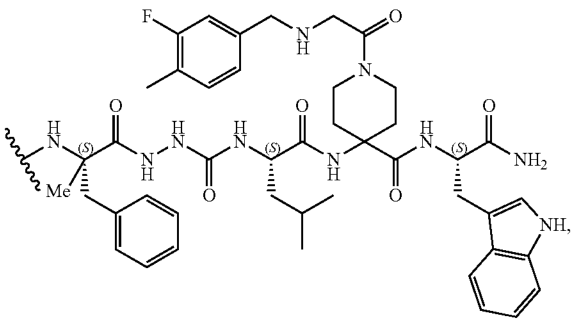
(SEQ ID NO: 59)
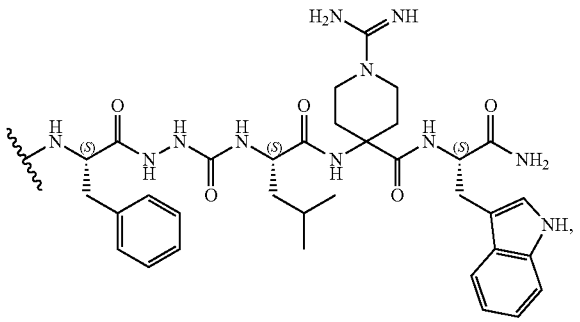
(SEQ ID NO: 60)
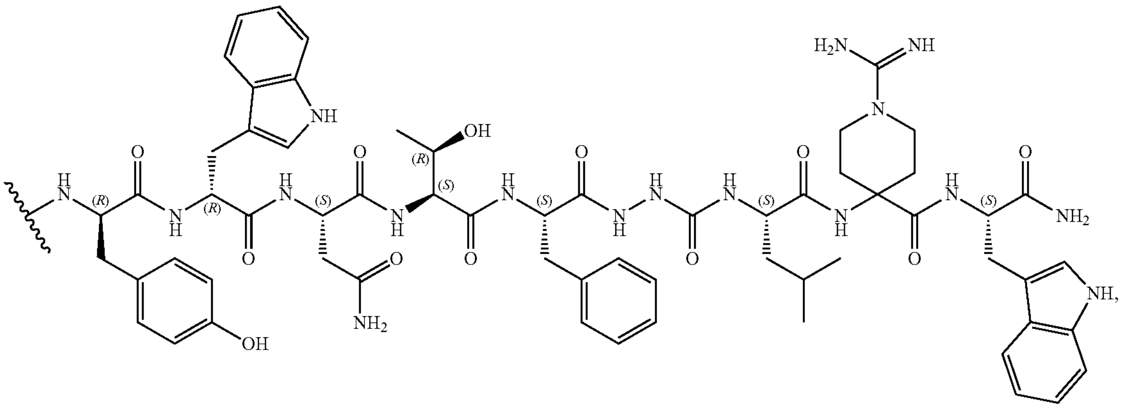
(SEQ ID NO: 61)
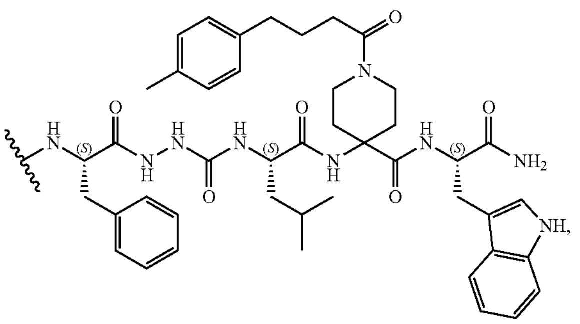
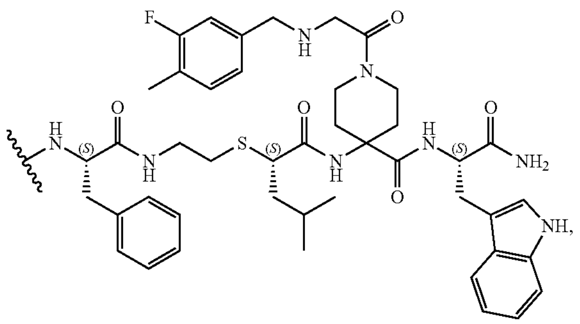
(SEQ ID NO: 63)
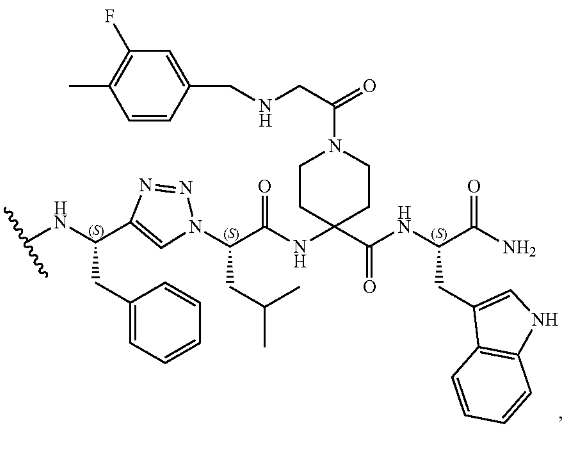
(SEQ ID NO: 64)
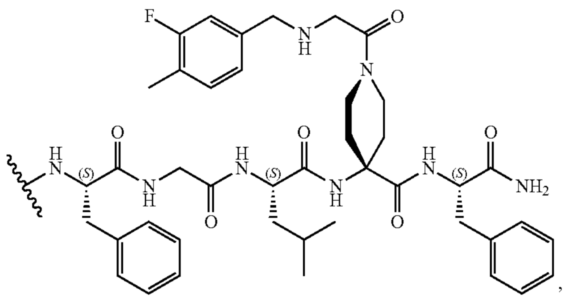

-continued
(SEQ ID NO: 65)
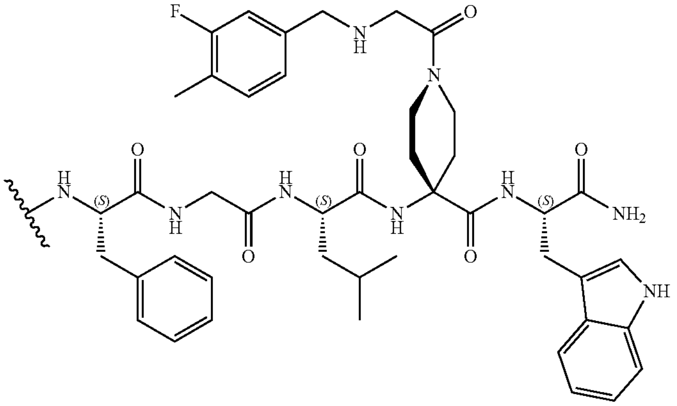
(SEQ ID NO: 65)
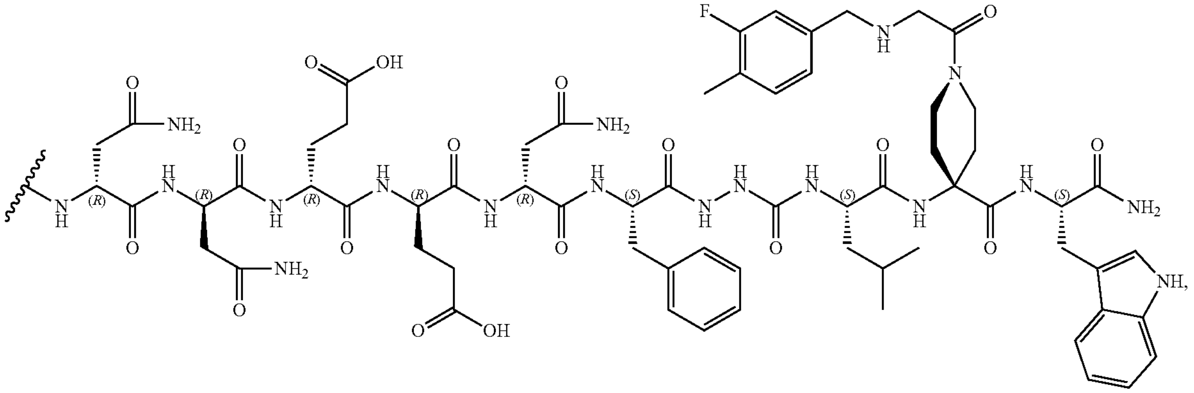
(SEQ ID NO: 66)
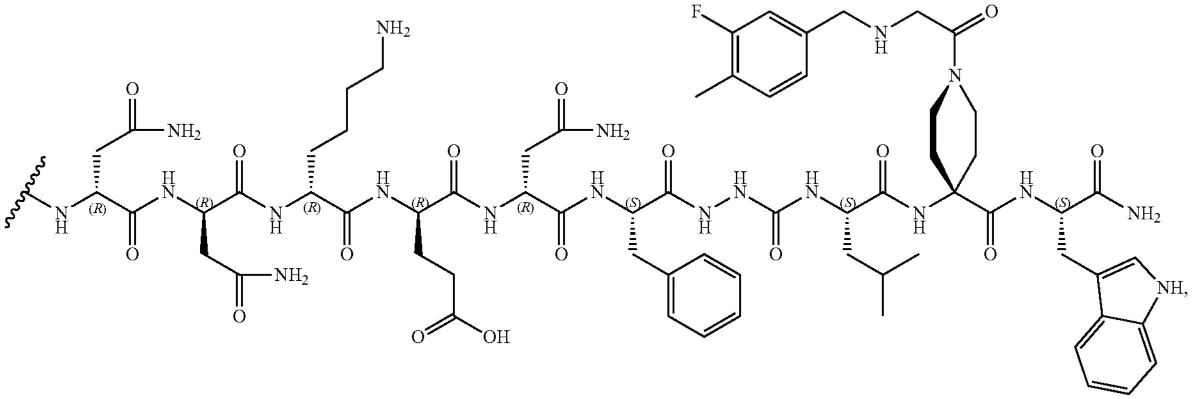
(SEQ ID NO: 67)
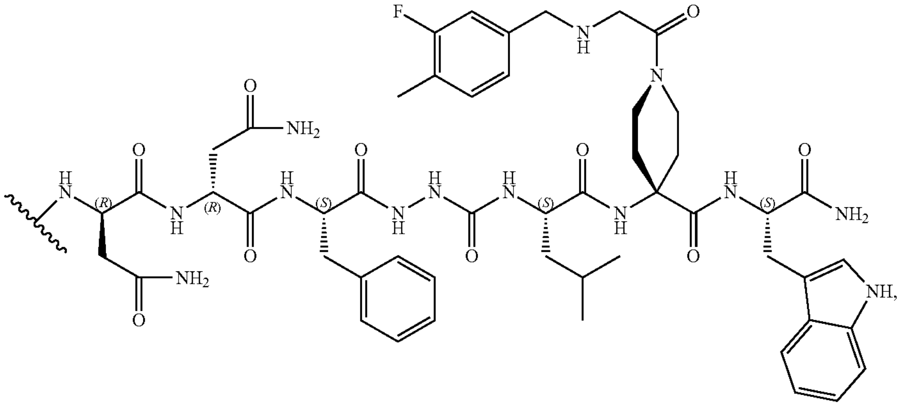

-continued
(SEQ ID NO: 68)
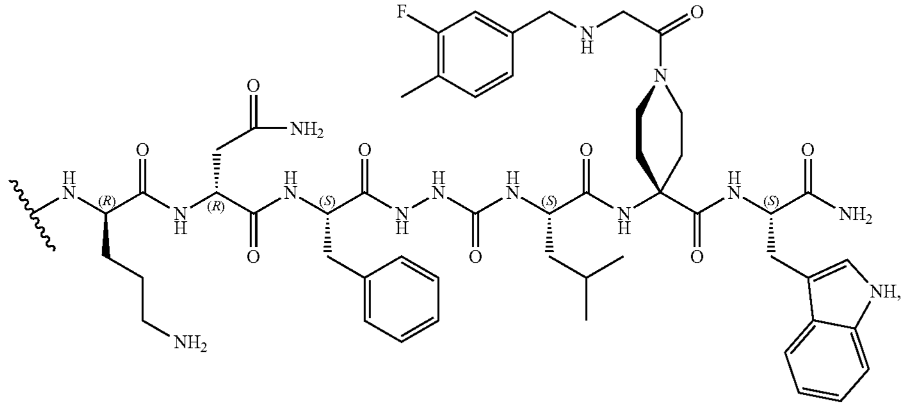
(SEQ ID NO: 69)
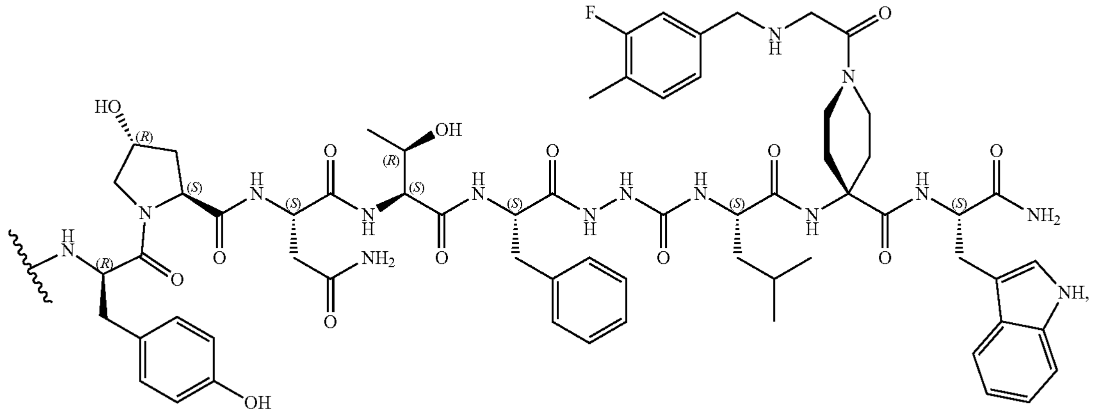
(SEQ ID NO: 70)
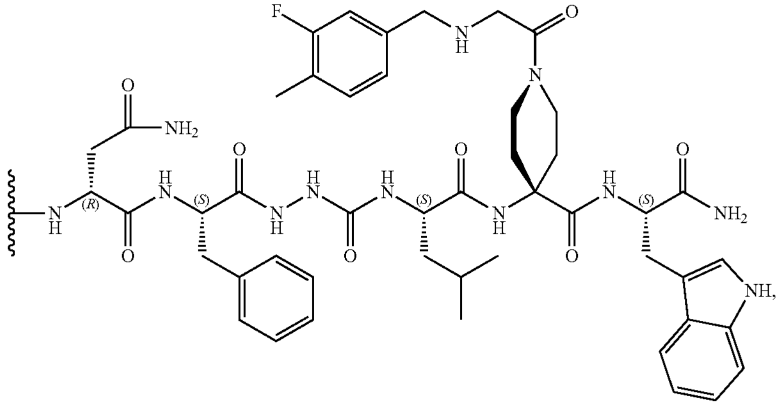
(SEQ ID NO: 71)
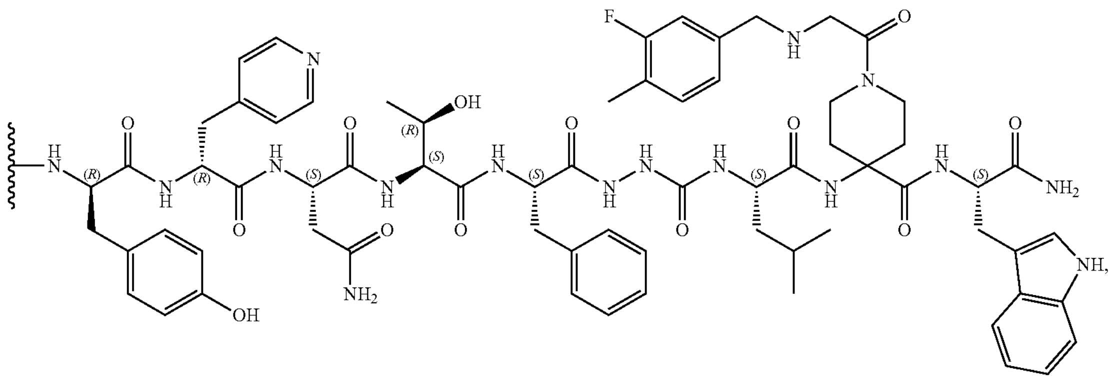

-continued
(SEQ ID NO: 72)
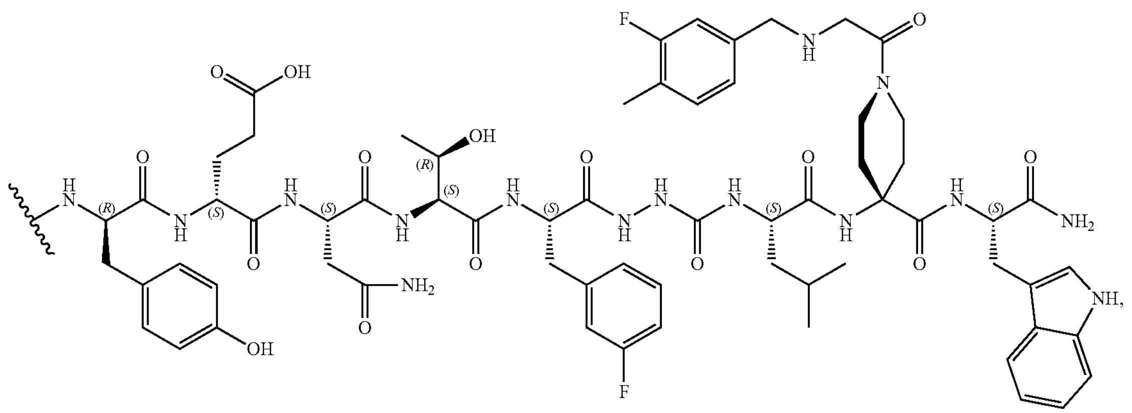
(SEQ ID NO: 73)
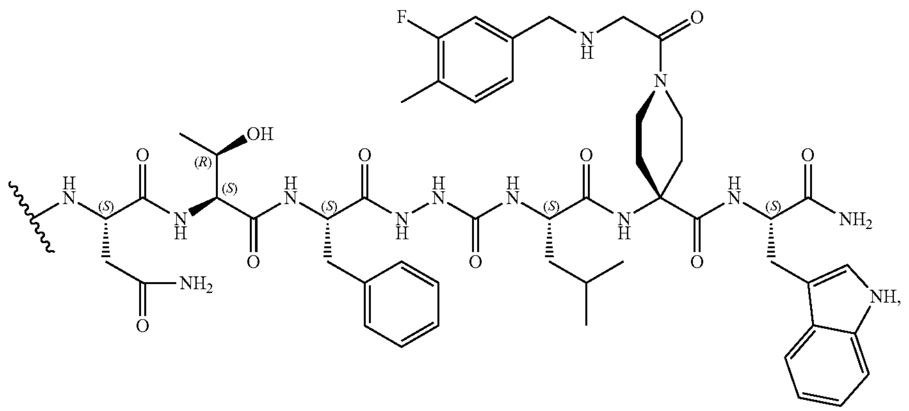
(SEQ ID NO: 74)
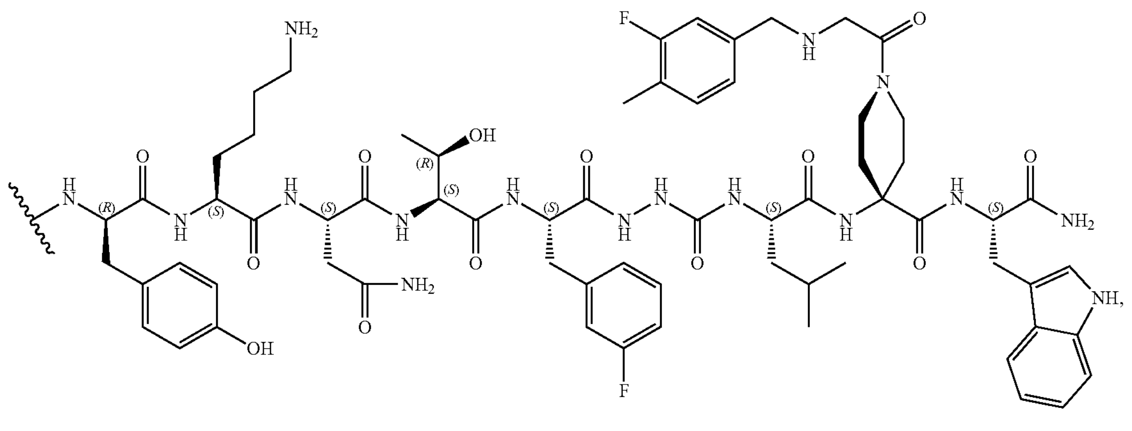

-continued
(SEQ ID NO: 75)
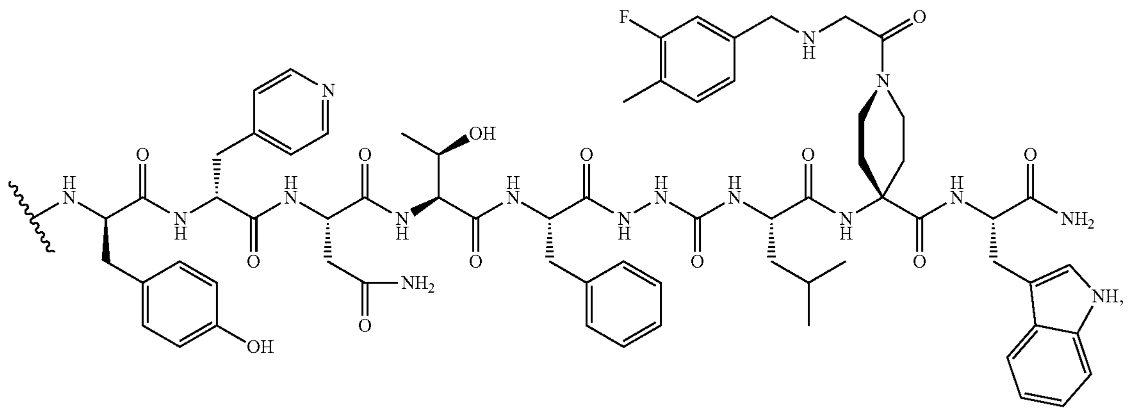
(SEQ ID NO: 76)
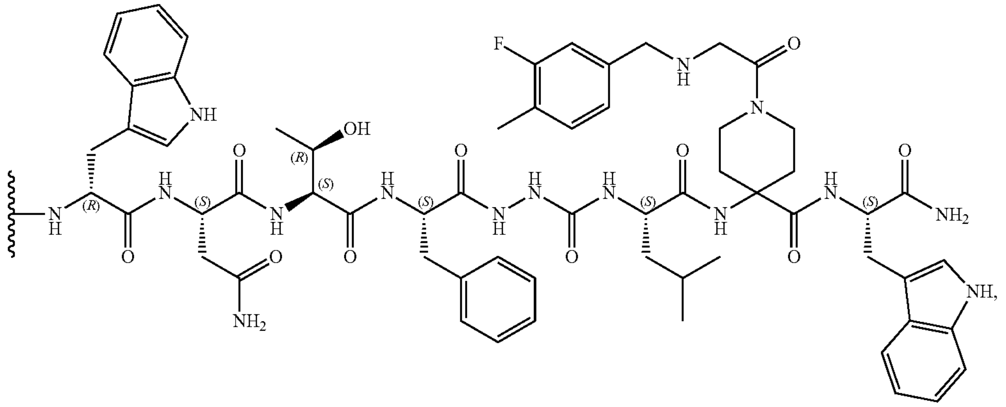
(SEQ ID NO: 77)
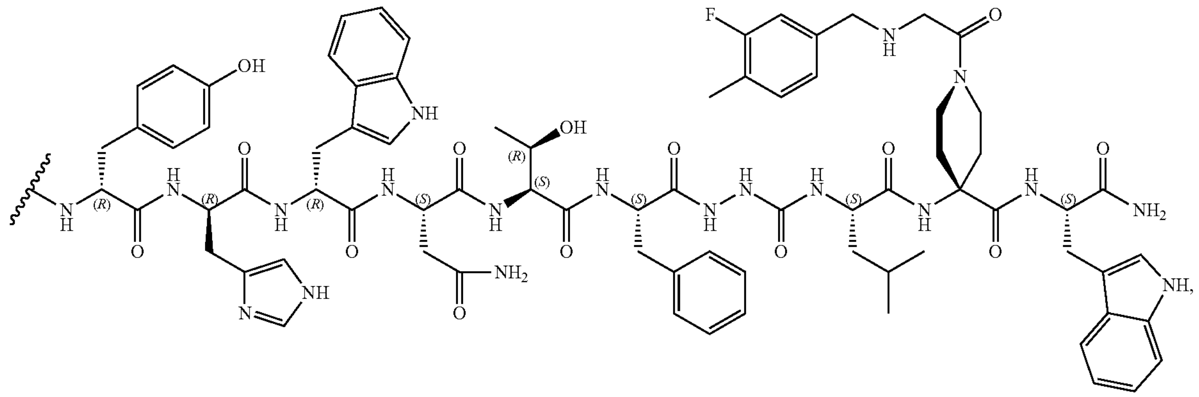

-continued
(SEQ ID NO: 78)
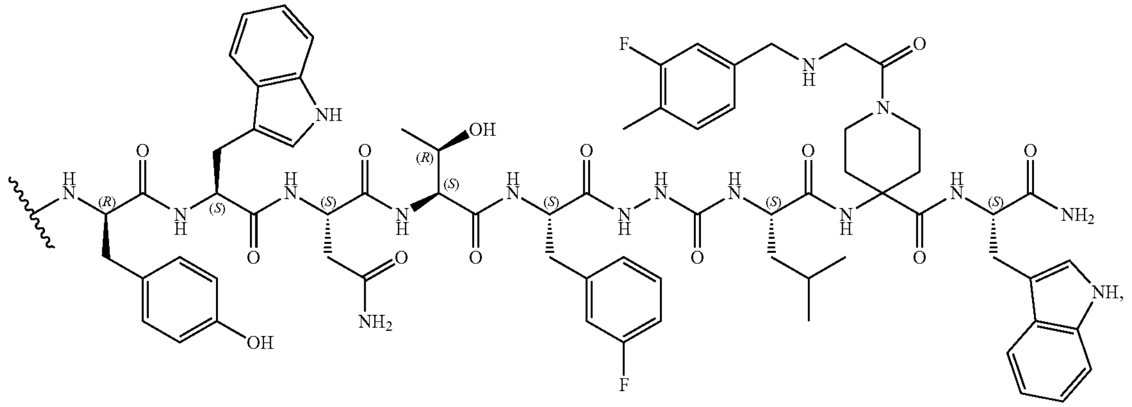
lp;4p
(SEQ ID NO: 79)
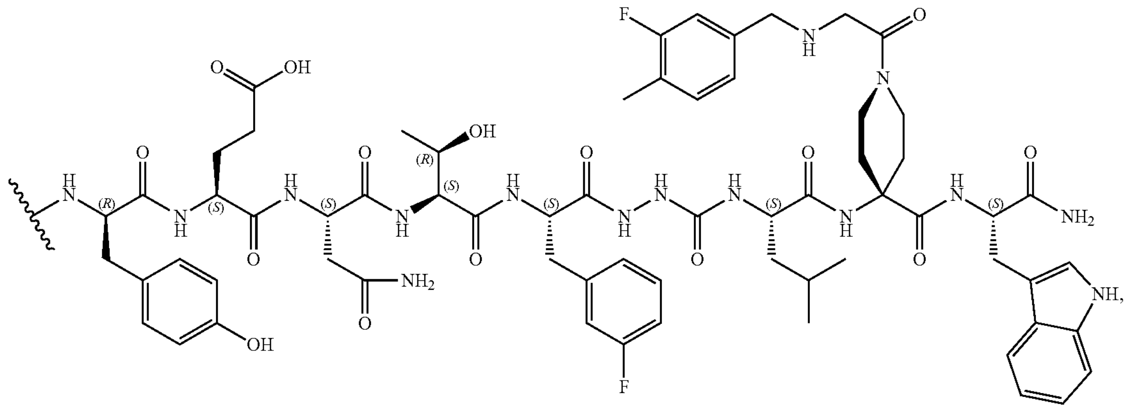
(SEQ ID NO: 80)
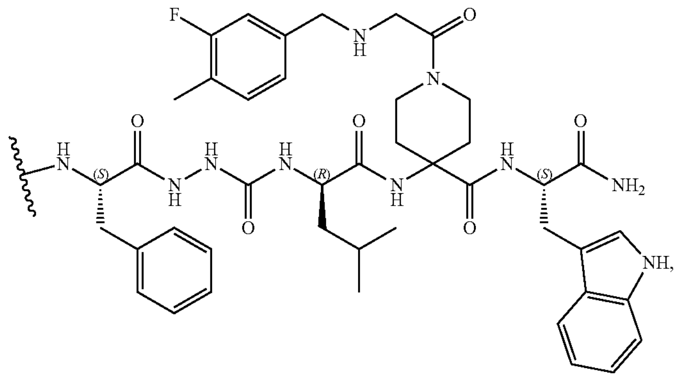

(SEQ ID NO: 81)
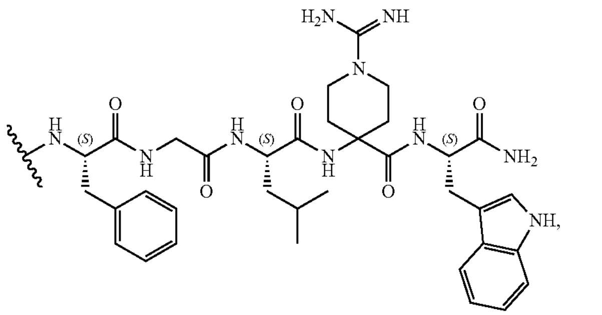
(SEQ ID NO: 82)
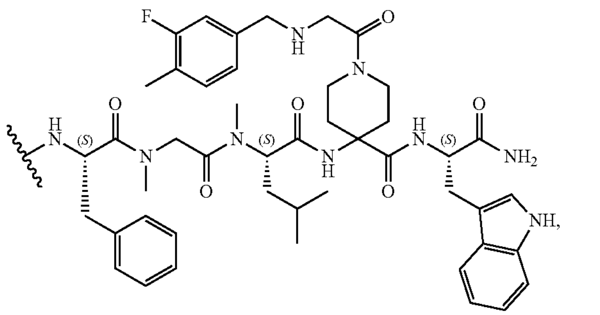
(SEQ ID NO: 83)
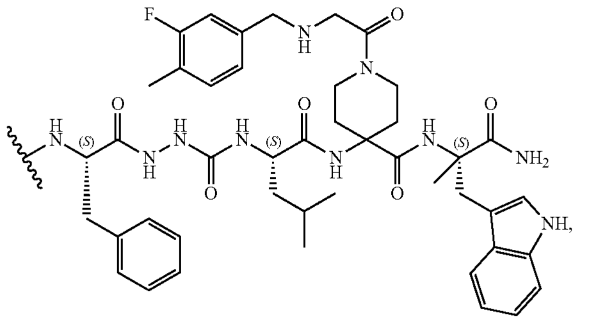
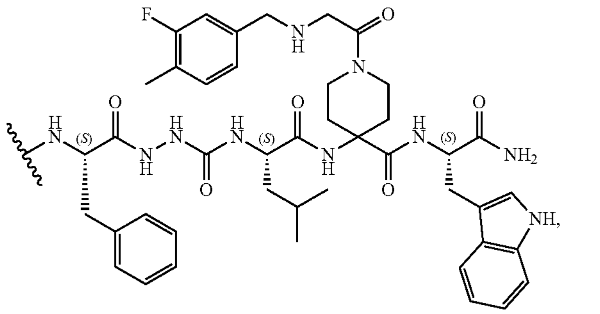
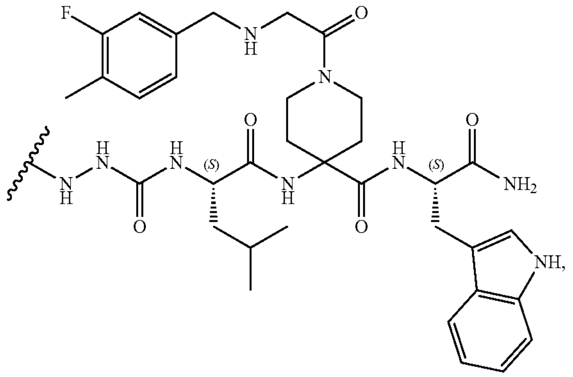
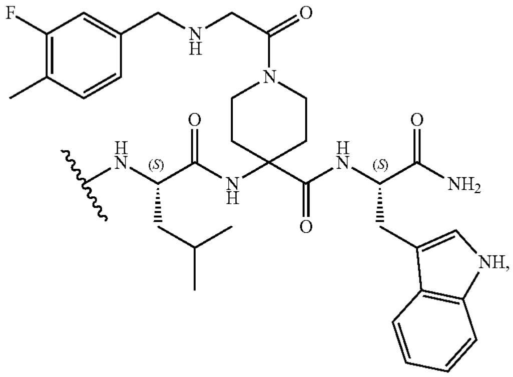
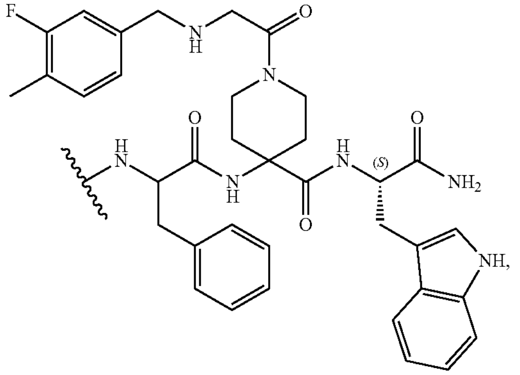
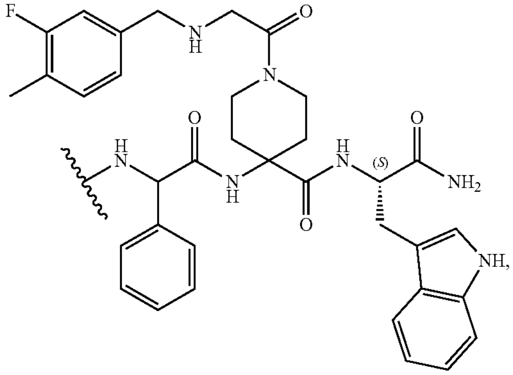

-continued
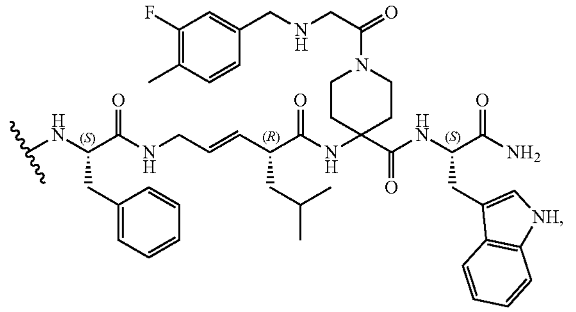
(SEQ ID NO: 87)
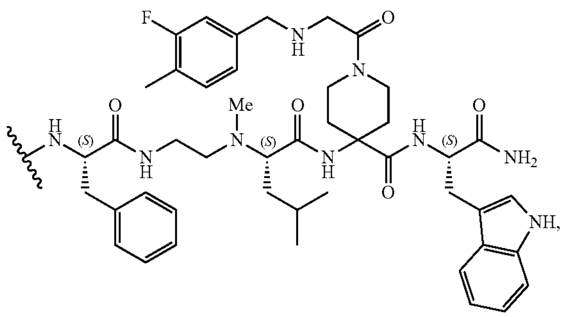
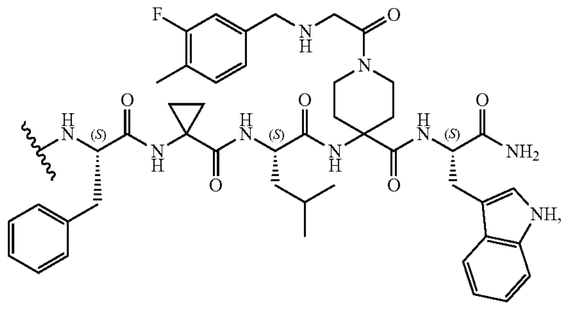
(SEQ ID NO: 89)
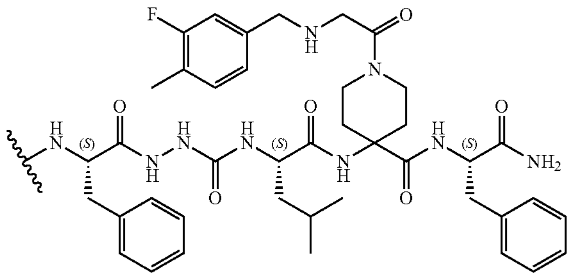
(SEQ ID NO: 90)
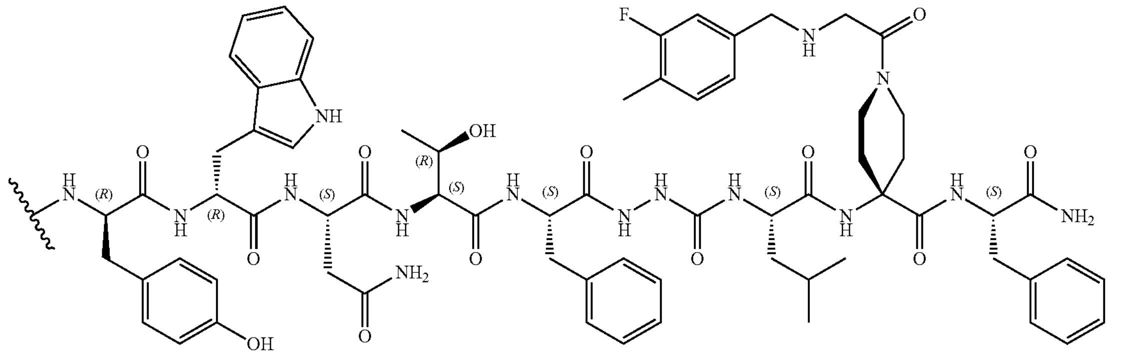
(SEQ ID NO: 91)
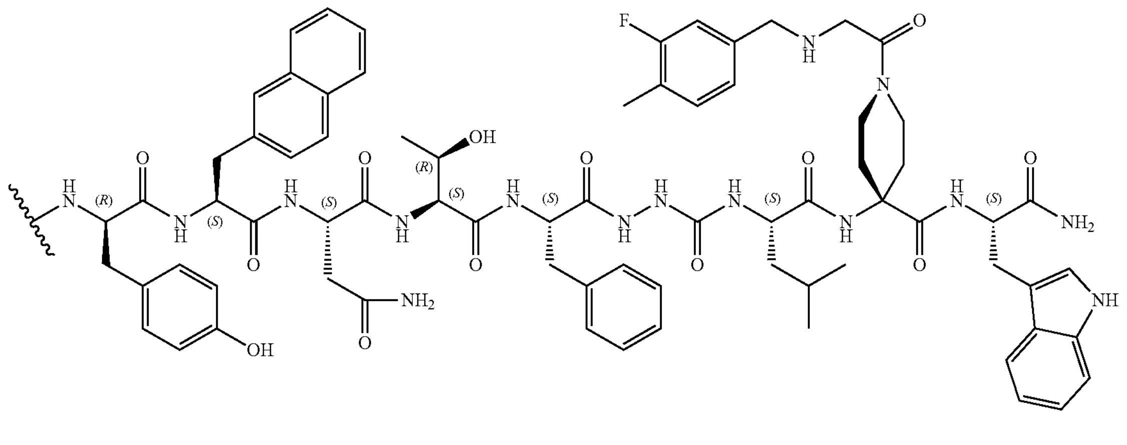

-continued
(SEQ ID NO: 92)
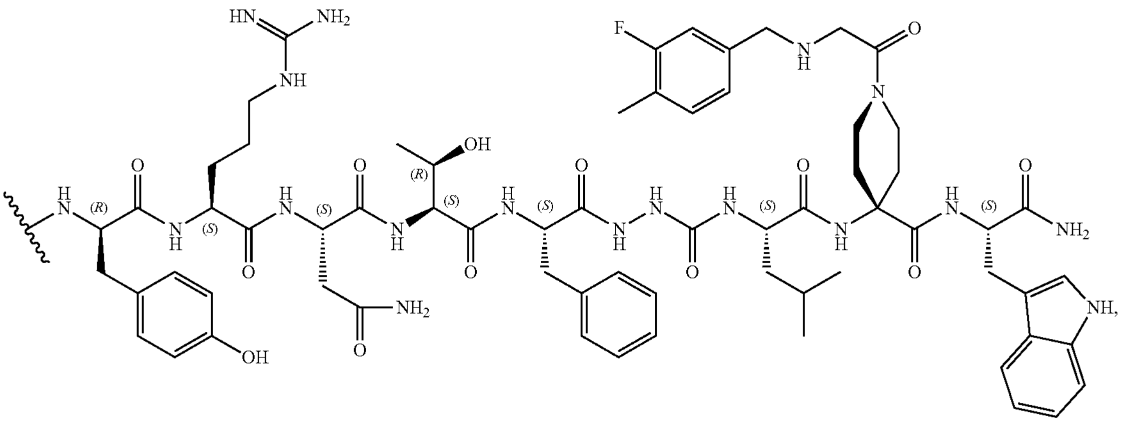
(SEQ ID NO: 93)
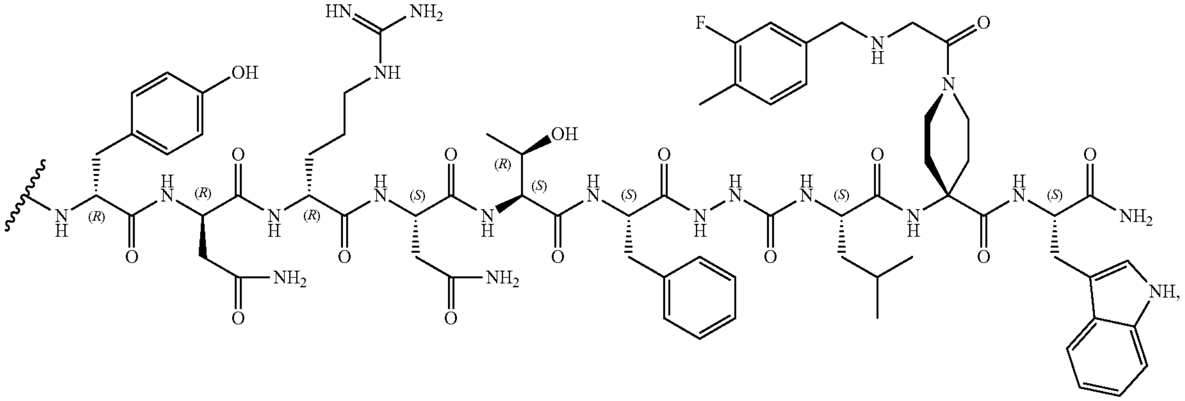
(SEQ ID NO: 94)
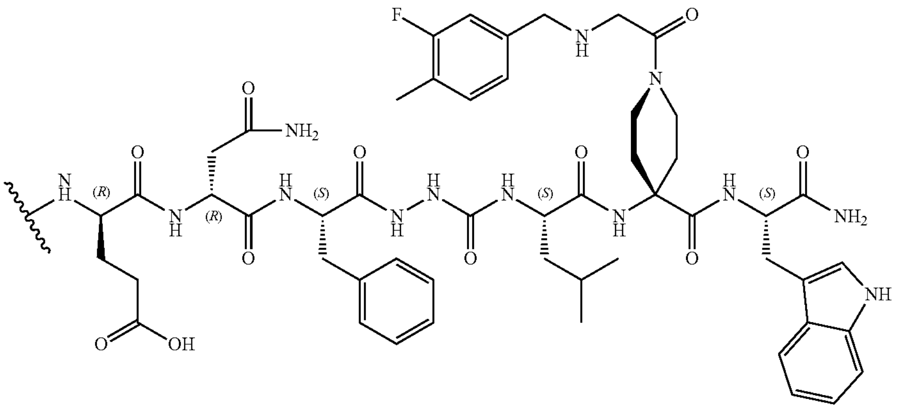

-continued
(SEQ ID NO: 95)
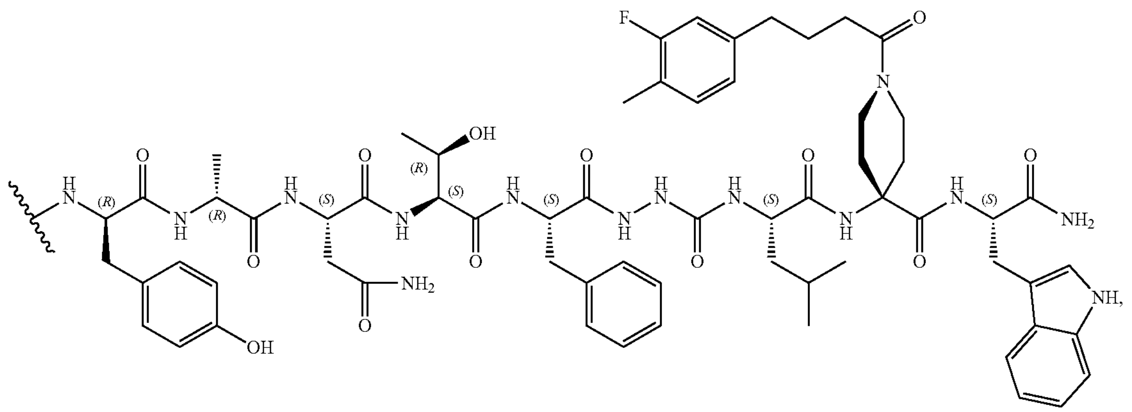
(SEQ ID NO: 96)
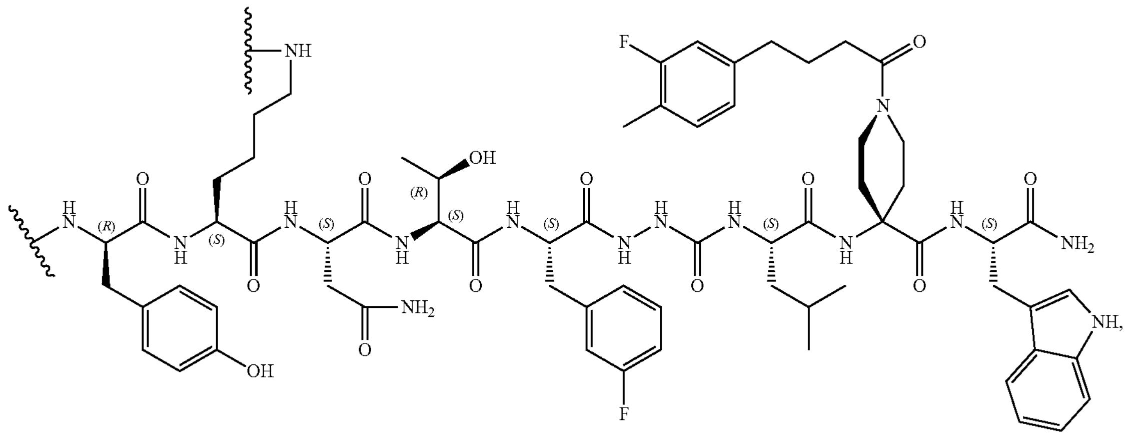
(SEQ ID NO: 97)
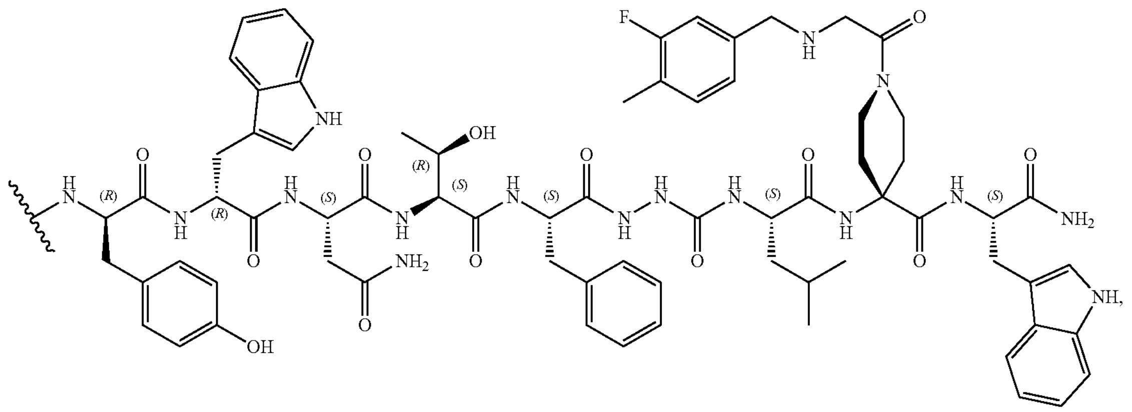

-continued
(SEQ ID NO: 98)
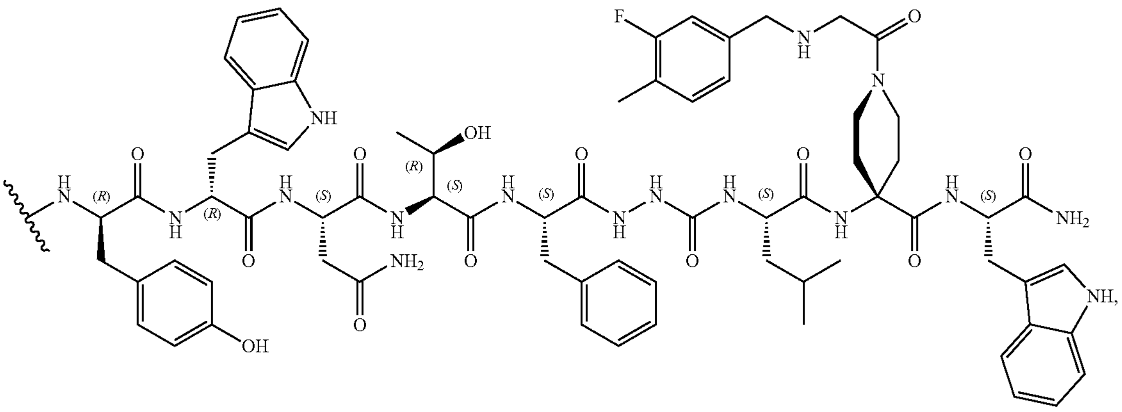
(SEQ ID NO: 99)
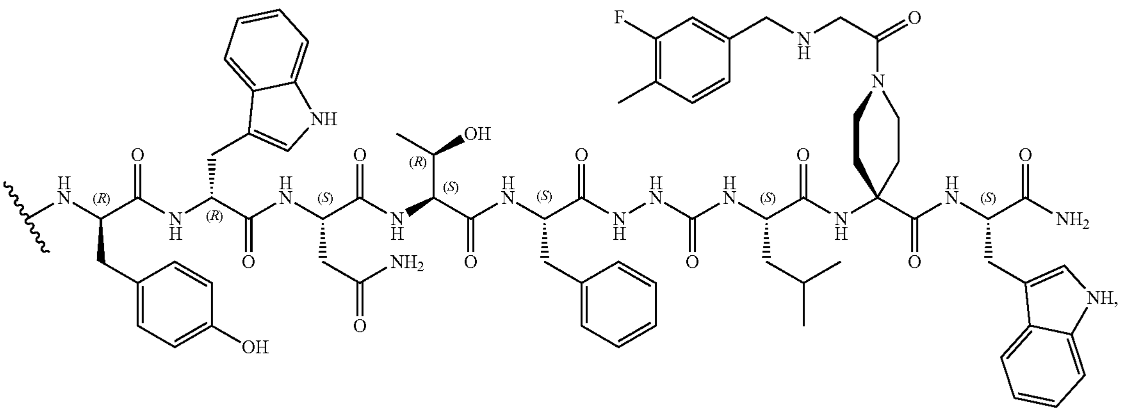
(SEQ ID NO: 100)
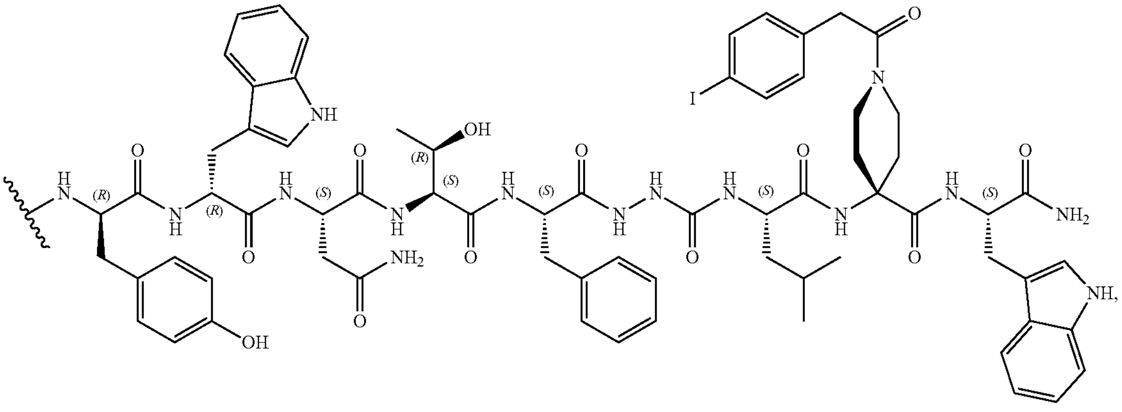

-continued
(SEQ ID NO: 101)
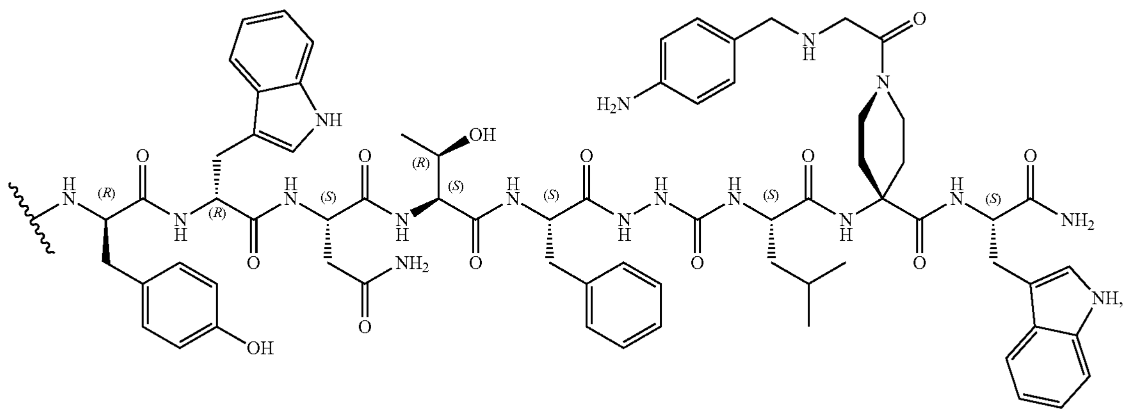
(SEQ ID NO: 102)
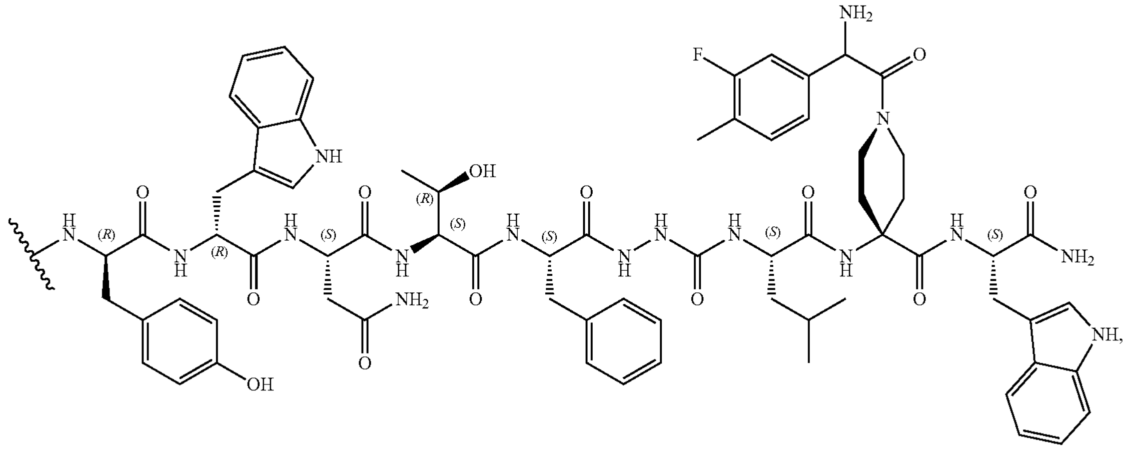
(SEQ ID NO: 103)
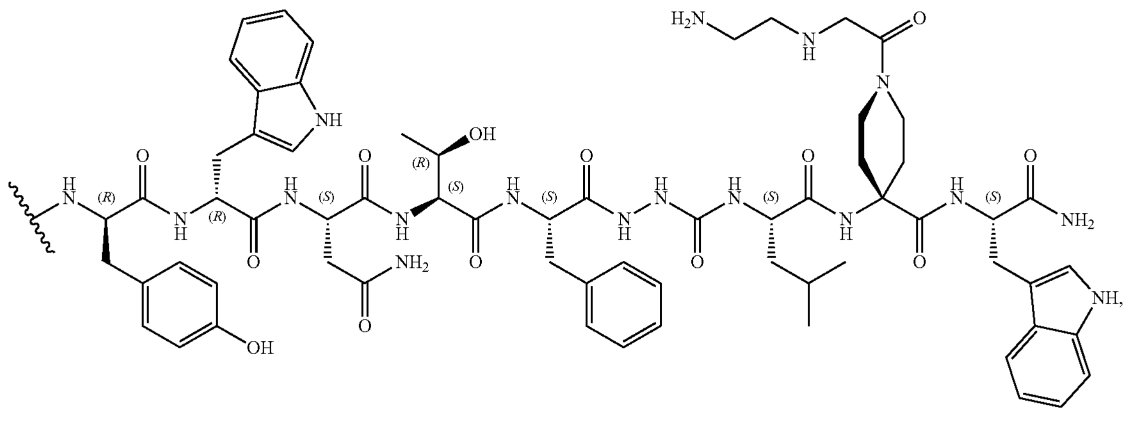

-continued
(SEQ ID NO: 104)
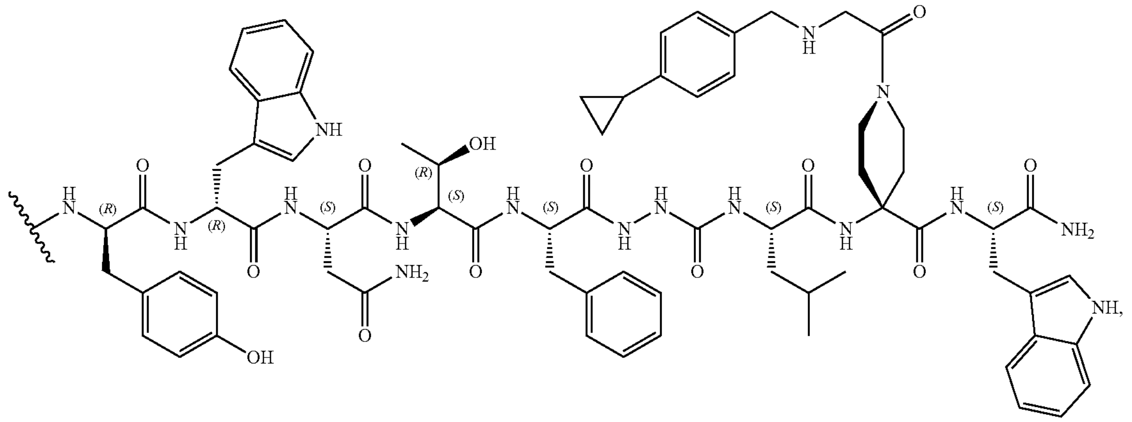
(SEQ ID NO: 105)
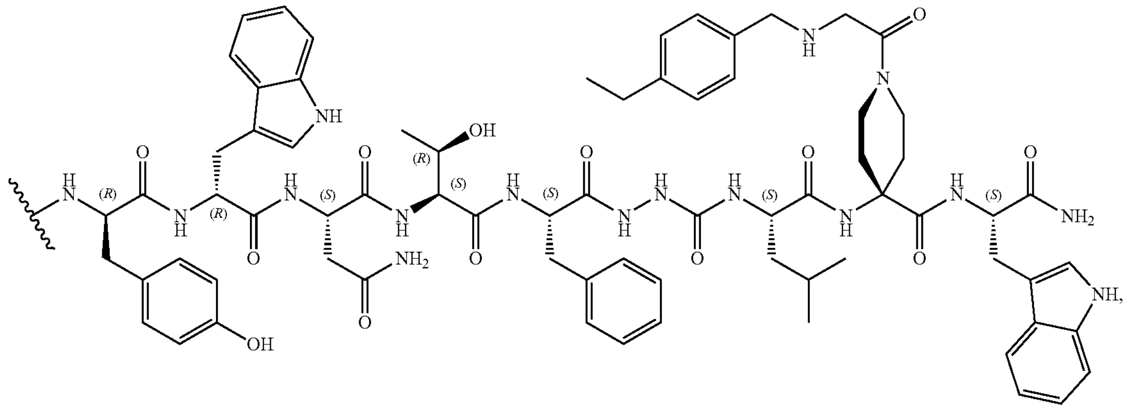
(SEQ ID NO: 106)
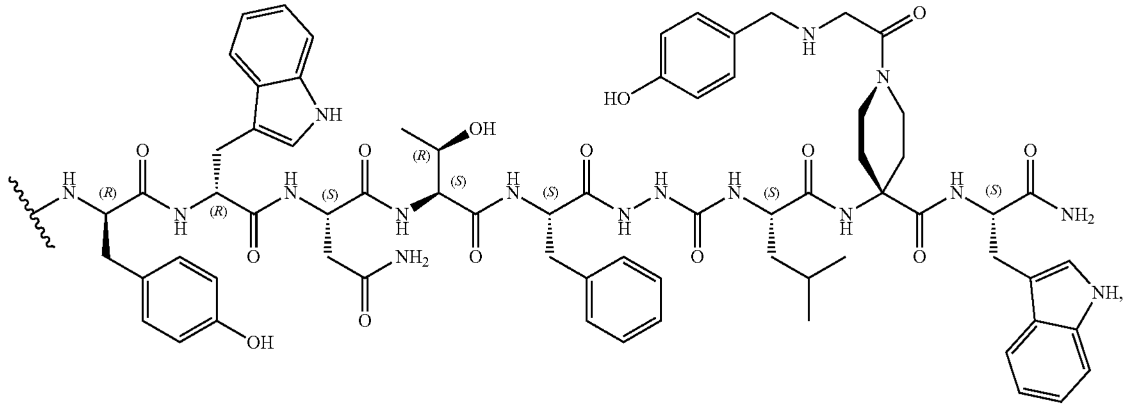

-continued
(SEQ ID NO: 107)
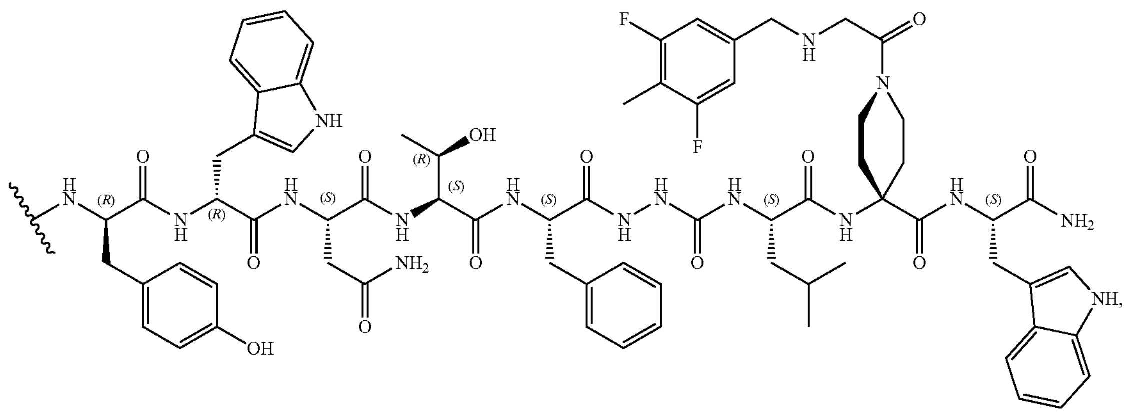
(SEQ ID NO: 108)
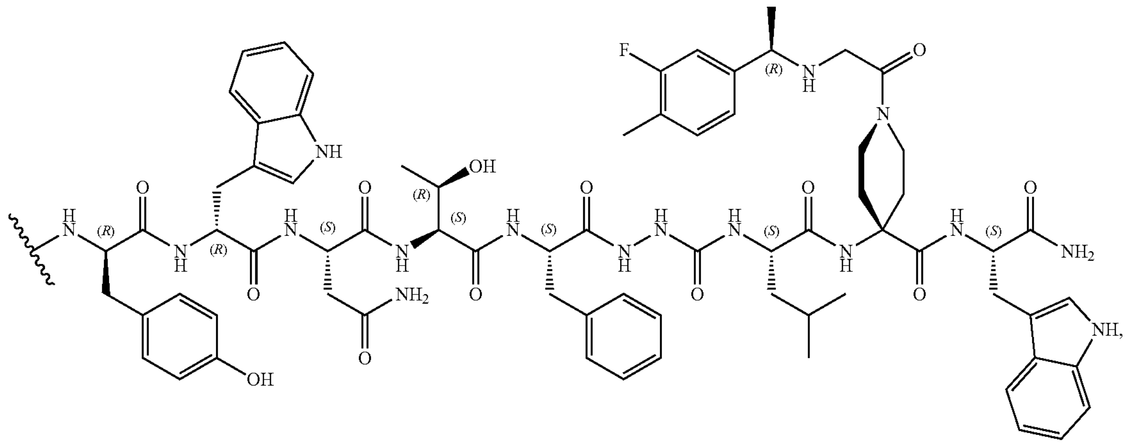
(SEQ ID NO: 109)
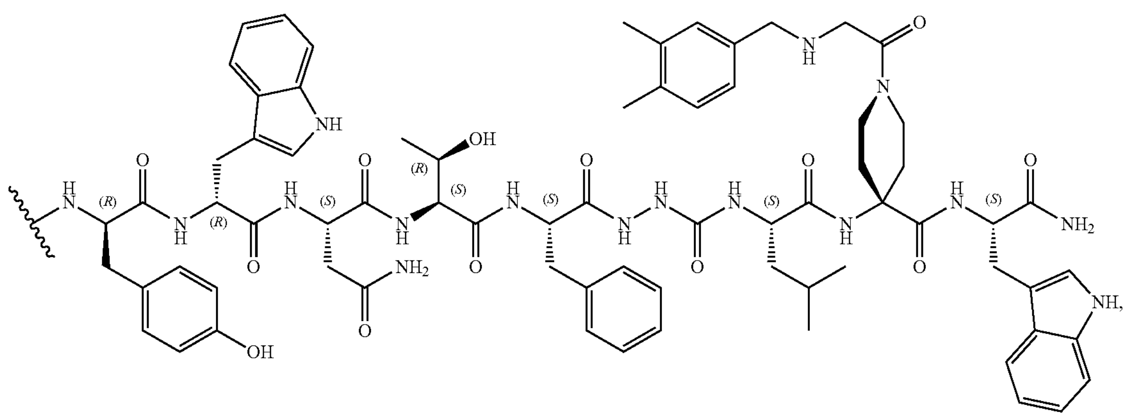

-continued
(SEQ ID NO: 110)
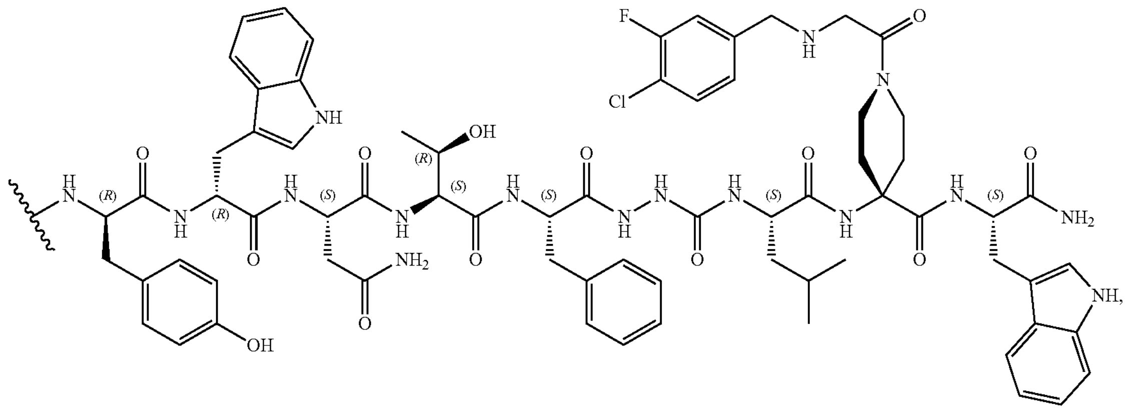
(SEQ ID NO: 111)
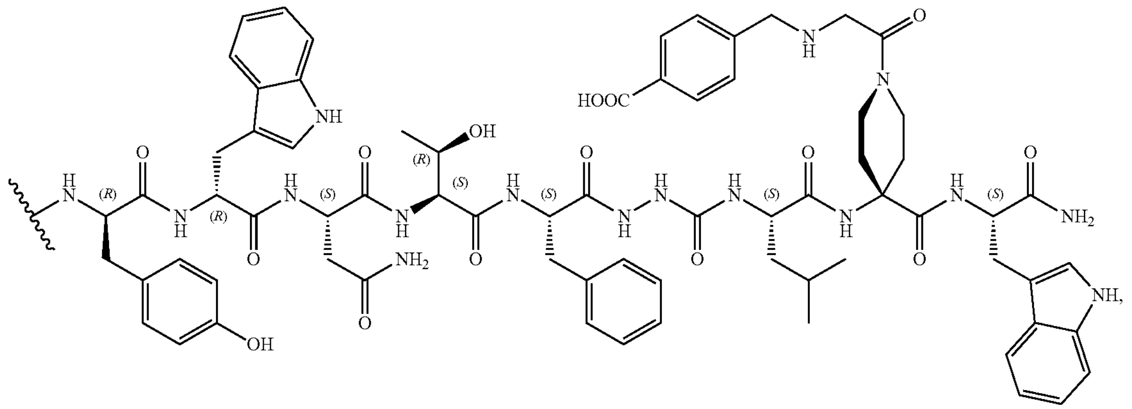
(SEQ ID NO: 112)
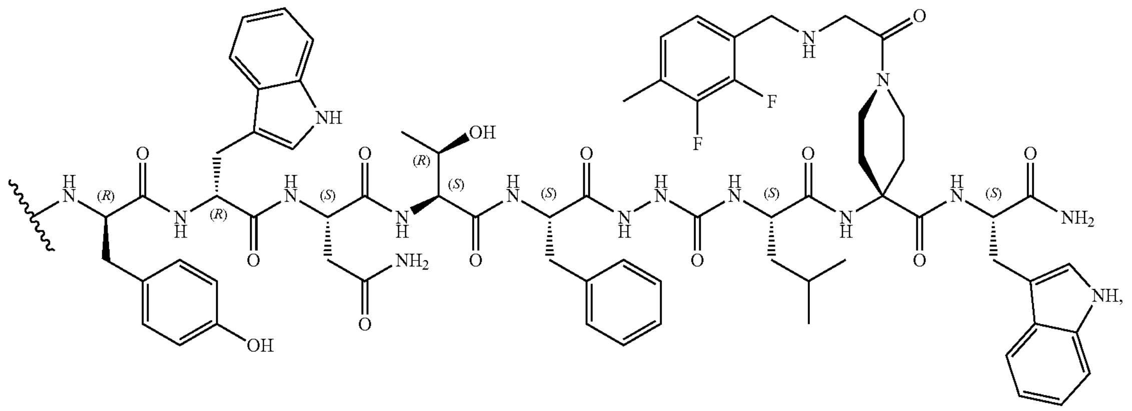

(SEQ ID NO: 113)
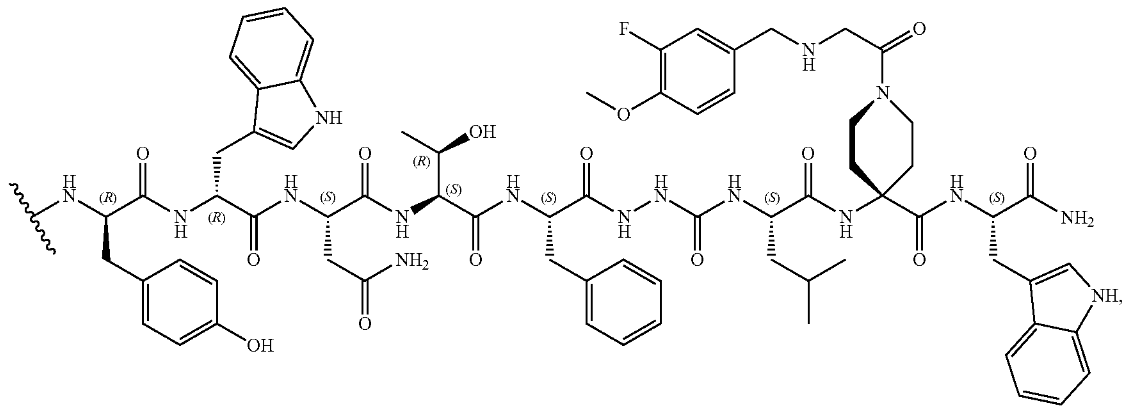
(SEQ ID NO: 114)
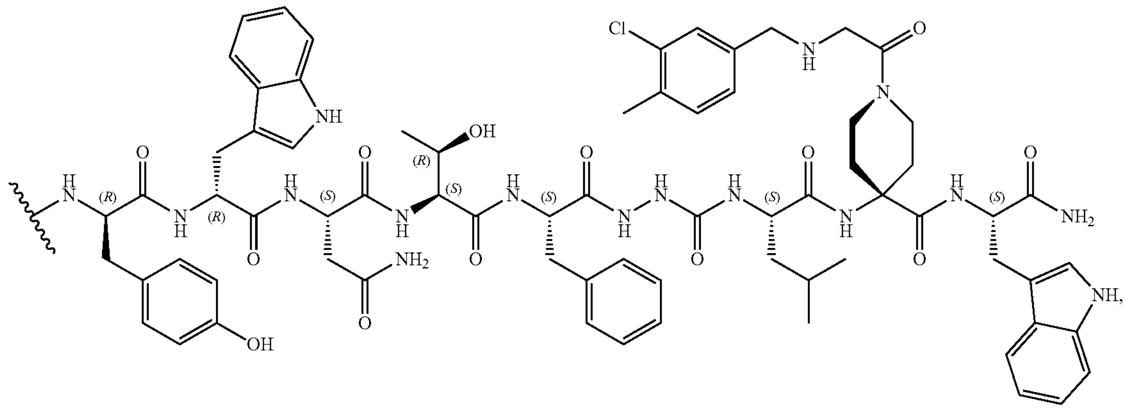
(SEQ ID NO: 115)
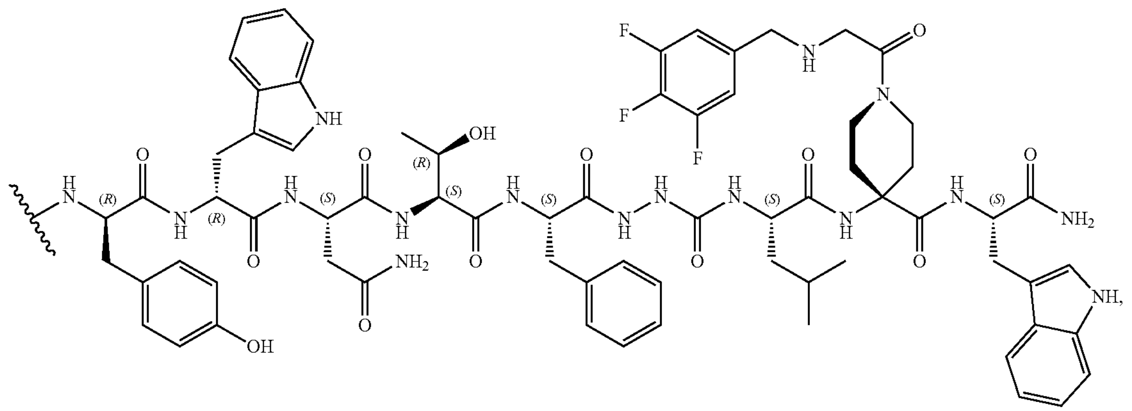

-continued
(SEQ ID NO: 116)
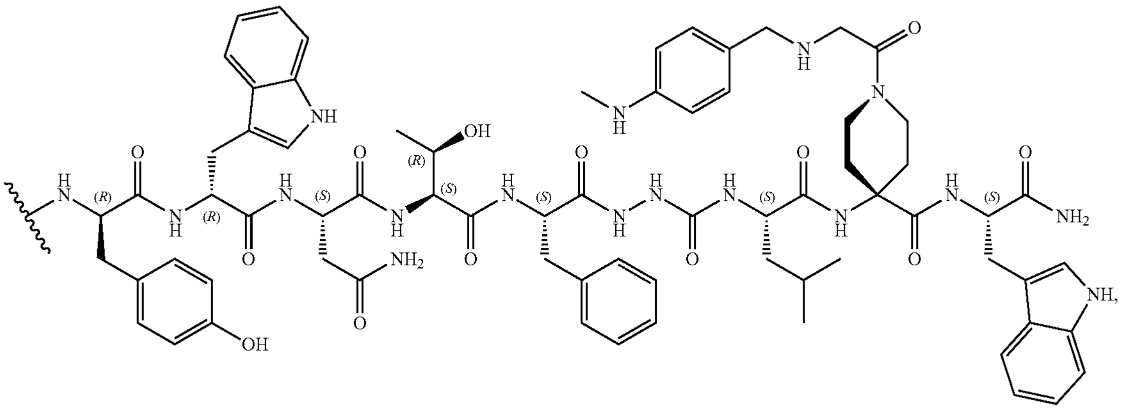
(SEQ ID NO: 117)
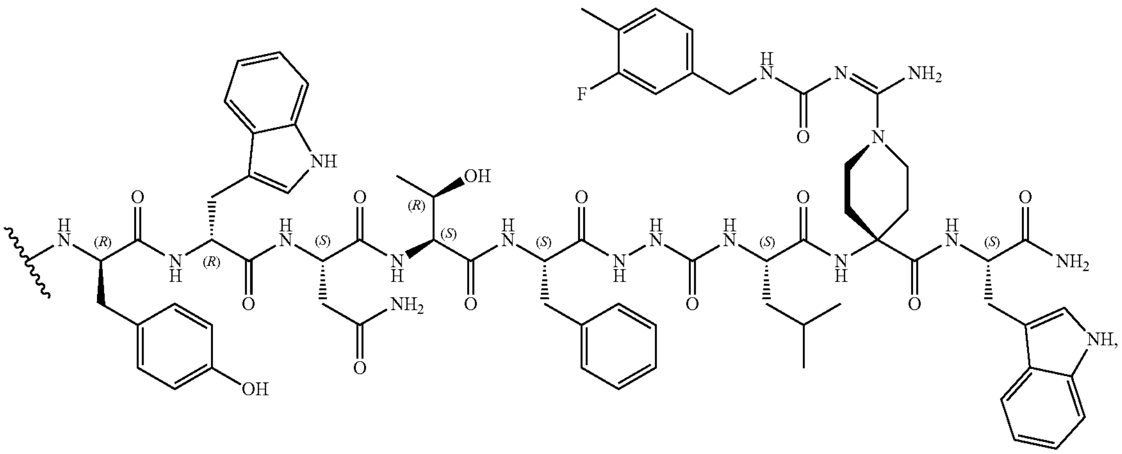
(SEQ ID NO: 118)
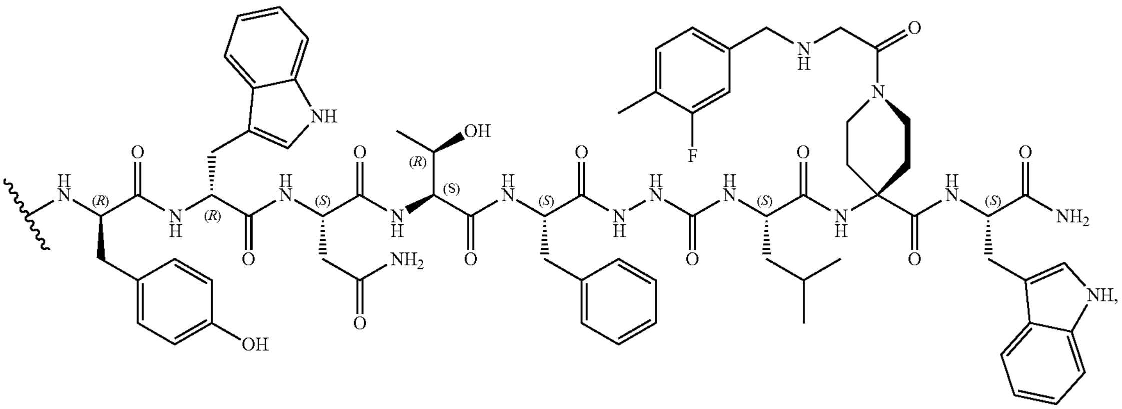

-continued
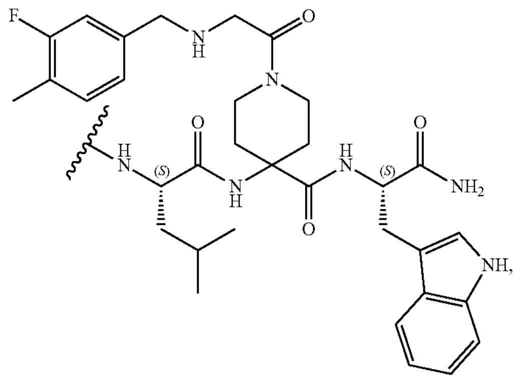
(SEQ ID NO: 119)
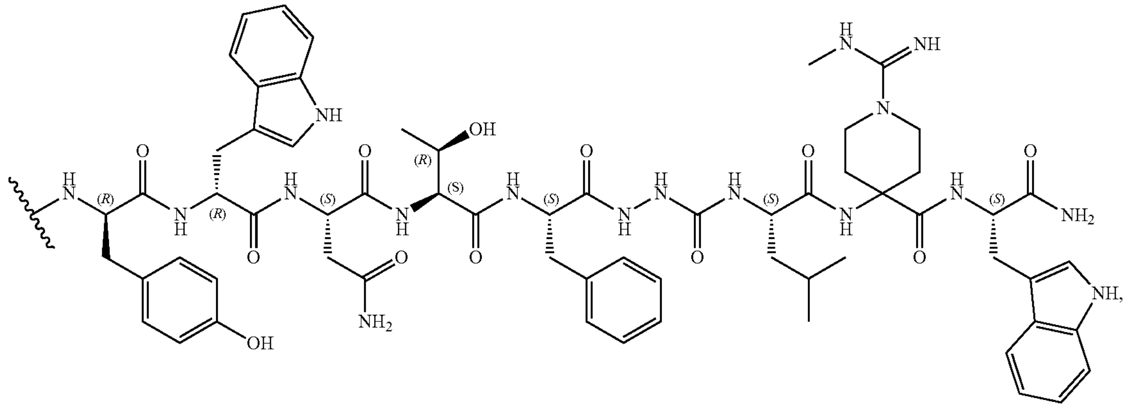
(SEQ ID NO: 120)
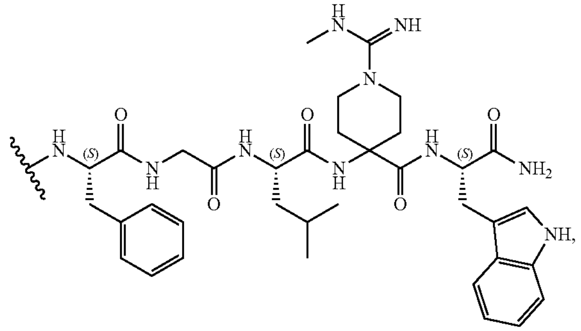
(SEQ ID NO: 121)
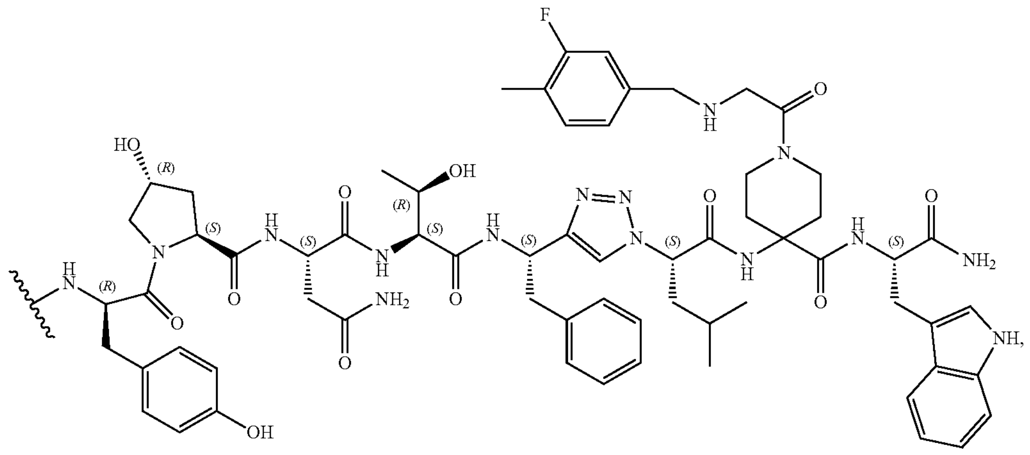

-continued
(SEQ ID NO: 122)
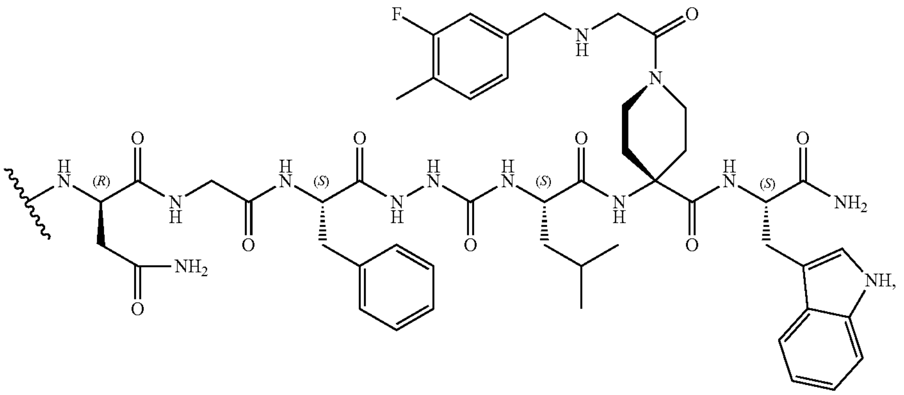
(SEQ ID NO: 123)
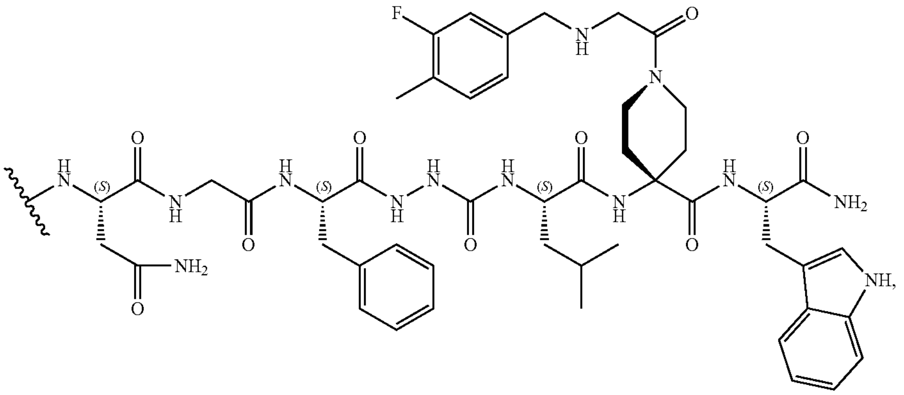
(SEQ ID NO: 124)
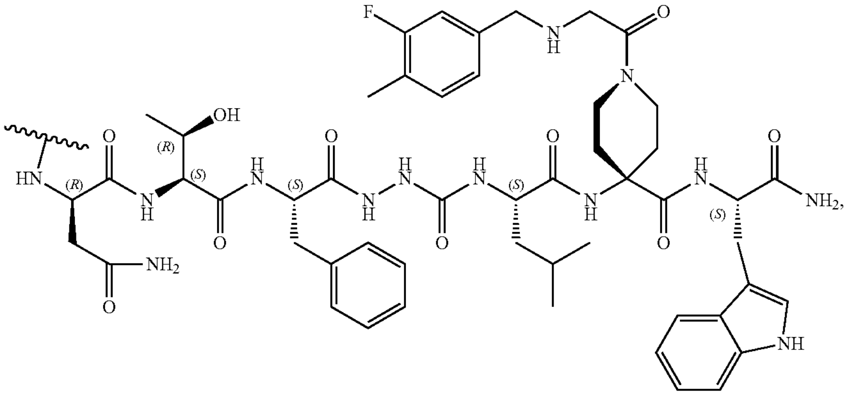
(SEQ ID NO: 125)
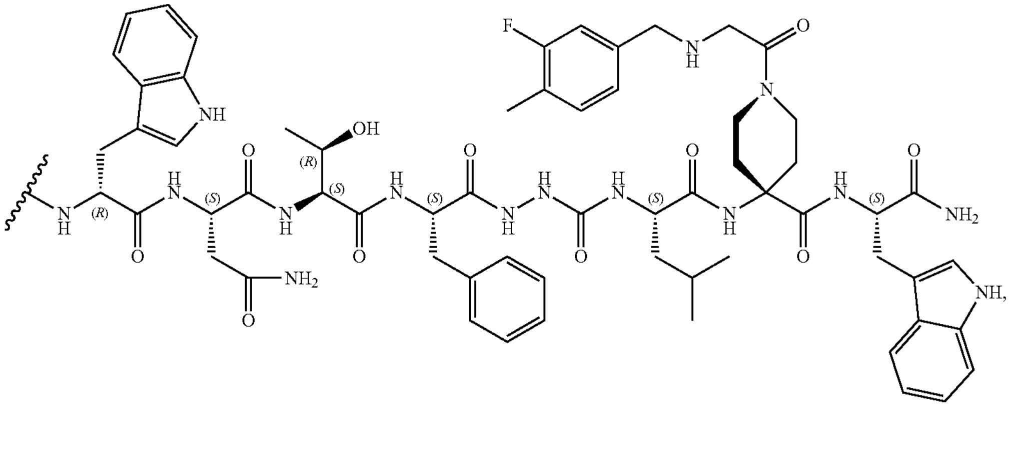

-continued
(SEQ ID NO: 126)
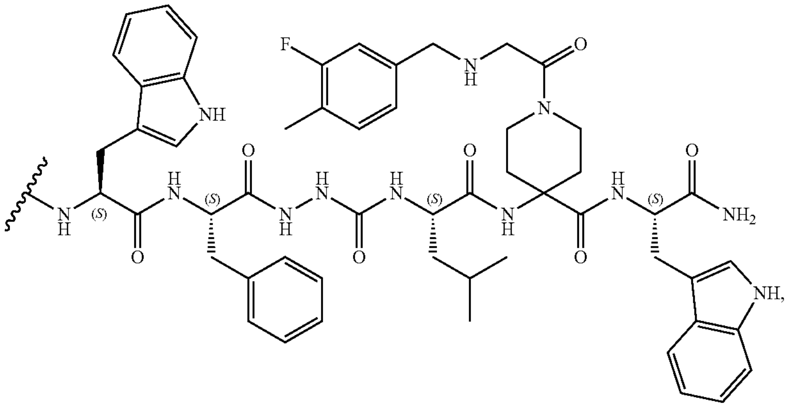
(SEQ ID NO: 127)
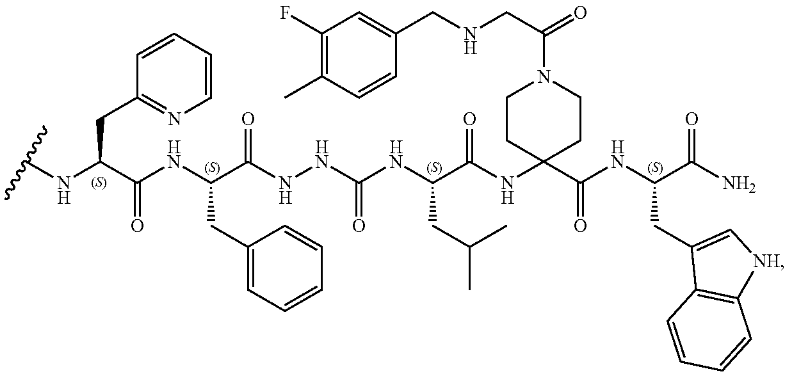
(SEQ ID NO: 128)
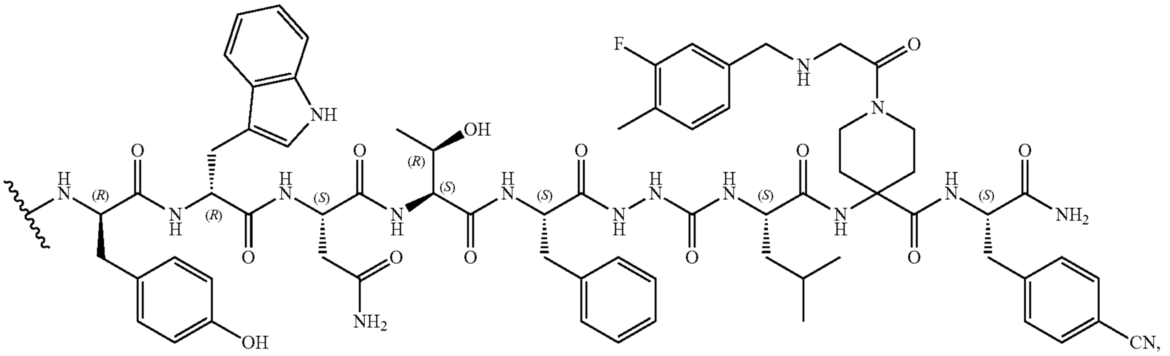
(SEQ ID NO: 129)
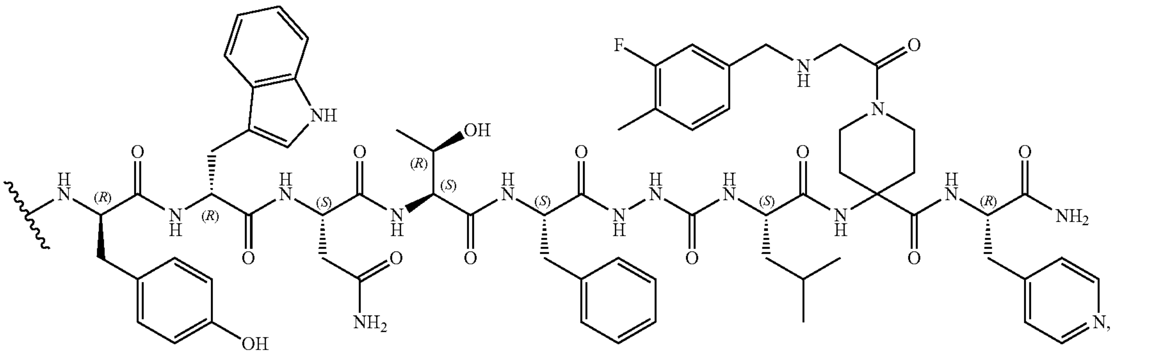

-continued
(SEQ ID NO: 130)
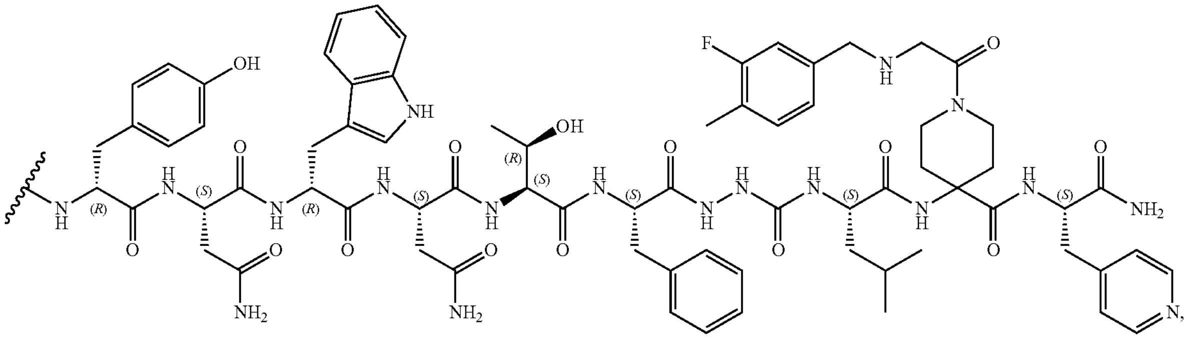
(SEQ ID NO: 131)
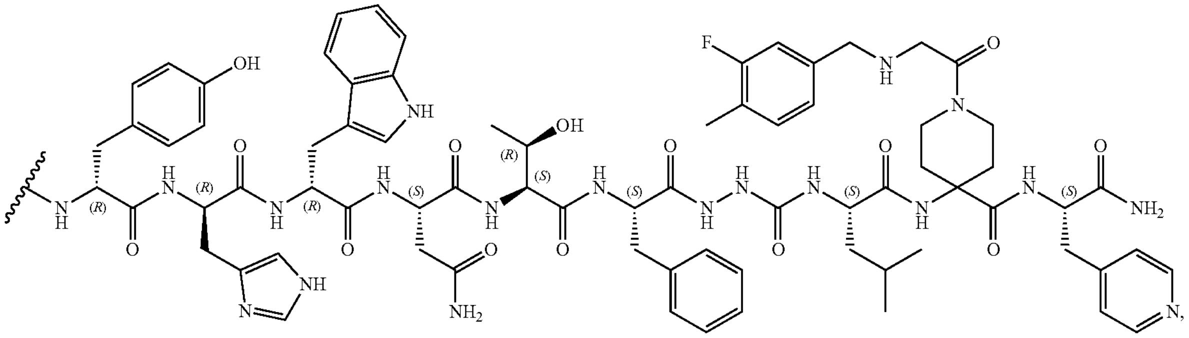
(SEQ ID NO: 132)
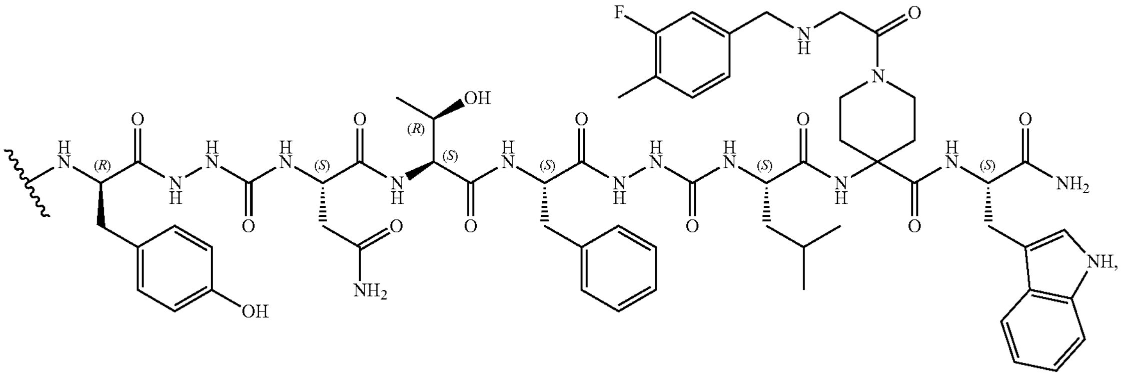
(SEQ ID NO: 133)
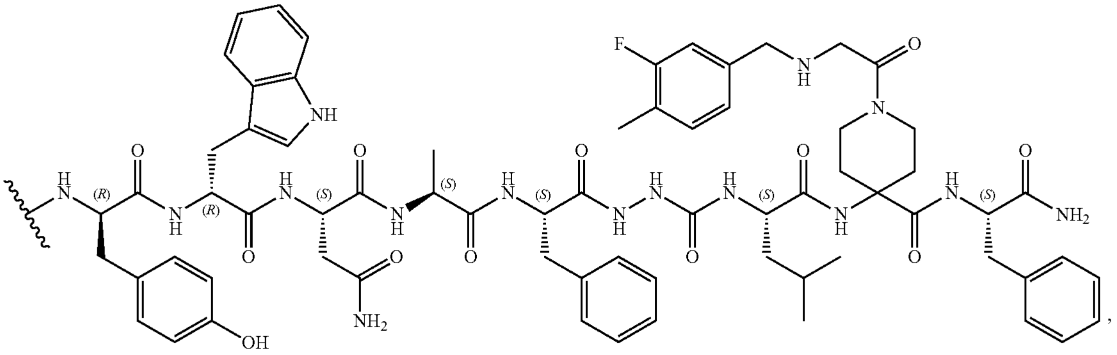

-continued
(SEQ ID NO: 134)
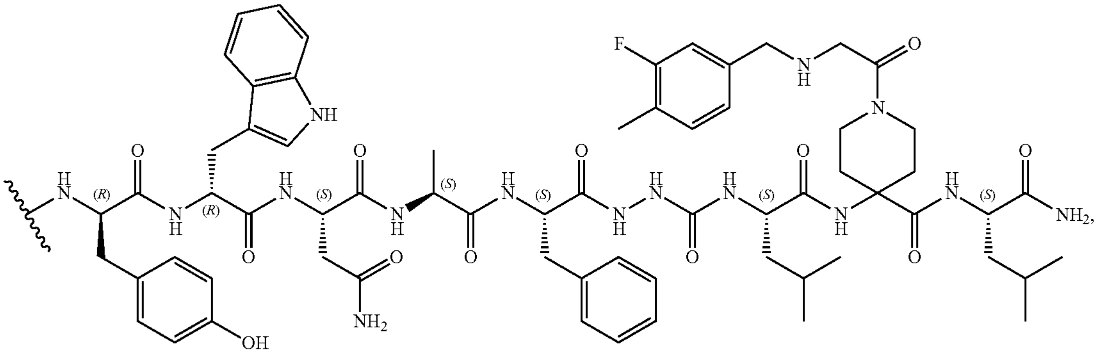
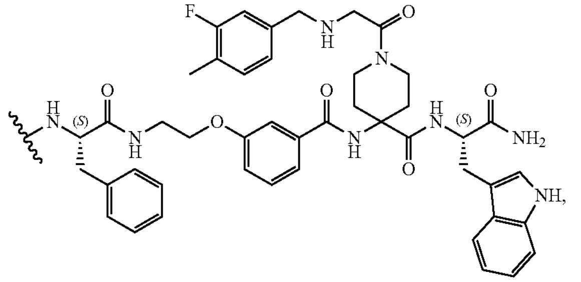
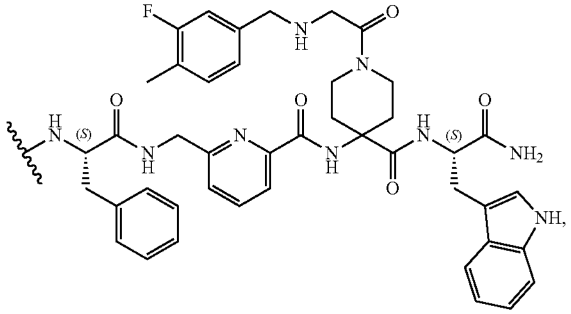
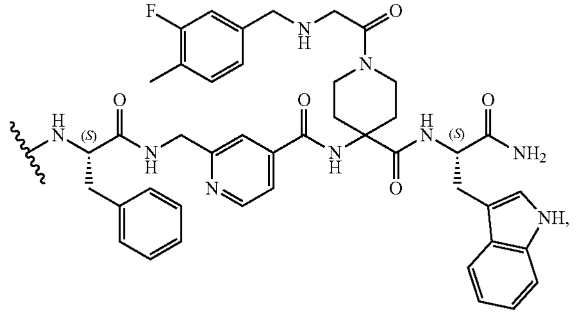
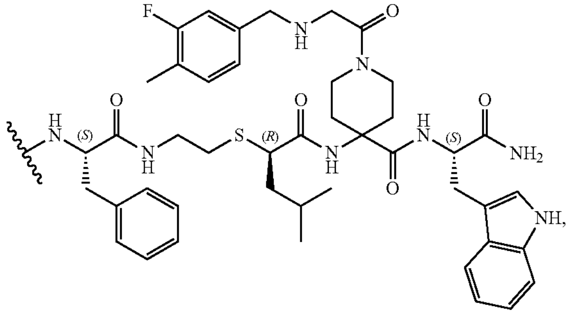
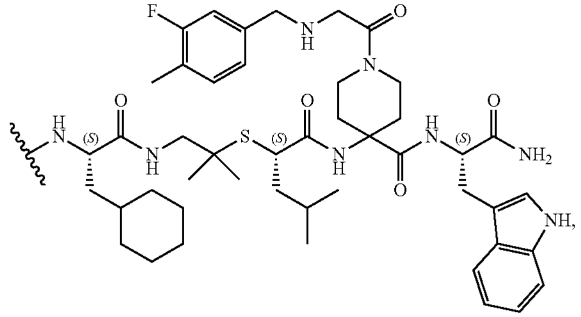
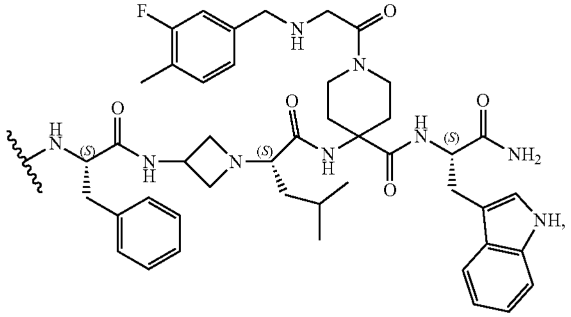
(SEQ ID NO: 141)
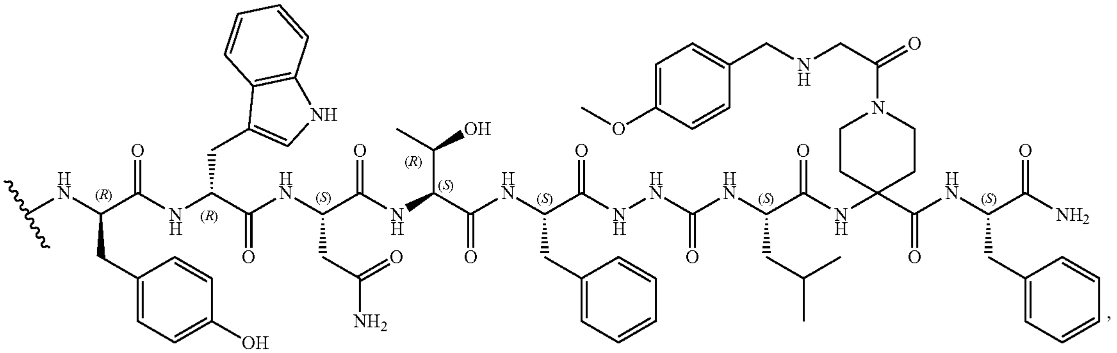

-continued
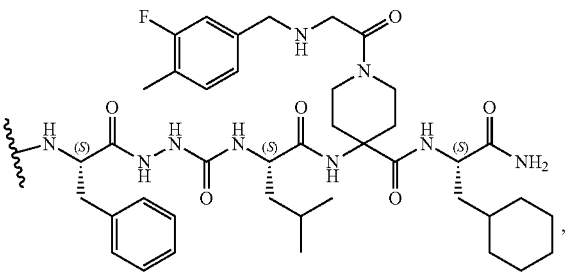
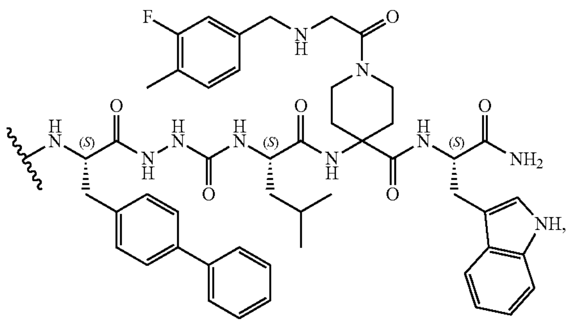
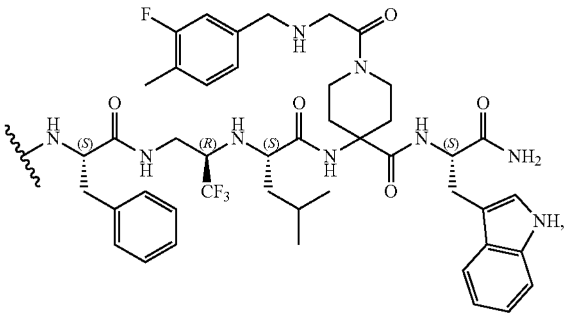
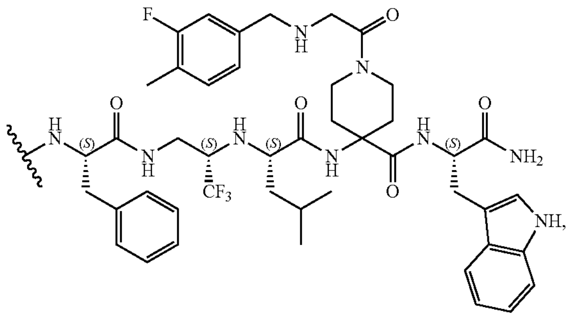
(SEQ ID NO: 146)
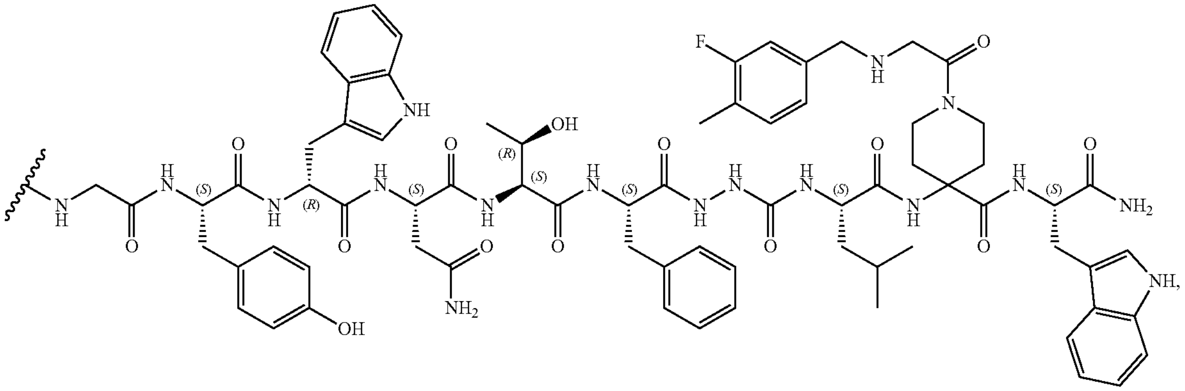
(SEQ ID NO: 147)
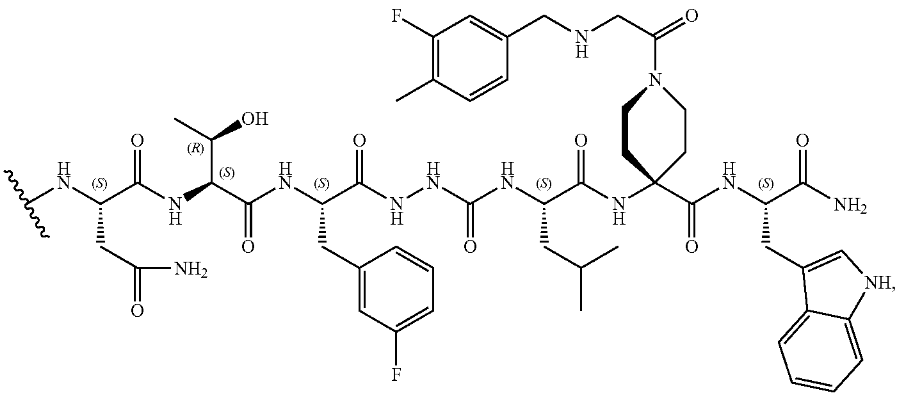

-continued
(SEQ ID NO: 148)
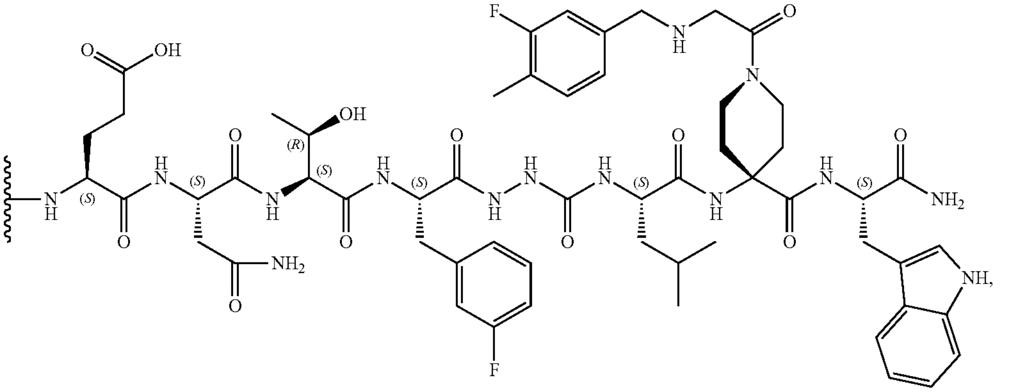
(SEQ ID NO: 149)
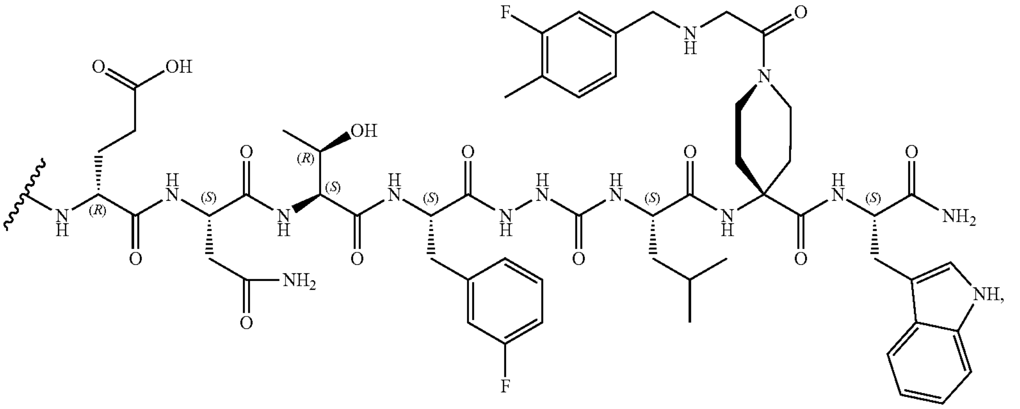
(SEQ ID NO: 150)
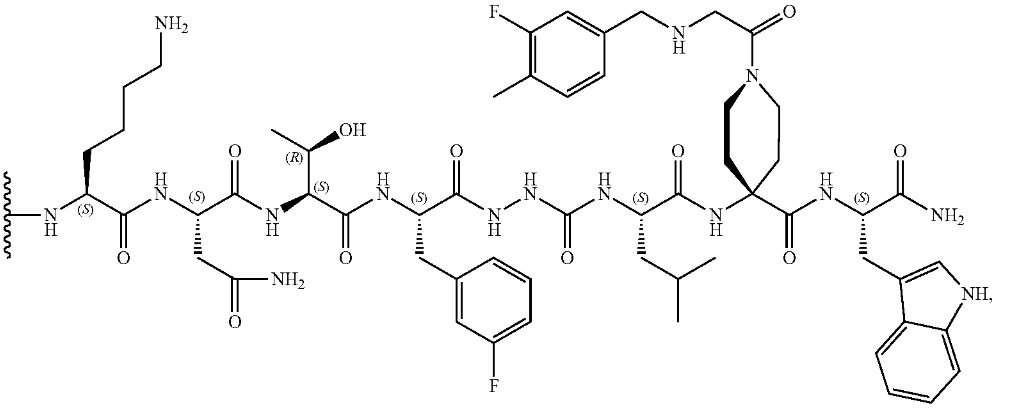

-continued
(SEQ ID NO: 151)
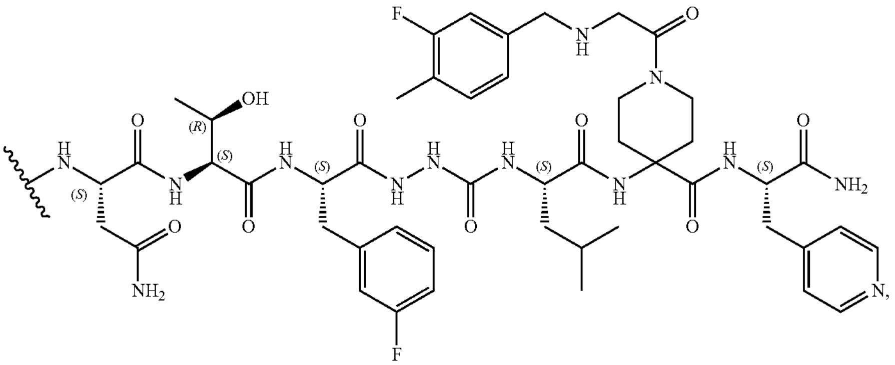
(SEQ ID NO: 152)
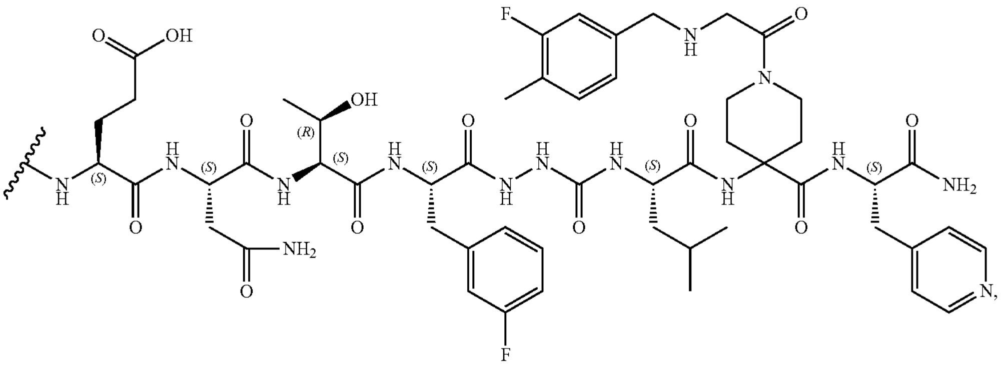
(SEQ ID NO: 153)
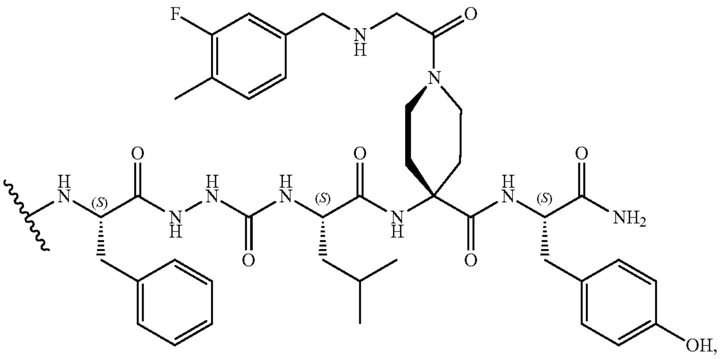
or
(SEQ ID NO: 154)
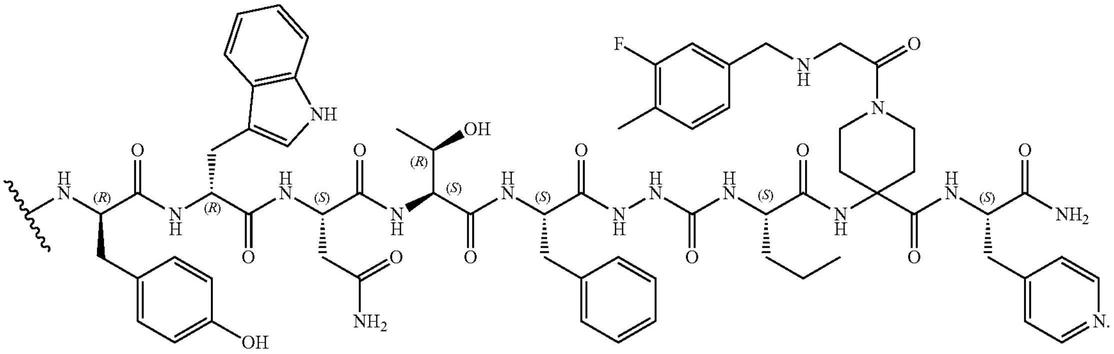

In some embodiments,
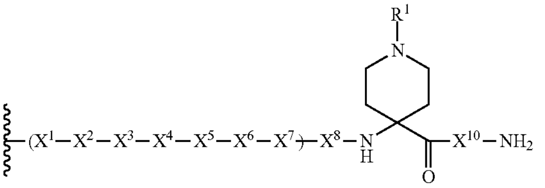
is
(SEQ ID NO: 155)
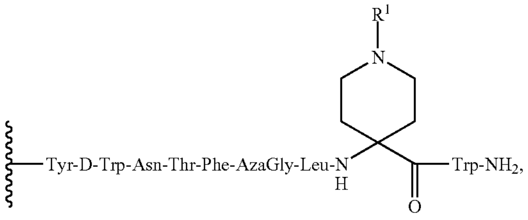
(SEQ ID NO: 156)
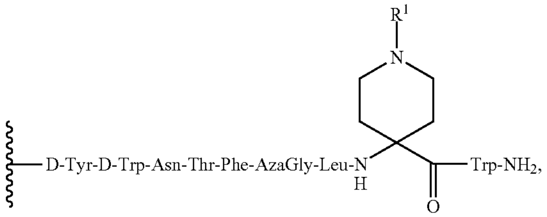
(SEQ ID NO: 157)
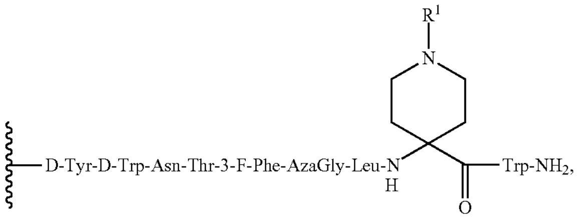
(SEQ ID NO: 158)
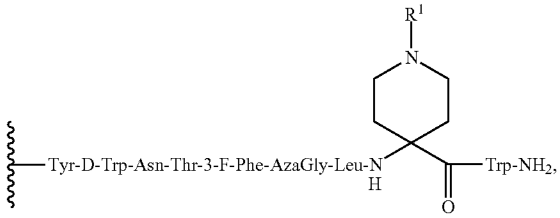
(SEQ ID NO: 159)
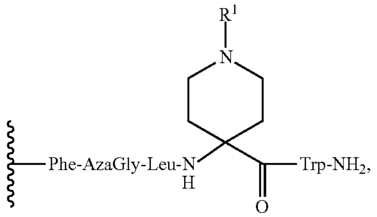
(SEQ ID NO: 160)
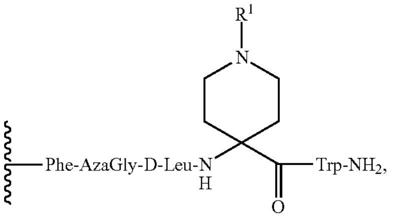
-continued
(SEQ ID NO: 161)
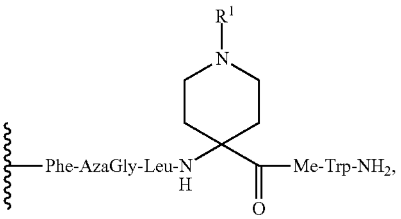
(SEQ ID NO: 162)
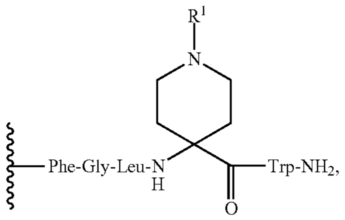
(SEQ ID NO: 163)
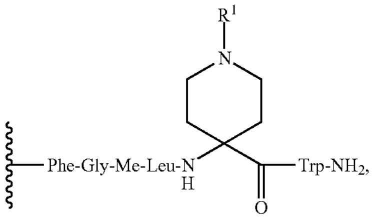
(SEQ ID NO: 164)
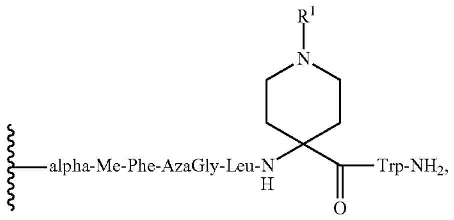
(SEQ ID NO: 165)
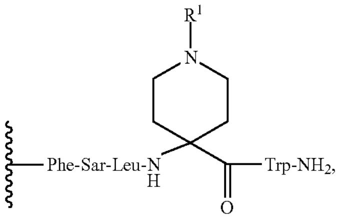
(SEQ ID NO: 166)
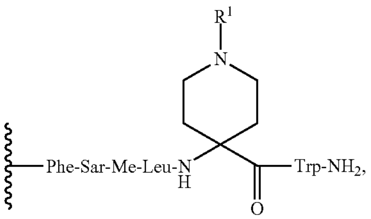
(SEQ ID NO: 167)
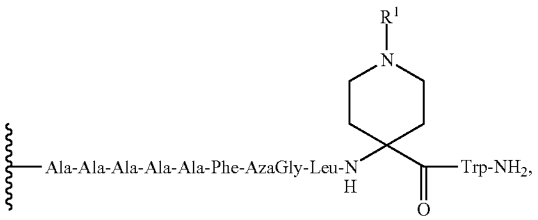

(SEQ ID NO: 168)
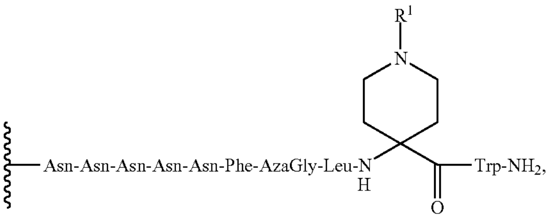
(SEQ ID NO: 169)
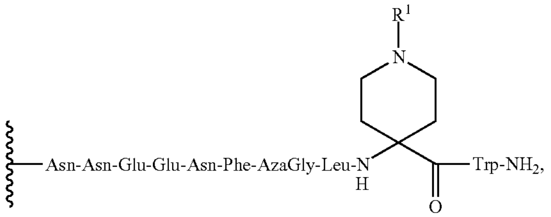
(SEQ ID NO: 170)
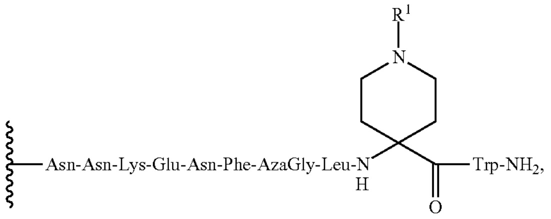
(SEQ ID NO: 171)
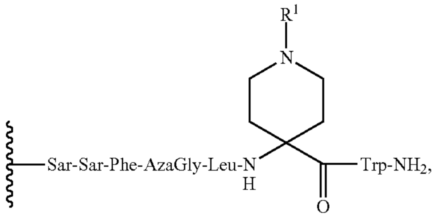
(SEQ ID NO: 172)
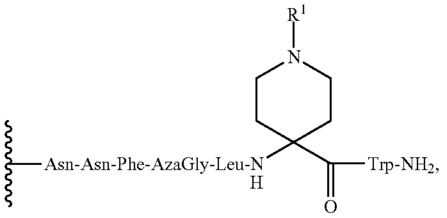
(SEQ ID NO: 173)
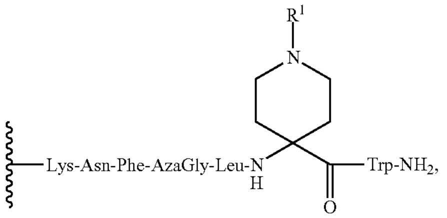
(SEQ ID NO: 174)
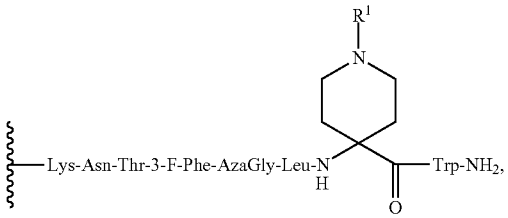
(SEQ ID NO: 175)
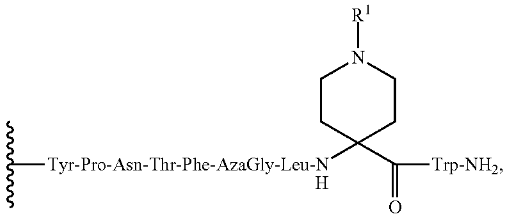
(SEQ ID NO: 176)
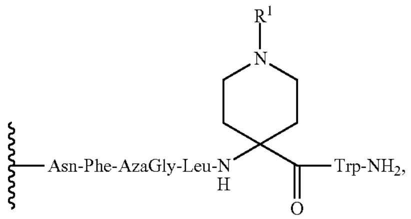
(SEQ ID NO: 177)
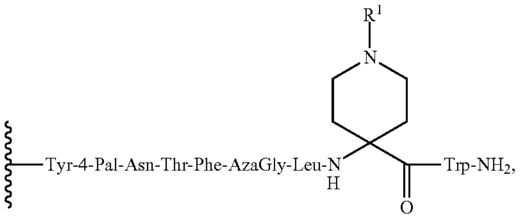
(SEQ ID NO: 178)
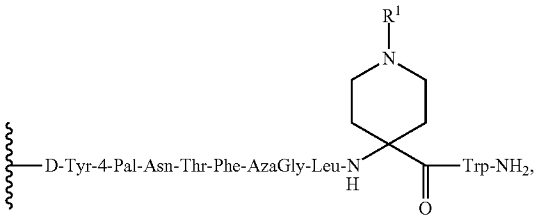
(SEQ ID NO: 179)
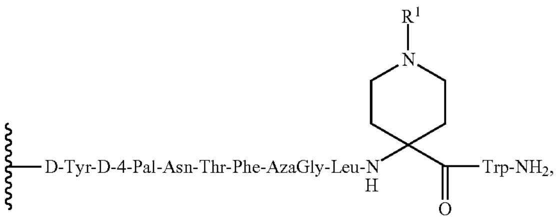

-continued
(SEQ ID NO: 180)
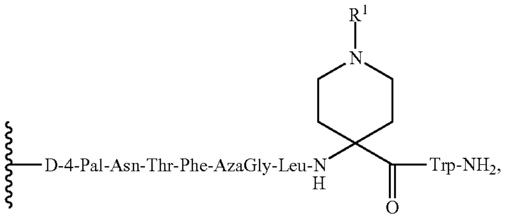
(SEQ ID NO: 181)
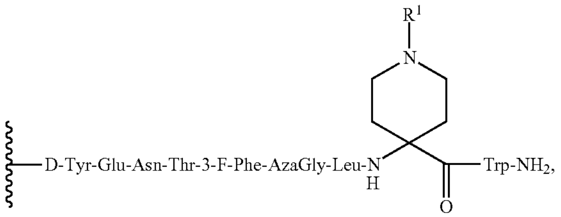
(SEQ ID NO: 182)
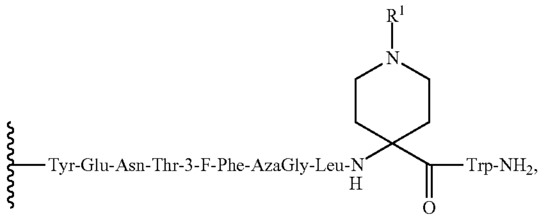
(SEQ ID NO: 183)
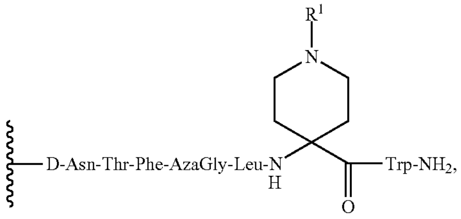
(SEQ ID NO: 184)
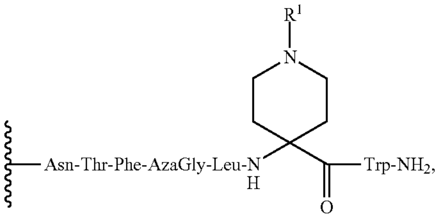
(SEQ ID NO: 185)
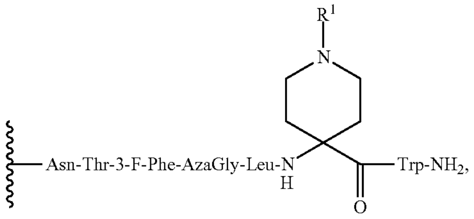
-continued
(SEQ ID NO: 186)
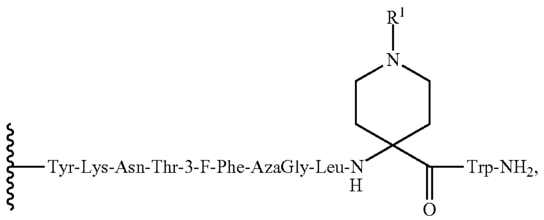
(SEQ ID NO: 187)
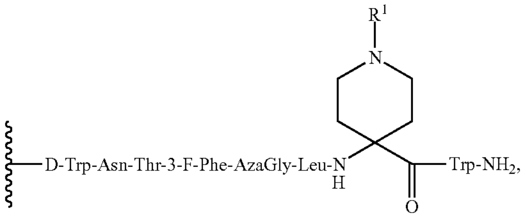
(SEQ ID NO: 188)
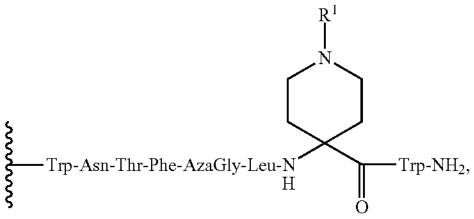
(SEQ ID NO: 189)
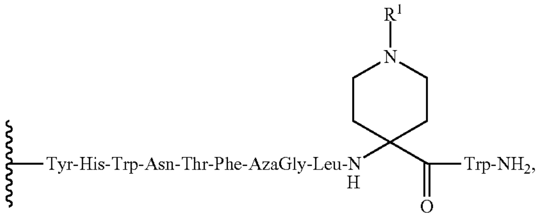
(SEQ ID NO: 190)
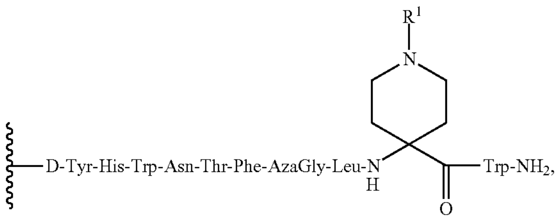
(SEQ ID NO: 191)
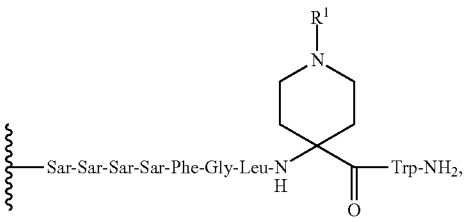

-continued
(SEQ ID NO: 192)
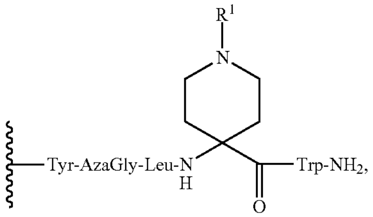
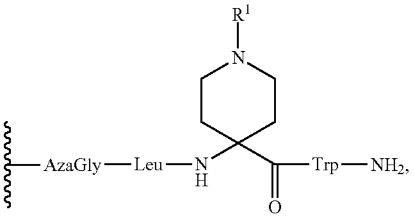
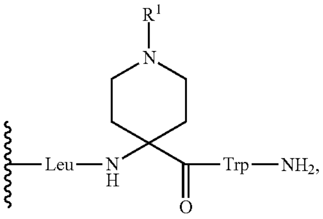
(SEQ ID NO: 194)
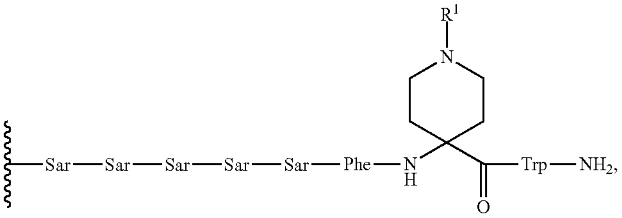
(SEQ ID NO: 195)
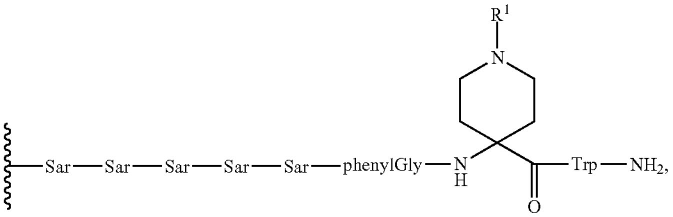
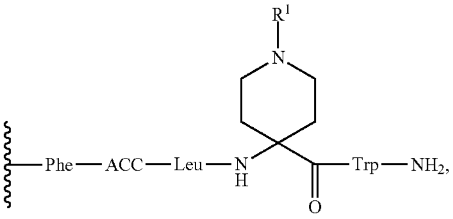
(SEQ ID NO: 197)
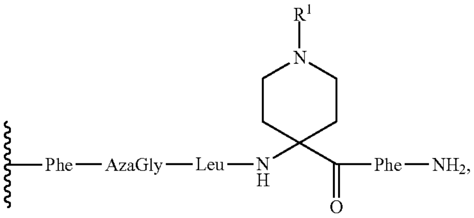
(SEQ ID NO: 198)
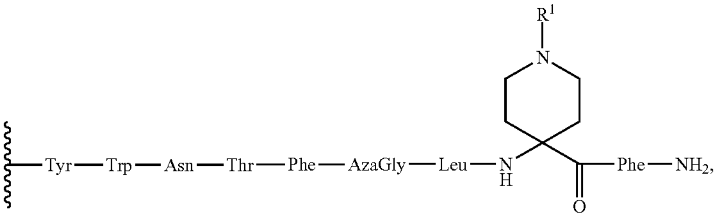

-continued
(SEQ ID NO: 199)
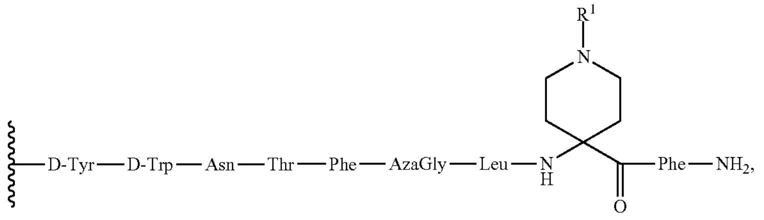
(SEQ ID NO: 200)
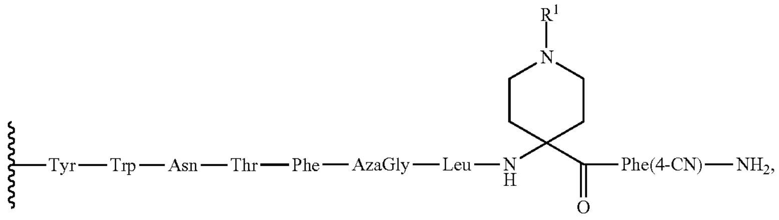
(SEQ ID NO: 201)
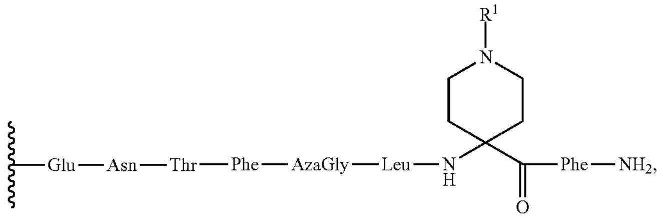
(SEQ ID NO: 202)
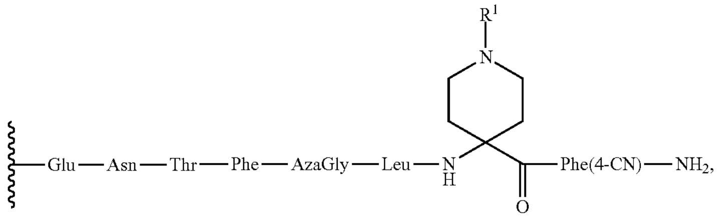
(SEQ ID NO: 203)
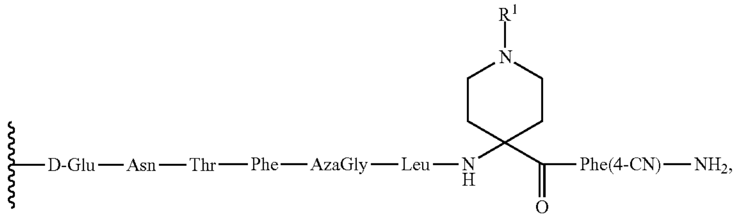
(SEQ ID NO: 204)
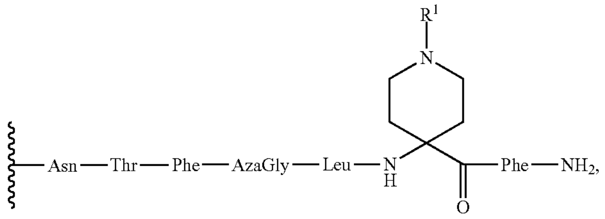
(SEQ ID NO: 205)
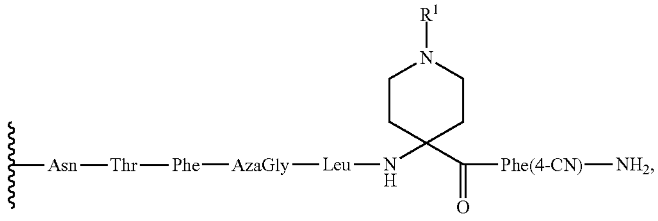

-continued
(SEQ ID NO: 206)
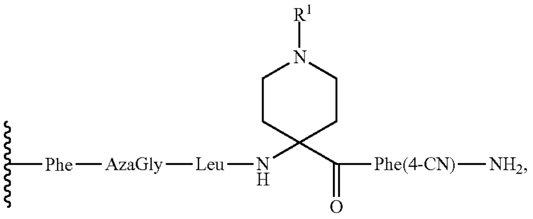
(SEQ ID NO: 207)
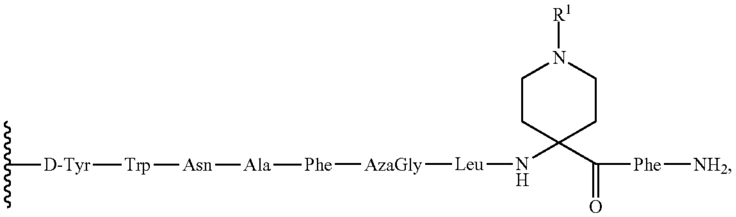
(SEQ ID NO. 208)
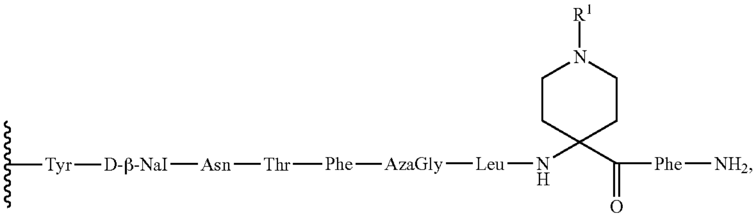
(SEQ ID NO: 209)
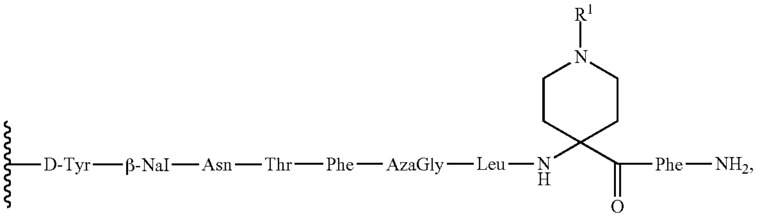
(SEQ ID NO: 210)
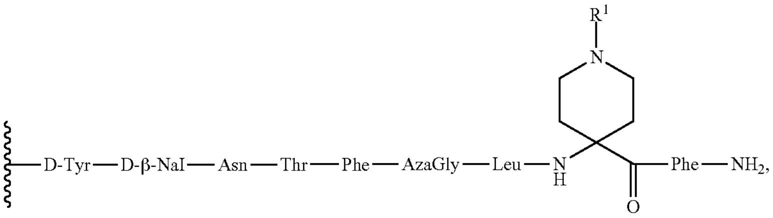
(SEQ ID NO: 211)
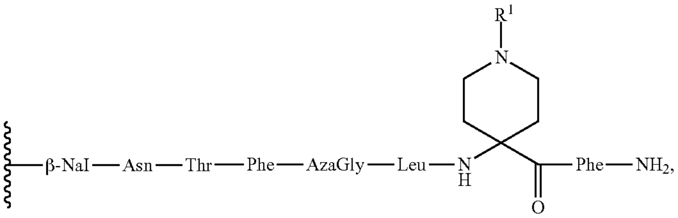
(SEQ ID NO: 212)
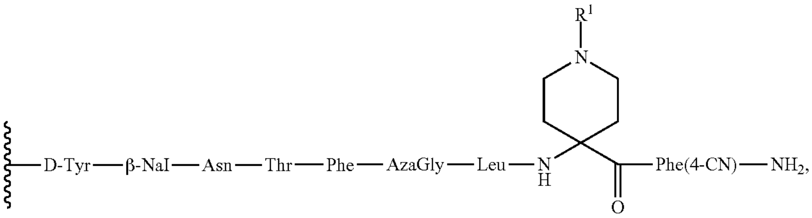

-continued
(SEQ ID NO: 213)
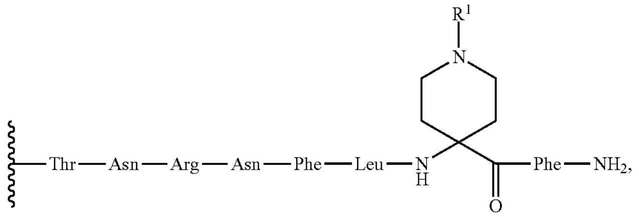
(SEQ ID NO: 214)
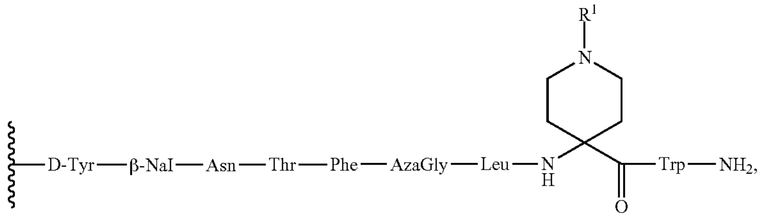
(SEQ ID NO: 215)
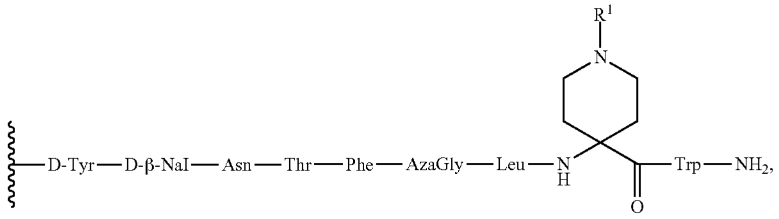
(SEQ ID NO: 216)
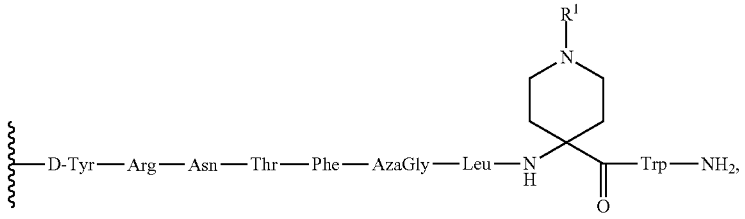
(SEQ ID NO: 217)
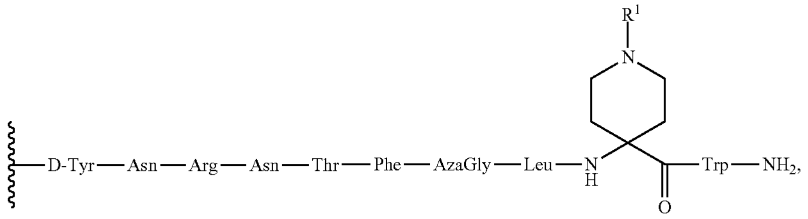
(SEQ ID NO: 218)
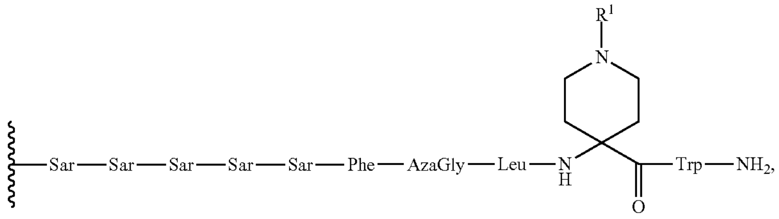
(SEQ ID NO: 219)
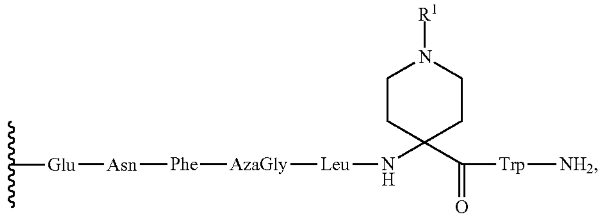

-continued
(SEQ ID NO: 220)
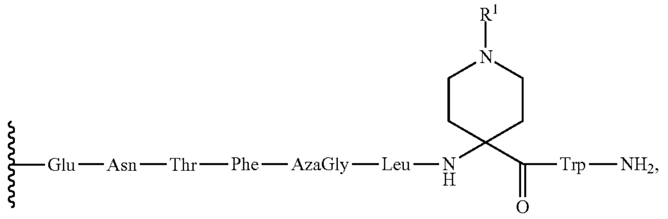
(SEQ ID NO: 221)
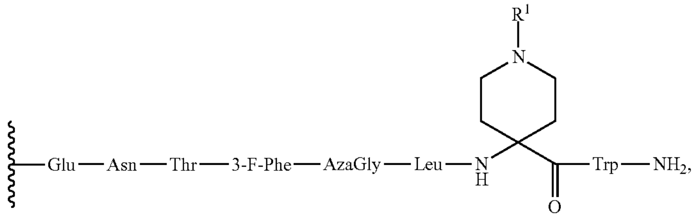
(SEQ ID NO: 222)
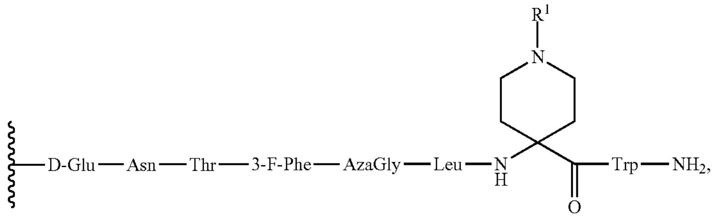
(SEQ ID NO: 223)
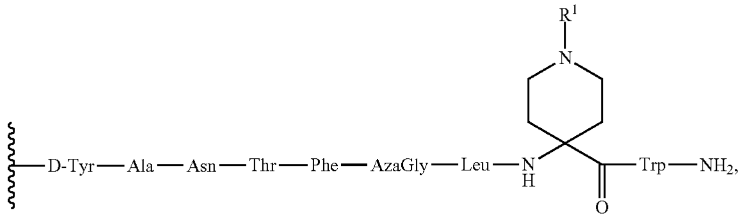
(SEQ ID NO: 224)
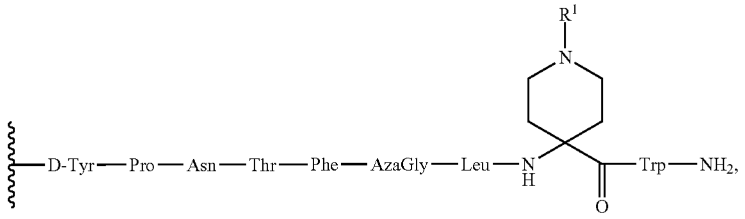
(SEQ ID NO: 225)
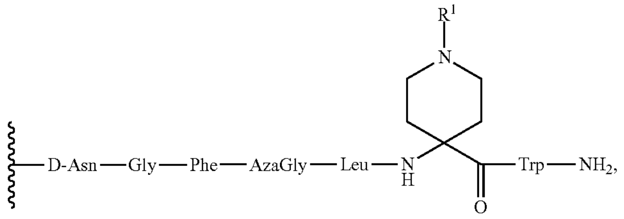
(SEQ ID NO: 226)
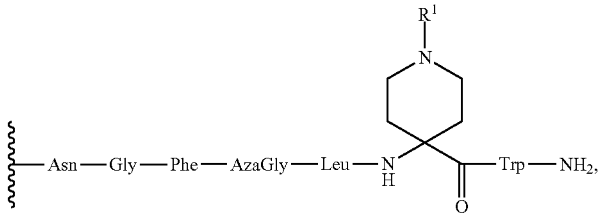

-continued
(SEQ ID NO: 227)
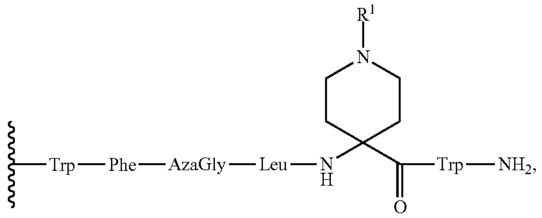
(SEQ ID NO: 228)
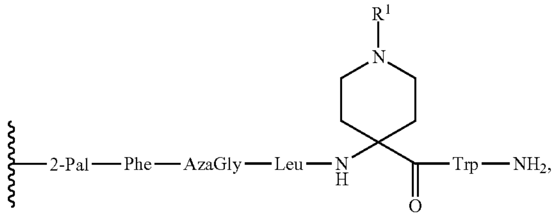
(SEQ ID NO: 229)
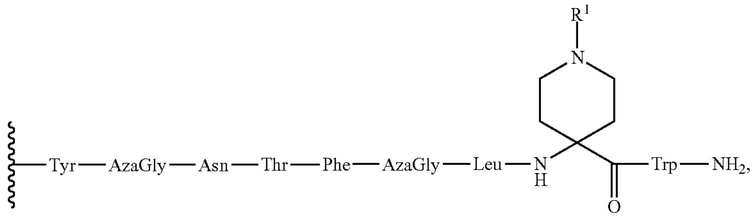
(SEQ ID NO: 230)
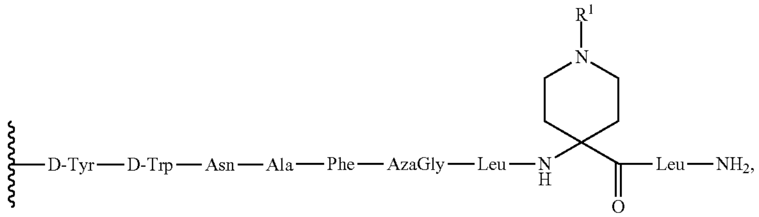
(SEQ ID NO: 231)
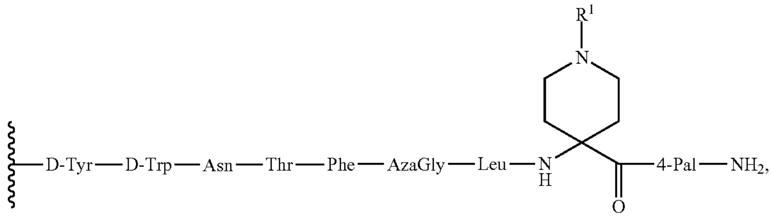
(SEQ ID NO: 232)
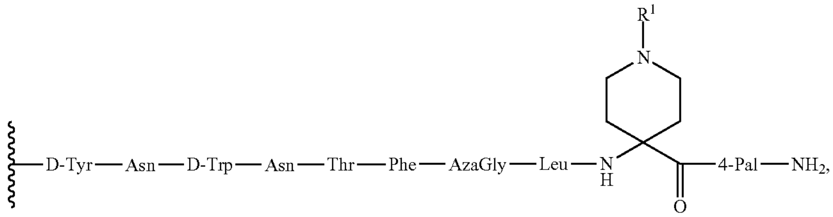
(SEQ ID NO: 233)
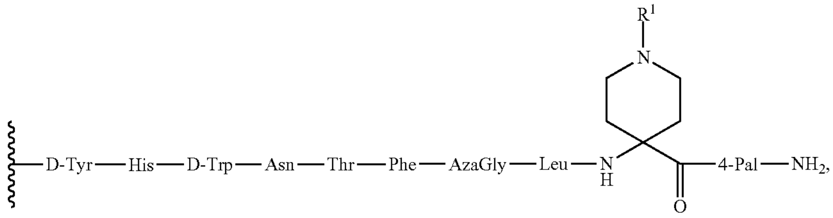

(SEQ ID NO: 233)
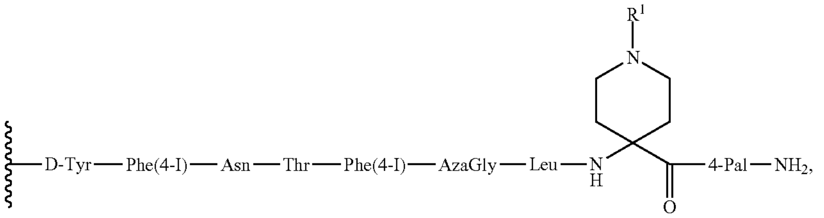
(SEQ ID NO: 234)
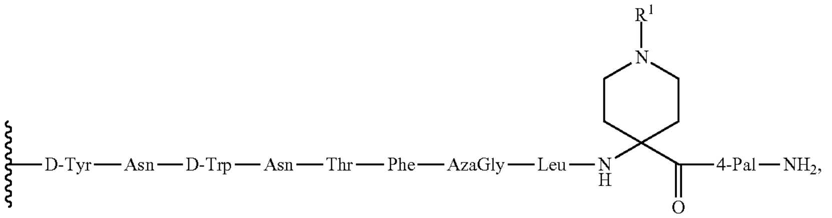
(SEQ ID NO: 235)
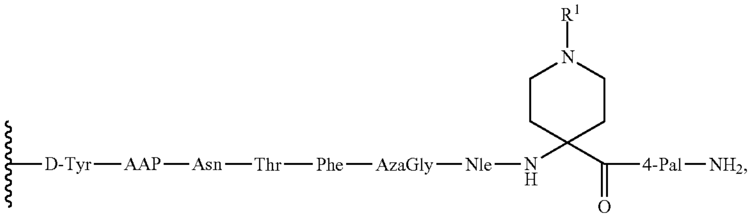
(SEQ ID NO: 236), 237)
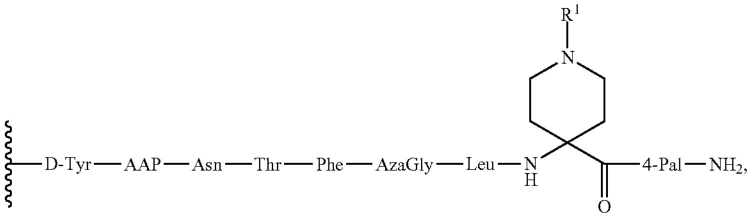
(SEQ ID NO: 238)
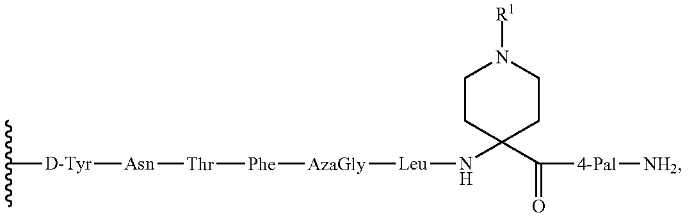
(SEQ ID NO: 239)
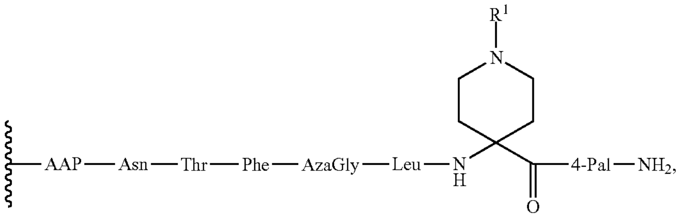
(SEQ ID NO: 240)
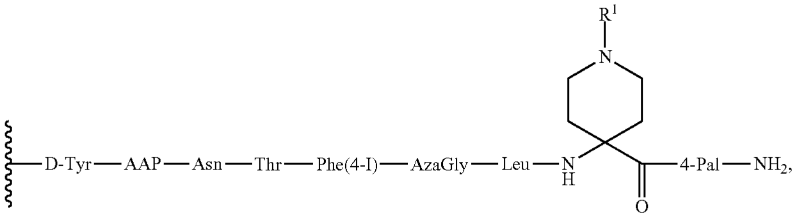

-continued
(SEQ ID NO: 241)
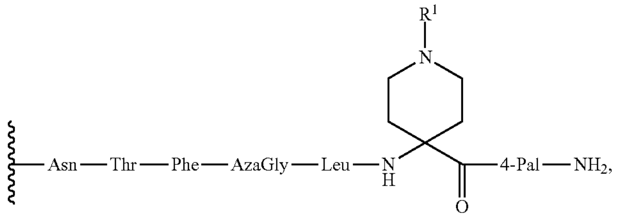
(SEQ ID NO: 242)
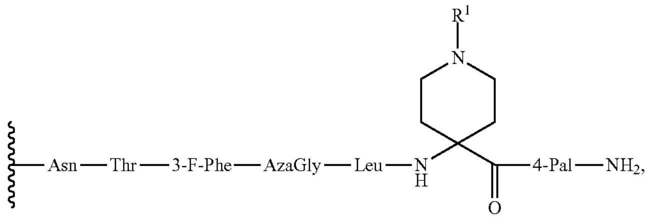
(SEQ ID NO: 243)
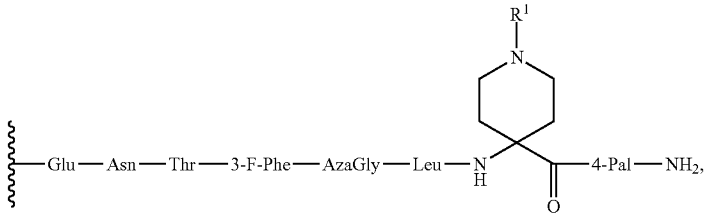
(SEQ ID NO: 244)
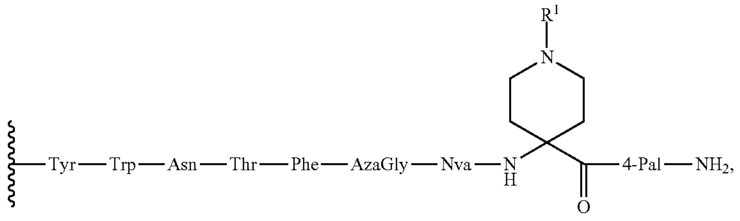
(SEQ ID NO: 245)
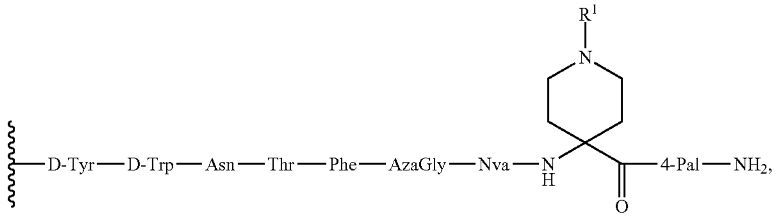
(SEQ ID NO: 246)
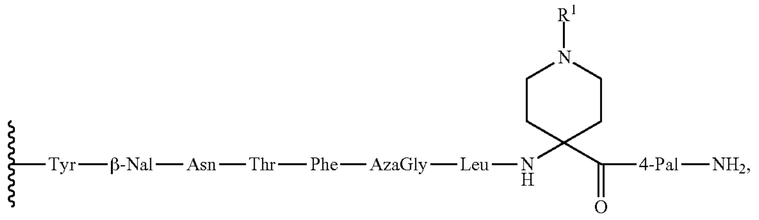
(SEQ ID NO: 247)
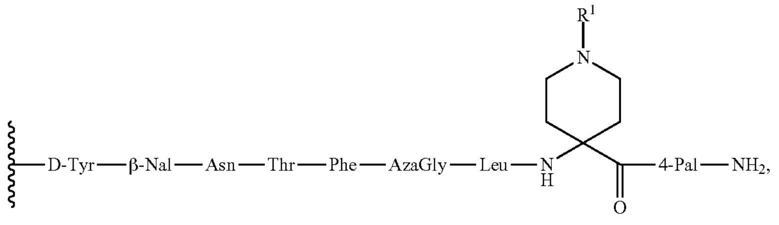

-continued
(SEQ ID NO: 248)
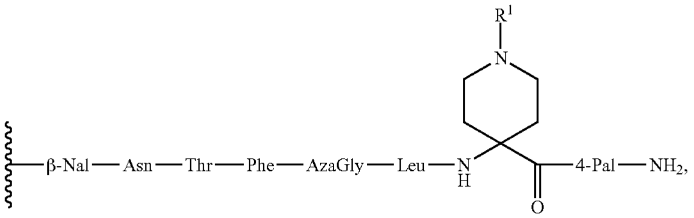
(SEQ ID NO: 249)
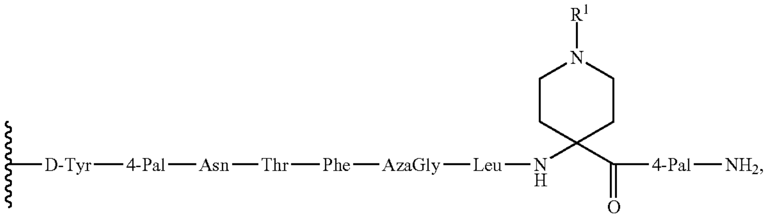
(SEQ ID NO: 250)
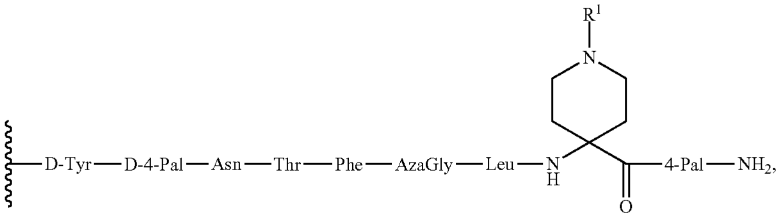
(SEQ ID NO: 251)
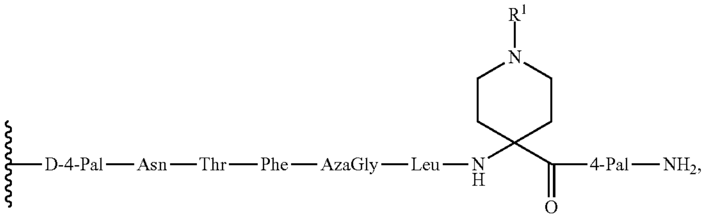
(SEQ ID NO: 252)
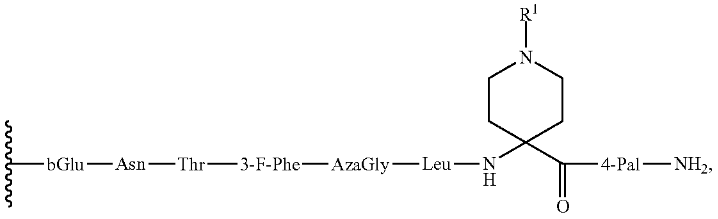
(SEQ ID NO: 253)
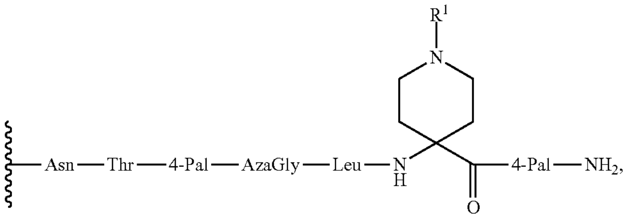
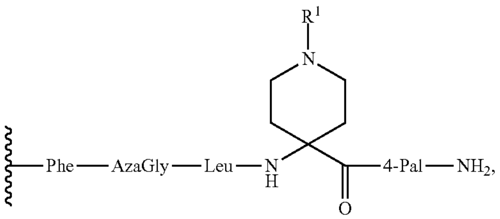
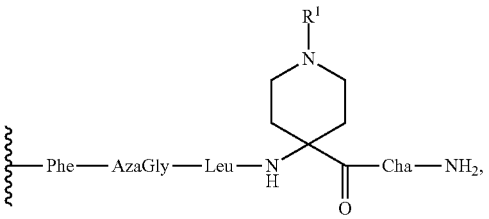

-continued
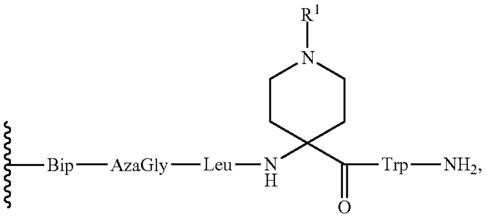
(SEQ ID NO: 257)
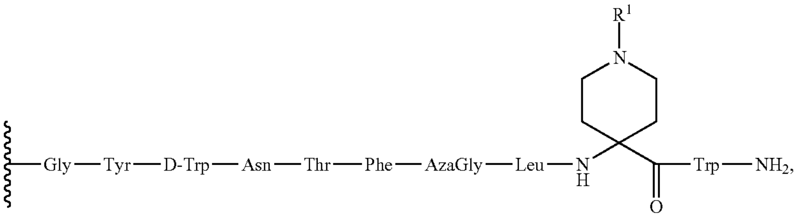
(SEQ ID NO: 258)
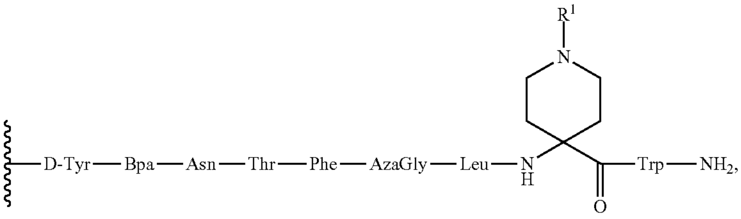
(SEQ ID NO: 259)
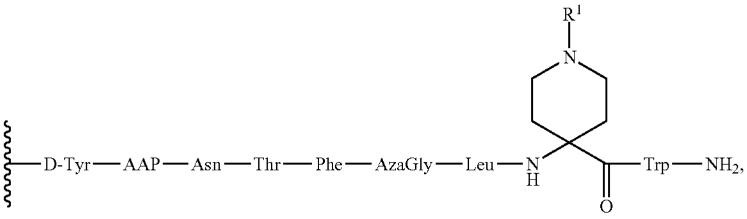
(SEQ ID NO: 261)
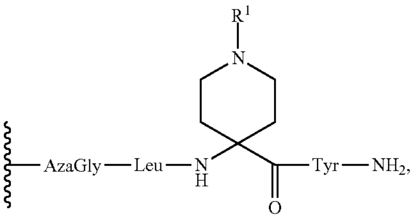
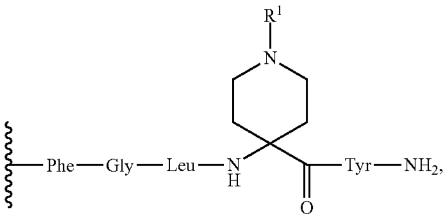
(SEQ ID NO: 262)
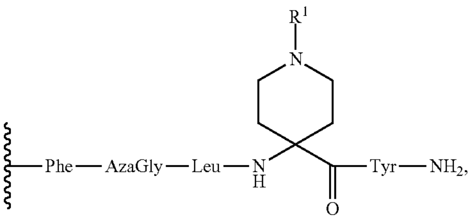
(SEQ ID NO: 263)
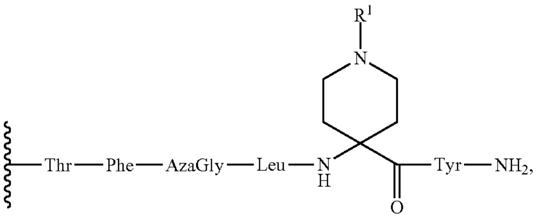

-continued
(SEQ ID NO: 264)
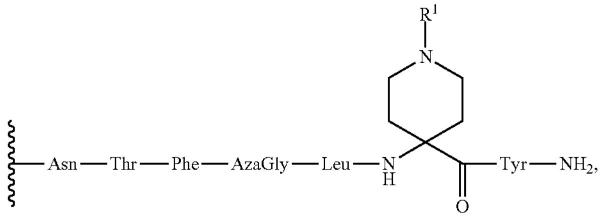
(SEQ ID NO: 265)
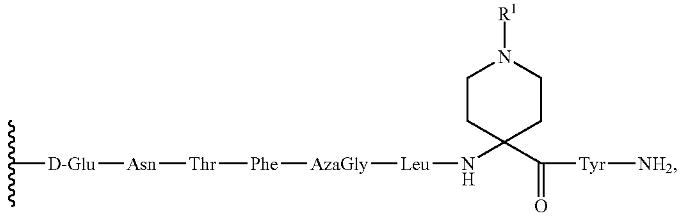
(SEQ ID NO: 266)
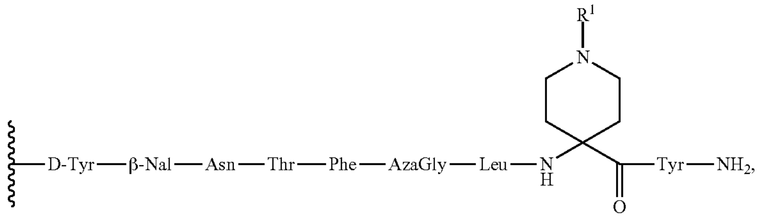
(SEQ ID NO: 267)
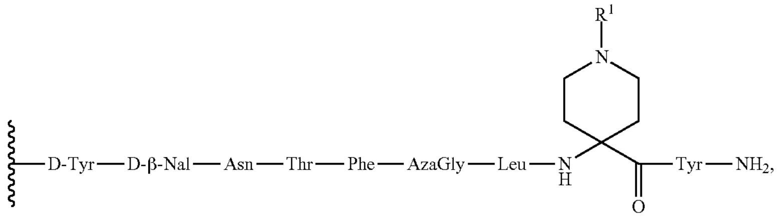
(SEQ ID NO: 268)
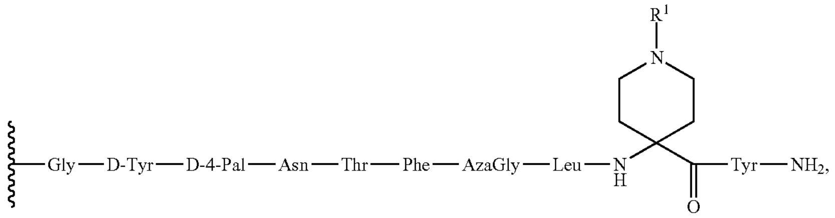
(SEQ ID NO: 269)
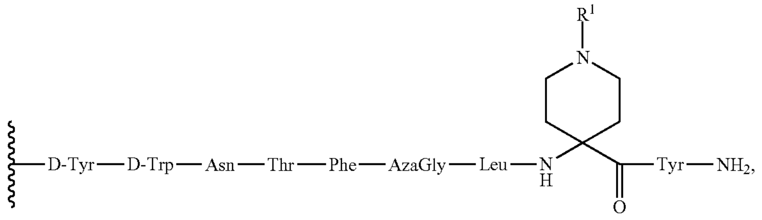
(SEQ ID NO: 270)
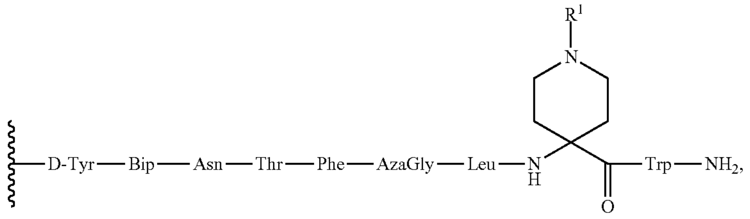

-continued
(SEQ ID NO: 271)
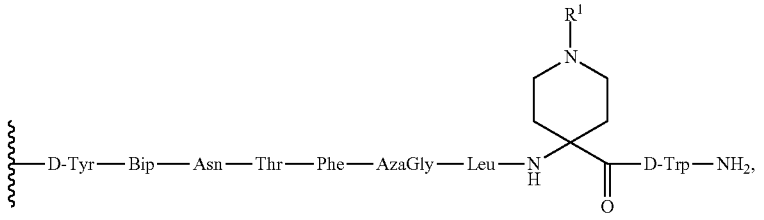
(SEQ ID NO: 272)
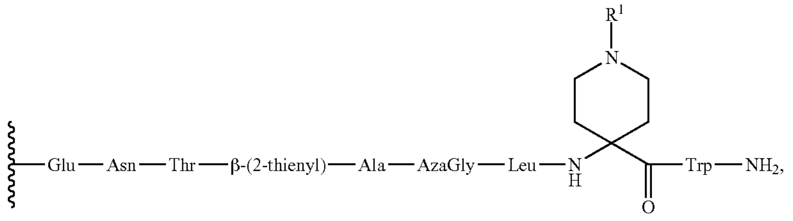
(SEQ ID NO: 273)
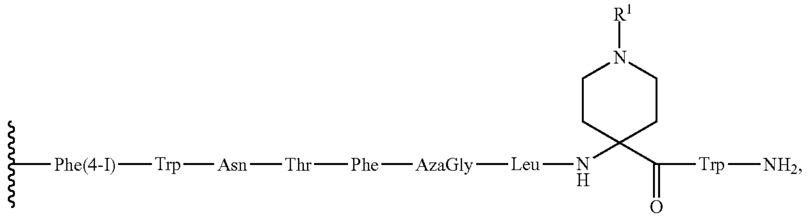
(SEQ ID NO: 274)
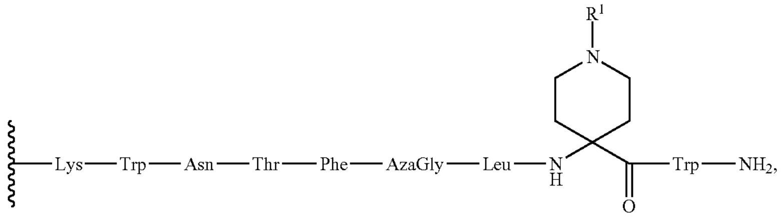
(SEQ ID NO: 275)
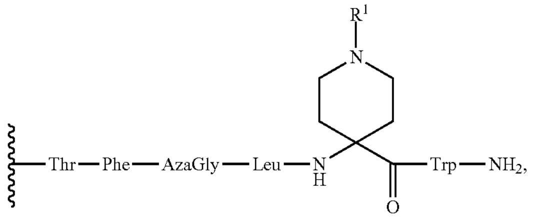
(SEQ ID NO: 276)
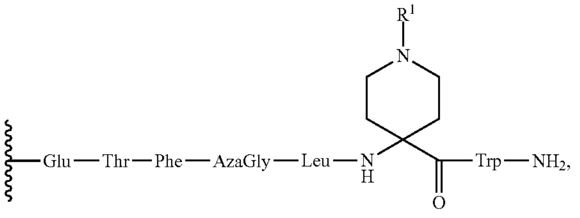
(SEQ ID NO: 277)
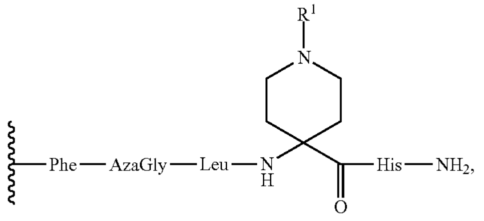

-continued
(SEQ ID NO: 278)
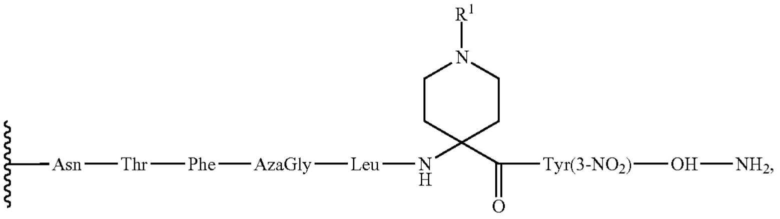
(SEQ ID NO: 279)
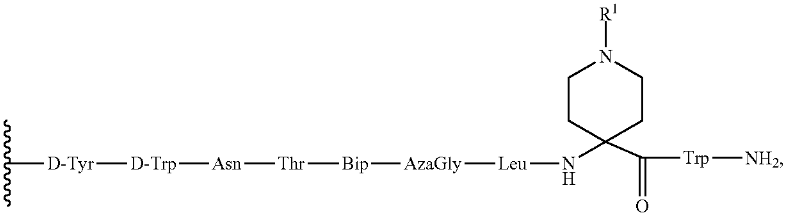
(SEQ ID NO: 280)
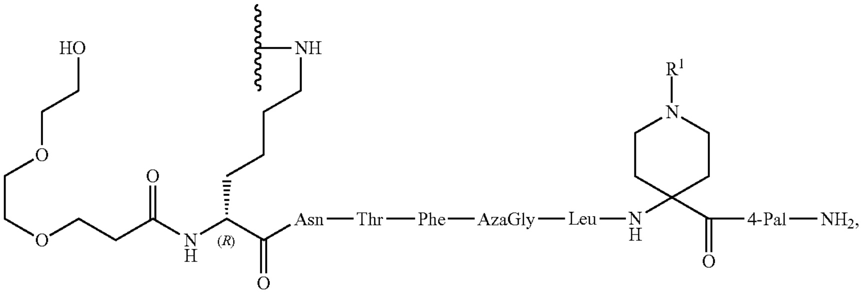
(SEQ ID NO: 281)
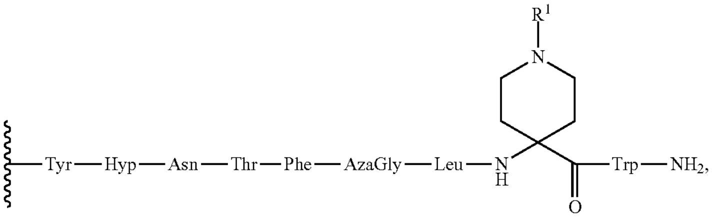
(SEQ ID NO: 282)
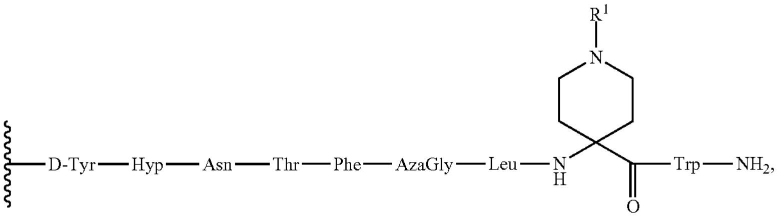
(SEQ ID NO: 283)
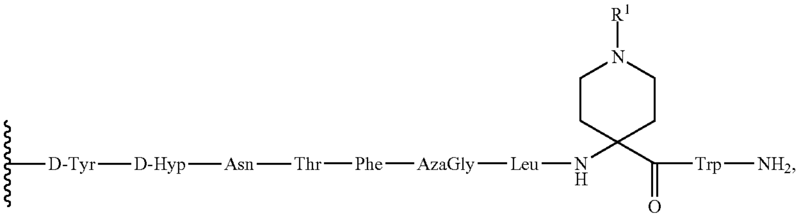

-continued
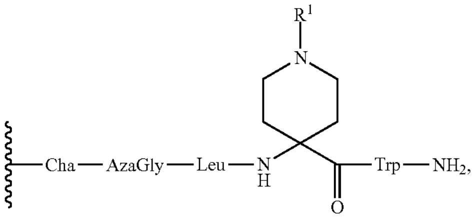
(SEQ ID NO: 285)
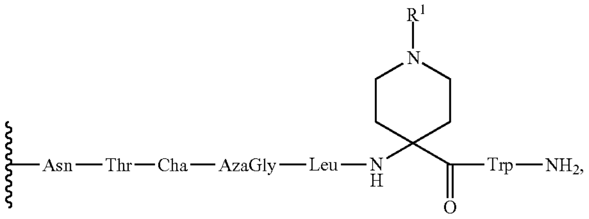
(SEQ ID NO: 286)
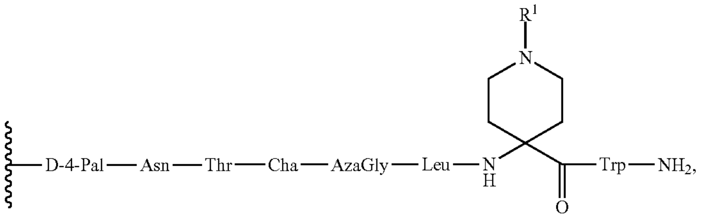
(SEQ ID NO: 287)
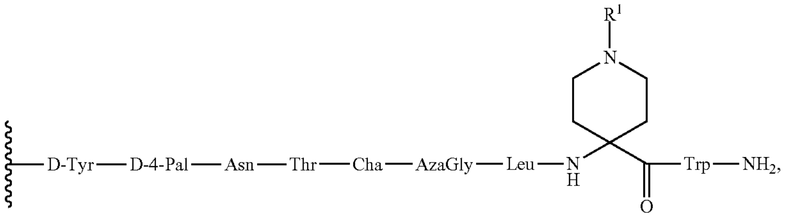
(SEQ ID NO: 288)
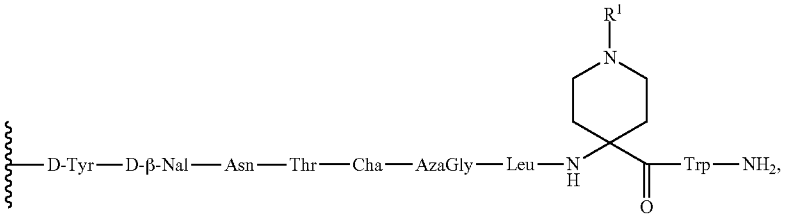
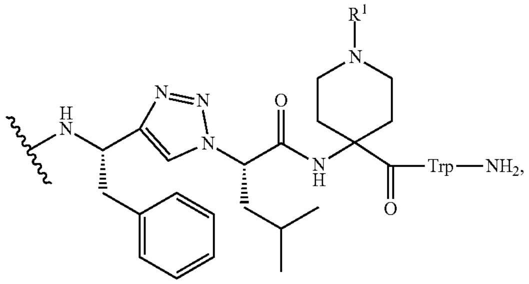
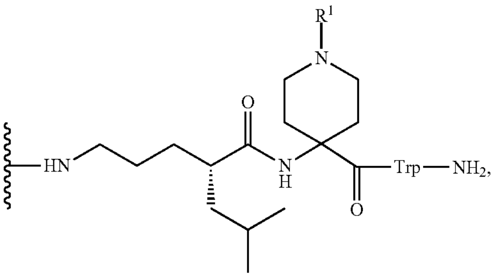
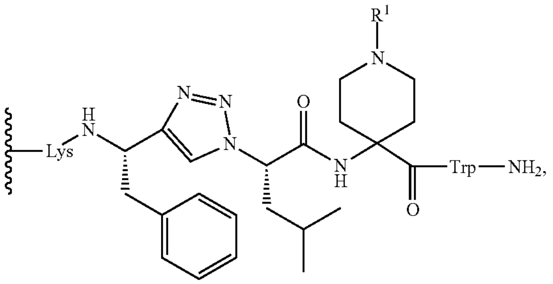

-continued
(SEQ ID NO: 290)
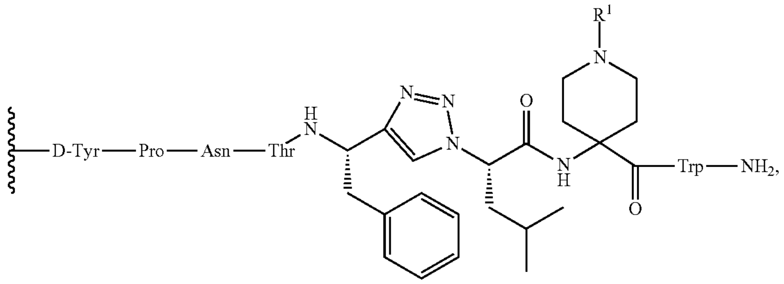
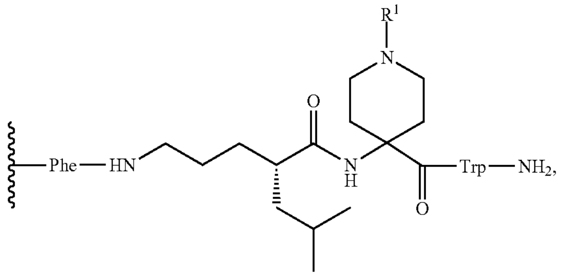
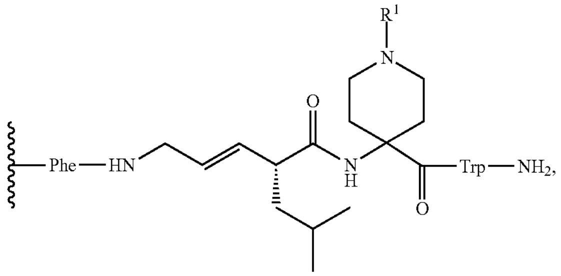
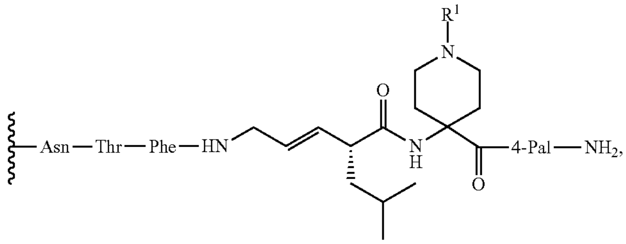
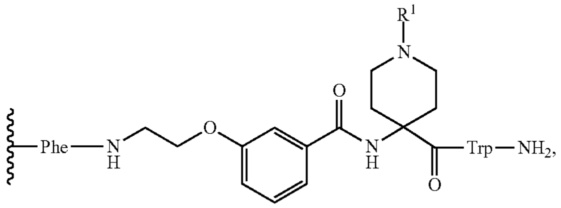
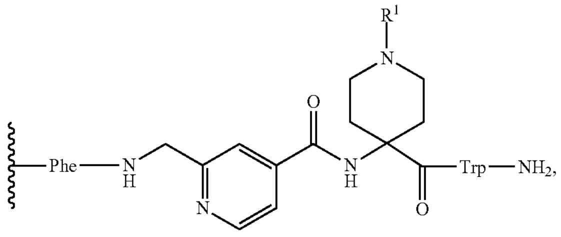
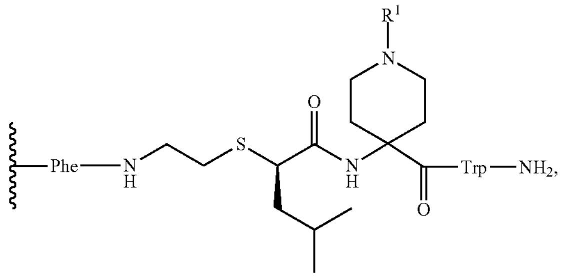
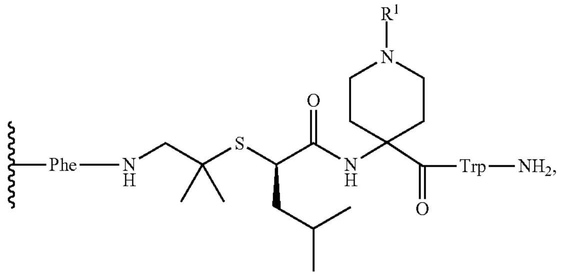
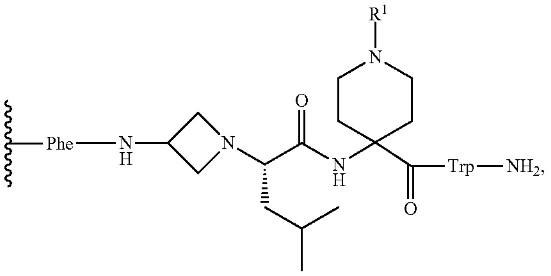
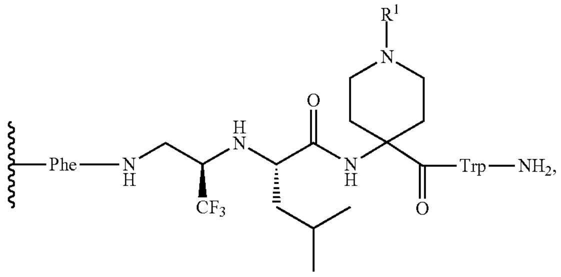
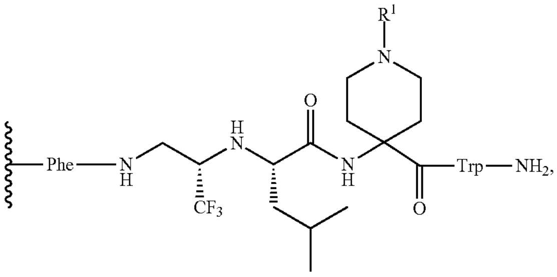

-continued
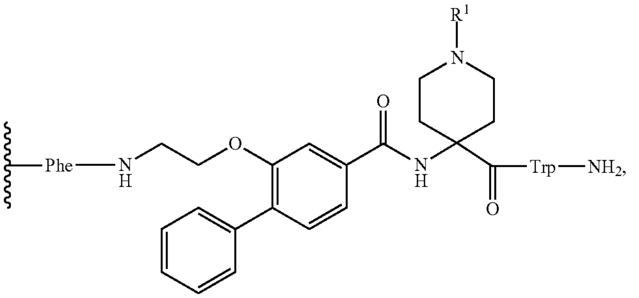
(SEQ ID NO: 302)
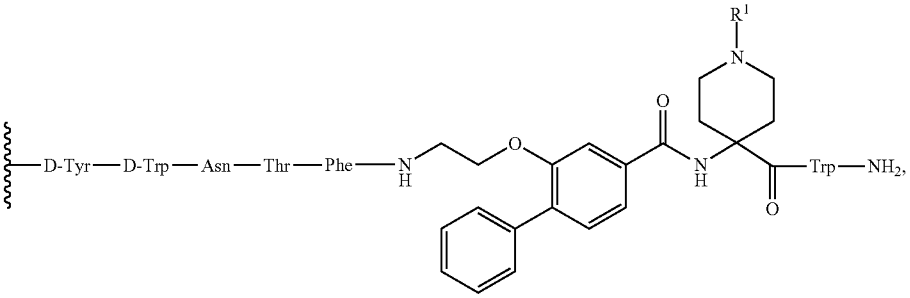
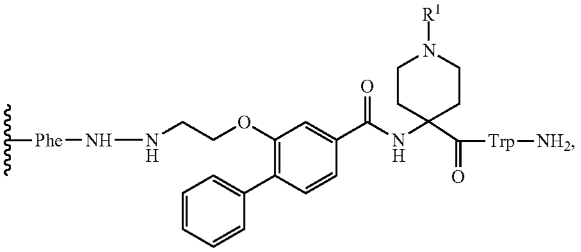
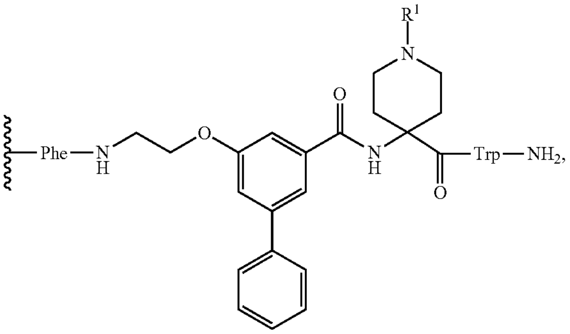
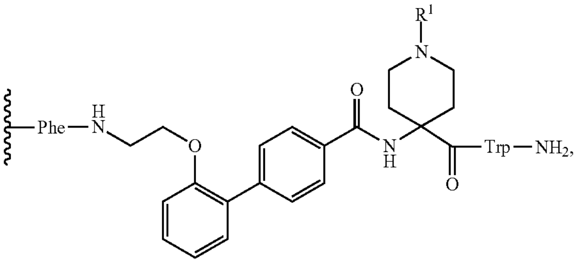
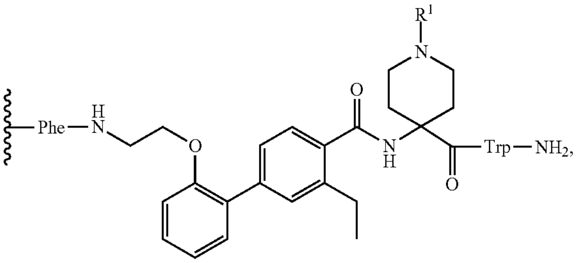
(SEQ ID NO: 306)
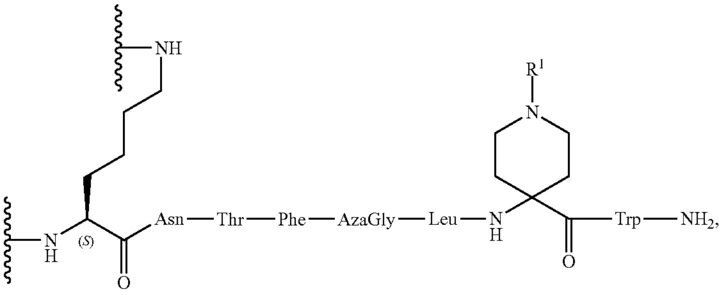

-continued
(SEQ ID NO: 307)
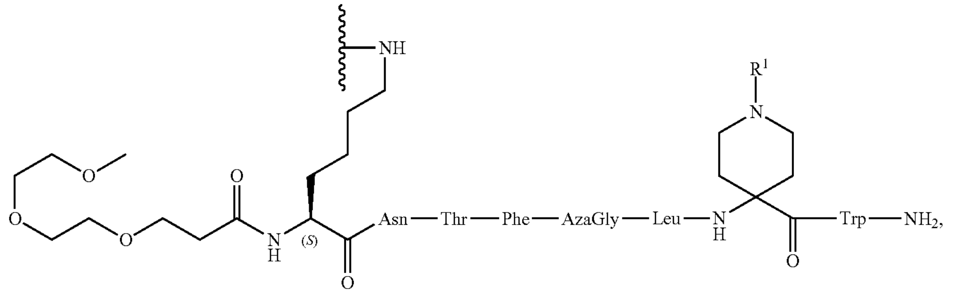
(SEQ ID NO: 308)
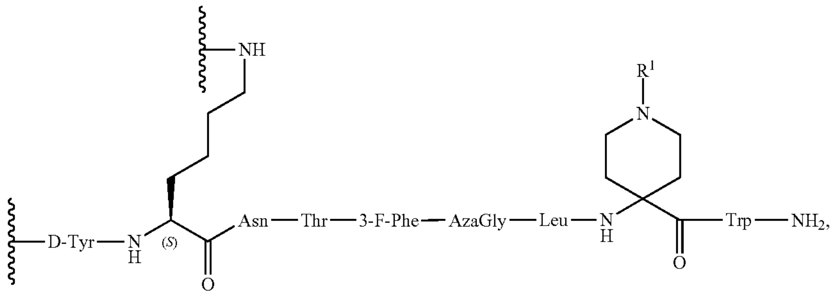
(SEQ ID NO: 309)
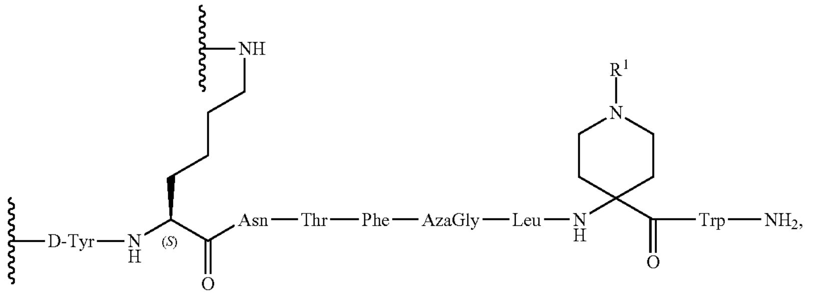
(SEQ ID NO: 310)
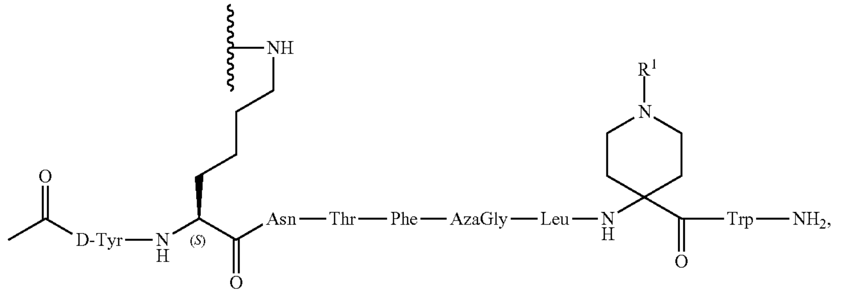
(SEQ ID NO: 311)
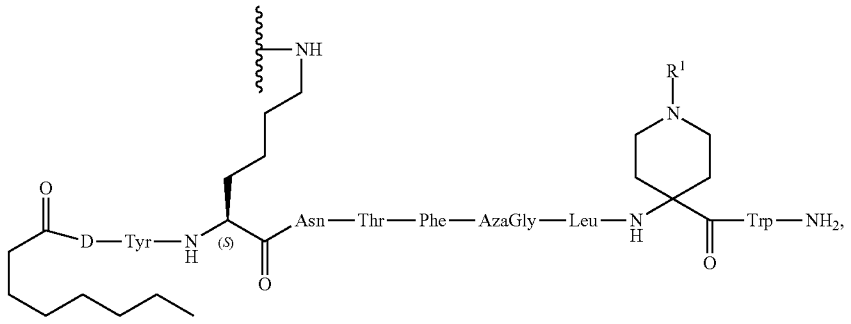

-continued
(SEQ ID NO: 312)
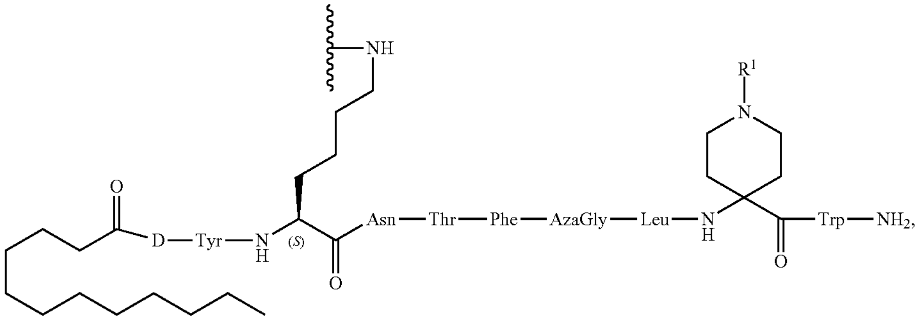
(SEQ ID NO: 313)
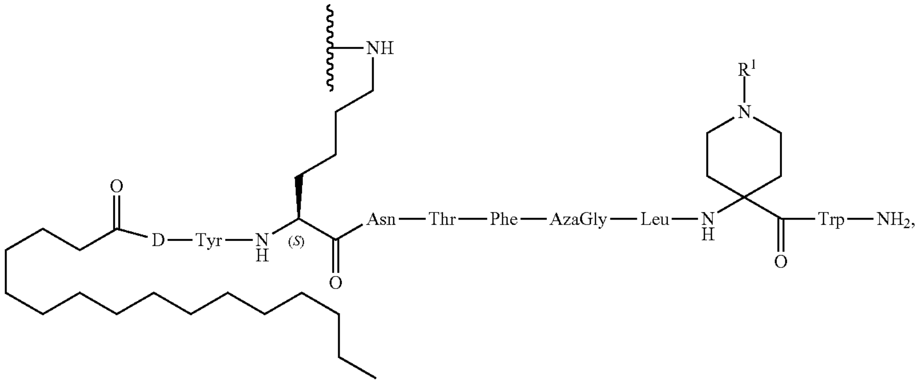
(SEQ ID NO: 314)
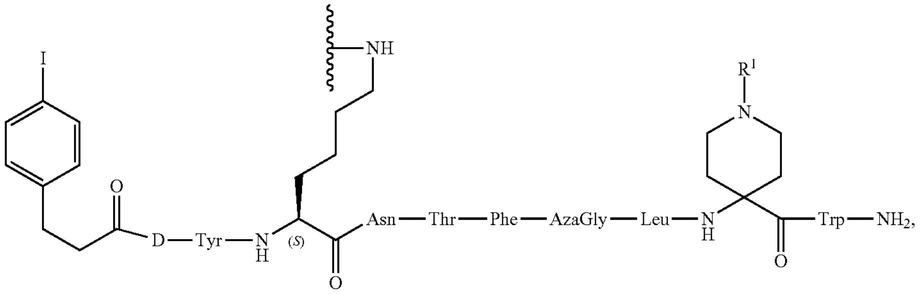
(SEQ ID NO: 315)
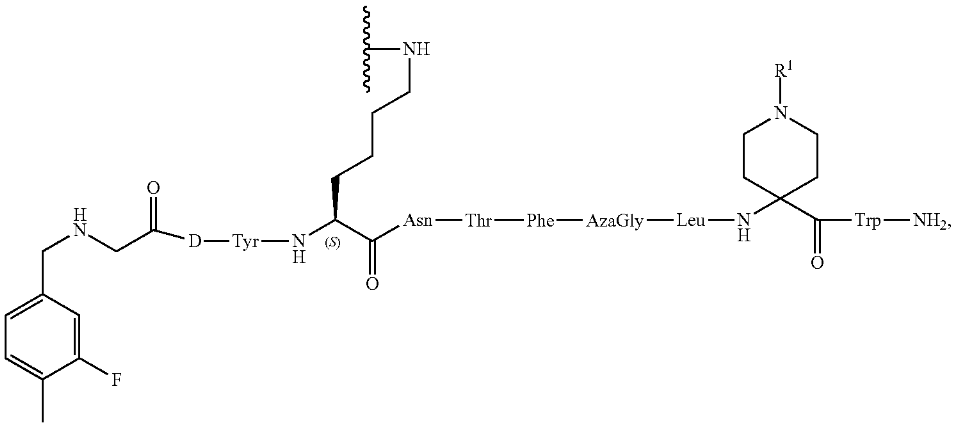

-continued
(SEQ ID NO: 316)
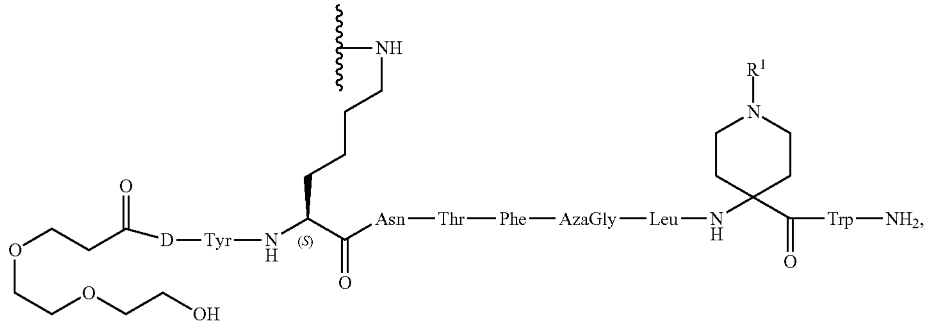
(SEQ ID NO: 317)
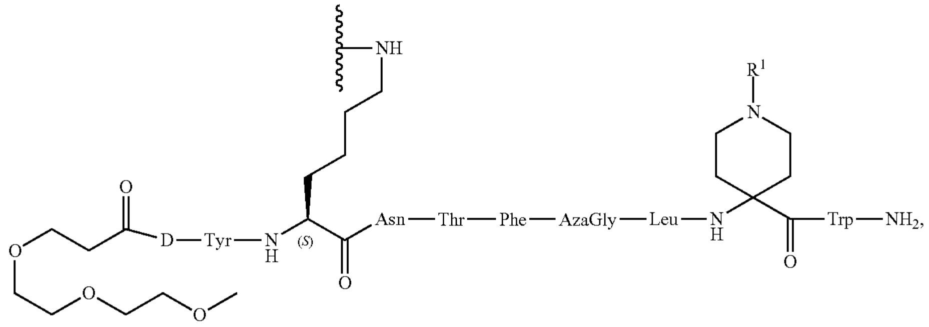
(SEQ ID NO: 318)
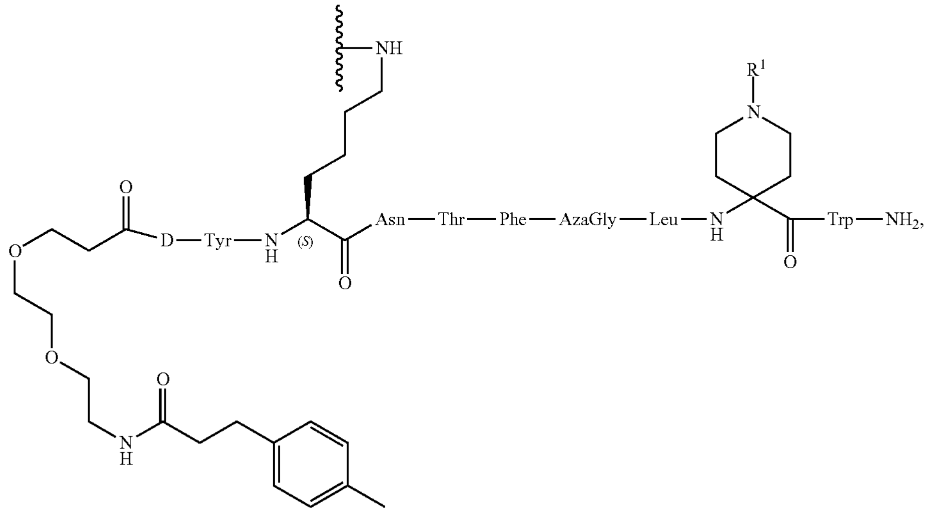

-continued
(SEQ ID NO: 319)
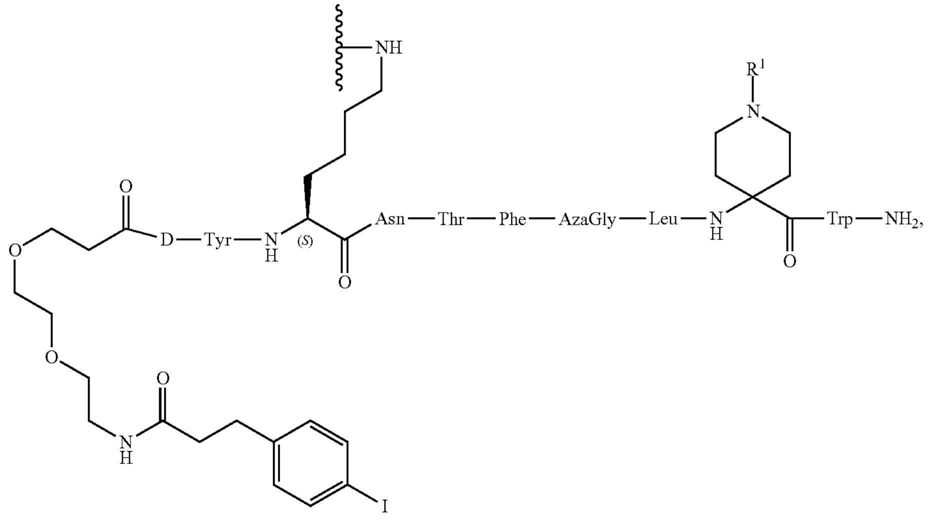
(SEQ ID NO: 320)
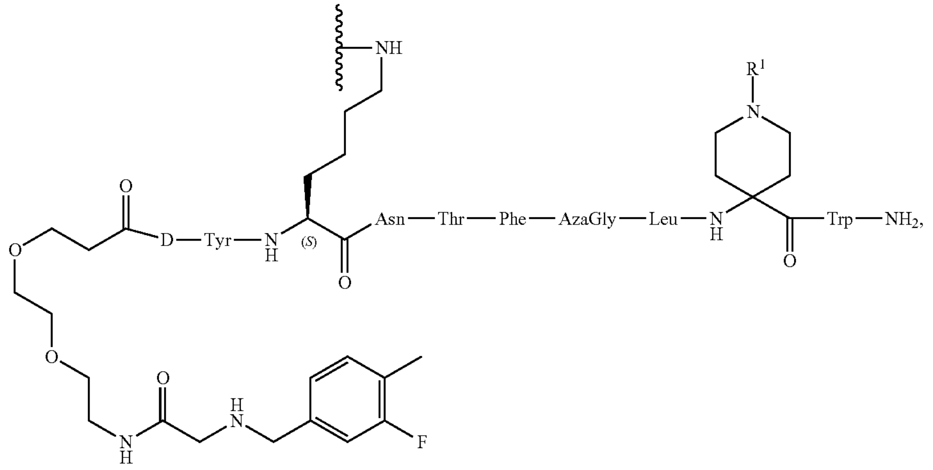
(SEQ ID NO: 321)
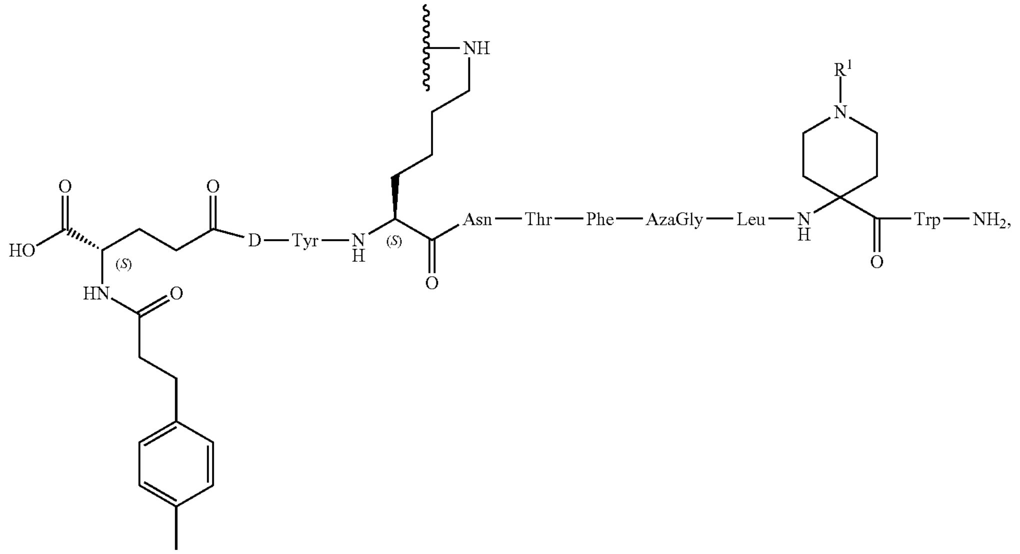

-continued
(SEQ ID NO: 322)
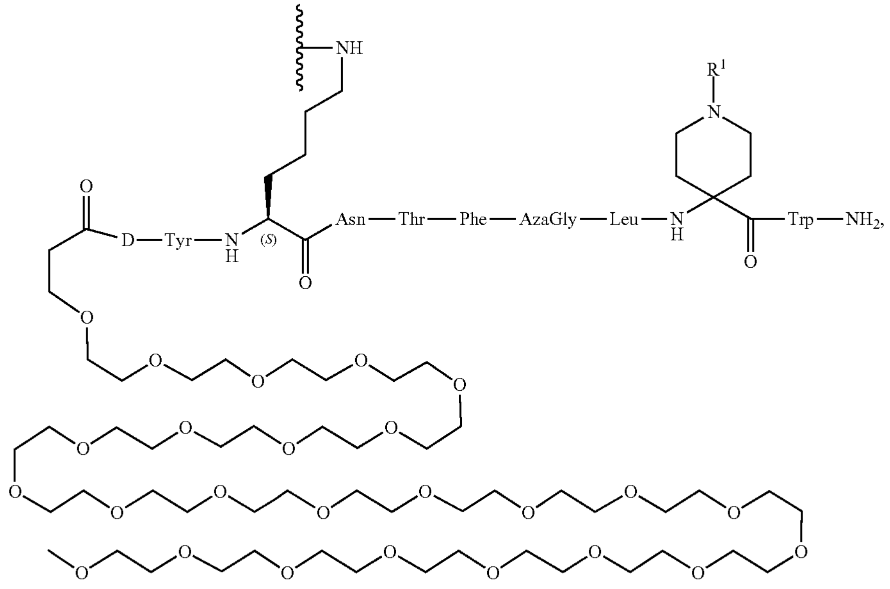
(SEQ ID NO: 323)
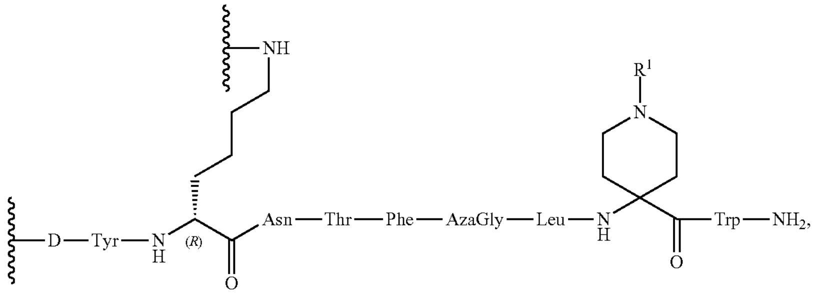
(SEQ ID NO: 324)
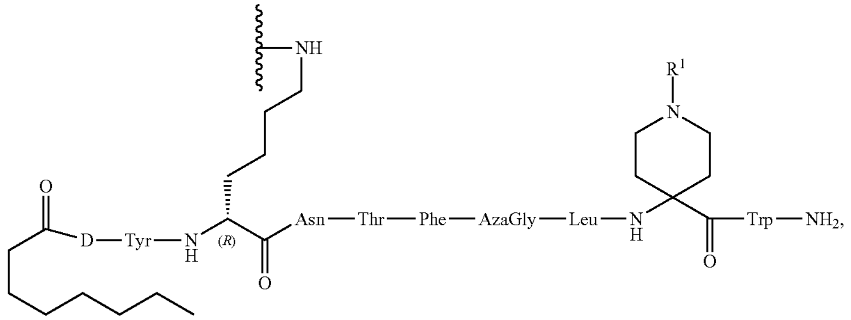

-continued
(SEQ ID NO: 325)
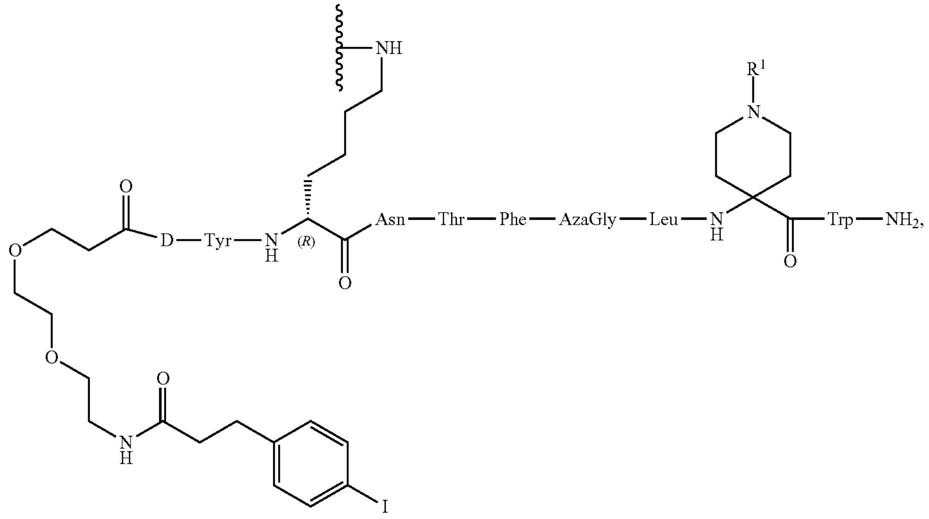
(SEQ ID NO: 326)
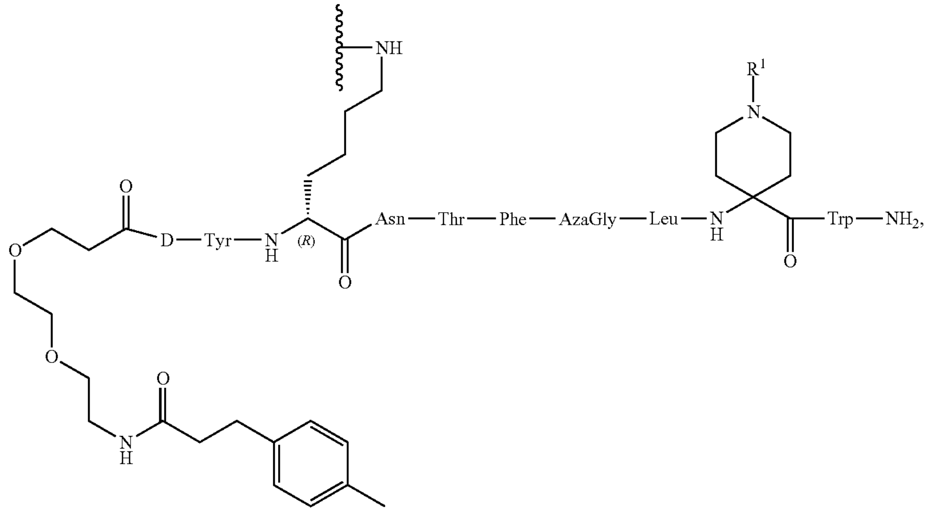
(SEQ ID NO: 327)
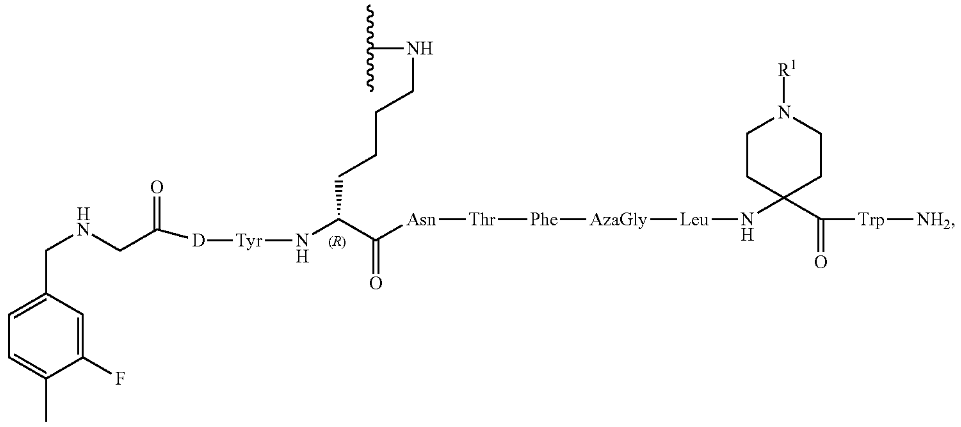

-continued
(SEQ ID NO: 328)
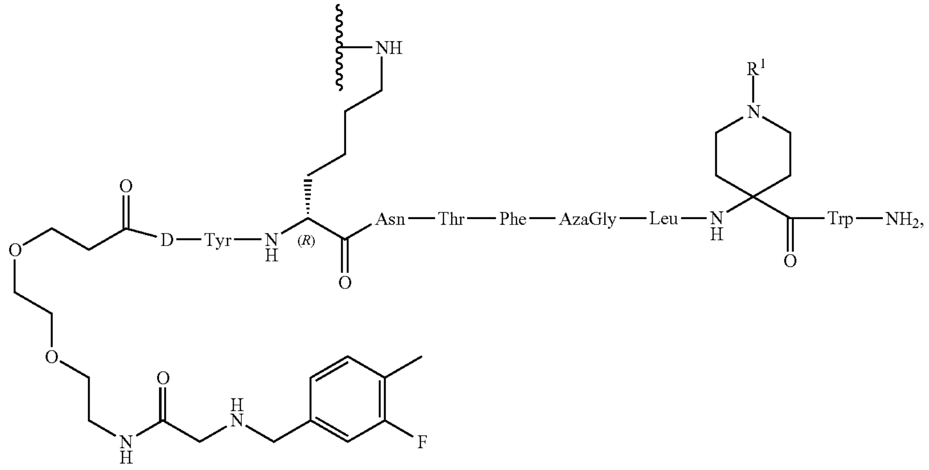
(SEQ ID NO: 329)
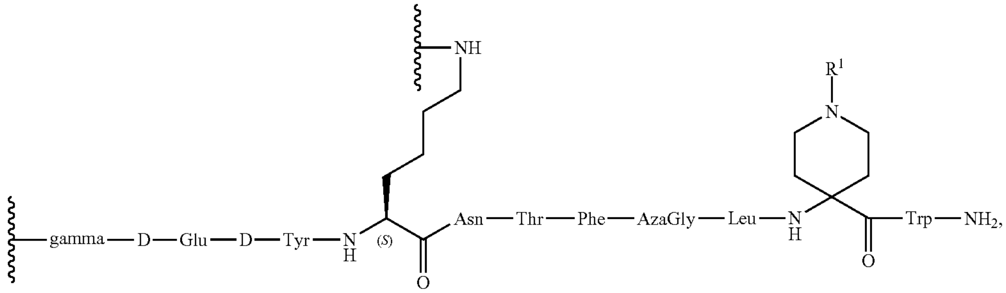
(SEQ ID NO: 330)
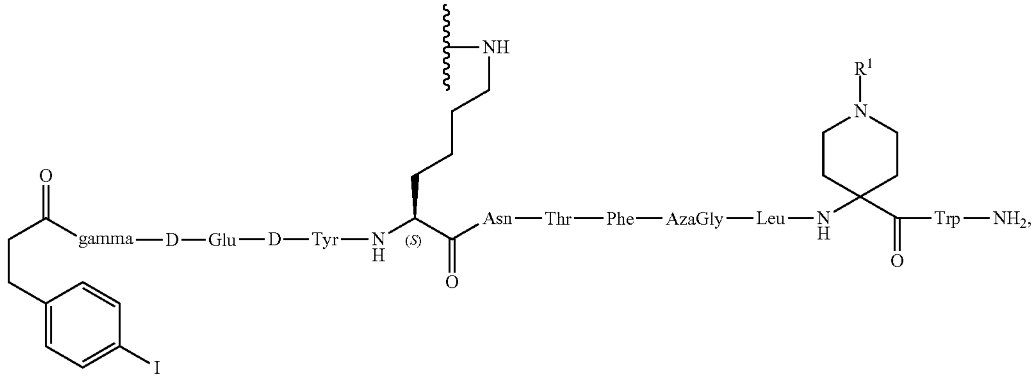
(SEQ ID NO: 331)
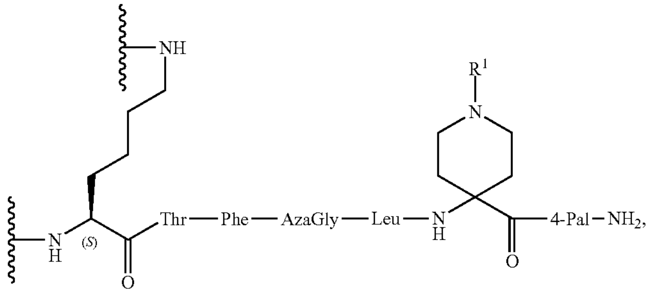

-continued
(SEQ ID NO: 332)
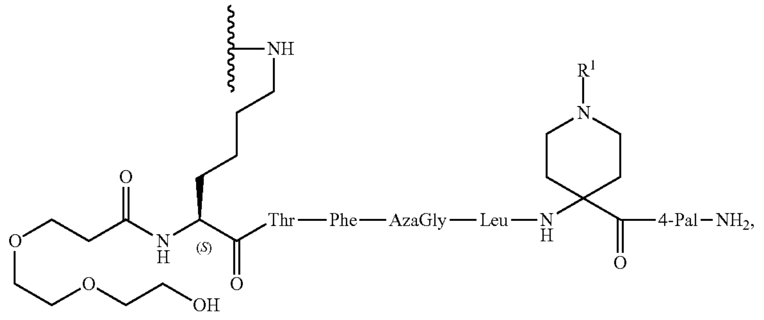
(SEQ ID NO: 333)
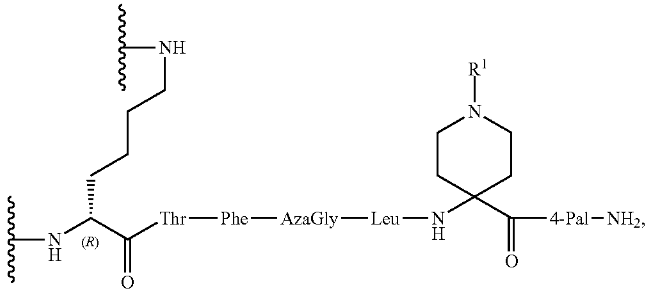
(SEQ ID NO: 334)
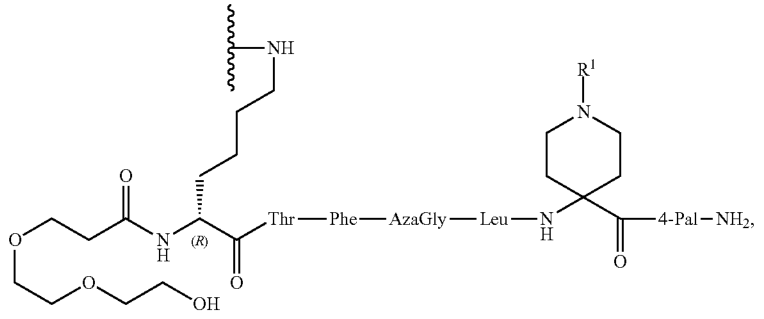
(SEQ ID NO: 335)
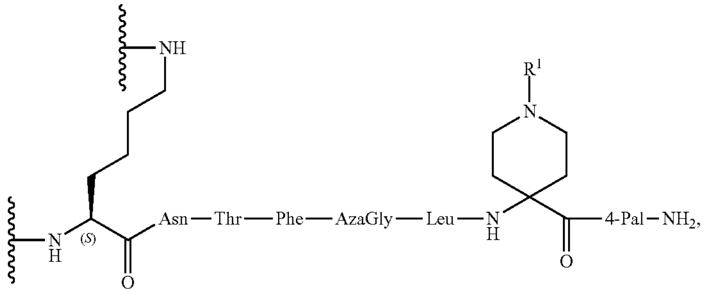
(SEQ ID NO:
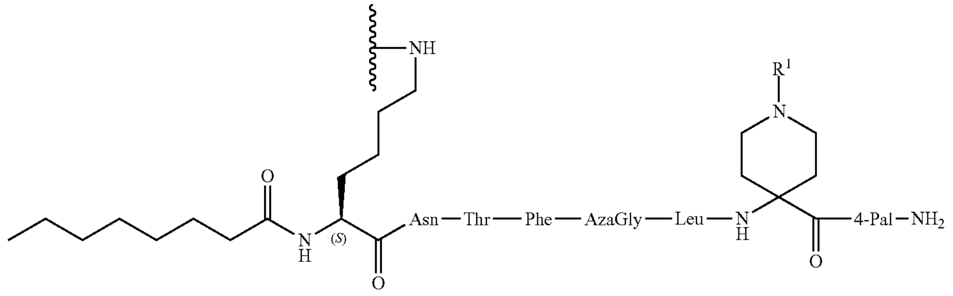

(SEQ ID NO: 337)
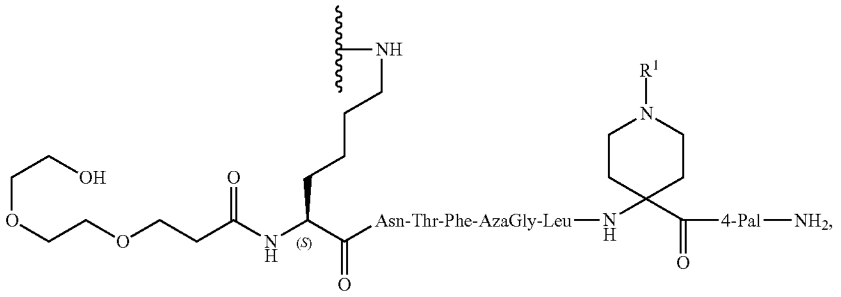
(SEQ ID NO: 338)
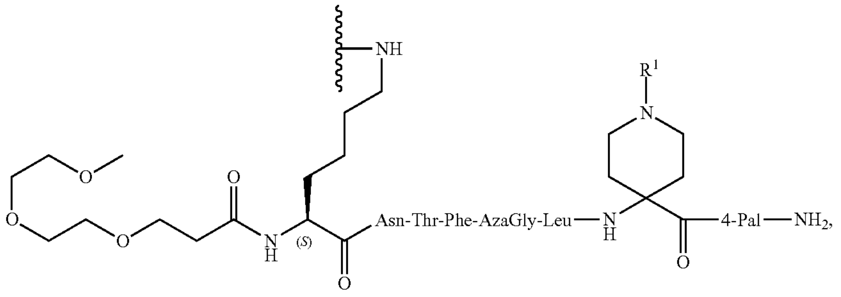
(SEQ ID NO: 339)
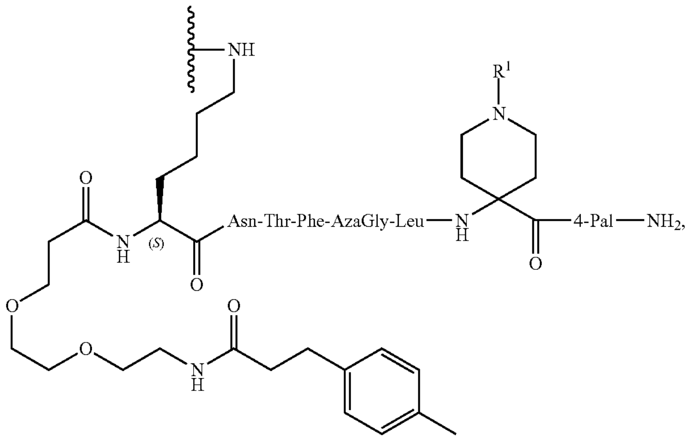
(SEQ ID NO: 340)
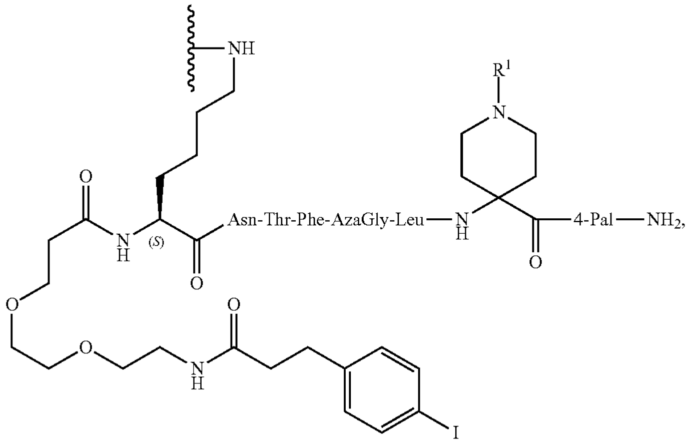

-continued
(SEQ ID NO: 341)
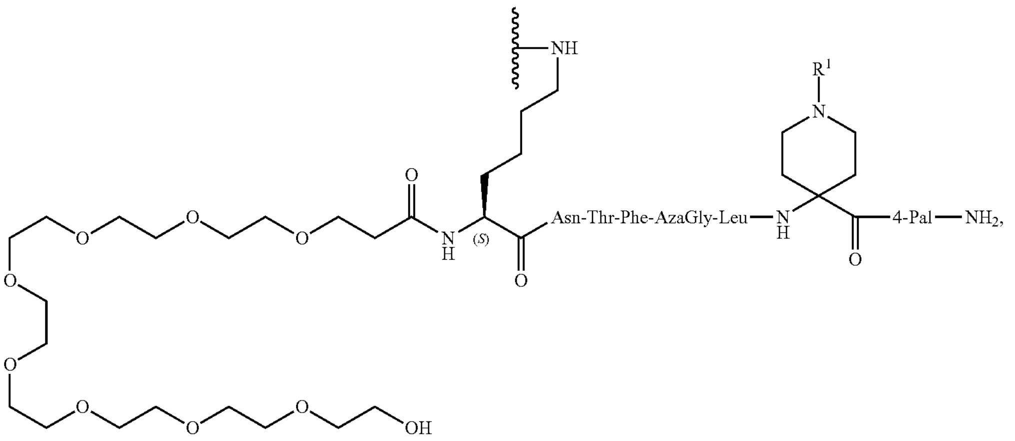
(SEQ ID NO: 342)
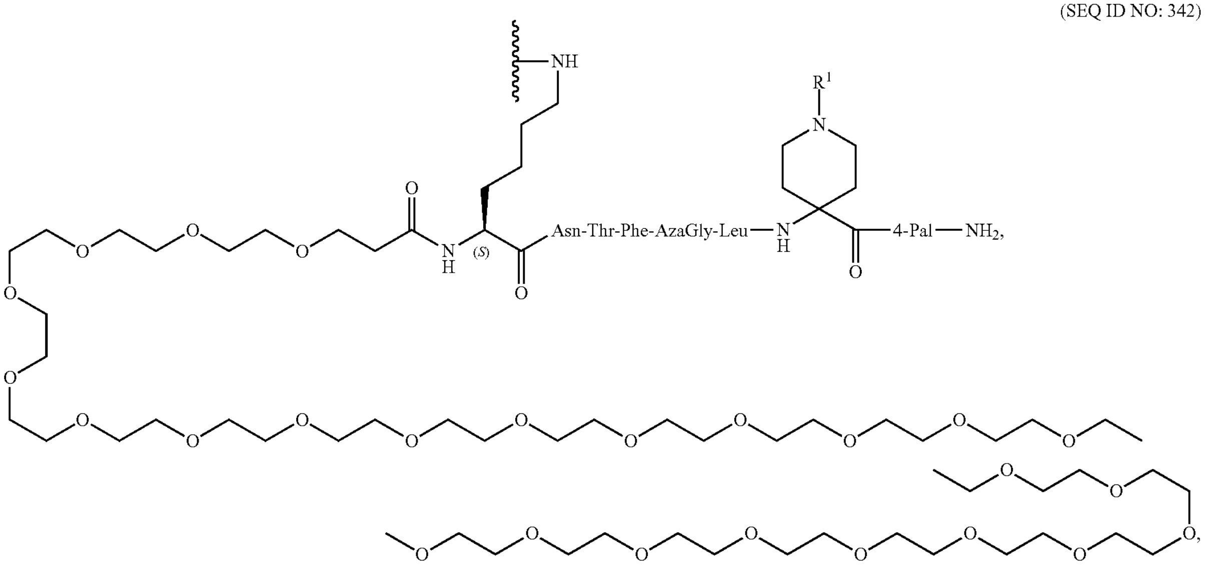
(SEQ ID NO: 343)
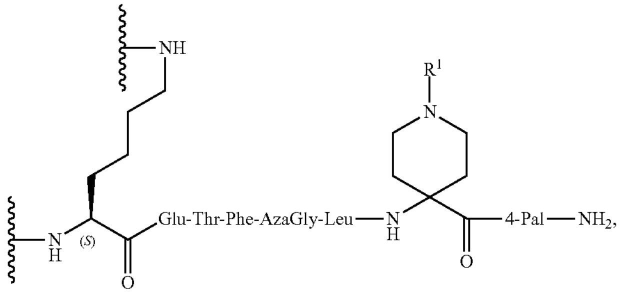
(SEQ ID NO: 344)
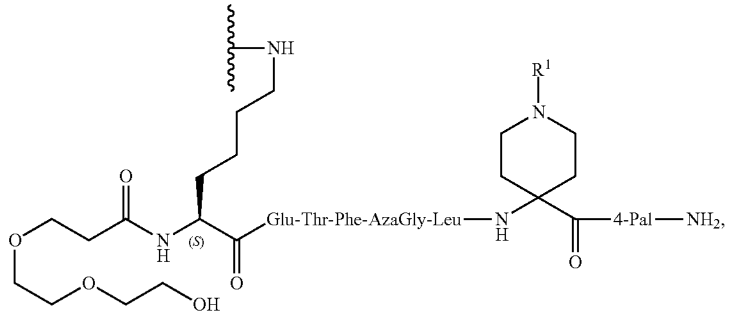

-continued
(SEQ ID NO: 345)
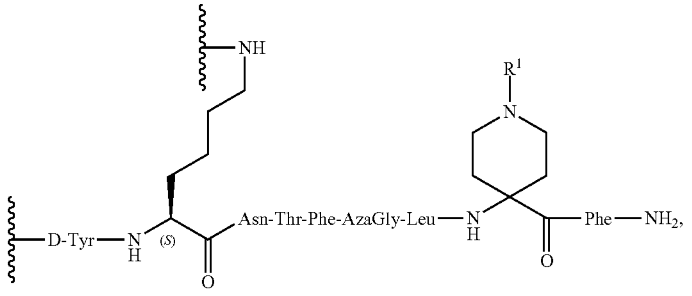
(SEQ ID NO: 346)
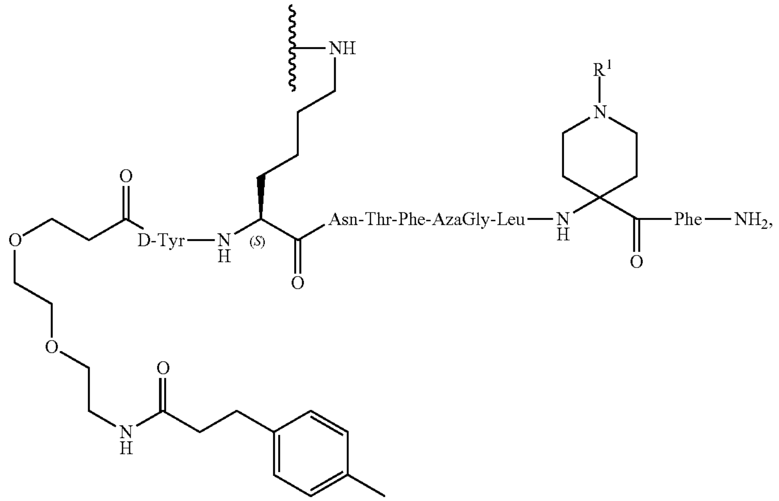
(SEQ ID NO: 347)
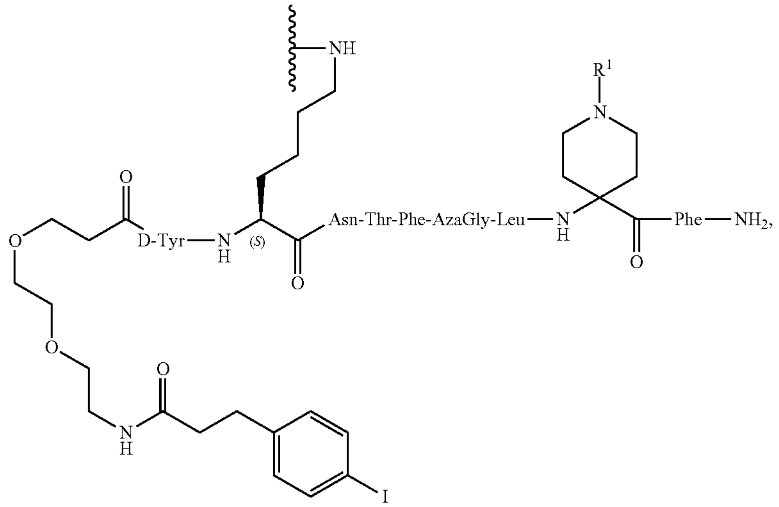
(SEQ ID NO: 348)
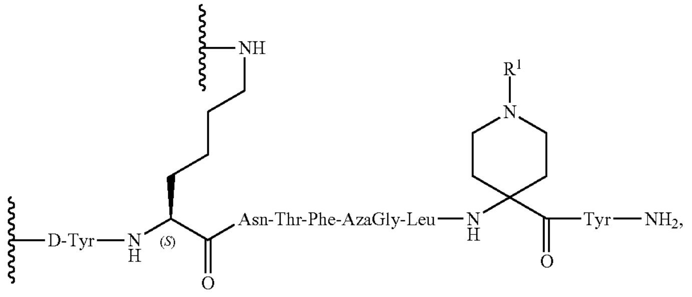

-continued
(SEQ ID NO: 349)
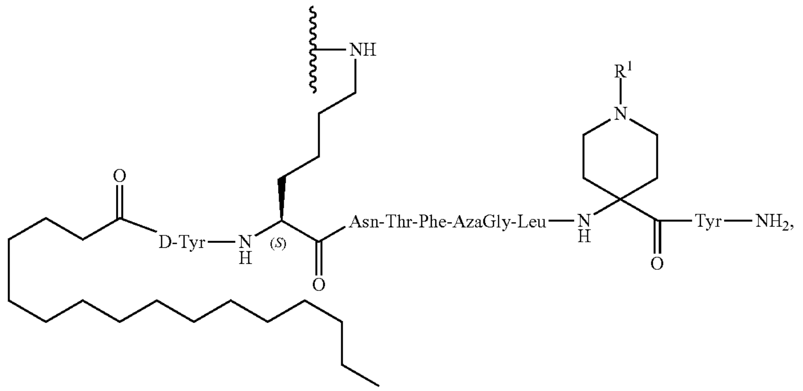
(SEQ ID NO: 350)
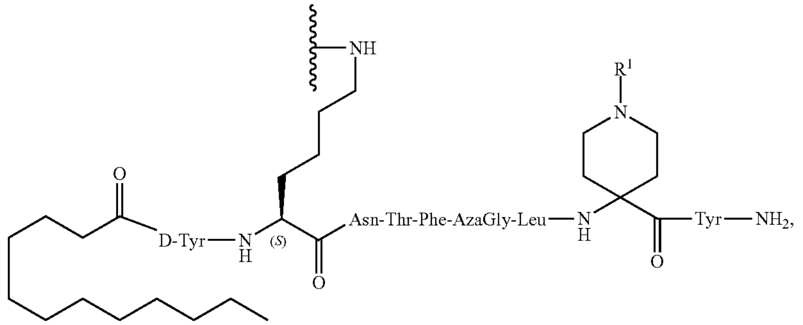
(SEQ ID NO: 351)
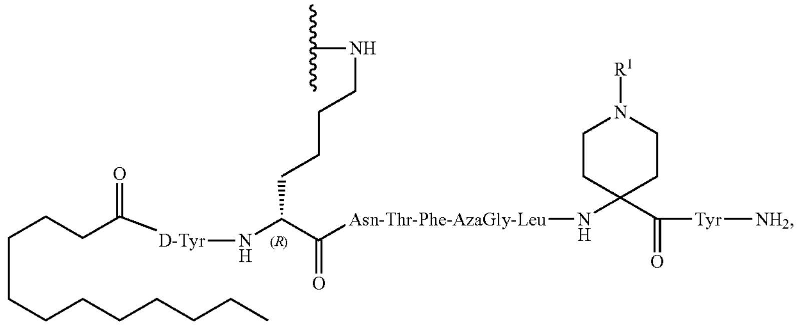
(SEQ ID NO: 352)
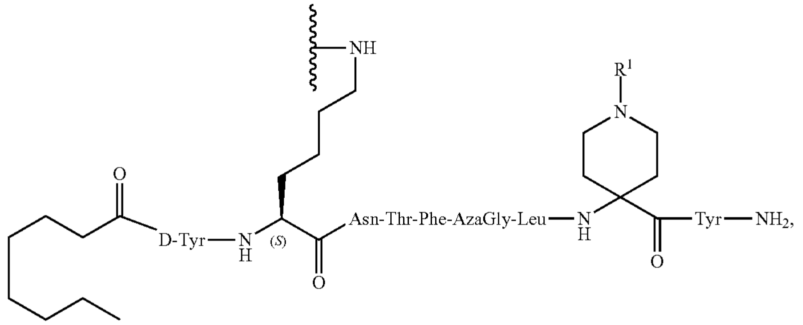

-continued
(SEQ ID NO: 353)
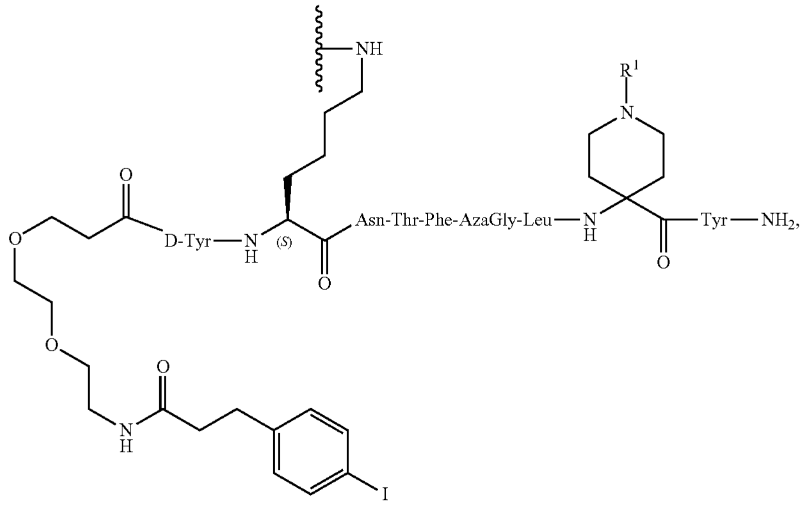
(SEQ ID NO: 354)
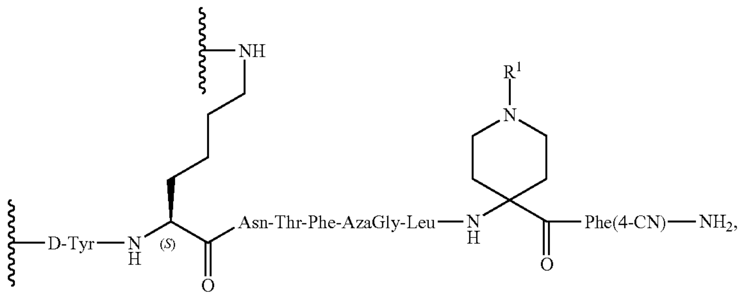
(SEQ ID NO: 355)
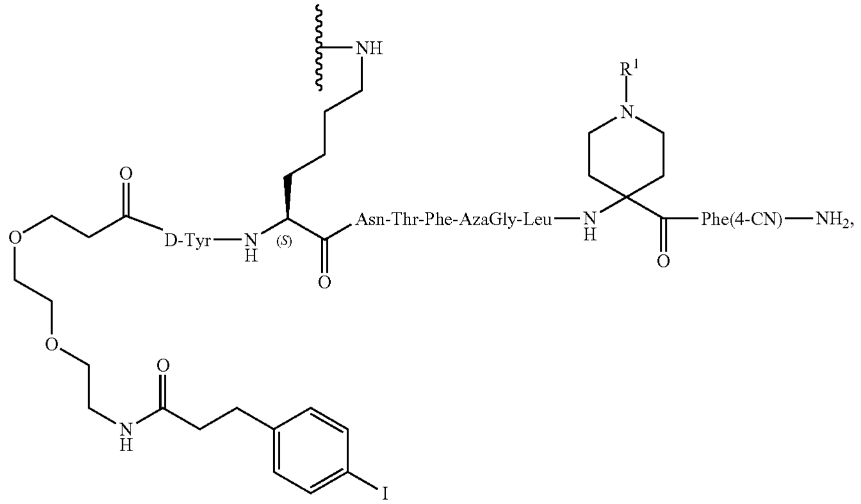

-continued
(SEQ ID NO: 356)
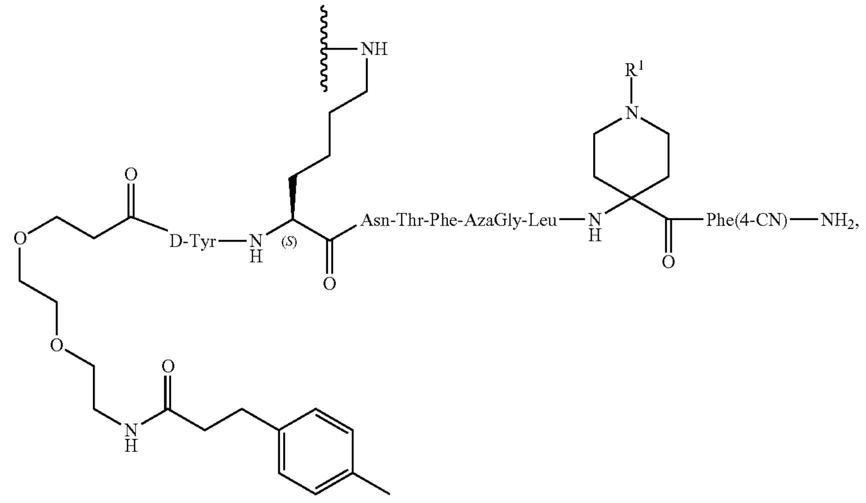
(SEQ ID NO: 357)
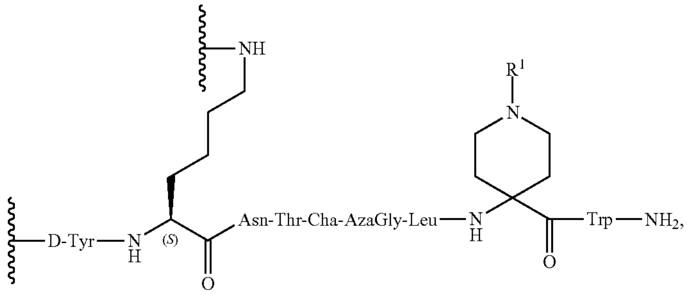
(SEQ ID NO: 358)
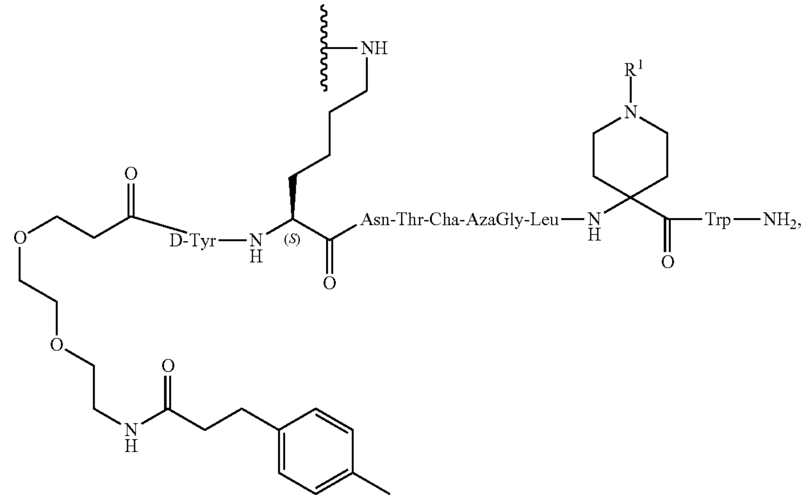

-continued
(SEQ ID NO: 359)
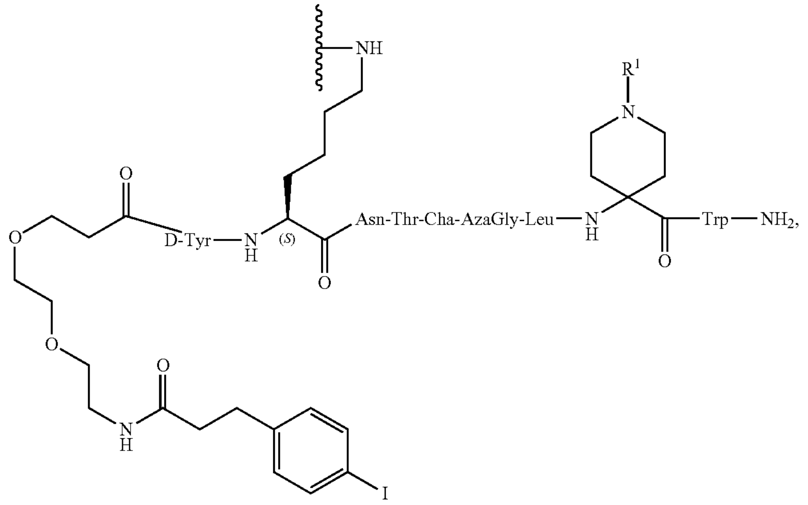
(SEQ ID NO: 360)
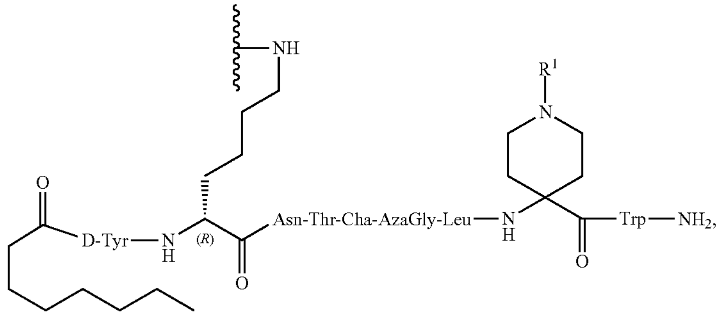
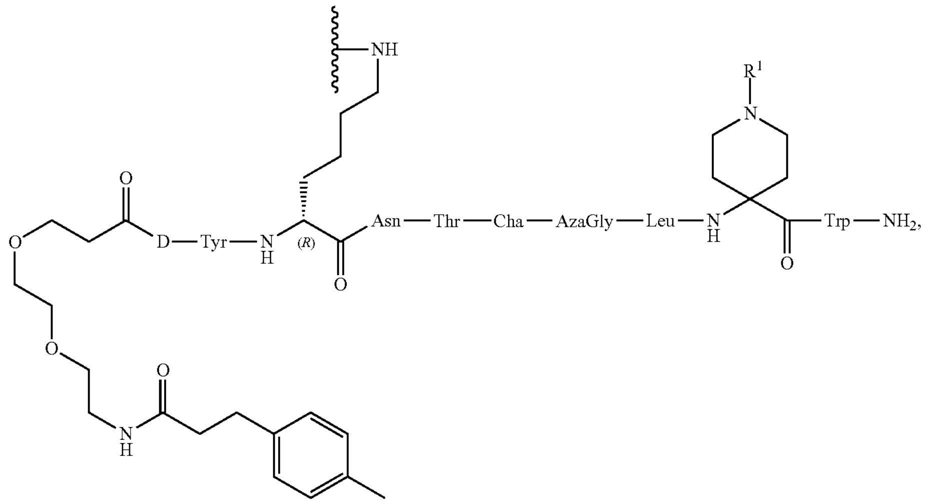

-continued
(SEQ ID NO: 361)
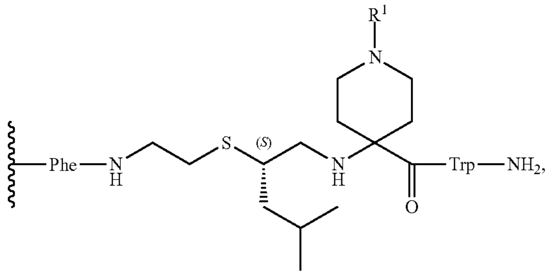
(SEQ ID NO: 363)
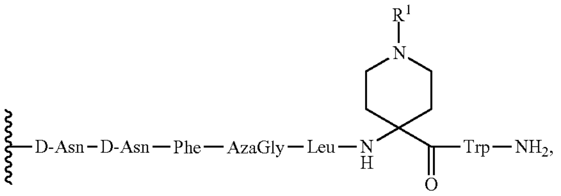
(SEQ ID NO: 364)
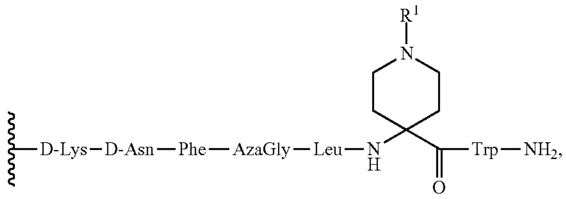
(SEQ ID NO: 365)
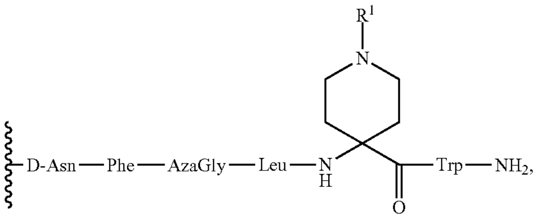
(SEQ ID NO: 366)
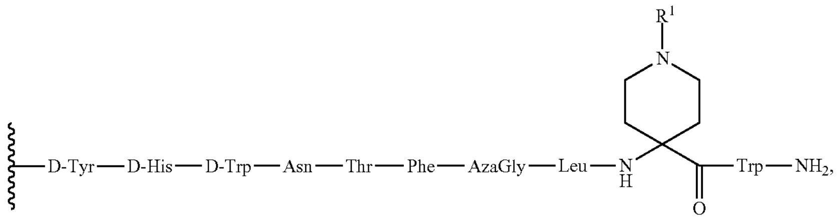
(SEQ ID NO: 367)
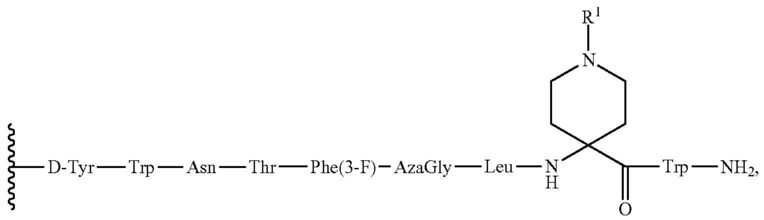
(SEQ ID NO: 368)
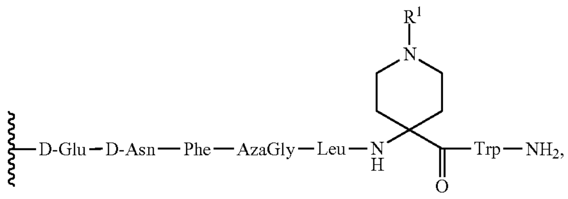
(SEQ ID NO: 369)
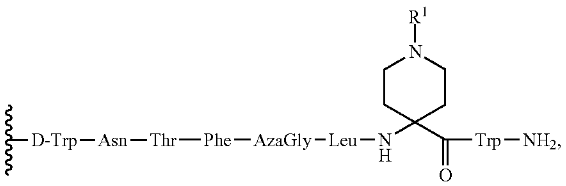
(SEQ ID NO: 370)
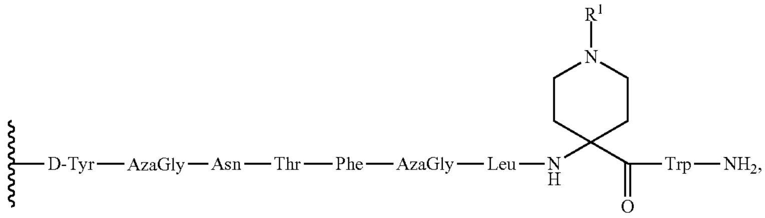

-continued
(SEQ ID NO: 371)
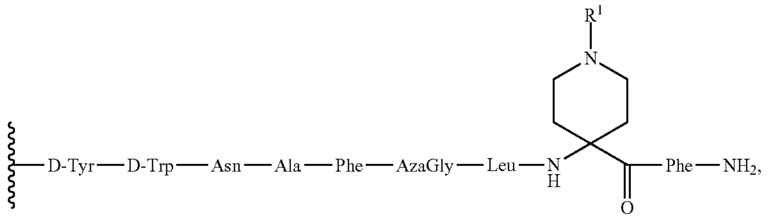
(SEQ ID NO: 372)
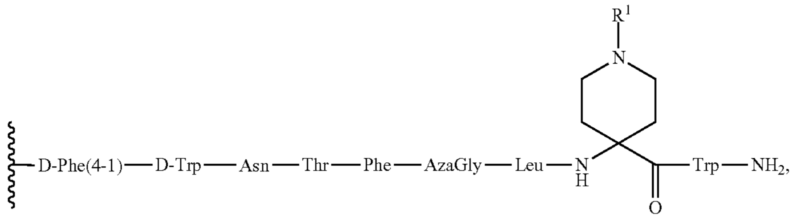
(SEQ ID NO: 373)
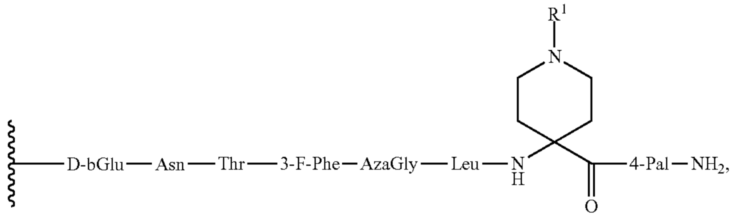
(SEQ ID NO: 374)
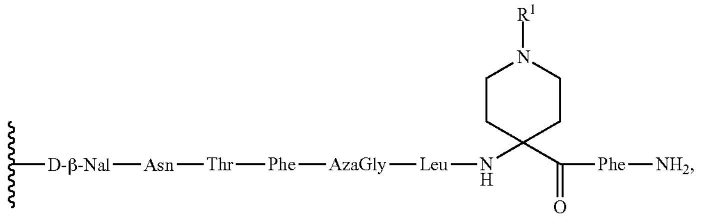
(SEQ ID NO: 375)
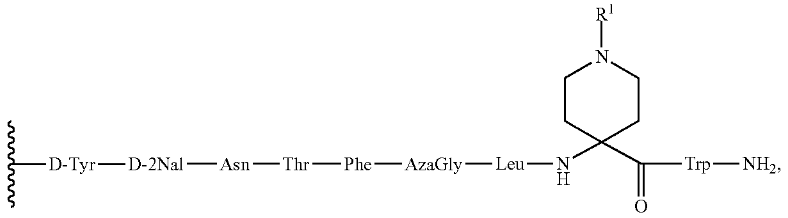
(SEQ ID NO: 376)
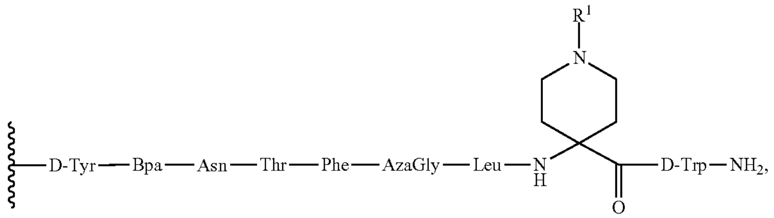

-continued
(SEQ ID NO: 377)
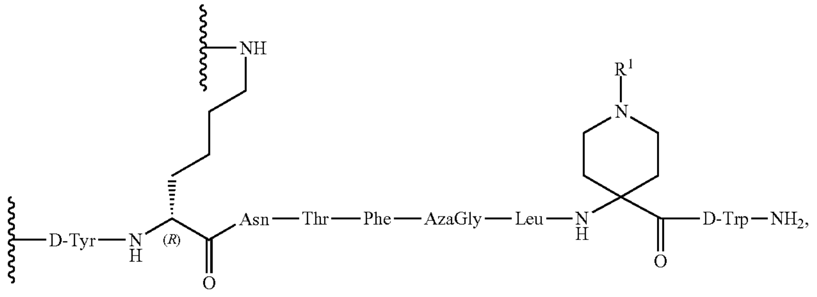
(SEQ ID NO: 378)
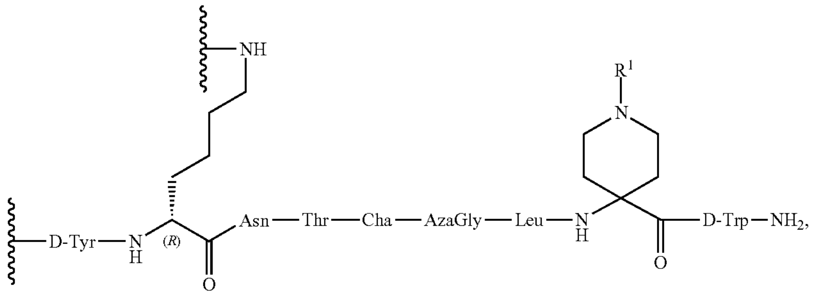
(SEQ ID NO: 379)
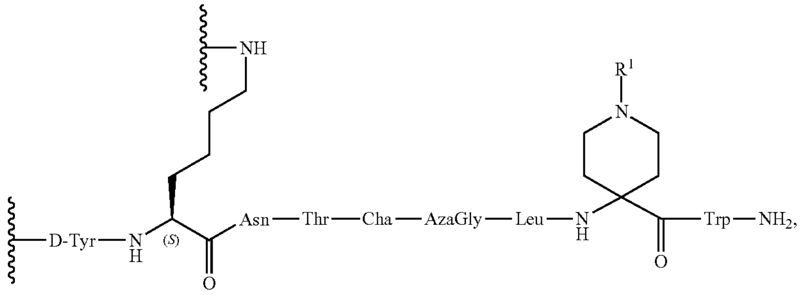
(SEQ ID NO: 380)
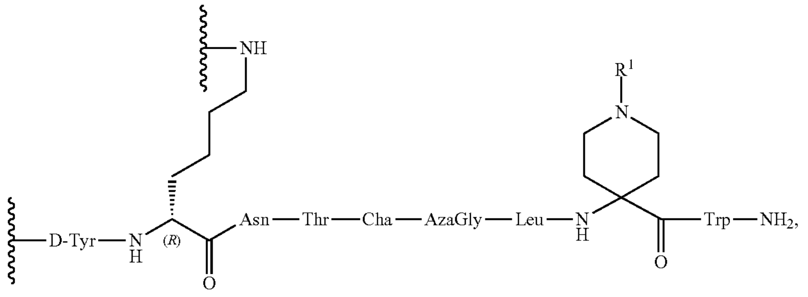
(SEQ ID NO: 381)
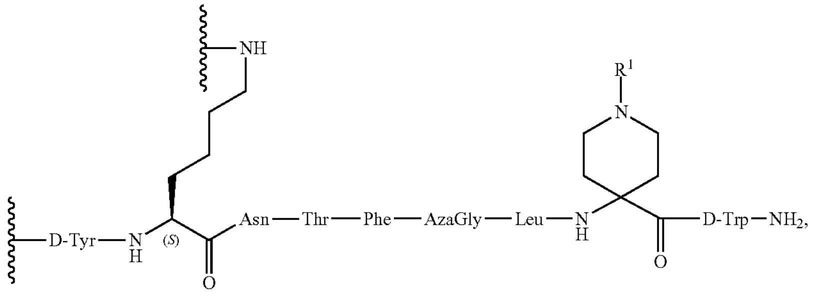
or -continued
(SEQ ID NO: 382)
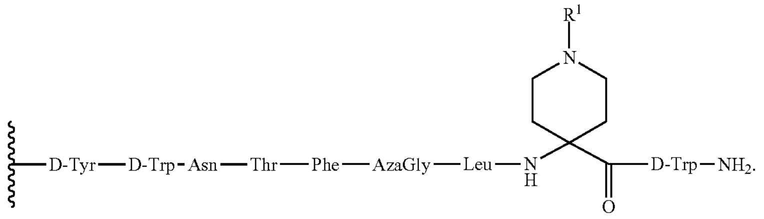
(SEQ ID NO: 383)
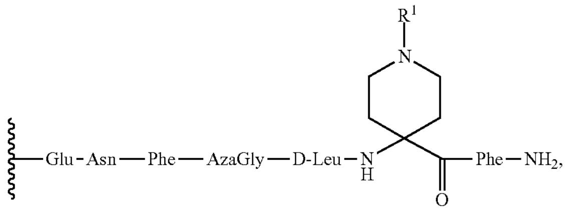
(SEQ ID NO: 384)
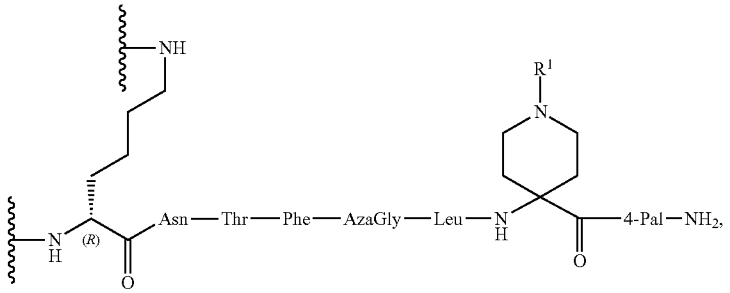
or
(SEQ ID NO: 385)
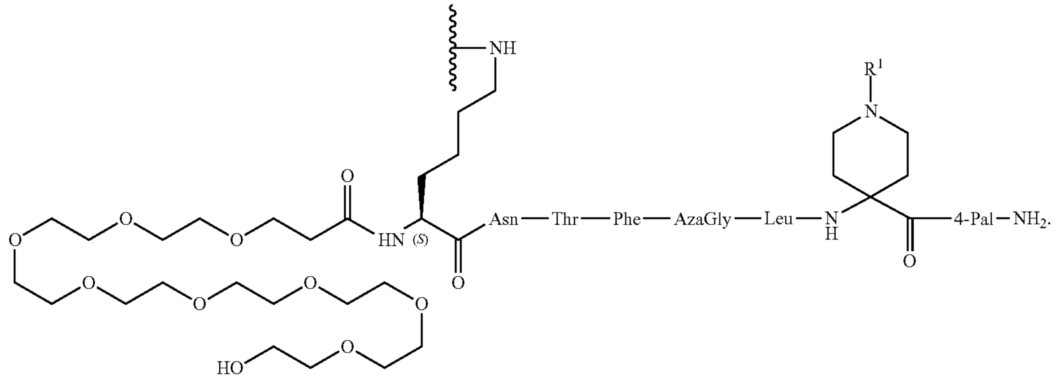
In some embodiments,
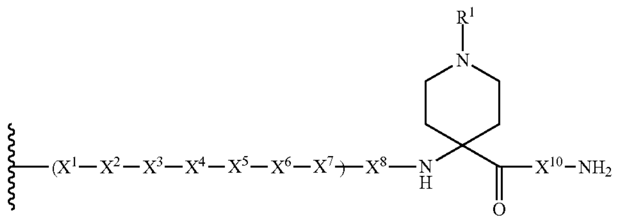
is -continued
(SEQ ID NO: 156)
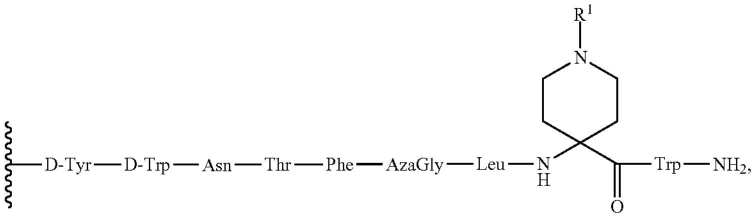
(SEQ ID NO: 268)
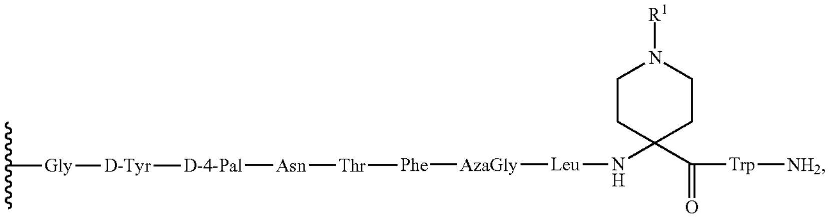
(SEQ ID NO: 214)
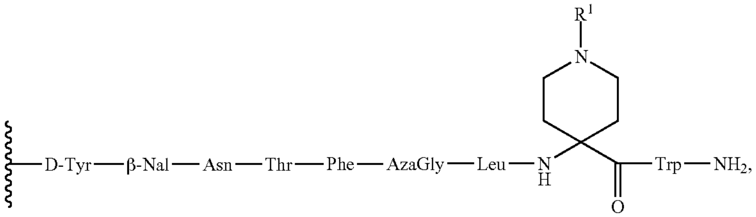
(SEQ ID NO: 269)
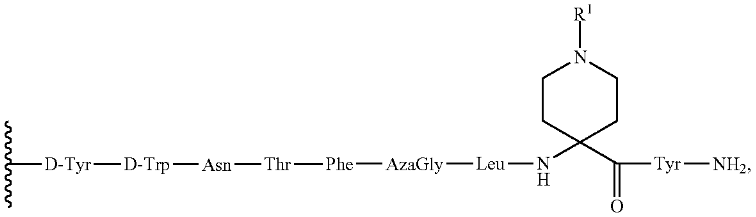
(SEQ ID NO: 348)
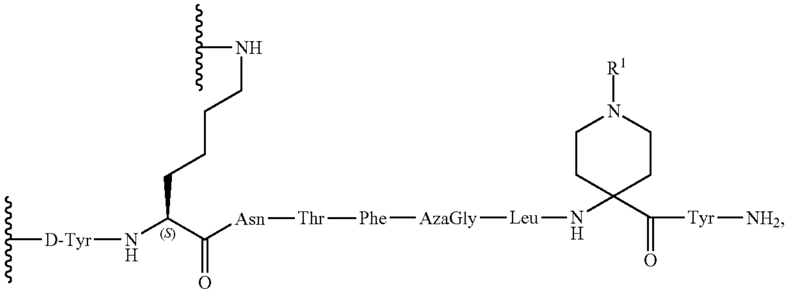
(SEQ ID NO: 352)
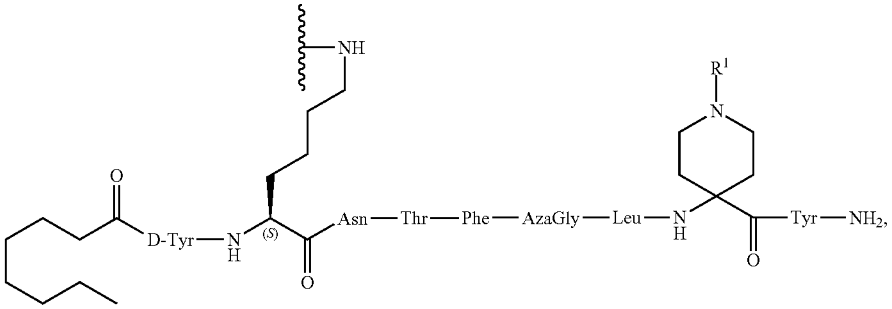

-continued
(SEQ ID NO: 231)
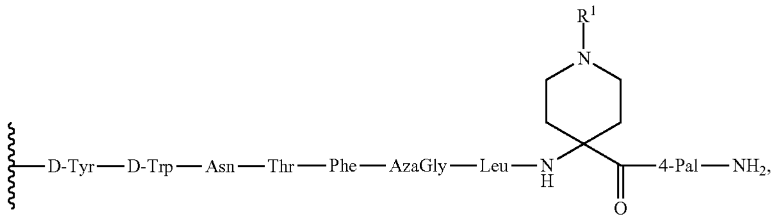
(SEQ ID NO: 156)
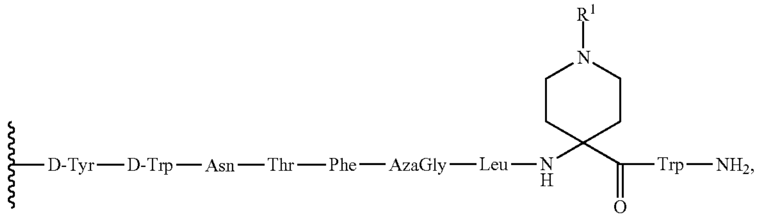
(SEQ ID NO: 215)
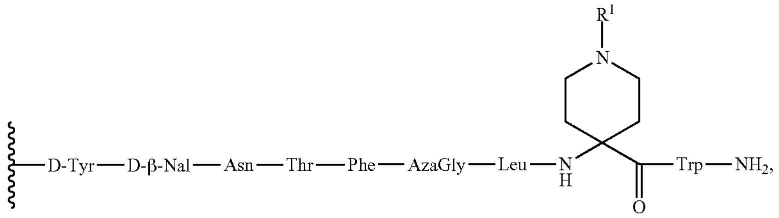
(SEQ ID NO: 309)
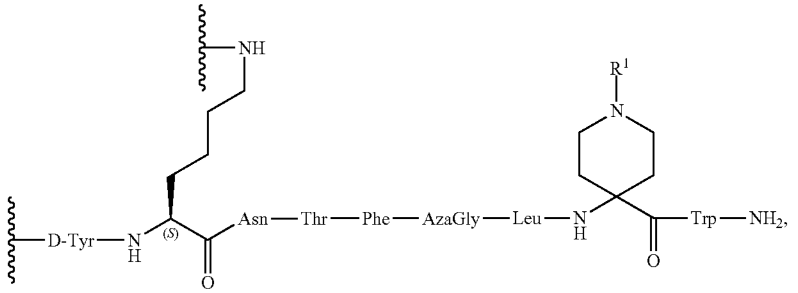
or
(SEQ ID NO: 318)
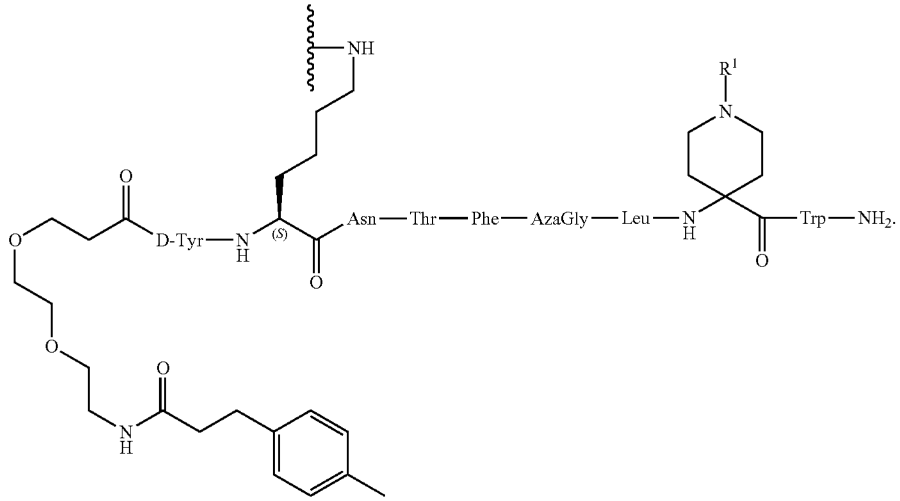

In some embodiments of the previous embodiment, $R^1$ is

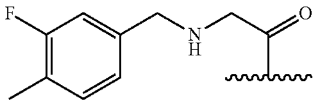

or

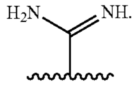

In some embodiments $R^1$ is

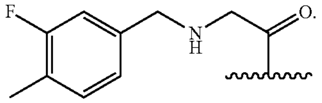 [SMILES: *C(=O)CNCc1ccc(C)c(F)c1]

In some embodiments $R^1$ is

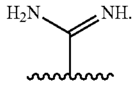

In some embodiments $R^1$ is

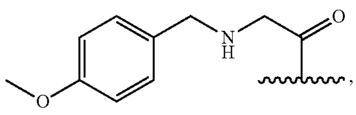

,

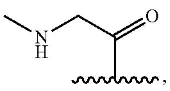

, or

-continued

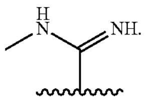

In some embodiments $R^1$ is

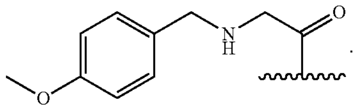 [SMILES: *C(=O)CNCc1ccc(OC)cc1]

In some embodiments $R^1$ is

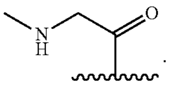 [SMILES: *C(=O)CNC]

In some embodiments $R^1$ is

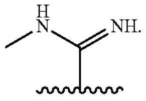 [SMILES: *C(=N)NC]

In some embodiments, the compound of Formula (I) has the following structure, or a pharmaceutically acceptable salt thereof:

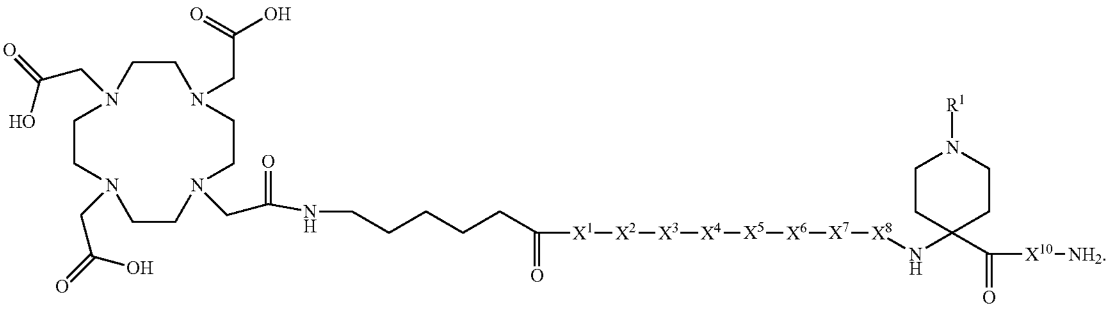

In some embodiments, the compound of Formula (I) has the following structure, or a pharmaceutically acceptable salt thereof:

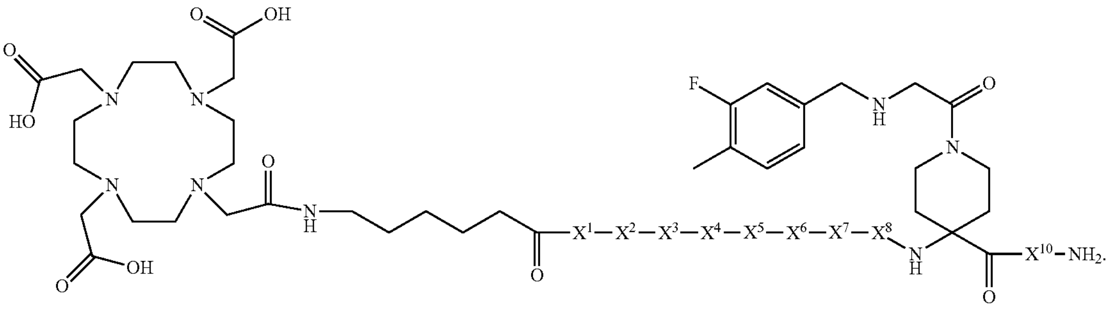

In some embodiments, the compound of Formula (I) has the following structure, or a pharmaceutically acceptable salt thereof:

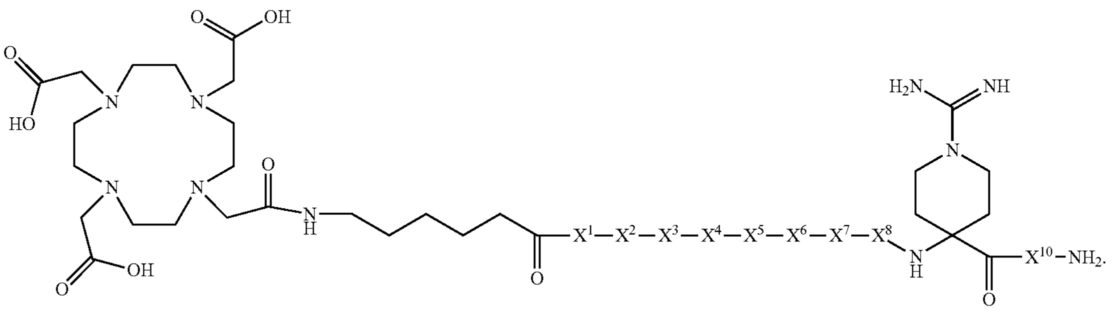

In some embodiments, the compound of Formula (I) has the following structure, or a pharmaceutically acceptable salt thereof:

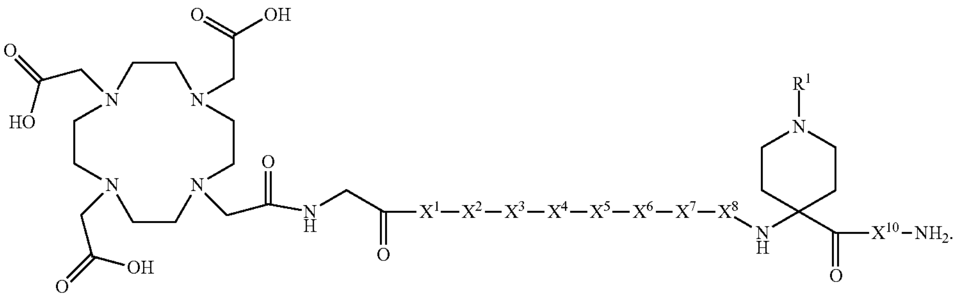

In some embodiments, the compound of Formula (I) has the following structure, or a pharmaceutically acceptable salt thereof:

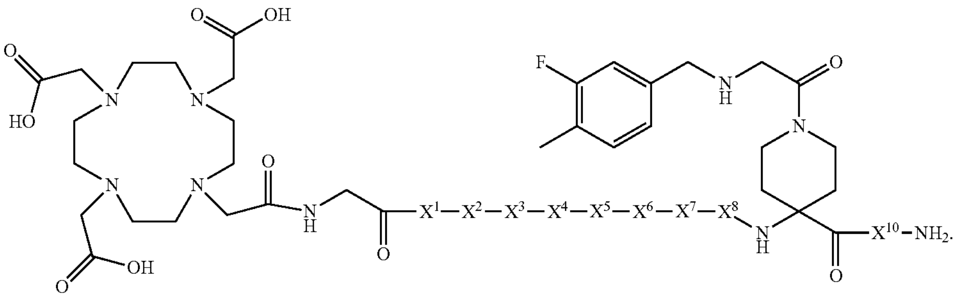

In some embodiments, the compound of Formula (I) has the following structure, or a pharmaceutically acceptable salt thereof:

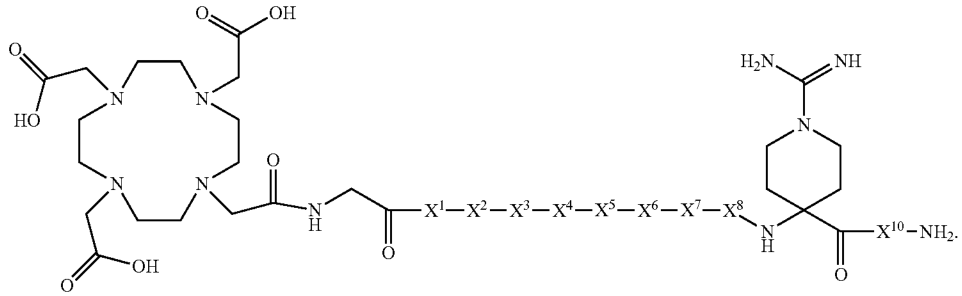

In some embodiments, the compound of Formula (I) has the following structure, or a pharmaceutically acceptable salt thereof:

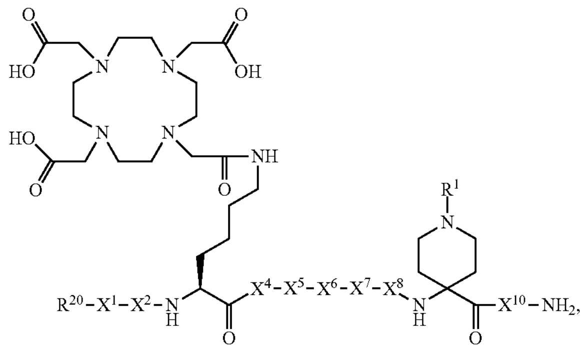

wherein $R^{20}$ is H, —C(=O)—$C_1$-$C_{20}$ alkyl, —C(=O)—$(CH_2CH_2O)_y$—$CH_2CH_2$—$R^{15}$, —$C_1$-$C_{20}$ alkyl, N-hexadecanoyl-Glu, —$C_4$-$C_{20}$ polyethylene glycol, a saccharide, —C(=O)—$(CH_2CH_2O)_x$—$CH_3$, —C(=O)—$(CH_2CH_2O)_x$—H, —C(=O)—$CH_2CH_2CH$(COOH)—$R^{15}$, —C(=O)—$(CH_2)_2R^{19}$, or —C(=O)$CH_2NHCH_2R^{19}$. In some embodiments, the compound of Formula (I) has the following structure, or a pharmaceutically acceptable salt thereof:

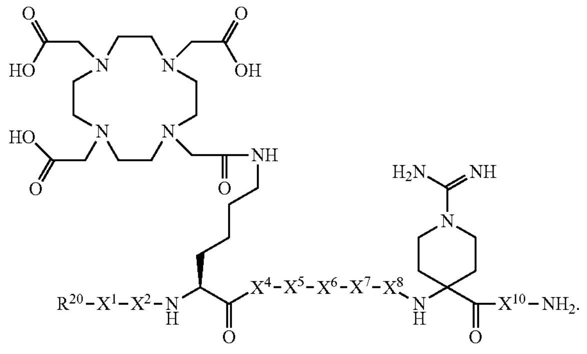

In some embodiments, the compound of Formula (I) has the following structure, or a pharmaceutically acceptable salt thereof:

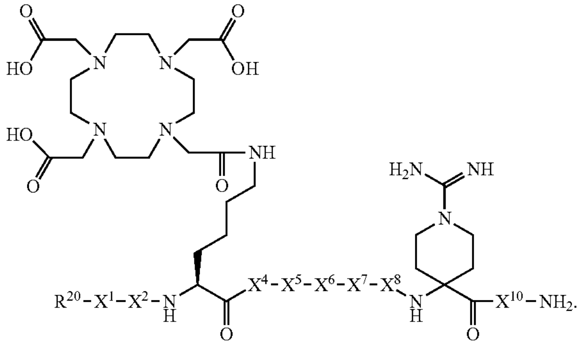

In some embodiments, the compound of Formula (I) has the following structure, or a pharmaceutically acceptable salt thereof:

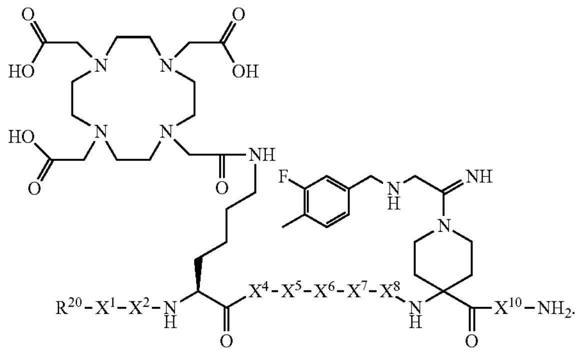

In some embodiments, $R^{20}$ is —C(=O)—$C_1$-$C_{10}$ alkyl. In some embodiments, $R^{20}$ is —C(=O)—$(CH_2CH_2O)_y$—$CH_2CH_2$—$R^{15}$; wherein v is 1, 2, 3, or 4. In some embodiments, $R^{15}$ is

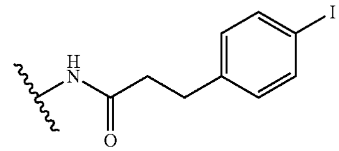

or

-continued

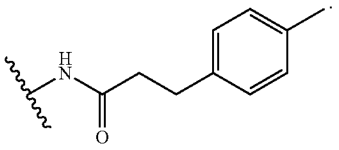

Radionuclide Complexes

Radiopharmaceuticals have increasingly become very useful tools for physicians to diagnose, stage, treat, and monitor the progression of several diseases, especially cancer. The primary difference between radiopharmaceuticals and other pharmaceutical drugs is that radiopharmaceuticals contain a radionuclide. The nuclear decay properties of the radionuclide determine whether a radiopharmaceutical will be used clinically as a diagnostic agent or as a therapeutic agent. Diagnostic radiopharmaceuticals require radionuclides that emit either gamma (γ) rays or positrons (β+), which subsequently annihilate with nearby electrons to produce two 511 keV annihilation photons emitted approximately 180° away from each other. Gamma ray-emitting radionuclides (e. g. $^{99m}$Tc, $^{111}$In, $^{201}$Tl, etc.) are useful for single photon emission computed tomography (SPECT), while positron-emitting radionuclides (e. g. $^{18}$F, $^{89}$Zr, $^{68}$Ga, etc.) are useful for positron emission tomography (PET).

In contrast, therapeutic radiopharmaceuticals require radionuclides that emit particulate radiation, such as alpha (α) particles, beta (β-) particles, or Auger electrons. These particles, which strongly interact with target tissues (e. g. cancerous tumor) and lead to extensive localized ionization, can damage chemical bonds in DNA molecules and potentially induce cytotoxicity.

For most nuclear medicine applications, it is desired that a diagnostic radiopharmaceutical is paired with a therapeutic radiopharmaceutical. This concept is commonly known as "theranostics". As a first step in the theranostic concept, a target molecule labeled with a diagnostic radionuclide is used for quantitative imaging of a tumor imaging biomarker, either by positron emission tomography (PET) or single photon emission computed tomography (SPECT). When it is demonstrated that, with this targeted molecule, a tumoricidal radiation absorbed dose can be delivered to tumor and metastases, as a second step, via administration of the same or a similar target molecule labeled with a therapeutic radionuclide.

In some embodiments, the chemical and pharmacokinetic behaviors of both the diagnostic and therapeutic radiopharmaceuticals match. In some embodiments, the diagnostic and therapeutic radionuclides are a chemically identical radioisotope pair (also known as a "matched pair"). One examples of a matched pair for theranostic radiopharmaceutical applications is the $^{123}$I/$^{131}$I pair, where $^{123}$I-labeled compounds are used for diagnosis, while $^{131}$I-labeled compounds are used for therapy. Other theranostic matched pairs include $^{44}$Sc/$^{47}$Sc, $^{64}$Cu/$^{67}$Cu, $^{72}$As/$^{77}$As, $^{86}$Y/$^{90}$Y, and $^{203}$Pb/$^{212}$Pb, among others. Alternatively, radionuclide pairs from different elements can be utilized for theranostic radiopharmaceutical development when their chemistry is very similar (e. g. $^{99m}$Tc/$^{186/188}$Re) and there is no significant difference in the pharmacokinetic behavior between the diagnostic and therapeutic analogues. Another example is the $^{68}$Ga/$^{177}$Lu pair, where $^{68}$Ga is used for diagnosis and $^{177}$Lu is used for therapy. For example, gastroenteropancreatic endocrine tumors express high amounts of sst2 receptor that can be targeted with somatostatin receptor scintigraphy for diagnostic purposes with a $^{68}$Ga sst2 ligand conjugate ([$^{68}$Ga]Ga-DOTA-TATE (NETSPOT™) or [$^{68}$Ga]Ga-DOTA-TOC (DOTA-(D-Phe1, Tyr3)-octreotide, SomaKit TOC®)), followed by treatment with a $^{177}$Lu sst2 ligand conjugate ([$^{177}$Lu]Lu-DOTA-TATE) for endoradiotherapy.

Chelating Moieties Used to Generate Metal (Radionuclide) Complexes

The compounds described herein comprise at least one $R^a$ group, wherein $R^a$ is a chelating moiety capable of chelating a radionuclide (Z'), or radionuclide complex thereof. In some embodiments, any suitable group or atom(s) of the chelator are used to connect, via an optional linker, to the KISS1R targeting ligand.

In some embodiments, the chelator is capable of binding a radioactive atom. In some embodiments, the binding is direct, e.g., the chelator makes hydrogen bonds or electrostatic interactions with a radioactive atom. In some embodiments, the binding is indirect, e.g., the chelator binds to a molecule that comprises a radioactive atom. In some embodiments, the chelator is or comprises a macrocycle.

In some embodiments, the chelator comprises one or more amine groups. In some embodiments, the metal chelator comprises two or more amine groups. In some embodiments, the chelator comprises three or more amine groups. In some embodiments, the chelator comprises four or more amine groups. In some embodiments, the chelator includes 4 or more N atoms, 4 or more carboxylic acid groups, or a combination thereof. In some embodiments, the chelator does not comprise S. In some embodiments, the chelator comprises a ring. In some embodiments, the ring comprises an O and/or a N atom. In some embodiments, the chelator is a ring that includes 3 or more N atoms, 3 or more carboxylic acid groups, or a combination thereof. In some embodiments, the chelator is polydentate ligand, bidentate ligand, or monodentate ligand. Polydentate ligands range in the number of atoms used to bond to a metal atom or ion. EDTA, a hexadentate ligand, is an example of a polydentate ligand that has six donor atoms with electron pairs that can be used to bond to a central metal atom or ion. Bidentate ligands have two donor atoms which allow them to bind to a central metal atom or ion at two points. Ethylenediamine (en) and the oxalate ion (ox) are examples of bidentate ligands.

In some embodiments, a chelator described herein comprises a cyclic chelating agent or an acyclic chelating agent. In some embodiments, a chelator described herein comprises a cyclic chelating agent. In some embodiments, a chelator described herein comprises an acyclic chelating agent.

In some embodiments, a chelator described herein comprises cyclen, DO2A, DO3A, HP-DO3A, DO3A-Nprop, DO3AP, DO3A$^{PrA}$, DO3AP$^{ABn}$, DO3AM$^{nBu}$ BT-DO3A, DOTA, PSC, DOTAGA, DOTA(GA)$_2$, DOTAM, DOTA-4AMP, DOTMA, DOTP, CB-DO2A, DOTPA, DOTMP, DOTAMAP, TRITA, L$^{Py}$, cyclam, TETA, CB-Cyclam, CB-TE2A, TE2A, NOTA, NODAGA, NODA-MPAA, TACN, TACN-TM, NOTP, Sarcophagine (Sar), DiAmSar, SarAr, AmBaSar, cis-DO2A2P, trans-DO2A2P, DOTEP, p-NO$_2$-Bn-DOTA, BAT, DO3TMP-Monoamide, CHX-A"-DTPA, c-DEPA, PCTA, p-NO$_2$-Bn-PCTA, TRAP, TRAPH, TRAP-OH, TRAP-Ph, NOPO, AAZTA, DATAM, HEHA, PEPA, DTA, EDTMP, DTPMP, NTA, EDTA, DTPA, CyDTPA, DFO, DFO*, deferiprone, TTHA, HBED, HBED-CC , HBED-CC TFP, H$_4$pypa, H$_4$py4pa, CP256, THP, YM103, t-Bu-calix[4]arene-tetracarboxylic acid, CHX-A"-DTPA, H$_6$phospha, p-NH$_2$-Bn-CHXA"-DTPA, DEDPA, H$_4$octox, H$_4$octapa, H$_4$CHXoctapa, HYNIC, macropa, crown, macropid, HOPO, Bis(2-mercaptoacetamide), Bis (aminothiolate), or $SBTG_2DAP$.

In some embodiments, a chelator described herein comprises DOTA, DOTAGA, $DOTA(GA)_2$, NOTA, NODAGA, TRITA, TETA, DOTA-MA, HP-DO3A, DOTMA, DOTA-pNB, DOTP, DOTMP, DOTEP, DOTMPE, F-DOTPME, DOTPP, DOTBzP, DOTA-monoamide, BAT, DO3TMP-Monoamide, and CHX-A"-DTPA.

In some embodiments, a chelator described herein comprises DTA, CyEDTA, EDTMP, DTPMP, DTPA, CyDTPA, Cy2DTPA, DTPA-MA, DTPA-BA, and BOPA.

In some embodiments, a chelator described herein comprises DOTA, DOTAGA, $DOTA(GA)_2$, DOTP, DOTMA, DOTAM, DTPA, NTA, EDTA, DO3A, DO2A, NOC, NOTA, TETA. TACN, DiAmSar, CB-Cyclam, CB-TE2A, DOTA-4AMP, or NOTP.

In some embodiments, a chelator described herein comprises HP-DO3A, BT-DO3A, DO3A-Nprop, DO3AP, DO2A2P, DOA3P, DOTP, DOTPMB, DOTAMAE, DOTAMAP, $DO3AM^{Bu}$, DOTMA, TCE-DOTA, DEPA, PCTA, $p\text{-}NO_2$-Bn-PCTA, $p\text{-}NO_2$-Bn-DOTA, symPC2APA, svmPCA2PA, asymPC2APA, asymPCA2PA, TRAP, AAZTA, $DATA^m$, THP, HEHA, HBED, or HBED-CC TFP.

In some embodiments, a chelator described herein comprises DOTA, NOTA, NODAGA, DOTAGA, HBED, HBED-CC TFP, H2DEPDPA, DFO-B, Deferiprone, CP256, YM103, TETA, CB-TE2A, TE2A, Sar, DiAmSar, TRAPH, TRAP-Pr, TRAP-OH, TRAP-Ph, NOPO, DEADPA, PCTA, EDTA, PEPA, HEHA, DTPA, EDTMP, AAZTA, DO3AP, $DO3AP^{PrA}$, $DO3AP^{ABn}$, or DOTAM.

In some embodiments, the chelator is or comprises DOTA, HBED-CC, DOTAGA, $DOTA(GA)_2$, NOTA, and DOTAM. In some embodiments, the chelator is or comprises NODAGA, NOTA, DOTAGA, $DOTA(GA)_2$, TRAP, NOPO, NCTA, DFO, DTPA, and HYNIC.

In some embodiments, the chelator comprises a macrocycle, e.g., a macrocycle comprising an O and/or a N atom, DOTA, HBED-CC , DOTAGA, $DOTA(GA)_2$, NOTA, DOTAM, one or more amines, one or more ethers, one or more carboxylic acids, EDTA, DTPA, TETA, DO3A, PCTA, or desferrioxamine.

In some embodiments, a metal chelator described herein comprises one of the following structures:

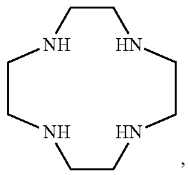
, (Cyclen)

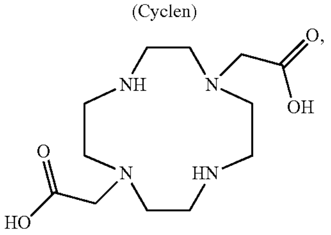

(DO2A)

-continued

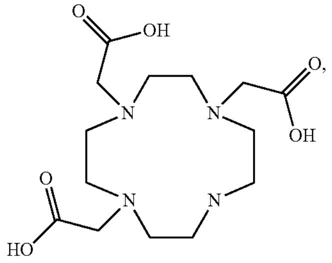

(DO3A)

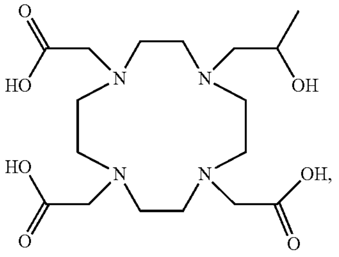

(HP-DO3A)

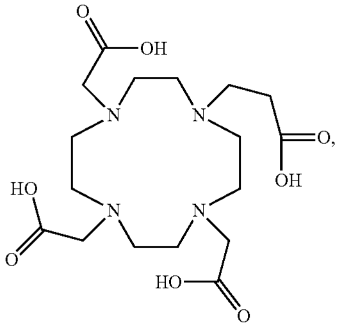

(DO3A-Nprop)

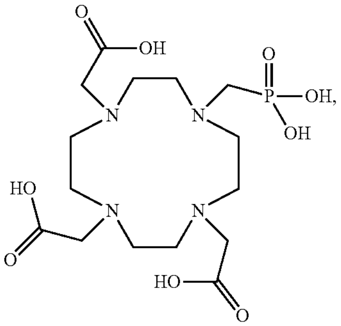

(DO3AP)

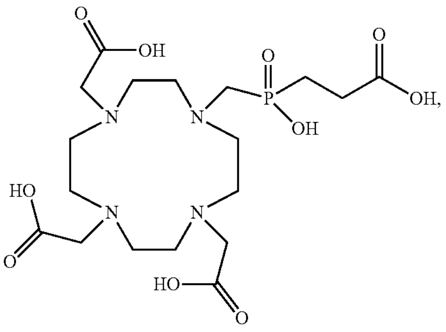

($DO3AP^{PrA}$)

-continued
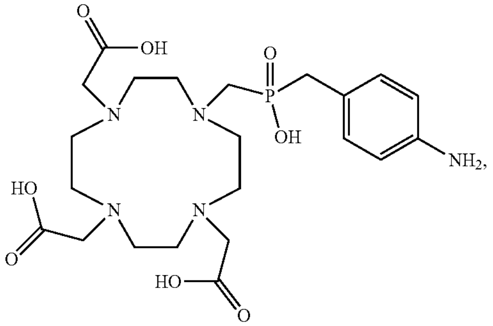
(DO3AP$^{ABn}$)
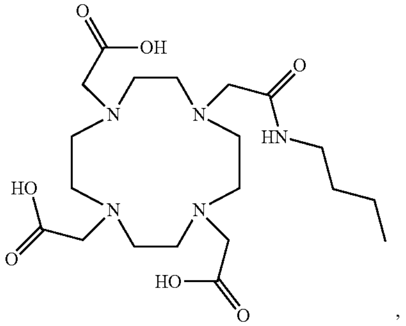
(DO3AM$^{nBu}$)
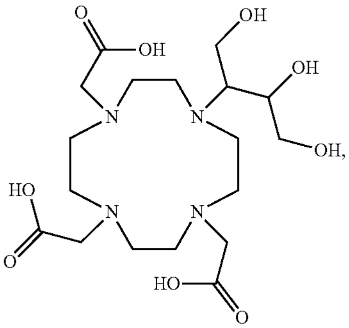
(BT-DO3A)
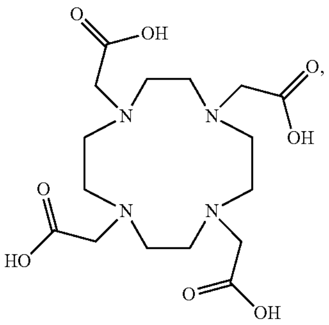
(DOTA)
-continued
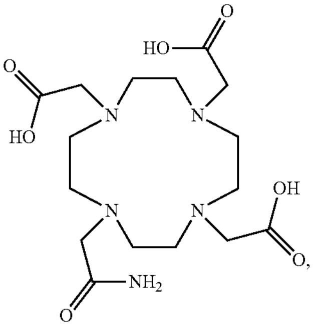
(PSC)
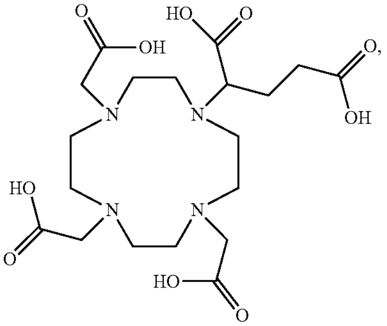
(DOTAGA)
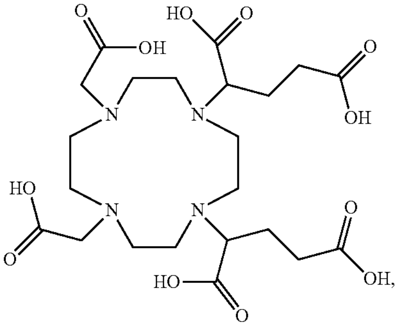
(DOTA(GA)$_2$)
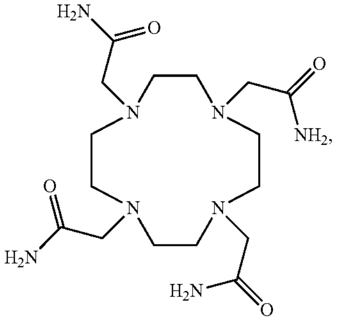
(DOTAM)
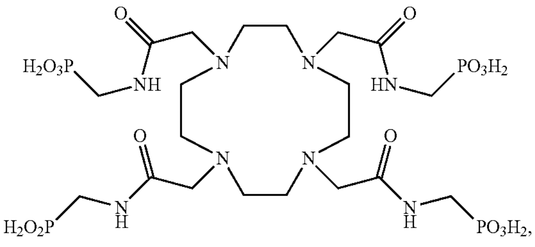
(DOTA-4AMP)

-continued
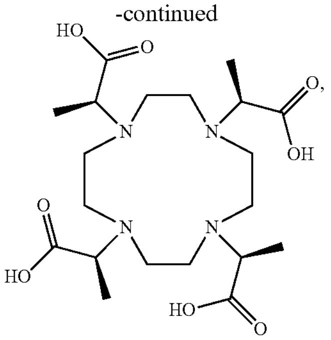
(DOTMA)
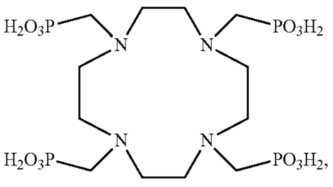
(DOTP)
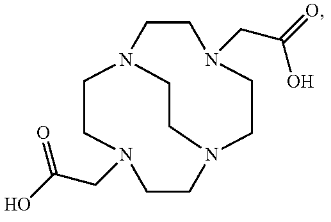
(CB-DO2A)
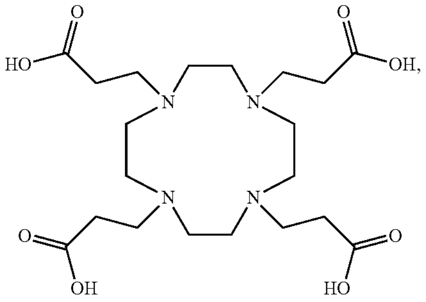
(DOTPA)
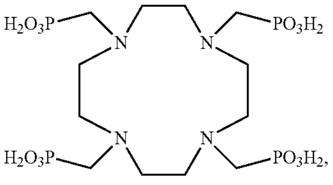
(DOTMP)
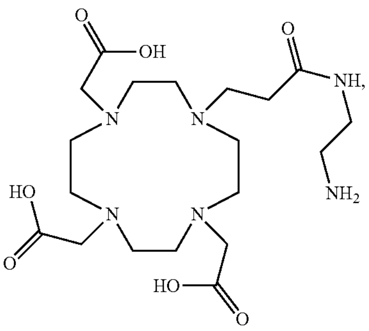
(DOTAMAP)
-continued
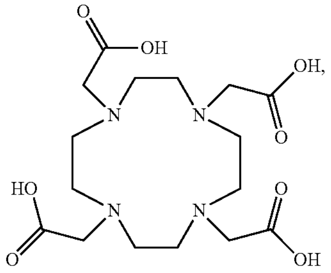
(TRITA)
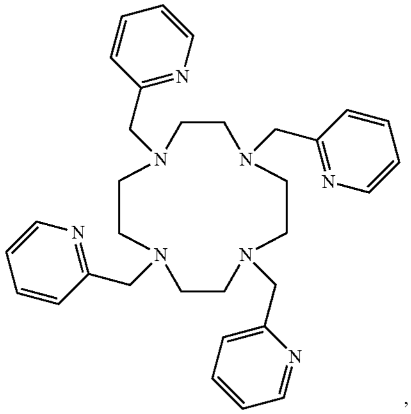
,
($L^{py}$)
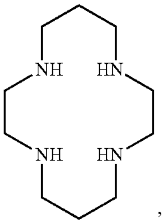
,
(cyclam)
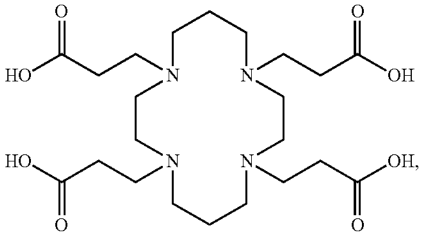
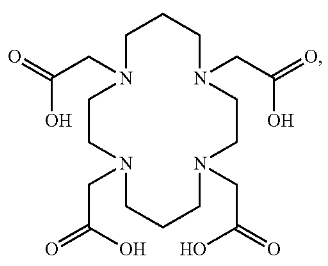
(TETA)

-continued
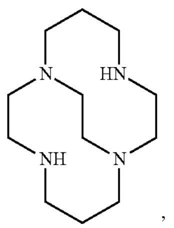
(CB-Cyclam)
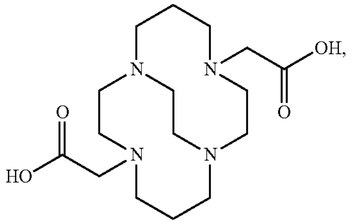
(CB-TE2A)
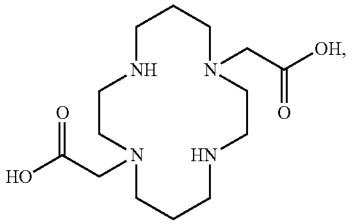
(TE2A)
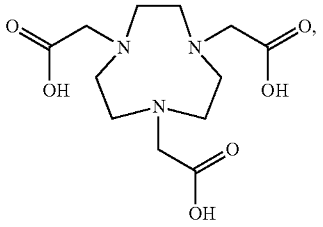
(NOTA)
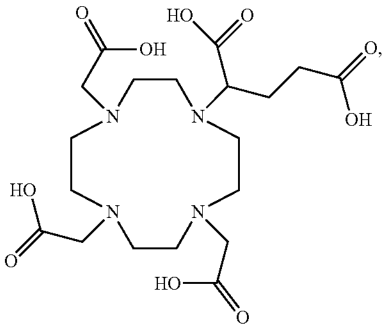
(NODAGA)
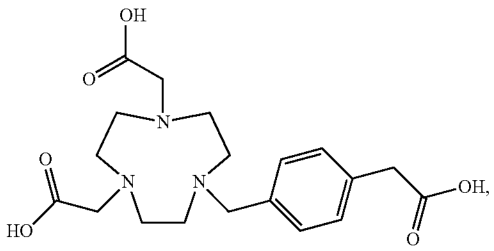
(NODA-MPAA)
-continued
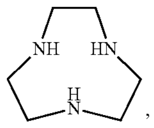
(TACN)
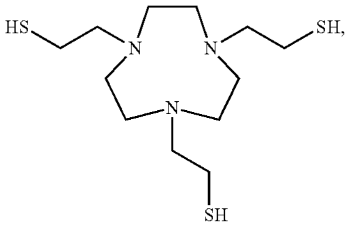
(TACN-TM)
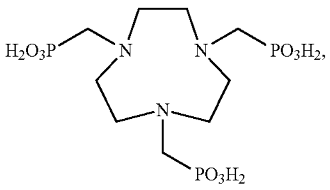
(NOTP)
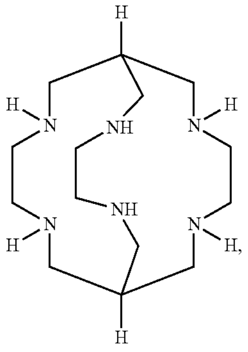
(Sar)
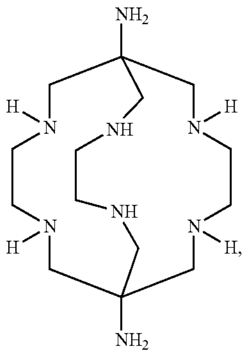
(DiAmSar)

-continued
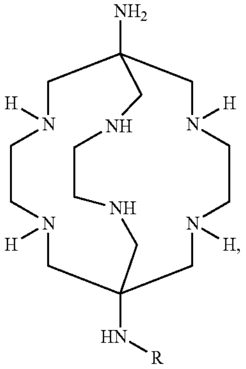
(SarAr, R = P—NH2—Bn;
AmBaSar = P—CO2H—Bn)
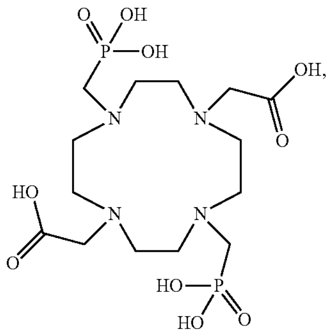
(*cis*-DO2A2P)
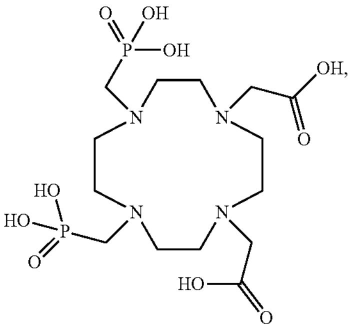
(*trans*-DO2A2P)
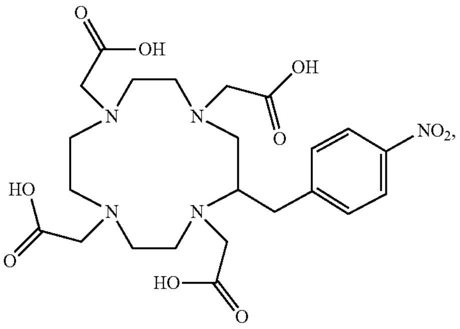
(p—NO2—Bn—DOTA)
-continued
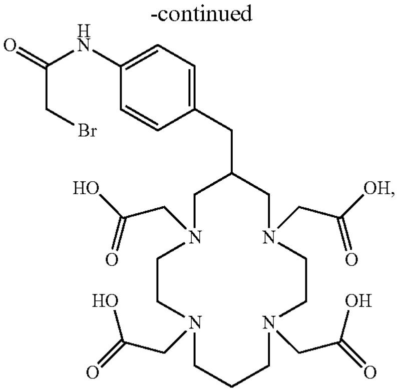
(BAT)
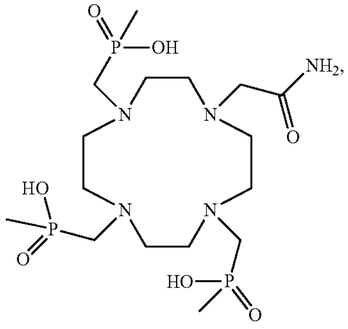
(DO3TMP-Monoamide)
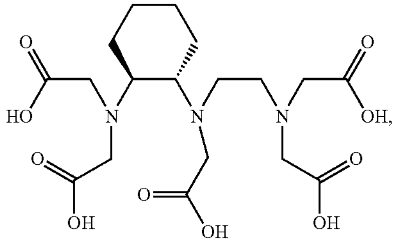
(CHX-A″-DTPA)
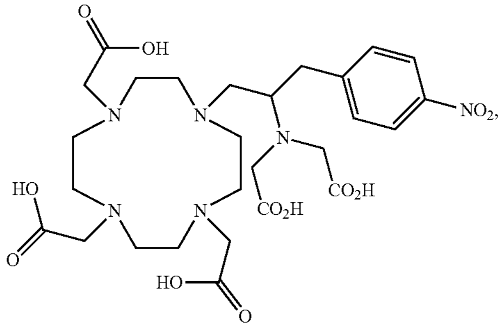
(c-DEPA)
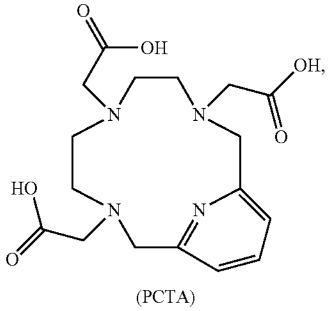
(PCTA)

-continued
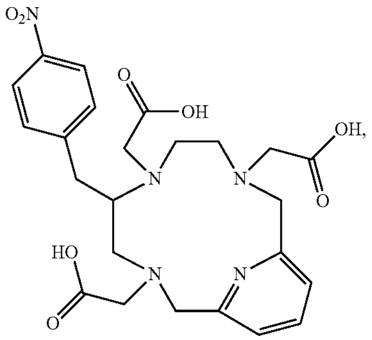
(p—$NO_2$—Bn—PCTA)
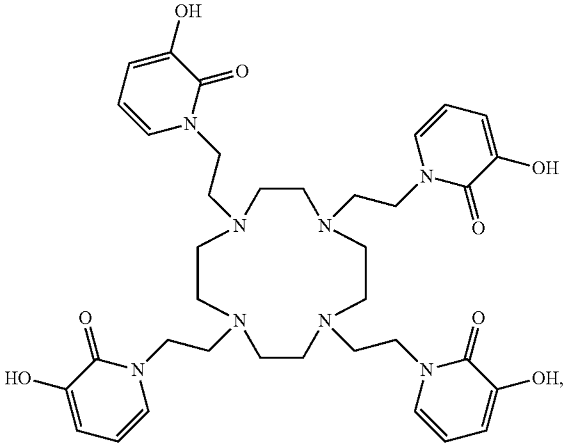
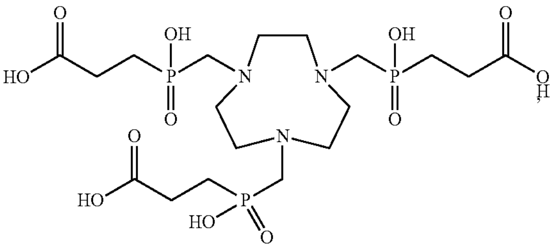
(TRAP)
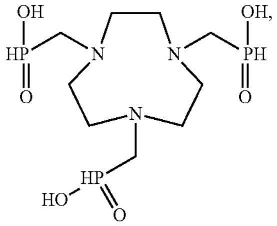
(TRAPH)
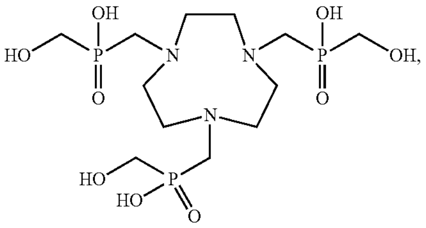
(TRAP—OH)
-continued
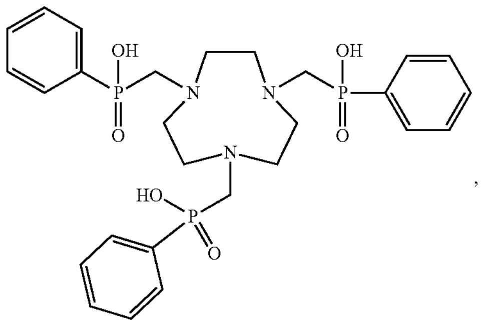
(TRAP—Ph)
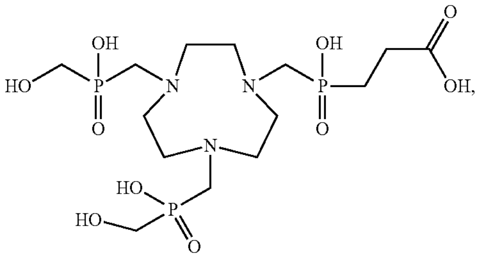
(NOPO)
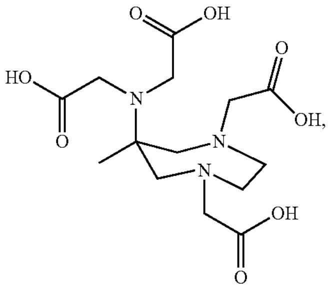
(AAZTA)
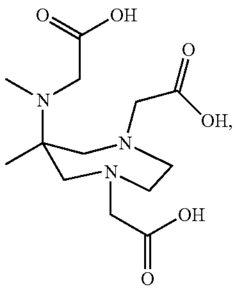
(DATAM)
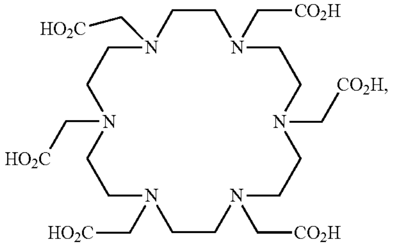
(HEHA)

-continued
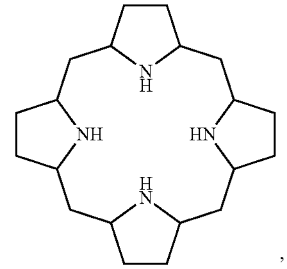
,
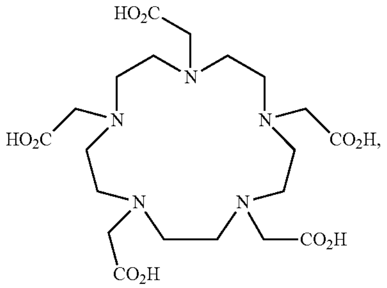
(PEPA)
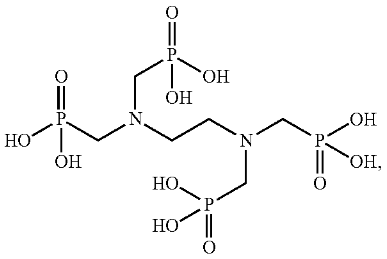
(EDTMP)
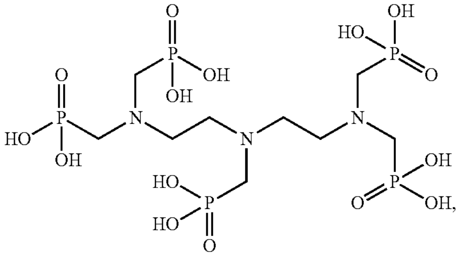
(DTPMP)
-continued
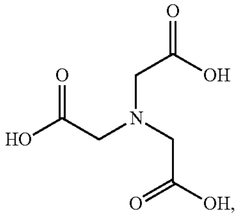
(NTA)
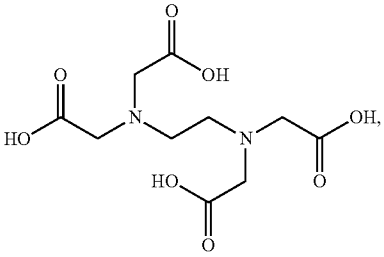
(EDTA)
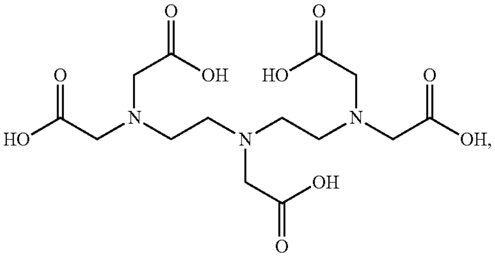
(DTPA)
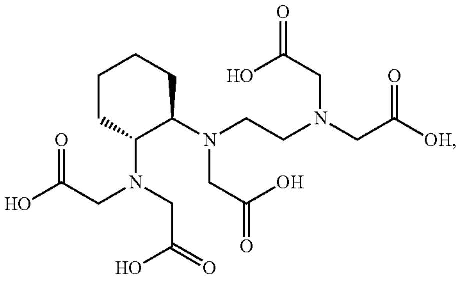
(CyDTPA)
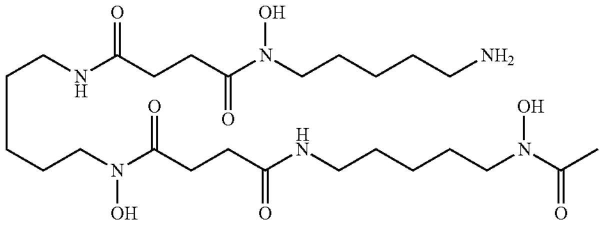
,
(DFO)

-continued
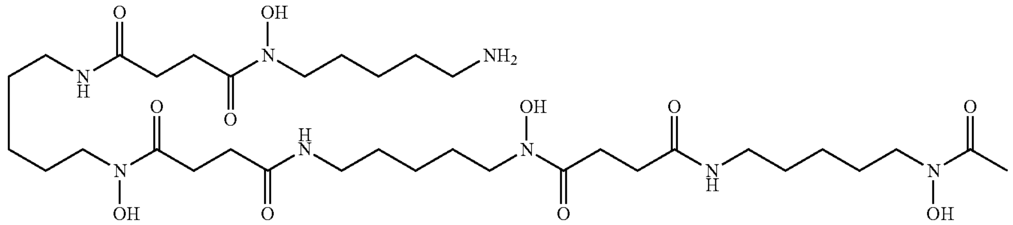
,
(DFO*)
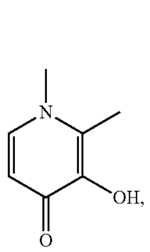
(deferiprone)
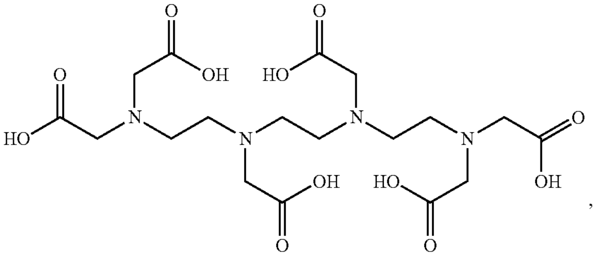
,
(TTHA)
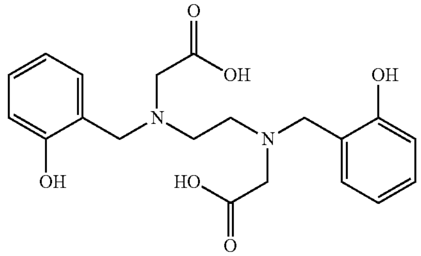
,
(HBED)
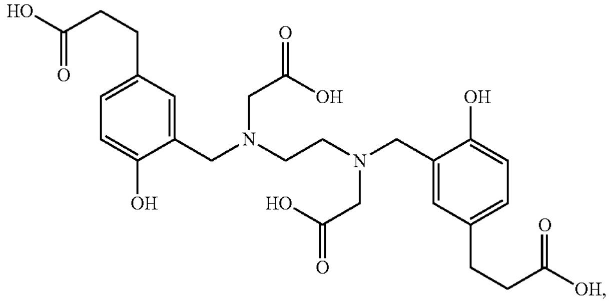
(HBED-CC)
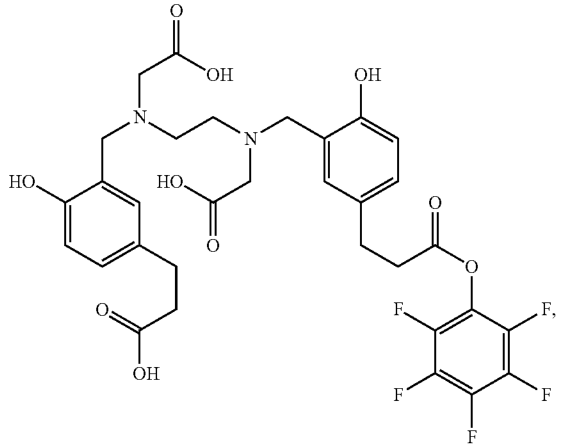
(HBED-CC-TFP)
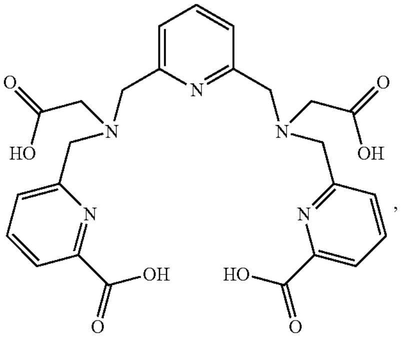
,
($H_4$pypa)

-continued
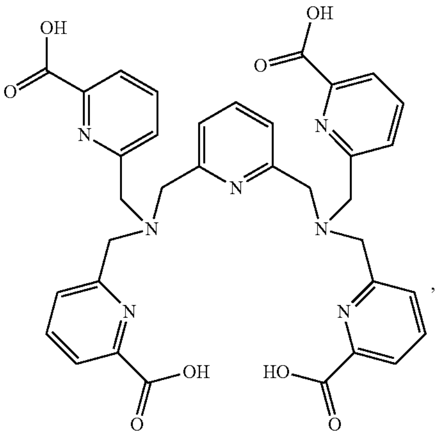
(H4py4pa)
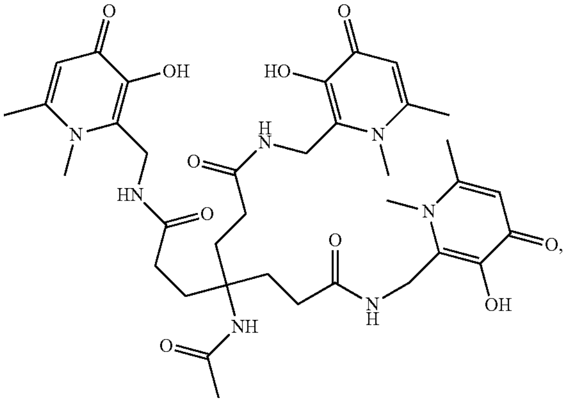
(CP256)
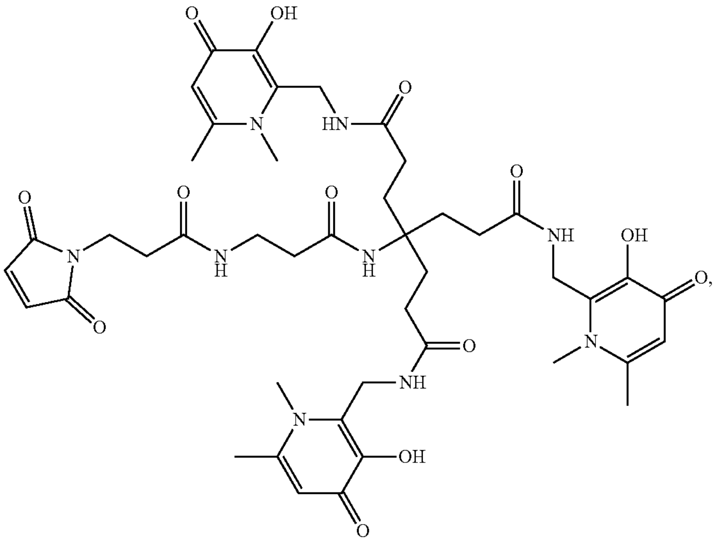
(YM103)
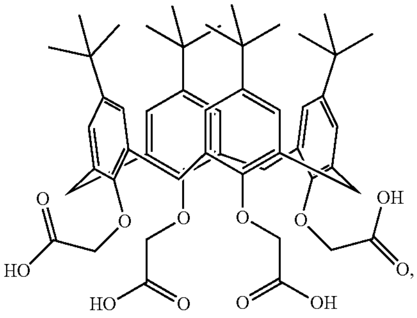
(t-Bu-calix[4]arene-tetracarboxylic acid)
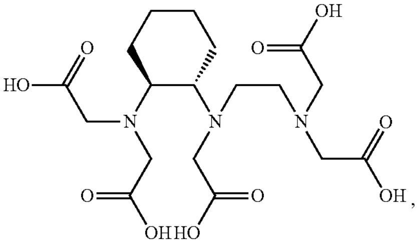
(CHX-A″-DTPA)

-continued
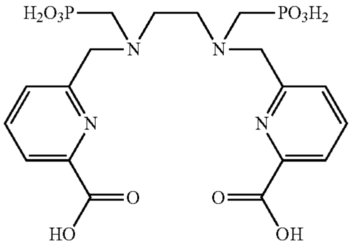
,
(H6phospha)
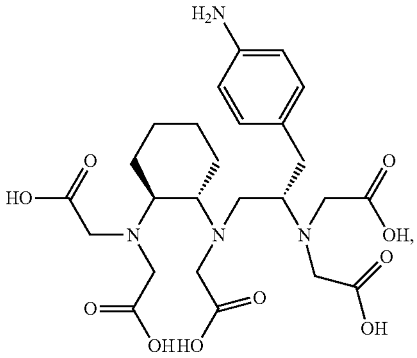
(p-NH2-Bn-CHXA″-DTPA)
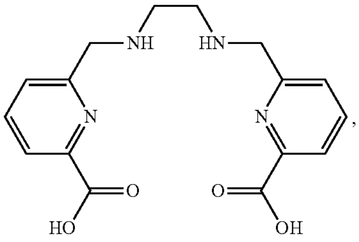
,
(DEDPA)
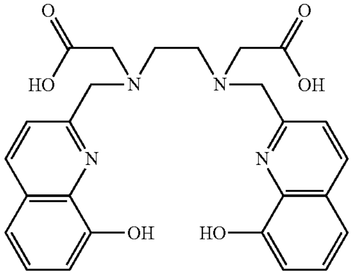
,
(H4octox)
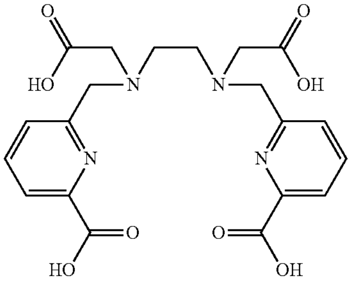
,
(H4octapa)
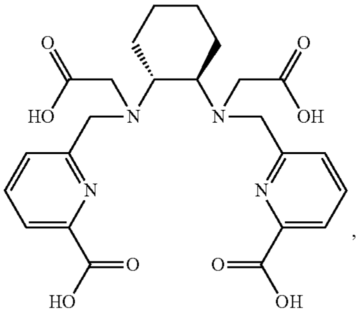
,
(H4CHXoctapa)
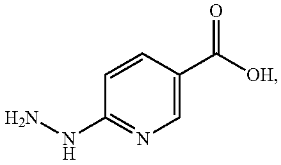
(HYNIC)
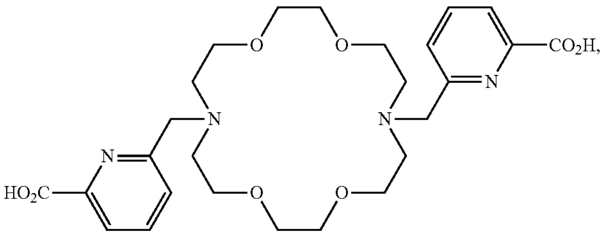
(macropa)
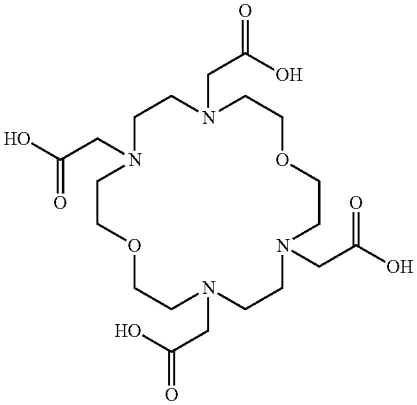
,
(crown)

-continued

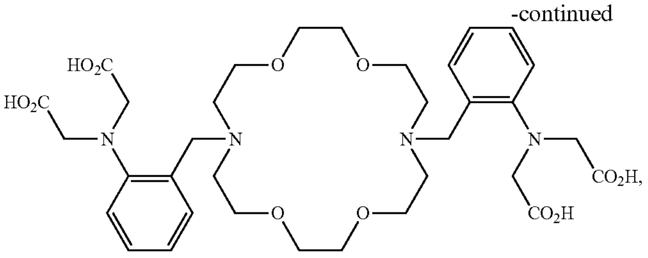

(macropid)

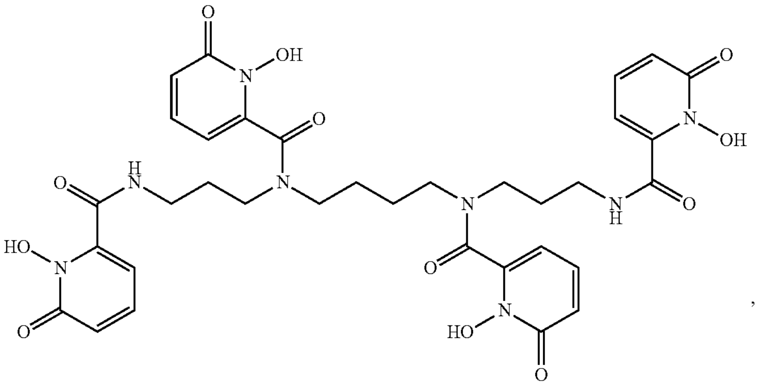

(HOPO)

,

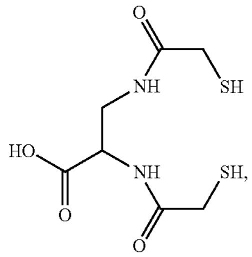

(Bis(2-mercaptoacetamide))

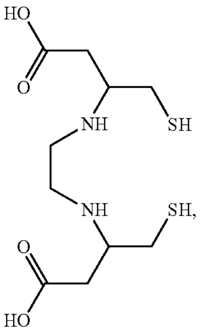

(Bis(aminothiolate))

or

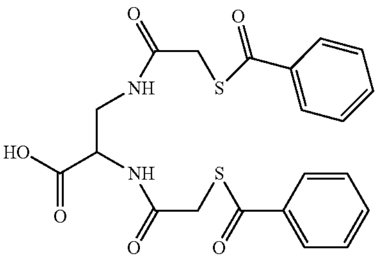

(SBTG$_2$DAP)

.

In some embodiments, the chelating moiety $R^a$ comprises a radionuclide and DOTA. In some embodiments, the chelating moiety $R^a$ comprises a radionuclide and a DOTA derivative. In some embodiments, the chelating moiety comprises two independent chelators, and at least one or both are DOTA.

In some embodiments, the chelating moiety comprises a radionuclide and a chelator configured to bind the radionuclide (Z'), wherein the chelator comprises DOTA, DOTP, DOTMA, DOTAM, DTPA, NOTA, NTA, NODAGA, EDTA, DO3A, DO2A, NOC, TETA, CB-TE2A, DiAmSar, CB-Cyclam, DOTA-4AMP, $H_4$pypa, $H_4$octox, $H_4$octapa, p-$NO_2$-Bn-neunpa, or NOTP.

In some embodiments, the metal chelator described herein comprises macropa or crown. In some embodiments, the metal chelator described herein comprises macropa. In some embodiments, the metal chelator described herein comprises crown. In some embodiments, the metal chelator described herein comprises

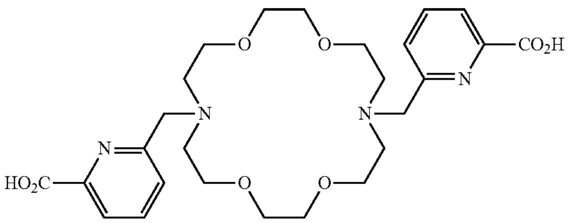 [SMILES: O=C(O)c1cccc(CN2CCOCCOCCN(Cc3cccc(C(=O)O)n3)CCOCCOCC2)n1]

(macropa). In some embodiments, the metal chelator described herein comprises

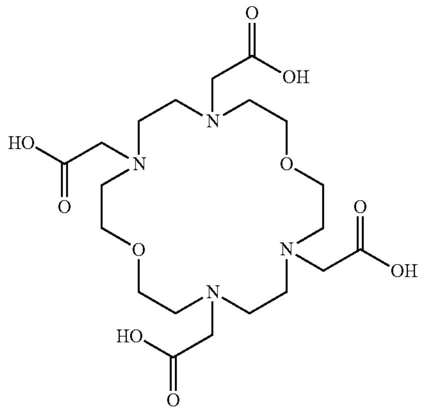 [SMILES: O=C(O)CN1CCOCCN(CC(=O)O)CCN(CC(=O)O)CCOCCN(CC(=O)O)CC1]

(crown).

In some embodiments, the chelating moiety of $R^a$ is independently selected from the group consisting of: cyclen, DO2A, DO3A, HP-DO3A, DO3A-Nprop, DO3AP, DO3AP$^{PrA}$ DO3AP$^{ABn}$, DO3AM$^{nBu}$, BT-DO3A, DOTA, DOTAGA, DOTA(GA)$_2$, DOTAM, DOTA-4AMP, DOTMA, DOTP, CB-DO2A, DOTPA, DOTMP, DOTAMAP, TRITA, L$^{py}$, cyclam, TETA, CB-Cyclam, CB-TE2A, TE2A, NOTA, NODAGA, NODA-MPAA, TACN, TACN-TM, NOTP, Sarcophagine (Sar), DiAmSar, SarAr, AmBaSar, cis-DO2A2P, trans-DO2A2P, DOTEP, p-$NO_2$-Bn-DOTA, BAT, DO3TMP-Monoamide, CHX-A"-DTPA, c-DEPA, PCTA, p-$NO_2$-Bn-PCTA, TRAP, TRAPH, TRAP-OH, TRAP-Ph, NOPO, AAZTA, DATAM, HEHA, PEPA, DTA, EDTMP, DTPMP, NTA, EDTA, DTPA, CyDTPA, DFO, DFO*, deferiprone, TTHA, HBED, HBED-CC , HBED-CC TFP, $H_4$pypa, $H_4$py4pa, CP256, THP, YM103, t-Bu-calix[4]arene-tetracarboxylic acid, CHX-A"-DTPA, $H_6$phospha, p-$NH_2$-Bn-CHXA"-DTPA, DEDPA, $H_4$octox, $H_4$octapa, $H_4$CHXoctapa, HYNIC, macropa, crown, macropid, HOPO, Bis(2-mercaptoacetamide), Bis (aminothiolate), and SBTG$_2$DAP.

In some embodiments, $R^a$ is a chelating moiety selected from the group consisting of: DOTA; 2,2',2"-(10-(2-amino-2-oxoethyl)-1,4,7,10-tetraazacyclododecane-1,4,7-triyl)triacetic acid (PSC); DO3A; DO2A; DOTMA; DOTAM; DOTPA; 2,2',2"-(10-(2-amino-2-oxoethyl)-1,4,7,10-tetraazacyclododecane-1,4,7-triyl)triacetic acid; Bn-DOTA; p-OH-Bn-DOTA; -$H_4$pypa; $H_4$pypa-benzyl; $H_4$py4pa; -$H_4$py4pa-benzyl; NOTA; macropa; crown; $H_4$octapa; H4octapa-benzyl; and TTHA; or a radionuclide complex thereof.

In some embodiments, the chelating moiety of $R^a$ is independently selected from the group consisting of: 1,4,7,10-tetraazacyclododecane-1,4,7,10-tetraacetic acid (DOTA); 1,4,7,10-tetraazacyclododecane-1,4,7-triacetic acid (DO3A); 1,4,7,10-tetraazacyclododecane-1,7-diacetic acid (DO2A); α,α',α",α'"-tetramethyl-1,4,7,10-tetraazacyclododecane-1,4,7,10-tetraacetic acid (DOTMA); 1,4,7,10-tetrakis(carbamoylmethyl)-1,4,7,10-tetraazacyclododecane (DOTAM); 1,4,7,10-tetraazacyclododecane-1,4,7,10-tetrapropionic acid (DOTPA); 2,2',2"-(10-(2-amino-2-oxoethyl)-1,4,7,10-tetraazacyclododecane-1,4,7-triyl)triacetic acid; benzyl-1,4,7,10-tetraazacyclododecane-1,4,7,10-tetraacetic acid (Bn-DOTA); p-hydroxy-benzyl-1,4,7,10-tetraazacyclododecane-1,4,7,10-tetraacetic acid (p-OH-Bn-DOTA); 6,6'-(((pyridine-2,6-diylbis(methylene))bis((carboxymethyl)azanediyl))bis(methylene))dipicolinic acid ($H_4$pypa); $H_4$pypa-benzyl; 6,6',6",6'"-(((pyridine-2,6-diylbis(methylene))bis(azanetriyl))tetrakis(methylene))-tetrapicolinic acid ($H_4$py4pa); $H_4$py4pa-benzyl; 2,2',2"-(1,4,7-triazacyclononane-1,4,7-triyl)triacetic acid (NOTA); 6,6'-((1,4,10,13-tetraoxa-7,16-diazacyclooctadecane-7,16-diyl)bis(methylene))dipicolinic acid (macropa); 2,2',2",2'"-(1,10-dioxa-4,7,13,16-tetraazacyclooctadecane-4,7,13,16-tetrayl)tetraacetic acid (crown); 6,6'-((ethane-1,2-diylbis((carboxymethyl)azanediyl))bis(methylene))dipicolinic acid ($H_4$octapa); $H_4$octapa-benzyl; and 3,6,9,12-tetrakis(carboxymethyl)-3,6,9,12-tetraazatetradecanedioic acid (TTHA); or a radionuclide complex thereof.

In some embodiments, the chelating moiety of $R^a$ is independently selected from the group consisting of: DOTA; DO3A, DO2A; DOTMA; DOTAM; DOTPA; 2,2',2"-(10-(2-amino-2-oxoethyl)-1,4,7,10-tetraazacyclododecane-1,4,7-triyl)triacetic acid; $H_4$pypa; $H_4$py4pa; NOTA; macropa; crown; $H_4$octapa; and TTHA; or a radionuclide complex thereof.

In some embodiments, $R^a$ is DOTA or a radionuclide complex thereof. In some embodiments, $R^a$ is DO3A or a radionuclide complex thereof. In some embodiments, $R^a$ is DO2A or a radionuclide complex thereof. In some embodiments, $R^a$ is DOTMA or a radionuclide complex thereof. In some embodiments, $R^a$ is DOTAM or a radionuclide complex thereof. In some embodiments, $R^a$ is DOTPA or a radionuclide complex thereof. In some embodiments, $R^a$ is 2,2',2"-(10-(2-amino-2-oxoethyl)-1,4,7,10-tetraazacyclododecane-1,4,7-triyl)triacetic acid or a radionuclide complex thereof. In some embodiments, $R^a$ is $H_4$pypa or a radionuclide complex thereof. In some embodiments, $R^a$ is $H_4$py4pa or a radionuclide complex thereof. In some embodiments, $R^a$ is NOTA or a radionuclide complex thereof. In some embodiments, $R^a$ is macropa or a radionuclide complex thereof. In some embodiments, $R^a$ is crown or a radionuclide complex thereof. In some embodiments, $R^a$ is $H_4$octapa or a radionuclide complex thereof. In some embodiments, $R^a$ is TTHA or a radionuclide complex thereof.

In some embodiments, $R^a$ is: DOTA or DO3A; or a radionuclide complex thereof.

In some embodiments, the chelating moiety of $R^a$ is independently selected from the group consisting of: DOTA; DO3A; DO2A; DOTMA; DOTAM; DOTPA; 2,2',2"-(10-(2-amino-2-oxoethyl)-1,4,7,10-tetraazacyclododecane-1,4,7-triyl)triacetic acid; $H_4$pypa; $H_4$py4pa; NOTA; macropa; crown; $H_4$octapa; and TTHA; or a radionuclide complex thereof.

In some embodiments, $R^a$ is DOTA or a radionuclide complex thereof. In some embodiments, $R^a$ is DO3A or a radionuclide complex thereof. In some embodiments, $R^a$ is DO2A or a radionuclide complex thereof. In some embodiments, $R^a$ is DOTMA or a radionuclide complex thereof. In some embodiments, $R^a$ is DOTAM or a radionuclide complex thereof. In some embodiments, $R^a$ is DOTPA or a radionuclide complex thereof. In some embodiments, $R^a$ is 2,2',2"-(10-(2-amino-2-oxoethyl)-1,4,7,10-tetraazacyclododecane-1,4,7-triyl)triacetic acid or a radionuclide complex thereof. In some embodiments, $R^a$ is $H_4$pypa or a radionuclide complex thereof. In some embodiments, $R^a$ is $H_4$py4pa or a radionuclide complex thereof. In some embodiments, $R^a$ is NOTA. In some embodiments, $R^a$ is macropa. In some embodiments, $R^a$ is crown. In some embodiments, $R^a$ is $H_4$octapa or a radionuclide complex thereof. In some embodiments, $R^a$ is TTHA or a radionuclide complex thereof.

In some embodiments, the chelating moiety of $R^a$ is: DOTA or DO3A; or a radionuclide complex thereof.

In some embodiments, $R^a$ is a chelating moiety selected from the group consisting of:

(CM-1)

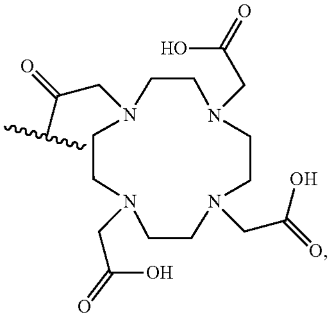

(CM-2)

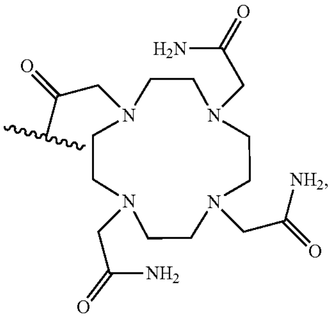

(CM-3)

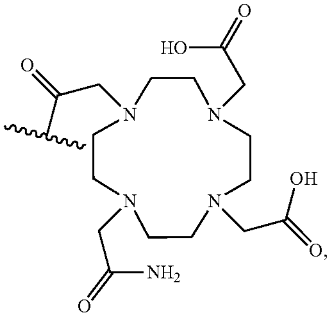

(CM-4)

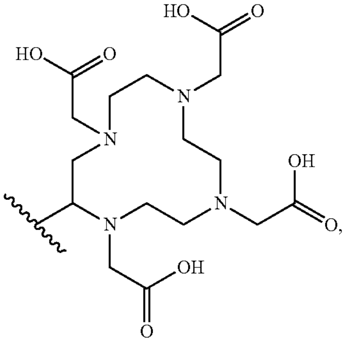

and

-continued (CM-5)

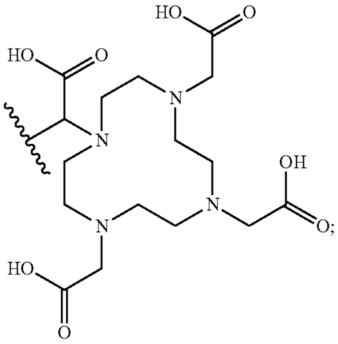

or a radionuclide complex thereof.

In some embodiments, $R^a$ is a chelating moiety selected from the group consisting of: (CM-1), (CM-2), (CM-4) and (CM-5); or a radionuclide complex thereof.

In some embodiments, $R^a$ is (CM-1)

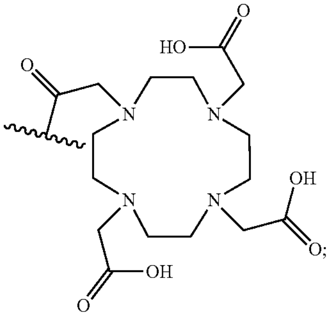

or a radionuclide complex thereof.

In some embodiments, $R^a$ is: (CM-2), (CM-3), (CM-4), or (CM-5); or a radionuclide complex thereof.

In some embodiments, $R^a$ is (CM-2), (CM-4), or (CM-5); or a radionuclide complex thereof.

In some embodiments, $R^a$ is: (CM-2); or a radionuclide complex thereof. In some embodiments, $R^a$ is: (CM-3); or a radionuclide complex thereof. In some embodiments, $R^a$ is: (CM-5); or a radionuclide complex thereof.

In some embodiments, $R^a$ is:

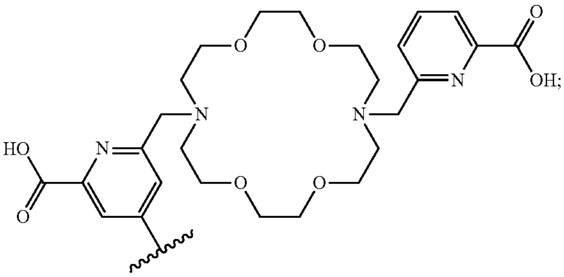 [SMILES: *c1cc(CN2CCOCCOCCN(Cc3cccc(C(=O)O)n3)CCOCCOCC2)nc(C(=O)O)c1]

or a radionuclide complex thereof. In some embodiments, $R^a$ is:

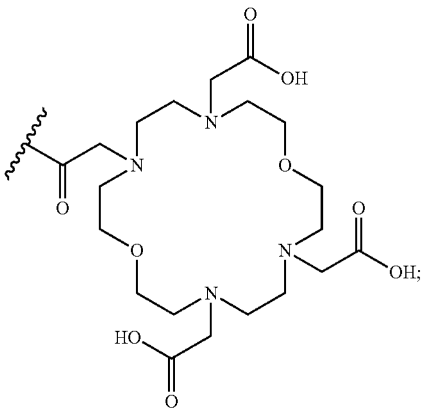 [SMILES: *C(=O)CN1CCOCCN(CC(=O)O)CCN(CC(=O)O)CCOCCN(CC(=O)O)CC1]

or a radionuclide complex thereof.

In some embodiments, $R^a$ is:

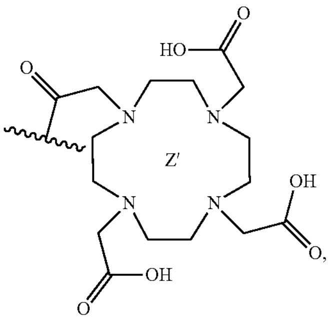

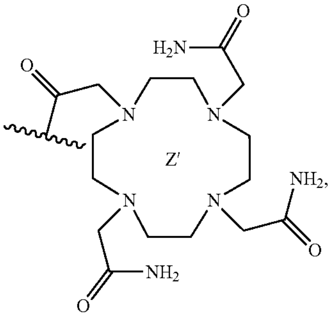

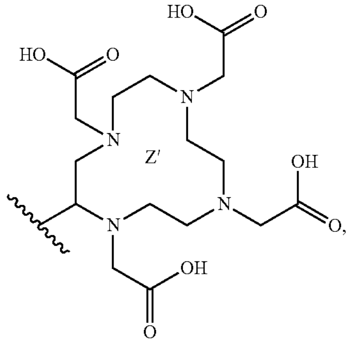

or

-continued

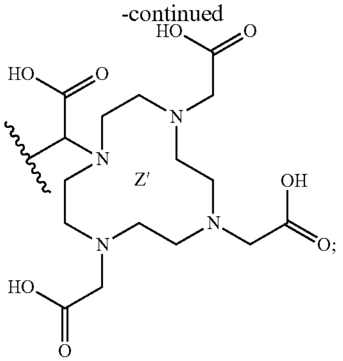

wherein Z' is a diagnostic or therapeutic radionuclide.

In some embodiments, $R^a$ is:

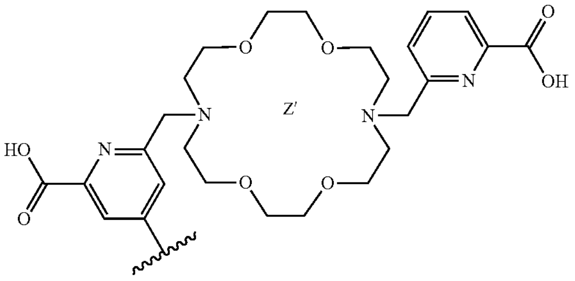

or

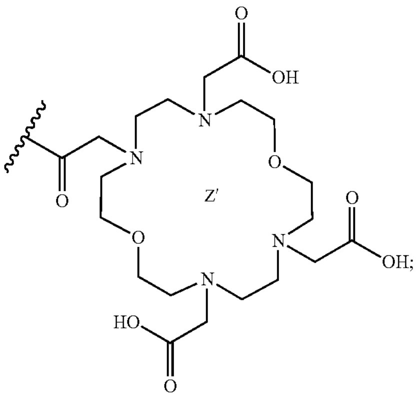

wherein Z' is a diagnostic or therapeutic radionuclide.

In some embodiments, Z' is an Auger electron-emitting radionuclide, c-emitting radionuclide, β-emitting radionuclide, or γ-emitting radionuclide. In some embodiments, Z' is an Auger electron-emitting radionuclide that is 111-indium ($^{111}In$), 67-gallium ($^{67}Ga$), 68-gallium ($^{68}Ga$), 99m-technetium ($^{99m}Tc$), 64-copper ($^{64}Cu$), or 195m-platinum ($^{195}Pt$).

In some embodiments, Z' is an α-emitting radionuclide that is 225-actinium ($^{225}Ac$), 213-bismuth ($^{213}Bi$), 223-Radium ($^{223}Ra$), or 212-lead ($^{212}Pb$). In some embodiments, Z' is a β-emitting radionuclide that is 90-yttrium ($^{90}Y$), 177-lutetium ($^{177}Lu$), iodine-131 ($^{131}$) 186-rhenium ($^{186}Re$), 188-rhenium ($^{188}Re$), 64-copper ($^{64}Cu$), 67-copper ($^{67}Cu$), 153-samarium ($^{153}Sm$), 89-strontium ($^{89}Sr$), 198-gold ($^{198}Au$), 169-Erbium ($^{169}Er$), 165-dysprosium ($^{165}Dy$), 99m-technetium ($^{99m}Tc$), 89-zirconium ($^{89}Zr$), or 52-manganese ($^{52}Mn$).

In some embodiments, Z' is a γ-emitting radionuclide that is 60-cobalt ($^{60}Co$), 103-palladium ($^{103}Pd$), 137-cesium ($^{137}Cs$), 169-ytterbium ($^{169}Yb$), 192-iridium ($^{192}Ir$), or 226-radium ($^{226}Ra$).

In some embodiments, $R^a$ comprises a radionuclide (Z') and a chelator configured to bind the radionuclide (Z'), wherein the radionuclide is suitable for positron emission tomography (PET) analysis, single-photon emission computerized tomography (SPECT), or magnetic resonance imaging (MRI). In some embodiments, the radionuclide is copper-64 ($^{64}Cu$), gallium-68 ($^{68}Ga$), 111-indium ($^{111}In$), or technetium-99m ($^{99m}Tc$).

Metals (Radionuclides)

In some embodiments, Z' is an Auger electron-emitting radionuclide. In some embodiments, Z' is an α-emitting radionuclide. In some embodiments, Z' is a β-emitting radionuclide. In some embodiments, Z' is a γ-emitting radionuclide. In some embodiments, the type of radionuclide used in a peptide targeted therapeutic compound can be tailored to the specific type of cancer, the type of targeting moiety (e.g., peptide ligand), etc. Radionuclides that undergo α-decay emit α-particles (helium ions with a +2 charge) from their nuclei. As a result of α-decay the daughter nuclide has 2 protons less and 2 neutrons less than the parent nuclide. This means that in α-decay, the proton number is reduced by 2 while the nucleon number is reduced by 4. Radionuclides that undergo β-decay emit β-particles (electrons) from their nuclei. During β-decay, one of the neutrons changes into a proton and an electron. The proton remains in the nucleus while the electron is emitted as a β-particle. This means that in β-decay, the nucleus loses a neutron but gains a proton. In γ-decay, a nucleus in an excited state (higher energy state) emits a γ-ray photon to change to a lower energy state. There is no change in the proton number and nucleon number during the γ-decay. The emission of γ-rays often accompanies the emission of α-particles and β-particles.

Auger electrons (AEs) are very low energy electrons that are emitted by radionuclides that decay by electron capture (EC) (e.g. $^{111}In$, $^{67}Ga$, $^{99m}Tc$, $^{195m}Pt$, $^{125}I$ and $^{123}I$). This energy is deposited over nanometer-micrometer distances, resulting in high linear energy transfer that is potent for causing lethal damage in cancer cells. Thus, AE-emitting radiotherapeutic agents have great potential for treatment of cancer.

β-Particles are electrons emitted from the nucleus. They typically have a longer range in tissue (of the order of 1-5 mm) and are the most frequently used.

α-Particles are helium nuclei (two protons and two neutrons) that are emitted from the nucleus of a radioactive atom. Depending on their emission energy, they can travel 50-100 μm in tissue. They are positively charged and are orders of magnitude larger than electrons. The amount of energy deposited per path length travelled (designated 'linear energy transfer') of a-particles is approximately 400 times greater than that of electrons. This leads to substantially more damage along their path than that caused by electrons. An α-particle track leads to a preponderance of complex and largely irreparable DNA double-strand breaks. The absorbed dose required to achieve cytotoxicity relates to the number of α-particles traversing the cell nucleus. With use of this as a measure, cytotoxicity may be achieved with a range of 1 to 20 α-particle traversals of the cell nucleus. The resulting high potency, combined with the short range of α-particles (which reduces normal organ toxicity), has led to substantial interest in developing α-particle-emitting agents. The α-particle emitters typically used include bismuth-212, lead-212, bismuth-213, actinium-225, radium-223 and thorium-227.

In some embodiments, Z' is a diagnostic or therapeutic radionuclide.

Representative Radionuclides

| Isotope | Radionuclide $t_{1/2}$ (h) | Decay mode |
|---|---|---|
| $^{60}Cu$ | 0.4 | β+ (93%), EC (7%) |
| $^{61}Cu$ | 3.3 | β+ (62%), EC (38%) |
| $^{62}Cu$ | 0.16 | β+ (98%), EC (2%) |
| $^{64}Cu$ | 12.7 | β+ (19%), EC (41%), β− (40%) |
| $^{67}Cu$ | 61.9 | |
| $^{66}Ga$ | 9.5 | β+ (56%), EC (44%) |
| $^{67}Ga$ | 78.2 | EC (100%) |
| $^{68}Ga$ | 1.1 | β+ (90%), EC (10%) |
| $^{44}Sc$ | 3.9 | β+ (94%), EC (6%) |
| $^{47}Sc$ | 80.2 | β− (100%) |
| $^{111}In$ | 67.2 | EC (100%) |
| $^{114m}In$ | 49.5 d | EC (100%) |
| $^{114}In$ (daughter) | 73 s | β− (100%) |
| $^{177}Lu$ | 159.4 | β− (100%) |
| $^{86}Y$ | 14.7 | β+ (33%), EC (66%) |
| $^{90}Y$ | 64.1 | β− (100%) |
| $^{89}Zr$ | 78.5 | β+ (23%), EC (77%) |
| $^{212}Bi$ | 1.1 | α (36%), β− (64%) |
| $^{213}Bi$ | 0.76 | α (2.2%), β− (97.8%) |
| $^{212}Pb$ (daughter is $^{212}Bi$) | 10.6 | β− (100%) |
| $^{225}Ac$ | 240 | α (100%) |
| $^{227}Th$ | 448.8 | α |
| $^{211}At$ | 7.2 | α |

In some embodiments, Z' is an Auger electron-emitting radionuclide. In some embodiments, Z' is an Auger electron-emitting radionuclide that is 111-indium ($^{111}In$), 67-gallium ($^{67}Ga$), 68-gallium ($^{68}Ga$), 99m-technetium ($^{99m}Tc$), or 195m-platinum ($^{195m}Pt$).

In some embodiments, Z' is an α-emitting radionuclide. In some embodiments, Z' is an α-emitting radionuclide that is 225-actinium ($^{225}Ac$), 213-bismuth ($^{213}Bi$), 223-Radium ($^{223}Ra$), or 212-lead ($^{212}Pb$).

In some embodiments, Z' is a β-emitting radionuclide. In some embodiments, Z' is a β-emitting radionuclide that is 90-yttrium ($^{90}Y$), 177-lutetium ($^{177}Lu$) 186-rhenium ($^{186}Re$), 188-rhenium ($^{188}Re$), 64-copper ($^{64}Cu$), 67-copper ($^{67}Cu$), 153-samarium ($^{153}Sm$), 89-strontium ($^{89}Sr$), 198-gold ($^{198}Au$), 169-Erbium ($^{169}Er$), 165-dysprosium ($^{165}Dy$), 99m-technetium ($^{99m}Tc$), 89-zirconium ($^{89}Zr$), or 52-manganese ($^{52}Mn$).

In some embodiments, Z' is a γ-emitting radionuclide. In some embodiments, Z' is a γ-emitting radionuclide that is 60-cobalt ($^{60}Co$), 103-pallidum ($^{103}Pd$), 137-cesium ($^{137}C$), 169-ytterbium ($^{169}Yb$), 192-iridium ($^{192}Ir$), or 226-radium ($^{226}Ra$).

In some embodiments, Z' is an Auger electron-emitting radionuclide that is 111-indium ($^{111}In$), 67-gallium ($^{67}Ga$), 68-gallium ($^{68}Ga$), 99m-technetium ($^{99m}Tc$), or 195m-platinum ($^{195m}Pt$); or Z' is an α-emitting radionuclide that is 225-actinium ($^{225}Ac$), 213-bismuth ($^{213}Bi$), 223-Radium ($^{223}Ra$), or 212-lead ($^{212}Pb$); or Z' is a β-emitting radionuclide that is 90-yttrium ($^{90}Y$), 177-lutetium ($^{177}Lu$), 186-rhenium ($^{186}Re$), 188-rhenium ($^{188}Re$), 64-copper ($^{64}Cu$), 67-copper ($^{67}Cu$), 153-samarium ($^{153}Sm$), 89-strontium ($^{89}Sr$), 198-gold ($^{198}Au$), 169-Erbium ($^{169}Er$), 165-dysprosium ($^{165}Dy$) 99m-technetium ($^{99m}Tc$), 89-zirconium ($^{89}Zr$), or 52-manganese ($^{52}Mn$); or Z' is a γ-emitting radionuclide that is 60-cobalt ($^{60}Co$), 103-pallidum ($^{103}Pd$), 137-cesium ($^{137}Cs$), 169-ytterbium ($^{169}Yb$), 192-iridium ($^{192}Ir$), or 226-radium ($^{226}Ra$).

In some embodiments, Z' is 90-yttrium ($^{90}Y$), 177-lutetium ($^{177}Lu$), 186-rhenium ($^{186}Re$), 188-rhenium ($^{188}Re$), 67-copper ($^{67}Cu$), 153-samarium ($^{153}Sm$), 89-strontium ($^{89}Sr$), 198-gold ($^{198}Au$), 169-Erbium ($^{169}Er$), 165-dysprosium ($^{165}Dy$), or technetium-99m ($^{99m}Tc$).

In some embodiments, Z' is $^{94}Tc$, $^{90}In$, $^{111}In$, $^{67}Ga$, $^{68}Ga$, $^{86}Y$, $^{90}Y$, $^{177}Lu$, $^{161}Tb$, $^{186}Re$, $^{188}Re$, $^{64}Cu$, $^{67}Cu$, $^{55}Co$, $^{57}Co$, $^{43}Sc$, $^{44}Sc$, $^{47}Sc$, $^{225}Ac$, $^{213}Bi$, $^{212}Bi$, $^{212}Pb$, $^{227}Th$, $^{153}Sm$, $^{160}Ho$, $^{152}Gd$, $^{153}Gd$, $^{157}Gd$, and $^{166}Dy$.

In some embodiments, Z' is $^{67}Cu$, $^{64}Cu$, $^{90}Y$, $^{109}Pd$, $^{111}Ag$, $^{149}Pm$, $^{153}Sm$, $^{166}Ho$, $^{99m}Tc$, $^{67}Ga$, $^{68}Ga$, $^{111}In$, $^{90}Y$, $^{177}Lu$, $^{186}Re$, $^{188}Re$, $^{197}Au$, $^{198}Au$, $^{199}Au$, $^{105}Rh$, $^{165}Ho$, $^{161}Tb$, $^{149}Pm$, $^{44}Sc$, $^{47}Sc$, $^{70}As$, $^{71}As$, $^{72}As$, $^{73}As$, $^{74}As$, $^{76}As$, $^{77}As$, $^{212}Pb$, $^{212}Bi$, $^{213}Bi$, $^{225}Ac$, $^{117m}Sn$, $^{67}Ga$, $^{201}Tl$, $^{160}Gd$, $^{148}Nd$, and $^{89}Sr$.

In some embodiments, Z' is $^{68}Ga$, $^{43}Sc$, $^{44}Sc$, $^{47}Sc$, $^{177}Lu$, $^{161}Tb$, $^{225}Ac$, $^{213}Bi$, $^{212}Bi$, or $^{212}Pb$. In some embodiments, Z' is $^{67}Ga$, $^{99m}Tc$, $^{111}In$, or $^{201}Tl$.

In some embodiments, the radionuclide (Z') is $^{44}Sc$, $^{64}Cu$, $^{67}Ga$, $^{68}Ga$, $^{86}Y$, $^{89}Zr$, $^{99m}Tc$, $^{111}In$, or $^{177}Lu$.

In some embodiments, Z' is $^{44}Sc$, $^{64}Cu$, $^{68}Ga$, $^{86}Y$ or $^{89}Zr$. In some embodiments, Z' is $^{67}Ga$, $^{99m}Tc$, $^{111}In$, $^{177}Lu$.

In some embodiments, Z' is $^{67}Cu$, $^{90}Y$, $^{111}In$, $^{177}Lu$, $^{225}Ac$, $^{212}Pb$, or $^{213}Bi$.

In some embodiments, Z' is 111-indium ($^{111}In$), 115-indium ($^{115}In$), $^{67}$-gallium ($^{67}Ga$), 68-gallium ($^{68}Ga$), 69-gallium ($^{69}Ga$), 71-gallium ($^{71}Ga$), 225-actinium ($^{225}Ac$), 175-lutetium ($^{175}Lu$), 177-lutetium ($^{177}Lu$), 204-lead ($^{204}Pb$), 206-lead ($^{206}Pb$), 207-lead ($^{207}Pb$), 208-lead ($^{208}Pb$), 212-lead ($^{212}Pb$), 63-copper ($^{63}Cu$), 64-copper ($^{64}Cu$), 65-copper ($^{65}CU$), or 67-copper ($^{67}Cu$).

In some embodiments, Z' is 111-indium ($^{111}In$). In some embodiments, Z' is 115-indium ($^{115}In$). In some embodiments, Z' is 67-gallium ($^{67}Ga$). In some embodiments, Z' is 68-gallium ($^{68}Ga$). In some embodiments, Z' is 69-gallium ($^{69}Ga$), 71-gallium ($^{71}Ga$), or a mixture thereof. In some embodiments, Z' is 225-actinium ($^{225}Ac$). In some embodiments, Z' is 175-lutetium ($^{175}Lu$). In some embodiments, Z' is 177-lutetium ($^{177}Lu$). In some embodiments, Z' is 204-lead ($^{204}Pb$), 206-lead ($^{206}Pb$), 207-lead ($^{207}Pb$) 208-lead ($^{208}Pb$), or a mixture thereof. In some embodiments, Z' is 212-lead ($^{212}Pb$). In some embodiments, Z' is 64-copper ($^{64}Cu$). In some embodiments, Z' is 63-copper ($^{63}Cu$), 65-copper ($^{65}Cu$), or a mixture thereof. In some embodiments, Z' is 67-copper ($^{67}Cu$).

In some embodiments, Z' is 111-indium ($^{111}In$), 115-indium ($^{115}In$), 67-gallium ($^{67}Ga$), 68-gallium ($^{68}Ga$), 225-actinium ($^{225}Ac$), 175-lutetium ($^{175}Lu$) or 177-lutetium ($^{177}Lu$).

Exemplary Chelator and Radionuclide Complexes

Radionuclides have useful emission properties that can be used for diagnostic imaging techniques, such as single photon emission computed tomography (SPECT, e.g. $^{67}Ga$, $^{99m}Tc$, $^{111}In$, $^{177}Lu$) and positron emission tomography (PET, e.g. $^{68}Ga$, $^{64}Cu$, $^{44}Sc$, $^{86}Y$, $^{89}Zr$), as well as therapeutic applications (e.g. $^{47}Sc$, $^{114}$mIn, $^{177}Lu$, $^{90}Y$, $^{212/213}Bi$, $^{212}Pb$, $^{225}Ac$, $^{186/188}Re$). A fundamental component of a radiometal-based radiopharmaceutical is the chelator, the ligand system that binds the radiometal ion in a tight stable coordination complex so that it can be properly directed to a desirable molecular target in vivo. Guidance for selecting the optimal match between chelator and radiometal for a particular use is provided in the art (e.g., see Price et al., "Matching chelators to radiometals for radiopharmaceuticals", *Chem. Soc. Rev.,* 2014, 43, 260-290).

In some embodiments, $R^a$ is a chelating moiety selected from the group consisting of: DOTA; DO3A; DO2A; DOTMA; DOTAM; DOTPA; Bn-DOTA; p-OH-Bn-DOTA; $H_4$pypa; $H_4$pypa-benzyl; $H_4$py4pa; $H_4$py4pa-benzyl; $H_4$octapa; $H_4$octapa-benzyl; and TTHA; or a radionuclide complex thereof.

In some embodiments, $R^a$ is:

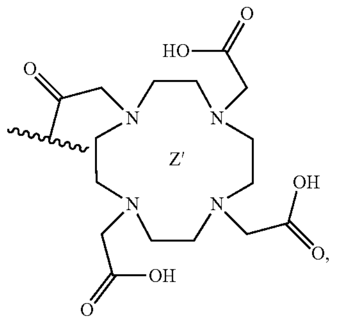

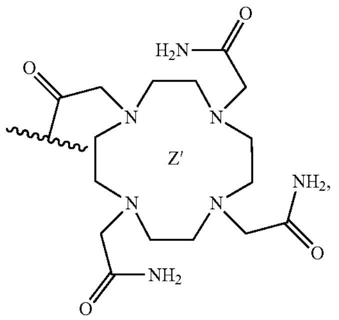

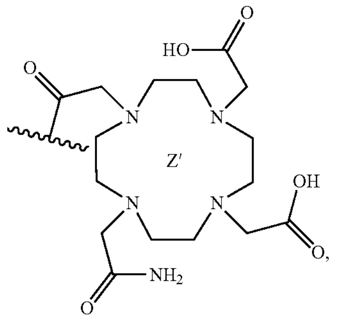

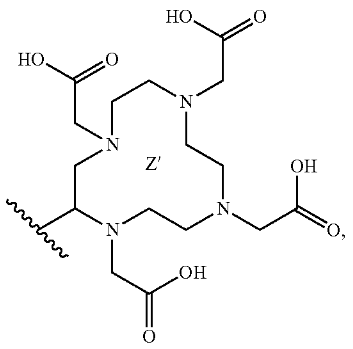

or

-continued

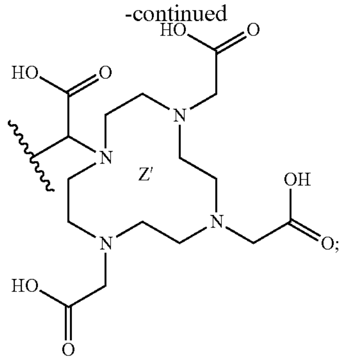

wherein Z' is a diagnostic or therapeutic radionuclide.

In some embodiments, the radionuclide (Z') is $^{44}Sc$, $^{64}Cu$, $^{67}Ga$, $^{68}Ga$, $^{86}Y$, $^{89}Zr$, $^{99m}Tc$, $^{111}In$, or $^{177}Lu$. In some embodiments, the radionuclide (Z') is $^{44}Sc$, $^{64}Cu$, $^{68}Ga$, $^{86}Y$, or $^{89}Zr$. In some embodiments, the radionuclide (Z') is $^{67}Ga$, $^{99m}Tc$, $^{111}In$, or $^{177}Lu$.

In some embodiments, the radionuclide (Z') is $^{67}Cu$, $^{90}Y$, $^{111}In$, $^{177}Lu$, $^{225}Ac$, $^{212}Pb$, or 213Bi In some embodiments, the radionuclide (Z') is 111-indium ($^{111}In$), 115-indium ($^{115}In$), 67-gallium ($^{67}Ga$), 68-gallium ($^{68}Ga$), 69-gallium ($^{69}Ga$), 71-gallium ($^{71}Ga$), 225-actinium ($^{225}Ac$), 175-lutetium ($^{175}Lu$), 177-lutetium ($^{177}Lu$), 206-lead ($^{206}Pb$), 207-lead ($^{207}Pb$), 208-lead ($^{208}Pb$), 212-lead ($^{212}Pb$), 60-copper ($^{60}Cu$), 61-copper (61Cu), 62-copper ($^{62}Cu$), 63-copper ($^{63}Cu$), 64-copper ($^{64}Cu$), 65-copper ($^{65}Cu$), or 67-copper ($^{67}Cu$).

In some embodiments, the radionuclide (Z') is 111-indium ($^{111}In$) or 115-indium ($^{115}In$), or a mixture thereof. In some embodiments, the radionuclide (Z') is 67-gallium ($^{67}Ga$), 68-gallium ($^{68}Ga$), 69-gallium ($^{69}Ga$), or 71-gallium ($^{71}Ga$), or a mixture thereof. In some embodiments, the radionuclide (Z') is 225-actinium ($^{225}Ac$). In some embodiments, the radionuclide (Z') is 175-lutetium ($^{175}Lu$) or 177-lutetium ($^{177}Lu$), or a mixture thereof. In some embodiments, the radionuclide (Z') is 206-lead ($^{206}Pb$), 207-lead ($^{207}Pb$), 208-lead ($^{208}Pb$), or 212-lead ($^{212}Pb$), or a mixture thereof. In some embodiments, the radionuclide (Z') is 60-copper ($^{60}Cu$), 61-copper ($^{61}Cu$), 62-copper ($^{62}Cu$), 63-copper ($^{63}Cu$), 64-copper ($^{64}Cu$), 65-copper ($^{65}Cu$), or 67-copper ($^{67}Cu$), or a mixture thereof.

In some embodiments, the radionuclide (Z') is 111-indium ($^{111}In$), 115-indium ($^{115}In$), 67-gallium ($^{67}Ga$), 68-gallium ($^{68}Ga$), 225-actinium ($^{225}Ac$), 175-lutetium ($^{175}Lu$) or 177-lutetium ($^{177}Lu$).

In some embodiments, the radionuclide (Z') is 90-yttrium ($^{90}Y$), 177-lutetium ($^{177}Lu$), 186-rhenium ($^{186}Re$), 188-rhenium ($^{188}Re$), 67-copper ($^{67}Cu$), 153-samarium ($^{153}Sm$), 89-strontium ($^{19}Sr$), 198-gold ($^{198}Au$), 169-Erbium ($^{169}Er$), 165-dysprosium ($^{165}Dy$), or technetium-99m ($^{99m}Tc$)

Emission Tomography

In some embodiments, $R^a$ comprises a chelated radionuclide that is suitable for positron emission tomography (PET) analysis or single-photon emission computerized tomography (SPECT). In some embodiments, $R^a$ comprises a chelated radionuclide that is suitable for single-photon emission computerized tomography (SPECT). In some embodiments, $R^a$ comprises a chelated radionuclide that is suitable for positron emission tomography (PET) analysis. In some embodiments, $R^a$ comprises a chelated radionuclide that is suitable for positron emission tomography imaging, positron emission tomography with computed tomography imaging, or positron emission tomography with magnetic resonance imaging (MRI).

In some embodiments, $R^a$ is a chelating moiety selected from the group consisting of: DOTA; DO3A; DO2A; DOTMA; DOTAM; DOTPA; En-DOTA; p-OH-Bn-DOTA; $H_4$pypa; $H_4$pypa-benzyl; $H_4$py4pa; $H_4$py4pa-benzyl; $H_4$octapa; $H_4$octapa-benzyl; and TTHA; or a radionuclide complex thereof. In some embodiments, the radionuclide is copper-64 ($^{64}Cu$, gallium-68 ($^{68}Ga$), or technetium-99m ($^{99m}Tc$).

In some embodiments, a conjugate described herein is designed to have a prescribed elimination profile. The elimination profile can be designed by adjusting the sequence and length of the peptide ligand, the property of the linker, the type of radionuclide, etc. In some embodiments, the conjugate has an elimination half-life of about 5 minutes to about 12 hours. In some embodiments, the conjugate has an elimination half-life of about 10 minutes to about 8 hours. In some embodiments, the conjugate has an elimination half-life of at least about 15 minutes, at least about 30 minutes, at least about 1 hour, at least about 2 hours, at least about 3 hours, at least about 4 hours, at least about 5 hours, at least about 6 hours, or at least about 8 hours. In some embodiments, the conjugate has an elimination half-life of at most about 15 minutes, at most about 30 minutes, at most about 1 hour, at most about 2 hours, at most about 3 hours, at most about 4 hours, at most about 5 hours, at most about 6 hours, or at most about 8 hours. In some embodiments, the elimination half-life is determined in rats. In some embodiments, the elimination half-life is determined in humans.

A herein described conjugate can have an elimination half-life in a tumor and non-tumor tissue of the subject. The elimination half-life in a tumor can be the same as or different from (either longer or shorter than) the elimination half-life in a non-tumor issue. In some embodiments, the elimination half-life of the conjugate in a tumor is about 15 minutes to about 1 day. In some embodiments, the elimination half-life of the conjugate in a tumor is at least 1.1, at least 1.2, at least 1.3, at least 1.4, at least 1.5, at least 2.0, at least 2.5, at least 3.0, at least 4.0, or at least 5.0-fold of the elimination half-life of the conjugate in a non-tumor tissue of the subject.

As used herein, the "elimination half-life" can refer to the time it takes from the maximum concentration after administration to half maximum concentration. In some embodiments, the elimination half-life is determined after intravenous administration. In some embodiments, the elimination half-life is measured as biological half-life, which is the half-life of the pharmaceutical in the living system. In some embodiments, the elimination half-life is measured as effective half-life, which is the half-life of a radiopharmaceutical in a living system taking into account the half-life of the radionuclide.

Response and toxicity prediction is essential for the rational implementation of cancer therapy. The biological effects of radionuclide therapy are mediated by a well-defined physical quantity, the absorbed dose (D), which is defined as the energy absorbed per unit mass of tissue.

Radiation dosimetry is the measurement, calculation and assessment of the ionizing radiation dose absorbed by an object, usually the human body, and may be thought of as the ability to perform the equivalent of a pharmacodynamic study in treated patients in real time. This applies both internally, due to ingested or inhaled radioactive substances, or externally due to irradiation by sources of radiation. Dosimetry analysis may be performed as part of patient treatment to calculate tumor versus normal organ absorbed dose and therefore the likelihood of treatment success.

A conjugate described herein can have a prescribed time-integrated activity coefficient (i.e., ã) in a tumor or non-tumor tissues of a subject. As used herein, ã represents the cumulative number of nuclear transformations occurring in a source tissue over a dose-integration period per unit administered activity. The ã value of a conjugate can be tuned by modifications of the NPDC. The ã value can be determined using a method known in the art. In some embodiments, the ã value of the conjugate in a tumor is from about 10 minutes to about 1 day. The ã value of the conjugate in a tumor can be the same as the ã value of the conjugate in a non-tumor tissue of the subject. The ã value of the conjugate in a tumor can be longer or shorter than the ã value of the conjugate in a non-tumor tissue of the subject. In some embodiments, the ã value of the conjugate in a tumor is at least 1.1, at least 1.2, at least 1.3, at least 1.4, at least 1.5, at least 2.0, at least 2.5, at least 3.0, at least 4.0, or at least 5.0-fold of the ã value of the conjugate in a non-tumor tissue of the subject.

A conjugate described herein can have an ã value in an organ of a subject. In some embodiments, the conjugate has an ã value in a kidney of the subject of at most 24 hours. In some embodiments, the ã value of the conjugate in a kidney of the subject is at most 18 hours, 15 hours, 12 hours, 10 hours, 8 hours, 6 hours, or 5 hours. In some embodiments, the ã value of the conjugate in a kidney of the subject is about 30 minutes to about 24 hours. In some embodiments, the ã value of the conjugate in a kidney of the subject is about 2 to 24 hours. In some embodiments, the ã value of the conjugate in a kidney of the subject is more than 24 hours. In some embodiments, the ã value of the conjugate in a liver of the subject is at most 24 hours. In some embodiments, the ã value of the conjugate in a liver of the subject is at most 18 hours, 15 hours, 12 hours, 10 hours, 8 hours, 6 hours, or 5 hours. In some embodiments, the ã value of the conjugate in a liver of the subject is about 30 minutes to about 24 hours. In some embodiments, the ã value of the conjugate in a liver of the subject is about 2 to 24 hours. In some embodiments, the ã value of the conjugate in a liver of the subject is more than 24 hours.

Linkers

In some embodiments, the linker has a prescribed length thereby linking the Kisspeptin receptor (KISS1R) targeting ligand and the chelating moiety or a radionuclide complex thereof ($R^a$) while allowing an appropriate distance therebetween.

For the linkers described herein, no orientation of the linker is implied by the direction in which the formula of the linker is written. For example, the formula

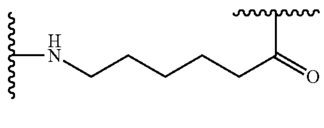

represents both

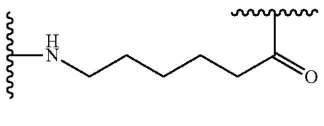 [SMILES: *NCCCCCC(*)=O]

and

-continued

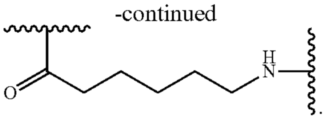

Additionally, the formula

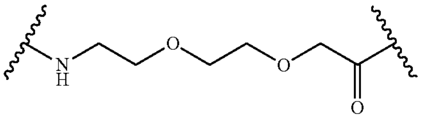 [SMILES: *NCCOCCOCC(*)=O]

represents both

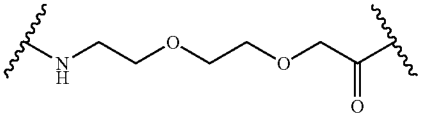 [SMILES: *NCCOCCOCC(*)=O]

and

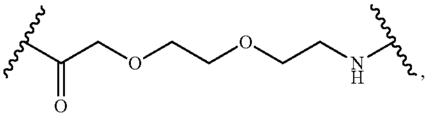 [SMILES: *NCCOCCOCC(*)=O]

, and the formula

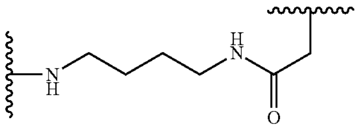 [SMILES: *CC(=O)NCCCCN*]

represents both

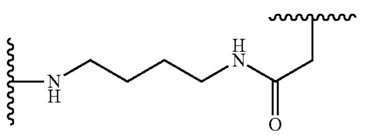

and

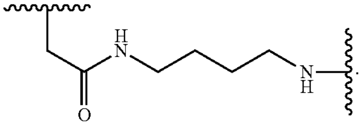

In some embodiments, the linker is flexible. In some embodiments, the linker is rigid.

In some embodiments, the linker comprises a linear structure. In some embodiments, the linker comprises a non-linear structure. In some embodiments, the linker comprises a branched structure. In some embodiments, the linker comprises a cyclic structure.

In some embodiments, the linker comprises one or more linear structures, one or more non-linear structures, one or more branched structures, one or more cyclic structures, one or more flexible moieties, one or more rigid moieties, or combinations thereof.

In some embodiments, a linker comprises one or more amino acid residues. In some embodiments, the linker comprises 1 to 3, 1 to 5, 1 to 10, 5 to 10, or 5 to 20 amino acid residues. In some embodiments, one or more amino acids of the linker are unnatural amino acids.

In some embodiments, the linker comprises a peptide linkage. The peptide linkage comprises L-amino acids and/or D-amino acids. In some embodiments, D-amino acids are preferred in order to minimize immunogenicity and nonspecific cleavage by background peptidases or proteases.

In some embodiments, a linker has 1 to 100 atoms, 1 to 50 atoms, 1 to 30 atoms, 1 to 20 atoms, 1 to 15 atoms, 1 to 10 atoms, or 1 to 5 atoms in length. In some embodiments, the linker has 1 to 10 atoms in length. In some embodiments, the linker has 1 to 20 atoms in length.

In some embodiments, a linker can comprise flexible and/or rigid regions. Exemplary flexible linker regions include those comprising Gly and Ser residues ("GS" linker), glycine residues, alkylene chain, PEG chain, etc. Exemplary rigid linker regions include those comprising alpha helix-forming sequences, proline-rich sequences, and regions rich in double and/or triple bonds.

In some embodiments, the linker comprises a click chemistry residue. In some embodiments, the linker is attached to a peptide ligand, to a metal chelator or both via click chemistry. For example, in some embodiments, a peptide ligand comprises an azide group that reacts with an alkyne moiety of the linker. For another example, in some embodiments, a peptide ligand comprises an alkyne group that reacts with an azide of the linker. The metal chelator and the linker can be attached similarly. In some embodiments, the linker comprises an azide moiety, an alkyne moiety, or both. In some embodiments, the linker comprises a triazole moiety.

In some embodiments,

-L- is absent, *-$L^1$, *—$NR^{17}$-$L^1$-, *—$NR^{17}$-$L^5$-$L^1$, *—$NR^{17}$-$L^5$-C(═O)-$L^1$-, *—$NR^{17}$-$L^5$-$NR^{17}$—C(═O)-$L^1$-, *-$L^5$-C(═O)-$L^1$-, *-$L^5$-$L^1$-, *—$NR^{17}$-$L^5$-$NR^{17}$-$L^1$-, *—$NR^{17}$-$L^5$-C(═O)$NR^{17}$-$L^1$-, *-$(L^3)_w$-, *—$NR^{17}$-$L^5$-C(═O)-$L^3$-$NR^{17}$-$L^5$-C(═O)—, or *-$(L^3)_w$-$NR^{17}$-$L^5$-C(═O)-$L^1$-; wherein * denotes the attachment point to $R^a$;

$L^5$ is substituted or unsubstituted —$C_1$-$C_6$ alkylene;

or $L^5$ and $R^{17}$ are taken together with the N atom to which they are attached to form N-heterocycloalkyl;

$R^{17}$ is selected from hydrogen, —$C_1$-$C_6$ alkyl, —$C_1$-$C_6$ alkyl-$CO_2H$, —$(CH_2CH_2O)_z$—$CH_2CH_2$—$CO_2H$;

$L^1$ is absent, -$L^2$-, -$L^2$-$(L^3)_w$-, -$(L^3)_w$-$L^2$-, or -$L^2$-$(L^3)_w$-$L^2$-$(L^3)_w$;

each $L^2$ is independently absent, —$C_0$-$C_6$ alkylene-(substituted or unsubstituted arylene)-$C_0$-$C_6$ alkylene-C(═O)—, —$C_0$-$C_6$ alkylene-(substituted or unsubstituted arylene)-$C_0$-$C_6$ alkylene-OC(═O)—, —$C_0$-$C_6$ alkylene-(substituted or unsubstituted cyclohexylene)-$C_0$-$C_6$ alkylene-C(═O)—, —$C_0$-$C_6$ alkylene-(substituted or unsubstituted heterocycloalkylene)-$C_0$-$C_6$ alkylene-C(═O)—, —$C_0$-$C_6$alkylene-(substituted or unsubstituted heteroarylene)-$C_0$-$C_6$ alkylene-C(═O)—, $C_0$-$C_6$ alkylene-(substituted or unsubstituted heteroarylene)-$C_0$-$C_6$alkylene-OC(═O)—, —$C_4$-$C_{20}$ polyethylene glycol, —$C_4$-$C_{20}$ polyethylene glycol-C(═O)—, substituted or unsubstituted $C_1$-$C_{20}$ alkylene, substituted or unsubstituted $C_1$-$C_{20}$ alkylene-C(═O)—, substituted or unsubstituted 2 to 20 membered heteroalkylene, —$(CH_2CH_2O)_z$—$CH_2$—, —$(CH_2CH_2O)_z$—$CH_2CH_2$—, —$(CH_2CH_2O)_z$—$CH_2$—C(═O)—; or —$(CH_2CH_2O)_z$—$CH_2CH_2$—C(═O)—;

each z is independently 1, 2, 3, 4, 5, or 6;

each $L^3$ is independently selected from natural or unnatural amino acids, wherein any free amine of an amino acid or peptide bond is optionally independently substituted with $L^4$, and wherein when two or more amino acids are present then the N atom of the amide linking the amino acids is optionally substituted with —$CH_3$;

each $L^4$ is independently selected from $C_1$-$C_6$ alkylene, C(═O)—$C_1$-$C_6$ alkylene-C(═O), C(═O)—NH—$C_1$-$C_6$ alkylene-C(═O), C(═O)—$C_1$-$C_6$ alkylene-(substituted or unsubstituted heteroarylene)-$C_1$-$C_6$ alkylene-C(═O), $C_1$-$C_6$ alkylene-C(═O), —C(═O)—$C_1$-$C_6$ alkylene-(substituted or unsubstituted arylene), and $C_1$-$C_6$ alkylene-(substituted or unsubstituted arylene)-C(═O); wherein if $L^4$ is present then: $L^4$ is attached to the any one of $X^1$, $X^2$, $X^3$, $X^4$, $X^5$, $X^6$, or $X^7$, or $L^4$ is attached to $X^8$ if $X^1$, $X^2$, $X^3$, $X^4$, $X^5$, $X^6$, and $X^7$ are absent;

each w is independently 1, 2, 3, 4, 5, or 6.

In some embodiments, each $L^2$ is independently absent, -(substituted or unsubstituted phenylene)-$C_0$-$C_6$ alkylene-C(═O)—, -(substituted or unsubstituted cyclohexylene)-$C_0$-$C_6$ alkylene-C(═O)—, -(substituted or unsubstituted heterocycloalkylene)-$C_0$-$C_6$ alkylene-C(═O)—, -(substituted or unsubstituted heteroarylene)-$C_0$-$C_6$alkylene-C(═O)—, substituted or unsubstituted $C_1$-$C_{20}$ alkylene-C(═O)—, —$(CH_2CH_2O)_z$—$CH_2$—, —$(CH_2CH_2O)_z$—$CH_2CH_2$—, —$(CH_2CH_2O)_z$—$CH_2$—C(═O)—; or —$(CH_2CH_2O)_z$—$CH_2CH_2$—C(═O)—, wherein each z is independently 1, 2, 3, 4, 5, or 6.

In some embodiments, each $L^2$ is independently absent, -(substituted or unsubstituted phenylene)-$C_0$-$C_6$ alkylene-C(═O)—, -(substituted or unsubstituted cyclohexylene)-$C_0$-$C_6$ alkylene-C(═O)—, -(substituted or unsubstituted heterocycloalkylene)-$C_0$-$C_6$ alkylene-C(═O)—, -(substituted or unsubstituted heteroarylene)-$C_0$-$C_6$alkyl-C(═O)—, substituted or unsubstituted $C_1$-$C_{20}$ alkylene-C(═O)—, —$(CH_2CH_2O)_z$—$CH_2$—C(═O)—, or —$(CH_2CH_2O)_z$—$CH_2CH_2$—C(═O)—, wherein each z is independently 1, 2, 3, 4, 5, or 6.

In some embodiments, -L- is *—$NR^{17}$—, *—$NR^{17}$-$L^5$, *—$NR^5$-$L^5$-C(═O)—, *—$NR^{17}$—$C_0$-$C_6$ alkylene-(substituted or unsubstituted phenylene)-$C_0$-$C_6$ alkylene-C(═O)—, *—$NR^{17}$—$C_0$-$C_6$ alkylene-(substituted or unsubstituted cyclohexylene)-$C_0$-$C_6$ alkylene-C(═O)—, *—$NR^{17}$—$C_0$-$C_6$ alkylene-(substituted or unsubstituted heterocycloalkylene)-$C_0$-$C_6$ alkylene-C(═O)—, *—$NR^{17}$—$C_0$-$C_6$ alkylene-(substituted or unsubstituted heteroarylene)-$C_0$-$C_6$ alkylene-C(═O)—, *—$NR^{17}$— substituted or unsubstituted $C_1$-$C_{20}$ alkylene-C(═O)—, *—$NR^{17}$—$(CH_2CH_2O)_z$—$CH_2$—C(═O)—, *$NR^{17}$—$(CH_2CH_2O)_z$—$CH_2CH_2$—C(═O)—, *—$R^{17}$-$L^5$-C(═O)-$(L^3)_w$-, *—$NR^5$-$L^5$-C(═O)$NR^{17}$—$C_0$-$C_6$ alkylene-(substituted or unsubstituted phenylene)-$C_0$-$C_6$ alkylene-C(═O)—, *—$NR^5$-$L^5$-C(═O)$NR^{17}$—$C_0$-$C_6$ alkylene-(substituted or unsubstituted cyclohexylene)-$C_0$-$C_6$ alkylene-C(═O)—, *—$NR^5$-$L^5$-C(═O)$NR^{17}$—$C_0$-$C_6$ alkylene-(substituted or unsubstituted heterocycloalkylene)-$C_0$-$C_6$ alkylene-C(═O)—, or *—$NR^5$-$L^5$-C(═O)$NR^{17}$—$C_0$-$C_6$ alkylene-(substituted or unsubstituted heteroarylene)-$C_0$-$C_6$ alkylene-C(═O)—, wherein each z is independently 1, 2, 3, 4, 5, or 6, and wherein * denotes the attachment point to $R^a$ In some embodiments, each $L^3$ is independently selected from the group consisting of alanine (Ala), arginine (Arg), asparagine (Asn), aspartate (Asp), glutamine (Gln), glutamate (Glu), glycine (Gly), leucine (Leu), lysine (Lys), 3-(2-naphthyl)-L-alanine (2-Nal), 3-(4-pyridyl)alanine (4-Pal), phenylalanine (Phe), serine (Ser), sarcosine, tyrosine (Tyr), 3-sulfo-alanine (Ala-$SO_3$H), methionine (Met), valine (Val), 2-(3-aminopropoxy)-[1,1-biphenyl]-4-carboxylic acid, 2'-(3-aminopropoxy)-[1,1'-biphenyl]-4-carboxylic acid, O-(dihydroxy(oxo)-16-phosphaneyl)-L-serine, (S)-2-amino-4-(2H-tetrazol-5-yl)butanoic acid, and (S)-2-amino-3-(anthracen-9-yl)propanoic acid, wherein any free amine of an amino acid or peptide bond is optionally independently substituted with $L^4$, and wherein when two or more amino acids are present then the N atom of the amide linking the amino acids is optionally substituted with —$CH_3$. In some embodiments, each $L^3$ is independently selected from the group consisting of alanine (Ala), glycine (Gly), serine (Ser), sarcosine, methionine (Met), 3-sulfo-alanine (Ala-$SO_3$H), and valine (Val), wherein any free amine of an amino acid or peptide bond is optionally independently substituted with $L^4$, wherein $L^4$ is —C(═O)—$C_1$-$C_6$ alkylene-C(═O)— or —C(═O)—NH—$C_1$-$C_6$ alkylene-C(═O)—, and wherein when two or more amino acids are present then the N atom of the amide linking the amino acids is optionally substituted with —$CH_3$.

In some embodiments, -$(L^3)_w$- is sarcosine, sarcosine-sarcosine, sarcosine-sarcosine-sarcosine, sarcosine-sarcosine-sarcosine-sarcosine (SEQ ID NO: 24), sarcosine-sarcosine-sarcosine-sarcosine-sarcosine (SEQ ID NO: 25), sarcosine-sarcosine-sarcosine-sarcosine-sarcosine-sarcosine (SEQ ID NO: 831), valine-citrulline, valine-alanine, methionine-valine-lysine, glycine-phenylalanine-glycine-glycine (SEQ ID NO: 832), tyrosine-arginine-valine, arginine-valine, 3-sulfo-alanine, 3-sulfo-alanine-3-sulfo-alanine, 3-sulfo-alanine-3-sulfo-alanine-3-sulfo-alanine, glycine-glutamate, glycine-glutamate-glycine, glycine-glutamate-glutamate, methionine-tryptophan-lysine, methionine-phenylalanine-lysine, methionine-valine, methionine-valine-lysine, or phenylalanine-lysine.

In some embodiments, -$(L^3)_w$- is sarcosine, sarcosine-sarcosine, sarcosine-sarcosine-sarcosine, sarcosine-sarcosine-sarcosine-sarcosine (SEQ ID NO: 24), sarcosine-sarcosine-sarcosine-sarcosine-sarcosine (SEQ ID NO: 25), sarcosine-sarcosine-sarcosine-sarcosine-sarcosine-sarcosine (SEQ ID NO: 831), valine-citrulline, valine-alanine, methionine-valine-lysine, glycine-phenylalanine-glycine-glycine (SEQ ID NTO: 832), tyrosine-arginine-valine, arginine-valine, 3-sulfo-alanine, 3-sulfo-alanine-3-sulfo-alanine, 3-sulfo-alanine-3-sulfo-alanine-3-sulfo-alanine, glycine-glutamate, glycine-glutamate-glycine, glycine-glutamate-glutamate, methionine-tryptophan-lysine, methionine-phenylalanine-lysine, methionine-valine, methionine-valine-lysine, or phenylalanine-lysine, wherein the free amine of lysine is optionally independently substituted with $L^4$; $L^4$ is —C(═O)—$(CH_2)_3$—C(═O)—, —C(═O)—$(CH_2)_4$—C(═O)—, —C(═O)—$(CH_2)_5$—C(═O)—, —C(═O)—$(CH_2)_6$—C(═O)—, —C(═O)NH—$(CH_2)_3$—C(═O)—, —C(═O)NH—$(CH_2)_4$—C(═O)—, —C(═O)NH—$(CH_2)_5$—C(═O)—, —C(═O)NH—$(CH_2)_6$—C(═O)—, —C(═O)—$(CH_2)_2$-(triazolylene)-$(CH_2)_1$—C(═O)— or —C(═O)—$(CH_2)_2$-(triazolylene)-$(CH_2)_2$—C(═O)—; wherein if $L^4$ is present then: L is attached to the any one of $X^1$, $X^2$, $X^3$, $X^4$, $X^5$, $X^6$, or $X^7$, or $L^4$ is attached to $X^8$ if $X^1$, $X^2$, $X^3$, $X^4$, $X^5$, $X^6$, and $X^7$ are absent.

In some embodiments, -L- is:

absent, 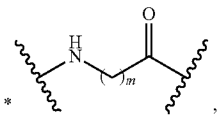, 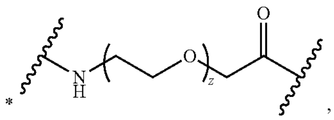, 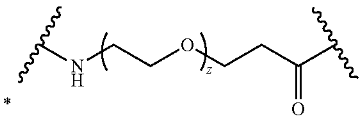, (SEQ ID NO: 833) (SEQ ID NO: 834)

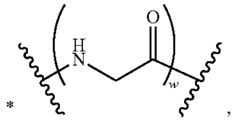, 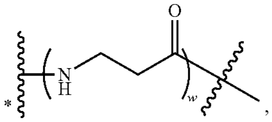, (SEQ ID NO: 835) (SEQ ID NO: 836)

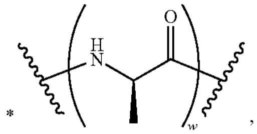, 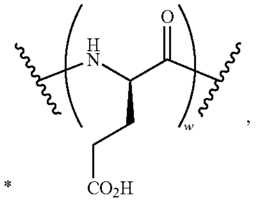, (SEQ ID NO: 837) (SEQ ID NO: 838)

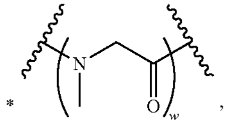, 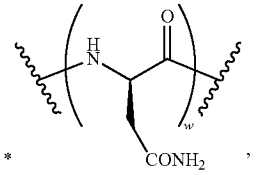,

-continued
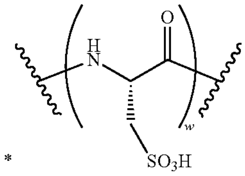, 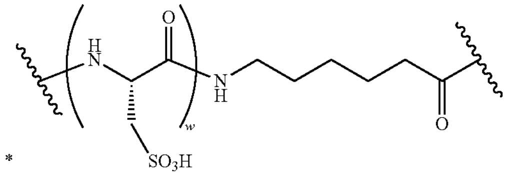,
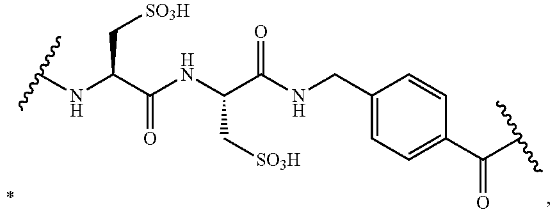, 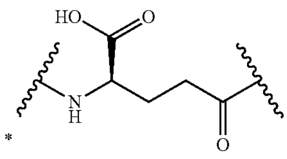,
(SEQ ID NO: 839)
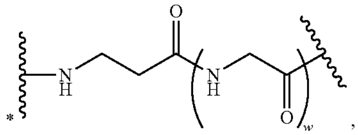,
(SEQ ID NO: 840)
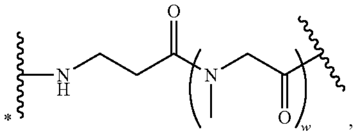,
(SEQ ID NO: 841)
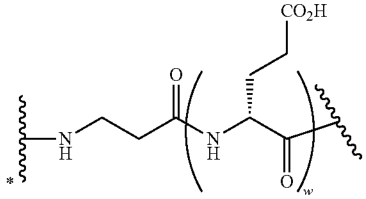,
(SEQ ID NO: 842)
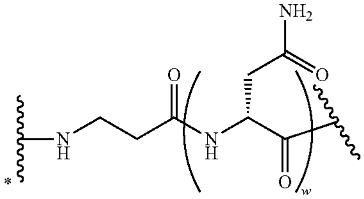,
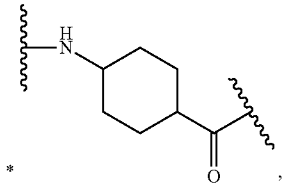, 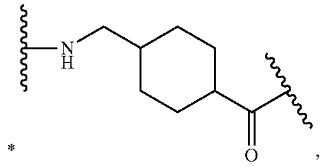, 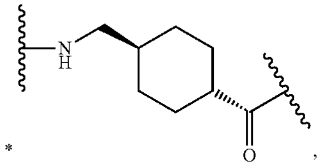,
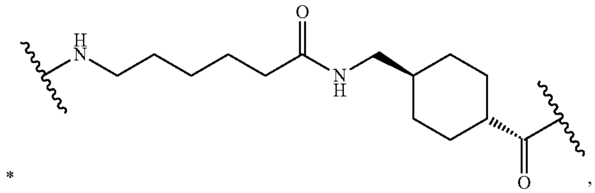, 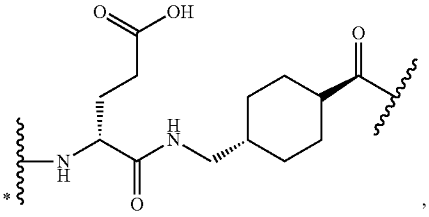,
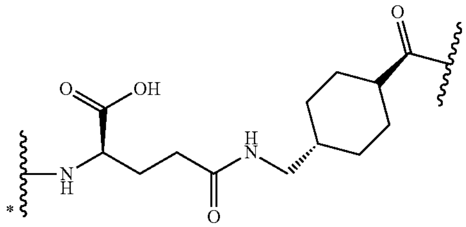, 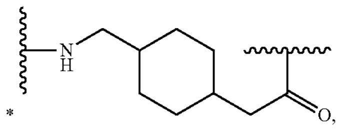, 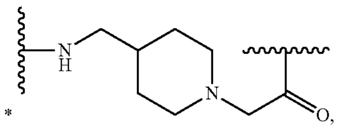,
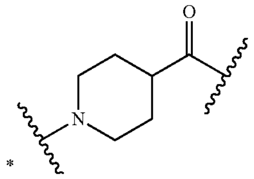, 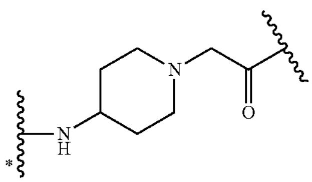, 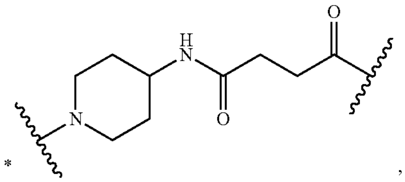, -continued
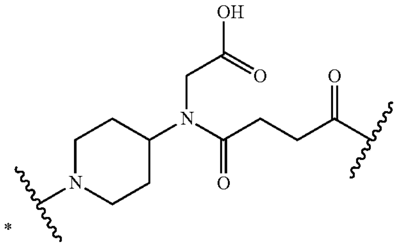,
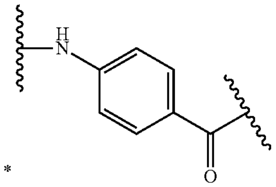,
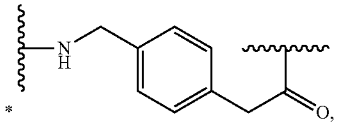,
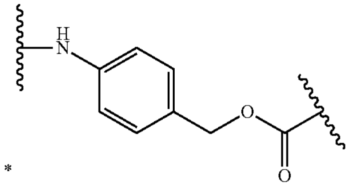,
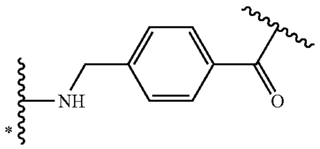,
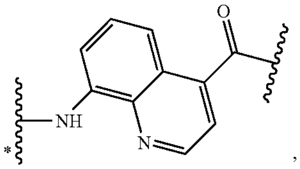,
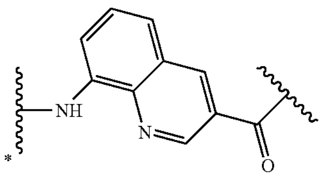,
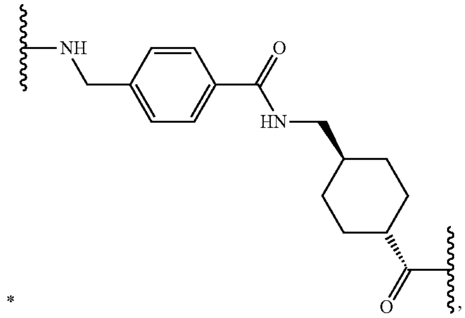,
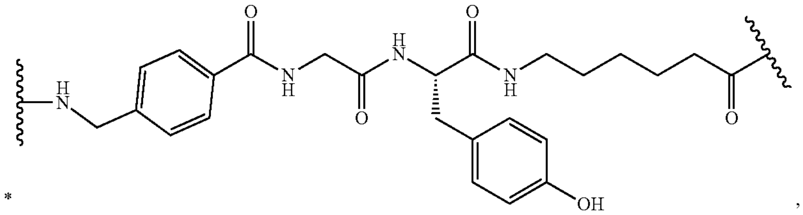,
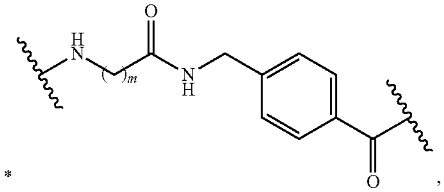,
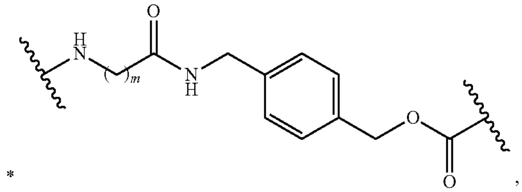,
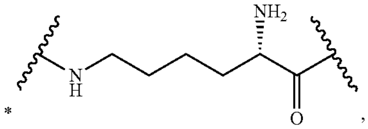,
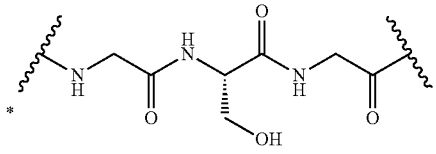,
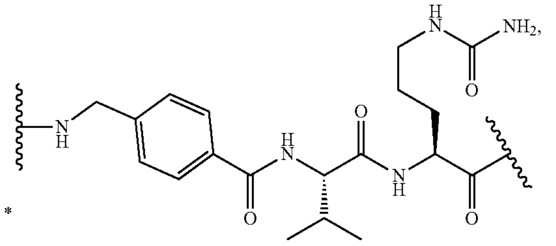
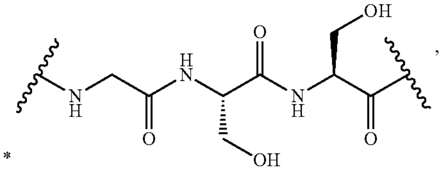, -continued
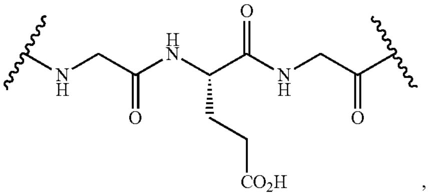
* ,
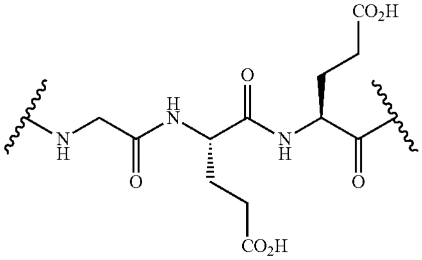
* ,
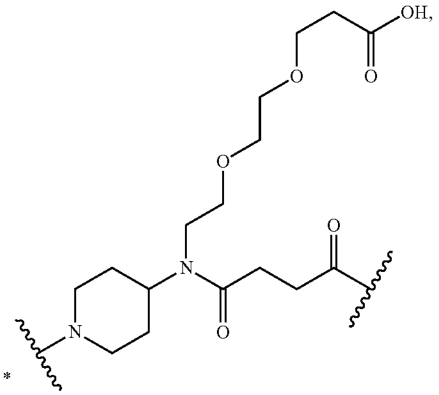
*
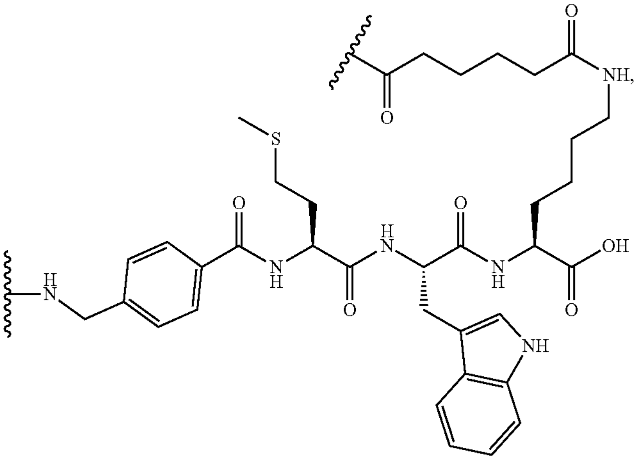
*
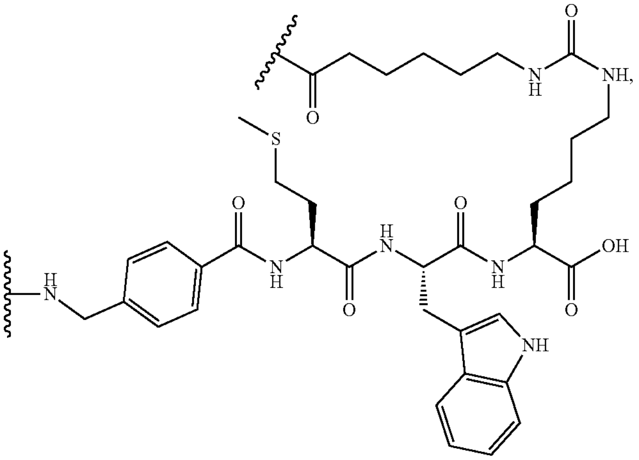
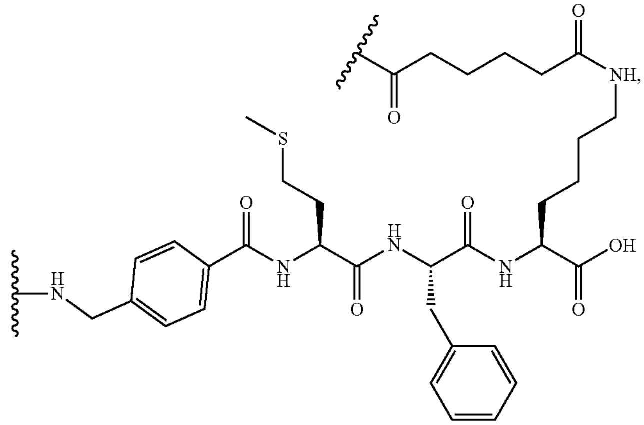
*

-continued
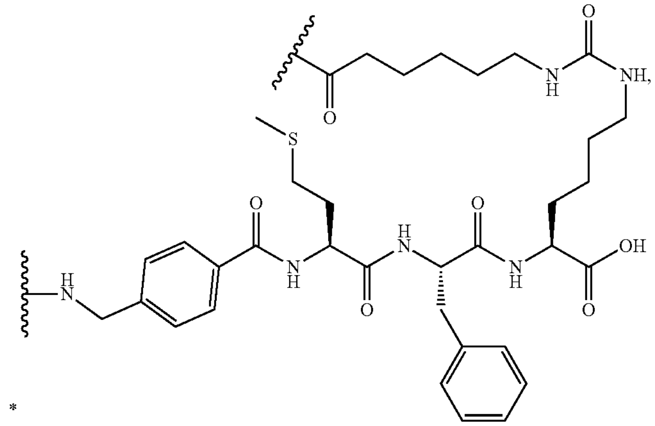
(SEQ ID NO: 796)
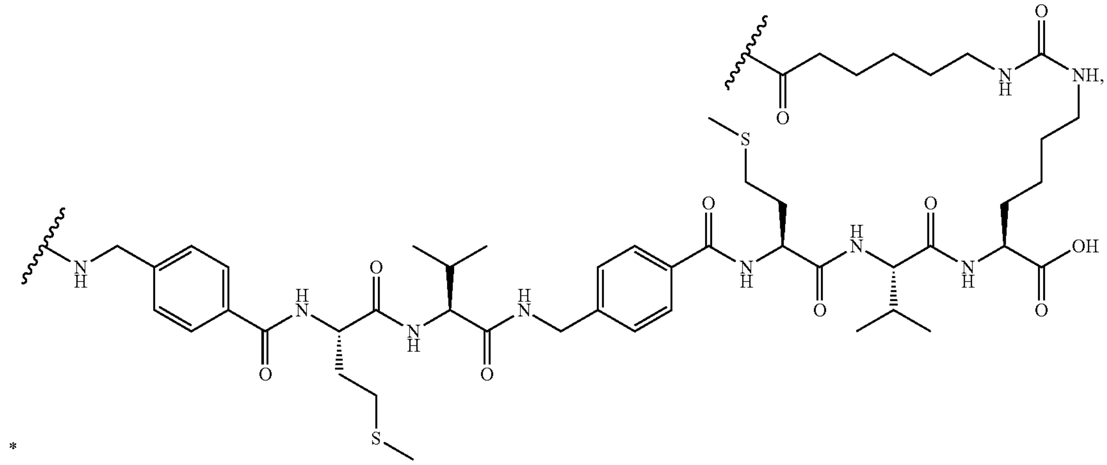
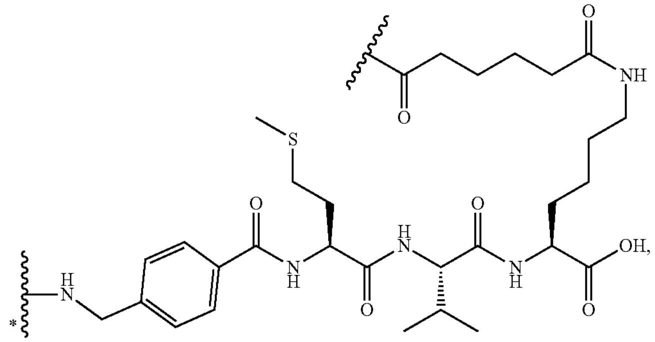
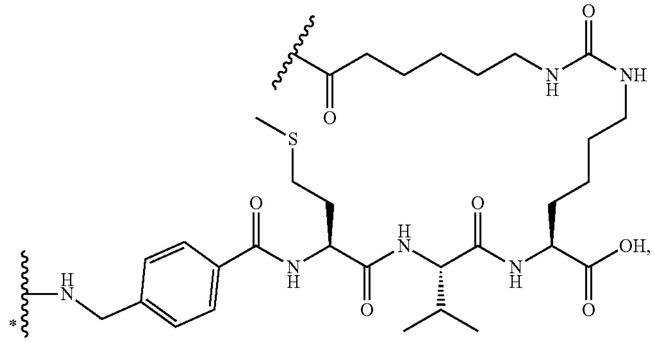

-continued
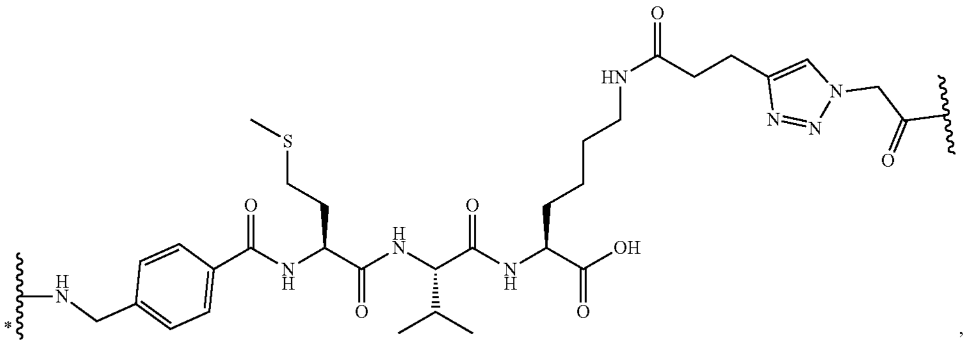
,
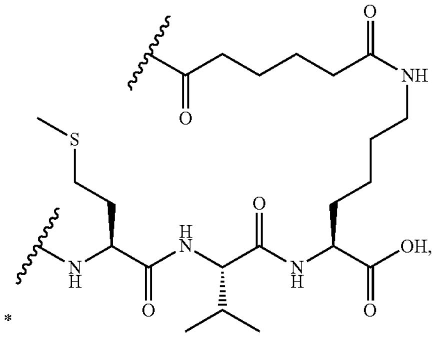
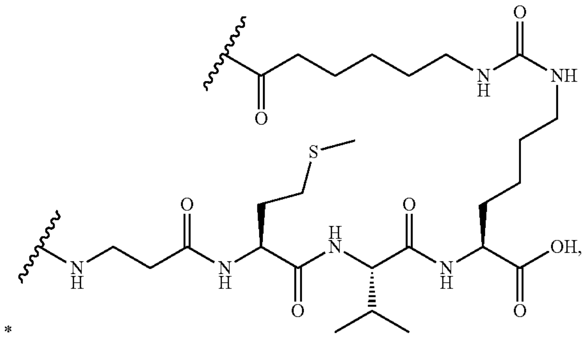
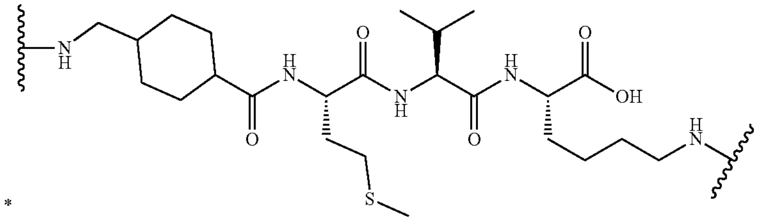
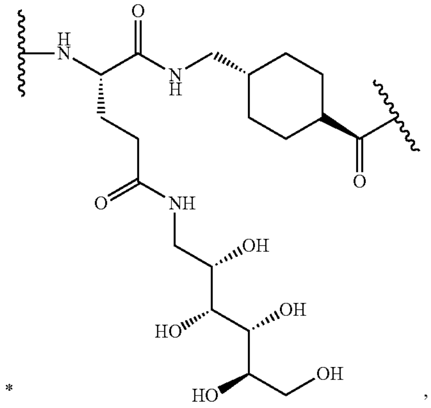
,
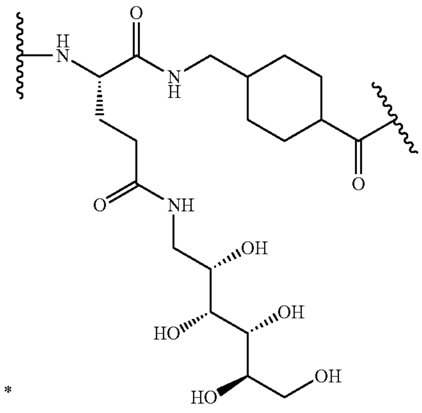
,
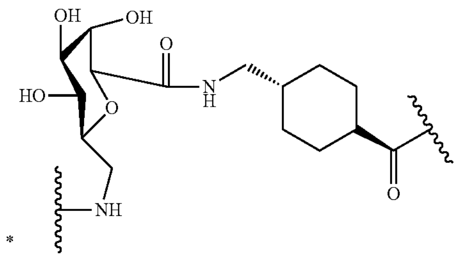
, -continued
* 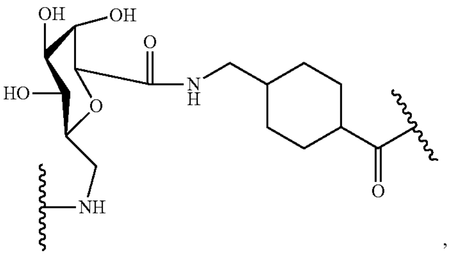 ,
* 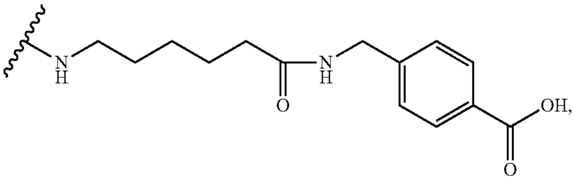
* 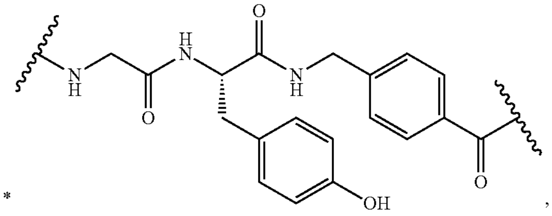 , * 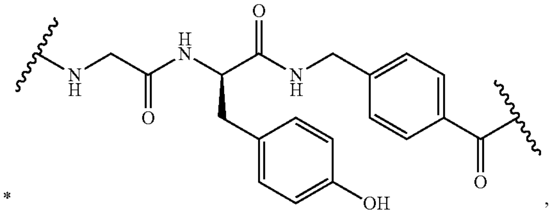 ,
* 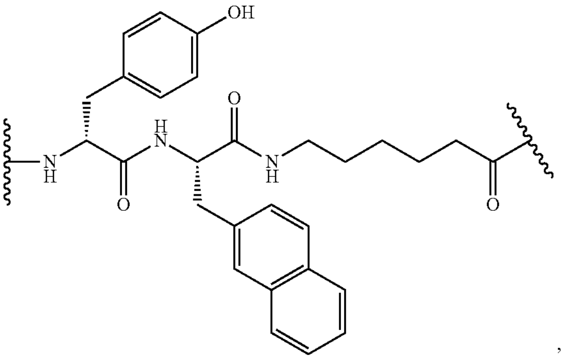 , * 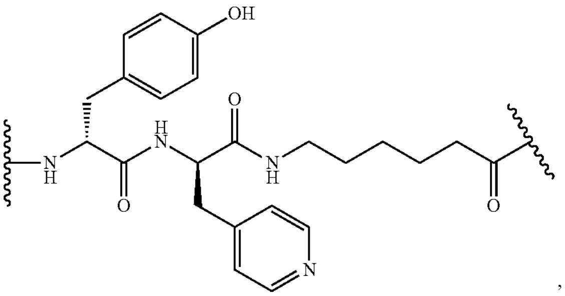 ,
* 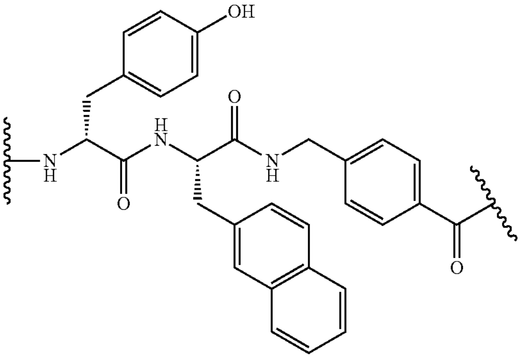 ,
* 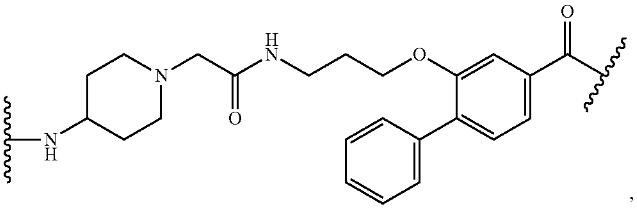 ,
* 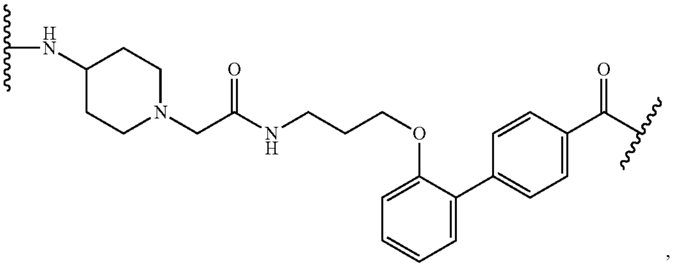 , * 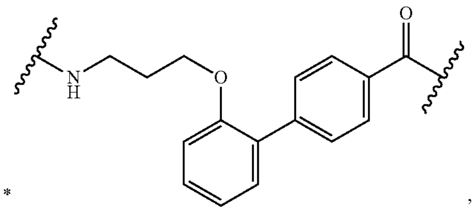 , -continued
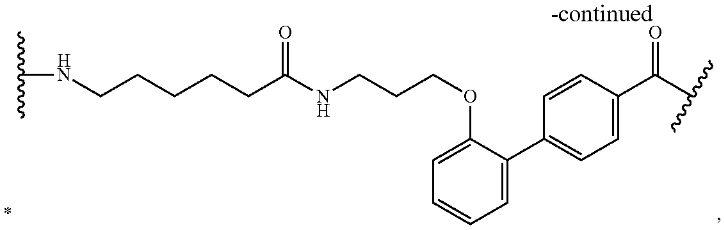
,
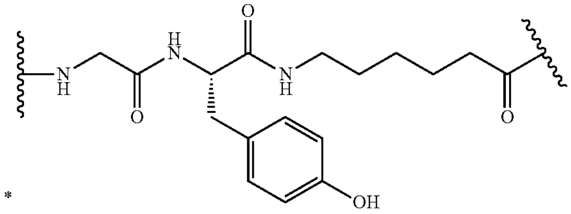
,
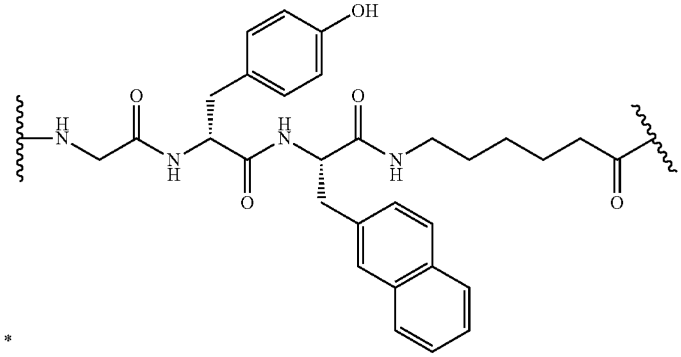
,
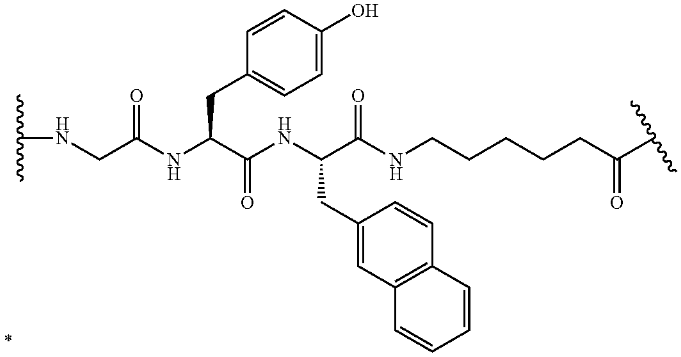
,
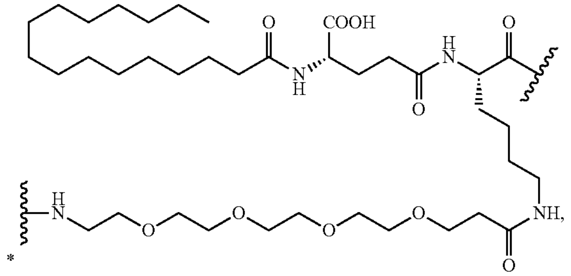
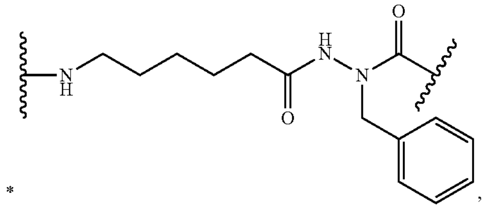
,
-continued
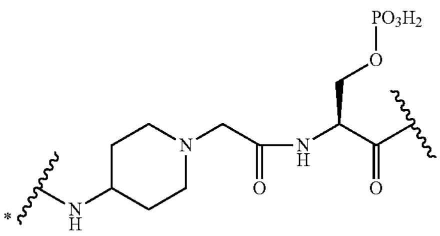
, -continued
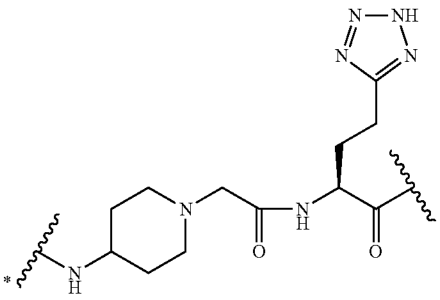
,
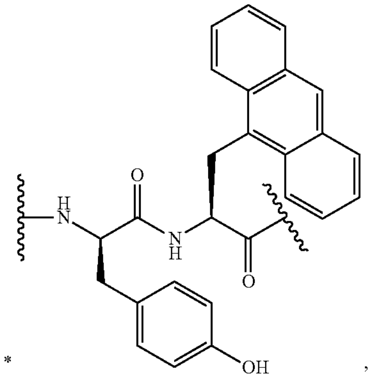
,
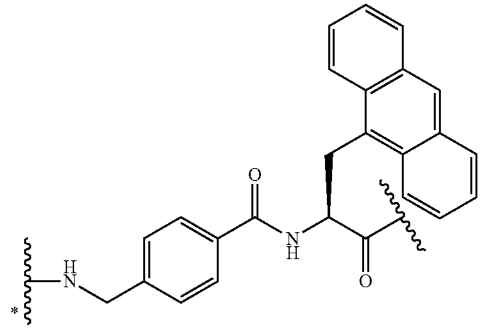
,
-continued
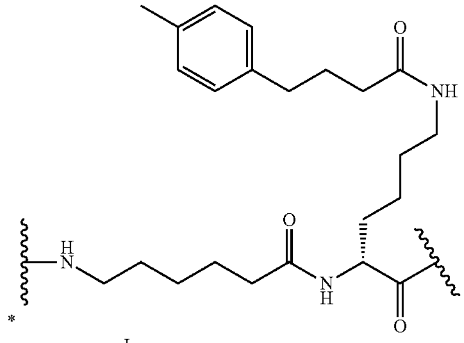
,
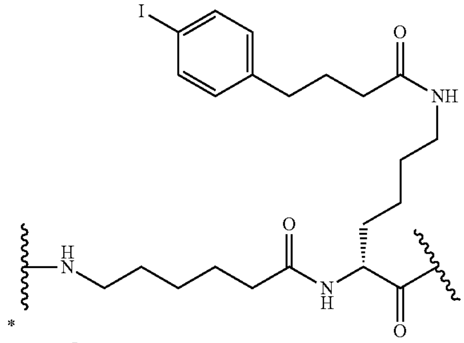
, or
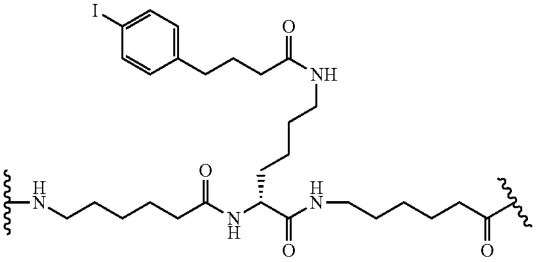
;
m is 1, 2, 3, 4, 5, or 6;
z is 1, 2, 3, 4, 5, or 6;
w is 1, 2, 3, 4, 5, or 6;
wherein * denotes the attachment point to $R^a$.
In some embodiments, -L- is:
absent,
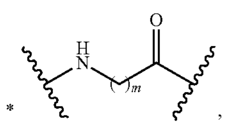
,
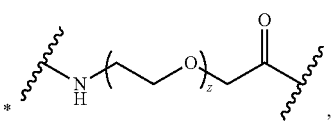
(SEQ ID NO: 833)
,
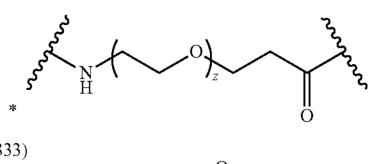
,
(SEQ ID NO: 834)
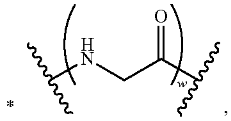
,
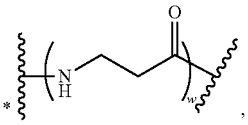
, -continued
(SEQ ID NO: 835)
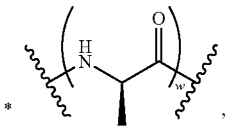,
(SEQ ID NO: 836)
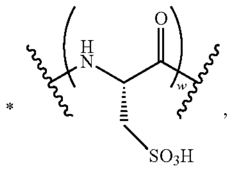,
(SEQ ID NO: 843)
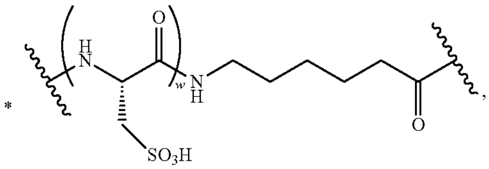,
(SEQ ID NO: 839)
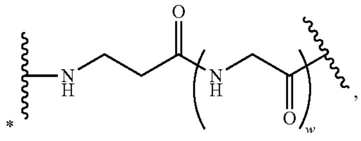,
(SEQ ID NO: 840)
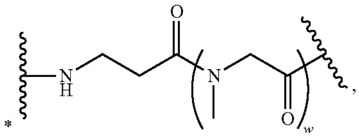,
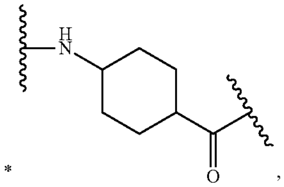, 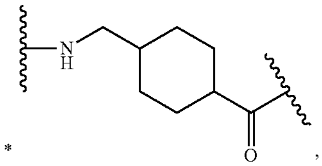, 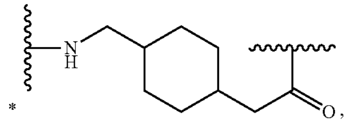,
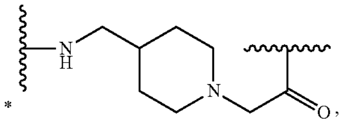, 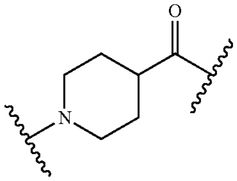, 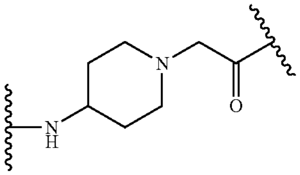,
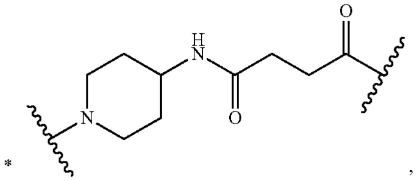, 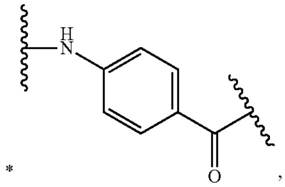, 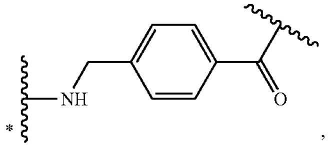,
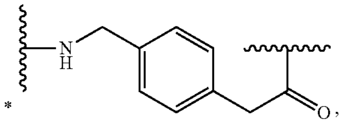, 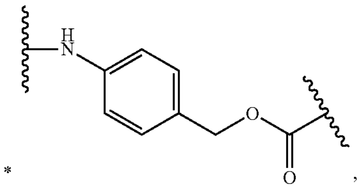, 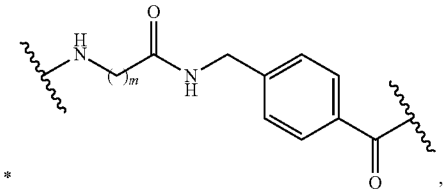,
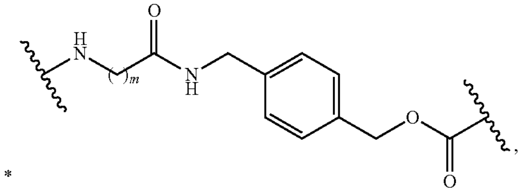, -continued
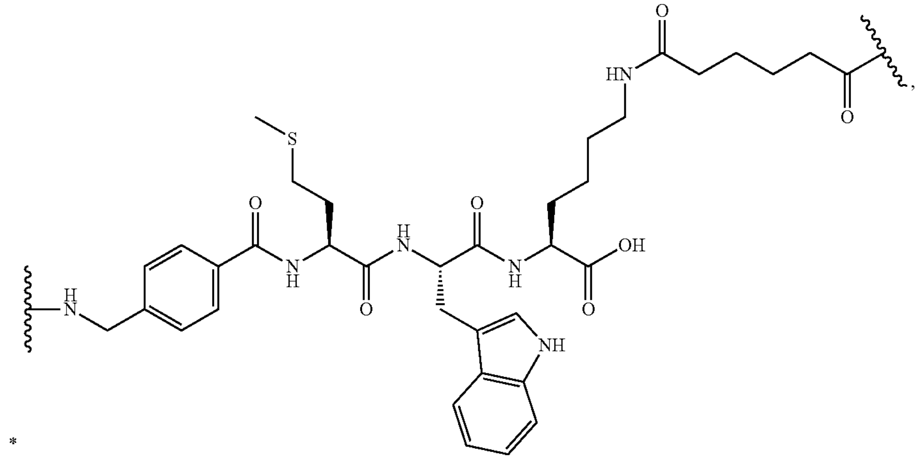
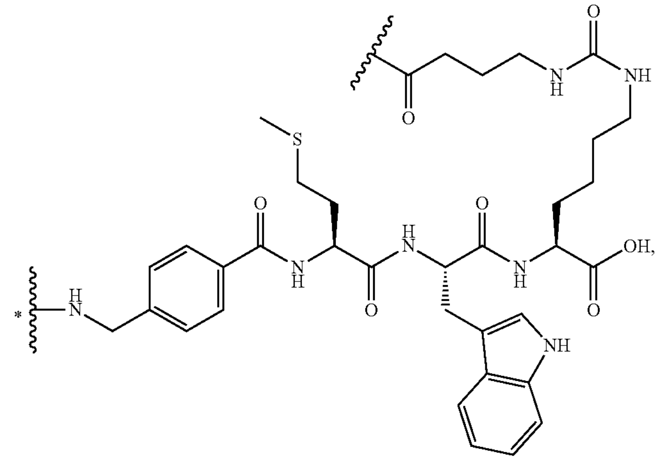
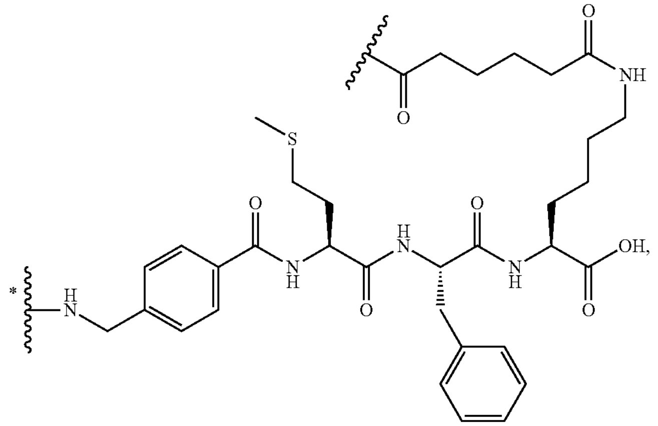

-continued
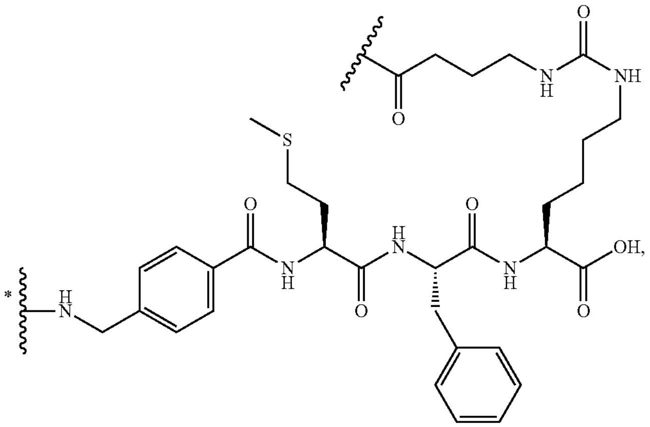
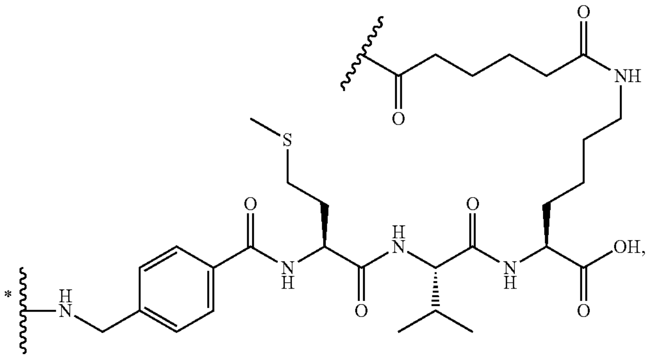
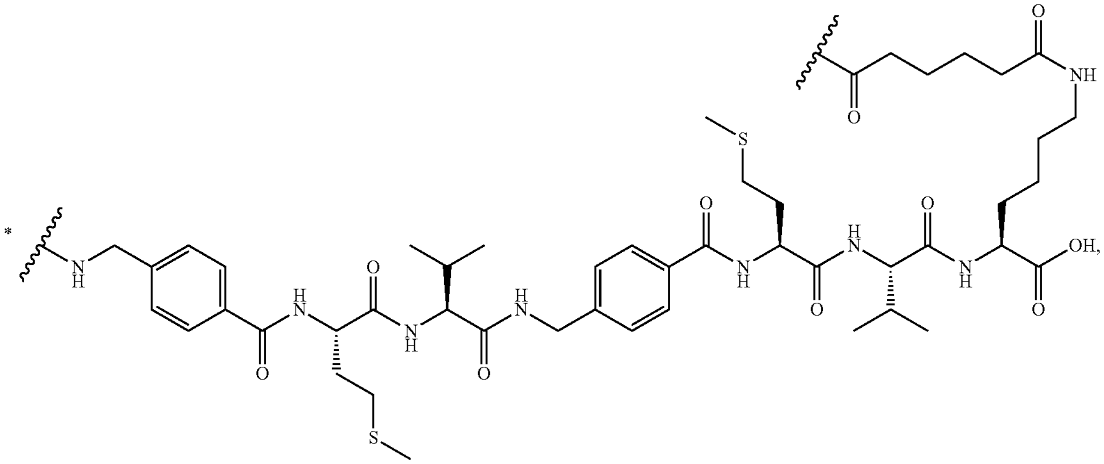
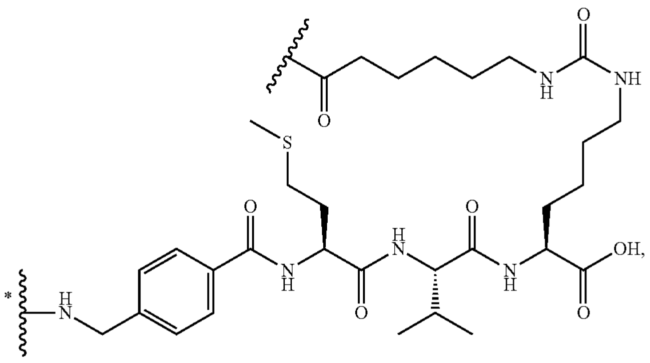
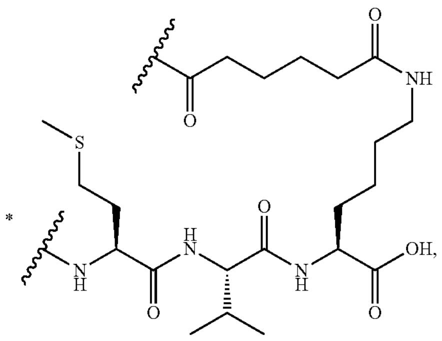

-continued

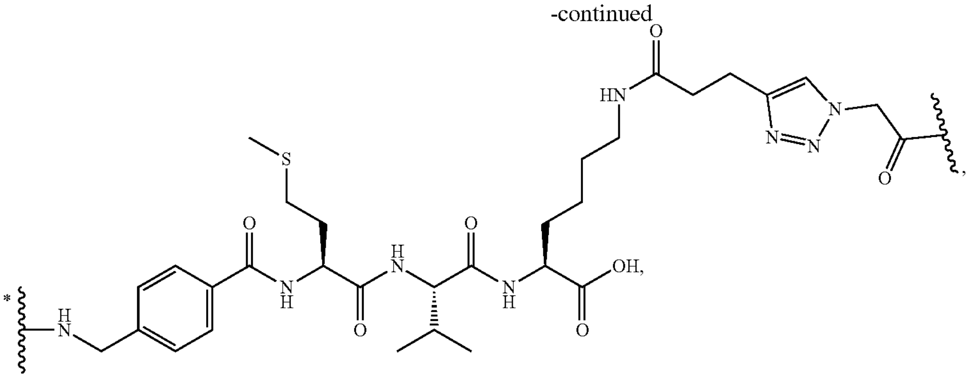

, or

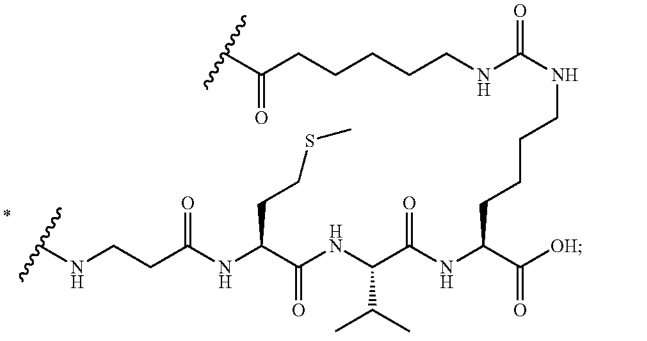

m is 1, 2, 3, 4, 5, or 6;

wherein * denotes the attachment point to $R^a$.

In some embodiments, m is 1. In some embodiments, m is 2. In some embodiments, m is 3. In some embodiments, m is 4. In some embodiments, m is 5. In some embodiments, m is 6.

In some embodiments, w is 1. In some embodiments, w is 2. In some embodiments, w is 3. In some embodiments, w is 4. In some embodiments, w is 5. In some embodiments, w is 6.

In some embodiments, z is 1. In some embodiments, z is 2. In some embodiments, z is 3. In some embodiments, z is 4. In some embodiments, z is 5. In some embodiments, z is 6.

In some embodiments, -L- is: absent:

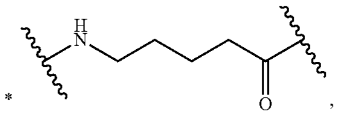

,

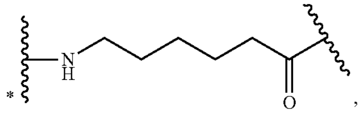

,

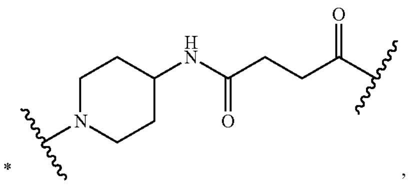

,

-continued (SEQ ID NO: 836)

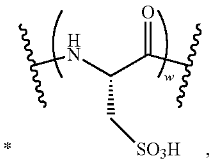

,

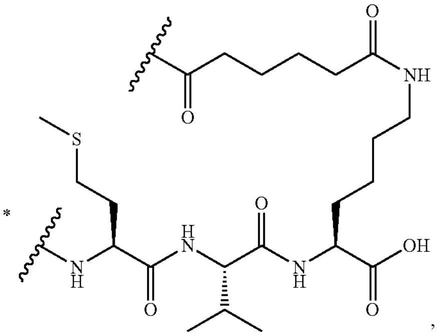

,

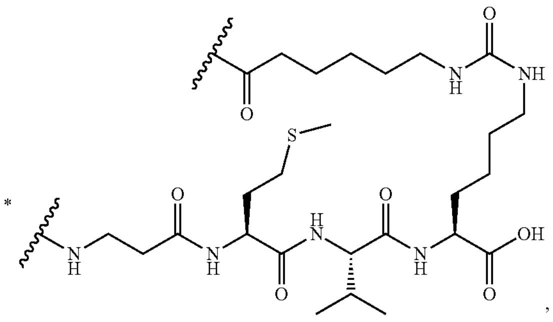

,

-continued
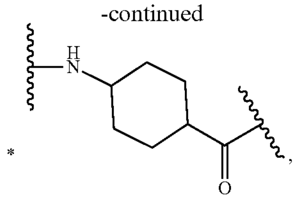
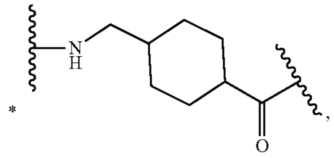
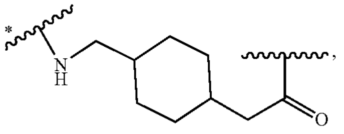
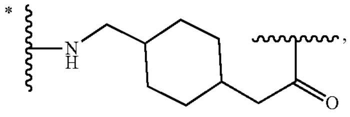
-continued
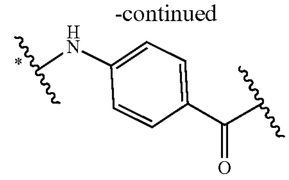
or
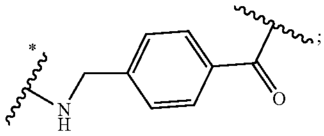
;
wherein * denotes the attachment point to $R^a$.
Representative Linker and Chelating Moieties
In some embodiments, $R^a$-L- is $R^a$,
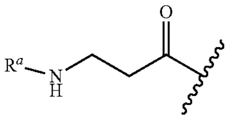
,
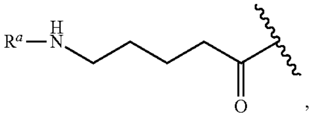
,
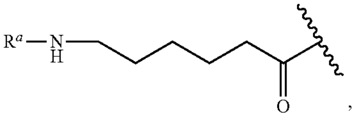
,
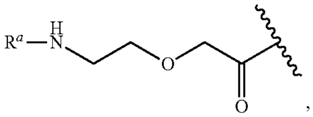
,
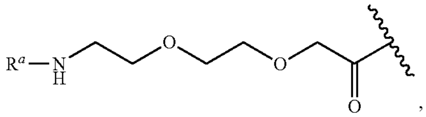
,
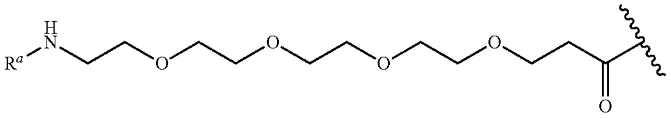
,
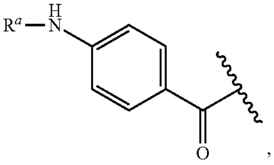
,
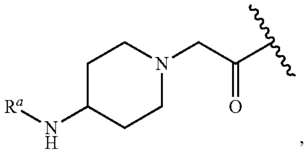
,
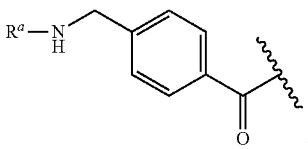
,
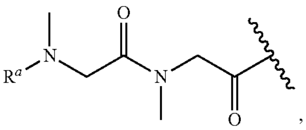
,
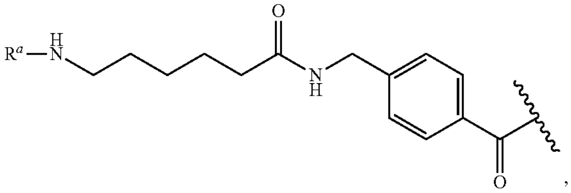
,
(SEQ ID NO: 797)
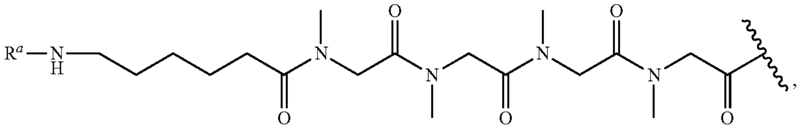
(SEQ ID NO: 386)
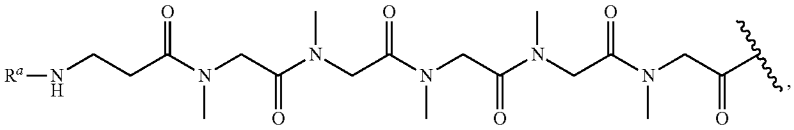

-continued
(SEQ ID NO: 387)
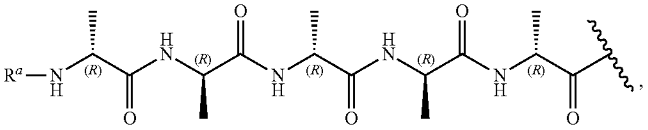
,
(SEQ ID NO: 388)
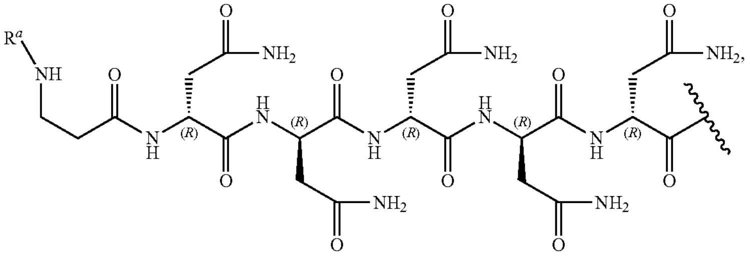
,
(SEQ ID NO: 389)
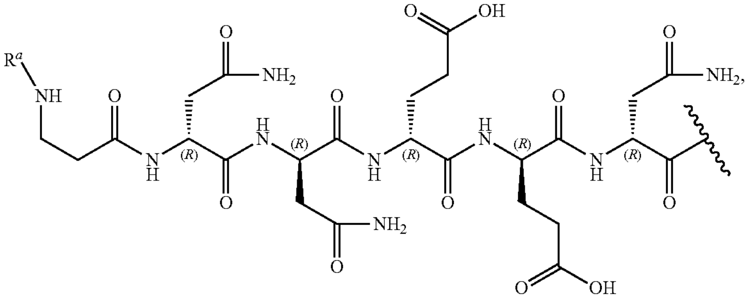
,
(SEQ ID NO: 390)
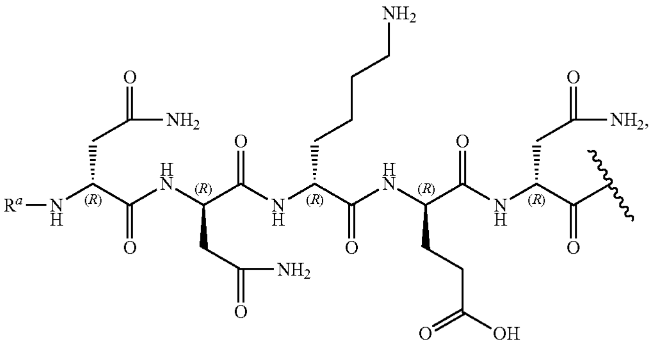
,
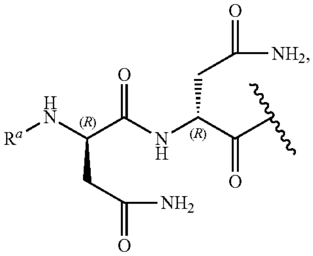
,
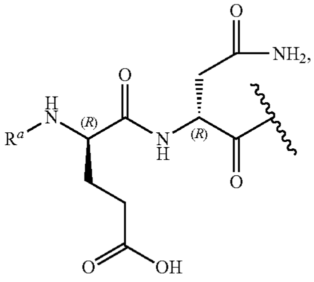
,
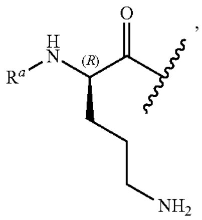
,
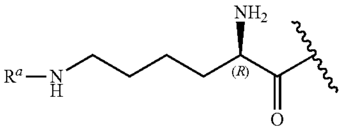
,
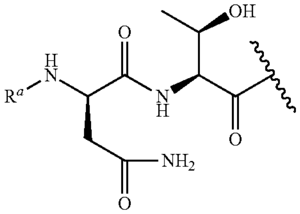
,
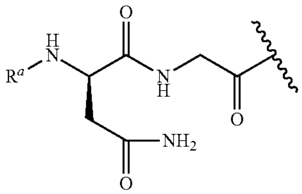
, -continued
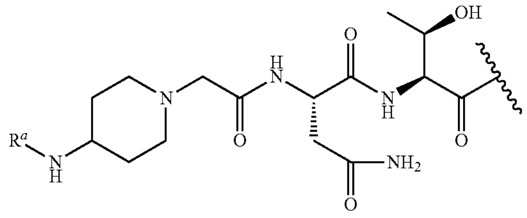,
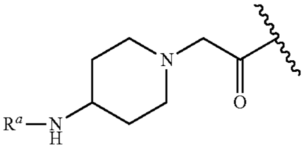,
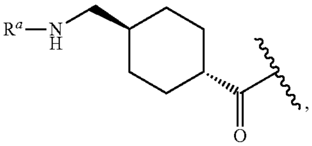,
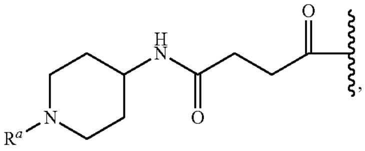,
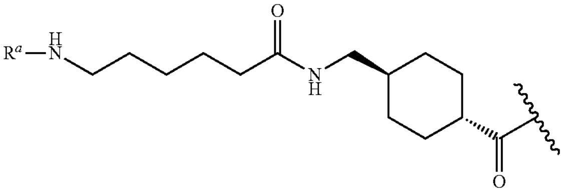,
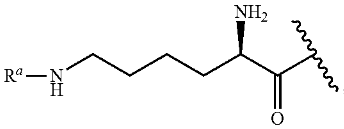,
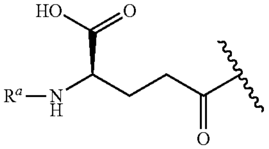,
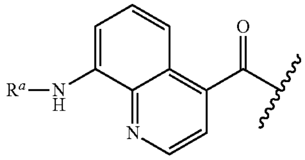,
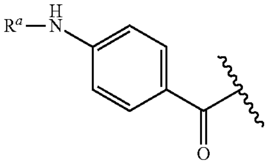,
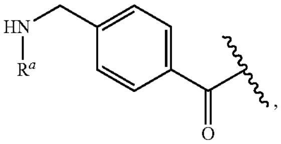,
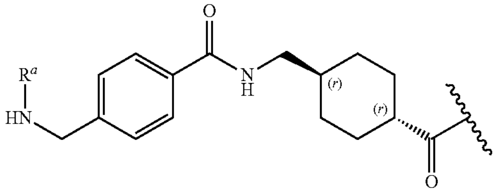,
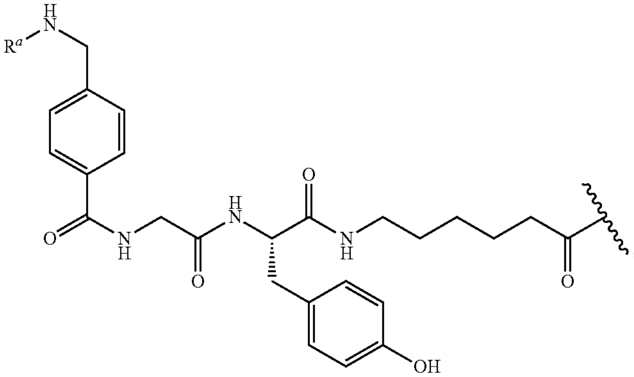,
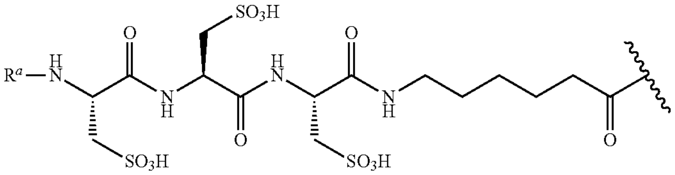,
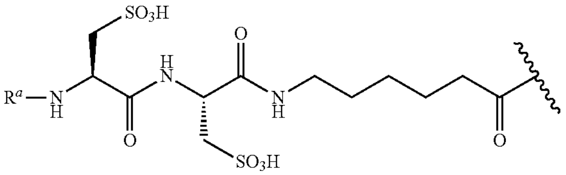,
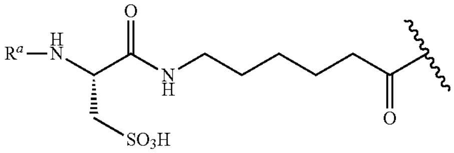, -continued
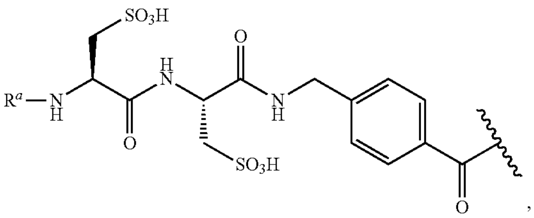
,
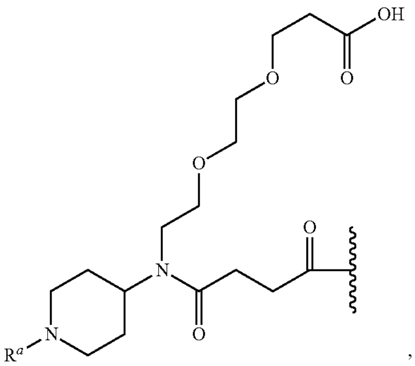
,
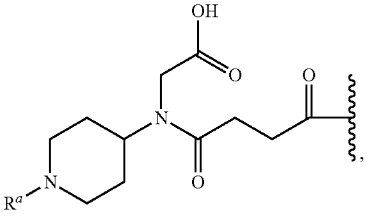
,
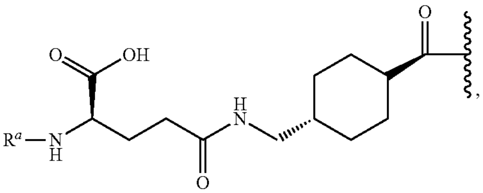
,
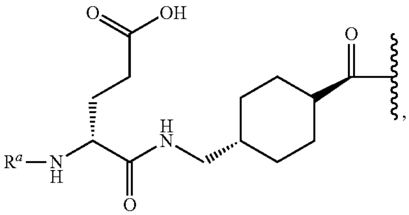
,
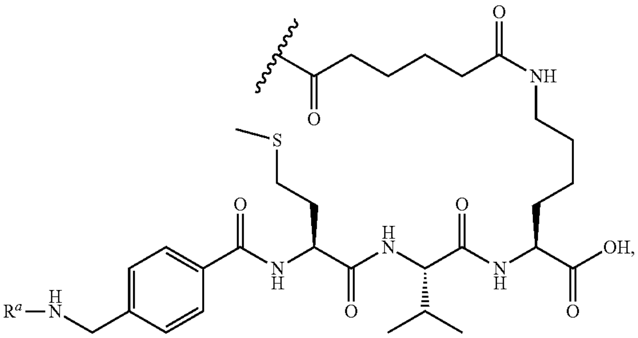
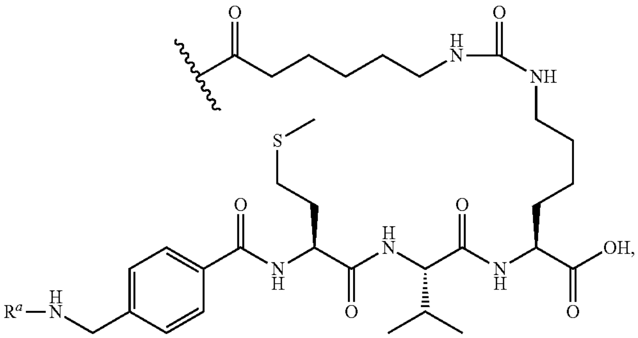
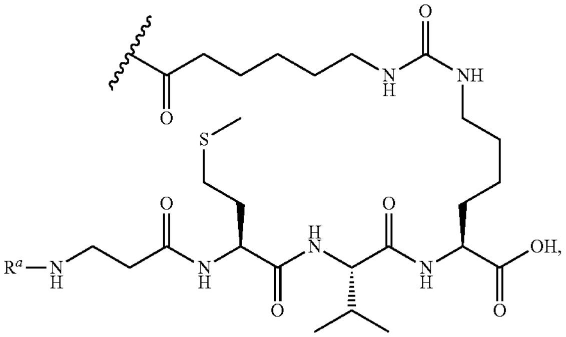
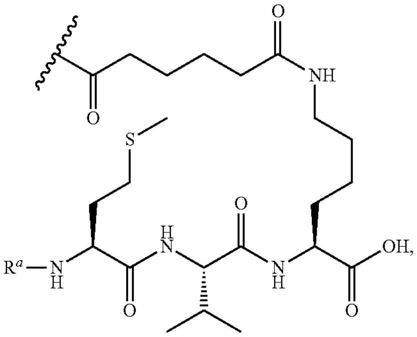

-continued
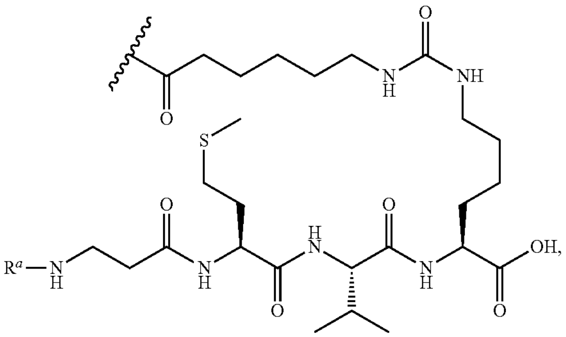
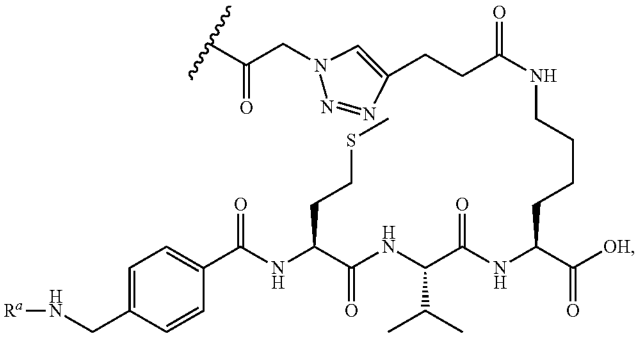
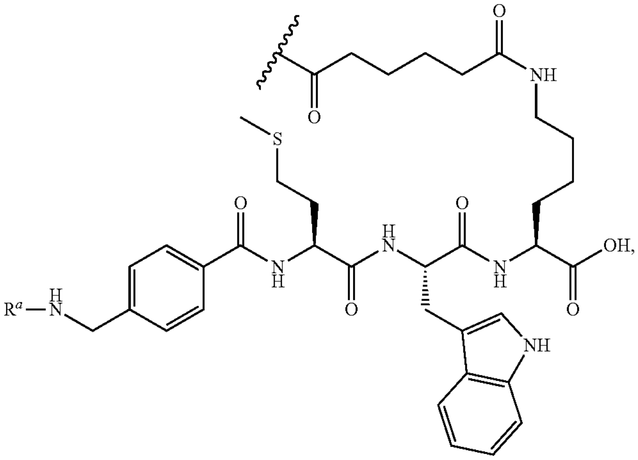
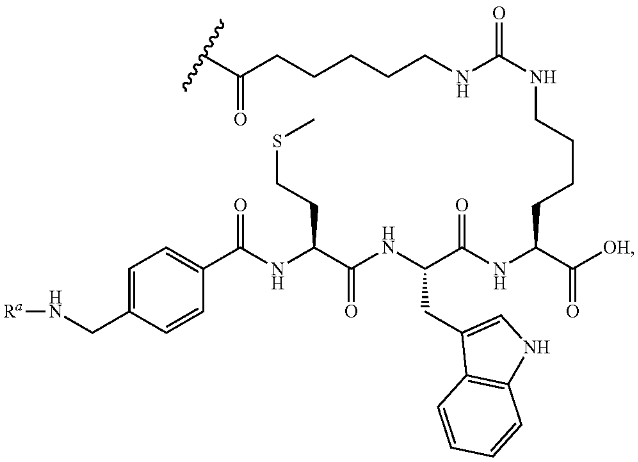

-continued

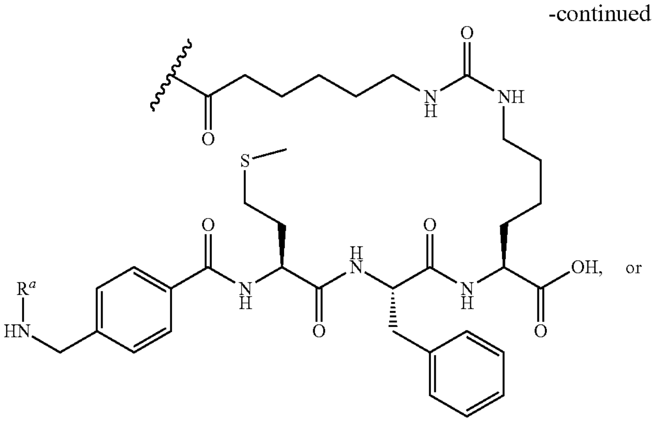

or (SEQ ID NO: 844)

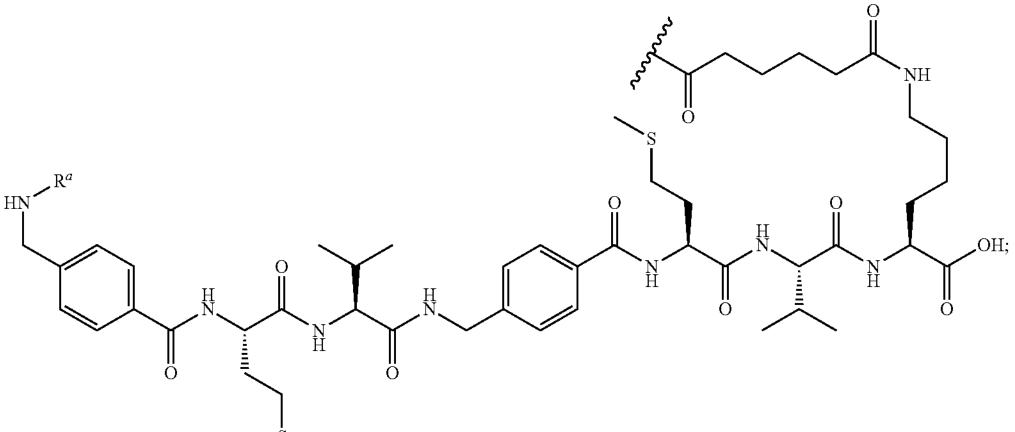

wherein $R^a$ is

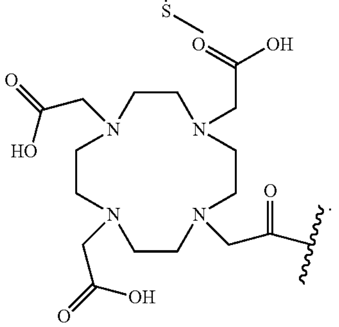

Representative Compounds

In some embodiments, the compound of Formula (I) is compound in Table A, or a pharmaceutically acceptable salt thereof:

TABLE A

| Cmp. # | Structure |
|---|---|
| 1 | SEQ ID NO: 391 |
| 1-In | In Complex of Compound 1<br>SEQ ID NO: 392 |
| 1-Lu | Lu Complex of Compound 1<br>SEQ ID NO: 393 |
| 1-Ga | Ga Complex of Compound 1<br>SEQ ID NO: 394 |
| 2 | SEQ ID NO: 395 |
| 2-In | In Complex of Compound 2<br>SEQ ID NO: 771 |
| 3 | SEQ ID NO: 396 |
| 4 | SEQ ID NO: 397 |

TABLE A-continued
| Cmp. # | Structure |
|---|---|
| 5 | SEQ ID NO: 398 |
| 6 | SEQ ID NO: 399 |
| 6-In | In Complex of Compound 6<br>SEQ ID NO: 772 |
| 7 | SEQ ID NO: 400 |
| 8 | 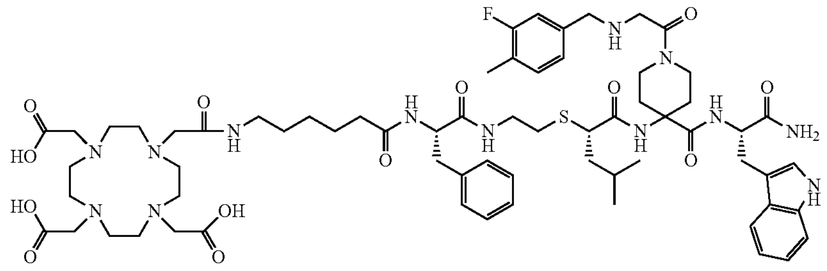 [SMILES: Cc1ccc(CNCC(=O)N2CCC(NC(=O)[C@H](CC(C)C)SCCNC(=O)[C@H](Cc3ccccc3)NC(=O)CCCCCNC(=O)CN3CCN(CC(=O)O)CCN(CC(=O)O)CCN(CC(=O)O)CC3)(C(=O)N[C@@H](Cc3c[nH]c4ccccc34)C(N)=O)CC2)cc1F] |
| 9 | 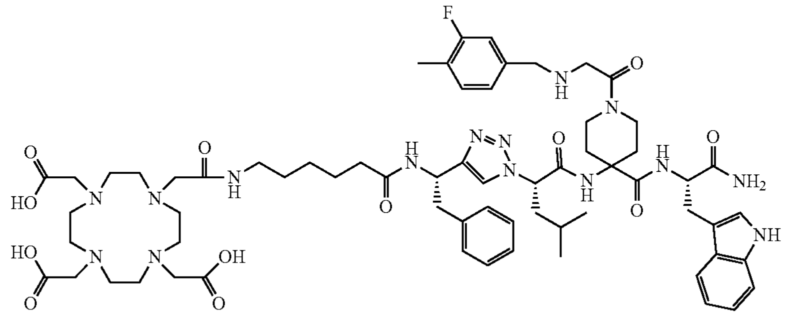 [SMILES: Cc1ccc(CNCC(=O)N2CCC(NC(=O)[C@H](CC(C)C)n3cc([C@H](Cc4ccccc4)NC(=O)CCCCCNC(=O)CN4CCN(CC(=O)O)CCN(CC(=O)O)CCN(CC(=O)O)CC4)nn3)(C(=O)N[C@@H](Cc3c[nH]c4ccccc34)C(N)=O)CC2)cc1F] |
| 10 | SEQ ID NO: 403 |
| 11 | SEQ ID NO: 404 |
| 12 | SEQ ID NO: 405 |
| 13 | SEQ ID NO: 406 |
| 14 | SEQ ID NO: 407 |
| 15 | SEQ ID NO: 408 |
| 16 | SEQ ID NO: 409 |
| 17 | SEQ ID NO: 410 |
| 18 | SEQ ID NO: 411 |
| 19 | SEQ ID NO: 412 |
| 20 | SEQ ID NO: 413 |
| 21 | SEQ ID NO: 414 |
| 22 | SEQ ID NO: 415 |
| 23 | SEQ ID NO: 416 |
| 24 | SEQ ID NO: 417 |
| 25 | SEQ ID NO: 418 |
| 26 | SEQ ID NO: 419 |
| 27 | SEQ ID NO: 420 |
| 28 | SEQ ID NO: 421 |
| 29 | SEQ ID NO: 422 |
| 30 | SEQ ID NO: 423 |
| 31 | SEQ ID NO: 424 |
| 32 | SEQ ID NO: 425 |
| 33 | SEQ ID NO: 426 |
| 34 | SEQ ID NO: 427 |
| 35 | SEQ ID NO: 428 |
| 36 | SEQ ID NO: 429 |
| 37 | SEQ ID NO: 430 |
| 38 | SEQ ID NO: 431 |

TABLE A-continued
| Cmp. # | Structure |
|---|---|
| 39 | 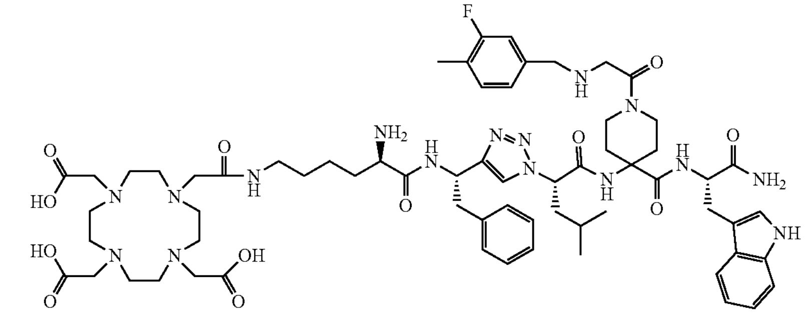 [SMILES: Cc1ccc(CNCC(=O)N2CCC(NC(=O)[C@H](CC(C)C)n3cc([C@H](Cc4ccccc4)NC(=O)[C@H](N)CCCCNC(=O)CN4CCN(CC(=O)O)CCN(CC(=O)O)CCN(CC(=O)O)CC4)nn3)(C(=O)N[C@@H](Cc3c[nH]c4ccccc34)C(N)=O)CC2)cc1F] |
| 49 | SEQ ID NO: 441 |
| 50 | SEQ ID NO: 442 |
| 51 | 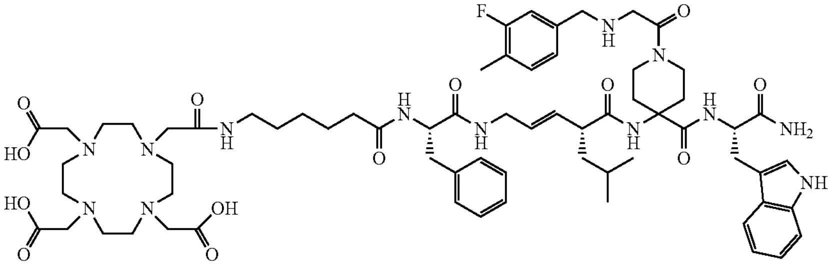 [SMILES: Cc1ccc(CNCC(=O)N2CCC(NC(=O)[C@@H](/C=C/CNC(=O)[C@H](Cc3ccccc3)NC(=O)CCCCCNC(=O)CN3CCN(CC(=O)O)CCN(CC(=O)O)CCN(CC(=O)O)CC3)CC(C)C)(C(=O)N[C@@H](Cc3c[nH]c4ccccc34)C(N)=O)CC2)cc1F] |
| 55 | SEQ ID NO: 447 |
| 57 | SEQ ID NO: 449 |
| 58 | SEQ ID NO: 450 |
| 64 | SEQ ID NO: 456 |
| 91 | SEQ ID NO: 479 |
| 104 | SEQ ID NO: 491 |
| 105 | SEQ ID NO: 492 |
| 105-In | In Complex of Compound 105<br>SEQ ID NO: 493 |
| 106 | SEQ ID NO: 494 |
| 107 | SEQ ID NO: 495 |
| 108 | SEQ ID NO: 496 |
| 109 | SEQ ID NO: 497 |
| 110 | SEQ ID NO: 498 |
| 113 | SEQ ID NO: 500 |
| 114 | SEQ ID NO: 501 |
| 115 | SEQ ID NO: 502 |
| 116 | SEQ ID NO: 503 |
| 117 | SEQ ID NO: 504 |
| 118 | SEQ ID NO: 505 |
| 118-Lu | Lu Complex of Compound 118<br>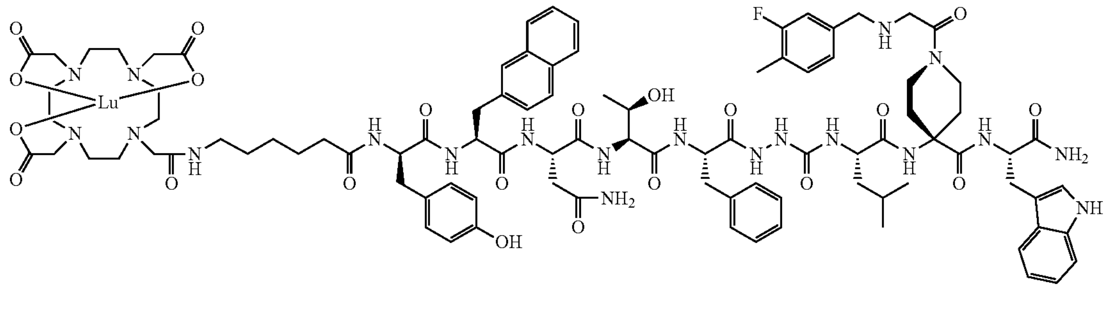 |
| 119 | SEQ ID NO: 506 |
| 120 | SEQ ID NO: 507 |
| 121 | SEQ ID NO: 508 |
| 123 | SEQ ID NO: 510 |
| 130 | SEQ ID NO: 511 |
| 131 | SEQ ID NO: 512 |
| 132 | SEQ ID NO: 513 |

TABLE A-continued
| Cmp. # | Structure |
|---|---|
| 133 | SEQ ID NO: 514 |
| 134 | 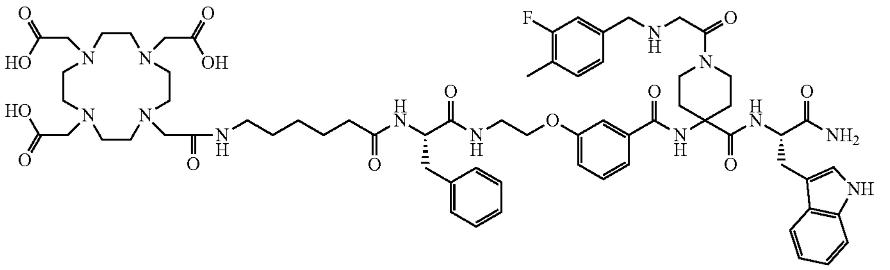 [SMILES: Cc1ccc(CNCC(=O)N2CCC(NC(=O)c3cccc(OCCNC(=O)[C@H](Cc4ccccc4)NC(=O)CCCCCNC(=O)CN4CCN(CC(=O)O)CCN(CC(=O)O)CCN(CC(=O)O)CC4)c3)(C(=O)N[C@@H](Cc3c[nH]c4ccccc34)C(N)=O)CC2)cc1F] |
| 135 | 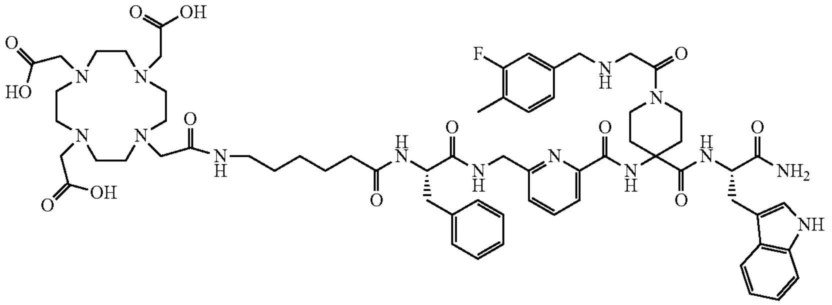 [SMILES: Cc1ccc(CNCC(=O)N2CCC(NC(=O)c3cccc(CNC(=O)[C@H](Cc4ccccc4)NC(=O)CCCCCNC(=O)CN4CCN(CC(=O)O)CCN(CC(=O)O)CCN(CC(=O)O)CC4)n3)(C(=O)N[C@@H](Cc3c[nH]c4ccccc34)C(N)=O)CC2)cc1F] |
| 136 | 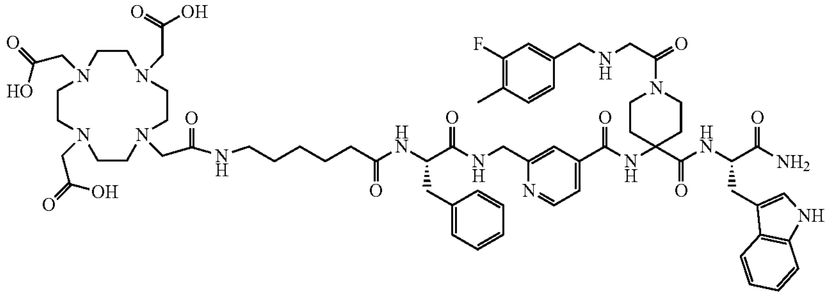 [SMILES: Cc1ccc(CNCC(=O)N2CCC(NC(=O)c3ccnc(CNC(=O)[C@H](Cc4ccccc4)NC(=O)CCCCCNC(=O)CN4CCN(CC(=O)O)CCN(CC(=O)O)CCN(CC(=O)O)CC4)c3)(C(=O)N[C@@H](Cc3c[nH]c4ccccc34)C(N)=O)CC2)cc1F] |
| 137 | 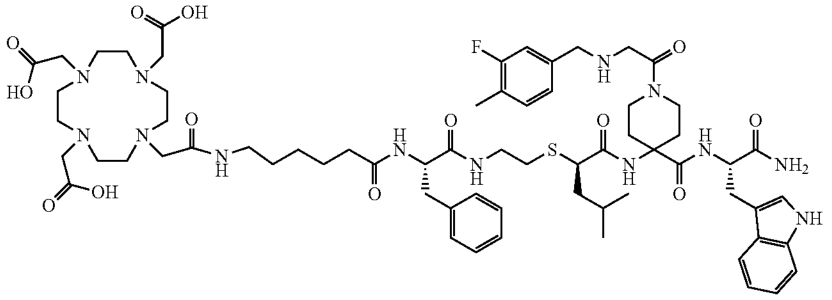 [SMILES: Cc1ccc(CNCC(=O)N2CCC(NC(=O)[C@@H](CC(C)C)SCCNC(=O)[C@H](Cc3ccccc3)NC(=O)CCCCCNC(=O)CN3CCN(CC(=O)O)CCN(CC(=O)O)CCN(CC(=O)O)CC3)(C(=O)N[C@@H](Cc3c[nH]c4ccccc34)C(N)=O)CC2)cc1F] |
| 138 | 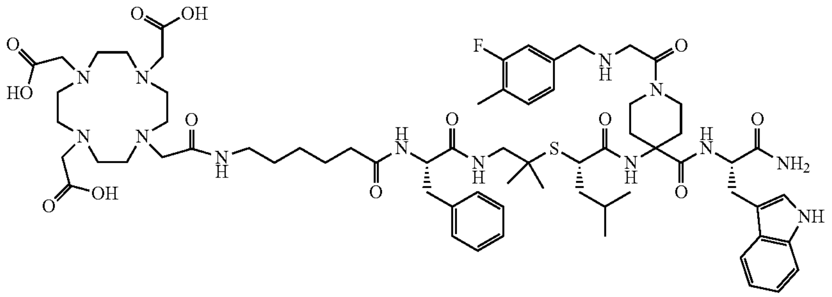 [SMILES: Cc1ccc(CNCC(=O)N2CCC(NC(=O)[C@H](CC(C)C)SC(C)(C)CNC(=O)[C@H](Cc3ccccc3)NC(=O)CCCCCNC(=O)CN3CCN(CC(=O)O)CCN(CC(=O)O)CCN(CC(=O)O)CC3)(C(=O)N[C@@H](Cc3c[nH]c4ccccc34)C(N)=O)CC2)cc1F] |

TABLE A-continued
| Cmp. # | Structure |
| --- | --- |
| 139 | 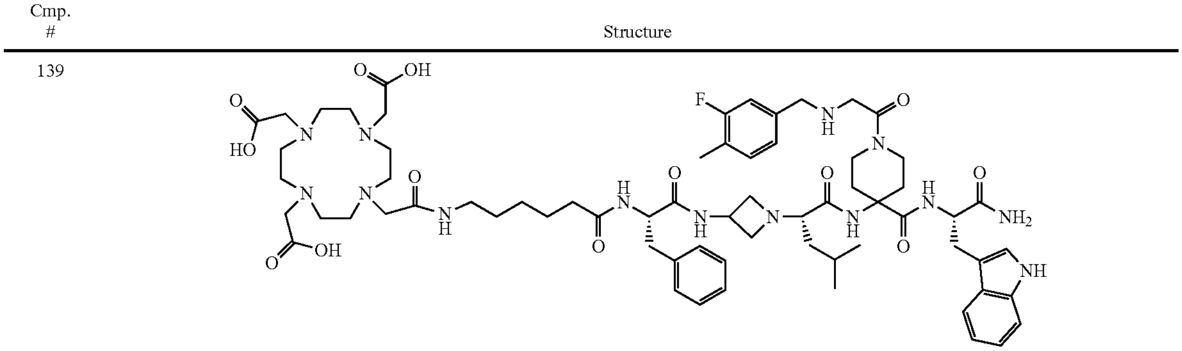 |
| 140 | SEQ ID NO: 521 |
| 141 | 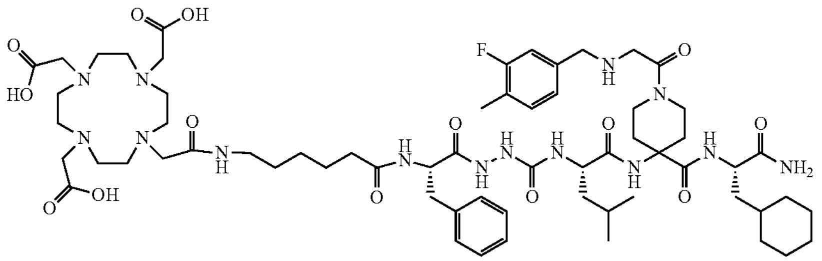 [SMILES: Cc1ccc(CNCC(=O)N2CCC(NC(=O)[C@H](CC(C)C)NC(=O)NNC(=O)[C@H](Cc3ccccc3)NC(=O)CCCCCNC(=O)CN3CCN(CC(=O)O)CCN(CC(=O)O)CCN(CC(=O)O)CC3)(C(=O)N[C@@H](CC3CCCCC3)C(N)=O)CC2)cc1F] |
| 142 | 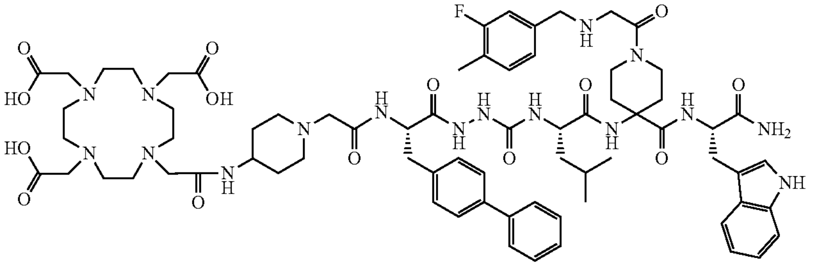 [SMILES: Cc1ccc(CNCC(=O)N2CCC(NC(=O)[C@H](CC(C)C)NC(=O)NNC(=O)[C@H](Cc3ccc(-c4ccccc4)cc3)NC(=O)CN3CCC(NC(=O)CN4CCN(CC(=O)O)CCN(CC(=O)O)CCN(CC(=O)O)CC4)CC3)(C(=O)N[C@@H](Cc3c[nH]c4ccccc34)C(N)=O)CC2)cc1F] |
| 146 | SEQ ID NO: 527 |
| 147 | 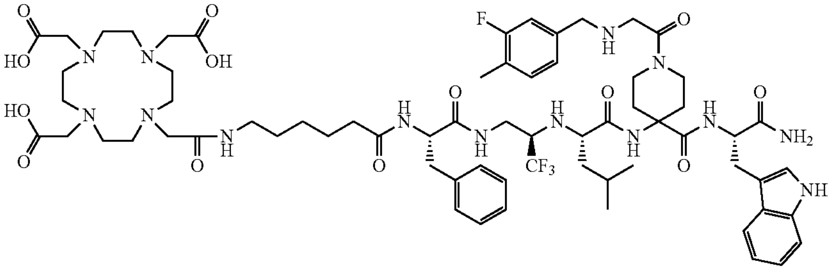 [SMILES: Cc1ccc(CNCC(=O)N2CCC(NC(=O)[C@H](CC(C)C)N[C@H](CNC(=O)[C@H](Cc3ccccc3)NC(=O)CCCCCNC(=O)CN3CCN(CC(=O)O)CCN(CC(=O)O)CCN(CC(=O)O)CC3)C(F)(F)F)(C(=O)N[C@@H](Cc3c[nH]c4ccccc34)C(N)=O)CC2)cc1F] |
| 148 | 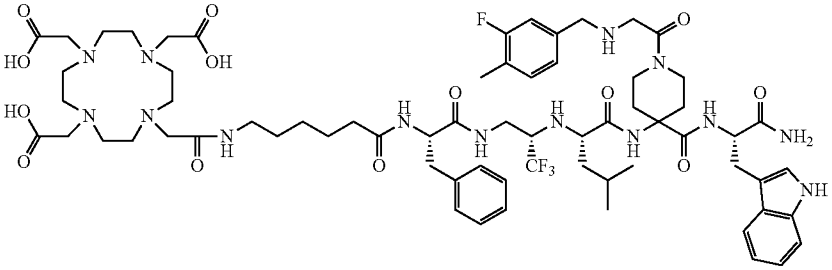 [SMILES: Cc1ccc(CNCC(=O)N2CCC(NC(=O)[C@H](CC(C)C)N[C@@H](CNC(=O)[C@H](Cc3ccccc3)NC(=O)CCCCCNC(=O)CN3CCN(CC(=O)O)CCN(CC(=O)O)CCN(CC(=O)O)CC3)C(F)(F)F)(C(=O)N[C@@H](Cc3c[nH]c4ccccc34)C(N)=O)CC2)cc1F] |
| 149 | SEQ ID NO: 530 |
| 151 | SEQ ID NO: 532 |
| 156 | SEQ ID NO: 537 |
| 158 | SEQ ID NO: 539 |

TABLE A-continued

| Cmp. # | Structure |
|---|---|
| 159 | SEQ ID NO: 540 |
| 160 | SEQ ID NO: 541 |
| 161 | SEQ ID NO: 542 |
| 164 | SEQ ID NO: 545 |
| 165 | SEQ ID NO: 546 |
| 166 | SEQ ID NO: 547 |
| 167 | SEQ ID NO: 548 |
| 168 | SEQ ID NO: 549 |
| 169 | SEQ ID NO: 550 |
| 170 | SEQ ID NO: 551 |
| 171 | SEQ ID NO: 552 |
| 176 | SEQ ID NO: 555 |
| 181 | SEQ ID NO: 560 |
| 182 | SEQ ID NO: 561 |
| 183 | SEQ ID NO: 562 |
| 184 | SEQ ID NO: 563 |
| 185 | SEQ ID NO: 564 |
| 186 | SEQ ID NO: 565 |
| 187 | SEQ ID NO: 566 |
| 188 | SEQ ID NO: 567 |
| 189 | SEQ ID NO: 568 |
| 192 | SEQ ID NO: 571 |
| 193 | SEQ ID NO: 572 |
| 193-In | Indium complex of Compound 193<br>SEQ ID NO: 573 |
| 195 | SEQ ID NO: 575 |
| 196 | SEQ ID NO: 576 |
| 196-In | In Complex of Compound 196<br>SEQ ID NO: 577 |
| 197 | SEQ ID NO: 578 |
| 198 | SEQ ID NO: 579 |
| 199 | SEQ ID NO: 580 |
| 201 | SEQ ID NO: 581 |
| 201-In | In Complex of Compound 201<br>SEQ ID NO: 582 |
| 202 | SEQ ID NO: 583 |
| 203 | SEQ ID NO: 584 |
| 204 | 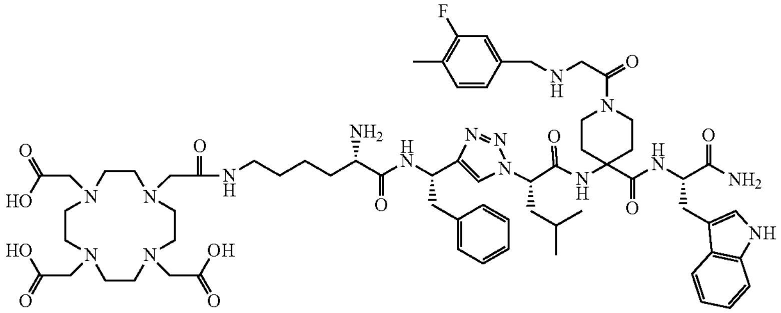 [SMILES: Cc1ccc(CNCC(=O)N2CCC(NC(=O)[C@H](CC(C)C)n3cc([C@H](Cc4ccccc4)NC(=O)[C@@H](N)CCCCNC(=O)CN4CCN(CC(=O)O)CCN(CC(=O)O)CCN(CC(=O)O)CC4)nn3)(C(=O)N[C@@H](Cc3c[nH]c4ccccc34)C(N)=O)CC2)cc1F] |
| 205 | SEQ ID NO: 586 |
| 206 | SEQ ID NO: 587 |
| 213 | SEQ ID NO: 594 |
| 214 | 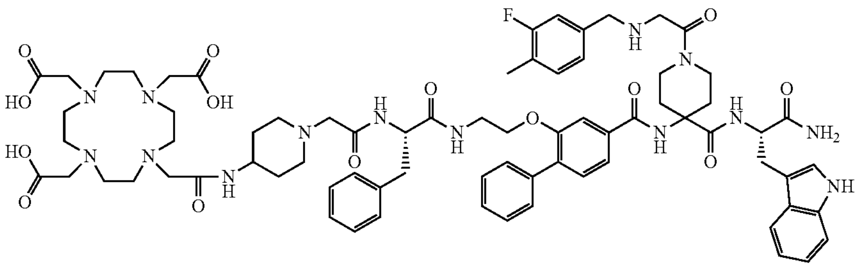 [SMILES: Cc1ccc(CNCC(=O)N2CCC(NC(=O)c3ccc(-c4ccccc4)c(OCCNC(=O)[C@H](Cc4ccccc4)NC(=O)CN4CCC(NC(=O)CN5CCN(CC(=O)O)CCN(CC(=O)O)CCN(CC(=O)O)CC5)CC4)c3)(C(=O)N[C@@H](Cc3c[nH]c4ccccc34)C(N)=O)CC2)cc1F] |

TABLE A-continued
| Cmp. # | Structure |
|---|---|
| 215 | 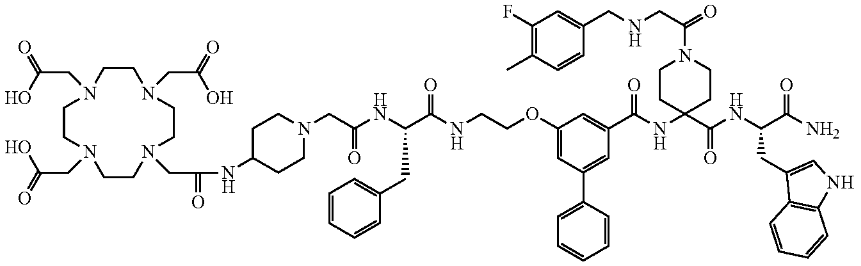 [SMILES: Cc1ccc(CNCC(=O)N2CCC(NC(=O)c3cc(OCCNC(=O)[C@H](Cc4ccccc4)NC(=O)CN4CCC(NC(=O)CN5CCN(CC(=O)O)CCN(CC(=O)O)CCN(CC(=O)O)CC5)CC4)cc(-c4ccccc4)c3)(C(=O)N[C@@H](Cc3c[nH]c4ccccc34)C(N)=O)CC2)cc1F] |
| 216 | 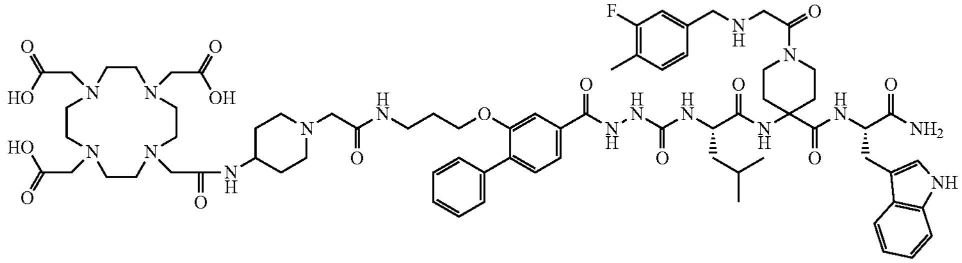 [SMILES: Cc1ccc(CNCC(=O)N2CCC(NC(=O)[C@H](CC(C)C)NC(=O)NNC(=O)c3ccc(-c4ccccc4)c(OCCCNC(=O)CN4CCC(NC(=O)CN5CCN(CC(=O)O)CCN(CC(=O)O)CCN(CC(=O)O)CC5)CC4)c3)(C(=O)N[C@@H](Cc3c[nH]c4ccccc34)C(N)=O)CC2)cc1F] |
| 217 | 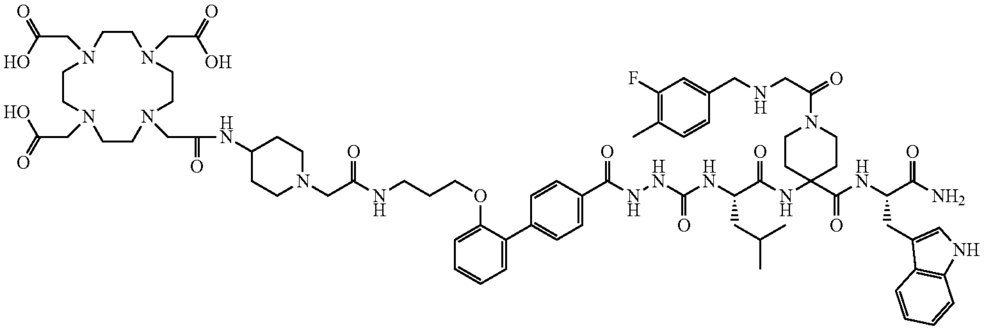 [SMILES: Cc1ccc(CNCC(=O)N2CCC(NC(=O)[C@H](CC(C)C)NC(=O)NNC(=O)c3ccc(-c4ccccc4OCCCNC(=O)CN4CCC(NC(=O)CN5CCN(CC(=O)O)CCN(CC(=O)O)CCN(CC(=O)O)CC5)CC4)cc3)(C(=O)N[C@@H](Cc3c[nH]c4ccccc34)C(N)=O)CC2)cc1F] |
| 218 | SEQ ID NO: 599 |
| 221 | SEQ ID NO: 602 |
| 222 | SEQ ID NO: 603 |
| 226 | SEQ ID NO: 607 |
| 230 | SEQ ID NO: 611 |
| 231 | SEQ ID NO: 612 |
| 232 | SEQ ID NO: 613 |
| 233 | SEQ ID NO: 614 |
| 234 | SEQ ID NO: 615 |
| 235 | SEQ ID NO: 616 |
| 236 | SEQ ID NO: 617 |
| 237 | SEQ ID NO: 618 |
| 238 | SEQ ID NO: 619 |
| 239 | SEQ ID NO: 620 |
| 240 | SEQ ID NO: 621 |
| 241 | SEQ ID NO: 622 |
| 242 | SEQ ID NO: 623 |
| 244 | SEQ ID NO: 625 |
| 245 | SEQ ID NO: 626 |
| 246 | 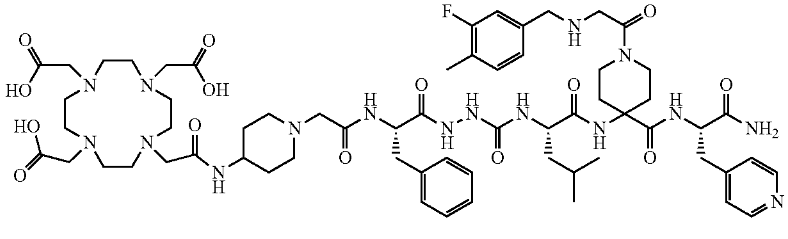 [SMILES: Cc1ccc(CNCC(=O)N2CCC(NC(=O)[C@H](CC(C)C)NC(=O)NNC(=O)[C@H](Cc3ccccc3)NC(=O)CN3CCC(NC(=O)CN4CCN(CC(=O)O)CCN(CC(=O)O)CCN(CC(=O)O)CC4)CC3)(C(=O)N[C@@H](Cc3ccncc3)C(N)=O)CC2)cc1F] |
| 247 | SEQ ID NO: 628 |
| 248 | SEQ ID NO: 629 |

TABLE A-continued
| Cmp. # | Structure |
|---|---|
| 249 | SEQ ID NO: 630 |
| 250 | SEQ ID NO: 631 |
| 251 | SEQ ID NO: 632 |
| 252 | SEQ ID NO: 633 |
| 253 | SEQ ID NO: 634 |
| 254 | SEQ ID NO: 635 |
| 255 | SEQ ID NO: 636 |
| 256 | SEQ ID NO: 637 |
| 258 | SEQ ID NO: 639 |
| 259 | SEQ ID NO: 640 |
| 260 | SEQ ID NO: 641 |
| 261 | 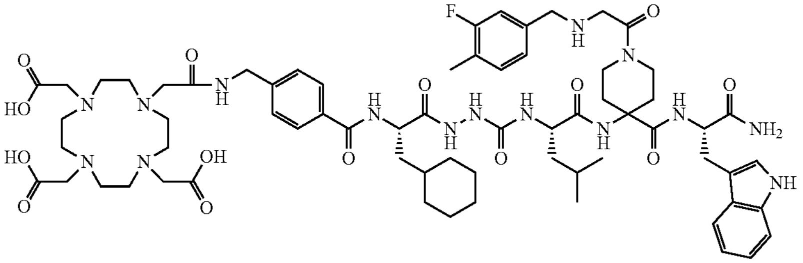 [SMILES: Cc1ccc(CNCC(=O)N2CCC(NC(=O)[C@H](CC(C)C)NC(=O)NNC(=O)[C@H](CC3CCCCC3)NC(=O)c3ccc(CNC(=O)CN4CCN(CC(=O)O)CCN(CC(=O)O)CCN(CC(=O)O)CC4)cc3)(C(=O)N[C@@H](Cc3c[nH]c4ccccc34)C(N)=O)CC2)cc1F] |
| 264 | SEQ ID NO: 645 |
| 266 | SEQ ID NO: 647 |
| 269 | SEQ ID NO: 650 |
| 269-In | In Complex of Compound 269<br>SEQ ID NO: 651 |
| 270 | SEQ ID NO: 652 |
| 271 | SEQ ID NO: 653 |
| 272 | SEQ ID NO: 654 |
| 273 | SEQ ID NO: 655 |
| 275 | SEQ ID NO: 657 |
| 276 | SEQ ID NO: 658 |
| 277 | SEQ ID NO: 659 |
| 278 | SEQ ID NO: 660 |
| 279 | SEQ ID NO: 661 |
| 280 | 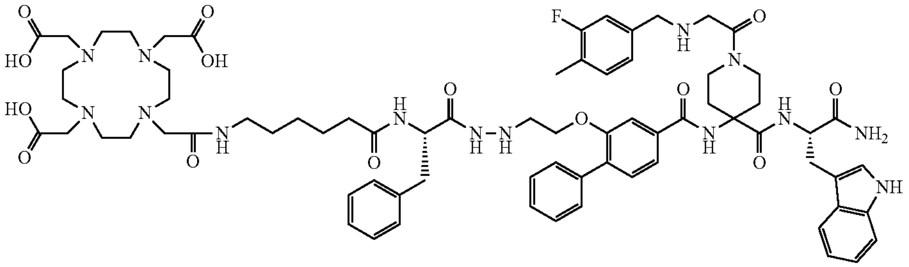 [SMILES: Cc1ccc(CNCC(=O)N2CCC(NC(=O)c3ccc(-c4ccccc4)c(OCCNNC(=O)[C@H](Cc4ccccc4)NC(=O)CCCCCNC(=O)CN4CCN(CC(=O)O)CCN(CC(=O)O)CCN(CC(=O)O)CC4)c3)(C(=O)N[C@@H](Cc3c[nH]c4ccccc34)C(N)=O)CC2)cc1F] |
| 281 | SEQ ID NO: 663 |
| 282 | 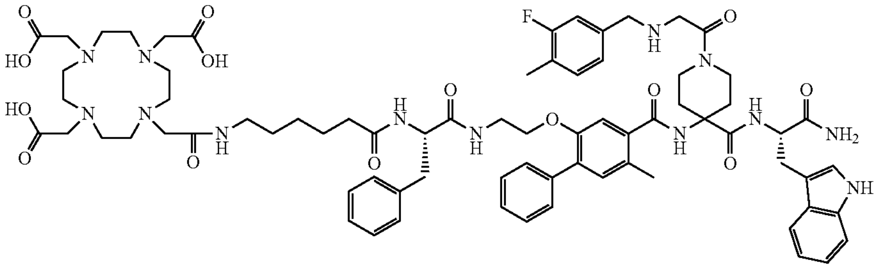 [SMILES: Cc1ccc(CNCC(=O)N2CCC(NC(=O)c3cc(OCCNC(=O)[C@H](Cc4ccccc4)NC(=O)CCCCCNC(=O)CN4CCN(CC(=O)O)CCN(CC(=O)O)CCN(CC(=O)O)CC4)c(-c4ccccc4)cc3C)(C(=O)N[C@@H](Cc3c[nH]c4ccccc34)C(N)=O)CC2)cc1F] |

TABLE A-continued
| Cmp. # | Structure |
|---|---|
| 283 | 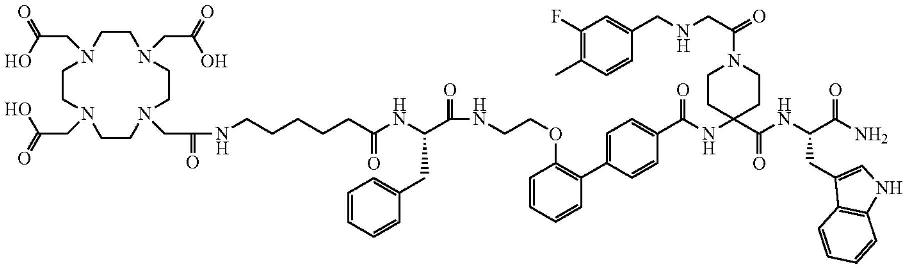 [SMILES: Cc1ccc(CNCC(=O)N2CCC(NC(=O)c3ccc(-c4ccccc4OCCNC(=O)[C@H](Cc4ccccc4)NC(=O)CCCCCNC(=O)CN4CCN(CC(=O)O)CCN(CC(=O)O)CCN(CC(=O)O)CC4)cc3)(C(=O)N[C@@H](Cc3c[nH]c4ccccc34)C(N)=O)CC2)cc1F] |
| 284 | 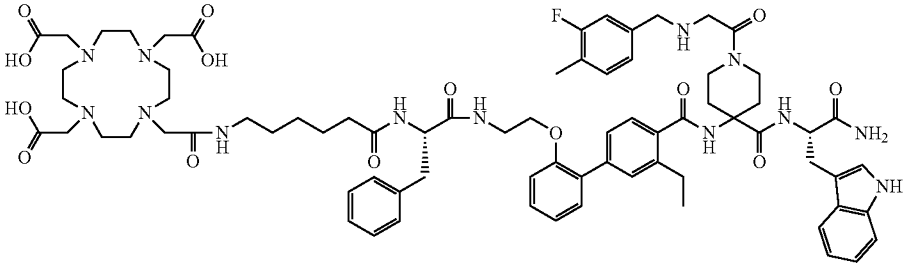 [SMILES: CCc1cc(-c2ccccc2OCCNC(=O)[C@H](Cc2ccccc2)NC(=O)CCCCCNC(=O)CN2CCN(CC(=O)O)CCN(CC(=O)O)CCN(CC(=O)O)CC2)ccc1C(=O)NC1(C(=O)N[C@@H](Cc2c[nH]c3ccccc23)C(N)=O)CCN(C(=O)CNCc2ccc(C)c(F)c2)CC1] |
| 285 | SEQ ID NO: 667 |
| 286 | SEQ ID NO: 668 |
| 287 | SEQ ID NO: 669 |
| 288 | SEQ ID NO: 670 |
| 289 | SEQ ID NO: 671 |
| 290 | SEQ ID NO: 672 |
| 291 | SEQ ID NO: 673 |
| 292 | SEQ ID NO: 674 |
| 293 | SEQ ID NO: 675 |
| 294 | SEQ ID NO: 676 |
| 295 | SEQ ID NO: 677 |
| 296 | SEQ ID NO: 678 |
| 297 | 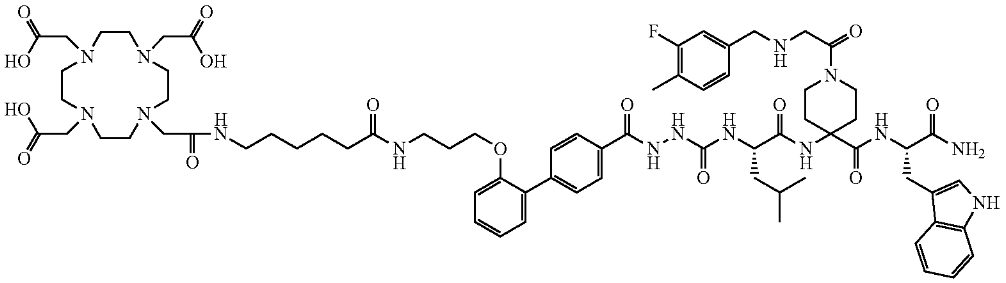 [SMILES: Cc1ccc(CNCC(=O)N2CCC(NC(=O)[C@H](CC(C)C)NC(=O)NNC(=O)c3ccc(-c4ccccc4OCCCNC(=O)CCCCCNC(=O)CN4CCN(CC(=O)O)CCN(CC(=O)O)CCN(CC(=O)O)CC4)cc3)(C(=O)N[C@@H](Cc3c[nH]c4ccccc34)C(N)=O)CC2)cc1F] |
| 298 | 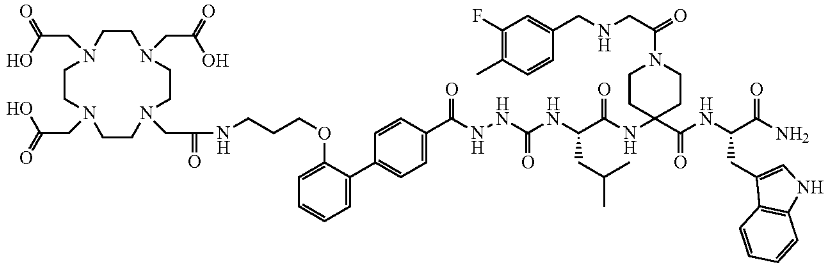 [SMILES: Cc1ccc(CNCC(=O)N2CCC(NC(=O)[C@H](CC(C)C)NC(=O)NNC(=O)c3ccc(-c4ccccc4OCCCNC(=O)CN4CCN(CC(=O)O)CCN(CC(=O)O)CCN(CC(=O)O)CC4)cc3)(C(=O)N[C@@H](Cc3c[nH]c4ccccc34)C(N)=O)CC2)cc1F] |
| 299 | SEQ ID NO: 681 |
| 300 | SEQ ID NO: 682 |
| 301 | SEQ ID NO: 683 |
| 302 | SEQ ID NO: 684 |
| 304 | SEQ ID NO: 686 |
| 305 | SEQ ID NO: 687 |
| 306 | SEQ ID NO: 688 |
| 307 | SEQ ID NO: 689 |
| 308 | SEQ ID NO: 690 |

TABLE A-continued

| Cmp. # | Structure |
|---|---|
| 309 | SEQ ID NO: 691 |
| 310 | SEQ ID NO: 692 |
| 311 | SEQ ID NO: 693 |
| 312 | SEQ ID NO: 694 |
| 313 | SEQ ID NO: 695 |
| 314 | SEQ ID NO: 696 |
| 315 | SEQ ID NO: 697 |
| 316 | SEQ ID NO: 698 |
| 317 | SEQ ID NO: 699 |
| 318 | SEQ ID NO: 700 |
| 319 | SEQ ID NO: 701 |
| 320 | SEQ ID NO: 702 |
| 321 | SEQ ID NO: 703 |
| 322 | SEQ ID NO: 704 |
| 323 | SEQ ID NO: 705 |
| 324 | SEQ ID NO: 706 |
| 325 | SEQ ID NO: 707 |
| 326 | SEQ ID NO: 708 |
| 327 | SEQ ID NO: 709 |
| 328 | SEQ ID NO: 710 |
| 329 | SEQ ID NO: 711 |
| 330 | SEQ ID NO: 712 |
| 33 | SEQ ID NO: 713 |
| 332 | SEQ ID NO: 714 |
| 333 | SEQ ID NO: 715 |
| 334 | SEQ ID NO: 716 |
| 335 | SEQ ID NO: 717 |
| 336 | SEQ ID NO: 718 |
| 337 | SEQ ID NO: 719 |
| 338 | SEQ ID NO: 720 |
| 339 | SEQ ID NO: 721 |
| 345 | SEQ ID NO: 727 |
| 346 | SEQ ID NO: 728 |
| 353 | SEQ ID NO: 735 |
| 354 | SEQ ID NO: 736 |
| 355 | SEQ ID NO: 737 |
| 356 | SEQ ID NO: 738 |
| 357 | SEQ ID NO: 739 |
| 358 | SEQ ID NO: 740 |
| 359 | SEQ ID NO: 741 |
| 360 | SEQ ID NO: 742 |
| 363 | SEQ ID NO: 745 |
| 364 | SEQ ID NO: 746 |
| 365 | SEQ ID NO: 747 |
| 366 | SEQ ID NO: 748 |
| 367 | SEQ ID NO: 749 |
| 368 | SEQ ID NO: 750 |
| 370 | SEQ ID NO: 752 |
| 371 | SEQ ID NO: 753 |
| 373 | SEQ ID NO: 755 |
| 374 | SEQ ID NO: 756 |
| 375 | SEQ ID NO: 757 |
| 376 | SEQ ID NO: 758 |
| 378 | SEQ ID NO: 759 |
| 379 | SEQ ID NO: 760 |
| 380 | SEQ ID NO: 761 |
| 381 | SEQ ID NO: 762 |
| 382 | SEQ ID NO: 763 |

TABLE A-continued
| Cmp. # | Structure |
|---|---|
| 383 | SEQ ID NO: 764 |
| 384 | SEQ ID NO: 765 |
| 386 | SEQ ID NO: 767 |
| 387 | SEQ ID NO: 768 |
| 388 | SEQ ID NO: 769 |
| 389 | SEQ ID NO: 770 |
In some embodiments, the compound of Formula (I) has a structure as shown in Table B-1, or a pharmaceutically acceptable salt thereof, wherein $R^a$ is
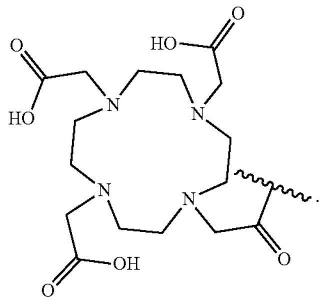 [SMILES: *C(=O)CN1CCN(CC(=O)O)CCN(CC(=O)O)CCN(CC(=O)O)CC1]

TABLE B-1
| Cmp. # | Structure |
| --- | --- |
| 40 | 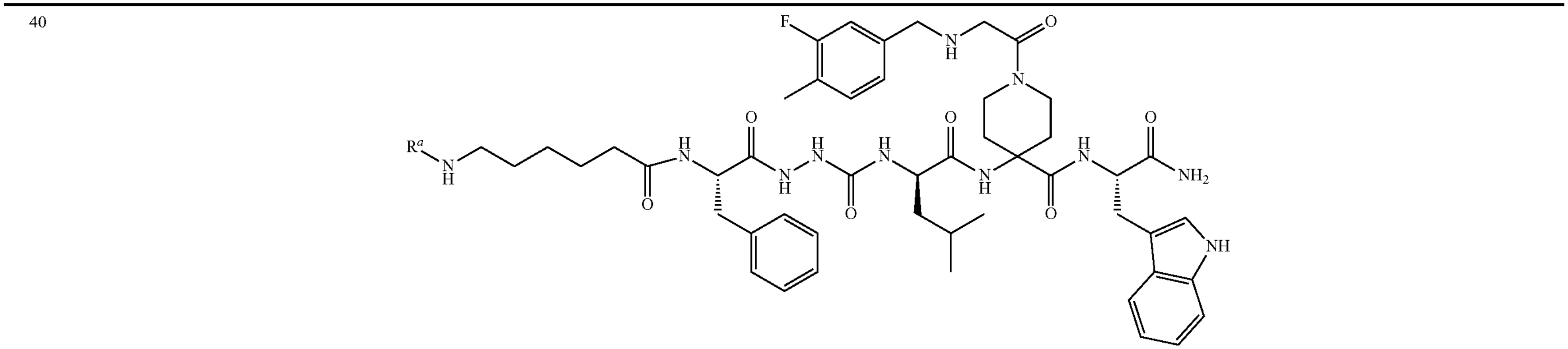<br>SEQ ID NO: 433 |
| 41 | 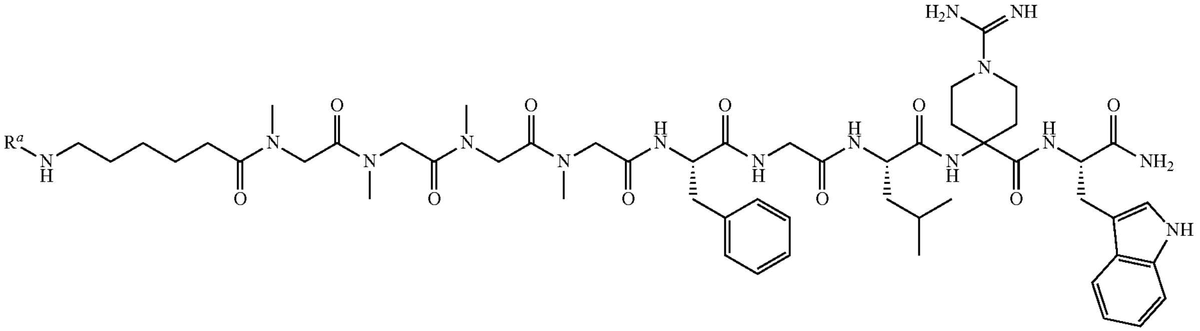<br>SEQ ID NO: 434 |

TABLE B-1-continued
| Cmp. # | Structure |
|---|---|
| 42 | 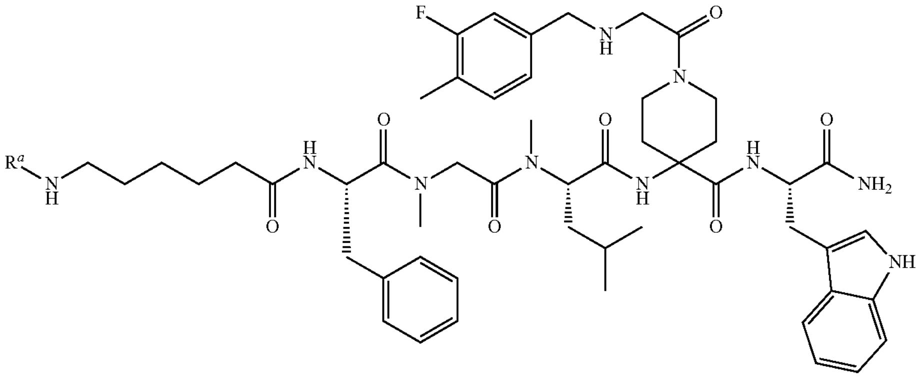<br>SEQ ID NO: 435 |
| 43 | 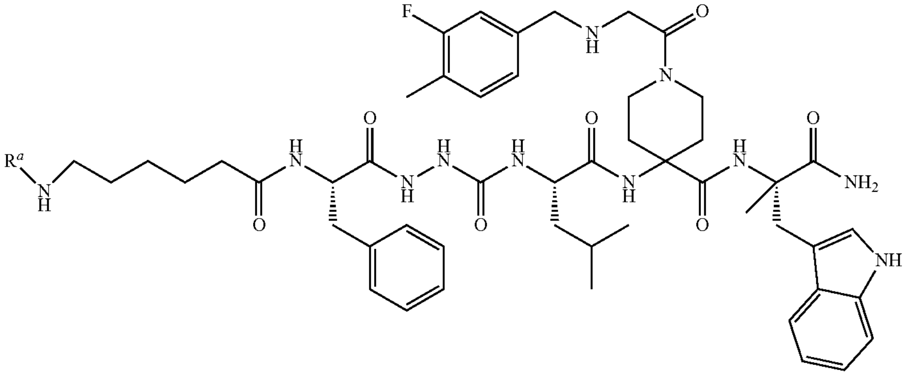<br>SEQ ID NO: 436 |

TABLE B-1-continued
| Cmp. # | Structure |
| --- | --- |
| 44 | 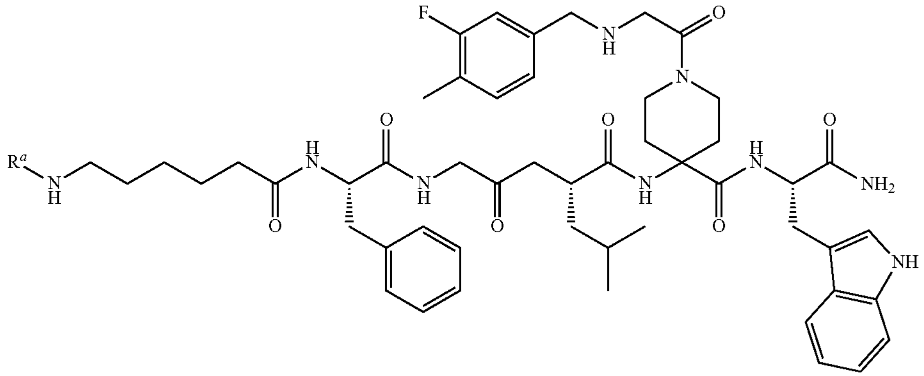 |
| 45 | 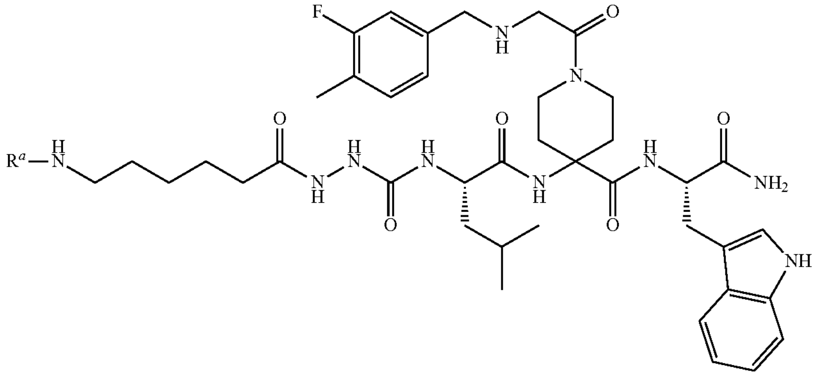 |

TABLE B-1-continued
| Cmp. # | Structure |
|---|---|
| 46 | 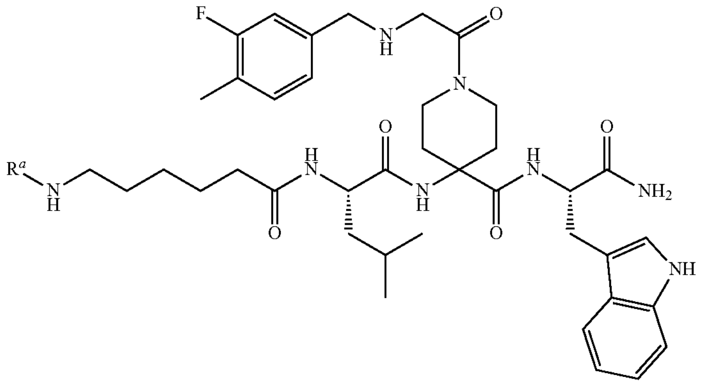 |
| 47 | 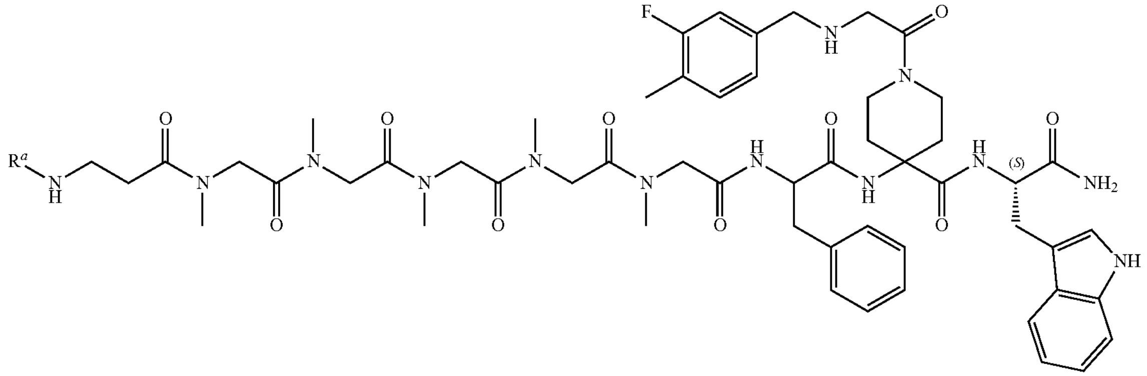 SEQ ID NO: 439 |

TABLE B-1-continued
| Cmp. # | Structure |
| --- | --- |
| 48 | 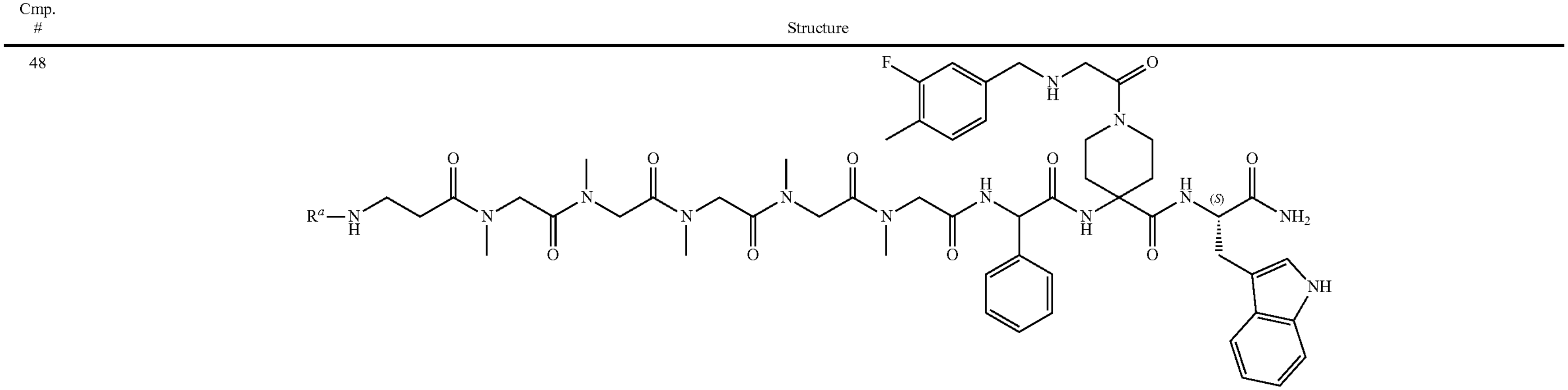 SEQ ID NO: 440 |
| 52 | 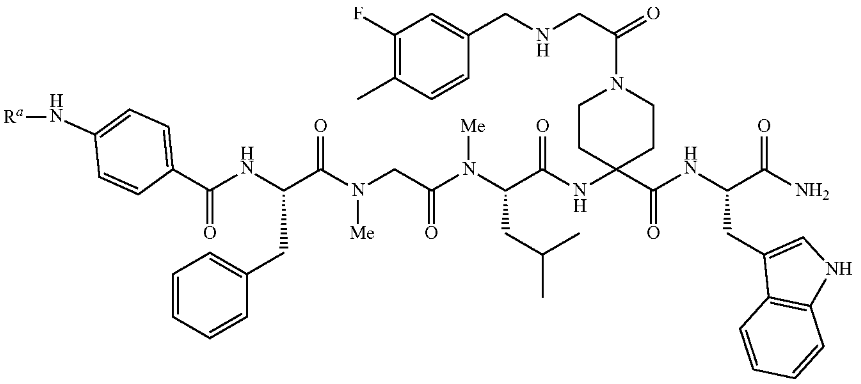 SEQ ID NO: 444 |

TABLE B-1-continued
| Cmp. # | Structure |
| --- | --- |
| 53 | 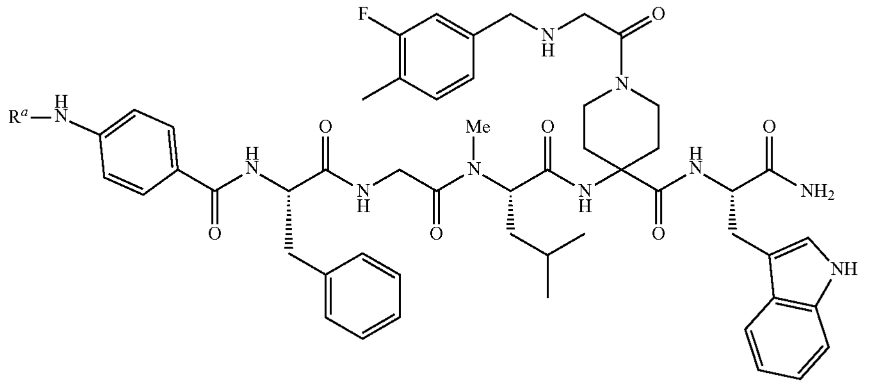 SEQ ID NO: 445 |
| 54 | 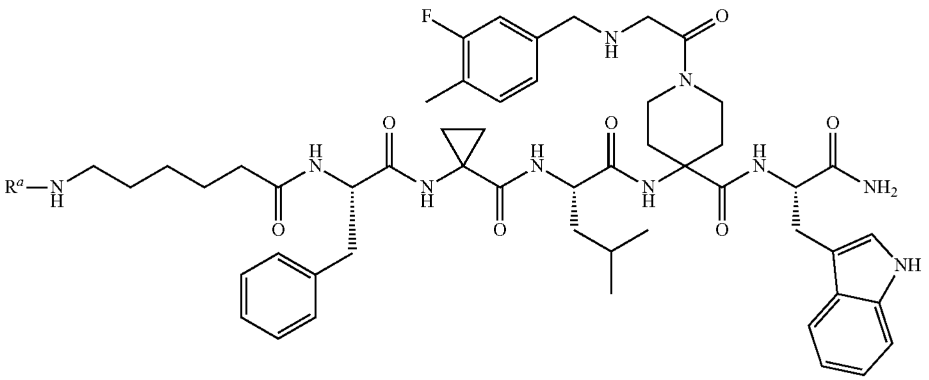 |

TABLE B-1-continued
| Cmp. # | Structure |
| --- | --- |
| 56 | 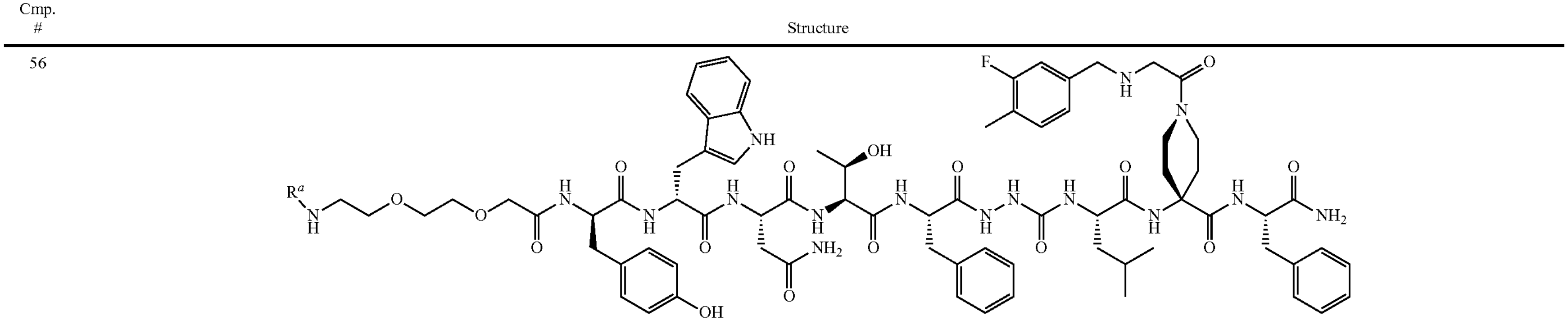 SEQ ID NO: 448 |
| 59 | 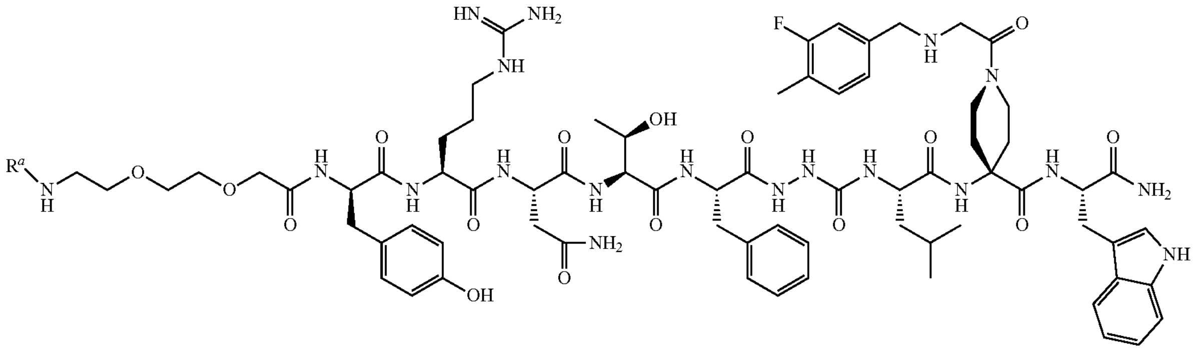 SEQ ID NO: 451 |

TABLE B-1-continued
| Cmp. # | Structure |
| --- | --- |
| 60 | 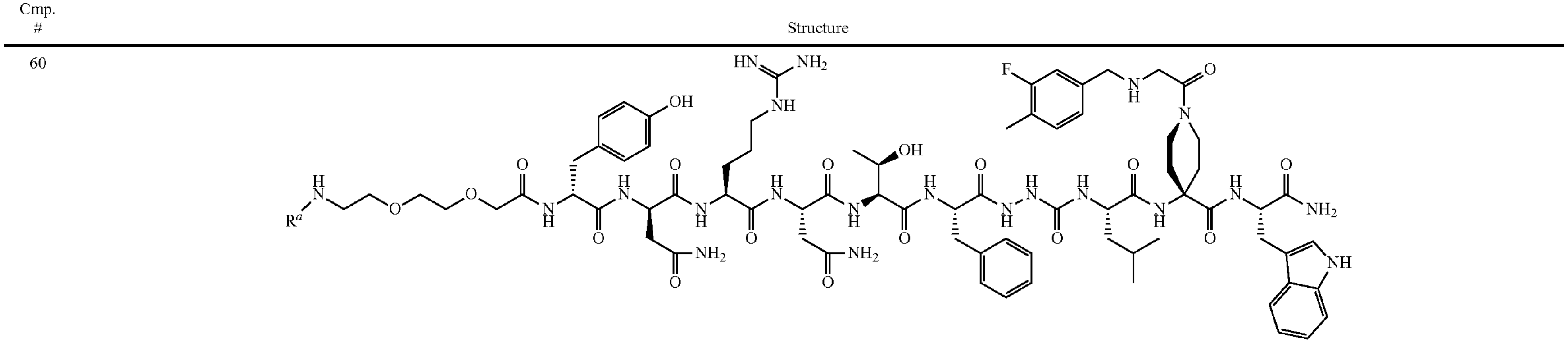 SEQ ID NO: 452 |
| 61 | 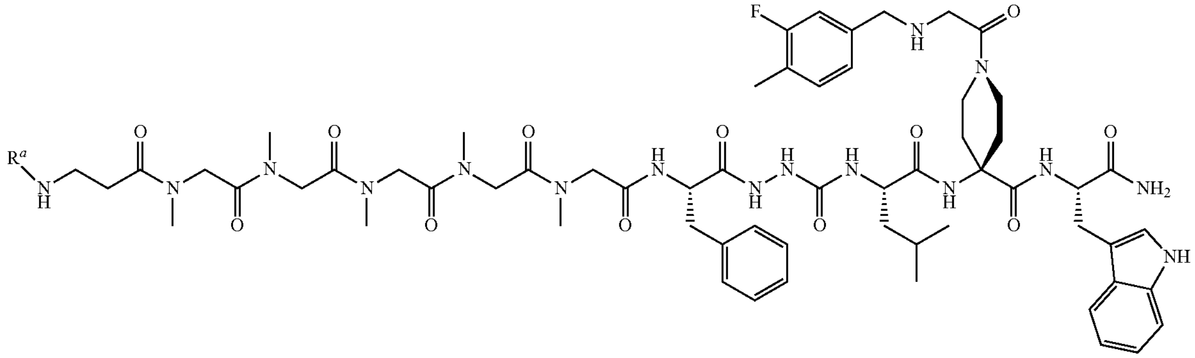 SEQ ID NO: 453 |

TABLE B-1-continued
| Cmp. # | Structure |
| --- | --- |
| 62 | 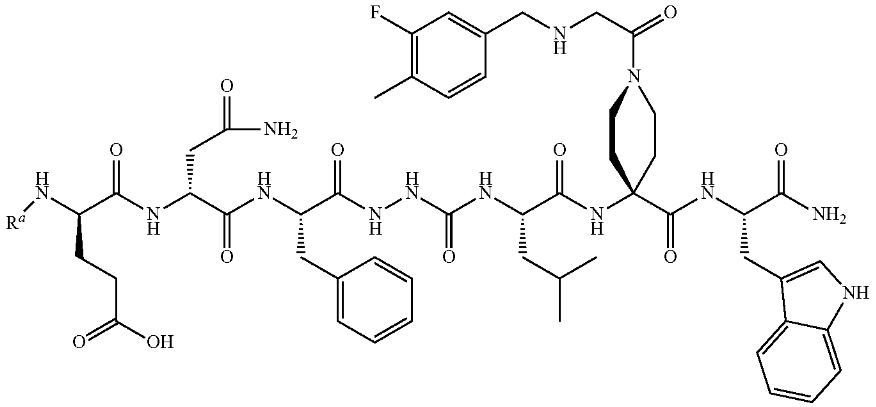 SEQ ID NO: 454 |
| 63 | 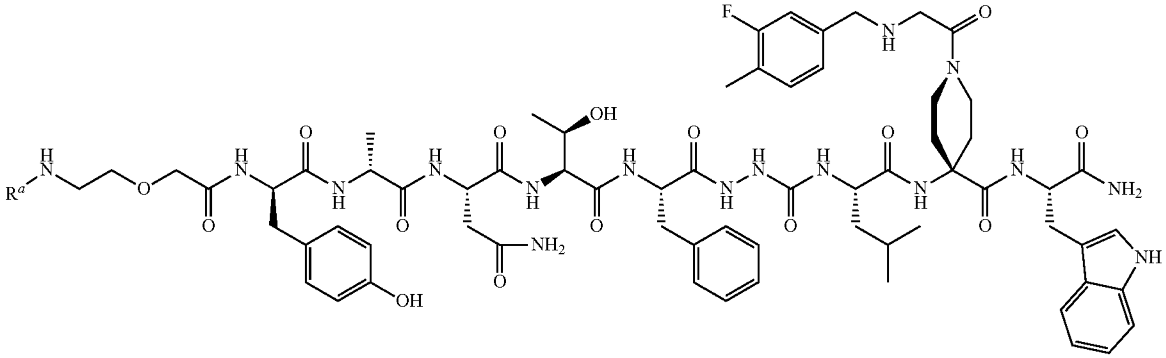 SEQ ID NO: 455 |

TABLE B-1-continued
| Cmp. # | Structure |
| --- | --- |
| 65 | 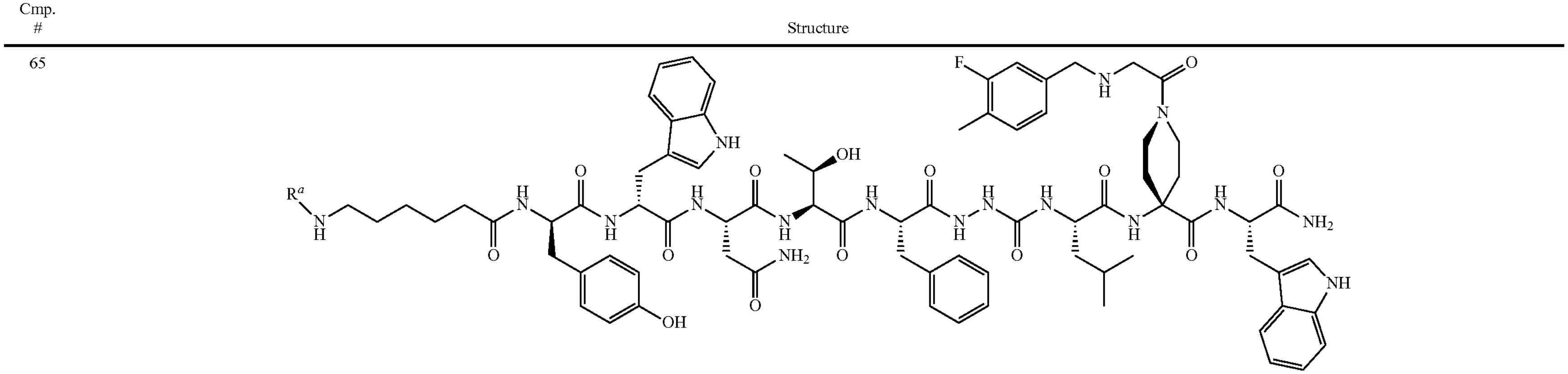<br>SEQ ID NO: 457 |
| 66 | 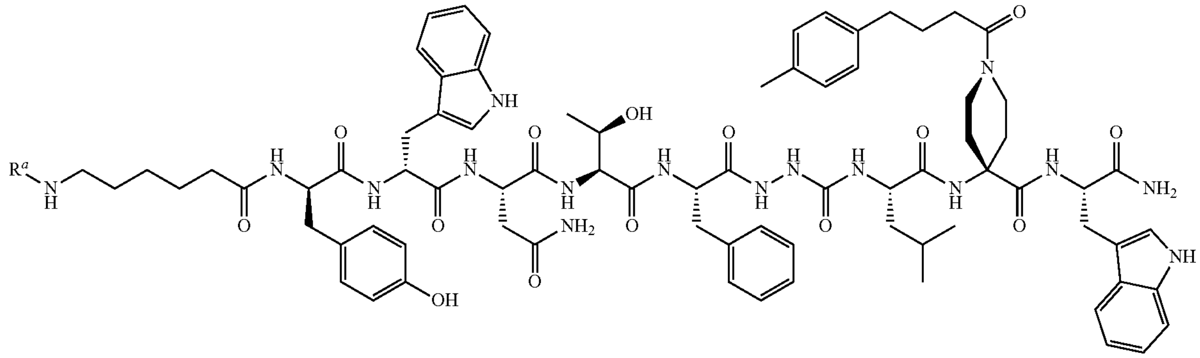<br>SEQ ID NO: 458 |

TABLE B-1-continued
| Cmp. # | Structure |
|---|---|
| 67 | 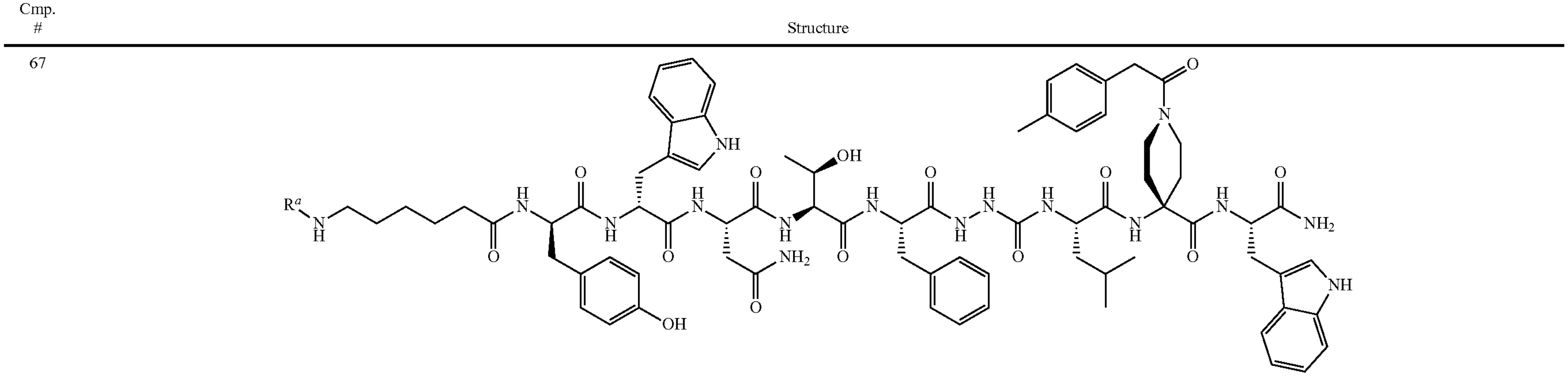 SEQ ID NO: 459 |
| 68 | 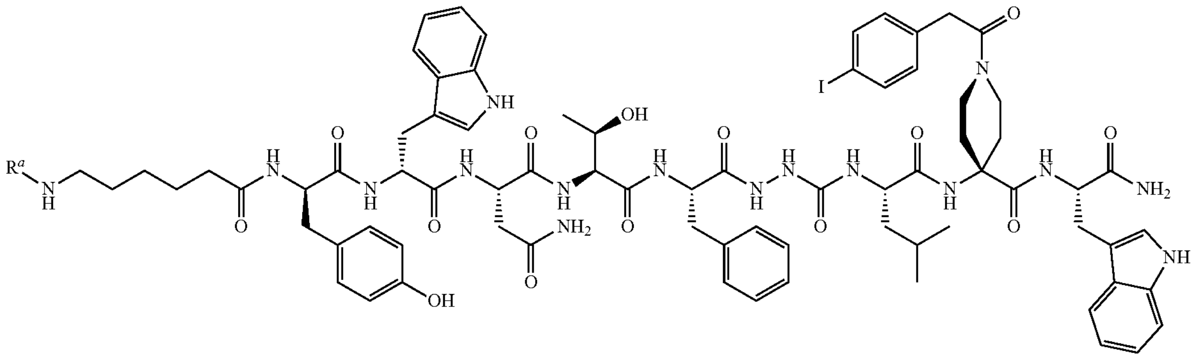 SEQ ID NO: 460 |

TABLE B-1-continued
| Cmp. # | Structure |
| --- | --- |
| 69 | 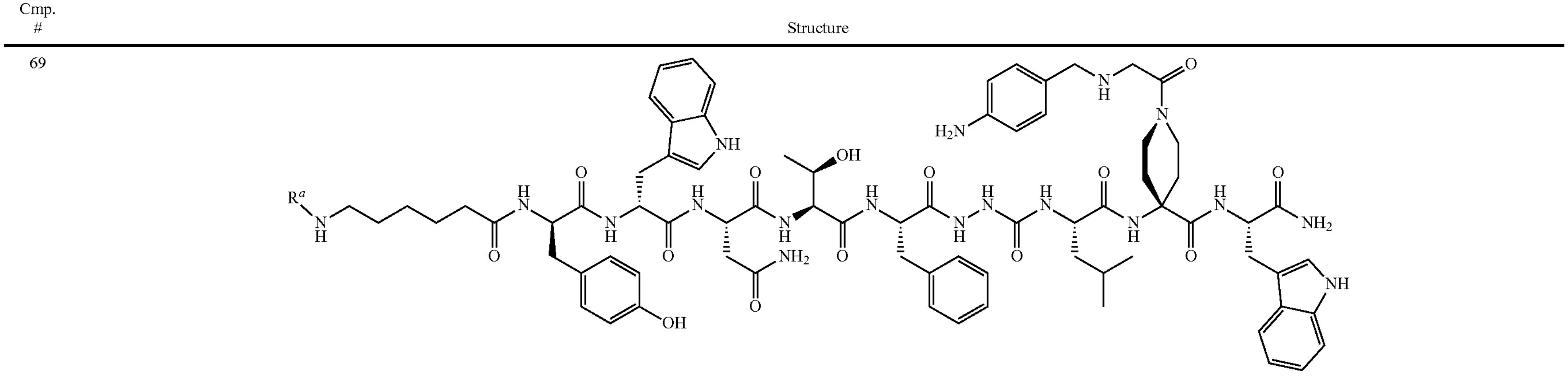 SEQ ID NO: 461 |
| 70 | 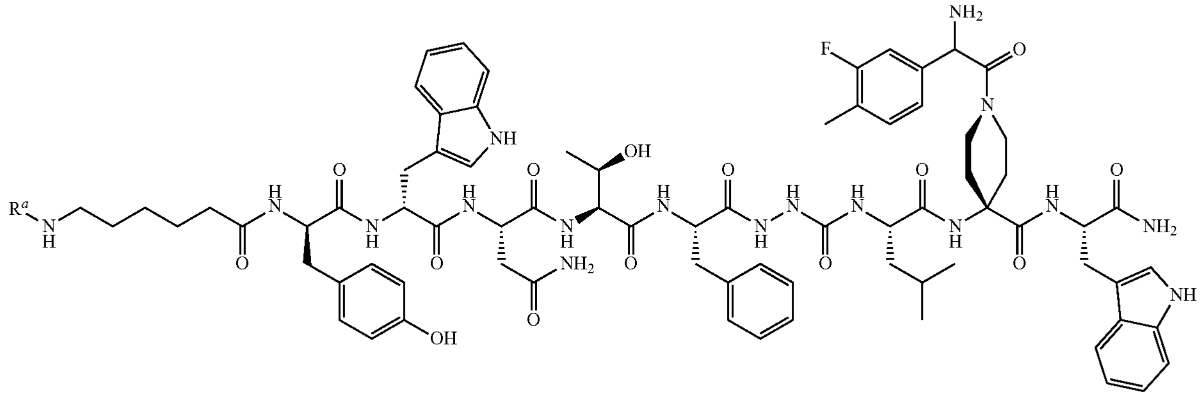 SEQ ID NO: 462 |

TABLE B-1-continued
| Cmp. # | Structure |
| --- | --- |
| 71 | 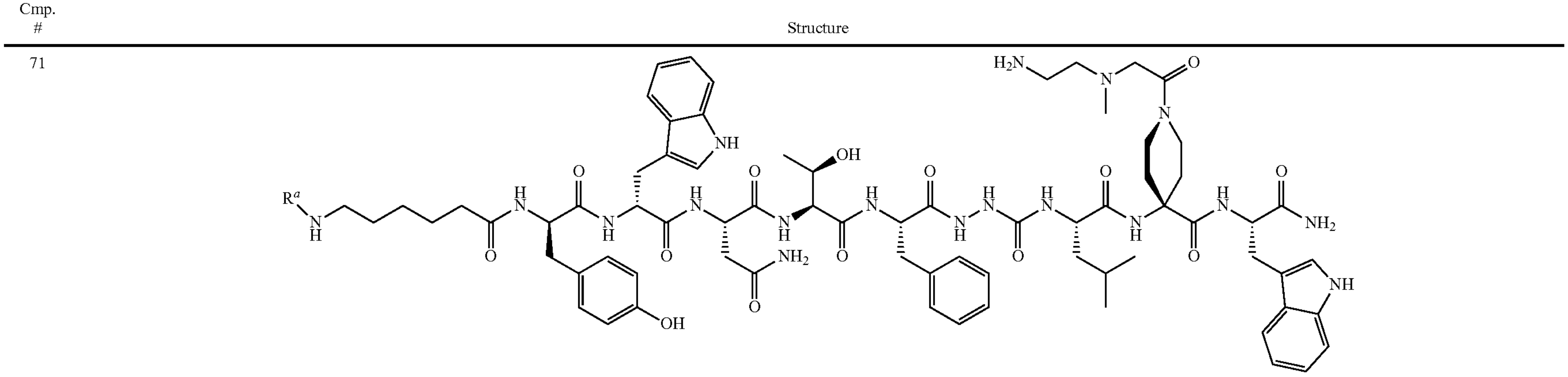 SEQ ID NO: 463 |
| 72 | 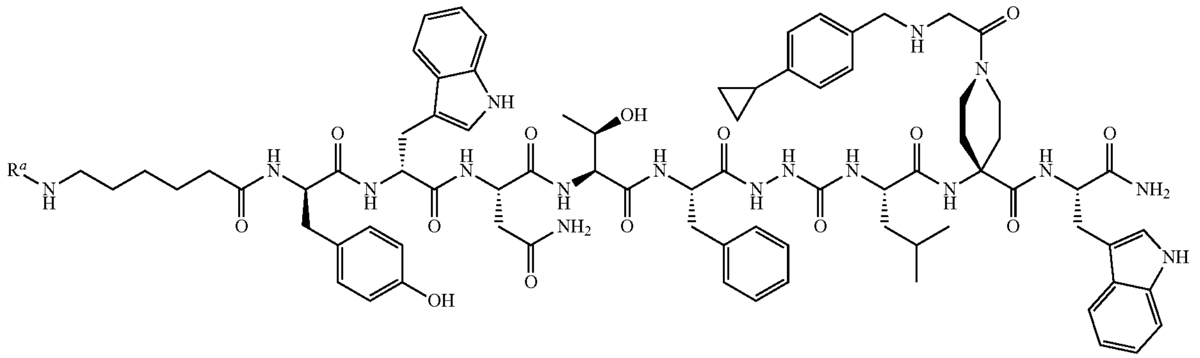 SEQ ID NO: 464 |

TABLE B-1-continued
| Cmp. # | Structure |
| --- | --- |
| 73 | 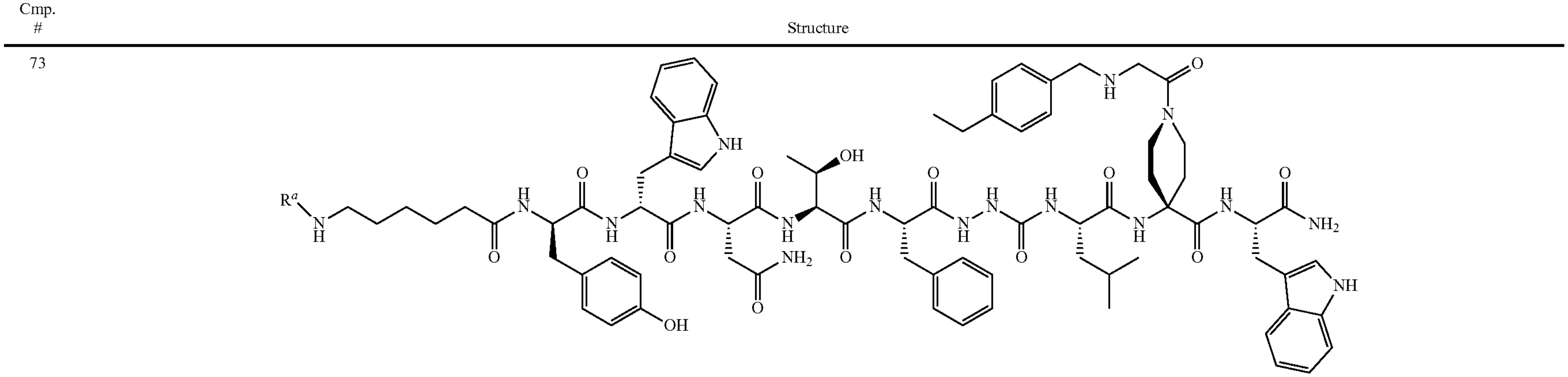<br>SEQ ID NO: 465 |
| 74 | 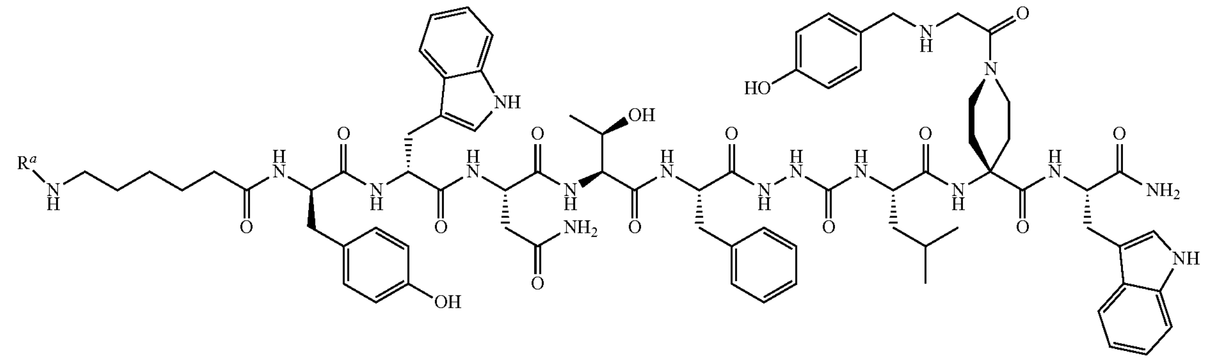<br>SEQ ID NO: 466 |

TABLE B-1-continued
| Cmp. # | Structure |
|---|---|
| 75 | 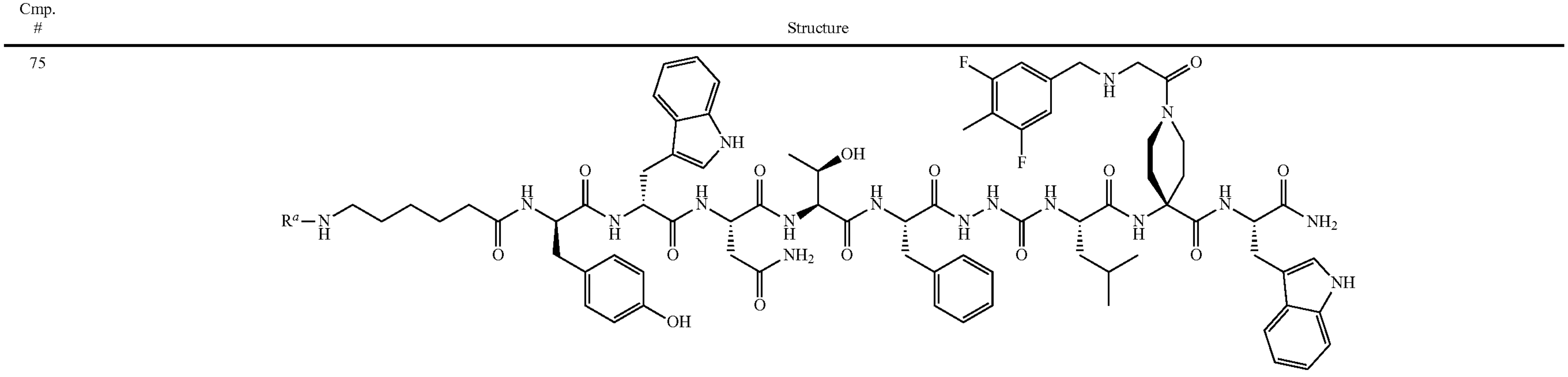 SEQ ID NO: 467 |
| 76 | 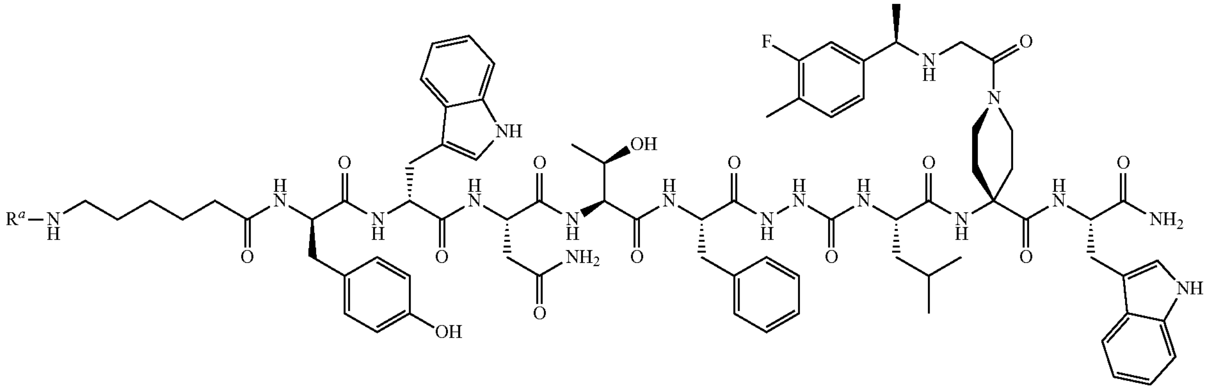 SEQ ID NO: 468 |

TABLE B-1-continued
| Cmp. # | Structure |
|---|---|
| 77 | 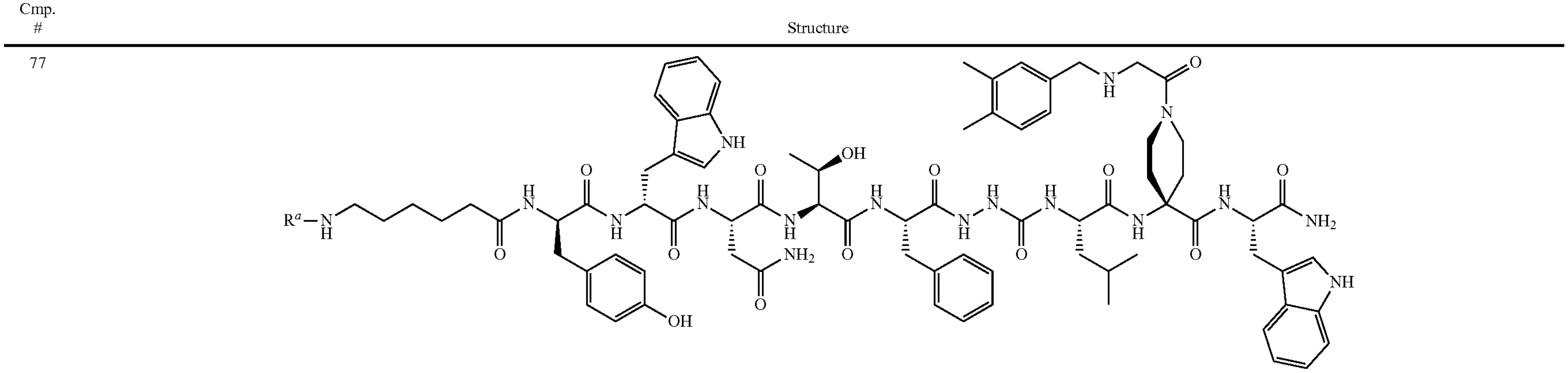<br>SEQ ID NO: 469 |
| 78 | 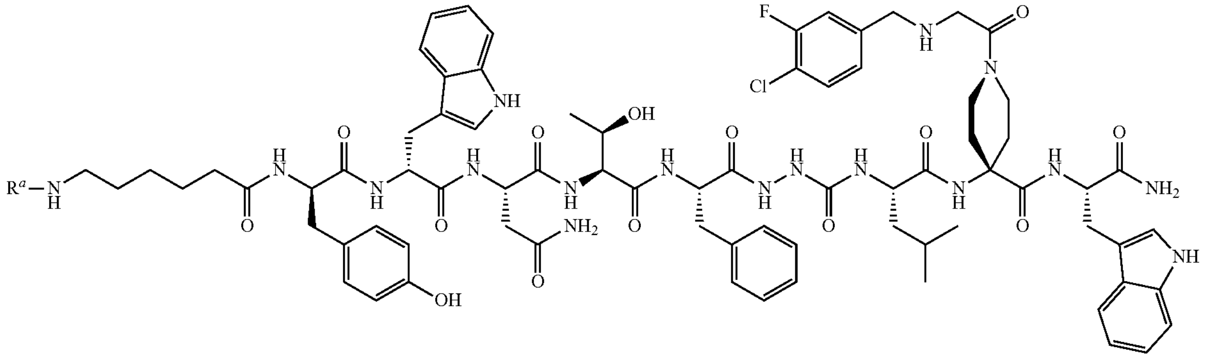<br>SEQ ID NO: 470 |

TABLE B-1-continued
| Cmp. # | Structure |
|---|---|
| 79 | 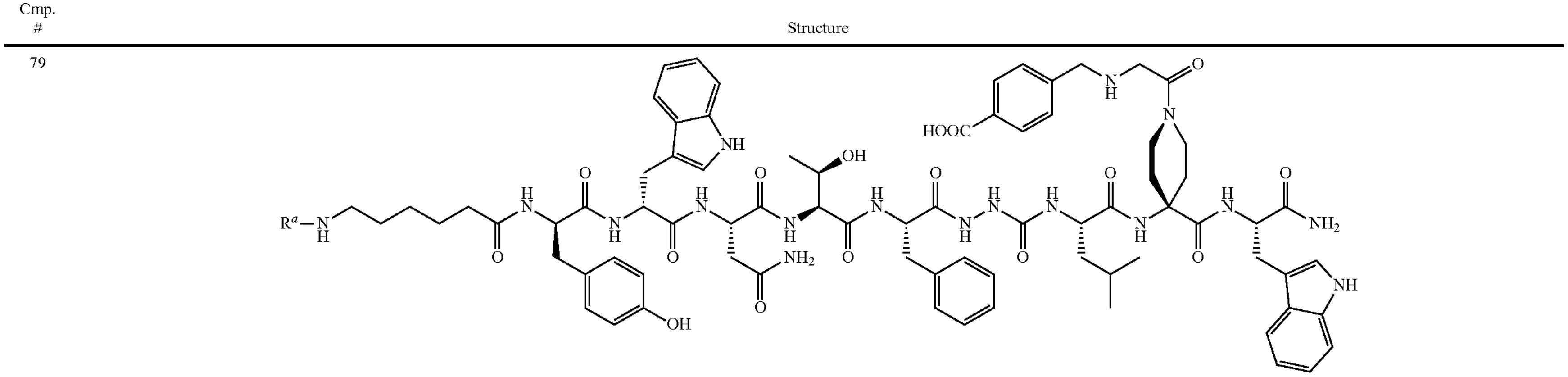 SEQ ID NO: 471 |
| 80 | 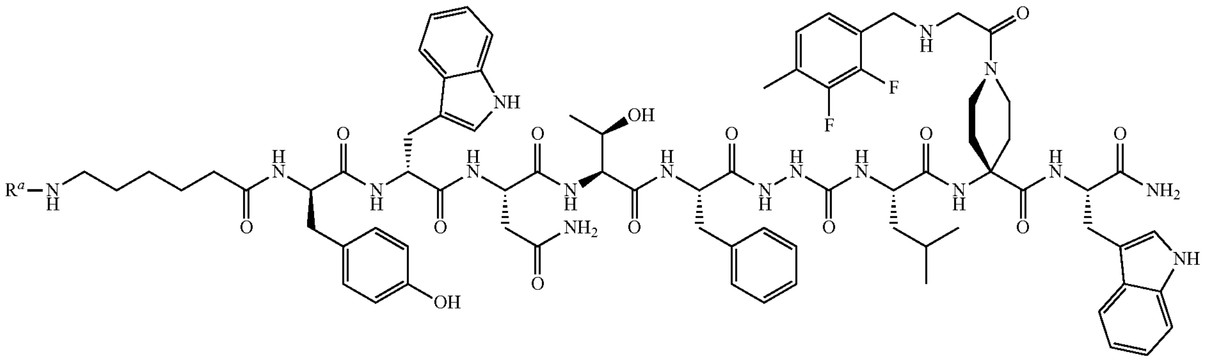 SEQ ID NO: 472 |

TABLE B-1-continued
| Cmp. # | Structure |
|---|---|
| 81 | 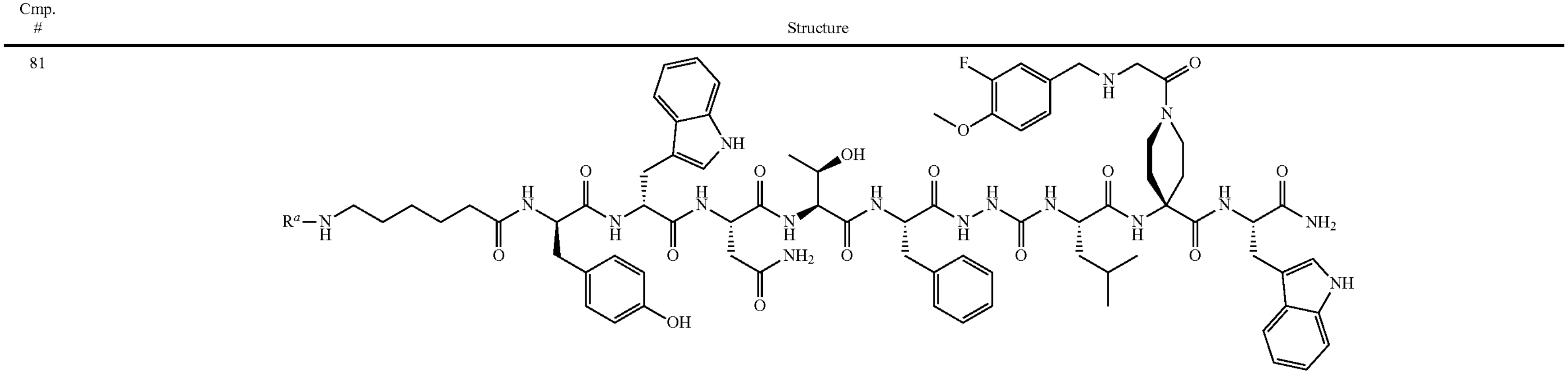 SEQ ID NO: 473 |
| 82 | 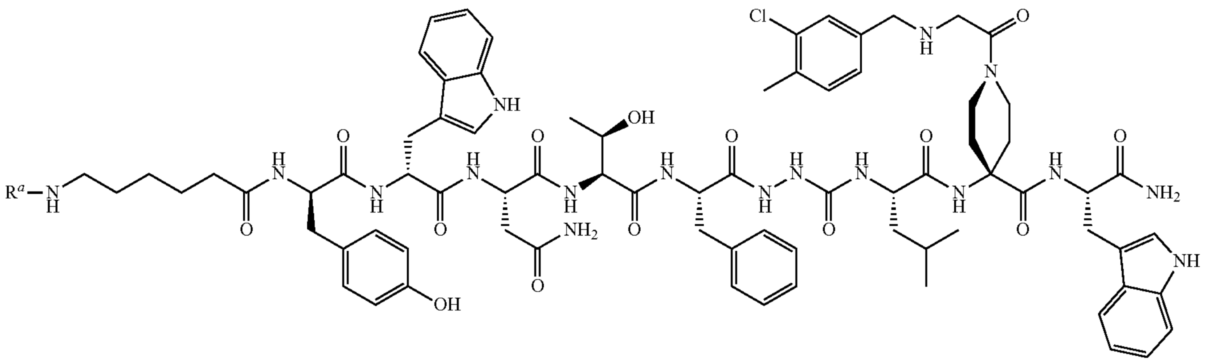 SEQ ID NO: 474 |

TABLE B-1-continued
| Cmp. # | Structure |
| --- | --- |
| 83 | 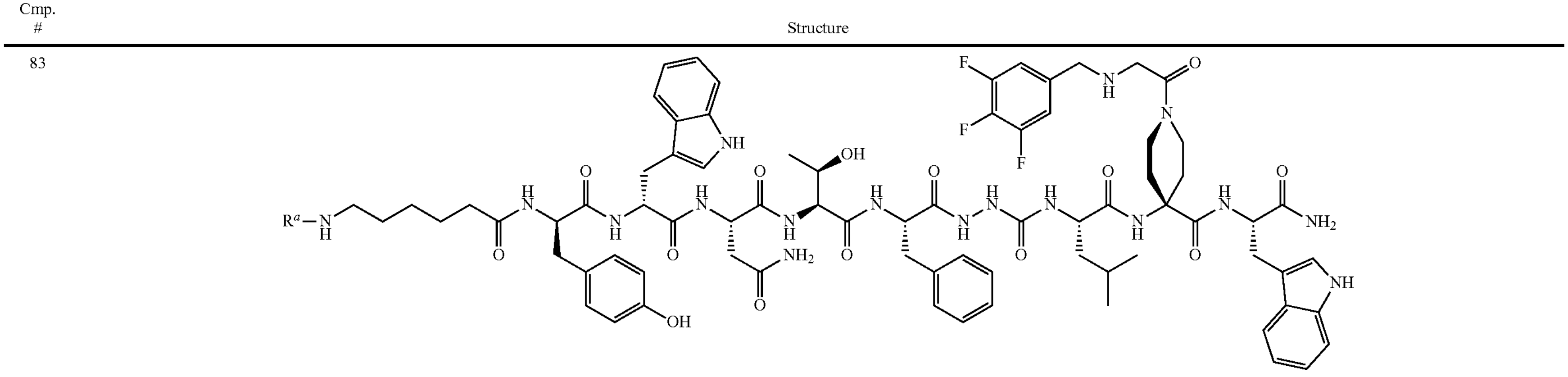 SEQ ID NO: 475 |
| 84 | 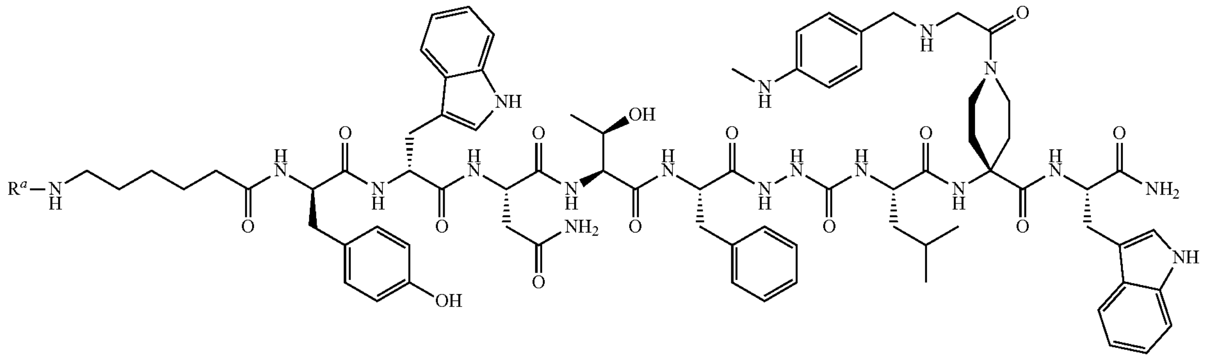 SEQ ID NO: 476 |

TABLE B-1-continued
| Cmp. # | Structure |
| --- | --- |
| 85 | 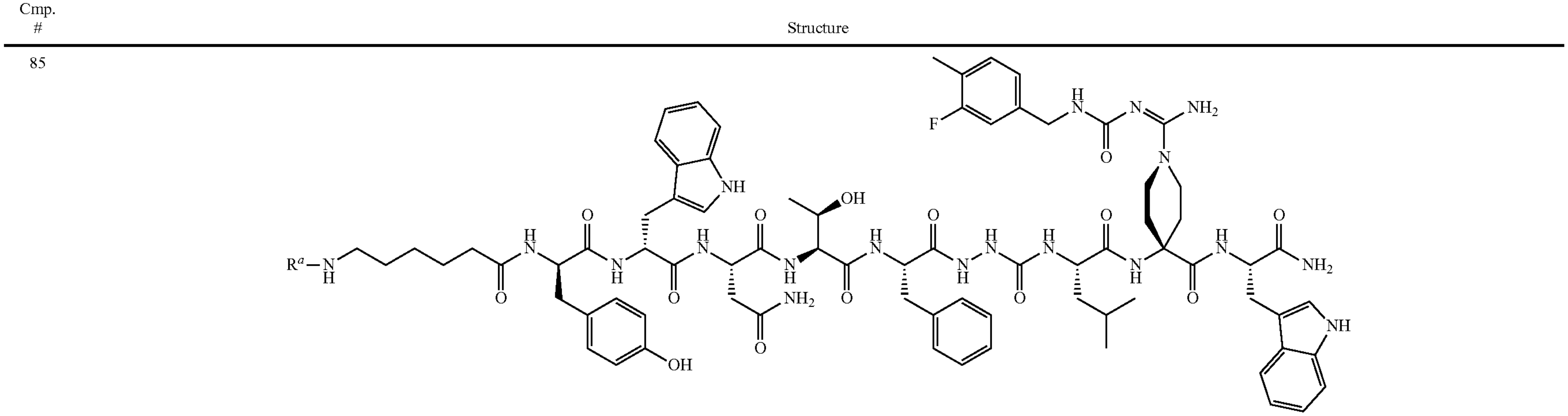<br>SEQ ID NO: 477 |
| 86 | 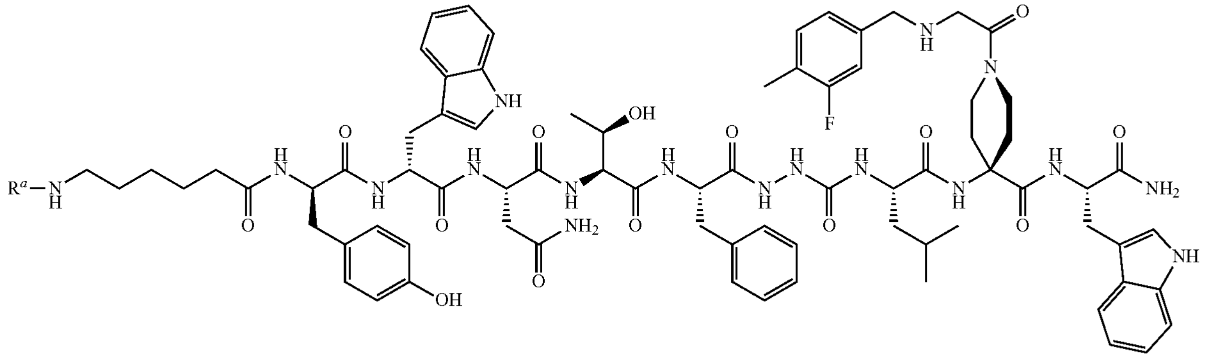<br>SEQ ID NO: 478 |

TABLE B-1-continued
| Cmp. # | Structure |
|---|---|
| 87 | 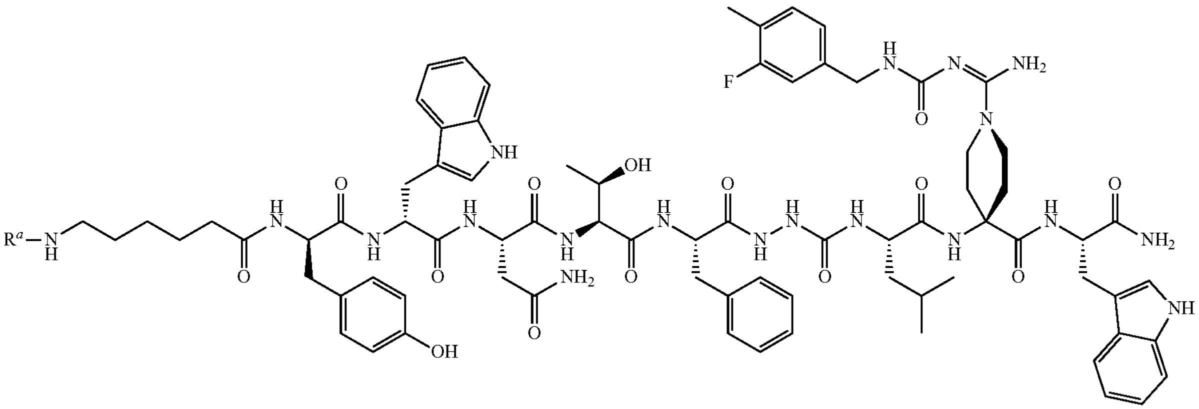 SEQ ID NO: 477 |
| 88 | 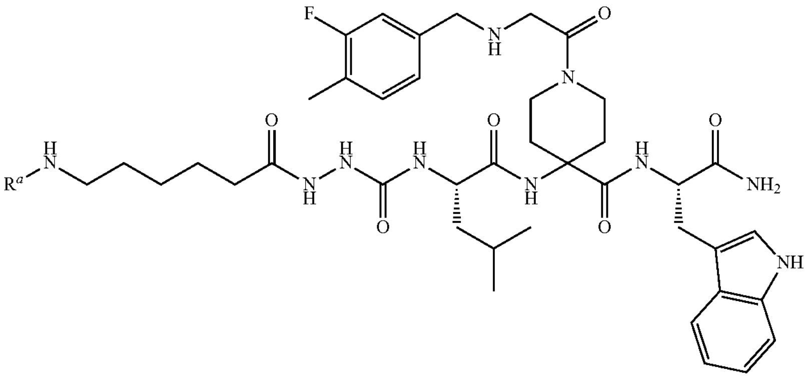 |

TABLE B-1-continued
| Cmp. # | Structure |
| --- | --- |
| 89 | 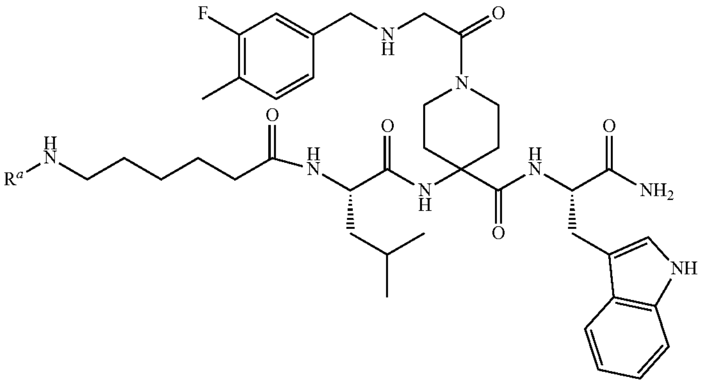 |
| 90 | 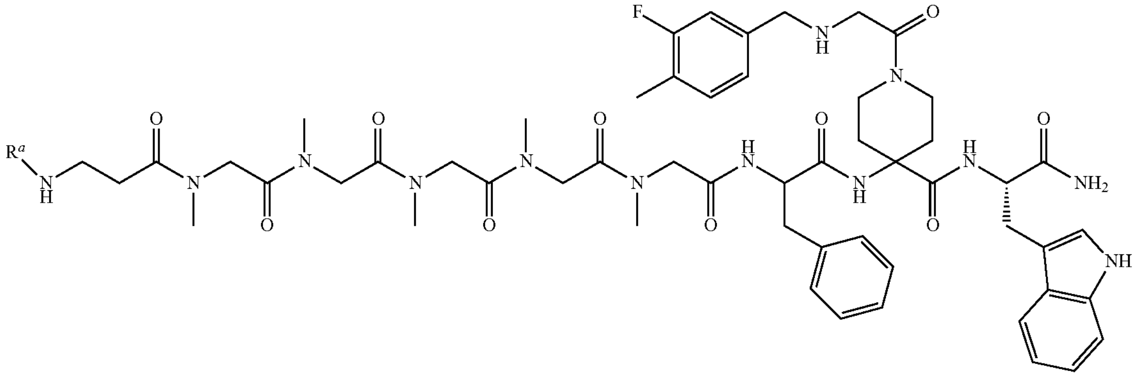<br>SEQ ID NO: 439 |

TABLE B-1-continued
| Cmp. # | Structure |
| --- | --- |
| 92 | 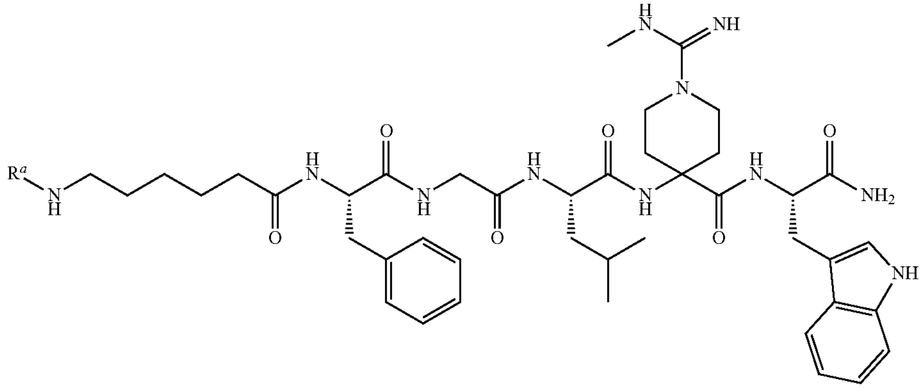<br>SEQ ID NO: 480 |
| 93 | 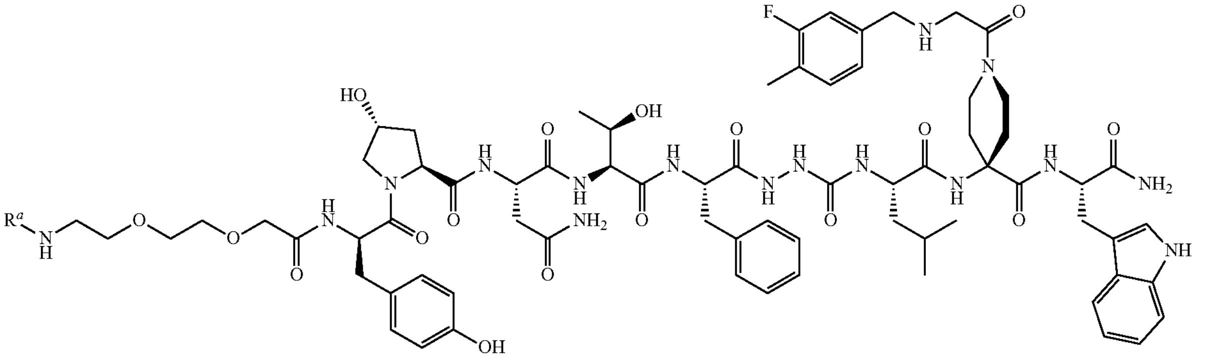<br>SEQ ID NO: 481 |

TABLE B-1-continued
| Cmp. # | Structure |
|---|---|
| 94 | 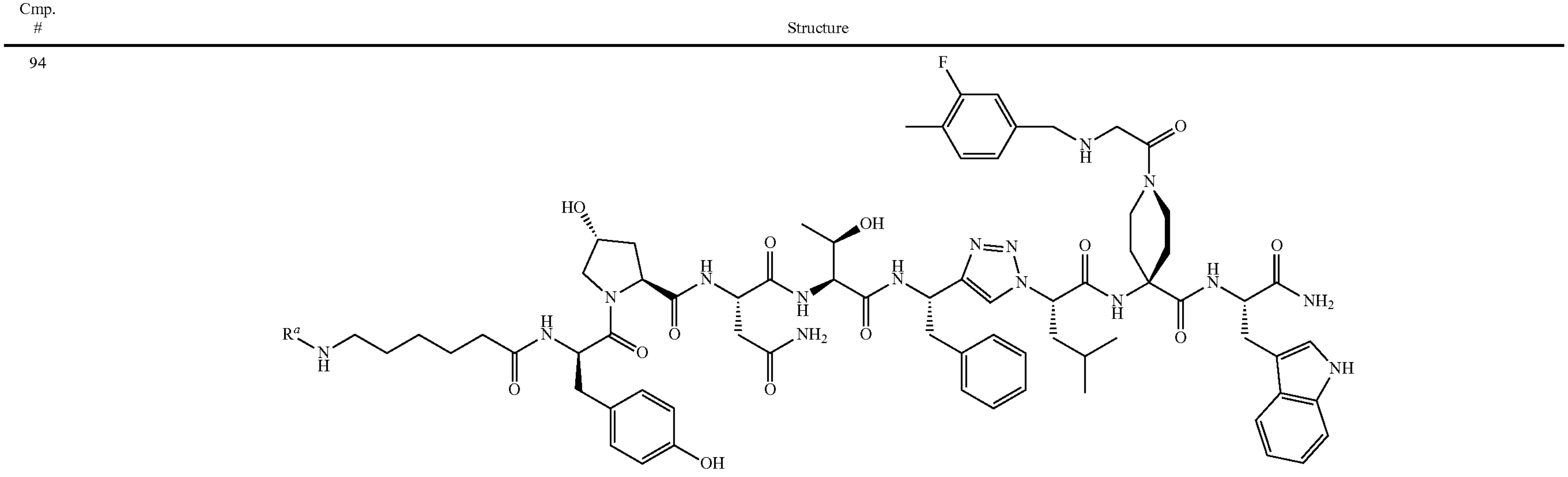<br>SEQ ID NO: 482 |
| 95 | 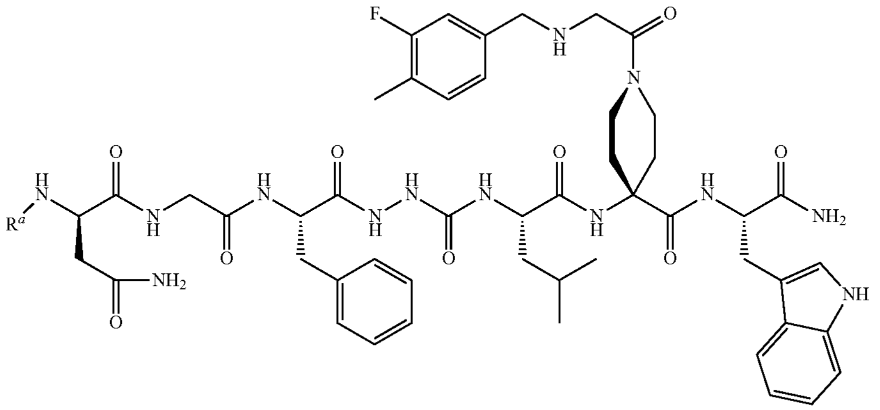<br>SEQ ID NO: 483 |

TABLE B-1-continued
| Cmp. # | Structure |
| --- | --- |
| 96 | 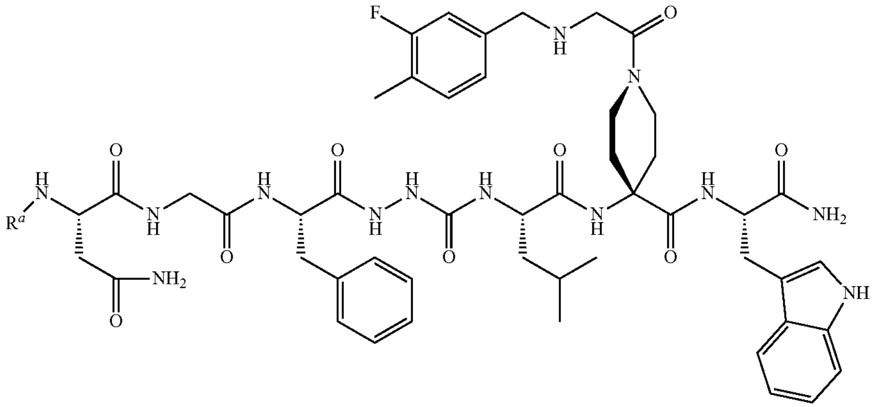 SEQ ID NO: 484 |
| 97 | 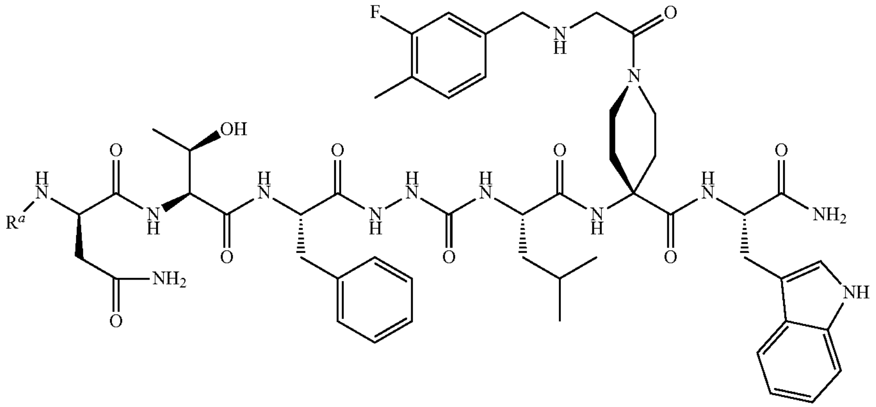 SEQ ID NO: 485 |

TABLE B-1-continued
| Cmp. # | Structure |
|---|---|
| 98 | 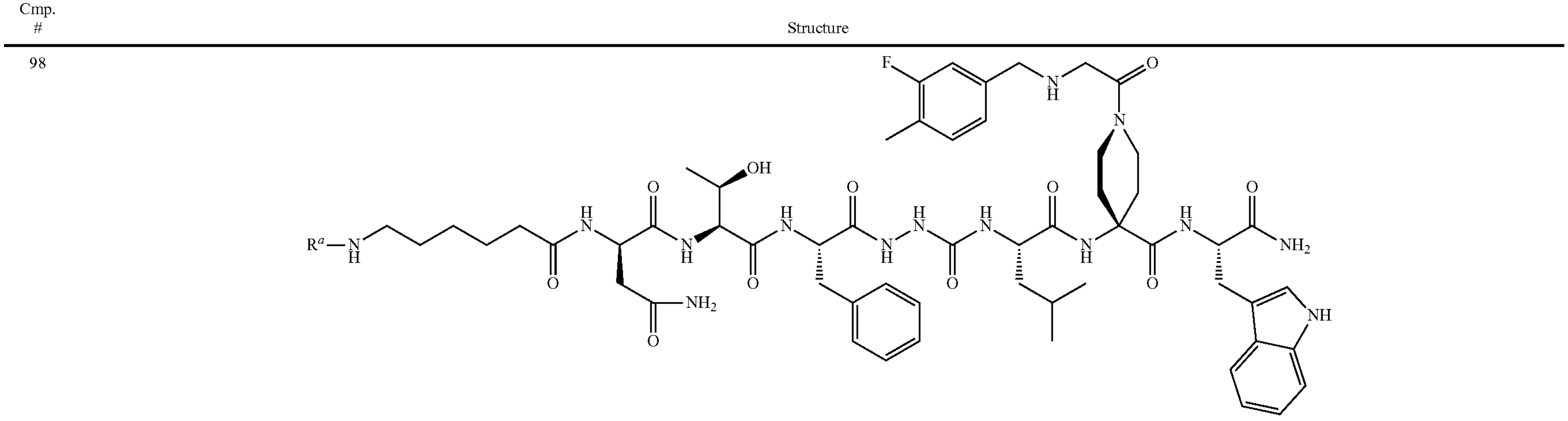 SEQ ID NO: 486 |
| 99 | 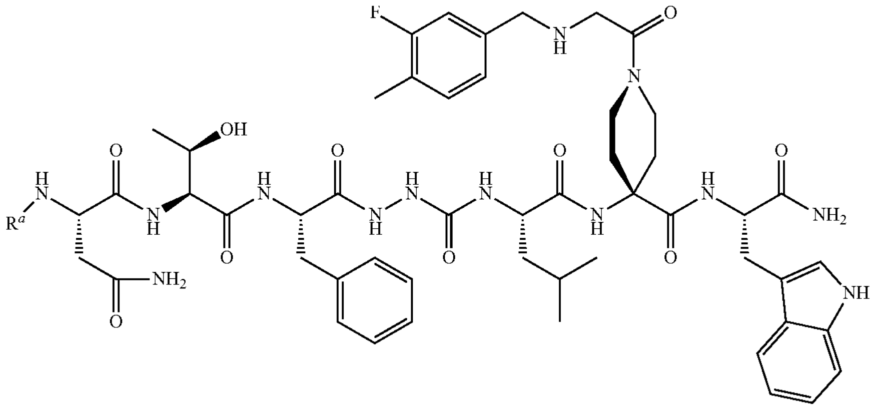 SEQ ID NO: 487 |

TABLE B-1-continued
| Cmp. # | Structure |
| --- | --- |
| 100 | 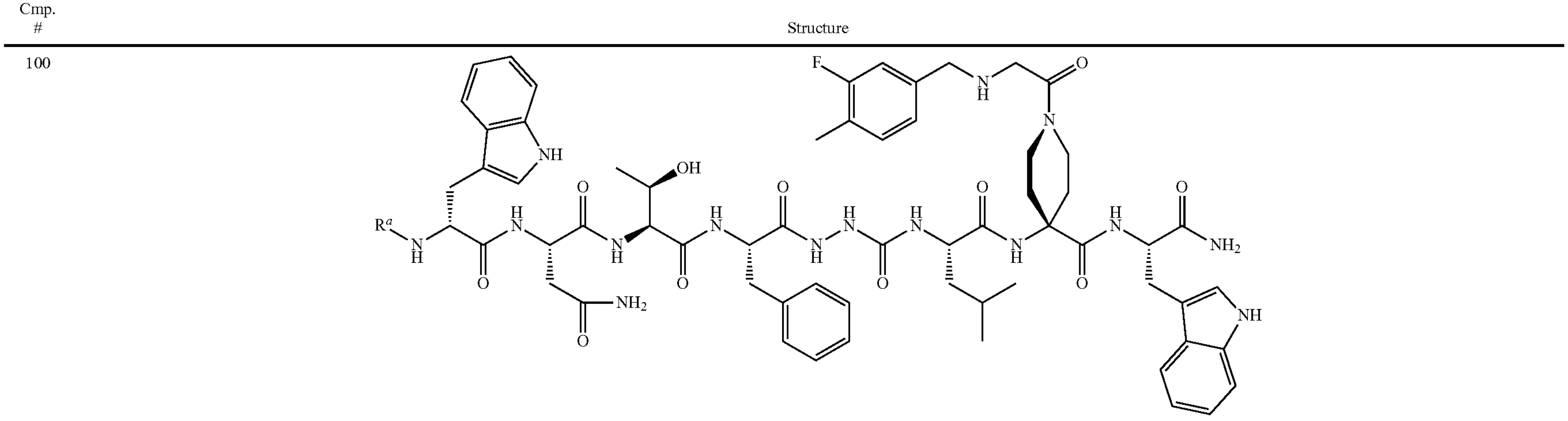 SEQ ID NO: 488 |
| 101 | 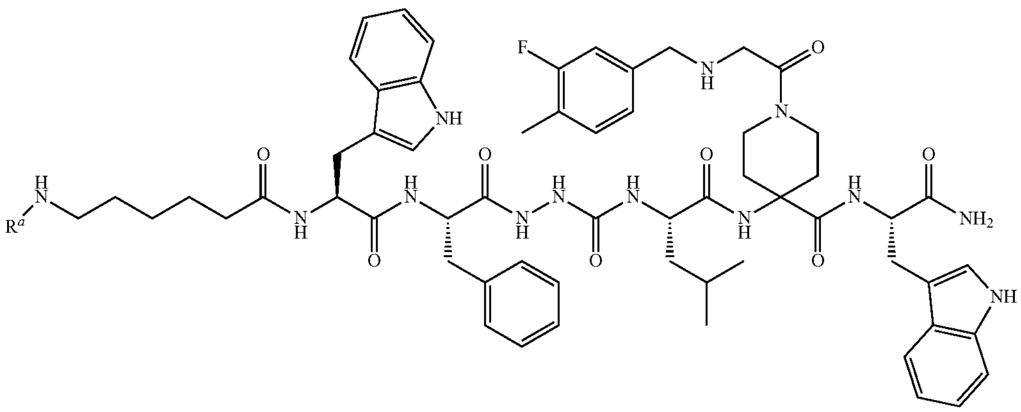 SEQ ID NO: 489 |

TABLE B-1-continued
| Cmp. # | Structure |
| --- | --- |
| 102 | 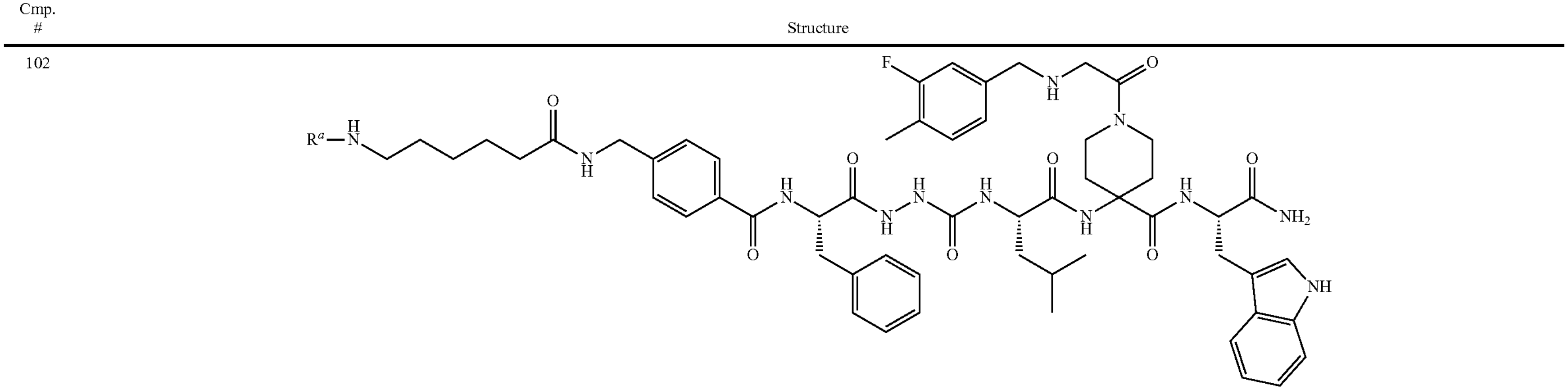 SEQ ID NO: 415 |
| 103 | 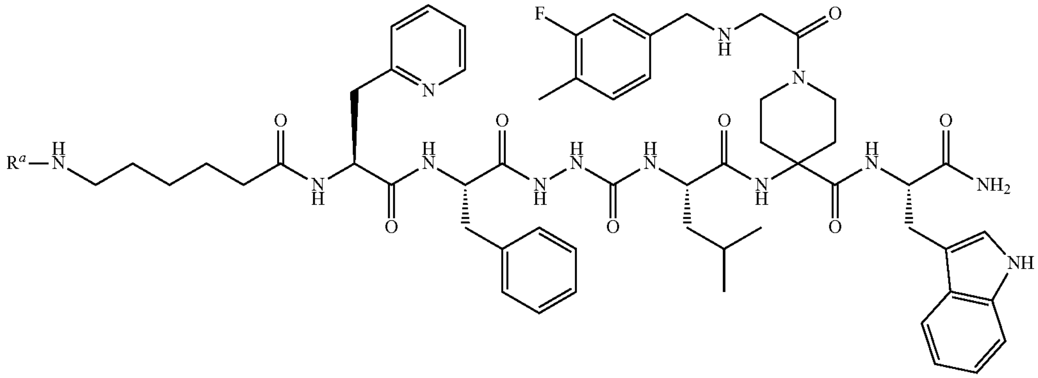 SEQ ID NO: 490 |

TABLE B-1-continued
| Cmp. # | Structure |
|---|---|
| 112 | 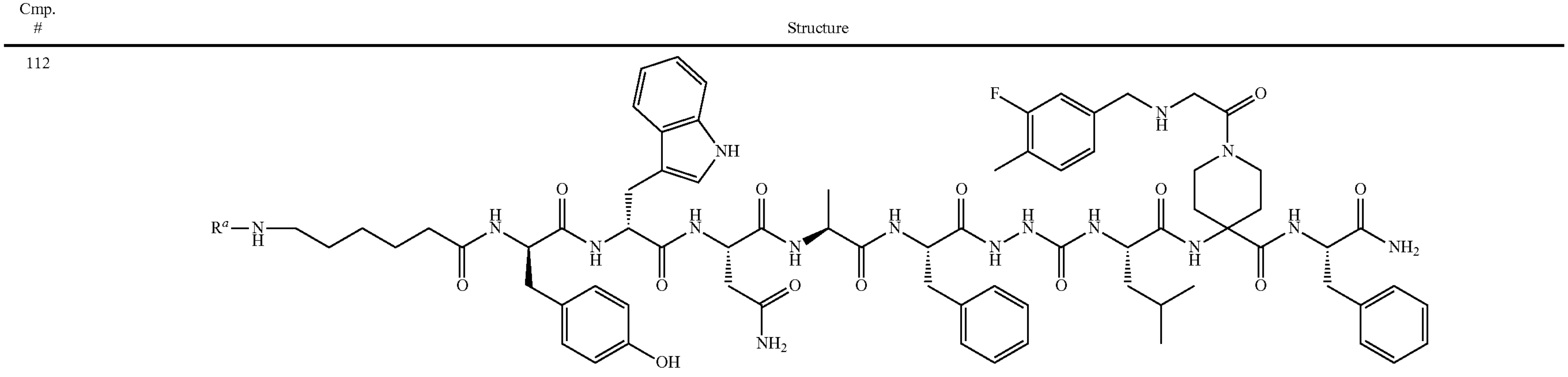 SEQ ID NO: 499 |
| 122 | 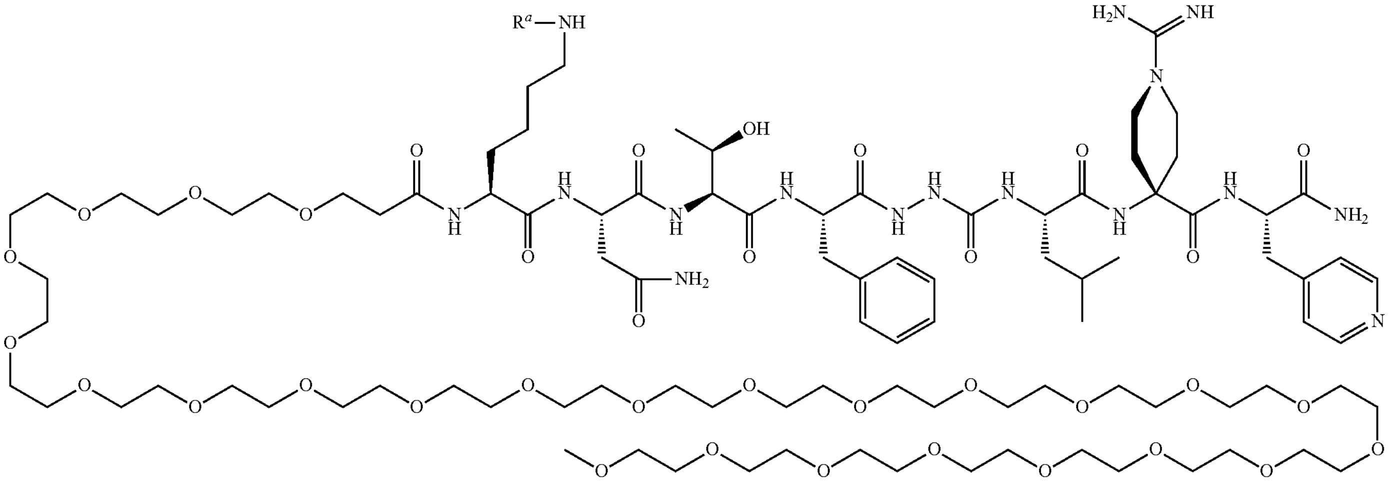 SEQ ID NO: 509 |

TABLE B-1-continued
| Cmp. # | Structure |
|---|---|
| 143 | 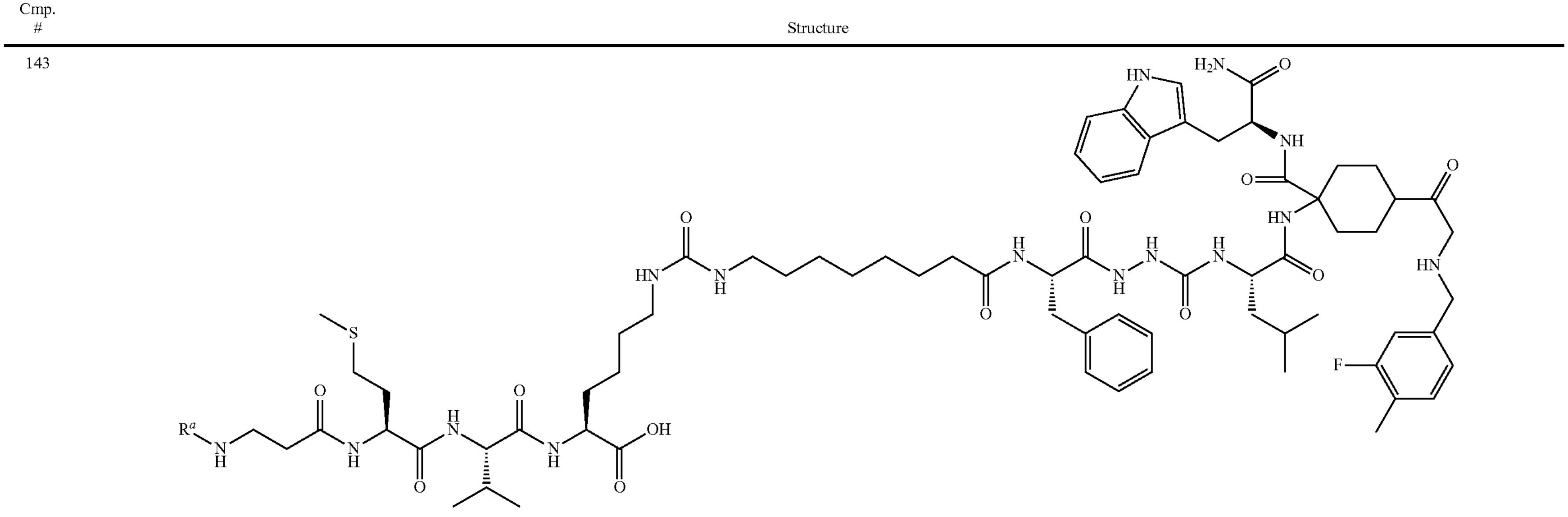<br>SEQ ID NO: 524 |
| 144 | 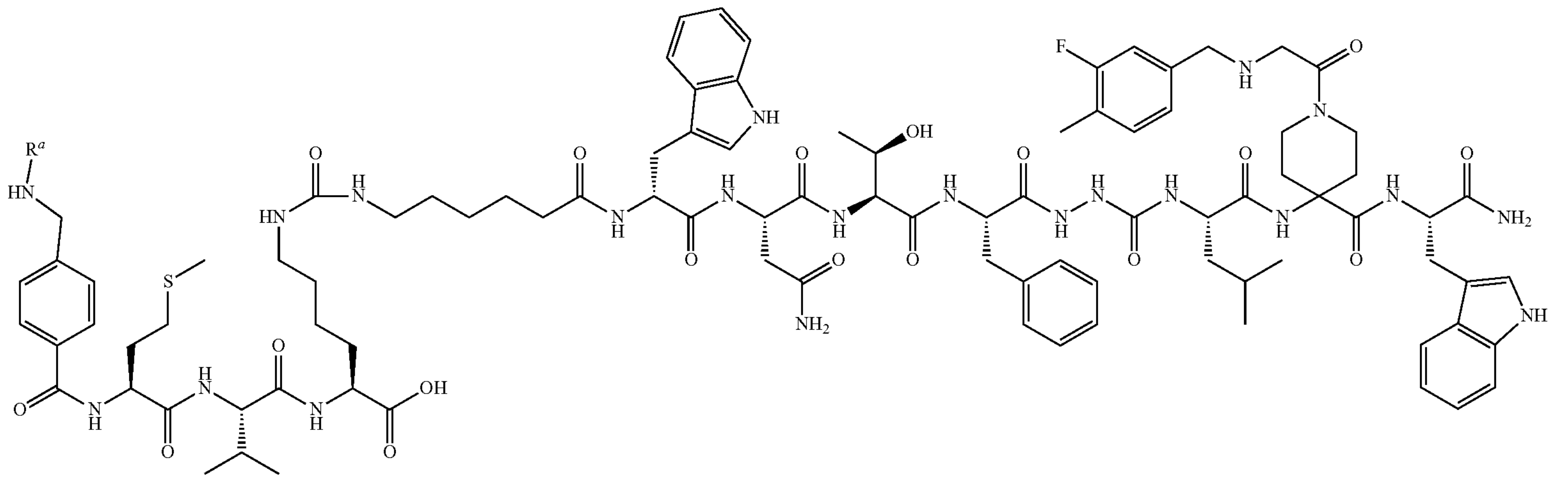 |

TABLE B-1-continued
| Cmp. # | Structure |
|---|---|
| | SEQ ID NO: 525 |
| 145 | 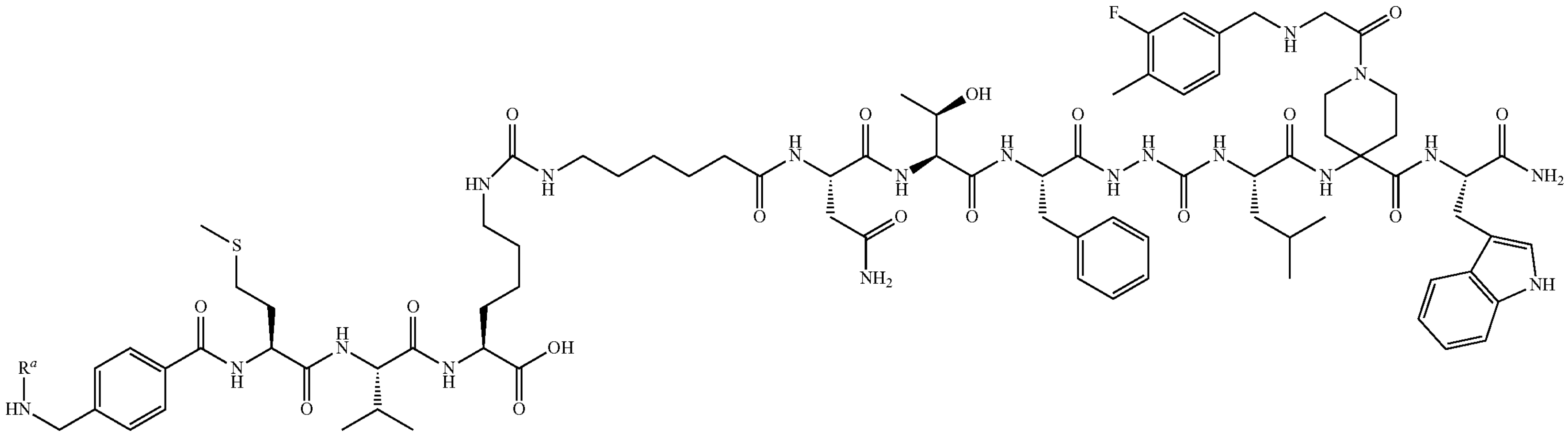 |
| | SEQ ID NO: 526 |
| 150 | 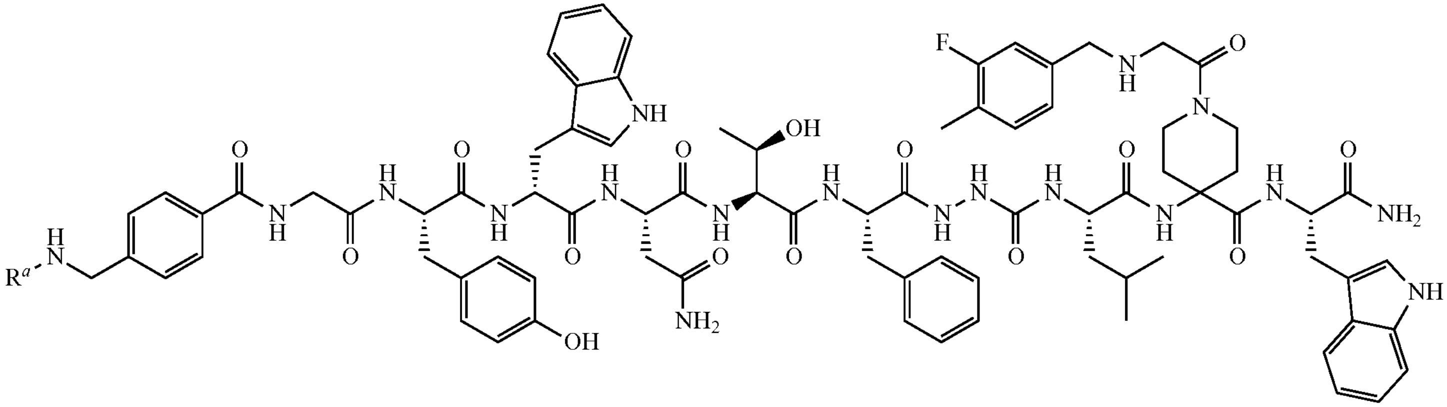 |
| | SEQ ID NO: 531 |

TABLE B-1-continued
| Cmp. # | Structure |
|---|---|
| 152 | 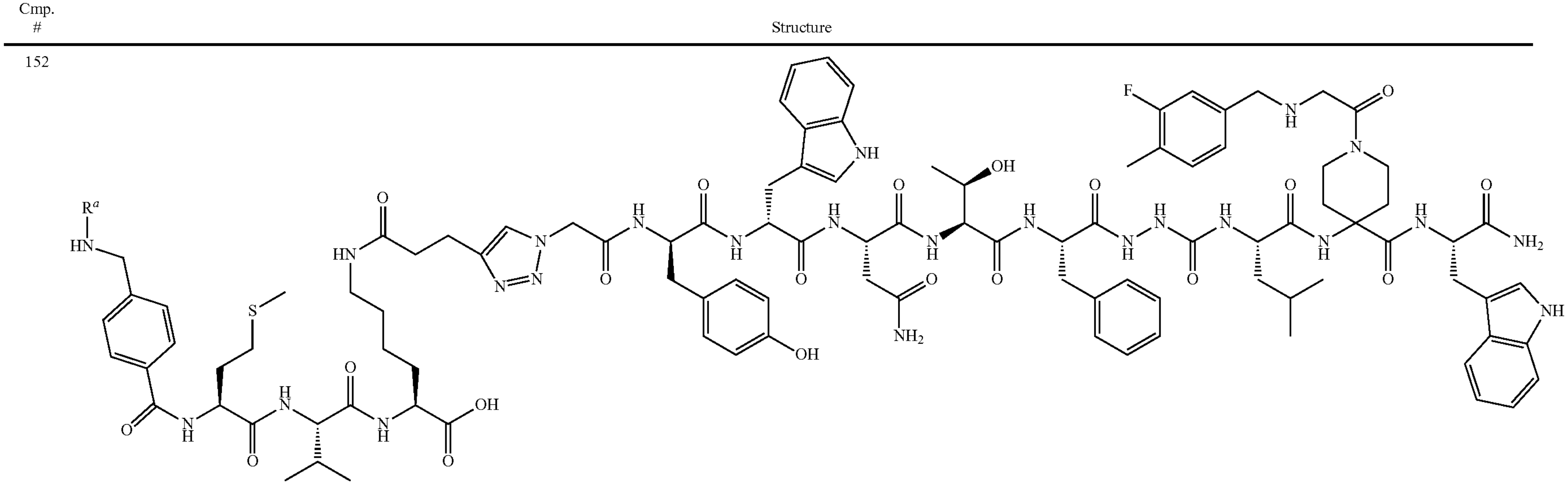 SEQ ID NO: 533 |
| 153 | 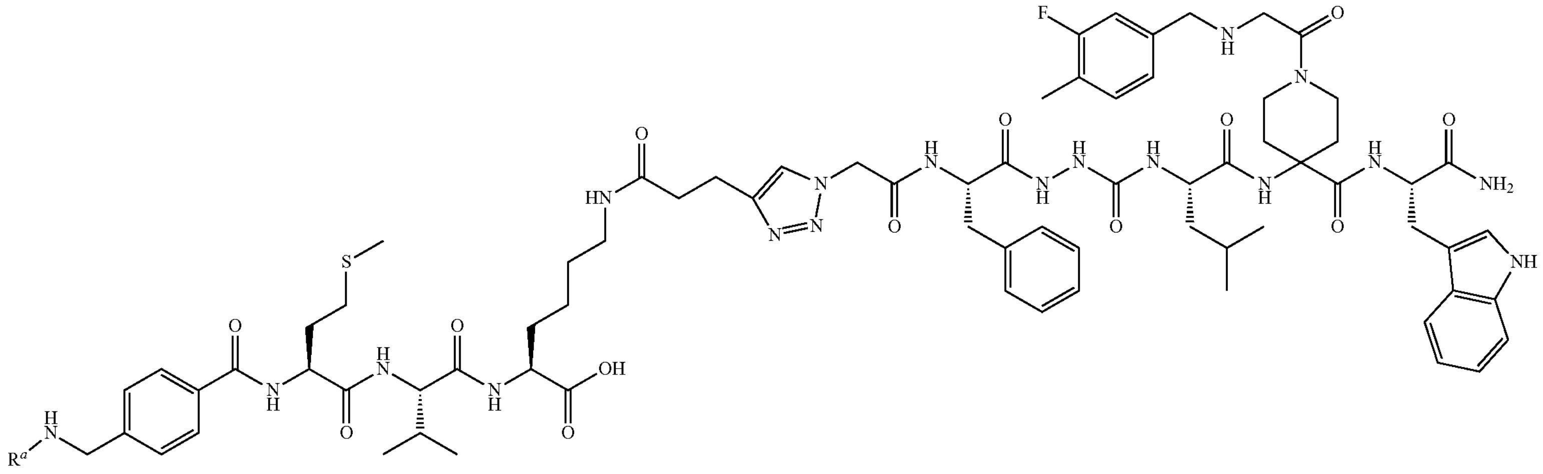 SEQ ID NO: 534 |

TABLE B-1-continued
| Cmp. # | Structure |
|---|---|
| 154 | 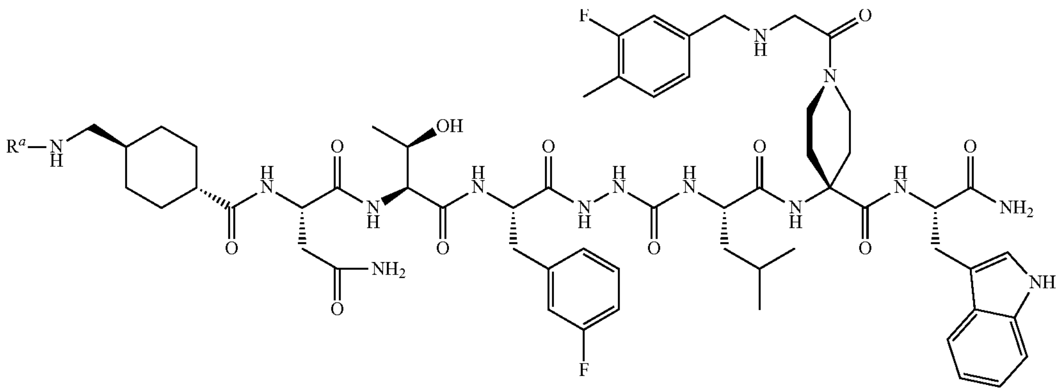 SEQ ID NO: 535 |
| 155 | 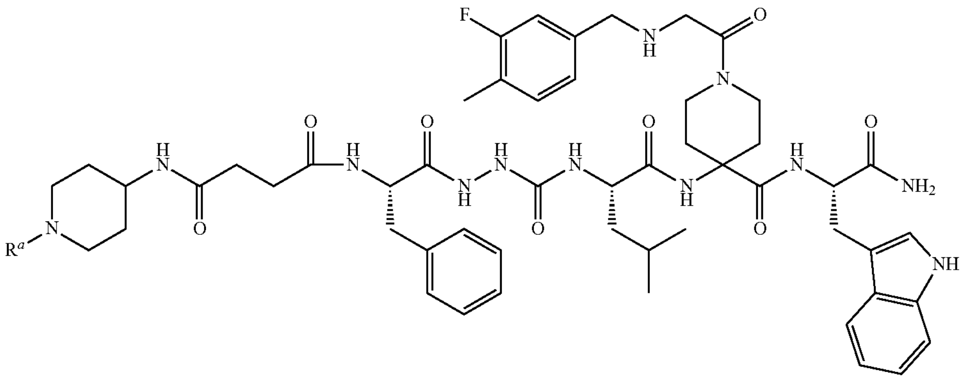 SEQ ID NO: 536 |

TABLE B-1-continued
| Cmp. # | Structure |
|---|---|
| 157 | 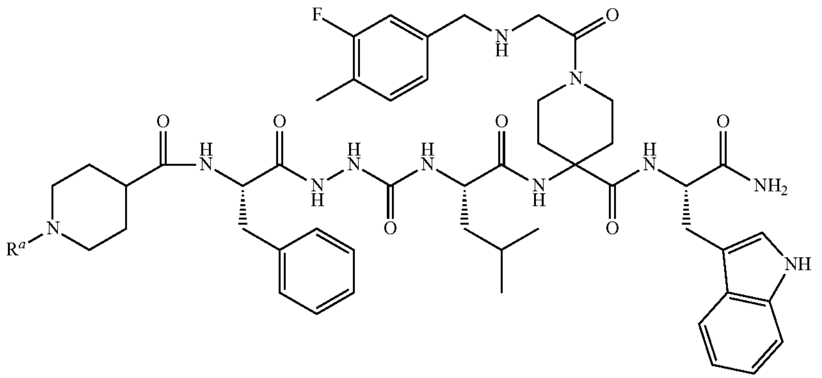<br>SEQ ID NO: 538 |
| 162 | 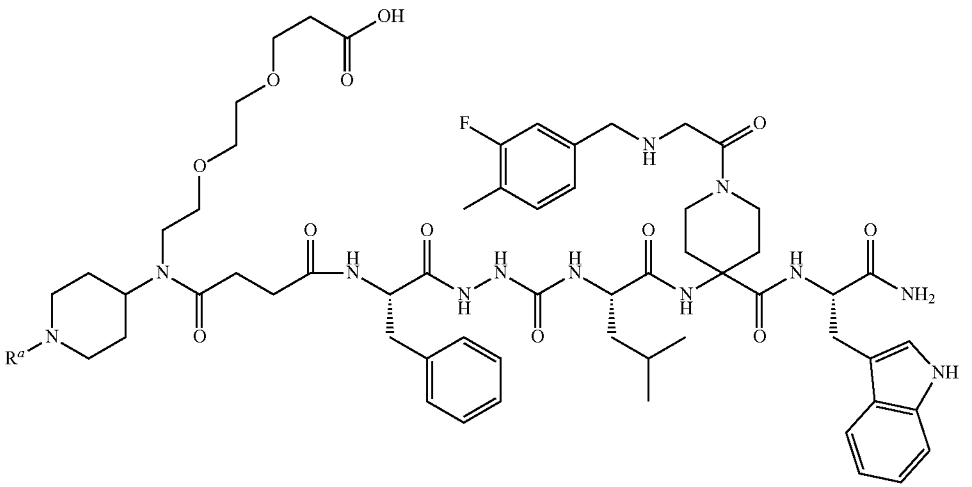<br>SEQ ID NO: 543 |

TABLE B-1-continued
| Cmp. # | Structure |
|---|---|
| 163 | 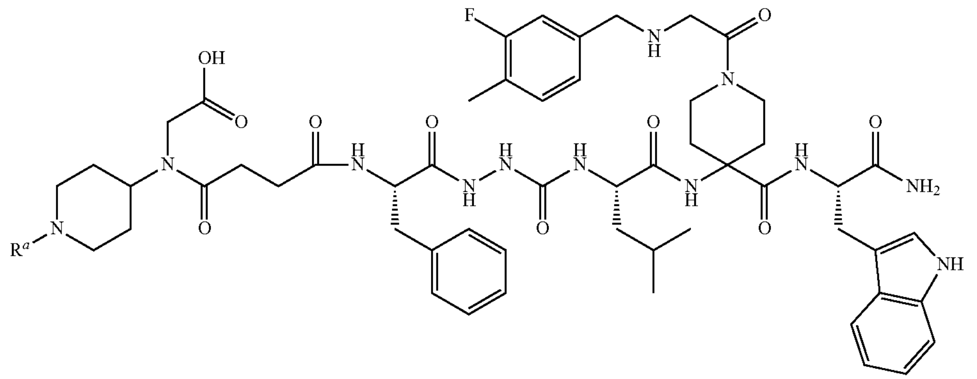 SEQ ID NO: 544 |
| 172 | 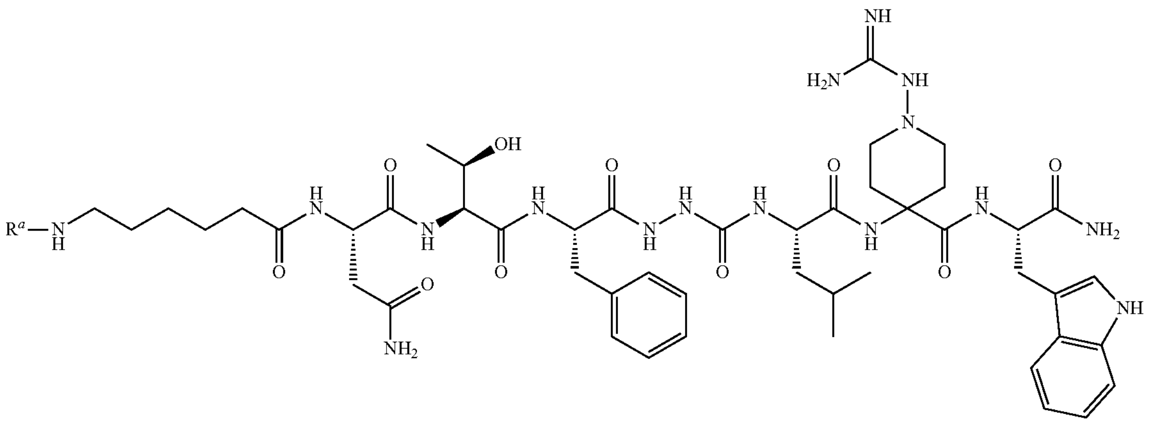 SEQ ID NO: 800 |

TABLE B-1-continued
| Cmp. # | Structure |
|---|---|
| 173 | 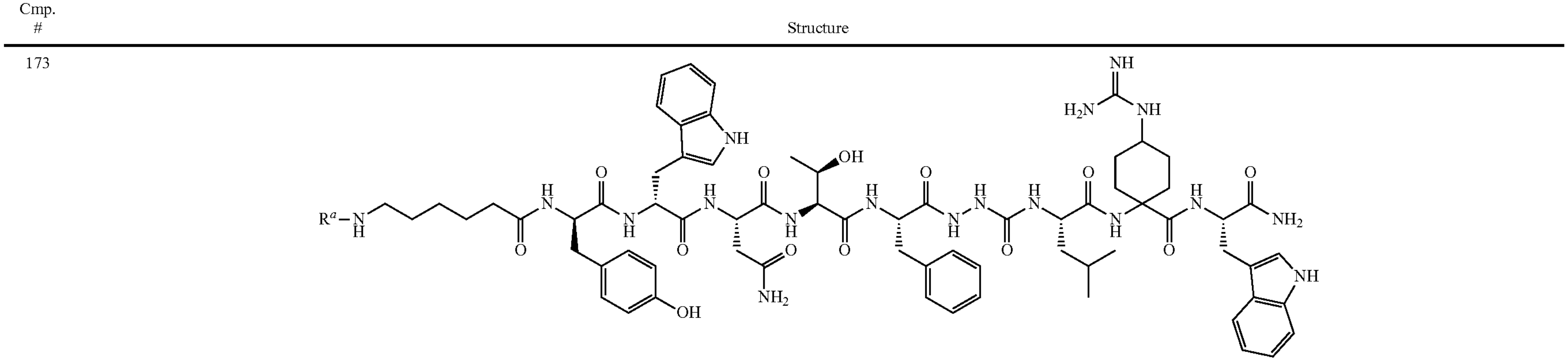 SEQ ID NO: 801 |
| 174 | 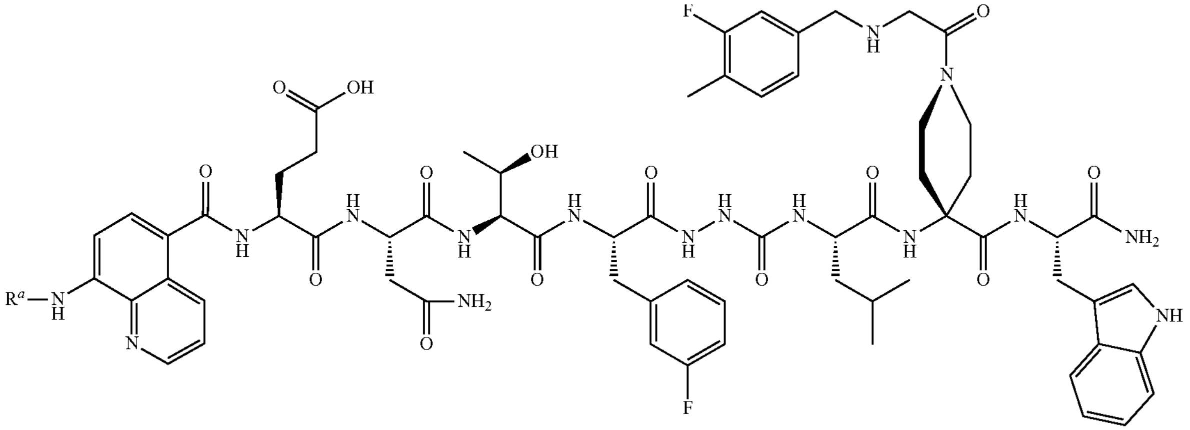 SEQ ID NO: 553 |

TABLE B-1-continued
| Cmp. # | Structure |
| --- | --- |
| 175 | 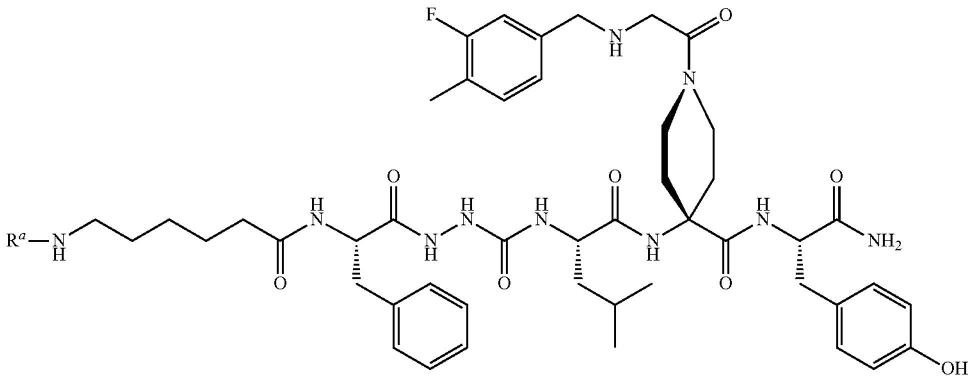 SEQ ID NO: 554 |
| 177 | 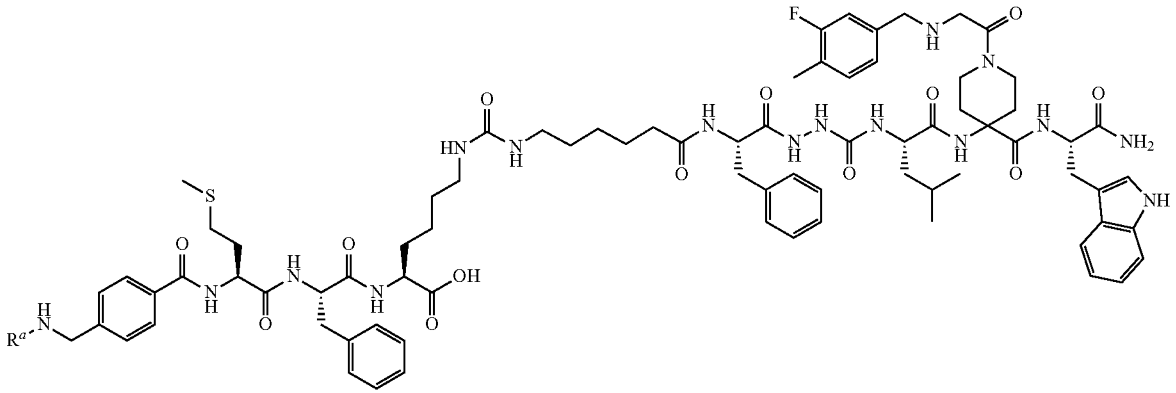 SEQ ID NO: 556 |

TABLE B-1-continued
| Cmp. # | Structure |
| --- | --- |
| 178 | 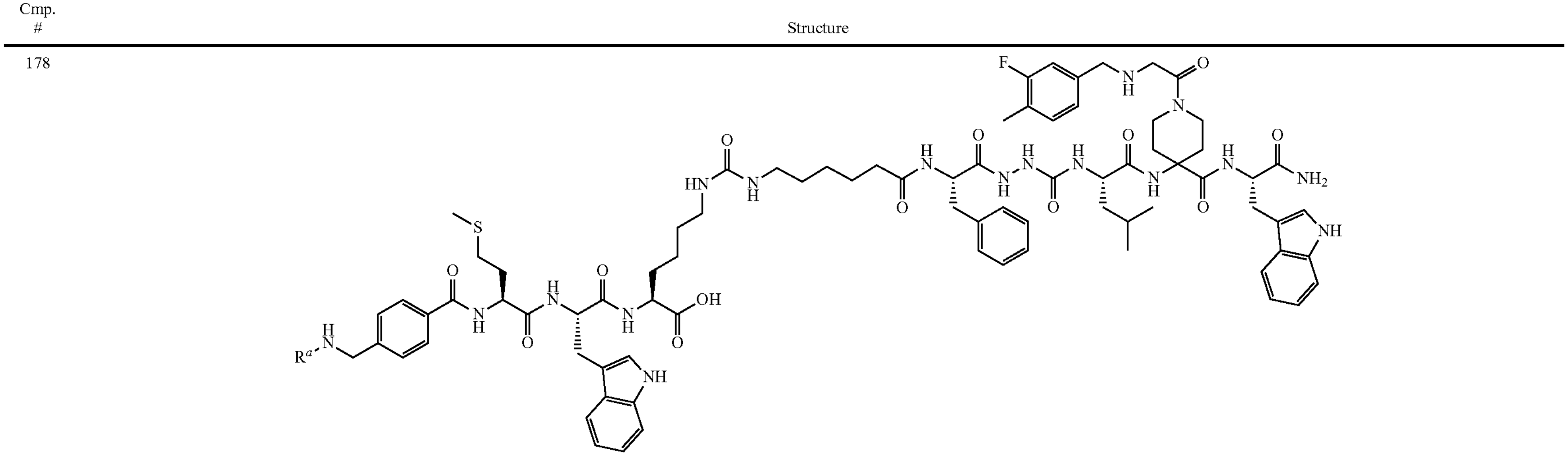 SEQ ID NO: 557 |
| 179 | 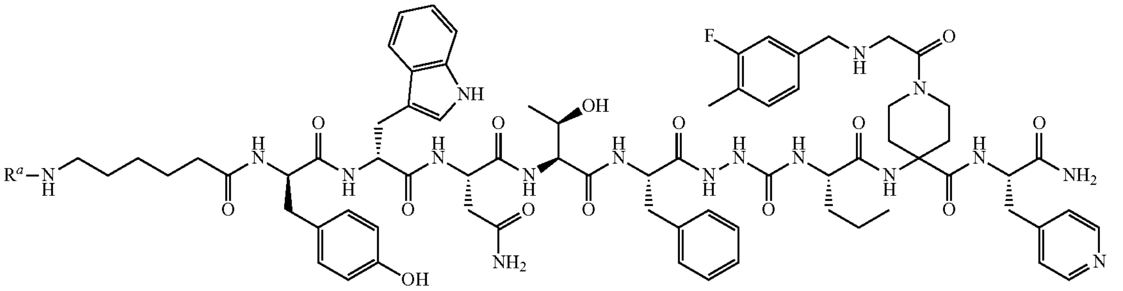 SEQ ID NO: 558 |

TABLE B-1-continued
| Cmp. # | Structure |
|---|---|
| 180 | 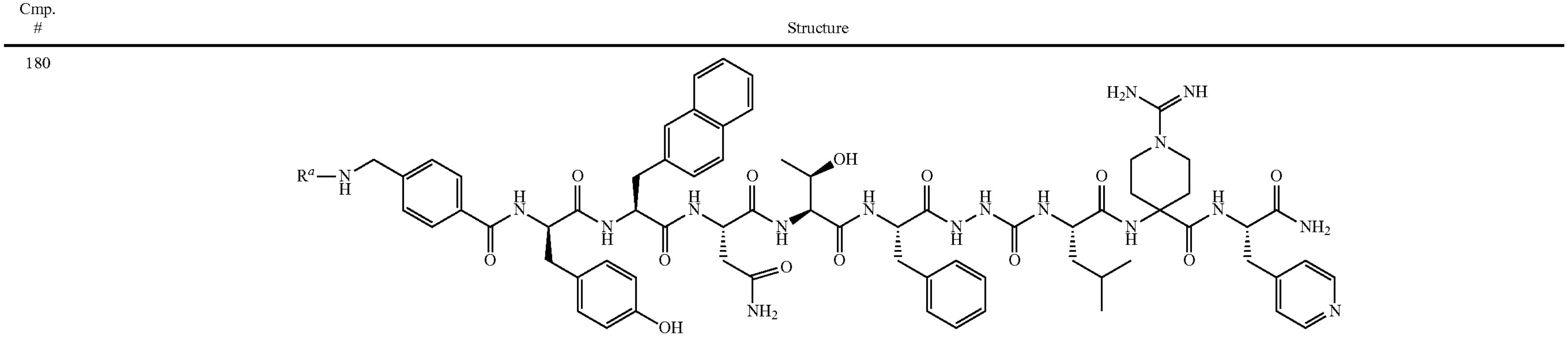 SEQ ID NO: 559 |
| 190 | 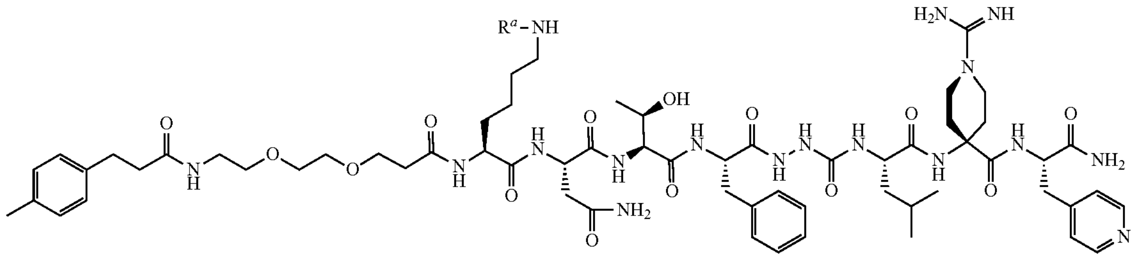 SEQ ID NO: 569 |
| 191 | 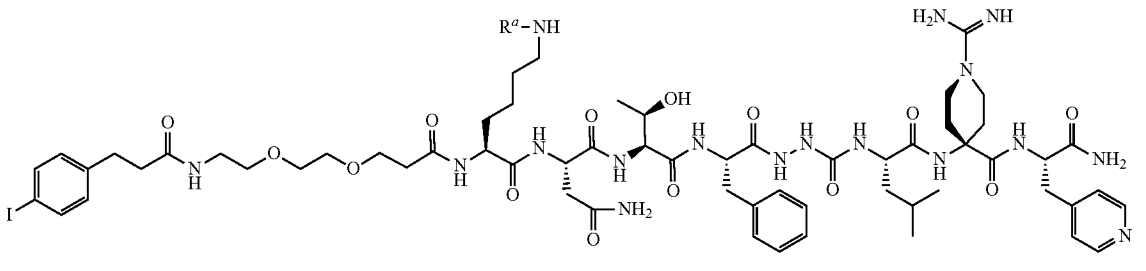 SEQ ID NO: 570 |

TABLE B-1-continued
| Cmp. # | Structure |
| --- | --- |
| 194 | 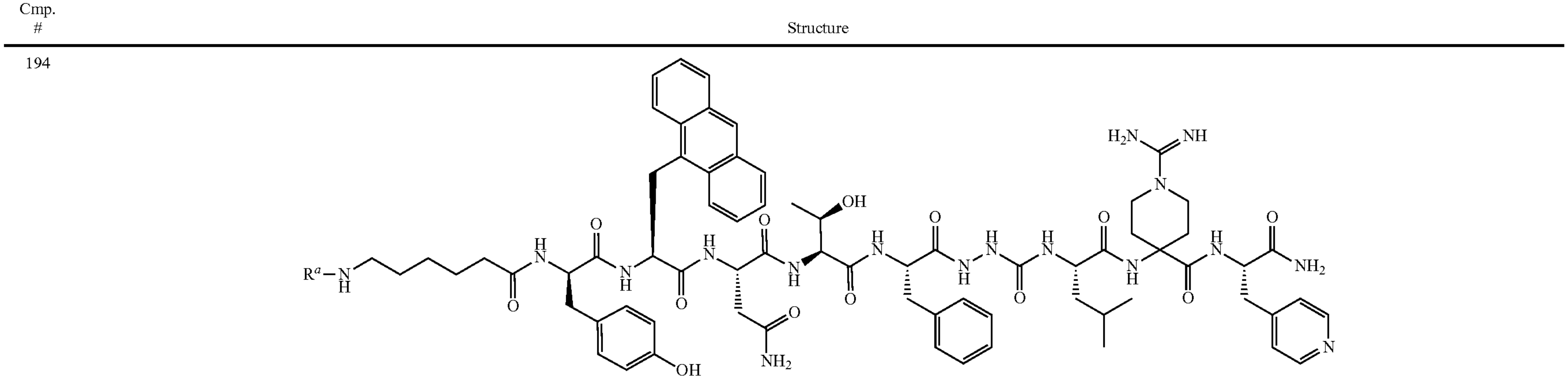<br>SEQ ID NO: 574 |
| 207 | 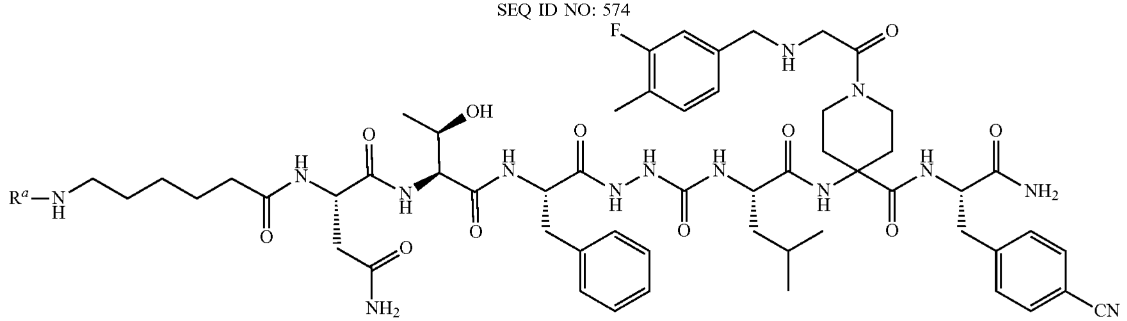<br>SEQ ID NO: 588 |
| 208 | 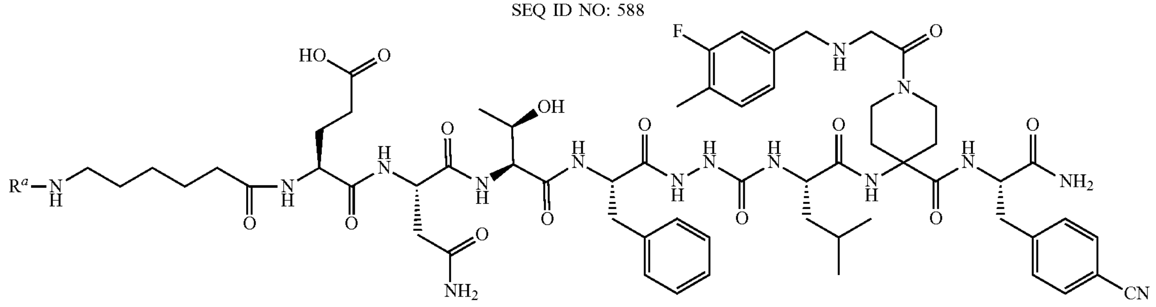<br>SEQ ID NO: 589 |

TABLE B-1-continued
| Cmp. # | Structure |
|---|---|
| 209 | 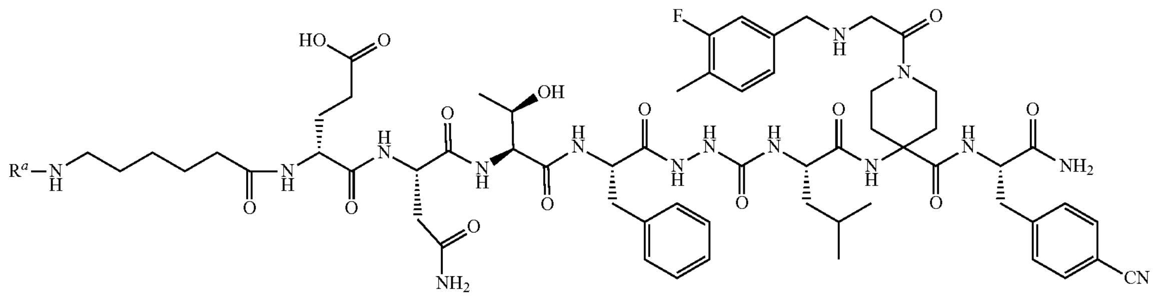 SEQ ID NO: 590 |
| 210 | 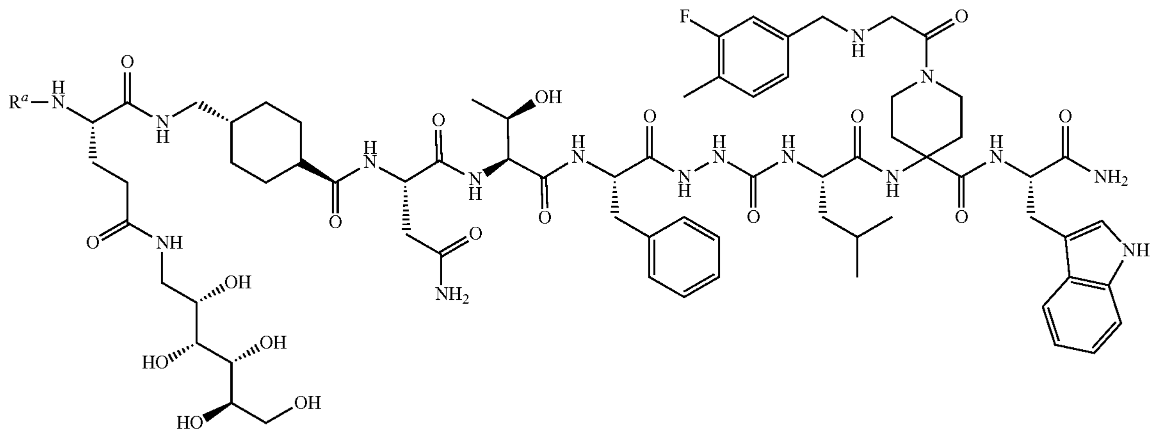 SEQ ID NO: 591 |

TABLE B-1-continued
| Cmp. # | Structure |
| --- | --- |
| 211 | 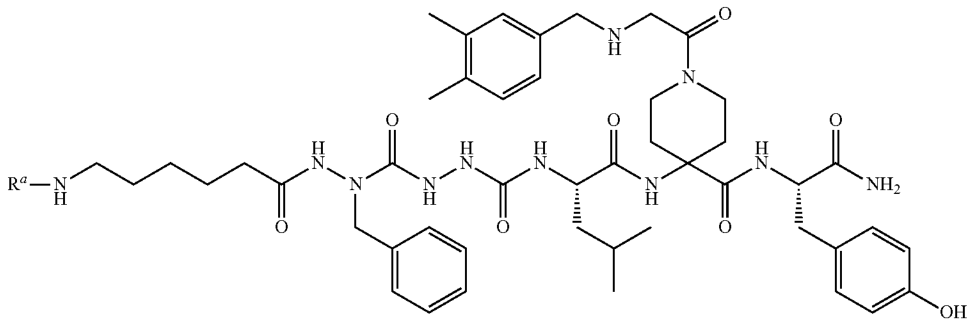 |
| 212 | 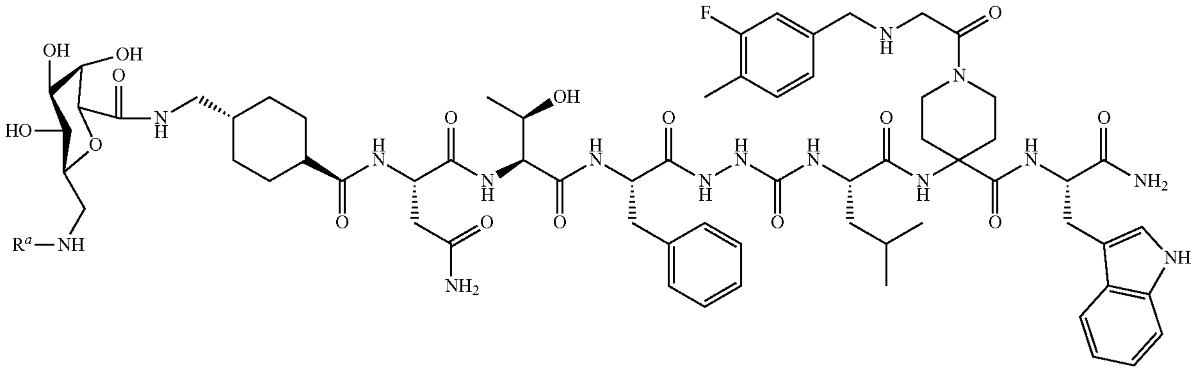<br>SEQ ID NO: 593 |

TABLE B-1-continued
| Cmp. # | Structure |
| --- | --- |
| 219 | 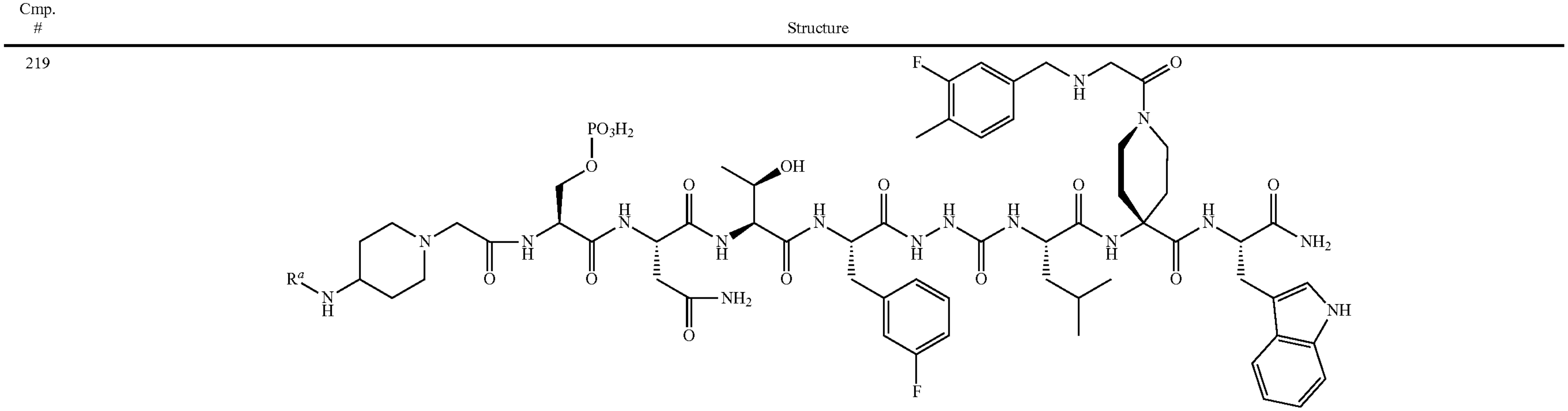 SEQ ID NO: 600 |
| 220 | 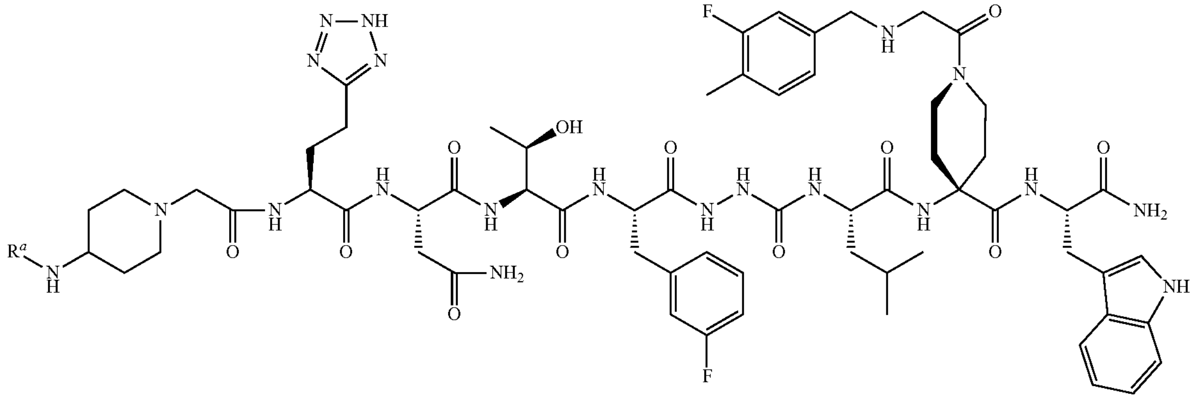 SEQ ID NO: 601 |

TABLE B-1-continued
| Cmp. # | Structure |
| --- | --- |
| 224 | 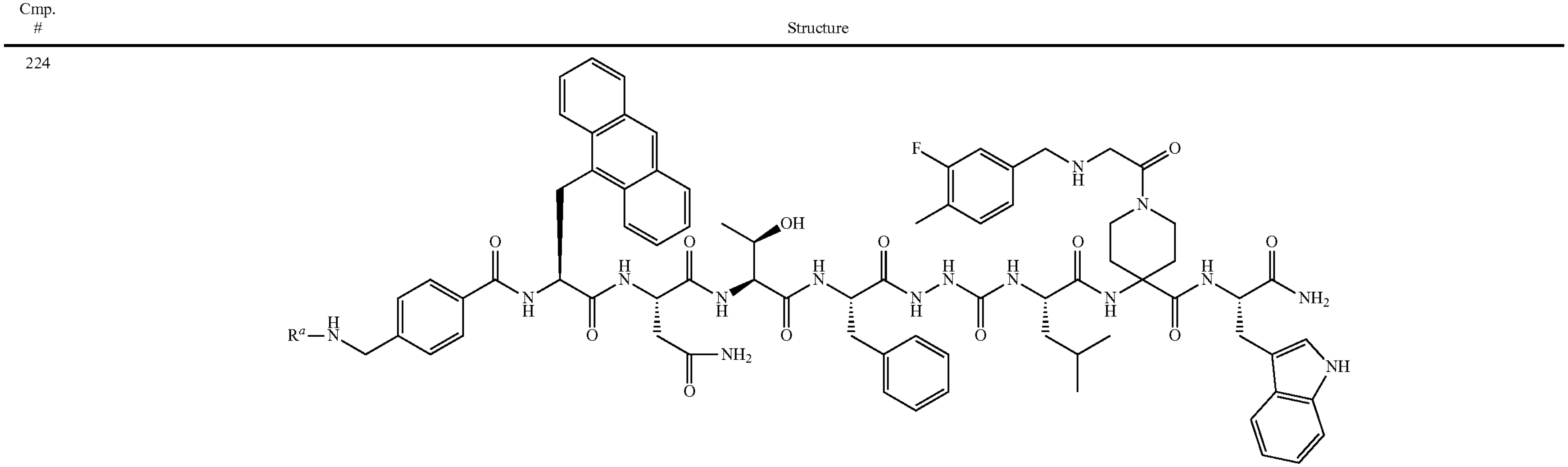<br>SEQ ID NO: 605 |
| 225 | 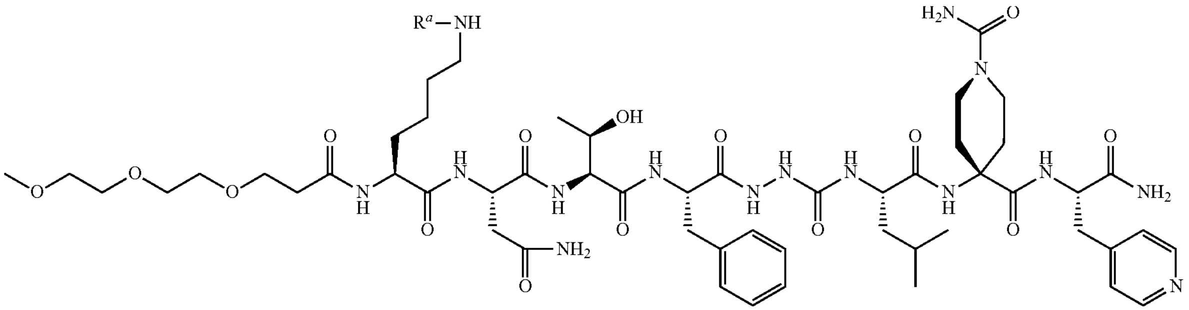<br>SEQ ID NO: 606 |

TABLE B-1-continued
| Cmp. # | Structure |
| --- | --- |
| 227 | 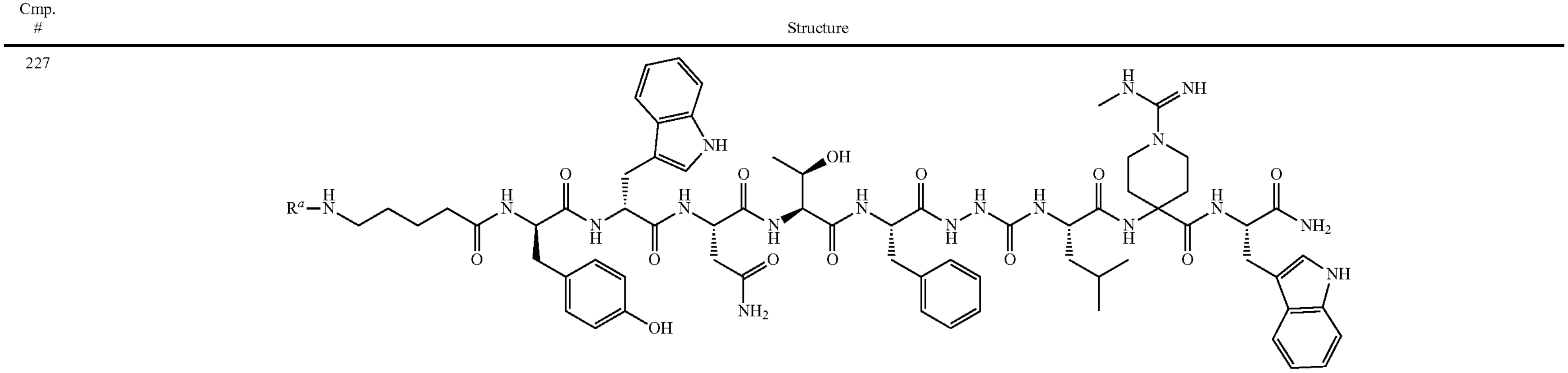<br>SEQ ID NO: 608 |
| 229 | 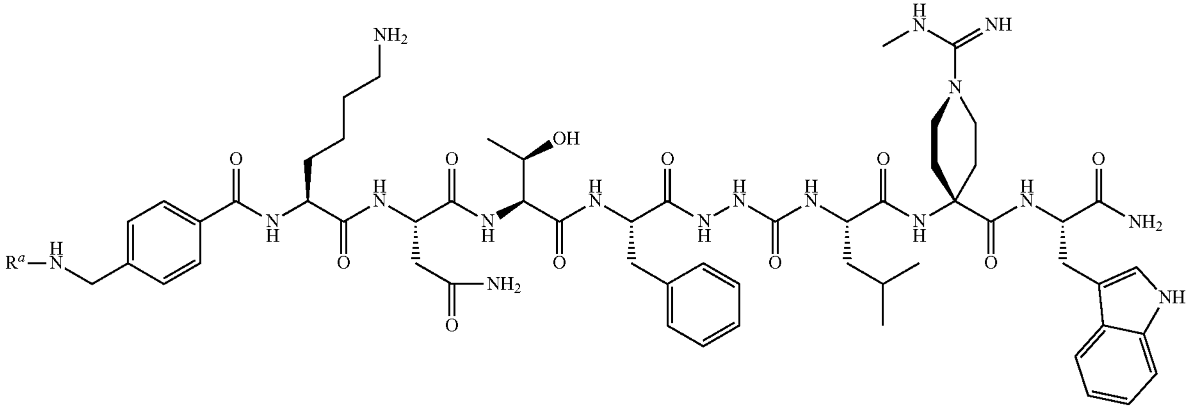<br>SEQ ID NO: 610 |

TABLE B-1-continued
| Cmp. # | Structure |
|---|---|
| 243 | 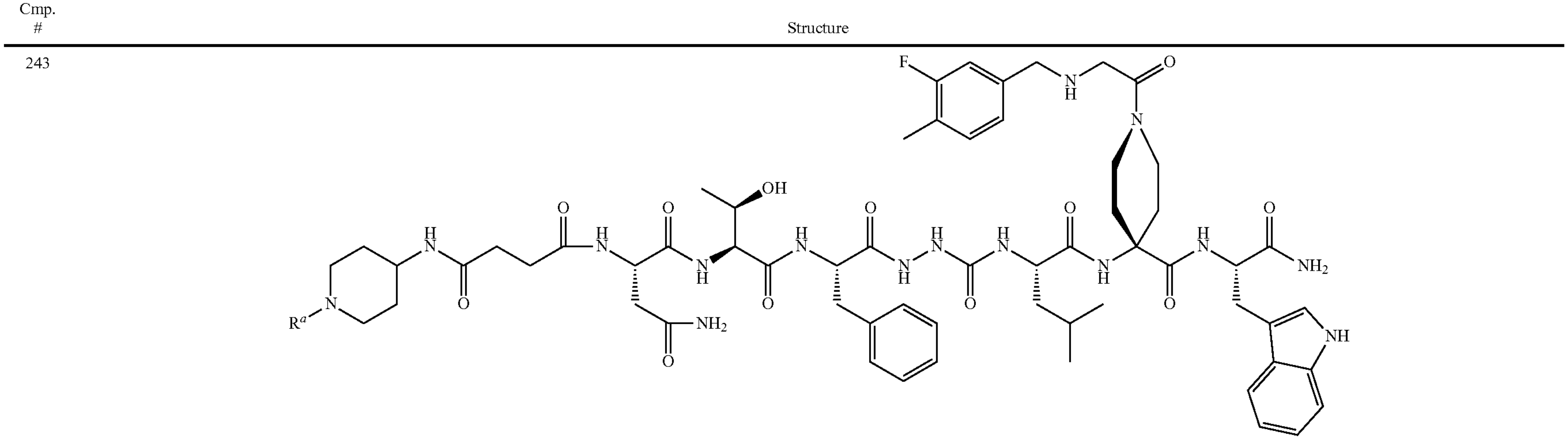<br>SEQ ID NO: 624 |
| 257 | 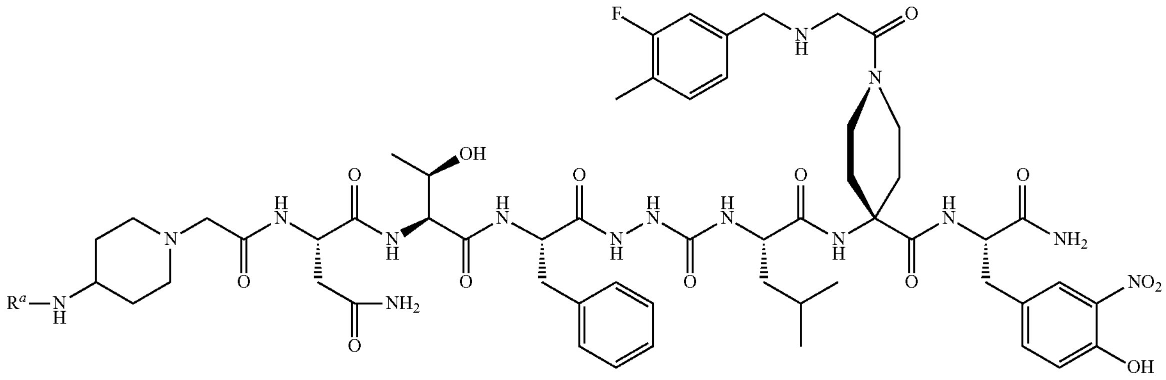<br>SEQ ID NO: 638 |

TABLE B-1-continued
| Cmp. # | Structure |
|---|---|
| 262 | 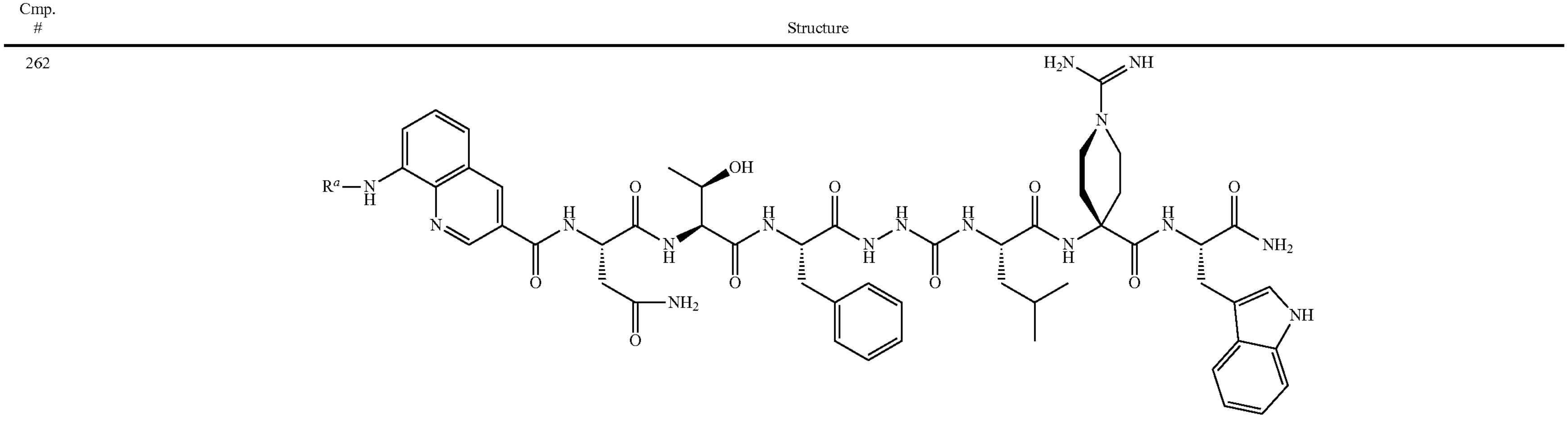 SEQ ID NO: 643 |
| 267 | 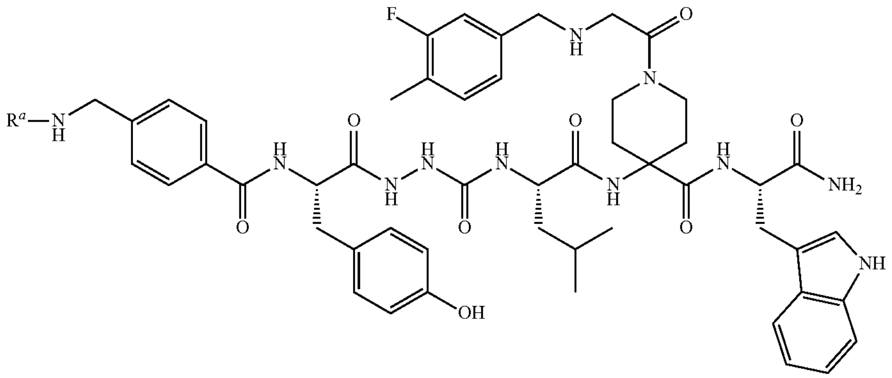 SEQ ID NO: 648 |

TABLE B-1-continued
| Cmp. # | Structure |
| --- | --- |
| 268 | 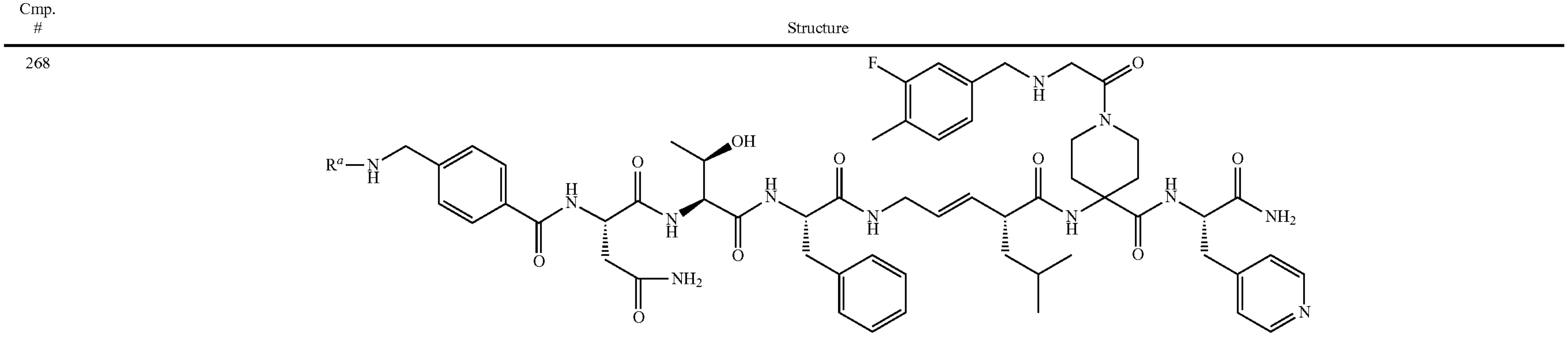 |
| 274 | 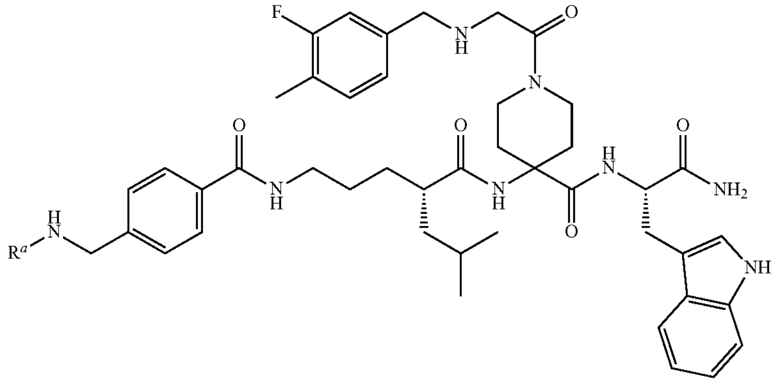 |

TABLE B-1-continued
| Cmp. # | Structure |
|---|---|
| 340 | 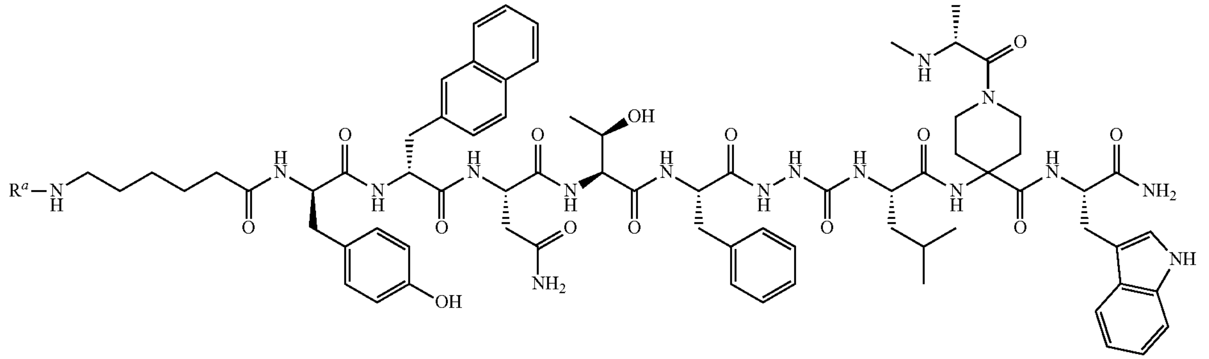 SEQ ID NO: 722 |
| 341 | 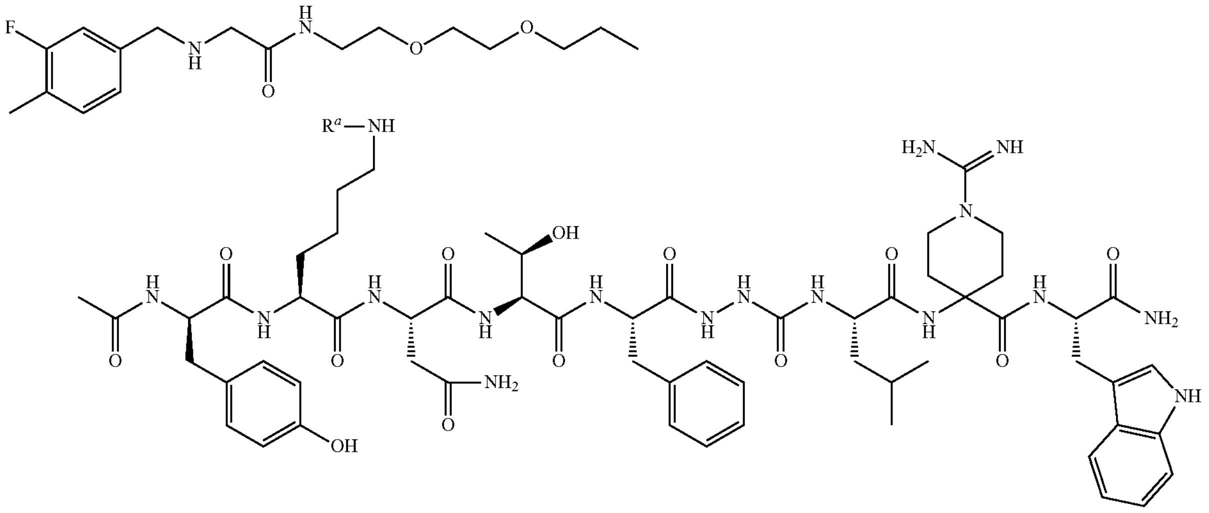 SEQ ID NO: 723 |

TABLE B-1-continued
| Cmp. # | Structure |
| --- | --- |
| 342 | 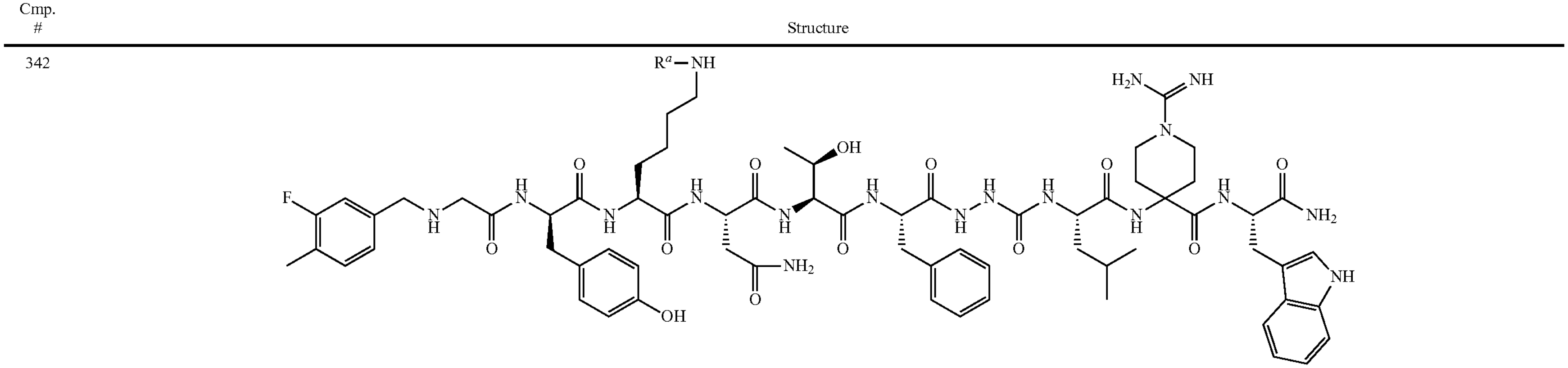 SEQ ID NO: 724 |
| 343 | 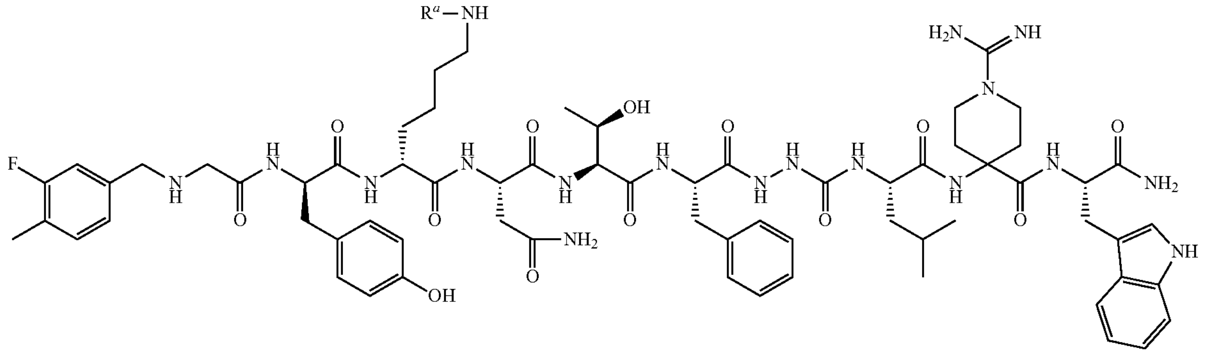 SEQ ID NO: 725 |
| 344 | 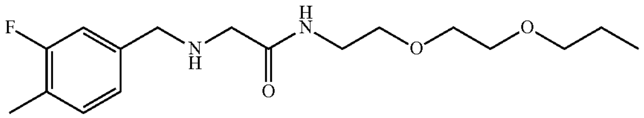 |

TABLE B-1-continued
| Cmp. # | Structure |
|---|---|
| | 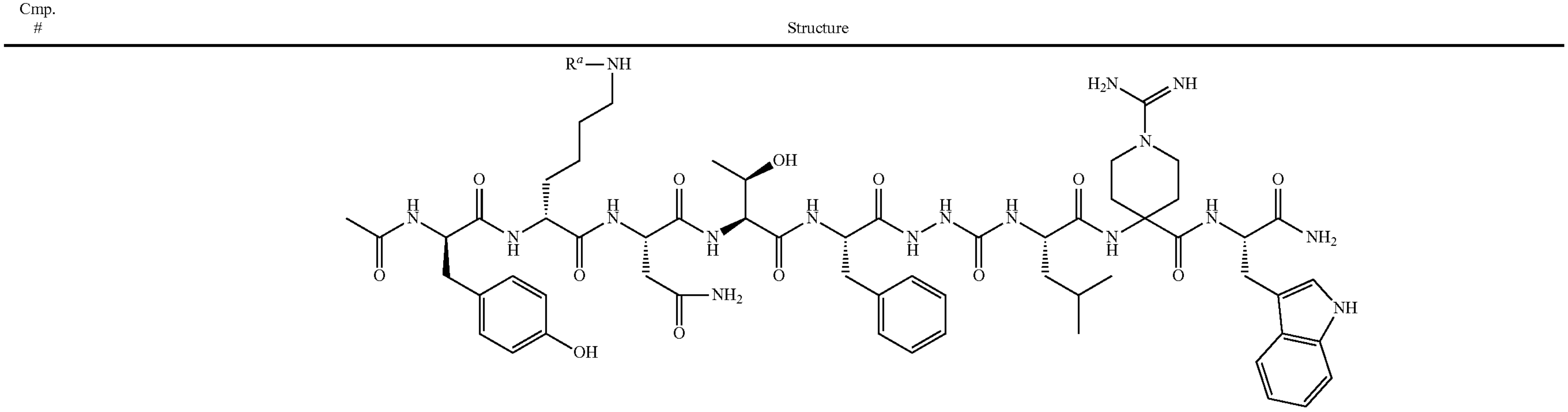<br>SEQ ID NO: 726 |
| 347 | 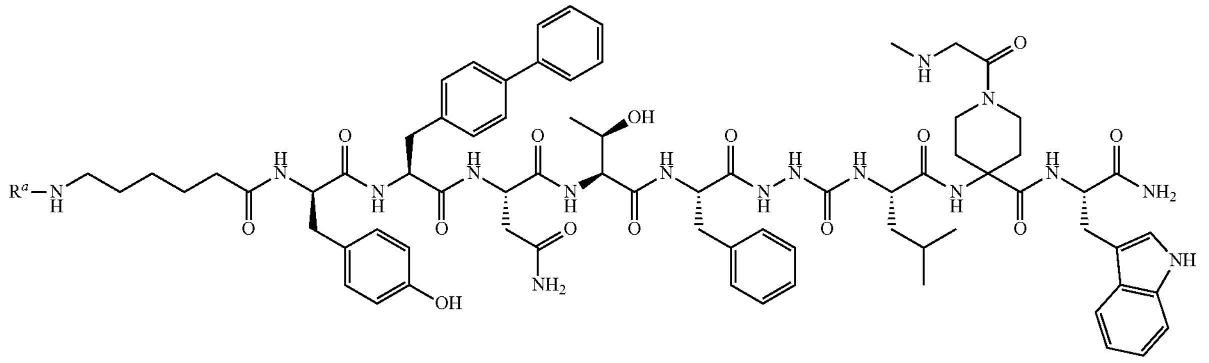<br>SEQ ID NO: 729 |

TABLE B-1-continued
| Cmp. # | Structure |
|---|---|
| 348 | 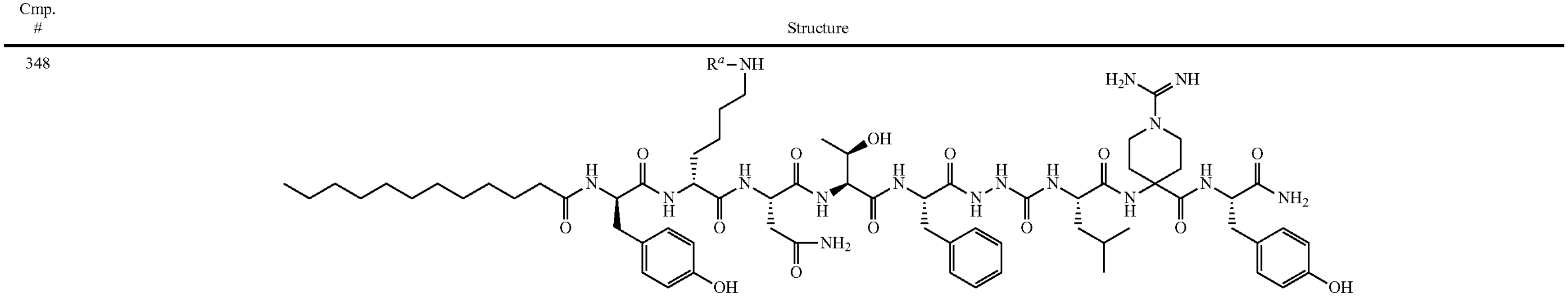 SEQ ID NO: 730 |
| 349 | 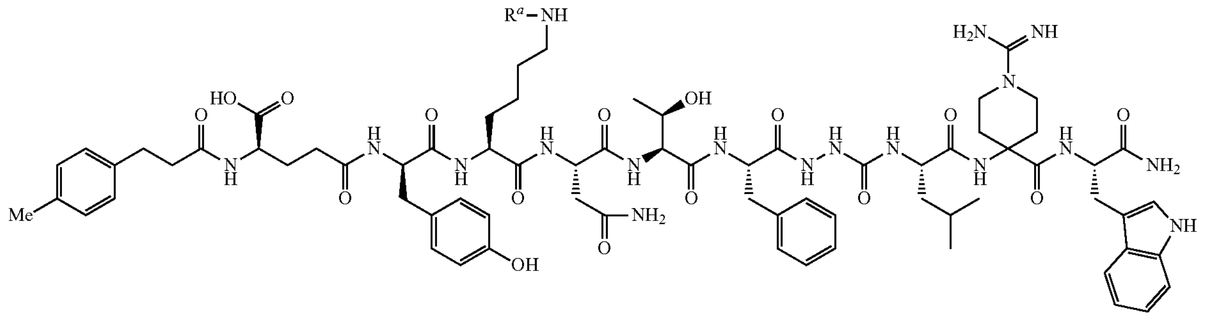 SEQ ID NO: 731 |
| 350 | 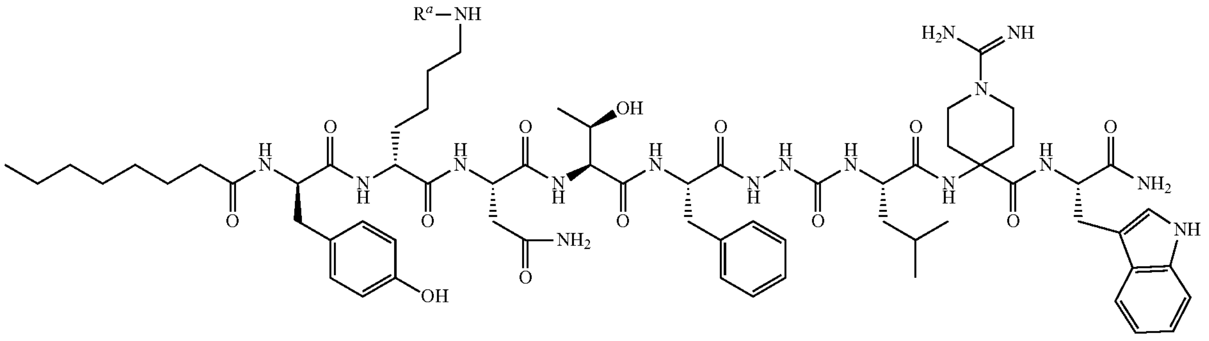 SEQ ID NO: 732 |

TABLE B-1-continued
| Cmp. # | Structure |
|---|---|
| 351 | 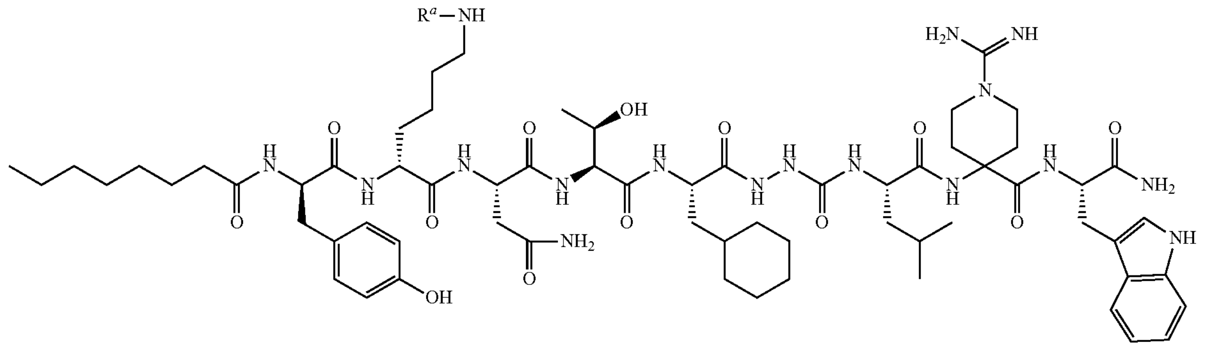 SEQ ID NO: 733 |
| 352 | 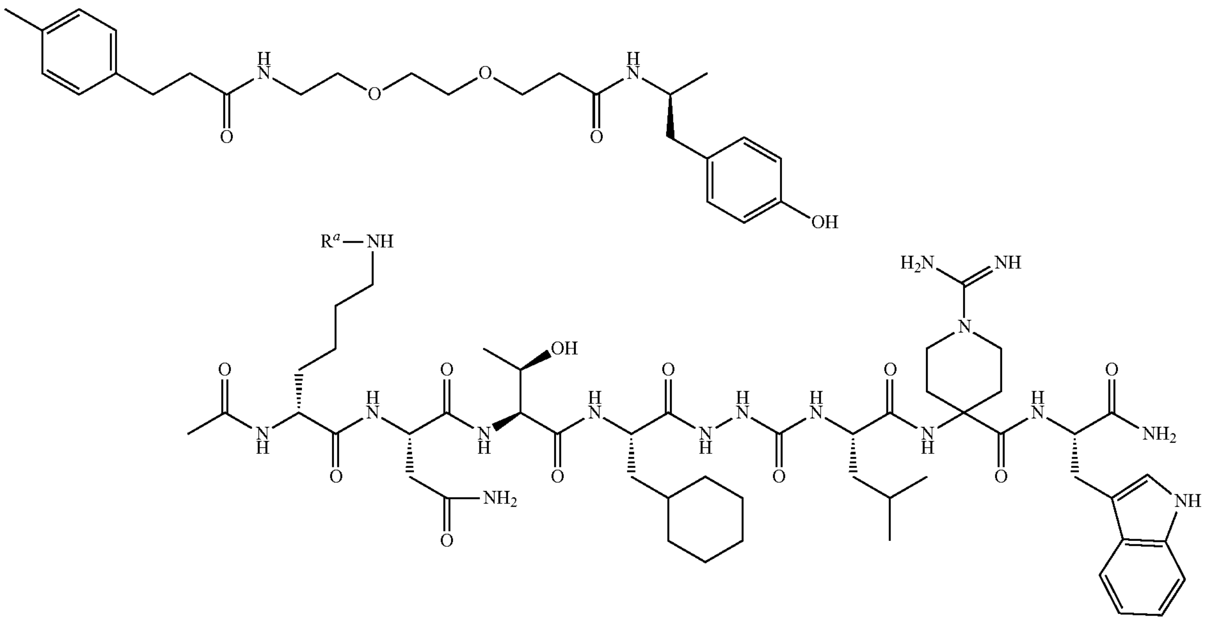 SEQ ID NO: 734 |

TABLE B-1-continued
| Cmp. # | Structure |
| --- | --- |
| 361 | 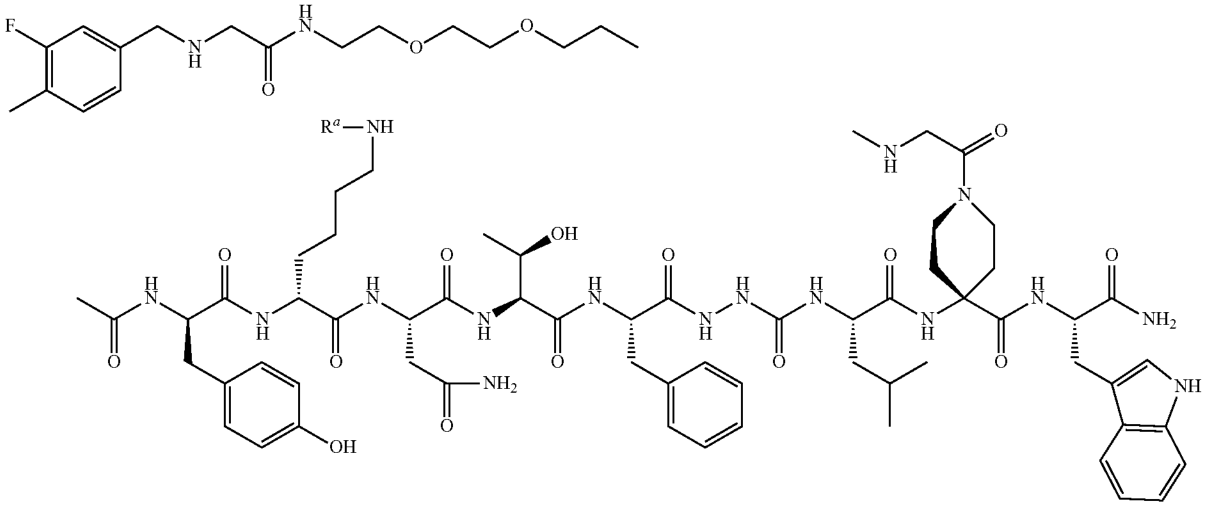 SEQ ID NO: 743 |
| 362 | 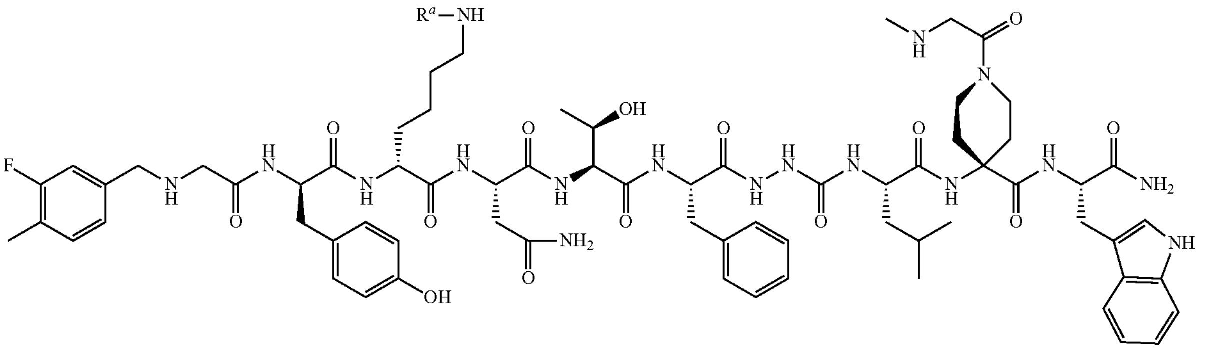 SEQ ID NO: 744 |

TABLE B-1-continued
| Cmp. # | Structure |
|---|---|
| 369 | 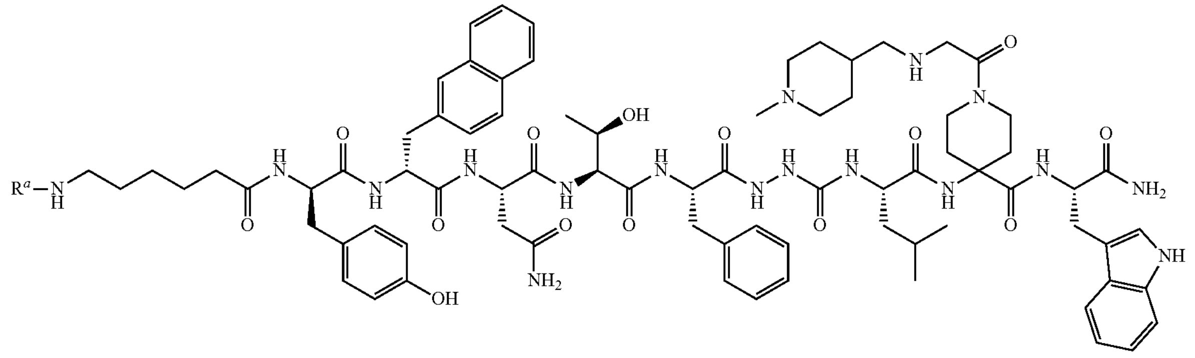 SEQ ID NO: 751 |
| 372 | 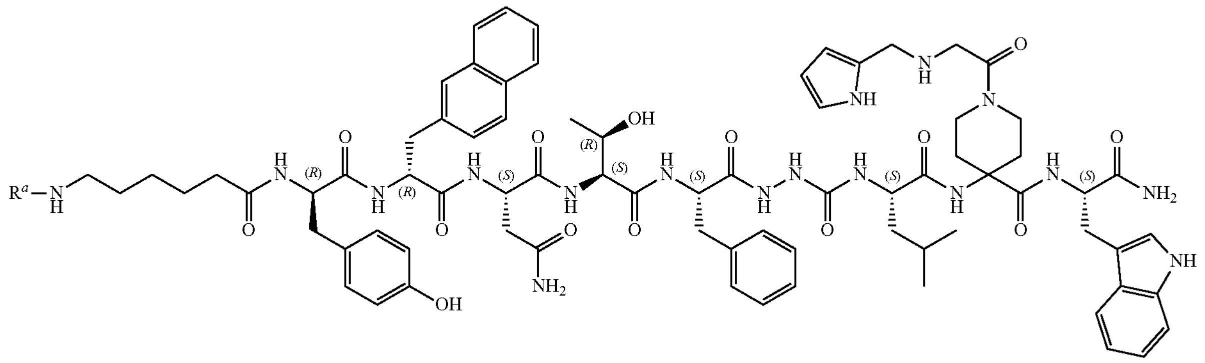 SEQ ID NO: 754 |

TABLE B-1-continued
| Cmp. # | Structure |
|---|---|
| 385 | 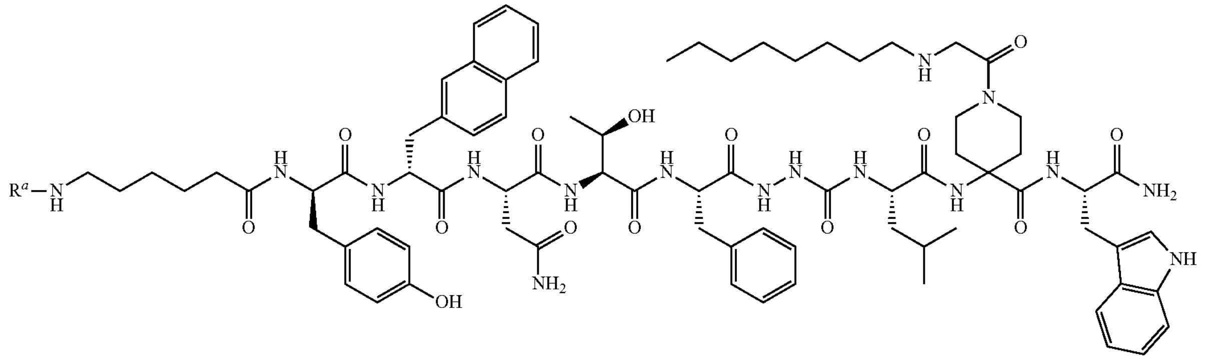 SEQ ID NO: 766 |

In some embodiments, the compound of Formula (I) is compound 1, a pharmaceutically acceptable salt thereof, or radionuclide complex thereof; compound 1-In, a pharmaceutically acceptable salt thereof; compound 1-Lu, a pharmaceutically acceptable salt thereof; compound 1-Ga, a pharmaceutically acceptable salt thereof, compound 2, a pharmaceutically acceptable salt thereof, or a radionuclide complex thereof; compound 2-In, a pharmaceutically acceptable salt thereof, or a radionuclide complex thereof; compound 3, a pharmaceutically acceptable salt thereof, or a radionuclide complex thereof, compound 4, a pharmaceutically acceptable salt thereof, or a radionuclide complex thereof; compound 5, a pharmaceutically acceptable salt thereof, or a radionuclide complex thereof; compound 6, a pharmaceutically acceptable salt thereof, or a radionuclide complex thereof; compound 6-In, a pharmaceutically acceptable salt thereof, or a radionuclide complex thereof; compound 7, a pharmaceutically acceptable salt thereof, or a radionuclide complex thereof; compound 8, a pharmaceutically acceptable salt thereof, or a radionuclide complex thereof: compound 9, a pharmaceutically acceptable salt thereof, or a radionuclide complex thereof; compound 10, a pharmaceutically acceptable salt thereof, or a radionuclide complex thereof; compound 11, a pharmaceutically acceptable salt thereof, or a radionuclide complex thereof; compound 12, a pharmaceutically acceptable salt thereof, or a radionuclide complex thereof; compound 13, a pharmaceutically acceptable salt thereof, or a radionuclide complex thereof; compound 14, a pharmaceutically acceptable salt thereof, or a radionuclide complex thereof; compound 15, a pharmaceutically acceptable salt thereof, or a radionuclide complex thereof; compound 16, a pharmaceutically acceptable salt thereof, or a radionuclide complex thereof; compound 17, a pharmaceutically acceptable salt thereof, or a radionuclide complex thereof; compound 18, a pharmaceutically acceptable salt thereof, or a radionuclide complex thereof; compound 19, a pharmaceutically acceptable salt thereof, or a radionuclide complex thereof; compound 20, a pharmaceutically acceptable salt thereof, or a radionuclide complex thereof; compound 21, a pharmaceutically acceptable salt thereof, or a radionuclide complex thereof; compound 22, a pharmaceutically acceptable salt thereof, or a radionuclide complex thereof; compound 23, a pharmaceutically acceptable salt thereof, or a radionuclide complex thereof; compound 24, a pharmaceutically acceptable salt thereof, or a radionuclide complex thereof; compound 25, a pharmaceutically acceptable salt thereof, or a radionuclide complex thereof; compound 26, a pharmaceutically acceptable salt thereof, or a radionuclide complex thereof; compound 27, a pharmaceutically acceptable salt thereof, or a radionuclide complex thereof; compound 28, a pharmaceutically acceptable salt thereof, or a radionuclide complex thereof; compound 29, a pharmaceutically acceptable salt thereof, or a radionuclide complex thereof; compound 30, a pharmaceutically acceptable salt thereof, or a radionuclide complex thereof; compound 31, a pharmaceutically acceptable salt thereof, or a radionuclide complex thereof; compound 32, a pharmaceutically acceptable salt thereof, or a radionuclide complex thereof: compound 33, a pharmaceutically acceptable salt thereof, or a radionuclide complex thereof; compound 34, a pharmaceutically acceptable salt thereof, or a radionuclide complex thereof; compound 35, a pharmaceutically acceptable salt thereof, or a radionuclide complex thereof; compound 36, a pharmaceutically acceptable salt thereof, or a radionuclide complex thereof; compound 37, a pharmaceutically acceptable salt thereof, or a radionuclide complex thereof; compound 38, a pharmaceutically acceptable salt thereof, or a radionuclide complex thereof; compound 39, a pharmaceutically acceptable salt thereof, or a radionuclide complex thereof; compound 40, a pharmaceutically acceptable salt thereof, or a radionuclide complex thereof, compound 41, a pharmaceutically acceptable salt thereof, or a radionuclide complex thereof; compound 42, a pharmaceutically acceptable salt thereof, or a radionuclide complex thereof; compound 43, a pharmaceutically acceptable salt thereof, or a radionuclide complex thereof; compound 44, a pharmaceutically acceptable salt thereof, or a radionuclide complex thereof; compound 45, a pharmaceutically acceptable salt thereof, or a radionuclide complex thereof; compound 46, a pharmaceutically acceptable salt thereof, or a radionuclide complex thereof; compound 47, a pharmaceutically acceptable salt thereof, or a radionuclide complex thereof; compound 48, a pharmaceutically acceptable salt thereof, or a radionuclide complex thereof; compound 49, a pharmaceutically acceptable salt thereof, or a radionuclide complex thereof; compound 50, a pharmaceutically acceptable salt thereof, or a radionuclide complex thereof; compound 51, a pharmaceutically acceptable salt thereof, or a radionuclide complex thereof; compound 52, a pharmaceutically acceptable salt thereof, or a radionuclide complex thereof; compound 53, a pharmaceutically acceptable salt thereof, or a radionuclide complex thereof; compound 54, a pharmaceutically acceptable salt thereof, or a radionuclide complex thereof; compound 55, a pharmaceutically acceptable salt thereof, or a radionuclide complex thereof; compound 56, a pharmaceutically acceptable salt thereof, or a radionuclide complex thereof; compound 57, a pharmaceutically acceptable salt thereof, or a radionuclide complex thereof; compound 58, a pharmaceutically acceptable salt thereof, or a radionuclide complex thereof; compound 59, a pharmaceutically acceptable salt thereof, or a radionuclide complex thereof; compound 60, a pharmaceutically acceptable salt thereof, or a radionuclide complex thereof; compound 61, a pharmaceutically acceptable salt thereof, or a radionuclide complex thereof; compound 62, a pharmaceutically acceptable salt thereof, or a radionuclide complex thereof; compound 63, a pharmaceutically acceptable salt thereof, or a radionuclide complex thereof: compound 64, a pharmaceutically acceptable salt thereof, or a radionuclide complex thereof; compound 65, a pharmaceutically acceptable salt thereof, or a radionuclide complex thereof; compound 66, a pharmaceutically acceptable salt thereof, or a radionuclide complex thereof; compound 67, a pharmaceutically acceptable salt thereof, or a radionuclide complex thereof; compound 68, a pharmaceutically acceptable salt thereof, or a radionuclide complex thereof; compound 69, a pharmaceutically acceptable salt thereof, or a radionuclide complex thereof; compound 70, a pharmaceutically acceptable salt thereof, or a radionuclide complex thereof; compound 71, a pharmaceutically acceptable salt thereof, or a radionuclide complex thereof: compound 72, a pharmaceutically acceptable salt thereof, or a radionuclide complex thereof; compound 73, a pharmaceutically acceptable salt thereof, or a radionuclide complex thereof; compound 74, a pharmaceutically acceptable salt thereof, or a radionuclide complex thereof; compound 75, a pharmaceutically acceptable salt thereof, or a radionuclide complex thereof; compound 76, a pharmaceutically acceptable salt thereof, or a radionuclide complex thereof; compound 77, a pharmaceutically acceptable salt thereof, or a radionuclide complex thereof, compound 78, a pharmaceutically acceptable salt thereof, or a radionuclide complex thereof; compound 79, a pharmaceutically acceptable salt thereof, or a radionuclide complex thereof; compound 80, a pharmaceutically acceptable salt thereof, or a radionuclide complex thereof; compound 81, a pharmaceutically acceptable salt thereof, or a radionuclide complex thereof, compound 82, a pharmaceutically acceptable salt thereof, or a radionuclide complex thereof; compound 83, a pharmaceutically acceptable salt thereof, or a radionuclide complex thereof; compound 84, a pharmaceutically acceptable salt thereof, or a radionuclide complex thereof; compound 85, a pharmaceutically acceptable salt thereof, or a radionuclide complex thereof; compound 86, a pharmaceutically acceptable salt thereof, or a radionuclide complex thereof; compound 87, a pharmaceutically acceptable salt thereof, or a radionuclide complex thereof; compound 88, a pharmaceutically acceptable salt thereof, or a radionuclide complex thereof; compound 89, a pharmaceutically acceptable salt thereof, or a radionuclide complex thereof; compound 90, a pharmaceutically acceptable salt thereof, or a radionuclide complex thereof; compound 91, a pharmaceutically acceptable salt thereof, or a radionuclide complex thereof; compound 92, a pharmaceutically acceptable salt thereof, or a radionuclide complex thereof; compound 93, a pharmaceutically acceptable salt thereof, or a radionuclide complex thereof; compound 94, a pharmaceutically acceptable salt thereof, or a radionuclide complex thereof; compound 95, a pharmaceutically acceptable salt thereof, or a radionuclide complex thereof: compound 96, a pharmaceutically acceptable salt thereof, or a radionuclide complex thereof; compound 96, a pharmaceutically acceptable salt thereof, or a radionuclide complex thereof; compound 98, a pharmaceutically acceptable salt thereof, or a radionuclide complex thereof; compound 99, a pharmaceutically acceptable salt thereof, or a radionuclide complex thereof; compound 100, a pharmaceutically acceptable salt thereof, or a radionuclide complex thereof; compound 101, a pharmaceutically acceptable salt thereof, or a radionuclide complex thereof: compound 102, a pharmaceutically acceptable salt thereof, or a radionuclide complex thereof; compound 103, a pharmaceutically acceptable salt thereof, or a radionuclide complex thereof; compound 104, a pharmaceutically acceptable salt thereof, or a radionuclide complex thereof; compound 105, a pharmaceutically acceptable salt thereof, or a radionuclide complex thereof; compound 105-In, a pharmaceutically acceptable salt thereof, or a radionuclide complex thereof; compound 106, a pharmaceutically acceptable salt thereof, or a radionuclide complex thereof; compound 107, a pharmaceutically acceptable salt thereof, or a radionuclide complex thereof, compound 108, a pharmaceutically acceptable salt thereof, or a radionuclide complex thereof; compound 109, a pharmaceutically acceptable salt thereof, or a radionuclide complex thereof; compound 110, a pharmaceutically acceptable salt thereof, or a radionuclide complex thereof; compound 112, a pharmaceutically acceptable salt thereof, or a radionuclide complex thereof, compound 113, a pharmaceutically acceptable salt thereof, or a radionuclide complex thereof; compound 114, a pharmaceutically acceptable salt thereof, or a radionuclide complex thereof; compound 115, a pharmaceutically acceptable salt thereof, or a radionuclide complex thereof; compound 116, a pharmaceutically acceptable salt thereof, or a radionuclide complex thereof; compound 117, a pharmaceutically acceptable salt thereof, or a radionuclide complex thereof; compound 118, a pharmaceutically acceptable salt thereof, or a radionuclide complex thereof; compound 118-Lu, a pharmaceutically acceptable salt thereof, or a radionuclide complex thereof; compound 119, a pharmaceutically acceptable salt thereof, or a radionuclide complex thereof; compound 120, a pharmaceutically acceptable salt thereof, or a radionuclide complex thereof; compound 121, a pharmaceutically acceptable salt thereof, or a radionuclide complex thereof; compound 122, a pharmaceutically acceptable salt thereof, or a radionuclide complex thereof; compound 123, a pharmaceutically acceptable salt thereof, or a radionuclide complex thereof; compound 130, a pharmaceutically acceptable salt thereof, or a radionuclide complex thereof; compound 131, a pharmaceutically acceptable salt thereof, or a radionuclide complex thereof; compound 132, a pharmaceutically acceptable salt thereof, or a radionuclide complex thereof; compound 133, a pharmaceutically acceptable salt thereof, or a radionuclide complex thereof; compound 134, a pharmaceutically acceptable salt thereof, or a radionuclide complex thereof; compound 135, a pharmaceutically acceptable salt thereof, or a radionuclide complex thereof; compound 136, a pharmaceutically acceptable salt thereof, or a radionuclide complex thereof; compound 137, a pharmaceutically acceptable salt thereof, or a radionuclide complex thereof; compound 138, a pharmaceutically acceptable salt thereof, or a radionuclide complex thereof; compound 139, a pharmaceutically acceptable salt thereof, or a radionuclide complex thereof; compound 140, a pharmaceutically acceptable salt thereof, or a radionuclide complex thereof; compound 141, a pharmaceutically acceptable salt thereof, or a radionuclide complex thereof; compound 142, a pharmaceutically acceptable salt thereof, or a radionuclide complex thereof; compound 143, a pharmaceutically acceptable salt thereof, or a radionuclide complex thereof; compound 144, a pharmaceutically acceptable salt thereof, or a radionuclide complex thereof; compound 145, a pharmaceutically acceptable salt thereof, or a radionuclide complex thereof; compound 146, a pharmaceutically acceptable salt thereof, or a radionuclide complex thereof; compound 147, a pharmaceutically acceptable salt thereof, or a radionuclide complex thereof; compound 148, a pharmaceutically acceptable salt thereof, or a radionuclide complex thereof; compound 149, a pharmaceutically acceptable salt thereof, or a radionuclide complex thereof; compound 150, a pharmaceutically acceptable salt thereof, or a radionuclide complex thereof; compound 151, a pharmaceutically acceptable salt thereof, or a radionuclide complex thereof; compound 152, a pharmaceutically acceptable salt thereof, or a radionuclide complex thereof; compound 153, a pharmaceutically acceptable salt thereof, or a radionuclide complex thereof; compound 154, a pharmaceutically acceptable salt thereof, or a radionuclide complex thereof; compound 155, a pharmaceutically acceptable salt thereof, or a radionuclide complex thereof; compound 156, a pharmaceutically acceptable salt thereof, or a radionuclide complex thereof; compound 157, a pharmaceutically acceptable salt thereof, or a radionuclide complex thereof; compound 158, a pharmaceutically acceptable salt thereof, or a radionuclide complex thereof; compound 159, a pharmaceutically acceptable salt thereof, or a radionuclide complex thereof; compound 160, a pharmaceutically acceptable salt thereof, or a radionuclide complex thereof; compound 161, a pharmaceutically acceptable salt thereof, or a radionuclide complex thereof; compound 162, a pharmaceutically acceptable salt thereof, or a radionuclide complex thereof; compound 163, a pharmaceutically acceptable salt thereof, or a radionuclide complex thereof; compound 164, a pharmaceutically acceptable salt thereof, or a radionuclide complex thereof; compound 165, a pharmaceutically acceptable salt thereof, or a radionuclide complex thereof; compound 166, a pharmaceutically acceptable salt thereof, or a radionuclide complex thereof; compound 167, a pharmaceutically acceptable salt thereof, or a radionuclide complex thereof; compound 168, a pharmaceutically acceptable salt thereof, or a radionuclide complex thereof; compound 169, a pharmaceutically acceptable salt thereof, or a radionuclide complex thereof; compound 170, a pharmaceutically acceptable salt thereof, or a radionuclide complex thereof; compound 171, a pharmaceutically acceptable salt thereof, or a radionuclide complex thereof; compound 174, a pharmaceutically acceptable salt thereof, or a radionuclide complex thereof; compound 175, a pharmaceutically acceptable salt thereof, or a radionuclide complex thereof; compound 176, a pharmaceutically acceptable salt thereof, or a radionuclide complex thereof; compound 177, a pharmaceutically acceptable salt thereof, or a radionuclide complex thereof; compound 178, a pharmaceutically acceptable salt thereof, or a radionuclide complex thereof; compound 179, a pharmaceutically acceptable salt thereof, or a radionuclide complex thereof; compound 180, a pharmaceutically acceptable salt thereof, or a radionuclide complex thereof; compound 181, a pharmaceutically acceptable salt thereof, or a radionuclide complex thereof; compound 182, a pharmaceutically acceptable salt thereof, or a radionuclide complex thereof; compound 183, a pharmaceutically acceptable salt thereof, or a radionuclide complex thereof; compound 184, a pharmaceutically acceptable salt thereof, or a radionuclide complex thereof; compound 185, a pharmaceutically acceptable salt thereof, or a radionuclide complex thereof; compound 186, a pharmaceutically acceptable salt thereof, or a radionuclide complex thereof; compound 187, a pharmaceutically acceptable salt thereof, or a radionuclide complex thereof; compound 188, a pharmaceutically acceptable salt thereof, or a radionuclide complex thereof; compound 189, a pharmaceutically acceptable salt thereof, or a radionuclide complex thereof; compound 180, a pharmaceutically acceptable salt thereof, or a radionuclide complex thereof; compound 181, a pharmaceutically acceptable salt thereof, or a radionuclide complex thereof; compound 182, a pharmaceutically acceptable salt thereof, or a radionuclide complex thereof; compound 183, a pharmaceutically acceptable salt thereof, or a radionuclide complex thereof; compound 184, a pharmaceutically acceptable salt thereof, or a radionuclide complex thereof; compound 185, a pharmaceutically acceptable salt thereof, or a radionuclide complex thereof; compound 186, a pharmaceutically acceptable salt thereof, or a radionuclide complex thereof; compound 187, a pharmaceutically acceptable salt thereof, or a radionuclide complex thereof; compound 188, a pharmaceutically acceptable salt thereof, or a radionuclide complex thereof; compound 189, a pharmaceutically acceptable salt thereof, or a radionuclide complex thereof; compound 190, a pharmaceutically acceptable salt thereof, or a radionuclide complex thereof; compound 191, a pharmaceutically acceptable salt thereof, or a radionuclide complex thereof; compound 192, a pharmaceutically acceptable salt thereof, or a radionuclide complex thereof; compound 193, a pharmaceutically acceptable salt thereof, or a radionuclide complex thereof; compound 193-In, a pharmaceutically acceptable salt thereof, or a radionuclide complex thereof; compound 194, a pharmaceutically acceptable salt thereof, or a radionuclide complex thereof; compound 195, a pharmaceutically acceptable salt thereof, or a radionuclide complex thereof; compound 196, a pharmaceutically acceptable salt thereof, or a radionuclide complex thereof; compound 196-In, a pharmaceutically acceptable salt thereof, or a radionuclide complex thereof; compound 197, a pharmaceutically acceptable salt thereof, or a radionuclide complex thereof; compound 198, a pharmaceutically acceptable salt thereof, or a radionuclide complex thereof; compound 199, a pharmaceutically acceptable salt thereof, or a radionuclide complex thereof; compound 201, a pharmaceutically acceptable salt thereof, or a radionuclide complex thereof; compound 201-In, a pharmaceutically acceptable salt thereof, or a radionuclide complex thereof; compound 202, a pharmaceutically acceptable salt thereof, or a radionuclide complex thereof; compound 203, a pharmaceutically acceptable salt thereof, or a radionuclide complex thereof; compound 204, a pharmaceutically acceptable salt thereof, or a radionuclide complex thereof; compound 205, a pharmaceutically acceptable salt thereof, or a radionuclide complex thereof; compound 206, a pharmaceutically acceptable salt thereof, or a radionuclide complex thereof; compound 207, a pharmaceutically acceptable salt thereof, or a radionuclide complex thereof; compound 208, a pharmaceutically acceptable salt thereof, or a radionuclide complex thereof; compound 209, a pharmaceutically acceptable salt thereof, or a radionuclide complex thereof; compound 210, a pharmaceutically acceptable salt thereof, or a radionuclide complex thereof; compound 211, a pharmaceutically acceptable salt thereof, or a radionuclide complex thereof; compound 212, a pharmaceutically acceptable salt thereof, or a radionuclide complex thereof; compound 213, a pharmaceutically acceptable salt thereof, or a radionuclide complex thereof; compound 214, a pharmaceutically acceptable salt thereof, or a radionuclide complex thereof; compound 215, a pharmaceutically acceptable salt thereof, or a radionuclide complex thereof; compound 216, a pharmaceutically acceptable salt thereof, or a radionuclide complex thereof; compound 217, a pharmaceutically acceptable salt thereof, or a radionuclide complex thereof; compound 218, a pharmaceutically acceptable salt thereof, or a radionuclide complex thereof; compound 219, a pharmaceutically acceptable salt thereof, or a radionuclide complex thereof; compound 220, a pharmaceutically acceptable salt thereof, or a radionuclide complex thereof; compound 221, a pharmaceutically acceptable salt thereof, or a radionuclide complex thereof; compound 222, a pharmaceutically acceptable salt thereof, or a radionuclide complex thereof; compound 224, a pharmaceutically acceptable salt thereof, or a radionuclide complex thereof; compound 225, a pharmaceutically acceptable salt thereof, or a radionuclide complex thereof; compound 226, a pharmaceutically acceptable salt thereof, or a radionuclide complex thereof; compound 227, a pharmaceutically acceptable salt thereof, or a radionuclide complex thereof; compound 229, a pharmaceutically acceptable salt thereof, or a radionuclide complex thereof; compound 230, a pharmaceutically acceptable salt thereof, or a radionuclide complex thereof; compound 231, a pharmaceutically acceptable salt thereof, or a radionuclide complex thereof; compound 232, a pharmaceutically acceptable salt thereof, or a radionuclide complex thereof; compound 233, a pharmaceutically acceptable salt thereof, or a radionuclide complex thereof; compound 234, a pharmaceutically acceptable salt thereof, or a radionuclide complex thereof; compound 235, a pharmaceutically acceptable salt thereof, or a radionuclide complex thereof; compound 236, a pharmaceutically acceptable salt thereof, or a radionuclide complex thereof; compound 237, a pharmaceutically acceptable salt thereof, or a radionuclide complex thereof; compound 238, a pharmaceutically acceptable salt thereof, or a radionuclide complex thereof; compound 239, a pharmaceutically acceptable salt thereof, or a radionuclide complex thereof; compound 240, a pharmaceutically acceptable salt thereof, or a radionuclide complex thereof; compound 241, a pharmaceutically acceptable salt thereof, or a radionuclide complex thereof; compound 242, a pharmaceutically acceptable salt thereof, or a radionuclide complex thereof; compound 243, a pharmaceutically acceptable salt thereof, or a radionuclide complex thereof; compound 244, a pharmaceutically acceptable salt thereof, or a radionuclide complex thereof; compound 245, a pharmaceutically acceptable salt thereof, or a radionuclide complex thereof; compound 246, a pharmaceutically acceptable salt thereof, or a radionuclide complex thereof; compound 247, a pharmaceutically acceptable salt thereof, or a radionuclide complex thereof; compound 248, a pharmaceutically acceptable salt thereof, or a radionuclide complex thereof; compound 249, a pharmaceutically acceptable salt thereof, or a radionuclide complex thereof; compound 240, a pharmaceutically acceptable salt thereof, or a radionuclide complex thereof; compound 241, a pharmaceutically acceptable salt thereof, or a radionuclide complex thereof; compound 242, a pharmaceutically acceptable salt thereof, or a radionuclide complex thereof; compound 243, a pharmaceutically acceptable salt thereof, or a radionuclide complex thereof; compound 244, a pharmaceutically acceptable salt thereof, or a radionuclide complex thereof; compound 245, a pharmaceutically acceptable salt thereof, or a radionuclide complex thereof; compound 246, a pharmaceutically acceptable salt thereof, or a radionuclide complex thereof; compound 247, a pharmaceutically acceptable salt thereof, or a radionuclide complex thereof; compound 248, a pharmaceutically acceptable salt thereof, or a radionuclide complex thereof; compound 249, a pharmaceutically acceptable salt thereof, or a radionuclide complex thereof; compound 250, a pharmaceutically acceptable salt thereof, or a radionuclide complex thereof; compound 251, a pharmaceutically acceptable salt thereof, or a radionuclide complex thereof; compound 252, a pharmaceutically acceptable salt thereof, or a radionuclide complex thereof; compound 253, a pharmaceutically acceptable salt thereof, or a radionuclide complex thereof; compound 254, a pharmaceutically acceptable salt thereof, or a radionuclide complex thereof; compound 255, a pharmaceutically acceptable salt thereof, or a radionuclide complex thereof; compound 256, a pharmaceutically acceptable salt thereof, or a radionuclide complex thereof; compound 257, a pharmaceutically acceptable salt thereof, or a radionuclide complex thereof; compound 258, a pharmaceutically acceptable salt thereof, or a radionuclide complex thereof; compound 259, a pharmaceutically acceptable salt thereof, or a radionuclide complex thereof; compound 260, a pharmaceutically acceptable salt thereof, or a radionuclide complex thereof; compound 261, a pharmaceutically acceptable salt thereof, or a radionuclide complex thereof; compound 262, a pharmaceutically acceptable salt thereof, or a radionuclide complex thereof; compound 264, a pharmaceutically acceptable salt thereof, or a radionuclide complex thereof; compound 266, a pharmaceutically acceptable salt thereof, or a radionuclide complex thereof; compound 267, a pharmaceutically acceptable salt thereof, or a radionuclide complex thereof; compound 268, a pharmaceutically acceptable salt thereof, or a radionuclide complex thereof; compound 269, a pharmaceutically acceptable salt thereof, or a radionuclide complex thereof, compound 269-In, a pharmaceutically acceptable salt thereof, or a radionuclide complex thereof; compound 270, a pharmaceutically acceptable salt thereof, or a radionuclide complex thereof; compound 271, a pharmaceutically acceptable salt thereof, or a radionuclide complex thereof; compound 272, a pharmaceutically acceptable salt thereof, or a radionuclide complex thereof; compound 273, a pharmaceutically acceptable salt thereof, or a radionuclide complex thereof; compound 274, a pharmaceutically acceptable salt thereof, or a radionuclide complex thereof; compound 275, a pharmaceutically acceptable salt thereof, or a radionuclide complex thereof; compound 276, a pharmaceutically acceptable salt thereof, or a radionuclide complex thereof; compound 277, a pharmaceutically acceptable salt thereof, or a radionuclide complex thereof; compound 278, a pharmaceutically acceptable salt thereof, or a radionuclide complex thereof; compound 279, a pharmaceutically acceptable salt thereof, or a radionuclide complex thereof; compound 280, a pharmaceutically acceptable salt thereof, or a radionuclide complex thereof; compound 281, a pharmaceutically acceptable salt thereof, or a radionuclide complex thereof; compound 282, a pharmaceutically acceptable salt thereof, or a radionuclide complex thereof; compound 283, a pharmaceutically acceptable salt thereof, or a radionuclide complex thereof; compound 284, a pharmaceutically acceptable salt thereof, or a radionuclide complex thereof; compound 285, a pharmaceutically acceptable salt thereof, or a radionuclide complex thereof; compound 286, a pharmaceutically acceptable salt thereof, or a radionuclide complex thereof; compound 287, a pharmaceutically acceptable salt thereof, or a radionuclide complex thereof; compound 288, a pharmaceutically acceptable salt thereof, or a radionuclide complex thereof; compound 289, a pharmaceutically acceptable salt thereof, or a radionuclide complex thereof; compound 290, a pharmaceutically acceptable salt thereof, or a radionuclide complex thereof; compound 291, a pharmaceutically acceptable salt thereof, or a radionuclide complex thereof; compound 292, a pharmaceutically acceptable salt thereof, or a radionuclide complex thereof; compound 293, a pharmaceutically acceptable salt thereof, or a radionuclide complex thereof; compound 294, a pharmaceutically acceptable salt thereof, or a radionuclide complex thereof; compound 295, a pharmaceutically acceptable salt thereof, or a radionuclide complex thereof; compound 296, a pharmaceutically acceptable salt thereof, or a radionuclide complex thereof; compound 297, a pharmaceutically acceptable salt thereof, or a radionuclide complex thereof; compound 298, a pharmaceutically acceptable salt thereof, or a radionuclide complex thereof; compound 299, a pharmaceutically acceptable salt thereof, or a radionuclide complex thereof; compound 300, a pharmaceutically acceptable salt thereof, or a radionuclide complex thereof; compound 301, a pharmaceutically acceptable salt thereof, or a radionuclide complex thereof; compound 302, a pharmaceutically acceptable salt thereof, or a radionuclide complex thereof; compound 304, a pharmaceutically acceptable salt thereof, or a radionuclide complex thereof: compound 305, a pharmaceutically acceptable salt thereof, or a radionuclide complex thereof; compound 306, a pharmaceutically acceptable salt thereof, or a radionuclide complex thereof; compound 307, a pharmaceutic ally acceptable salt thereof, or a radionuclide complex thereof; compound 308, a pharmaceutically acceptable salt thereof, or a radionuclide complex thereof; compound 309, a pharmaceutically acceptable salt thereof, or a radionuclide complex thereof; compound 310, a pharmaceutically acceptable salt thereof, or a radionuclide complex thereof; compound 311, a pharmaceutically acceptable salt thereof, or a radionuclide complex thereof; compound 312, a pharmaceutically acceptable salt thereof, or a radionuclide complex thereof; compound 313, a pharmaceutically acceptable salt thereof, or a radionuclide complex thereof; compound 314, a pharmaceutically acceptable salt thereof, or a radionuclide complex thereof; compound 315, a pharmaceutically acceptable salt thereof, or a radionuclide complex thereof; compound 316, a pharmaceutically acceptable salt thereof, or a radionuclide complex thereof; compound 317, a pharmaceutically acceptable salt thereof, or a radionuclide complex thereof; compound 318, a pharmaceutically acceptable salt thereof, or a radionuclide complex thereof; compound 319, a pharmaceutically acceptable salt thereof, or a radionuclide complex thereof; compound 320, a pharmaceutically acceptable salt thereof, or a radionuclide complex thereof; compound 321, a pharmaceutically acceptable salt thereof, or a radionuclide complex thereof; compound 322, a pharmaceutically acceptable salt thereof, or a radionuclide complex thereof; compound 323, a pharmaceutically acceptable salt thereof, or a radionuclide complex thereof; compound 324, a pharmaceutically acceptable salt thereof, or a radionuclide complex thereof; compound 325, a pharmaceutically acceptable salt thereof, or a radionuclide complex thereof; compound 326, a pharmaceutically acceptable salt thereof, or a radionuclide complex thereof; compound 327, a pharmaceutically acceptable salt thereof, or a radionuclide complex thereof; compound 328, a pharmaceutically acceptable salt thereof, or a radionuclide complex thereof; compound 329, a pharmaceutically acceptable salt thereof, or a radionuclide complex thereof; compound 330, a pharmaceutically acceptable salt thereof, or a radionuclide complex thereof; compound 331, a pharmaceutically acceptable salt thereof, or a radionuclide complex thereof; compound 332, a pharmaceutically acceptable salt thereof, or a radionuclide complex thereof; compound 333, a pharmaceutically acceptable salt thereof, or a radionuclide complex thereof; compound 334, a pharmaceutically acceptable salt thereof, or a radionuclide complex thereof; compound 335, a pharmaceutically acceptable salt thereof, or a radionuclide complex thereof; compound 336, a pharmaceutically acceptable salt thereof, or a radionuclide complex thereof; compound 337, a pharmaceutically acceptable salt thereof, or a radionuclide complex thereof; compound 338, a pharmaceutically acceptable salt thereof, or a radionuclide complex thereof; compound 339, a pharmaceutically acceptable salt thereof, or a radionuclide complex thereof; compound 340, a pharmaceutically acceptable salt thereof, or a radionuclide complex thereof; compound 341, a pharmaceutically acceptable salt thereof, or a radionuclide complex thereof; compound 342, a pharmaceutically acceptable salt thereof, or a radionuclide complex thereof; compound 343, a pharmaceutically acceptable salt thereof, or a radionuclide complex thereof; compound 344, a pharmaceutically acceptable salt thereof, or a radionuclide complex thereof; compound 345, a pharmaceutically acceptable salt thereof, or a radionuclide complex thereof; compound 346, a pharmaceutically acceptable salt thereof, or a radionuclide complex thereof; compound 347, a pharmaceutically acceptable salt thereof, or a radionuclide complex thereof; compound 348, a pharmaceutically acceptable salt thereof, or a radionuclide complex thereof; compound 349, a pharmaceutically acceptable salt thereof, or a radionuclide complex thereof; compound 350, a pharmaceutically acceptable salt thereof, or a radionuclide complex thereof; compound 351, a pharmaceutically acceptable salt thereof, or a radionuclide complex thereof; compound 352, a pharmaceutically acceptable salt thereof, or a radionuclide complex thereof; compound 353, a pharmaceutically acceptable salt thereof, or a radionuclide complex thereof; compound 354, a pharmaceutically acceptable salt thereof, or a radionuclide complex thereof; compound 355, a pharmaceutically acceptable salt thereof, or a radionuclide complex thereof; compound 356, a pharmaceutically acceptable salt thereof, or a radionuclide complex thereof; compound 357, a pharmaceutically acceptable salt thereof, or a radionuclide complex thereof; compound 358, a pharmaceutically acceptable salt thereof, or a radionuclide complex thereof; compound 359, a pharmaceutically acceptable salt thereof, or a radionuclide complex thereof; compound 360, a pharmaceutically acceptable salt thereof, or a radionuclide complex thereof; compound 361, a pharmaceutically acceptable salt thereof, or a radionuclide complex thereof; compound 362, a pharmaceutically acceptable salt thereof, or a radionuclide complex thereof; compound 363, a pharmaceutically acceptable salt thereof, or a radionuclide complex thereof; compound 364, a pharmaceutically acceptable salt thereof, or a radionuclide complex thereof; compound 365, a pharmaceutically acceptable salt thereof, or a radionuclide complex thereof; compound 366, a pharmaceutically acceptable salt thereof, or a radionuclide complex thereof; compound 367, a pharmaceutically acceptable salt thereof, or a radionuclide complex thereof; compound 368, a pharmaceutically acceptable salt thereof, or a radionuclide complex thereof; compound 369, a pharmaceutically acceptable salt thereof, or a radionuclide complex thereof; compound 370, a pharmaceutically acceptable salt thereof, or a radionuclide complex thereof; compound 371, a pharmaceutically acceptable salt thereof, or a radionuclide complex thereof; compound 372, a pharmaceutically acceptable salt thereof, or a radionuclide complex thereof; compound 373, a pharmaceutically acceptable salt thereof, or a radionuclide complex thereof; compound 374, a pharmaceutically acceptable salt thereof, or a radionuclide complex thereof; compound 375, a pharmaceutically acceptable salt thereof, or a radionuclide complex thereof; compound 376, a pharmaceutically acceptable salt thereof, or a radionuclide complex thereof; compound 378, a pharmaceutically acceptable salt thereof, or a radionuclide complex thereof; compound 379, a pharmaceutically acceptable salt thereof, or a radionuclide complex thereof; compound 380, a pharmaceutically acceptable salt thereof, or a radionuclide complex thereof; compound 381, a pharmaceutically acceptable salt thereof, or a radionuclide complex thereof; compound 382, a pharmaceutically acceptable salt thereof, or a radionuclide complex thereof; compound 383, a pharmaceutically acceptable salt thereof, or a radionuclide complex thereof; compound 384, a pharmaceutically acceptable salt thereof, or a radionuclide complex thereof; compound 385, a pharmaceutically acceptable salt thereof, or a radionuclide complex thereof; compound 386, a pharmaceutically acceptable salt thereof, or a radionuclide complex thereof; compound 387, a pharmaceutically acceptable salt thereof, or a radionuclide complex thereof; compound 388, a pharmaceutically acceptable salt thereof, or a radionuclide complex thereof, or compound 389, a pharmaceutically acceptable salt thereof, or a radionuclide complex thereof.

Any combination of the groups described above for the various variables is contemplated herein. Throughout the specification, groups and substituents thereof are chosen by one skilled in the field to provide stable moieties and compounds.

Representative Kisspeptin Receptor (KISS1R) Ligands

In one aspect, the Kisspeptin ligand described herein has the structure of Formula (II), or a pharmaceutically acceptable salt thereof. In some embodiments, described herein is a compound of Formula (II), or a pharmaceutically acceptable salt thereof:

Formula (II)

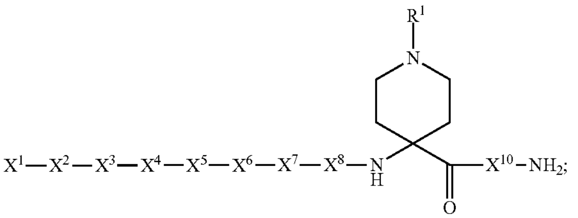

wherein:

$R^1$ is H,

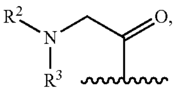, 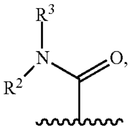, 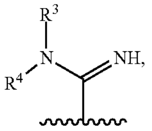 or

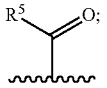

$R^2$ is $C_1$-$C_8$ alkyl, substituted or unsubstituted heteroalkyl, —$(CHR^6)_n$-heterocycloalkyl, —$(CHR^6)_n$-aryl, —$(CHR^6)_n$-heteroaryl, —C(═O)—$(CHR^6)_n$-aryl, or —C(═O)NH—$(CHR^6)_n$-aryl; wherein $C_1$-$C_6$ alkyl is optionally substituted with $R^7$, and wherein the heterocycloalkyl, aryl, or heteroaryl are each independently optionally substituted with $R^7$, $R^8$, $R^9$, $R^{10}$, and $R^{11}$;

$R^3$ is H or $C_1$-$C_4$ alkyl;

$R^4$ is H, $C_1$-$C_4$ alkyl, or $R^2$;

$R^5$ is substituted or unsubstituted alkyl, substituted or unsubstituted heteroalkyl, or —$(CHR^6)_n$-aryl; wherein aryl is optionally substituted with $R^7$, $R^8$, $R^9$, $R^{10}$, and $R^{11}$;

each $R^6$ is independently H, F, —$CH_3$, —$NH_2$, or —OH;

$R^7$, $R^8$, $R^9$, $R^{10}$, and $R^{11}$ are each independently selected from H, F, Cl, Br, I, —OH, —O—$C_1$-$C_4$ alkyl, —$NH_2$, —$NHC_1$-$C_4$ alkyl, —N($C_1$-$C_4$ alkyl)$_2$, —CN, —$CO_2H$, —$CO_2C_1$-$C_4$ alkyl, —$C_1$-$C_6$ alkyl, —$C_1$-$C_6$ fluroroalkyl or —$C_3$-$C_6$ cycloalkyl;

n is 0, 1, 2, 3, 4, 5, or 6;

$X^1$ is absent, tyrosine (Tyr), glycine (Gly), sarcosine (Sar), alanine (Ala), aspartic acid (Asp), lysine (Lys), phenylalanine (Phe), 3-(3-pyridyl)alanine (3-Pal) threonine (Thr), methionine (Met), 4-iodophenylalanine (Phe(4-I)), N6-(4-(p-tolyl)butanoyl)-lysine, N6-(4-(4-iodophenyl)butanoyl)-lysine, or γ-glutamic acid (γ-Glu));

$X^2$ is absent, asparagine (Asn), glutamine (Gln), aspartic acid (Asp), glutamic acid (Glu), serine (Ser), histidine (His), alanine (Ala), sarcosine (Sar), tyrosine (Tyr), proline (Pro), hydroxyproline (Hyp), azetidine-2-carboxylic acid (Aze), 2,3,4,5-tetrahydroisoquinoline-3-carboxylic acid (Tic), phenylalanine (Phe), 3-(2-pyridyl)alanine (2-Pal), 3-(3-pyridyl)alanine (3-Pal), or 3-(4-pyridyl)alanine (4-Pal);

$X^3$ is absent, tryptophan (Trp), serine (Ser), leucine (Leu), isoleucine (Ile), phenylalanine (Phe), 4-iodophenylalanine (Phe(4-I)), 3-(2-pyridyl)alanine (2-Pal), 3-(3-pyridyl)alanine (3-Pal), 3-(4-pyridyl)alanine 4-Pal), 2-amino-3-(naphthalen-2-yl)propanoic acid (H-2-NAL-OH), lysine (Lys), asparagine (Asn), glutamine (Gln), aspartic acid (Asp), glutamic acid (Glu), arginine (Arg), methyl arginine (Arg(Me)), norarginine (AGBA), methyl norarginine (AGBA(Me)), homoarginine (HArg), methyl homoarginine (HArg(Me)), citrulline (Cit), methyl citrulline (Cit(Me)), canavanine, methyl-canavanine, glycine (Gly), alanine (Ala), sarcosine (Sar), tyrosine (Tyr), cyclohexylalanine(Cha), 3-(1-naphthyl)alanine (α-Nal), 3-(2-naphthyl)alanine (β-Nal), or threonine (Thr), proline (Pro), hydroxyproline (Hyp), or tetrahydroisoquinoline-3-carboxylic acid (Tic); O-phospho-serine (SOP), 2-amino-4-(2H-tetrazol-5-yl)butanoic acid, β-glutamic acid, 8-aminoquinoline-3-carboxylic acid, biphenylalanine (Bip), 4-benzoylphenylalanine (Bpa), or 3-(9-anthryl)-alanine (H-Ala (9-Anth)-OH or AAFP);

$X^4$ is absent, asparagine (Asn), glutamine (Gln), aspartic acid (Asp), glutamic acid (Glu), tryptophan (Tip), glycine (Gly), tyrosine (Tyr), alanine (Ala), or sarcosine (Sar);

$X^5$ is absent, serine (Ser), threonine (Thr), lysine (Lys), asparagine (Asn), glutamine (Gln), aspartic acid (Asp), glutamic acid (Glu), glycine (Gly), alanine (Ala), sarcosine (Sar), or arginine (Arg);

$X^6$ is absent, phenylalanine (Phe), alpha-methylphenylalanine (α-Me-Phe), N-methylphenylalanine (N-Me-Phe), 2-fluorophenylalanine (2-F-Phe), 3-fluorophenylalanine (3-F-Phe), 4-fluorophenylalanine (4-F-Phe), 4-iodophenylalanine (Phe(4-L)), 2-amino-2-indancarboxylic acid (Aic), biphenylalanine (Bip), (β-(2-thienyl)-Ala), tryptophan (Trp), 2-aminotetralin-2-carboxylic acid (Atc); 3-(2-thienyl)-alanine, 3-(4-pyridyl) alanine (4-Pal), cyclohexylalanine (Cha), or tyrosine (Tyr);

$X^7$ is absent, glycine (Gly), aza-glycine (aza-Gly), alanine (Ala), N-methylglycine (Sar), or 1-aminocyclopropane-1-carboxylic acid (ACC);

$X^8$ is leucine (Leu), norvaline (Nva), valine (Val), isoleucine (Ile), homoalanine (HAla), tryptophan (Tip), phenylalanine (Phe), or phenylglycine (Phg);

or —$X^7$—$X^8$— is

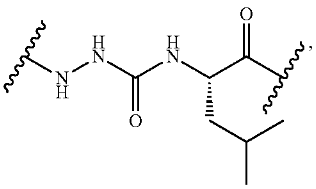,

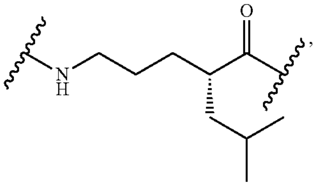,

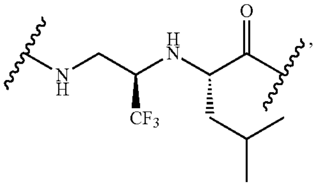,

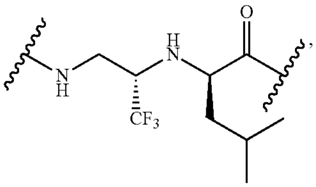,

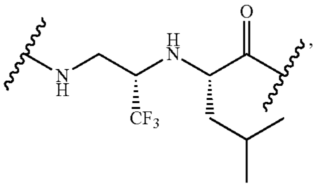,

-continued
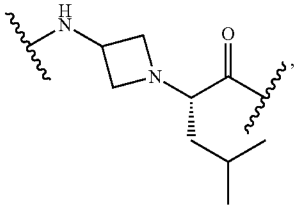
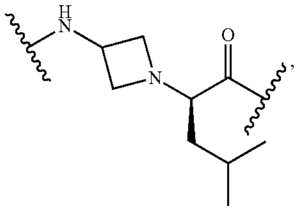
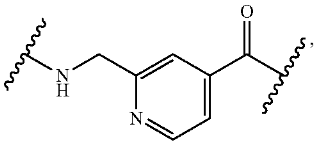
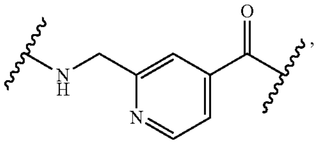
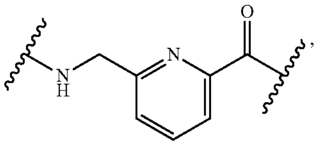
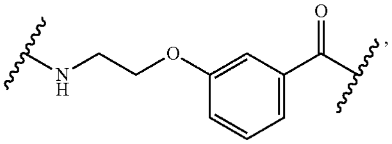
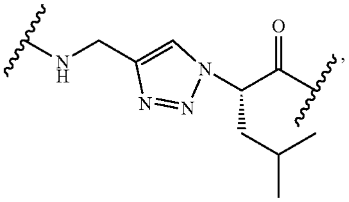
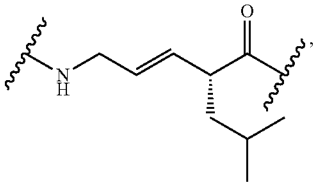
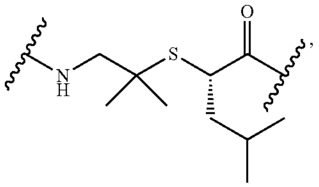
-continued
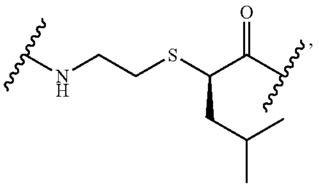
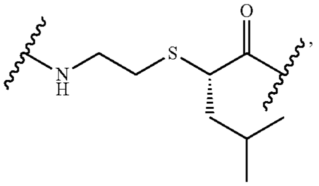
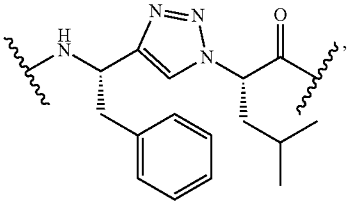
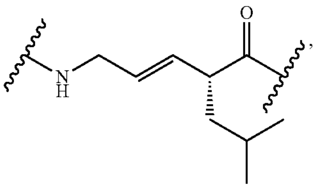
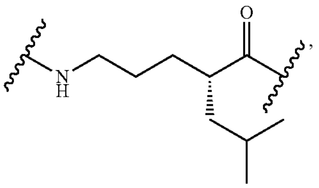
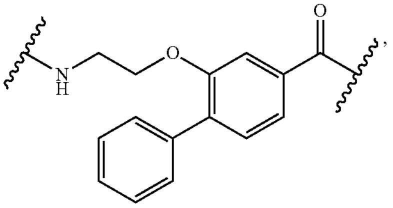
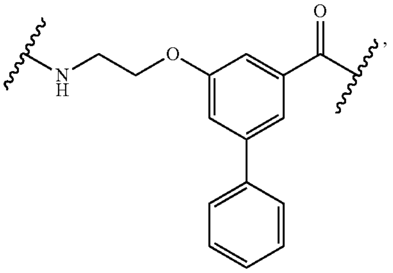
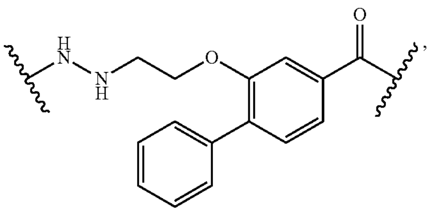

-continued

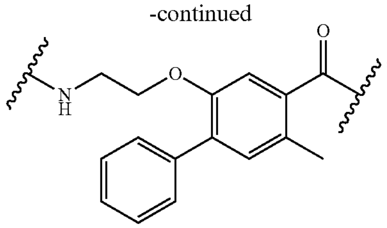

,

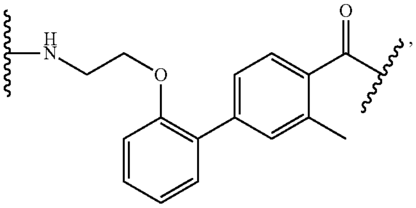

, or

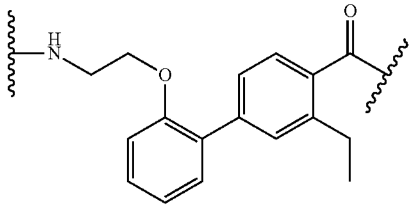

;

or $—X^6—X^7—X^8—$ is

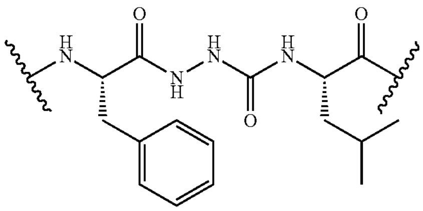

,

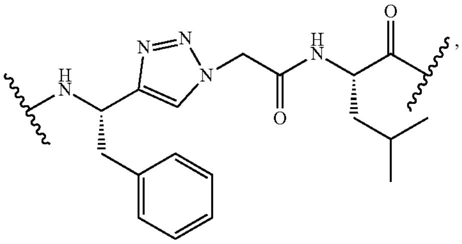

, or

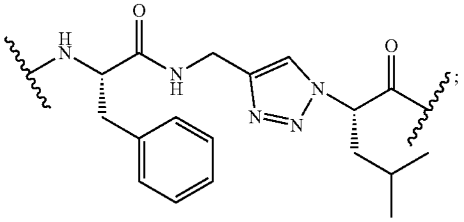

;

$X^{10}$ is tryptophan (Trp), 1-methyltryptophan (1MT), tyrosine (Tyr), phenylalanine (Phe), 4-cyano phenylalanine (Phe(4-CN)), 3-(4-pyridyl )alanine (4-Pal), leucine (Leu), phenylglycine (Phg), cyclohexylalanine (Cha), 3-(1-naphthyl)alanine (α-Nal), 3-(2-naphthyl)-alanine (β-NaI), histidine (His), or 3-nitro-tyrosine (Tyr(3-$NO_2$));

wherein the N-terminal amino acid or the compound of Formula (II) is optionally substituted with $—C(=O)—C_1-C_{20}$ alkyl, $—C(=O)—(CH_2CH_2O)_y—CH_2CH_2—R^{15}$, $—C_1-C_{20}$ alkyl, N-hexadecanoyl-Glu, $—C_4-C_{20}$ polyethylene glycol, a saccharide, $—R^{16}$, $—C(=O)—(CH_2CH_2O)_x—CH_3$, $—C(=O)—(CH_2CH_2O)_x—H$, $—C(=O)—CH_2CH_2CH(COOH)—R^{15}$, $—C(=O)—(CH_2)_2R^{19}$, or $—C(=O)CH_2NHCH_2R^{19}$;

$R^{15}$ is selected from $—OR^{16}$, $—N(R^{16})_2$, $—C(=O)OR^{16}$, or $—C(=O)N(R^{16})_2$;

each $R^{16}$ is independently H, $—C_1-C_6$ alkyl, $—C(=O)—(CH_2)_vR^{19}$, $—C(=O)CH_2NHCH_2R^{19}$, or a saccharide or derivative thereof;

$R^{19}$ is 4-iodophenylene, 4-methylphenylene, or 3-fluoro-4-methylphenylene;

y is 0, 1, 2, 3, 4, 5, 6, 7, 8, 9, or 10;

x is an integer from 1 and 25; and v is 1, 2, 3, or 4;

wherein any free —NH— of a peptide bond is optionally independently substituted with $—CH_3$ or $—CH_2CH_3$; and wherein any alpha position of an amino acid is optionally independently substituted with $—CH_3$ or $—CH_2CH_3$.

In some embodiments, $R^1$ is

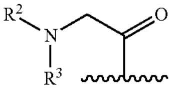

or

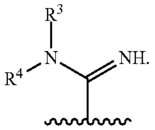

.

In some embodiments, $R^2$ is H and $R^3$ is H or $C_1-C_4$ alkyl. In some embodiments, $R^2$ is H and $R^3$ is H. In some embodiments, $R^2$ is H and $R^3$ is $CH_3$.

In some embodiments, $R^3$ is H and $R^4$ is H or $C_1-C_4$ alkyl.

In some embodiments, $R^2$ is $—(CHR^6)_n$-aryl.

In some embodiments, n is 1.

In some embodiments, $R^6$ is H.

In some embodiments, $R^1$ is

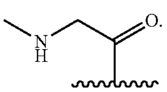 [SMILES: *C(=O)CNC]

.

In some embodiments, $R^1$ is

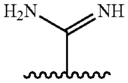

or

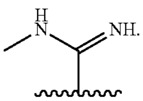 [SMILES: *C(=N)NC]

.

In some embodiments, $R^1$ is

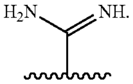

.

In some embodiments, $R^1$ is

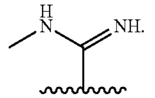 [SMILES: *C(=N)NC]

In some embodiments $R^1$ is

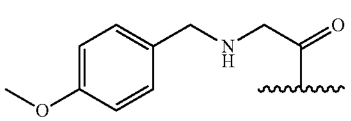

or

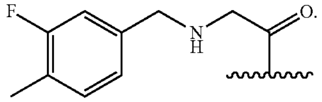

In some embodiments, $R^1$ is

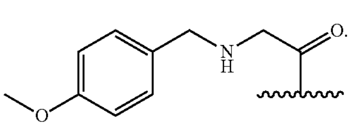 [SMILES: *C(=O)CNCc1ccc(OC)cc1]

In some embodiments, $R^1$ is

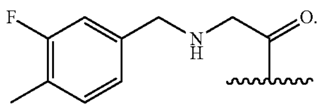 [SMILES: *C(=O)CNCc1ccc(C)c(F)c1]

In some embodiments, $R^1$ is

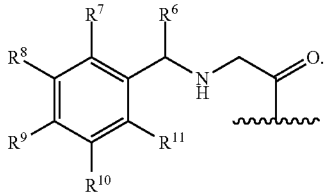

In some embodiments, $R^7$, $R^8$, $R^9$, $R^{10}$, and $R^{11}$ are each independently selected from H, F, Cl, Br, I, —OH, —O—$C_1$-$C_4$ alkyl, —$NH_2$, or —$C_1$-$C_6$ alkyl. In some embodiments, $R^7$, $R^8$, $R^9$, $R^{10}$, and $R^{11}$ are each independently selected from H, F, Cl, Br, I, —OH, —$OCH_3$, —$NH_2$, or —$CH_3$. In some embodiments, $R^7$ is H. In some embodiments, $R^7$ is F. In some embodiments, $R^7$ is Cl. In some embodiments, $R^7$ is Br. In some embodiments, $R^7$ is I. In some embodiments, R is —OH. In some embodiments, $R^7$ is —$OCH_3$. In some embodiments, $R^7$ is —$NH_2$. In some embodiments, $R^7$ is —$CH_3$. In some embodiments, $R^8$ is H. In some embodiments, $R^8$ is F. In some embodiments, $R^8$ is Cl. In some embodiments, $R^8$ is Br. In some embodiments, $R^8$ is I. In some embodiments, $R^8$ is —OH. In some embodiments, $R^8$ is —$OCH_3$. In some embodiments, $R^8$ is —$NH_2$. In some embodiments, $R^8$ is —$CH_3$. In some embodiments, $R^9$ is H. In some embodiments, $R^9$ is F. In some embodiments, $R^9$ is Cl. In some embodiments, $R^9$ is Br. In some embodiments, $R^9$ is I. In some embodiments, $R^9$ is —OH. In some embodiments, $R^9$ is —$OCH_3$. In some embodiments, $R^9$ is —$NH_2$. In some embodiments, $R^9$ is —$CH_3$. In some embodiments, $R^{10}$ is H. In some embodiments, $R^{10}$ is F. In some embodiments, $R^{10}$ is Cl. In some embodiments, $R^{10}$ is Br. In some embodiments, $R^{10}$ is I. In some embodiments, $R^{10}$ is —OH. In some embodiments, $R^{10}$ is —$OCH_3$. In some embodiments, $R^{10}$ is —$NH_2$. In some embodiments, $R^{10}$ is —$CH_3$. In some embodiments, $R^{11}$ is H. In some embodiments, $R^{11}$ is F. In some embodiments, $R^{11}$ is Cl. In some embodiments, $R^{11}$ is Br. In some embodiments, $R^{11}$ is I. In some embodiments, $R^{11}$ is —OH. In some embodiments, $R^{11}$ is —$OCH_3$. In some embodiments, $R^{11}$ is —$NH_2$. In some embodiments, $R^{11}$ is —$CH_3$. In some embodiments, $R^8$ is F and $R^9$ is $CH_3$.

In some embodiments, $X^1$ is tyrosine (Tyr

In some embodiments, $X^2$ is absent.

In some embodiments, $X^3$ is 3-(2-naphthyl)alanine (β-Nal). In some embodiments, $X^3$ is tryptophan (Trp).

In some embodiments, $X^4$ is asparagine (Asn).

In some embodiments, $X^5$ is threonine (Thr).

In some embodiments, $X^6$ is phenylalanine (Phe). In some embodiments, $X^6$ is cyclohexylalanine (Cha).

In some embodiments, $X^7$ is azaglycine (aza-gly).

In some embodiments, $X^8$ is leucine (Leu).

In some embodiments, $X^{10}$ is tryptophan (Trp), 1-methyltryptophan (1MT), tyrosine (Tyr), phenylalanine (Phe), 4-cyanophenylalanine (Phe(4-CN)), 3-(4-pyridyl)alanine (4-Pal), or leucine (Leu). In some embodiments, $X^{10}$ is tryptophan (Trp), tyrosine (Tyr), or phenylalanine (Phe). In some embodiments, $X^{11}$ is tryptophan (Trp). In some embodiments, $X^{10}$ is 1-methyltryptophan (1MT). In some embodiments, $X^{10}$ is tyrosine (Tyr). In some embodiments, $X^{10}$ is phenylalanine (Phe). In some embodiments, $X^{10}$ is 4-cyano phenylalanine (Phe(4-CN)). In some embodiments, $X^{10}$ is 3-(4-pyridyl)alanine (4-Pal). In some embodiments, $X^{10}$ is leucine (Leu).

In some embodiments, $X^1$ is absent, tyrosine (Tyr), or 3-(3-pyridyl)alanine (3-Pal));

$X^2$ is absent, asparagine (Asn), glutamine (Gln), serine (Ser), D-histidine (His), or phenylalanine (Phe);

$X^3$ is absent, tryptophan (Trp), isoleucine (Ile), 3-(4-pyridyl)alanine (4-Pal), lysine (Lys), aspartic acid (Asp), glutamic acid (Glu), glycine (Gly), alanine (Ala), cyclohexylalanine (Cha), (Hyp), biphenylalanine (Bip); 4-benzoylphenylalanine (Bpa), or 3-(9-anthryl)-alanine (AAP);

$X^4$ is absent, asparagine (Asn), or glutamine (Gln); and $X^5$ is absent, serine (Ser), threonine (Thr), glycine (Gly), or alanine (Ala).

In some embodiments, XV is D-tyrosine (D-Tyr);

$X^2$ is absent;

$X^3$ is D-tryptophan (D-Trp), biphenylalanine (Bip); 4-benzoylphenylalanine (Bpa), or 3-(9-anthryl)-alanine (AAP);

$X^4$ is asparagine (Asn); and $X^5$ is serine (Ser) or threonine (Thr).

In some embodiments, $X^6$ is phenylalanine (Phe), 3-fluorophenylalanine (3-F-Phe), biphenylalanine (Bip), or cyclohexylalanine (Cha); $X^7$ is glycine (Gly) or aza-glycine (aza-Gly); and $X^8$ is leucine (Leu) or norvaline (Nva). In some embodiments, $X^6$ is phenylalanine (Phe) or cyclohexylalanine (Cha); $X^7$ is aza-glycine (aza-Gly); and $X^8$ is leucine (Leu).

In some embodiments, $X^8$ is Leu, Nya, Ile, Hala, or Phe; and $X^{10}$ is Trp, 1MT, Tyr, 4-Pal, Phe(4-CN), or Phe.

In some embodiments,

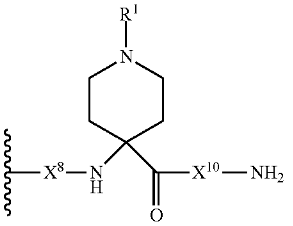 is

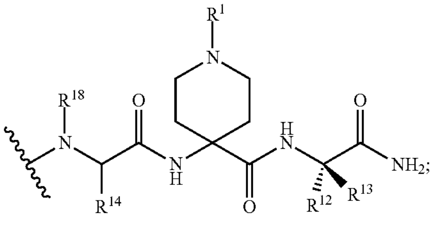

wherein, $R^{18}$ is H or —$CH_3$;

$R^{12}$ is

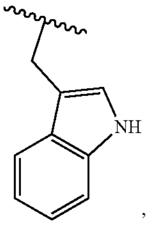,
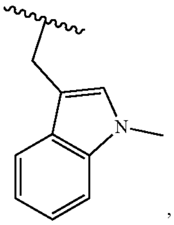,
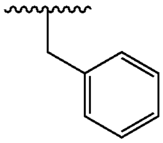,
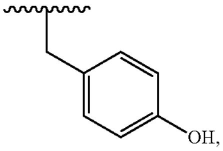
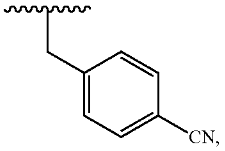
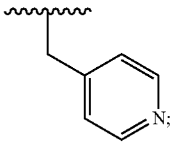

$R^{13}$ is H or —$CH_3$; and $R^{14}$ is

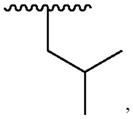,
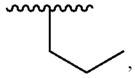,
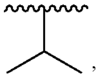,
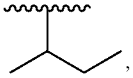, or
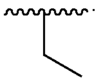

In some embodiments, the N-terminal amino acid or the compound of Formula (II) is optionally substituted with —C(═O)—$C_1$-$C_{20}$ alkyl, —C(═O)—$(CH_2CH_2O)_y$—$CH_2CH_2$—$R^{15}$, —$C_1$-$C_{20}$ alkyl, N-hexadecanoyl-Glu, —$C_4$-$C_{20}$ polyethylene glycol, a saccharide, —$R^{16}$, —C(═O)—$(CH_2CH_2O)_x$—$CH_3$, —C(═O)—$(CH_2CH_2O)_x$—H, —C(═O)—$CH_2CH_2CH$(COOH)—$R^{15}$, —C(═O)—$(CH_2)_2R^{19}$, or —C(═O)$CH_2NHCH_2R^{19}$;

$R^{15}$ is selected from —$OR^{16}$, —$N(R^{16})_2$, —C(═O)$OR^{16}$, or —C(═O)$N(R^{16})_2$;

each $R^{16}$ is independently H, —$C_1$-$C_6$ alkyl, —C(═O)—$(CH_2)_vR^{19}$, —C(═O)$CH_2NHCH_2R^{19}$, or a saccharide or derivative thereof;

$R^{19}$ is 4-iodophenylene, 4-methylphenylene, or 3-fluoro-4-methylphenylene;

y is 0, 1, 2, 3, 4, 5, 6, 7, 8, 9, or 10;

x is an integer from 1 and 25; and v is 1, 2, 3, or 4.

In some embodiments, the N-terminal amino acid or the compound of Formula (II) is optionally substituted with —C(═O)—$C_1$-$C_{12}$ alkyl.

In some embodiments, the N-terminal amino acid or the compound of Formula (II) is optionally substituted with —C(═O)—$(CH_2CH_2O)_y$—$CH_2CH_2$—$R^{15}$. In some embodiments, y is 2. In some embodiments, $R^{15}$ is —$N(R^{16})_2$ and both $R^{16}$ are H. In some embodiments, $R^{15}$ is —$N(R^{16})_2$, one $R^{16}$ is H and the other $R^{16}$ is —C(═O)—$(CH_2)_vR^{19}$. In some embodiments, the N-terminal amino acid or the compound of Formula (II) is optionally substituted with —$R^{16}$. In some embodiments, $R^{16}$ is —C(═O)—$(CH_2)_vR^{19}$. In some embodiments, v is 2 or 3. In some embodiments, $R^{19}$ is 4-iodophenylene or 4-methylphenylene In some embodiments, the N-terminal amino acid or the compound of Formula (II) is optionally substituted with

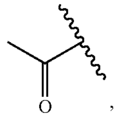,
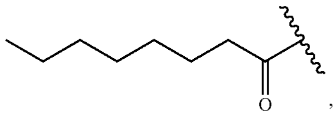,
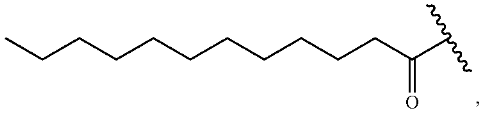,
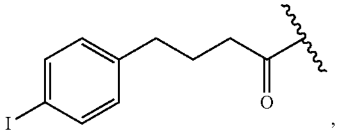,
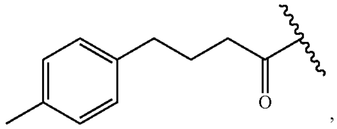,
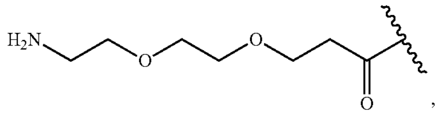, or
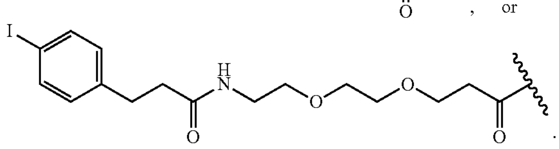.

In some embodiments, the N-terminal amino acid or the compound of Formula (II) is optionally substituted with

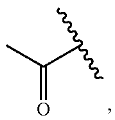,
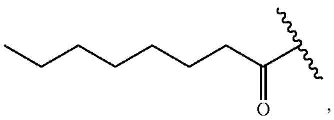, or

-continued

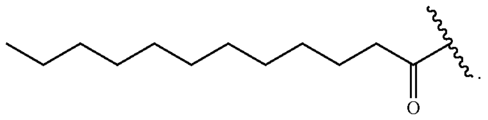

In some embodiments, the N-terminal amino acid or the compound of Formula (II) is optionally substituted with

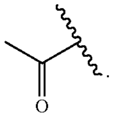 [SMILES: *C(C)=O]

In some embodiments, the N-terminal amino acid or the compound of Formula (II) is optionally substituted with

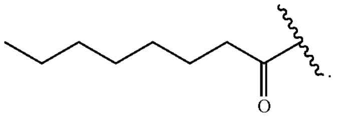 [SMILES: *C(=O)CCCCCCC]

In some embodiments, the N-terminal amino acid or the compound of Formula (II) is optionally substituted with

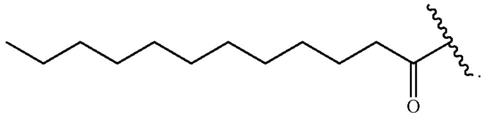 [SMILES: *C(=O)CCCCCCCCCCC]

In some embodiments, the N-terminal amino acid or the compound of Formula (II) is optionally substituted with

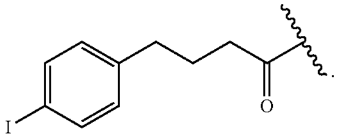 [SMILES: *C(=O)CCCc1ccc(I)cc1]

In some embodiments, the N-terminal amino acid or the compound of Formula (II) is optionally substituted with

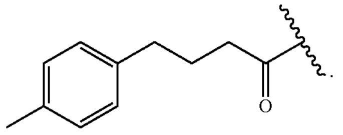 [SMILES: *C(=O)CCCc1ccc(C)cc1]

In some embodiments, the N-terminal amino acid or the compound of Formula (II) is optionally substituted with

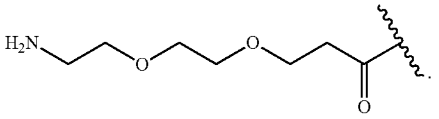 [SMILES: *C(=O)CCOCCOCCN]

In some embodiments, the N-terminal amino acid or the compound of Formula (II) is optionally substituted with

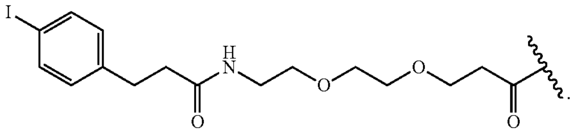 [SMILES: *C(=O)CCOCCOCCNC(=O)CCc1ccc(I)cc1]

In some embodiments, the compound of Formula (II) has the following structure, or a pharmaceutically acceptable salt thereof:

(SEQ ID NO: 802)

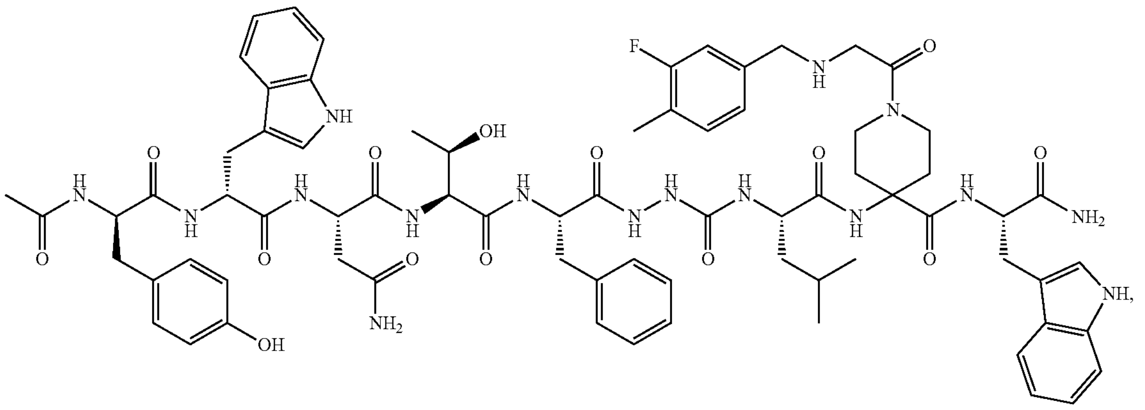

-continued
(SEQ ID NO: 803)
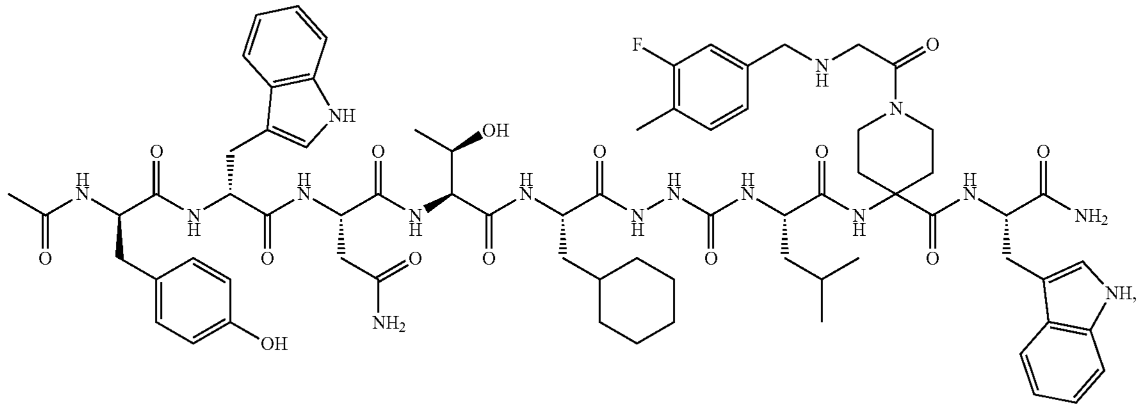
(SEQ ID NO: 804)
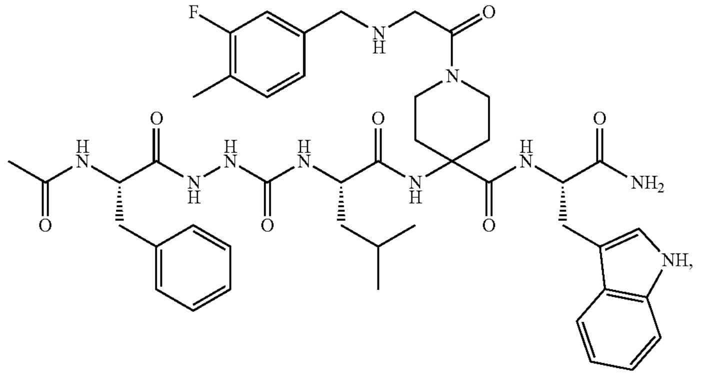
(SEQ ID NO: 805)
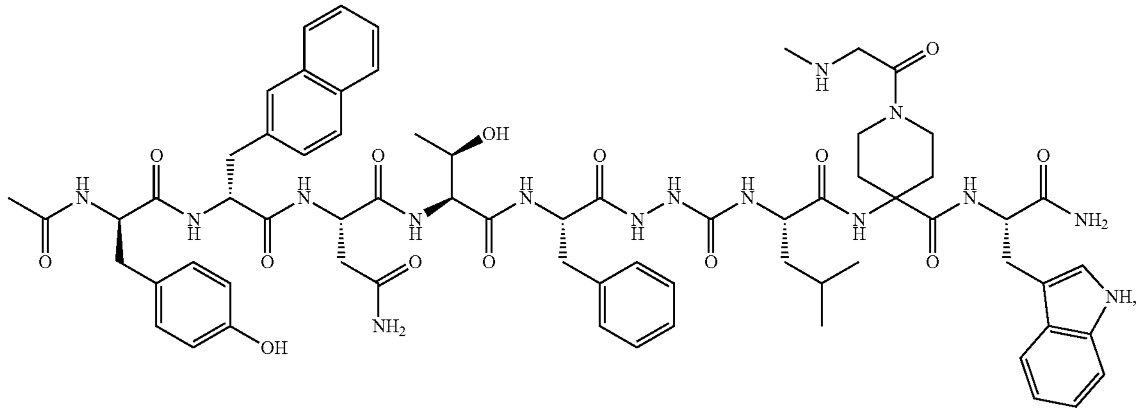
(SEQ ID NO: 806)
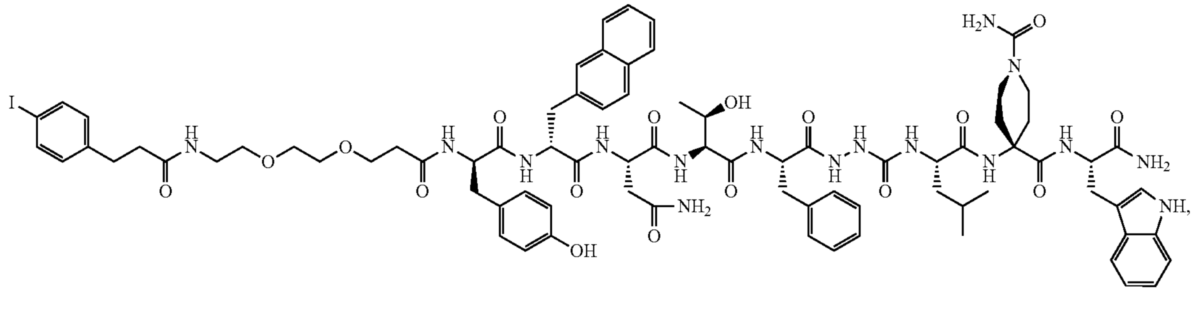

-continued
(SEQ ID NO: 807)
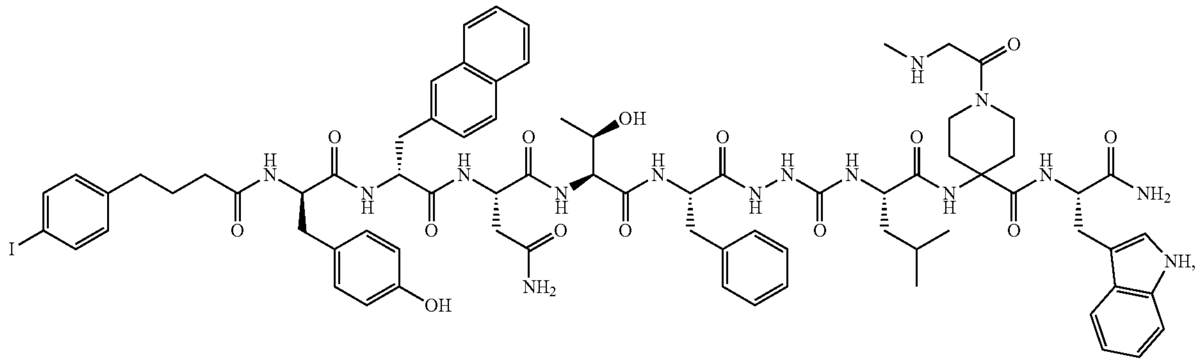
(SEQ ID NO: 808)
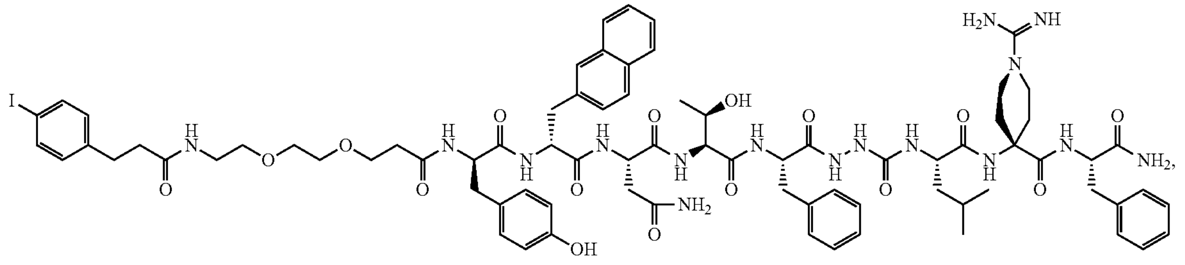
(SEQ ID NO: 809)
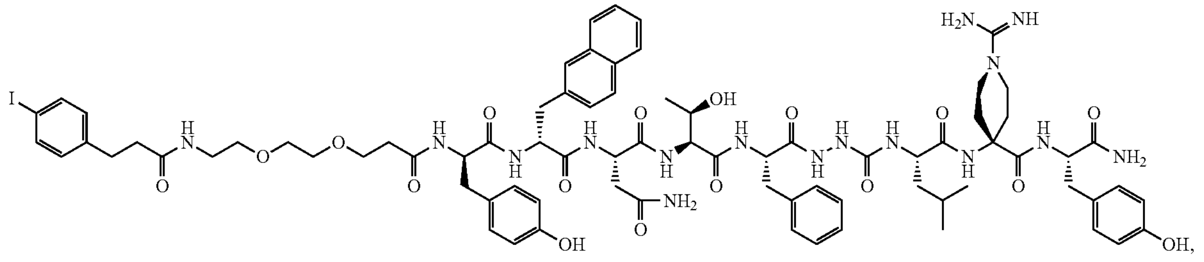
(SEQ ID NO: 810)
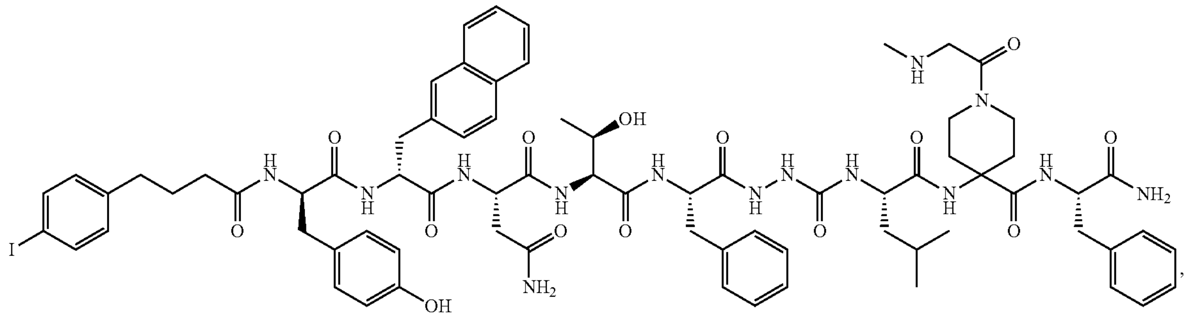
(SEQ ID NO: 811)
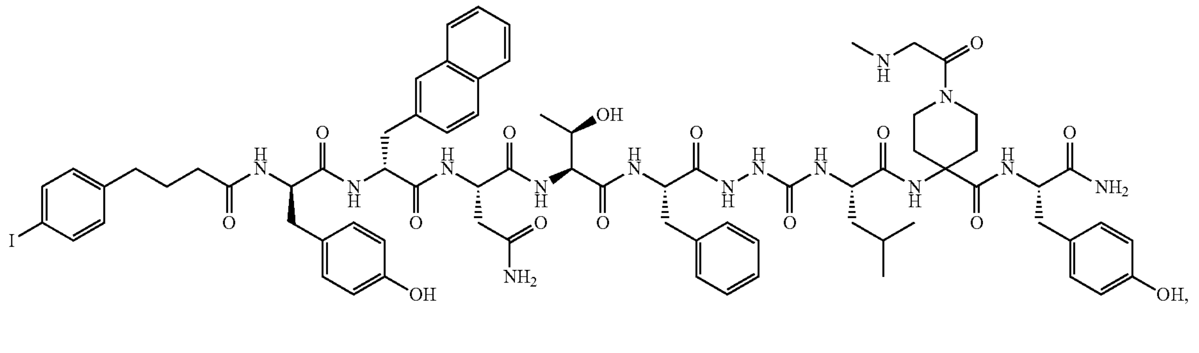

-continued
(SEQ ID NO: 812)
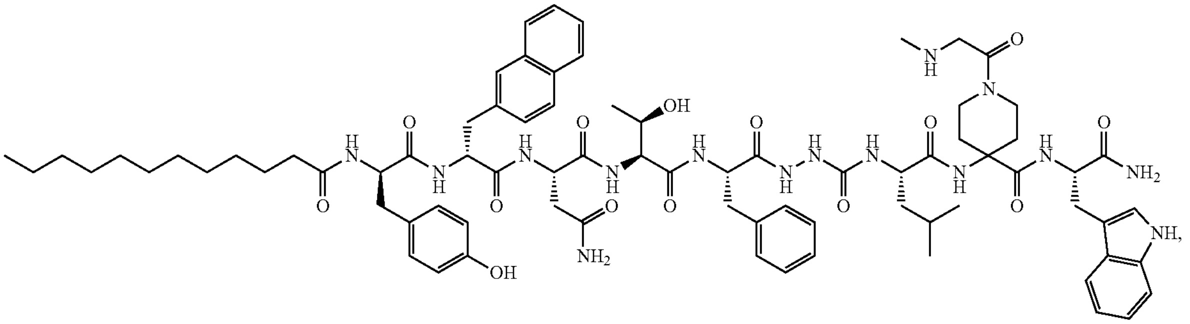
(SEQ ID NO: 813)
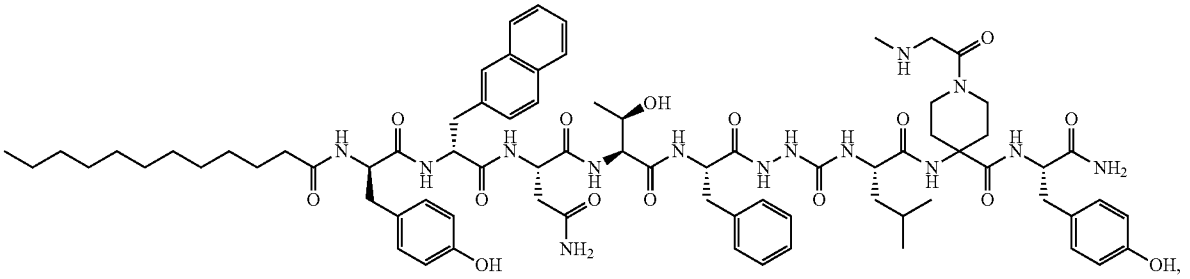
(SEQ ID NO: 814)
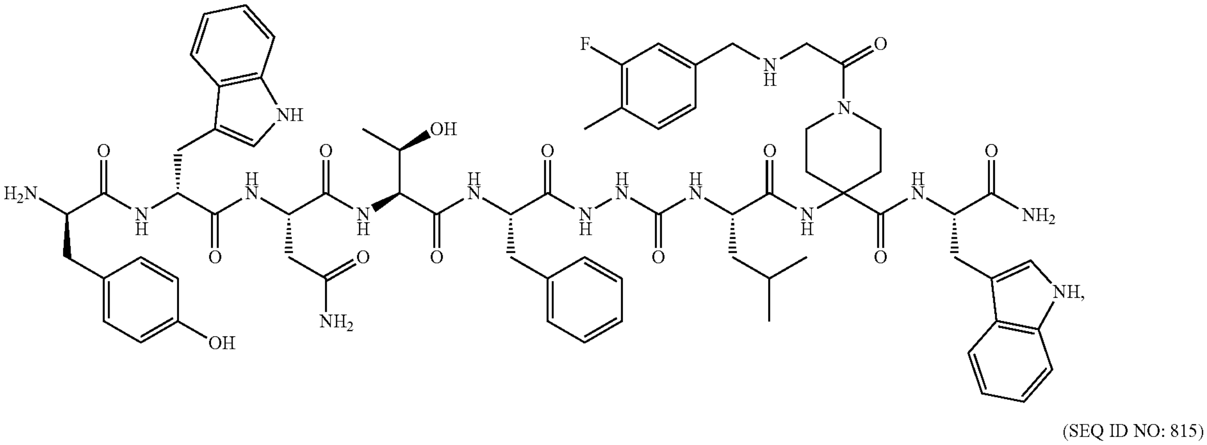
(SEQ ID NO: 815)
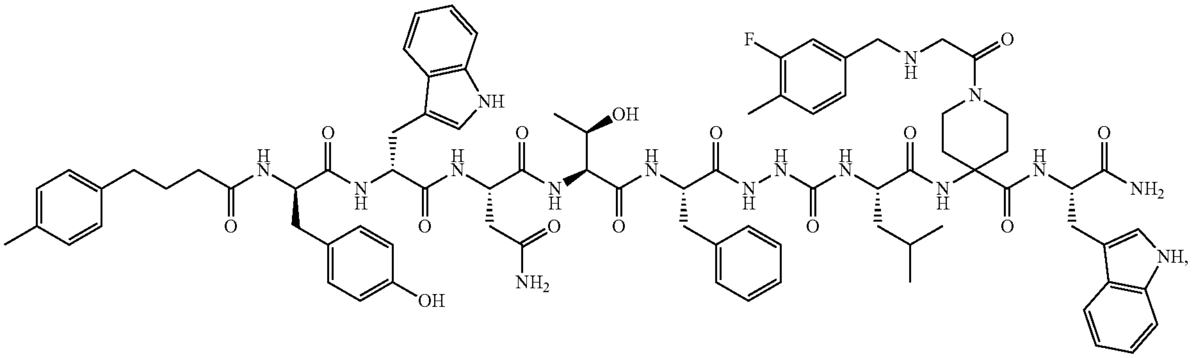

-continued
(SEQ ID NO: 816)
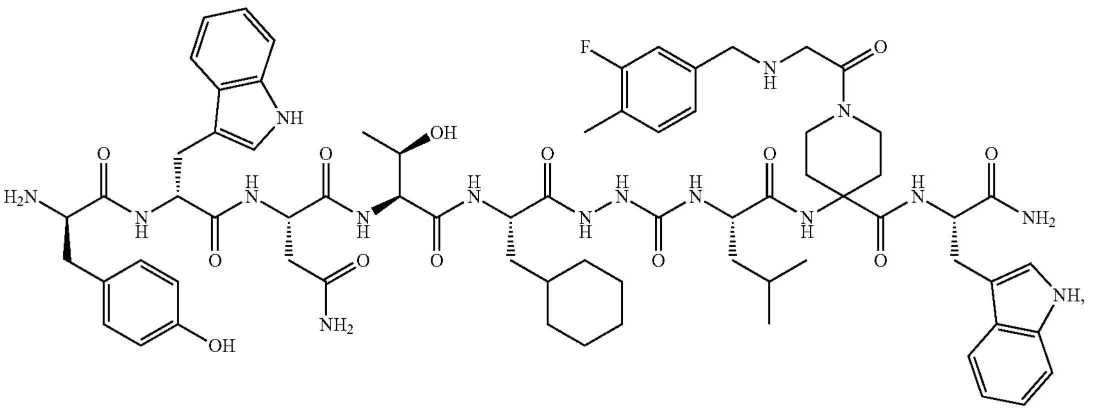
(SEQ ID NO: 817)
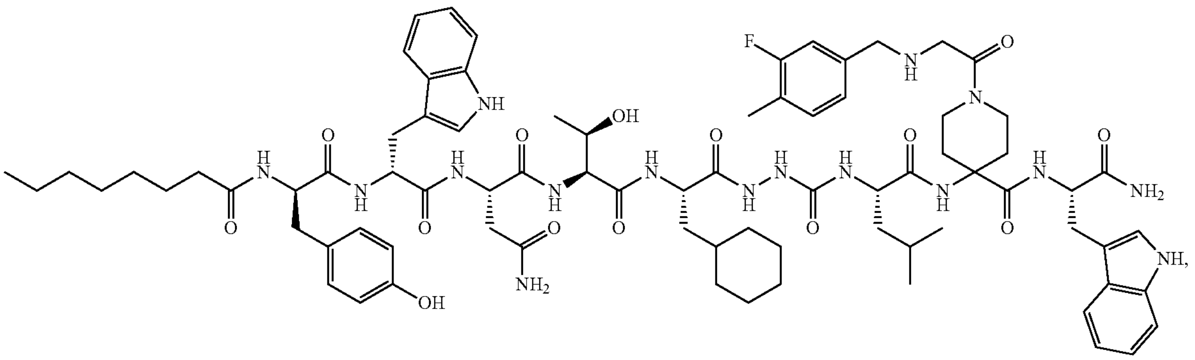
(SEQ ID NO: 818)
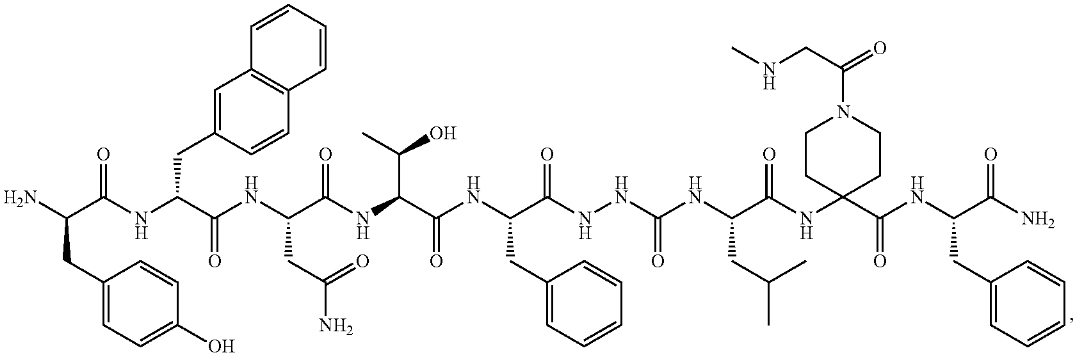
(SEQ ID NO: 819)
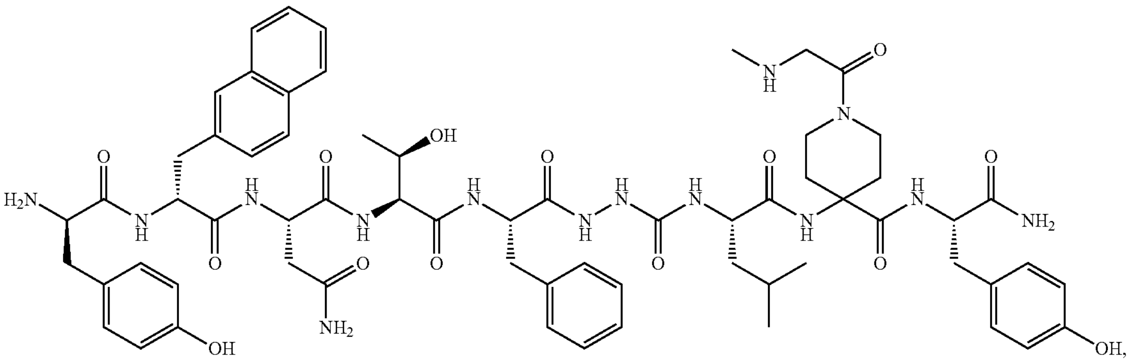

-continued
(SEQ ID NO: 820)
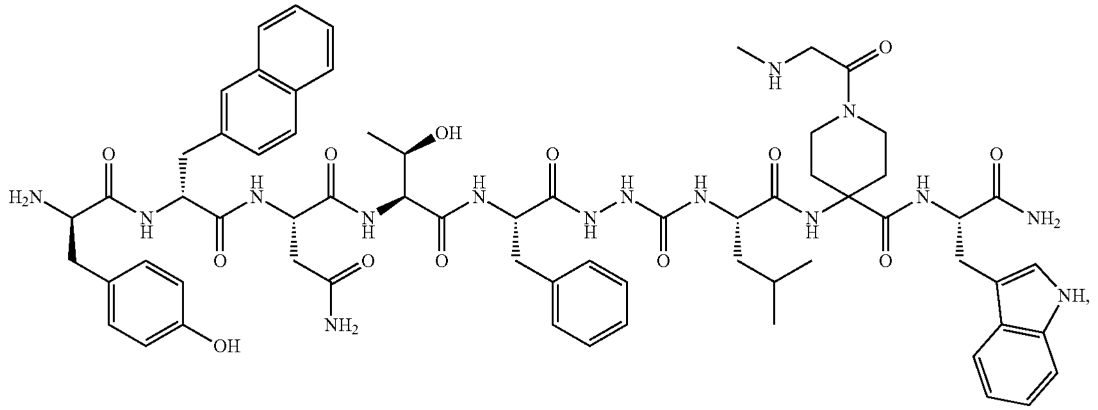
(SEQ ID NO: 821)
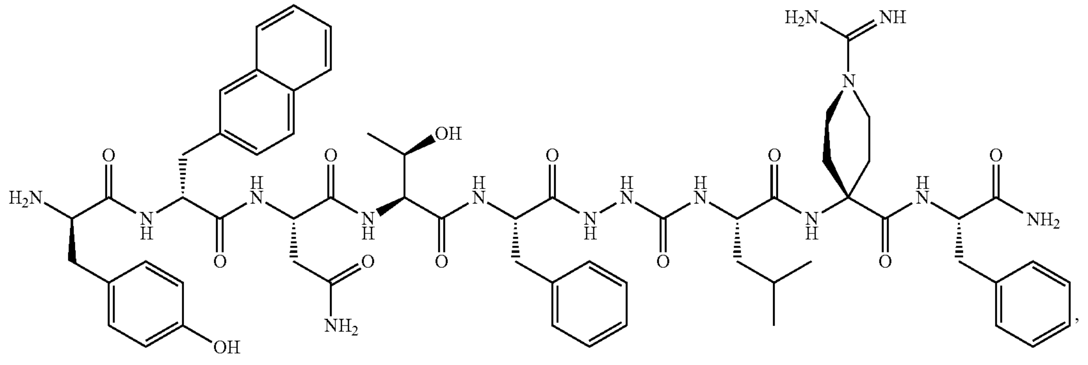
(SEQ ID NO: 822)
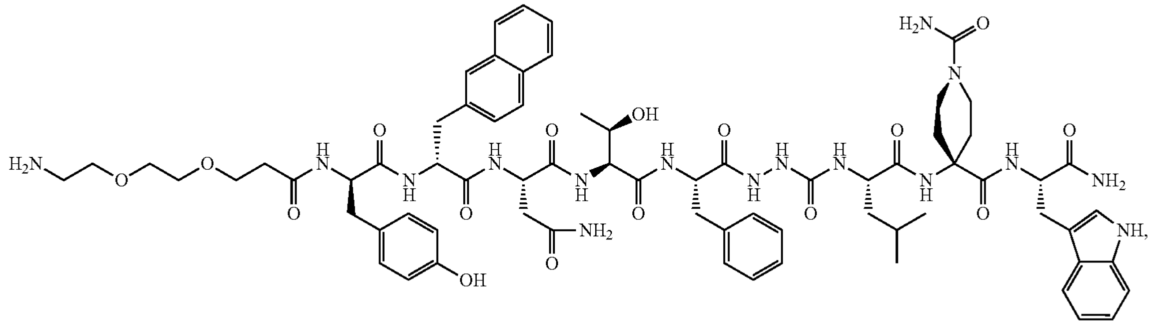
or
(SEQ ID NO: 823)
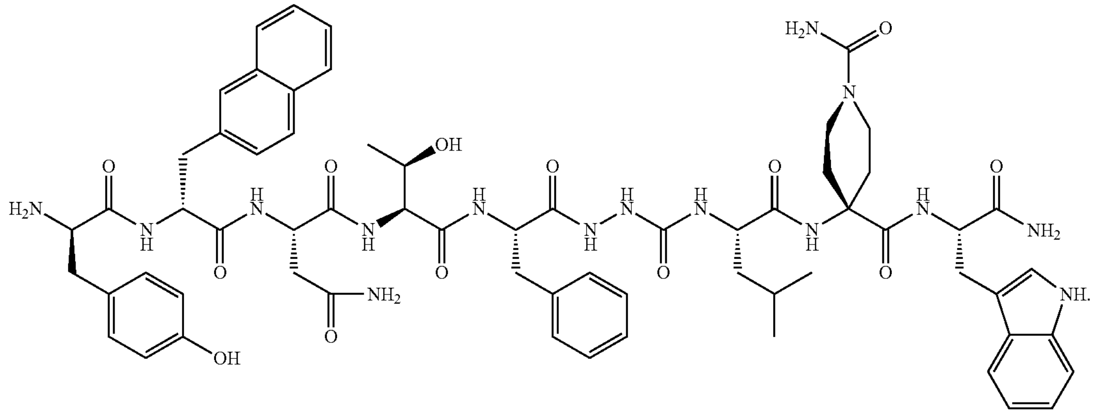

In some embodiments, the compound of Formula (II) is compound 390, or a pharmaceutically acceptable salt thereof; compound 391, or a pharmaceutically acceptable salt thereof; compound 392, or a pharmaceutically acceptable salt thereof; compound 393, or a pharmaceutically acceptable salt thereof; compound 394, or a pharmaceutically acceptable salt thereof; compound 395, or a pharmaceutically acceptable salt thereof; compound 396, or a pharmaceutically acceptable salt thereof; compound 397, or a pharmaceutically acceptable salt thereof; compound 398, or a pharmaceutically acceptable salt thereof; compound 399, or a pharmaceutically acceptable salt thereof; compound 400, or a pharmaceutically acceptable salt thereof; compound 398, or a pharmaceutically acceptable salt thereof; compound 401, or a pharmaceutically acceptable salt thereof; compound 402, or a pharmaceutically acceptable salt thereof; compound 403, or a pharmaceutically acceptable salt thereof; compound 404, or a pharmaceutically acceptable salt thereof; compound 405, or a pharmaceutically acceptable salt thereof; compound 406, or a pharmaceutically acceptable salt thereof; compound 407, or a pharmaceutically acceptable salt thereof; compound 408, or a pharmaceutically acceptable salt thereof; compound 409, or a pharmaceutically acceptable salt thereof; compound 410, or a pharmaceutically acceptable salt thereof; or compound 411, or a pharmaceutically acceptable salt thereof.

In some embodiments, the compound of Formula (II) is compound 402, or a pharmaceutically acceptable salt thereof. In some embodiments, the compound of Formula (II) is compound 403, or a pharmaceutically acceptable salt thereof. In some embodiments, the compound of Formula (II) is compound 404, or a pharmaceutically acceptable salt thereof. In some embodiments, the compound of Formula (II) is compound 405, or a pharmaceutically acceptable salt thereof. In some embodiments, the compound of Formula (II) is compound 406, or a pharmaceutically acceptable salt thereof. In some embodiments, the compound of Formula (II) is compound 407, or a pharmaceutically acceptable salt thereof. In some embodiments, the compound of Formula (II) is compound 408, or a pharmaceutically acceptable salt thereof. In some embodiments, the compound of Formula (II) is compound 409, or a pharmaceutically acceptable salt thereof. In some embodiments, the compound of Formula (II) is compound 410, or a pharmaceutically acceptable salt thereof. In some embodiments, the compound of Formula (II) is compound 411, or a pharmaceutically acceptable salt thereof.

Further Forms of Compounds

In one aspect, compounds described herein are in the form of pharmaceutically acceptable salts. In addition, the compounds described herein can exist in unsolvated as well as solvated forms with pharmaceutically acceptable solvents such as water, ethanol, and the like. The solvated forms of the compounds presented herein are also considered to be disclosed herein.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. See for example Handbook of Pharmaceutical Salts: Properties, Selection and Use; International Union of Pure and Applied Chemistry, Wiley-VCH 2002; S. M. Berge, L. D. Bighley, D. C. Monkhouse, J. Pharm. Sci. 1977, 66, 1-19; and P. H. Stahl and C. G. Wermuth, editors, *Handbook of Pharmaceutical Salts: Properties, Selection and Use*, Weinheim/Zürich:Wiley-VCH/VHCA, 2002; which are incorporated herein by reference. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible, and this capability can be manipulated as one aspect of delayed and sustained release behaviors. Also, because the salt-forming molecule can be in equilibrium with a neutral form, passage through biological membranes can be adjusted.

In some embodiments, pharmaceutically acceptable salts are obtained by reacting a compound of Formula (I) with an acid. In some embodiments, the acid is an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to: I-hydroxy-2-naphthoic acid; 2,2-dichloroacetic acid; 2-hydroxyethanesulfonic acid; 2-oxoglutaric acid; 4-acetamidobenzoic acid; 4-aminosalicyclic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (−L); malonic acid; mandelic acid (DL); methanesulfonic acid; naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid.

In some embodiments, a compound of Formula (I), is prepared as a chloride salt, sulfate salt, bromide salt, mesylate salt, maleate salt, citrate salt or phosphate salt.

In some embodiments, pharmaceutically acceptable salts are obtained by reacting a compound of Formula (I), with a base. In some cases, compounds described herein coordinate with an organic base, such as, but not limited to, ethanolamine, diethanolamine, triethanolamine, tromethamine, meglumine, N-methylglucamine, dicyclohexylamine, or tris (hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, magnesium salt, meglumine salt, N-methylglucamine salt or ammonium salt.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

In some embodiments, any one of the hydrogen atoms on the organic radicals (e.g., alkyl groups, aromatic rings) of compounds described herein are replaced with deuterium.

In some embodiments, the compounds of Formula (I), possess one or more stereocenters and each stereocenter exists independently in either the R or S configuration. The compounds presented herein include all diastereomeric, individual enantiomers, atropisomers, and epimeric forms as well as the appropriate mixtures thereof. The compounds and methods provided herein include all cis, trans, syn, anti, entgegen (E), and zusammen (Z) isomers as well as the appropriate mixtures thereof.

Individual stereoisomers are obtained, if desired, by methods such as, stereoselective synthesis and/or the separation of stereoisomers by chiral chromatographic columns or the separation of diastereomers by either non-chiral or chiral chromatographic columns or crystallization and recrystallization in a proper solvent or a mixture of solvents. In certain embodiments, compounds described herein, are prepared as their individual stereoisomers by reacting a racemic mixture of the compound with an optically active resolving agent to form a pair of diastereoisomeric compounds/salts, separating the diastereomers and recovering the optically pure individual enantiomers. In some embodiments, resolution of individual enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the formation of diastereomeric salts and separation by recrystallization, or chromatography, or any combination thereof. See for example Jean Jacques, Andre Collet, Samuel H. Wilen, "Enantiomers, Racemates and Resolutions", John Wiley And Sons, Inc., 1981, which is incorporated herein by reference. In some embodiments, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they are easier to administer than the parent drug. They are, for instance, bioavailable by oral administration whereas the parent is not. Further or alternatively, the prodrug also has improved solubility in pharmaceutical compositions over the parent drug. In some embodiments, the design of a prodrug increases the effective water solubility. See for example Design of Prodrugs, Bundgaard, A. Ed., Elsevier, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference.

A "metabolite" of a compound disclosed herein is a derivative of that compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulfhydryl groups. Metabolites of the compounds disclosed herein are optionally identified either by administration of compounds to a host and analysis of tissue samples from the host, or by incubation of compounds with hepatic cells in vitro and analysis of the resulting compounds.

Synthesis of Compounds

Compounds described herein are synthesized using standard synthetic techniques or using methods known in the art in combination with methods described herein.

Unless otherwise indicated, conventional methods of mass spectroscopy, NMR, and HPLC are employed.

Compounds are prepared using standard organic chemistry techniques such as those described in, for example, March's Advanced Organic Chemistry, $6^{th}$ Edition, John Wiley and Sons, Inc. Compounds may also be prepared using solid-phase peptide synthesis techniques such as those described in, for example, Solid Phase Peptide Synthesis, $2^{nd}$ Edition, The Pierce Chemical Co., Rockford, Ill. (1984). Alternative reaction conditions for the synthetic transformations described herein may be employed such as variation of solvent, reaction temperature, reaction time, as well as different chemical reagents and other reaction conditions.

Peptide Synthesis

A peptide of the present disclosure may be prepared through known methods, including solid-phase peptide synthesis (SPPS). (See, for example, Palomo, Jose M. (2014); "Solid-phase peptide synthesis: An overview focused on the preparation of biologically relevant peptides" *RSC Adv.* 4 (62): 32658-32672; Krchňák, V; Holladay, Mark W. (2002); "Solid Phase Heterocyclic Chemistry" *Chemical Reviews.* 102 (1): 61-92; Merrifield, B. (1986-04-18); "Solid phase synthesis" *Science.* 232 (4748): 341-347; Guillier, F; et al., (2000). "Linkers and Cleavage Strategies in Solid-Phase Organic Synthesis and Combinatorial Chemistry." *Chemical Reviews.* 100 (6): 2091-2158; Amblard M, et al., "Methods and protocols of modern solid phase Peptide synthesis." *Mol Biotechnol.* 2006 July; 33(3):239-54).

In some embodiments, the solid-phase peptide synthesis is Fmoc solid-phase peptide synthesis. See, for example, Behrendt, R., et al., (2016) Advances in Fmoc solid-phase peptide synthesis. *J. Pept. Sci.,* 22: 4-27.

SPPS is a common technique for peptide synthesis. Usually, peptides are synthesized from the carbonyl group side (C-terminus) to amino group side (N-terminus) of the amino acid chain in the SPPS method, although peptides are biologically synthesized in the opposite direction in cells. In peptide synthesis, an amino-protected amino acid is bound to a solid phase material or resin (most commonly, low cross-linked polystyrene beads), forming a covalent bond between the carbonyl group and the resin, most often an amido or an ester bond. Then the amino group is deprotected and reacted with the carbonyl group of the next N-protected amino acid. The solid phase now bears a dipeptide. This cycle is repeated to form the desired peptide chain. After all reactions are complete, the synthesized peptide is cleaved from the bead.

The protecting groups for the amino groups mostly used in the peptide synthesis are 9-fluorenylmethyloxycarbonyl group (Fmoc) and t-butyloxycarbonyl (Boc). A number of amino acids bear functional groups in the side chain which must be protected specifically from reacting with the incoming N-protected amino acids. In contrast to Boc and Fmoc groups, these have to be stable over the course of peptide synthesis although they are also removed during the final deprotection of peptides.

An example solid-phase peptide synthesis may be carried out as follows. An esterification reaction occurs between the carboxyl group of a first amino acid (with a protected α-amino group) and the hydroxyl group of a hydroxyl-containing resin. The α-amino protecting group of the first amino acid is removed and a second amino acid is coupled with the first through its carboxyl group (all other functional groups are protected) to form a peptide bond between the first and second amino acids. The α-amino protecting group of the second amino acid is removed and a third amino acid is coupled with the second through its carboxyl group (all other functional groups are protected) to form a peptide bond between the second and third amino acids. These steps are repeated until the peptide of desired length is synthesized. Any remaining functional groups on the peptide chain are then deprotected. The peptide chain can then be cleaved from the resin.

Examples of resins used for SPPS include Merrifield resin, Rink amide resin, Wang resin, Sieber amide resin, MBHA resin, CTC resin, HMBA resin, DHP resin, and PAL resin. In some embodiments, the resin for SPPS is Rink amide resin. In some embodiments, the resin for SPPS is Wang resin. In some embodiments, the resin for SPPS is 2-chlorotrityl resin. In some embodiments, the resin for SPPS is Sieber amide resin.

Examples of α-amino protecting groups include benzyloxycarbonyl (Cbz), tertbutoxycarbonyl (Boc), fluorenylmethoxycarbonyl (Fmoc), an d allyloxycarbonyl (Alloc) groups. In some embodiments, the α-amino protecting group is Fmoc. In some embodiments, the α-amino protecting group can be deprotected using acid, such as hydrofluoric acid or trifluoroacetic acid. In some embodiments, the α-amino protecting group can be deprotected using base, such as piperidine.

Examples of condensation agents used to activate a carboxyl group for an amidification or esterification reaction include HATU, DCC, EDC, BOP, and HBTU. In some embodiments, the condensation agent is HATU.

Examples of acids use to cleave a peptide chain from the resin include TFA.

In some embodiments, compounds are prepared as described in the Examples.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins, 1999), herein incorporated by reference for such disclosure.

In some embodiments, the compounds described herein are administered either alone or in combination with pharmaceutically acceptable carriers, excipients or diluents, in a pharmaceutical composition. Administration of the compounds and compositions described herein can be affected by any method that enables delivery of the compounds to the site of action. These methods include, though are not limited to, delivery via parenteral routes (including injection or infusion, and subcutaneous).

In some embodiments, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and contain optional agents as excipients such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use.

Methods of Treatment

In some embodiments, the methods comprise administering to a subject a therapeutically effective amount of a compound of Formula (I), or a pharmaceutically acceptable salt or solvate thereof. In some embodiments, the compound of Formula (I) or pharmaceutically acceptable salt or solvate thereof is administered in a pharmaceutical composition. In some embodiments, the subject has cancer. In some embodiments, the cancer is a solid tumor. In some embodiments, the subject has a noncancerous tumor. In some embodiments, the subject has an adenoma.

In some embodiments, the treatment is sufficient to reduce or inhibit the growth of the subject's tumor, reduce the number or size of metastatic lesions, reduce tumor load, reduce primary tumor load, reduce invasiveness, prolong survival time, or maintain or improve the quality of life, or combinations thereof.

In some embodiments, provided herein are methods for killing a tumor cell comprising contacting the tumor cell with a compound of Formula (I), or a pharmaceutically acceptable salt or solvate thereof. In some embodiments, the compound of Formula (I), or pharmaceutically acceptable salt or solvate thereof releases a number of alpha particles by natural radioactive decay. In some embodiments, the released alpha particles are sufficient to kill the tumor cell. In some embodiments, the released alpha particles are sufficient to stop cell growth. In some embodiments, the tumor cell is a malignant tumor cell. In some embodiments, the tumor cell is a benign tumor cell. In some embodiments, the method comprises killing a tumor cell with a beta-particle emitting radionuclide. In some embodiments, the method comprises killing a tumor cell with an alpha-particle emitting radionuclide. In some embodiments, the method comprises killing a tumor cell with a gamma-particle emitting radionuclide.

In one aspect, provided herein are methods and compositions for treating cancers. In some embodiments, the cancer is ovarian cancer. In some embodiments, the cancer is breast cancer. In some embodiments, the cancer is endometrial cancer. In some embodiments, the cancer is prostate cancer. In some embodiments, the cancer is renal cell carcinoma. In some embodiments, the cancer is lung cancer.

In one aspect, provided herein are methods and compositions for treating an adenoma.

In one aspect, provided herein are methods and compositions for treating a carcinoma.

In one aspect, provided herein is a method for identifying tissues or organs in a mammal that overexpress KISS1R comprising: (i) administering to the mammal a KISS1R radiopharmaceutical described herein, or a pharmaceutically acceptable salt thereof; and (ii) performing single-photon emission computerized tomography (SPECT) or positron emission tomography (PET) analysis on the mammal. In some embodiments, the method comprises: (i) administering to the mammal a KISS1R radiopharmaceutical described herein, or a pharmaceutically acceptable salt thereof; and (ii) performing positron emission tomography (PET) analysis on the mammal.

In some embodiments, the mammal was diagnosed with cancer. In some embodiments, the mammal was diagnosed with ovarian cancer. In sone embodiments, the mammal was diagnosed with breast cancer. In some embodiments, the mammal was diagnosed with endometrial cancer. In some embodiments, the mammal was diagnosed with prostate cancer. In some embodiments, the tissues in the mammal that overexpress KISS1R are tumors.

In some embodiments, a KISS1R radiopharmaceutical described herein, or a pharmaceutically acceptable salt thereof are used in a method for in vivo imaging of a subject. In some embodiments, the method includes the steps of:

(i) administering to the mammal KISS1R radiopharmaceutical described herein, or a pharmaceutically acceptable salt thereof;
(ii) waiting a sufficient amount of time to allow the KISS1R radiopharmaceutical, to accumulate at a tissue or cell site to be imaged; and
(iii) imaging the cells or tissues with a non-invasive imaging technique.

In some embodiments, the non-invasive imaging technique is single-photon emission computerized tomography (SPECT) or positron emission tomography (PET) analysis. In some embodiments, the non-invasive imaging technique is single-photon emission computerized tomography (SPECT). In some embodiments, the non-invasive imaging technique is selected from positron emission tomography imaging, or positron emission tomography with computed tomography imaging, and positron emission tomography with magnetic resonance imaging.

In some embodiments, the methods comprise administering to a subject a therapeutically effective amount of a compound of Formula (II), or a pharmaceutically acceptable salt or solvate thereof. In some embodiments, the compound of Formula (II), or pharmaceutically acceptable salt or solvate thereof is administered in a pharmaceutical composition. In some embodiments, the pharmaceutical composition is formulated for administration to a mammal by oral administration. In some embodiments, the subject has cancer. In some embodiments, the cancer is breast cancer. In some embodiments, the cancer is prostate cancer. In some embodiments, the subject has an endocrine condition. In some embodiments, the subject has is polycystic ovary syndrome (PCOS). In some embodiments, the subject suffers from infertility.

In one aspect, provided herein are methods and compositions for treating an endocrine condition. In some embodiments, the endocrine condition is polycystic ovary syndrome (PCOS). In some embodiments, the endocrine condition is infertility.

In one aspect, provided herein are methods and compositions for treating cancer. In some embodiments, the cancer is breast cancer. In some embodiments, the cancer is prostate cancer.

In one aspect, provided herein are methods and compositions for treating infertility.

Methods of Dosing and Treatment Regimens

In one embodiment, the KISS1R radiopharmaceutical described herein, or a pharmaceutically acceptable salt thereof, are used in the preparation of medicaments for the treatment of tumors in a mammal. Methods for treating any of the diseases or conditions described herein in a mammal in need of such treatment, involves administration of pharmaceutical compositions that include at least one compound of Formula (I), or a pharmaceutically acceptable salt thereof, in therapeutically effective amounts to said mammal.

In certain embodiments, the compositions containing the compound(s) described herein are administered for diagnostic and/or therapeutic treatments.

The amount of a given agent that corresponds to such an amount varies depending upon factors such as the particular conjugate, specific cancer or tumor to be treated (and its severity), the identity (e.g., weight, sex) of the subject or host in need of treatment, but nevertheless is determined according to the particular circumstances surrounding the case, including, e.g., the specific conjugate being administered, the route of administration, the condition being treated, and the subject or host being treated. Optimal doses are generally determined using experimental models and/or clinical trials. The optimal dose depends upon the body mass, weight, or blood volume of the subject.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans.

The amount of a compound of Formula (I), or pharmaceutically acceptable salts thereof, that are administered are sufficient to deliver a therapeutically effective dose to the particular subject. In some embodiments, dosages of a compound of Formula (I), are between about 0.1 pg and about 50 mg per kilogram of body weight, 1 μg and about 50 mg per kilogram of body weight, or between about 0.1 and about 10 mg/kg of body weight. Therapeutically effective dosages can also be determined at the discretion of a physician. By way of example only, the dose of a compound of Formula (I), or a pharmaceutically acceptable salt thereof described herein for methods of treating a disease as described herein is about 0.001 mg/kg to about 1 mg/kg body weight of the subject per dose. In some embodiments, the dose is about 0.001 mg to about 1000 mg per dose for the subject being treated. In some embodiments, a compound of Formula (I), or a pharmaceutically acceptable salt thereof described herein is administered to a subject at a dosage of from about 0.01 mg to about 500 mg, from about 0.01 mg to about 100 mg, or from about 0.01 mg to about 50 mg.

In some embodiments, a compound of Formula (I), or a pharmaceutically acceptable salt thereof described herein is administered to a subject at a dosage of about 0.01 picomole to about 1 mole, about 0.1 picomole to about 0.1 mole, about 1 nanomole to about 0.1 mole, or about 0.01 micromole to about 0.1 millimole.

In some embodiments, a compound of Formula (I), or a pharmaceutically acceptable salt thereof described herein is administered to a subject at a dosage of about 0.01 Gbq to about 1000 Gbq, about 0.5 Gbq to about 100 Gbq, or about 1 Gbq to about 50 Gbq.

In some embodiments, the dose is administered once a day, 1 to 3 times a week, 1 to 4 times a month, or 1 to 12 times a year.

In any of the aforementioned aspects are further embodiments in which the effective amount of the KISS1R radiopharmaceutical described herein, or a pharmaceutically acceptable salt thereof, is: (a) systemically administered to the mammal; and/or (b) intravenously administered to the mammal; and/or (c) administered by injection to the mammal.

In certain instances, it is appropriate to administer at least one KISS1R radiopharmaceutical described herein, or a pharmaceutically acceptable salt thereof, in combination with one or more other therapeutic agents.

Certain Terminology

Unless otherwise stated, the following terms used in this application have the definitions given below. The use of the term "including" as well as other forms, such as "include," "includes," and "included," is not limiting. The section headings used herein are for organizational purposes only and are not to be construed as limiting the subject matter described.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As used herein, $C_1$-$C_x$ includes $C_1$-$C_2$, $C_1$-$C_3$ . . . $C_1$-$C_x$. By way of example only, a group designated as "$C_1$-$C_6$" indicates that there are one to six carbon atoms in the moiety, i.e., groups containing 1 carbon atom, 2 carbon atoms, 3 carbon atoms, 4 carbon atoms, 5 carbon atoms or 6 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

An "alkyl" group refers to an aliphatic hydrocarbon group. The alkyl group is branched or straight chain. In some embodiments, the "alkyl" group has 1 to 10 carbon atoms, i.e., a —$C_1$-$C_{10}$ alkyl. Whenever it appears herein, a numerical range such as "1 to 10" refers to each integer in the given range; e.g., "1 to 10 carbon atoms" means that the alkyl group consists of 1 carbon atom, 2 carbon atoms, 3 carbon atoms, etc., up to and including 10 carbon atoms, although the present definition also covers the occurrence of the term "alkyl" where no numerical range is designated. In some embodiments, an alkyl is a —$C_1$-$C_6$ alkyl. In one aspect the alkyl is methyl, ethyl, propyl, iso-propyl, n-butyl, iso-butyl, sec-butyl, or t-butyl. Typical alkyl groups include, but are in no way limited to, methyl, ethyl, propyl, isopropyl, butyl, isobutyl, sec-butyl, tertiary butyl, pentyl, neopentyl, or hexyl. In some embodiments, the alkyl group is an "alkenyl" or "alkynyl" group.

An "alkylene" group refers to a divalent alkyl radical. Any of the above-mentioned monovalent alkyl groups may be an alkylene by abstraction of a second hydrogen atom from the alkyl. In some embodiments, an alkylene is a —$C_1$-$C_6$alkylene. In other embodiments, an alkylene is a —$C_1$-$C_4$ alkylene. Typical alkylene groups include, but are not limited to: —$CH_2$—, —$CH_2CH_2$—, —$CH_2CH_2CH_2$—, —$CH_2CH_2CH_2CH_2$—, and the like. In some embodiments, an alkylene is —$CH_2$—. In some embodiments, an alkylene is —$CH_2CH_2$—.

An "alkoxy" group refers to an (alkyl)O— group, where alkyl is as defined herein.

The term "alkenyl" refers to a type of alkyl group in which at least one carbon-carbon double bond is present. In one embodiment, an alkenyl group has the formula: —C(R)=$CR_2$, wherein R refers to the remaining portions of the alkenyl group, which may be the same or different. In some embodiments, each R is independently H or an alkyl. In some embodiments, an alkenyl is selected from ethenyl (i.e., vinyl), propenyl (i.e., allyl), butenyl, pentenyl, pentadienyl, and the like. Non-limiting examples of an alkenyl group include —CH=$CH_2$, —C($CH_3$)=$CH_2$, —CH=$CHCH_3$, —C($CH_3$)=$CHCH_3$, and —$CH_2$CH=$CH_2$.

The term "alkynyl" refers to a type of alkyl group in which at least one carbon-carbon triple bond is present. In one embodiment, an alkenyl group has the formula —C≡C—R, wherein R refers to the remaining portion of the alkynyl group. In some embodiments, R is H or an alkyl. In some embodiments, an alkynyl is selected from ethynyl, propynyl, butynyl, pentynyl, hexynyl, and the like. Non-limiting examples of an alkynyl group include —C≡CH, —C≡$CCH_3$—C≡$CCH_2CH_3$, and —$CH_2$C≡CH.

The term "heteroalkyl" refers to an alkyl group in which one or more skeletal atoms of the alkyl are selected from an atom other than carbon, e.g., oxygen, nitrogen (e.g., —NH—, —N(alkyl)-), sulfur, or combinations thereof. In some embodiments, the "heteroalkyl" group has 2 to 10 atoms in the backbone, which include a combination of carbon atoms and heteroatoms (e.g. N, O, S), i.e., a 2 to 10-membered heteroalkyl. In some embodiments, the heteroalkyl is attached to the rest of the molecule at a carbon atom of the heteroalkyl. In one embodiment, a heteroalkyl is a 2 to 8 membered heteroalkyl.

A "heteroalkylene" group refers to a divalent alkyl radical derived from heteroalkyl, as exemplified, but not limited by, —$CH_2$—$CH_2$—O—$CH_2CH_2$— and —$CH_2$—O—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(=O)O— represents both —C(=O)O— and —OC(=O)—. Additionally, the formula —C(=O)NH— represents both —C(=O)NH— and —NHC(=O)—.

The term "carbocyclic" or "carbocycle" refers to a ring or ring system where the atoms forming the backbone of the ring are all carbon atoms. The term thus distinguishes carbocyclic from "heterocyclic" rings or "heterocycles" in which the ring backbone contains at least one atom which is different from carbon. In some embodiments, at least one of the two rings of a bicyclic carbocycle is aromatic. In some embodiments, both rings of a bicyclic carbocycle are aromatic. Carbocycles include aryls and cycloalkyls.

As used herein, the term "aryl" refers to an aromatic ring wherein each of the atoms forming the ring is a carbon atom. In one aspect, aryl is phenyl or a naphthyl. In some embodiments, an aryl is a phenyl. In some embodiments, an aryl is a phenyl, naphthyl, indanyl, indenyl, or tetrahydronaphthyl. In some embodiments, an aryl is a $C_6$-$C_{10}$ aryl. Depending on the structure, an aryl group is a monoradical or a diradical (i.e., an arylene group).

The term "cycloalkyl" refers to a monocyclic or polycyclic aliphatic, non-aromatic radical, wherein each of the atoms forming the ring (i.e., skeletal atoms) is a carbon atom. In some embodiments, cycloalkyls are spirocyclic or bridged cycloalkyls. In some embodiments, cycloalkyls are optionally fused with an aromatic ring, and the point of attachment is at a carbon that is not an aromatic ring carbon atom. Cycloalkyl groups include groups having from 3 to 12 ring atoms. In some embodiments, cycloalkyl groups are selected from cyclopropyl, cyclobutyl, cyclopentyl, cyclopentenyl, cyclohexyl, cyclohexenyl, cycloheptyl, cyclooctyl, spiro[2.2]pentyl, norbornyl and bicycle[0.1.1]pentyl. In some embodiments, a cycloalkyl is a $C_3$-$C_6$ cycloalkyl. In some embodiments, a cycloalkyl is a $C_3$-$C_4$ cycloalkyl. In some embodiments, a cycloalkyl is a $C_5$-$C_6$ cycloalkyl.

The term "halo" or, alternatively, "halogen" or "halide" means fluoro, chloro, bromo or iodo. In some embodiments, halo is fluoro, chloro, or bromo.

The term "fluoroalkyl" refers to an alkyl in which one or more hydrogen atoms are replaced by a fluorine atom. In one aspect, a fluoroalkyl is a $—C_1$-$C_6$ fluoroalkyl.

The term "heterocycle" or"heterocyclic" refers to heteroaromatic rings (also known as heteroaryls) and heterocycloalkyl rings containing one to four heteroatoms in the ring(s), where each heteroatom in the ring(s) is selected from O, S and N, wherein each heterocyclic group has from 3 to 12 atoms in its ring system, and with the proviso that any ring does not contain two adjacent O or S atoms. Non-aromatic heterocyclic groups (also known as heterocycloalkyls) include rings having 3 to 12 atoms in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo [4.1.0]heptanyl, 3-1-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1l-benzo[d] imidazol-2(31H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (=O) moieties, such as pyrrolidin-2-one. In some embodiments, at least one of the two rings of a bicyclic heterocycle is aromatic. In some embodiments, both rings of a bicyclic heterocycle are aromatic.

The terms "heteroaryl" or, alternatively, "heteroaromatic" refers to an aryl group that includes one or more ring heteroatoms selected from nitrogen, oxygen and sulfur. Illustrative examples of heteroaryl groups include monocyclic heteroaryls and bicyclic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, a heteroaryl contains 1 O atom. In some embodiments, a heteroaryl contains 1 S atom in the ring. In some embodiments, heteroaryl is a 5 to 10-membered heteroaryl. In some embodiments, a monocyclic heteroaryl is a 5 to 6 membered heteroaryl. In some embodiments, a monocyclic heteroaryl is a 5-membered heteroaryl. In some embodiments, a monocyclic heteroaryl is a 6-membered heteroaryl. In some embodiments, bicyclic heteroaryl is a 10-membered heteroaryl A "heterocycloalkyl" group refers to a cycloalkyl group that includes at least one heteroatom selected from nitrogen, oxygen and sulfur. In some embodiments, a heterocycloalkyl is fused with an aryl or heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. In one aspect, a heterocycloalkyl is a 3 to 12 membered heterocycloalkyl. In another aspect, a heterocycloalkyl is a 5 to 10-membered heterocycloalkyl. In some embodiments, a heterocycloalkyl is a 5-membered heterocycloalkyl. In some embodiments, a heterocycloalkyl is a 6-membered heterocycloalkyl. In some embodiments, a heterocycloalkyl is monocyclic or bicyclic. In some embodiments, a heterocycloalkyl is monocyclic and is a 3, 4, 5, 6, 7, or 8-membered ring. In some embodiments, a heterocycloalkyl is monocyclic and is a 3, 4, 5, or 6-membered ring. In some embodiments, a heterocycloalkyl is monocyclic and is a 3 or 4-membered ring. In some embodiments, a heterocycloalkyl contains 1-4 nitrogen (N)

atoms in the ring. In some embodiments, a heterocycloalkyl contains 0-2 N atoms, 0-2 oxygen (O) atoms and 0-1 sulfur (S) atoms in the ring.

The term "bond" or "single bond" refers to a chemical bond between two atoms, or two moieties when the atoms joined by the bond are considered to be part of a larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "optionally substituted" or "substituted" means that the referenced group is optionally substituted with one or more additional group(s) individually and independently selected from halogen, —CN, —$NH_2$, —NH(alkyl), —N(alkyl)$_2$, —OH, —$CO_2$H, —$CO_2$alkyl, —C(=O)$NH_2$, —C(=O)NH(alkyl), —C(=O)N(alkyl)$_2$, —S(=O)$_2NH_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from halogen, —CN, —$NH_2$, —NH($CH_3$), —N($CH_3$), —OH, —$CO_2$H, —$CO_2$($C_1$-$C_4$ alkyl), —C(=O)$NH_2$, —C(=O)NH($C_1$-$C_4$ alkyl), —C(=O)N($C_1$-$C_4$ alkyl)$_2$, —S(=O)$_2NH_2$, —S(=O)$_2$NH($C_1$-$C_4$alkyl), —S(=O)$_2$N($C_1$-$C_4$ alkyl)$_2$, —$C_1$-$C_4$, alkyl, $C_3$-$C_6$ cycloalkyl, —$C_1$-$C_4$ fluoroalkyl, —$C_1$-$C_4$heteroalkyl, —$C_1$-$C_4$ alkoxy, —$C_1$-$C_4$ fluoroalkoxy, —S$C_1$-$C_4$alkyl, —S(=O)$C_1$-$C_4$alkyl, and —S(=O)$_2C_1$-$C_4$ alkyl. In some embodiments, optional substituents are independently selected from halogen. —CN, —$NH_2$, —OH, —NH($CH_3$), —N($CH_3$)$_2$, —$CH_3$, —$CH_2CH_3$, —$CHF_2$, —$CF_3$, —$OCH_3$, —$OCHF_2$, and —$OCF_3$. In some embodiments, substituted groups are substituted with one or two of the preceding groups. In some embodiments, an optional substituent on an aliphatic carbon atom (acyclic or cyclic) includes oxo (=O).

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an agonist.

The terms "administer," "administering," "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion). Those of skill in the art are familiar with administration techniques that can be employed with the compounds and methods described herein.

The terms "co-administration" or the like, as used herein, are meant to encompass administration of the selected therapeutic agents to a single patient and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "article of manufacture" and "kit" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition.

Chemical structures depicted herein include all stereochemical forms of the structure, unless otherwise stated.

The term "peptide" as used herein refers to a compound comprising two or more amino acids in a serial array, linked through peptide bonds. The amino acids making up the polypeptide may be naturally derived, or may be synthetic.

The term "amino acid" as used herein refers to both natural and unnatural amino acids. The term "unnatural amino acid" as used herein refers to an amino acid that is not part of the 20 amino acids that occur naturally in protein.

As used herein, amino acid residue refers to an amino acid formed upon chemical digestion (hydrolysis) of a polypeptide at its peptide linkages. The amino acid residues described herein are, in certain embodiments, in the "L" isomeric form. Residues in the "D" isomeric form can be substituted for any "L" amino acid residue, as long as the desired functional property is retained by the polypeptide. "—$NH_2$" refers to the free amino group present at the amino terminus of a polypeptide. "—COH" refers to the free carboxy group present at the carboxyl terminus of a polypeptide. In keeping with standard polypeptide nomenclature described in *J. Biol. Chem*, 243:3552 59 (1969) and adopted at 37 C.F.R. §§ 1.821-1.822, abbreviations for amino acid residues are shown in the following Table B:

TABLE B

| Table of Correspondence | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| X | Xaa | Unknown or other |

It should be noted that all amino, acid residue sequences represented herein by formulae have a left to right orientation in the conventional direction of amino terminus to carboxyl terminus. In addition, the phrase "amino acid residue" is broadly defined to include the amino acids listed in the Table of Correspondence and modified and unusual amino acids, such as those referred to in 37 C.F.R. §§ 1.821-1.822, and incorporated herein by reference. Furthermore, it should be noted that a dash at the beginning or end of an amino acid residue sequence indicates a peptide bond to a further sequence of one or more amino acid residues or to an amino terminal group such as $—NH_2$ or to a carboxyl terminal group such as $—CO_2H$.

In a peptide, suitable conservative substitutions of amino acids are known to those of skill in this art and can be made generally without altering the biological activity of the resulting molecule, Those of skill in this art recognize that, in general, single amino acid substitutions in non-essential regions of a polypeptide do not substantially alter biological activity, (see, e.g., Watson et al. Molecular Biology of the Gene, 4th Edition, 1987, The Benjamin/Cummings Pub. co., p. 224). Such substitutions can be made in accordance with those set forth in Table C as follows:

TABLE C

| Original residue | Conservative substitution |
|---|---|
| Ala (A) | Gly; Ser |
| Arg (R) | Lys |
| Asn (N) | Gln; His |
| Asp (D) | Glu |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln |
| Met (M) | Leu; Tyr; Ile |
| Phe (F) | Met; Leu; Tyr |

TABLE C-continued

| Original residue | Conservative substitution |
|---|---|
| Ser (S) | Thr |
| Thr (T) | Ser |
| Trp (W) | Tyr |
| Tyr (Y) | Trp; Phe |
| Val (V) | Ile; Leu |

Representative amino acid side chains are shown in Table D.

TABLE D

Representative amino acid side chains

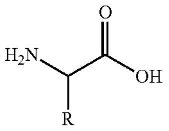

| R |
|---|
| —H<br>Glycine (Gly) |
| 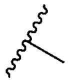<br>Alanine (Ala) |
| 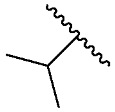 [SMILES: *C(C)C]<br>Valine (Val) |
| 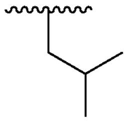<br>Leucine (Leu) |
| 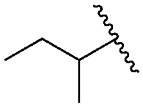 [SMILES: *C(C)CC]<br>Isoleucine (Ile) |
| 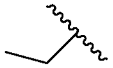 [SMILES: *CC]<br>Homoalanine (HAla) |
| 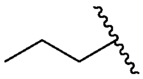 [SMILES: *CCC]<br>Norvaline (Nva) |

TABLE D-continued

| Representative amino acid side chains<br>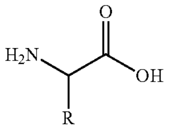<br>R |
|---|
| 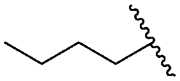 [SMILES: *CCCC]<br>Norleucine (Nle) |
| 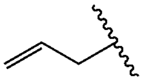 [SMILES: *CC=C]<br>Allylglycine (Allylgly) |
| 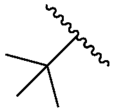 [SMILES: *C(C)(C)C]<br>tert-Leucine (Tle) |
| 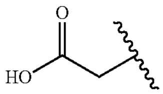<br>Aspartic Acid (Asp) |
| 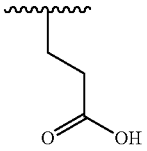 [SMILES: *CCC(=O)O]<br>Glutamic acid (Glu) |
| 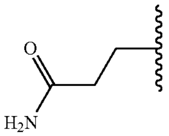<br>Glutamine (Gln) |
| 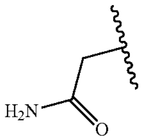 [SMILES: *CC(N)=O]<br>Asparagine (Asn) |
| 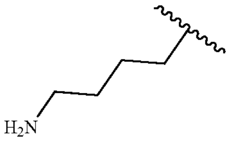 [SMILES: *CCCCN]<br>Lysine (Lys) |

TABLE D-continued

| Representative amino acid side chains<br>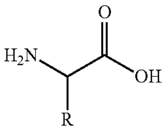<br>R |
|---|
| 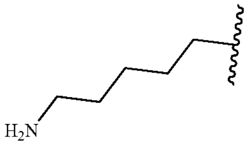 [SMILES: *CCCCCN]<br>Homolysine (HLys) |
| 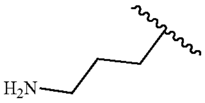<br>Ornithine (Orn) |
| 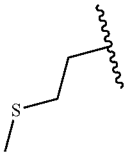 [SMILES: *CCSC]<br>Methionine (Met) |
| 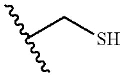<br>Cysteine (Cys) |
| 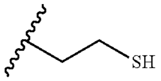 [SMILES: *CCS]<br>Homocysteine (HCys) |
| 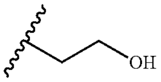 [SMILES: *CCO]<br>Homoserine (HSer) |
| 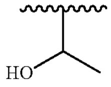<br>Threonine (Thr) |
| 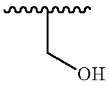<br>Serine (Ser) |

TABLE D-continued
| Representative amino acid side chains |
| --- |
| 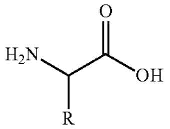 |
| R |
| 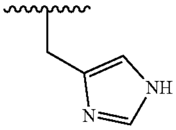 [SMILES: *Cc1c[nH]cn1] |
| Histidine (His) |
| 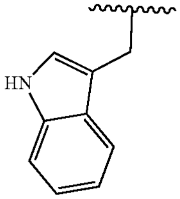 [SMILES: *Cc1c[nH]c2ccccc12] |
| Tryptophan (Trp) |
| 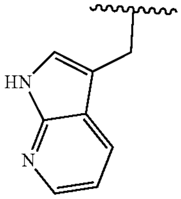 [SMILES: *Cc1c[nH]c2ncccc12] |
| 7-aza-Trp |
| 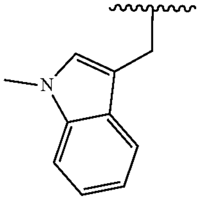 [SMILES: *Cc1cn(C)c2ccccc12] |
| 1-methyltryptophan (1MT) |
| 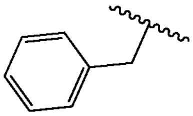 [SMILES: *Cc1ccccc1] |
| Phenylalanine (Phe) |
| 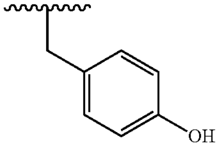 [SMILES: *Cc1ccc(O)cc1] |
| Tyrosine (Tyr) |
TABLE D-continued
| Representative amino acid side chains |
| --- |
| 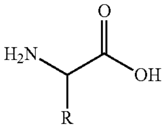 |
| R |
| 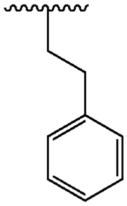 [SMILES: *CCc1ccccc1] |
| Homophenylalanine (HPhe) |
| 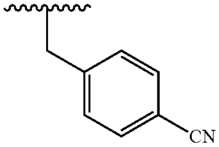 [SMILES: *Cc1ccc(C#N)cc1] |
| 4-cyano phenylalanine (Phe(4-CN)) |
| 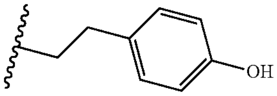 [SMILES: *CCc1ccc(O)cc1] |
| Homotyrosine (HTyr) |
| 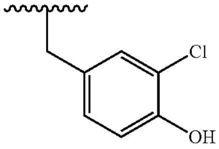 [SMILES: *Cc1ccc(O)c(Cl)c1] |
| 3-chlorotyrosine (Tyr(3-Cl)) |
| 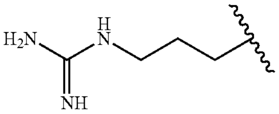 [SMILES: *CCCNC(=N)N] |
| Arginine (Arg) |
| 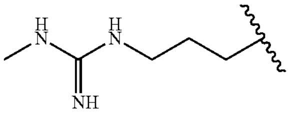 [SMILES: *CCCNC(=N)NC] |
| Arg(Me) |
| 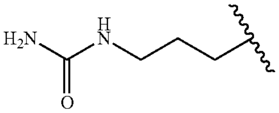 [SMILES: *CCCNC(N)=O] |
| Citrulline (Cit) |

TABLE D-continued

| Representative amino acid side chains |
|---|
| 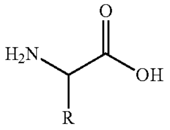 |
| R |
| 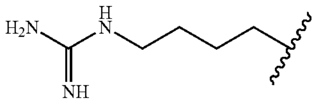 [SMILES: *CCCCNC(=N)N] Homoarginine (HArg) |
| 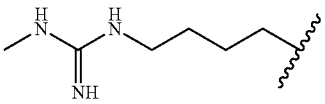 [SMILES: *CCCCNC(=N)NC] Methyl homoarginine (homo-Arg(Me)) |
| 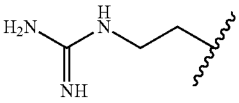 [SMILES: *CCNC(=N)N] Norarginine (AGBA) |
| 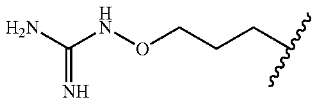 [SMILES: *CCCONC(=N)N] Canavanine |
| 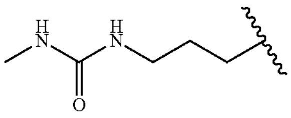 [SMILES: *CCCNC(=O)NC] Methyl Citrulline (Cit(Me)) |
| 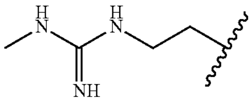 [SMILES: *CCNC(=N)NC] Methyl Norarginine (AGBA(Me)) |
| 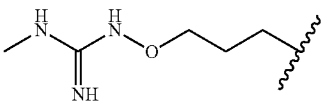 [SMILES: *CCCONC(=N)NC] Methyl Canavanine |
| 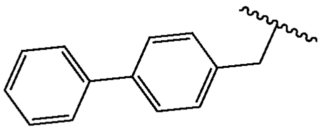 [SMILES: *Cc1ccc(-c2ccccc2)cc1] Biphenylalanine (Bip) |

TABLE D-continued

| Representative amino acid side chains |
|---|
| 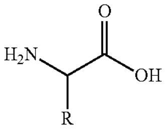 |
| R |
| 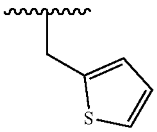 [SMILES: *Cc1cccs1] β-(2-thienyl)-Ala |
| 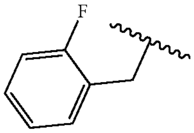 [SMILES: *Cc1ccccc1F] 2-Fluorophenylalanine (Phe(2-F)) |
| 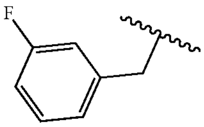 [SMILES: *Cc1cccc(F)c1] 3-Fluorophenylalanine (Phe(3-F)) |
| 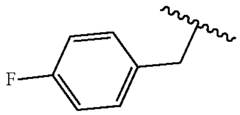 [SMILES: *Cc1ccc(F)cc1] 4-Fluorophenylalanine (Phe(4-F)) |
| 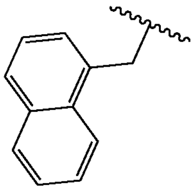 [SMILES: *Cc1cccc2ccccc12] 3-(1-Naphthyl)alanine (α-Nal) |
| 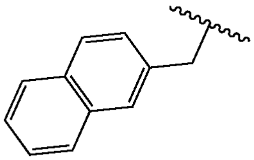 [SMILES: *Cc1ccc2ccccc2c1] 3-(2-Naphthyl)alanine or 2-amino-3-(naphthalen-2-yl)propanoic acid (β-Nal or 2Nal) |

TABLE D-continued

| Representative amino acid side chains |
|---|
| 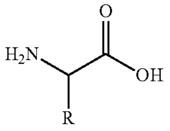 R |
| 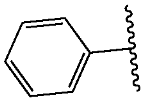 [SMILES: *c1ccccc1] Phenylglycine (Phg) |
| 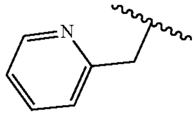 [SMILES: *Cc1ccccn1] 3-(2-pyridyl)alanine (2-Pal) |
| 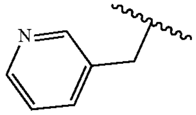 [SMILES: *Cc1cccnc1] 3-(3-pyridyl)alanine (3-Pal) |
| 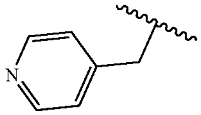 [SMILES: *Cc1ccncc1] 3-(4-pyridyl)alanine (4-Pal) |
| 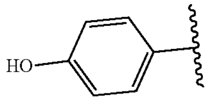 [SMILES: *c1ccc(O)cc1] 4-hydroxyphenylglycine (Phg(4-OH)) |
| 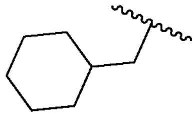 [SMILES: *CC1CCCCC1] Cyclohexylalanine (Cha) |
| 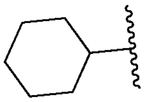 [SMILES: *C1CCCCC1] Cyclohexylglycine (Chg) |

TABLE D-continued

| Representative amino acid side chains |
|---|
| 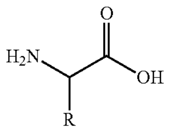 R |
| 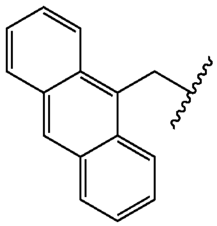 [SMILES: *Cc1c2ccccc2cc2ccccc12] 3-(9-anthryl)-alanine (H-Ala(9-Anth)-OH, AAP) |
| 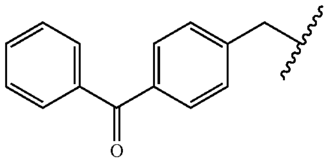 [SMILES: *Cc1ccc(C(=O)c2ccccc2)cc1] 4-Benzoyl-L-phenylalanine (Bpa) |
| 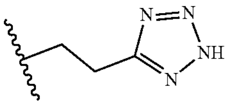 [SMILES: *CCc1nn[nH]n1] (S)-2-amino-4-(2H-tetrazol-5-yl)butanoic acid |
| 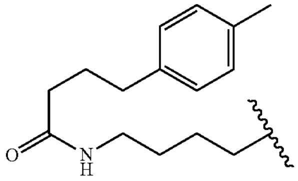 [SMILES: *CCCCNC(=O)CCCc1ccc(C)cc1] O-phospho-serine (SOP) |
| 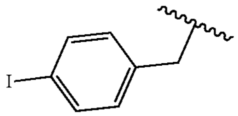 [SMILES: *Cc1ccc(I)cc1] 4-Iodophenylalanine (Phe(4-I)) |
| 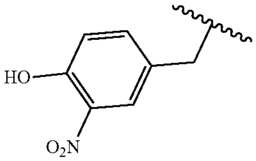 [SMILES: *Cc1ccc(O)c([N+](=O)[O-])c1] 3-nitro-tyrosine Tyr(3-$NO_2$) |

TABLE D-continued

| Representative amino acid side chains |
| --- |
| 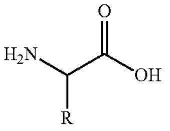 |
| R |
| 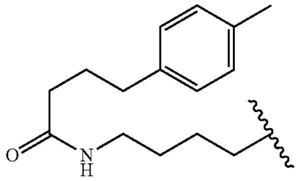 [SMILES: *CCCCNC(=O)CCCc1ccc(C)cc1] |
| N6-(4-(p-tolyl)butanoyl)-lysine |
| 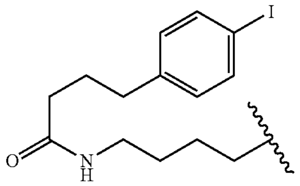 [SMILES: *CCCCNC(=O)CCCc1ccc(I)cc1] |
| N6-(4-(4-iodophenyl) butanoyl)-lysine |

Additional amino acids are shown in Tables E and F.

TABLE E

| Representative cyclic and unnatural amino acids |
| --- |
| 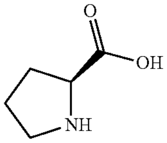 |
| Proline (Pro) |
| 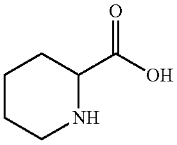 |
| Piperidine-2-carboxylic acid |
| 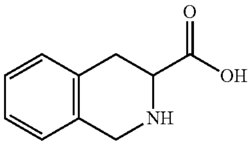 [SMILES: O=C(O)C1Cc2ccccc2CN1] |
| 2,3,4,5-Tetrahydroisoquinoline-3-carboxylic acid (Tic) |

TABLE E-continued

| Representative cyclic and unnatural amino acids |
| --- |
| 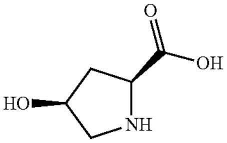 |
| Hydroxyproline (Hyp) |
| 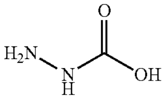 |
| Azaglycine (AzaGly) |
| 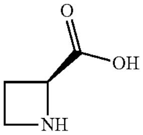 |
| Azetidine-2-carboxylic acid (Aze) |
| 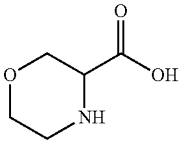 |
| Morpholine-2-carboxylic acid |
| 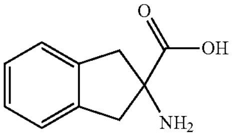 |
| 2-Amino-2-indancarboxylic acid (Aic) |
| 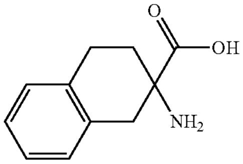 [SMILES: NC1(C(=O)O)CCc2ccccc2C1] |
| 2-aminotetralin-2-carboxylic acid (Atc) |
| 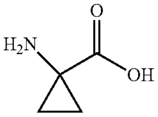 |
| 1-Aminocyclopropane-1-carboxylic acid (ACC) |
| 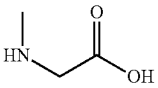 |
| Sarcosine (Sar) |

TABLE E-continued

Representative cyclic and unnatural amino acids

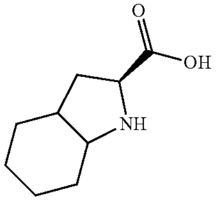 [SMILES: O=C(O)[C@@H]1CC2CCCCC2N1]

Octahydroindole-2-carboxylic acid (Oic)

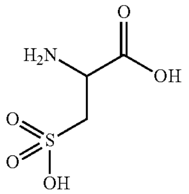

3-sulfo-alanine (Ala-$SO_3H$)

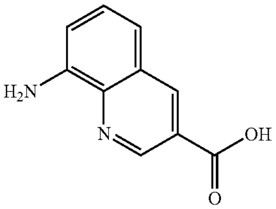 [SMILES: Nc1cccc2cc(C(=O)O)cnc12]

8-aminoquinoline-3-carboxylic acid

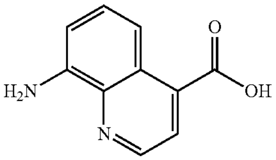 [SMILES: Nc1cccc2c(C(=O)O)ccnc12]

8-aminoquinoline-4-carboxylic acid

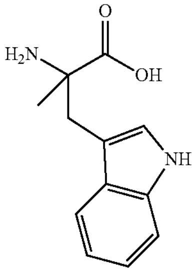 [SMILES: CC(N)(Cc1c[nH]c2ccccc12)C(=O)O]

Methyl-tryptophan (Me-Trp)

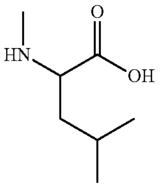

Methyl-leucine (Me-Leu)

TABLE E-continued

Representative cyclic and unnatural amino acids

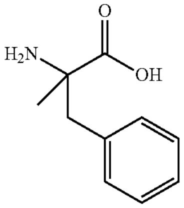

Methyl-phenylalanine (Me-Phe)

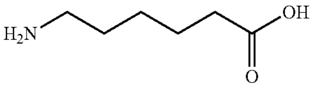

H2N 6-aminohexanoic acid (Ahx)

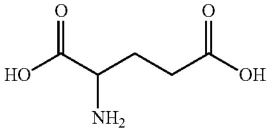

γ-Glutamic acid (γ-Glu)

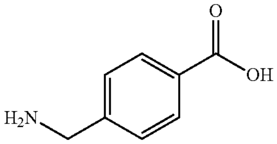 [SMILES: NCc1ccc(C(=O)O)cc1]

4-(aminomethyl)benzoic acid (AMBA)

TABLE F

Representative B-amino acids

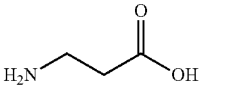

β-alanine (bAla or β-Ala)

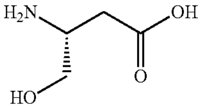

$\beta^3$-homoserine

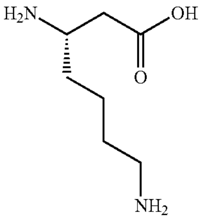

$\beta^3$-homolysine

TABLE F-continued

| Representative B-amino acids |
| --- |
| 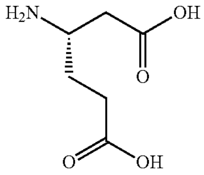<br>$\beta^3$-homoglutamic acid |
| 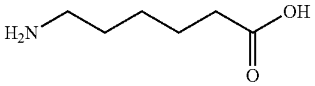<br>6-aminohexanoic acid (Ahx) |
| 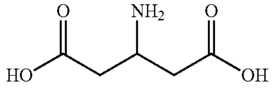<br>β-Glutamic acid<br>(β-glu or bglu) |

NUMBERED EMBODIMENTS

Embodiment 1. A compound of Formula (I), or a pharmaceutically acceptable salt thereof:

Formula (I)

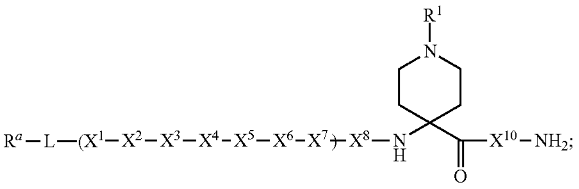

wherein:

$R^a$ is a chelating moiety or a radionuclide complex thereof;

L is an optional linker that is attached to any one of $X^1$, $X^2$, $X^3$, $X^4$, $X^5$, $X^6$, or $X^7$; or L is attached to $X^8$ if $X^1$, $X^2$, $X^3$, $X^4$, $X^5$, $X^6$, and $X^7$ are absent; and $R^1$ is H,

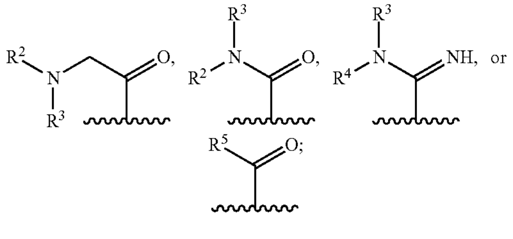

$R^2$ is $C_1$-$C_8$ alkyl, substituted or unsubstituted heteroalkyl, —$(CHR^6)_n$-heterocycloalkyl, —$(CHR^6)_n$-aryl, —$(CHR^6)_n$-heteroaryl, —C(═O)—$(CHR^6)_n$-aryl, or —C(═O)NH—$(CHR^6)_n$-aryl; wherein $C_1$-$C_6$ alkyl is optionally substituted with $R^7$, and wherein the heterocycloalkyl, aryl, or heteroaryl are each independently optionally substituted with $R^7$, $R^8$, $R^9$, $R^{10}$, and $R^{11}$;

$R^3$ is H or $C_1$-$C_4$, alkyl;

$R^4$ is H, $C_1$-$C_4$ alkyl, or $R^2$;

$R^5$ is substituted or unsubstituted alkyl, substituted or unsubstituted heteroalkyl, or —$(CHR^6)_n$-aryl; wherein aryl is optionally substituted with $R^7$, $R^8$, $R^9$, $R^{10}$, and $R^{11}$;

each $R^6$ is independently H, F, —$CH_3$, —$NH_2$, or —OH;

$R^7$, $R^8$, $R^9$, $R^{10}$, and $R^{11}$ are each independently selected from H, F, Cl, Br, I, —OH, —O—$C_1$-$C_4$ alkyl, —$NH_2$, —$NHC_1$-$C_4$, alkyl, —N($C_1$-$C_4$ alkyl)$_2$, —CN, —$CO_2H$, —$CO_2C_1$-$C_4$, alkyl, —$C_1$-$C_6$ alkyl, —$C_1$-$C_6$ fluroroalkyl or —$C_3$-$C_6$ cycloalkyl;

n is 0, 1, 2, 3, 4, 5, or 6;

$X^1$ is absent, tyrosine (Tyr), glycine (Gly), sarcosine (Sar), alanine (Ala), aspartic acid (Asp), lysine (Lys), phenylalanine (Phe), 3-(3-pyridyl)alanine (3-Pal), threonine (Thr), methionine (Met), 4-iodophenylalanine (Phe(4-I)), N6-(4-(p-tolyl)butanoyl)-lysine, N6-(4-(4-iodophenyl)butanoyl)-lysine, or γ-glutamic acid (γ-Glu));

$X^2$ is absent, asparagine (Asn), glutamine (Gln), aspartic acid (Asp), glutamic acid (Glu), serine (Ser), histidine (His), alanine (Ala), sarcosine (Sar), tyrosine (Tyr), proline (Pro), hydroxyproline (Hyp), azetidine-2-carboxylic acid (Aze), 2,3,4,5-tetrahydroisoquinoline-3-carboxylic acid (Tic), phenylalanine (Phe), 3-(2-pyridyl)alanine (2-Pal), 3-(3-pyridyl)alanine (3-Pal), or 3-(4-pyridyl)alanine (4-Pal);

$X^3$ is absent, tryptophan (Trp), serine (Ser), leucine (Leu), isoleucine (Ile), phenylalanine (Phe), 4-iodophenylalanine (Phe(4-I)), 3-(2-pyridyl)alanine (2-Pal), 3-(3-pyridyl)alanine (3-Pal), 3-(4-pyridyl)alanine (4-Pal), 2-amino-3-(naphthalen-2-yl)propanoic acid (H-2-NAL-OH), lysine (Lys), asparagine (Asn), glutamine (Gln), aspartic acid (Asp), glutamic acid (Glu), arginine (Arg), methyl arginine (Arg(Me)), norarginine (AGBA), methyl norarginine(AGBA(Me)), homoarginine (Harg), methyl homoarginine (Harg(Me)), citrulline (Cit), methyl citrulline (Cit(Me)), canavanine, methyl-canavanine, glycine (Gly), alanine (Ala), sarcosine (Sar), tyrosine (Tyr), cyclohexylalanine (Cha), 3-(1-naphthyl)alanine (α-Nal), 3-(2-naphthyl)alanine (β-Nal), threonine (Thr), proline (Pro), hydroxyproline (Hyp), tetrahydroisoquinoline-3-carboxylic acid (Tic), O-phospho-serine (SOP), 2-amino-4-(2H-tetrazol-5-yl) butanoic acid, β-glutamic acid, 8-aminoquinoline-3-carboxylic acid, biphenylalanine (Bip), 4-benzoylphenylalanine (Bpa), or 3-(9-anthryl)-alanine (H-Ala(9-Anth)-OH or AAP);

$X^4$ is absent, asparagine (Asn), glutamine (Gln), aspartic acid (Asp), glutamic acid (Glu), tryptophan (Trp), glycine (Gly), tyrosine (Tyr), alanine (Ala), sarcosine (Sar), or arginine (Arg);

$X^5$ is absent, serine (Ser), threonine (Thr), lysine (Lys), asparagine (Asn), glutamine (Gln), aspartic acid (Asp), glutamic acid (Glu), glycine (Gly), alanine (Ala), or sarcosine (Sar);

$X^6$ is absent, phenylalanine (Phe), alpha-methylphenylalanine (α-Me-Phe), N-methylphenylalanine (N-Me-Phe), 2-fluorophenylalanine (2-F-Phe), 3-fluorophenylalanine (3-F-Phe), 4-fluorophenylalanine (4-F-Phe), 4-iodophenylalanine (Phe(4-I)), 2-amino-2-indancarboxylic acid (Aic), biphenylalanine (Bip), (β-(2-thienyl)-Ala), tryptophan (Trp), 2-aminotetralin-2-carboxylic acid (Atc), 3-(2-thienyl)-alanine, 3-(4-pyridyl) alanine (4-Pal), cyclohexylalanine (Cha), or tyrosine (Tyr);

$X^7$ is absent, glycine (Gly), aza-glycine (aza-Gly), alanine (Ala), N-methylglycine (Sar) or 1-aminocyclopropane-1-carboxylic acid (ACC);

$X^8$ is leucine (Leu), norvaline (Nva), valine (Val), isoleucine (Ile), homoalanine (Hala), tryptophan (Trp), phenylalanine (Phe), or phenylglycine (Phg);

or —$X^7$—$X^8$— is

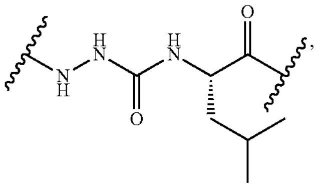,

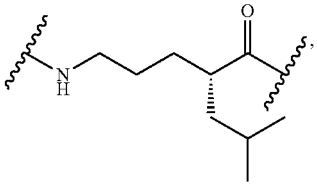,

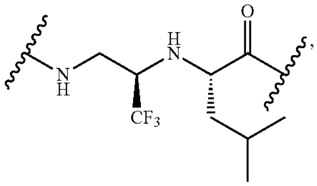,

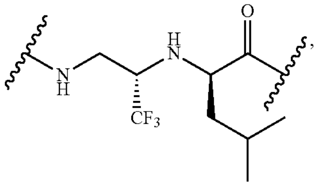,

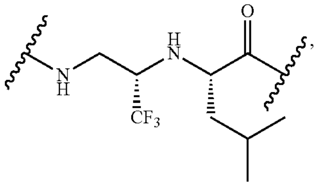,

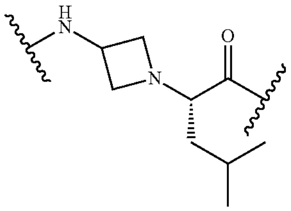,

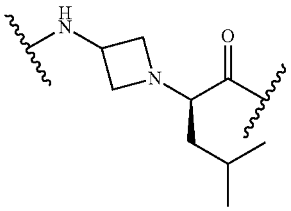,

-continued

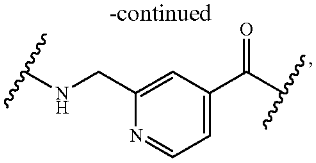,

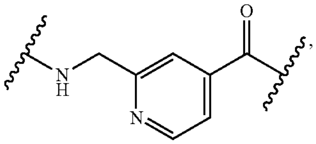,

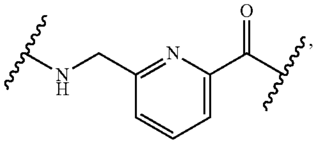,

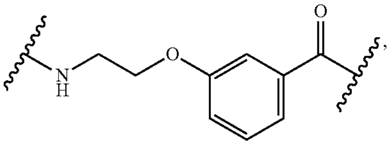,

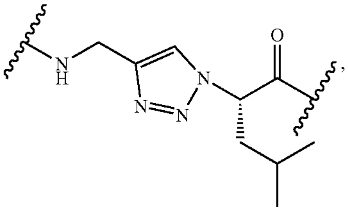,

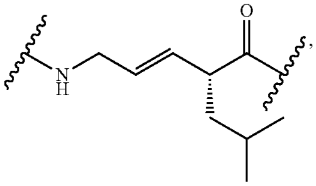,

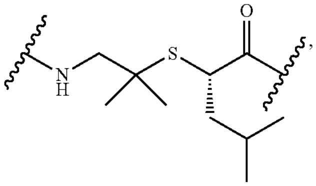,

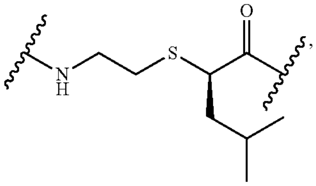,

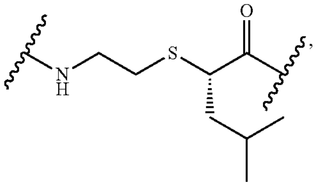,

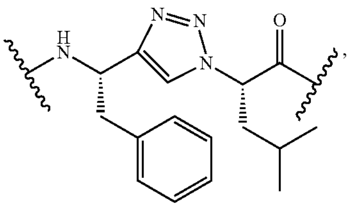,

-continued
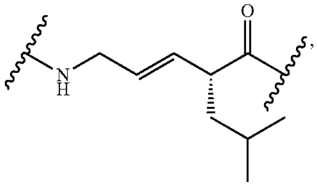
,
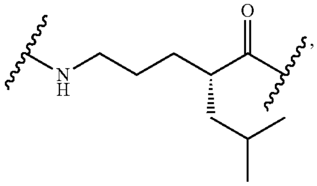
,
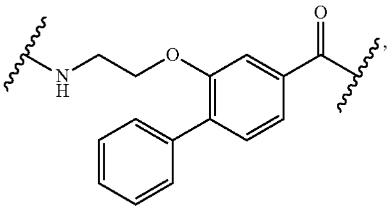
,
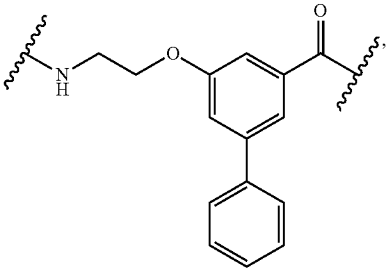
,
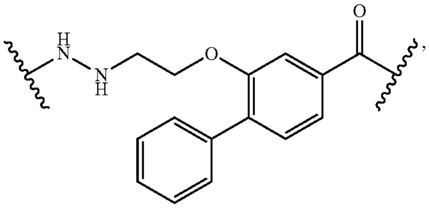
,
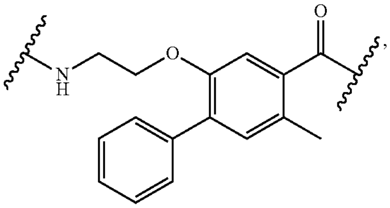
,
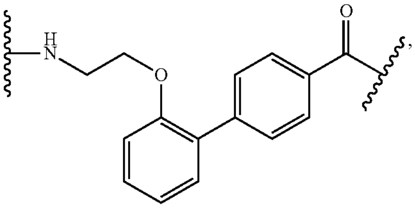
, or
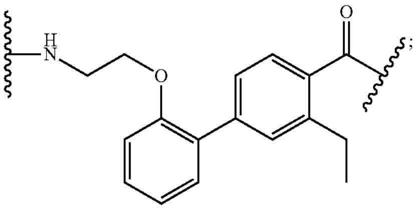
;
-continued
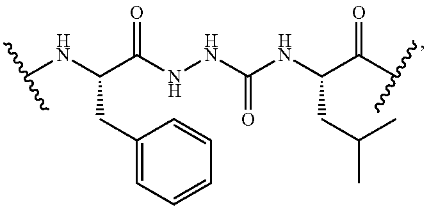
,
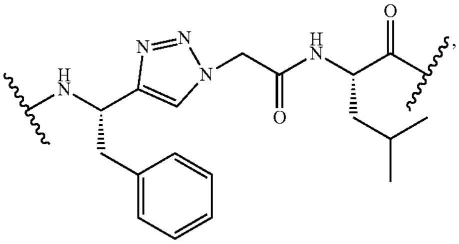
,
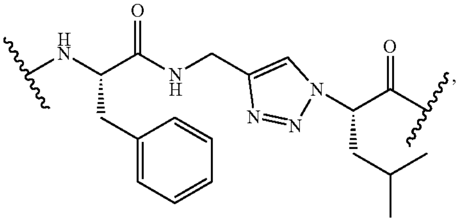
, or
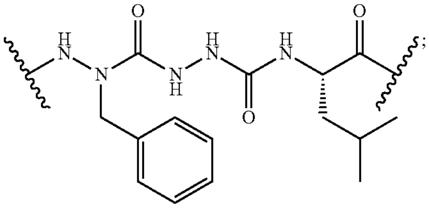
;
or —$X^6$—$X^7$—$X^8$— is
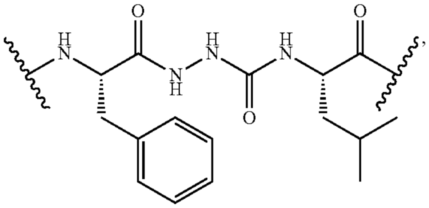
,
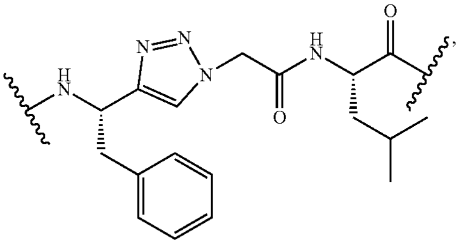
,
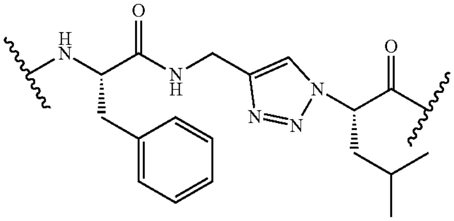
, or -continued

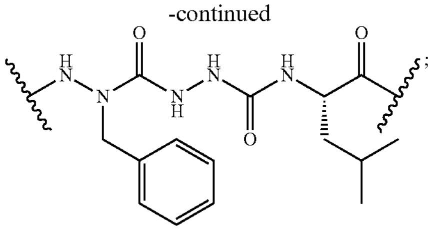

$X^{10}$ is tryptophan (Trp), 1-methyltryptophan (1MT), tyrosine (Tyr), phenylalanine (Phe), 4-cyano phenylalanine (Phe(4-CN)), 3-(4-pyridyl)alanine (4-Pal), leucine (Leu), phenylglycine (Phg), cyclohexylalanine (Cha), 3-(1-naphthyl)alanine (α-Nal), 3-(2-naphthyl)-alanine (β-Nal), histidine (His), or 3-nitro-tyrosine (Tyr(3-$NO_2$));

wherein the N-terminal amino acid or the compound of Formula (I) is optionally substituted with —C(═O)—$C_1$-$C_{20}$ alkyl, —C(═O)—$(CH_2CH_2O)_y$—$CH_2CH_2$—$R^{15}$, $C_1$-$C_{20}$ alkyl, N-hexadecanoyl-Glu, $C_4$-$C_{20}$ polyethylene glycol, a saccharide, —$R^{16}$, —C(═O)—$(CH_2CH_2O)_x$—$CH_3$, —C(═O)—$(CH_2CH_2O)_x$—H, —C(═O)—$CH_2CH_2CH(COOH)$—$R^{15}$, —C(═O)—$(CH_2)_2R^{19}$, or —C(═O)$CH_2NHCH_2R^{19}$ $R^{15}$ is selected from —$OR^{16}$, —$N(R^{16})_2$, —C(═O)$OR^{16}$, or —C(═O)$N(R^{16})_2$;

each $R^{16}$ is independently H, —$C_1$-$C_6$ alkyl, —C(═O)—$(CH_2)_vR^{19}$, —C(═O)$CH_2NHCH_2R^{19}$, or a saccharide or derivative thereof;

$R^{19}$ is 4-iodophenylene, 4-methylphenylene, or 3-fluoro-4-methylphenylene;

y is 0, 1, 2, 3, 4, 5, 6, 7, 8, 9, or 10;

x is an integer from 1 and 25; and v is 1, 2, 3, or 4;

wherein any free —NH— of a peptide bond is optionally independently substituted with —$CH_3$ or —$CH_2CH_3$; and wherein any alpha position of an amino acid is optionally independently substituted with —$CH_3$ or —$CH_2CH_3$.

Embodiment 2. The compound of embodiment 1, or a pharmaceutically acceptable salt thereof, wherein:

$X^1$ is absent, tyrosine (Tyr), glycine (Gly), sarcosine (Sar), alanine (Ala), aspartic acid (Asp), lysine (Lys), phenylalanine (Phe), 3-(3-pyridyl)alanine (3-Pal), threonine (Thr), methionine (Met), 4-iodophenylalanine (Phe(4-I)), N6-(4-(p-tolyl)butanoyl)-lysine or N6-(4-(4-iodophenyl)butanoyl)-lysine, or γ-glutamic acid (γ-Glu);

$X^2$ is absent, asparagine (Asn), glutamine (Gln), aspartic acid (Asp), glutamic acid (Glu), serine (Ser), D-histidine (His), alanine (Ala), sarcosine (Sar), tyrosine (Tyr), proline (Pro), hydroxyproline (Hyp), azetidine-2-carboxylic acid (Aze), 2,3,4,5-tetrahydroisoquinoline-3-carboxylic acid (Tic), phenylalanine (Phe), 3-(2-pyridyl)alanine (2-Pal), 3-(3-pyridyl)alanine (3-Pal), or 3-(4-pyridyl)alanine (4-Pal);

$X^3$ is absent, tryptophan (Trp), serine (Ser), leucine (Leu), isoleucine (Ile), phenylalanine (Phe), 4-iodophenylalanine (Phe(4-I)), 3-(2-pyridyl)alanine (2-Pal), 3-(3-pyridyl)alanine (3-Pal), 3-(4-pyridyl)alanine (4-Pal), 2-amino-3-(naphthalen-2-yl)propanoic acid (H-2-NAL-OH), lysine (Lys), asparagine (Asn), glutamine (Gln), aspartic acid (Asp), glutamic acid (Glu), arginine (Arg), methyl arginine (Arg(Me)), norarginine (AGBA), methyl norarginine (AGBA(Me)), homoarginine (Harg), methyl homoarginine (Harg(Me)), citrulline (Cit), methyl citrulline (Cit(Me)), canavanine, methyl-canavanine, glycine (Gly), alanine (Ala), sarcosine (Sar), tyrosine (Tyr), cyclohexylalanine (Cha), 3-(1-naphthyl)alanine (α-Nal), 3-(2-naphthyl)alanine (β-Nal), threonine (Thr), proline (Pro), hydroxyproline (Hyp), tetrahydroisoquinoline -3-carboxylic acid (Tic), O-phospho-serine (SOP), 2-amino-4-(2H-tetrazol-5-yl) butanoic acid, beta-glutamic acid (bGlu), 8-aminoquinoline-3-carboxylic acid, biphenylalanine (Bip); 4-benzoylphenylalanine (Bpa), or 3-(9-anthryl)-alanine (H-Ala(9-Anth)-OH or AAP);

$X^4$ is absent, -asparagine (-Asn), glutamine (Gln), aspartic acid (Asp), glutamic acid (Glu), tryptophan (Trp), glycine (Gly), alanine (Ala), sarcosine ( ), or arginine (Arg); and $X^5$ is absent, serine (Ser), threonine (Thr), lysine (Lys), asparagine (-Asn), glutamine (Gln), aspartic acid (Asp), glutamic acid (Glu), glycine (Gly), alanine (Ala), or sarcosine (Sar).

Embodiment 3. The compound of embodiment 1, or a pharmaceutically acceptable salt thereof, wherein:

$X^1$ is absent, tyrosine (Tyr), or 3-(3-pyridyl)alanine (3-Pal));

$X^2$ is absent, asparagine (Asn), glutamine (Gln), serine (Ser), D-histidine (His), or phenylalanine (Phe);

$X^3$ is absent, tryptophan (Trp), isoleucine (fie), 3-(4-pyridyl)alanine (4-Pal), lysine (Lys), aspartic acid (Asp), glutamic acid (Glu), glycine (Gly), alanine (Ala), cyclohexylalanine (Cha), (Hyp), biphenylalanine (Bip); 4-benzoylphenylalanine (Bpa), or 3-(9-anthryl)-alanine (AAP);

$X^4$ is absent, asparagine (Asn), or glutamine (Gln); and $X^5$ is absent, serine (Ser), threonine (Thr), glycine (Gly), or alanine (Ala).

Embodiment 4. The compound of embodiment 1, or a pharmaceutically acceptable salt thereof, wherein:

$X^1$ is D-tyrosine (D-Tyr);

$X^2$ is absent;

$X^3$ is D-tryptophan (D-Trp), biphenylalanine (Bip); 4-benzoylphenylalanine (Bpa), or 3-(9-anthryl)-alanine (AAP);

$X^4$ is asparagine (Asn); and $X^5$ is serine (Ser) or threonine (Thr).

Embodiment 5. The compound of any one of embodiments 1-4, or a pharmaceutically acceptable salt thereof, wherein:

$X^8$ is Leu, Nva, Ile, Hala, or Phe; and $X^{10}$ is Trp, 1MT, Tyr, 4-Pal, Phe(4-CN), or Phe.

Embodiment 6. The compound of any one of embodiments 1-4, or a pharmaceutically acceptable salt thereof, wherein:

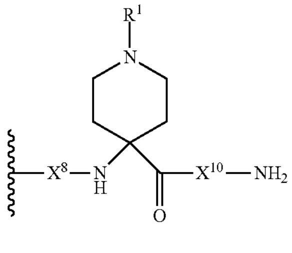 is

-continued

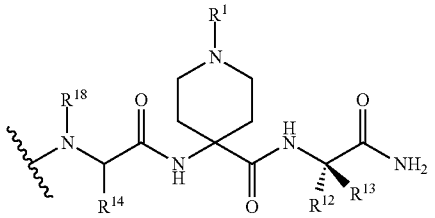

wherein, $R^{18}$ is H or —$CH_3$;

$R^{12}$ is

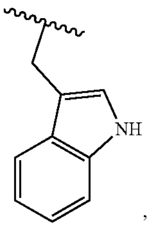
,
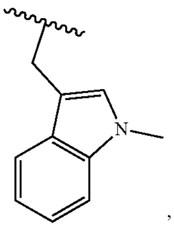
,
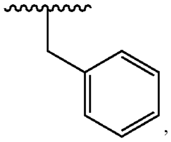
,
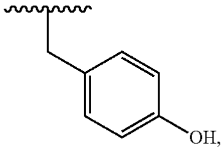
OH,
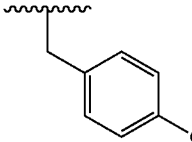
CN,
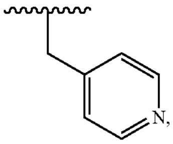
N, or
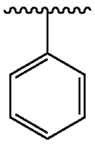
;

$R^{13}$ is H or —$CH_3$; and $R^{14}$ is

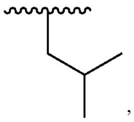
,
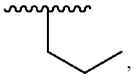
,
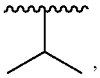
,
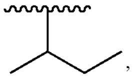
,
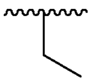
,
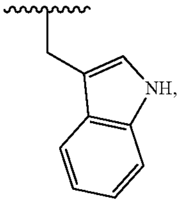
NH,
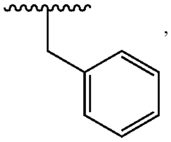
, or
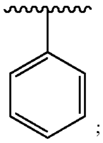
;

Embodiment 7. The compound of embodiment 6, or a pharmaceutically acceptable salt thereof, wherein:

$R^{14}$ is

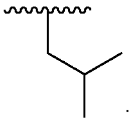 [SMILES: *CC(C)C]
.

Embodiment 8. The compound of embodiment 6 or 7, or a pharmaceutically acceptable salt thereof, wherein:

$R^{12}$ is

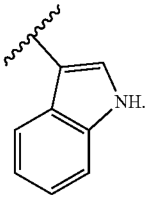 [SMILES: *c1c[nH]c2ccccc12]
NH.

Embodiment 9. The compound of embodiment 6, 7, or 8, or a pharmaceutically acceptable salt thereof, wherein:

$R^{11}$ is H or —$CH_3$;

$R^{12}$ is

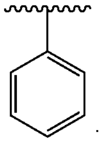
.

Embodiment 10 The compound of embodiment 1, or a pharmaceutically acceptable salt thereof, wherein:

$X^6$ is phenylalanine (Phe), 3-fluorophenylalanine (3-F-Phe), biphenylalanine (Bip), or cyclohexylalanine (Cha);

$X^7$ is glycine (Gly) or aza-glycine (aza-Gly); and $X^8$ is leucine (Leu) or norvaline (Nva).

Embodiment 11. The compound of embodiment 1, or a pharmaceutically acceptable salt thereof, wherein:

$X^6$ is phenylalanine (Phe) or cyclohexylalanine (Cha);

$X^7$ is aza-glycine (aza-Gly); and $X^8$ is leucine (Leu).

Embodiment 12. The compound of embodiment 1, or a pharmaceutically acceptable salt thereof, wherein:

$X^6$ is

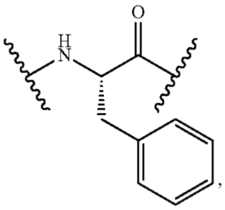
,
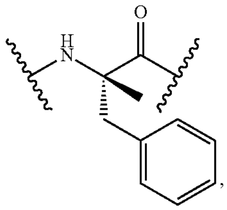
,
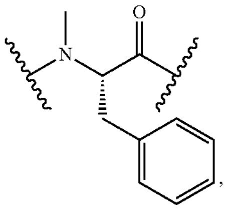
,
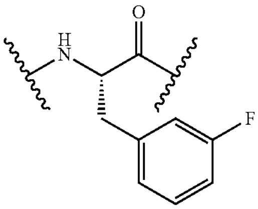
,

-continued

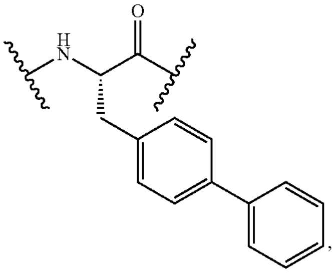, or 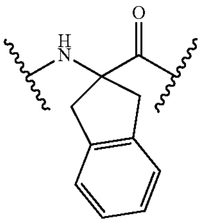;

$X^7$ is 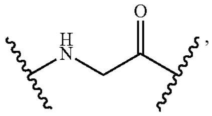, 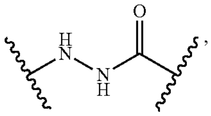,

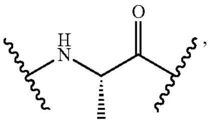, 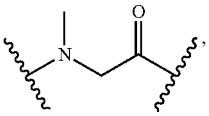, or

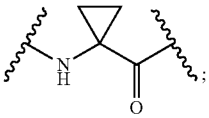;

$X^8$ is 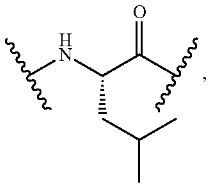, 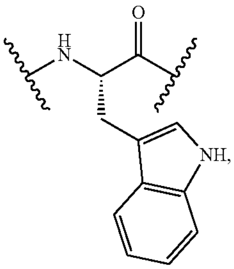

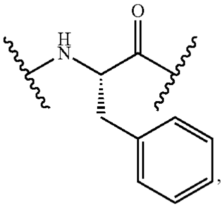, or 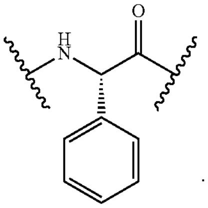.

Embodiment 13. The compound of embodiment 12, or a pharmaceutically acceptable salt thereof, wherein:

$X^6$ is

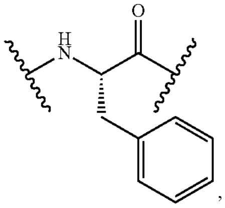, 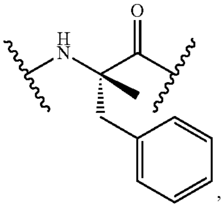,

-continued

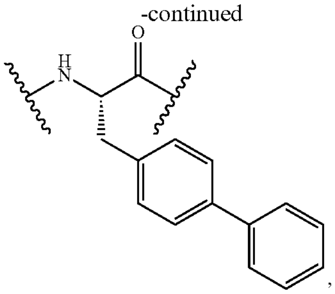, or

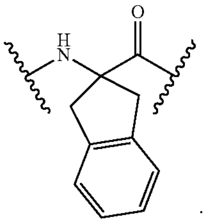.

Embodiment 14 The compound of embodiment 12 or 13, or a pharmaceutically acceptable salt thereof, wherein:

$X^7$ is

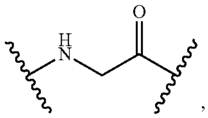, 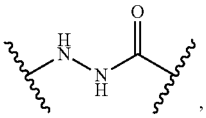, or

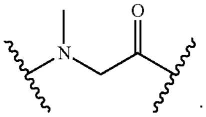.

Embodiment 15. The compound of embodiment 12, 13, or 14, or a pharmaceutically acceptable salt thereof, wherein:

$X^8$ is

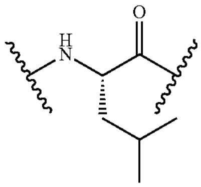 or 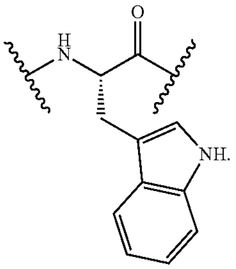

Embodiment 16. The compound of embodiment 1, or a pharmaceutically acceptable salt thereof, wherein:

$X^6$ is

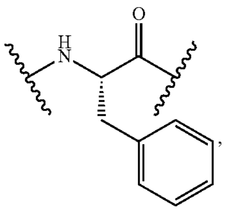, 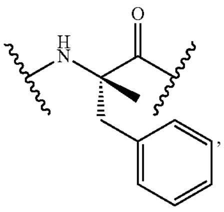,

-continued
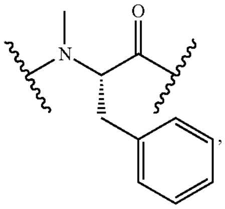, or 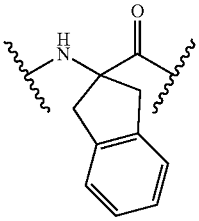;
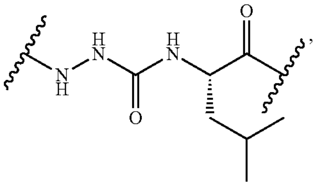,
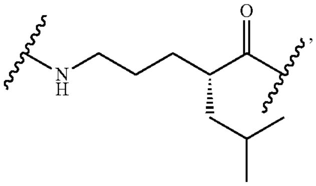,
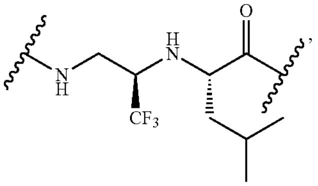,
X7-X8- is 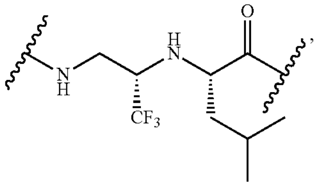,
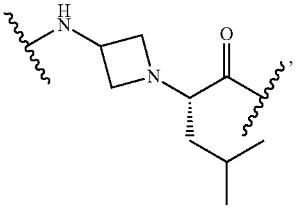,
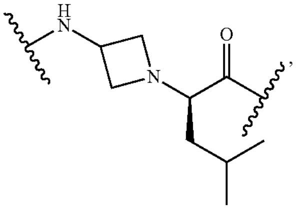,
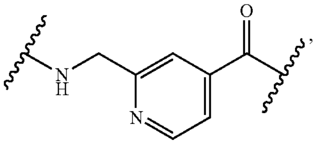,
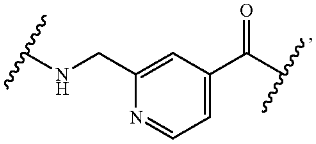,
-continued
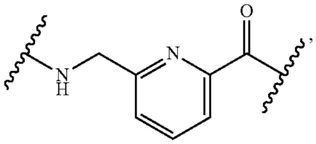,
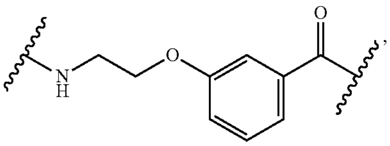,
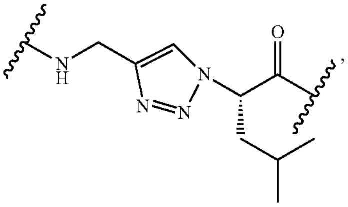,
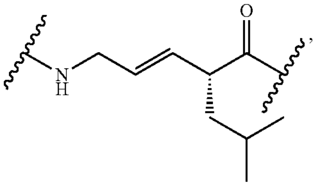,
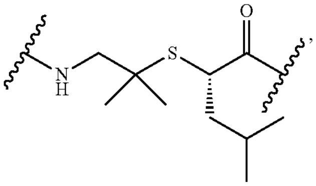,
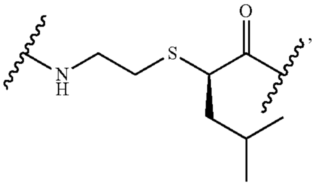, or
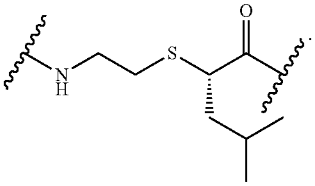.
Embodiment 17. The compound of embodiment 1, or a pharmaceutically acceptable salt thereof, wherein:
—X6—X7—X8— is
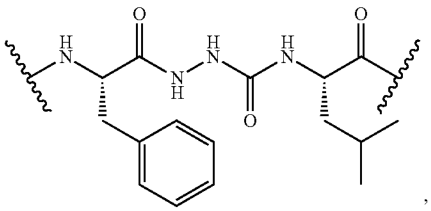, -continued
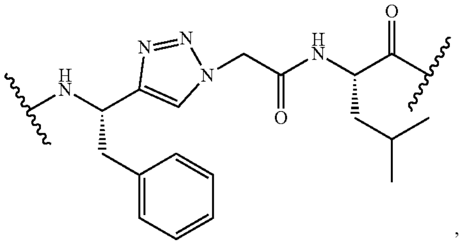
,
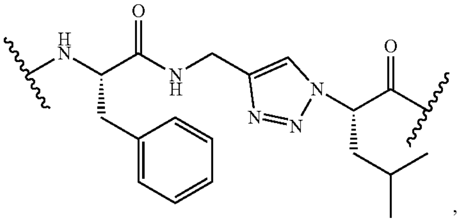
, or
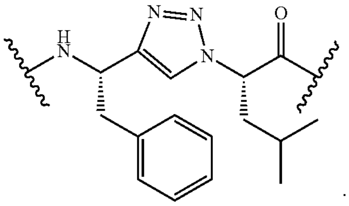
.
Embodiment 18. The compound of embodiment 1, or a pharmaceutically acceptable salt thereof, wherein:
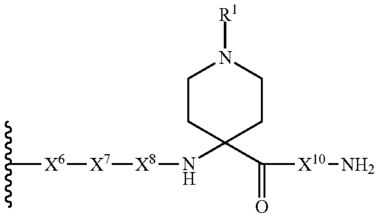
is
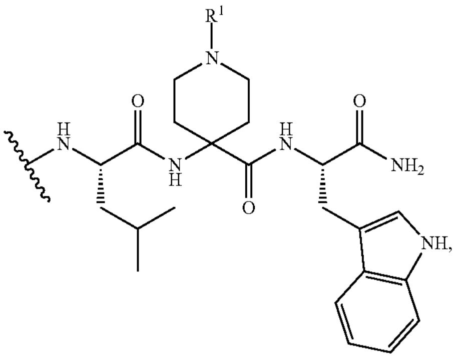
-continued
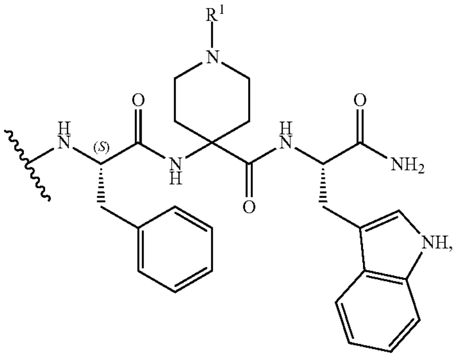
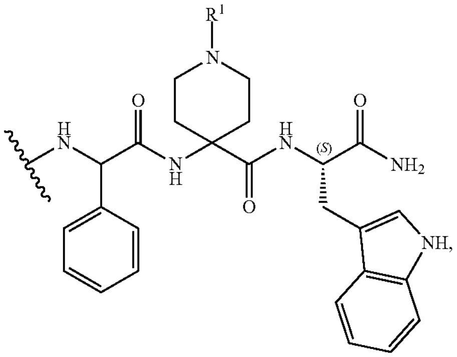
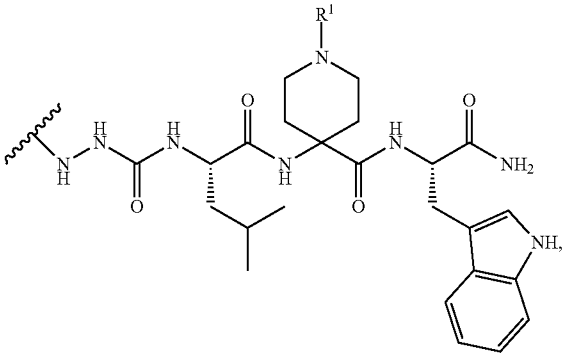
(SEQ ID NO: 159)
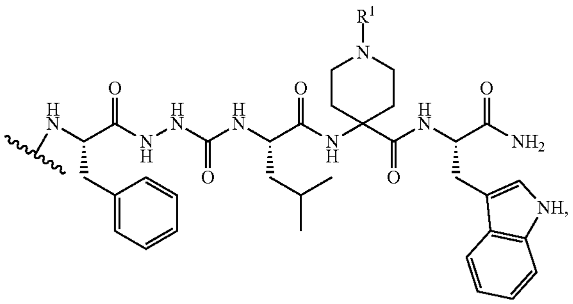

-continued
(SEQ ID NO: 162)
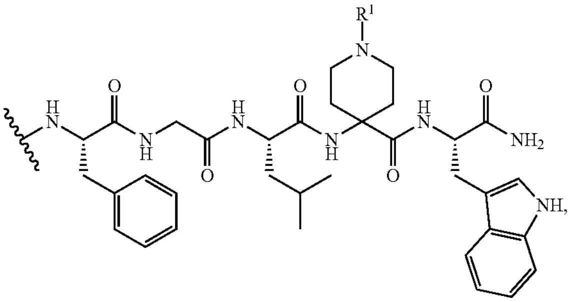
(SEQ ID NO: 164)
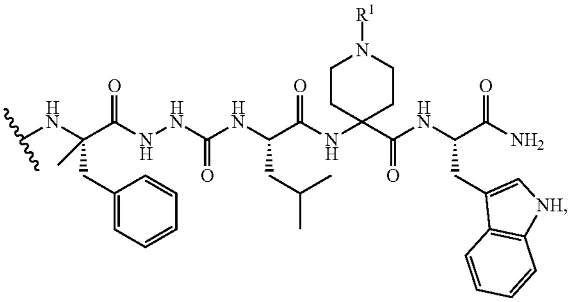
(SEQ ID NO: 161)
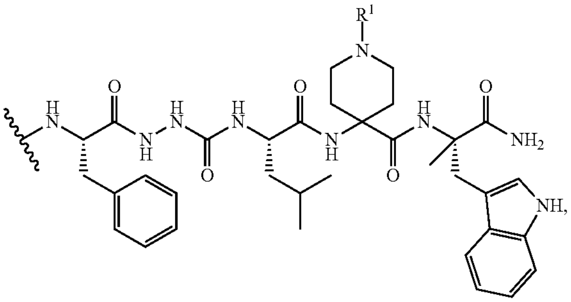
(SEQ ID NO: 166)
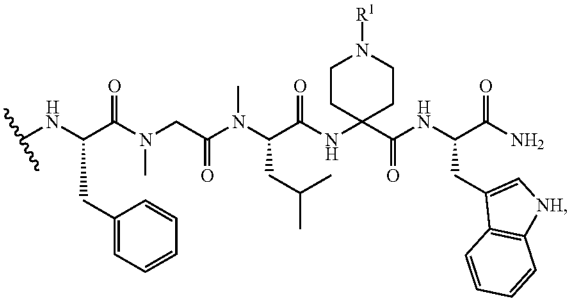
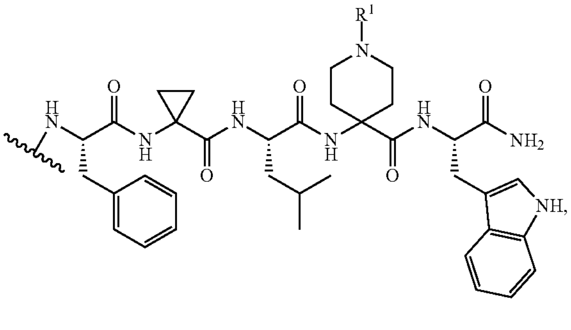
-continued
(SEQ ID NO: 163)
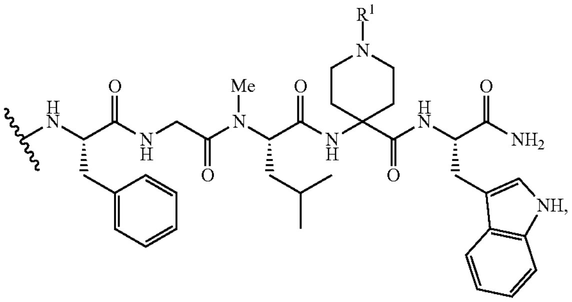
(SEQ ID NO: 165)
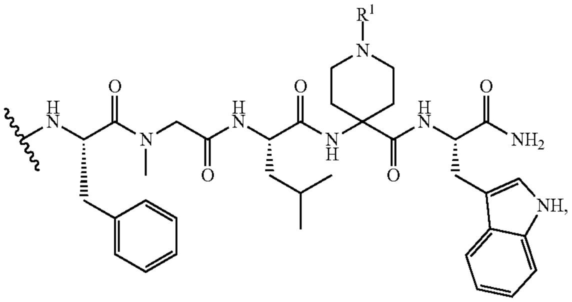
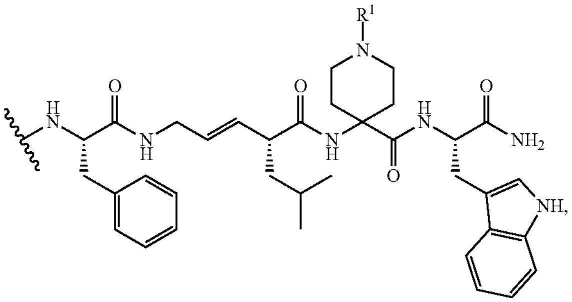
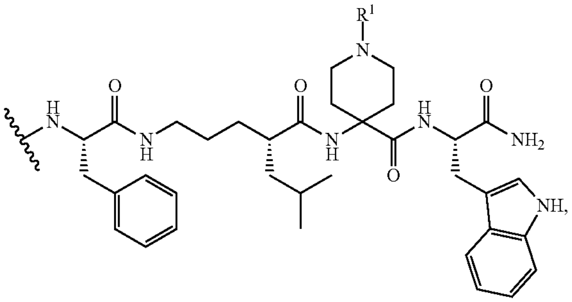
(SEQ ID NO: 160)
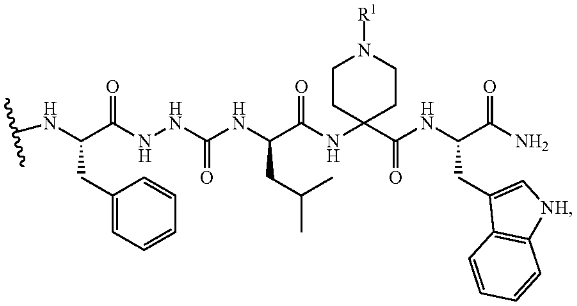

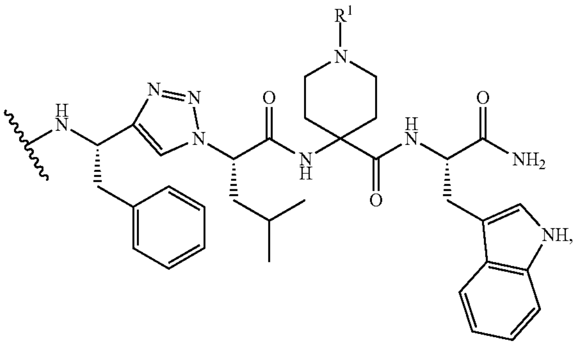
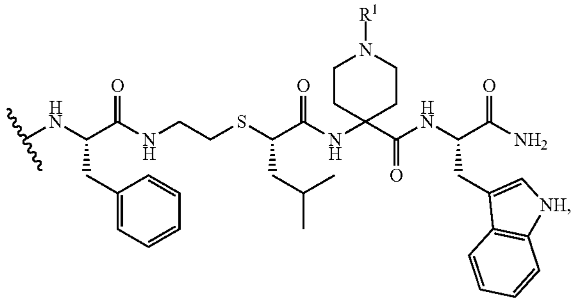
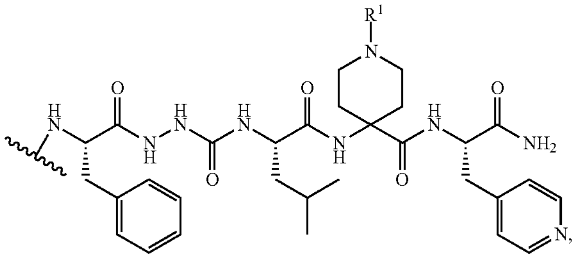
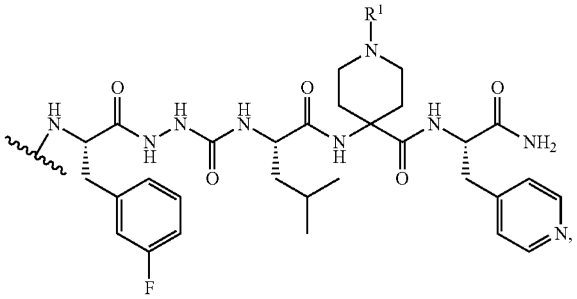
(SEQ ID NO: 197)
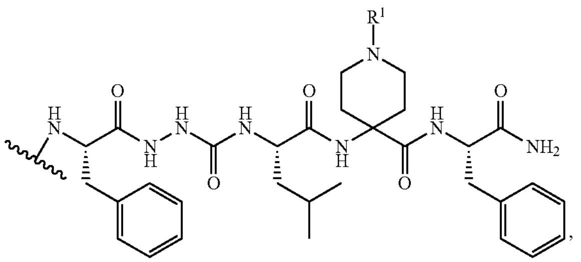
(SEQ ID NO: 774)
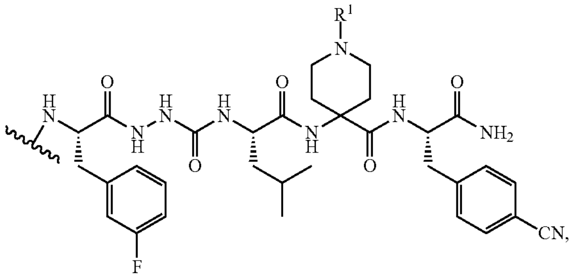
(SEQ ID NO: 775)
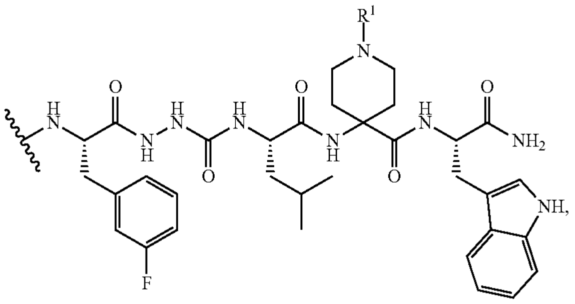
(SEQ ID NO: 160)
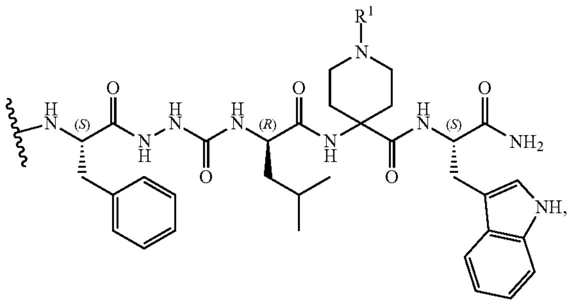
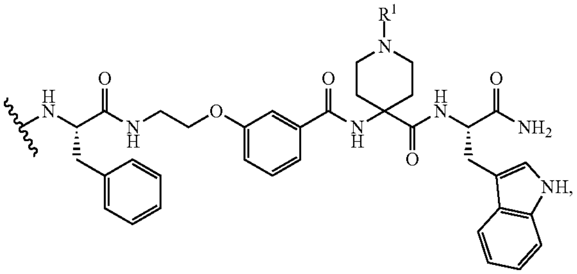
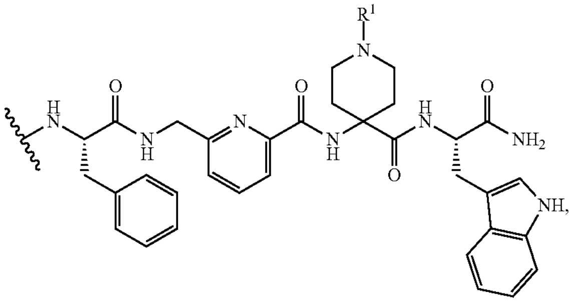

-continued
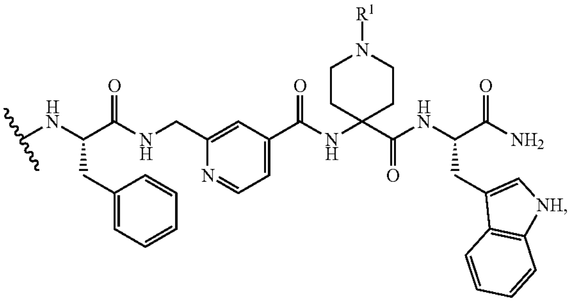
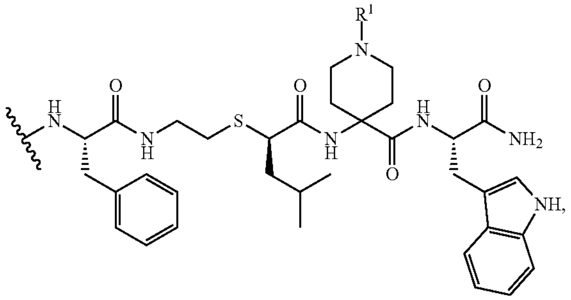
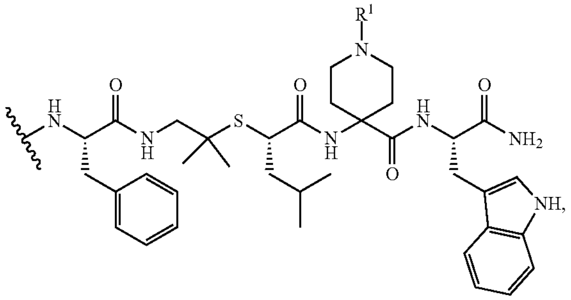
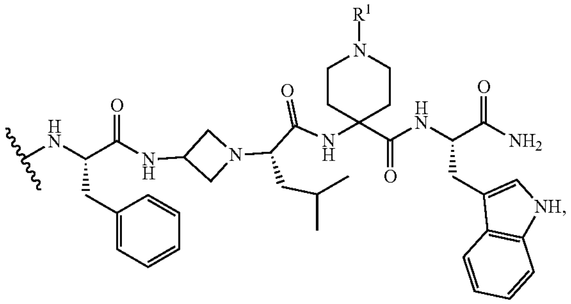
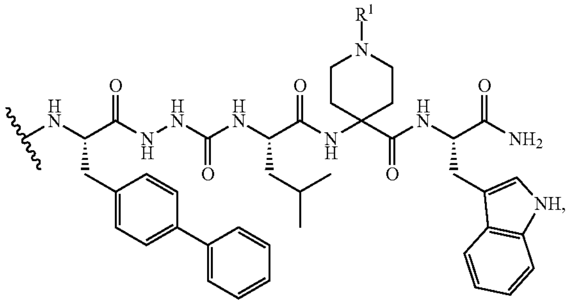
-continued
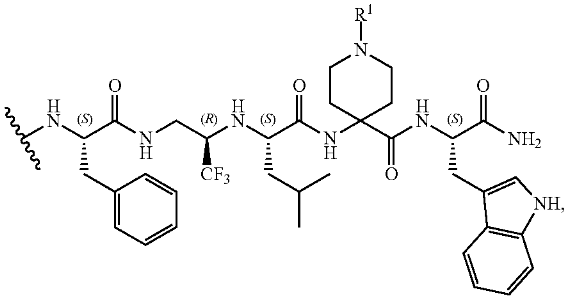
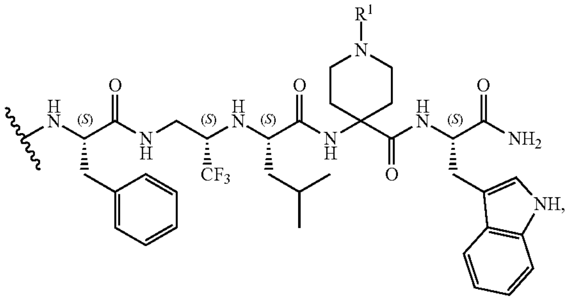
(SEQ ID NO: 206)
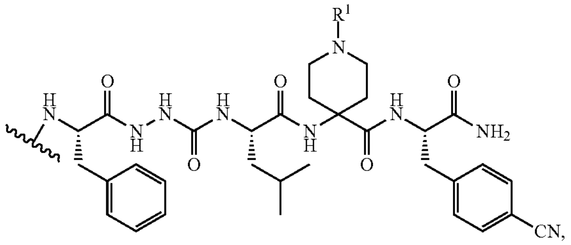
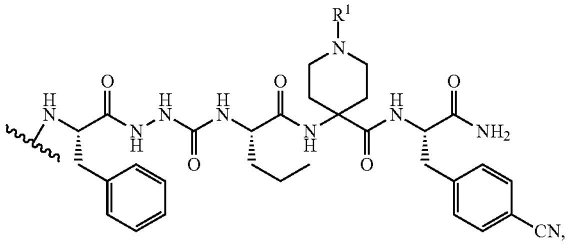
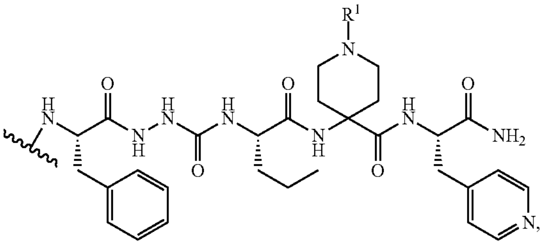
or
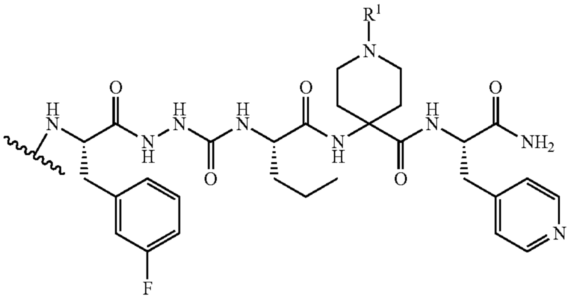

Embodiment 19. The compound of any one of embodiments 1-4 or 10-18, or a pharmaceutically acceptable salt thereof, wherein: $X^{10}$ is tryptophan (Trp), 1-methyltryptophan (1MT), tyrosine (Tyr), phenylalanine (Phe), 4-cyano phenylalanine (Phe(4-CN)), 3-(4-pyridyl)alanine (4-Pal), or leucine (Leu).

Embodiment 20. The compound of any one of embodiments 1-4 or 10-18, or a pharmaceutically acceptable salt thereof, wherein: $X^{10}$ is tryptophan (Trp), tyrosine (Tyr), phenylalanine (Phe), or 4-cyano phenylalanine (Phe(4-CN)).

Embodiment 21. The compound of any one of embodiments 1-20, or a pharmaceutically acceptable salt thereof, wherein:

$R^3$ is H or $—CH_3$;

$R^4$ is H, $—CH_3$, or $R^2$.

Embodiment 22. The compound of any one of embodiments 1-21, or a pharmaceutically acceptable salt thereof, wherein:

$R^1$ is

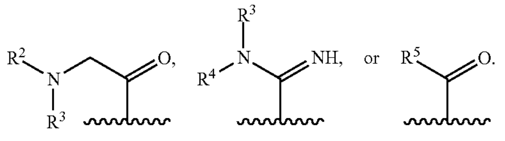

Embodiment 23. The compound of any one of embodiments 1-21, or a pharmaceutically acceptable salt thereof, wherein $R^1$ is H.

Embodiment 24. The compound of any one of embodiments 1-21, or a pharmaceutically acceptable salt thereof, wherein:

$R^1$ is

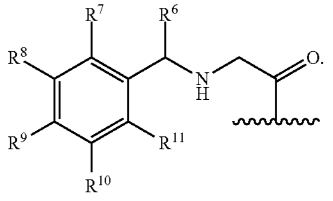

Embodiment 25. The compound of any one of embodiments 1-21, or a pharmaceutically acceptable salt thereof, wherein: $R^1$ is

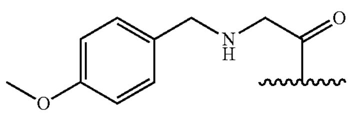

or

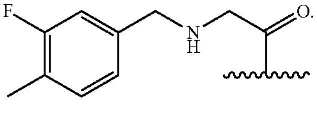

Embodiment 26. The compound of any one of embodiments 1-21, or a pharmaceutically acceptable salt thereof, wherein:

$R^1$ is

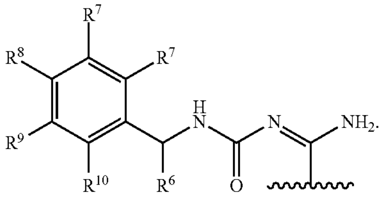

Embodiment 27. The compound of any one of embodiments 1-26, or a pharmaceutically acceptable salt thereof, wherein:

$R^2$ is

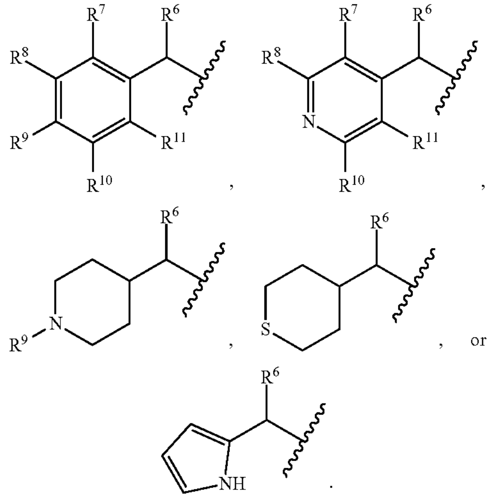

Embodiment 28. The compound of any one of embodiments 1-26, or a pharmaceutically acceptable salt thereof, wherein:

$R^2$ is

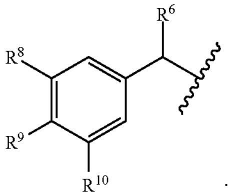

Embodiment 29. The compound of any one of embodiments 1-26, or a pharmaceutically acceptable salt thereof, wherein:

$R^2$ is $C_1$-$C_6$ alkyl, wherein $C_1$-$C_6$ alkyl is optionally substituted with $R^7$.

Embodiment 30, The compound of any one of embodiments 1-29, or a pharmaceutically acceptable salt thereof, wherein:

$R^5$ is

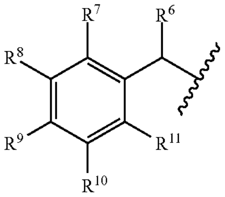
,
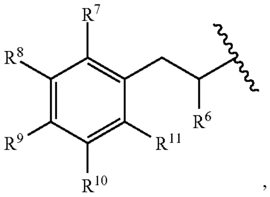
, or
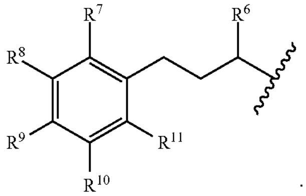
.

Embodiment 31 The compound of any one of embodiments 1-30, or a pharmaceutically acceptable salt thereof, wherein:

$R^7$, $R^8$, $R^9$, $R^{10}$, and $R^{10}$ are independently selected from H, F, Cl, Br, I, —OH, —$OCH_3$, —$OCH_2CH_3$, —$NH_2$, —$NHCH_3$, —$N(CH_3)_2$, —CN, —$CO_2H$, —$CO_2CH_3$, —$CO_2CH_2CH_3$, —$CH_3$, —$CH_2CH_3$, —$CH(CH_3)_2$, —$(CH_3)_3$, —$CF_3$, —$CH_2F$, —$CH_2F$, or cyclopropyl.

Embodiment 32. The compound of any one of embodiments 1-21, or a pharmaceutically acceptable salt thereof, wherein:

$R^1$ is

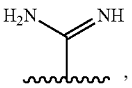
,
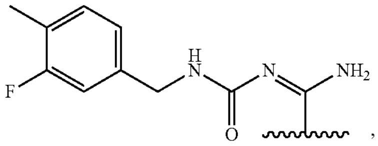
,
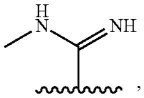
,
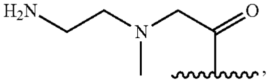
,
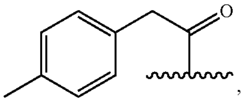
,
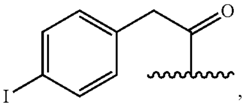
,
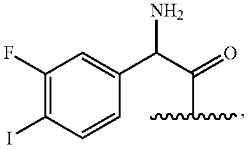
,
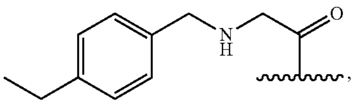
,
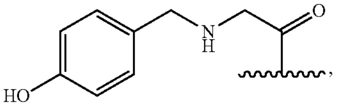
,
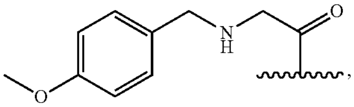
,
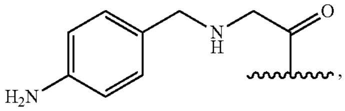
, -continued

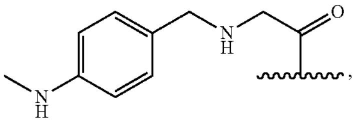
,
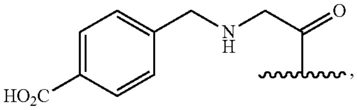
,
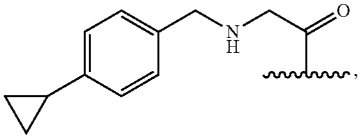
,
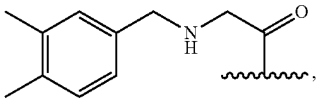
,
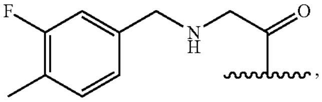
,
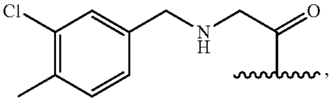
,
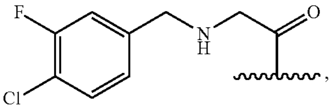
,
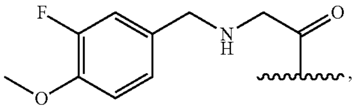
,
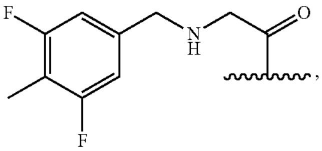
,
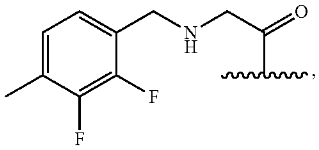
,
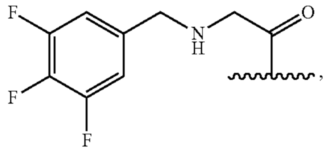
,
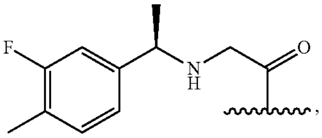
,
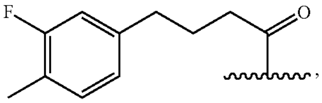
,
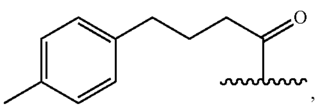
,
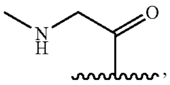
, -continued

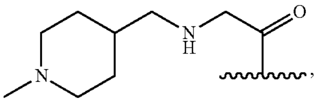,

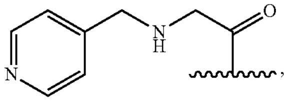,

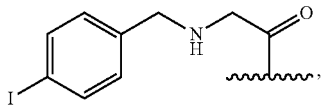,

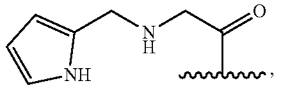,

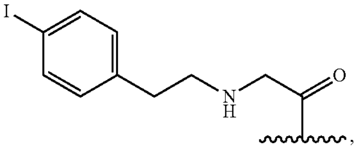,

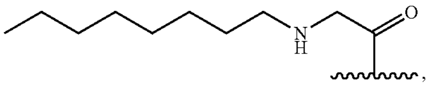,

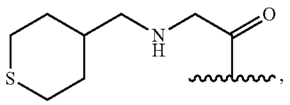,

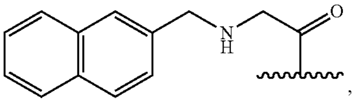, or 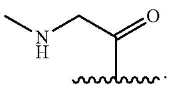.

Embodiment 33 The compound of any one of embodiments 1-21, or a pharmaceutically acceptable salt thereof, wherein:

$R^1$ is

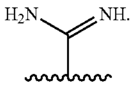

Embodiment 34. The compound of any one of embodiments 1-21, or a pharmaceutically acceptable salt thereof, wherein: $R^1$ is

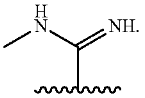 [SMILES: *C(=N)NC]

Embodiment 35. The compound of any one of embodiments 1-21, or a pharmaceutically acceptable salt thereof, wherein:

$R^1$ is

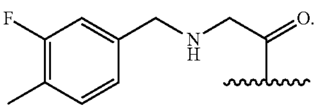 [SMILES: *C(=O)CNCc1ccc(C)c(F)c1]

Embodiment 36. The compound of any one of embodiments 1-21, or a pharmaceutically acceptable salt thereof, wherein:

$R^1$ is

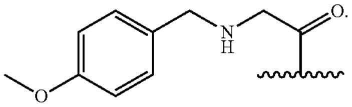 [SMILES: *C(=O)CNCc1ccc(OC)cc1]

Embodiment 37. The compound of any one of embodiments 1-21, or a pharmaceutically acceptable salt thereof, wherein.

$X^1$ is absent, Tyr, Asp, Lys, 3-Pal, Sar, or Phe; and $X^2$ is absent, Asn, Gln, Asp, Glu, Ser, His, Ala, Sar, Pro, Hyp, Aze, Tic, Phe, or 4-Pal.

Embodiment 38. The compound of any one of embodiments 1-21, or a pharmaceutically acceptable salt thereof, wherein:

$X^1$ is absent, D-Tyr, Asp, Lys, D-3-Pal, Sar, or Phe; and $X^2$ is absent, D-Asn, Gln, Asp, Glu, Ser, His, Ala, Sar, Pro, Hyp, Aze, Tic, Phe, or 4-Pal.

Embodiment 39. The compound of any one of embodiments 1-38, or a pharmaceutically acceptable salt thereof, wherein $X^3$ is absent, Trp, Ser, Ile, Phe, 4-Pal, Lys, Asn, Gln, Asp, Glu, Arg, Arg(Me), AGBA, AGBA(Me), Harg, Harg (Me), Cit, Cit(Me), canavanine, methyl-canavanine, Gly, Ala, Sar, Tyr, Cha, β-Nal, Hyp, Thr, Bip, Bpa, or H-Ala(9-Anth)-OH;

$X^4$ is absent, Asn, Gln, Asp, Glu, Trp, Gly, Ala, or Sar; and $X^5$ is absent, Ser, Thr, Asn, Gln, Asp, Glu, Gly, Ala or Sar.

Embodiment 40. The compound of any one of embodiments 1-38, or a pharmaceutically acceptable salt thereof, wherein:

$X^3$ is absent, Trp, Ser, Ile, Phe, 4-Pal, Lys, Asn, Gln, Asp, Glu, Arg, Arg(Me), AGBA, AGBA(Me), Harg, Harg (Me), Cit, Cit(Me), canavanine, methyl-canavanine, Gly, Ala, Sar, Tyr, Cha, β-Nal, Hyp, Thr, Bip, Bpa, or AAP;

$X^4$ is absent, -Asn, Gln, Asp, Glu, Trp, Gly, Ala, or Sar; and $X^5$ is absent, Thr, Ser or Ala.

Embodiment 41. The compound of any one of embodiments 1-38, or a pharmaceutically acceptable salt thereof, wherein:

$X^1$ is absent, Tyr, Asp, Lys, 3-Pal, Sar, or Phe;

$X^2$ is absent, Asn, Gln, Asp, Glu, Ser, His, Ala, Sar, Pro, Hyp, Aze, Tic, Phe, or 4-Pal;

$X^3$ is absent, Trp, Ser, Ile, Phe, 4-Pal, Lys, Asn, Gln, Asp, Glu, Arg, Arg(Me), Gly, Ala, Sar, Tyr, Cha, β-Nal, Hyp, Thr, Bip, Bpa, or AAP;

$X^4$ is absent, Asn, Gln, Asp, Glu, Trp, Gly, Ala, or Sar; and $X^5$ is absent, Thr, Ser, Gly, or Ala.

Embodiment 42. The compound of any one of embodiments 1-38, or a pharmaceutically acceptable salt thereof, wherein

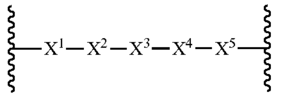

is absent, (SEQ ID NO: 1)
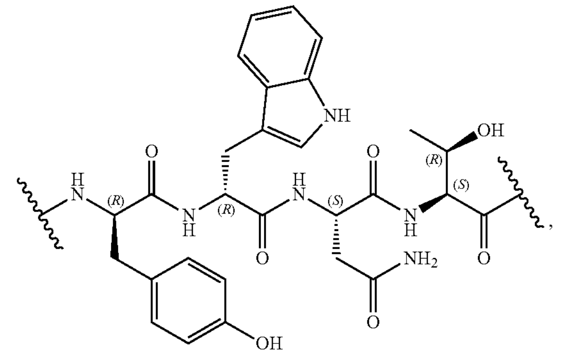
(SEQ ID NO: 2)
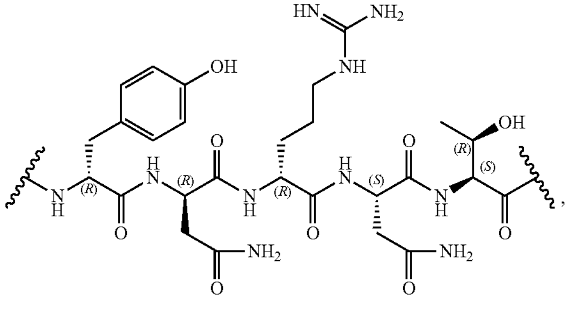
(SEQ ID NO: 3)
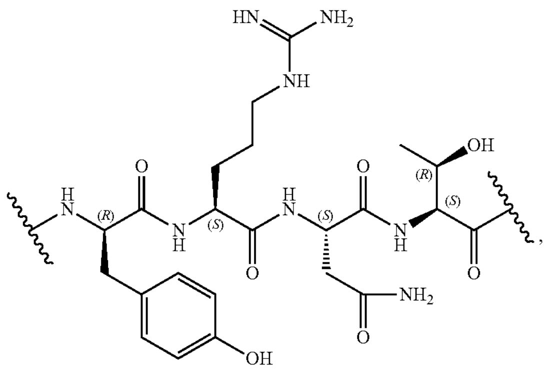
(SEQ ID NO: 4)
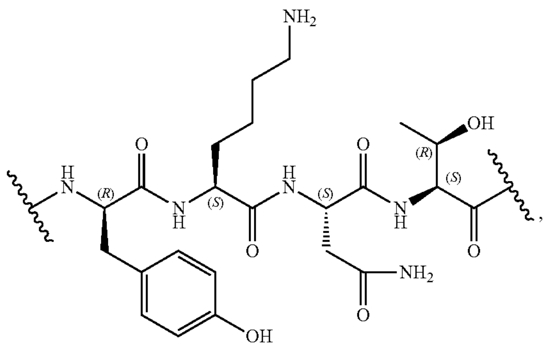
-continued
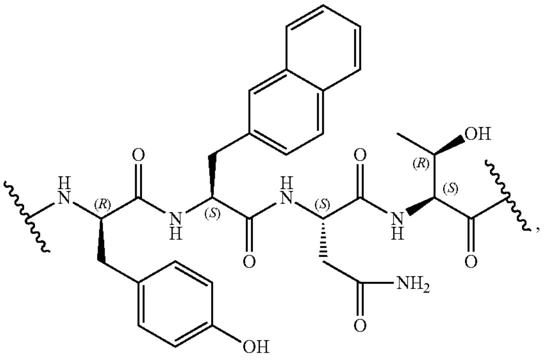
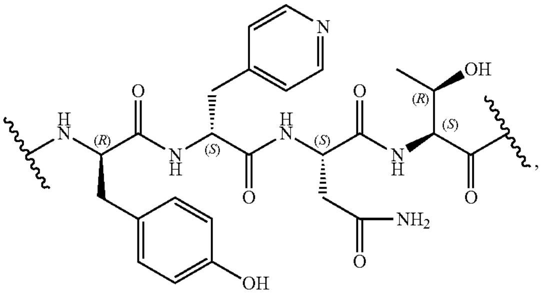
(SEQ ID NO: 7)
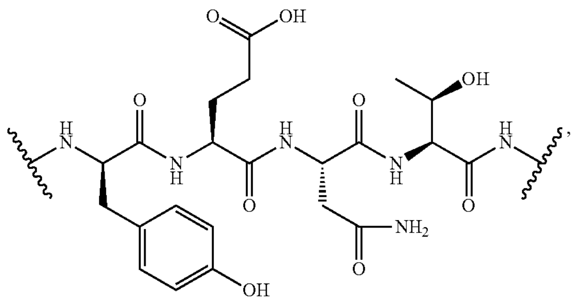
(SEQ ID NO: 8)
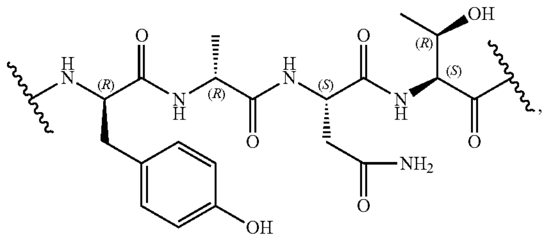
(SEQ ID NO: 9)
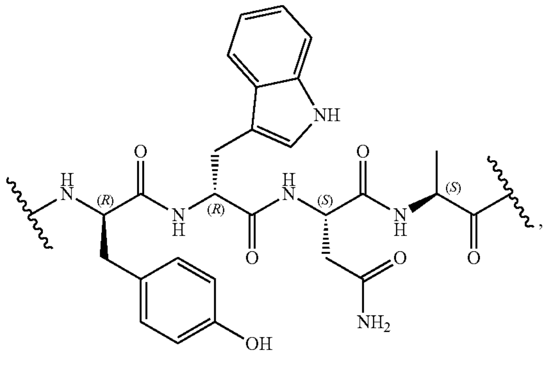

-continued
(SEQ ID NO: 10)
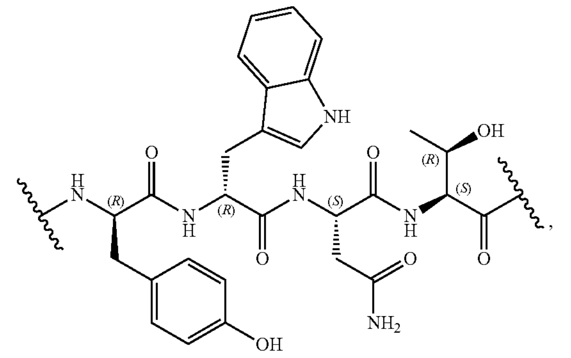
(SEQ ID NO: 11)
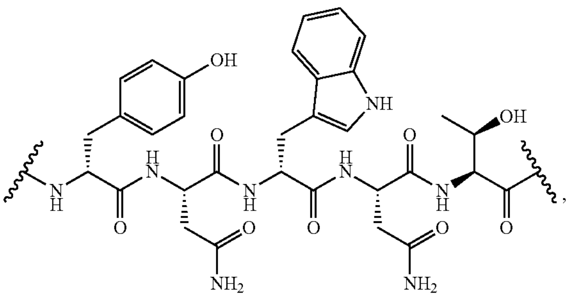
(SEQ ID NO: 12)
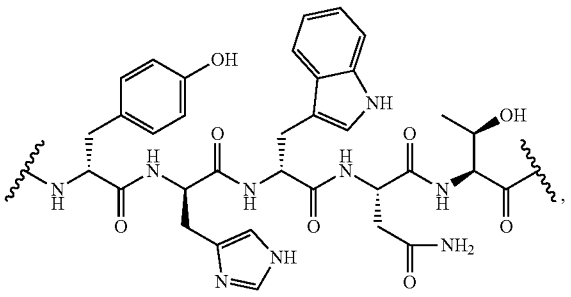
(SEQ ID NO: 13)
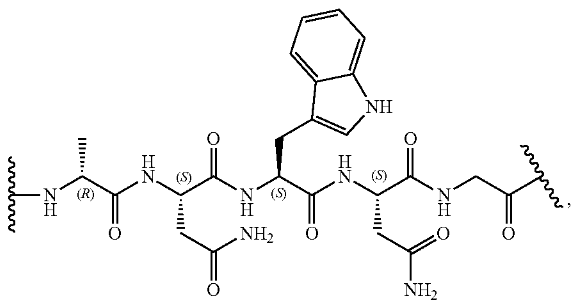
-continued
(SEQ ID NO: 14)
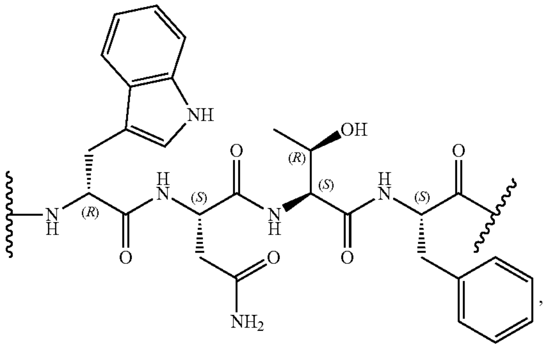
(SEQ ID NO: 15)
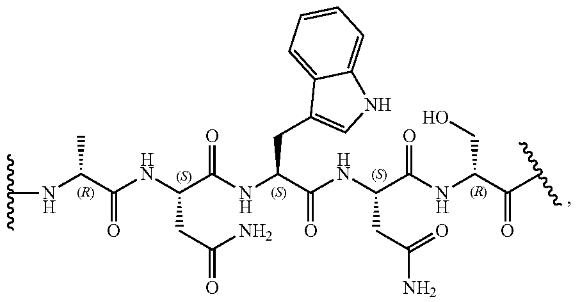
(SEQ ID NO: 16)
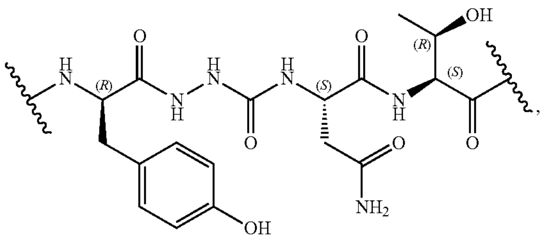
(SEQ ID NO: 17)
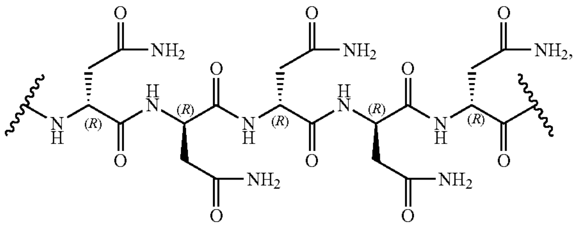
(SEQ ID NO: 18)
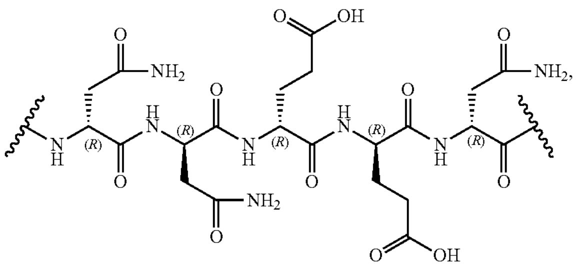

-continued
(SEQ ID NO: 19)
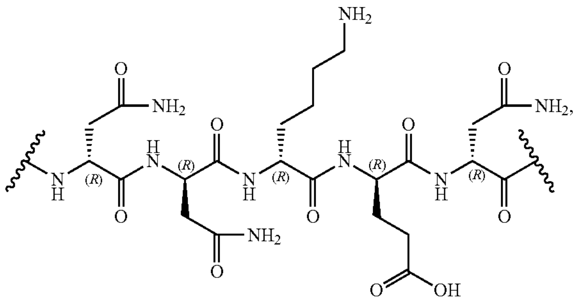
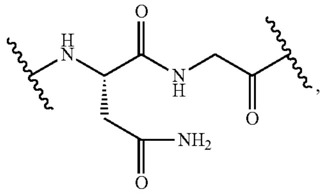
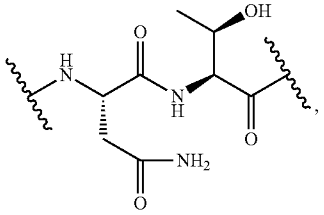
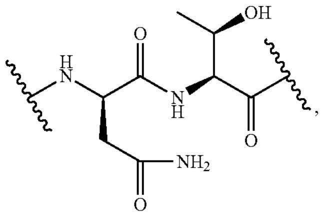
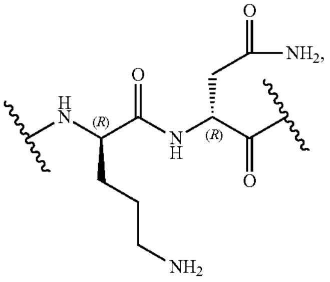
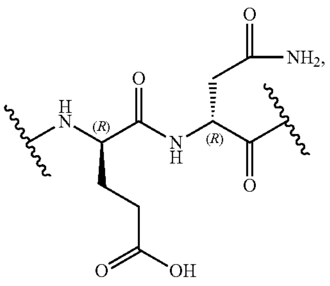
-continued
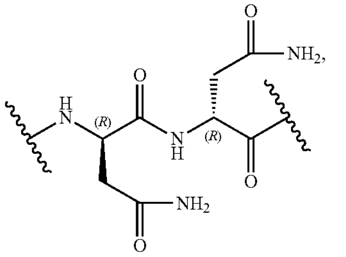
(SEQ ID NO: 20)
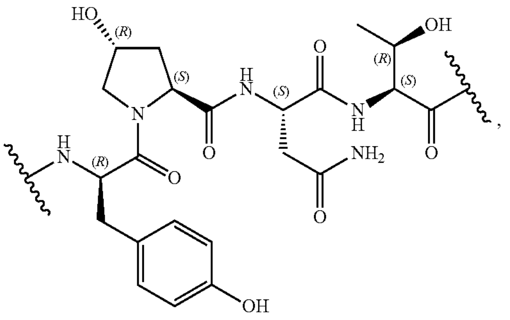
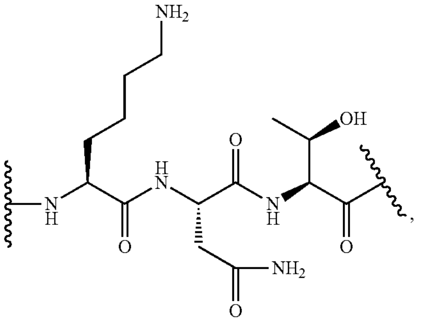
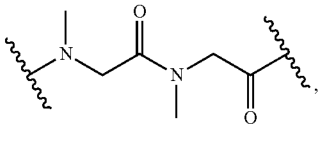
(SEQ ID NO: 24)
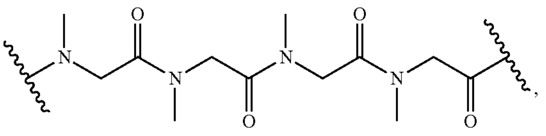
(SEQ ID NO: 25)
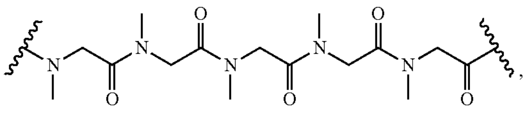
or
(SEQ ID NO: 26)
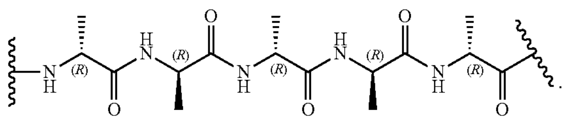
Embodiment 43. The compound of any one of embodiments 1-3, or a pharmaceutically acceptable salt thereof, wherein

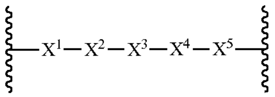

is absent, Asn-, -Lys-, -2-Pal-, -Thr-, -Trp-, -Asn-Asn-, -Asn-Gly-, -Asn-Thr-, -Glu-Asn-, -Glu-Thr-, -Lys-Asn-, -Lys(DOTA)-Asn-, -Lys-Thr-, -Lys(DOTA)-Thr-, -Lys-Glu-, -Lys(DOTA)-Glu-, -Sar-Sar-, -AAP-Asn-Thr, -Asn-Phe-Thr-, -Glu-Asn-Thr-, -D-Glu-Asn-Thr-, -bGlu-Asn-Thr-, -Gly-Tyr-Ahx-, -Lys-Asn-Thr-, -D-β-Nal-Asn-Thr-, -D-4Pal-Asn-Thr-, -Thr-Asn-Arg-, -Trp-Asn-Thr-, -D-Trp-Asn-Thr-, -D-Tyr-Asn-Thr-, -Lys-Asn-Thr-, -Lys(DOTA)-Asn-Thr-, -Gly-Tyr-β-Nal-Ahx-, -Lys-Trp-Asn-Thr- (SEQ ID NO: 28), -Phe(4-I)-Trp-Asn-Thr- (SEQ ID NO: 29), -D-Phe(4-I)-D-Trp-Asn-Thr- (SEQ ID NO: 30), -Sar-Sar-Sar-Sar- (SEQ ID NO: 24), D-Trp-Asn-Thr-Phe-(SEQ ID NO: 14), -D-Tyr-AAP-Asn-Thr-, -D-Tyr-Arg-Asn-Thr- (SEQ ID NO: 3), -D-Tyr-D-Ala-Asn-Thr-(SEQ ID NO: 8), -Tyr-AzaGly-Asn-Thr- (SEQ ID NO: 32), -D-Tyr-AzaGly-Asn-Thr-(SEQ ID NO: 16), -D-Tyr-Bip-Asn-Thr-, -D-Tyr-Bpa-Asn-Thr-, -D-Tyr-Glu-Asn-Thr-(SEQ ID NO: 7), -D-Tyr-Hyp-Asn-Thr-, -D-Tyr-D-Hyp-Asn-Thr-, -Tyr-Hyp-Asn-Thr-, -D-Tyr-Lys-Asn-Thr- (SEQ ID NO: 4), -D-Tyr-Lys(DOTA)-Asn-Thr- (SEQ ID NO: 38), 1H10-$(CH_2CH_2O)_2$—$CH_2C(=O)$-D-Tyr-Lys(DOTA)-Asn-Thr- (SEQ ID NO: 21), -Tyr-D-Lys-Asn-Thr-, -Tyr-D-Lys(DOTA)-Asn-Thr- (SEQ ID NO: 39), -D-Tyr-D-Lys-Asn-Thr-, -D-Tyr-D-Lys(DOTA)-Asn-Thr-(SEQ ID NO: 40), -Tyr-β-Nal-Asn-Thr-, -D-Tyr-β-Nal-Asn-Thr-, -D-Tyr-D-β-Nal-Asn-Thr-, -Tyr-4Pal-Asn-Thr-, -D-Tyr-4Pal-Asn-Thr-, -D-Tyr-D-4Pal-Asn-Thr-, -D-Tyr-Phe(4-I)-Asn-Thr- (SEQ ID NO: 45), -Tyr-Pro-Asn-Thr- (SEQ ID NO: 46), -D-Tyr-Pro-Asn-Thr-(SEQ ID NO: 20), D-Tyr-Trp-Asn-Ala- (SEQ ID NO: 9), -D-Tyr-D-Trp-Asn-Ala-(SEQ ID NO: 47), -D-Tyr-Trp-Asn-Thr- (SEQ ID NO: 10), -D-Tyr-D-Trp-Asn-Thr- (SEQ ID NO: 1), -D-Ala-D-Ala-D-Ala-D-Ala-D-Ala- (SEQ ID NO: 26), D-Ala-Asn-Trp-Asn-Gly- (SEQ ID NO: 13), D-Ala-Asn-Trp-Asn-D-Ser (SEQ ID NO: 15), -D-Asn-D-Asn-D-Asn-D-Asn-D-Asn-(SEQ ID NO: 17), -D-Asn-D-Asn-D-Glu-D-Glu-D-Asn- (SEQ ID NO: 18), -D-Asn-D-Asn-D-Lys-D-Glu-D-Asn-(SEQ ID NO: 19), -γ-D-Glu-D-Tyr-Lys(DOTA)-Asn-Tin- (SEQ ID NO: 48) -Gly-D-Tyr-β-Nal-Asn-Thr- (SEQ ID NO: 49), -Gly-Tyr-D-Trp-Asn-Thr- (SEQ ID NO: 50), -Sar-Sar-Sar-Sar-Sar- (SEQ ID NO: 25), -Tyr-Asn-Trp-Asn-Ser- (SEQ ID NO: 51), -D-Tyr-D-Asn-D-Arg-Asn-Thr-(SEQ ID NO: 2), -D-Tyr-Asn-D-Trp-Asn-Thr (SEQ ID NO: 11), -Tyr-Glu-Asn-Thr-3-F-Phe- (SEQ ID NO: 52), -D-Tyr-D-His-D-Trp-Asn-Thr- (SEQ ID NO: 12), -Tyr-D-Trp-Asn-Thr-3-F-Phe- (SEQ ID NO: 53), -D-Tyr-D-Trp-Asn-Thr-3-F-Phe- (SEQ ID NO: 54), Palmitic Acid-γGlu-Lys(DOTA)-Tyr-Asn-Trp-Asn-Ser- (SEQ ID NO: 846), or Ac-γGlu-Lys(DOTA )-D-Ala-Asn-Trp-Asn-Gly- (SEQ ID NO: 23).

Embodiment 44. The compound of embodiment 1, or a pharmaceutically acceptable salt, thereof, wherein:

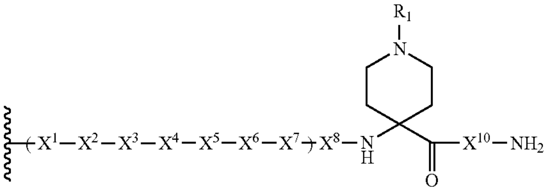

is (SEQ ID NO: 55)

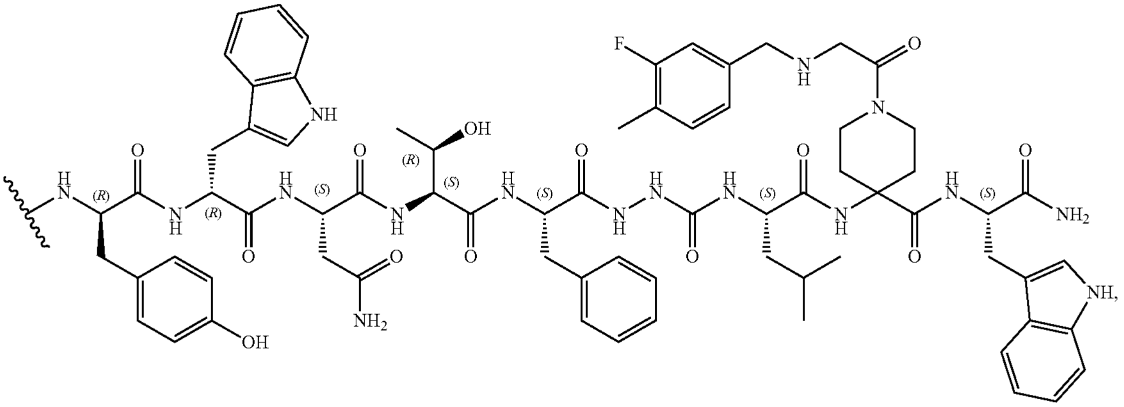

-continued
(SEQ ID NO: 56)
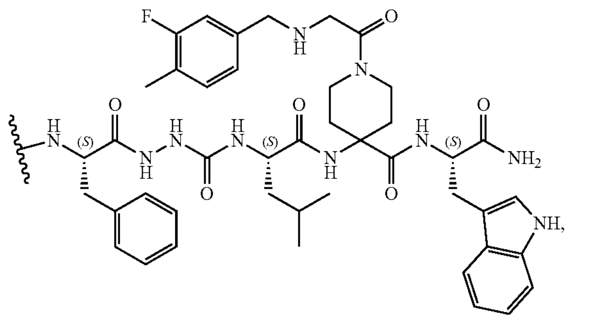
(SEQ ID NO: 57)
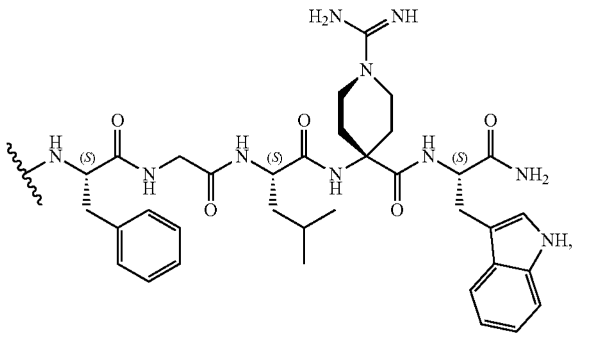
(SEQ ID NO: 58)
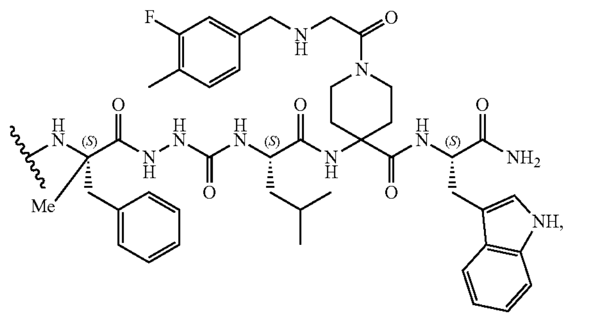
(SEQ ID NO: 59)
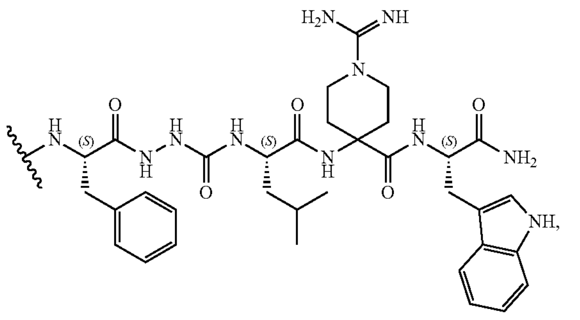
(SEQ ID NO: 60)
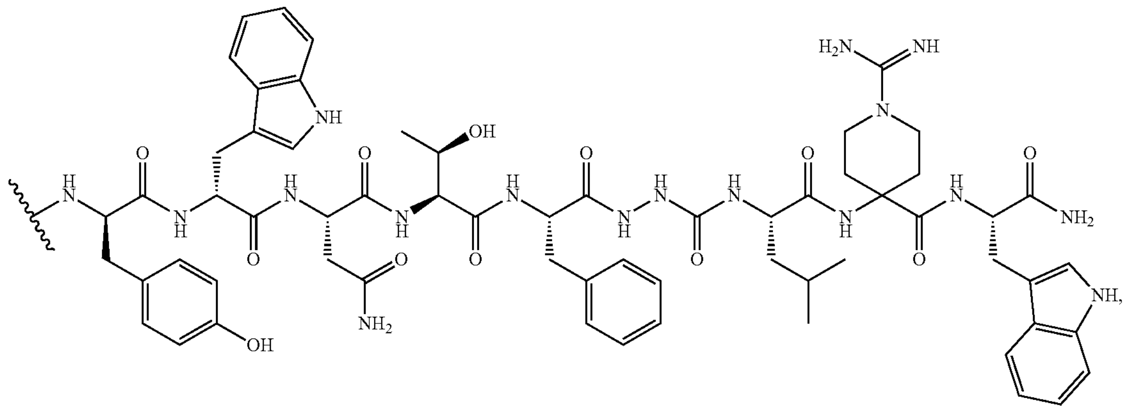
(SEQ ID NO: 61)
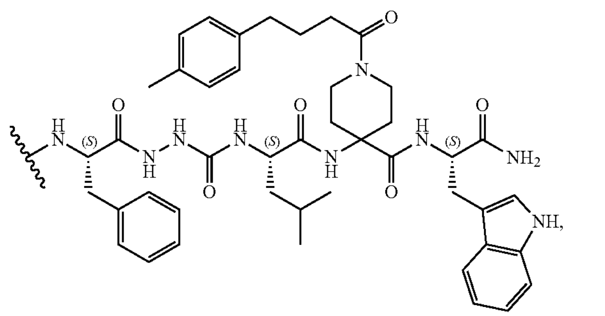
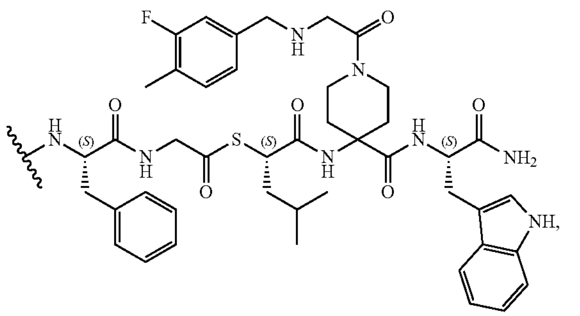

-continued
(SEQ ID NO: 63)
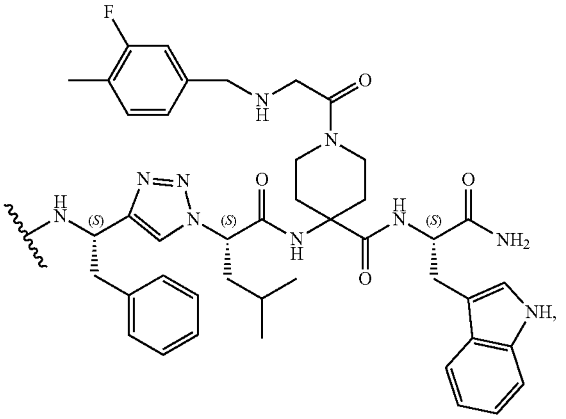
(SEQ ID NO: 64)
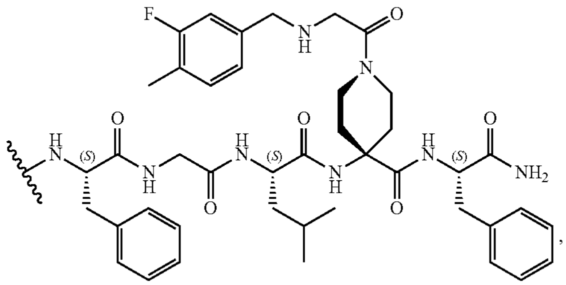
(SEQ ID NO: 65)
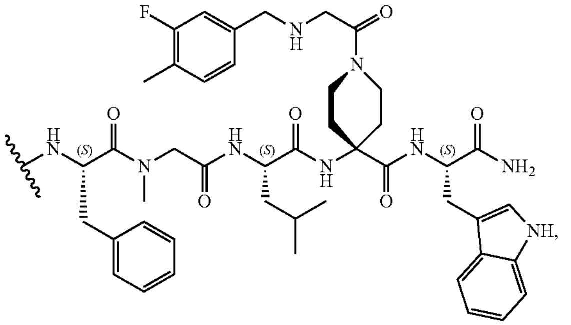
(SEQ ID NO: 65)
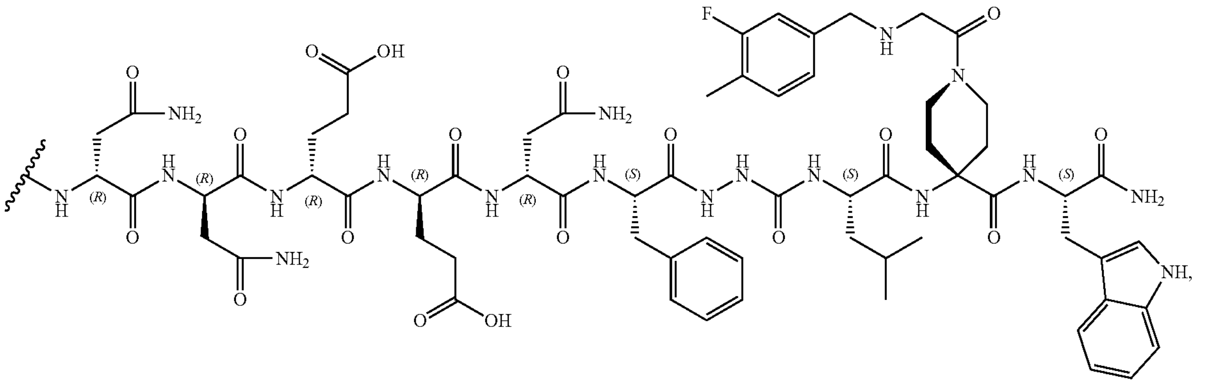
(SEQ ID NO: 66)
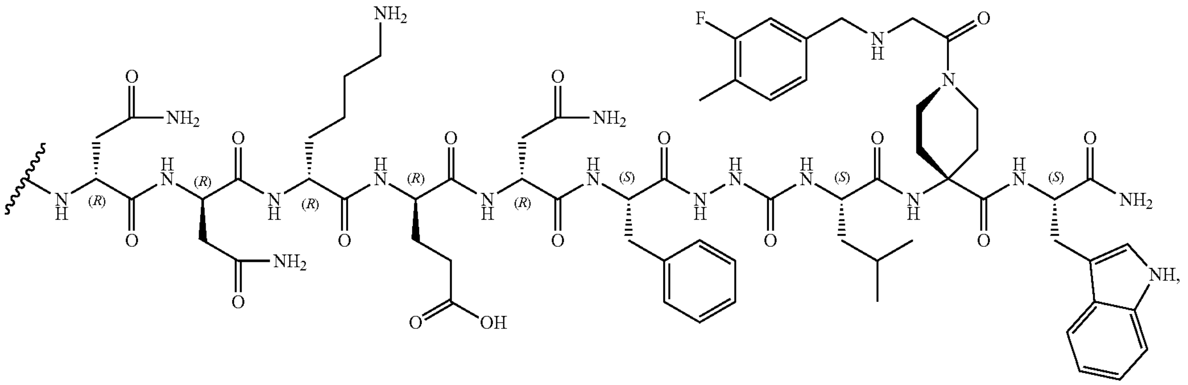

-continued
(SEQ ID NO: 67)
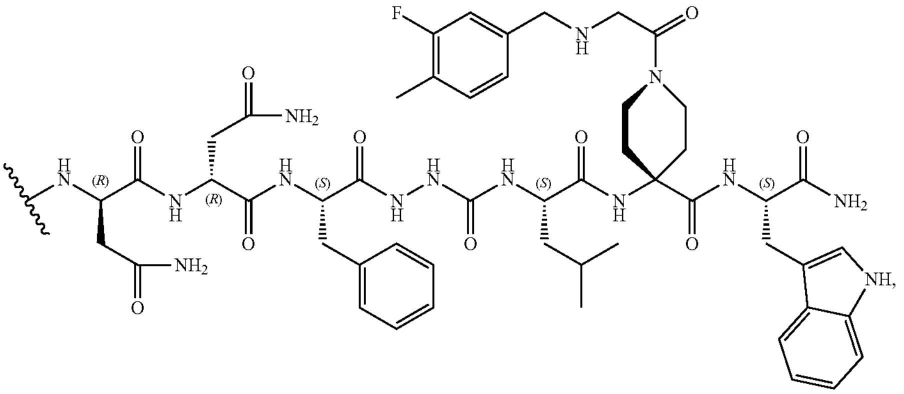
(SEQ ID NO: 68)
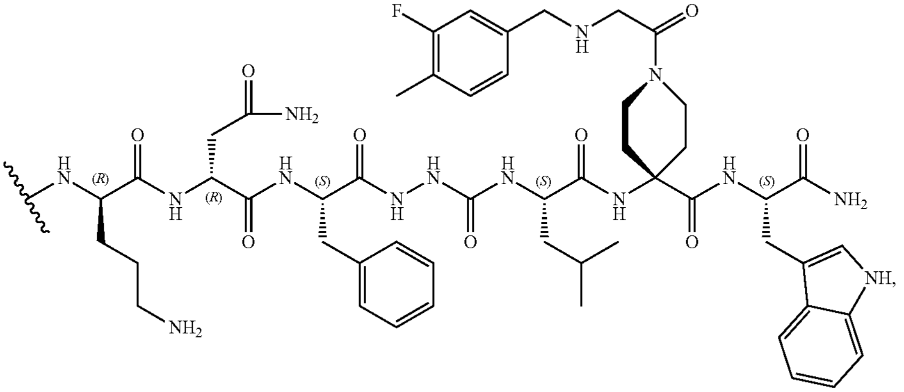
(SEQ ID NO: 69)
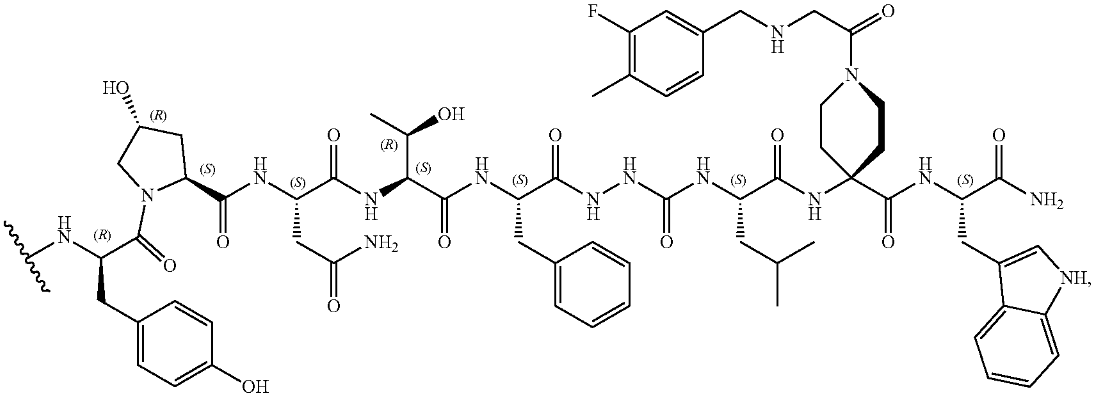
(SEQ ID NO: 70)
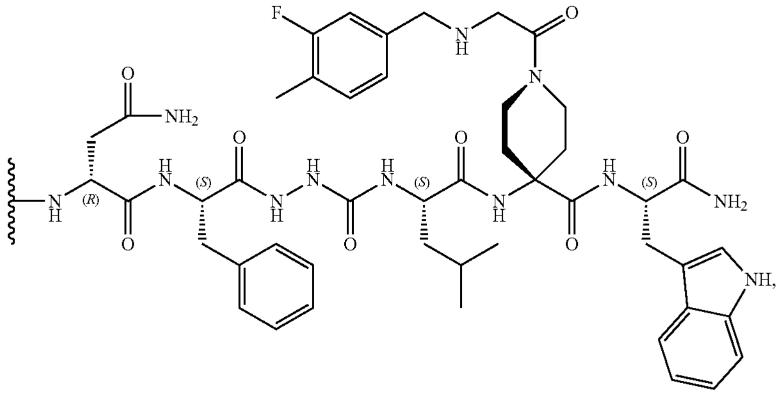

-continued
(SEQ ID NO: 71)
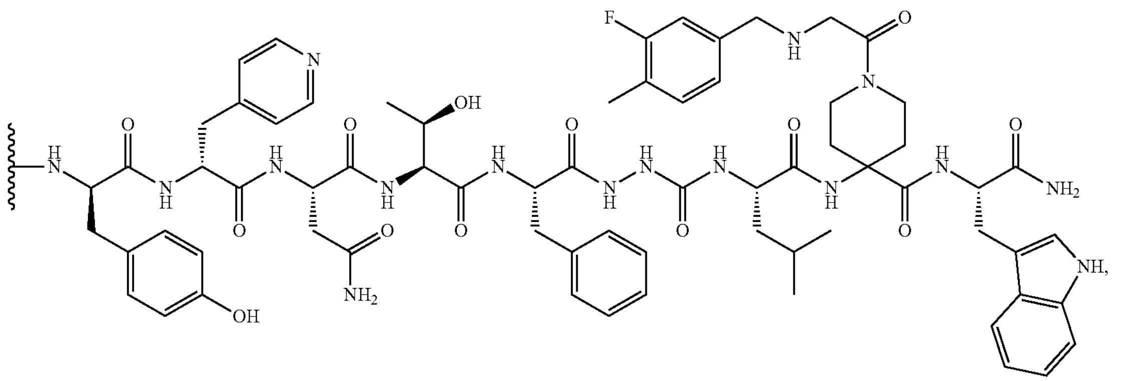
(SEQ ID NO: 72)
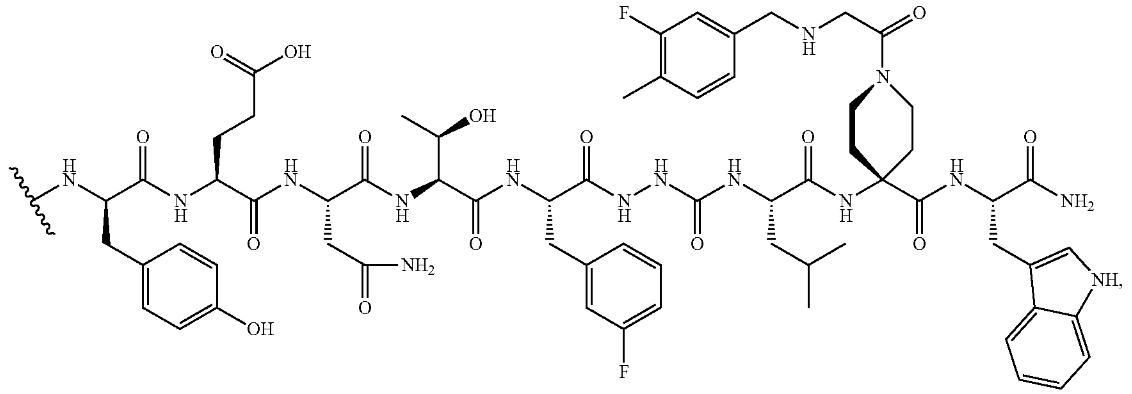
(SEQ ID NO: 73)
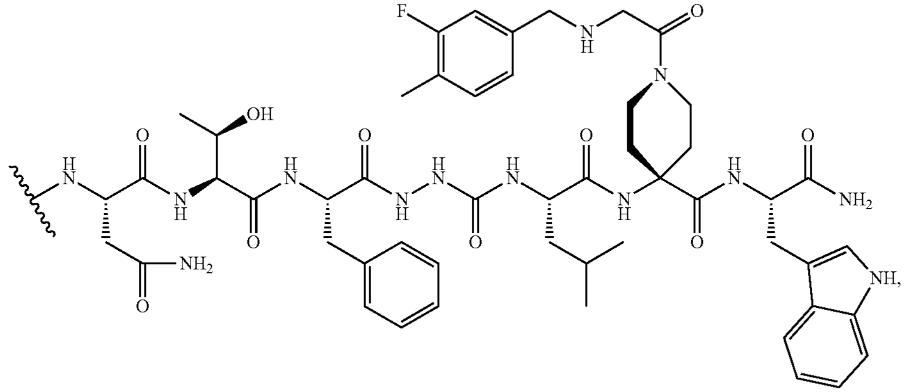
(SEQ ID NO: 74)
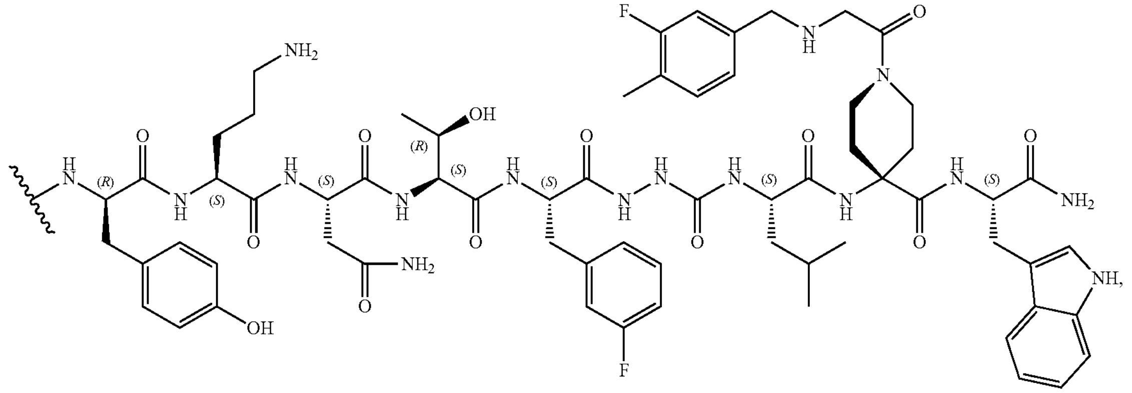

-continued
(SEQ ID NO: 75)
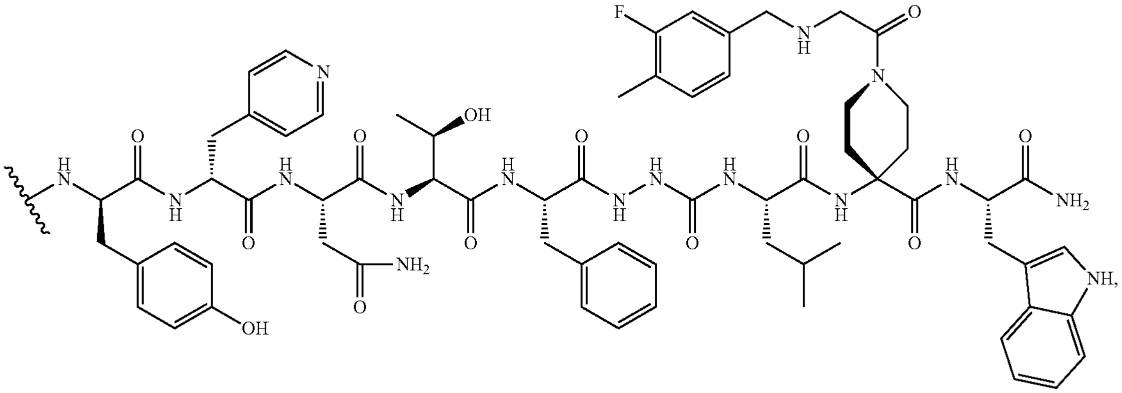
(SEQ ID NO: 76)
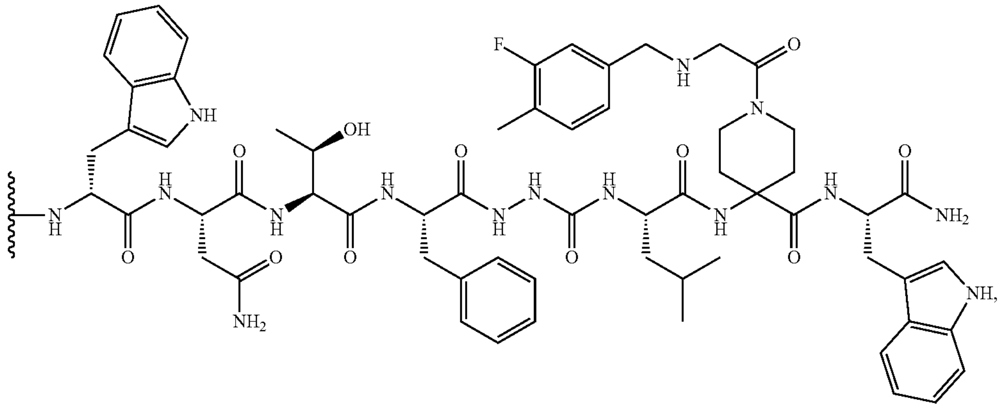
(SEQ ID NO: 77)
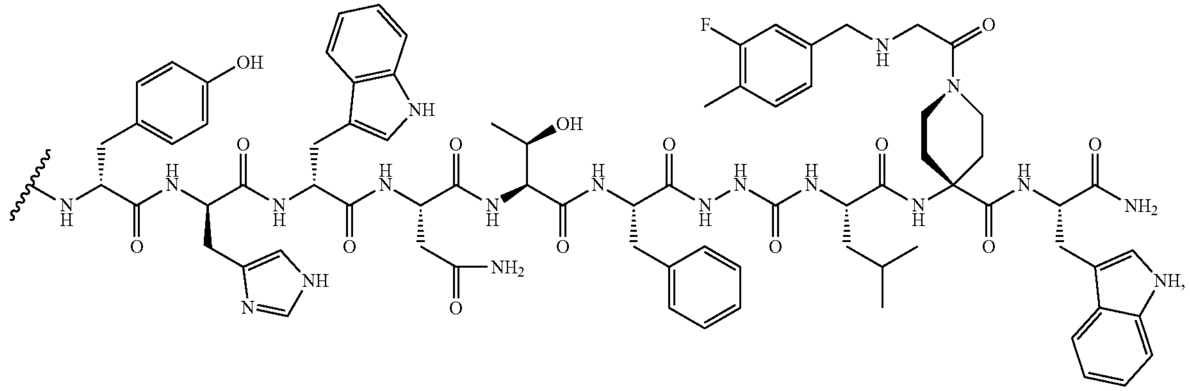

-continued
(SEQ ID NO: 78)
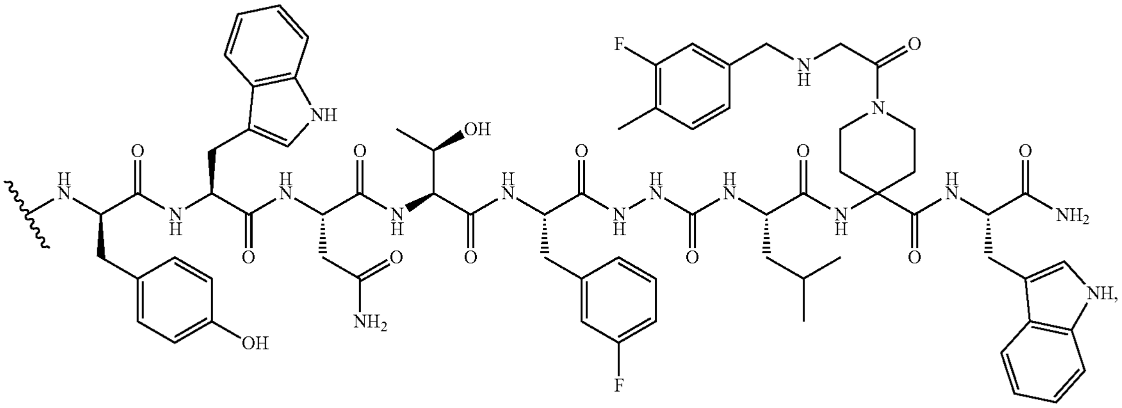
(SEQ ID NO: 79)
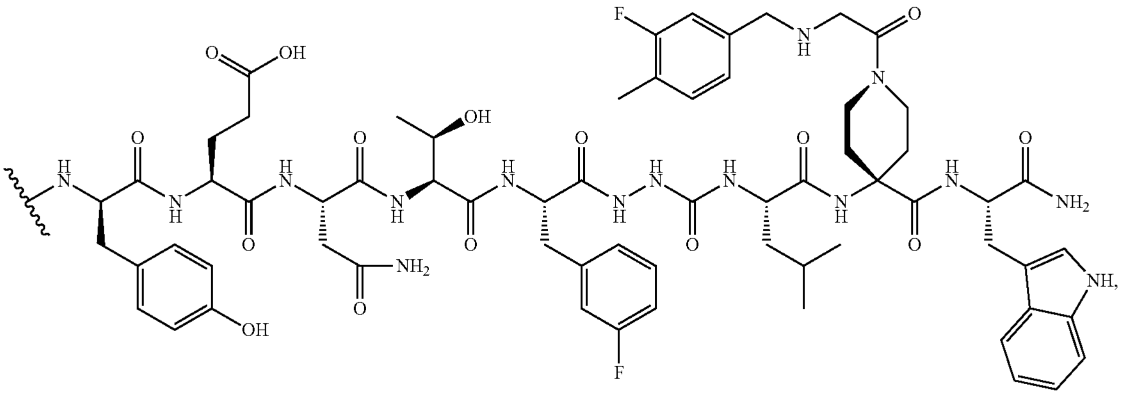
(SEQ ID NO: 80)
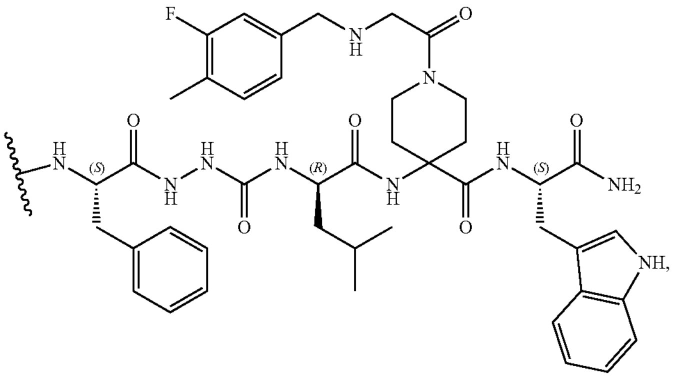
(SEQ ID NO: 81)
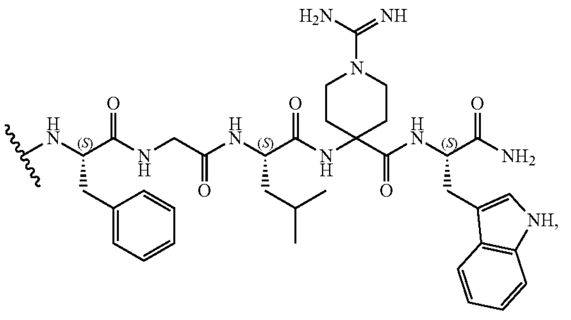
(SEQ ID NO: 82)
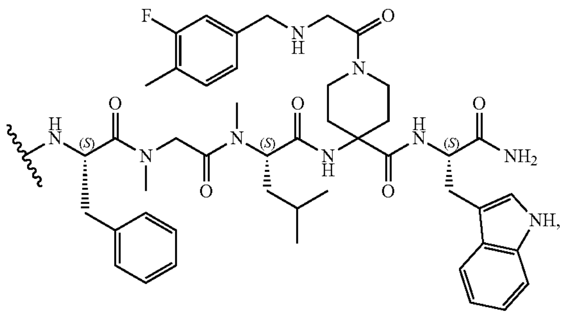

-continued
(SEQ ID NO: 83)
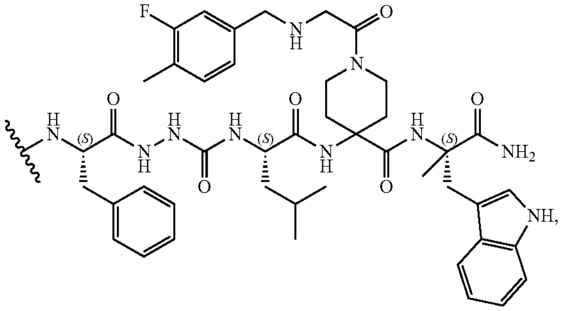
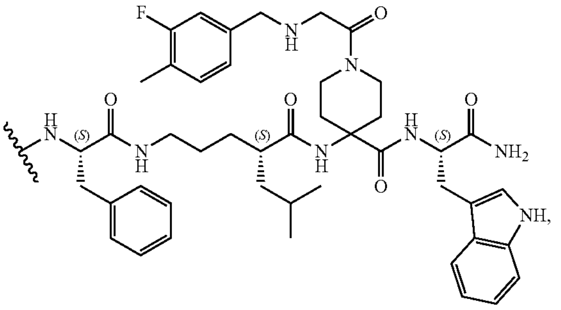
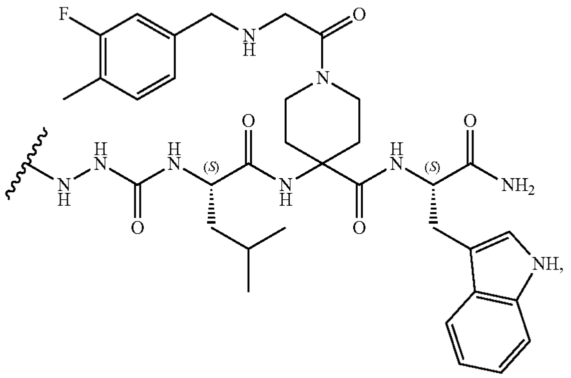
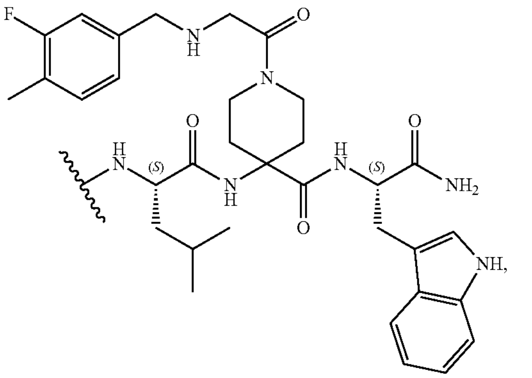
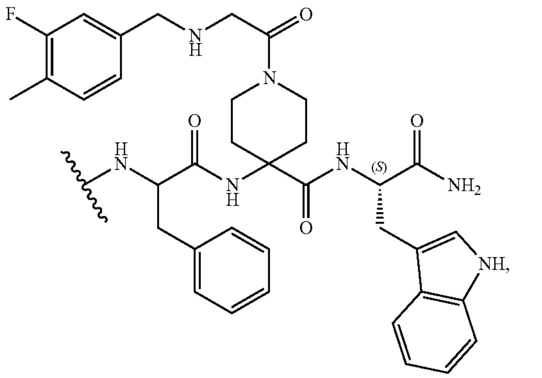
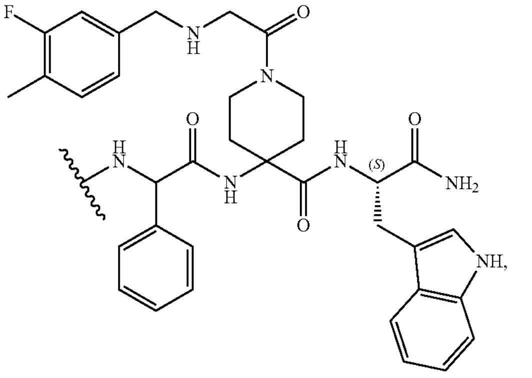
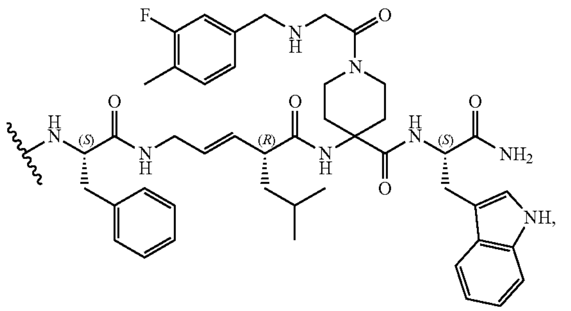

-continued
(SEQ ID NO: 87)
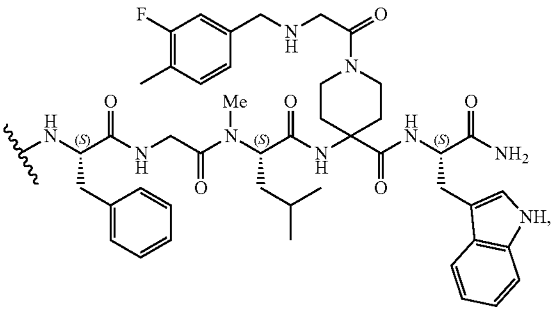
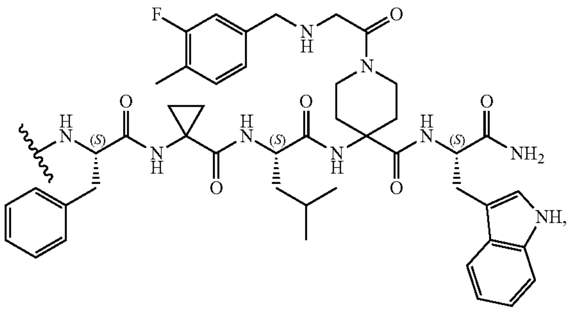
(SEQ ID NO: 89)
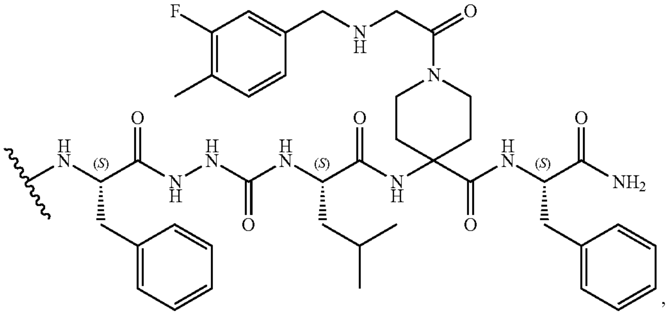
(SEQ ID NO: 90)
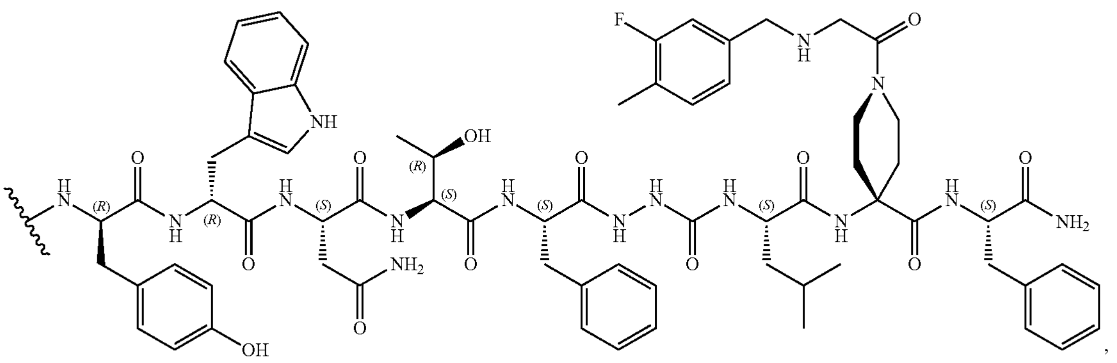
(SEQ ID NO: 91)
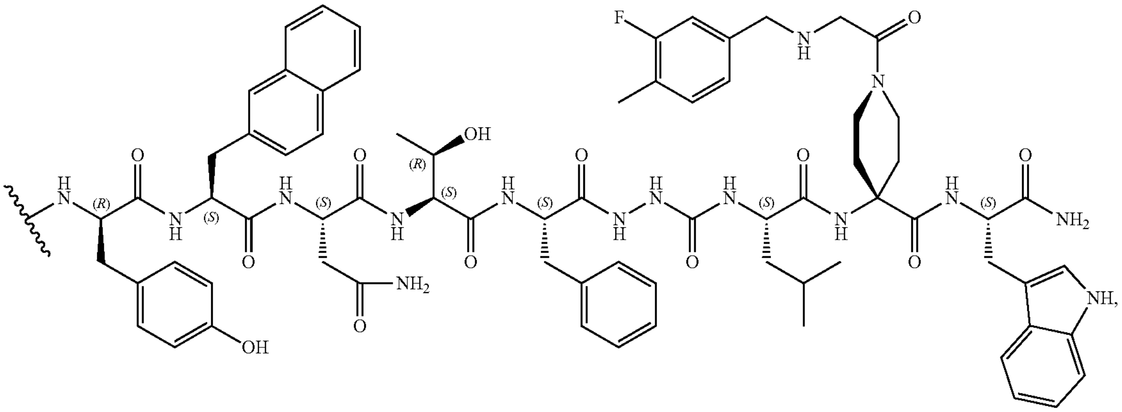

-continued
(SEQ ID NO: 92)
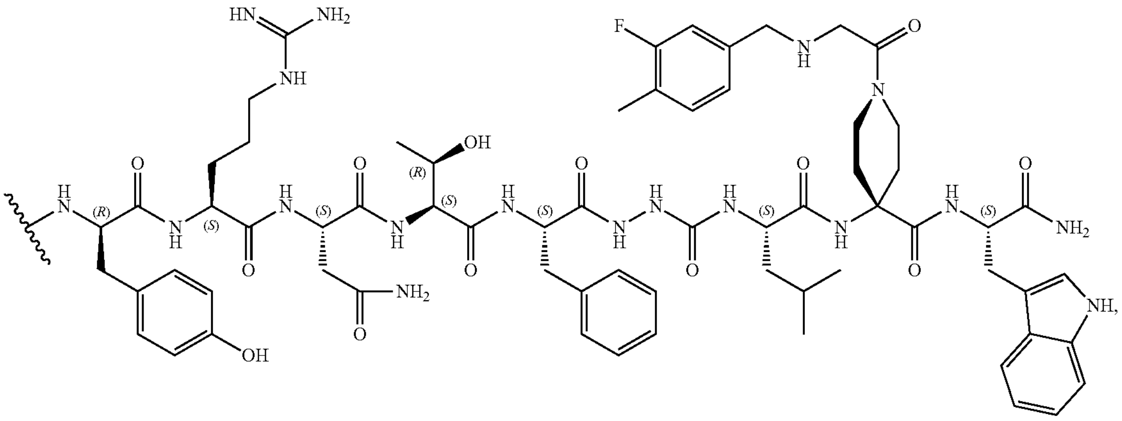
(SEQ ID NO: 93)
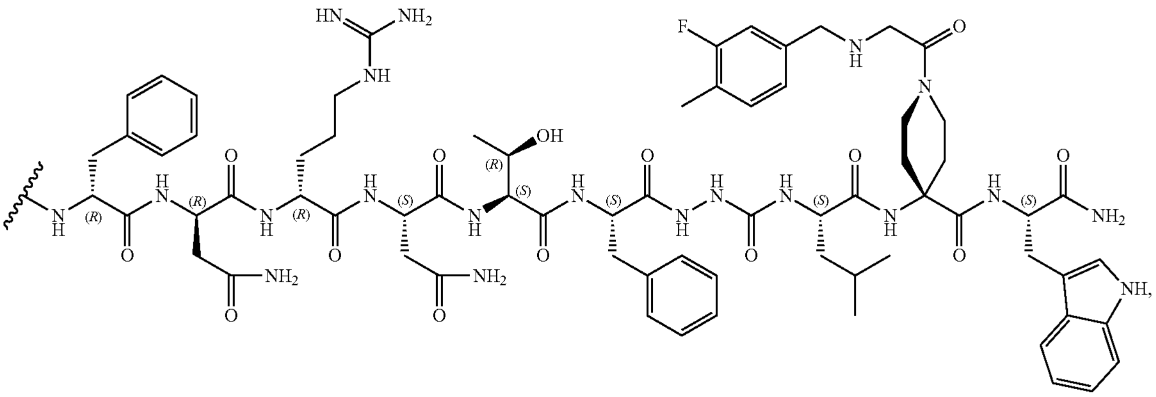
(SEQ ID NO: 94)
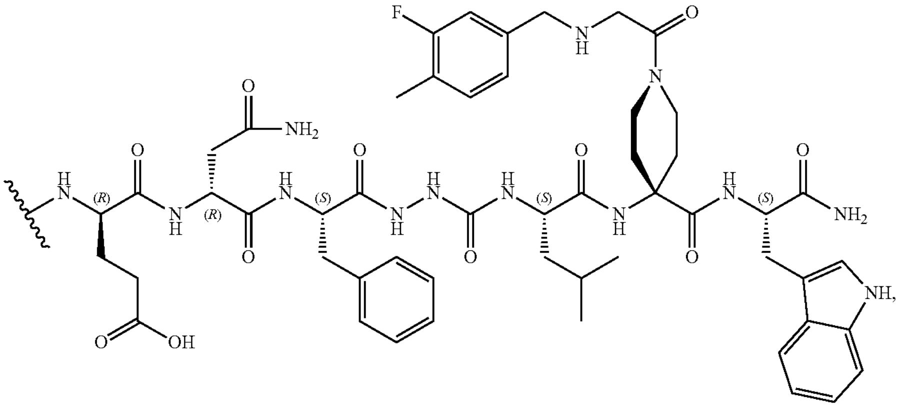

-continued
(SEQ ID NO: 95)
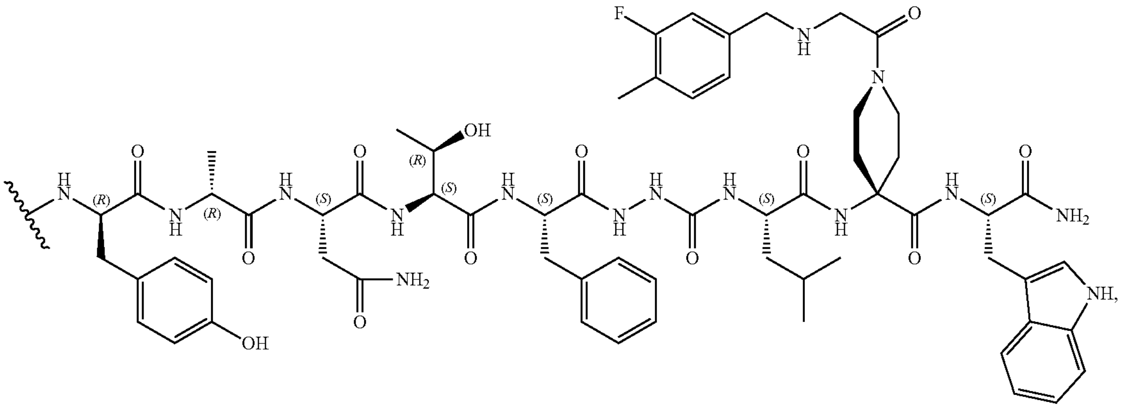
(SEQ ID NO: 96)
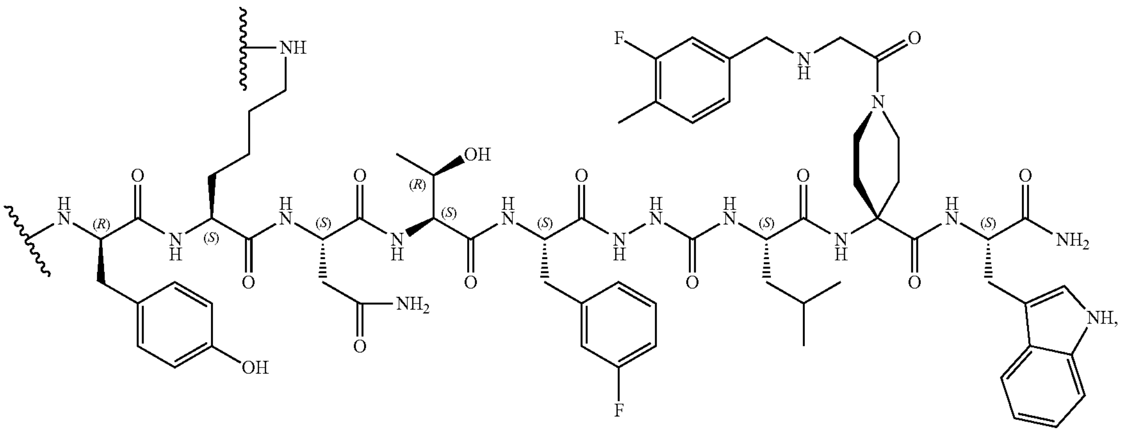
(SEQ ID NO: 97)
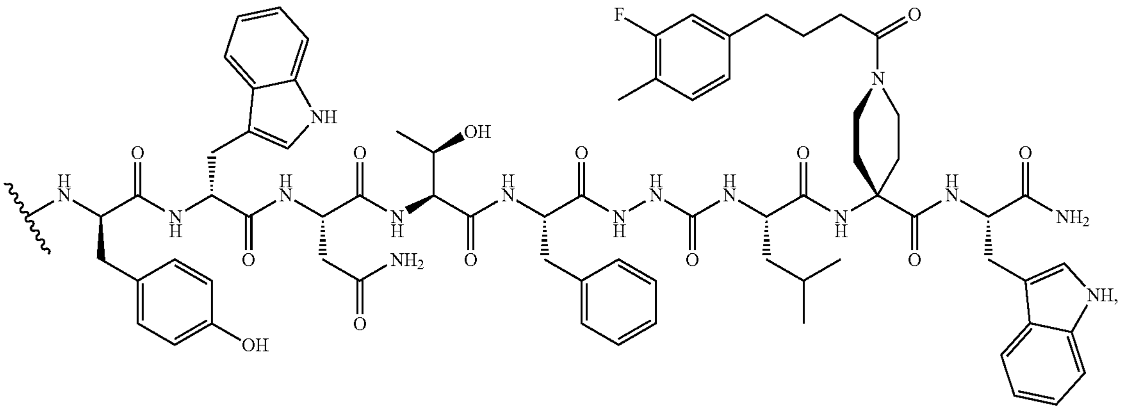

-continued
(SEQ ID NO: 98)
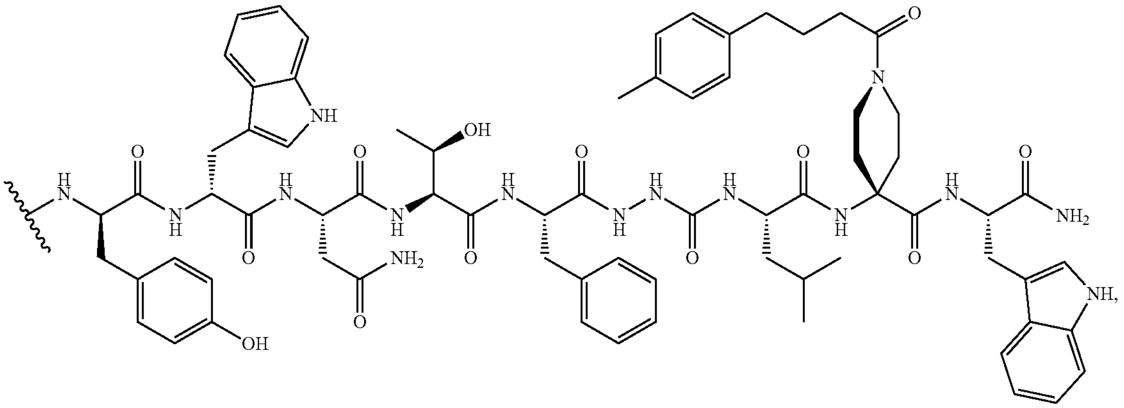
(SEQ ID NO: 99)
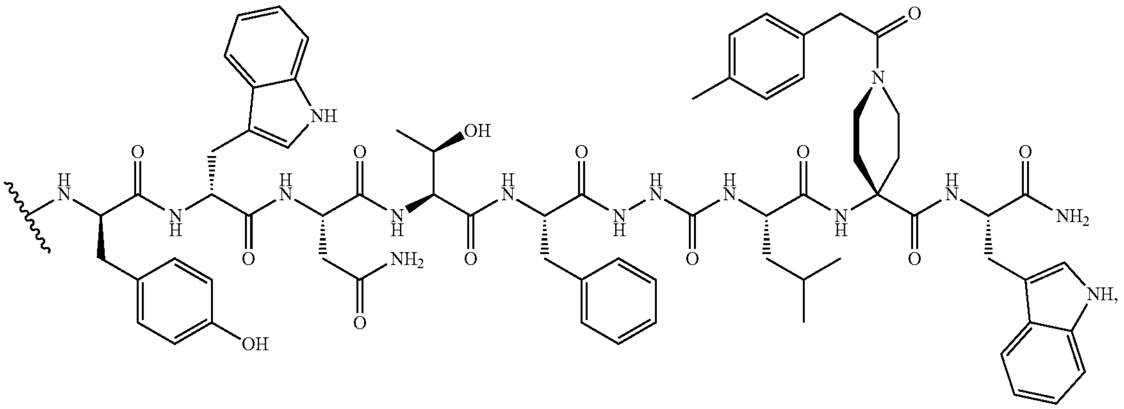
(SEQ ID NO: 100)
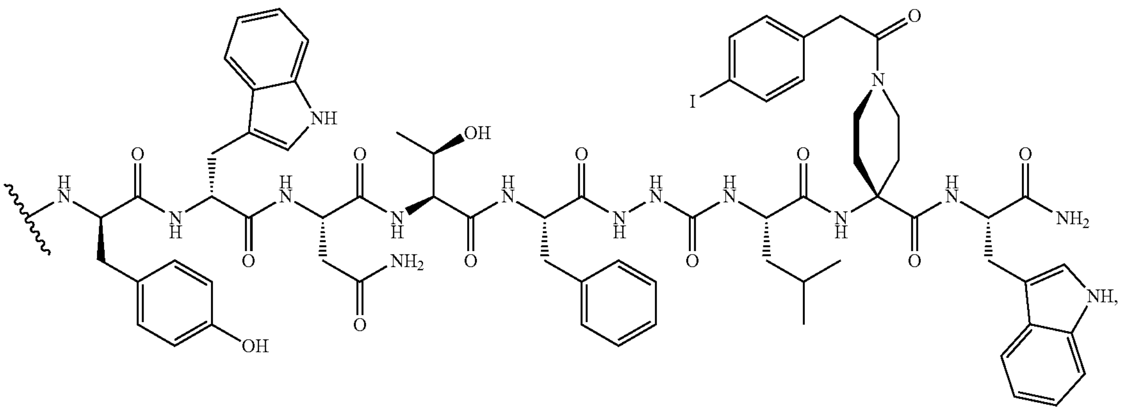

-continued
(SEQ ID NO: 101)
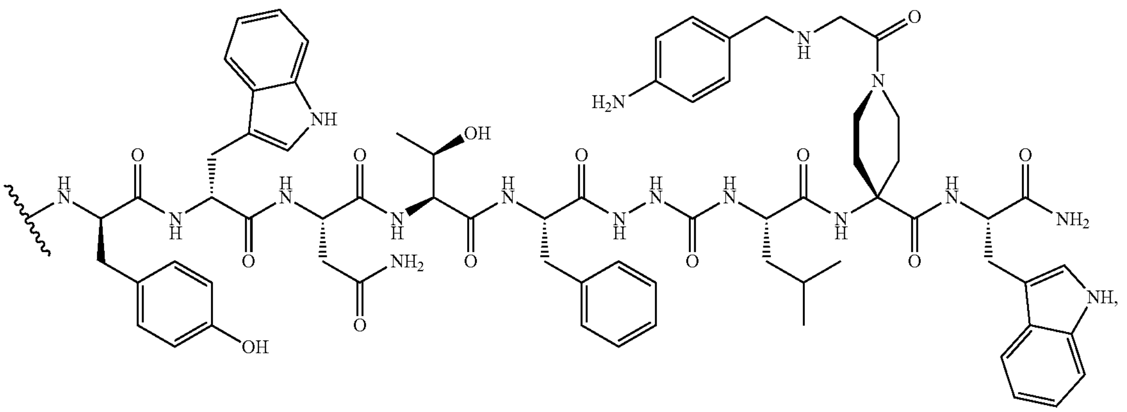
(SEQ ID NO: 102)
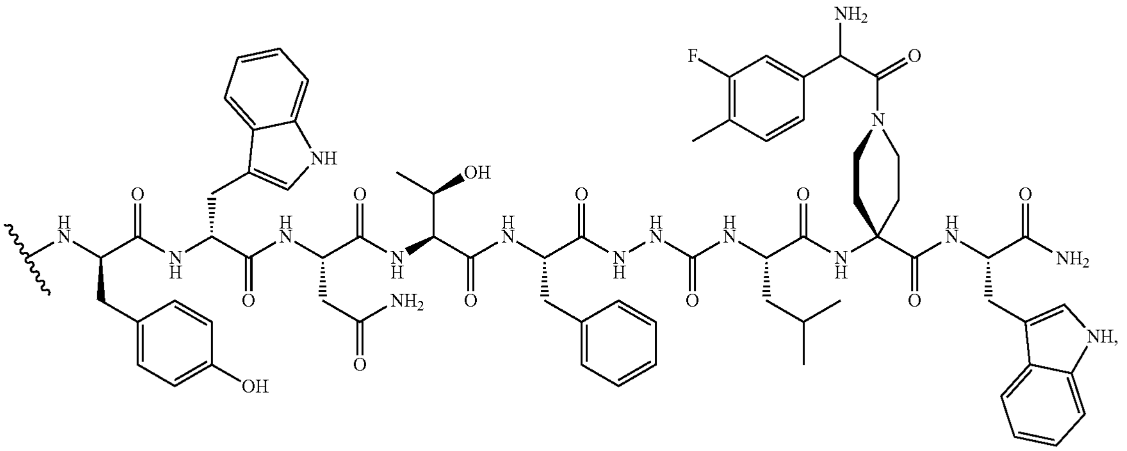
(SEQ ID NO: 103)
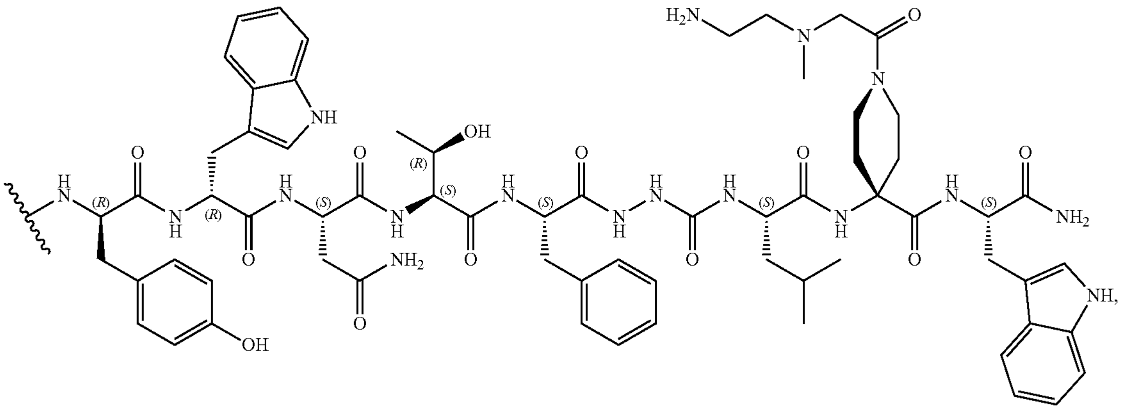

-continued
(SEQ ID NO: 104)
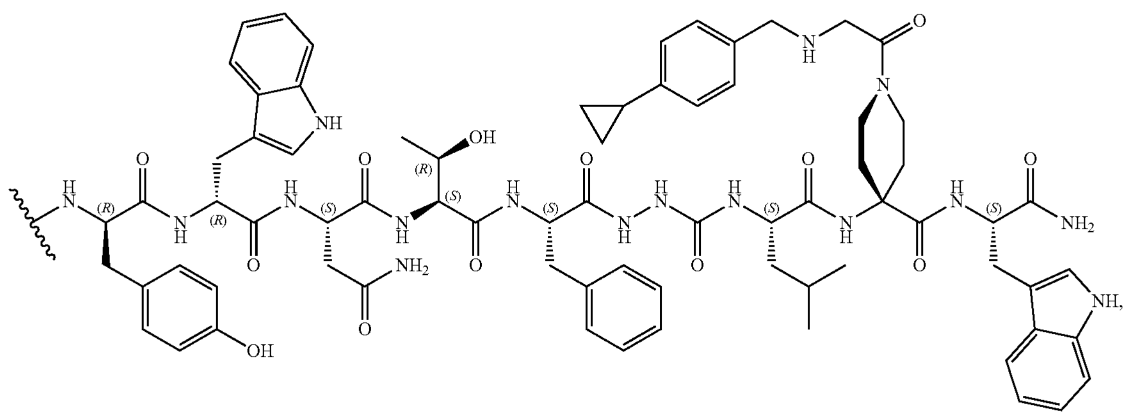
(SEQ ID NO: 105)
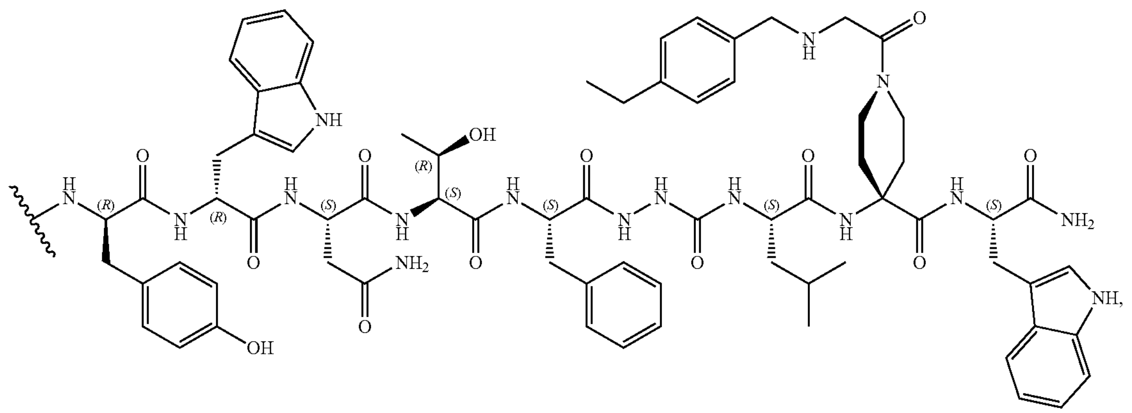
(SEQ ID NO: 106)
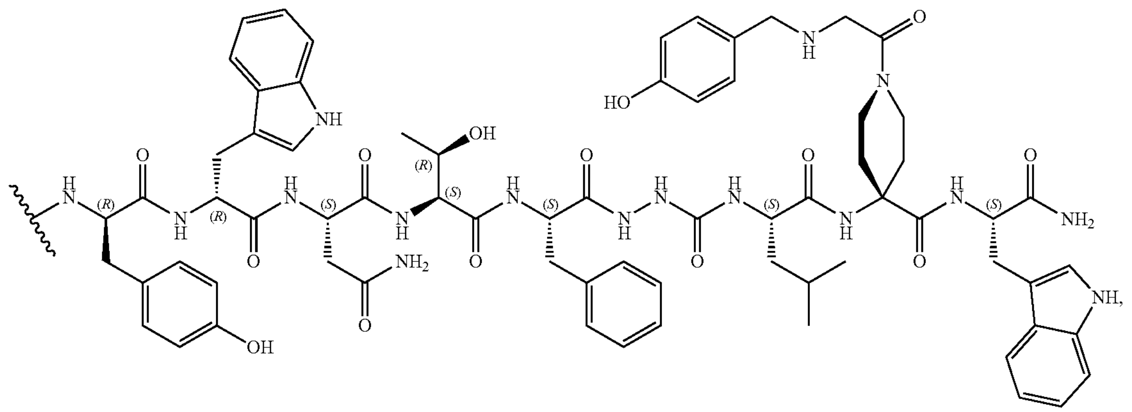

-continued
(SEQ ID NO: 107)
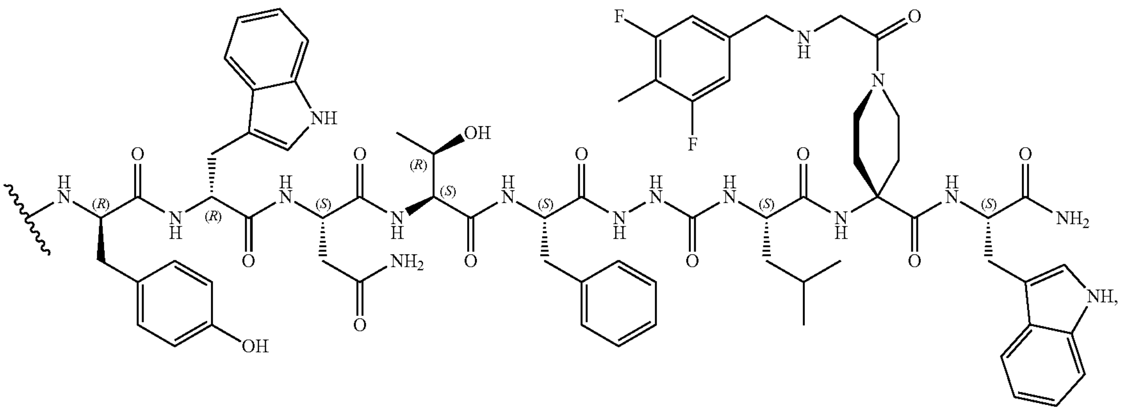
(SEQ ID NO: 108)
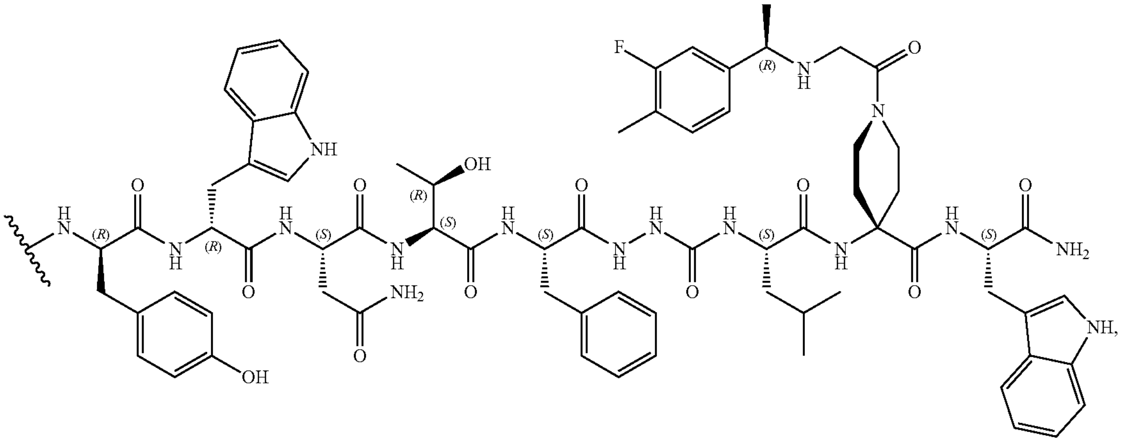
(SEQ ID NO: 109)
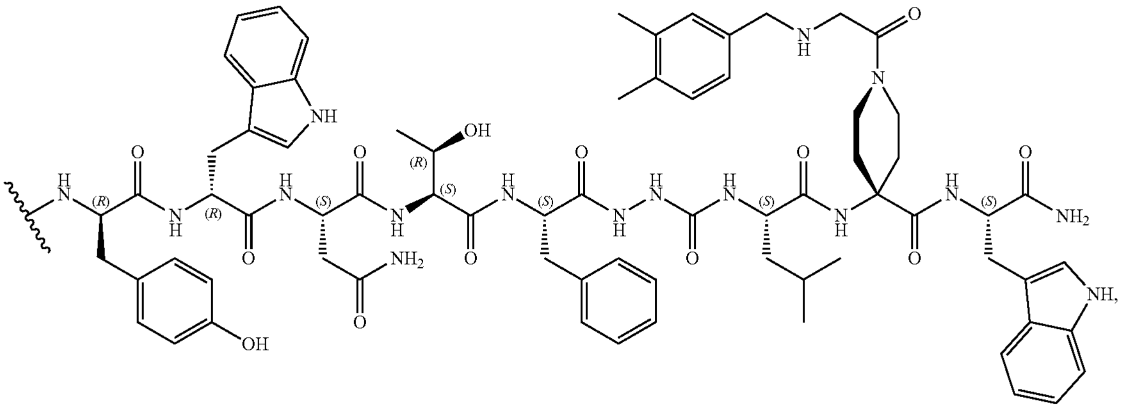

-continued
(SEQ ID NO: 110)
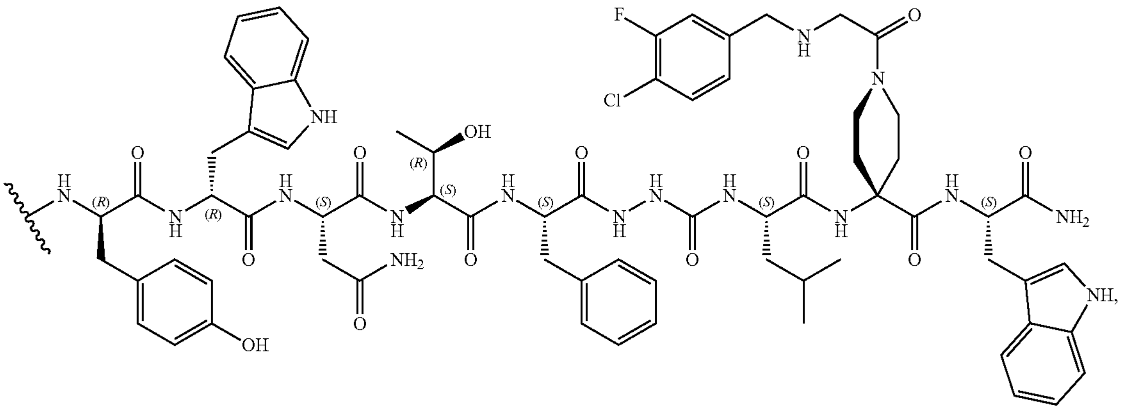
(SEQ ID NO: 111)
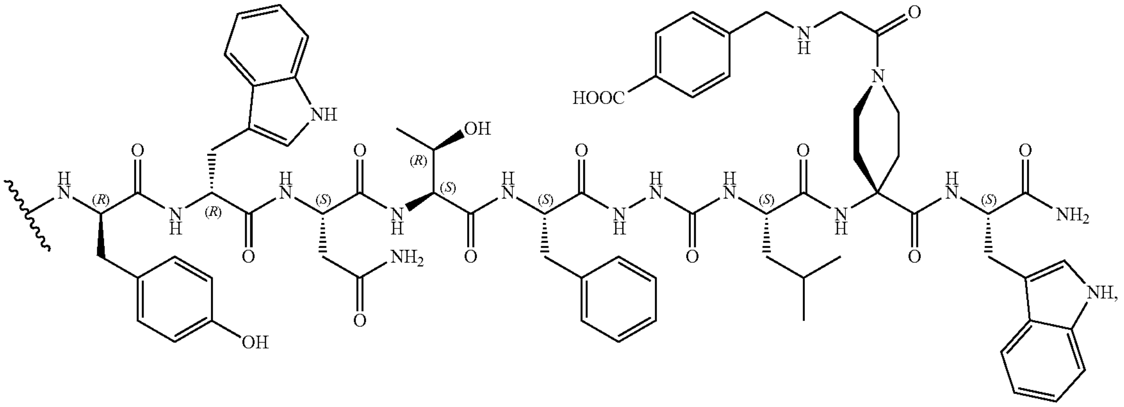
(SEQ ID NO: 112)
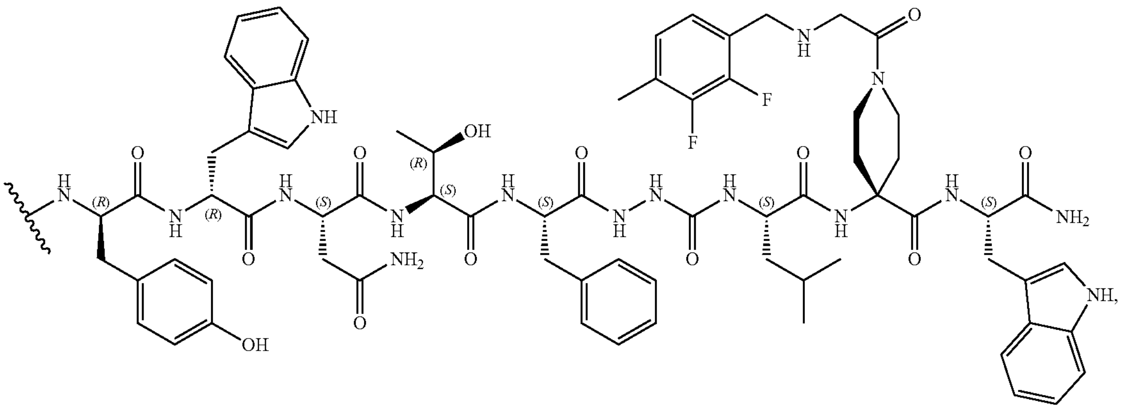

-continued
(SEQ ID NO: 113)
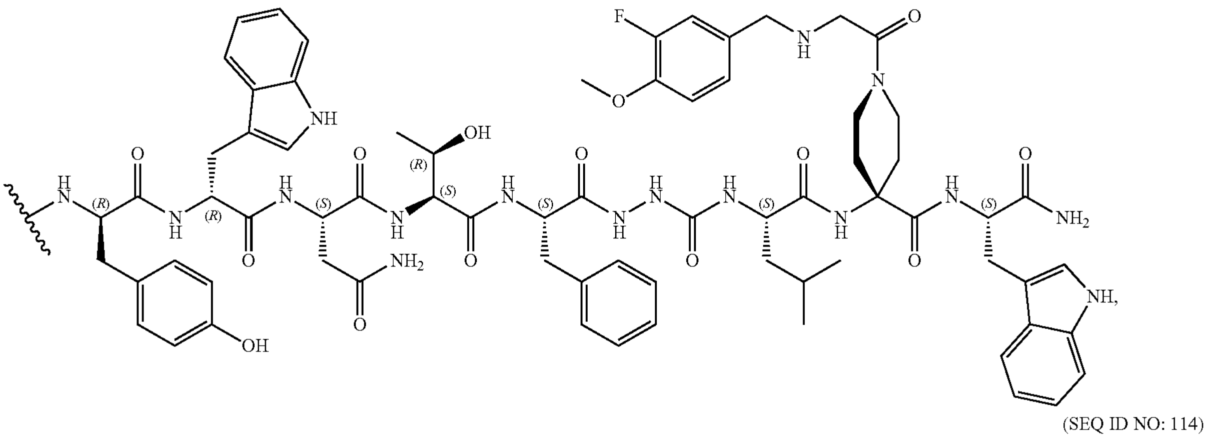
(SEQ ID NO: 114)
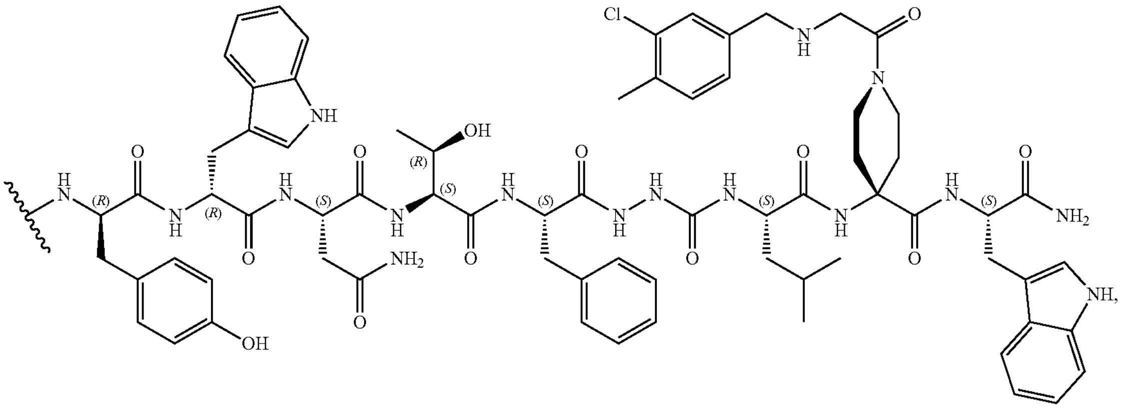
(SEQ ID NO: 115)
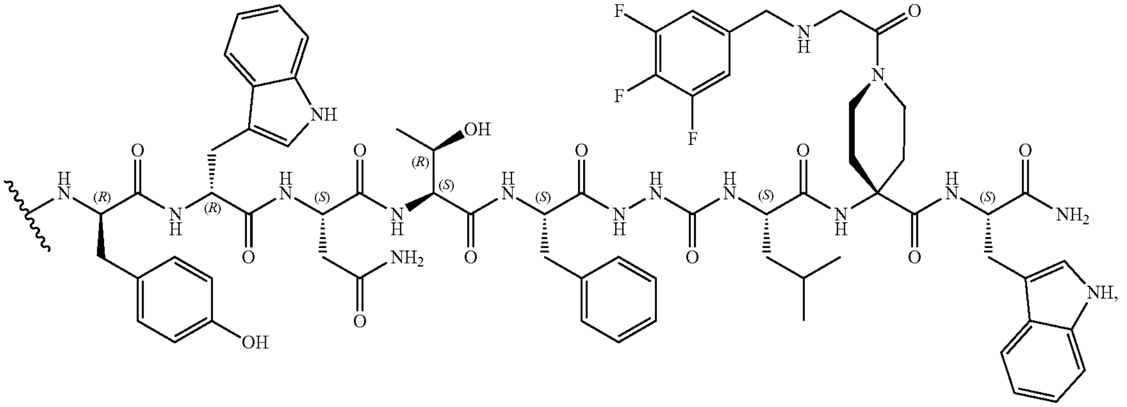

-continued
(SEQ ID NO: 116)
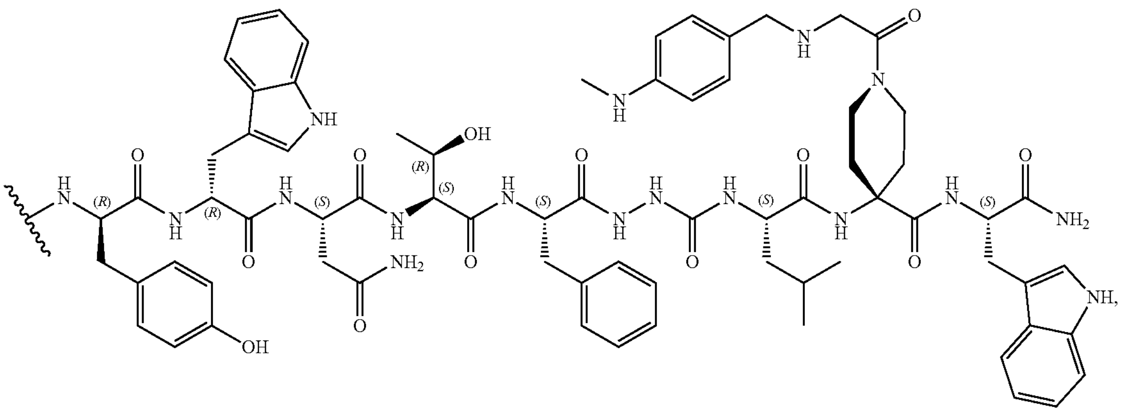
(SEQ ID NO: 117)
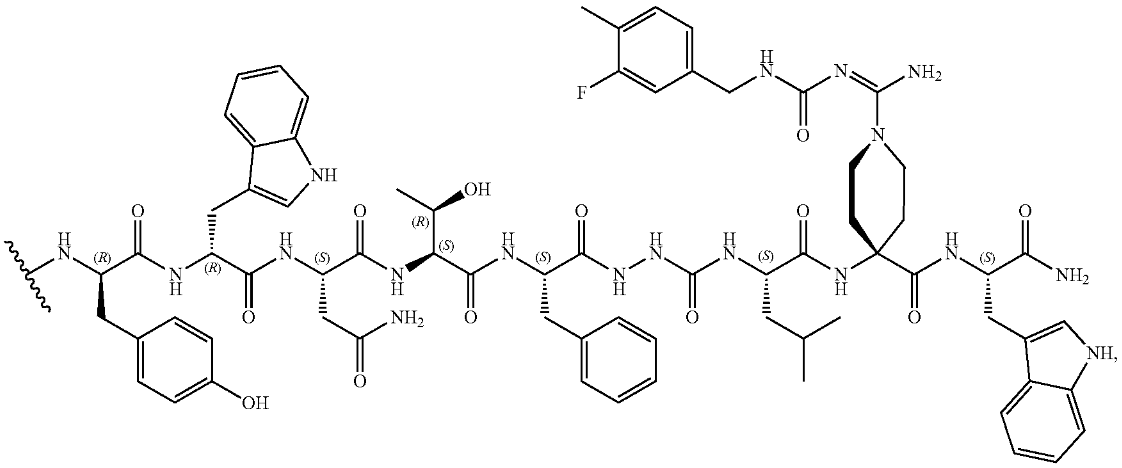
(SEQ ID NO: 118)
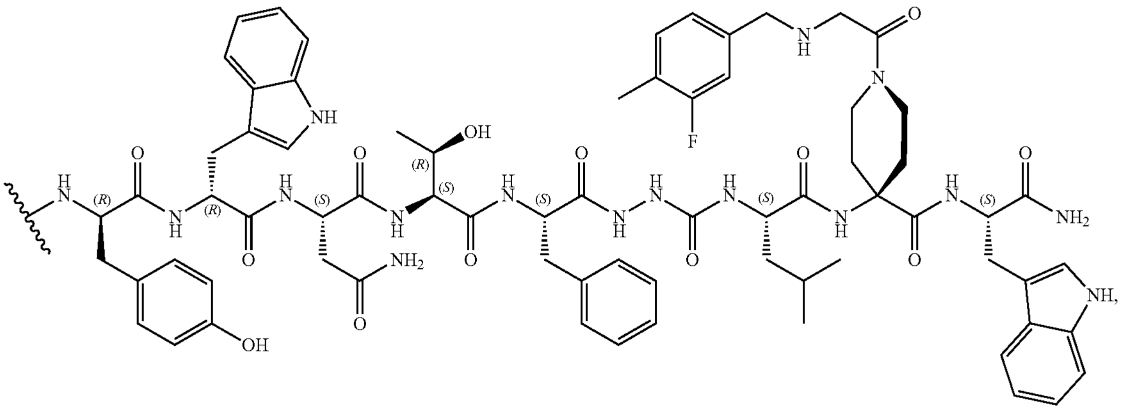

-continued
(SEQ ID NO: 120)
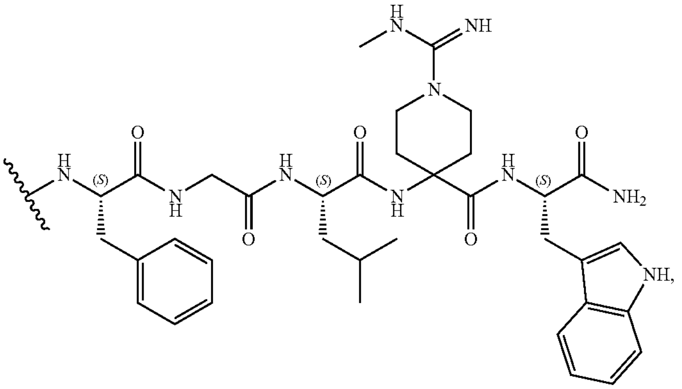
(SEQ ID NO: 119)
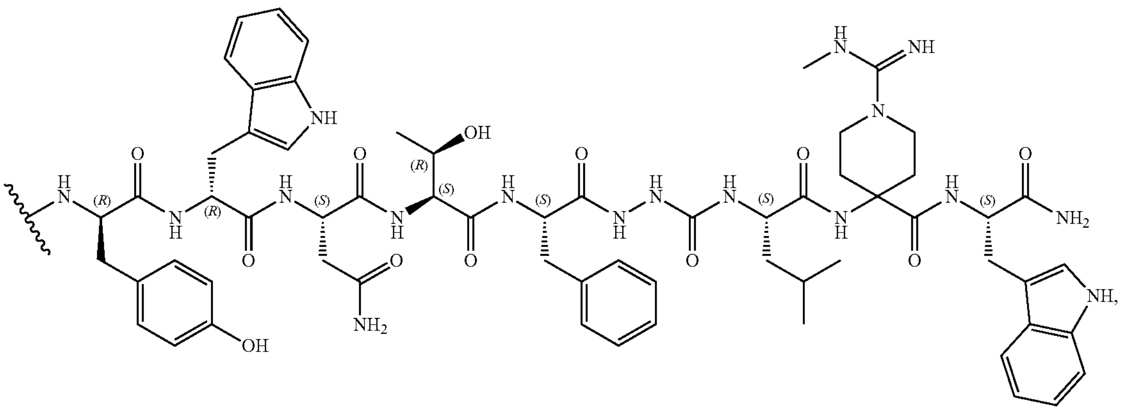
(SEQ ID NO: 121)
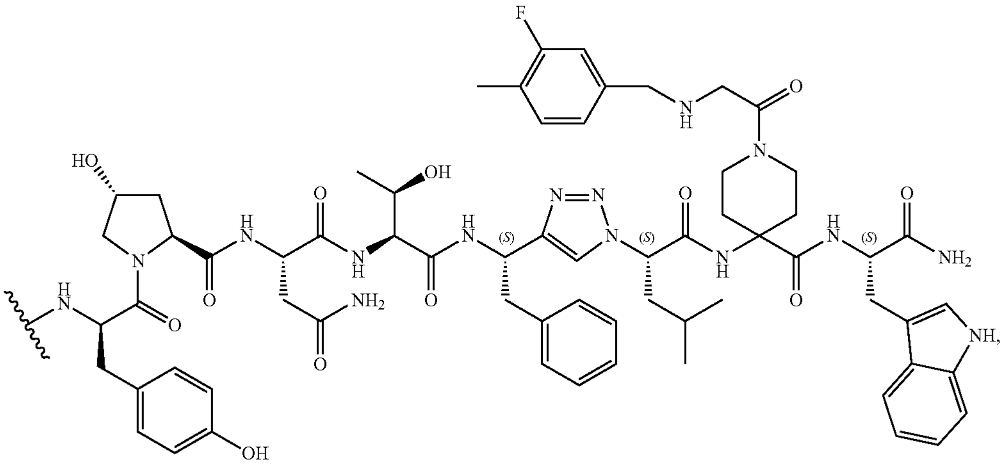

-continued
(SEQ ID NO: 122)
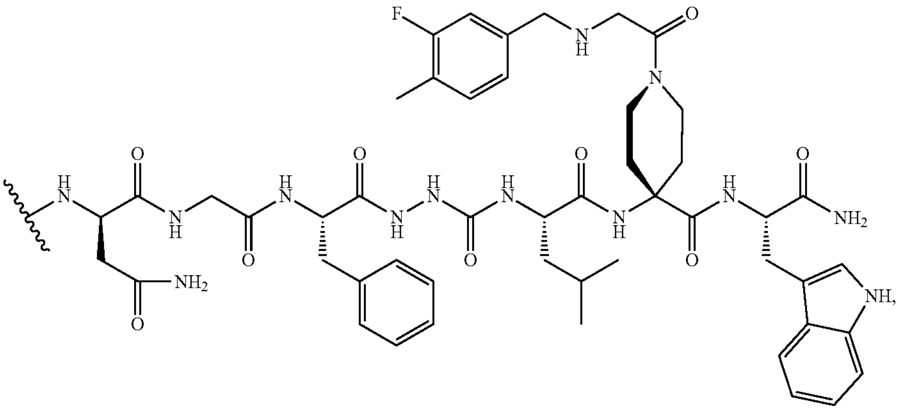
(SEQ ID NO: 123)
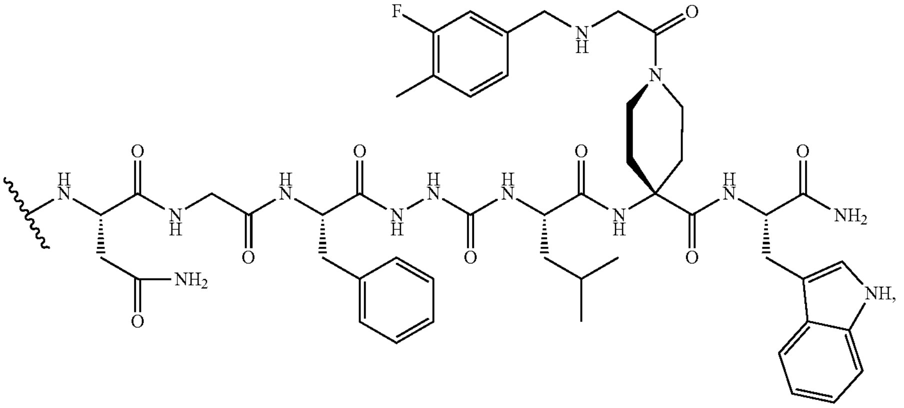
(SEQ ID NO: 124)
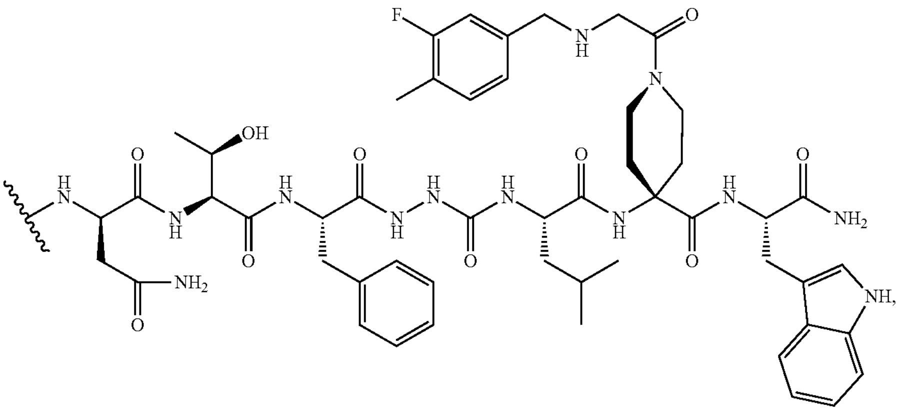
(SEQ ID NO: 127)
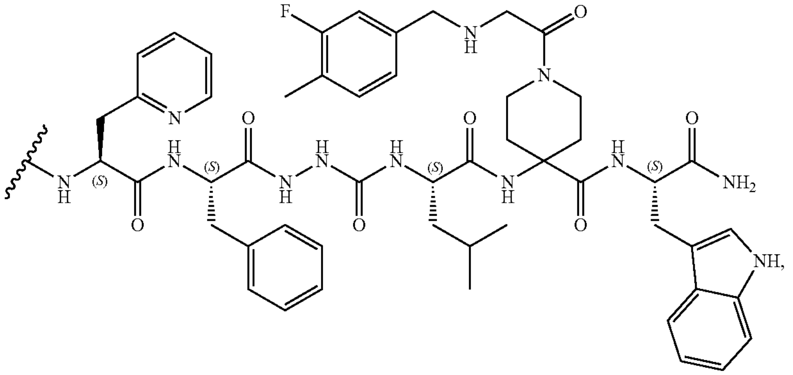

-continued
(SEQ ID NO: 125)
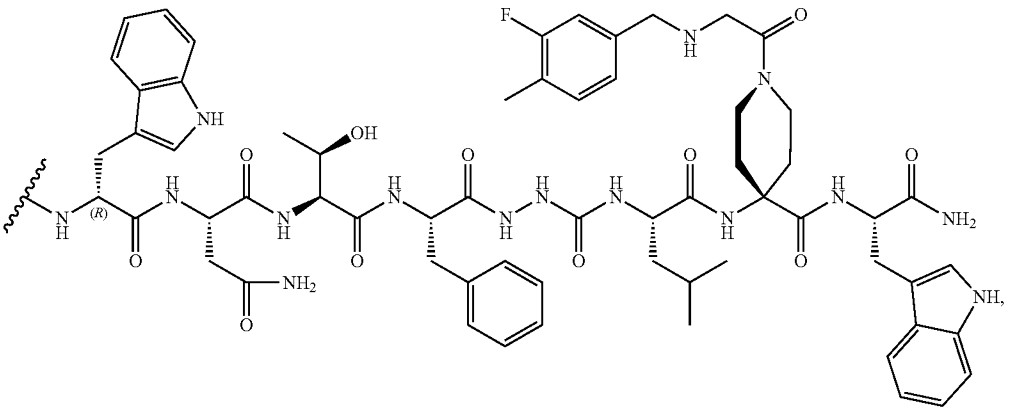
(SEQ ID NO: 126)
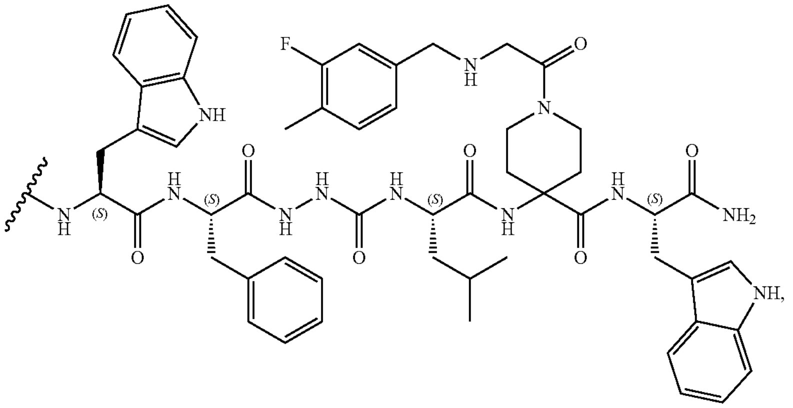
(SEQ ID NO: 128)
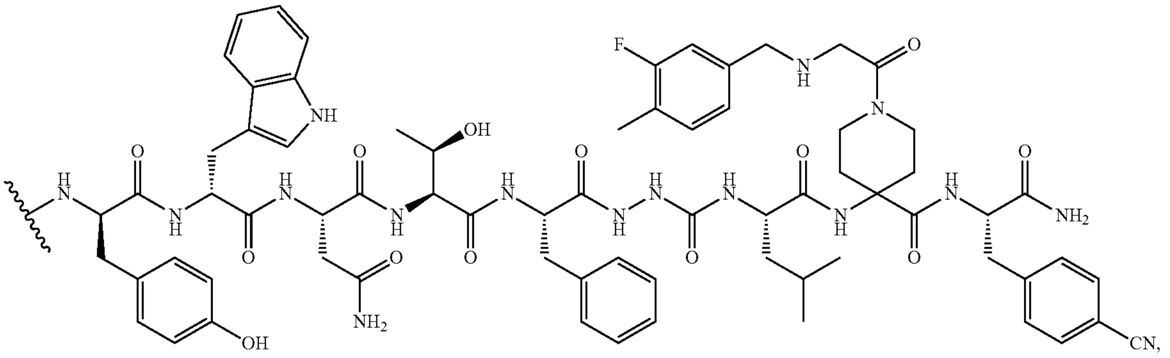
(SEQ ID NO: 129)
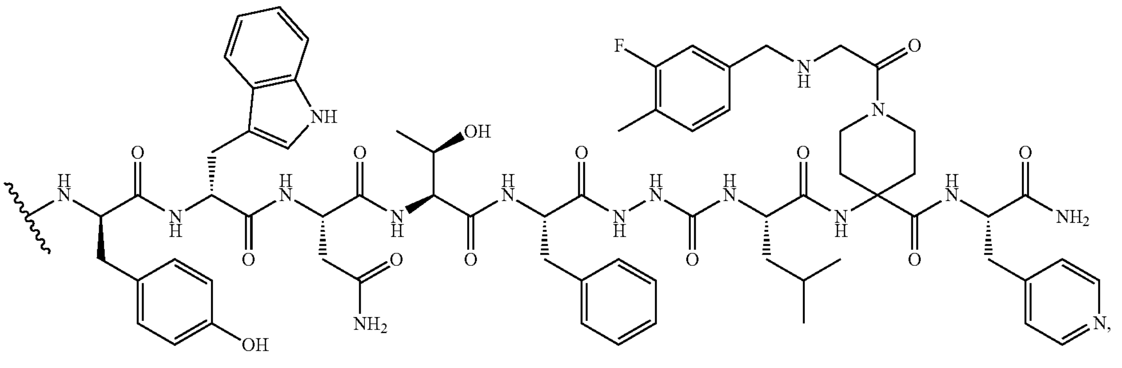

-continued
(SEQ ID NO: 130)
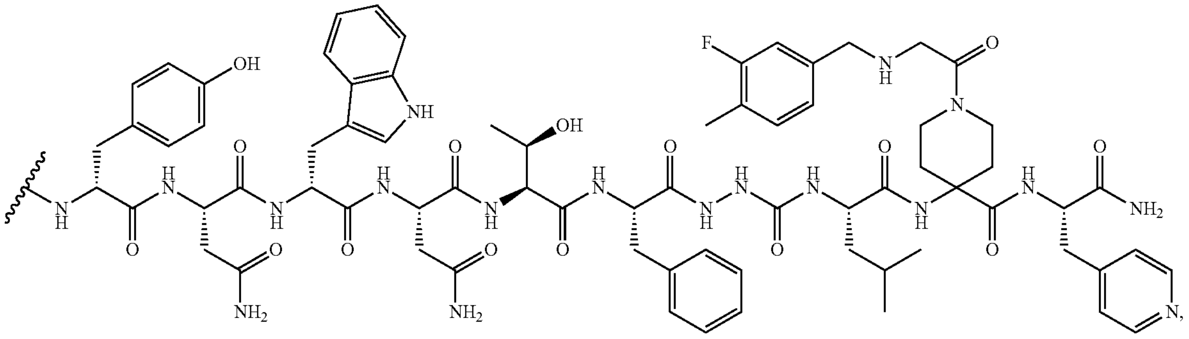
(SEQ ID NO: 131)
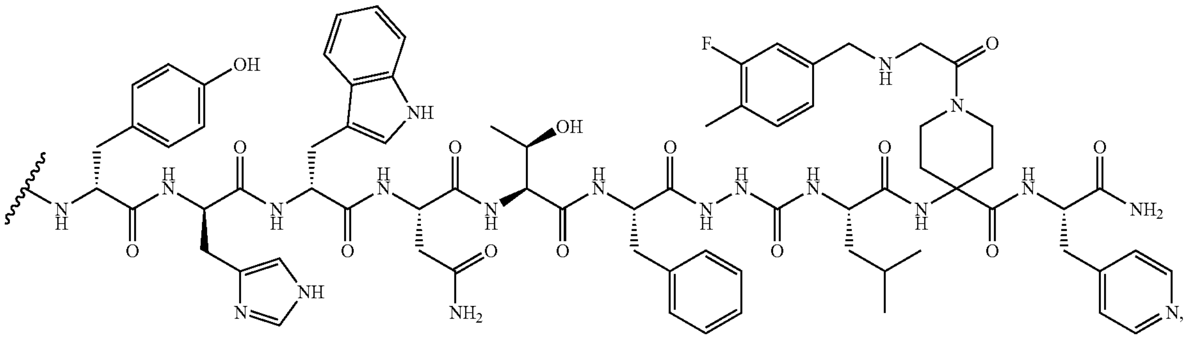
(SEQ ID NO: 132)
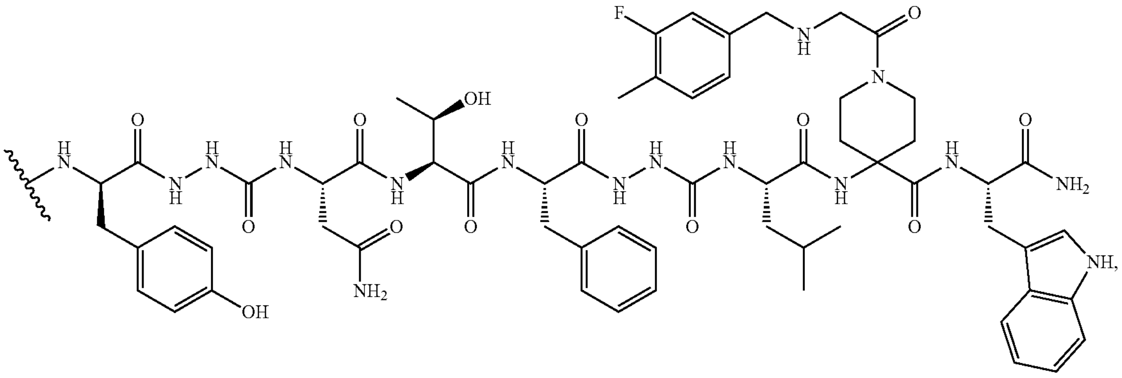
(SEQ ID NO: 133)
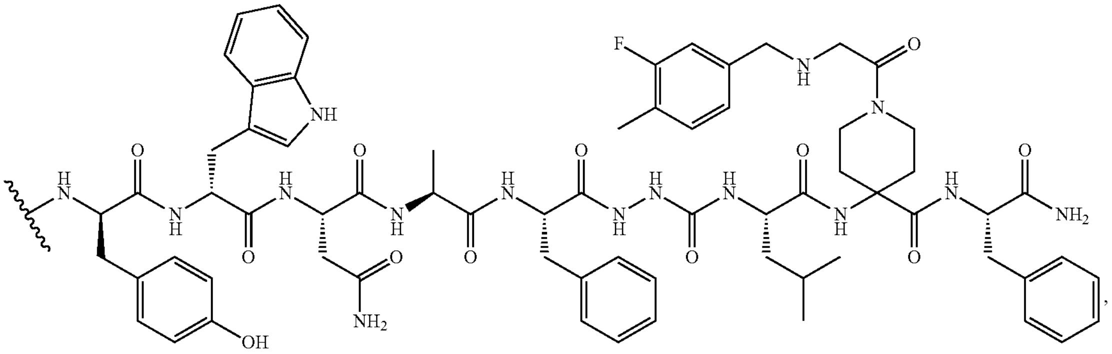

-continued
(SEQ ID NO: 134)
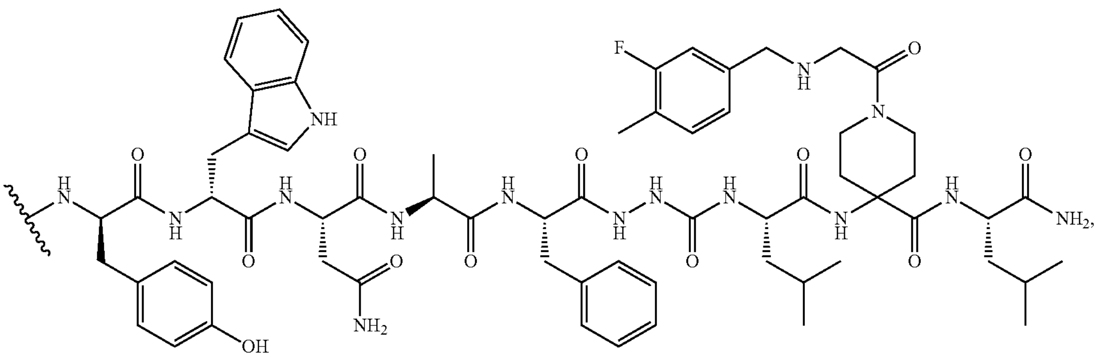
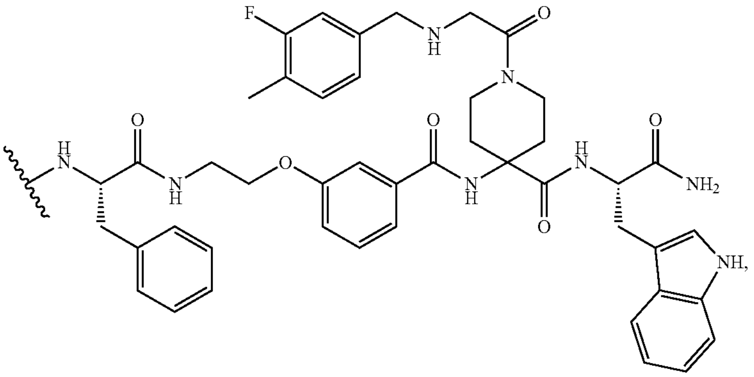
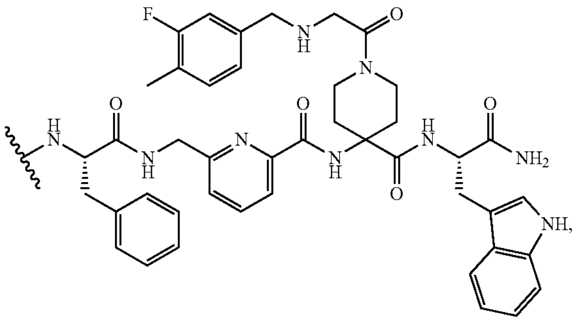
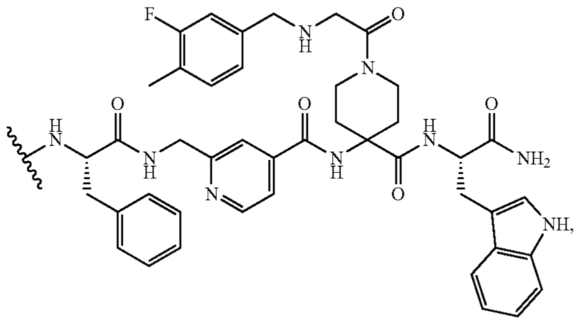
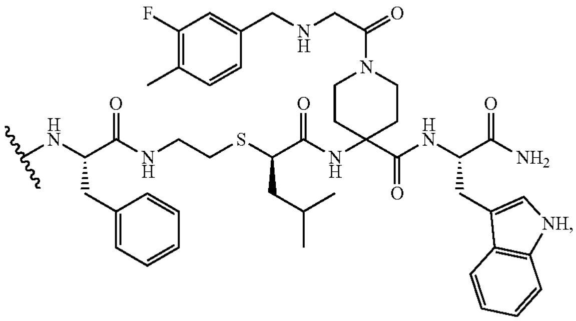
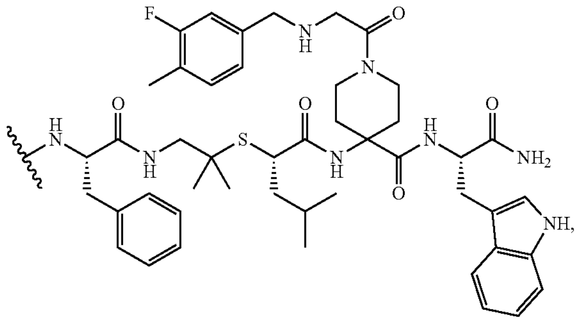

-continued
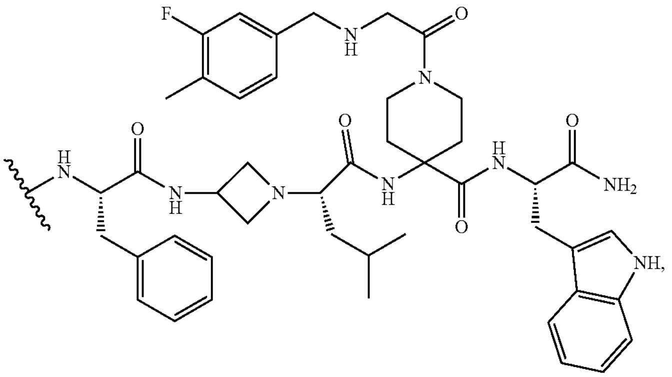
(SEQ ID NO: 141)
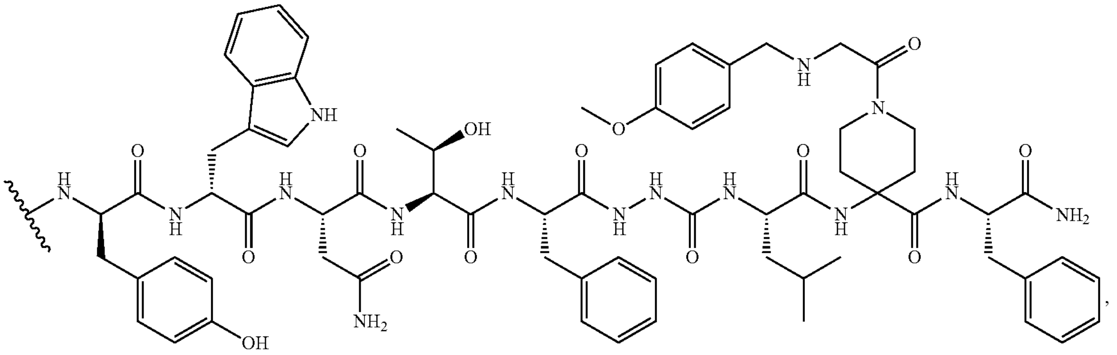
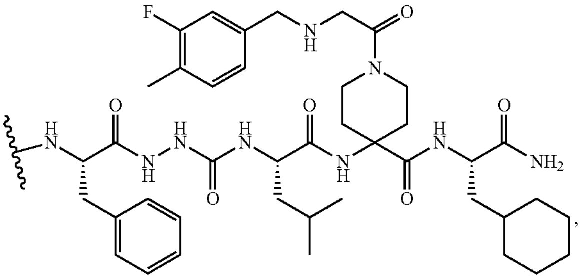
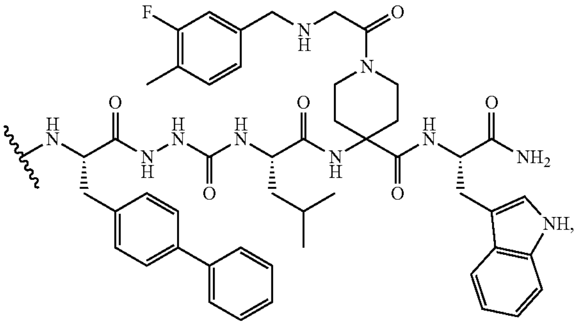
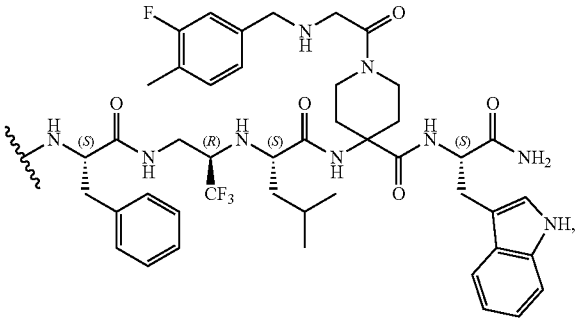
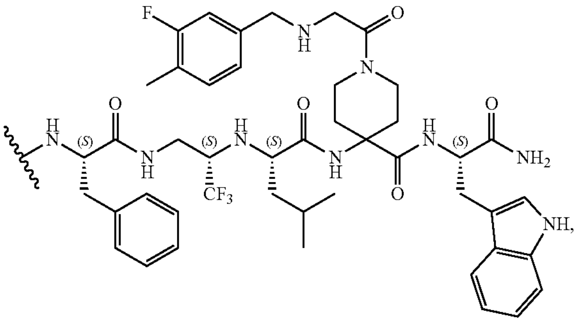

-continued
(SEQ ID NO: 146)
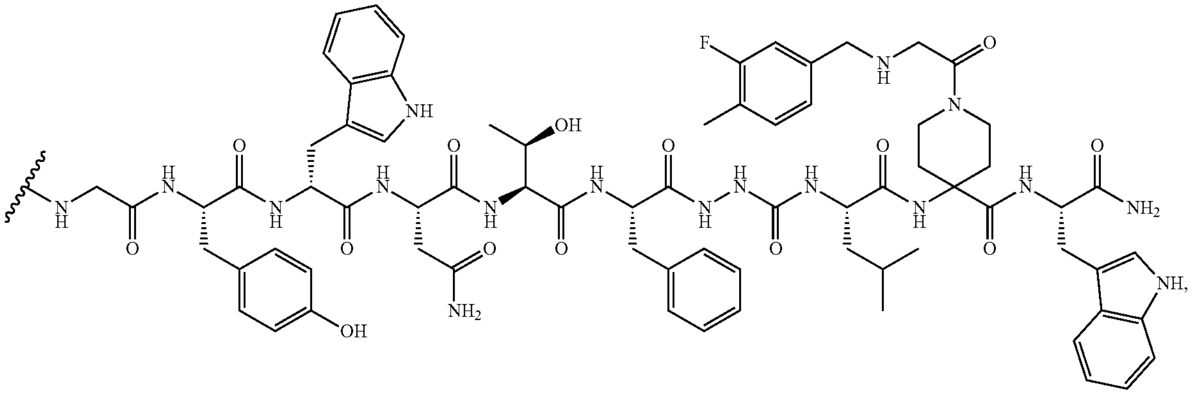
(SEQ ID NO: 147)
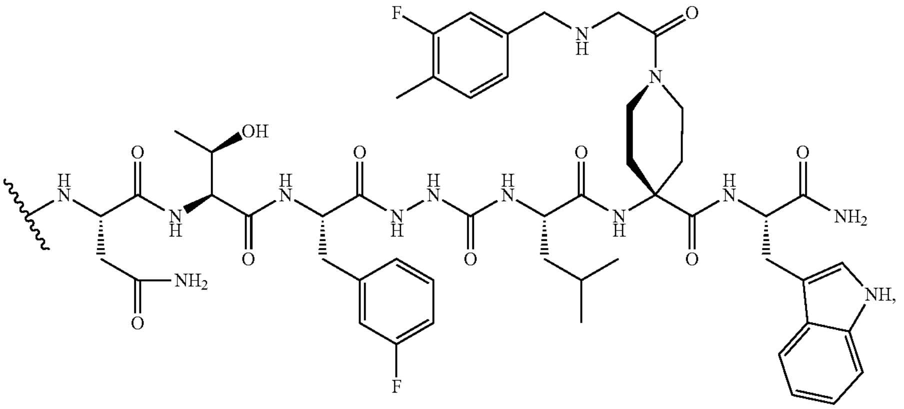
(SEQ ID NO: 148)
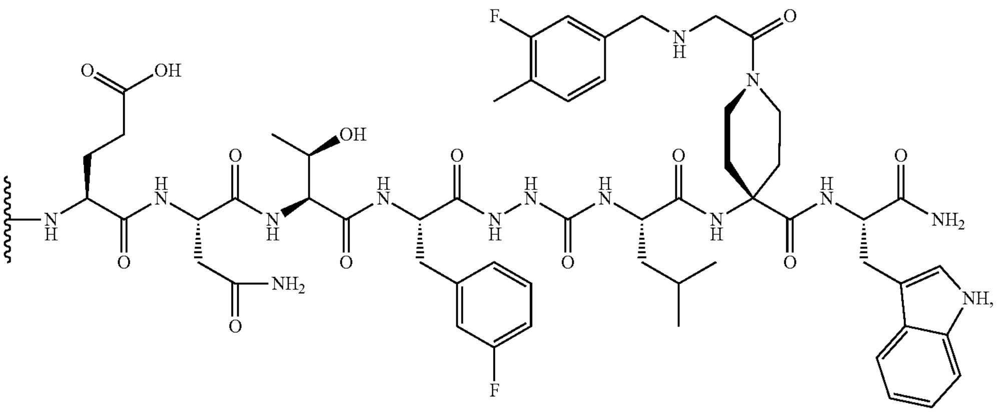

-continued
(SEQ ID NO: 149)
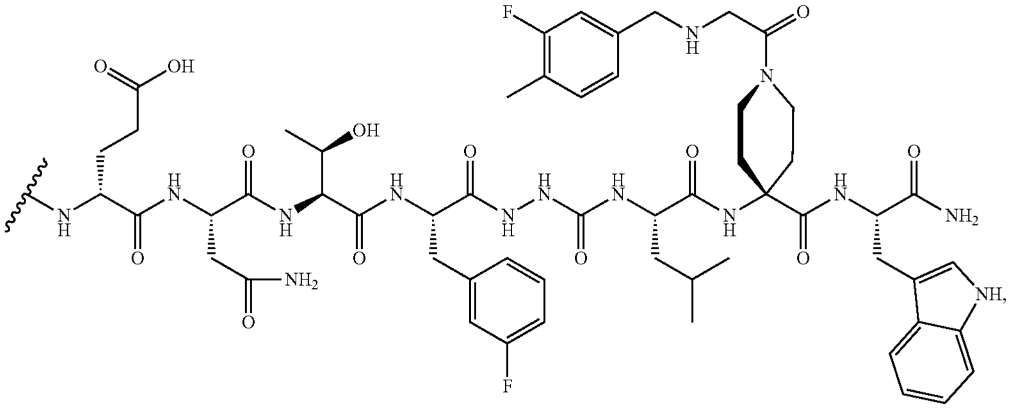
(SEQ ID NO: 150)
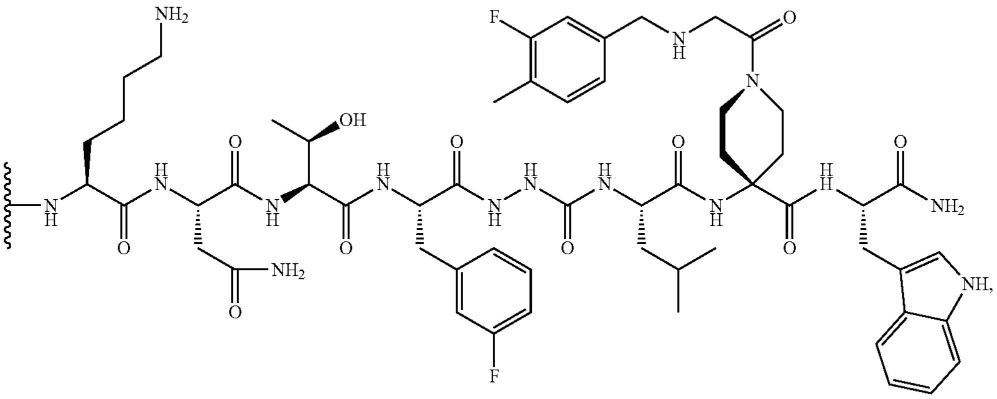
(SEQ ID NO: 151)
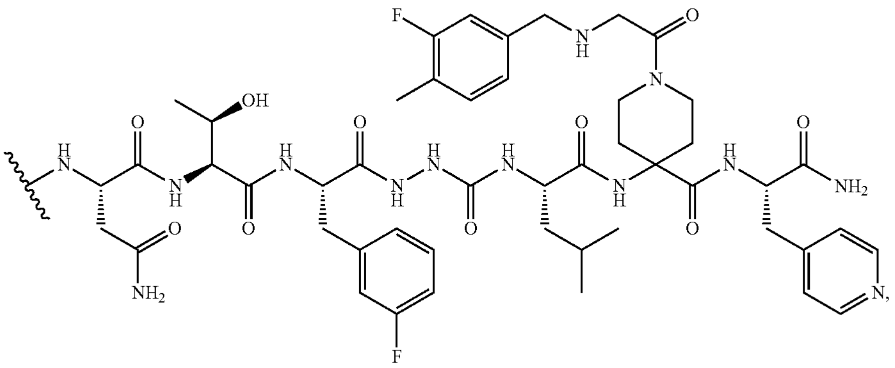

-continued
(SEQ ID NO: 152)
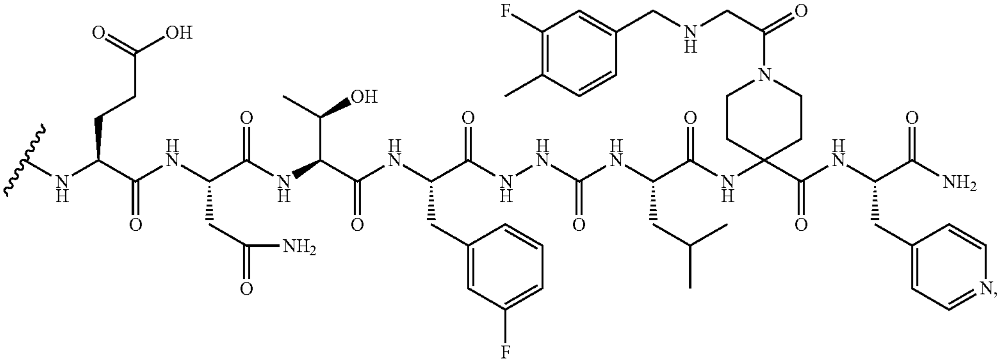
(SEQ ID NO: 153)
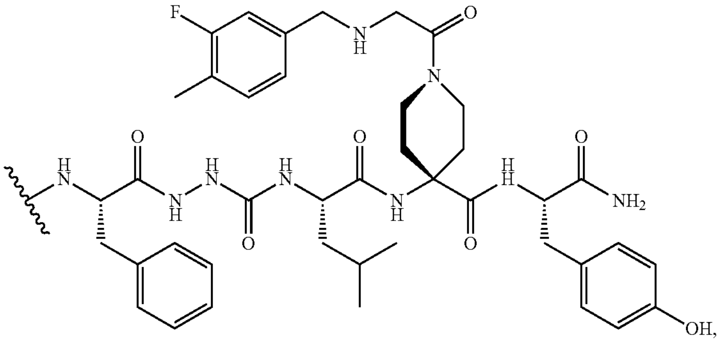
or
(SEQ ID NO: 154
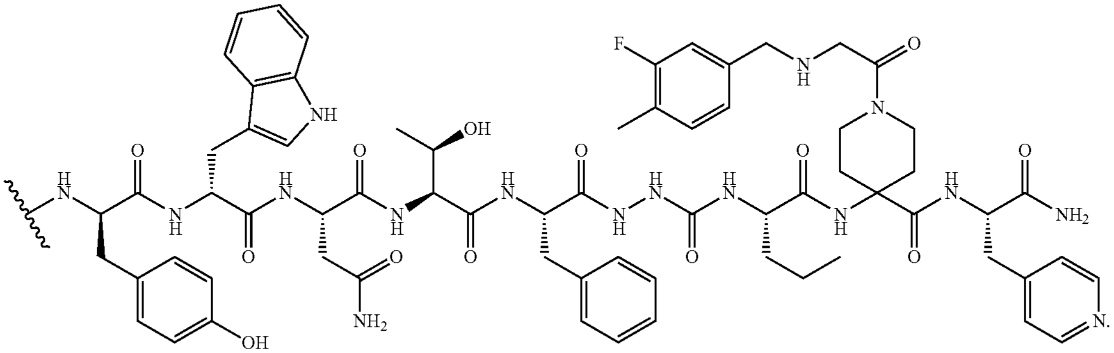
Embodiment 45. The compound of embodiment 1, or a pharmaceutically acceptable salt hereof, wherein:
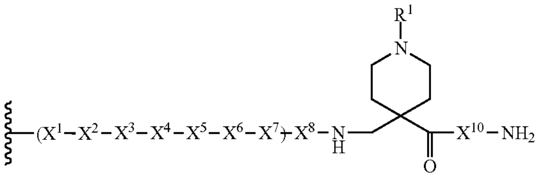
is
-continued
(SEQ ID NO: 155)
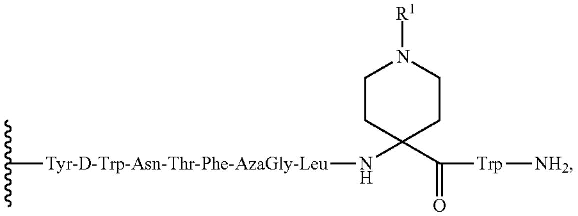

-continued
(SEQ ID NO: 156)
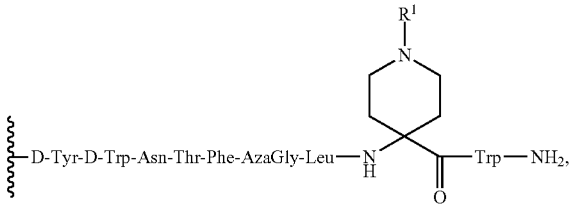
(SEQ ID NO: 157)
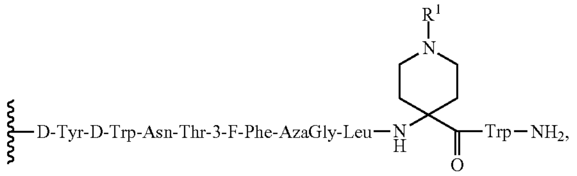
(SEQ ID NO: 158)
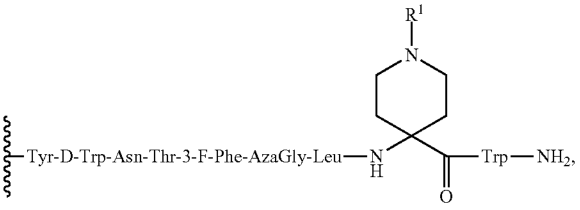
(SEQ ID NO: 159)
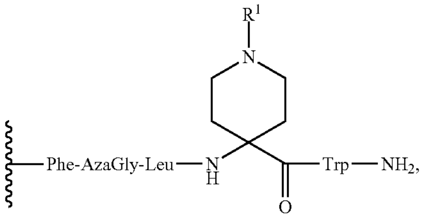
(SEQ ID NO: 160)
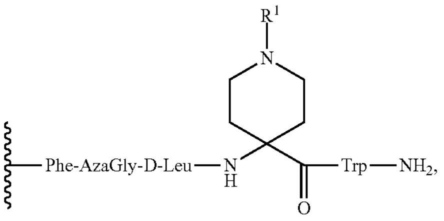
(SEQ ID NO: 161)
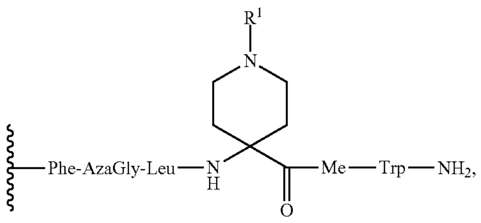
-continued
(SEQ ID NO: 162)
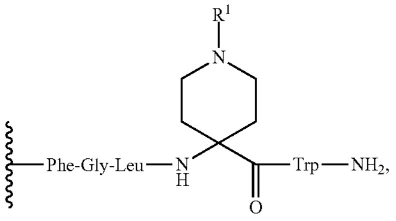
(SEQ ID NO: 163)
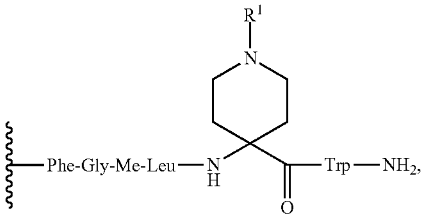
(SEQ ID NO: 164)
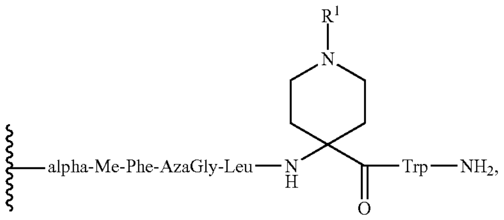
(SEQ ID NO: 165)
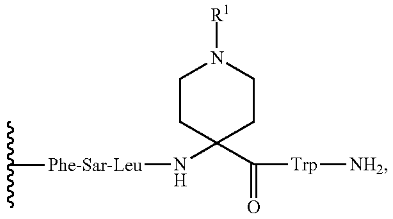
(SEQ ID NO: 166)
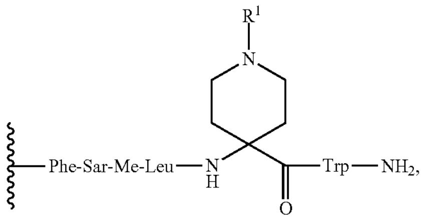
(SEQ ID NO: 167)
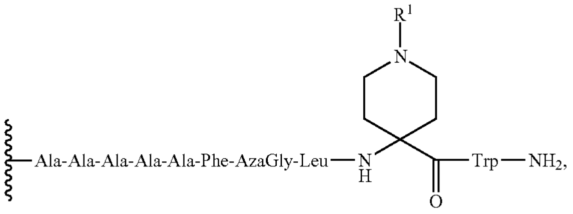

-continued
(SEQ ID NO: 168)
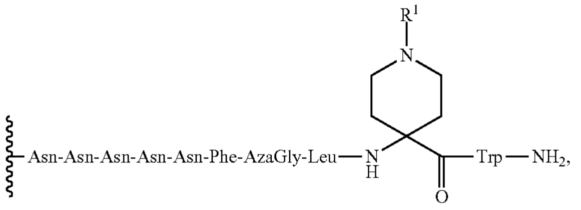
(SEQ ID NO: 169)
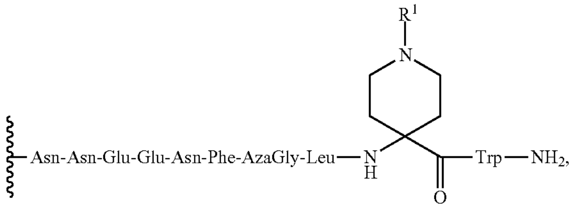
(SEQ ID NO: 170)
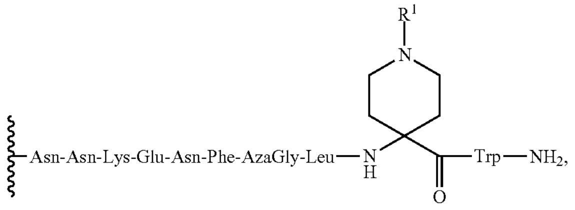
(SEQ ID NO: 171)
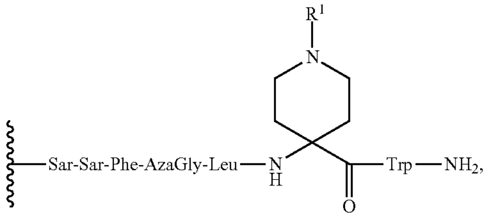
(SEQ ID NO: 172)
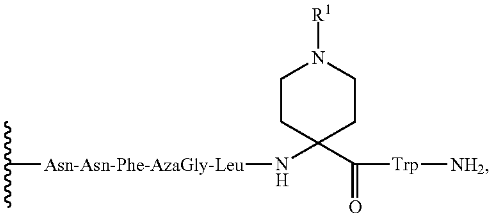
(SEQ ID NO: 173)
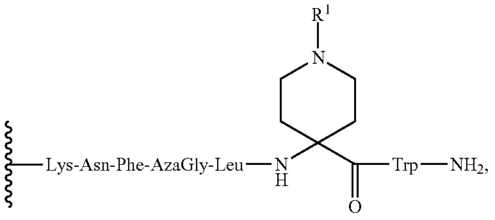
-continued
(SEQ ID NO: 174)
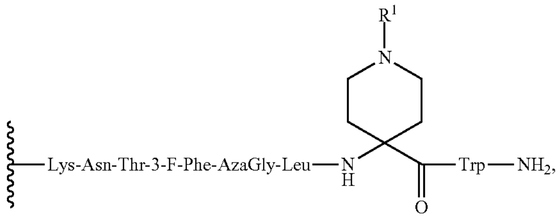
(SEQ ID NO: 175)
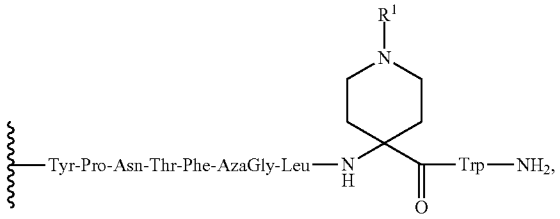
(SEQ ID NO: 176)
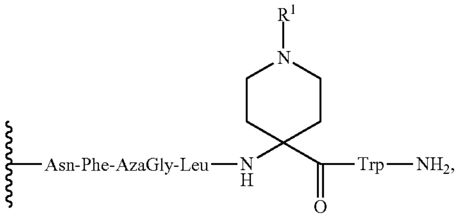
(SEQ ID NO: 177)
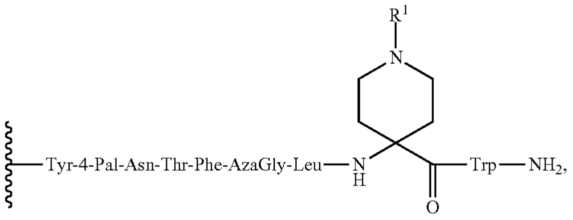
(SEQ ID NO: 178)
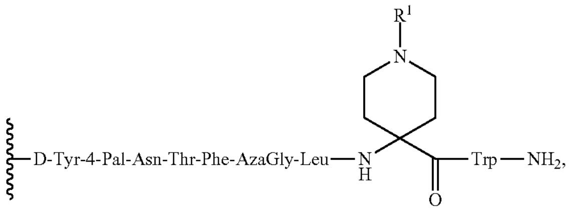
(SEQ ID NO: 179)
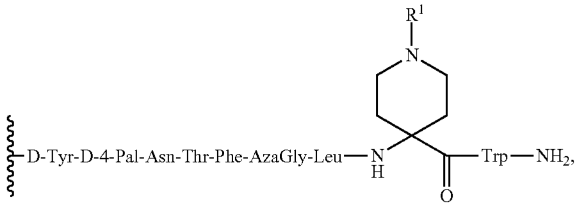

-continued
(SEQ ID NO: 180)
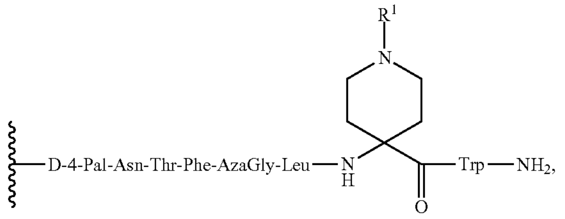
(SEQ ID NO: 181)
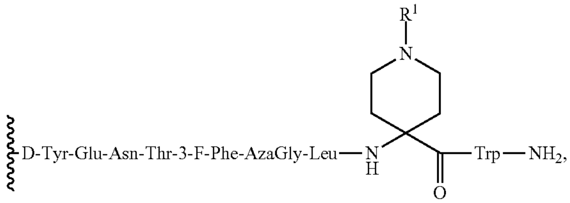
(SEQ ID NO: 182)
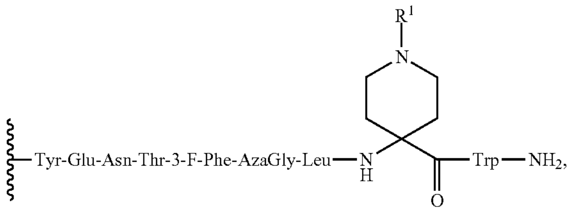
(SEQ ID NO: 183)
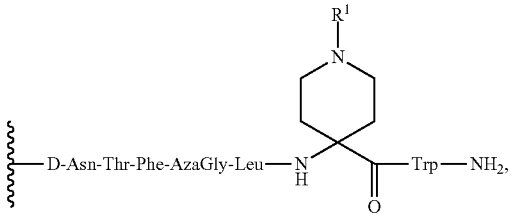
(SEQ ID NO: 184)
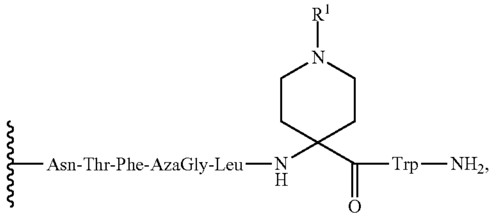
(SEQ ID NO: 185)
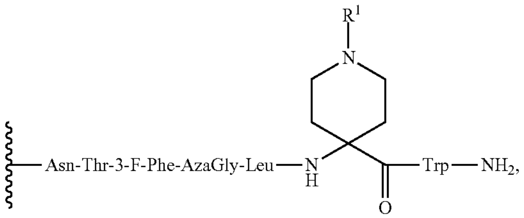
-continued
(SEQ ID NO: 186)
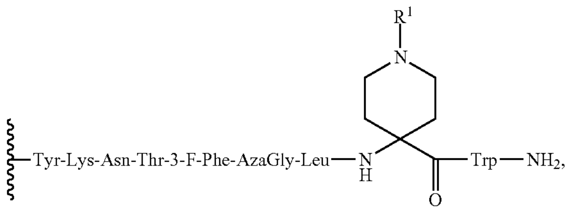
(SEQ ID NO: 187)
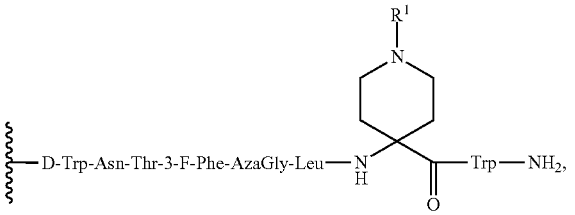
(SEQ ID NO: 188)
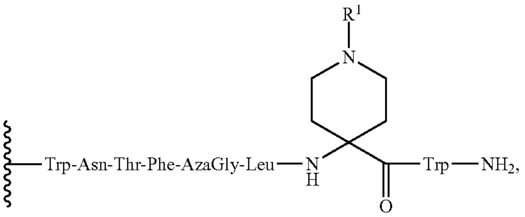
(SEQ ID NO: 189)
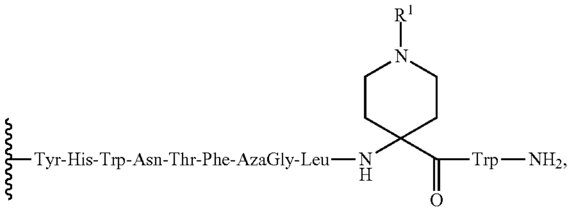
(SEQ ID NO: 190)
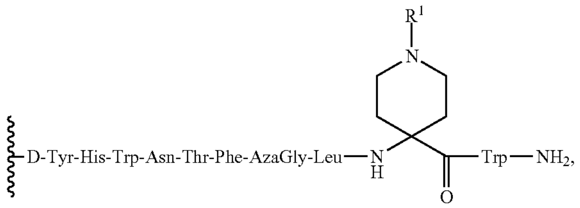
(SEQ ID NO: 191)
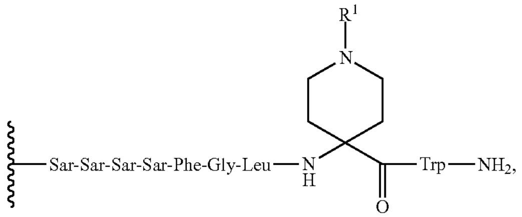

-continued
(SEQ ID NO: 192)
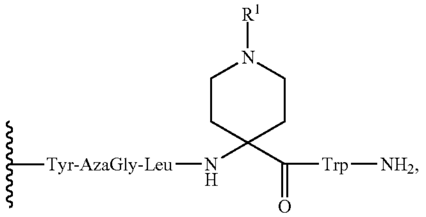
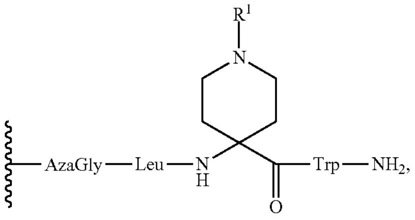
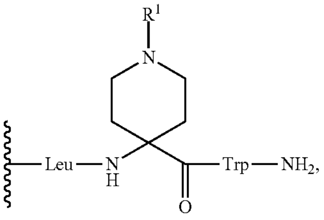
(SEQ ID NO: 194)
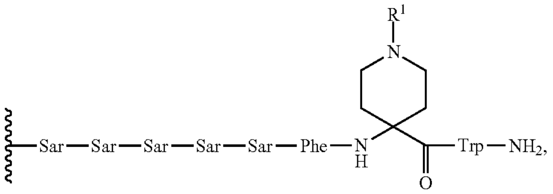
(SEQ ID NO: 195)
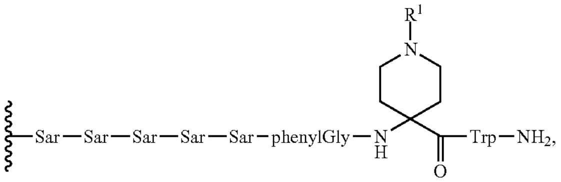
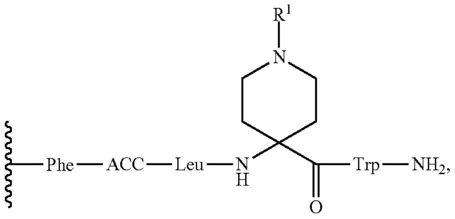
(SEQ ID NO: 197)
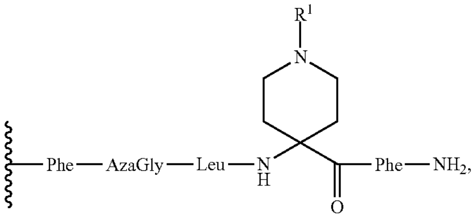
(SEQ ID NO: 198)
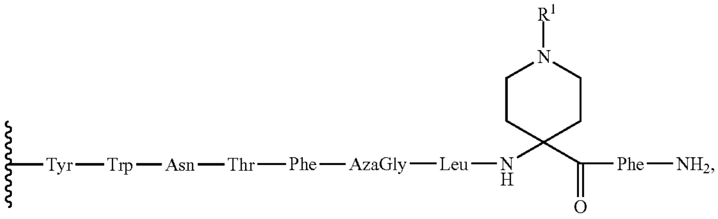
(SEQ ID NO: 199)
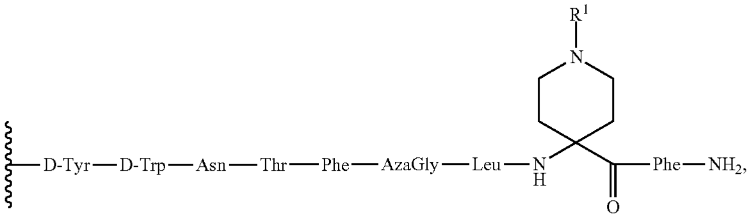

-continued
(SEQ ID NO: 200)
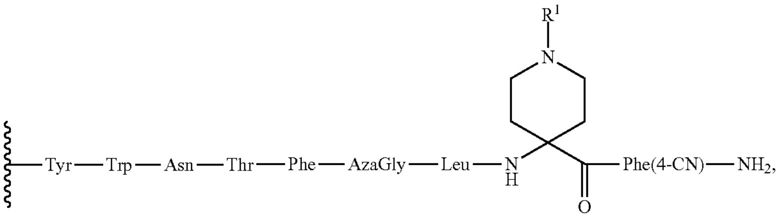
(SEQ ID NO: 201)
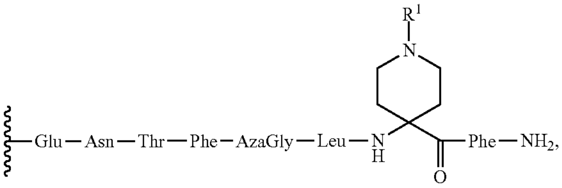
(SEQ ID NO: 202)
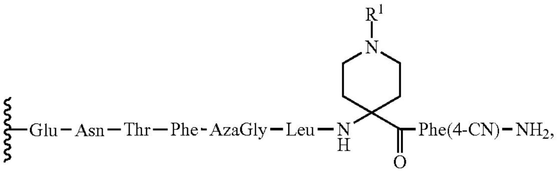
(SEQ ID NO: 203)
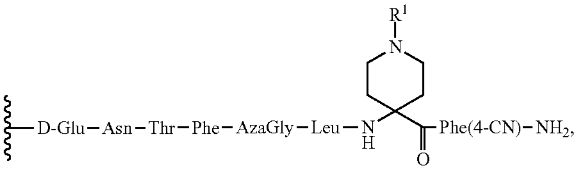
(SEQ ID NO: 204)
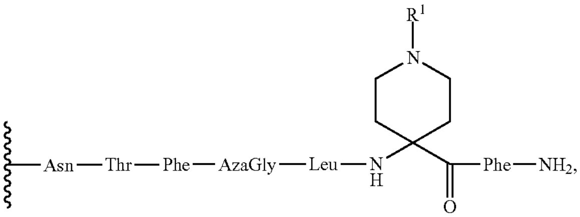
(SEQ ID NO: 205)
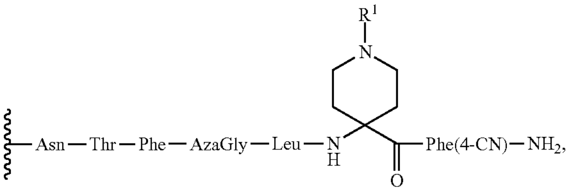
(SEQ ID NO: 206)
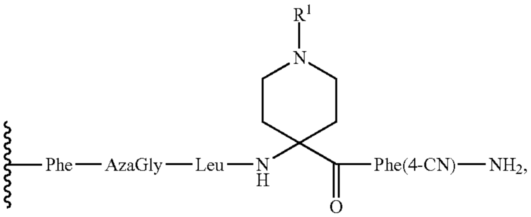
(SEQ ID NO: 207)
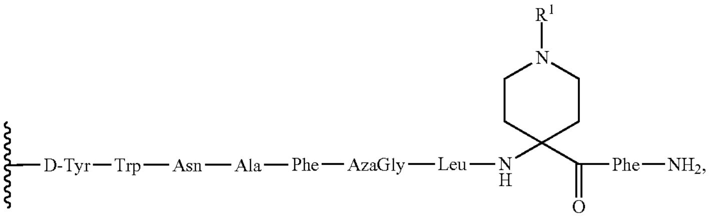
(SEQ ID NO: 208)
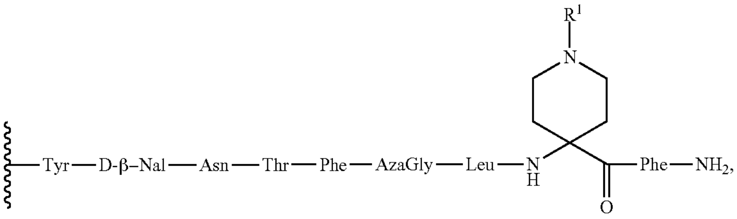
(SEQ ID NO: 209)
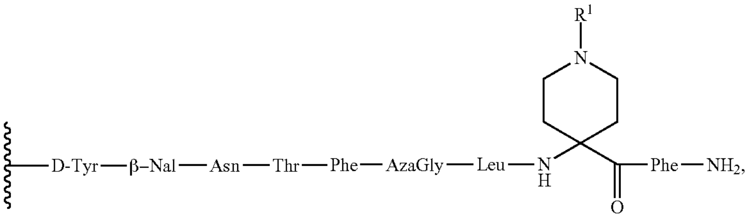

-continued
(SEQ ID NO: 210)
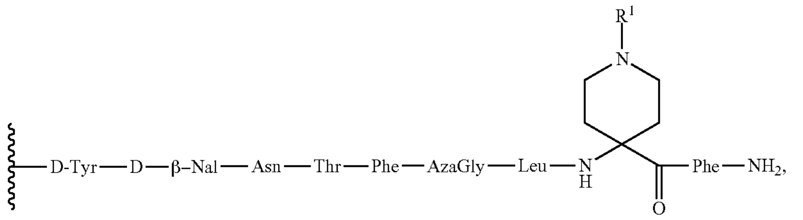
(SEQ ID NO: 211)
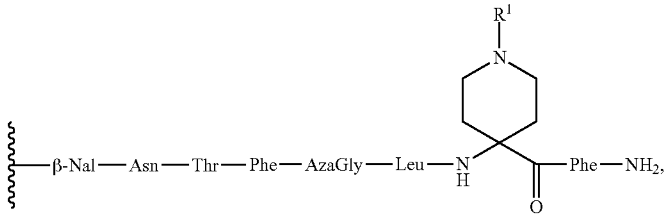
(SEQ ID NO: 212)
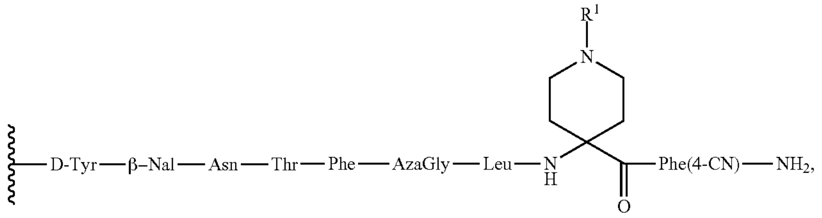
(SEQ ID NO: 213)
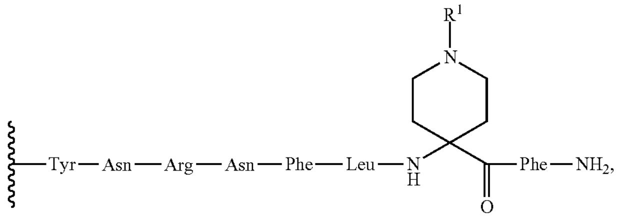
(SEQ ID NO: 214)
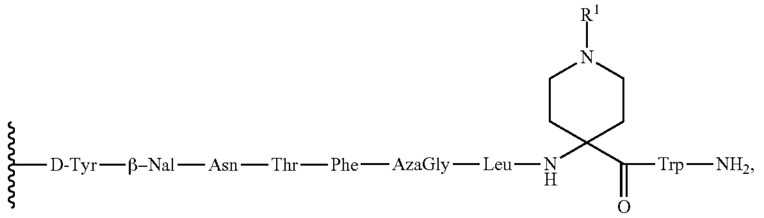
(SEQ ID NO: 215)
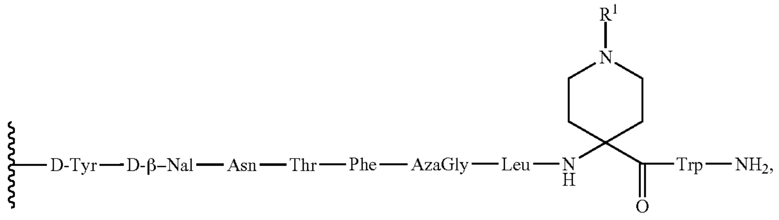
(SEQ ID NO: 216)
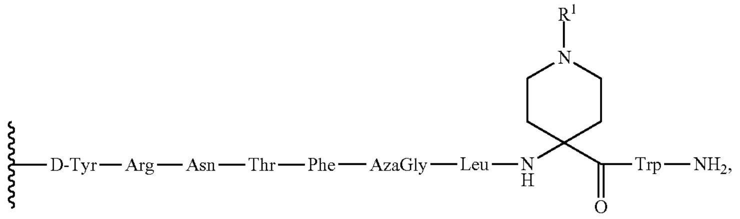

-continued
(SEQ ID NO: 217)
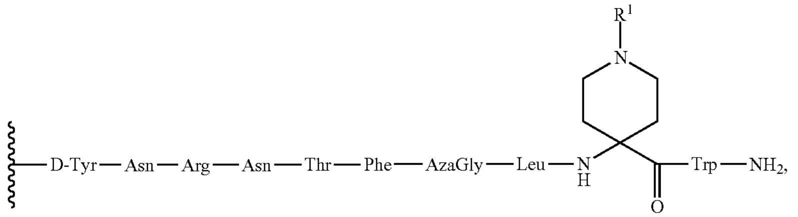
(SEQ ID NO: 218)
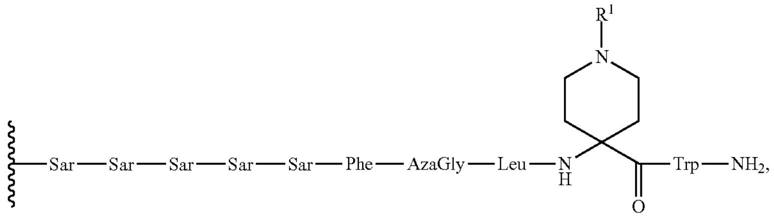
(SEQ ID NO: 219)
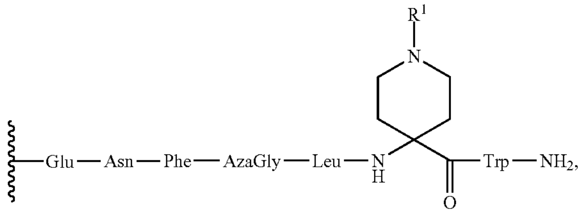
(SEQ ID NO: 220)
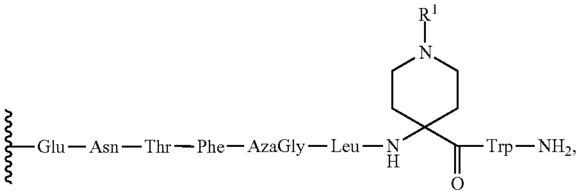
(SEQ ID NO: 221)
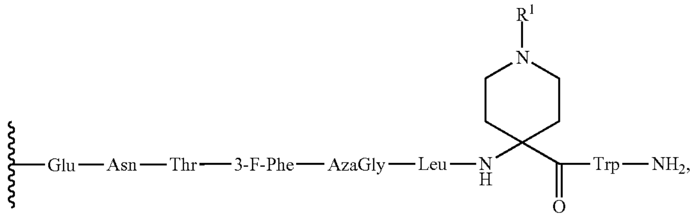
(SEQ ID NO: 222)
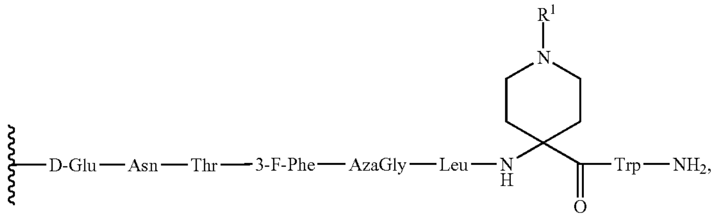
(SEQ ID NO: 223)
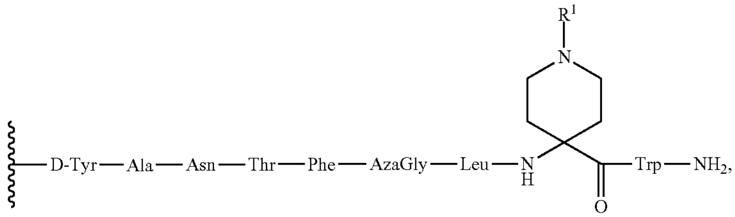
(SEQ ID NO: 224)
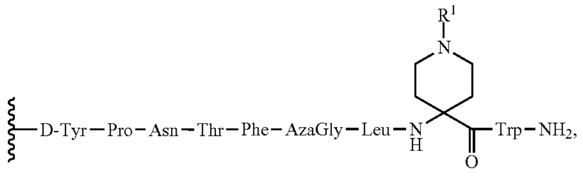
(SEQ ID NO: 225)
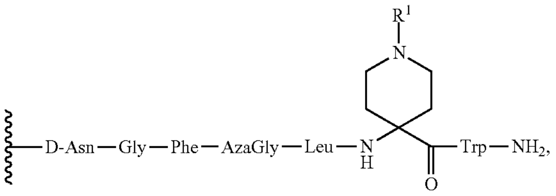

-continued
(SEQ ID NO: 226)
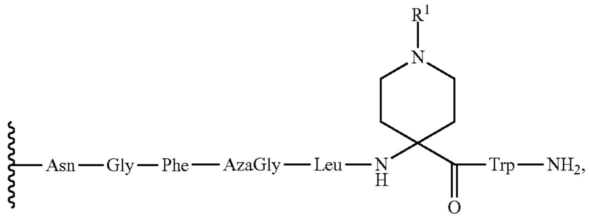
(SEQ ID NO: 227)
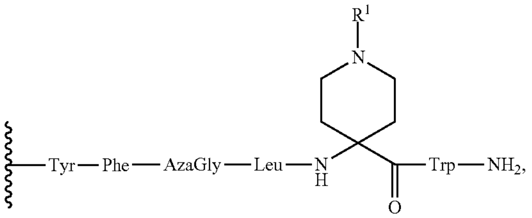
(SEQ ID NO: 228)
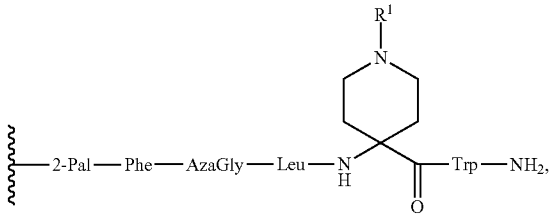
(SEQ ID NO: 229)
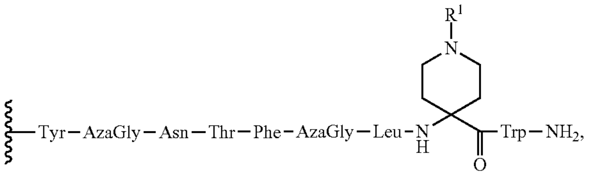
(SEQ ID NO: 230)
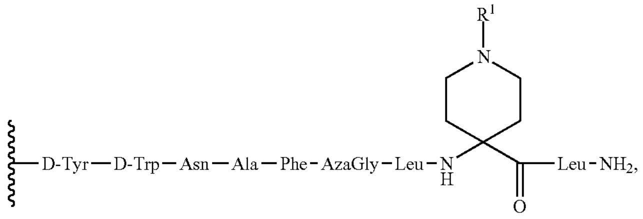
(SEQ ID NO: 231)
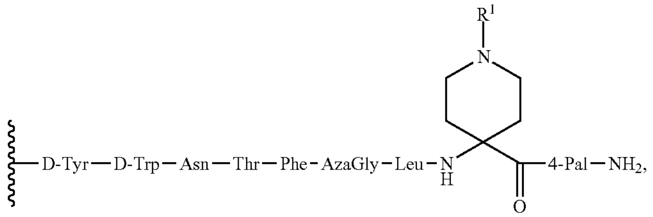
(SEQ ID NO: 232)
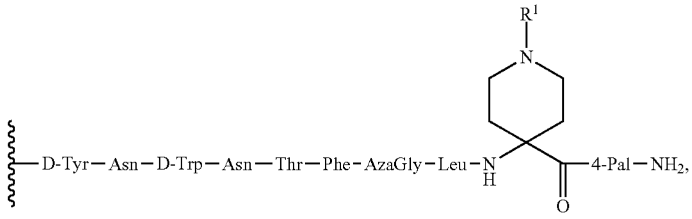
(SEQ ID NO: 233)
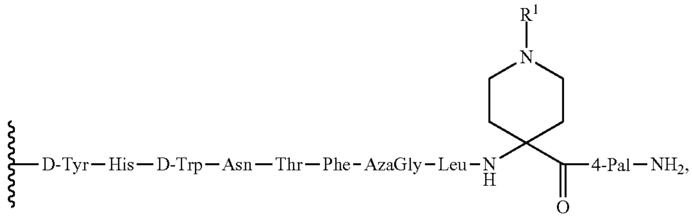

-continued
(SEQ ID NO: 234)
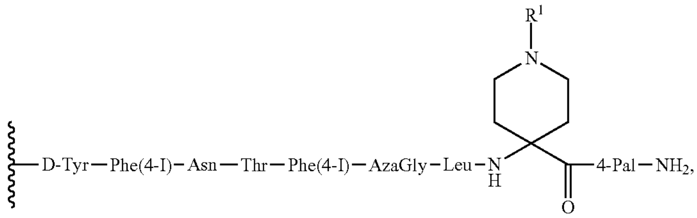
(SEQ ID NO: 235)
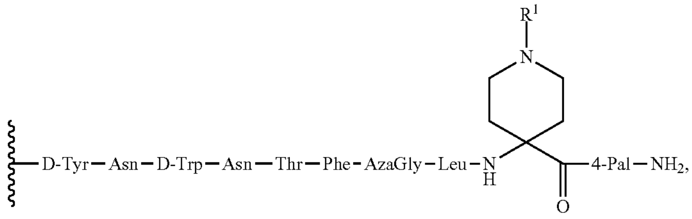
(SEQ ID NO: 236)
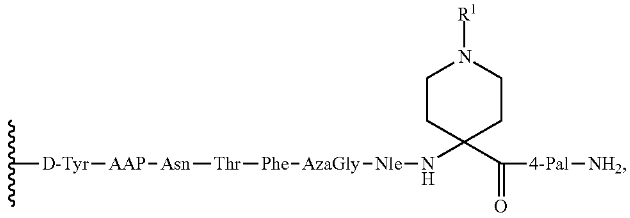
(SEQ ID NO: 237)
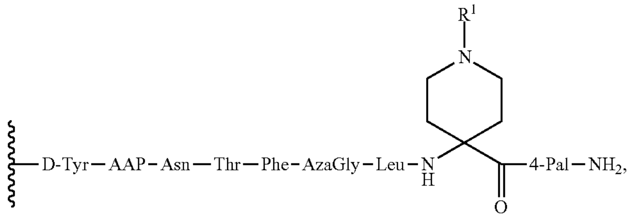
(SEQ ID NO: 238)
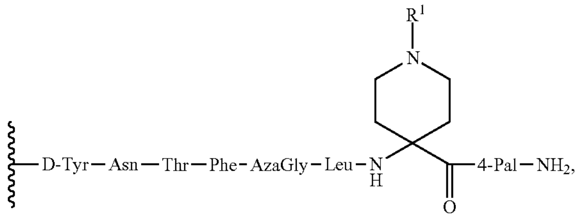
(SEQ ID NO: 239)
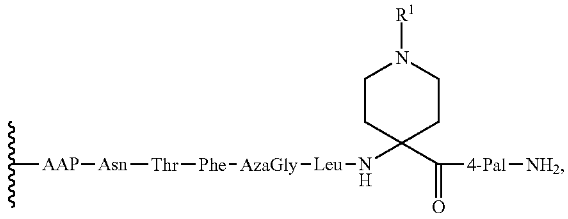

-continued
(SEQ ID NO: 240)
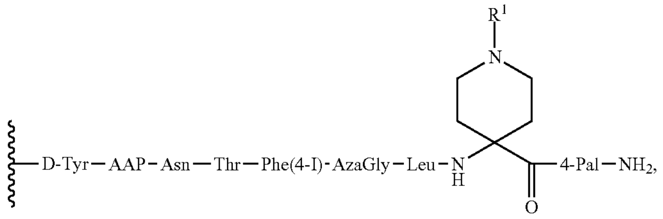
(SEQ ID NO: 241)
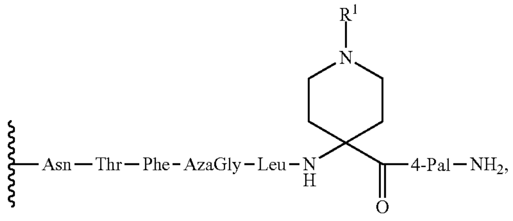
(SEQ ID NO: 242)
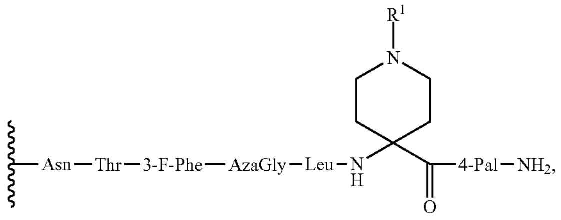
(SEQ ID NO: 243)
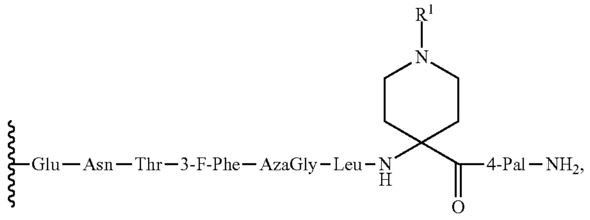
(SEQ ID NO: 244)
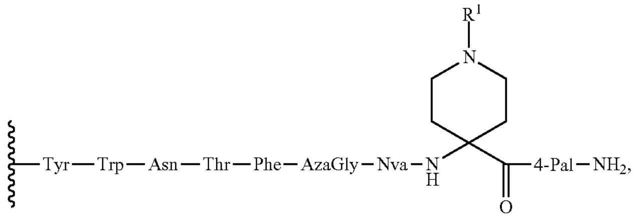
(SEQ ID NO: 245)
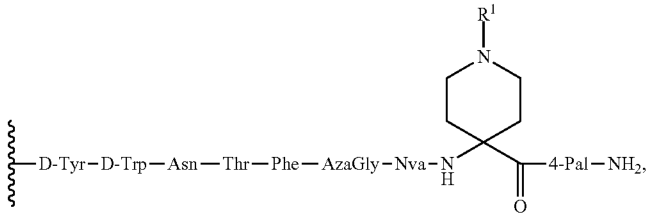
(SEQ ID NO: 246)
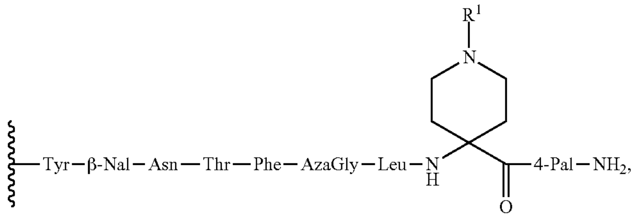

-continued
(SEQ ID NO: 247)
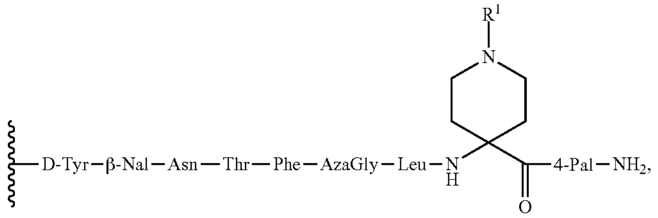
(SEQ ID NO: 248)
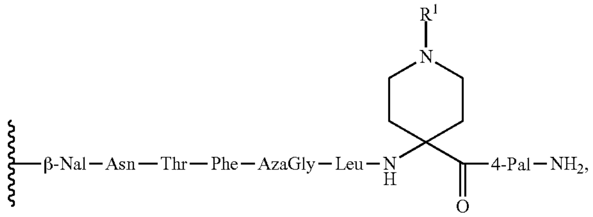
(SEQ ID NO: 249)
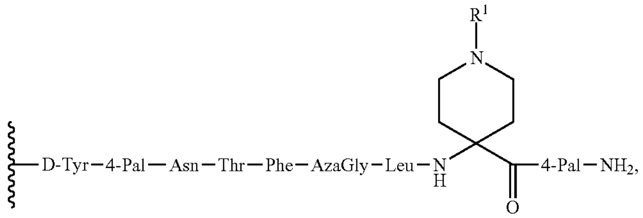
(SEQ ID NO: 250)
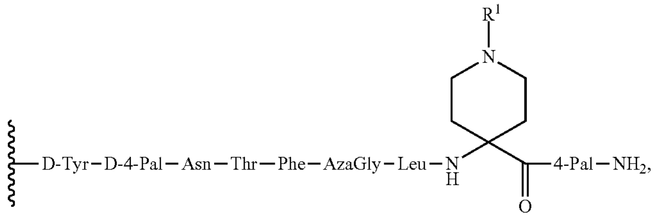
(SEQ ID NO: 251)
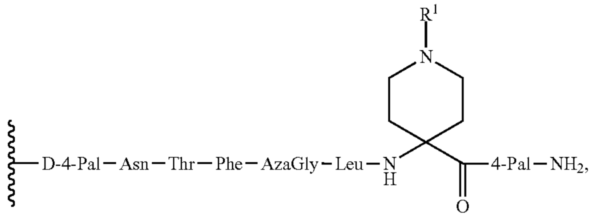
(SEQ ID NO: 252)
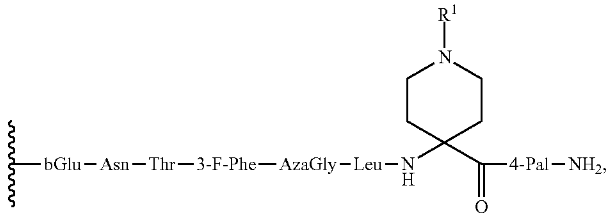
(SEQ ID NO: 253)
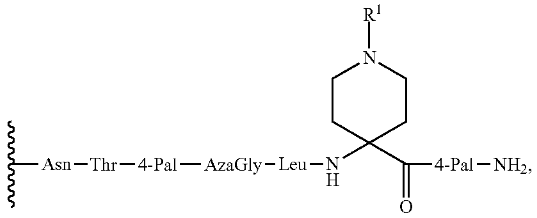

-continued
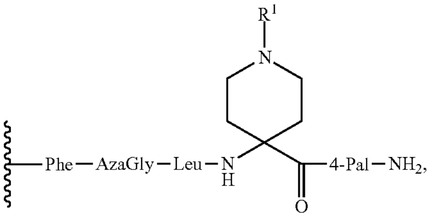
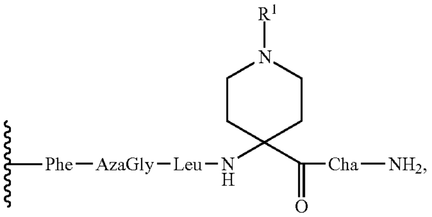
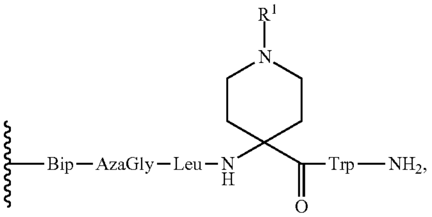
(SEQ ID NO: 257)
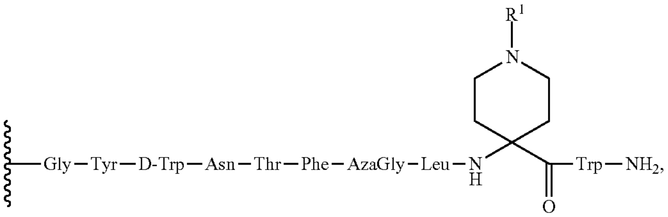
(SEQ ID NO: 258)
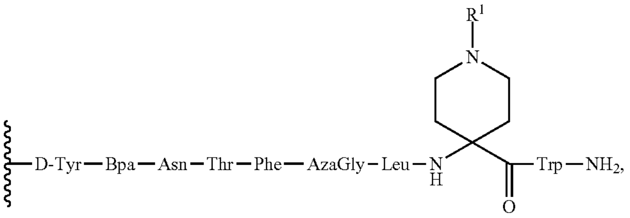
(SEQ ID NO: 259)
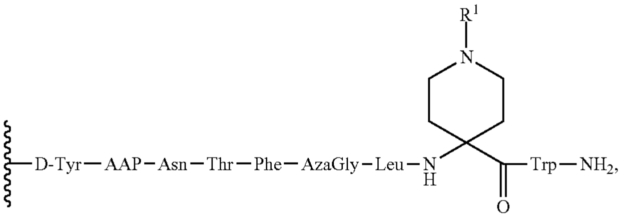
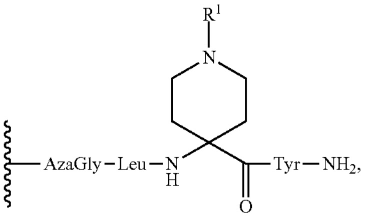

-continued
(SEQ ID NO: 261)
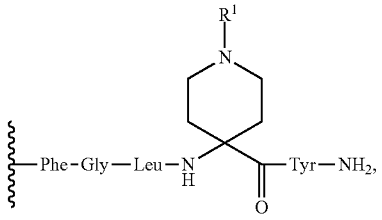
(SEQ ID NO: 262)
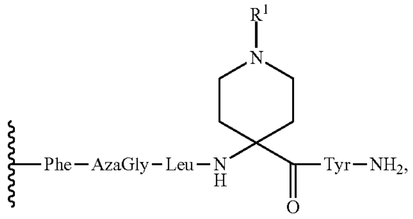
(SEQ ID NO: 263)
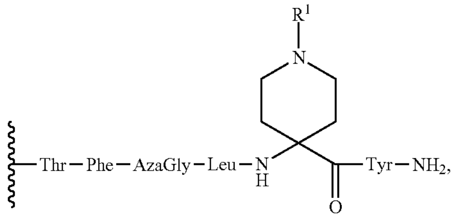
(SEQ ID NO: 264)
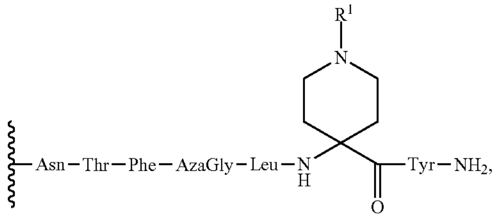
(SEQ ID NO: 265)
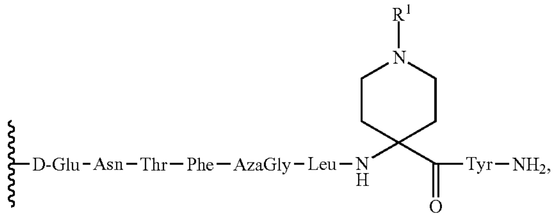
(SEQ ID NO: 266)
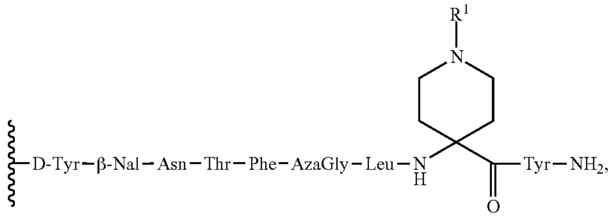

-continued
(SEQ ID NO: 267)
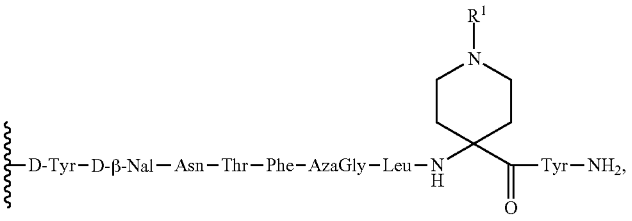
(SEQ ID NO: 268)
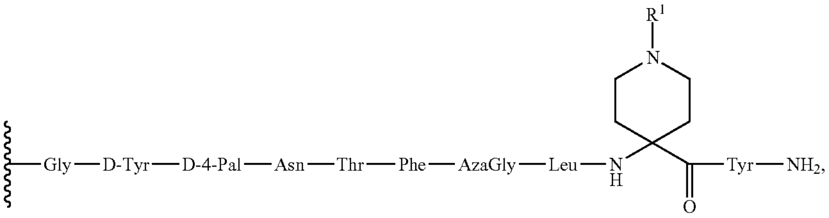
(SEQ ID NO: 269)
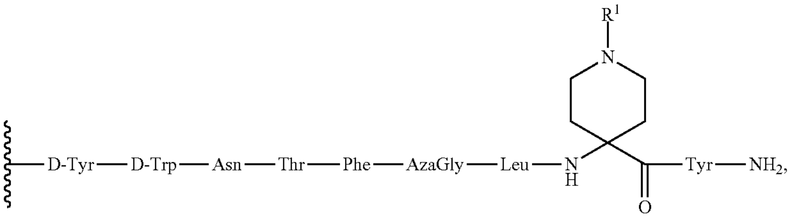
(SEQ ID NO: 270)
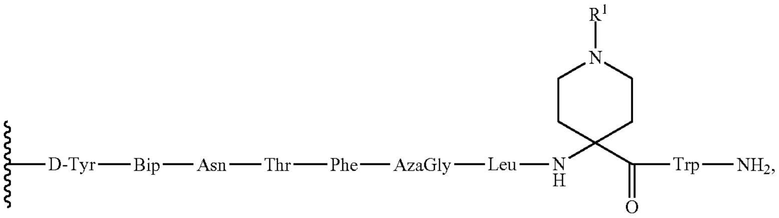
(SEQ ID NO: 271)
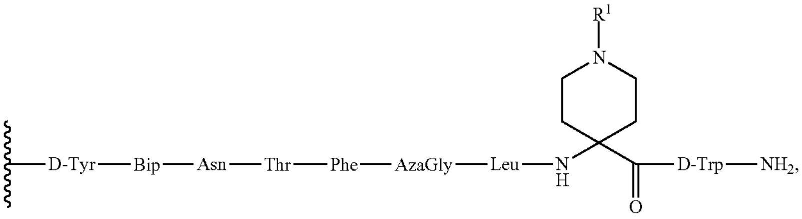
(SEQ ID NO: 272)
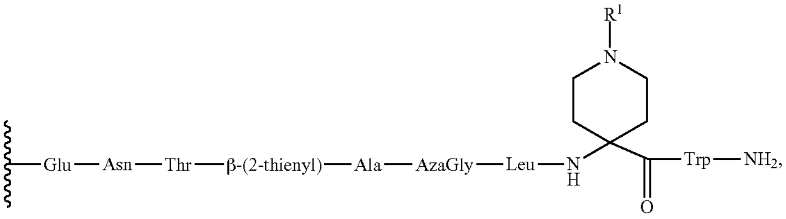

-continued
(SEQ ID NO: 273)
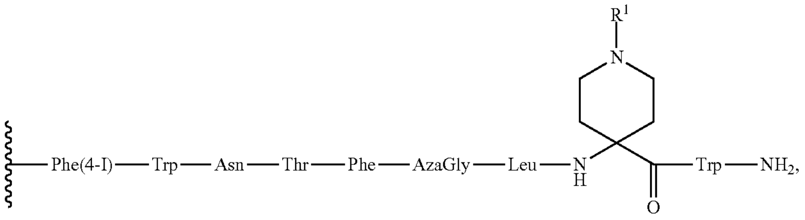
(SEQ ID NO: 274)
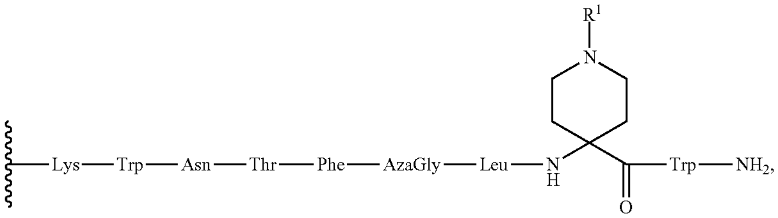
(SEQ ID NO: 275)
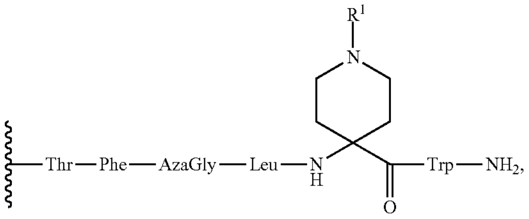
(SEQ ID NO: 276)
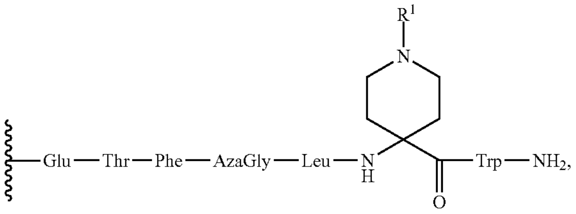
(SEQ ID NO: 277)
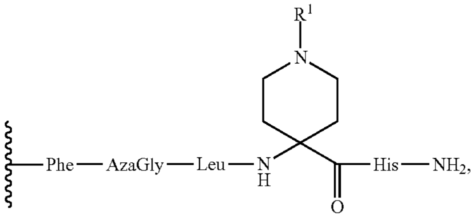
(SEQ ID NO: 278)
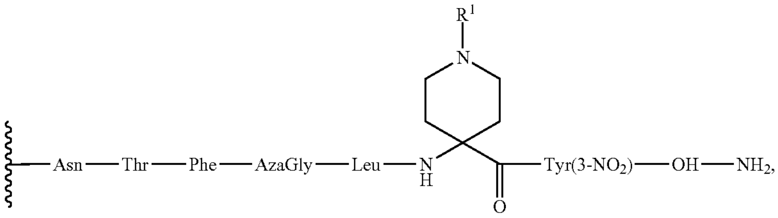
(SEQ ID NO: 279)
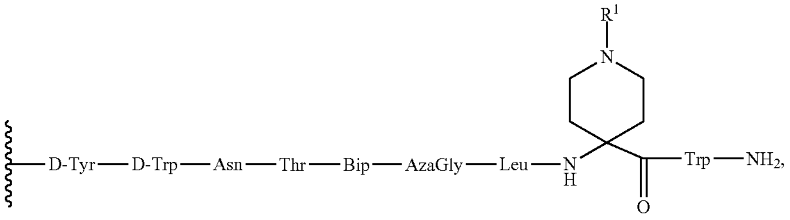

-continued
(SEQ ID NO: 280)
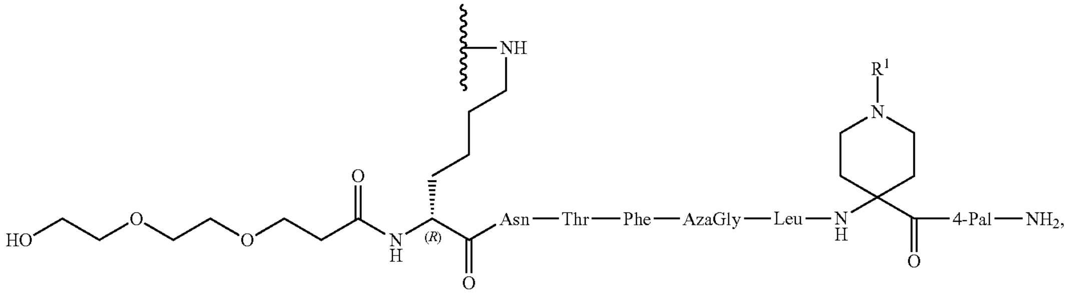
(SEQ ID NO: 281)
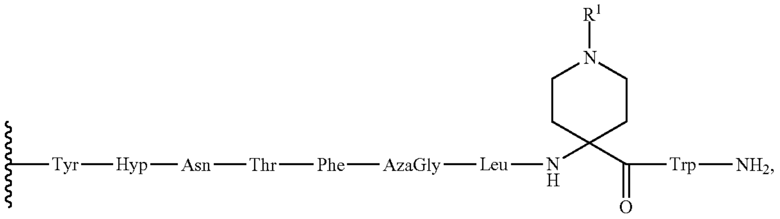
(SEQ ID NO: 282)
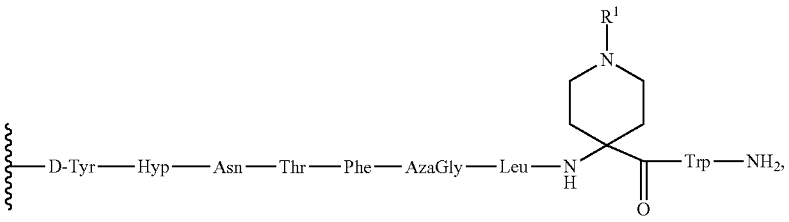
(SEQ ID NO: 283)
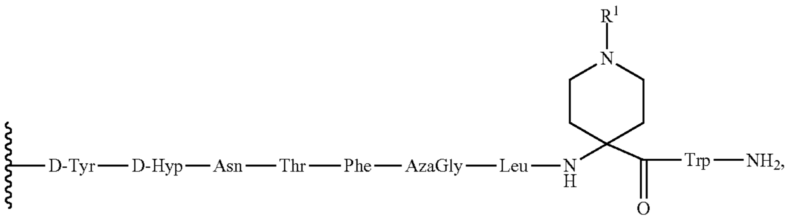
(SEQ ID NO: 285)
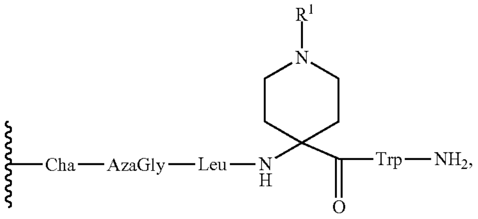
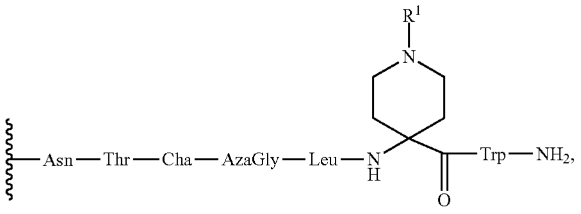
(SEQ ID NO: 286)
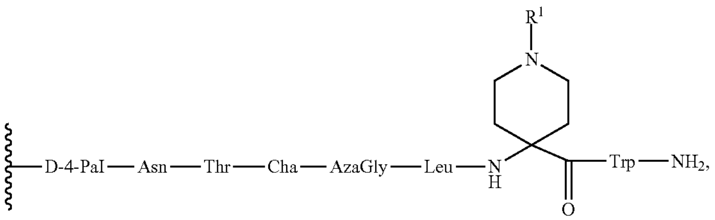

-continued
(SEQ ID NO: 287)
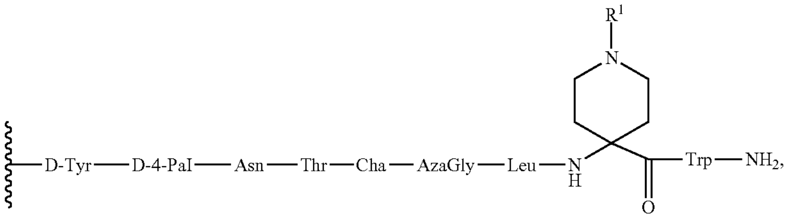
(SEQ ID NO: 288)
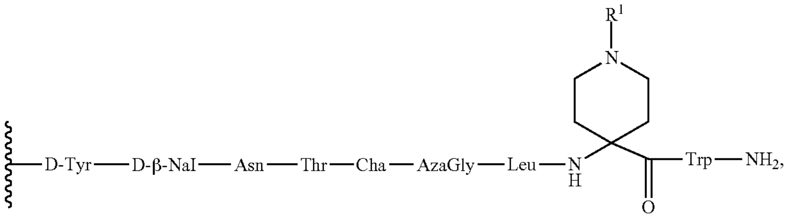
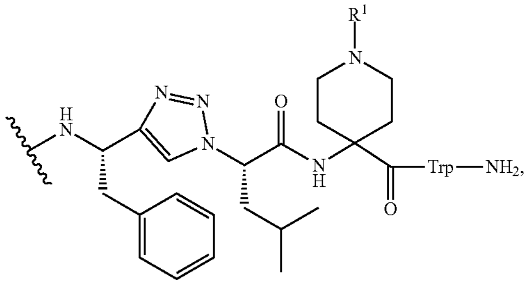
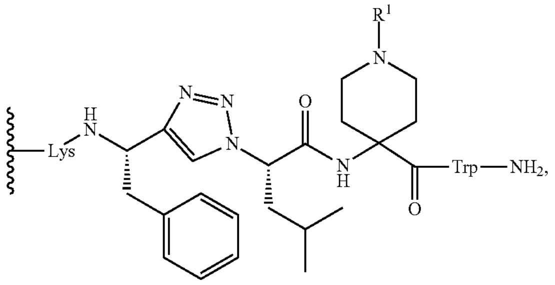
(SEQ ID NO: 290)
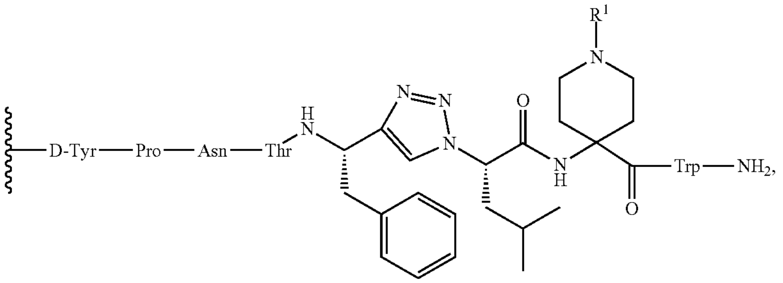
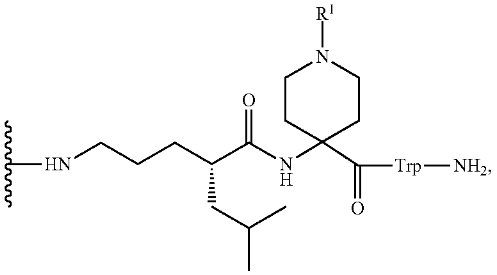
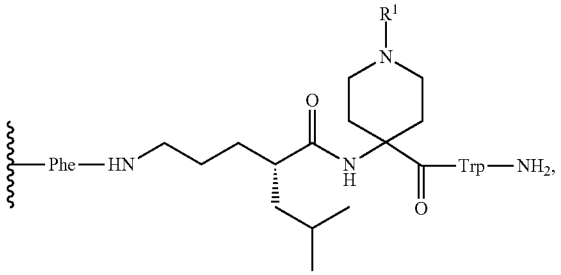
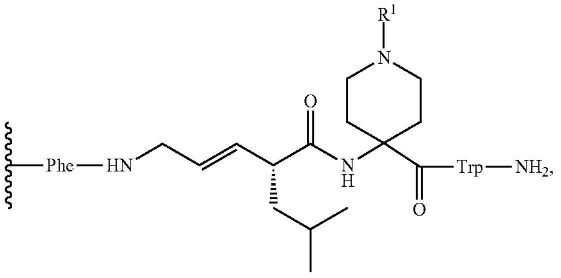
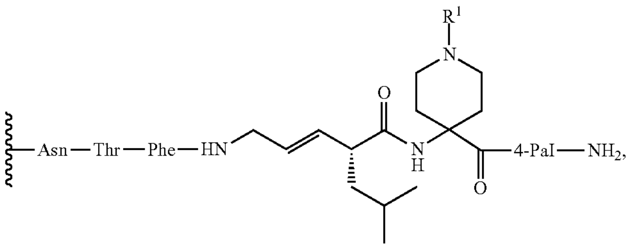

-continued
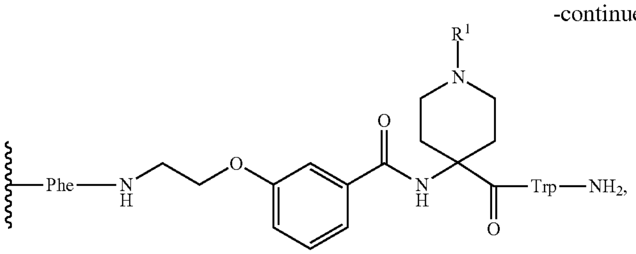,
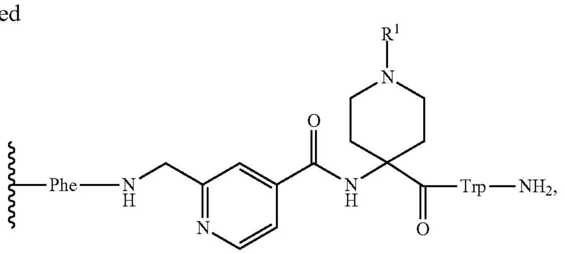,
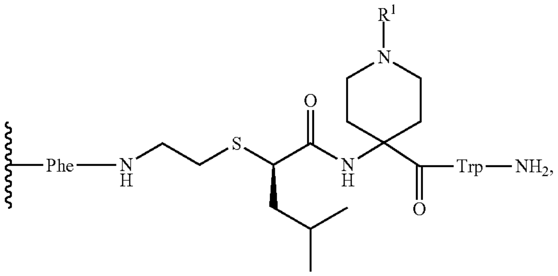,
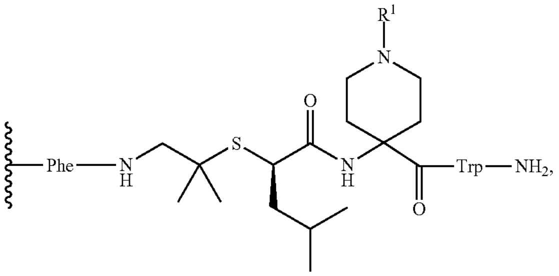,
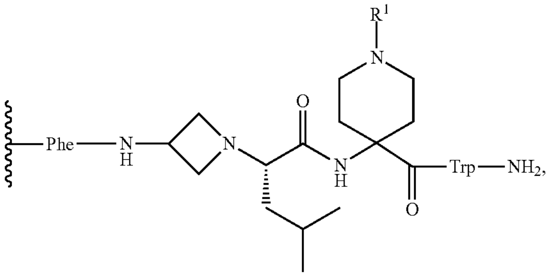,
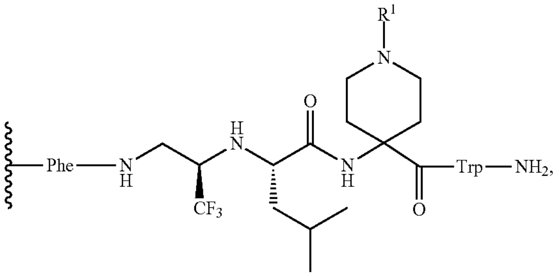,
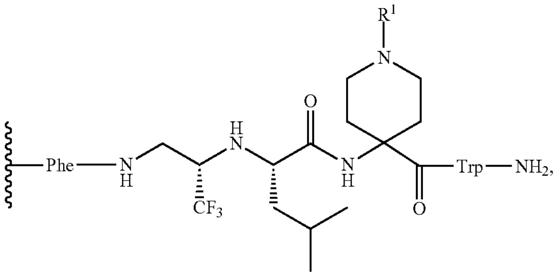,
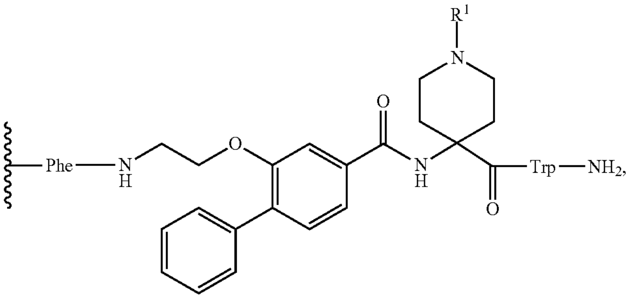,
(SEQ ID NO: 302)
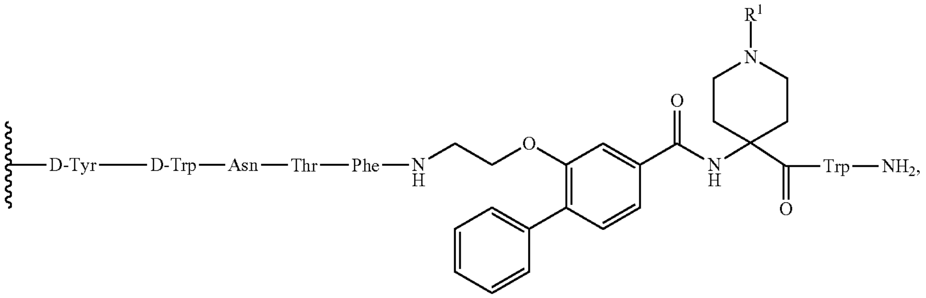,
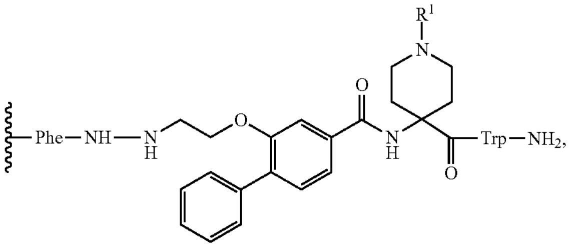,
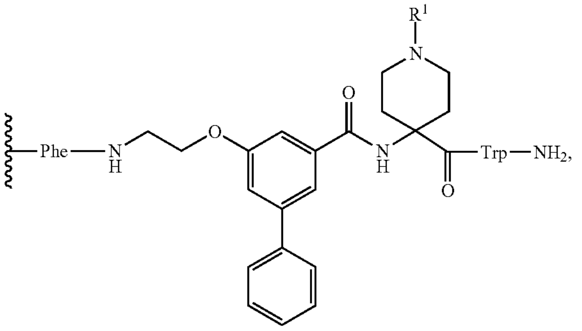, -continued
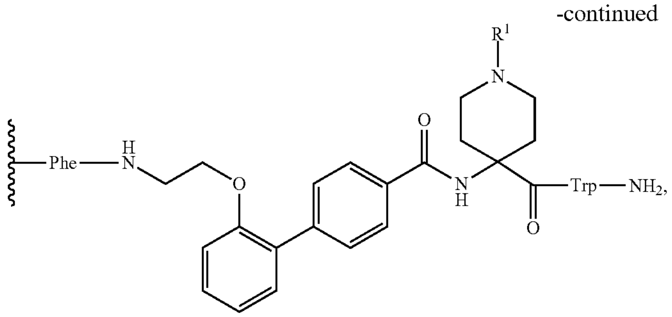
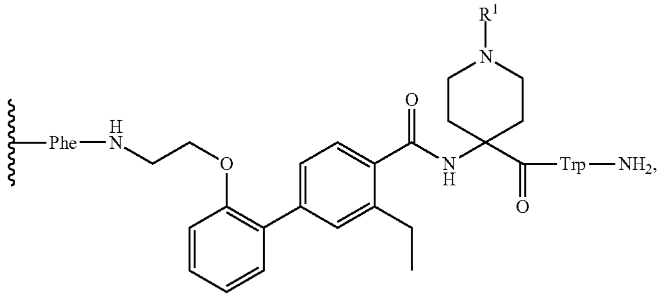
(SEQ ID NO: 306)
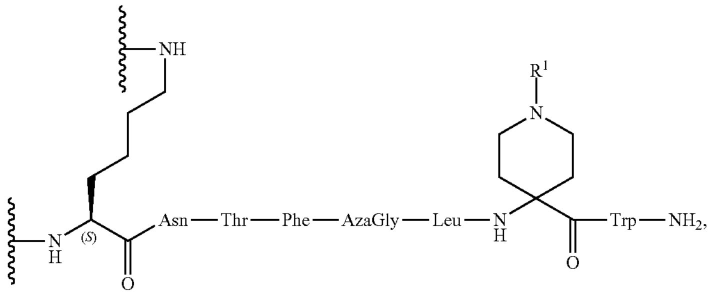
(SEQ ID NO: 307)
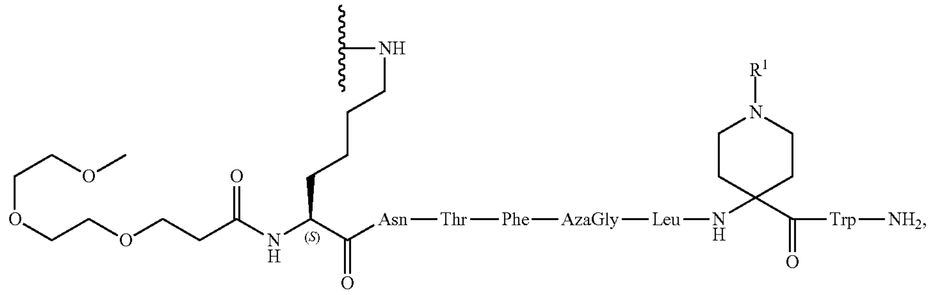
(SEQ ID NO: 308)
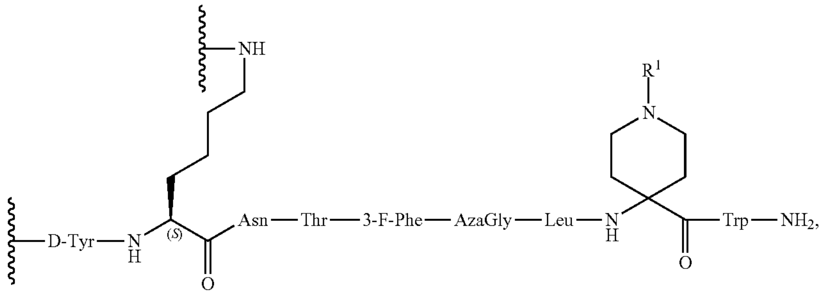

-continued
(SEQ ID NO: 309)
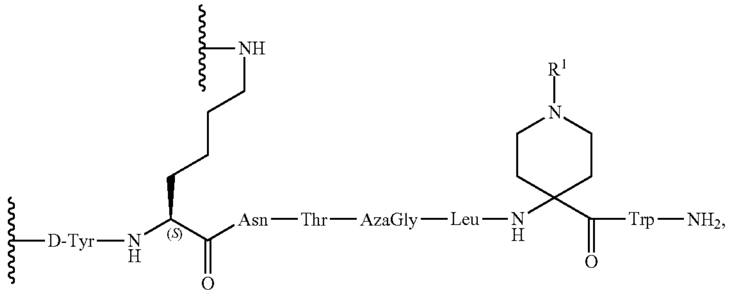
(SEQ ID NO: 310)
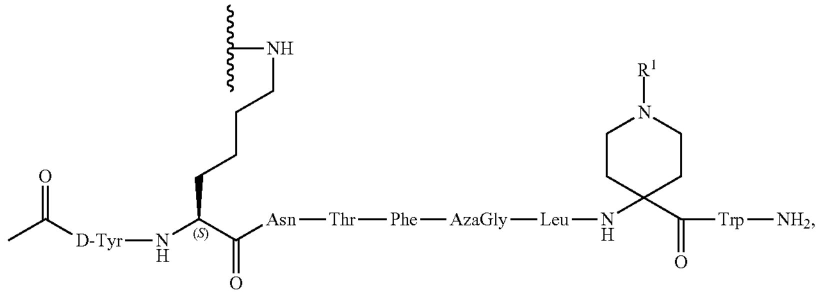
(SEQ ID NO: 311)
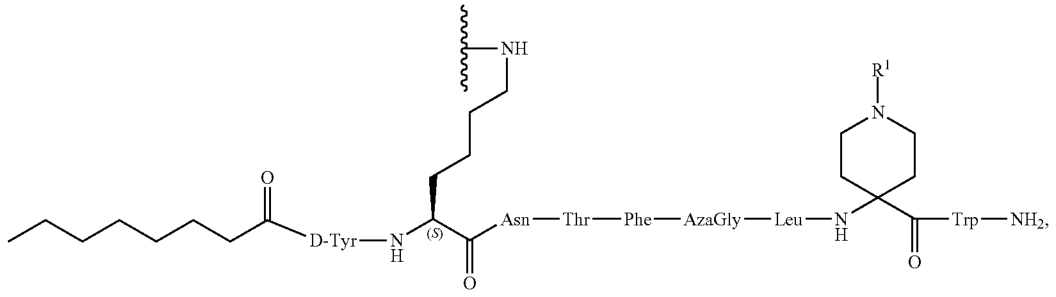
(SEQ ID NO: 312)
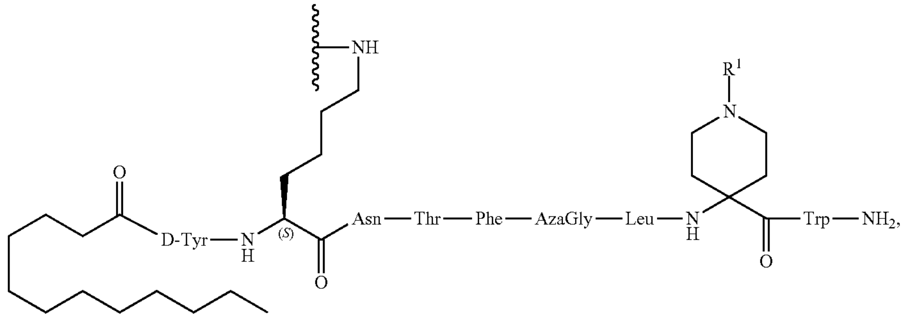
(SEQ ID NO: 313)
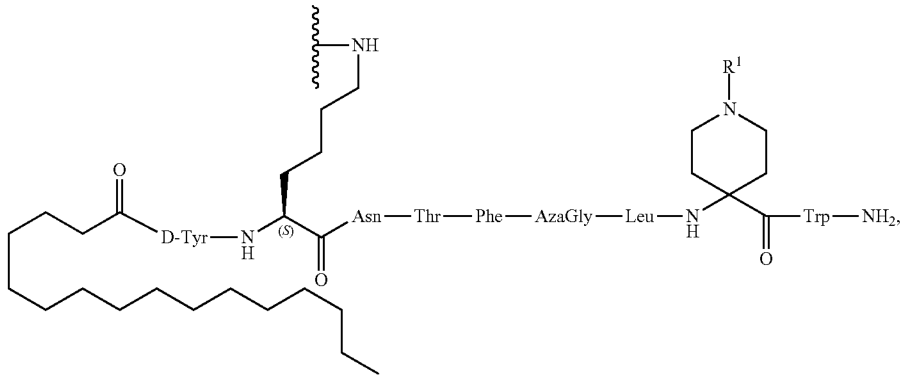

-continued
(SEQ ID NO: 314)
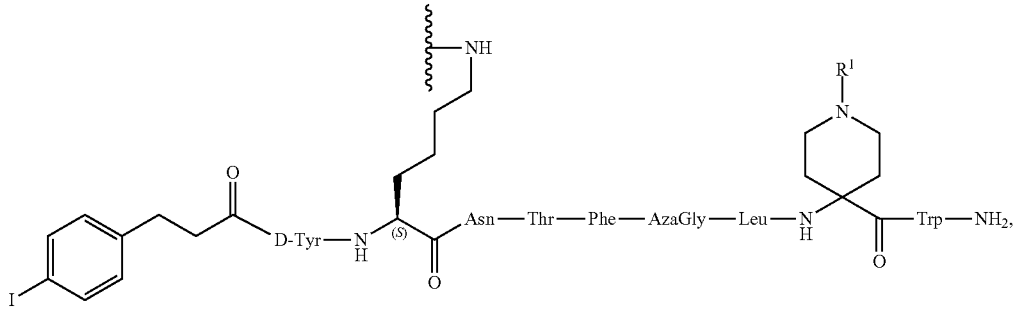
(SEQ ID NO: 315)
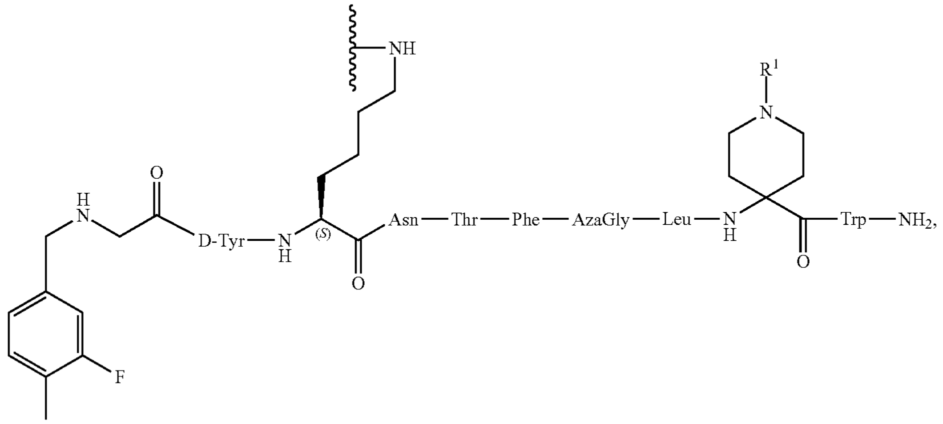
(SEQ ID NO: 316)
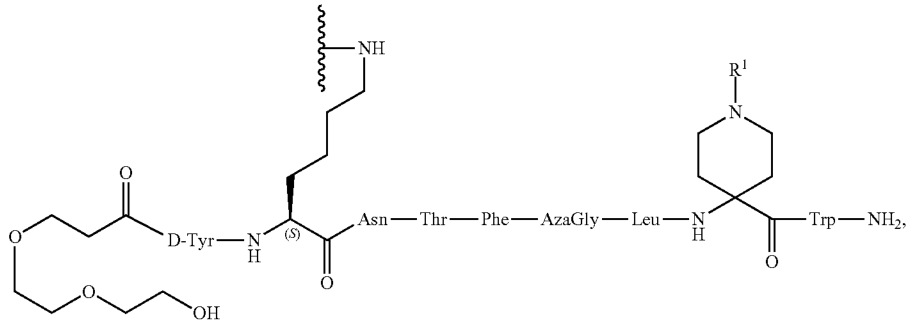
(SEQ ID NO: 316)
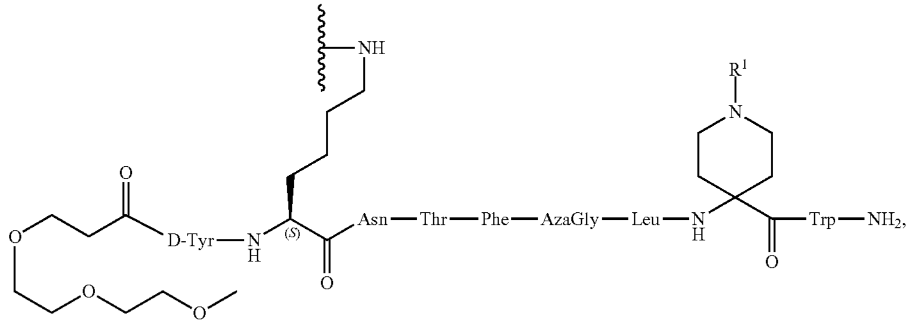

-continued
(SEQ ID NO: 317)
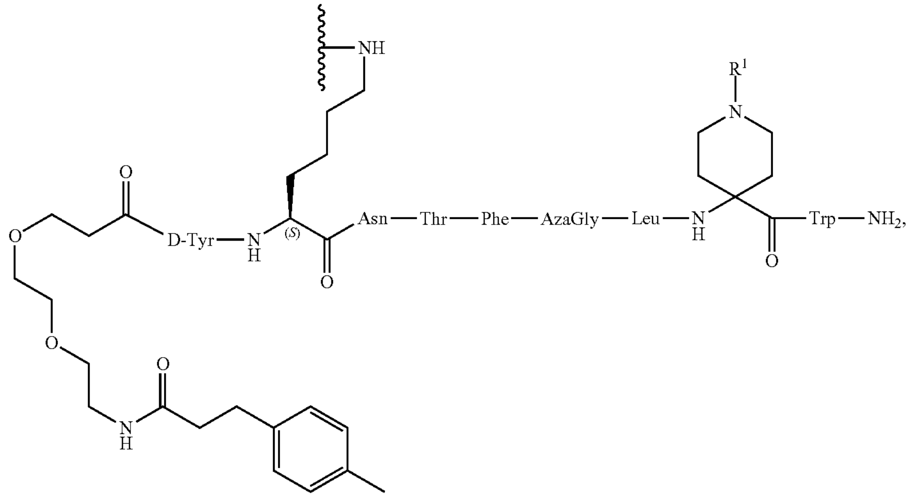
(SEQ ID NO: 318)
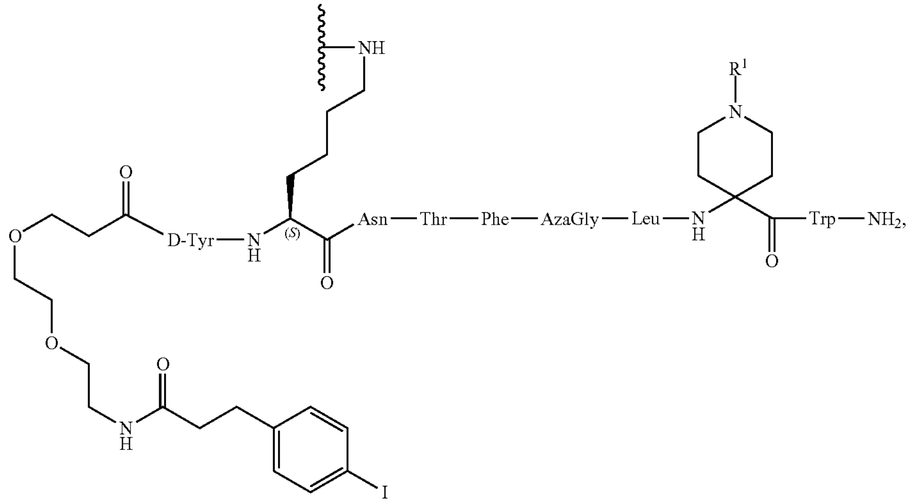
(SEQ ID NO: 319)
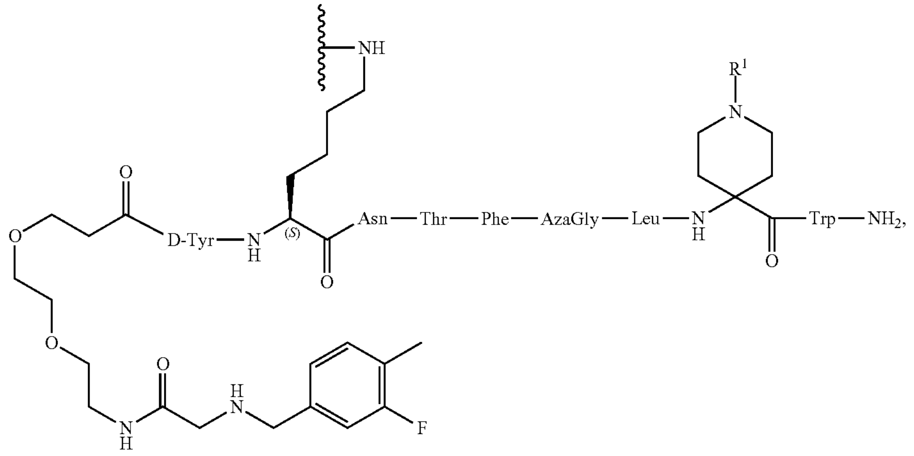

-continued
(SEQ ID NO: 320)
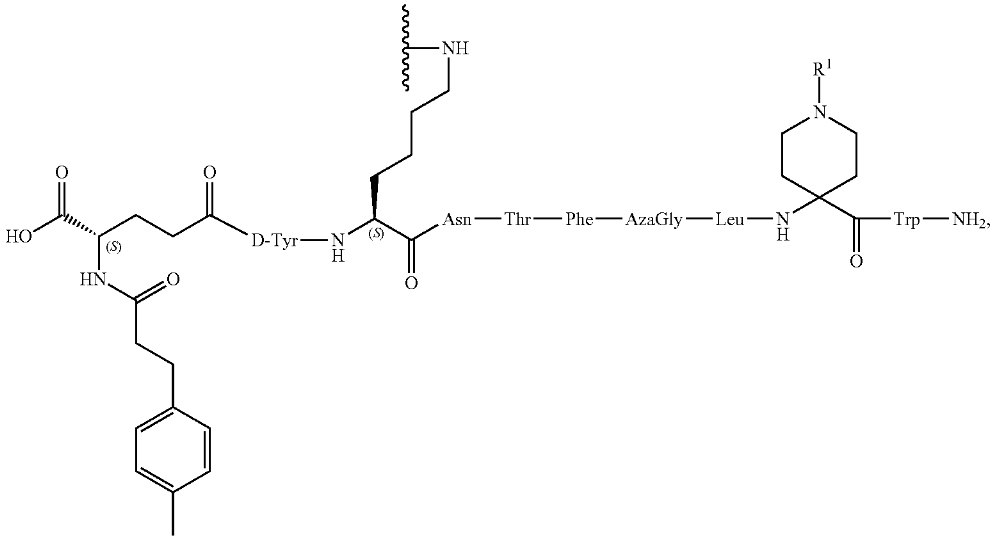
(SEQ ID NO: 321)
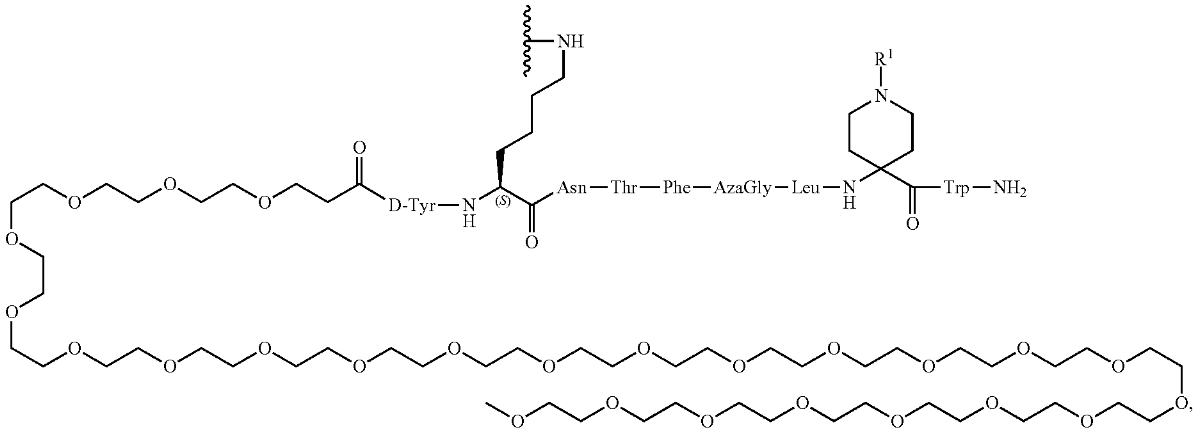
(SEQ ID NO: 322)
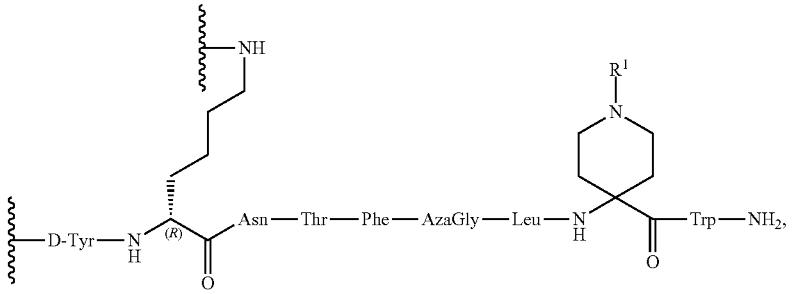
(SEQ ID NO: 323)
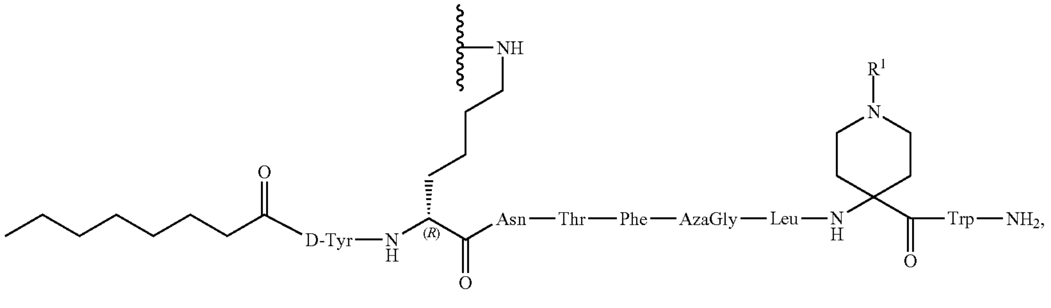

-continued
(SEQ ID NO: 324)
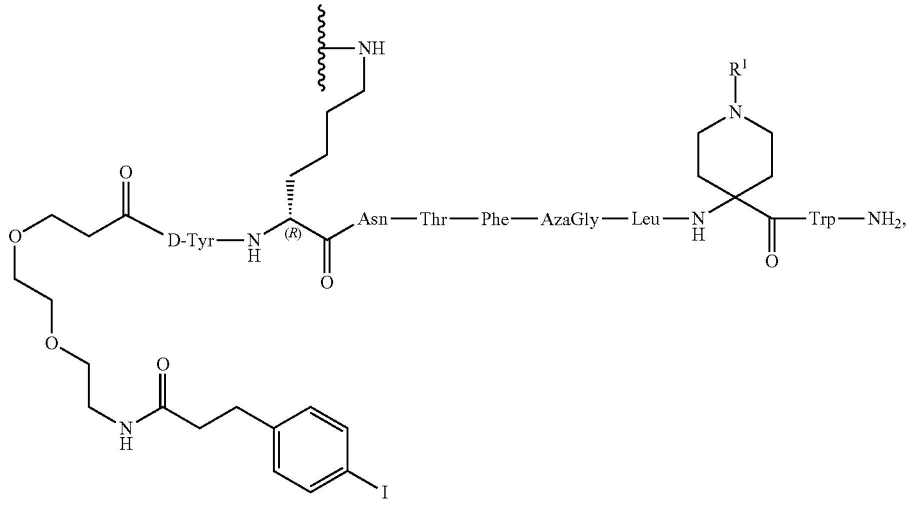
(SEQ ID NO: 325)
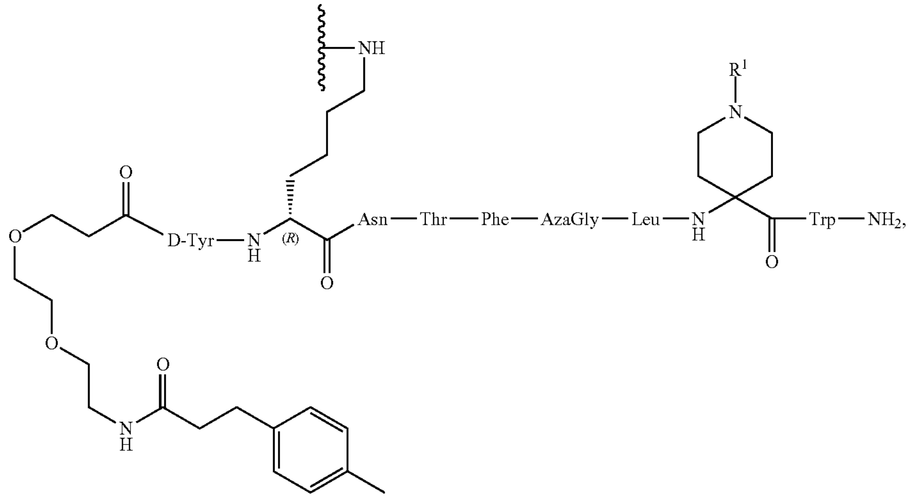
(SEQ ID NO: 326)
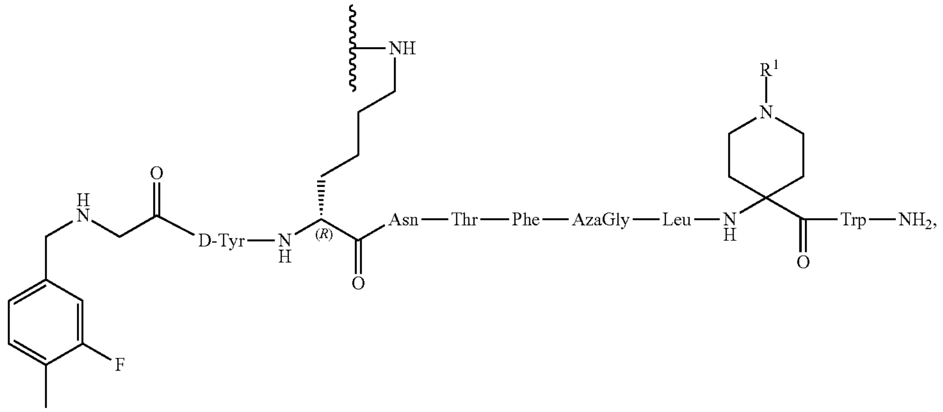

-continued
(SEQ ID NO: 327)
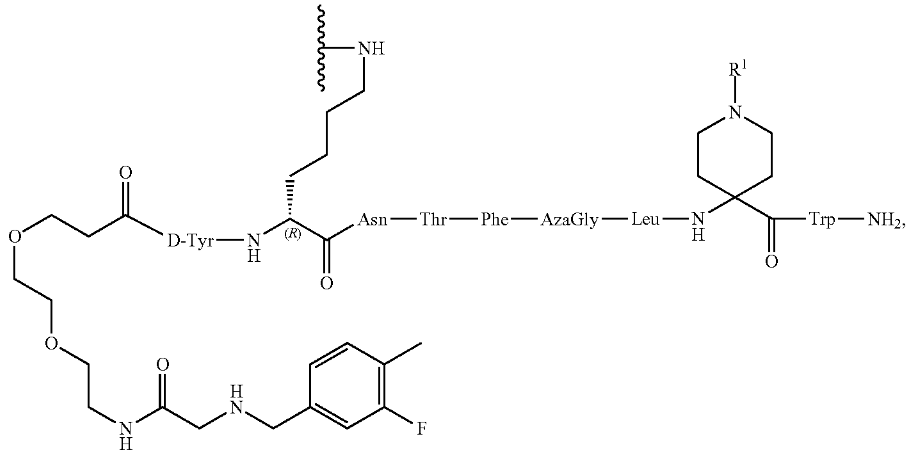
(SEQ ID NO: 328)
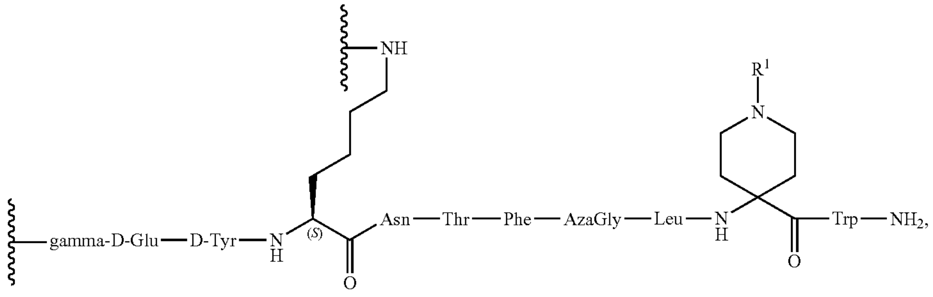
(SEQ ID NO: 330)
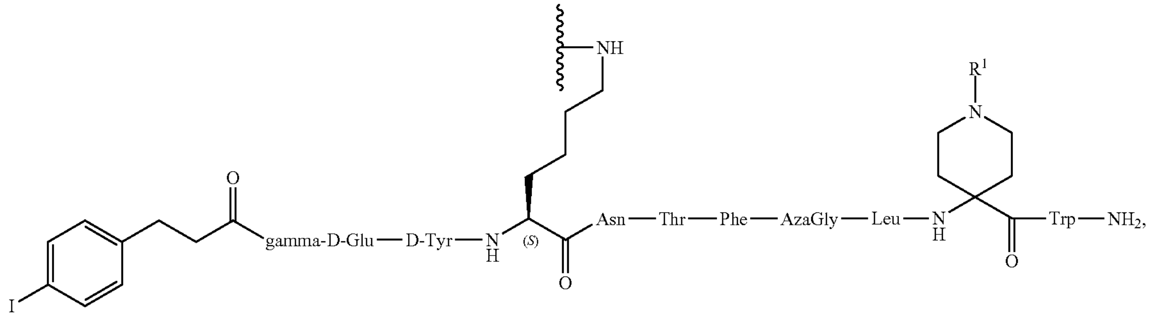
(SEQ ID NO: 331)
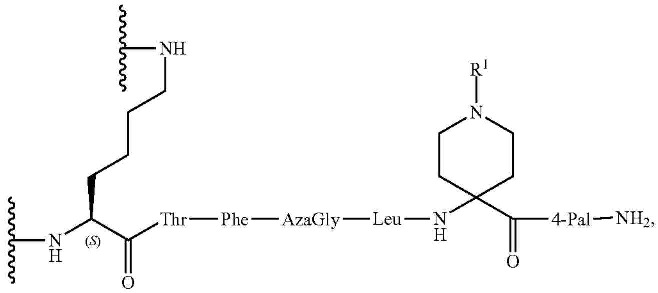

-continued
(SEQ ID NO: 332)
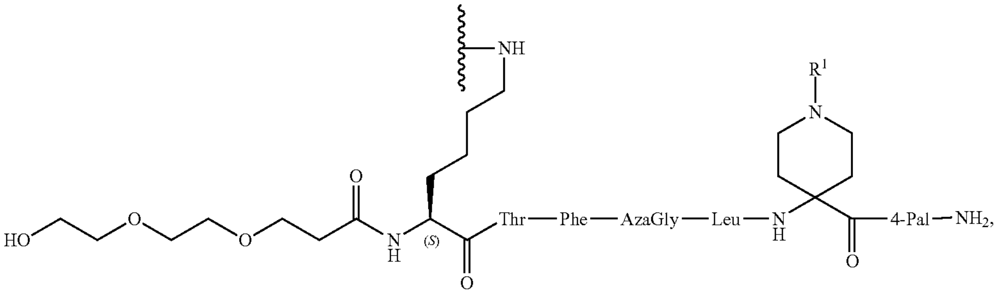
(SEQ ID NO: 333)
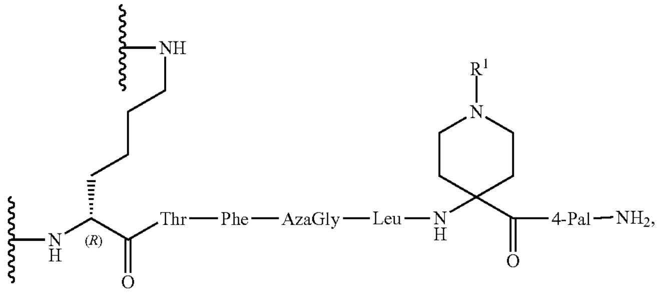
(SEQ ID NO: 334)
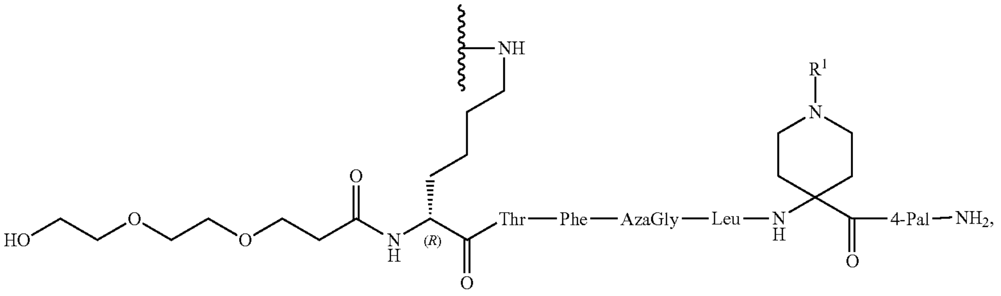
(SEQ ID NO: 335)
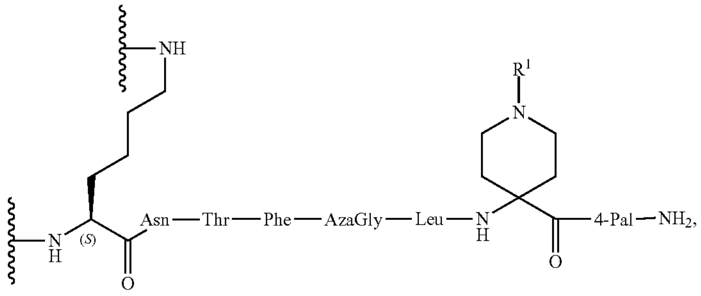
(SEQ ID NO: 336)
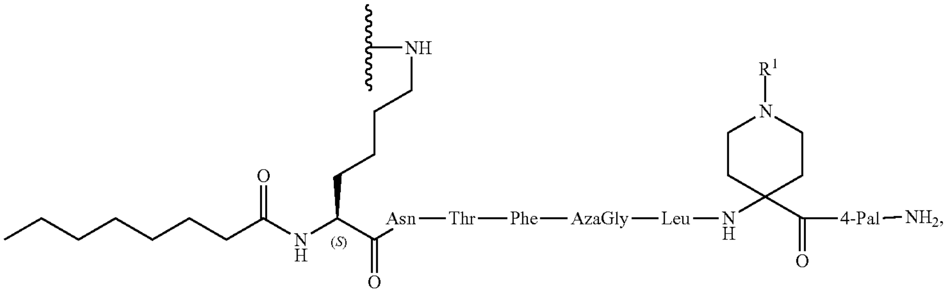

-continued
(SEQ ID NO: 337)
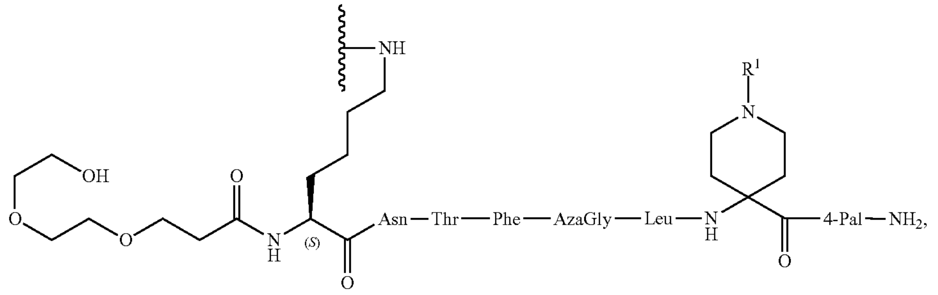
(SEQ ID NO: 338)
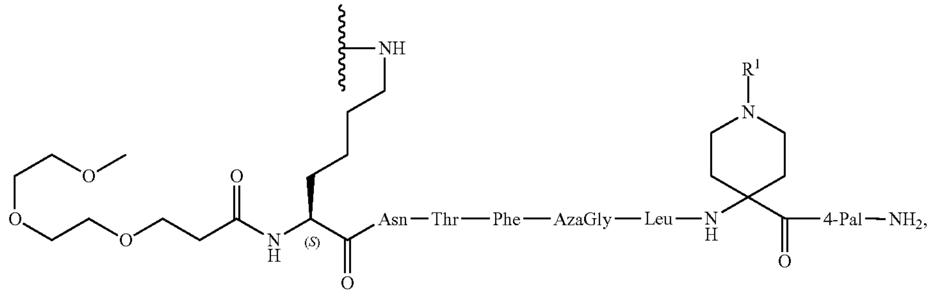
(SEQ ID NO: 339)
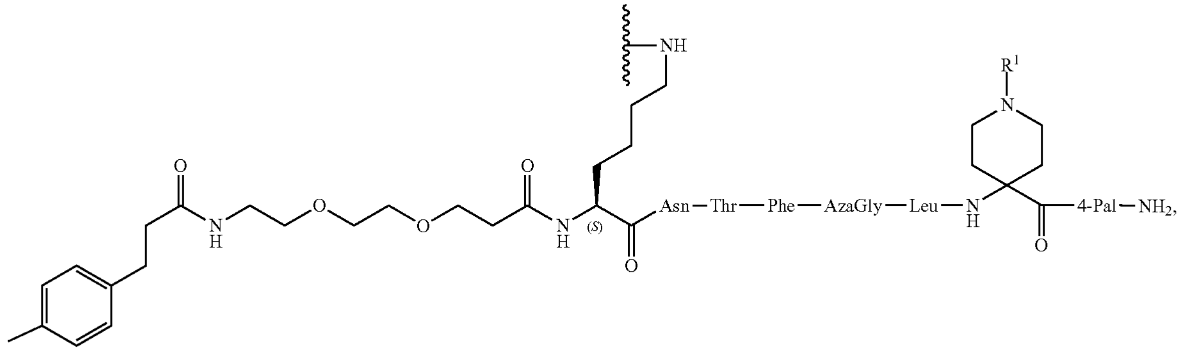
(SEQ ID NO: 340)
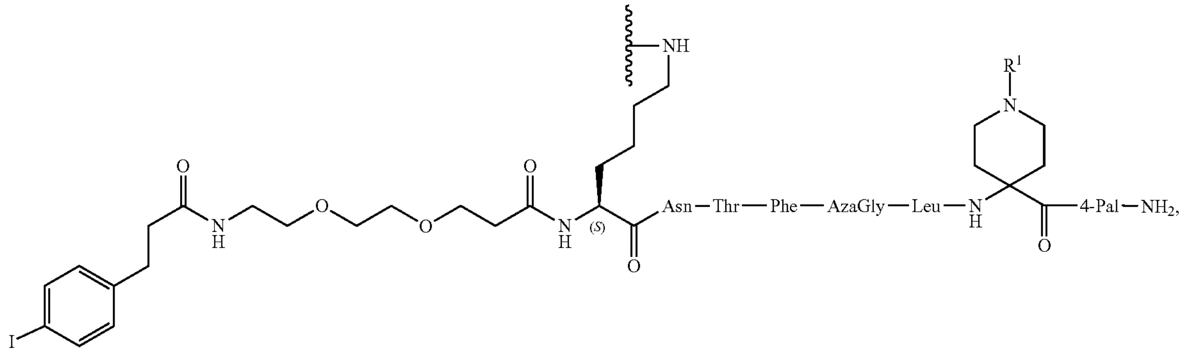

-continued
(SEQ ID NO: 341)
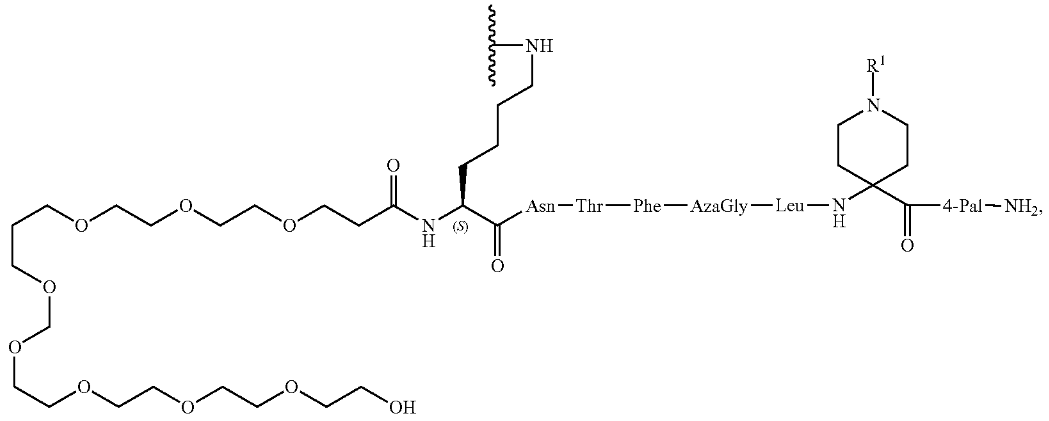
(SEQ ID NO: 342)
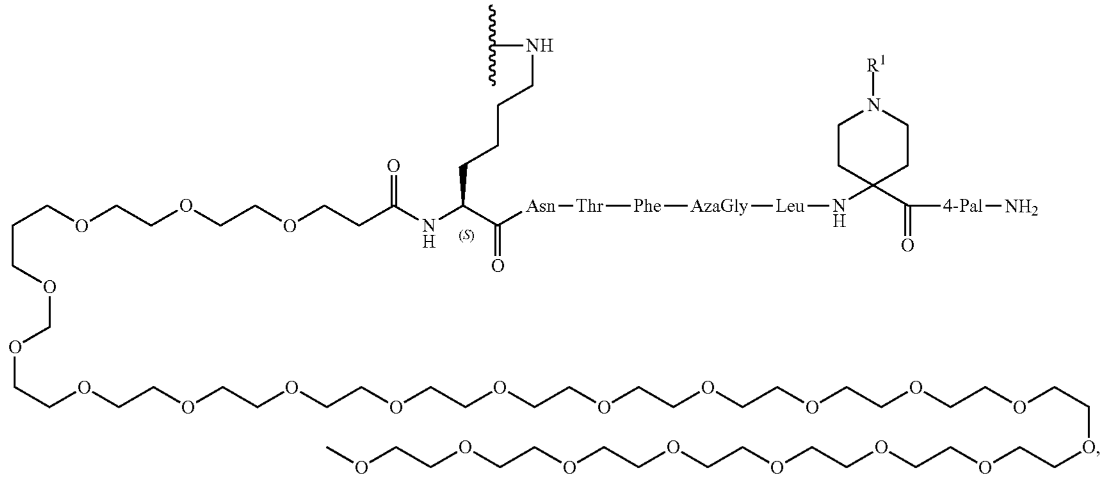
(SEQ ID NO: 343)
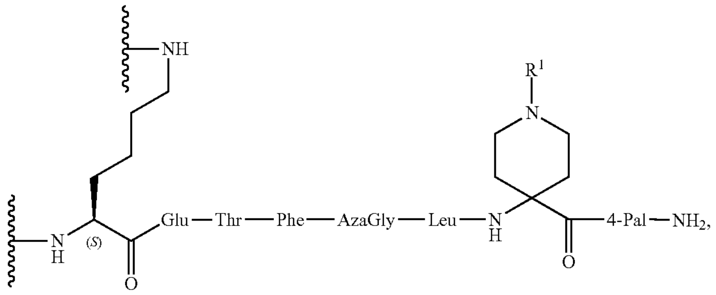
(SEQ ID NO: 344)
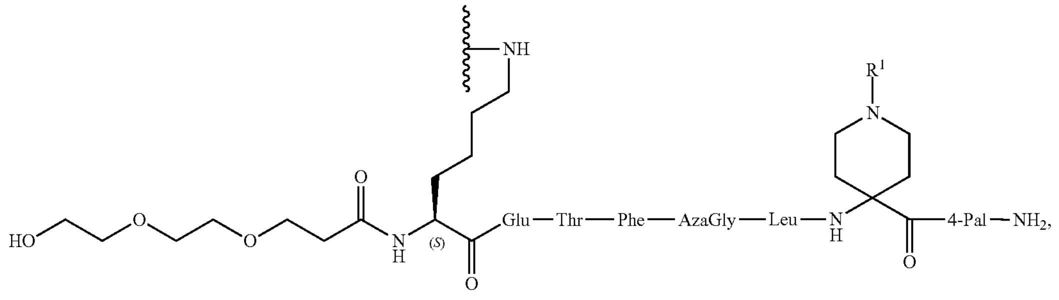

-continued
(SEQ ID NO: 345)
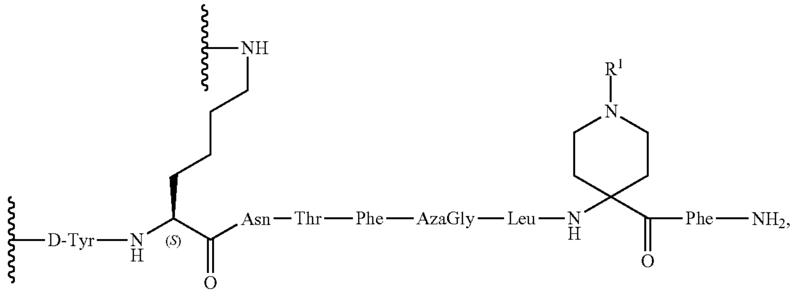
(SEQ ID NO: 346)
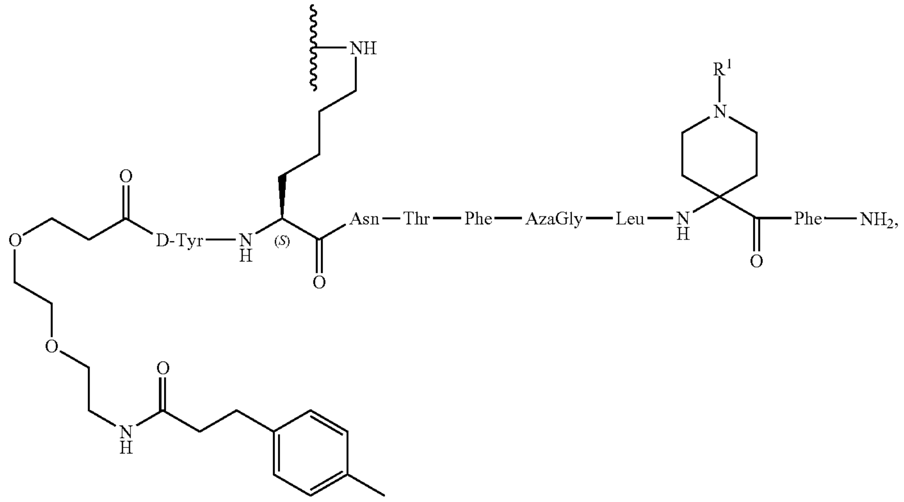
(SEQ ID NO: 347)
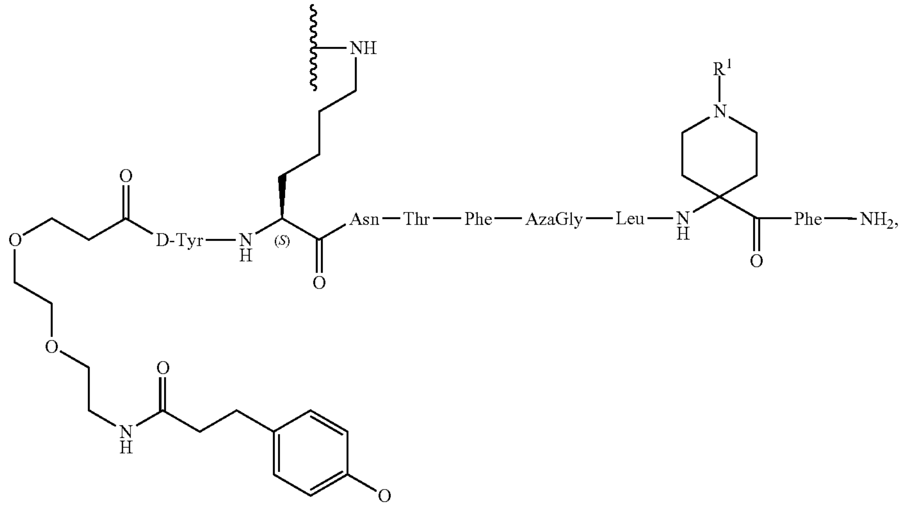
(SEQ ID NO: 348)
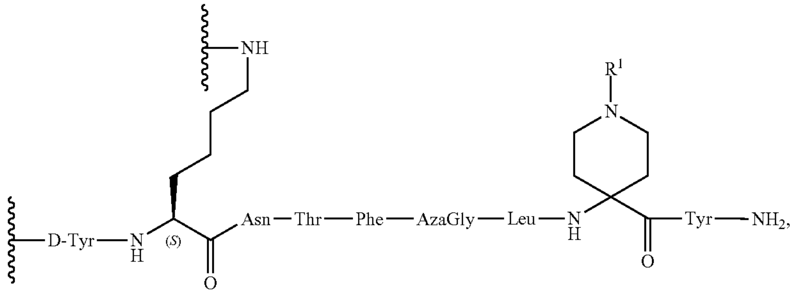

-continued
(SEQ ID NO: 349)
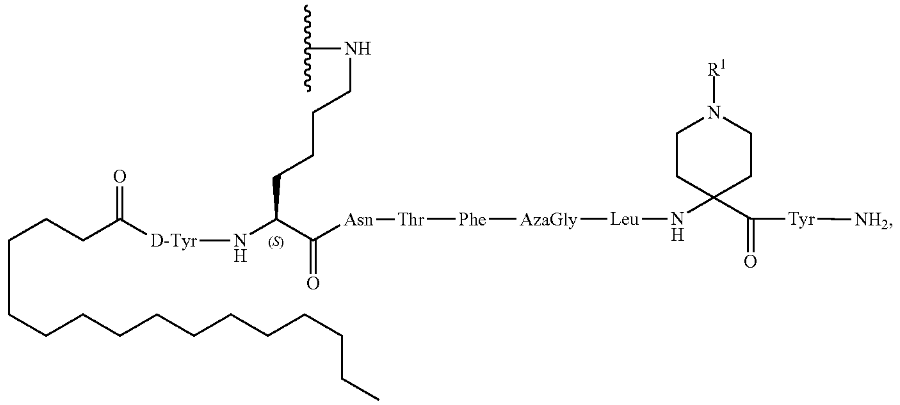
(SEQ ID NO: 350)
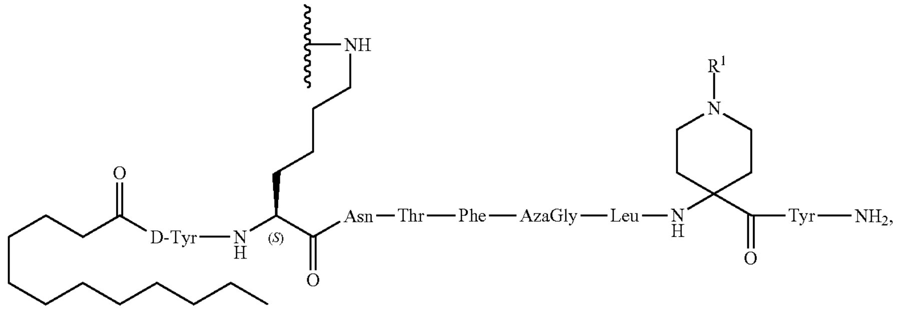
(SEQ ID NO: 351)
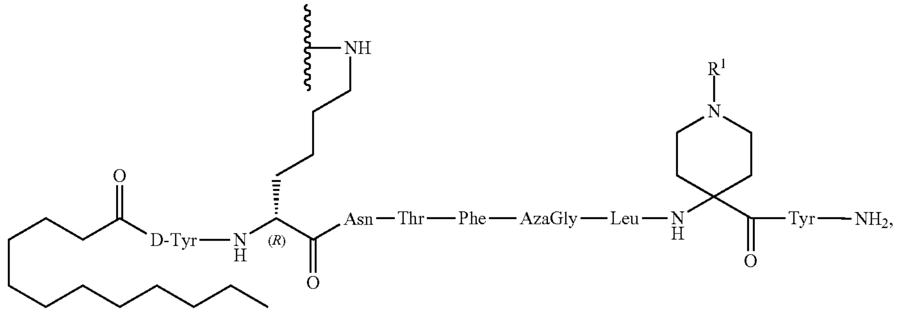
(SEQ ID NO: 352)
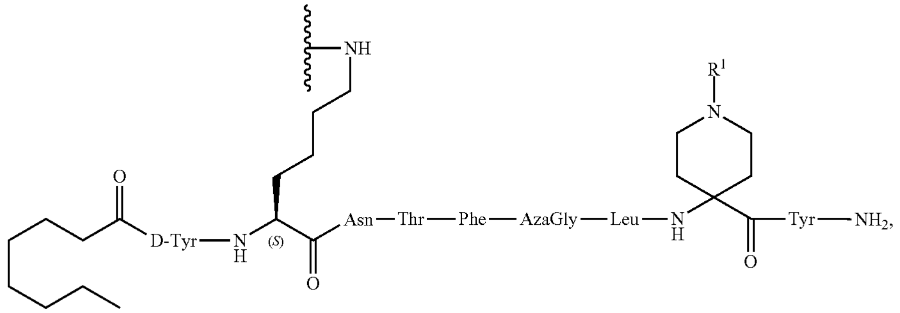

-continued
(SEQ ID NO: 353)
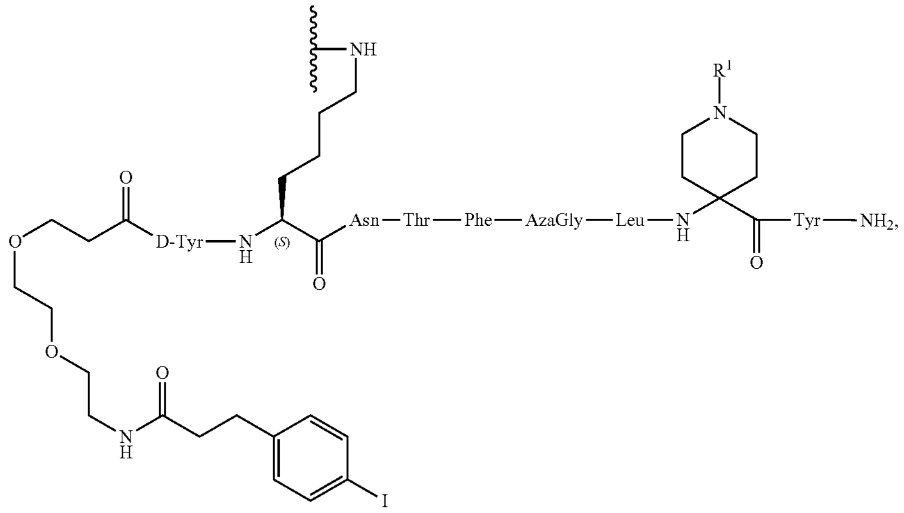
(SEQ ID NO: 354)
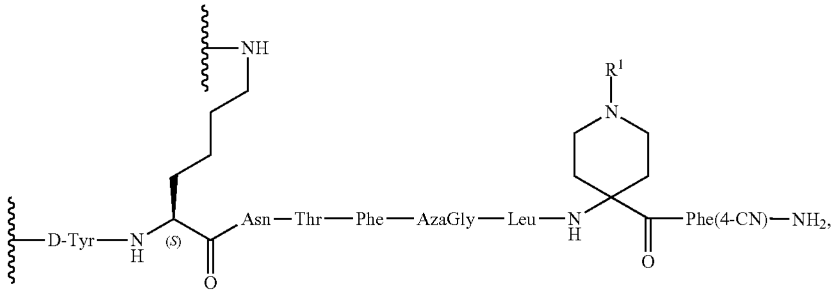
(SEQ ID NO: 355)
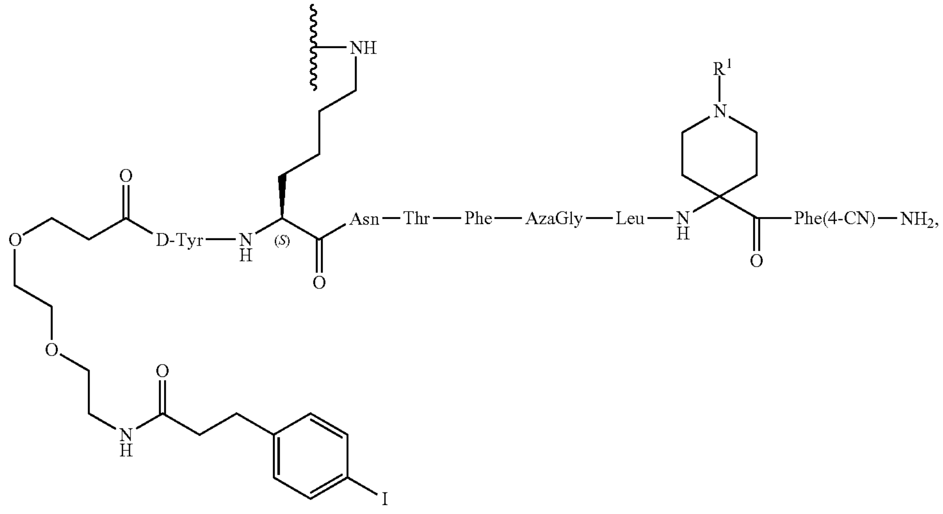

(SEQ ID NO: 356)
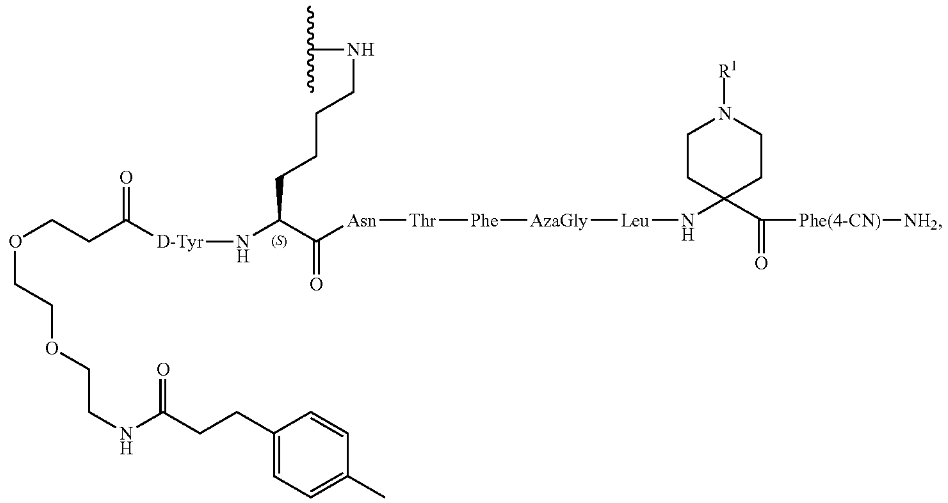
(SEQ ID NO: 357)
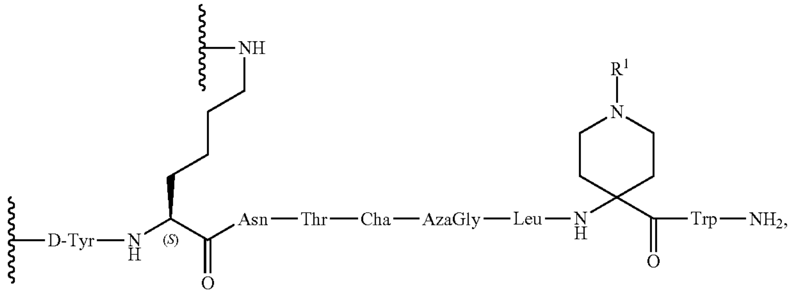
(SEQ ID NO: 358)
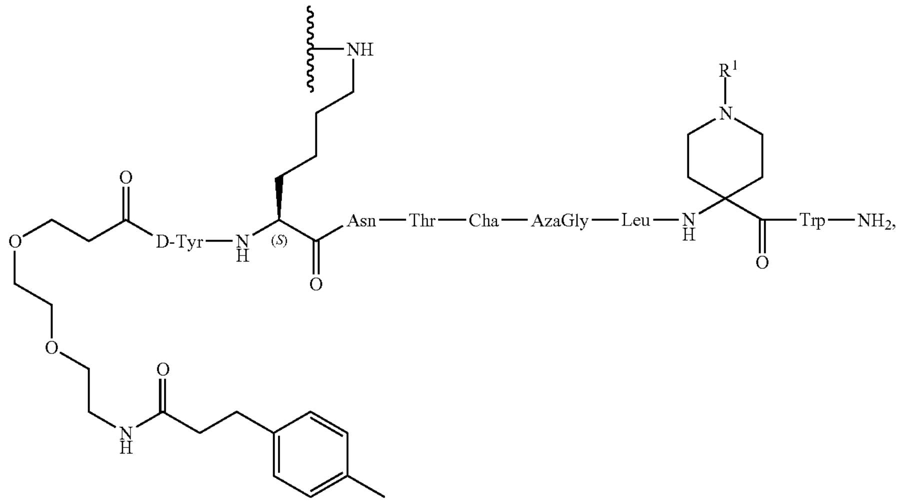

-continued
(SEQ ID NO: 359)
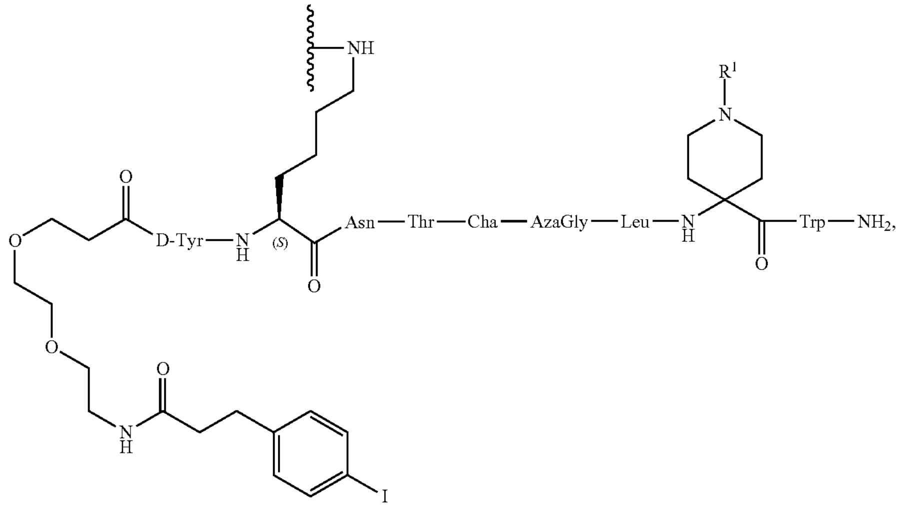
(SEQ ID NO: 360)
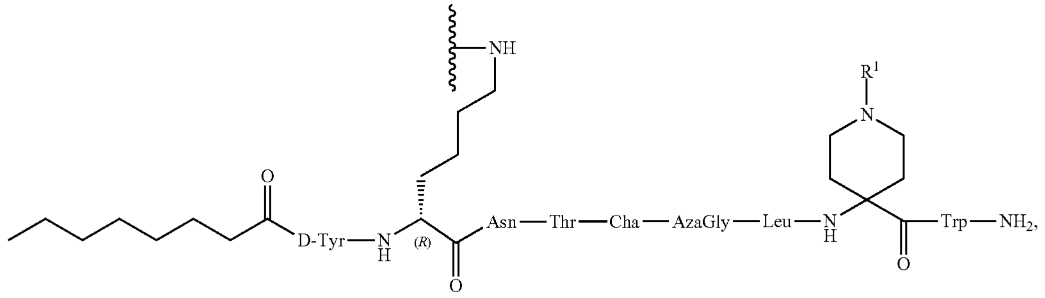
(SEQ ID NO: 361)
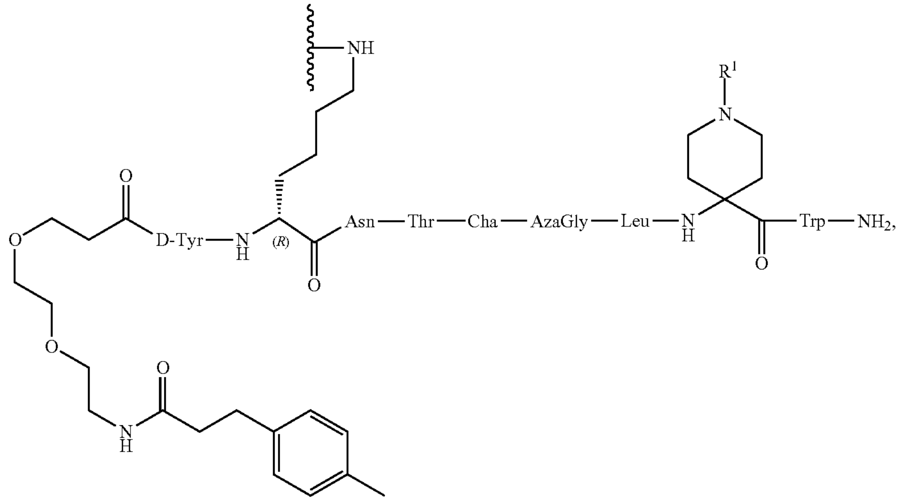
(SEQ ID NO: 362)
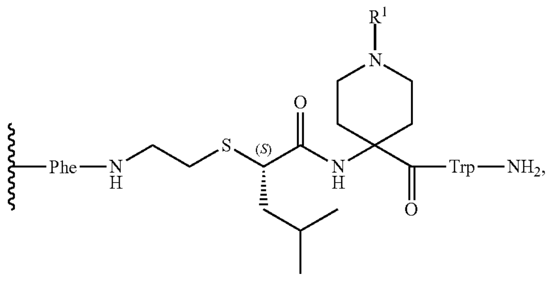
(SEQ ID NO: 363)
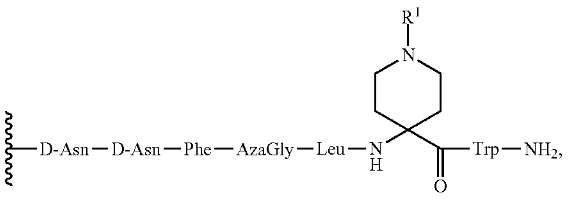

-continued
(SEQ ID NO: 364)
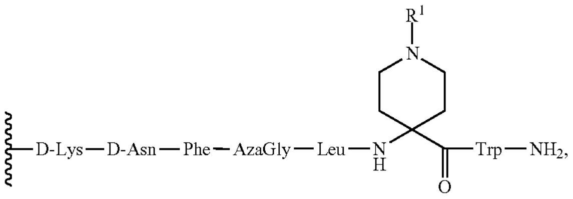
(SEQ ID NO: 365)
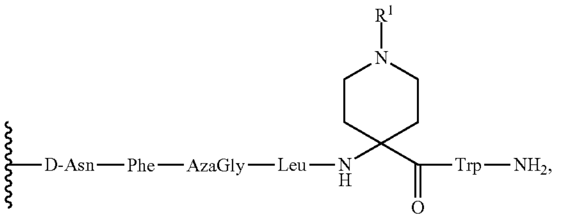
(SEQ ID NO: 366)
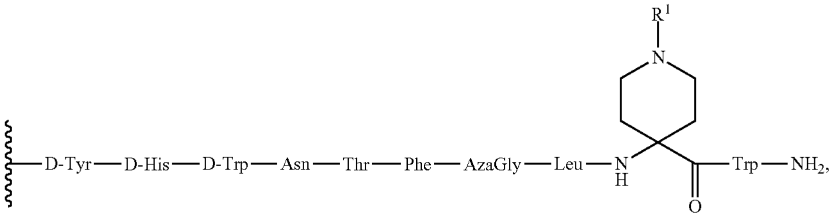
(SEQ ID NO: 367)
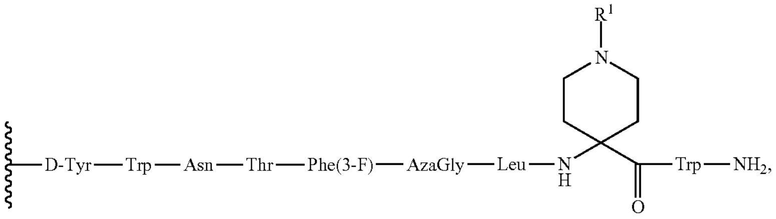
(SEQ ID NO: 368)
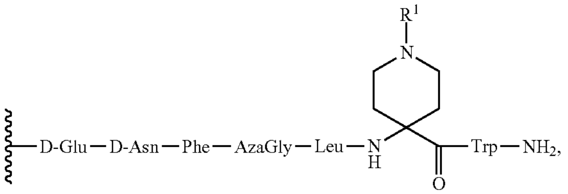
(SEQ ID NO: 369)
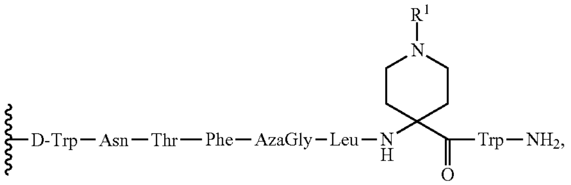
(SEQ ID NO: 370)
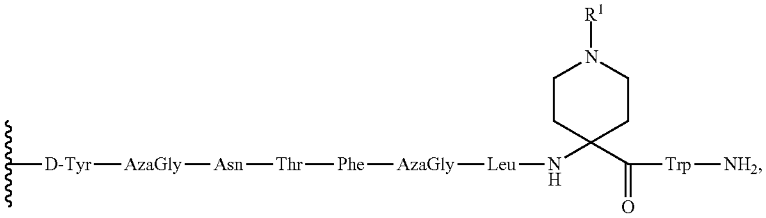
(SEQ ID NO: 371)
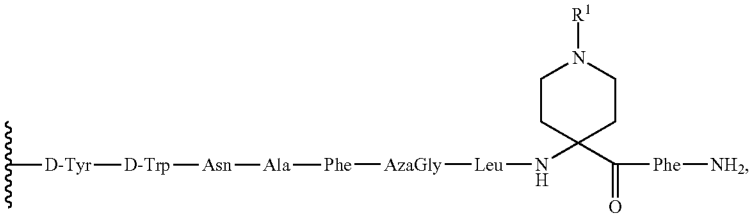
(SEQ ID NO: 372)
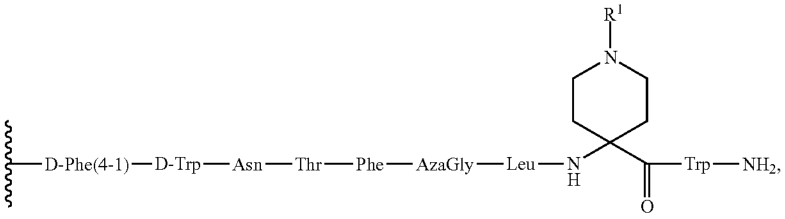

-continued
(SEQ ID NO: 373)
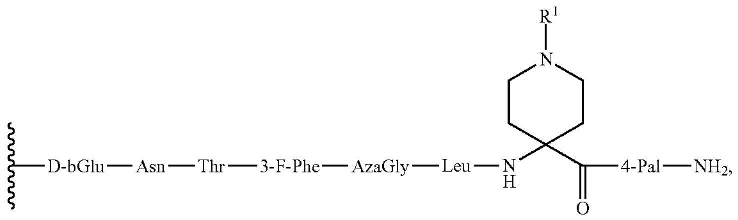
(SEQ ID NO: 374)
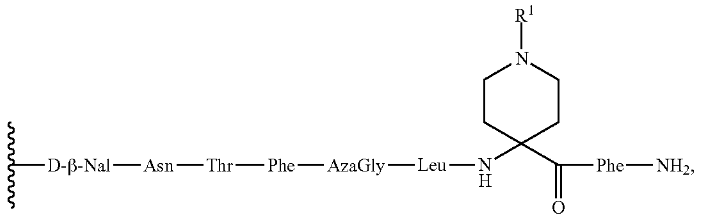
(SEQ ID NO: 375)
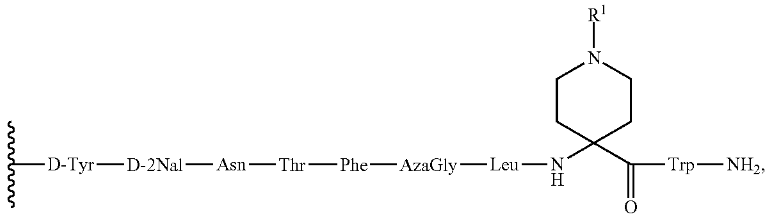
(SEQ ID NO: 376)
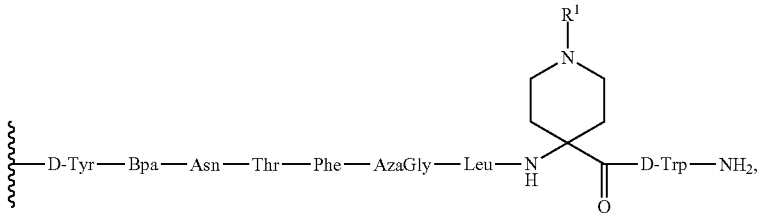
(SEQ ID NO: 377)
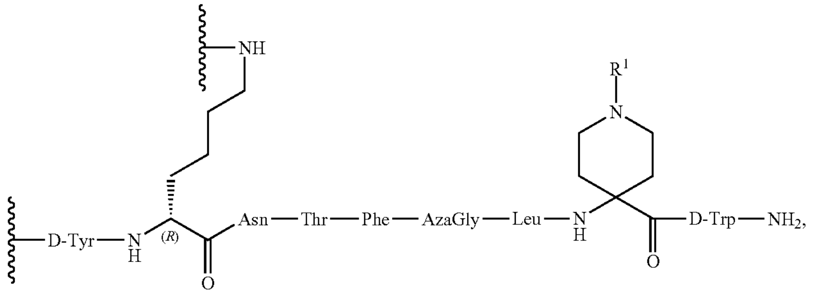
(SEQ ID NO: 378)
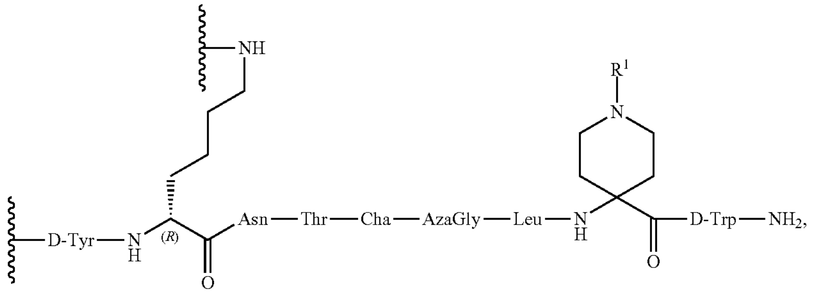

-continued
(SEQ ID NO: 379)
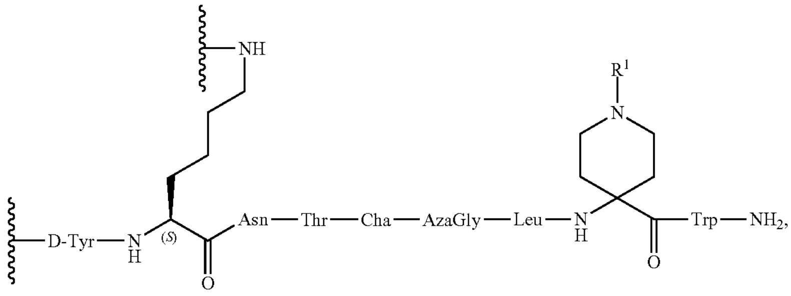
,
(SEQ ID NO: 380)
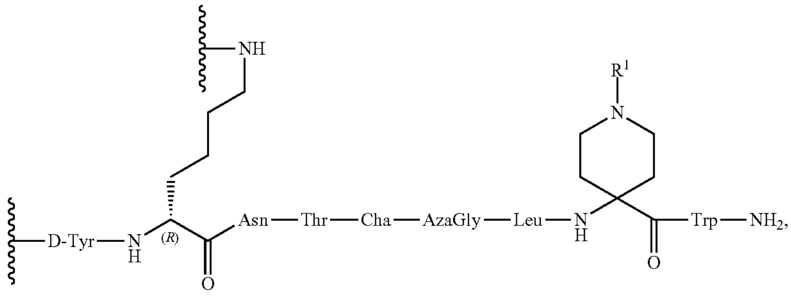
,
(SEQ ID NO: 381)
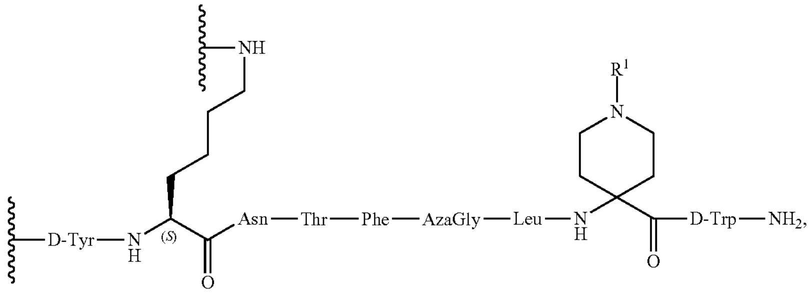
, or
(SEQ ID NO: 382)
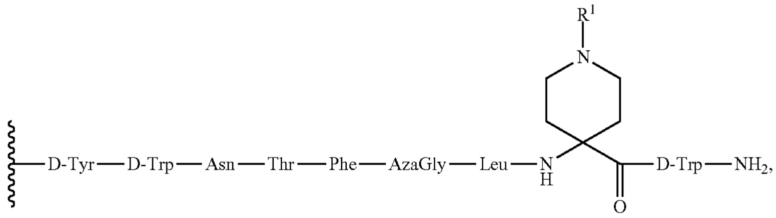
,
(SEQ ID NO: 383)
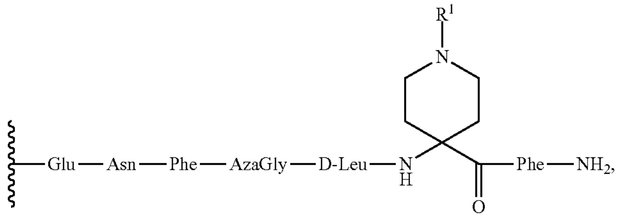
, -continued (SEQ ID NO: 384)

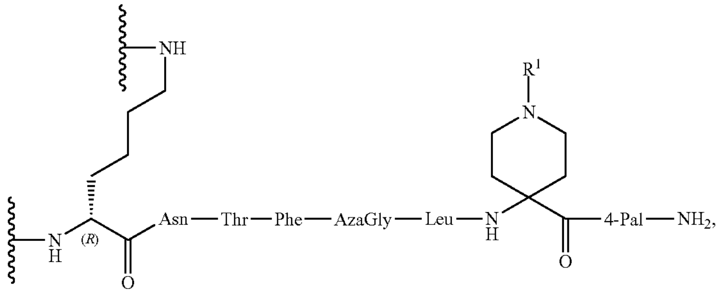

or (SEQ ID NO: 385)

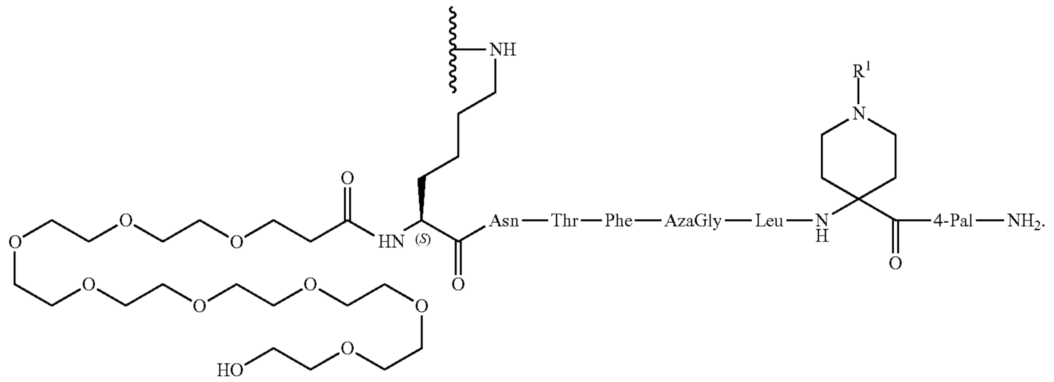

Embodiment 46. The compound of any one of embodiments 1-45, or a pharmaceutically acceptable salt thereof, wherein $R^a$ is a chelating moiety independently selected from the group consisting of:

1,4,7,10-tetraazacyclododecane-1,4,7,10-tetraacetic acid (DOTA);

2,2',2"(10-(2-amino-2-oxoethyl)-1,4,7,10-tetraazacyclododecane-1,4,7-triyl)triacetic acid (PSC);

1,4,7,10-tetraazacyclododecane-1,4,7-triacetic acid (DO3A);

1,4,7,10-tetraazacyclododecane-1,7-diacetic acid (DO2A);

α,α',α",α'"-tetramethyl-1,4,7,10-tetraazacyclododecane-1,4,7,10-tetraacetic acid (DOTMA);

1,4,7,10-tetrakis(carbamoylmethyl)-1,4,7,10-tetraazacyclododecane (DOTAM);

1,4,7,10-tetraazacyclododecane-1,4,7,10-tetrapropionic acid (DOTPA);

2,2',2"-(10-(2-amino-2-oxoethyl)-1,4,7,10-tetraazacyclododecane-1,4,7-triyl)triacetic acid:

benzyl-1,4,7,10-tetraazacyclododecane-1,4,7,10-tetraacetic acid (Bn-DOTA); p-hydroxy-benzyl-1,4,7,10-tetraazacyclododecane-1,4,7,10-tetraacetic acid (p-OH-Bn-DOTA);

6,6'-(((pyridine-2,6-diylbis(methylene))bis((carboxy methyl)azanediyl))bis(methylene))dipicolinic acid ($H_4$pypa);

H4pypa-benzyl;

6,6',6",6'"-(((pyridine-2,6-diylbis(methylene))bis(azanetriyl))tetrakis(methylene))-tetrapicolinic acid ($H_4$py4pa);

H-$_4$py4pa-benzyl;

2,2',2"-(1,4,7-triazacyclononane-1,4,7-triyl)triacetic acid (NOTA);

6,6'-((1,4,10,13-tetraoxa-7,16-diazacyclooctadecane-7,16-diyl)bis(methylene))dipicolinic acid (macropa);

2,2',2",2'"-(1,10-dioxa-4,7,13,16-tetraazacyclooctadecane-4,7,13,16-tetrayl)tetraacetic acid (crown);

6,6'-((ethane-1,2-diylbis((carboxymethyl)azanediyl))bis(methylene))dipicolinic acid ($H_4$octapa);

$H_4$octapa-benzyl; and 3,6,9,12-tetrakis(carboxymethyl)-3,6,9,12-tetraazatetradecanedioic acid (TTHA);

or a radionuclide complex thereof.

Embodiment 47. The compound of any one of embodiments 1-45, or a pharmaceutically acceptable salt thereof, wherein $R^a$ is a chelating moiety selected from the group consisting of:

1,4,7,10-tetraazacyclododecane-1,4,7,10-tetraacetic acid (DOTA) and 1,4,7,10-tetraazacyclododecane-1,4,7-triacetic acid (DO3A); or a radionuclide complex thereof.

Embodiment 48. The compound of any one of embodiments 1-45, or a pharmaceutically acceptable salt thereof, wherein $R^a$ is a chelating moiety independently selected from the group consisting of:

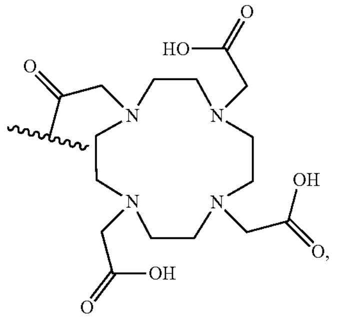

-continued

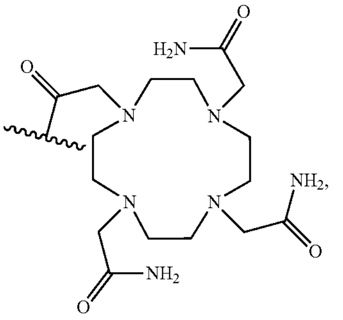

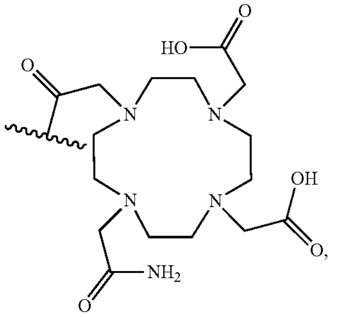 [SMILES: *C(=O)CN1CCN(CC(=O)O)CCN(CC(=O)O)CCN(CC(=O)O)CC1]

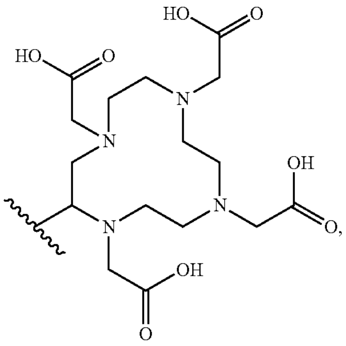

and

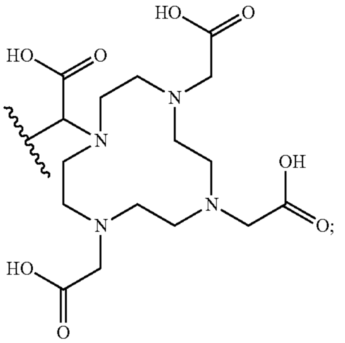

or a radionuclide complex thereof.

Embodiment 49. The compound of any one of embodiments 1-45, or a pharmaceutically acceptable salt thereof, wherein $R^a$ is

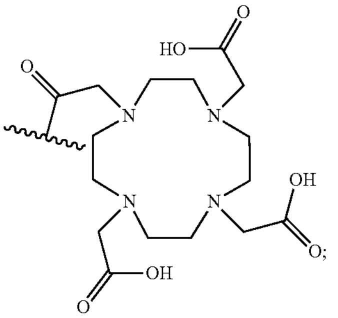

or a radionuclide complex thereof.

Embodiment 50. The compound of any one of embodiments 1-45, or a pharmaceutically acceptable salt thereof, wherein $R^a$ is independently selected from:

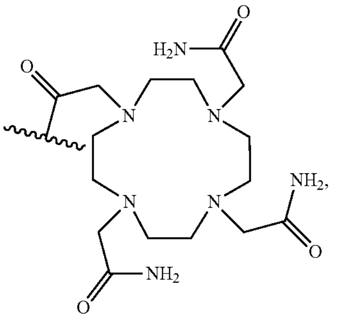

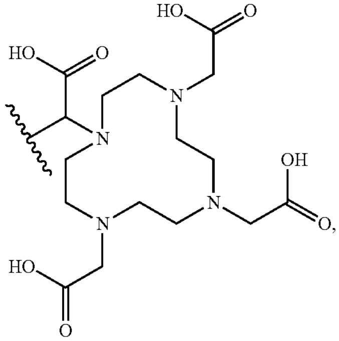

or

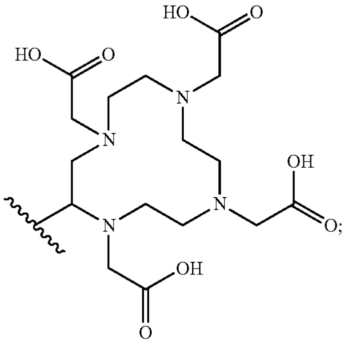

or a radionuclide complex thereof.

Embodiment 51. The compound of any one of embodiments 1-50, or a pharmaceutically acceptable salt thereof, wherein:

-L- is absent, $*\text{-}L^1\text{-}$, $*\text{—}NR^{17}\text{-}L^1\text{-}$, $*\text{—}NR^{17}\text{-}L^5\text{-}L^1$, $*\text{—}NR^{17}\text{-}L^5\text{-}C(\text{=}O)\text{-}L^1$, $*\text{—}NR^{17}\text{-}L^5\text{-}NR^{17}\text{—}C(\text{=}O)\text{-}L^1\text{-}$, $*\text{-}L^5\text{-}C(\text{=}O)\text{-}L^1\text{-}$, $*\text{-}L^5\text{-}L^1\text{-}$, $*\text{—}NR^{17}\text{-}L^5\text{-}$ $NR^{17}$-$L^1$-, *—$NR^{17}$-$L^5$-C(═O)$NR^{17}$-$L^1$-, *-($L^3$)-$_w$, *—$NR^{17}$-$L^5$-C(═O)-$L^3$-$NR^{17}$-$L^5$-C(═O)—, or *-($L^3$)$_w$-$NR^{17}$-$L^5$-C(═O)-$L^1$-;

wherein * denotes the attachment point to $R^a$;

$L^5$ is substituted or unsubstituted $C_1$-$C_6$ alkylene;

or $L^5$ and $R^{17}$ are taken together with the N atom to which they are attached to form N-heterocyclyl;

$R^{17}$ is selected from hydrogen, $C_1$-$C_6$ alkyl, $C_1$-$C_6$ alkyl-$CO_2H$, —$(CH_2CH_2O)_z$—$CH_2CH_2$—$CO_2H$;

$L^1$ is absent, -$L^2$-, -$L^2$-($L^3$)$_w$-, -($L^3$)$_w$-$L^2$-, or -$L^2$-($L^3$)$_w$-$L^2$-($L^3$)$_w$-;

each $L^2$ is independently absent, —$C_0$-$C_6$ alkylene-(substituted or unsubstituted aryl)-$C_0$-$C_6$ alkylene-C(═O)—, —$C_0$-$C_6$ alkylene-(substituted or unsubstituted arylene)-$C_0$-$C_6$ alkylene-OC(═O)—, —$C_0$-$C_6$ alkylene-(substituted or unsubstituted cyclohexylene)-$C_0$-$C_6$ alkylene-C(═O)—, —$C_0$-$C_6$ alkylene-(substituted or unsubstituted heterocycloalkylene)-$C_0$-$C_6$ alkylene-C(═O)—, —$C_0$-$C_6$ alkylene-(substituted or unsubstituted heteroarylene)-$C_0$-$C_6$ alkylene-C(═O)—, —$C_0$-$C_6$ alkylene-(substituted or unsubstituted heteroarylene)-$C_0$-$C_6$alkylene-OC(═O)—, —$C_4$-$C_{20}$ polyethylene glycol, —$C_4$-$C_{20}$ polyethylene glycol-C(═O)—, substituted or unsubstituted —$C_1$-$C_{20}$ alkylene, substituted or unsubstituted —$C_1$-$C_{20}$ alkylene-C(═O)—, substituted or unsubstituted 2 to 20 membered heteroalkylene, —$(CH_2CH_2O)_z$—$CH_2$—, —$(CH_2CH_2O)_z$—$CH_2CH_2$—, —$(CH_2CH_2O)_z$—$CH_2$—C(═O)—, or —$(CH_2CH_2O)_z$—$CH_2CH_2$—C(═O)—;

each z is independently 1, 2, 3, 4, 5, or 6;

each $L^3$ is independently selected from natural or unnatural amino acids, wherein any free amine of an amino acid or peptide bond is optionally independently substituted with $L^4$, and wherein when two or more amino acids are present then the N atom of the amide linking the amino acids is optionally substituted with —$CH_3$;

each $L^4$ is independently selected from $C_1$-$C_6$ alkylene, C(═O)—$C_1$-$C_6$ alkylene-(═O), C(═O)—NH—$C_1$-$C_6$ alkylene-C(═O), C(═O)—$C_1$-$C_6$ alkylene-(substituted or unsubstituted heteroarylene)-$C_1$-$C_6$ alkylene-C(═O), $C_1$-$C_6$ alkylene-C(═O), —C(═O)—$C_1$-$C_6$ alkylene-(substituted or unsubstituted arylene), and $C_1$-$C_6$ alkylene-(substituted or unsubstituted arylene)-C(═O), wherein if $L^4$ is present then: $L^4$ is attached to the any one of $X^1$, $X^2$, $X^3$, $X^4$, $X^5$, $X^6$, or $X^7$, or $L^4$ is attached to $X^8$ if $X^1$, $X^2$, $X^3$, $X^4$, $X^5$, $X^6$, and $X^7$ are absent; and each w is independently 1, 2, 3, 4, 5, or 6.

Embodiment 52. The compound of embodiment 51, or a pharmaceutically acceptable salt thereof, wherein:

each $L^2$ is independently absent, -(substituted or unsubstituted phenylene)-$C_0$-$C_6$ alkylene-C(═O)—, -(substituted or unsubstituted cyclohexylene)-$C_0$-$C_6$ alkylene-C(═O)—, -(substituted or unsubstituted heterocycloalkylene)-$C_0$-$C_6$ alkylene-C(═O)—, -(substituted or unsubstituted heteroarylene)-$C_0$-$C_6$ alkylene-C(═O)—, substituted or unsubstituted $C_1$-$C_{20}$ alkylene-C(═O)—, —$(CH_2CH_2O)_z$—$CH_2$—, —$(CH_2CH_2O)_z$—$CH_2CH_2$—, —$(CH_2CH_2O)_z$—$CH_2$—C(═O)—, or —$(CH_2CH_2O)_z$—$CH_2CH_2$—C(═O)—; and each z is independently 1, 2, 3, 4, 5, or 6.

Embodiment 53. The compound of embodiment 51, or a pharmaceutically acceptable salt thereof, wherein:

each $L^2$ is independently absent, -(substituted or unsubstituted phenylene)-$C_0$-$C_6$ alkylene-C(═O)—, -(substituted or unsubstituted cyclohexylene)-$C_0$-$C_6$ alkylene-C(═O)—, -(substituted or unsubstituted heterocycloalkylene)-$C_0$-$C_6$ alkylene-C(═O)—, -(substituted or unsubstituted heteroarylene)-$C_0$-$C_6$ alkylene-C(═O)—, substituted or unsubstituted $C_1$-$C_{20}$ alkylene-C(═O)—, —$(CH_2CH_2O)_z$—$CH_2$—C(═O)—, or —$(CH_2CH_2O)_z$—$CH_2CH_2$—C(═O)—; and each z is independently 1, 2, 3, 4, 5, or 6.

Embodiment 54. The compound of any one of embodiments 51-53, or a pharmaceutically acceptable salt thereof, wherein:

-L- is *—$NR^{17}$—, *—$NR^{17}$-$L^5$, *—$NR^5$-$L^5$-C(═O)—, *—$NR^{17}$—$C_0$-$C_6$ alkylene-(substituted or unsubstituted phenylene)-$C_0$-$C_6$alkylene-C(═O)—, *—$NR^{17}$—$C_0$-$C_6$ alkylene-(substituted or unsubstituted cyclohexylene)-$C_0$-$C_6$ alkylene-C(═O)—, *—$NR^{17}$—$C_0$-$C_6$ alkylene-(substituted or unsubstituted heterocycloalkylene)-$C_0$-$C_6$ alkylene-C(═O)—, *—$NR^{17}$—$C_0$-$C_6$ alkylene-(substituted or unsubstituted heteroarylene)-$C_0$-$C_6$ alkylene-C(═O)—, *—$NR^{17}$-substituted or unsubstituted $C_1$-$C_{20}$ alkylene-C(═O)—, *—$NR^{17}$—$(CH_2CH_2O)_z$—$CH_2$—C(═O)—, *—$NR^{17}$—$(CH_2CH_2O)_z$—$CH_2CH_2$—C(═O)—, *—$R^{17}$-$L^5$-C(═O)-($L^3$)$_w$-, *—$NR^5$-$L^5$—C(═O)$NR^{17}$—$C_0$-$C_6$ alkylene-(substituted or unsubstituted phenylene)-$C_0$-$C_6$ alkylene-C(═O)—, *—$NR^5$-$L^5$-C(═O)$NR^{17}$—$C_0$-$C_6$ alkylene-(substituted or unsubstituted cyclohexylene)-$C_0$-$C_6$ alkylene-C(═O)—, *—$NR^5$-$L^5$-C(═O)$NR^{17}$—$C_0$-$C_6$ alkylene-(substituted or unsubstituted heterocycloalkylene)-$C_0$-$C_6$ alkylene-C(═O)—, or *—$NR^5$-$L^5$-C(═O)$NR^{17}$—$C_0$-$C_6$ alkylene-(substituted or unsubstituted heteroarylene)-$C_0$-$C_6$ alkylene-C(═O)—; and z is 1, 2, 3, 4, 5, or 6;

wherein * denotes the attachment point to $R^a$.

Embodiment 55. The compound of any one of embodiments 51-53, or a pharmaceutically acceptable salt thereof, wherein:

each $L^3$ is independently selected from the group consisting of alanine (Ala), arginine (Arg), asparagine (Asn), aspartate (Asp), glutamine (Gln), glutamate (Glu), glycine (Gly), leucine (Leu), lysine (Lys), 3-(2-naphthyl)-L-alanine (2-Nal), 3-(4-pyridyl)alanine (4-Pal), phenylalanine (Phe), serine (Ser), sarcosine, tyrosine (Tyr), 3-sulfo-alanine (Ala-$SO_3H$), methionine (Met), valine (Val), 2-(3-aminopropoxy)-[1,1-biphenyl]-4-carboxylic acid, 2'-(3-aminopropoxy)-[1,1'-biphenyl]-4-carboxylic acid, O-(dihydroxy(oxo)-16-phosphaneyl)-L-serine, (S)-2-amino-4-(2H-tetrazol-5-yl)butanoic acid, and (S)-2-amino-3-(anthracen-9-yl)propanoic acid, wherein any free amine of an amino acid or peptide bond is optionally independently substituted with $L^4$, and wherein when two or more amino acids are present then the N atom of the amide linking the amino acids is optionally substituted with —$CH_3$.

Embodiment 56. The compound of any one of embodiments 51-53, or a pharmaceutically acceptable salt thereof, wherein:

each $L^3$ is independently selected from the group consisting of alanine (Ala), glycine (Gly), serine (Ser), sarcosine, methionine (Met), 3-sulfo-alanine (Ala-$SO_3H$), and valine (Val), wherein any free amine of an amino acid or peptide bond is optionally independently substituted with $L^4$, wherein $L^4$ is —C(═O)—$C_1$-$C_6$ alkylene-C(═O)— or —C(═O)—NH—$C_1$-$C_6$ alkyl-C(═O)—, and wherein when two or more amino acids are present then the N atom of the amide linking the amino acids is optionally substituted with $—CH_3$.

Embodiment 57. The compound of any one of embodiments 51-53, or a pharmaceutically acceptable salt thereof, wherein $-(L^3)_w-$ is sarcosine, sarcosine-sarcosine, sarcosine-sarcosine-sarcosine, sarcosine-sarcosine-sarcosine-sarcosine, sarcosine-sarcosine-sarcosine-sarcosine-sarcosine, sarcosine-sarcosine-sarcosine-sarcosine-sarcosine-sarcosine, valine-citrulline, valine-alanine, methionine-valine-lysine, glycine-phenylalanine-glycine-glycine, tyrosine-arginine-valine, arginine-valine, 3-sulfo-alanine, 3-sulfo-alanine-3-sulfo-alanine, 3-sulfo-alanine-3-sulfo-alanine-3-sulfo-alanine, glycine-glutamate, gly % cine-glutamate-glycine, glycine-glutamate-glutamate, methionine-tryptophan-lysine, methionine-phenylalanine-lysine, methionine-valine, methionine-valine-lysine, or phenylalanine-lysine, wherein the free amine of lysine is optionally substituted with $L^4$; $L^4$ is $—C(=O)(CH_2)_3—C(=O)—$, $—C(=O)—(CH_2)_4—C(=O)—$, $—C(=O)—(CH_2)_5—C(=O)—$, $—C(=O)—(CH_2)_6—C(=O)—$, $—C(=O)NH—(CH_2)_3—C(=O)$, $—(C(=O)N—(CH_2)_4—C(=O)—$, $—C(=O)NH—(CH_2)_5—C(=O)—$, $—C(=O)NH—(CH_2)_6—C(=O)—$, $—C(=O)—(CH_2)_2$-(triazolylene)-$(CH_2)_1—C(=O)—$ or $—C(=O)—(CH_2)_2$-(triazolylene)-$(CH_2)_2—C(=O)—$; wherein if $L^4$ is present then: $L^4$ is attached to the any one of $X^1$, $X^2$, $X^3$, $X^4$, $X^5$, $X^6$, or $X^7$, or $L^4$ is attached to $X^8$ if $X^1$, $X^2$, $X^3$, $X^4$, $X^5$, $X^6$, and $X^7$ are absent.

Embodiment 58. The compound of any one of embodiments 1-50, or a pharmaceutically acceptable salt thereof, wherein: -L- is: absent,

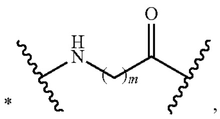
,
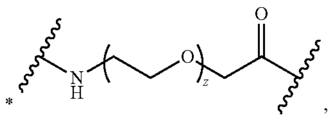
,
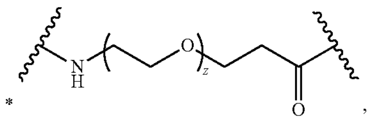
, (SEQ ID NO: 833)

(SEQ ID NO: 834)

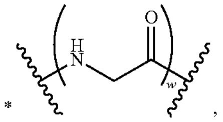
,
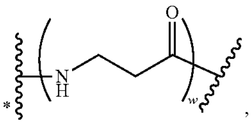
, (SEQ ID NO: 835)

(SEQ ID NO: 836)

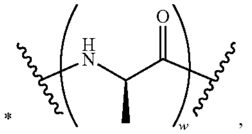
,
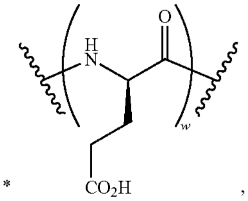
, (SEQ ID NO: 837)

(SEQ ID NO: 838)

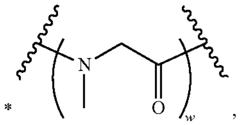
,
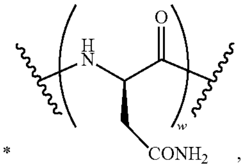
,

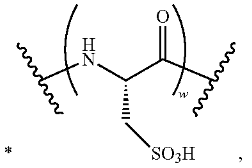
,
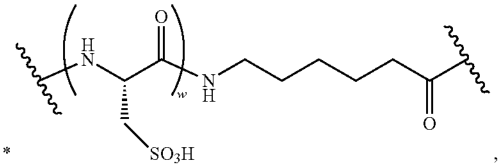
,

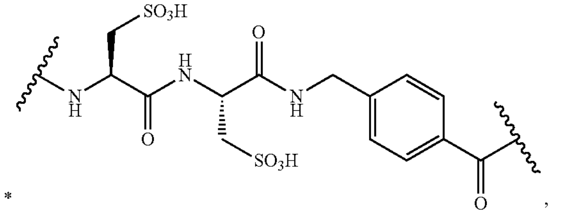
,
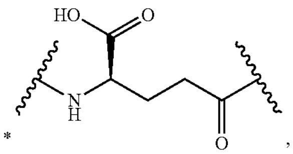
, (SEQ ID NO: 839)

(SEQ ID NO: 840)

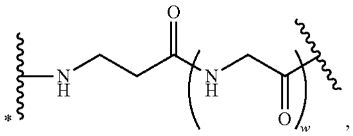
,
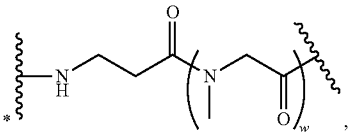
,

-continued
(SEQ ID NO: 841)
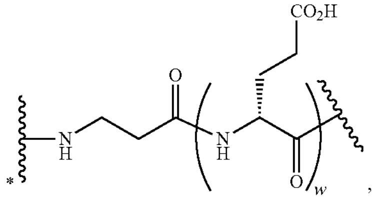,
(SEQ ID NO: 842)
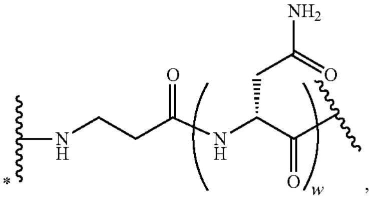,
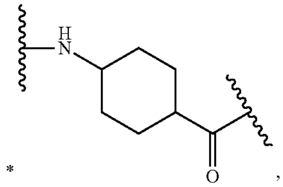, 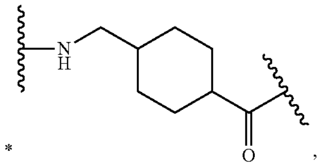, 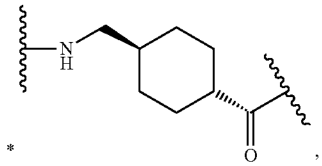,
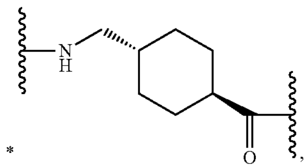, 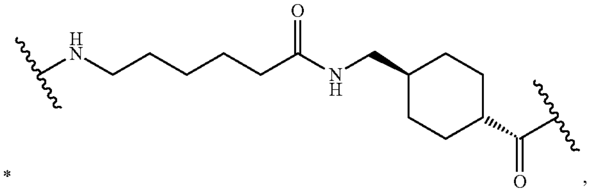,
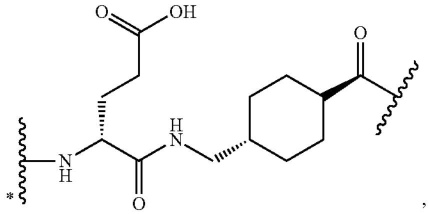, 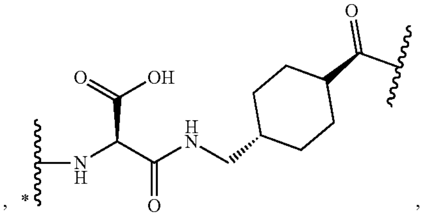, 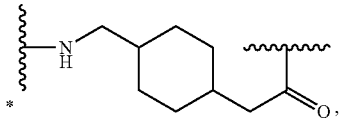,
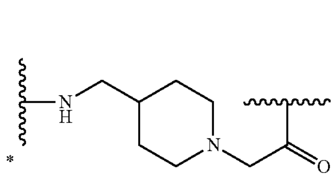, 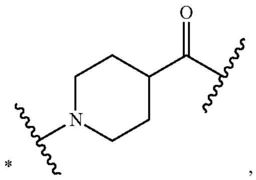, 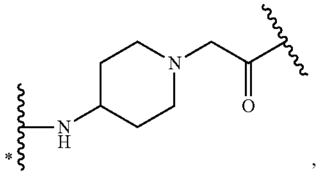,
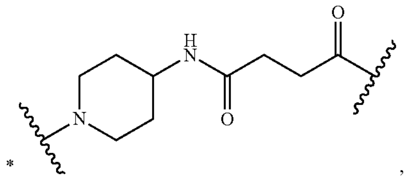, 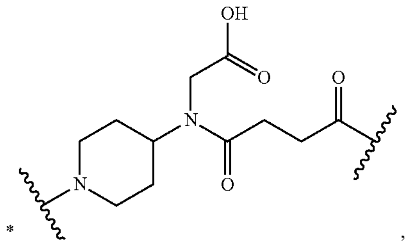, 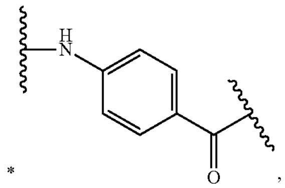,
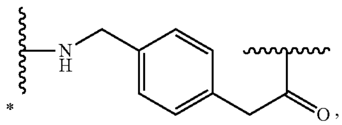, 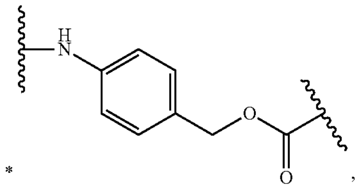, 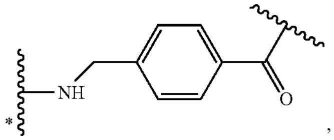,
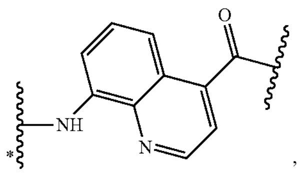, 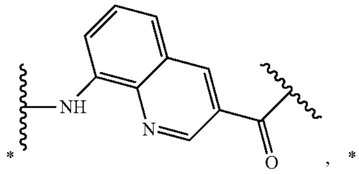, 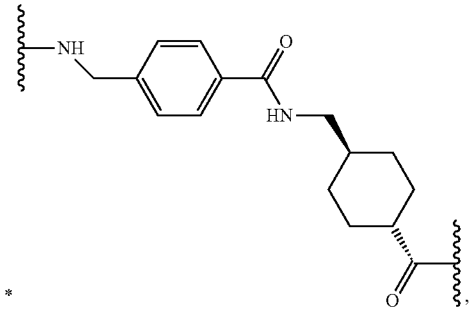, -continued
*
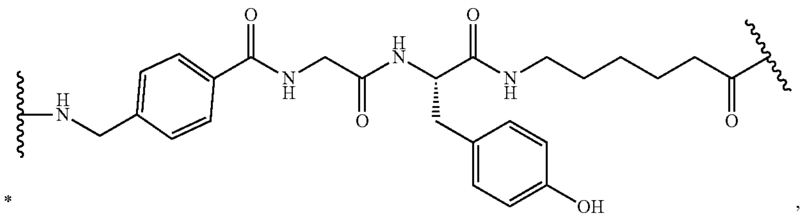
,
*
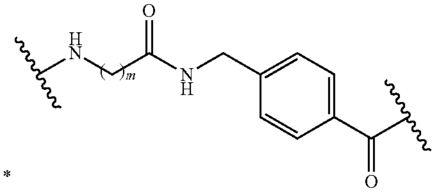
, *
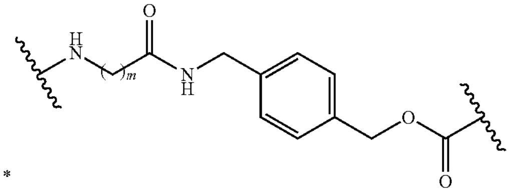
,
*
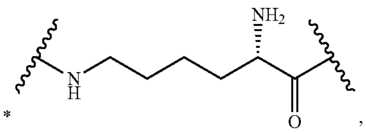
, *
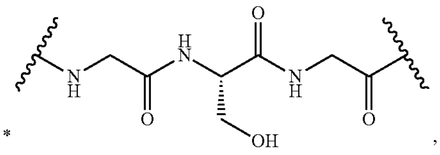
,
*
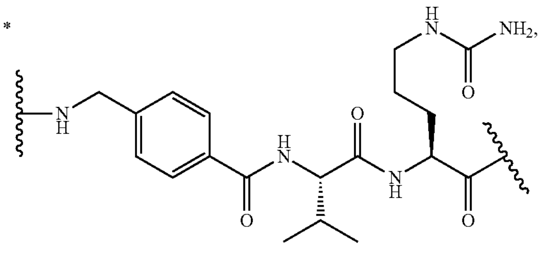
*
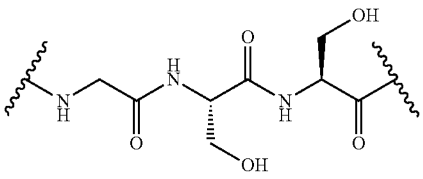
,
*
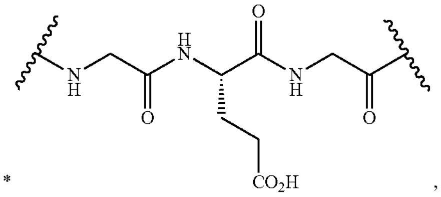
, *
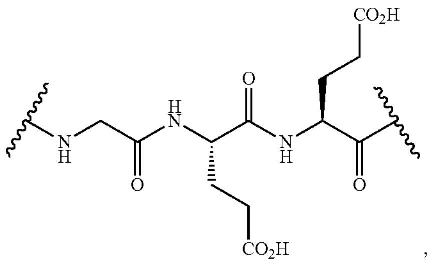
,
*
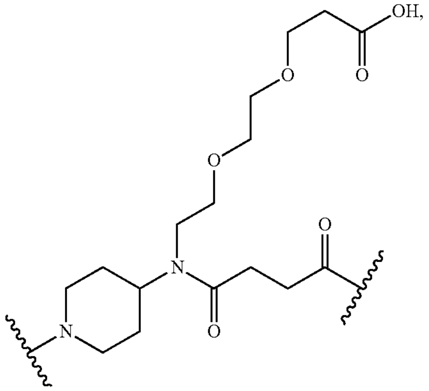
*
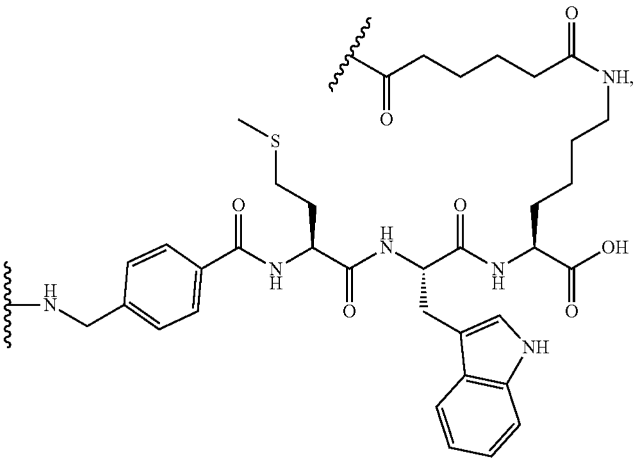

-continued
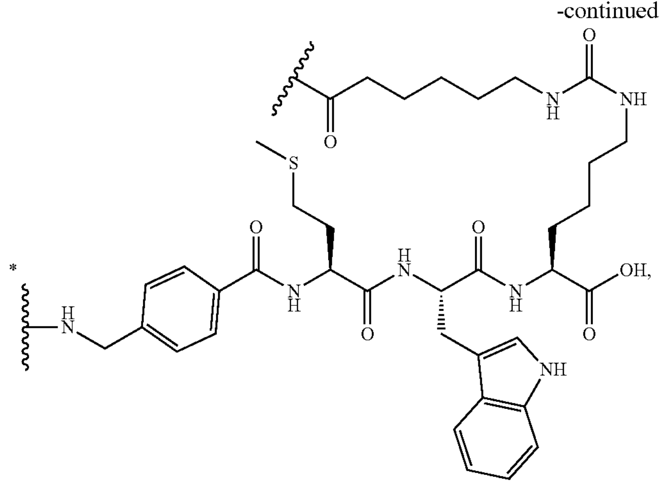
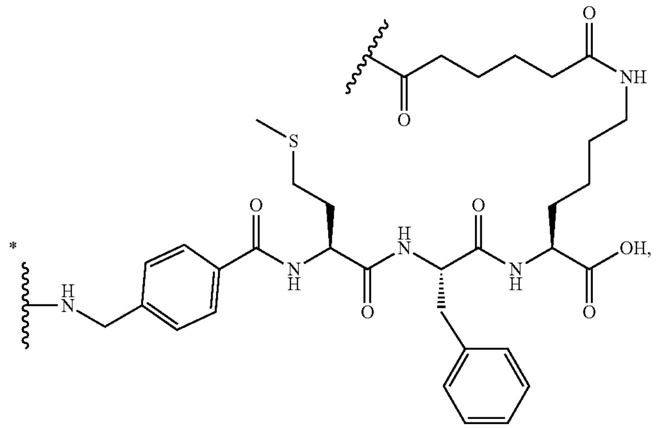
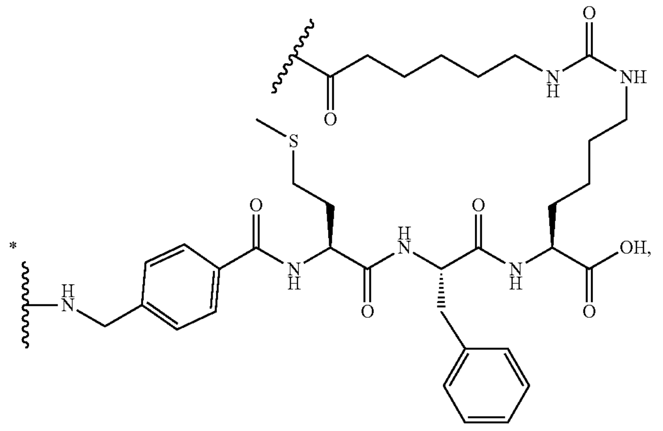

-continued
(SEQ ID NO: 796)
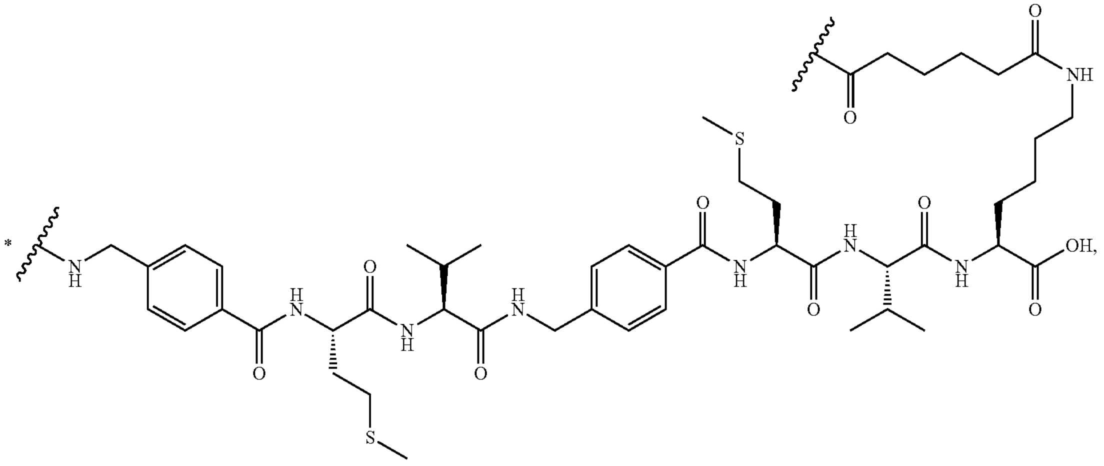
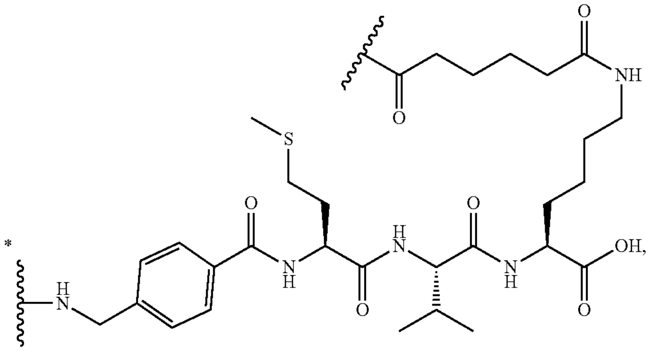
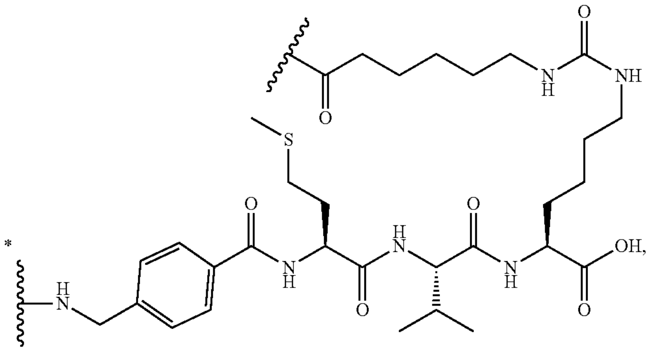
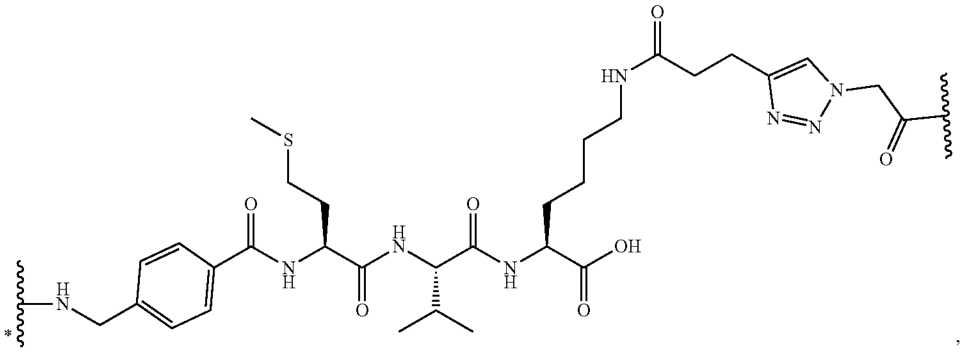
, -continued
* 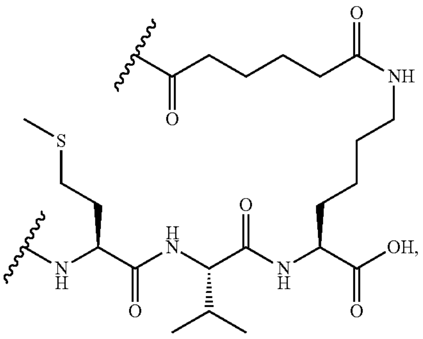 * 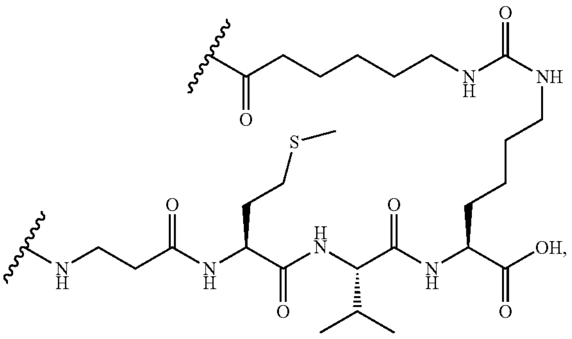
* 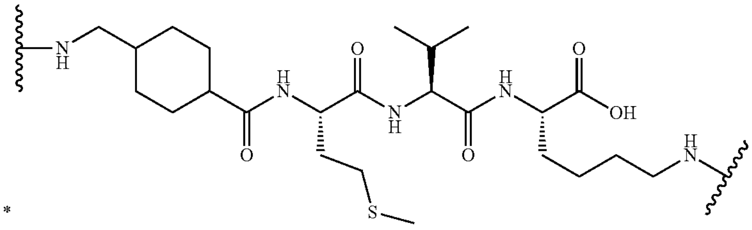 ,
* 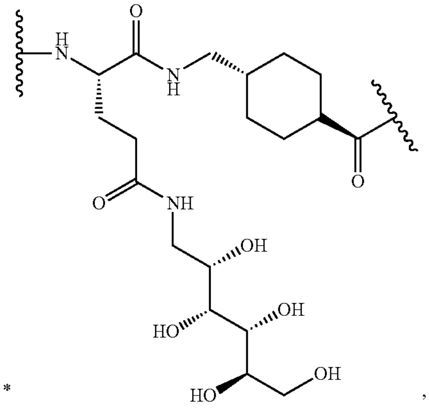 , * 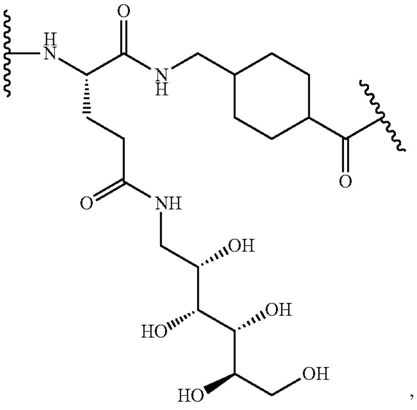 ,
* 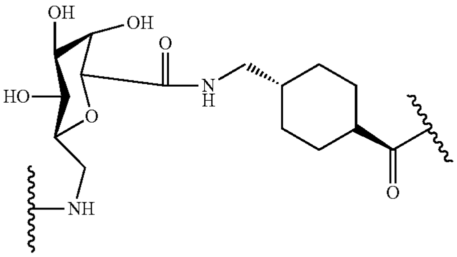 , * 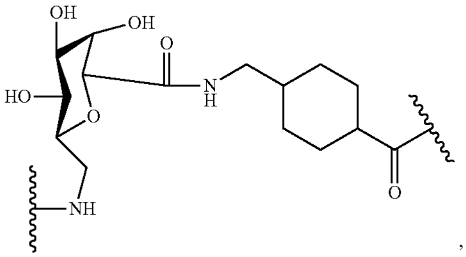 ,
* 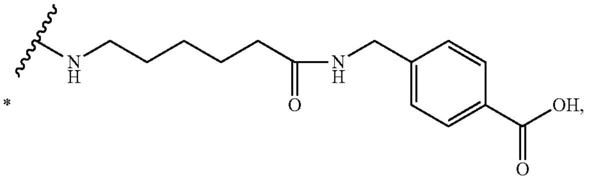 * 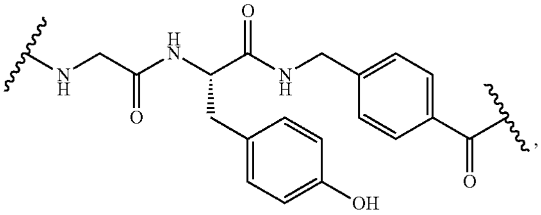

-continued
* 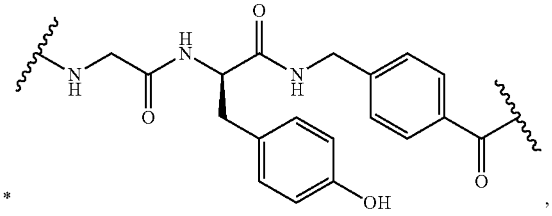 , * 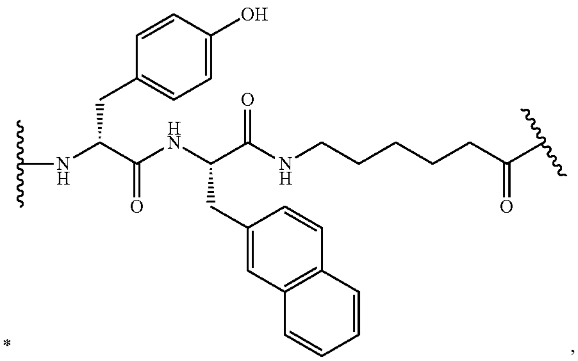 ,
* 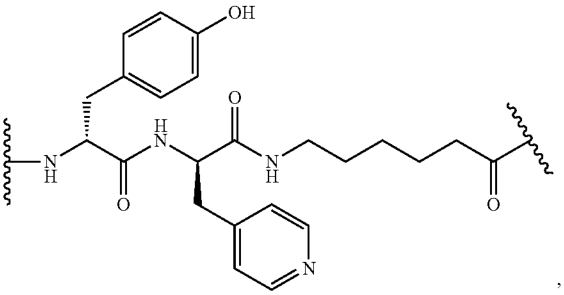 , * 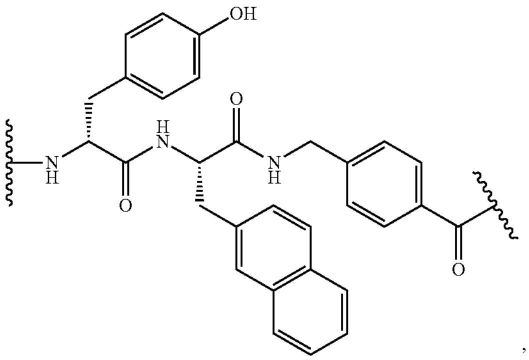 ,
* 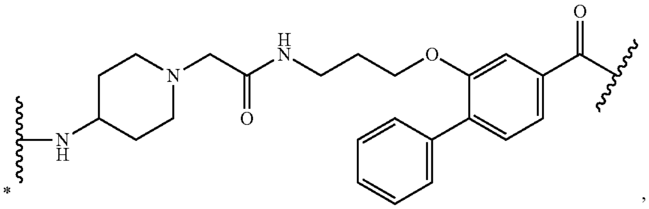 ,
* 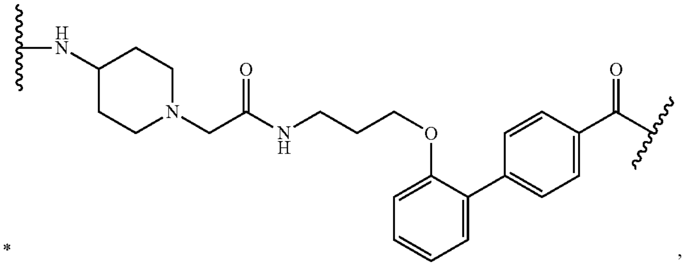 , * 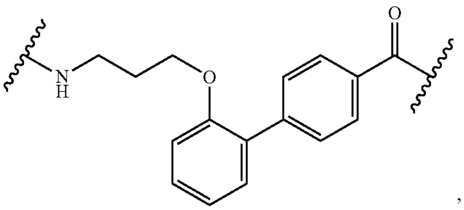 ,
* 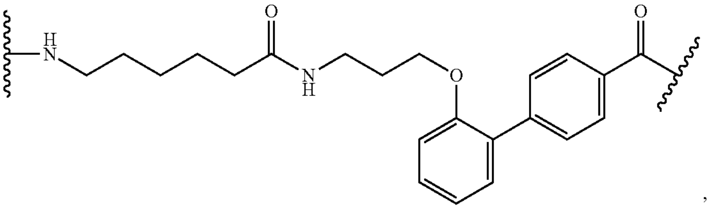 ,
* 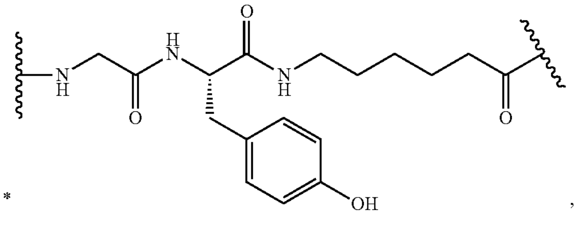 , -continued
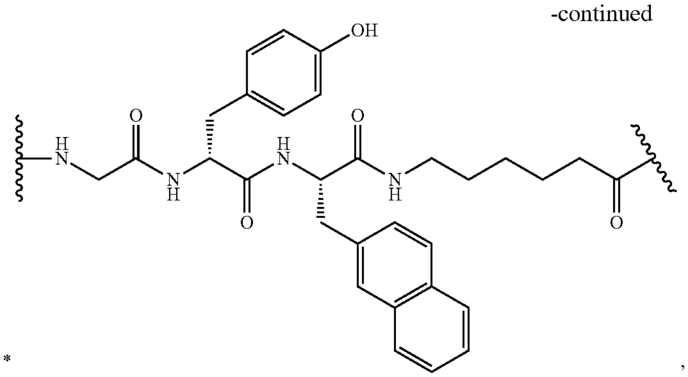
*
,
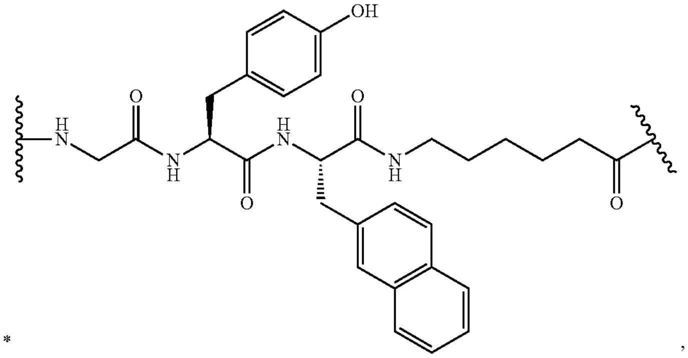
*
,
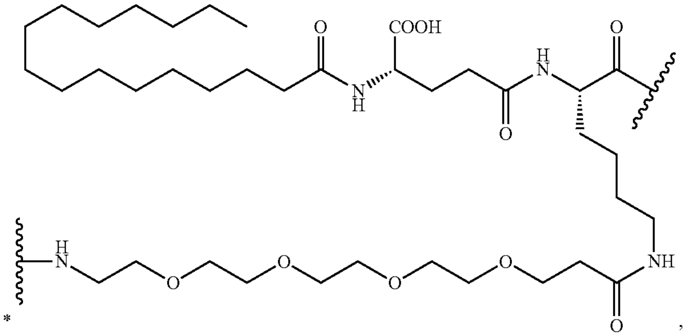
*
,
*
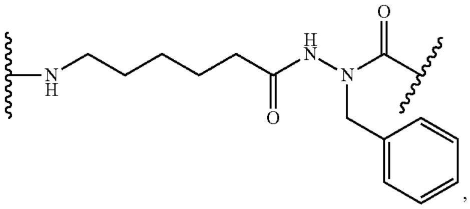
,
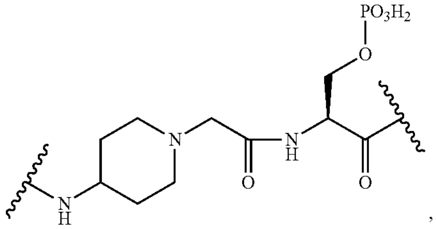
*
,
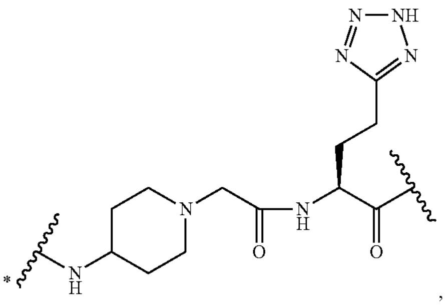
*
,
-continued
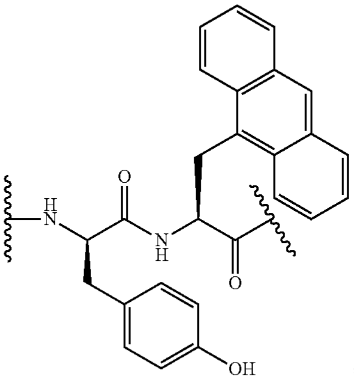
*
, -continued
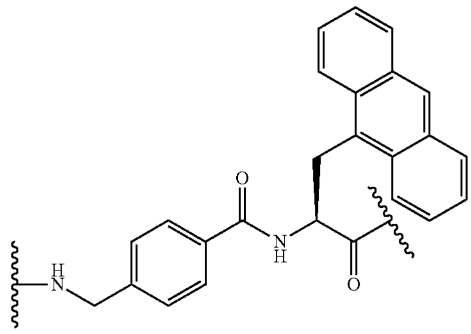
*, *
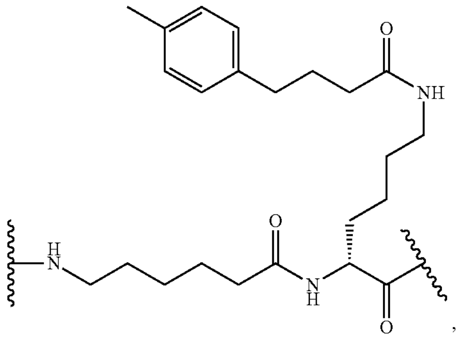
, *
-continued
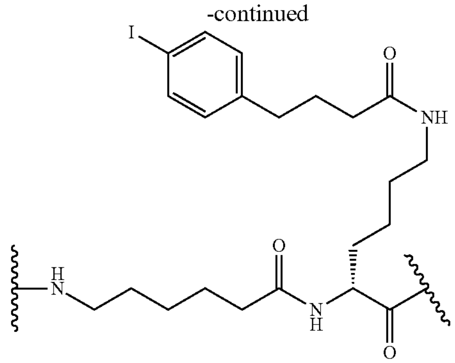
, or
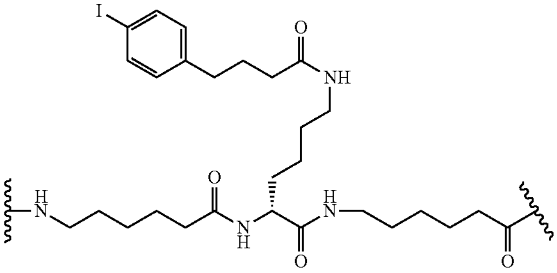
;
m is 1, 2, 3, 4, 5, or 6;
z is 1, 2, 3, 4, 5, or 6;
w is 1, 2, 3, 4, 5, or 6;
wherein * denotes the attachment point to $R^a$,
Embodiment 59. The compound of any one of embodiments 1-50, or a pharmaceutically acceptable salt thereof, wherein: -L- is: absent,
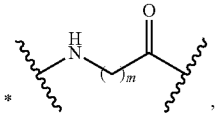
,
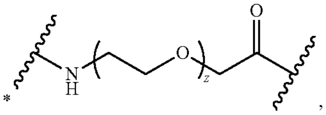
,
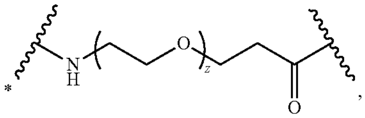
,
(SEQ ID NO: 833)
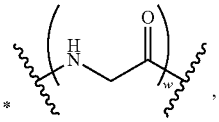
,
(SEQ ID NO: 834)
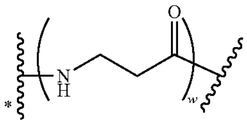
,
(SEQ ID NO: 835)
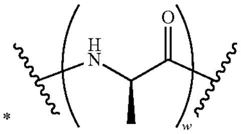
,
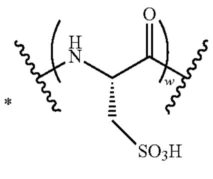
,
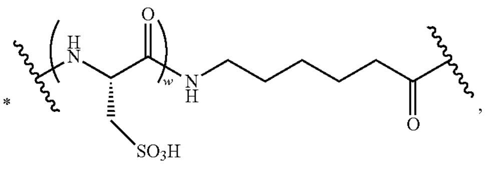
, -continued
(SEQ ID NO: 839)
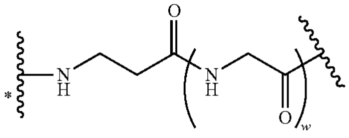,
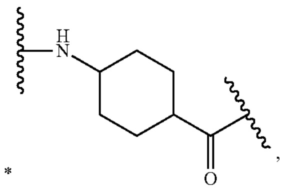,
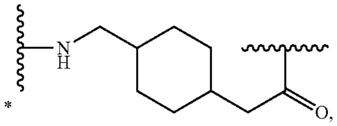
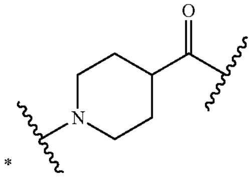,
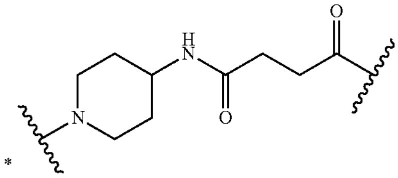
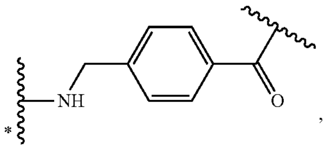,
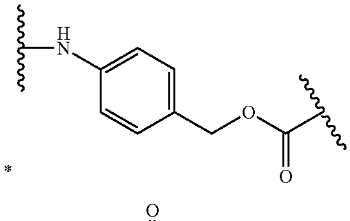,
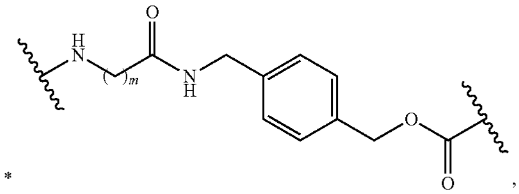,
(SEQ ID NO: 840)
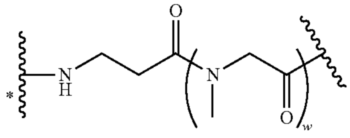,
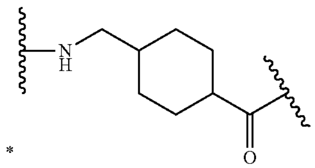,
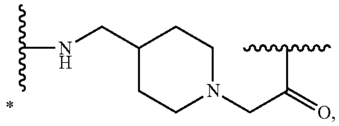
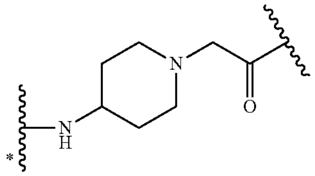,
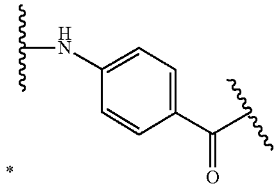,
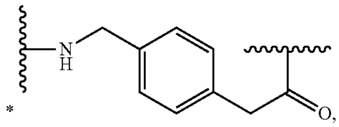
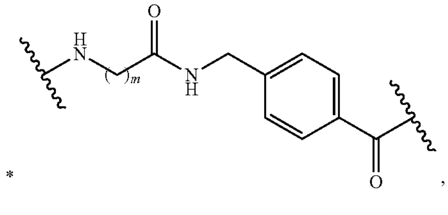,
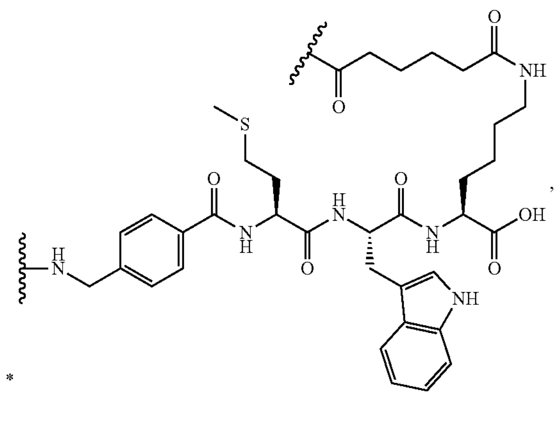, -continued
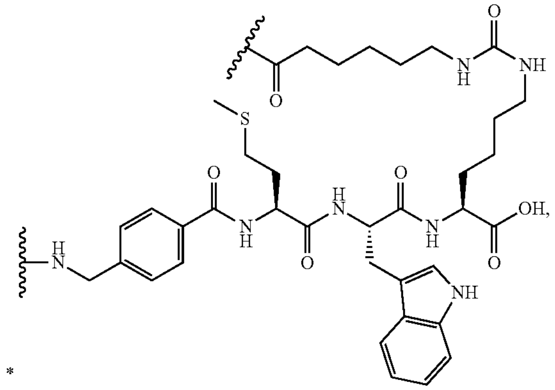
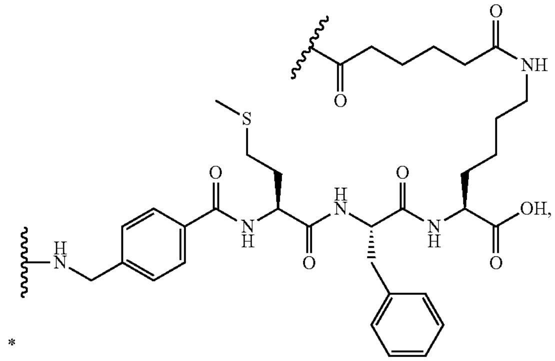
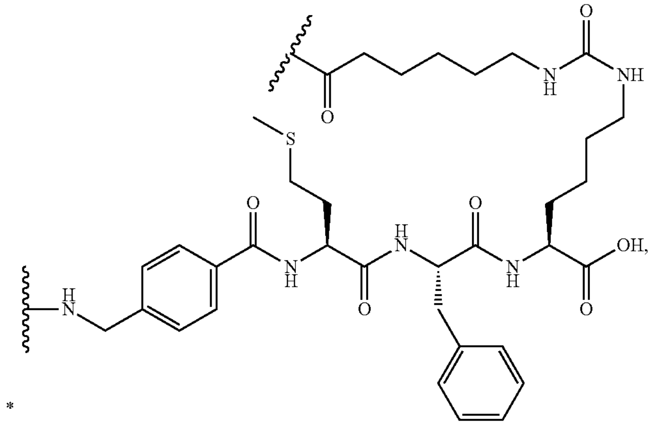
(SEQ ID NO: 796)
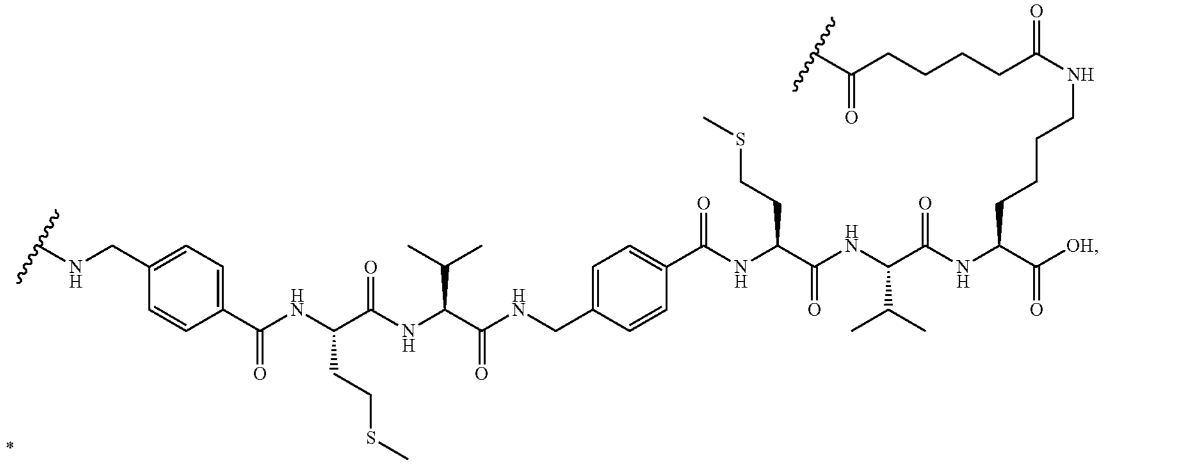
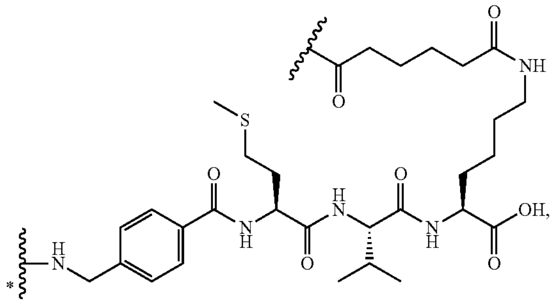
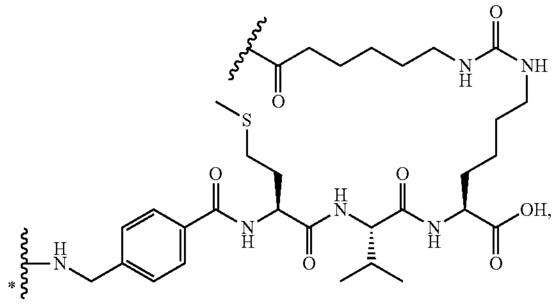

-continued
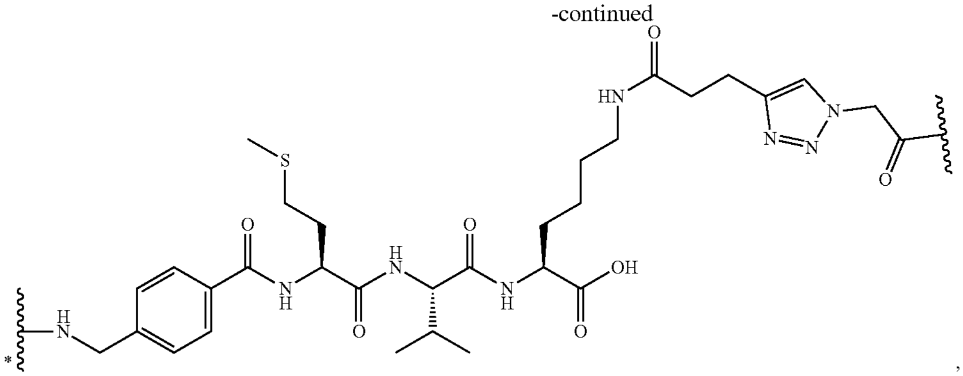
,
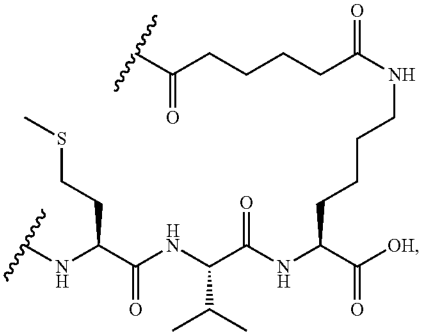
or
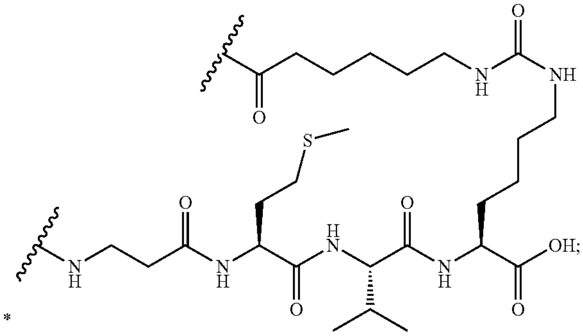
m is 1, 2, 3, 4, 5, or 6;
wherein * denotes the attachment point to $R^a$.
Embodiment 60. The compound of any one of embodiments 1-50, or a pharmaceutically acceptable salt thereof, wherein -L- is: absent,
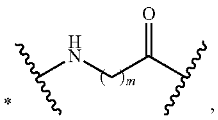
,
(SEQ ID NO: 834)
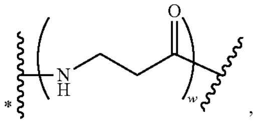
,
(SEQ ID NO: 835)
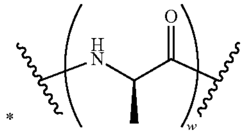
,
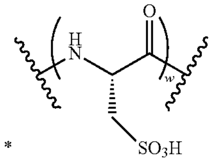
,
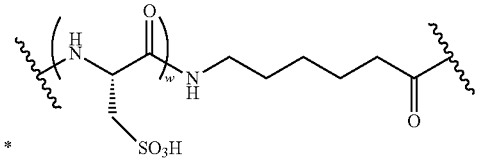
,
(SEQ ID NO: 839)
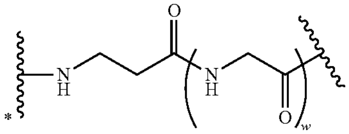
,
(SEQ ID NO: 840)
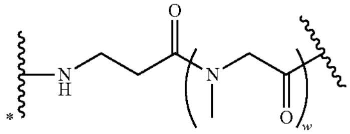
,
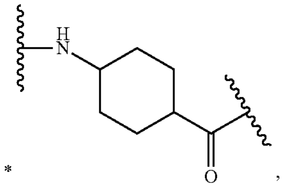
,
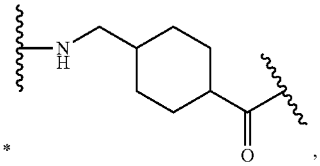
,
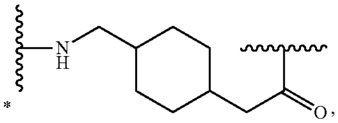

-continued
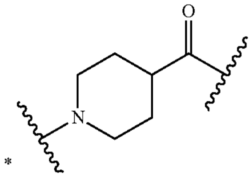 , 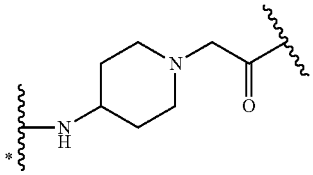 , 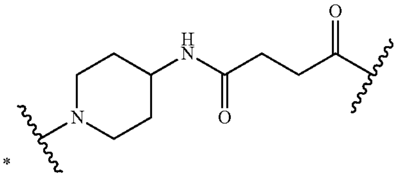 ,
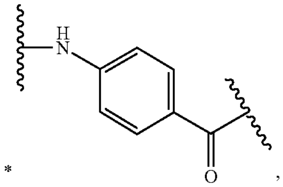 , 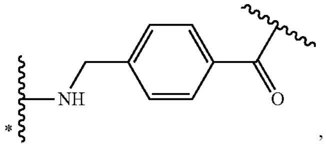 , 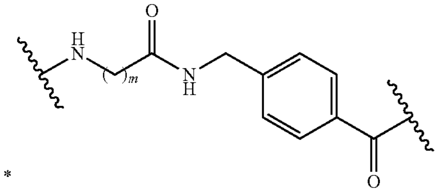 ,
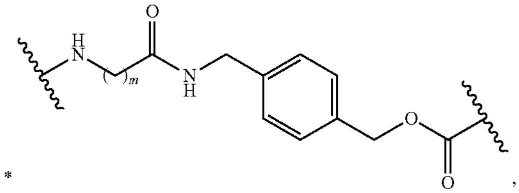 ,
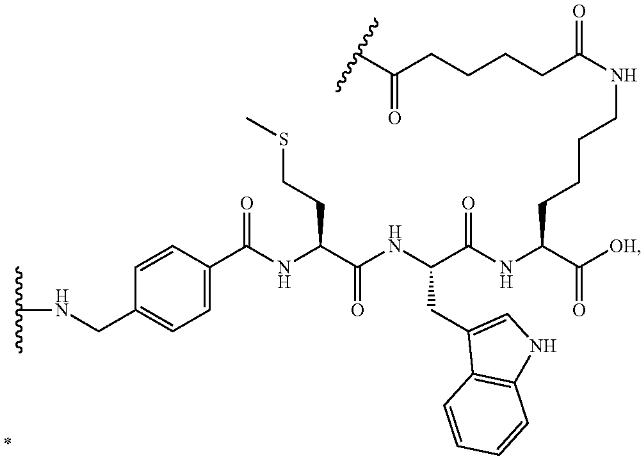
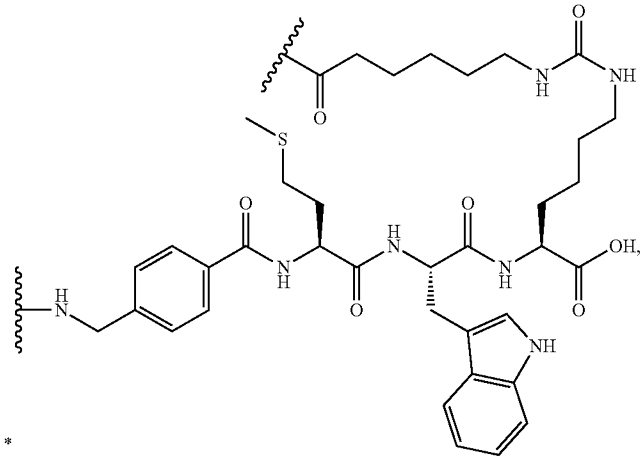

-continued
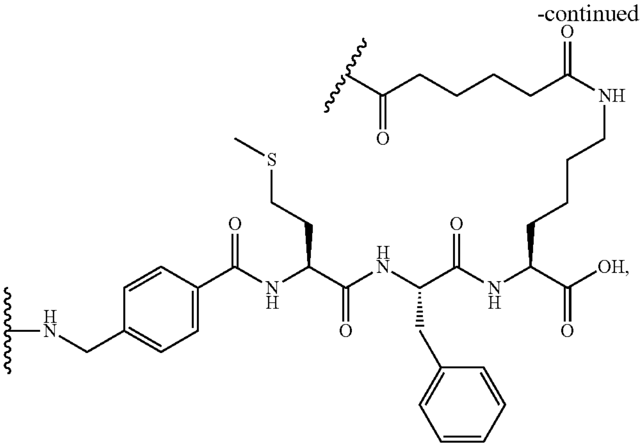
*
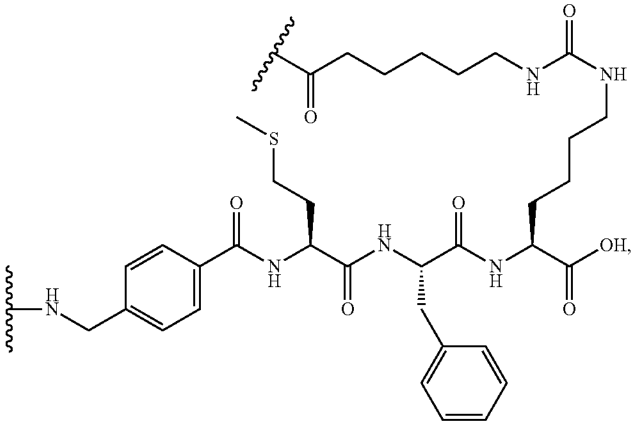
*
(SEQ ID NO: 796)
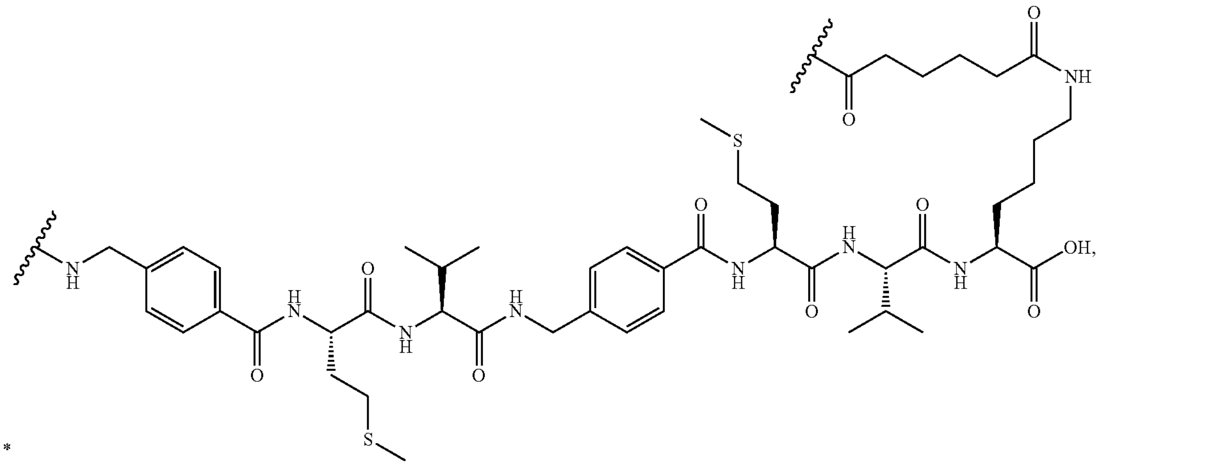
*
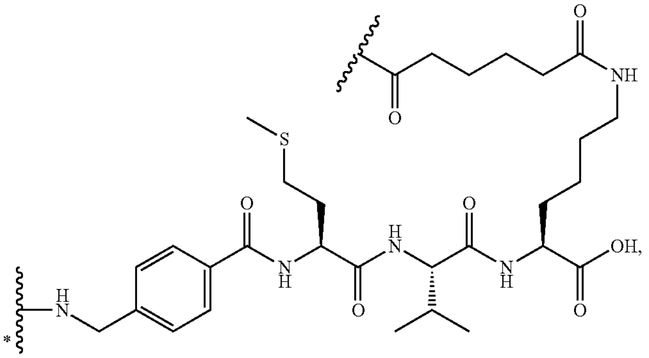
*

-continued
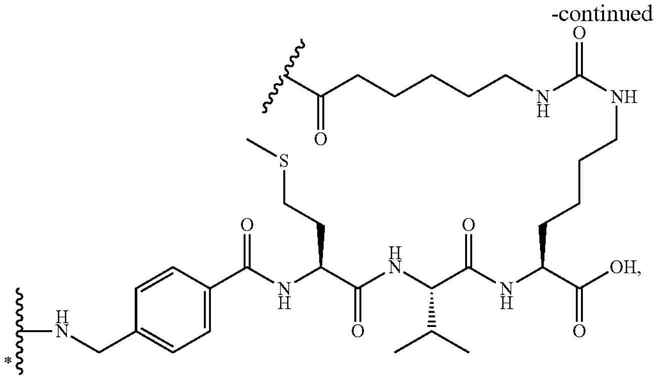
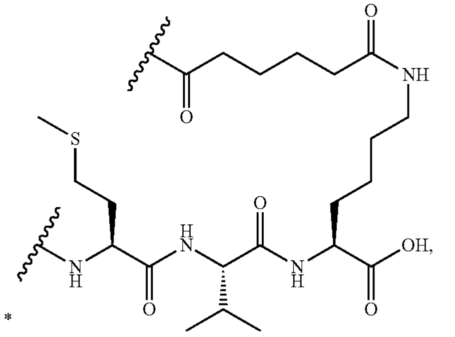
or
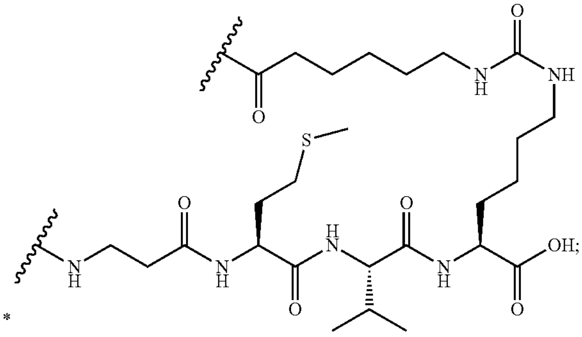
m is 1, 2, 3, 4, 5, or 6,
wherein * denotes the attachment point to $R^a$.
Embodiment 61. The compound of any one of embodiments 58-60, or a pharmaceutically acceptable salt thereof, wherein:
m is 5.
Embodiment 62. The compound of any one of embodiments 1-50, or a pharmaceutically acceptable salt thereof, wherein -L- is:
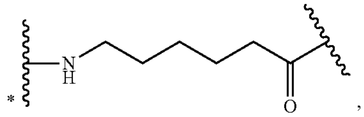
,
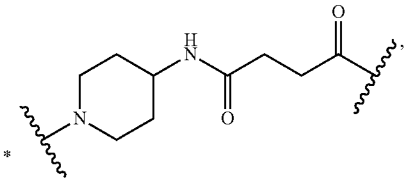
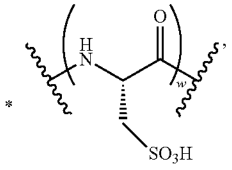
-continued
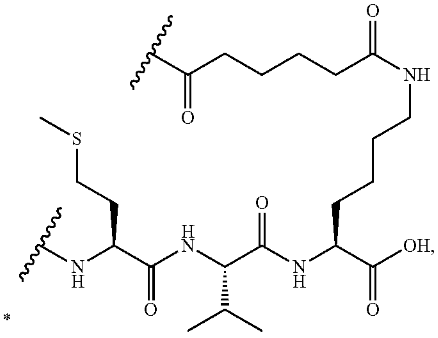
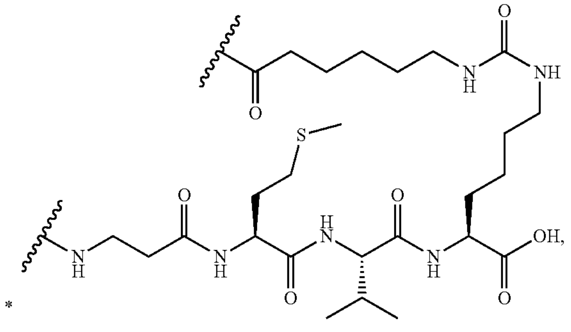
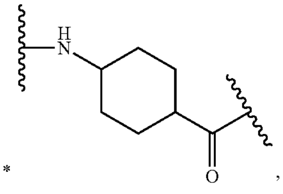
, -continued
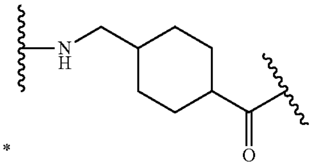
,
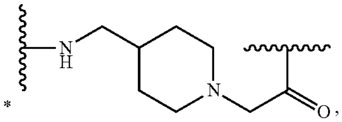
,
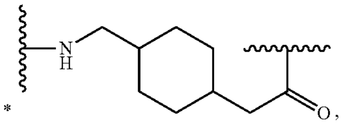
,
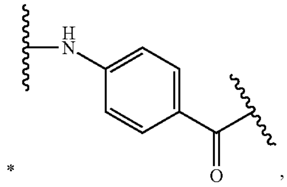
, or
-continued
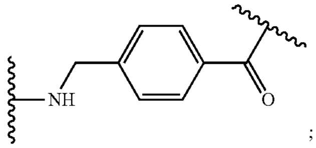
;
wherein * denotes the attachment point to $R^a$.
Embodiment 63. The compound of any one of embodiments 1-50, or a pharmaceutically acceptable salt thereof, wherein: -L- is:
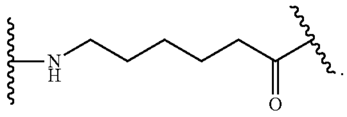 [SMILES: *NCCCCCC(*)=O]
.
Embodiment 64. The compound of any one of embodiments 1-50, or a pharmaceutically acceptable salt thereof, wherein $R^a$-L- is:
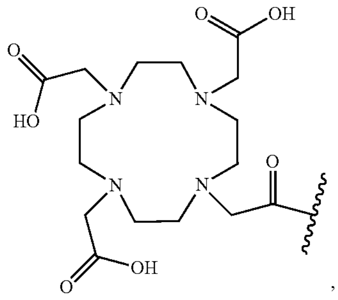
,
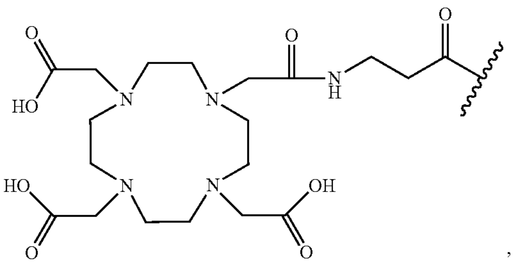
,
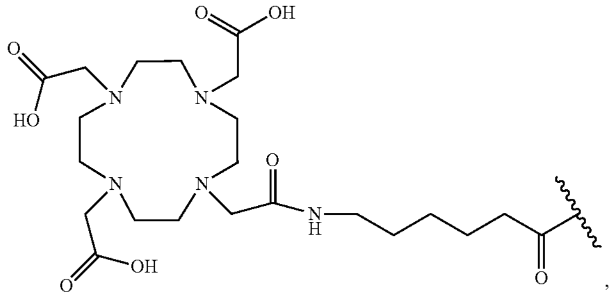
,
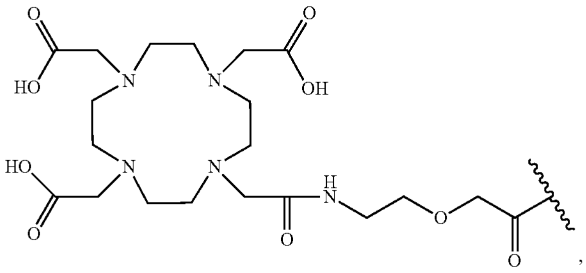
,
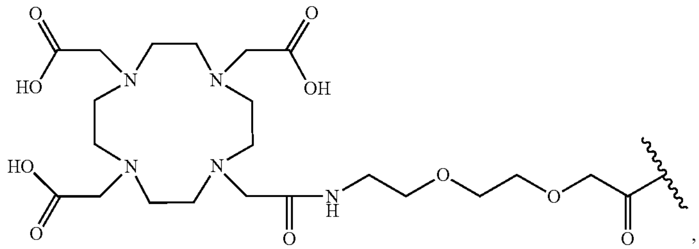
, -continued
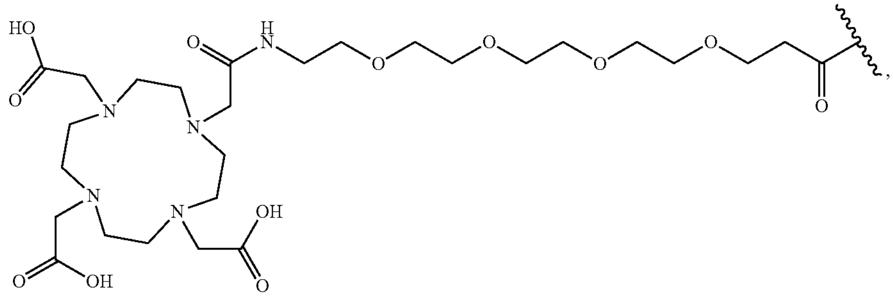
,
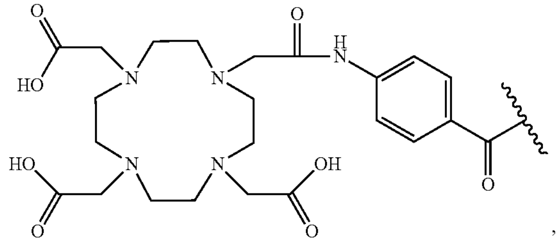
,
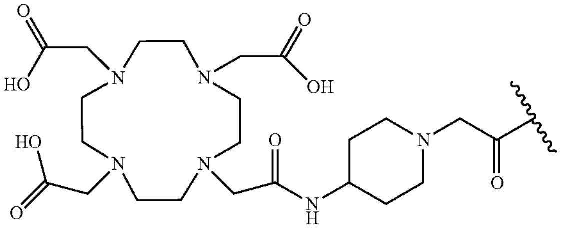
,
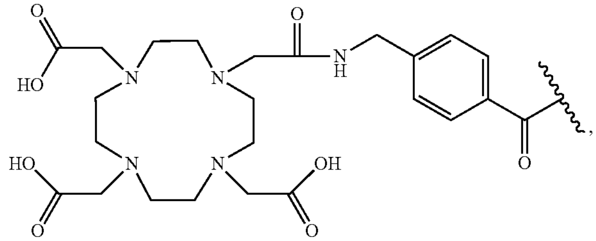
,
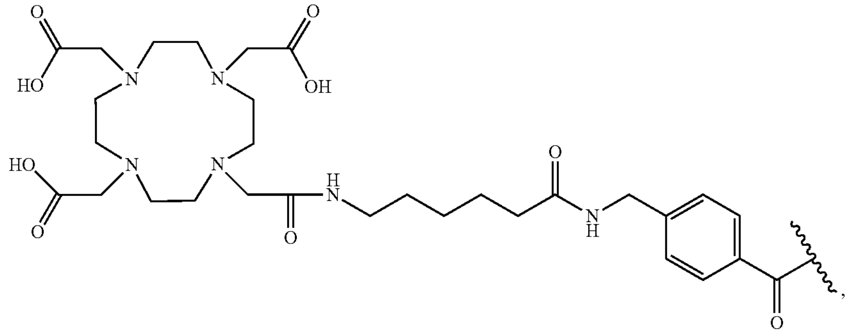
,
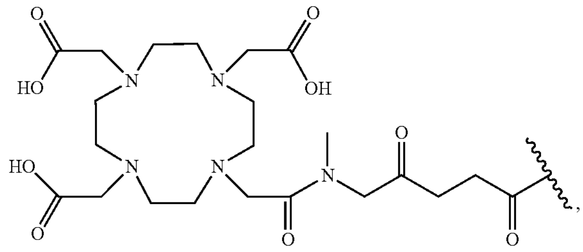
,
(SEQ ID NO: 798)
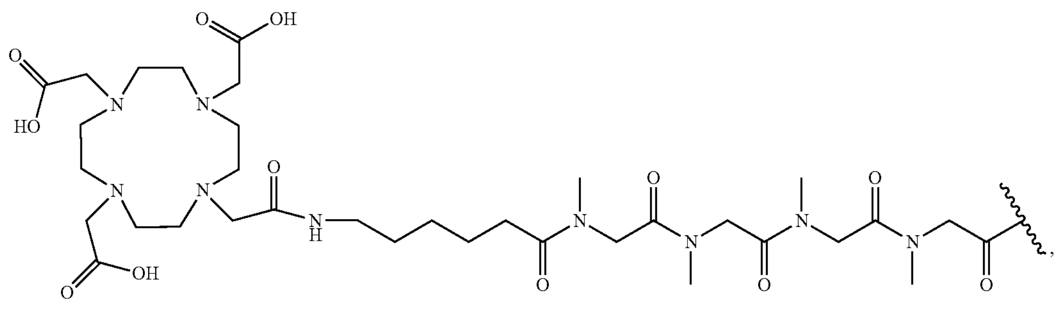
, -continued
(SEQ ID NO: 386)
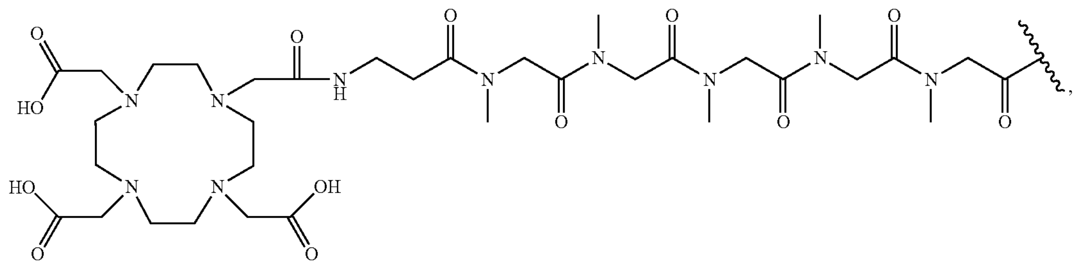
(SEQ ID NO: 387)
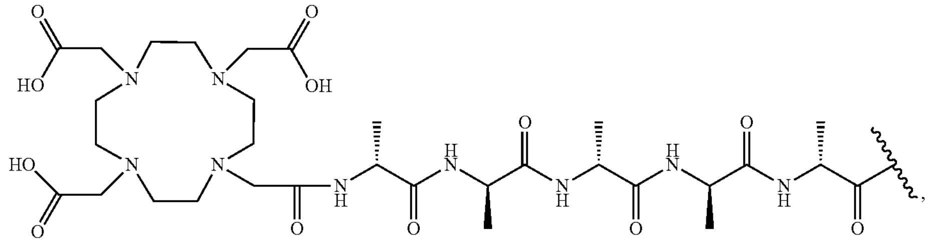
(SEQ ID NO: 388)
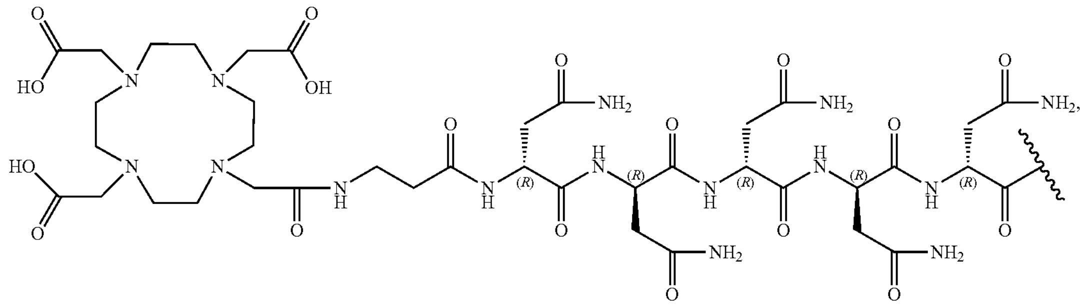
(SEQ ID NO: 389)
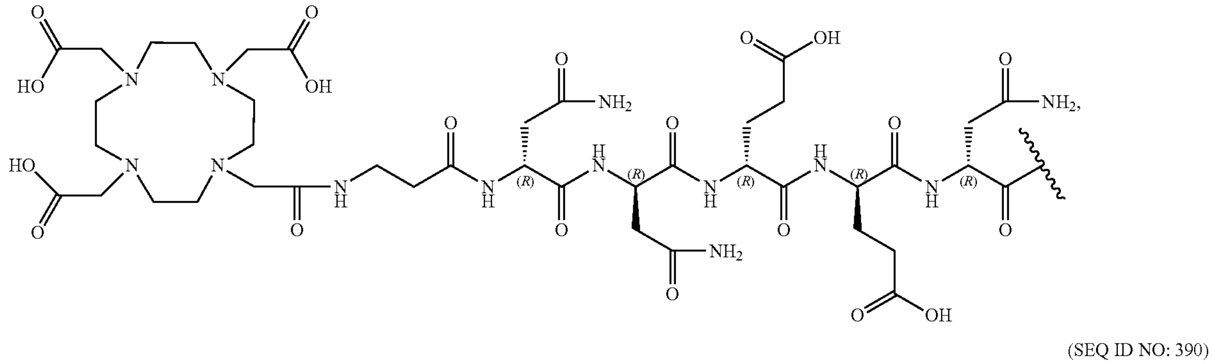
(SEQ ID NO: 390)
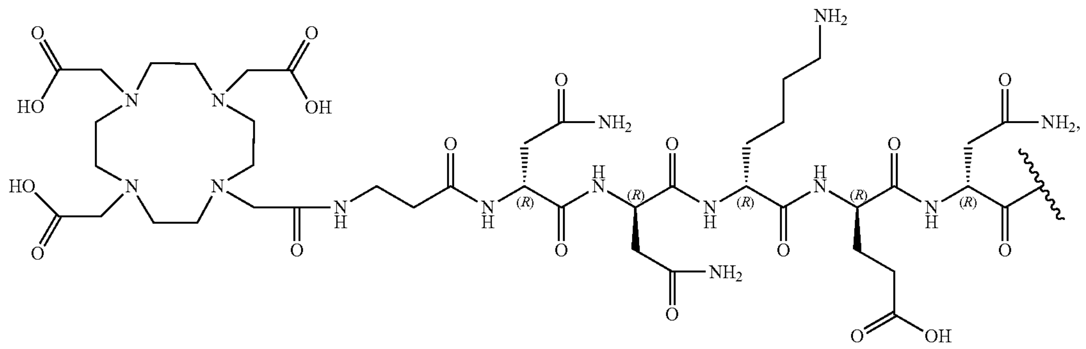

-continued
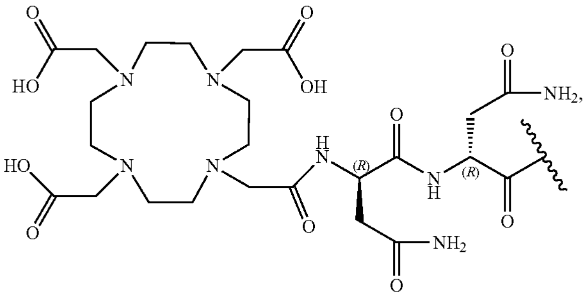
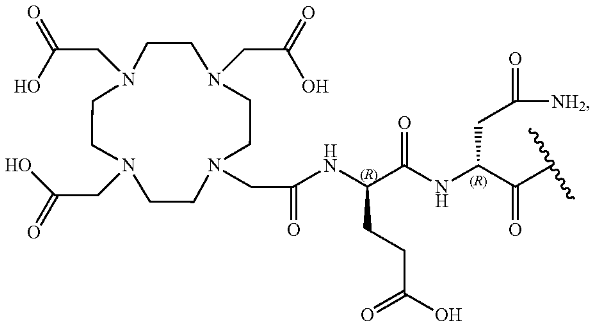
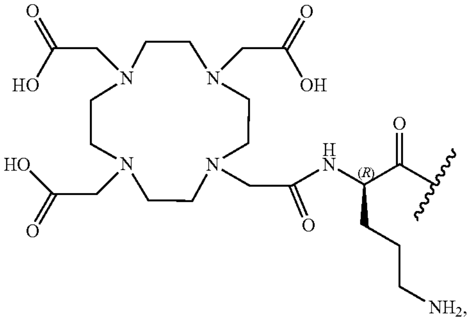
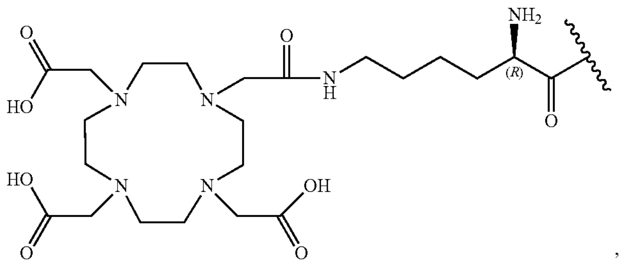
,
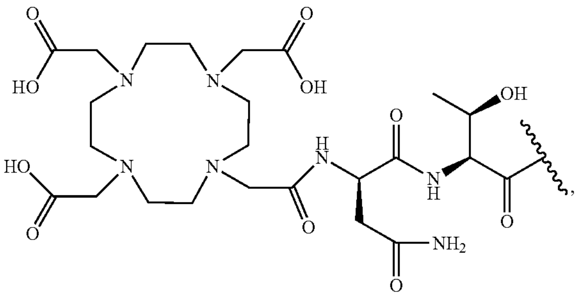
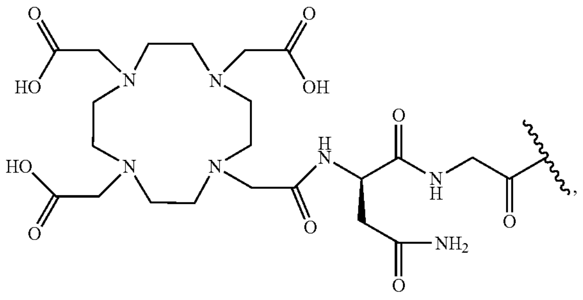
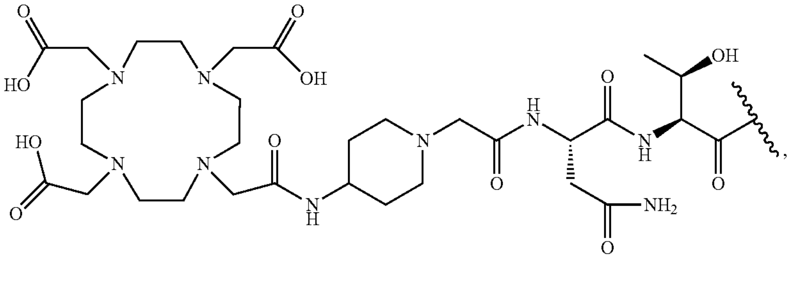
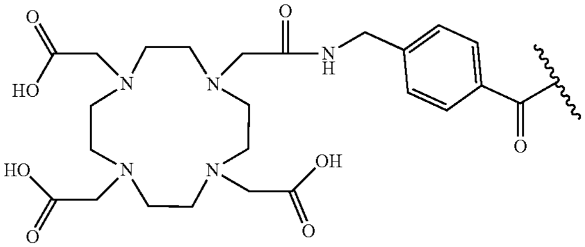
,
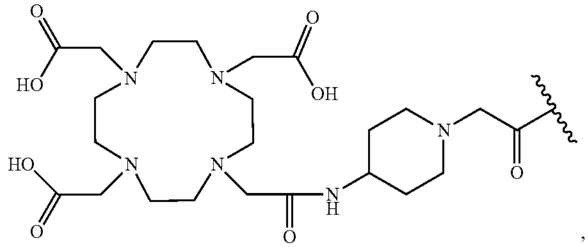
, -continued
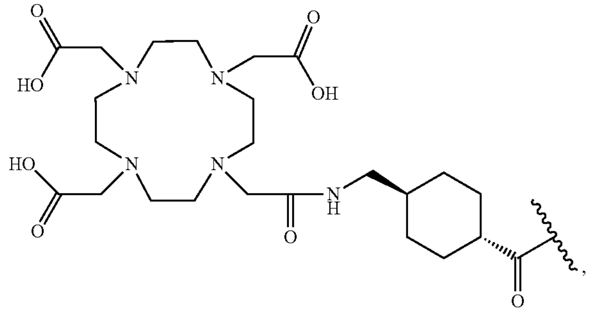
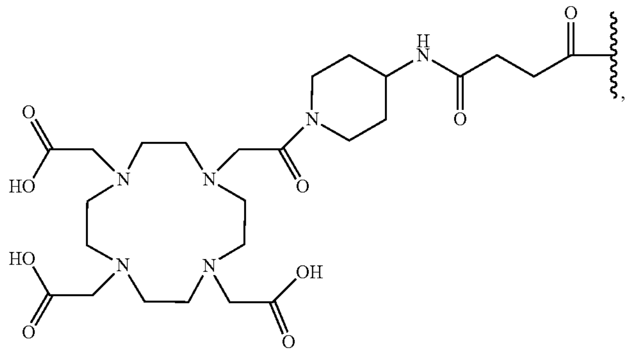
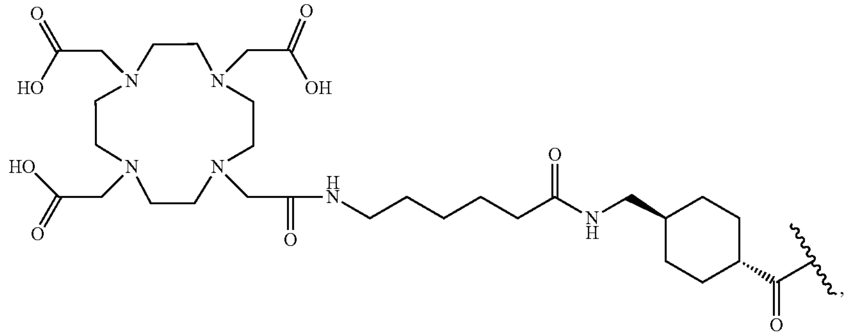
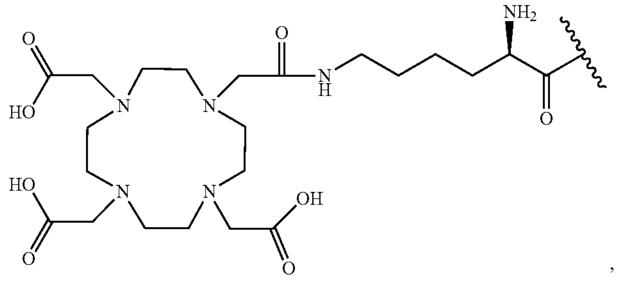
,
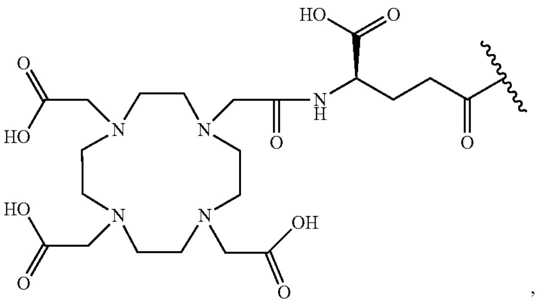
,
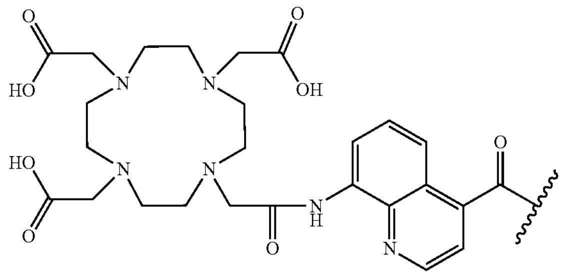
,
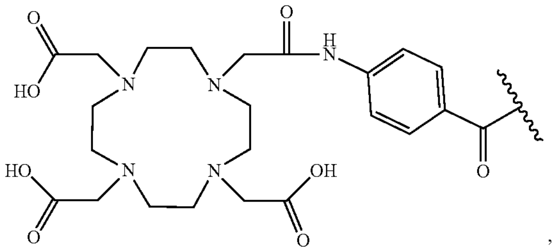
, -continued
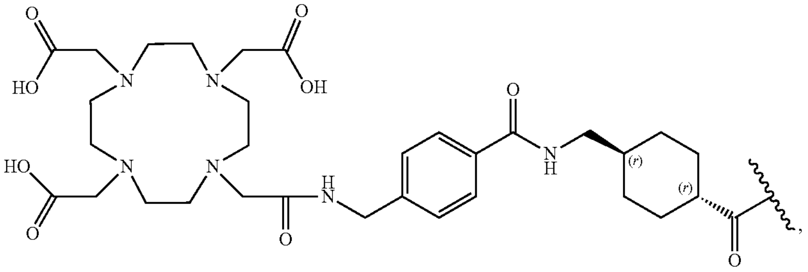
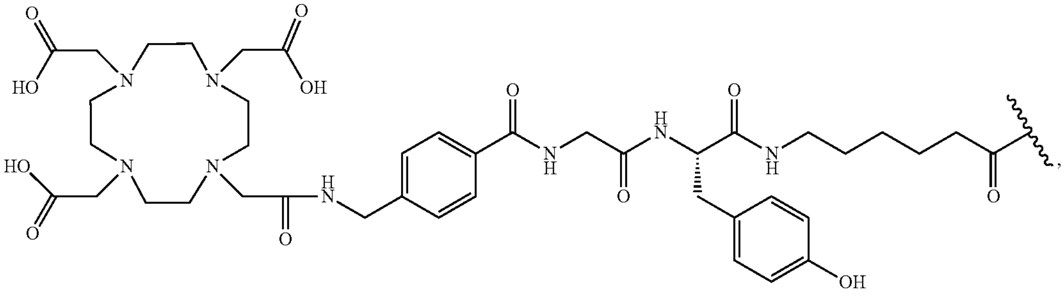
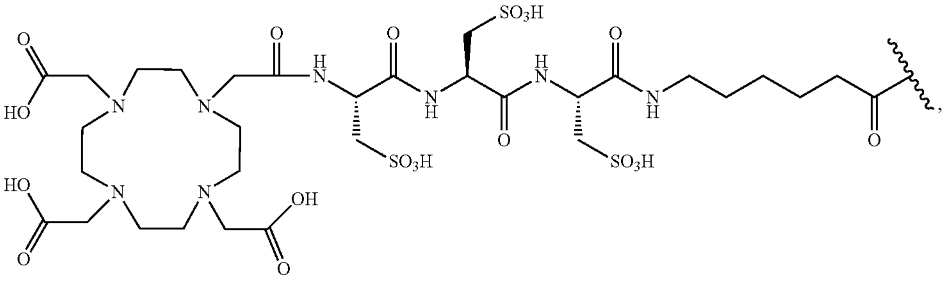
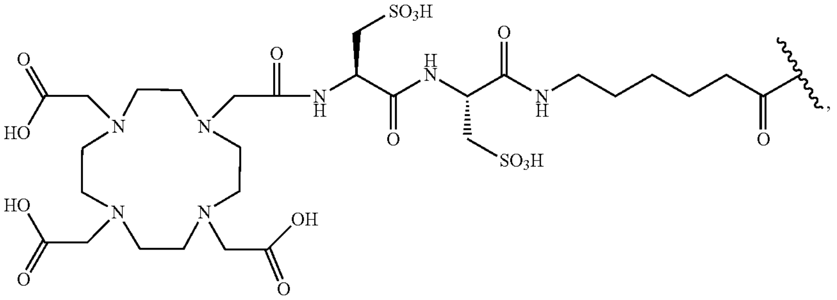
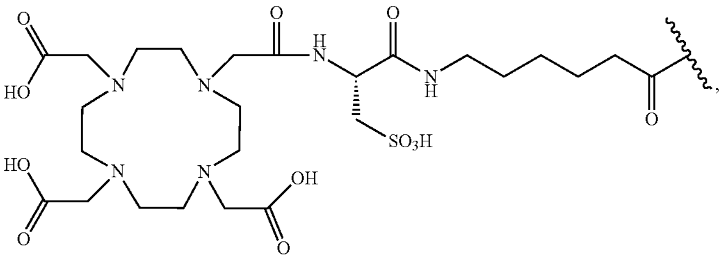
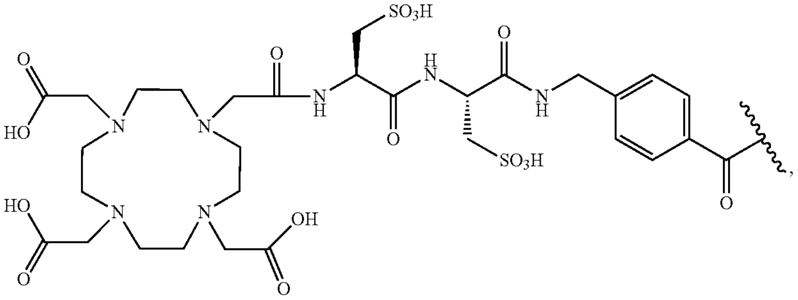

-continued
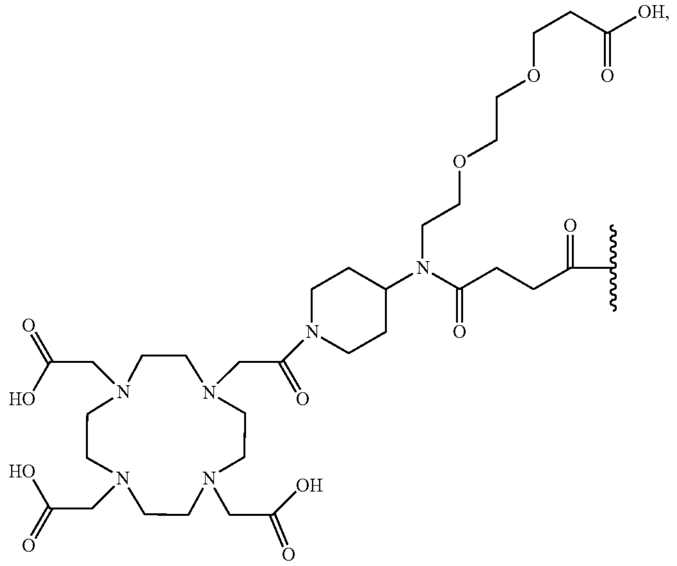
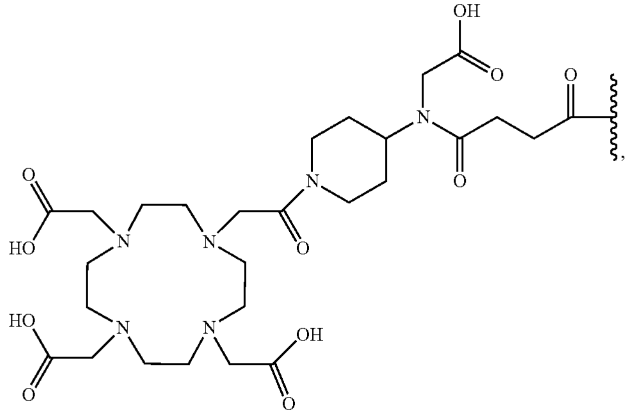
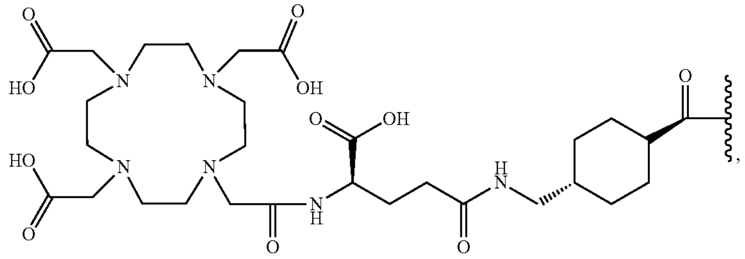
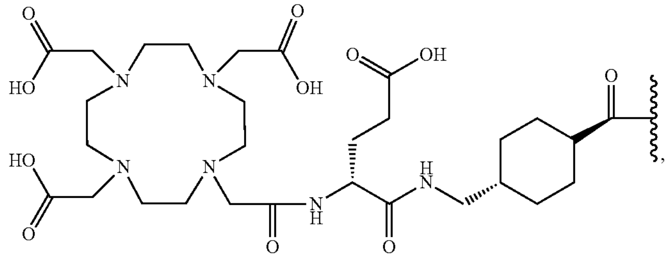

-continued
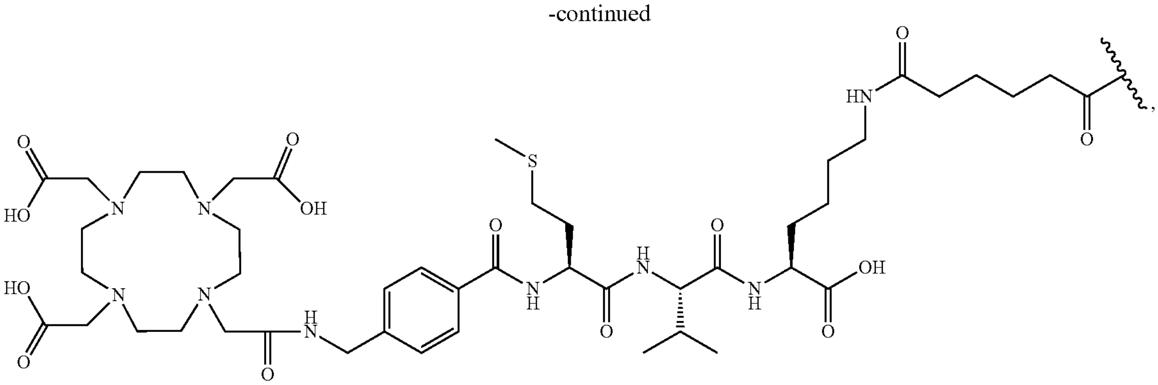
,
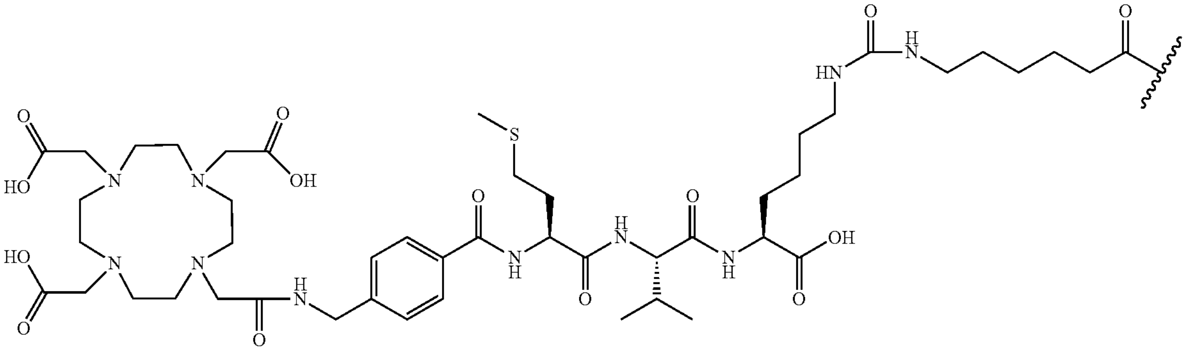
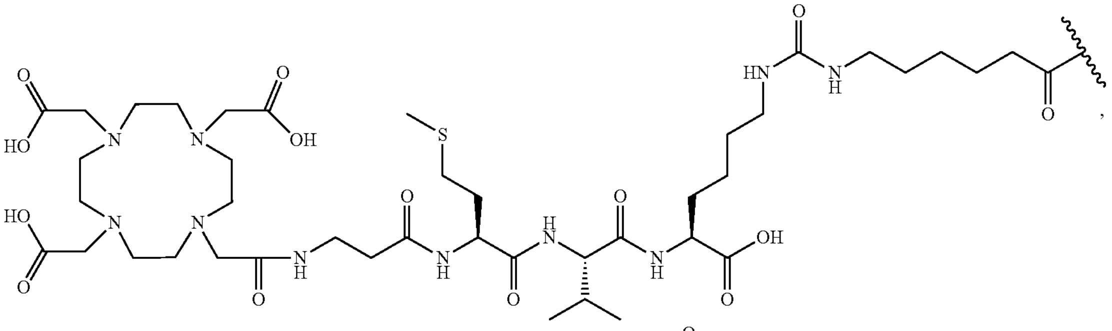
,
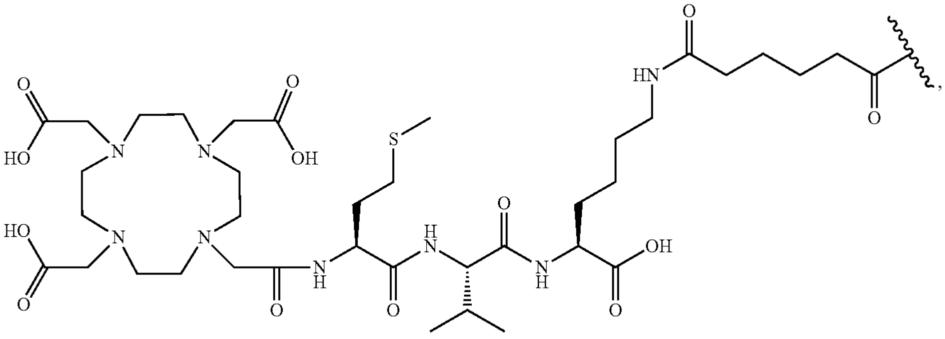
,
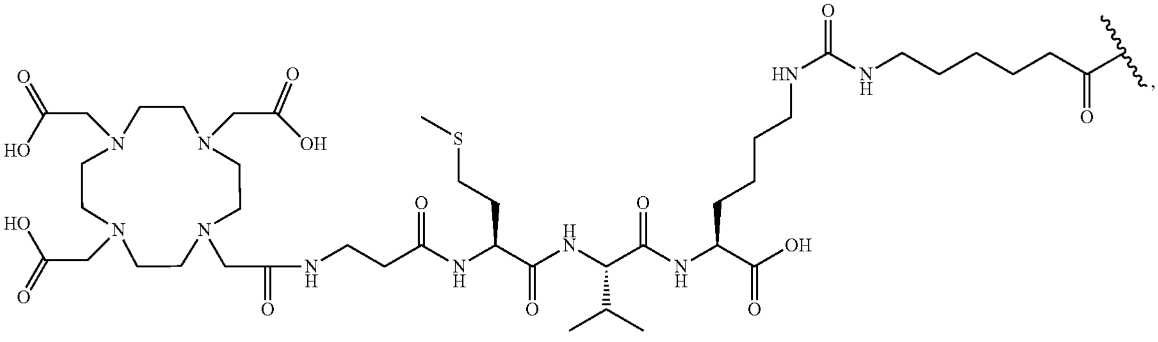
,

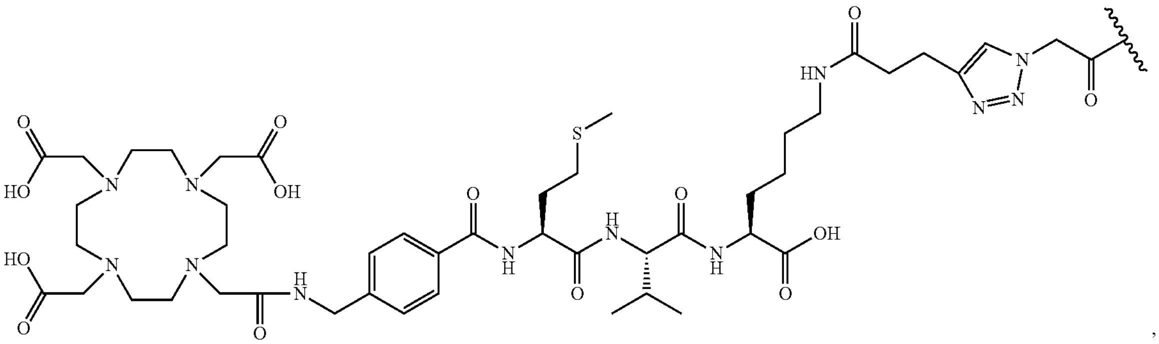
,
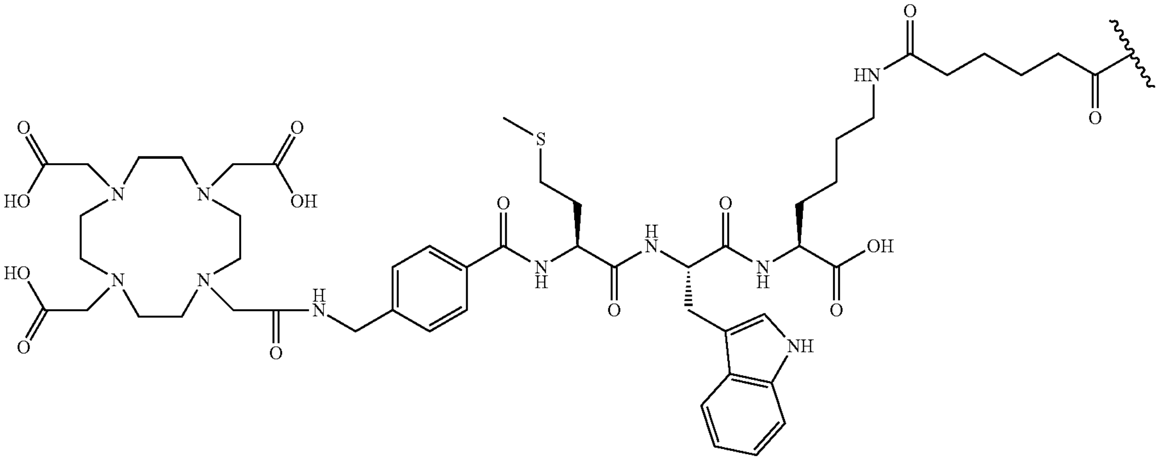
,
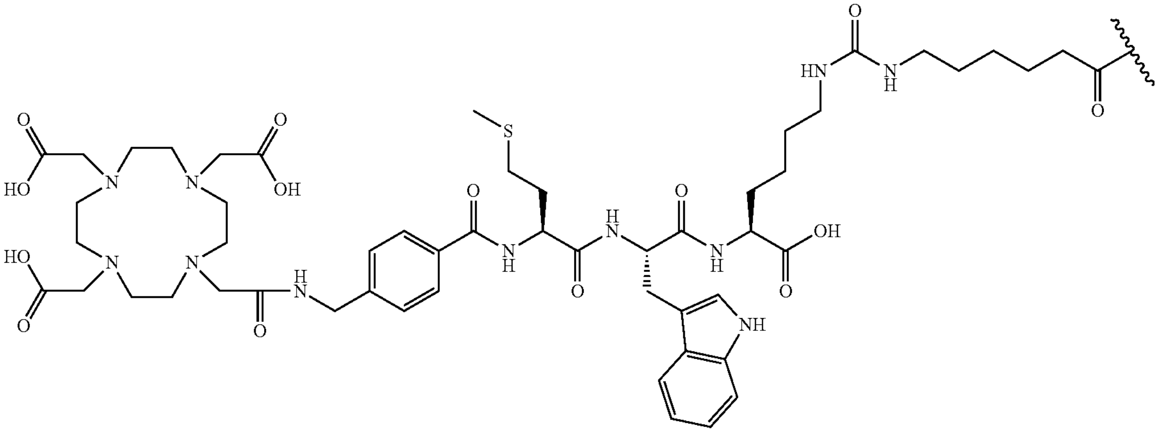
,
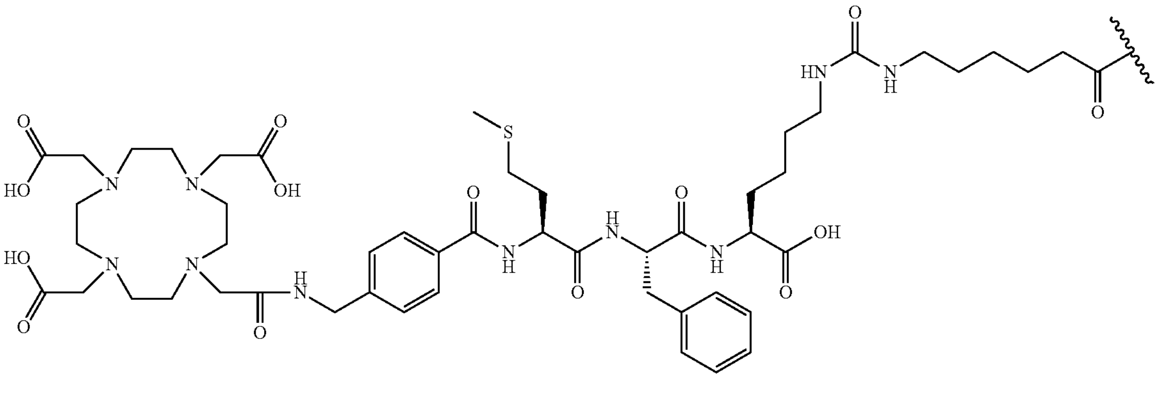
,
or

-continued

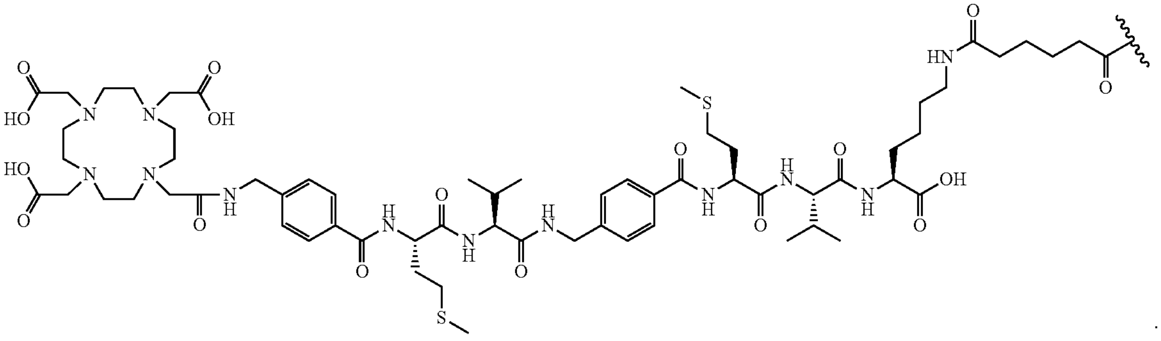

(SEQ ID NO: 799)

Embodiment 65. The compound of embodiment 1, or a pharmaceutically acceptable salt thereof, wherein the compound of Formula (I) has the chemical structure corresponding to one of the following SEQ ID numbers, or a pharmaceutically acceptable salt thereof: (SEQ ID NO: 391), (SEQ ID NO: 392), (SEQ ID NO: 393), (SEQ ID NO: 394), (SEQ ID NO: 395), (SEQ ID NO: 771), (SEQ ID NO: 396), (SEQ ID NO: 397), (SEQ ID NO: 398), (SEQ ID NO: 399), (SEQ ID NO: 772), (SEQ ID NO: 400),

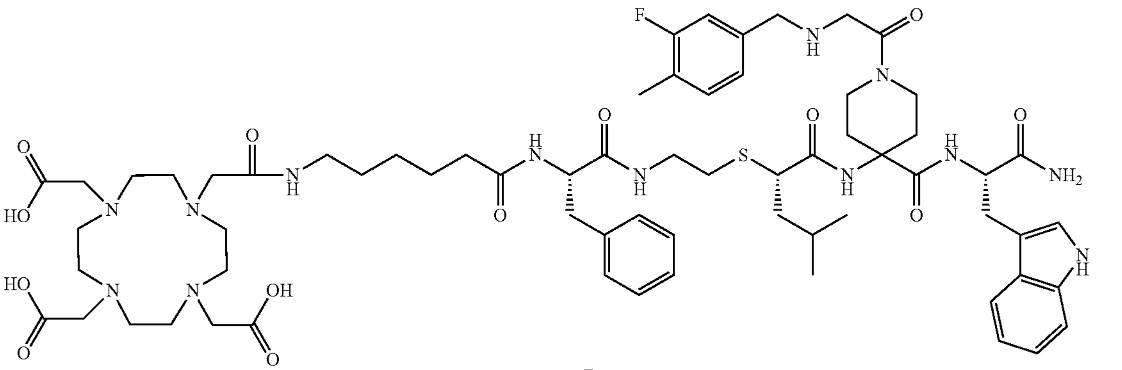

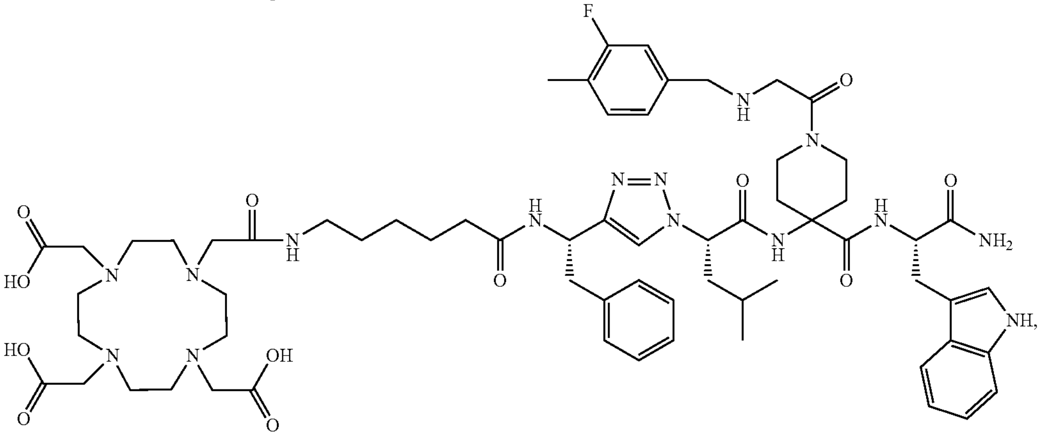

(SEQ ID NO: 403), (SEQ ID NO: 404), (SEQ ID NO: 405), (SEQ ID NO: 406), (SEQ ID NO: 407), (SEQ ID NO: 408), (SEQ ID NO: 409), (SEQ ID NO: 410), (SEQ ID NO: 411), (SEQ ID NO: 412), (SEQ ID NO: 413), (SEQ ID NO: 414), (SEQ ID NO: 415), (SEQ ID NO: 416), (SEQ ID NO: 417), (SEQ ID NO: 418), (SEQ ID NO: 419), (SEQ ID NO: 420), (SEQ ID NO: 421), (SEQ ID NO: 422), (SEQ ID NO: 423), (SEQ ID NO: 424), (SEQ ID NO: 425), (SEQ ID NO: 426), (SEQ ID NO: 427), (SEQ ID NO: 428), (SEQ ID NO: 429), (SEQ ID NO: 430), (SEQ ID NO: 431),

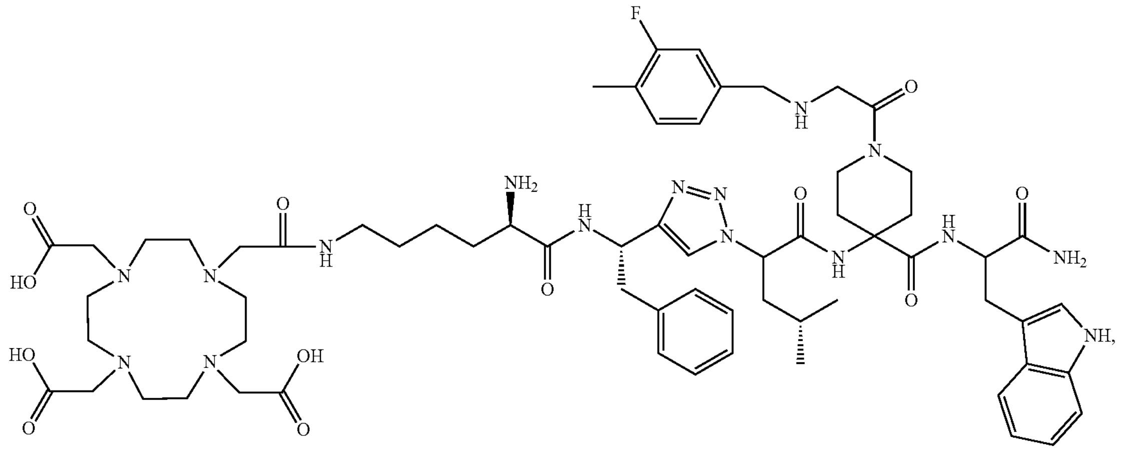
(SEQ ID NO: 433), (SEQ ID NO: 434), (SEQ ID NO: 435), (SEQ ID NO: 436),
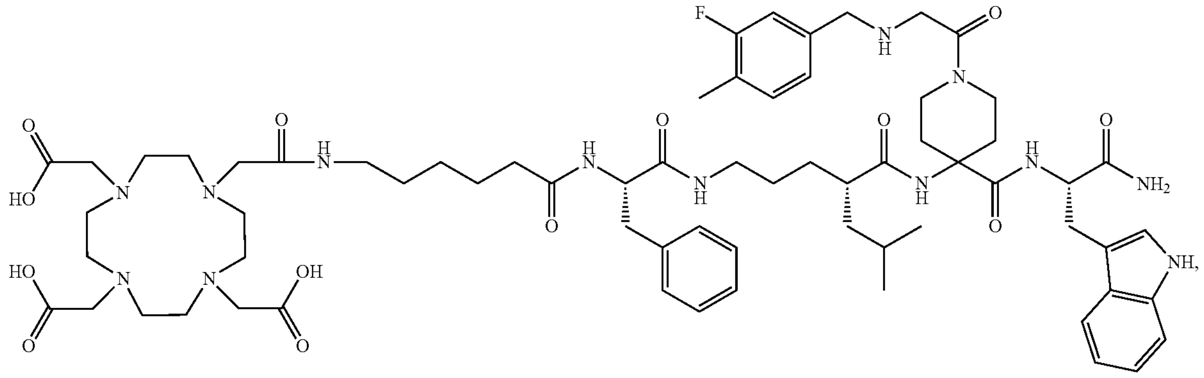
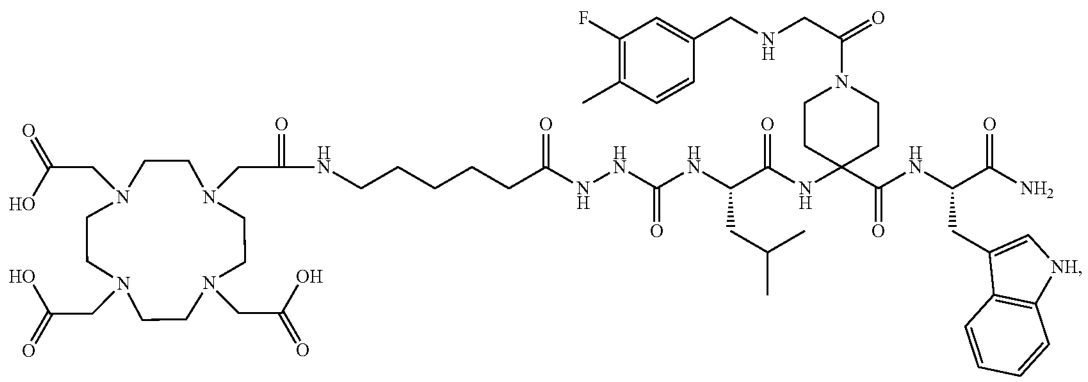

-continued

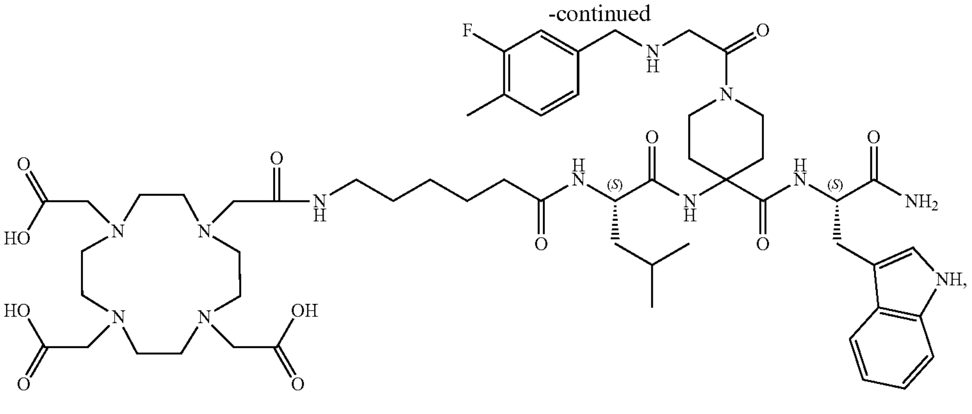

(SEQ ID NO: 439), (SEQ ID NO: 440), (SEQ ID NO: 441), (SEQ ID NO: 442),

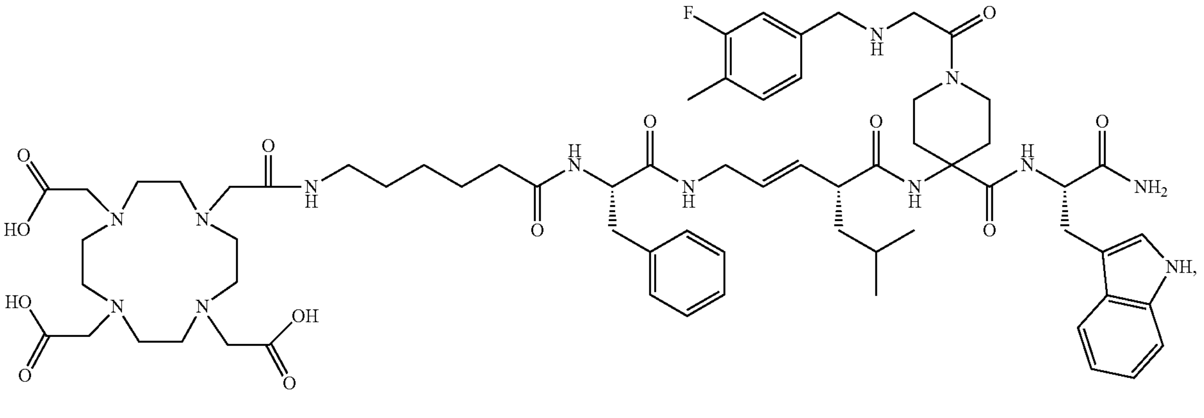 [SMILES: Cc1ccc(CNCC(=O)N2CCC(NC(=O)[C@@H](/C=C/CNC(=O)[C@H](Cc3ccccc3)NC(=O)CCCCCNC(=O)CN3CCN(CC(=O)O)CCN(CC(=O)O)CCN(CC(=O)O)CC3)CC(C)C)(C(=O)N[C@@H](Cc3c[nH]c4ccccc34)C(N)=O)CC2)cc1F]

(SEQ ID NO: 444), (SEQ ID NO: 445),

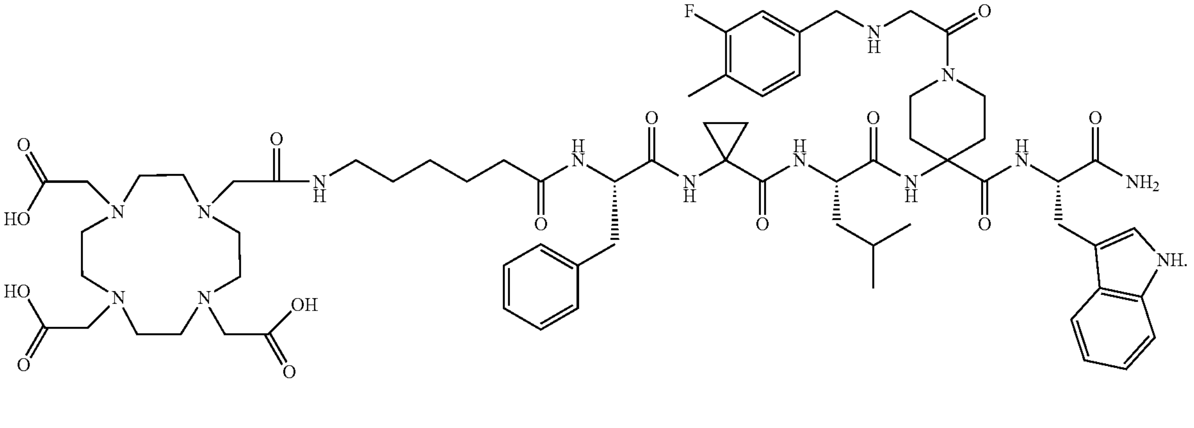 [SMILES: Cc1ccc(CNCC(=O)N2CCC(NC(=O)[C@H](CC(C)C)NC(=O)C3(NC(=O)[C@H](Cc4ccccc4)NC(=O)CCCCCNC(=O)CN4CCN(CC(=O)O)CCN(CC(=O)O)CCN(CC(=O)O)CC4)CC3)(C(=O)N[C@@H](Cc3c[nH]c4ccccc34)C(N)=O)CC2)cc1F]

(SEQ ID NO: 447), (SEQ ID NO: 448), (SEQ ID NO: 449), (SEQ ID NO: 450), (SEQ ID NO: 451), (SEQ ID NO: 452), (SEQ ID NO: 453), (SEQ ID NO: 154), (SEQ ID NO: 455), (SEQ ID NO: 456), (SEQ ID NO: 457), (SEQ ID NO: 458), (SEQ ID NO: 459), (SEQ ID NO: 460), (SEQ ID NO: 461), (SEQ ID NO: 462), (SEQ ID NO: 463), (SEQ ID NO: 464), (SEQ ID NO: 465), (SEQ ID NO: 466), (SEQ ID NO: 467), (SEQ ID NO: 468), (SEQ ID NO: 469), (SEQ ID NO: 470), (SEQ ID NO: 471) (SEQ ID NO: 472), (SEQ ID NO: 473), (SEQ ID NO: 474), (SEQ ID NO: 475), (SEQ ID NO: 476), (SEQ ID NO: 477), (SEQ ID NO: 478), (SEQ ID NO: 479), (SEQ ID NO: 480), (SEQ ID NO: 481), (SEQ ID NO: 482), (SEQ ID NO: 483), (SEQ ID NO: 484), (SEQ ID NO: 485), (SEQ ID NO: 486), (SEQ ID NO: 487), (SEQ ID NO: 488), (SEQ ID NO: 489), (SEQ ID NO: 490), (SEQ ID NO: 491), (SEQ ID NO: 492), (SEQ ID NO: 493), (SEQ ID NO: 494), (SEQ ID NO: 495), (SEQ ID NO: 496), (SEQ ID NO: 497), (SEQ ID NO: 498), (SEQ ID NO: 499), (SEQ ID NO: 500), (SEQ ID NO: 501), (SEQ ID NO: 502), (SEQ ID NO: 503), (SEQ ID NO: 504), (SEQ ID NO: 505),

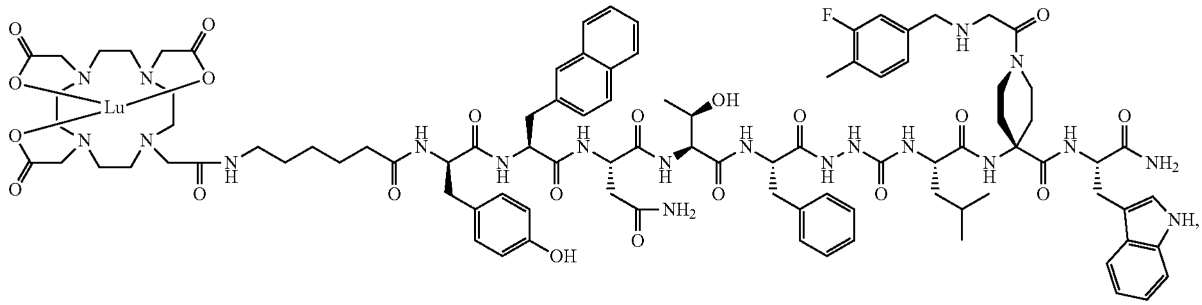
(SEQ ID NO: 506), (SEQ ID NO: 507), (SEQ ID NO: 508), (SEQ ID NO: 509 (SEQ ID NO: 510), (SEQ ID NO: 511), (SEQ ID NO: 512), (SEQ ID NO. 513), (SEQ ID NO: 514),
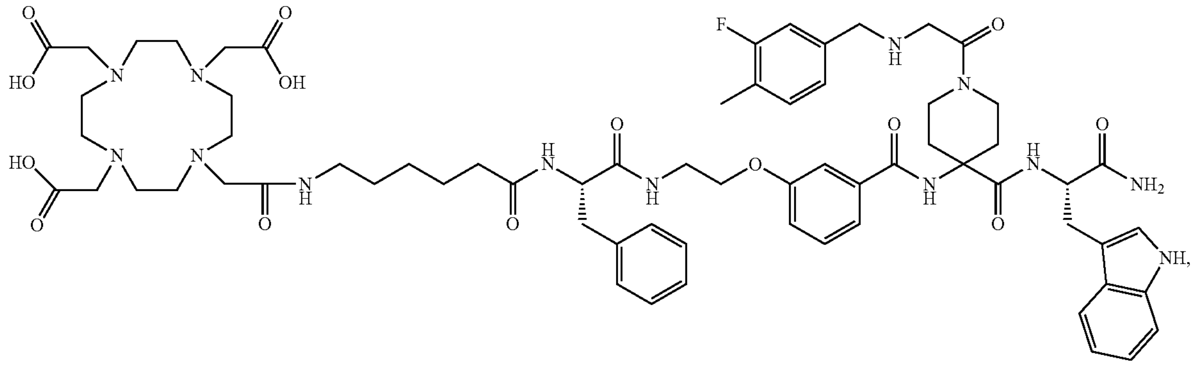
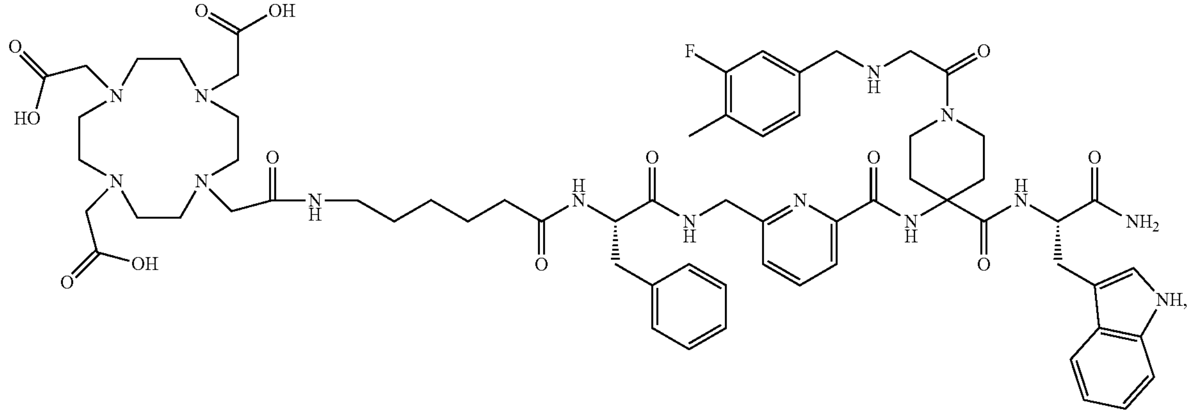
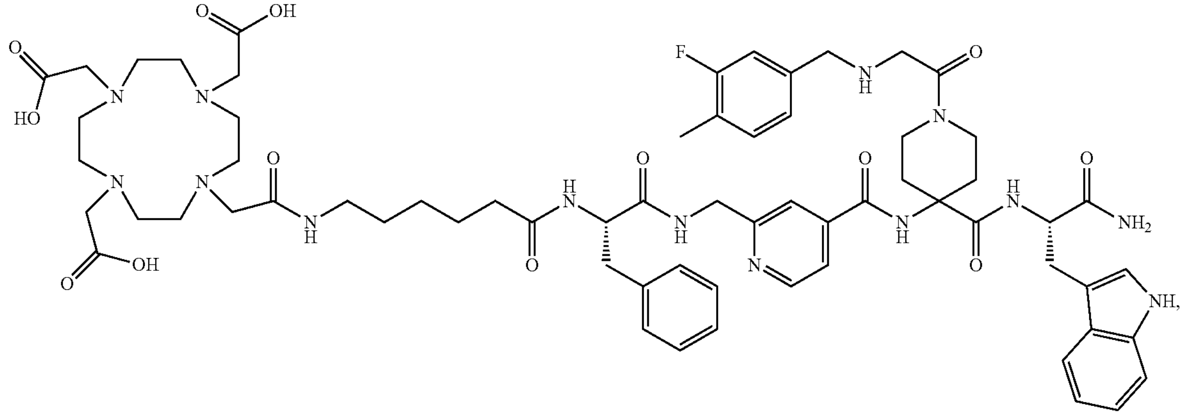

-continued
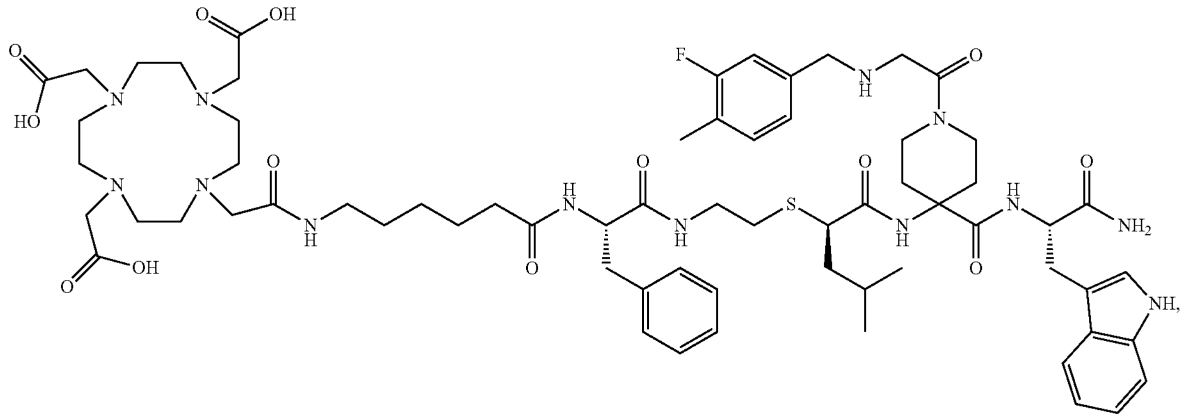
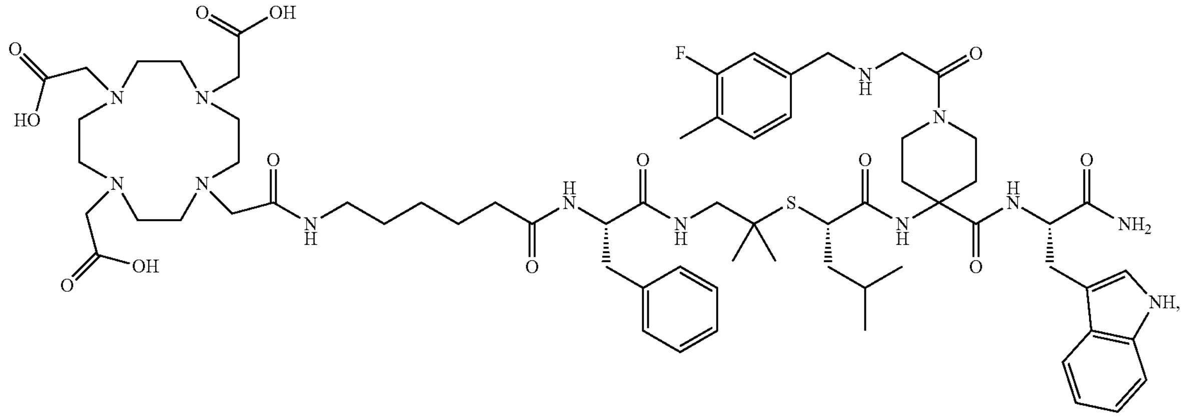
(SEQ ID NO: 521)
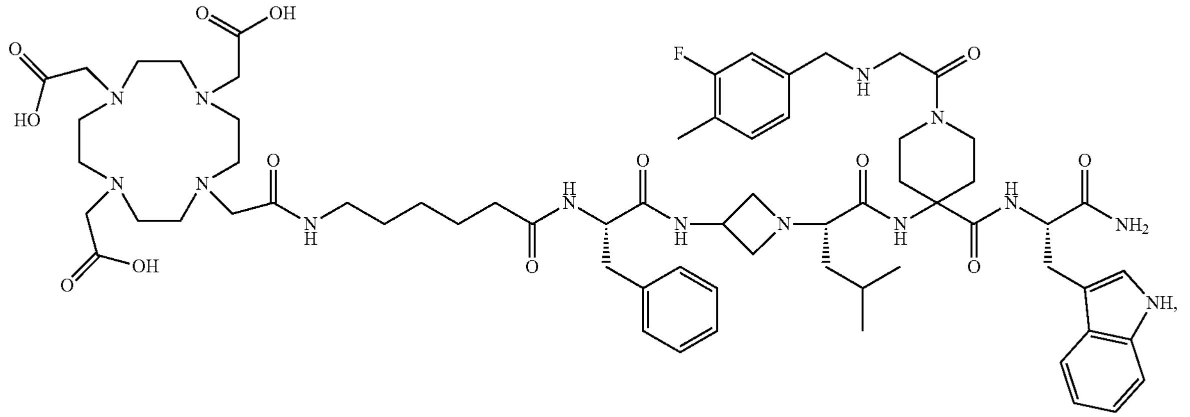
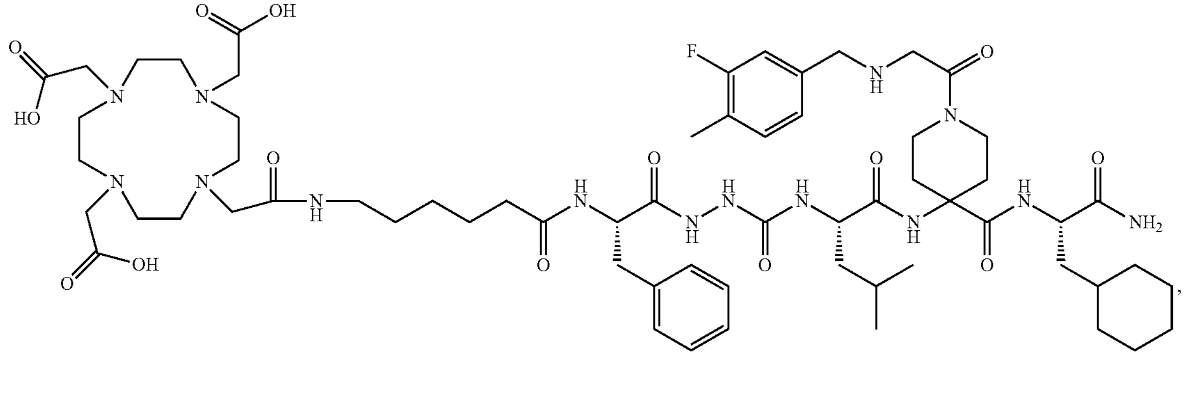

-continued

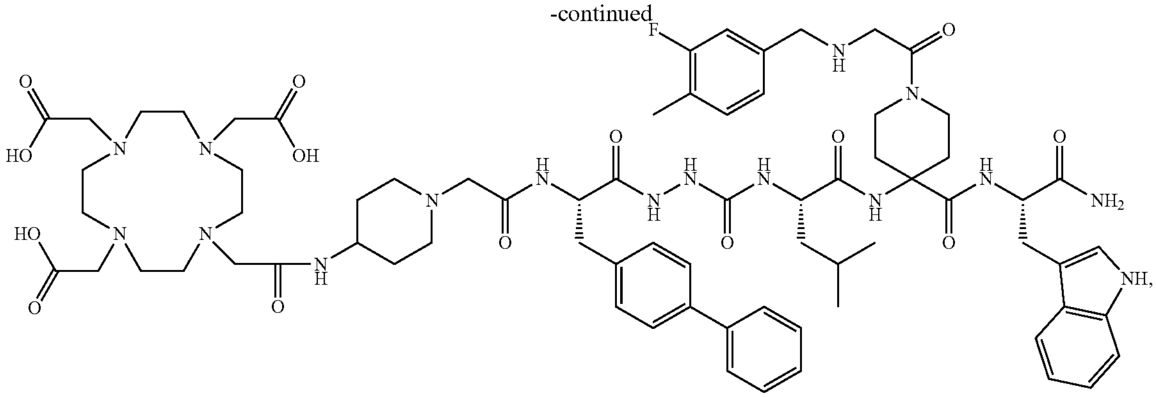

(SEQ ID NO: 524), (SEQ ID NO: 525), (SEQ ID NO: 526), (SEQ ID NO: 527),

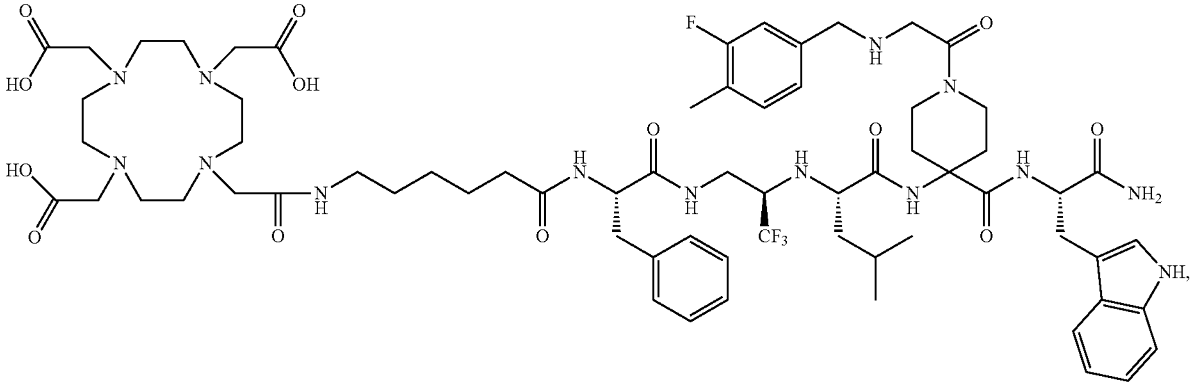

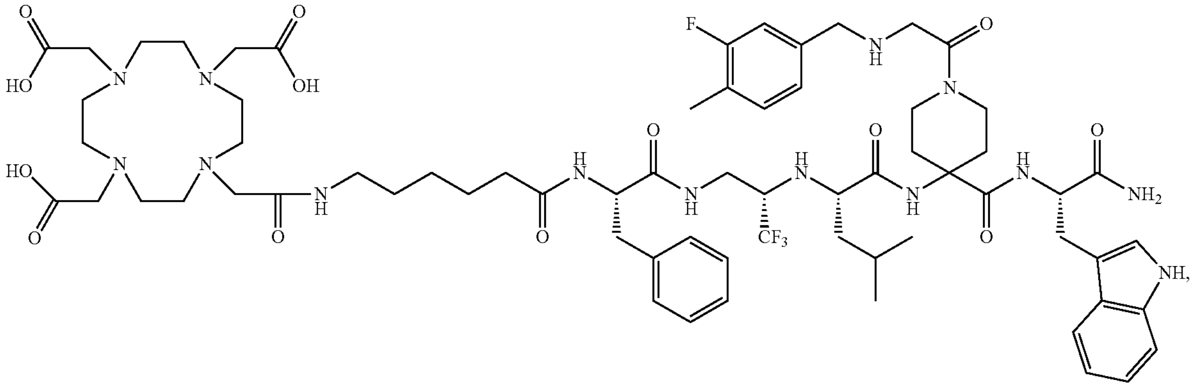 [SMILES: Cc1ccc(CNCC(=O)N2CCC(NC(=O)[C@H](CC(C)C)N[C@@H](CNC(=O)[C@H](Cc3ccccc3)NC(=O)CCCCCNC(=O)CN3CCN(CC(=O)O)CCN(CC(=O)O)CCN(CC(=O)O)CC3)C(F)(F)F)(C(=O)N[C@@H](Cc3c[nH]c4ccccc34)C(N)=O)CC2)cc1F]

(SEQ ID NO: 530), (SEQ ID NO: 531), (SEQ ID NO: 532 (SEQ ID NO: 533), (SEQ ID NO: 534), (SEQ ID NO: 535), (SEQ ID NO: 536), (SEQ ID NO: 537), (SEQ ID NO: 538), (SEQ ID NO: 539), (SEQ ID NO: 540), (SEQ ID NO: 541), (SEQ ID NO: 542), (SEQ ID NO: 543), (SEQ ID NO: 544), (SEQ ID NO: 545), (SEQ ID NO: 546), (SEQ ID NO: 547), (SEQ ID NO: 548), (SEQ ID NO: 549), (SEQ ID NO: 550), (SEQ ID NO: 551), (SEQ ID NO: 552), (SEQ ID NO: 553), (SEQ ID NO: 554), (SEQ ID NO: 555), (SEQ ID NO: 556), (SEQ ID NO: 557), (SEQ ID NO: 558), (SEQ ID NO: 559), (SEQ ID NO: 560), (SEQ ID NO: 561), (SEQ ID NO: 562), (SEQ ID NO: 563), (SEQ ID NO: 564), (SEQ ID NO: 565), (SEQ ID NO: 566), (SEQ ID NO: 567), (SEQ ID NO: 568), (SEQ ID NO: 569), (SEQ ID NO: 570), (SEQ ID NO: 571 (SEQ ID NO: 572), (SEQ ID NO: 573), (SEQ ID NO: 574), (SEQ ID NO: 575), (SEQ ID NO: 576 (SEQ ID NO: 577), (SEQ ID NO: 578), (SEQ ID NO: 579), (SEQ ID NO: 580), (SEQ ID NO: 581), (SEQ ID NO: 582), (SEQ ID NO: 583), (SEQ ID NO: 584),

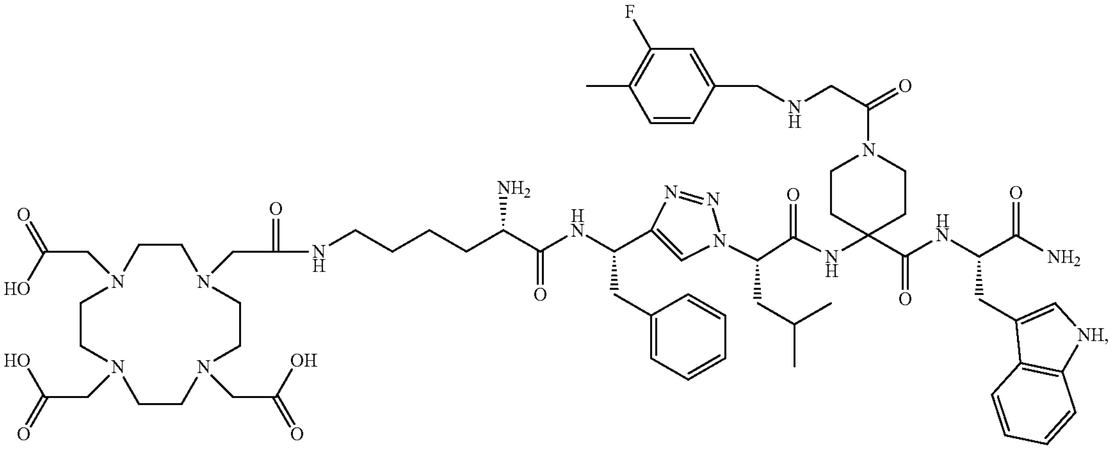 [SMILES: Cc1ccc(CNCC(=O)N2CCC(NC(=O)[C@H](CC(C)C)n3cc([C@H](Cc4ccccc4)NC(=O)[C@@H](N)CCCCNC(=O)CN4CCN(CC(=O)O)CCN(CC(=O)O)CCN(CC(=O)O)CC4)nn3)(C(=O)N[C@@H](Cc3c[nH]c4ccccc34)C(N)=O)CC2)cc1F]
(SEQ ID NO: 586), (SEQ ID NO: 587), (SEQ ID NO: 588), (SEQ ID NO: 589), (SEQ ID NO. 590), (SEQ ID NO: 591),
(SEQ ID NO: 593)
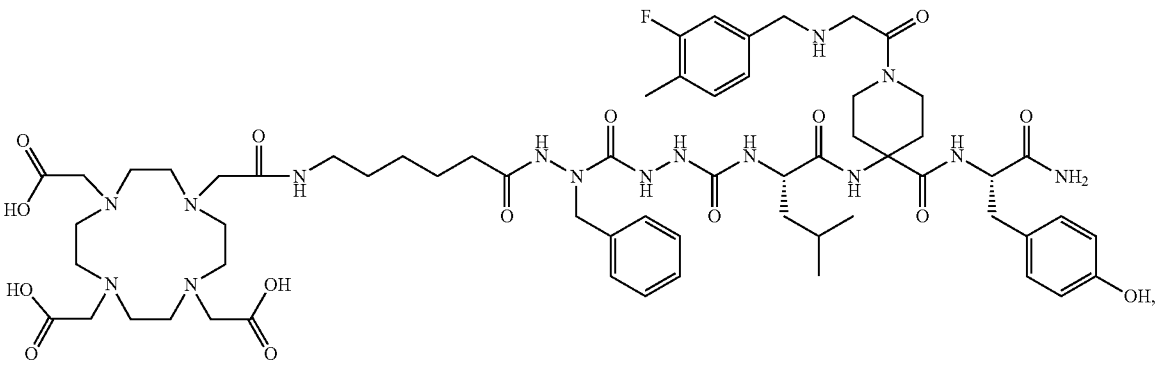
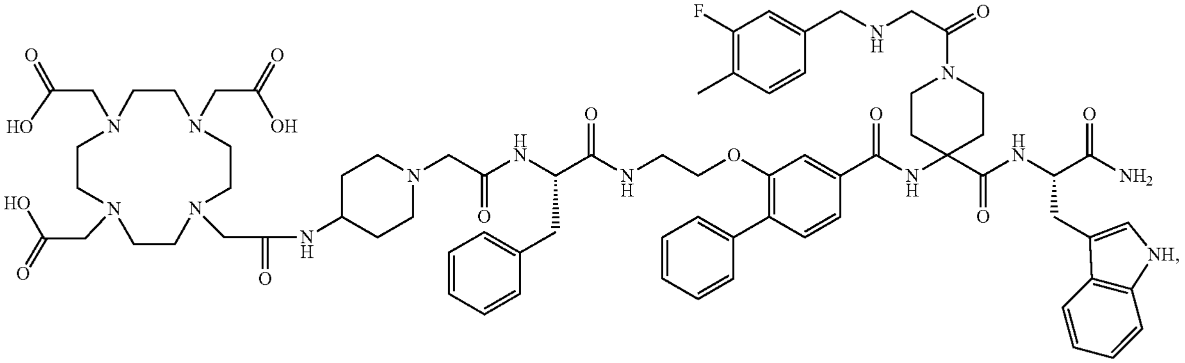

-continued
(SEQ ID NO: 594)
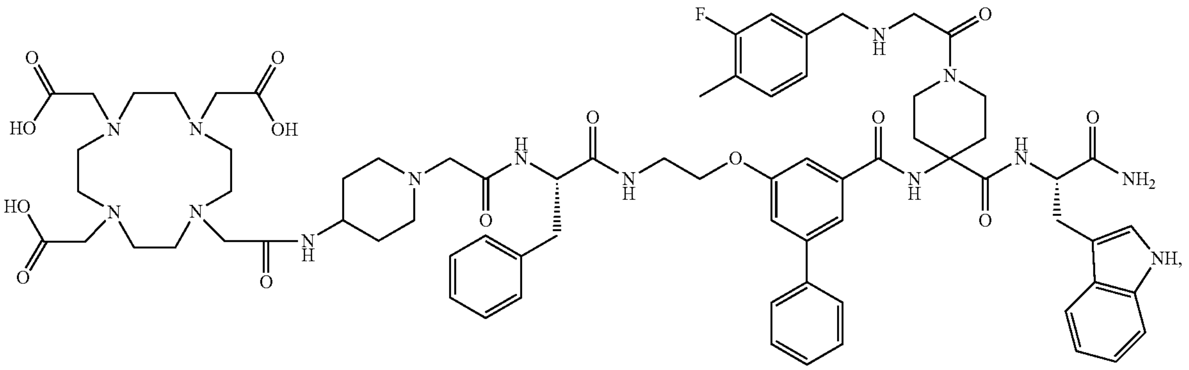
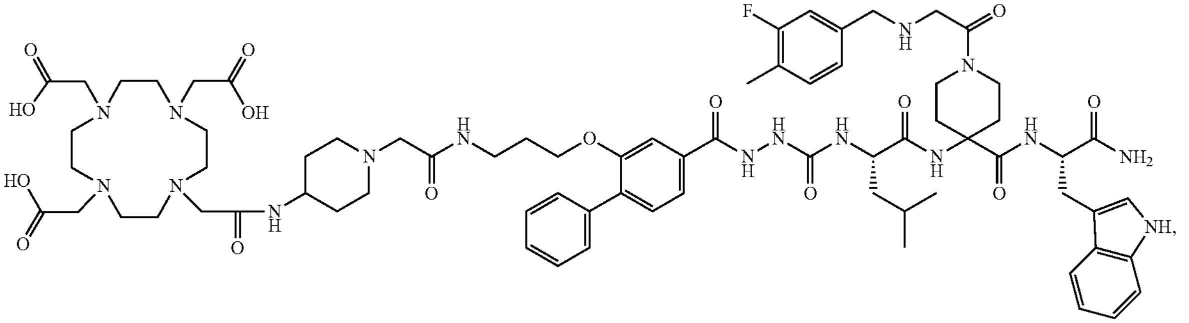
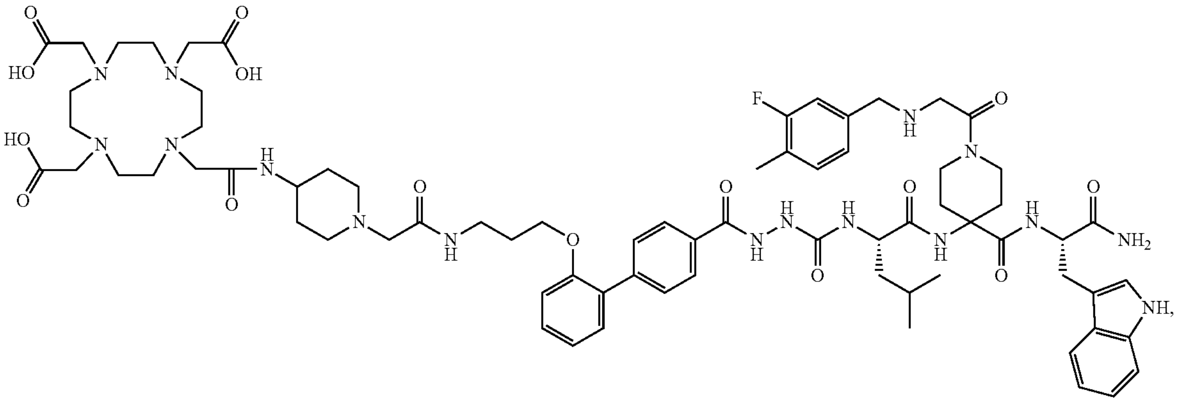 [SMILES: Cc1ccc(CNCC(=O)N2CCC(NC(=O)[C@H](CC(C)C)NC(=O)NNC(=O)c3ccc(-c4ccccc4OCCCNC(=O)CN4CCC(NC(=O)CN5CCN(CC(=O)O)CCN(CC(=O)O)CCN(CC(=O)O)CC5)CC4)cc3)(C(=O)N[C@@H](Cc3c[nH]c4ccccc34)C(N)=O)CC2)cc1F]
(SEQ ID NO: 599), (SEQ ID NO: 600), (SEQ ID NO: 601), (SEQ ID NO: 602), (SEQ ID NO: 603), (SEQ ID NO: 605), (SEQ ID NO: 606), (SEQ ID NO: 607), (SEQ ID NO: 608), (SEQ ID NO: 610), (SEQ ID NO: 611), (SEQ ID NO: 612), (SEQ ID NO: 613), (SEQ ID NO: 614), (SEQ ID NO: 615), (SEQ ID NO: 616), (SEQ ID NO: 617), (SEQ ID NO: 618), (SEQ ID NO: 619), (SEQ ID NO: 620), (SEQ ID NO: 621), (SEQ ID NO: 622), (SEQ ID NO: 623 (SEQ ID NO: 624), (SEQ ID NO: 625), (SEQ ID NO: 626)
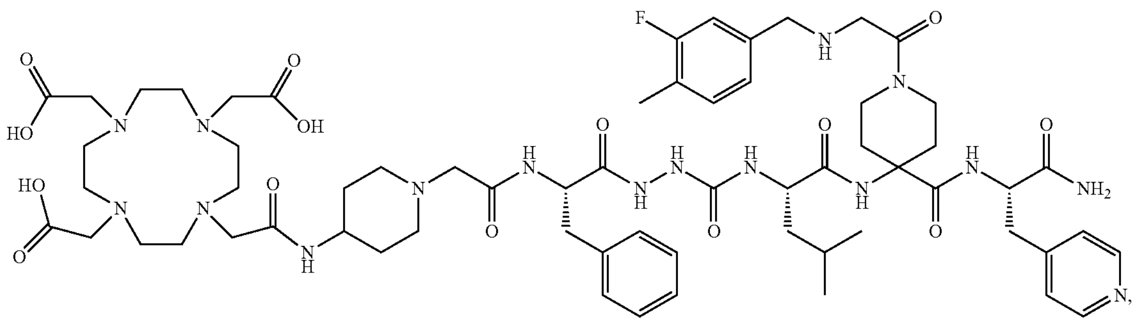 [SMILES: Cc1ccc(CNCC(=O)N2CCC(NC(=O)[C@H](CC(C)C)NC(=O)NNC(=O)[C@H](Cc3ccccc3)NC(=O)CN3CCC(NC(=O)CN4CCN(CC(=O)O)CCN(CC(=O)O)CCN(CC(=O)O)CC4)CC3)(C(=O)N[C@@H](Cc3ccncc3)C(N)=O)CC2)cc1F]

(SEQ ID NO: 628), (SEQ ID NO: 629 (SEQ ID NO: 630), (SEQ ID NO: 631), (SEQ ID NO: 632), (SEQ ID NO: 633), (SEQ ID NO: 634), (SEQ ID NO: 635); (SEQ ID NO: 636), (SEQ ID NO: 637), (SEQ ID NO: 638), (SEQ ID NO: 639), (SEQ ID NO: 640), (SEQ ID NO: 641)
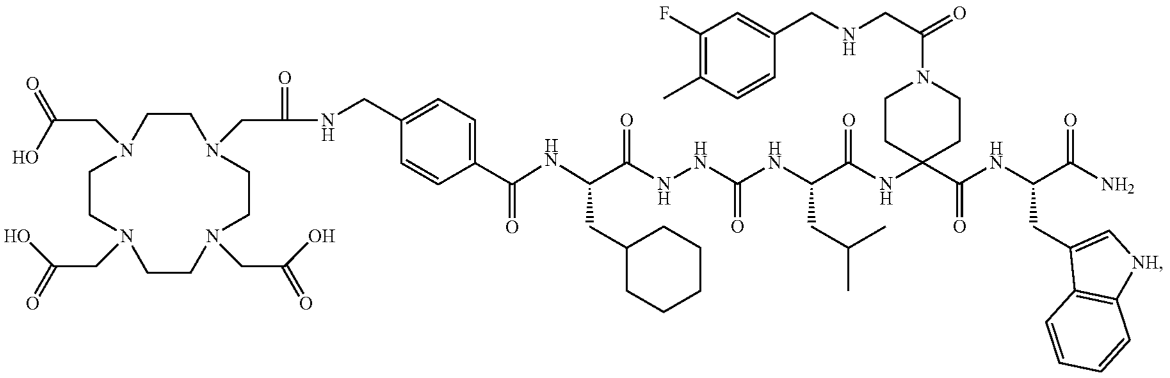 [SMILES: Cc1ccc(CNCC(=O)N2CCC(NC(=O)[C@H](CC(C)C)NC(=O)NNC(=O)[C@H](CC3CCCCC3)NC(=O)c3ccc(CNC(=O)CN4CCN(CC(=O)O)CCN(CC(=O)O)CCN(CC(=O)O)CC4)cc3)(C(=O)N[C@@H](Cc3c[nH]c4ccccc34)C(N)=O)CC2)cc1F]
(SEQ ID NO: 643), (SEQ ID NO: 645 (SEQ ID NO: 647), (SEQ ID NO: 648),
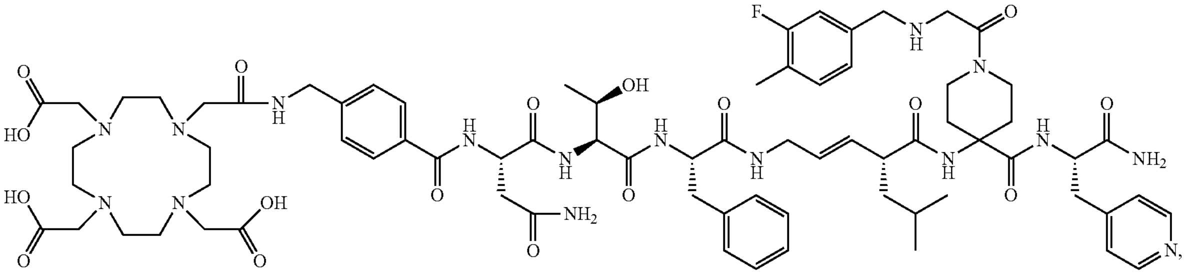 [SMILES: Cc1ccc(CNCC(=O)N2CCC(NC(=O)[C@@H](/C=C/CNC(=O)[C@H](Cc3ccccc3)NC(=O)[C@@H](NC(=O)[C@H](CC(N)=O)NC(=O)c3ccc(CNC(=O)CN4CCN(CC(=O)O)CCN(CC(=O)O)CCN(CC(=O)O)CC4)cc3)[C@@H](C)O)CC(C)C)(C(=O)N[C@@H](Cc3ccncc3)C(N)=O)CC2)cc1F]
(SEQ ID NO: 650), (SEQ ID NO: 651), (SEQ ID NO: 652), (SEQ ID NO: 653), (SEQ ID NO: 654), (SEQ ID NO: 655),
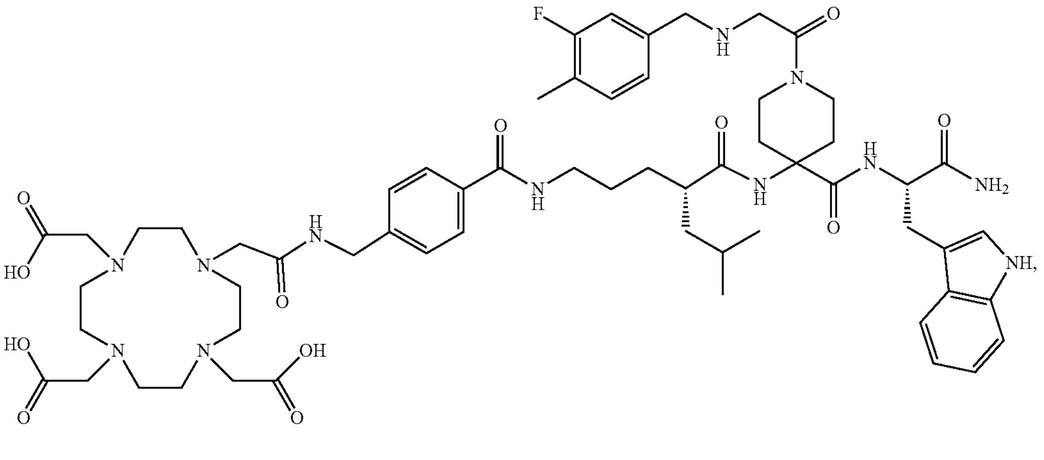 [SMILES: Cc1ccc(CNCC(=O)N2CCC(NC(=O)[C@@H](CCCNC(=O)c3ccc(CNC(=O)CN4CCN(CC(=O)O)CCN(CC(=O)O)CCN(CC(=O)O)CC4)cc3)CC(C)C)(C(=O)N[C@@H](Cc3c[nH]c4ccccc34)C(N)=O)CC2)cc1F]
65
(SEQ ID NO: 657), (SEQ ID NO: 658), (SEQ ID NO: 659), (SEQ ID NO: 660), (SEQ ID NO: 661), (SEQ ID NO:63)
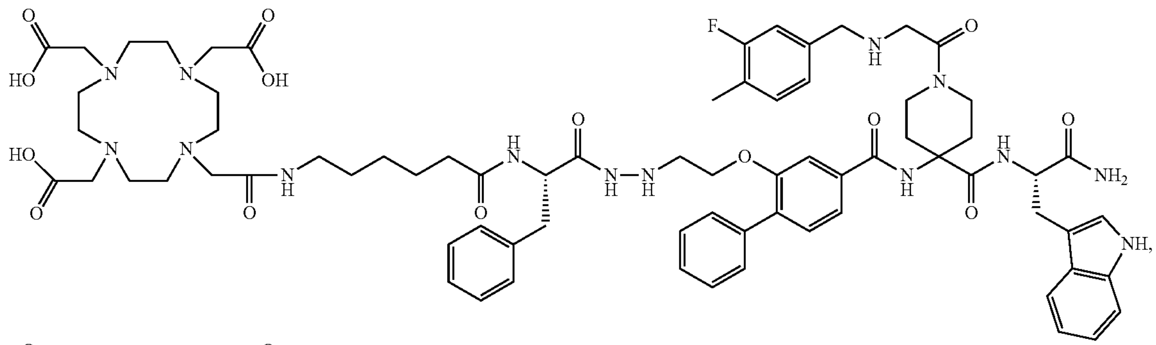
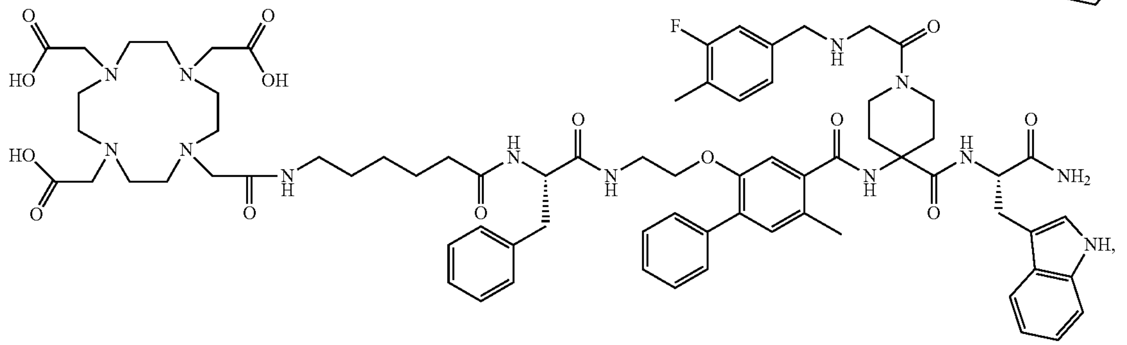
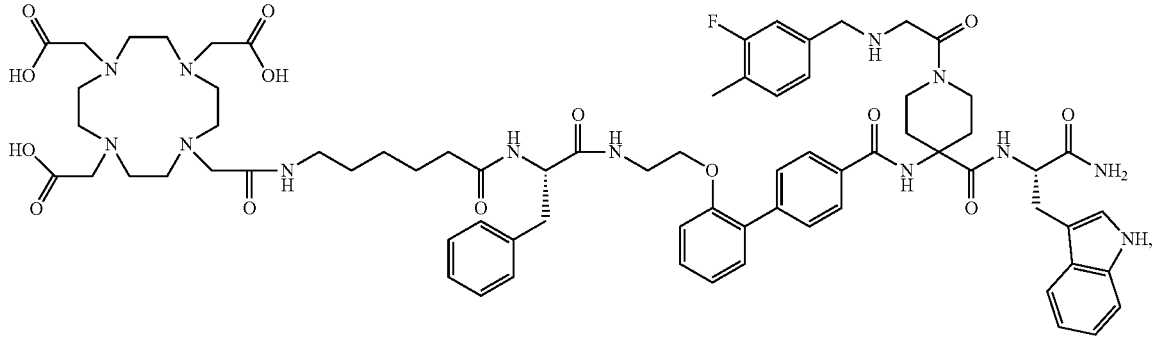
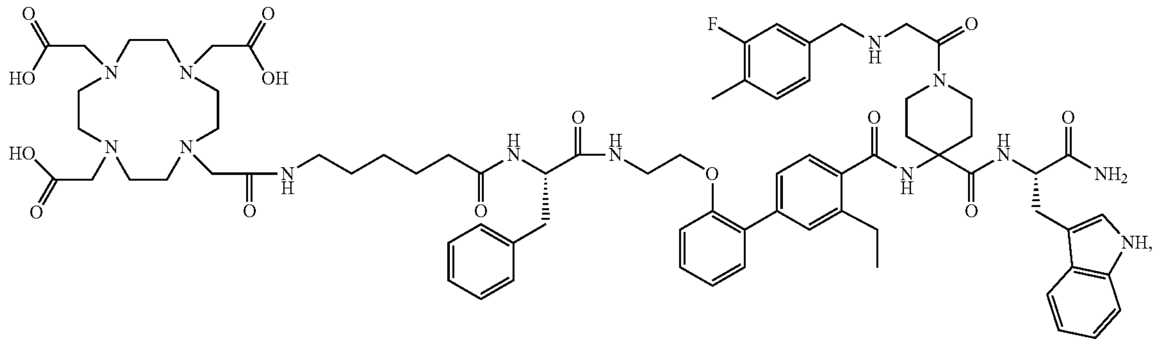
(SEQ ID NO: 667), (SEQ ID NO: 668), (SEQ ID NO: 669), (SEQ ID NO: 670), (SEQ ID NO: 671), (SEQ ID NO: 672), (SEQ ID NO: 673), (SEQ ID NO: 674), (SEQ ID NO: 675), (SEQ ID NO: 676), (SEQ ID NO: 677), (SEQ ID NO: 678),

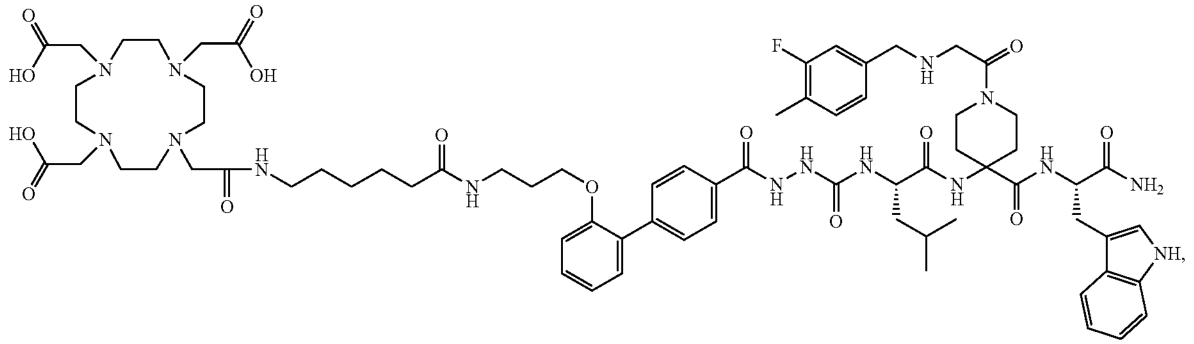

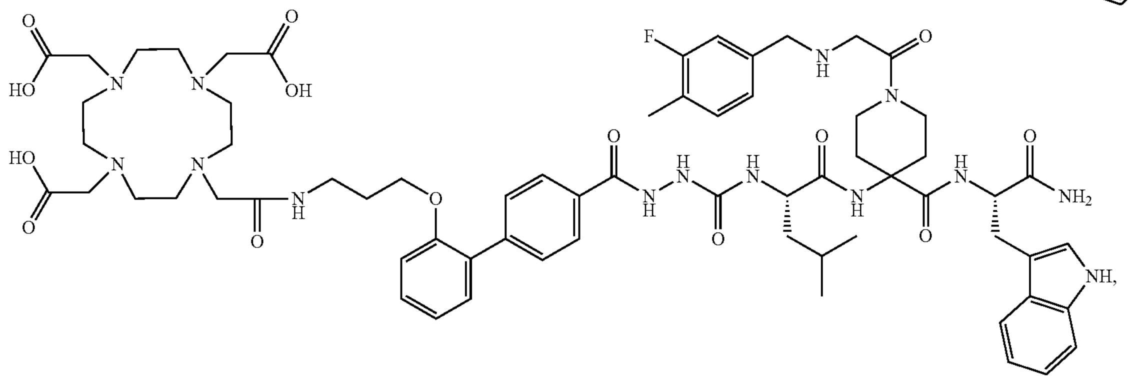

(SEQ ID NO: 681), (SEQ ID NO: 682), (SEQ ID NO: 683), (SEQ ID NO: 684), (SEQ ID NO: 686), (SEQ ID NO: 687), (SEQ ID NO: 688), (SEQ ID NO: 689), (SEQ ID NO: 690), (SEQ ID NO: 691), (SEQ ID NO: 692), (SEQ ID NO: 693), (SEQ ID NO: 694), (SEQ ID NO: 695), (SEQ ID NO: 696), (SEQ ID NO: 697), (SEQ ID NO: 698), (SEQ ID NO: 699), (SEQ ID NO: 700), (SEQ ID NO: 701), (SEQ ID NO: 702), (SEQ ID NO: 703), (SEQ ID NO: 704), (SEQ ID NO: 705), (SEQ ID NO: 706), (SEQ ID NO: 707), (SEQ ID NO: 708), (SEQ ID NO: 709), (SEQ ID NO: 710), (SEQ ID NO: 711), (SEQ ID NO: 712), (SEQ ID NO: 713), (SEQ ID NO: 714), (SEQ ID NO: 715), (SEQ ID NO: 716), (SEQ ID NO: 717), (SEQ ID NO: 718), (SEQ ID NO: 719), (SEQ ID NO: 720), (SEQ ID NO: 721), (SEQ ID NO: 722), (SEQ ID NO: 723), (SEQ ID NO: 724), (SEQ ID NO: 725), (SEQ ID NO: 726), (SEQ ID NO: 727), (SEQ ID NO: 728), (SEQ ID NO: 729), (SEQ ID NO: 730), (SEQ ID NO: 731), (SEQ ID NO: 732), (SEQ ID NO: 733), (SEQ ID NO: 734), (SEQ ID NO: 735), (SEQ ID NO: 736), (SEQ ID NO: 737), (SEQ ID NO: 738), (SEQ ID NO: 739), (SEQ ID NO: 740), (SEQ ID NO: 741), (SEQ ID NO: 742), (SEQ ID NO: 743), (SEQ ID NO: 744), (SEQ ID NO: 745), (SEQ ID NO: 746), (SEQ ID NO: 747), (SEQ ID NO: 748), (SEQ ID NO: 749), (SEQ ID NO: 750), (SEQ ID NO: 751), (SEQ ID NO: 752), (SEQ ID NO: 753), (SEQ ID NO: 754), (SEQ ID NO: 755), (SEQ ID NO: 756), (SEQ ID NO: 757), (SEQ ID NO: 758), (SEQ ID NO: 759), (SEQ ID NO: 760), (SEQ ID NO: 761), (SEQ ID NO: 762), (SEQ ID NO: 763), (SEQ ID NO: 764), (SEQ ID NO: 765), (SEQ ID NO: 766), (SEQ ID NO: 767), (SEQ ID NO: 768), (SEQ ID NO: 769), or (SEQ ID NO: 770), or a radionuclide complex thereof.

Embodiment 66. The compound of any one of embodiments 1-65, or a pharmaceutically acceptable salt thereof, wherein: the radionuclide of the radionuclide complex is a lanthanide or an actinide.

Embodiment 67. The compound of any one of embodiments 1-65, or a pharmaceutically acceptable salt thereof, wherein: the radionuclide of the radionuclide complex is actinium, bismuth, cesium, cobalt, copper, dysprosium, erbium, gold, indium, iridium, gallium, lead, lutetium, manganese, palladium, platinum, radium, rhenium, samarium, strontium, technetium, ytterbium, yttrium, or zirconium.

Embodiment 68. The compound of any one of embodiments 1-65, or a pharmaceutically acceptable salt thereof, wherein: the radionuclide of the radionuclide complex is a diagnostic or therapeutic radionuclide.

Embodiment 69. The compound of any one of embodiments 1-65, or a pharmaceutically acceptable salt thereof, wherein: the radionuclide of the radionuclide complex is an Auger electron-emitting radionuclide, α-emitting radionuclide, β-emitting radionuclide, or γ-emitting radionuclide.

Embodiment 70. The compound of any one of embodiments 1-65, or a pharmaceutically acceptable salt thereof, wherein the radionuclide of the radionuclide complex is:

an Auger electron-emitting radionuclide that is 111-indium ($^{111}In$), 67-gallium ($^{67}Ga$), 68-gallium ($^{68}Ga$), 99m-technetium ($^{99m}Tc$), or 195m-platinum ($^{195m}Pt$); or an α-emitting radionuclide that is 225-actinium ($^{225}Ac$), 213-bismuth ($^{213}Bi$), 223-Radium ($^{223}Re$), or 212-lead ($^{212}Pb$); or a β-emitting radionuclide that is 90-yttrium ($^{90}Y$), 177-lutetium ($^{177}Lu$), 186-rhenium ($^{186}Re$), 188-rhenium ($^{188}Re$), 64-copper ($^{64}Cu$), 67-copper ($^{67}Cu$), 153-samarium ($^{153}Sm$), 89-strontium ($^{89}Sr$), 198-gold ($^{198}Au$), 169-Erbium ($^{169}Er$), 165-dysprosium ($^{165}Dy$), 99m-technetium ($^{99m}Tc$), 89-zirconium ($^{89}Zr$), or 52-manganese ($^{52}Mn$) or a γ-emitting radionuclide that is 60-cobalt ($^{60}Co$)), 103-pallidum ($^{103}Pd$), 137-cesium ($^{137}Cs$), 169-ytterbium ($^{169}Yb$), 192-iridium ($^{192}Ir$), or 226-radium (226Ra).

Embodiment 71. The compound of any one of embodiments 1-65, or a pharmaceutically acceptable salt thereof, wherein: the radionuclide of the radionuclide complex is 111-indium ($^{111}In$), 67-gallium ($^{67}Ga$), 68-gallium ($^{68}Ga$), 69-gallium ($^{69}Ga$), 71-gallium ($^{71}Ga$), 225-actinium (225Ac), 175-lutetium ($^{175}Lu$), 177-lutetium ($^{177}Lu$), 204-lead ($^{204}Pb$), 206-lead ($^{206}Pb$), 207-lead ($^{207}Pb$), 208-lead ($^{208}Pb$), 212-lead ($^{212}Pb$), 63-copper ($^{63}Cu$), 64-copper ($^{64}Cu$), 65-copper ($^{65}Cu$), or 67-copper ($^{67}Cu$).

Embodiment 72. The compound of any one of embodiments 1-65, or a pharmaceutically acceptable salt thereof, wherein: the radionuclide of the radionuclide complex is 64-copper ($^{64}Cu$), 67-copper ($^{67}Cu$), 90-yttrium ($^{90}Y$), 111-indium ($^{111}In$), 67-gallium ($^{67}Ga$), 68-gallium ($^{68}Ga$), 225-actinium ($^{225}Ac$), or 177-lutetium ($^{177}Lu$) or 212-lead ($^{212}Pb$).

Embodiment 73. A pharmaceutical composition comprising a compound of any one of embodiments 1-72, or a pharmaceutically acceptable salt thereof, and at least one pharmaceutically acceptable excipient.

Embodiment 74. The pharmaceutical composition of embodiment 73, wherein the pharmaceutical composition is formulated for administration to a mammal by intravenous administration.

Embodiment 75. A method for the treatment of cancer comprising administering to a mammal with cancer an effective amount of a compound of any one of embodiments 1-72, or a pharmaceutically acceptable salt thereof.

Embodiment 76. The method of embodiment 75, wherein the cancer comprises tumors and the tumors overexpress Kisspeptin receptor (KISS1R).

Embodiment 77. The method of embodiment 75 or embodiment 76, wherein the cancer is glioma, thyroid cancer, lung cancer, colorectal cancer, stomach cancer, liver cancer, pancreatic cancer, renal cancer, prostate cancer, testis cancer, breast cancer, cervical cancer, endometrial cancer, ovarian cancer, or melanoma.

Embodiment 78. The method of embodiment 75 or embodiment 76, wherein the cancer is breast cancer, renal cancer, or lung cancer.

Embodiment 79. A method of killing tumors in a mammal that overexpress Kisspeptin receptor (KISS1R) comprising administering to the mammal a compound of any one of embodiments 1-72, or a pharmaceutically acceptable salt thereof, wherein the compound of any one of embodiments 1-72, or a pharmaceutically acceptable salt thereof, comprises a therapeutic radionuclide.

Embodiment 80. The method of embodiment 79, wherein the mammal has been diagnosed with glioma, thyroid cancer, lung cancer, colorectal cancer, stomach cancer, liver cancer, pancreatic cancer, renal cancer, prostate cancer, testis cancer, breast cancer, cervical cancer, endometrial cancer, ovarian cancer, or melanoma.

Embodiment 81. The method of embodiment 79, wherein the mammal has been diagnosed with breast cancer, renal cancer, or lung cancer.

Embodiment 82. A method for identifying tumors expressing Kisspeptin receptor (KISS1R) in a mammal comprising administering to the mammal a compound of any one of embodiments 1-72, or a pharmaceutically acceptable salt thereof; and performing positron emission tomography (PET) analysis, single-photon emission computerized tomography (SPECT), or magnetic resonance imaging (MRI) wherein the compound of any one of embodiments 1-72, or a pharmaceutically acceptable salt thereof, comprises a diagnostic radionuclide.

Embodiment 83. A method for the in vivo imaging of tissues or organs in a mammal with tumors expressing the Kisspeptin receptor (KISS1R) comprising administering to the mammal a compound of any one of embodiments 1-72, or a pharmaceutically acceptable salt thereof; and performing positron emission tomography (PET) analysis, single-photon emission computerized tomography (SPECT), or magnetic resonance imaging (MRI); wherein the compound of any one of embodiments 1-72, or a pharmaceutically acceptable salt thereof, comprises a diagnostic radionuclide.

Embodiment 84. A compound of Formula (II), or a pharmaceutically acceptable salt thereof:

Formula (II)

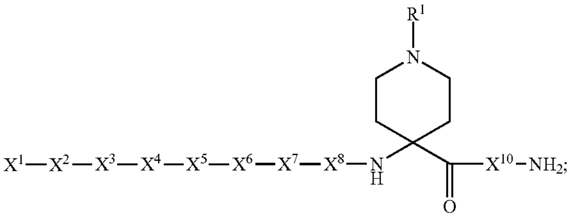

wherein:

$R^1$ is H,

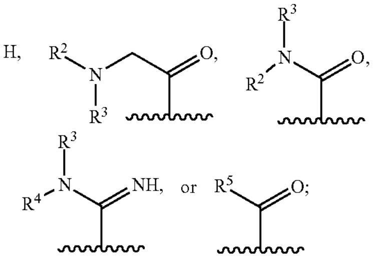

$R^2$ is $C_1$-$C_8$ alkyl, substituted or unsubstituted heteroalkyl, —$(CHR^6)_n$-heterocycloalkyl, —$(CHR^6)_n$-aryl, —$(CHR^6)_n$-heteroaryl, —C(═O)—$(CHR^6)_n$-aryl, or —C(═O)NH—$(CHR^6)_n$-aryl; wherein $C_1$-$C_6$ alkyl is optionally substituted with $R^7$, and wherein the heterocycloalkyl, aryl, or heteroaryl are each independently optionally substituted with $R^7$, $R^8$, $R^9$, $R^{10}$, and $R^{11}$;

$R^3$ is H or $C_1$-$C_4$ alkyl;

$R^4$ is H, $C_1$-$C_4$ alkyl, or $R^2$;

$R^5$ is substituted or unsubstituted alkyl, substituted or unsubstituted heteroalkyl, or —$(CHR^6)_n$-aryl; wherein aryl is optionally substituted with $R^7$, $R^8$, $R^9$, $R^{10}$, and $R^{11}$;

each $R^6$ is independently H, F, —$CH_3$, —$NH_2$, or —OH;

$R^7$, $R^8$, $^9$, $R^{10}$, and $R^{11}$ are each independently selected from H, F, Cl, Br, I, —OH, —O—$C_1$-$C_4$ alkyl, —$NH_2$, —$NHC_1$-$C_4$ alkyl, —$N(C_1$-$C_4$ alkyl$)_2$, —CN, —$CO_2H$, —$CO_2C_1$-$C_4$ alkyl, —$C_1$-$C_6$ alkyl, —$C_1$-$C_6$ fluroroalkyl or —$C_3$-$C_6$ cycloalkyl;

n is 0, 1, 2, 3, 4, 5, or 6;

$X^1$ is absent, tyrosine (Tyr), glycine (Gly), sarcosine (Sar), alanine (Ala), aspartic acid (Asp), lysine (Lys), phenylalanine (Phe), 3-(3-pyridyl)alanine (3-Pal) threonine (Thr), methionine (Met), 4-iodophenylalanine (Phe(4-4)), N6-(4-(p-tolyl)butanoyl)-lysine, N6-(4-(4-iodophenyl)butanoyl)-lysine, or γ-glutamic acid (γ-Glu));

$X^2$ is absent, asparagine (Asn), glutamine (Gln), aspartic acid (Asp), glutamic acid (Glu), serine (Ser), histidine (His), alanine (Ala), sarcosine (Sar), tyrosine (Tyr), proline (Pro), hydroxyproline (Hyp), azetidine-2-carboxylic acid (Aze), 2,3,4,5-tetrahydroisoquinoline-3-carboxylic acid (Tic), phenylalanine (Phe), 3-(2-

Pyridyl)alanine (2-Pal), 3-(3-Pyridyl)alanine (3-Pal), or 3-(4-pyridyl)alanine (4-Pal);

$X^3$ is absent, tryptophan (Trp), serine (Ser), leucine (Leu), isoleucine (Ile), phenylalanine (Phe), 4-iodophenylalanine (Phe(4-I)), 3-(2-pyridyl)alanine (2-Pal), 3-(3-pyridyl)alanine (3-Pal), 3-(4-pyridyl)alanine (4-Pal), 2-amino-3-(naphthalen-2-yl)propanoic acid (H-2-NAL-OH), lysine (Lys), asparagine (Asn), glutamine (Gln), aspartic acid (Asp), glutamic acid (Glu), arginine (Arg), methyl arginine (Arg(Me)), norarginine (AGBA), methyl norarginine (AGBA(Me)), homoarginine (HArg), methyl homoarginine (HArg(Me)), citrulline (Cit), methyl citrulline (Cit(Me)), canavanine, methyl-canavanine, glycine (Gly), alanine (Ala), sarcosine (Sar), tyrosine (Tyr), cyclohexylalanine (Cha), 3-(1-naphthyl)alanine (α-Nal), 3-(2-naphthyl)alanine (β-Nal), or threonine (Thr), proline (Pro), hydroxyproline (Hyp), or tetrahydroisoquinoline-3-carboxylic acid (Tic); O-phospho-serine (SOP), 2-amino-4-(2H-tetrazol-5-yl)butanoic acid, β-glutamic acid, 8-aminoquinoline-3-carboxylic acid, biphenylalanine (Bip), 4-benzoylphenylalanine (Bpa), or 3-(9-anthryl)-alanine (H-Ala (9-Anth)-OH or AAP);

$X^4$ is absent, asparagine (Asn), glutamine (Gln), aspartic acid (Asp), glutamic acid (Glu), tryptophan (Trp), glycine ((Gly), tyrosine (Tyr), alanine (Ala), or sarcosine (Sar);

$X^5$ is absent, serine (Ser), threonine (Thr), lysine (Lys), asparagine (Asn), glutamine (Gln), aspartic acid (Asp), glutamic acid (Glu), glycine (Gly), alanine (Ala), sarcosine (San) or arginine (Arg);

$X^6$ is absent, phenylalanine (Phe), alpha-methylphenylalanine (α-Me-Phe), N-methylphenylalanine (N-Me-Phe), 2-fluorophenylalanine (2-F-Phe), 3-fluorophenylalanine (3-F-Phe), 4-fluorophenylalanine (4-F-Phe), 4-iodophenylalanine (Phe(4-I)), 2-amino-2-indancarboxylic acid (Aic), biphenylalanine (Bip), (β-(2-thienyl)-Ala), tryptophan (Trp), 2-aminotetralin-2-carboxylic acid (Atc); 3-(2-thienyl)-alanine, 3-(4-pyridyl) alanine (4-Pal), cyclohexylalanine (Cha), or tyrosine (Tyr);

$X^7$ is absent, glycine (Gly), aza-glycine (aza-Gly), alanine (Ala), N-methylglycine (Sar), or 1-aminocyclopropane-1-carboxylic acid (ACC);

$X^8$ is leucine (Leu) norvaline (Nva), valine (Val), isoleucine (Ile), homoalanine (HAla), tryptophan (Trp), phenylalanine (Phe), or phenylglycine (Phg);

or —$X^7$—$X^8$— is

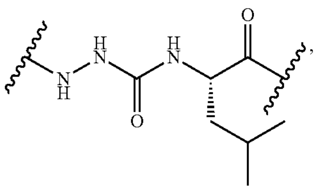

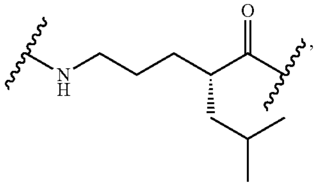

-continued

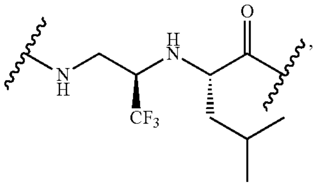

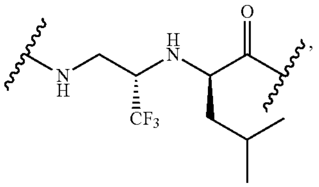

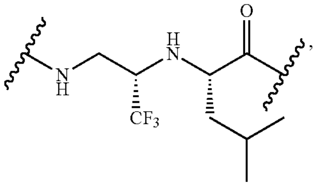

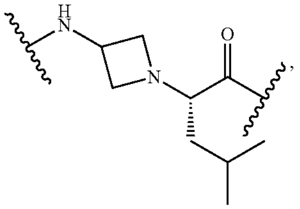

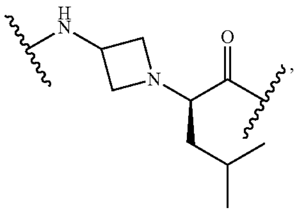

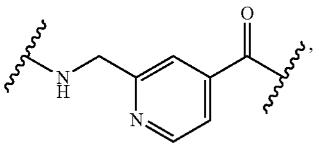

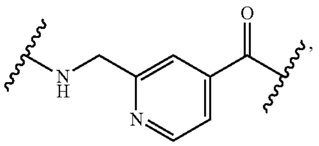

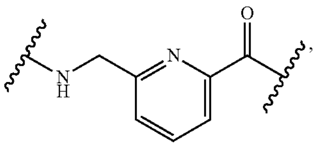

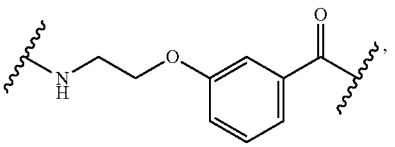

-continued
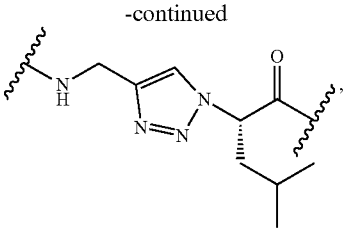
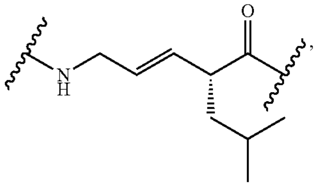
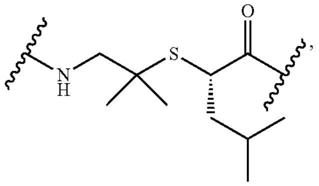
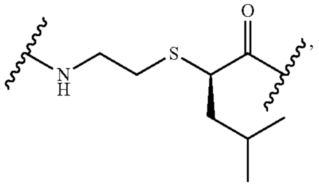
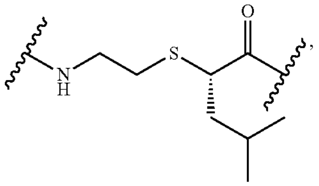
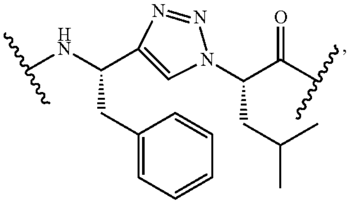
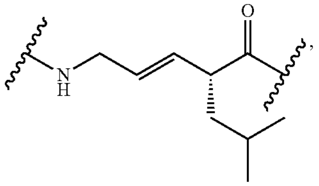
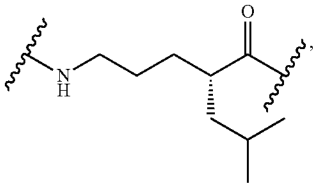
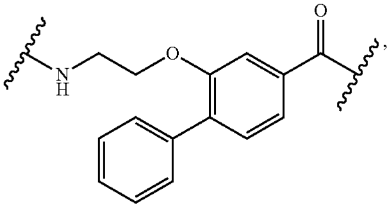
-continued
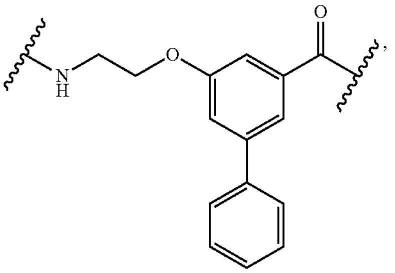
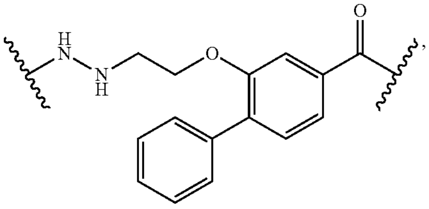
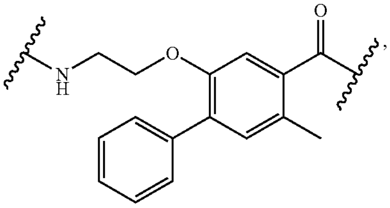
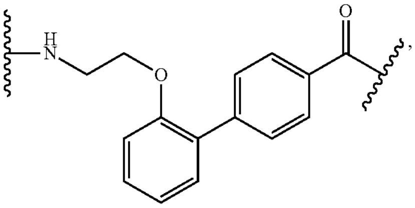
or
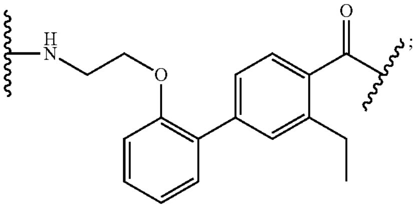 [SMILES: *NCCOc1ccccc1-c1ccc(C(*)=O)c(CC)c1]
or —$X^6$—$X^7$—$X^8$— is
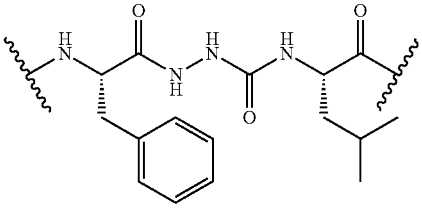
,
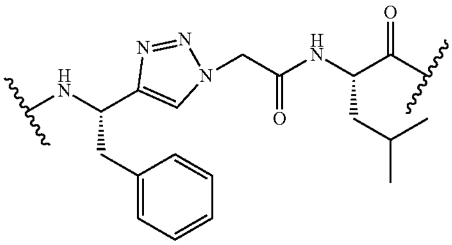
, or -continued

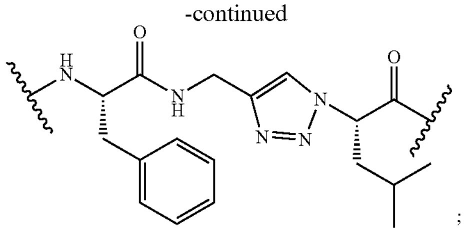

;

$X^{10}$ is tryptophan (Trp), 1-methyltryptophan (1MT), tyrosine (Tyr), phenylalanine (Phe), 4-cyano phenylalanine (Phe (4-CN)), 3-(4-pyridyl)alanine (4-Pal), leucine (Leu), phenylglycine (Phg), cyclohexylalanine (Cha), 3-(1-naphthyl) alanine (α-Nal), 3-(2-naphthyl)-alanine (β-Nal), histidine (His), or 3-nitro-tyrosine (Tyr(3-$NO_2$));

wherein the N-terminal amino acid or the compound of Formula (H1) is optionally substituted with —C(═O)—$C_1$-$C_{20}$ alkyl, —C(═O)—$(CH_2CH_2O)_y$—$CH_2CH_2$—$R^{15}$, —$C_1$-$C_{20}$ alkyl, N-hexadecanoyl-Glu, —$C_4$-$C_{20}$ polyethylene glycol, a saccharide, —$R^{16}$, —C(═O)—$(CH_2CH_2O)_x$—$CH_3$, —C(═O)—$(CH_2CH_2O)_x$—H, —C(═O)—$CH_2CH_2CH$(COOH)—$R^{15}$, —C(═O)—$(CH_2)_2R^{19}$, or —C(═O) $CH_2NHCH_2R^{19}$;

$R^{15}$ is selected from —$OR^{16}$, —$N(R^{16})_2$, —C(═O)$OR^{16}$, or —C(═O)$N(R^{16})_2$;

each $R^{16}$ is independently H, —$C_1$-$C_6$ alkyl, —C(═O)—$(CH)_vR^{19}$, —C(═O)$CH_2NHCH_2R^{19}$, or a saccharide or derivative thereof;

$R^{19}$ is 4-iodophenylene, 4-methylphenylene, or 3-fluoro-4-methylphenylene;

y is 0, 1, 2, 3, 4, 5, 6, 7, 8, 9, or 10;

x is an integer from 1 and 25; and v is 1,2,3, or 4;

wherein any free —NH— of a peptide bond is optionally independently substituted with —$CH_3$ or —$CH_2CH_3$; and wherein any alpha position of an amino acid is optionally independently substituted with —$CH_3$ or —$CH_2CH_3$.

Embodiment 85. The compound of embodiment 84, or a pharmaceutically acceptable salt thereof, wherein $R^1$ is

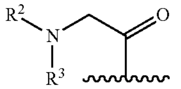 or 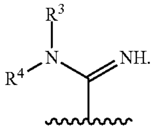

Embodiment 86. The compound of embodiment 84 or 85, or a pharmaceutically acceptable salt thereof, wherein $R^2$ is H and $R^3$ is H or $C_1$-$C_4$ alkyl.

Embodiment 87. The compound of embodiment 84 or 85, or a pharmaceutically acceptable salt thereof, wherein $R^3$ is H and $R^4$ is H or $C_1$-$C_4$ alkyl.

Embodiment 88. The compound of embodiment 84 or 85, or a pharmaceutically acceptable salt thereof, wherein $R^2$ is —$(CHR^6)_n$-aryl.

Embodiment 89. The compound of embodiment 88, or a pharmaceutically acceptable salt thereof, wherein n is 1.

Embodiment 90. The compound of embodiment 88 or 89, or a pharmaceutically acceptable salt thereof, wherein $R^6$ is H.

Embodiment 91. The compound of embodiment 84 or 85, or a pharmaceutically acceptable salt thereof, wherein $R^1$ is H,

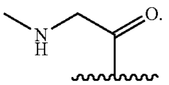 [SMILES: *C(=O)CNC]

Embodiment 92. The compound of embodiment 84 or 85, or a pharmaceutically acceptable salt thereof, wherein $R^1$ is

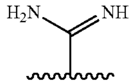 or 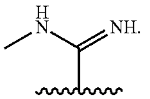

Embodiment 93. The compound of embodiment 84 or 85, or a pharmaceutically acceptable salt thereof, wherein $R^1$ is

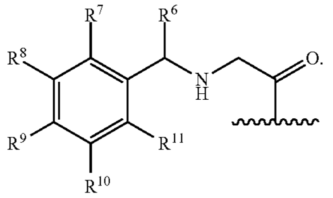

Embodiment 94. The compound of embodiment 84 or 85, or a pharmaceutically acceptable salt thereof, wherein $R^1$ is

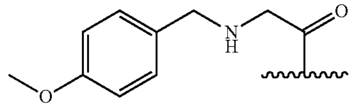 or

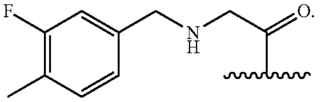

Embodiment 95 The compound of embodiment 93, or a pharmaceutically acceptable salt thereof, wherein $R^7$, $R^8$, $R^9$, $R^{10}$, and $R^{11}$ are each independently selected from H, F, Cl, Br, I, —OH, —O—$C_1$-$C_4$, alkyl, —$NH_2$, or —$C_1$-$C_6$ alkyl.

Embodiment 96. The compound of embodiment 93, or a pharmaceutically acceptable salt thereof, wherein $R^7$, $R^8$, $R^9$, $R^{10}$, and $R^{11}$ are each independently selected from H, F, Cl, Br, I, —OH, —$OCH_3$, —$NH_2$, or —$CH_3$.

Embodiment 97. The compound of embodiment 93, or a pharmaceutically acceptable salt thereof, wherein $R^8$ is F and $R^9$ is $CH_3$.

Embodiment 98. The compound of any one of embodiments 84-97, or a pharmaceutically acceptable salt thereof, wherein: $X^1$ is tyrosine (Tyr).

Embodiment 99. The compound of any one of embodiments 84-97, or a pharmaceutically acceptable salt thereof, wherein: $X^2$ is absent.

Embodiment 100. The compound of any one of embodiments 84-97, or a pharmaceutically acceptable salt thereof, wherein: $X^3$ is 3-(2-naphthyl)alanine (β-Nal) or tryptophan (Trp).

Embodiment 101. The compound of any one of embodiments 84-97, or a pharmaceutically acceptable salt thereof, wherein: $X^4$ is asparagine (Asn).

Embodiment 102. The compound of any one of embodiments 84-97, or a pharmaceutically acceptable salt thereof, wherein: $X^5$ is threonine (Thr).

Embodiment 103. The compound of any one of embodiments 84-97, or a pharmaceutically acceptable salt thereof, wherein: $X^6$ is phenylalanine (Phe) or cyclohexylalanine (Cha).

Embodiment 104. The compound of any one of embodiments 84-97, or a pharmaceutically acceptable salt thereof, wherein: $X^7$ is azaglycine (aza-gly).

Embodiment 105. The compound of any one of embodiments 84-97, or a pharmaceutically acceptable salt thereof, wherein: $X^8$ is leucine (Leu).

Embodiment 106. The compound of any one of embodiments 84-97, or a pharmaceutically acceptable salt thereof, wherein: $X^{10}$ is tryptophan (Trp), 1-methyltryptophan (1MT), tyrosine (Tyr), phenylalanine (Phe), 4-cyano phenylalanine (Phe(4-CN)), 3-(4-pyridyl)alanine (4-Pal), or leucine (Leu).

Embodiment 107. The compound of any one of embodiments 84-97, or a pharmaceutically acceptable salt thereof, wherein: $X^{10}$ is tryptophan (Trp), tyrosine (Tyr), or phenylalanine (Phe).

Embodiment 108. The compound of any one of embodiments 84-97, or a pharmaceutically acceptable salt thereof, wherein:

$X^1$ is absent, tyrosine (Tyr), or 3-(3-pyridyl)alanine (3-Pal));

$X^2$ is absent, asparagine (Asn), glutamine (Gln), serine (Ser), D-histidine (His), or phenylalanine (Phe);

$X^3$ is absent, tryptophan (Trp), isoleucine (Ile), 3-(4-pyridyl)alanine (4-Pal), lysine (Lys), aspartic acid (Asp), glutamic acid (Glu), glycine (Gly), alanine (Ala), cyclohexylalanine (Cha), (Hyp), biphenylalanine (Bip); 4-benzoylphenylalanine (Bpa), or 3-(9-anthryl)-alanine (AAP);

$X^4$ is absent, asparagine (Asn), or glutamine (Gln); and $X^5$ is absent, serine (Ser), threonine (Thr), glycine (Gly), or alanine (Ala).

Embodiment 109. The compound of any one of embodiments 84-97, or a pharmaceutically acceptable salt thereof, wherein:

$X^1$ is D-tyrosine (D-Tyr);

$X^2$ is absent;

$X^3$ is D-tryptophan (D-Trp), biphenylalanine (Bip); 4-benzoylphenylalanine (Bpa), or 3-(9-anthryl)-alanine (AAP);

$X^4$ is asparagine (Asn); and $X^5$ is serine (Ser) or threonine (Thr).

Embodiment 110. The compound of any one of embodiments 84-97, or a pharmaceutically acceptable salt thereof, wherein:

$X^6$ is phenylalanine (Phe), 3-fluorophenylalanine (3-F-Phe), biphenylalanine (Bip), or cyclohexylalanine (Cha);

$X^7$ is glycine (Gly) or aza-glycine (aza-Gly); and $X^8$ is leucine (Leu) or norvaline (Nva).

Embodiment 111. The compound of any one of embodiments 84-97, or a pharmaceutically acceptable salt thereof, wherein:

$X^6$ is phenylalanine (Phe) or cyclohexylalanine (Cha);

$X^7$ is aza-glycine (aza-Gly); and $X^8$ is leucine (Leu).

Embodiment 112. The compound of any one of embodiments 84-97, or a pharmaceutically acceptable salt thereof, wherein:

$X^8$ is Leu, Nva, Ile, Hala, or Phe; and $X^{10}$ is Trp, 1MT, Tyr, 4-Pal, Phe(4-CN), or Phe.

Embodiment 113. The compound of any one of embodiments 84-97, or a pharmaceutically acceptable salt thereof, wherein:

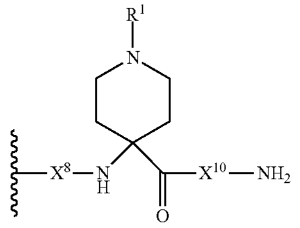 is

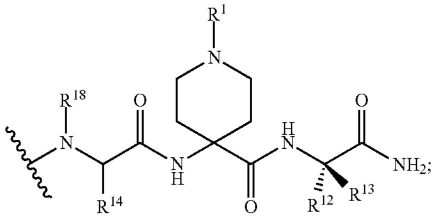

wherein, $R^{18}$ is H or —$CH_3$;

$R^{12}$ is

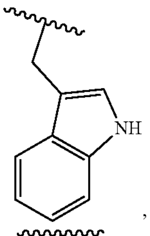,
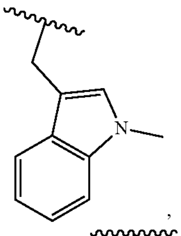,
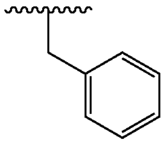,
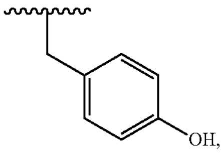
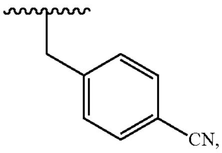 or
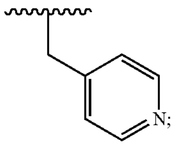

$R^{13}$ is H or —$CH_3$; and $R^{14}$ is

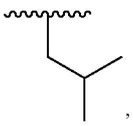,
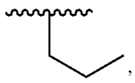,
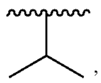,
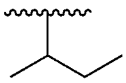, or
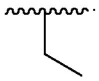

Embodiment 114. The compound of any one of embodiments 84-113, or a pharmaceutically acceptable salt thereof, wherein the N-terminal amino acid or the compound of Formula (II) is optionally substituted with —C(═O)—$C_1$-$C_{20}$ alkyl, —C(═O)—$(CH_2CH_2O)_y$—$CH_2CH_2$—$R^{15}$, —$C_1$-$C_{20}$alkyl, N-hexadecanoyl-Glu, —$C_4$-$C_{20}$ polyethylene glycol, a saccharide, —$R^{16}$, —C(═O)—$(CH_2CH_2O)_x$—$CH_3$, —C(═O)—$(CH_2CH_2O)_x$—H, —C(═O)—$CH_2CH_2CH(COOH)$—$R^{15}$, —C(═O)—$(CH_2)_2R^{19}$, or —C(═O)$CH_2NHCH_2R^{19}$;

$R^{15}$ is selected from —$OR^6$, —$N(R^{16})_2$, —C(═O)$OR^{16}$, or —C(═O)$N(R^6)_2$;

each $R^{16}$ is independently H, —$C_1$-$C_6$ alkyl, —C(═O)—$(CH_2)_vR^{19}$, —C(═O)$CH_2NHCH_2R^{19}$, or a saccharide or derivative thereof;

$R^{19}$ is 4-iodophenylene, 4-methylphenylene, or 3-fluoro-4-methylphenylene;

y is 0, 1, 2, 3, 4, 5, 6, 7, 8, 9, or 10;

x is an integer from 1 and 25; and v is 1, 2, 3, or 4.

Embodiment 115. The compound of any one of embodiments 84-113, or a pharmaceutically acceptable salt thereof, wherein the N-terminal amino acid or the compound of Formula (II) is optionally substituted with —C(═O)—$C_1$-$C_{12}$ alkyl.

Embodiment 116. The compound of embodiment 115, or a pharmaceutically acceptable salt thereof, wherein the N-terminal amino acid or the compound of Formula (II) is optionally substituted with

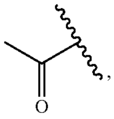, 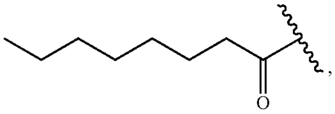, or

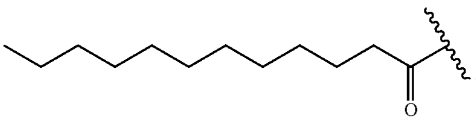.

Embodiment 117. The compound of any one of embodiments 84-113, or a pharmaceutically acceptable salt thereof, wherein the N-terminal amino acid or the compound of Formula (II) is optionally substituted with —C(═O)—$(CH_2CH_2O)_y$—$CH_2CH_2$—$R^{15}$.

Embodiment 118. The compound of embodiment 117, wherein y is 2.

Embodiment 119. The compound of embodiment 117 or 118, wherein $R^{15}$ is —$N(R^{16})_2$ and both $R^{16}$ are H.

Embodiment 120. The compound of embodiment 117 or 118, wherein $R^{15}$ is —$N(R^{16})_2$, one $R^{16}$ is H and the other $R^{16}$ is —C(═O)—$(CH_2)_vR^{19}$ Embodiment 121. The compound of any one of embodiments 84-113, or a pharmaceutically acceptable salt thereof, wherein the N-terminal amino acid or the compound of Formula (II) is optionally substituted with —$R^{16}$.

Embodiment 122. The compound of embodiment 123, wherein $R^{16}$ is —C(═O)—$(CH_2)_vR^{19}$, Embodiment 123. The compound of embodiment 120 or 122, wherein v is 2 or 3.

Embodiment 124. The compound of any one of embodiments 120, 122, or 123 wherein $R^{19}$ is 4-iodophenylene or 4-methylphenylene.

Embodiment 125. The compound of any one of embodiments 84-113, or a pharmaceutically acceptable salt thereof, wherein the N-terminal amino acid or the compound of Formula (II) is optionally substituted with

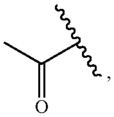, 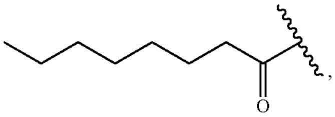, or

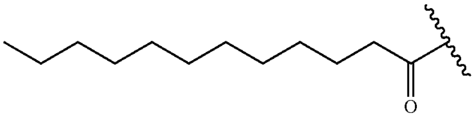.

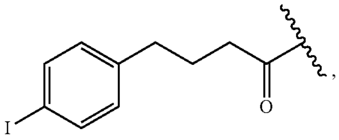,

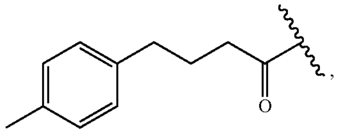,

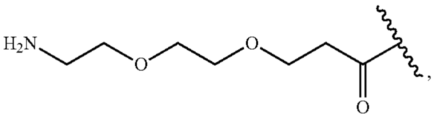, or

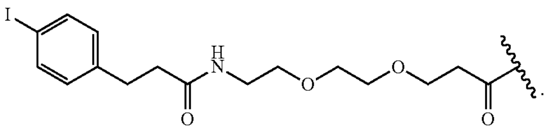.

Embodiment 126. The compound of embodiment 84, or a pharmaceutically acceptable salt thereof, wherein the compound of Formula (II) has one of the following structures, or a pharmaceutically acceptable salt thereof:

(SEQ ID NO: 802)
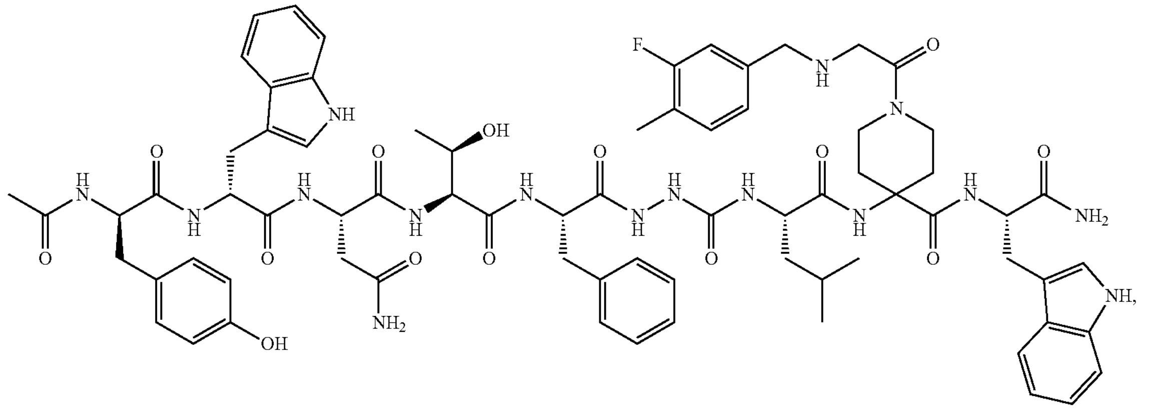
(SEQ ID NO: 803)
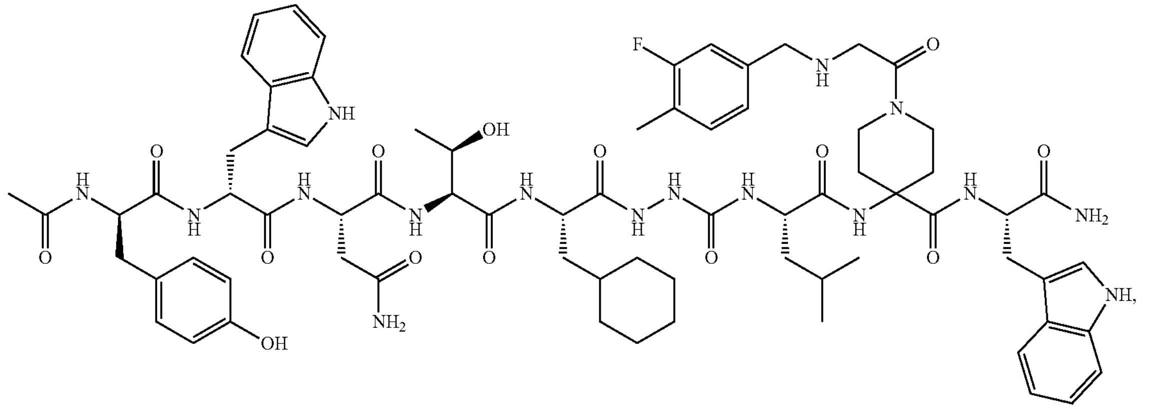
(SEQ ID NO: 804)
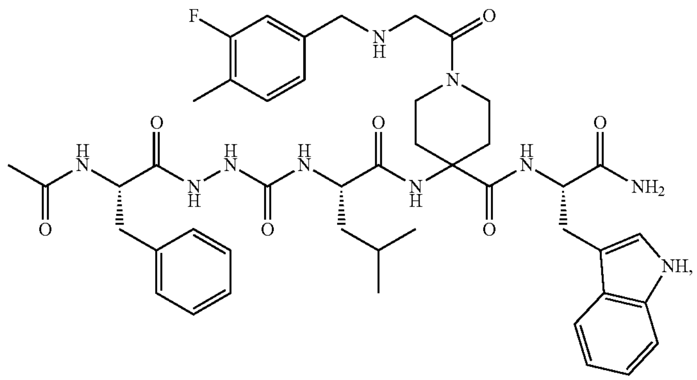

-continued
(SEQ ID NO: 805)
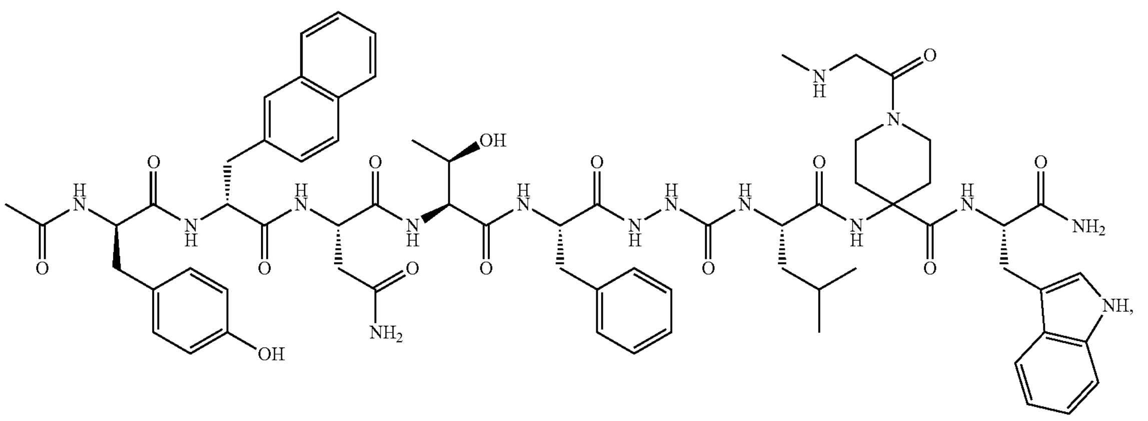
(SEQ ID NO: 806)
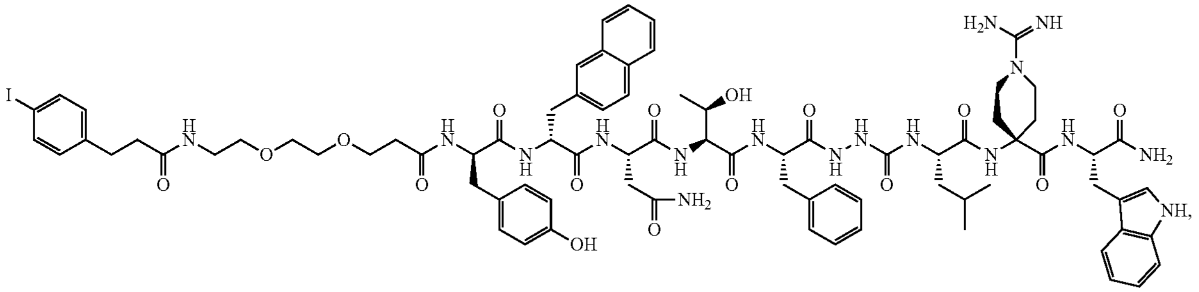
(SEQ ID NO: 807)
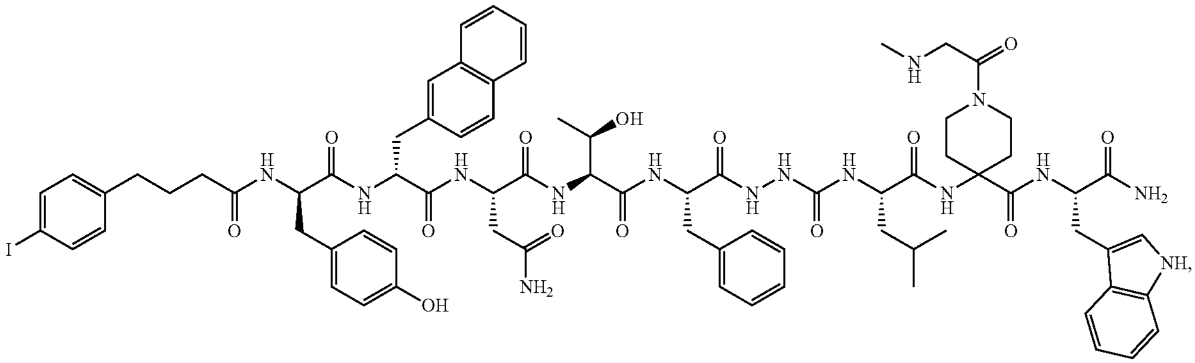
(SEQ ID NO: 808)
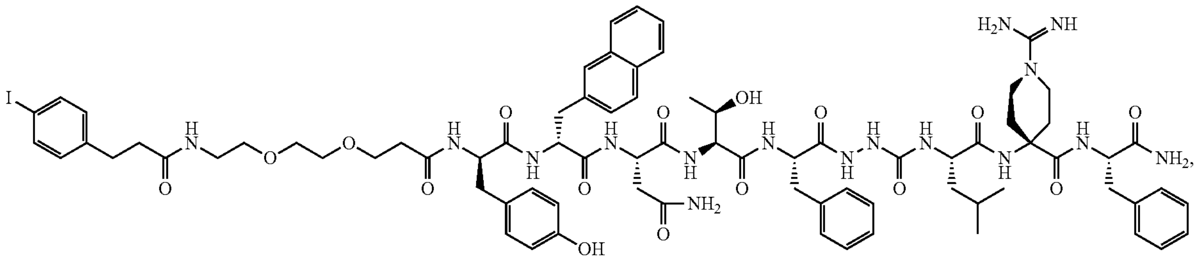

-continued
(SEQ ID NO: 809)
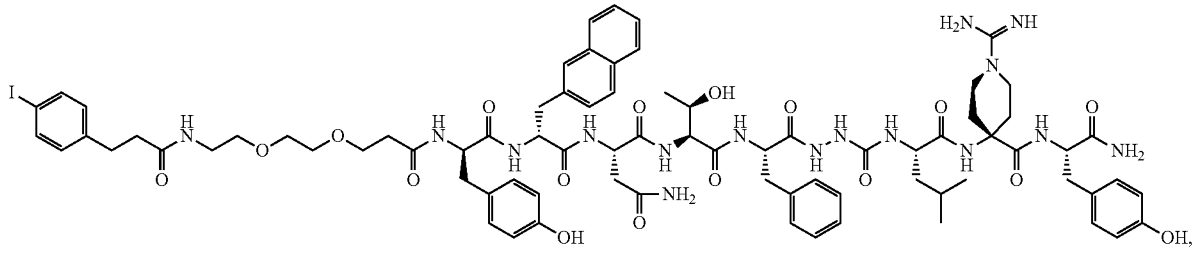
(SEQ ID NO: 810)
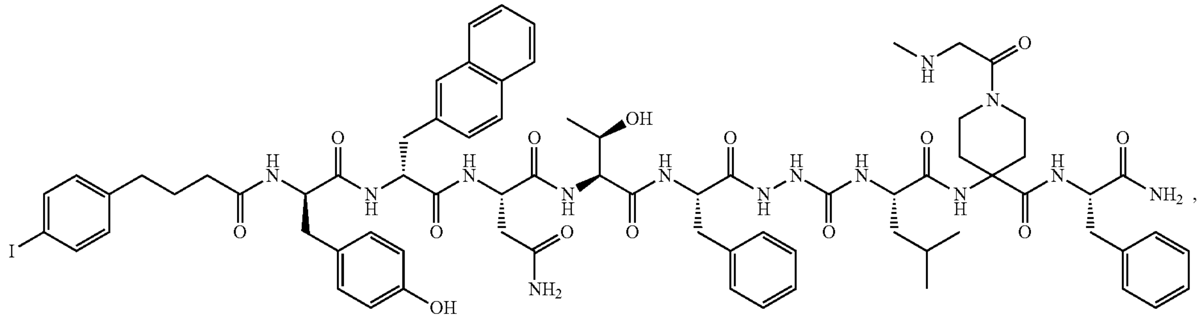
(SEQ ID NO: 811)
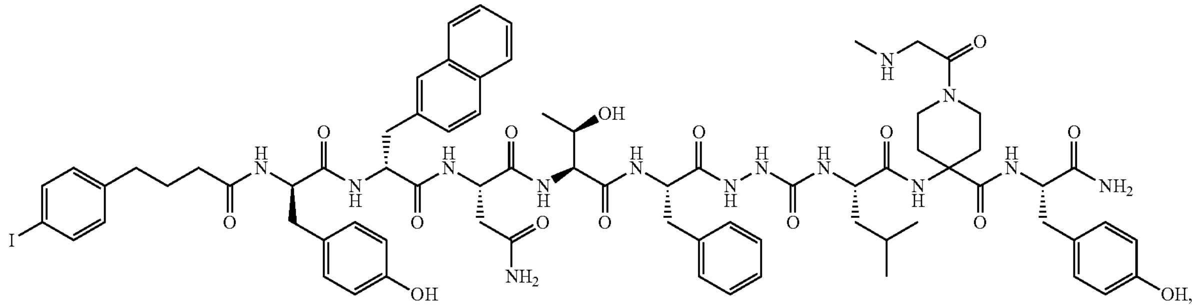
(SEQ ID NO: 812)
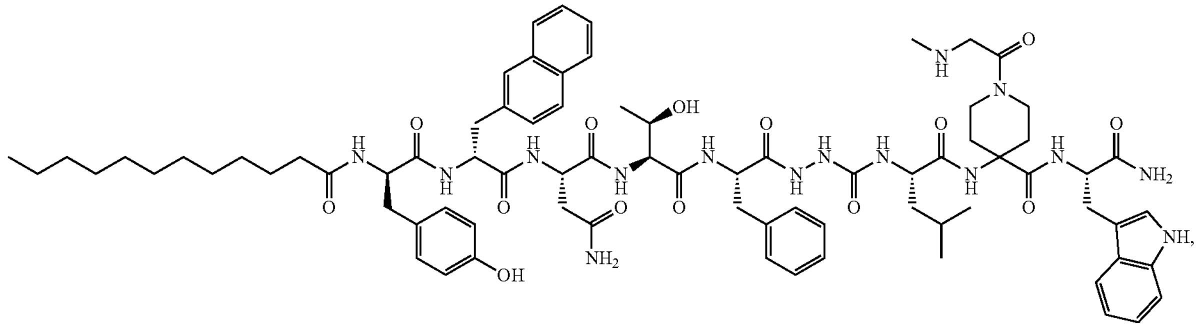
(SEQ ID NO: 813)
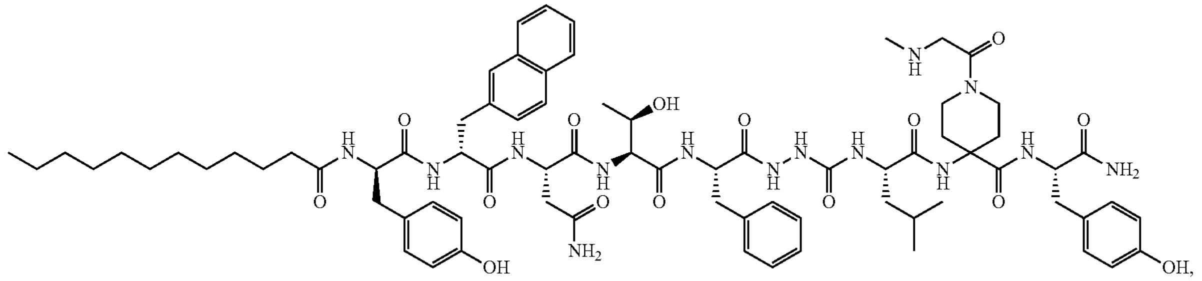

-continued
(SEQ ID NO: 814)
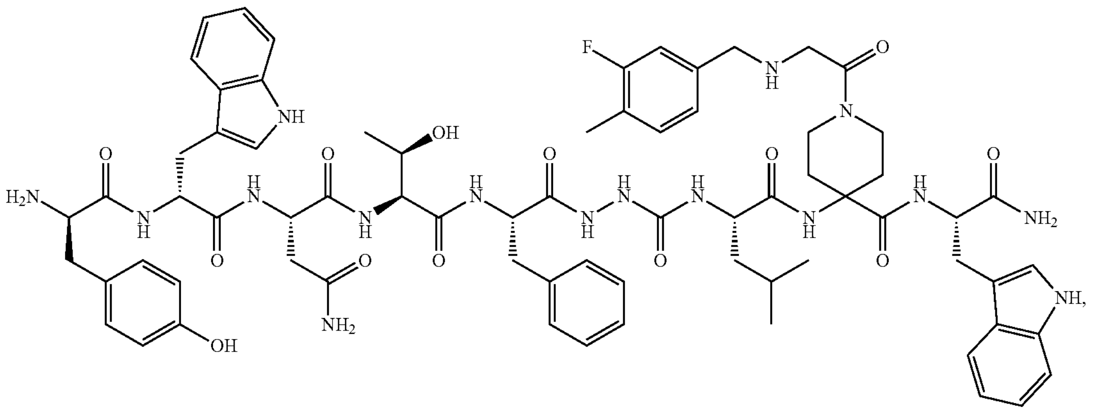
(SEQ ID NO: 815)
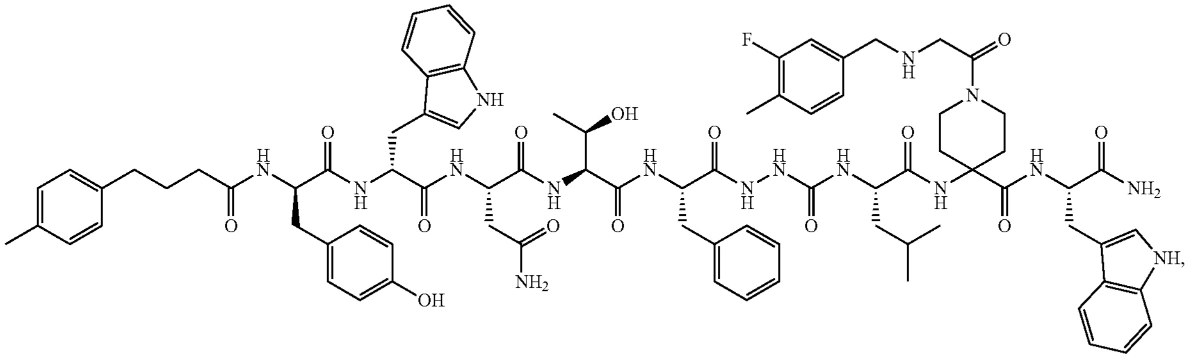
(SEQ ID NO: 816)
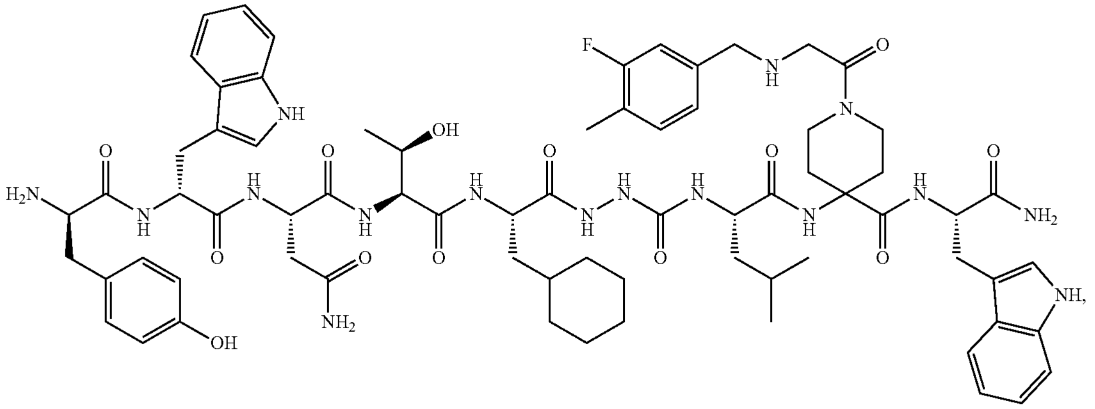
(SEQ ID NO: 817)
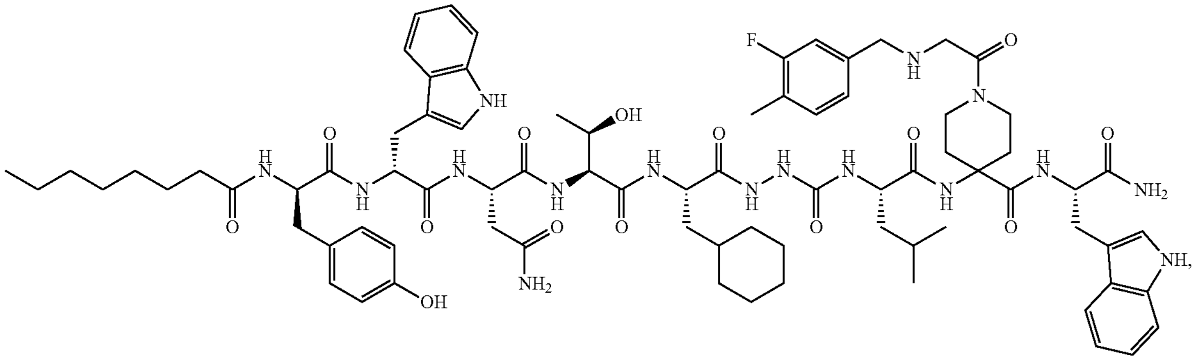

-continued
(SEQ ID NO: 818)
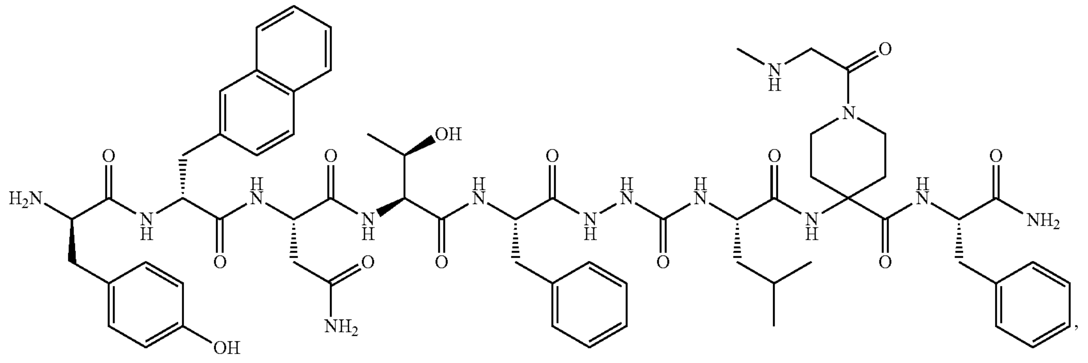
(SEQ ID NO: 819)
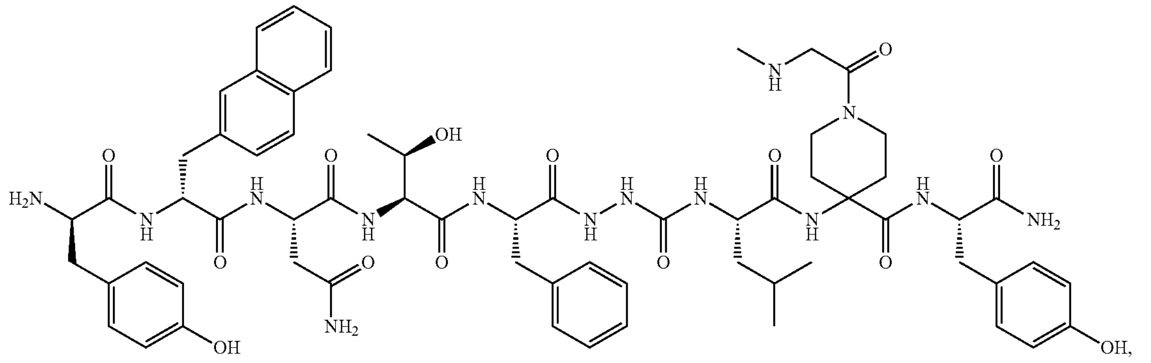
(SEQ ID NO: 820)
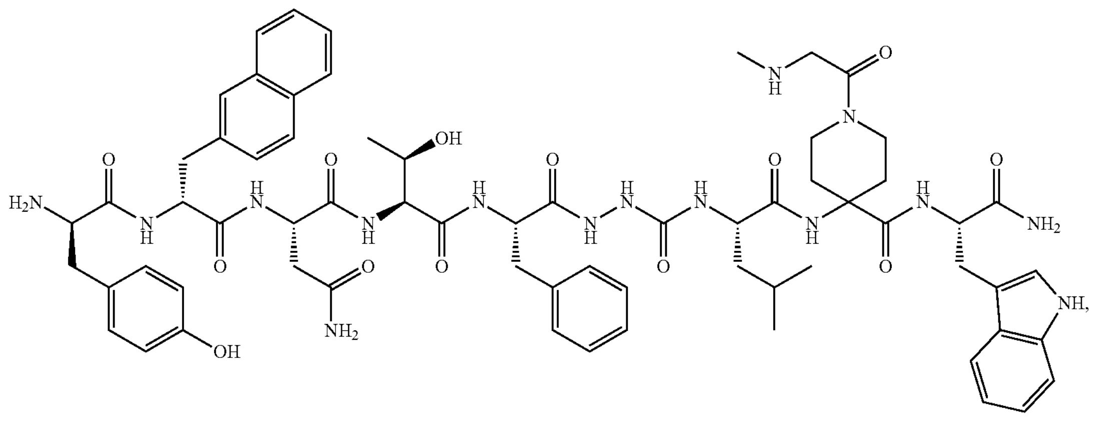
(SEQ ID NO: 821)
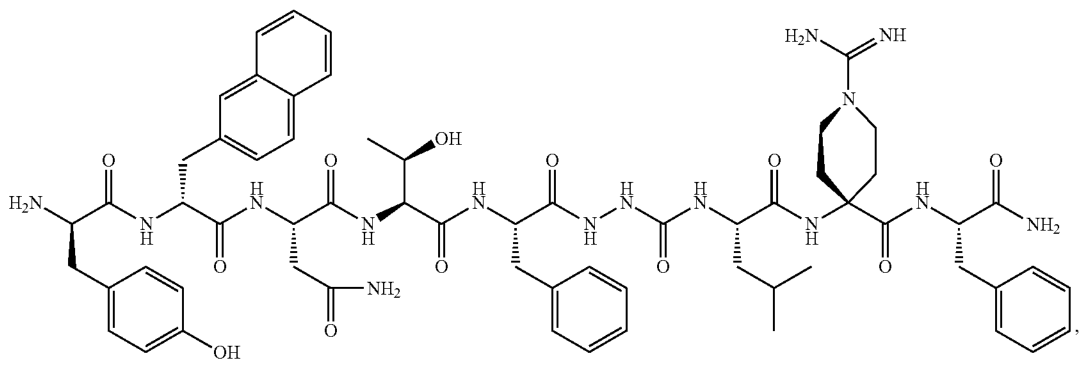

-continued (SEQ ID NO: 822)

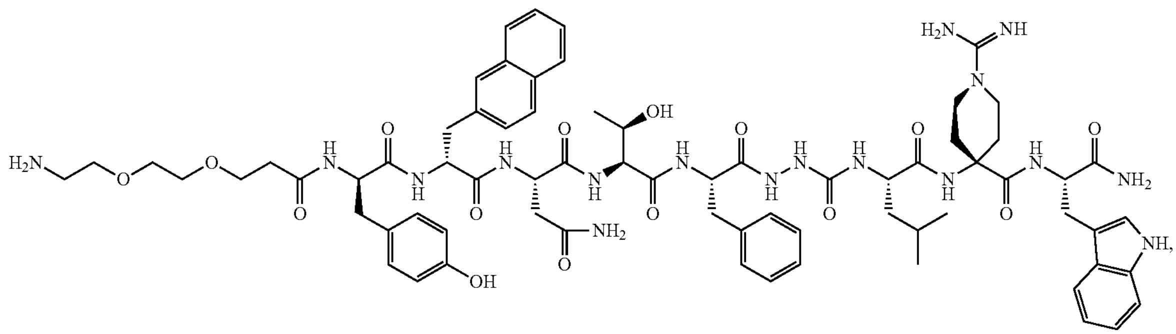

, or (SEQ ID NO: 823)

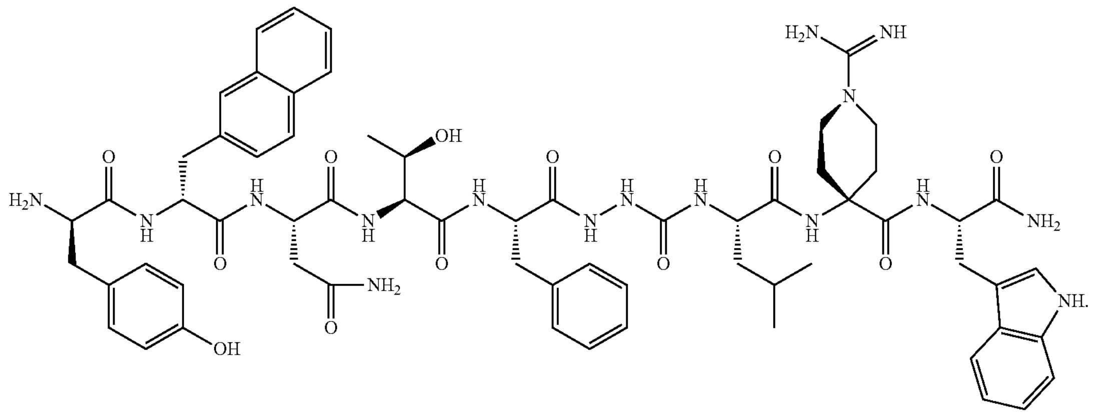

.

Embodiment 127. A pharmaceutical composition comprising a compound of any one of embodiments 84-126, or a pharmaceutically acceptable salt thereof, and at least one pharmaceutically acceptable excipient.

Embodiment 128. The pharmaceutical composition of embodiment 127, wherein the pharmaceutical composition is formulated for administration to a mammal by oral administration.

Embodiment 129. A method for the treatment of an endocrine condition comprising administering to a mammal an effective amount of a compound of any one of embodiments 84-126, or a pharmaceutically acceptable salt thereof.

Embodiment 130. The method of embodiment 129, wherein the endocrine condition is polycystic ovary syndrome (PCOS).

Embodiment 131. The method of embodiment 129, wherein the endocrine condition is infertility.

Embodiment 132. A method for the treatment of cancer comprising administering to a mammal an effective amount of a compound of any one of embodiments 84-126, or a pharmaceutically acceptable salt thereof.

Embodiment 133. The method of embodiment 117, wherein cancer is prostate cancer or breast cancer.

Embodiment 134. A method for the treatment of infertility comprising administering to a mammal an effective amount of a compound of any one of embodiments 84-126, or a pharmaceutically acceptable salt thereof.

EXAMPLES

The following examples are provided for illustrative purposes only and not to limit the scope of the claims provided herein.

Abbreviations

ACN or MeCN or $CH_3CN$: acetonitrile; $BBr_3$: boron tribromide; brine: saturated NaCl solution;

BOP: Benzotriazole-1-yl-oxy-tris-(dimethylamino)-phosphonium hexafluorophosphate;

CDT: 1,1'-carbonyl-di-(1,2,4-triazole); CTC resin: chlorotrityl chloride resin;

DBAD: Di-tert-butyl azodicarboxylate; DCC: dicyclohexylcarbodiimide;

DCM: dichloromethane; Dde-OH: 2-Acetyldimedone;

DHP resin: dihydropyranylmethoxymethyl resin;

DODT: 3,6-dioxa-1,8-octanedithiol; DIEA or DIPEA: N,N-diisopropylethylamine;

DMF: dimethylformamide; DMSO: dimethyl sulfoxide;

DOTA: 2,2',2'',2'''-(1,4,7,10-tetraazacyclododecane-1,4,7,10-tetrayl)tetraacetic acid or 1,4,7,10-tetraazacyclododecane-1,4,7,10-tetraacetic acid;

EDC: (1-ethyl-3-(3-dimethylaminopropyl)carbodiimide hydrochloride);

EtOAc or EA: ethyl acetate; Fu catalyst complex: tris (dibenzylideneacetone)dipalladium(0) tri-tert-butylphosphonium tetrafluoroborate Fmoc: fluorenylmethoxycarbonyl; Fmoc-OSu: N-(9-Fluorenylmethoxycarbonyloxy)succinimide HATU: 1-[Bis(dimethylamino)methylene]-1H-1,2,3-triazolo[4,5-b]pyridinium 3-oxide hexafluorophosphate; HCl: hydrochloric acid or hydrochloride; Hex: hexanes; $H_2O$: water;

HBTU: N,N,N',N'-Tetramethyl-O-(1H-benzotriazol-1-yl) uronium hexafluorophosphate;

HOBt: hydroxybenzotriazole; HMBA: hydroxymethyl benzoic acid resin;

HPLC: high-performance liquid chromatography; $InCl_3$: indium trichloride;

$K_2CO_3$: potassium carbonate; KOAc: potassium acetate; KOt-Bu: potassium t-butoxide $K_3PO_4$: potassium phosphate; ICMS: Liquid chromatography-mass spectrometry;

$LuCl_3$: lutetium (III) chloride; MBHA resin: methylbenzhydryl amine resin;

MeOH: methanol; MPLC: Medium pressure liquid chromatography;

MS: mass spectrometry; NaH: sodium hydride; $NaHCO_3$: sodium bicarbonate;

$NaIO_4$: sodium periodate; $NaN[(CH_3)_3Si]_2$: sodium bis (trimethylsilyl)amide NaOAc: sodium acetate; $Na_2SO_4$: sodium sulfate; NMP: N-Methyl-2-pyrrolidone;

Pd(dppf)$Cl_2$: [1,1'-Bis(diphenylphosphino)ferrocene]dichloropalladium(II);

Pd(DTBPF)$Cl_2$: [1,1'-Bis(di-tert-butylphosphino)ferrocene]dichloropalladium(II);

PE: petroleum ether; $PPh_3$: triphenyl phosphine; $RuCl_3$: ruthenium(III) chloride;

Prep-HPLC: preparative high-performance liquid chromatography;

RP-HPLC: reversed-phase high-performance liquid chromatography;

SPPS: solid-phase peptide synthesis; TFA: trifluoroacetic acid; THF: tetrahydrofuran;

TIS: triisopropylsilane; rt: room temperature; hrs: hours; h or Ir: hour; min: minute;

mg: milligrams; kg: kilograms; mL or ml: milliliter;

Eq: equivalents; mmol: millimole; mol: moles; UV: ultraviolet; v/v: volume/volume.

Reagents were obtained from commercial suppliers and used without further purification, unless otherwise noted.

Reactions were carried out in Syro II (Biotage) and/or manual shaker using Fmoc chemistry, unless otherwise noted.

$N^{\alpha}$-Fmoc-Rink amide resin purchased from Novabiochem (100-200 mesh, 0.62 mmol/g loading) was used for SPPS.

MPLC purifications were performed with a Orinedia preparative HPLC (BRIX 2802) on silica gel columns.

RP-HPLC purifications were performed on a Waters preparative HPLC (2767) at room temperature with reverse-phase C18 columns (X Select CSH C18 5 μm, 30 mm×150 mm).

HPLC solvents are $H_2O$ containing 0.05% trifluoroacetic acid (mobile phase A) and acetonitrile (mobile phase B).

HPLC analysis was carried out with a Shimadzu LCMS (2020 series) containing a binary pump (LC-20AD), micro vacuum degasser, auto sampler (SIL-20AC HT), thermostat column compartment (CTO-20A), variable wavelength detector (SPD-M20A). HPLC data was analyzed using Lab Solutions software from the Shimadzu LCMS (2020 series). A Kinetex EVO column (2.6 μm, 100 Å, 4.6×100 mm) was used with a flow rate of 1.0 mL/min.

LCMS analysis was carried out with a Shimadzu LCMS (2020 series) containing a binary pump (LC-20ADXR), micro vacuum degasser, auto sampler (SIL-20AC XR), thermostat column compartment (CTO-20AC), variable wavelength detector (SPD-M20A). LCMS data was analyzed using Lab Solutions software from Agilent Technologies. An Ascentis Express C18 column (2.7 μm, 3.0×50 mm) was used with a flow rate of 1.5 mL/min.

$^1$H NMR spectra were recorded using an AVANCE III HD 300 MHz, AVANCE NEO 400 MHz, or Bruker 300 MHz or 400 MHz. Chemical shifts are reported in 6 (ppm) relative to $TMS_4Si$ (in $CDCl_3$) as internal standard using Bruker TopSpin software unless otherwise noted.

A peptide of the present disclosure may be prepared through known methods, including procedures referenced in "Design and synthesis of downsized metastin (45-54) analogs with maintenance of high GPR54 activity" Niida et al., *Bioorganic & Medicinal Chemistry Letters* 16: 134-137 (2006); "A synthetic kisspeptin analog that triggers ovulation and advances puberty" Decourt et al., *Scientific Reports* 6: 26908 (2016); "A kisspeptin-10 analog with greater in vivo bioactivity than kisspeptin-10" Curtis et al., *American Journal of Physiology—Endocrinology and Metabolism* 298: E296-E3303 (2010); "RFamide Peptides: Structure, Function, Mechanisms and Pharmaceutical Potential" Pharmaceuticals 4: 1248-1280 (2011). Findeisen et al.; "Serum stability of selected decapeptide agonists of KISS1R using pseudopeptides" Asami et al., Bioorganic & Medicinal Chemistry Letters 22: 6391-6396 (2012); "Rational design of triazololipopeptides analogs of kisspeptin inducing a long-lasting increase of gonadotropins" Beltramo et al., *Journal of Medicinal Chemistry* 58: 3459-3470 (2015); "Design, synthesis, and biological evaluation of novel investigational nonapeptide KISS1R agonists with testosterone-suppressive activity" Asami et al., *Journal of Medicinal Chemistry* 56: 8298-8307 (2013); "Trypsin resistance of a decapeptide KISS1R agonist containing an $N^{\omega}$-methylarginine substitution" Asami et al., *Bioorganic & Medicinal Chemistry Letters* 22: 6328-6332 (2012); U.S. Pat. No. 9,884,891; PCT Appl. No. PCT/EP2014/051886; U.S. Pat. Nos. 8,404,643; 8,778,871; 8,361,968; U.S. application Ser. No. 12/989,346; U.S. Pat. No. 6,800,611; JP Appl. No. JP2003433643.

Solid-Phase Peptide Synthesis (SPPS)

Procedure A: General Procedure for SPPS

Procedure A-1: Resin Swelling and Attachment of First Amino Acid on Resin (CTC Resin)

2-Chlorotrityl chloride resin (1.1 mmol/g) and DCM (10 mL/g resin) were added into a sealed tube at room temperature under nitrogen. The mixture was swollen for 15 min at room temperature under nitrogen. The resin was washed with DCM (3×100 mL). The appropriate amino acid (1.0 eq.), DIEA (1.0 eq.), and DCM (10 mL/resin) were added to the mixture. The mixture was agitated for 5 min at room temperature under nitrogen. DIEA was added (1.5 eq.), and the mixture was agitated for another 60 min. MeOH (I-PLC grade, 0.8 mL/g resin) was added to endcap any remaining reactive trityl groups. The resin was filtered and washed twice with DCM (10 mL/g resin), twice with DMF, and three times with MeOH. The resin was dried under vacuum and the loading was calculated by weight gain.

Procedure A-2: Resin Swelling (Rink Amide Resin)

The resin (100 mg/tube) was swollen with NMP (1 mL/tube) for 1-5 minutes at room temperature under nitrogen. The resin was washed four times with NMP (1 mL/tube).

Procedure A-3: Fmoc Deprotection

The resin (100 mg/tube) was treated with 20% piperidine in NMP (1 mL) for 20 minutes at room temperature under nitrogen. The resin was washed four times with NMP (1 mL/tube).

Procedure A-4: HATU Coupling

The resin (100 mg/tube) was treated with a mixture of amino acid (4.0 eq.), HATU (4.0 eq.), and DIEA (8.0 eq.) in NMP for 45 min at 30° C. under nitrogen. The resin was washed four times with NMP (1 mL/tube).

Procedure A-5: Resin Capping

The resin (100 mg/tube) was capped with a solution of $Ac_2O$/DIEA/NMP (31.5:8.5:160 v/v/v) for 1 hour at room temperature under nitrogen. The resin was washed four times with NMP (1 mL/tube).

Procedure A-6: Cleavage and Purification (CTC Resin)

The crude peptide was cleaved from the resin with a solution of 1,1,1,3,3,3-hexafluoropropan-2-ol/DCM (1:4 v/v) for 30 min at room temperature. The crude product was purified by prep-HPLC.

Procedure A-7: Cleavage and Purification (Rink Amide Resin)

The crude peptide was cleaved from the resin with a solution of TFA/$H_2O$/TIS/DODT (37:1:1:1 v/v/v/v) for 2 h at room temperature. The mixture was filtered, and the filtrate was concentrated under reduced pressure. The residue was precipitated with cold ether, then the precipitate was centrifuged. The crude product was purified by prep-HPLC and dried by lyophilization.

Procedure B: Synthesis of (S)-2-(4-((S)-1-((((9H-fluoren-9-yl)methoxy)carbonyl)amino)-2-phenylethyl)-1H-1,2,3-triazol-1-yl)-4-methylpentanoic acid

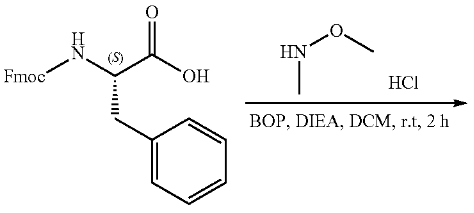

B-1

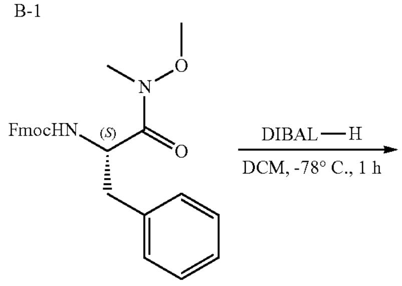

B-2

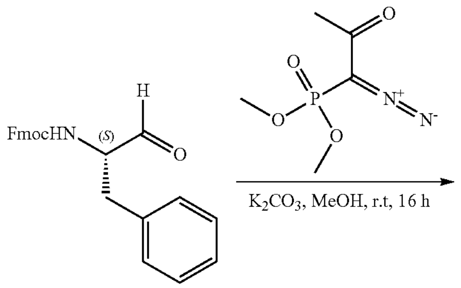

B-3

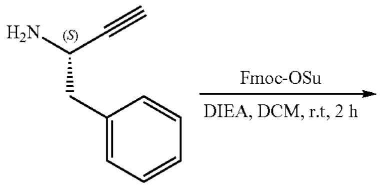

B-4

-continued

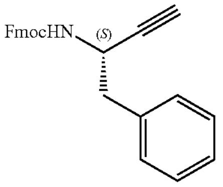

B-5

Into a 250-mL round bottom flask were added B-1 (10 g, 26 mmol, 1.0 eq), BOP (14 g, 32 mmol, 1.2 eq), DIEA (10 g, 13 mL, 77 mmol, 3.0 eq) and DCM (100 mL). The reaction mixture was stirred at 20° C. for 10 minutes, then N,O-dimethylhydroxylamine hydrochloride (3.8 g, 39 mmol, 1.5 eq) was added. The reaction mixture was stirred at 25° C. for an additional 2 h. The mixture was diluted with water (500 mL), extracted with EtOAc (3×200 mL), and the combined organic layers were washed with brine (200 mL), dried over anhydrous $Na_2SO_4$, filtered and concentrated under reduced pressure. The residue was purified by MPLC using a silica gel column (330 g) with a PE/EtOAc mobile phase (0% to 12% EtOAc in 25 min, 100 mL/min flow rate, UV 254 nm). The collected fractions were concentrated under reduced pressure to afford B-2 (9.2 g, 21 mmol, 83%) as a yellow solid. LCMS: (ESI, m/z): $[M+Na]^+$=453.3.

To a solution of B-2 (9.2 g, 21 mmol, 1.0 eq) in DCM (90 mL) was added diisobutylaluminum hydride (40 mL, 2 M in toluene, 80 mmol. 3.7 eq) dropwise at −78° C. over a period of 10 minutes under a nitrogen atmosphere. The reaction mixture was stirred at −78° C. for 1 h and quenched by dropwise addition of MeOH (100 mL). After the solvent was removed, the crude B-3 (8.0 g, 13 mmol, 60%) was carried forward without further purification.

Into a 500-mL three-neck round bottom flask was added B-3 (8.0 g, 60% Wt, 13 mmol, 1.0 eq), followed by $K_2CO_3$ (4.0 g, 29 mmol, 2.2 eq) and dimethyl (1-diazo-2-oxopropyl) phosphonate (3.7 g, 19 mmol, 1.5 eq). The reaction mixture was stirred at 25° C. for 16 h. The mixture was diluted with 200 mL of potassium sodium tartrate solution and stirred at 25° C. for 2 h. The mixture was extracted with DCM (3×100 mL), and the combined organic layers were washed with brine (100 mL), dried over anhydrous $Na_2SO_4$, and concentrated under reduced pressure to afford B-4 (6.0 g, 12 mmol, 96%) as a yellow oil, which was used without further purification.

To a mixture of B-4 (6.0 g, 12 mmol, 1.0 eq), DIEA (4.8 g, 6.5 mL, 37 mmol, 3.0 eq) and DCM (60 mL) was added Fmoc-OSu (6.3 g, 19 mmol, 1.5 eq). The reaction mixture was stirred at 20° C. for 2 h. The mixture was concentrated under reduced pressure. The residue was purified by MPLC using a silica gel column (80 g) with a PE/EtOAc mobile phase (0% to 12% EtOAc in 40 min, 80 mL/min flow rate, UV 220 nm). The collected fractions were concentrated under reduced pressure to afford B-5 (3.6 g, 9.8 mmol, 79%) as a white solid. LCMS: (ESI, m/z): $[M+H]^+$=368.1. $^1H$ NMR (300 MHz, Chloroform-d) δ 7.80 (d, J=7.5 Hz, 2H), 7.59 (d, J=7.4 Hz, 2H), 7.43-7.38 (m, 2H), 7.39-7.21 (m, 7H), 4.98-4.90 (m, 1H), 4.82-4.76 (m, 1H), 4.56-4.38 (in 2H), 4.23 (t, J=6.8 Hz, 1H), 3.04-2.91 (m, 2H), 2.34 (d, J=2.3 Hz, 1H).

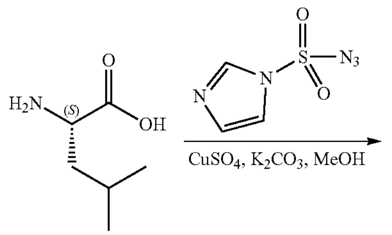

B-6

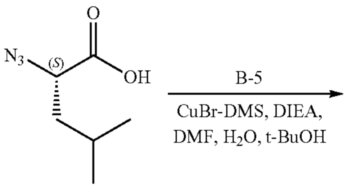

B-7

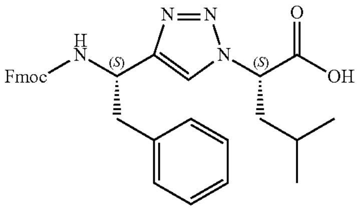

B-8

A solution of L-leucine (3 g, 22.9 mmol, 1 Eq), imidazole-1-sulfonyl azide (4.75 g, 27.4 mmol, 1.2 Eq), $CuSO_4$ (73.0 mg, 0.46 mmol, 0.02 Eq) and $K_2CO_3$ (6.32 g, 45.7 mmol, 2.0 Eq) in MeOH (120 mL) was stirred at 25° C. overnight and concentrated in vacuo. To the residue was added water (40 mL), and the mixture was acidified to pH 2 with HCl (aq.). The resulting mixture was extracted with EtOAc (4×50 mL). The combined organic layers were dried over anhydrous $Na_2SO_4$. After filtration, the filtrate was concentrated under reduced pressure to afford B-7 (2.9 g, 64.5%) as a green oil. Crude B-7 was used without further purification. LCMS: (ESI, m/z): $[M-H]^-$=156.00

A solution of B-7 (700 mg, 4.5 mmol, 1 Eq), B-5 (1.72 mg, 4.7 mmol, 1.05 Eq), DIPEA (575.63 mg, 4.5 mmol, 1 Eq), CuBr-DMS (91.56 ng, 0.45 mmol, 0.1 Eq) in DMF (4.5 mL), t-BuOH (3.2 mL) and $H_2O$ (0.9 mL) was stirred for 30 min at 25° C. The mixture was acidified to pH2 with HCl (aq.). The resulting mixture was extracted with EtOAc (3×20 mL). The combined organic layers were dried over anhydrous $Na_2SO_4$. After filtration, the filtrate was concentrated under reduced pressure. The residue was purified by Prep-HPLC to afford B-8 (900 mg, 48.5%) as a white solid. LCMS: (ESI, m/z): $[M+H]^+$=525.25. $^1H$ NMR (400 MHz, DMSO-d6) δ 0.83 (ddt, =16.1, 9.5, 5.4 Hz, 6H), 1.08 (s, 1H), 1.92 (ddd, J=14.2, 9.5, 4.7 Hz, 1H), 2.06-2.24 (m, 1H), 2.97-3.12 (m, 1H), 3.20 (dd, J=13.8, 5.9 Hz, 1H), 4.18 (ddt, J=25.7, 13.8, 7.3 Hz, 3H), 4.95 (dt, J=9.9, 4.8 Hz, 1H), 5.39 (dd, J=11.6, 4.2 Hz, 1H), 7.12-7.25 (m, 5H), 7.30 (td, J=7.3, 4.9 Hz, 2H), 7.41 (t, J=7.4 Hz, 2H), 7.64 (d, J=7.4 Hz, 2H), 7.90 (dd, J=15.2, 8.4 Hz, 3H), 8.00 (d, J=7.2 Hz, 1H), 13.44 (s, 11H).

Procedure C: Synthesis of 4-((((9H-fluoren-9-yl)methoxy)carbonyl)amino)-1-(4-(p-tolyl)butanoyl)piperidine-4-carboxylic acid

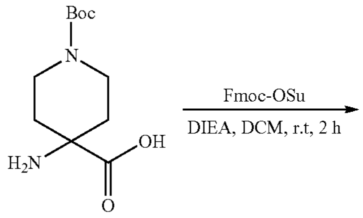

C-1

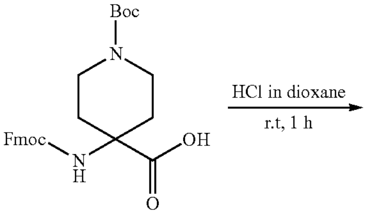

C-2

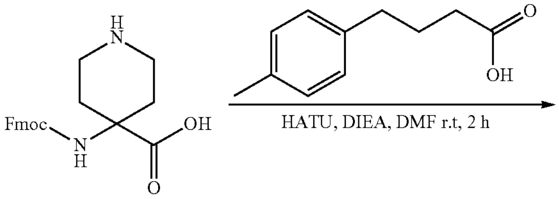

C-3

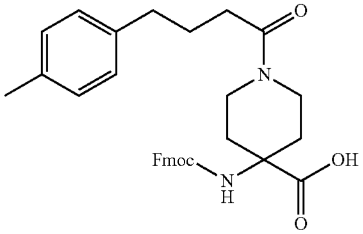

C-4

To a mixture of C-1 (2.0 g, 8.2 mmol, 1.0 eq), N-ethyl-N-isopropylpropan-2-amine (3.0 g, 23 mmol, 2.8 eq) and DCM (30 mL) was added (9H-fluoren-9-yl)methyl (2,5-dioxopyrrolidin-1-yl) carbonate (2.8 g, 8.3 mmol, 1.0 eq). The reaction mixture was stirred at 25° C. for 2 h. The mixture was concentrated, diluted with water (100 mL), and extracted with EtOAc (3×50 mL). The combined organic layers were washed with water (2×50 mL), brine (50 mL), dried over anhydrous $Na_2SO_4$, filtered and concentrated under reduced pressure. The residue was purified by MPLC using a silica gel column (40 g) with a PE/EtOAc mobile phase (0% to 35% EtOAc in 30 min, 40 m/min flow rate, UV 254 nm). The collected fractions were concentrated under reduced pressure to provide C-2 (3.8 g, 7.3 mmol, 90%) as a yellow oil. LCMS: (ESI, m/z): $[M+H]^+$=467.3.

To a solution of C-2 (2.0 g, 4.3 mmol, 1.0 eq) and 1,4-dioxane (15 mL) was added a 4 M HCl/dioxane solution (15 mL, 60 mmol, 14.0 eq). The reaction mixture was stirred at 25° C. for 2 h. The mixture was concentrated under reduced pressure, diluted with water (100 mL), and washed with EtOAc (3×50 mL). The aqueous phase was concentrated under reduced pressure to provide C-3 (2.8 g, 31 mmol, 71%) as a white solid. LCMS: (ESI, m/z): $[M+H+MeCN]^+$=408.4.

Into a 100-mL round bottom flask was added C-3 (1.5 g, 8.4 mmol, 1.2 eq), HATU (3.2 g, 8.4 mmol, 1.2 eq), DIEA (2.7 g, 3.6 mL, 21 mmol, 3.0 eq) and DMF (25 mL). The reaction mixture was stirred at 20° C. for 10 minutes.

4-((((9H-fluoren-9-yl)methoxy)carbonyl)amino)piperidine-4-carboxylic acid hydrochloride (2.8 g, 6.9 mmol, 1.0 eq) was added. The resulting reaction mixture was stirred for an additional 2 h at 25° C. The mixture was diluted with water (150 mL) and extracted with EtOAc (3x50 mL). The combined organic layers were washed with water (2x50 mL), brine (50 mL), dried over anhydrous $Na_2SO_4$, and concentrated under reduced pressure. The crude product was purified by MPLC using a silica gel column (80 g) with a PE/EtOAc mobile phase (0% to 85% EtOAc in 45 min, 80 mL/min flow rate, UV 254 nm). The collected fractions were concentrated under reduced pressure to afford C-4 (2.18 g, 4.14 mmol, 60%) as a white solid. LCMS: (ESI, m/z): $[M+H]^+$=527.2. $^1$H NMR (300 MHz, DMSO-$d_6$) δ 12.56 (brs, 1H), 7.90 (d, J=7.5 Hz, 2H), 7.78-7.70 (m, 3H), 7.48-7.23 (m, 4H), 7.08 (s, 4H), 4.3-4.18 (m, 3H), 4.11-3.99 (m, 1H), 3.68-3.58 (m, 1H), 3.25-2.15 (m, 1H), 2.96-2.82 (m, 1H), 2.60-2.52 (m, 2H), 2.31-2.20 (m, 5H), 2.00-1.82 (m, 2H), 1.76-1.58 (m, 4H).

Procedure D: Synthesis of (S)-2-((2-((((9H-fluoren-9-yl)methoxy)carbonyl)amino)ethyl)thio)-4-methylpentanoic acid

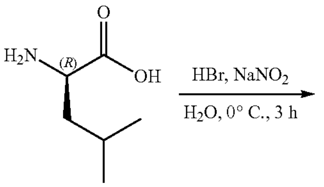

D-1

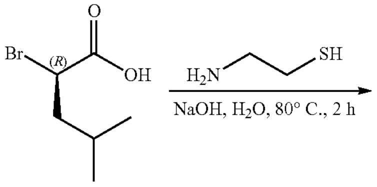

D-2

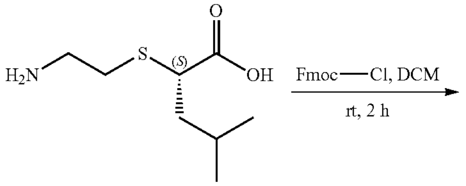

D-3

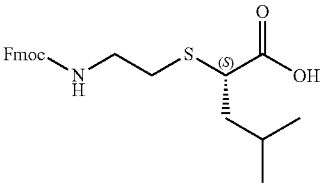

D-4

To a mixture of D-1 (6.0 g, 46 mmol, 1.0 eq) in 1420 (60 mL) were added an aqueous HBr solution (22 mL, 48 wt %, 0.19 mol, 4.3 eq), a solution of sodium nitrite (4.1 g, 2.6 mL, 59 mmol, 1.3 eq) in $H_2O$ (40 mL) at 0° C. The reaction mixture was stirred at 0° C. for 1 hour and an additional 3 h at 25° C. The mixture was extracted with EtOAc (3x50 mL) and the combined organic layers were washed with brine (100 mL), dried over anhydrous $Na_2SO_4$, and concentrated under reduced pressure to afford D-2 (4.6 g, 24 mmol, 52%) as a brown crude oil, which was used without further purification. LCMS: (ESI, m/z): $[M-H]^-$=193.0, 195.0.

Into a 250-mL round bottom flask were added crude D-2 (4.6 g, 1 Eq, 24 mmol), 2-aminoethane-1-thiol (1.9 g, 1.0 Eq, 25 mmol), NaOH (1.9 g, 2.0 Eq, 48 mmol) and $H_2O$ (25 mL). The reaction mixture was stirred at 80° C. for 2 h. The crude D-3 (4.5 g, 9.6 mmol, 41%) was used directly without further purification. LCMS: (ESI, m/z): $[M-H]^-$=190.1

To a solution of crude D-3 (4.5 g, 41 wt. %, 9.6 mmol, 1.0 eq) in DCM (40 mL) was added (9H-fluoren-9-yl)methyl carbonochloridate (3.5 g, 1.4 Eq, 14 mmol) and DCM (40 mL). The reaction mixture was stirred at 20° C. for 2 h and diluted with water (60 mL). The mixture was extracted with DCM (3x50 mL), and the combined organic layers were washed with brine (50 mL), dried over anhydrous $Na_2SO_4$, and concentrated under reduced pressure. The residue was purified by MPLC using a silica gel column (120 g) with a PE/EtOAc mobile phase (0% to 75% EtOAc in 40 min, flow rate 100 mL/min, LV 254 nm). The collected fractions were concentrated under reduced pressure and dried by lyophilization to afford D-4 (1.3 g, 3.1 mmol, 33%) as a yellow solid. LCMS: (ESI, m/z): $[M+H]^+$=414.1. $^1$H NMR (300 MHz, DMSO-$d_6$) δ 12.53 (s, 1H), 7.90 (d, J=7.4 Hz, 2H), 7.69 (d, J=7.4 Hz, 2H), 7.49-7.28 (n. 51H), 4.35-4.17 (m, 3H), 3.29-3.12 (m, 3H), 2.70-2.55 (m, 2H), 1.75-1.55 (m, 2H), 1.49-1.35 (m, 1H), 0.99-0.82 (m, 6H).

Procedure E: Synthesis of 1-((((9H-fluoren-9-yl)methoxy)carbonyl)amino)-4-((tert-butoxycarbonyl)amino)cyclohexane-1-carboxylic acid

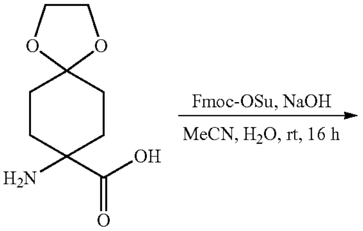

E-1

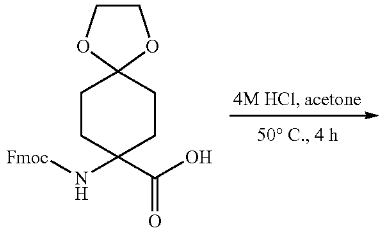

E-2

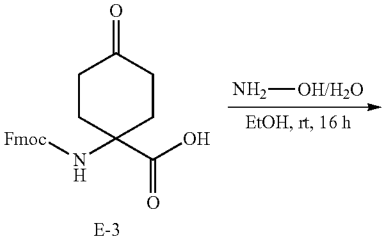

E-3

-continued

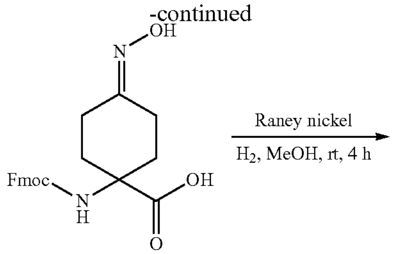

E-4

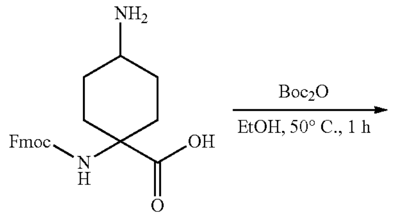

E-5

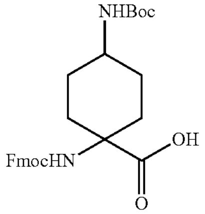

E-6

Into a 250-mL round bottom flask were added E-1 (5.0 g, 1 Eq, 25 mmol), NaOH (1.0 g, 25 mmol, 1.0 Eq), (9H-fluoren-9-yl)methyl (2,5-dioxopyrrolidin-1-yl) carbonate (8.4 g, 25 mmol, 1.0 Eq), $H_2O$ (80 mL), and MeCN (80 mL). The reaction mixture was stirred at 25° C. for 16 h. The mixture was diluted with water (250 mL) and the pH was adjusted to 6.0 by 2N HCl solution. The mixture was extracted with EtOAc (3×250 mL), and the combined organic layers were washed with water (2×150 mL), brine (50 mL), dried over anhydrous $Na_2SO_4$, and concentrated under reduced pressure. The crude product was triturated with 200 ml of a 5:1 mixture of EtOAc:hexanes, filtered, and dried to afford E-2 (6.9 g, 16 mmol, 66%) as a white solid. LCMS: (ESI, m/z): $[M-H]^+$=:424.1.

Into a 250-mL round bottom flask was added E-2 (6.9 g, 1 Eq, 16 mmol), acetone (70 mL) and 4M aqueous HCl solution (70 mL). The reaction mixture was stirred at 50° C. for 2 h. The mixture was concentrated under reduced pressure, filtered, and dried to afford E-3 (1-((((9H-fluoren-9-yl)methoxy)carbonyl)amino)-4-oxocyclohexane-1-carboxylic acid) (53 g, 14 mmol, 86%) as a white solid. LCMS: (ESI, m/z): $[M+H]^+$=380.1.

Into a 250-mL round bottom flask were added E-3 (5.3 g, 1 Eq, 14 mmol), hydroxylamine (60 g, 55 mL, 50 wt. %, 0.91 mol, 65 Eq), and EtOH (55 mL). The reaction mixture was stirred at 25° C. for 16 h and concentrated. The residue was purified by MPLC The collected fractions were concentrated under reduced pressure to provide E-4 (4.4 g, 8.9 mmol, 64%) as ax white solid. LCMS: (ESI, m/z): $[M+H]^+$ =395.1.

To a solution of E-4 (4.4 g. 80 wt. % 8.9 mmol, 1.0 eq) in MeOH (100 mL) was carefully added Raney Nickel (1.4 g) under a $N_2$ atmosphere. The flask was evacuated and flushed with hydrogen three times, followed by flushing with hydrogen. The mixture was stirred at 25° C. for 2 h under $H_2$. The reaction mixture was filtered through a pad of celite and the filtrate was concentrated under reduced pressure to afford E-5 (2.8 g, 4.8 mmol, 54%) as a yellow crude oil, which was used without further purification. LCMS: (ESI, m/z): $[M+H]^+$=381.2.

Into a 250-mL round bottom flask was added crude E-5 (2.9 g, 75 wt %, 5.7 mmol, 1.0 eq), di-tert-butyl dicarbonate (1.5 g, 6.9 mmol, 1.2 eq), and EtOH (40 mL). The reaction mixture was stirred at 50° C. for 2 h and concentrated in vacuo. The residue was purified by MPLC The collected fractions were concentrated under reduced pressure and dried by lyophilization to provide E-6 (1.53 g, 3.14 mmol, 55%) as a white solid. LCMS: (ESI, m/z): $[M-H]^-$=479.2. $^1$H NMR (300 MHz, DMSO-$d_6$) δ 7.89 (d, J=7.4 Hz, 2H), 7.81-7.60 (m, 2H), 7.51 (s, 1H), 7.42 (td, J=7.4, 1.4 Hz, 2H), 7.40-7.31 (m, 2H), 6.85-6.78 (m, 1H), 4.22 (s, 3H), 3.23-3.18 (m, 1H), 2.20-2.06 (m, 2H), 1.68-1.52 (m, 4H), 1.48-1.30 (s, 11H).

Procedure F: Synthesis of 4-((((9H-fluoren-9-yl)methoxy)carbonyl)amino)-1-(N-(tert-butoxycarbonyl)-N-(3-fluoro-4-methylbenzyl)glycyl)piperidine-4-carboxylic acid

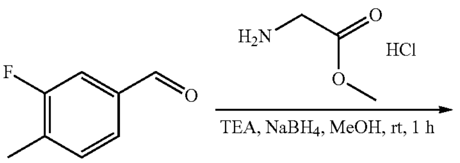

F-1

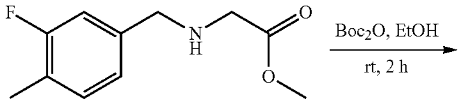

F-2

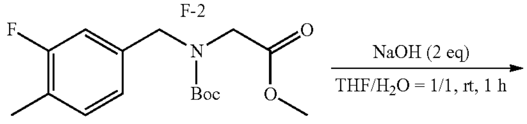

F-3

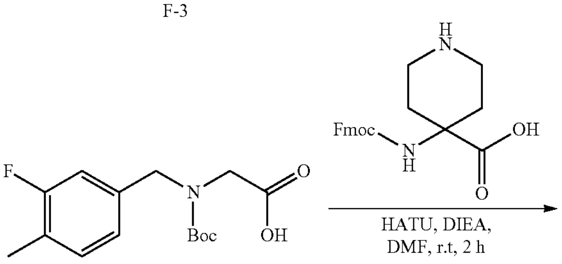

F-4

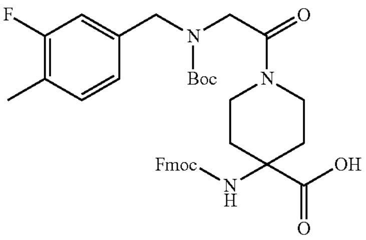

F-5

Into a 500 mL round bottom flask were added methyl glycinate hydrochloride (27 g, 0.22 mol, 2.0 eq), TEA (22 g, 30 mL, 0.22 nol. 2.0 eq), F-1 (3-fluoro-4-methylbenzaldehyde) (15 g, 0.11 mol, 1.0 eq), and MeOH (150 mL). The reaction mixture was stirred at 0° C. for 30 min., then $NaBH_4$ (8.2 g, 0.22 mol, 2.0 eq) was added slowly under a nitrogen atmosphere at 0° C. The reaction mixture was stirred at 25° C. for an additional 1 h, and concentrated under reduced pressure. The residue was diluted with water (300 mL) and extracted with EtOAc (3x300 mL), then the combined organic layers were washed with brine (200 mL), dried over anhydrous $Na_2SO_4$, and concentrated under reduced pressure. The crude residue was purified by MPLC to afford F-2 (methyl (3-fluoro-4-methylbenzyl)glycinate) (115 g, 54.4 mmol, 50%) as a colorless oil. LCMS: (ESI, m/z): $[M+H]^+$=212.3, $^1$H NMR (400 MHz, DMSO-$d_6$) δ 7.19 (t, J=8.0 Hz, 1H), 7.07 (d, J=11.2 Hz, 1H), 7.02 (d, J=8.0 Hz, 1H), 3.69-3.67 (m, 2H), 3.62 (s, 3H), 3.30-3.27 (m, 2H), 2.20 (s, 3H).

To a solution of F-2 (methyl (3-fluoro-4-methylbenzyl) glycinate) (11.5 g, 54.4 mmol, 1.0 eq) and EtOH (120 mL) was added di-tert-butyl dicarbonate (1.1 g, 5.0 mmol, 1.1 eq). The reaction mixture was stirred at 25° C. for 2 h, then concentrated under reduced pressure to provide F-3 (17.0 g, 54.6 mmol, 100%) as a white solid, which was used without further purification. LCMS: (ESL, m/z): $[M+H-Boc]^+$=212.3.

To a solution of F-3 (17 g, 55 mmol, 1.0 eq) in THF (100 mL) at 0° C. was slowly added sodium hydroxide (4.4 g, 2.0 Eq, 0.11 mol) in water (100 mL). The reaction mixture was stirred at 25° C. for 1 h. The mixture was acidified to pH=5 by addition of a HCl (aq. 1 N), diluted with water (200 mL), and extracted with EtOAc (3x300 mL). The combined organic layers were washed with brine (300 mL), dried over anhydrous $Na_2SO_4$, filtered and concentrated under reduced pressure to provide F-4 (15.6 g, 52.5 mmol, 96%) as a colorless oil. LCMS: (ESI, m/z): $[M+H-Boc]^+$=198.1.

Into a 500-mL round bottom flask were added F-4 (N-(tert-butoxycarbonyl)-N-(3-fluoro-4-methylbenzyl)glycine (13.2 g, 44.4 mmol, 1.05 eq), 2-(3H-[1,2,3]triazolo[4,5-b]pyridin-3-yl)-1,1,3,3-tetramethylisouronium hexafluorophosphate(V) (16.8 g, 44.2 mmol, 1.05 eq), N-ethyl-N-isopropylpropan-2-amine (16.4 g, 127 mmol, 3.0 eq), and DMF (200 mL). The reaction mixture was stirred at 20° C. for 10 minutes, then 4-((((9H-fluoren-9-yl)methoxy)carbonyl)amino)piperidine-4-carboxylic acid hydrochloride (17.0 g, 1.00 Eq, 42.2 mmol) was added. The reaction mixture was stirred at 25° C. for an additional 2 h and concentrated. The residue was purified by MPLC and the collected fractions were concentrated under reduced pressure and dried by lyophilization to provide F-5 (11.6 g, 18.0 mmol, 42.6%) as a white solid. LCMS: (ESI, m/z): $[M+H]^+$=646.3. $^1$H NMR (300 M-Hz, DMSO-$d_6$) δ 7.89 (d, J=7.5 Hz, 2H), 7.73 (d, J=7.4 Hz, 2H), 7.67 (s, 1H), 7.42 (td, J=7.4, 1.2 Hz, 2H), 7.33 (t, J=7.4 Hz, 2H), 7.23 (t, J=8.0 Hz, 1H), 7.08-6.95 (m, 2H), 4.45-4.17 (m, 5H), 4.05-3.90 (m, 3H), 3.60-3.50 (m, 1H), 3.20-3.10 (m, 1H), 3.03-2.90 (m, 1H), 2.21 (s, 3H), 2.05-1.95 (m, 2H, 1.88-1.65 (m, 2H), 1.38-1.32 (m, 9H).

Procedure G: (S)-6-((5-((((9H-fluoren-9-yl)methoxy)carbonyl)amino)-6-(tert-butoxy)-6-oxohexyl)amino)-6-oxohexanoic acid

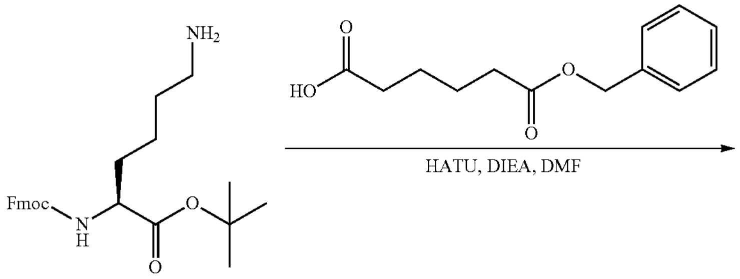

G-1

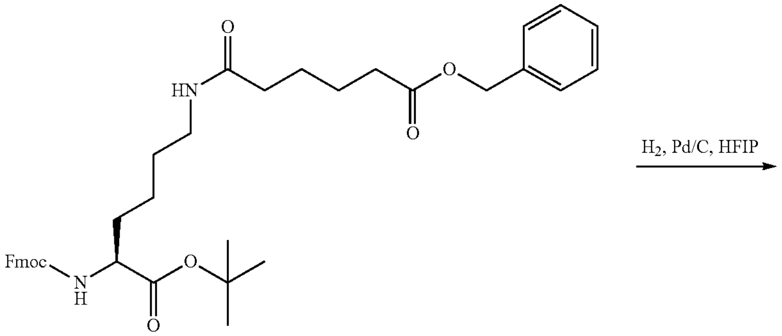

G-2

-continued

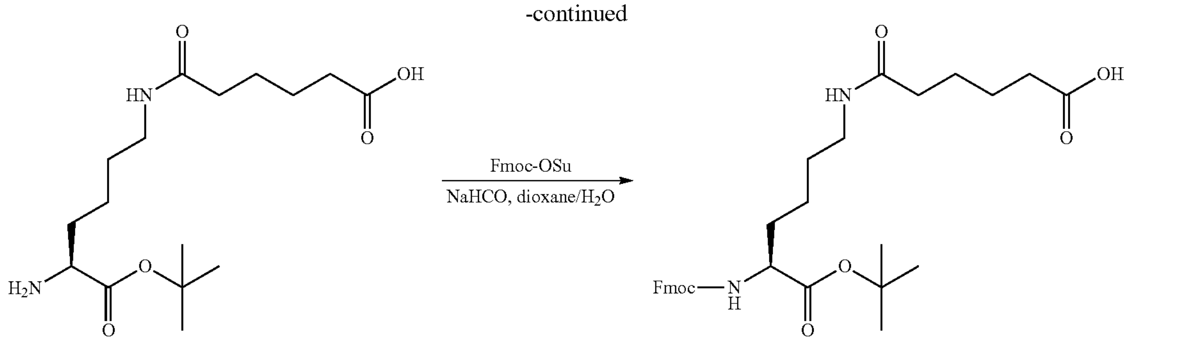

G-3 G-4

To a solution of 6-(benzyloxy)-6-oxohexanoic acid (5.0 g, 21.16 mmol, 1.5 Eq) and G-1 (6.50 g, 14.11 mmol, 1.0 Eq) in DMF (50 mL) were added HATU (8.05 g, 21.16 mmol, 1.5 eq) and DIEA (7.29 g, 56.43 mmol, 4.0 eq). The mixture was stirred for 1 h at 25° C. and extracted with EtOAc (3×500 mL). The combined organic layers were washed with brine (3×500 mL), then dried over anhydrous $Na_2SO_4$. After filtration, the filtrate was concentrated under reduced pressure. The residue was purified by reversed-phase flash chromatography with the following conditions: column, C18 silica gel; mobile phase, MeCN in Water (0.1% FA), 10% to 90% gradient in 30 min; detector, UV 254 nm to afford G-2 (8.1 g, 83.6%) as a white solid. LCMS: (ESI, m/z): $[M+H^+]$=643.40. $^1H$ NMR (400 MHz, DMSO-$d_6$) δ 7.90 (d, J=7.5 Hz, 2H), 7.78 (t, J=5.6 Hz, 1H), 7.73 (d, J=7.5 Hz, 1H), 7.65 (d, J=7.8 Hz, 1H), 7.46-7.39 (m, 2H), 7.37-7.31 (m, 6H), 5.08 (s, 2H), 4.36-4.19 (m, 3H), 3.90-3.80 (m, 11H), 3.09-2.95 (m, 2H), 2.39-2.31 (m, 2H), 2.08 (s, 4H), 1.69-1.56 (m, 2H), 1.51 (p, J=2.6 Hz, 4H), 1.39 (s, 13H).

To a solution of G-2 (3.0 g, 4.67 mmol, 1.0 Eq) in 1,1,1,3,3,3-hexafluoroisopropanol (30 mL) was added Pd/C (0.1 g, 0.94 mmol, 20 wt. %) in a 100 mL round-bottom flask. The mixture was hydrogenated at room temperature overnight under hydrogen atmosphere using a hydrogen balloon, filtered through a celite pad and concentrated under reduced pressure to afford G-3 (2.9 g, crude) as a white solid. The product was used in the next step without further purification. LCMS: (ESI, m/z): $[M+H^+]$331.30.

To a mixture of G-3 (2.9 g, 9.08 mmol, 1.0 Eq) in 1,4-dioxane (225 mL) and water (75 mL) was added solid $NaHCO_3$. After the pH of the solution was adjusted to 8~9, Fmoc-OSu (1.84 g, 5.45 mmol, 0.60 Eq) was added in portions at room temperature. The resulting mixture was stirred for 16 h at room temperature and extracted with EtOAc (3×750 mL). The combined organic layers were washed with water (3×700 mL), dried over anhydrous $Na_2SO_4$. After filtration, the filtrate was concentrated under reduced pressure. The residue was purified by reversed-phase flash chromatography with the following conditions: column, C18 silica gel; mobile phase, MeCN in Water (0.1% PFA), 40% to 70% gradient in 15 min; detector, UV 254 nm to afford G-4 (4.5 g, 73.6%) as a light brown oil. LCMS: (ESI, m/z): $[M+H^+]$=553.35. $^1H$ NMR (400 MHz, DMSO-$d_6$) δ 12.00 (s, 11H), 7.98-7.83 (m, 2H), 7.73 (tt, J=13.7, 6.9 Hz, 31H), 7.64 (d, J=7.8 Hz, 1H), 7.49-7.36 (m, 21H), 7.33 (td, J=7.4, 1.2 Hz, 2H), 4.27 (qt, J=14.0, 7.2 Hz, 3H), 3.01 (q, J=6.6 Hz, 2H), 2.19 (t, J=6.7 Hz, 2H), 2.08 (s, 4H), 1.60 (dq, J=22.8, 8.4, 7.7 Hz, 2H), 1.47 (dq, J=6.9, 4.0 Hz, 4H), 1.39 (s, 11H).

Procedure H: Synthesis of Compound 1 (H-3 disclosed as SEQ ID NO: 824 and Compound 1 disclosed as SEQ ID NO: 391)

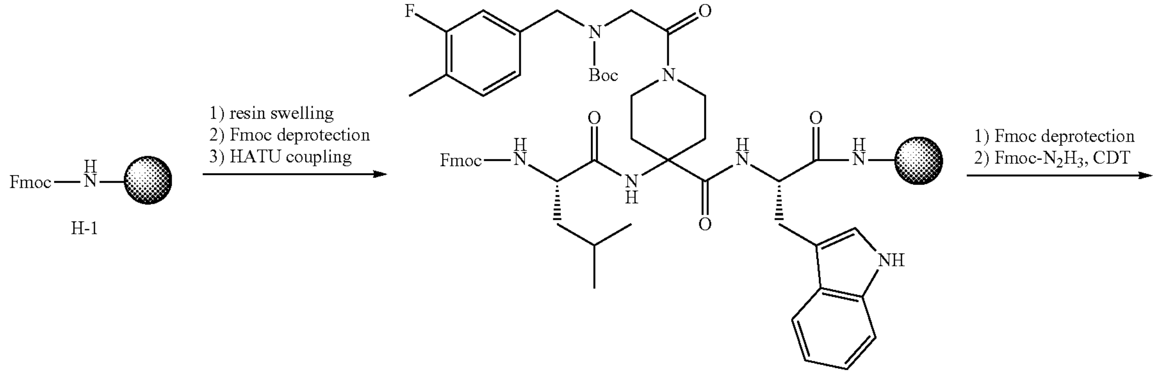

H-1

H-2

-continued

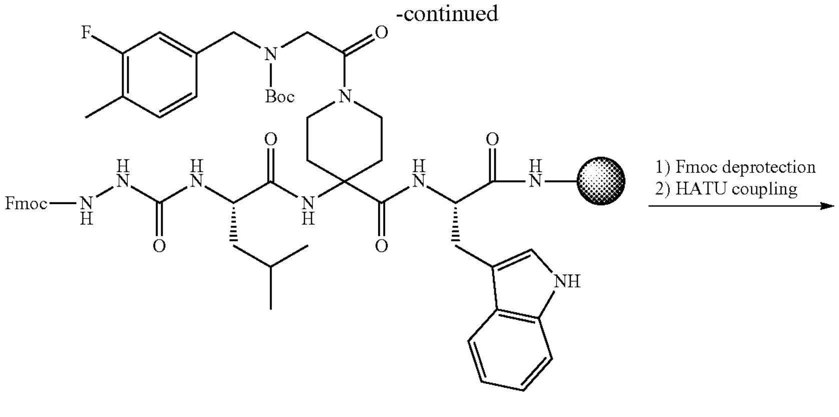

H-3

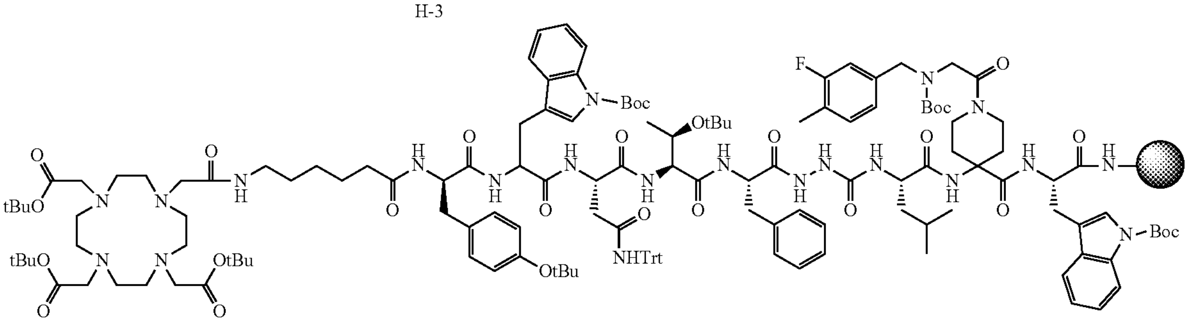

H-4

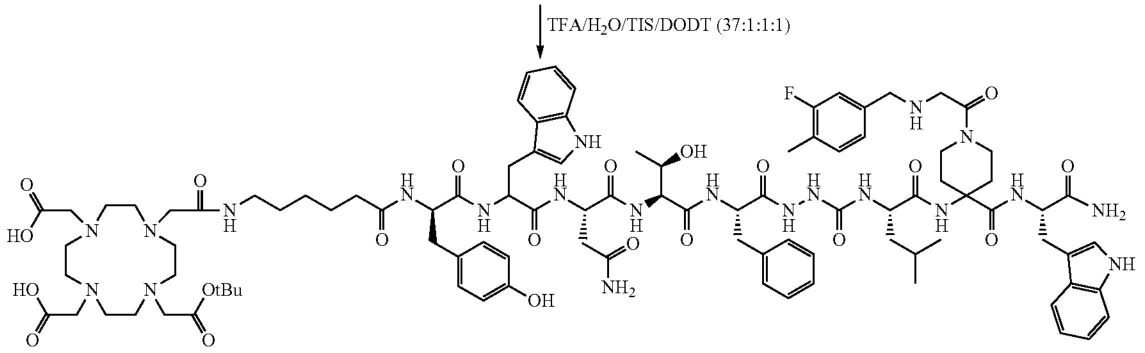

Compound 1

Peptide H-2 was prepared by standard Fmoc-based SPPS using $N^{\alpha}$-Fmoc-Rink amide resin. The details were outlined in Procedure A above. The coupling reaction with precursor F-5 was performed twice with HATU at 60° C.

Peptide H-2 was treated with the mixture of Fmoc-$N_2H_3$ (3.0 Eq) and CDT (3.0 Eq) in NMP (10 mL/g resin) overnight, at room temperature, and under nitrogen atmosphere. The reaction was operated manually. The reaction was washed with NMP (3×2 mL) to afford peptide H-3 on resin.

Elongation of 113 was carried out by repeating Procedures A-3 and A-4 until peptide H-4 was obtained.

Peptide H-4 was cleaved from the resin, followed by purification by RP-HPLC according to Procedures A-7. The desired fractions were concentrated and lyophilized to afford Compound 1 as a white solid (overall yield 8.54%, 98.5% purity). MS: Calc'd for $C_{93}H_{124}FN_{21}O_{21}$: 1889.9, found $[M+2H]^{2+}$: 946.4.

Procedure I: Synthesis of Compound 332 (I-3 disclosed as SEQ ID NO: 825, I-4 disclosed as SEQ ID NO: 826, I-5 disclosed as SEQ ID NO: 827 and Compound 332 disclosed as SEQ ID NO: 714)

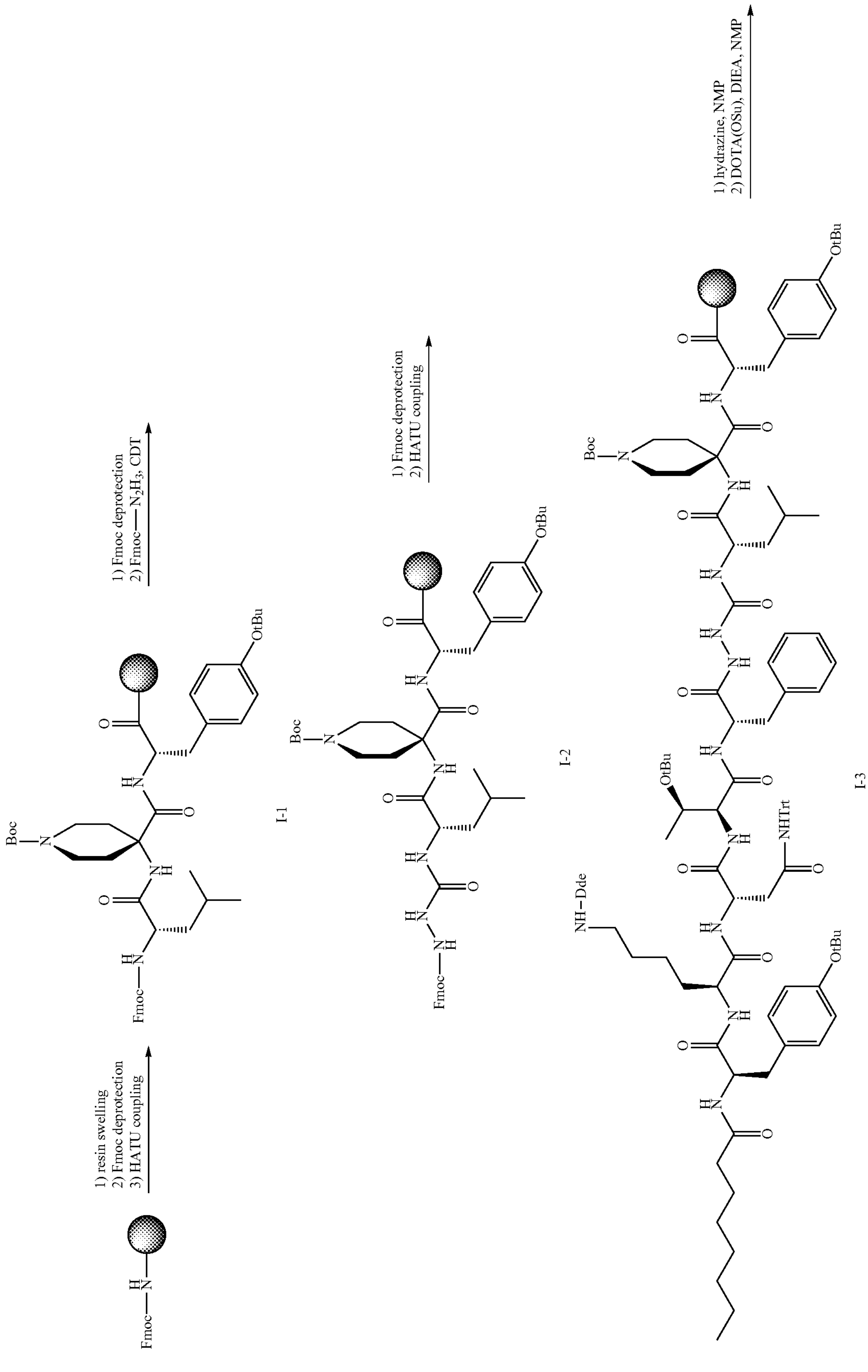
I-1
I-2
I-3

-continued
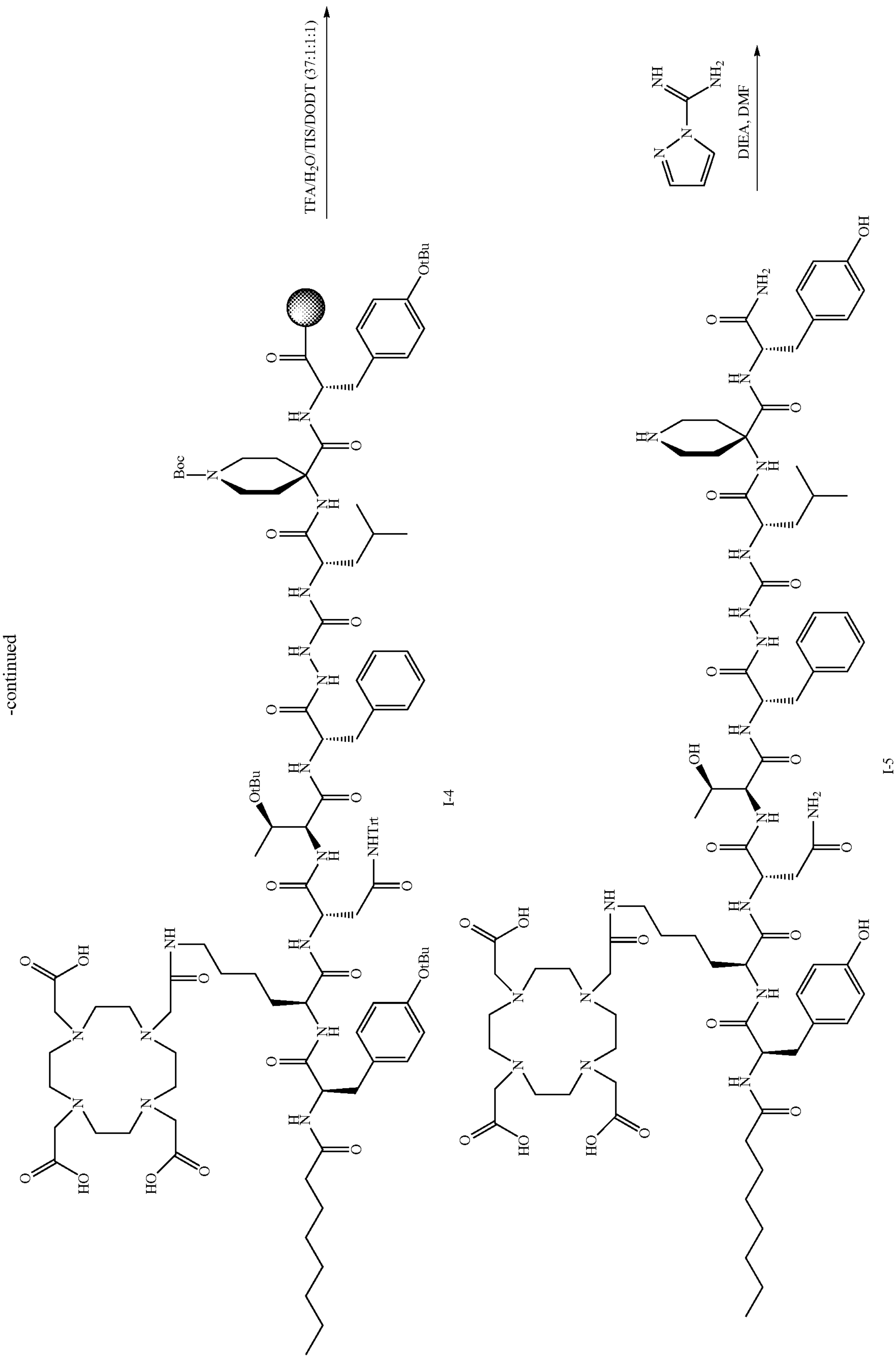
I-4
I-5

-continued
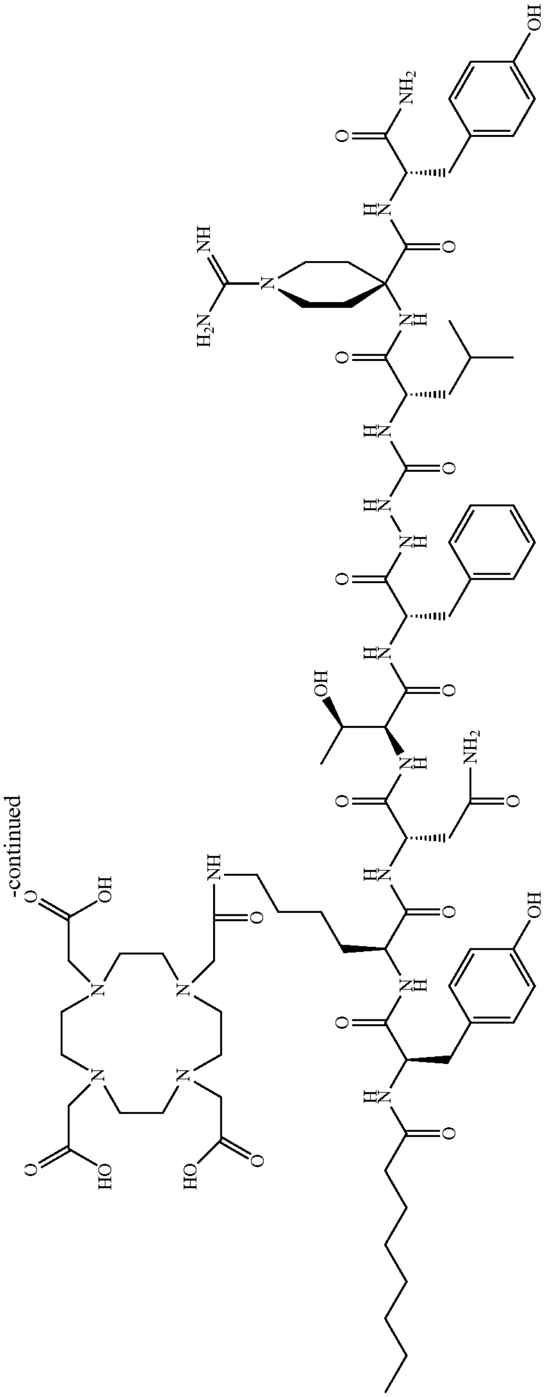
Compound 332

Peptide I-1 was prepared by standard Fmoc-based SPPS using $N^{\alpha}$/Fmoc-Rink amide resin. The details were outlined in Procedure A above (A-2, A-3, and A-4).

Peptide I-1 was treated with the mixture of Fmoc-$N_2H_3$ (3.0 Eq) and CDT (3.0 Eq) in NMP (10 mL/g resin) overnight at room temperature under nitrogen atmosphere. The reaction was operated manually. The reaction was washed with NMP (3×2 mL) to afford peptide I-2 on resin.

Elongation of I-2 was carried outby repeating Procedures A-3 and A-4 until peptide I-3 was obtained.

I-3 on resin (0.45 g) was treated with 2% hydrazine hydrate in NMP (5 mL) for 2 h under nitrogen atmosphere and then washed with NP (6×15 mL). To the resin in NMP (15 mL) were added DOTA(OSu) (279.8 mg, 0.56 mmol, 2.0 Eq) and DIEA (144.0 mg, 1.12 mmol, 4.0 Eq). The mixture was incubated for 2 h at room temperature and washed with NMP (6×15 mL) to afford I-4. The crude peptide was cleaved from the resin with a solution of TFA/$H_2O$/TIS/DODT (37:1:1:1 v/v/v/v, 15 mL) for 2 h at room temperature. The mixture was filtered, and the filtrate was concentrated under reduced pressure. The crude product was purified by RP-HPLC. The desired fractions were combined, concentrated and lyophilized to afford peptide I-5 (90.0 mg, overall yield 19.6%) as a white solid.

To a solution of peptide I-5 (90.0 mg, 0.055 mmol, 1.0 Eq) in DMF (1.0 mL) were added 1H-pyrazole-1-carboxamidine (60.3 mg, 0.550 mmol, 100 Eq) and DIEA (708 ng, 0.550 mmol, 10.0 Eq). The resulting mixture was stirred for 4 h at 30° C. The crude product was purified by RP-HPLC. The desired fractions were combined, concentrated and lyophilized to afford Compound 332 (69.2 mg, 98.9% purity, 74.2% yield) as a white solid. MS: Calc'd 1684.89, found $[M+2H]^{2+}$: 843.95.

Procedure J: General Synthesis Procedure for Metal Complexation

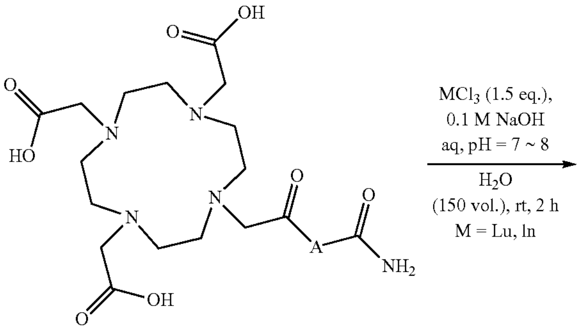

J-1

-continued

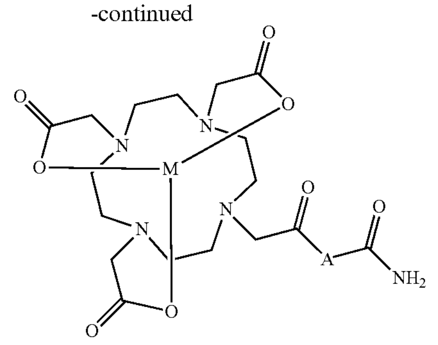

J-2

Compound J-1 (1.0 Eq) and $MCl_3$ (1.5 Eq) were dissolved in $H_2O$ (150.0 vol). The mixture was neutralized with 0.1 M aq. NaOH to pH=7-8. The mixture was stirred for 2 h at room temperature. The reaction was monitored by LCMS. Upon completion, the mixture was centrifuged, and the precipitate was purified by prep-HPLC and dried by lyophilization to afford J-2.

In compounds J-1 and J-2, "A" is a generic representation for the portion of each radionuclide conjugate molecule that connects the DOTA group to the amidated C-terminal carboxyl group of the peptide ligand. In other words, "A" is a generic representation for the portion of each radionuclide conjugate molecule that connects $R^a$ (or $R^a$ acomplexed with a metal) to the amidated C-terminal carboxyl group of the peptide ligand.

Procedure K: General Synthesis Procedure for $^{111}$In-Labeling

[$^{111}$In]In $Cl_3$ in HCl was added to a solution of a ligand in $NH_4OAc$ or NaOAc buffer (0.1 M, pH 5.0-5.5). The resulting mixture was heated at 60-95° C. in a thermal mixer for 15-30 min. Radiochemical purity was determined using iTLC or radio-HPLC analytical methods. The typical molar activities used in the studies ranged from 5-7 MBq/nmol to 10-15 MBq/nmol. The radiotracer solution for in vivo studies was formulated by dilution of the reaction mixture with 0.9% saline containing proper excipients based on stability studies.

Examples disclosed herein were prepared according to the procedures outlined above.

EXAMPLES

Example 1: Compound 1 (SEQ ID NO: 391)

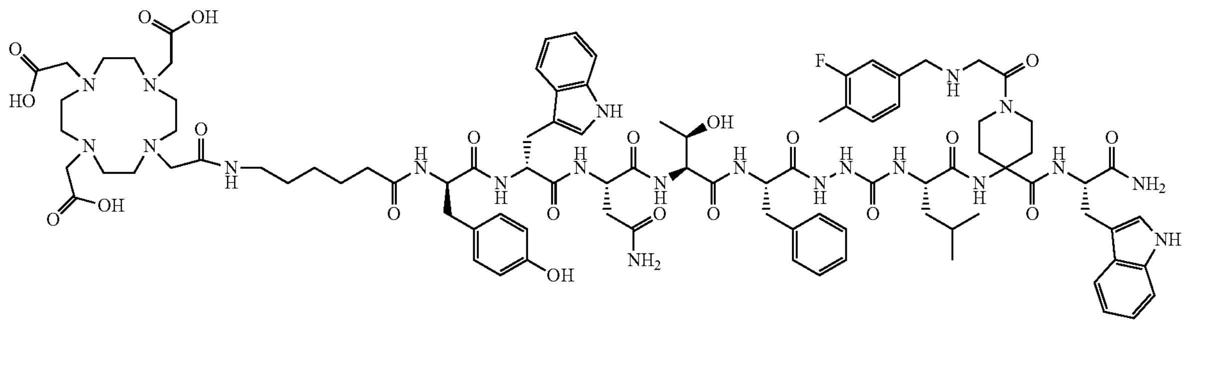 [SMILES: Cc1ccc(CNCC(=O)N2CCC(NC(=O)[C@H](CC(C)C)NC(=O)NNC(=O)[C@H](Cc3ccccc3)NC(=O)[C@@H](NC(=O)[C@H](CC(N)=O)NC(=O)[C@@H](Cc3c[nH]c4ccccc34)NC(=O)[C@@H](Cc3ccc(O)cc3)NC(=O)CCCCCNC(=O)CN3CCN(CC(=O)O)CCN(CC(=O)O)CCN(CC(=O)O)CC3)[C@@H](C)O)(C(=O)N[C@@H](Cc3c[nH]c4ccccc34)C(N)=O)CC2)cc1F]

MS: Calc'd for $C_{93}H_{124}FN_{21}O_{21}$: 1889.9, found $[M+2H]^{2+}$: 946.4.
Compound 1-In (SEQ ID NO: 392)
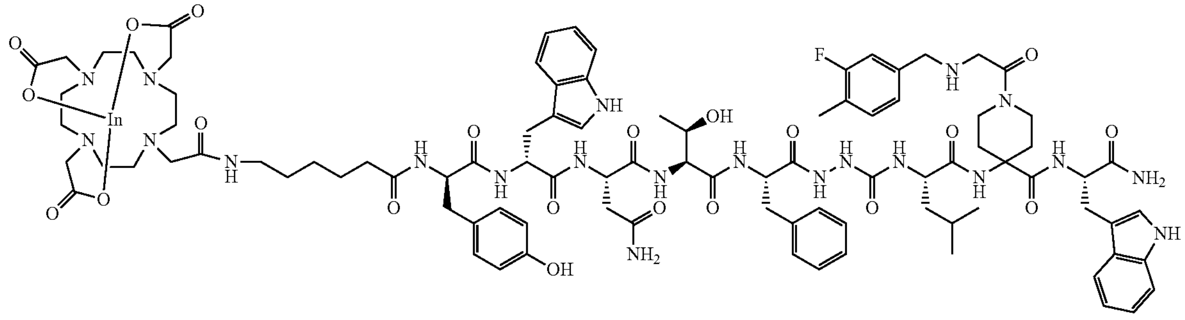
MS: Calc'd for $C_{93}H_{121}FInN_{21}O_{21}$: 2001.8, found $[M+2H]^{2+}$: 1002.5.
Compound 1-Lu (SEQ ID NO: 393)
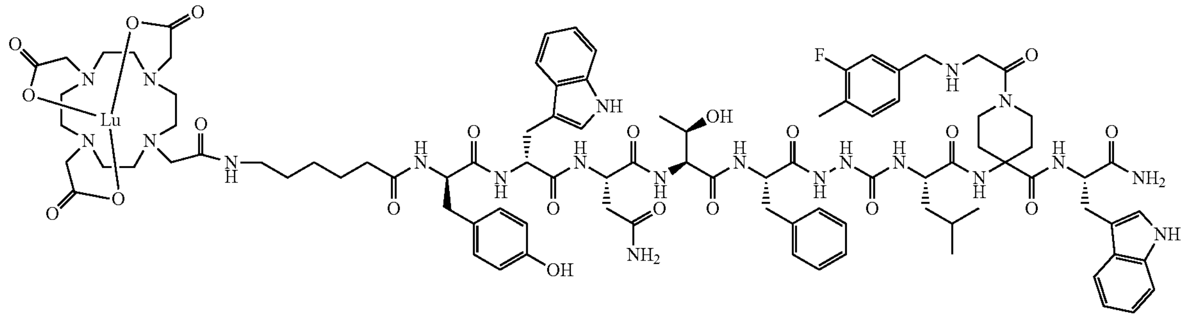
MS: Calc'd for $C_{93}H_{121}FLuN_{21}O_{21}$: 2061.8, found $[M+H]^{+}$: 2062.8.
Compound 1-Ga (SEQ ID NO: 394)
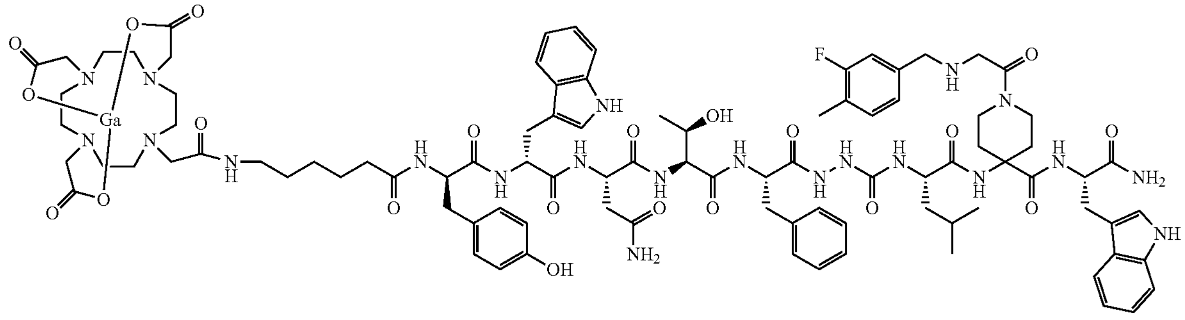
MS: Calc'd for $C_{93}H_{121}FGaN_{21}O_{21}$: 1955.83, found $[M+2H]^{2+}$: 979.75.

Example 2: Compound 2 (SEQ ID NO: 395)
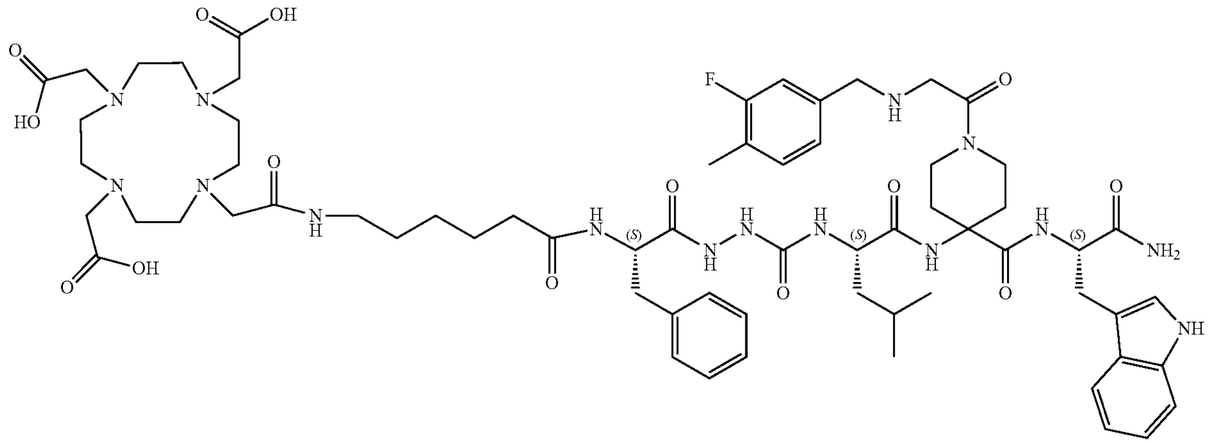
MS: Calc'd for $C_{65}H_{92}FN_{15}O_{14}$: 1325.7, found $[M+H]^+$: 1326.6.
Compound 2-In (SEQ ID NO: 771)
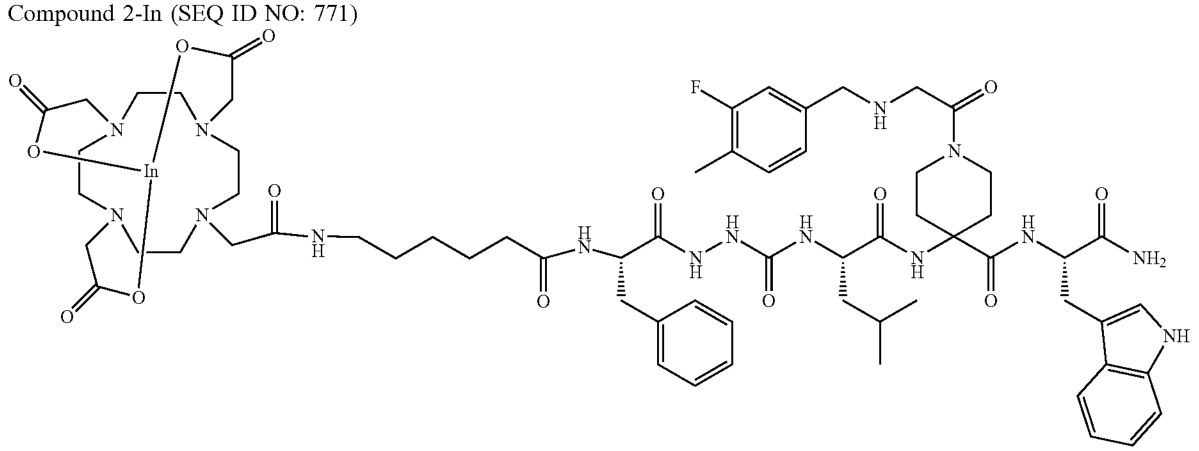
MS: Calc'd for $Cs_{65}H_{89}FInN_{15}O_{14}$: 1437.6, found $[M+H]^+$: 1439.0.
Example 3: Compound 3 (SEQ ID NO: 396)
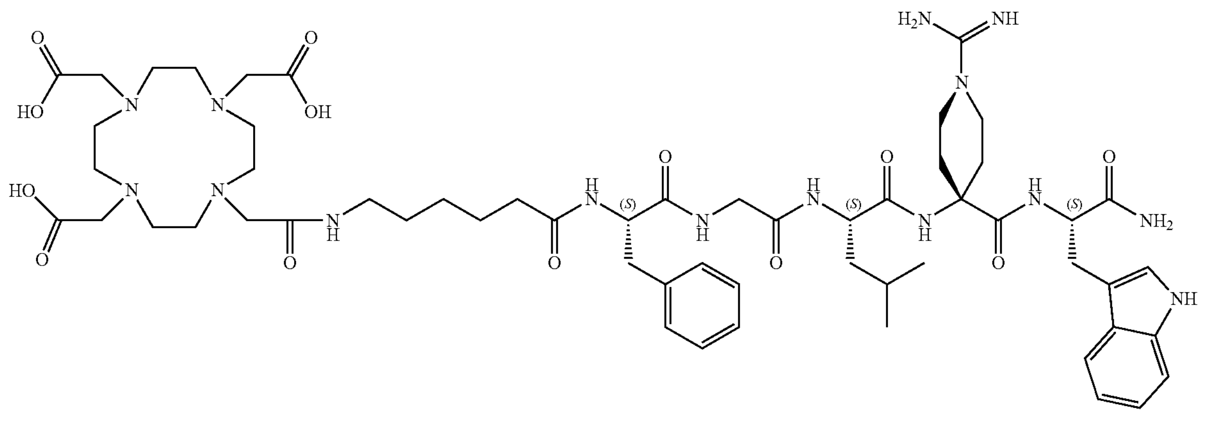
MS: Calc'd for $C_{57}H_{85}N_{15}O_{13}$: 1187.6, found $[M+2H]^{2+}$: 595.2.

Example 4: Compound 4 (SEQ ID NO. 397)
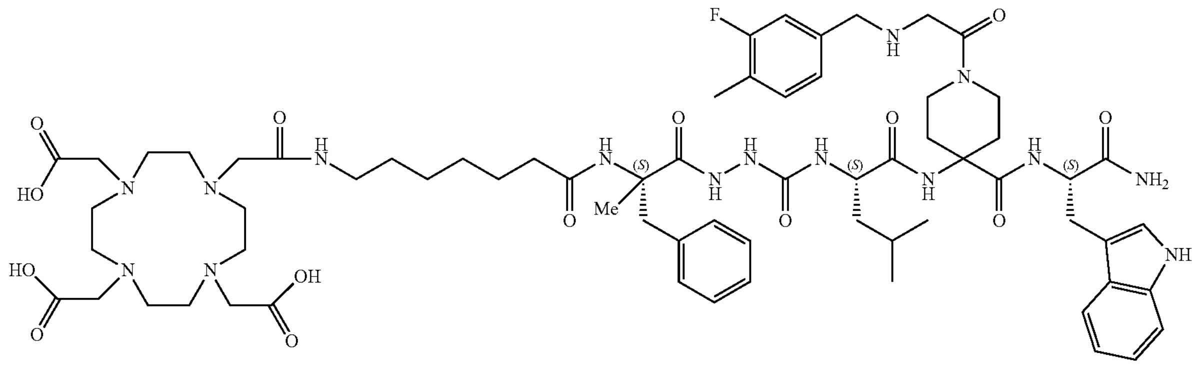
MS: Calc'd for $C_{85}H_{118}N_{22}O_{20}$: 1766.9, found $[M+2H]^{2+}$: 885.0.
Example 5: Compound 5 (SEQ ID NO: 398)
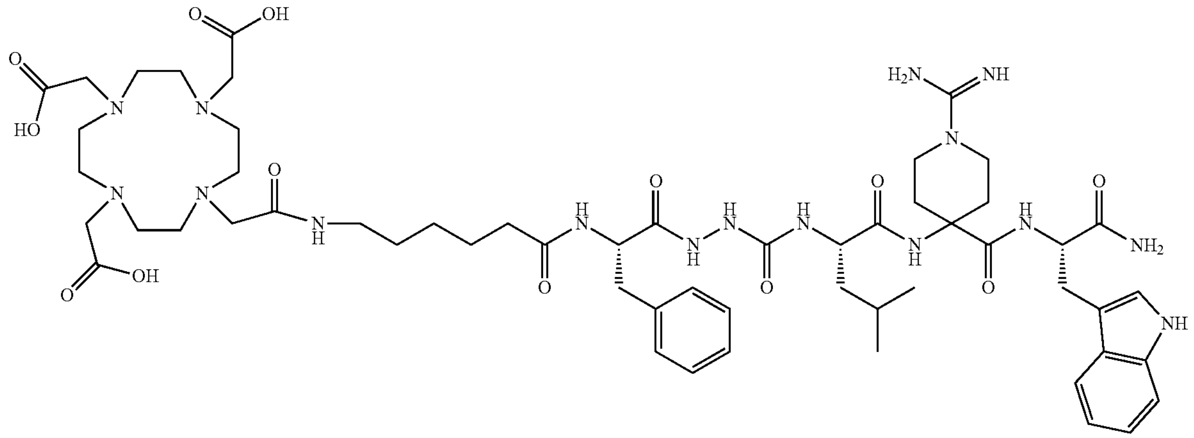 [SMILES: CC(C)C[C@H](NC(=O)NNC(=O)[C@H](Cc1ccccc1)NC(=O)CCCCCNC(=O)CN1CCN(CC(=O)O)CCN(CC(=O)O)CCN(CC(=O)O)CC1)C(=O)NC1(C(=O)N[C@@H](Cc2c[nH]c3ccccc23)C(N)=O)CCN(C(=N)N)CC1]
MS: Calc'd for $C_{56}H_{84}N_{16}O_{13}$: 1188.6, found $[M+2H]^{2+}$: 595.6.
Example 6: Compound 6 (SEQ ID NO: 399)
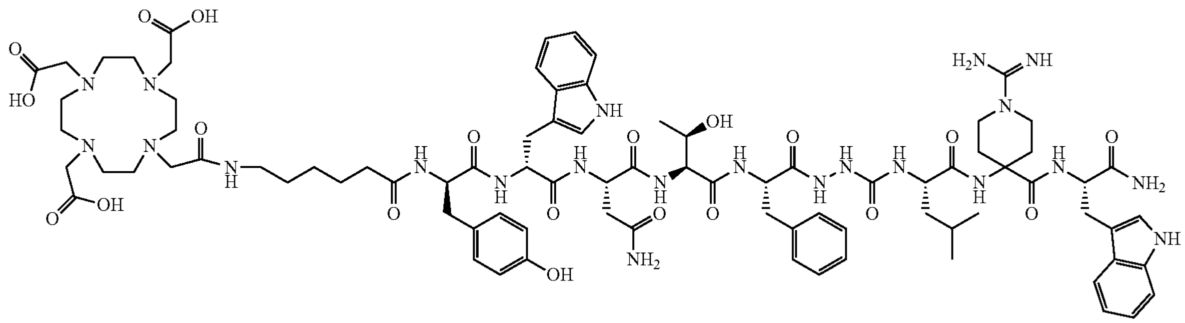 [SMILES: CC(C)C[C@H](NC(=O)NNC(=O)[C@H](Cc1ccccc1)NC(=O)[C@@H](NC(=O)[C@H](CC(N)=O)NC(=O)[C@@H](Cc1c[nH]c2ccccc12)NC(=O)[C@@H](Cc1ccc(O)cc1)NC(=O)CCCCCNC(=O)CN1CCN(CC(=O)O)CCN(CC(=O)O)CCN(CC(=O)O)CC1)[C@@H](C)O)C(=O)NC1(C(=O)N[C@@H](Cc2c[nH]c3ccccc23)C(N)=O)CCN(C(=N)N)CC1]
MS: Calc'd for $C_{84}H_{116}N_{22}O_{20}$: 1752.9, found $[M+2H]^{2+}$: 877.6.

Compound 6-In (SEQ ID NO: 772)
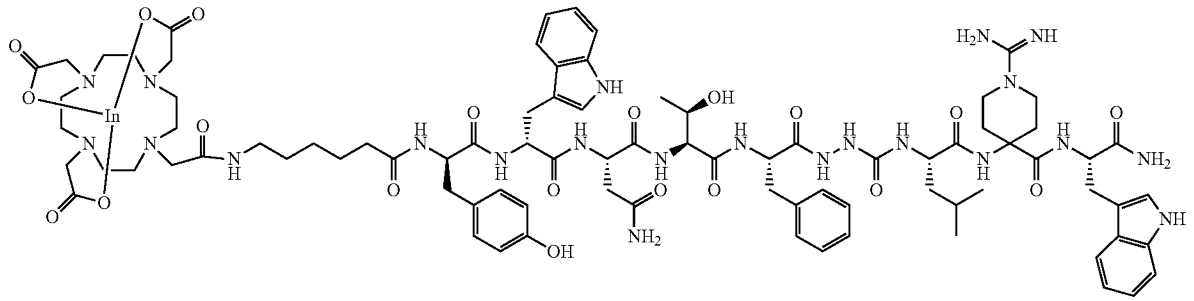
MS: Calc'd for $C_{84}H_{116}InN_{22}O_{20}$: 1864.8, found $[M-H]^-$: 1863.9.
Example 7: Compound 7 (SEQ ID NO: 400)
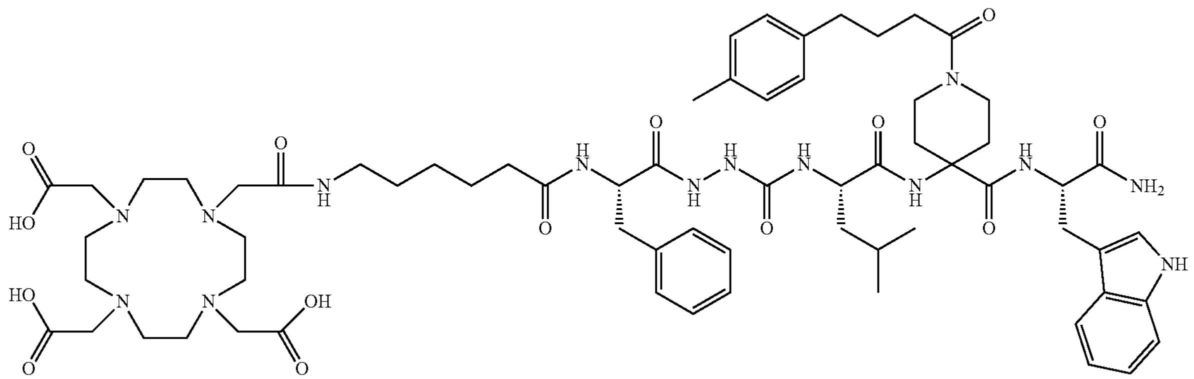 [SMILES: Cc1ccc(CCCC(=O)N2CCC(NC(=O)[C@H](CC(C)C)NC(=O)NNC(=O)[C@H](Cc3ccccc3)NC(=O)CCCCCNC(=O)CN3CCN(CC(=O)O)CCN(CC(=O)O)CCN(CC(=O)O)CC3)(C(=O)N[C@@H](Cc3c[nH]c4ccccc34)C(N)=O)CC2)cc1]
MS: Calc'd for $C_{66}H_{94}N_{14}O_{14}$: 1306.7, found $[M+H]^+$: 1307.8.
Example 8: Compound 8
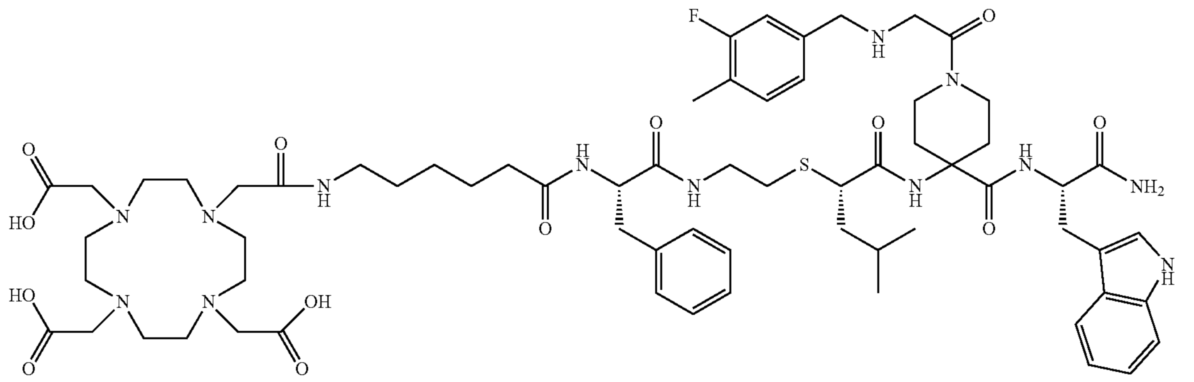 [SMILES: Cc1ccc(CNCC(=O)N2CCC(NC(=O)[C@H](CC(C)C)SCCNC(=O)[C@H](Cc3ccccc3)NC(=O)CCCCCNC(=O)CN3CCN(CC(=O)O)CCN(CC(=O)O)CCN(CC(=O)O)CC3)(C(=O)N[C@@H](Cc3c[nH]c4ccccc34)C(N)=O)CC2)cc1F]
MS: Calc'd for $C_{66}H_{94}FN_{13}O_{13}S$: 1327.7, found $[M+H]^+$: 1328.3.

Example 9: Compound 9
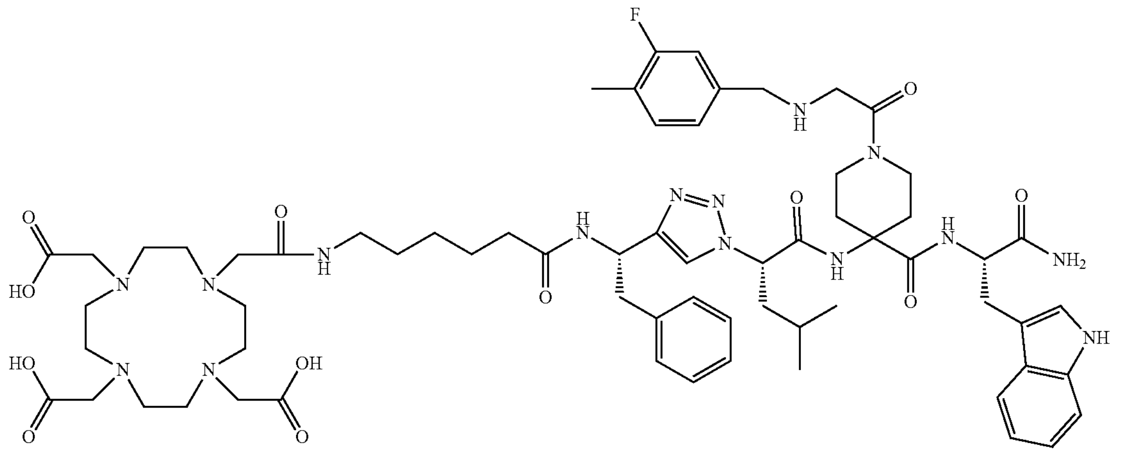 [SMILES: Cc1ccc(CNCC(=O)N2CCC(NC(=O)[C@H](CC(C)C)n3cc([C@H](Cc4ccccc4)NC(=O)CCCCCNC(=O)CN4CCN(CC(=O)O)CCN(CC(=O)O)CCN(CC(=O)O)CC4)nn3)(C(=O)N[C@@H](Cc3c[nH]c4ccccc34)C(N)=O)CC2)cc1F]
MS: Calc'd 1291.7, found $[M+2H]^{2+}$: 647.2.
Example 10: Compound 10 (SEQ ID NO. 403)
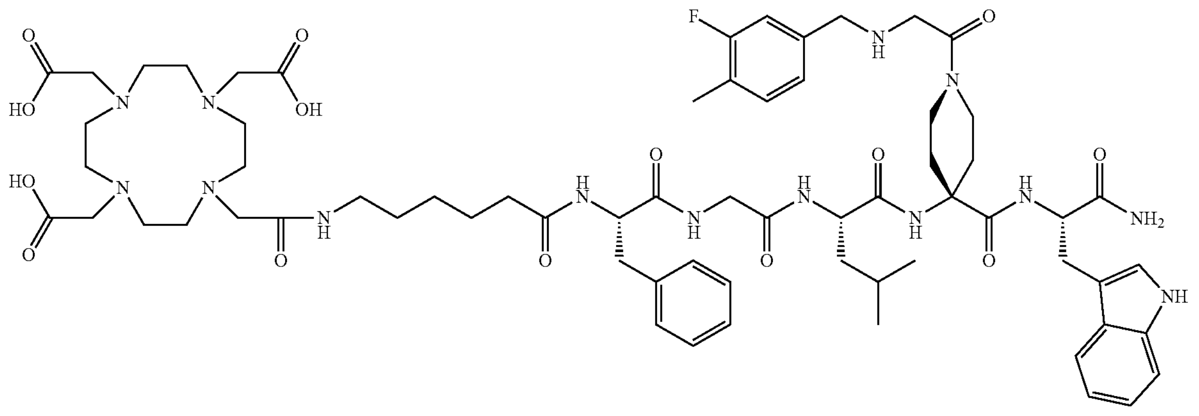
MS: Calc'd for $C_{66}H_{93}FN_{14}O_{14}$: 1324.7, found $[M+H]^+$: 1325.7.
Example 11: Compound 11 (SEQ ID NO: 404)
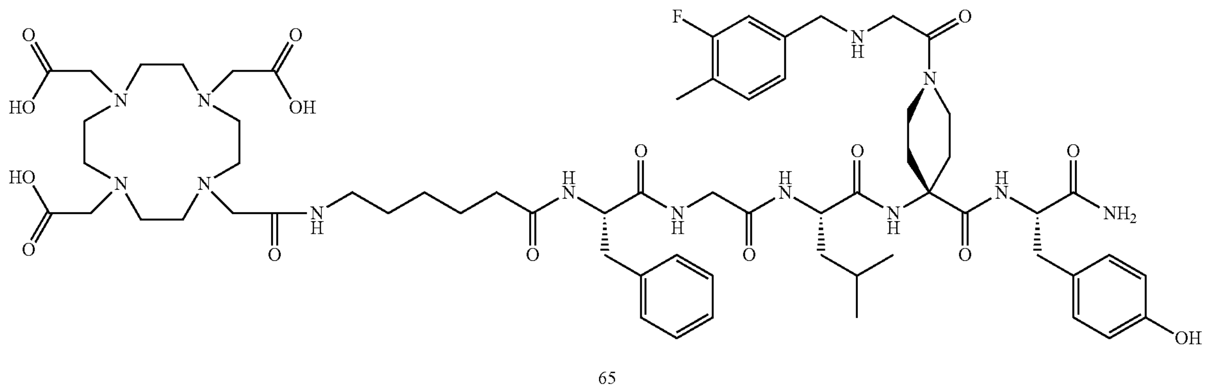
MS: Calc'd for $C_{64}H_{92}FN_{13}O_{15}$: 1301.7, found $[M+H]^+$: 1302.8.

Example 12: Compound 12 (SEQ ID NO: 405)
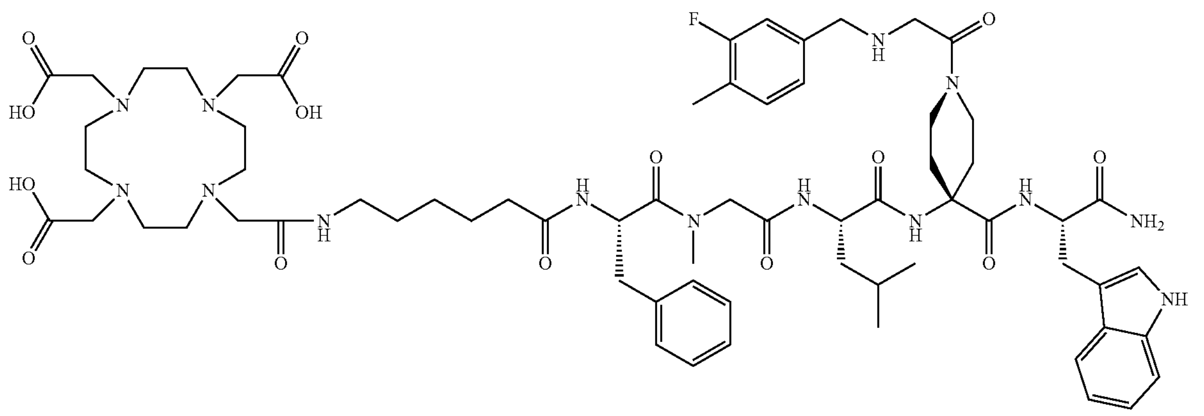
MS: Calc'd for $C_{67}H_{95}FN_{14}O_{14}$: 1338.7, found $[M+2H]^{2+}$: 670.8.
Example 13: Compound 13 (SEQ ID NO: 406)
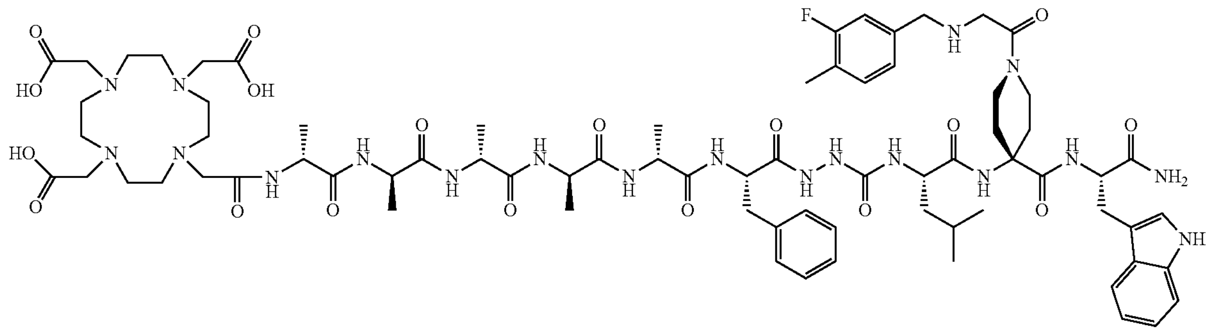
MS: Calc'd for $C_{74}H_{106}FN_{19}O_{18}$: 1567.8, found $[M+2H]^{2+}$: 785.4.
Example 14: Compound 14 (SEQ ID NO: 407)
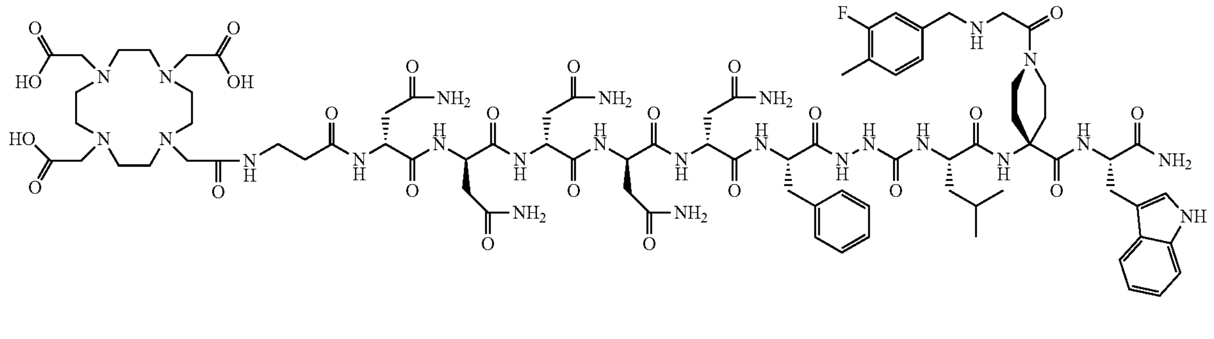
MS: Calc'd for $C_{82}H_{116}FN_{25}O_{24}$: 1853.9, found $[M+2H]^{2+}$: 928.5.

Example 15: Compound 15 (SEQ ID NO: 408)
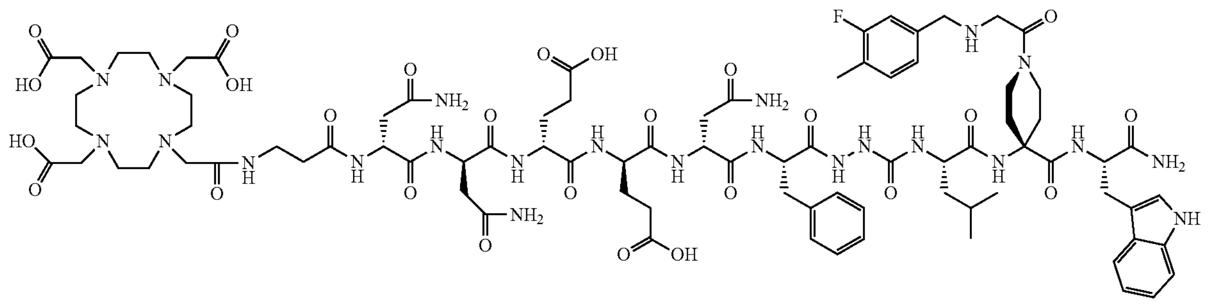
MS: Calc'd for $C_{84}H_{118}FN_{23}O_{26}$: 1883.9, found $[M+2H]^{2+}$: 943.5.
Example 16: Compound 16 (SEQ ID NO: 409)
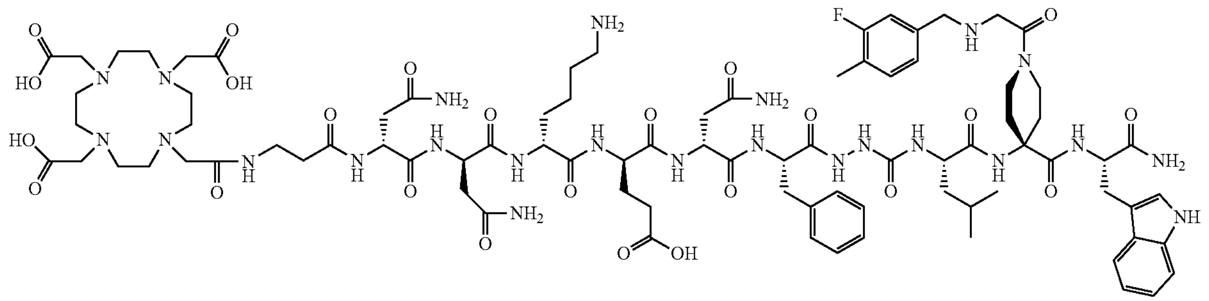
MS: Calc'd for $C_{85}H_{123}FN_{24}O_{24}$: 1882.9, found $[M+2H]^{2+}$: 943.1.
Example 17: Compound 17 (SEQ ID NO: 410)
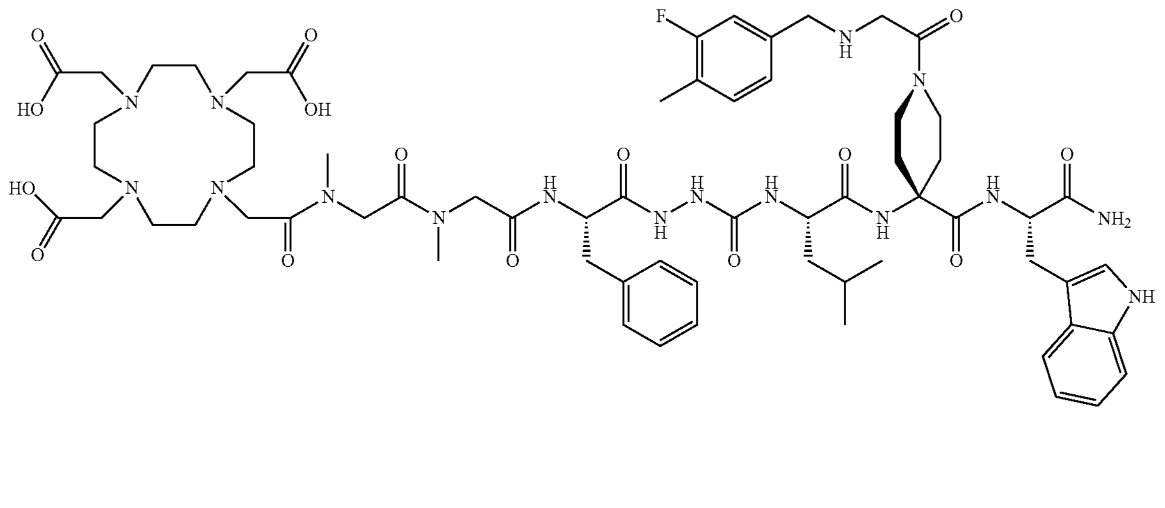
MS: Calc'd for 1354.7, found $[M+H]^{+}$: 1355.8.

Example 18: Compound 18 (SEQ ID NO: 411)
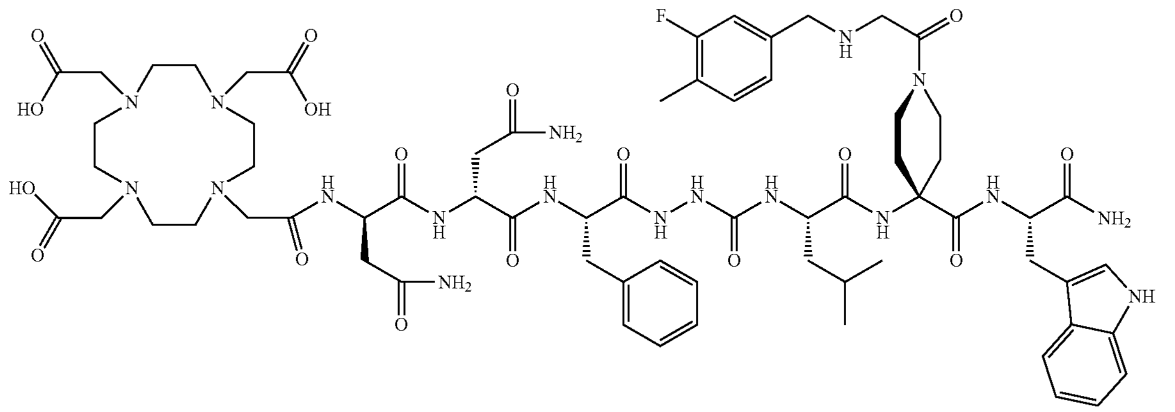
MS: Calc'd for $C_{67}H_{93}FN_{18}O_{17}$: 1440.7, found $[M+2H]^{2+}$: 721.9.
Example 19: Compound 19 (SEQ ID NO: 412)
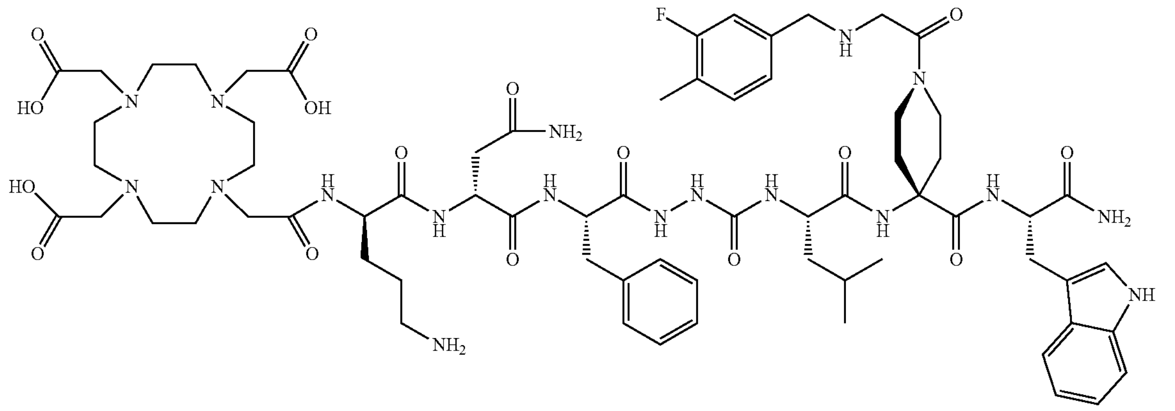
MS: Calc'd for $C_{68}H_{97}FN_{18}O_{16}$: 1410.7, found $[M+2H]^{2+}$: 721.8.
Example 20: Compound 20 (SEQ ID NO. 413)
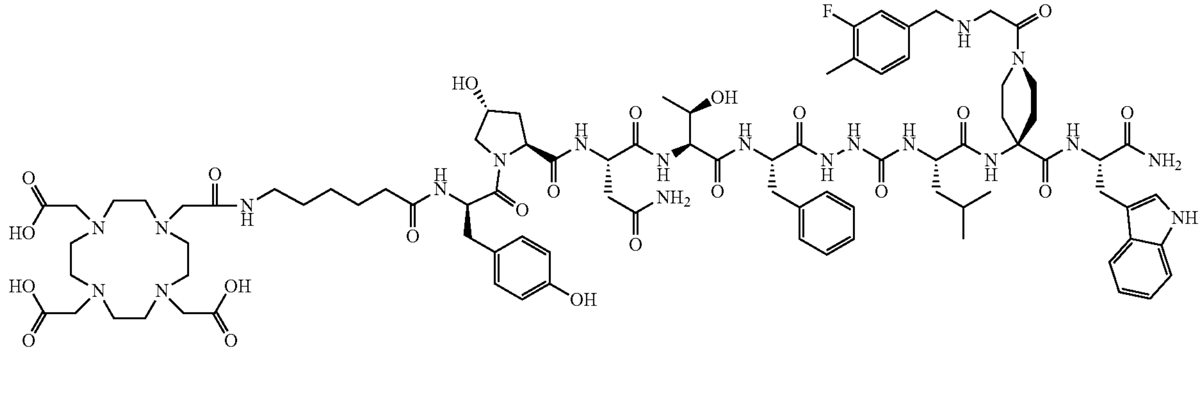
MS: Calc'd 1816.9, found $[M+H]^{+}$: 1818.2.

Example 21: Compound 21 (SEQ ID NO: 414)
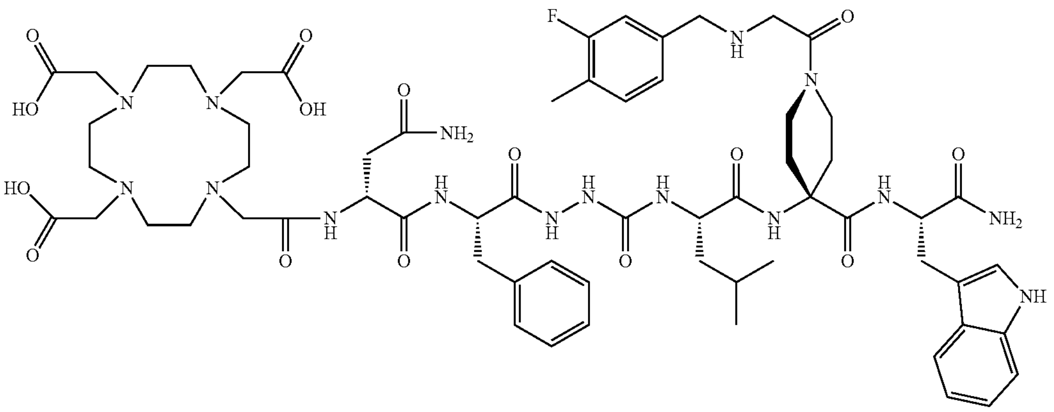
MS: Calc'd 1326.7, found $[M+H]^+$: 1327.8.
Example 22: Compound 22 (SEQ ID NO: 415)
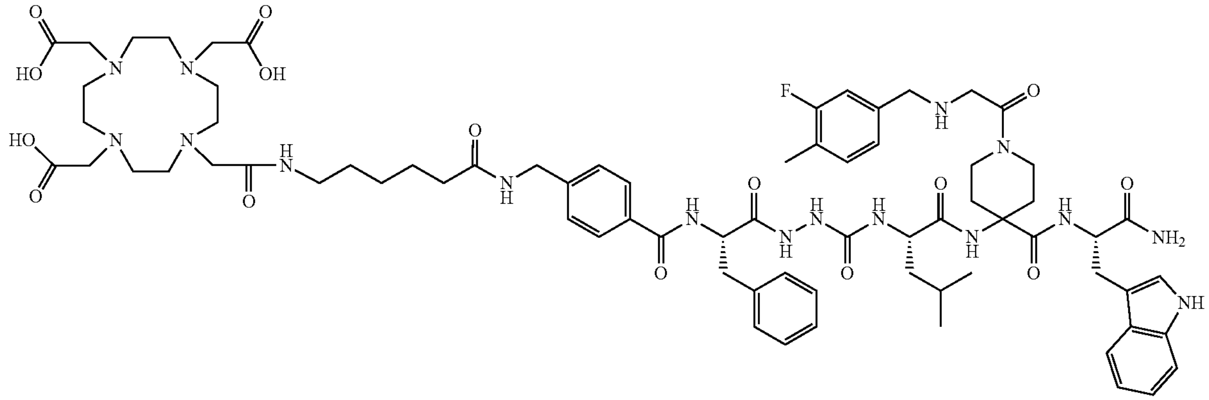 [SMILES: Cc1ccc(CNCC(=O)N2CCC(NC(=O)[C@H](CC(C)C)NC(=O)NNC(=O)[C@H](Cc3ccccc3)NC(=O)c3ccc(CNC(=O)CCCCCNC(=O)CN4CCN(CC(=O)O)CCN(CC(=O)O)CCN(CC(=O)O)CC4)cc3)(C(=O)N[C@@H](Cc3c[nH]c4ccccc34)C(N)=O)CC2)cc1F]
MS: Calc'd 1458.7, found $[M+H]^+$: 1459.9.
Example 23: Compound 23 (SEQ ID NO: 416)
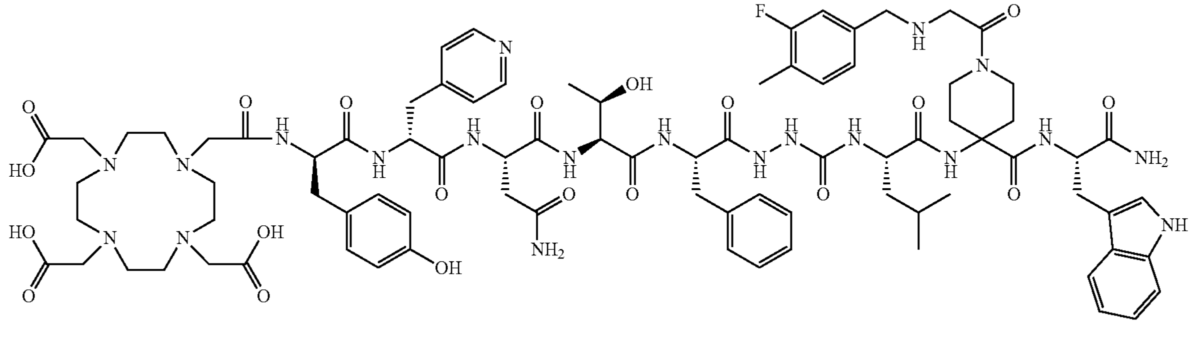 [SMILES: Cc1ccc(CNCC(=O)N2CCC(NC(=O)[C@H](CC(C)C)NC(=O)NNC(=O)[C@H](Cc3ccccc3)NC(=O)[C@@H](NC(=O)[C@H](CC(N)=O)NC(=O)[C@@H](Cc3ccncc3)NC(=O)[C@@H](Cc3ccc(O)cc3)NC(=O)CN3CCN(CC(=O)O)CCN(CC(=O)O)CCN(CC(=O)O)CC3)[C@@H](C)O)(C(=O)N[C@@H](Cc3c[nH]c4ccccc34)C(N)=O)CC2)cc1F]
MS: Calc'd 1738.8, found $[M+2H]^{2+}$: 870.9.

Example 24: Compound 24 (SEQ ID NO: 417)
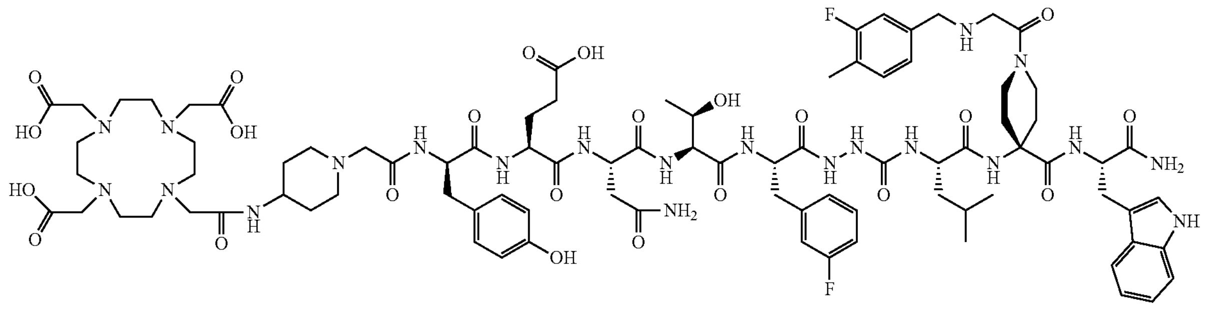
MS: Calc'd 1877.9, found $[M+2H]^{2+}$: 940.5.
Example 25: Compound 25 (SEQ ID NO: 418)
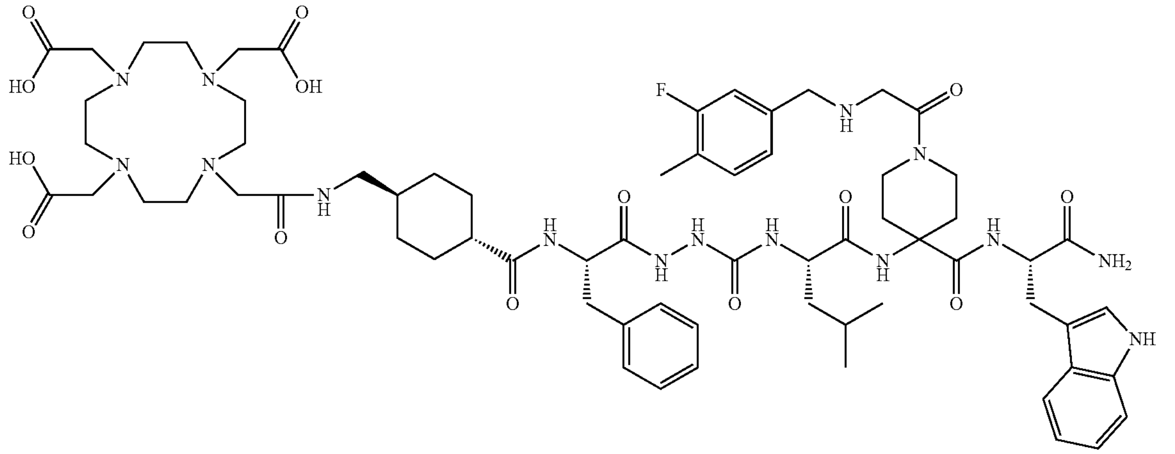 [SMILES: Cc1ccc(CNCC(=O)N2CCC(NC(=O)[C@H](CC(C)C)NC(=O)NNC(=O)[C@H](Cc3ccccc3)NC(=O)[C@H]3CC[C@H](CNC(=O)CN4CCN(CC(=O)O)CCN(CC(=O)O)CCN(CC(=O)O)CC4)CC3)(C(=O)N[C@@H](Cc3c[nH]c4ccccc34)C(N)=O)CC2)cc1F]
MS: Calc'd 1351.7, found $[M+2H]^{2+}$: 676.9.
Example 26: Compound 26 (SEQ ID NO: 419)
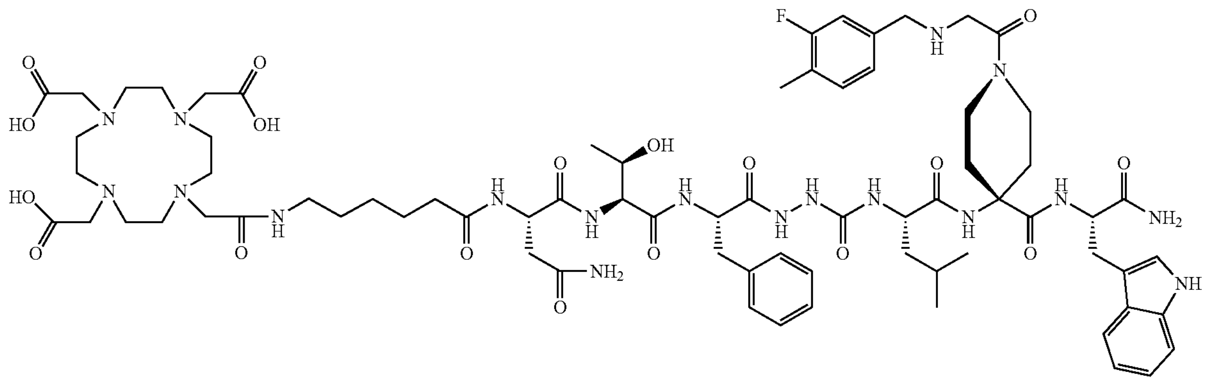
MS: Calc'd 1540.8, found $[M+2H]^{2+}$: 771.8.

Example 27: Compound 27 (SEQ ID NO. 420)
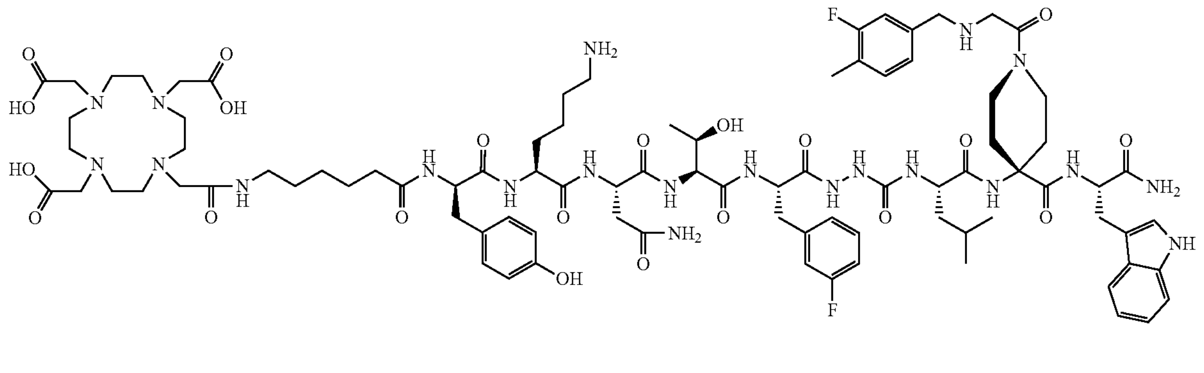
MS: Calc'd 1850.0, found $[M+2H]^{2+}$: 926.5.
Example 28: Compound 28 (SEQ ID NO 421)
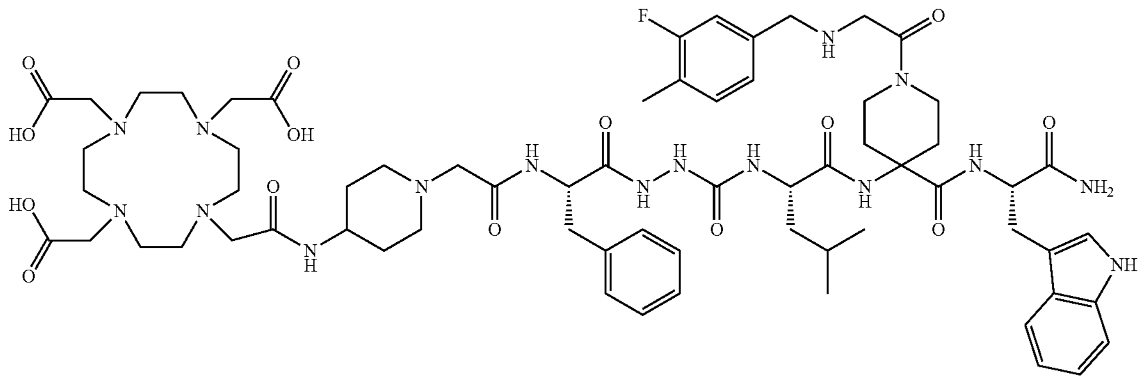 [SMILES: Cc1ccc(CNCC(=O)N2CCC(NC(=O)[C@H](CC(C)C)NC(=O)NNC(=O)[C@H](Cc3ccccc3)NC(=O)CN3CCC(NC(=O)CN4CCN(CC(=O)O)CCN(CC(=O)O)CCN(CC(=O)O)CC4)CC3)(C(=O)N[C@@H](Cc3c[nH]c4ccccc34)C(N)=O)CC2)cc1F]
MS: Calc'd 1352.7, found $[M+2H]^{2+}$: 677.7.
Example 29. Compound 29 (SEQ ID NO: 422)
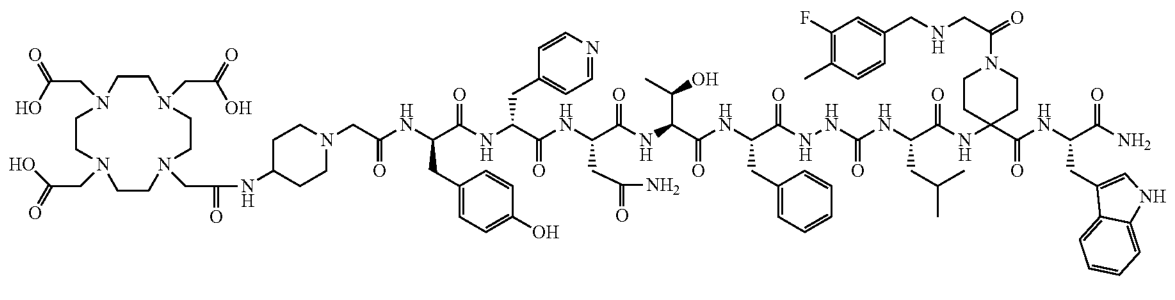 [SMILES: Cc1ccc(CNCC(=O)N2CCC(NC(=O)[C@H](CC(C)C)NC(=O)NNC(=O)[C@H](Cc3ccccc3)NC(=O)[C@@H](NC(=O)[C@H](CC(N)=O)NC(=O)[C@@H](Cc3ccncc3)NC(=O)[C@@H](Cc3ccc(O)cc3)NC(=O)CN3CCC(NC(=O)CN4CCN(CC(=O)O)CCN(CC(=O)O)CCN(CC(=O)O)CC4)CC3)[C@@H](C)O)(C(=O)N[C@@H](Cc3c[nH]c4ccccc34)C(N)=O)CC2)cc1F]
MS: Calc'd 1878.9, found $[M+2H]^{2+}$: 940.9.

Example 30: Compound 30 (SEQ ID NO: 423)
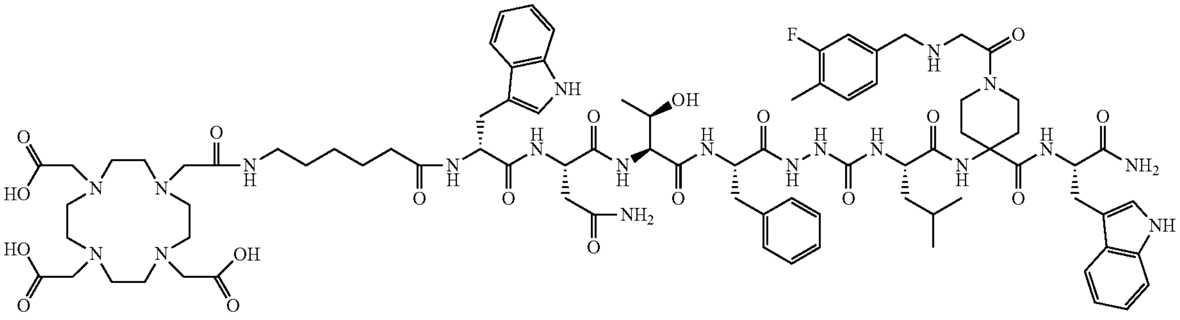 [SMILES: Cc1ccc(CNCC(=O)N2CCC(NC(=O)[C@H](CC(C)C)NC(=O)NNC(=O)[C@H](Cc3ccccc3)NC(=O)[C@@H](NC(=O)[C@H](CC(N)=O)NC(=O)[C@@H](Cc3c[nH]c4ccccc34)NC(=O)CCCCCNC(=O)CN3CCN(CC(=O)O)CCN(CC(=O)O)CCN(CC(=O)O)CC3)[C@@H](C)O)(C(=O)N[C@@H](Cc3c[nH]c4ccccc34)C(N)=O)CC2)cc1F]
MS: Calc'd 1726.9, found $[M+2H]^{2+}$: 864.8.
Example 31: Compound 31 (SEQ ID NO. 424)
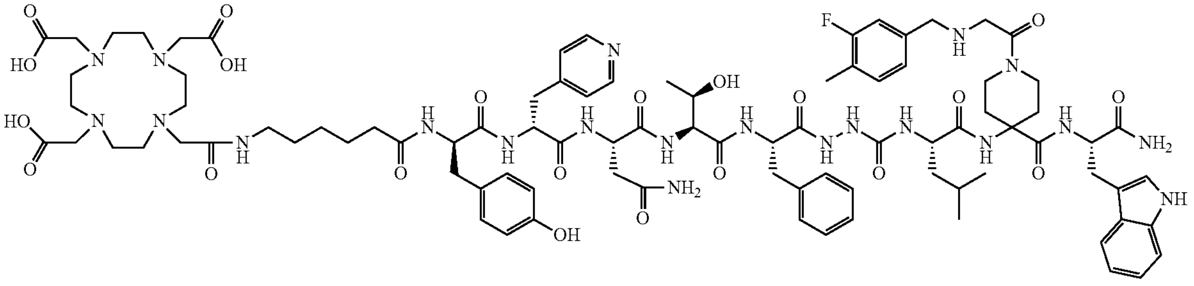 [SMILES: Cc1ccc(CNCC(=O)N2CCC(NC(=O)[C@H](CC(C)C)NC(=O)NNC(=O)[C@H](Cc3ccccc3)NC(=O)[C@@H](NC(=O)[C@H](CC(N)=O)NC(=O)[C@@H](Cc3ccncc3)NC(=O)[C@@H](Cc3ccc(O)cc3)NC(=O)CCCCCNC(=O)CN3CCN(CC(=O)O)CCN(CC(=O)O)CCN(CC(=O)O)CC3)[C@@H](C)O)(C(=O)N[C@@H](Cc3c[nH]c4ccccc34)C(N)=O)CC2)cc1F]
MS: Calc'd 1851.9, found $[M+2H]^{2+}$: 927.6.
Example 32: Compound 32 (SEQ ID NO: 425)
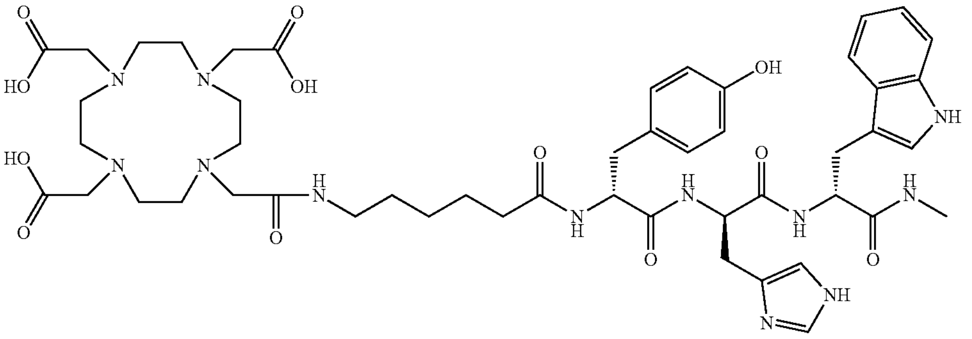

-continued
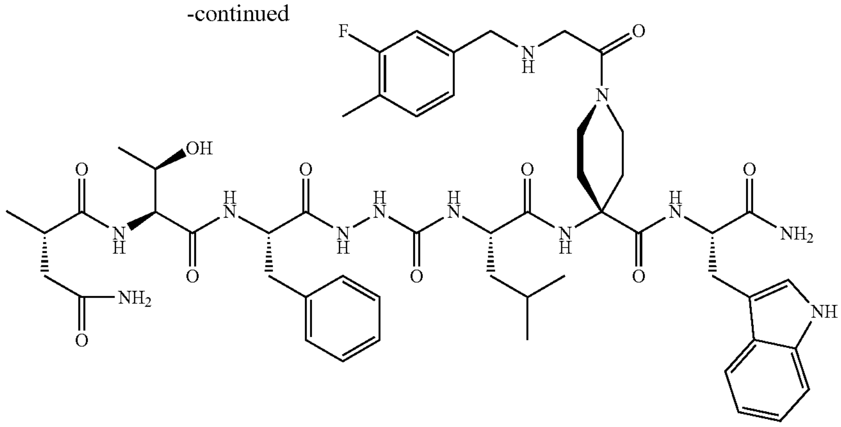
MS: Calc'd 2027.0, found $[M+2H]^{2+}$: 1014.8.
Example 33: Compound 33 (SEQ ID NO: 426)
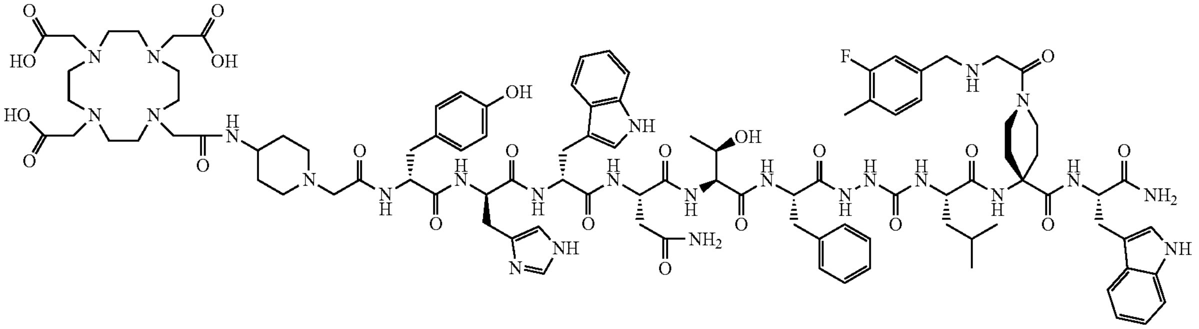
MS: Calc'd 2054.0, found $[M+2H]^{2+}$: 1028.6.
Example 34: Compound 34 (SEQ ID NO: 427)
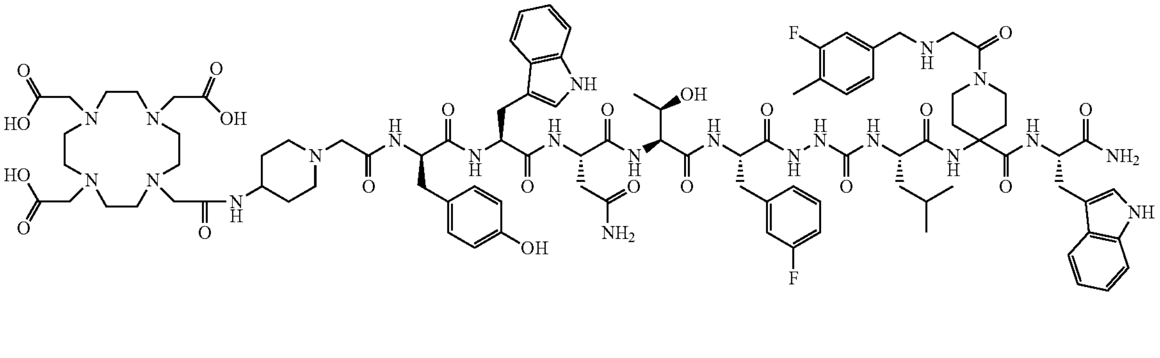 [SMILES: Cc1ccc(CNCC(=O)N2CCC(NC(=O)[C@H](CC(C)C)NC(=O)NNC(=O)[C@H](Cc3cccc(F)c3)NC(=O)[C@@H](NC(=O)[C@H](CC(N)=O)NC(=O)[C@H](Cc3c[nH]c4ccccc34)NC(=O)[C@@H](Cc3ccc(O)cc3)NC(=O)CN3CCC(NC(=O)CN4CCN(CC(=O)O)CCN(CC(=O)O)CCN(CC(=O)O)CC4)CC3)[C@@H](C)O)(C(=O)N[C@@H](Cc3c[nH]c4ccccc34)C(N)=O)CC2)cc1F]
MS: Calc'd 1935.0, found $[M+2H]^{2+}$: 969.0.

Example 35: Compound 35 (SEQ ID NO: 428)
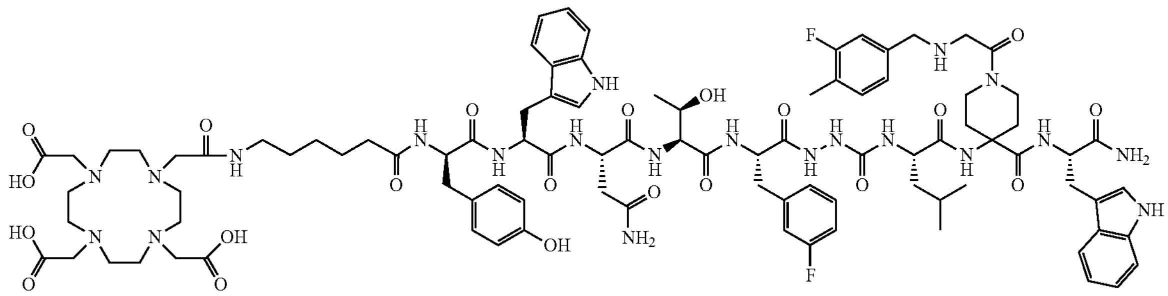 [SMILES: Cc1ccc(CNCC(=O)N2CCC(NC(=O)[C@H](CC(C)C)NC(=O)NNC(=O)[C@H](Cc3cccc(F)c3)NC(=O)[C@@H](NC(=O)[C@H](CC(N)=O)NC(=O)[C@H](Cc3c[nH]c4ccccc34)NC(=O)[C@@H](Cc3ccc(O)cc3)NC(=O)CCCCCNC(=O)CN3CCN(CC(=O)O)CCN(CC(=O)O)CCN(CC(=O)O)CC3)[C@@H](C)O)(C(=O)N[C@@H](Cc3c[nH]c4ccccc34)C(N)=O)CC2)cc1F]
MS: Calc'd 1907.9, found $[M+2H]^{2+}$: 955.5.
Example 36: Compound 36 (SEQ ID NO: 429)
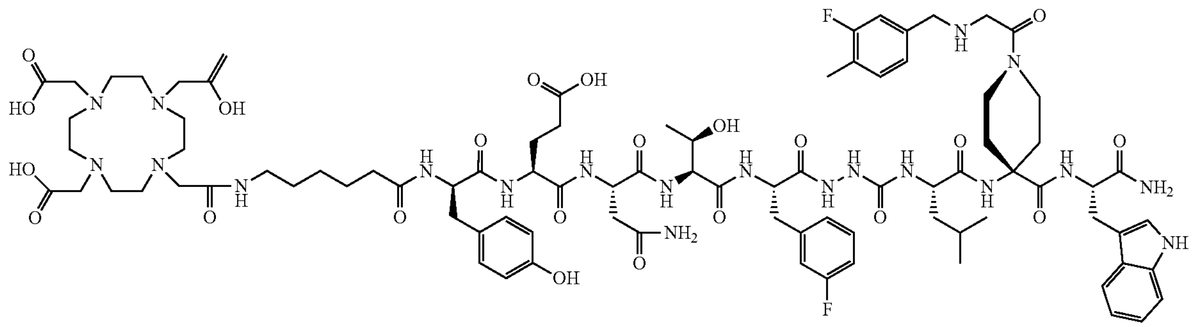
MS: Calc'd 1850.9, found $[M+3H]^{3+}$: 618.4.
Example 37: Compound 37 (SEQ ID NO: 430)
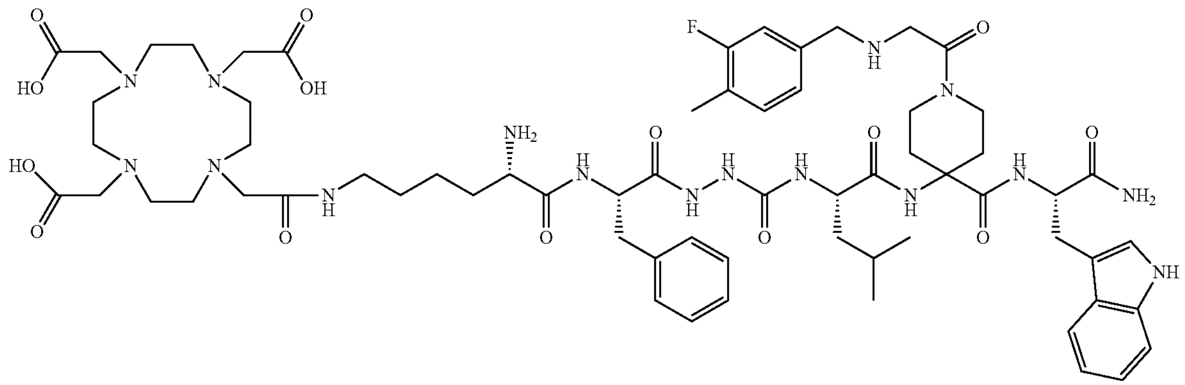 [SMILES: Cc1ccc(CNCC(=O)N2CCC(NC(=O)[C@H](CC(C)C)NC(=O)NNC(=O)[C@H](Cc3ccccc3)NC(=O)[C@@H](N)CCCCNC(=O)CN3CCN(CC(=O)O)CCN(CC(=O)O)CCN(CC(=O)O)CC3)(C(=O)N[C@@H](Cc3c[nH]c4ccccc34)C(N)=O)CC2)cc1F]
MS: Calc'd 1340.71 found $[M+H]^{+}$: 1341.7.

Example 38: Compound 38 (SEQ ID NO: 431)
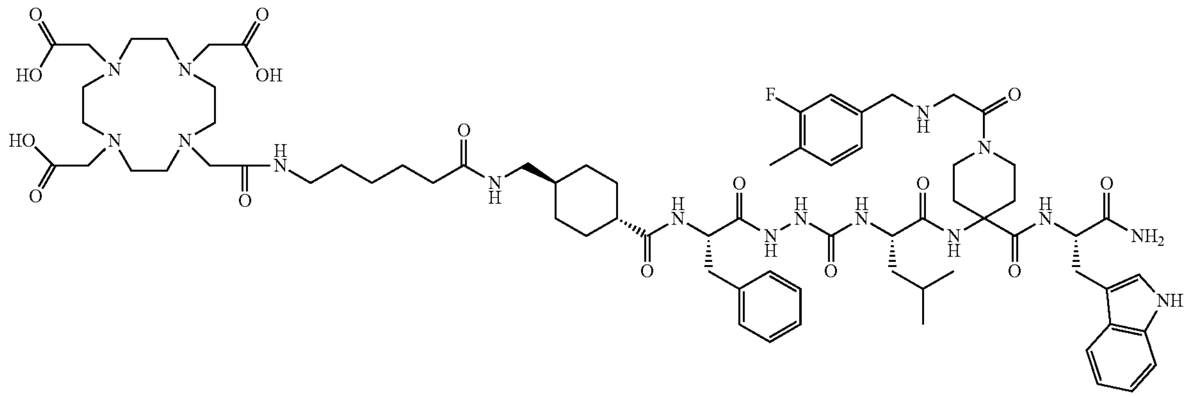 [SMILES: Cc1ccc(CNCC(=O)N2CCC(NC(=O)[C@H](CC(C)C)NC(=O)NNC(=O)[C@H](Cc3ccccc3)NC(=O)[C@H]3CC[C@H](CNC(=O)CCCCCNC(=O)CN4CCN(CC(=O)O)CCN(CC(=O)O)CCN(CC(=O)O)CC4)CC3)(C(=O)N[C@@H](Cc3c[nH]c4ccccc34)C(N)=O)CC2)cc1F]
MS: Calc'd 1464.8, found $[M+H]^+$: 1465.8.
Example 39: Compound 39
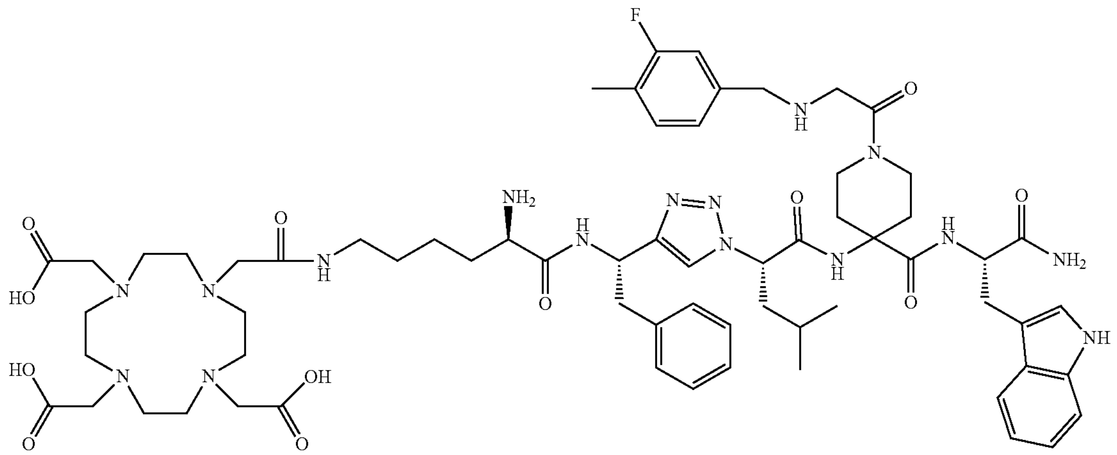 [SMILES: Cc1ccc(CNCC(=O)N2CCC(NC(=O)[C@H](CC(C)C)n3cc([C@H](Cc4ccccc4)NC(=O)[C@H](N)CCCCNC(=O)CN4CCN(CC(=O)O)CCN(CC(=O)O)CCN(CC(=O)O)CC4)nn3)(C(=O)N[C@@H](Cc3c[nH]c4ccccc34)C(N)=O)CC2)cc1F]
MS: Calc'd 1306.7, found $[M+2H]^{2+}$: 654.8.
Example 40: Compound 49 (SEQ ID NO: 441)
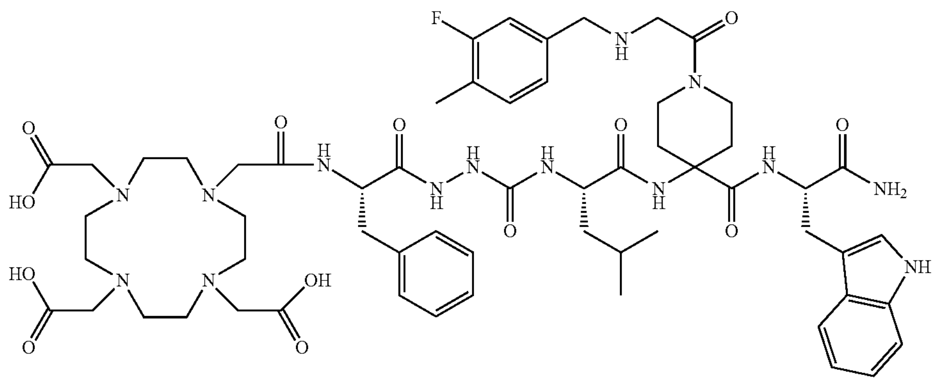 [SMILES: Cc1ccc(CNCC(=O)N2CCC(NC(=O)[C@H](CC(C)C)NC(=O)NNC(=O)[C@H](Cc3ccccc3)NC(=O)CN3CCN(CC(=O)O)CCN(CC(=O)O)CCN(CC(=O)O)CC3)(C(=O)N[C@@H](Cc3c[nH]c4ccccc34)C(N)=O)CC2)cc1F]
MS: Calc'd 1212.61 found $[M+2H]^{2+}$: 607.7.

Example 41: Compound 50 (SEQ ID NO: 442)
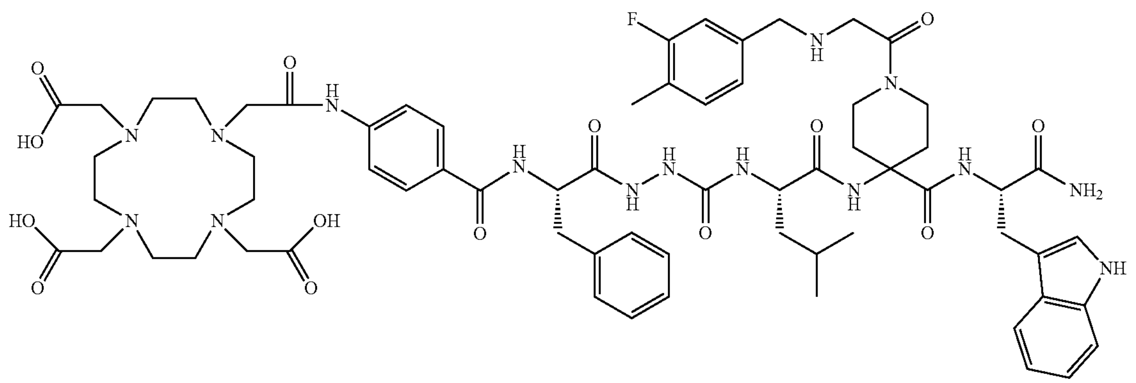 [SMILES: Cc1ccc(CNCC(=O)N2CCC(NC(=O)[C@H](CC(C)C)NC(=O)NNC(=O)[C@H](Cc3ccccc3)NC(=O)c3ccc(NC(=O)CN4CCN(CC(=O)O)CCN(CC(=O)O)CCN(CC(=O)O)CC4)cc3)(C(=O)N[C@@H](Cc3c[nH]c4ccccc34)C(N)=O)CC2)cc1F]
MS: Calc'd 1331.65, found $[M+2H]^{2+}$: 667.3.
Example 42: Compound 51
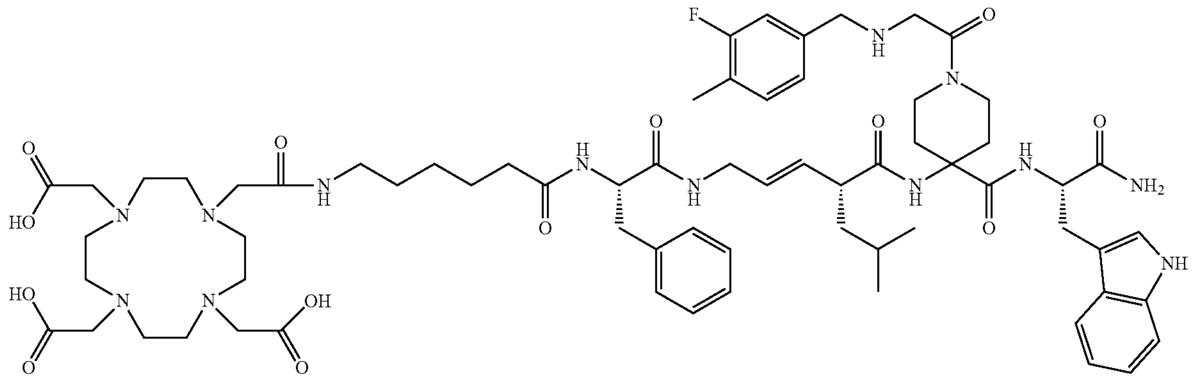 [SMILES: Cc1ccc(CNCC(=O)N2CCC(NC(=O)[C@@H](/C=C/CNC(=O)[C@H](Cc3ccccc3)NC(=O)CCCCCNC(=O)CN3CCN(CC(=O)O)CCN(CC(=O)O)CCN(CC(=O)O)CC3)CC(C)C)(C(=O)N[C@@H](Cc3c[nH]c4ccccc34)C(N)=O)CC2)cc1F]
MS: Calc'd 1307.71, found $[M+2H]^{2+}$: 655.3.
Example 43: Compound 55 (SEQ ID NO: 447)
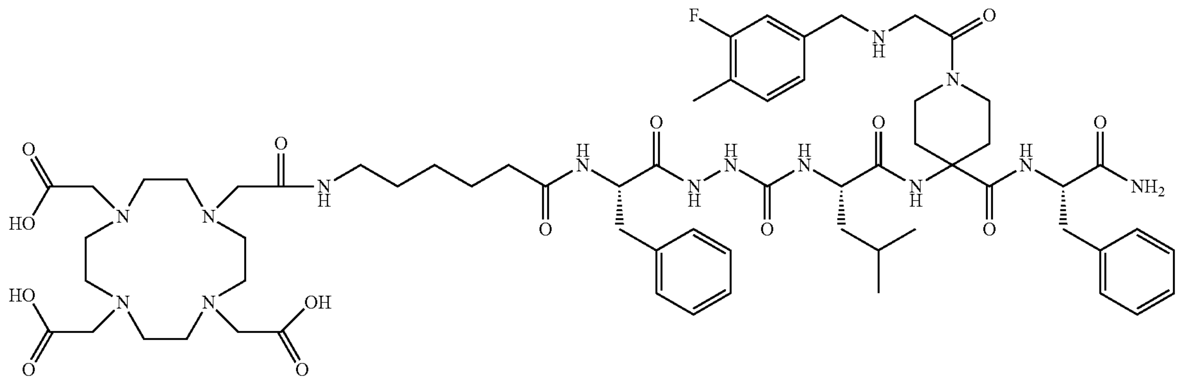 [SMILES: Cc1ccc(CNCC(=O)N2CCC(NC(=O)[C@H](CC(C)C)NC(=O)NNC(=O)[C@H](Cc3ccccc3)NC(=O)CCCCCNC(=O)CN3CCN(CC(=O)O)CCN(CC(=O)O)CCN(CC(=O)O)CC3)(C(=O)N[C@@H](Cc3ccccc3)C(N)=O)CC2)cc1F]
MS: Calc'd 1286.68, found $[M+2H]^{2+}$: 644.75.

Example 44: Compound 57 (SEQ ID NO: 449)
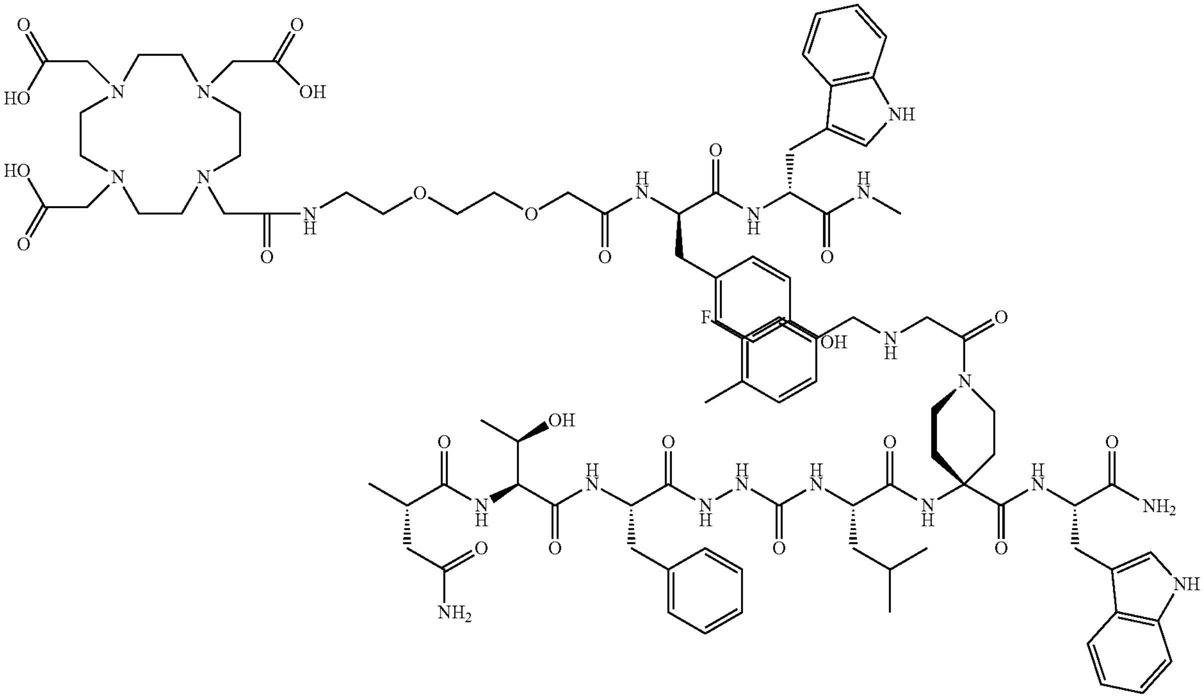
MS: Calc'd 1921.92, found $[M+3H]^{3+}$: 642.1.
Example 45: Compound 58 (SEQ ID NO: 450)
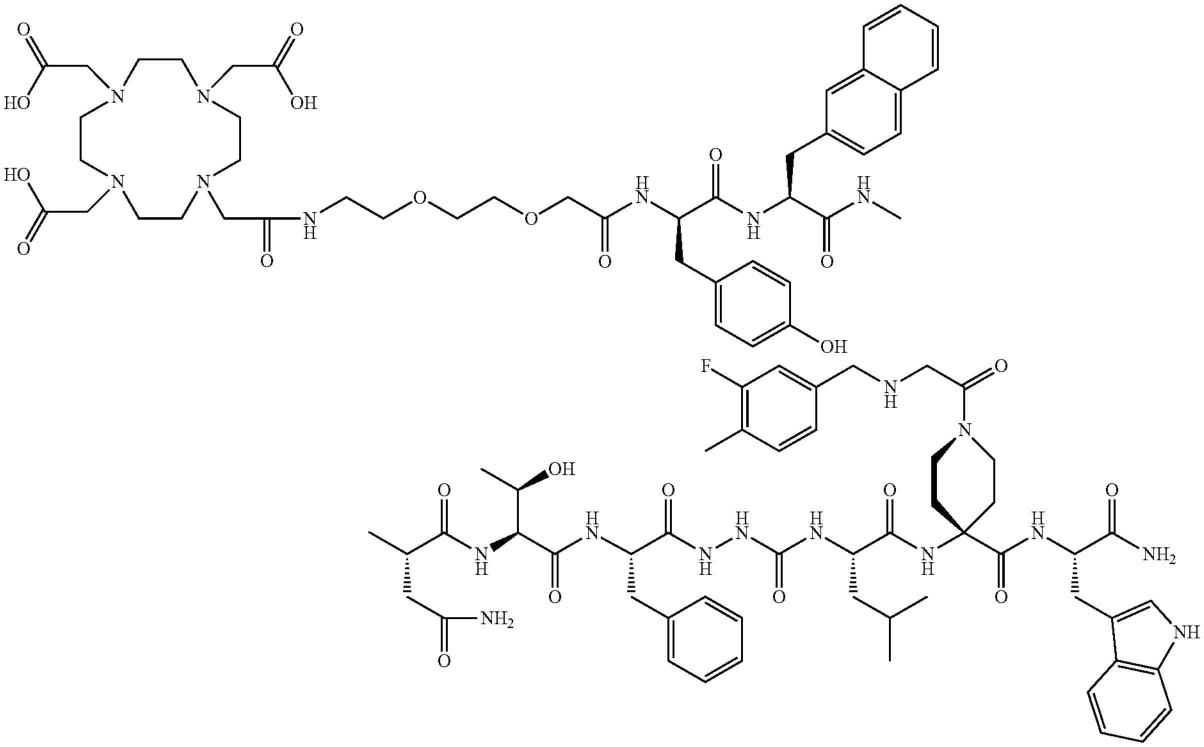
MS: Calc'd 1932.92, found $[M+2H]^{2+}$: 986.05.

Example 46: Compound 64 (SEQ ID NO: 456)
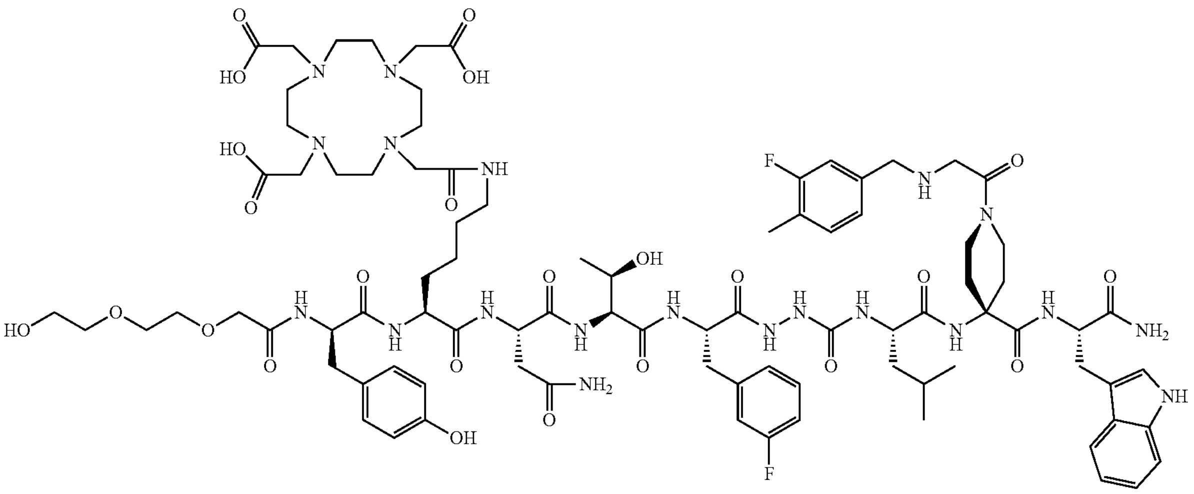
MS: Calc'd 1882.91, found $[M+3H]^{3+}$:629.1.
Example 47: Compound 91 (SEQ ID NO: 479)
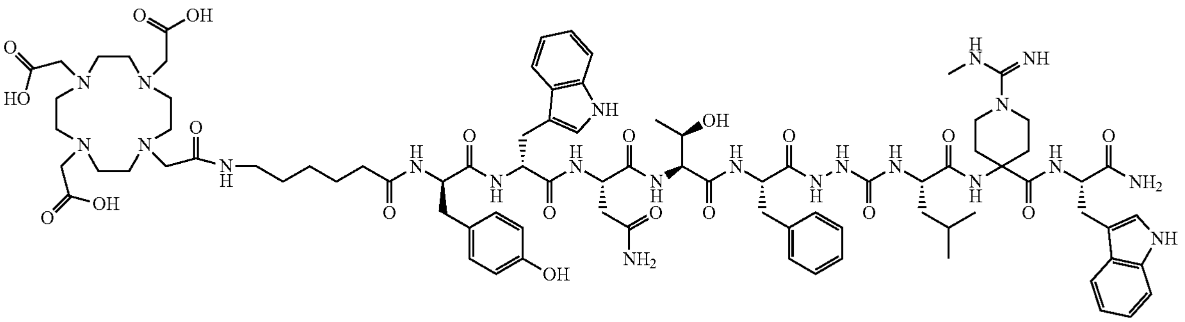 [SMILES: CNC(=N)N1CCC(NC(=O)[C@H](CC(C)C)NC(=O)NNC(=O)[C@H](Cc2ccccc2)NC(=O)[C@@H](NC(=O)[C@H](CC(N)=O)NC(=O)[C@@H](Cc2c[nH]c3ccccc23)NC(=O)[C@@H](Cc2ccc(O)cc2)NC(=O)CCCCCNC(=O)CN2CCN(CC(=O)O)CCN(CC(=O)O)CCN(CC(=O)O)CC2)[C@@H](C)O)(C(=O)N[C@@H](Cc2c[nH]c3ccccc23)C(N)=O)CC1]
MS: Calc'd 1776.89, found $[M+2H]^{2+}$: 885.0.
Example 48: Compound 104 (SEQ ID NO: 491)
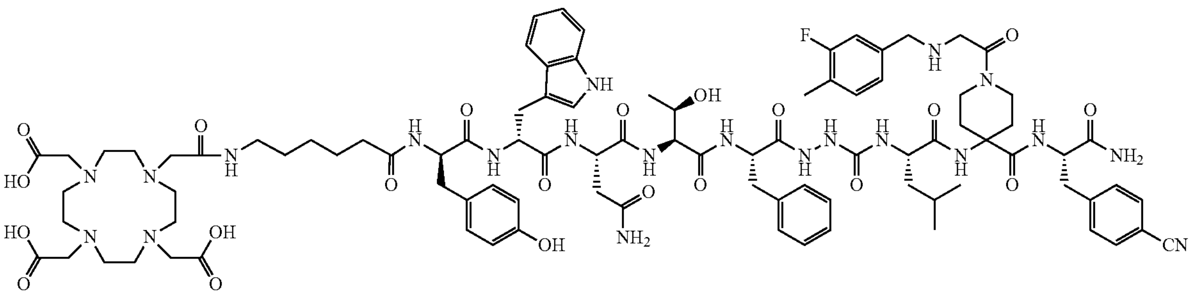 [SMILES: Cc1ccc(CNCC(=O)N2CCC(NC(=O)[C@H](CC(C)C)NC(=O)NNC(=O)[C@H](Cc3ccccc3)NC(=O)[C@@H](NC(=O)[C@H](CC(N)=O)NC(=O)[C@@H](Cc3c[nH]c4ccccc34)NC(=O)[C@@H](Cc3ccc(O)cc3)NC(=O)CCCCCNC(=O)CN3CCN(CC(=O)O)CCN(CC(=O)O)CCN(CC(=O)O)CC3)[C@@H](C)O)(C(=O)N[C@@H](Cc3ccc(C#N)cc3)C(N)=O)CC2)cc1F]
MS: Calc'd 1875.91, found $[M+2H]^{2+}$: 939.55.

Example 49: Compound 105 (SEQ ID NO: 492)
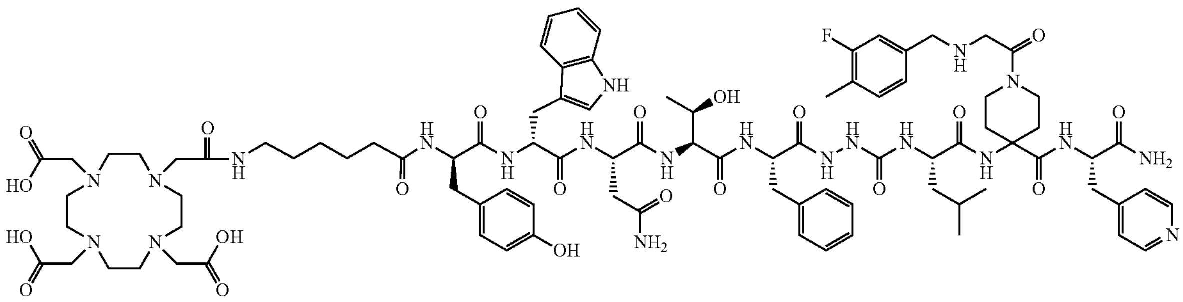 [SMILES: Cc1ccc(CNCC(=O)N2CCC(NC(=O)[C@H](CC(C)C)NC(=O)NNC(=O)[C@H](Cc3ccccc3)NC(=O)[C@@H](NC(=O)[C@H](CC(N)=O)NC(=O)[C@@H](Cc3c[nH]c4ccccc34)NC(=O)[C@@H](Cc3ccc(O)cc3)NC(=O)CCCCCNC(=O)CN3CCN(CC(=O)O)CCN(CC(=O)O)CCN(CC(=O)O)CC3)[C@@H](C)O)(C(=O)N[C@@H](Cc3ccncc3)C(N)=O)CC2)cc1F]
MS: Calc'd 1851.91, found $[M+2H]^{2+}$: 927.3.
Compound 105-In (SEQ ID NO: 493)
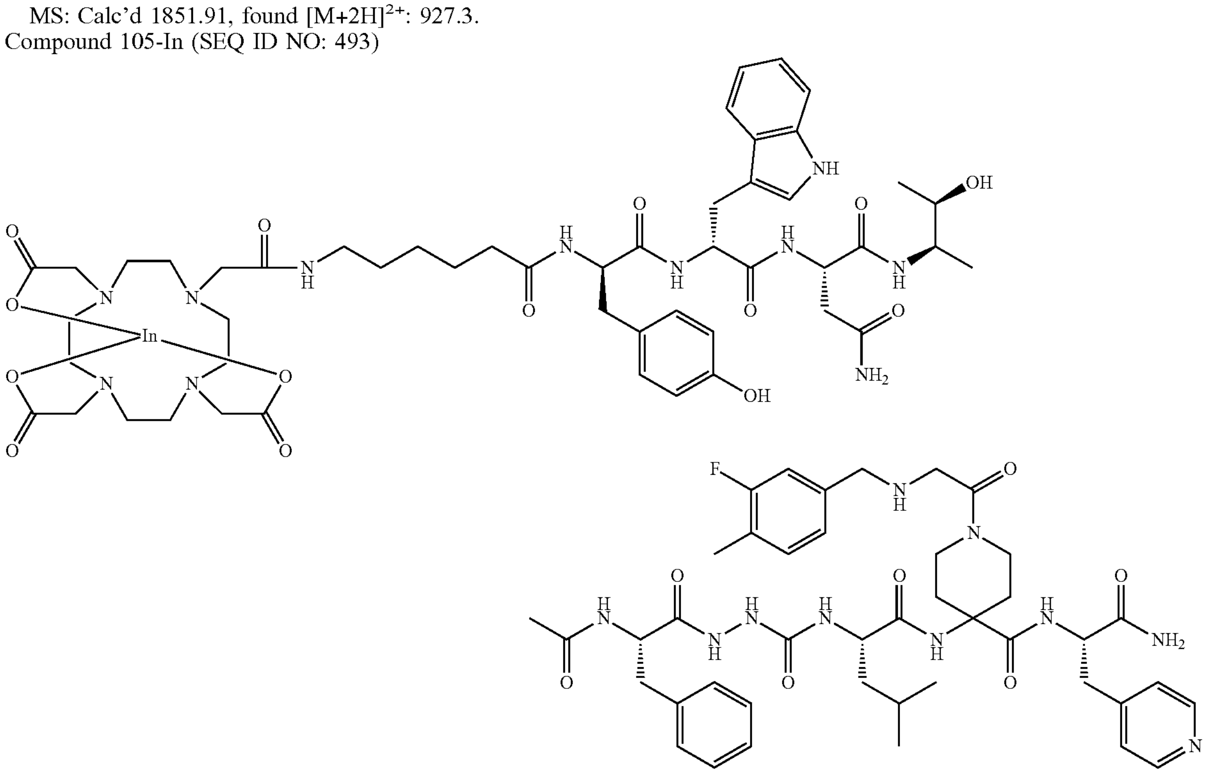
MS: Calc'd 1963.79, found $[M+2H]^{2+}$: 983.35.
Example 50: Compound 106 (SEQ ID NO: 494)
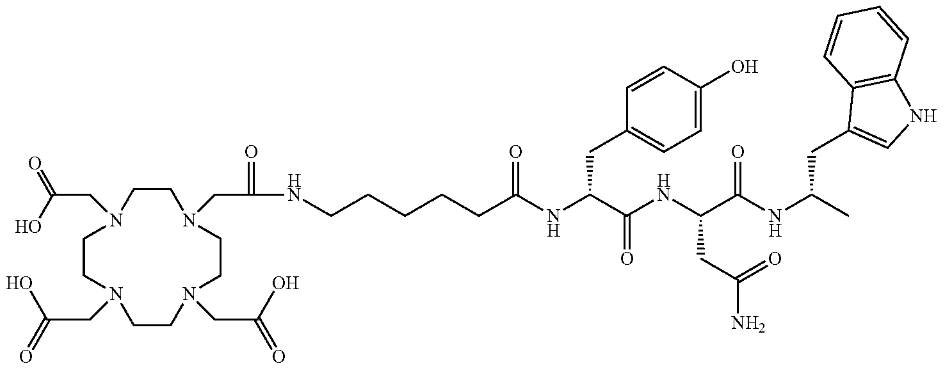

-continued
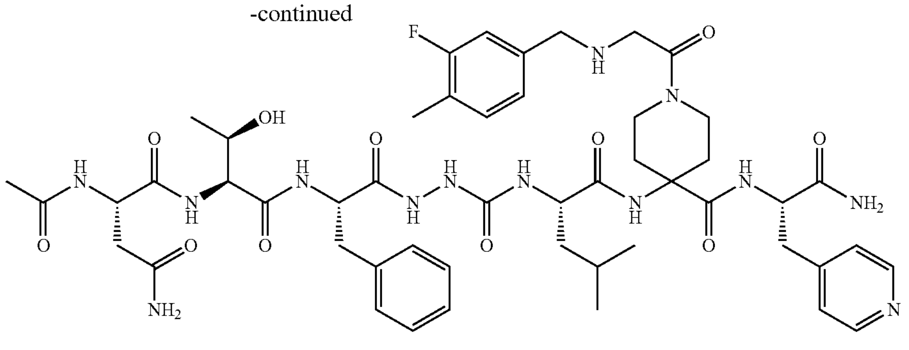
MS: Calc'd 1965.95, found $[M+3H]^{3+}$. 656.7.
Example 51: Compound 1071 (SEQ ID NO: 495)
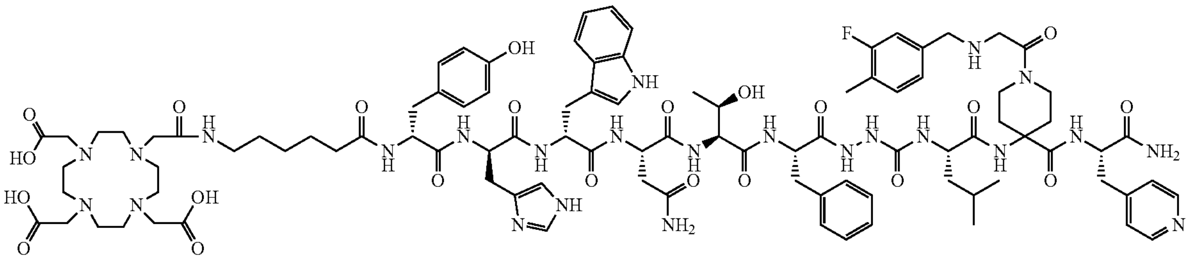 [SMILES: Cc1ccc(CNCC(=O)N2CCC(NC(=O)[C@H](CC(C)C)NC(=O)NNC(=O)[C@H](Cc3ccccc3)NC(=O)[C@@H](NC(=O)[C@H](CC(N)=O)NC(=O)[C@@H](Cc3c[nH]c4ccccc34)NC(=O)[C@@H](Cc3c[nH]cn3)NC(=O)[C@@H](Cc3ccc(O)cc3)NC(=O)CCCCCNC(=O)CN3CCN(CC(=O)O)CCN(CC(=O)O)CCN(CC(=O)O)CC3)[C@@H](C)O)(C(=O)N[C@@H](Cc3ccncc3)C(N)=O)CC2)cc1F]
MS: Calc'd 1988.97, found $[M+3H]^{3+}$: 664.45.
Example 51: Compound 108 (SEQ ID NO: 496)
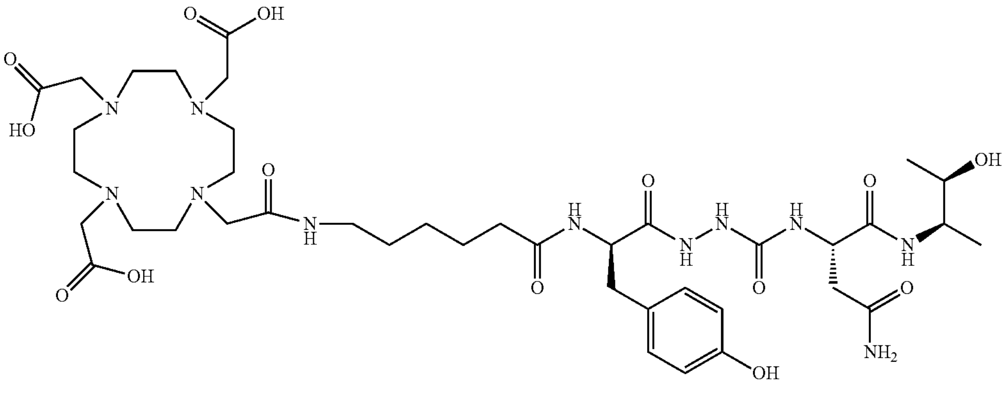

-continued
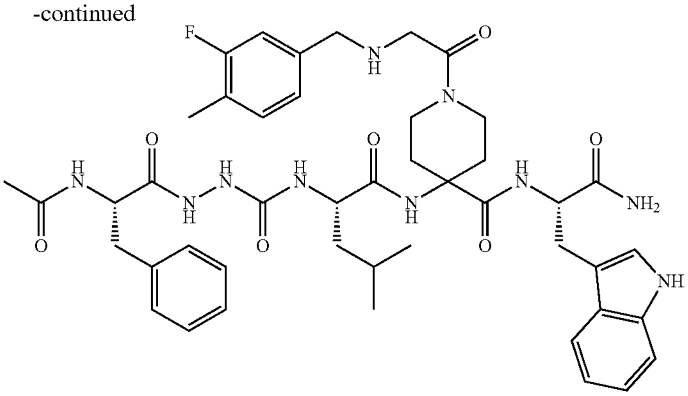
MS: Calc'd 1761.86, found $[M+3H]^{3+}$: 588.75.
Example 53: Compound 109 (SEQ ID NO: 497)
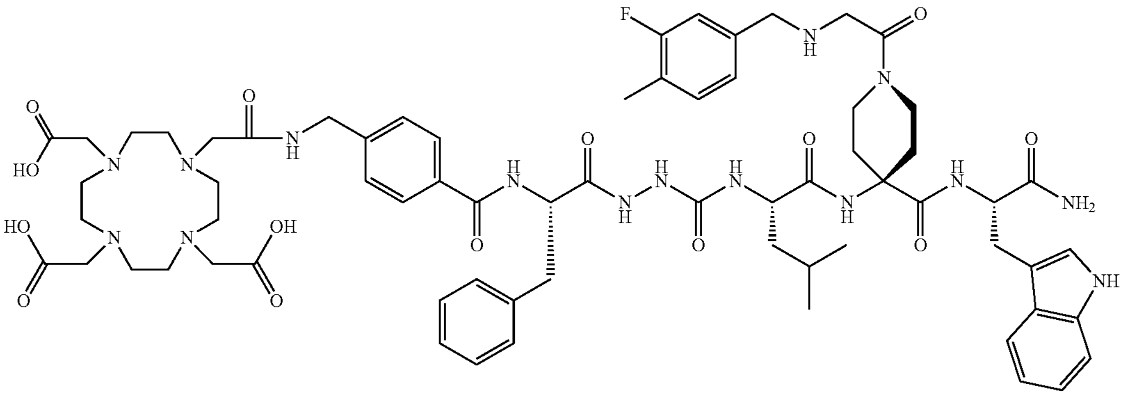
MS: Calc'd 13415.66, found $[M+2H]^{2+}$: 674.3.
Example 54: Compound 110 (SEQ ID NO: 498)
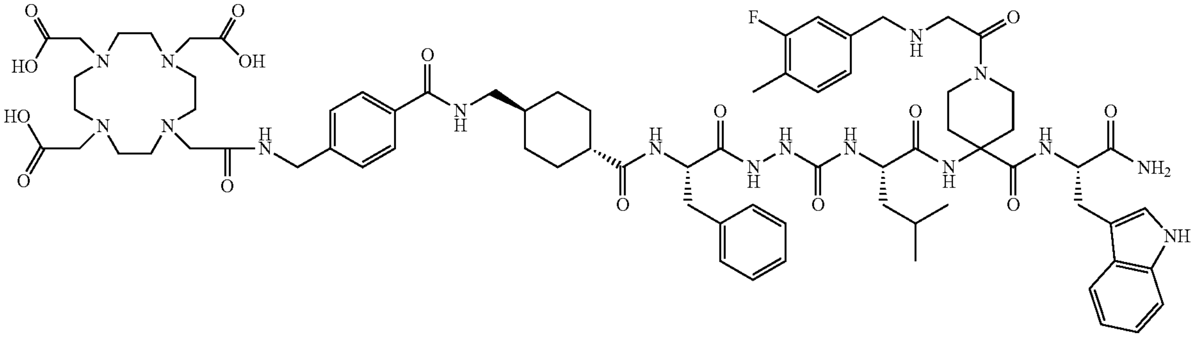 [SMILES: Cc1ccc(CNCC(=O)N2CCC(NC(=O)[C@H](CC(C)C)NC(=O)NNC(=O)[C@H](Cc3ccccc3)NC(=O)[C@H]3CC[C@H](CNC(=O)c4ccc(CNC(=O)CN5CCN(CC(=O)O)CCN(CC(=O)O)CCN(CC(=O)O)CC5)cc4)CC3)(C(=O)N[C@@H](Cc3c[nH]c4ccccc34)C(N)=O)CC2)cc1F]
MS: Calc'd 1484.76, found $[M+2H]^{2+}$: 743.9.

Example 55. Compound 113 (SEQ ID NO: 500)
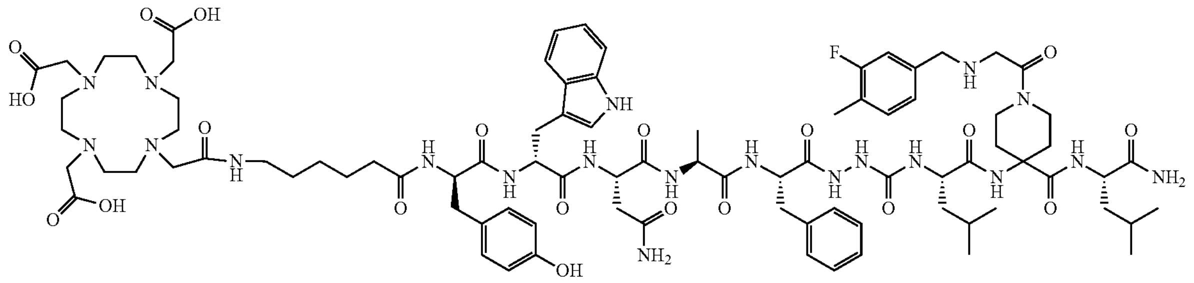 [SMILES: Cc1ccc(CNCC(=O)N2CCC(NC(=O)[C@H](CC(C)C)NC(=O)NNC(=O)[C@H](Cc3ccccc3)NC(=O)[C@H](C)NC(=O)[C@H](CC(N)=O)NC(=O)[C@@H](Cc3c[nH]c4ccccc34)NC(=O)[C@@H](Cc3ccc(O)cc3)NC(=O)CCCCCNC(=O)CN3CCN(CC(=O)O)CCN(CC(=O)O)CCN(CC(=O)O)CC3)(C(=O)N[C@@H](CC(C)C)C(N)=O)CC2)cc1F]
MS: Calc'd 1786.9, found $[M+H]^+$: 1788.0.
Example 56: Compound 114 (SEQ ID NO: 501)
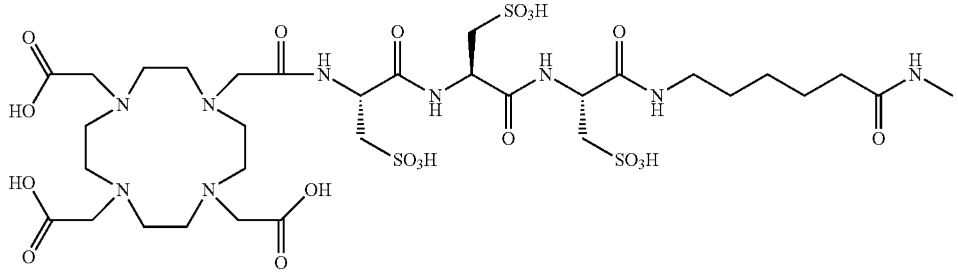
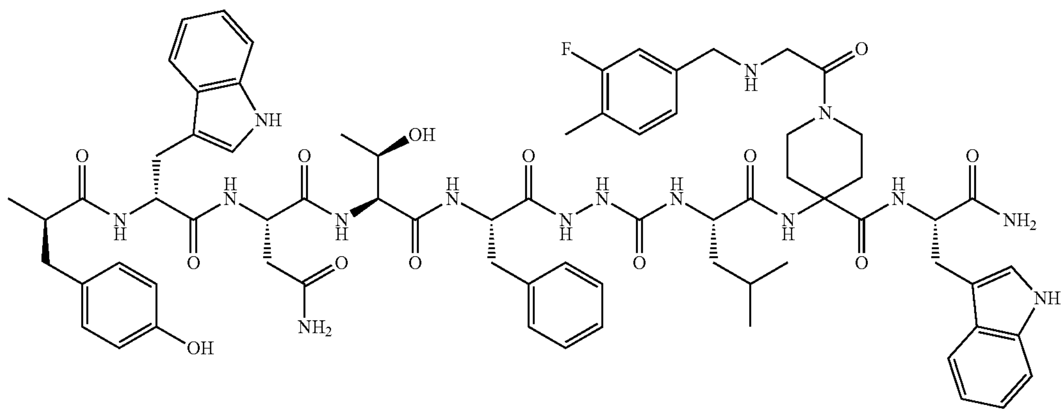
MS: Calc'd 2342.91 found $[M+2H]^{2+}$: 1173.3.

Example 57: Compound 115 (SEQ ID NO: 502)
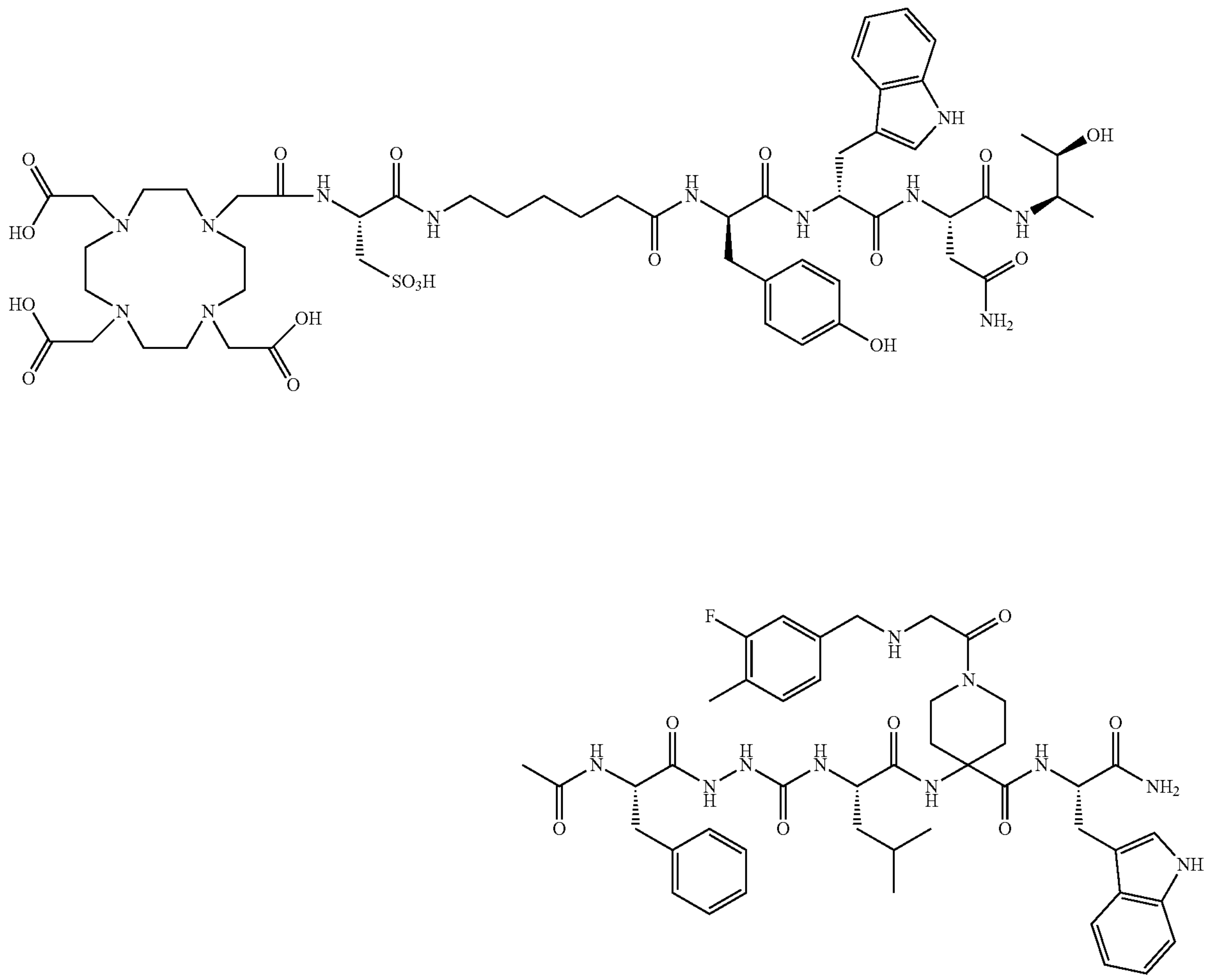
MS: Calc'd 2040.92, found $[M+2H]^{2+}$: 1022.05.
Example 58 Compound 116 (SEQ ID NO 503)
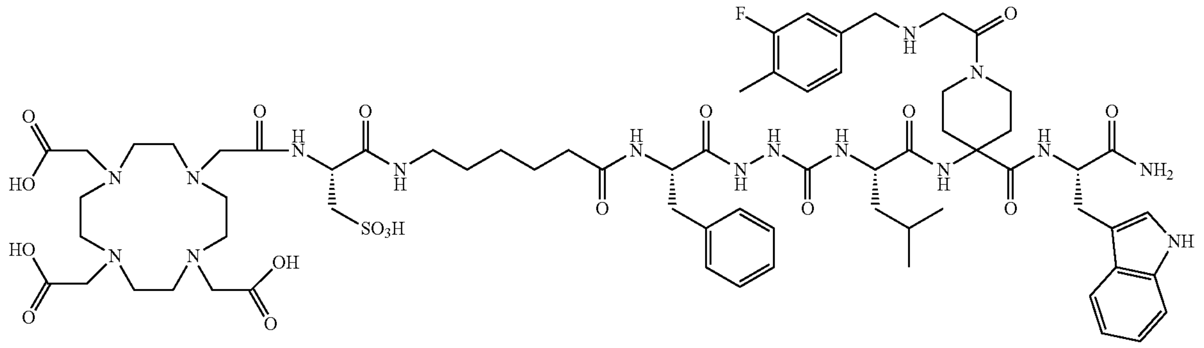 [SMILES: Cc1ccc(CNCC(=O)N2CCC(NC(=O)[C@H](CC(C)C)NC(=O)NNC(=O)[C@H](Cc3ccccc3)NC(=O)CCCCCNC(=O)[C@H](CS(=O)(=O)O)NC(=O)CN3CCN(CC(=O)O)CCN(CC(=O)O)CCN(CC(=O)O)CC3)(C(=O)N[C@@H](Cc3c[nH]c4ccccc34)C(N)=O)CC2)cc1F]
MS: Calc'd 1476.69, found $[M+2H]^{2+}$: 739.8.

Example 59: Compound 117 (SEQ ID NO: 504)
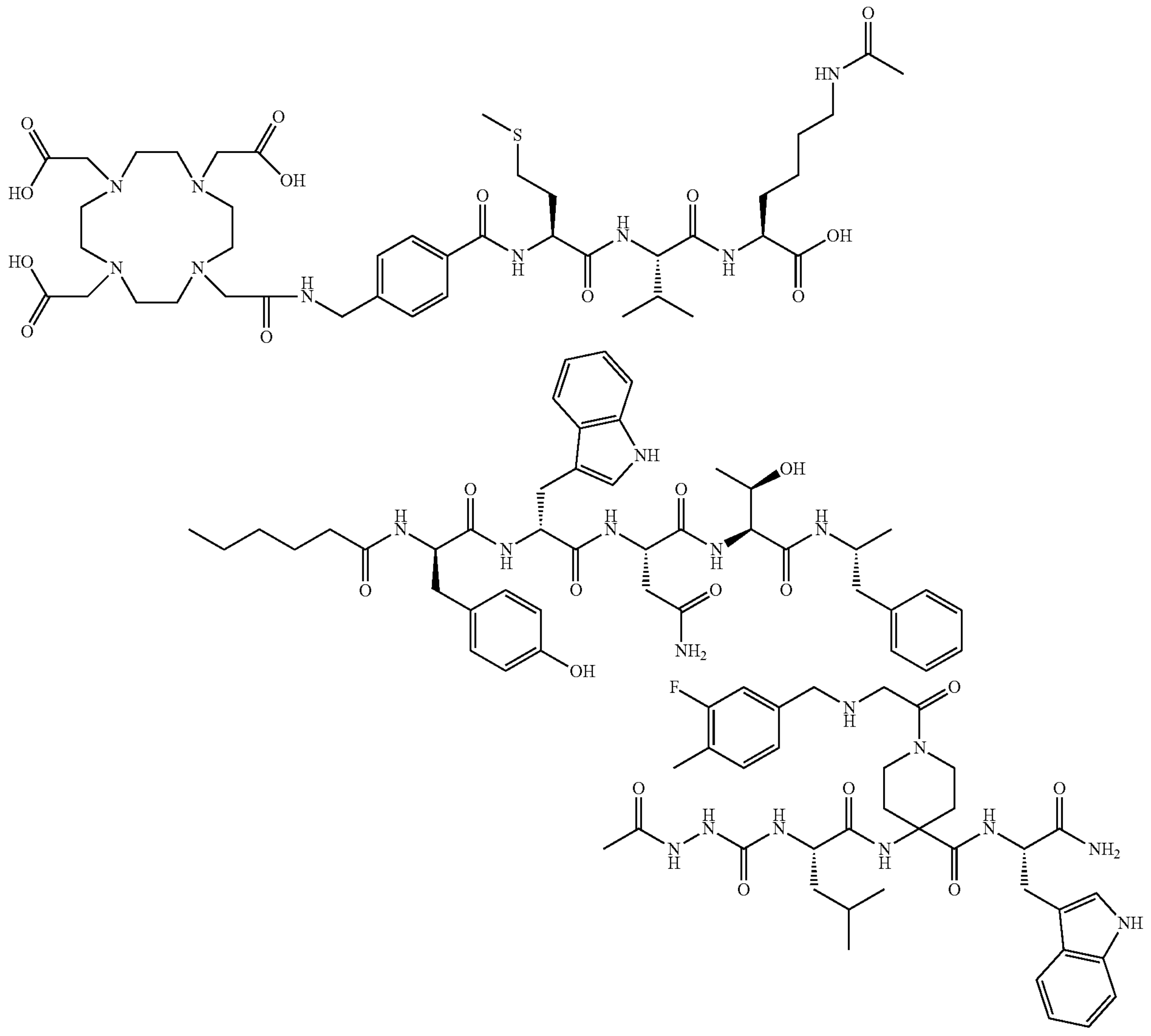
MS: Calc'd 2396.14, found $[M+3H]^{3+}$: 800.3.
Example 60: Compound 118 (SEQ ID NO: 505)
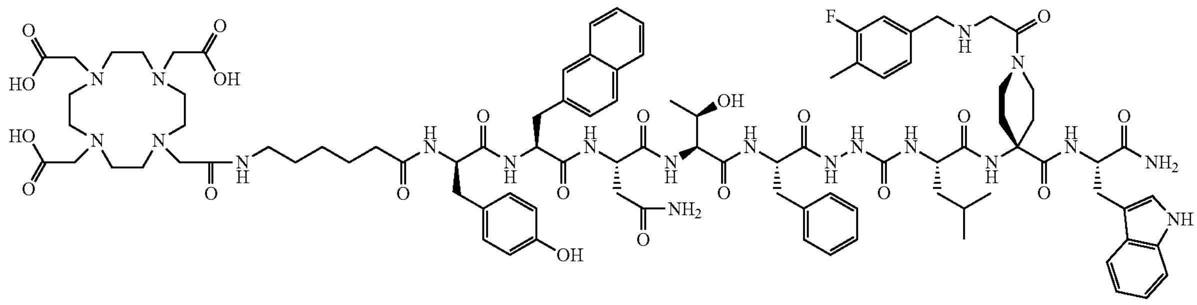
MS: Calc'd 1900.93, found $[M+3H]^{3+}$: 635.1.

Compound 118-Lu
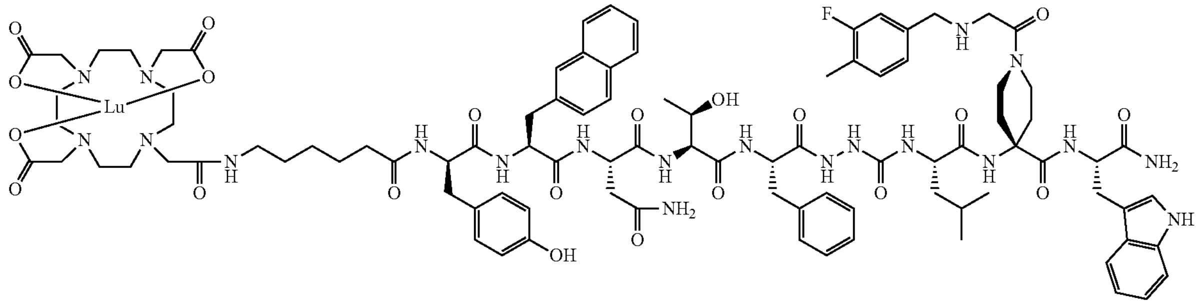
MS: Calc'd 2072.85, found $[M+2H]^{2+}$: 1038.05.
Example 61: Compound 119 (SEQ ID NO: 506)
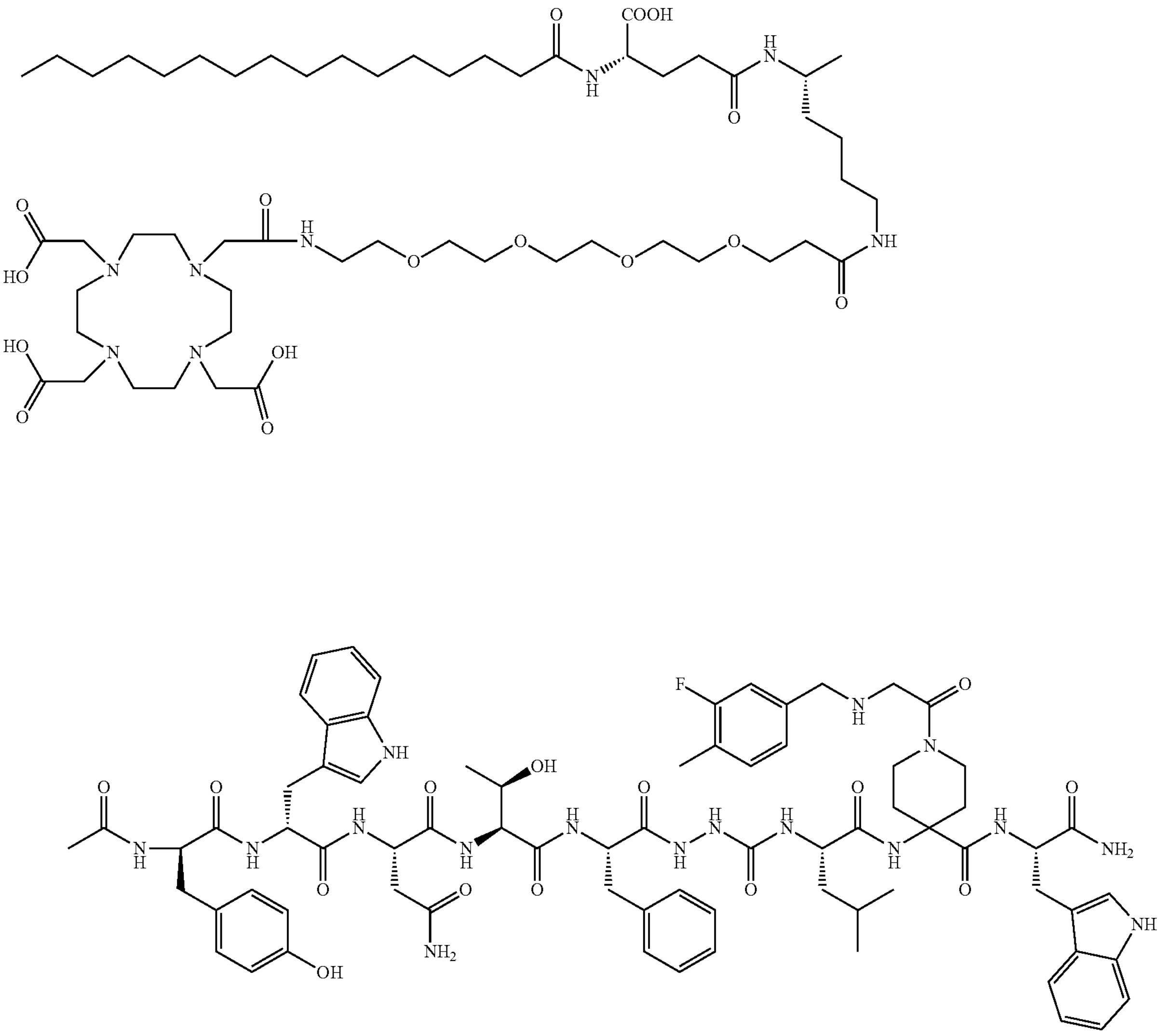
MS: Calc'd 2519.35, found $[M+3H]^{3+}$: 841.4.

Example 62: Compound 120 (SEQ ID NO: 507)
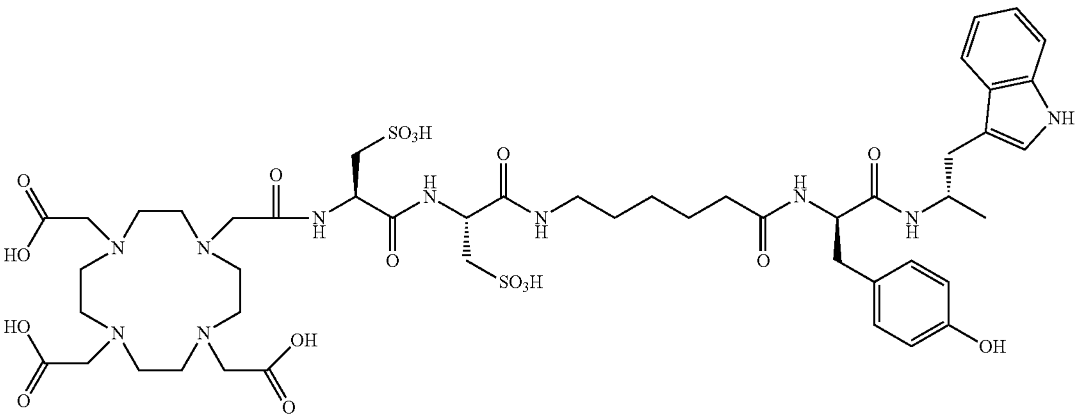
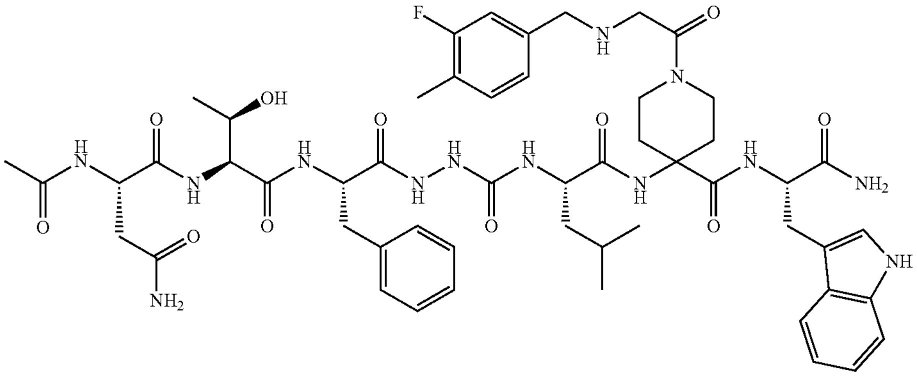
MS: Calc'd, found $[M+2H]^{2+}$:
Example 63: Compound 121 (SEQ ID NO: 508)
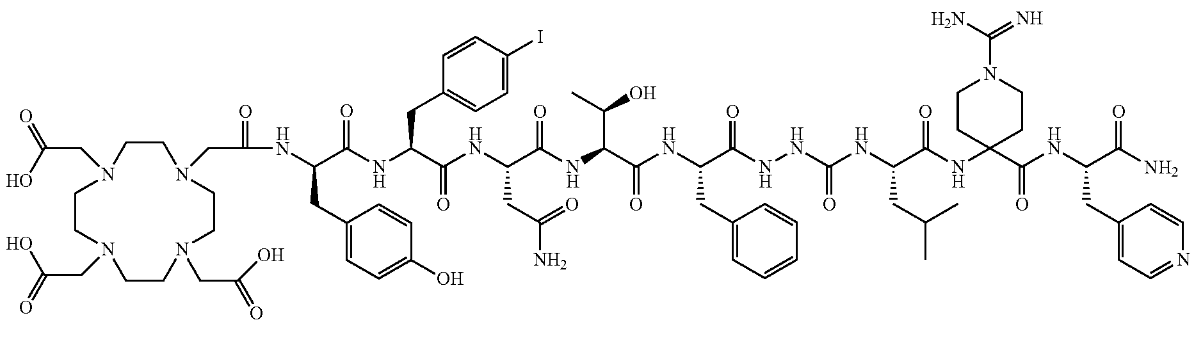 [SMILES: CC(C)C[C@H](NC(=O)NNC(=O)[C@H](Cc1ccccc1)NC(=O)[C@@H](NC(=O)[C@H](CC(N)=O)NC(=O)[C@H](Cc1ccc(I)cc1)NC(=O)[C@@H](Cc1ccc(O)cc1)NC(=O)CN1CCN(CC(=O)O)CCN(CC(=O)O)CCN(CC(=O)O)CC1)[C@@H](C)O)C(=O)NC1(C(=O)N[C@@H](Cc2ccncc2)C(N)=O)CCN(C(=N)N)CC1]
MS: Calc'd 1814.56, found $[M+3H]^{3+}$: 606.25.

Example 64: Compound 123 (SEQ ID NO: 510)
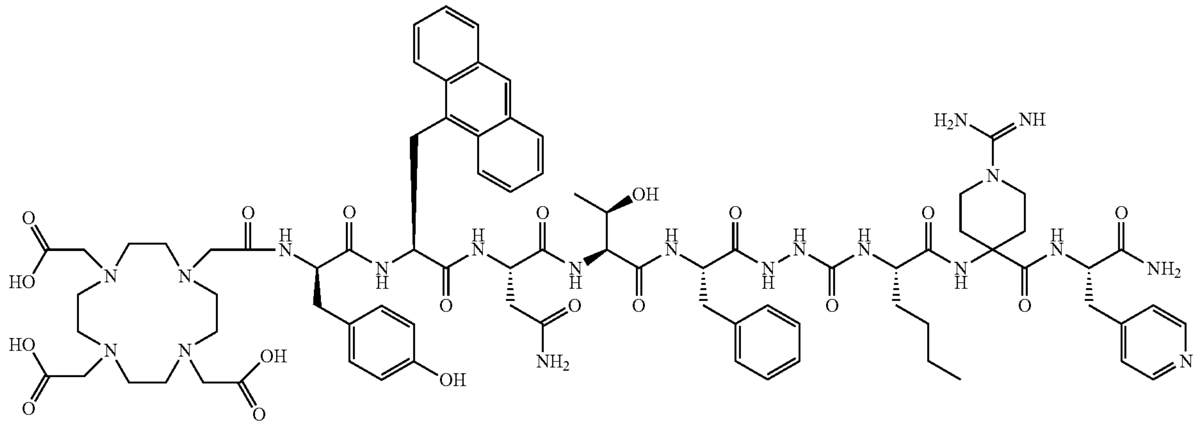 [SMILES: CCCC[C@H](NC(=O)NNC(=O)[C@H](Cc1ccccc1)NC(=O)[C@@H](NC(=O)[C@H](CC(N)=O)NC(=O)[C@H](Cc1c2ccccc2cc2ccccc12)NC(=O)[C@@H](Cc1ccc(O)cc1)NC(=O)CN1CCN(CC(=O)O)CCN(CC(=O)O)CCN(CC(=O)O)CC1)[C@@H](C)O)C(=O)NC1(C(=O)N[C@@H](Cc2ccncc2)C(N)=O)CCN(C(=N)N)CC1]
MS: Calc'd 1662.79, found $[M+3H]^{3+}$: 555.65.
Example 65: Compound 130 (SEQ ID NO: 511)
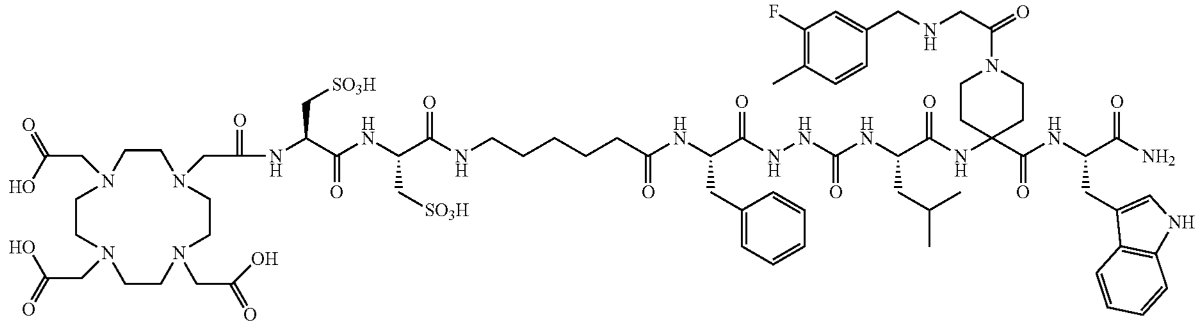 [SMILES: Cc1ccc(CNCC(=O)N2CCC(NC(=O)[C@H](CC(C)C)NC(=O)NNC(=O)[C@H](Cc3ccccc3)NC(=O)CCCCCNC(=O)[C@H](CS(=O)(=O)O)NC(=O)[C@H](CS(=O)(=O)O)NC(=O)CN3CCN(CC(=O)O)CCN(CC(=O)O)CCN(CC(=O)O)CC3)(C(=O)N[C@@H](Cc3c[nH]c4ccccc34)C(N)=O)CC2)cc1F]
MS: Calc'd 1627.68, found $[M+2H]^{2+}$: 815.4.
Example 66: Compound 131 (SEQ ID NO: 512)
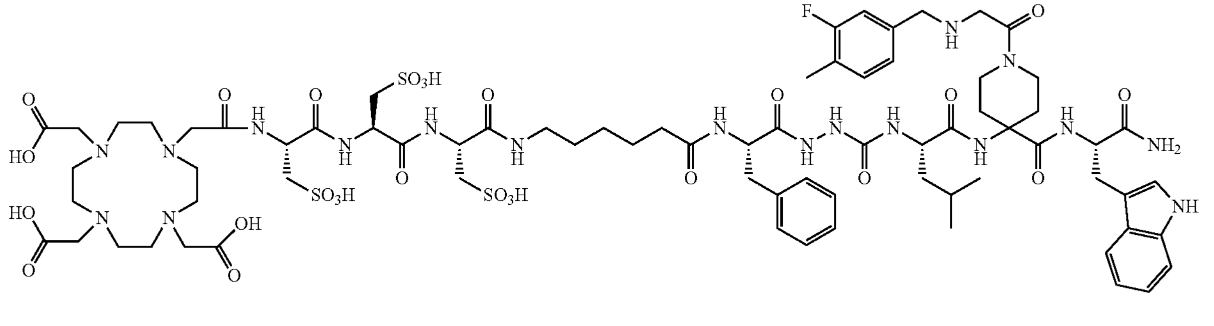 [SMILES: Cc1ccc(CNCC(=O)N2CCC(NC(=O)[C@H](CC(C)C)NC(=O)NNC(=O)[C@H](Cc3ccccc3)NC(=O)CCCCCNC(=O)[C@H](CS(=O)(=O)O)NC(=O)[C@H](CS(=O)(=O)O)NC(=O)[C@H](CS(=O)(=O)O)NC(=O)CN3CCN(CC(=O)O)CCN(CC(=O)O)CCN(CC(=O)O)CC3)(C(=O)N[C@@H](Cc3c[nH]c4ccccc34)C(N)=O)CC2)cc1F]
MS: Calc'd 1778.68, found $[M+2H]^{2+}$: 890.95.

Example 67: Compound 132 (SEQ ID NO: 513)
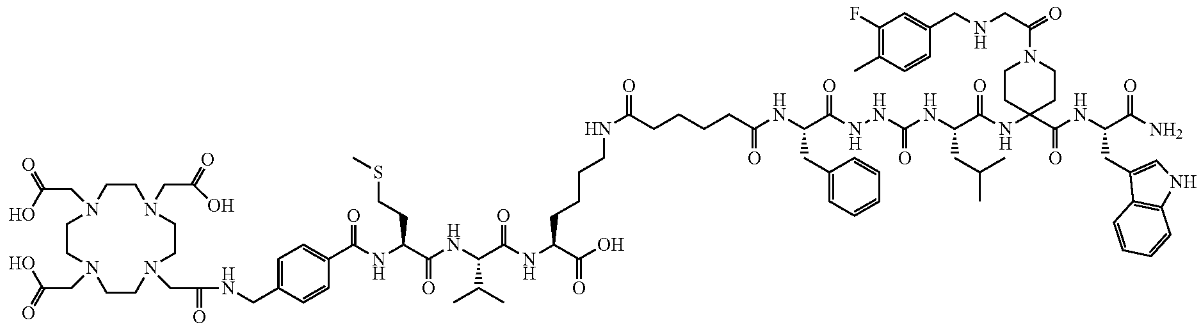 [SMILES: CSCC[C@H](NC(=O)c1ccc(CNC(=O)CN2CCN(CC(=O)O)CCN(CC(=O)O)CCN(CC(=O)O)CC2)cc1)C(=O)N[C@H](C(=O)N[C@@H](CCCCNC(=O)CCCCC(=O)N[C@@H](Cc1ccccc1)C(=O)NNC(=O)N[C@@H](CC(C)C)C(=O)NC1(C(=O)N[C@@H](Cc2c[nH]c3ccccc23)C(N)=O)CCN(C(=O)CNCc2ccc(C)c(F)c2)CC1)C(=O)O)C(C)C]
MS: Calc'd 1831.91, found $[M+2H]^{2+}$: 612.15.
Example 68: Compound 133 (SEQ ID NO: 514)
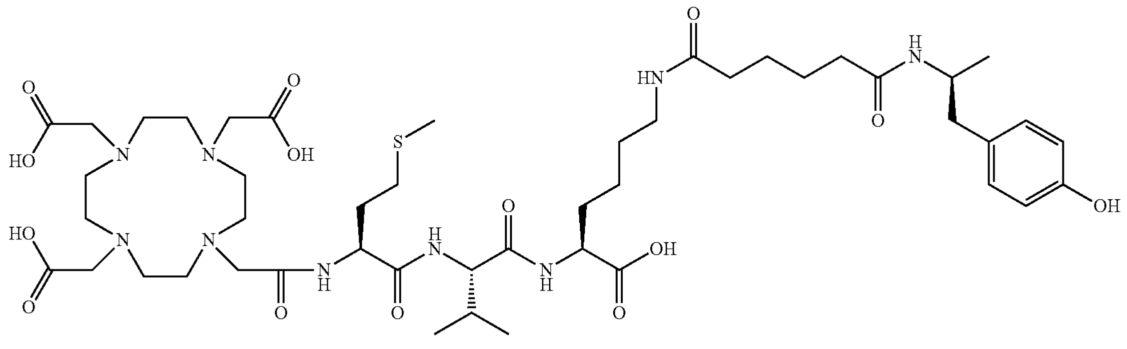
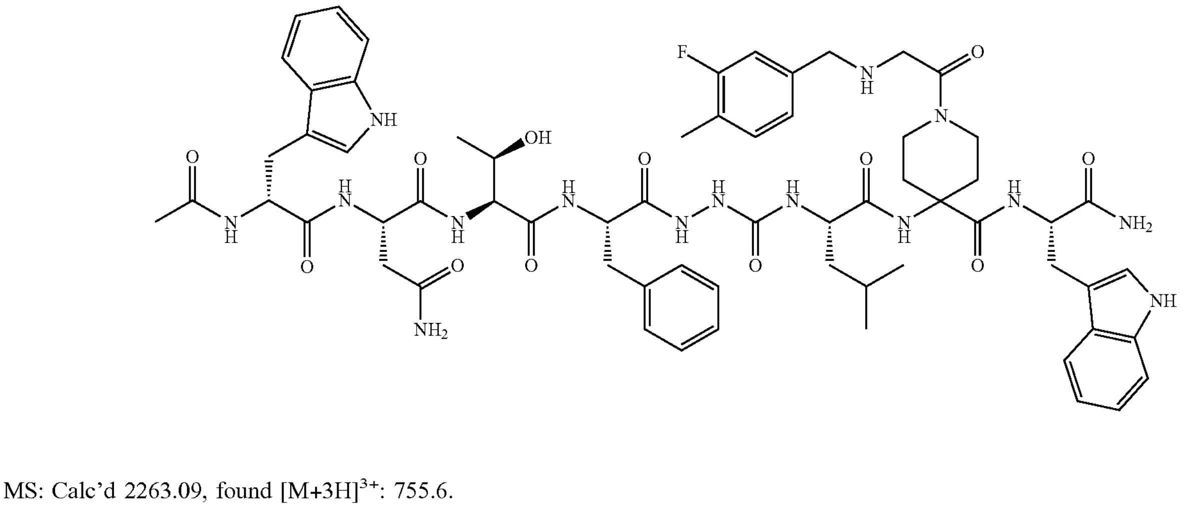
MS: Calc'd 2263.09, found $[M+3H]^{3+}$: 755.6.

Example 69: Compound 134
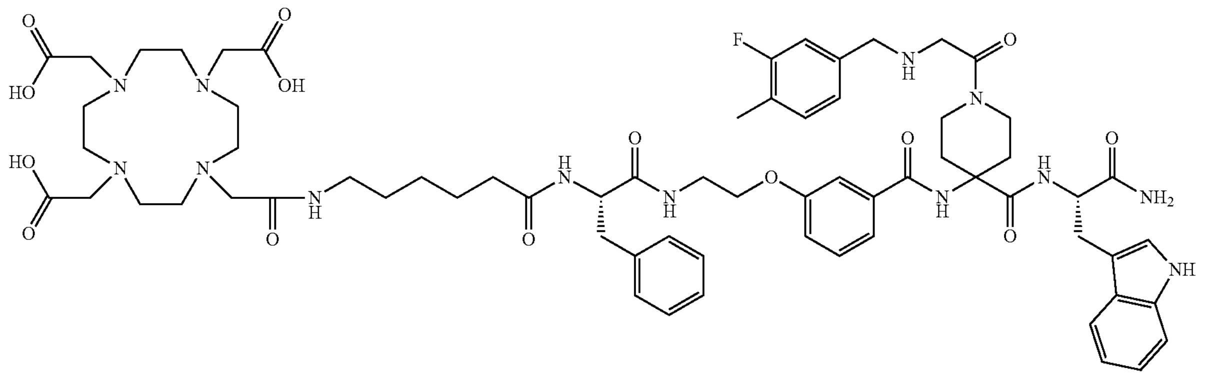 [SMILES: Cc1ccc(CNCC(=O)N2CCC(NC(=O)c3cccc(OCCNC(=O)[C@H](Cc4ccccc4)NC(=O)CCCCCNC(=O)CN4CCN(CC(=O)O)CCN(CC(=O)O)CCN(CC(=O)O)CC4)c3)(C(=O)N[C@@H](Cc3c[nH]c4ccccc34)C(N)=O)CC2)cc1F]
MS: Calc'd 1317.66, found $[M+H]^+$: 1318.7.
Example 70: Compound 135
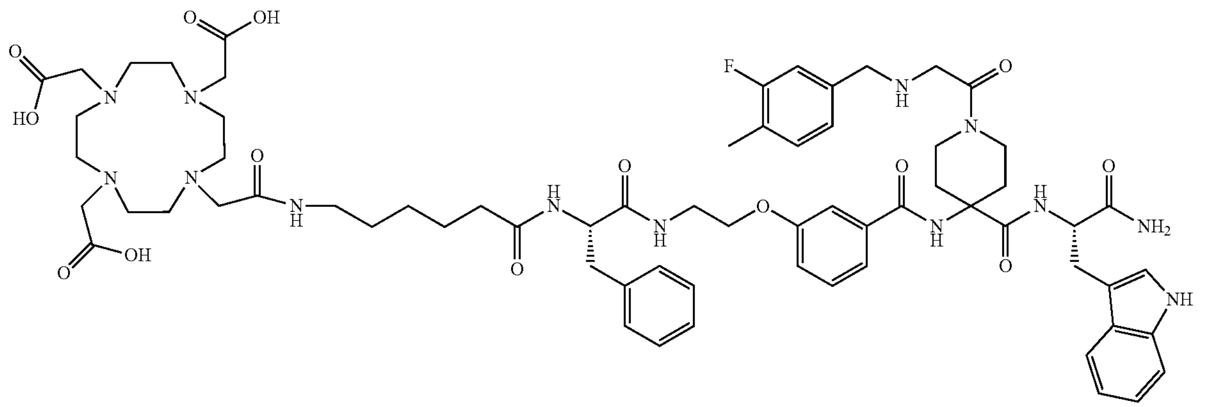 [SMILES: Cc1ccc(CNCC(=O)N2CCC(NC(=O)c3cccc(OCCNC(=O)[C@H](Cc4ccccc4)NC(=O)CCCCCNC(=O)CN4CCN(CC(=O)O)CCN(CC(=O)O)CCN(CC(=O)O)CC4)c3)(C(=O)N[C@@H](Cc3c[nH]c4ccccc34)C(N)=O)CC2)cc1F]
MS: Calc'd 1288.64, found $[M+H]^+$: 1289.7.
Example 71: Compound 136
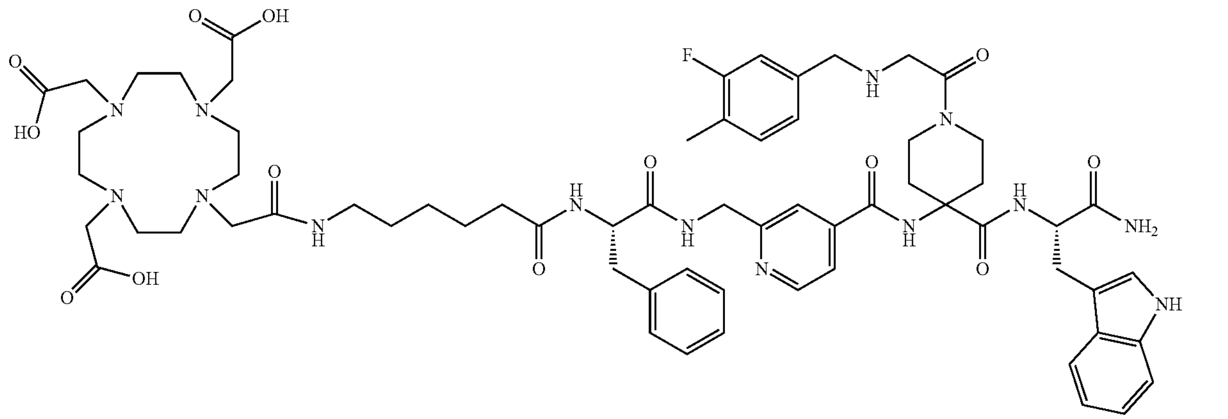 [SMILES: Cc1ccc(CNCC(=O)N2CCC(NC(=O)c3ccnc(CNC(=O)[C@H](Cc4ccccc4)NC(=O)CCCCCNC(=O)CN4CCN(CC(=O)O)CCN(CC(=O)O)CCN(CC(=O)O)CC4)c3)(C(=O)N[C@@H](Cc3c[nH]c4ccccc34)C(N)=O)CC2)cc1F]
MS: Calc'd 1288.64, found $[M+H]^+$: 12897.

Example 72: Compound 137
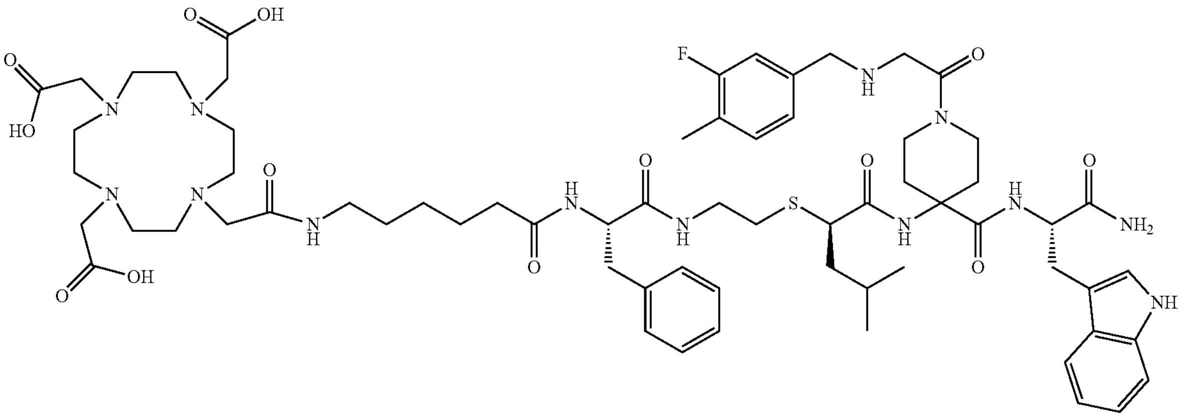 [SMILES: Cc1ccc(CNCC(=O)N2CCC(NC(=O)[C@@H](CC(C)C)SCCNC(=O)[C@H](Cc3ccccc3)NC(=O)CCCCCNC(=O)CN3CCN(CC(=O)O)CCN(CC(=O)O)CCN(CC(=O)O)CC3)(C(=O)N[C@@H](Cc3c[nH]c4ccccc34)C(N)=O)CC2)cc1F]
MS: Calc'd 1327.68, found $[M+H]^+$: 1328.7.
Example 73: Compound 138
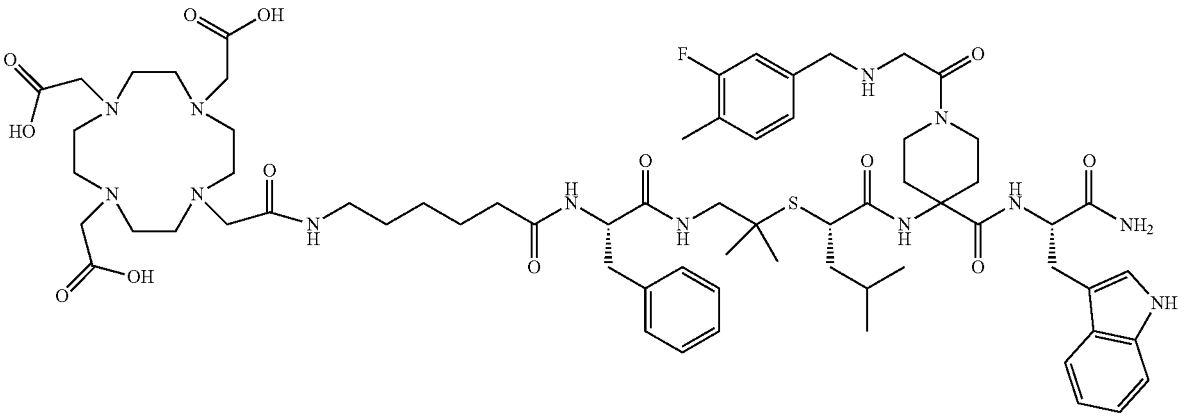 [SMILES: Cc1ccc(CNCC(=O)N2CCC(NC(=O)[C@H](CC(C)C)SC(C)(C)CNC(=O)[C@H](Cc3ccccc3)NC(=O)CCCCCNC(=O)CN3CCN(CC(=O)O)CCN(CC(=O)O)CCN(CC(=O)O)CC3)(C(=O)N[C@@H](Cc3c[nH]c4ccccc34)C(N)=O)CC2)cc1F]
MS: Calc'd 1355.71, found $[M+H]^+$: 1356.8.
Example 74: Compound 139
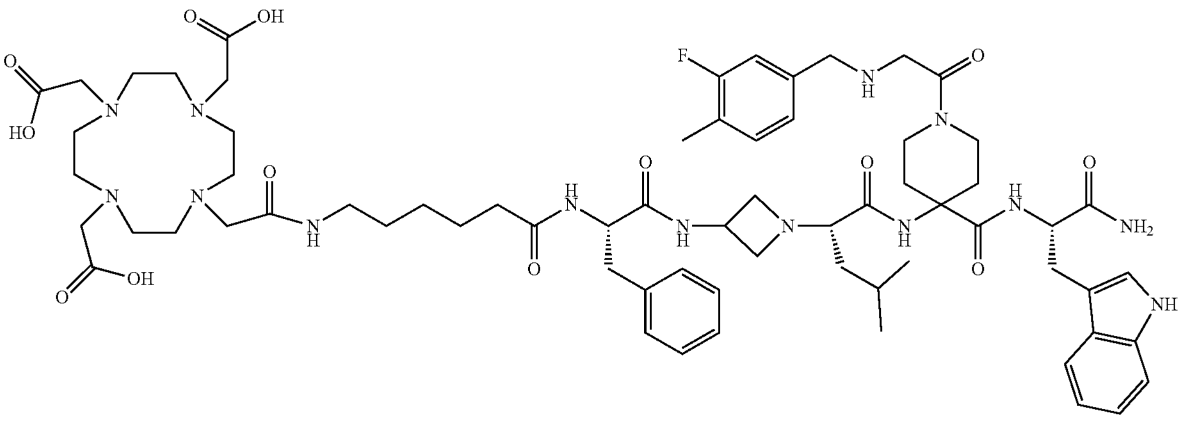 [SMILES: Cc1ccc(CNCC(=O)N2CCC(NC(=O)[C@H](CC(C)C)N3CC(NC(=O)[C@H](Cc4ccccc4)NC(=O)CCCCCNC(=O)CN4CCN(CC(=O)O)CCN(CC(=O)O)CCN(CC(=O)O)CC4)C3)(C(=O)N[C@@H](Cc3c[nH]c4ccccc34)C(N)=O)CC2)cc1F]
MS: Calc'd 1322.72, found $[M+H]^+$: 1323.7.

Example 75: Compound 140 (SEQ ID NO: 521)
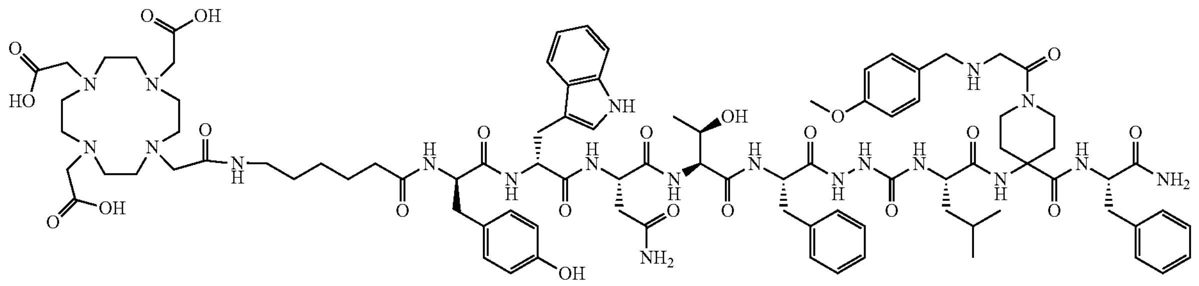 [SMILES: COc1ccc(CNCC(=O)N2CCC(NC(=O)[C@H](CC(C)C)NC(=O)NNC(=O)[C@H](Cc3ccccc3)NC(=O)[C@@H](NC(=O)[C@H](CC(N)=O)NC(=O)[C@@H](Cc3c[nH]c4ccccc34)NC(=O)[C@@H](Cc3ccc(O)cc3)NC(=O)CCCCCNC(=O)CN3CCN(CC(=O)O)CCN(CC(=O)O)CCN(CC(=O)O)CC3)[C@@H](C)O)(C(=O)N[C@@H](Cc3ccccc3)C(N)=O)CC2)cc1]
MS: Calc'd 1848.92, found $[M+H]^+$: 1849.9.
Example 76: Compound 141
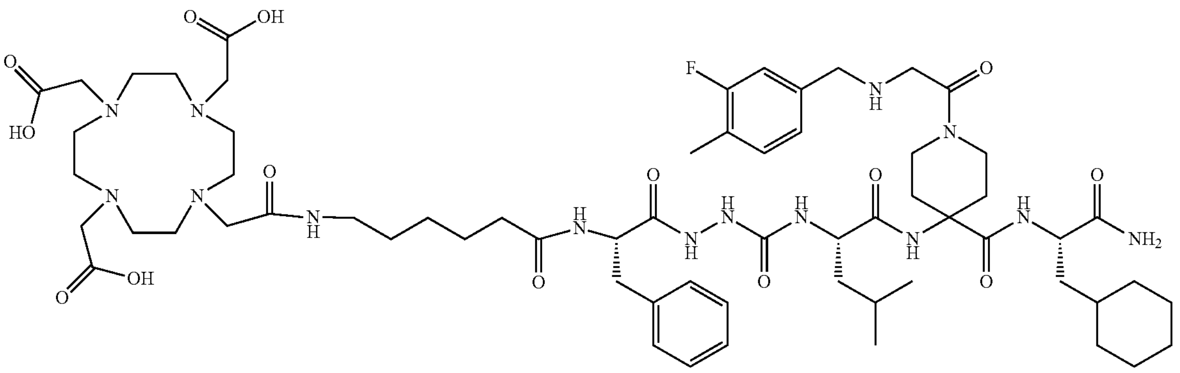 [SMILES: Cc1ccc(CNCC(=O)N2CCC(NC(=O)[C@H](CC(C)C)NC(=O)NNC(=O)[C@H](Cc3ccccc3)NC(=O)CCCCCNC(=O)CN3CCN(CC(=O)O)CCN(CC(=O)O)CCN(CC(=O)O)CC3)(C(=O)N[C@@H](CC3CCCCC3)C(N)=O)CC2)cc1F]
MS: Calc'd 1292.73, found $[M+H]^+$: 1293.4.
Example 77: Compound 142
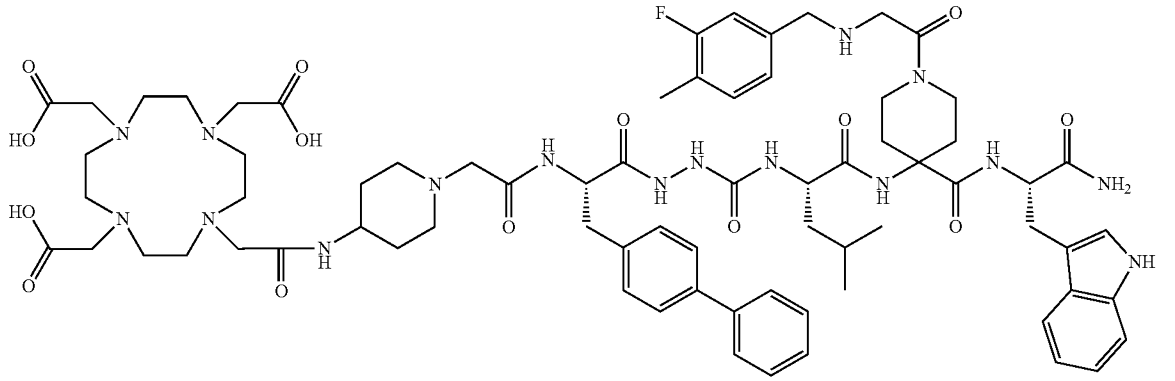 [SMILES: Cc1ccc(CNCC(=O)N2CCC(NC(=O)[C@H](CC(C)C)NC(=O)NNC(=O)[C@H](Cc3ccc(-c4ccccc4)cc3)NC(=O)CN3CCC(NC(=O)CN4CCN(CC(=O)O)CCN(CC(=O)O)CCN(CC(=O)O)CC4)CC3)(C(=O)N[C@@H](Cc3c[nH]c4ccccc34)C(N)=O)CC2)cc1F]
MS: Calc'd 1428.74, found $[M+H]^+$: 1429.6.

Example 78: Compound 146 (SEQ ID NO: 527)
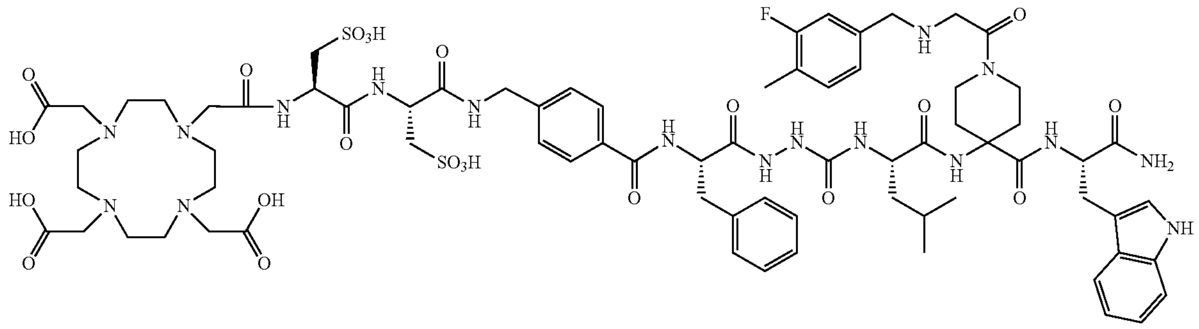 [SMILES: Cc1ccc(CNCC(=O)N2CCC(NC(=O)[C@H](CC(C)C)NC(=O)NNC(=O)[C@H](Cc3ccccc3)NC(=O)c3ccc(CNC(=O)[C@H](CS(=O)(=O)O)NC(=O)[C@H](CS(=O)(=O)O)NC(=O)CN4CCN(CC(=O)O)CCN(CC(=O)O)CCN(CC(=O)O)CC4)cc3)(C(=O)N[C@@H](Cc3c[nH]c4ccccc34)C(N)=O)CC2)cc1F]
MS: Calc'd 1647.65, found $[M+2H]^{2+}$: 1648.6.
Example 79: Compound 147
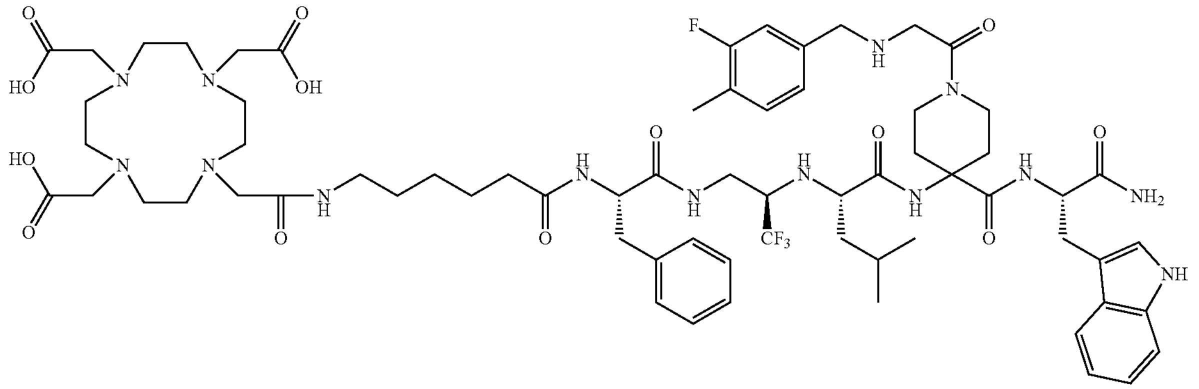 [SMILES: Cc1ccc(CNCC(=O)N2CCC(NC(=O)[C@H](CC(C)C)N[C@H](CNC(=O)[C@H](Cc3ccccc3)NC(=O)CCCCCNC(=O)CN3CCN(CC(=O)O)CCN(CC(=O)O)CCN(CC(=O)O)CC3)C(F)(F)F)(C(=O)N[C@@H](Cc3c[nH]c4ccccc34)C(N)=O)CC2)cc1F]
MS: Calc'd 1378.71, found $[M+2H]^{2+}$: 1379.7.
Example 80: Compound 148
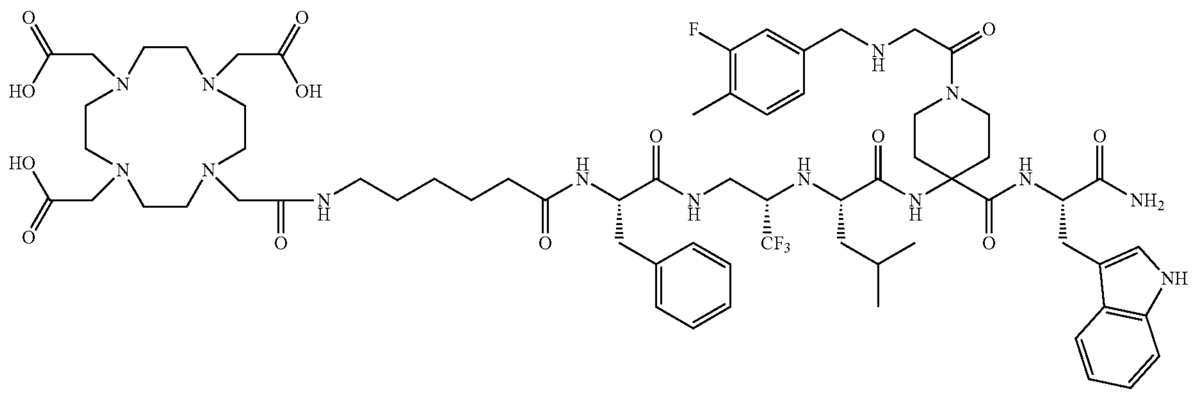 [SMILES: Cc1ccc(CNCC(=O)N2CCC(NC(=O)[C@H](CC(C)C)N[C@@H](CNC(=O)[C@H](Cc3ccccc3)NC(=O)CCCCCNC(=O)CN3CCN(CC(=O)O)CCN(CC(=O)O)CCN(CC(=O)O)CC3)C(F)(F)F)(C(=O)N[C@@H](Cc3c[nH]c4ccccc34)C(N)=O)CC2)cc1F]
MS: Calc'd 1378.71, found $[M+2H]^{2+}$: 1379.7.

Example 81: Compound 149 (SEQ ID NO: 530)
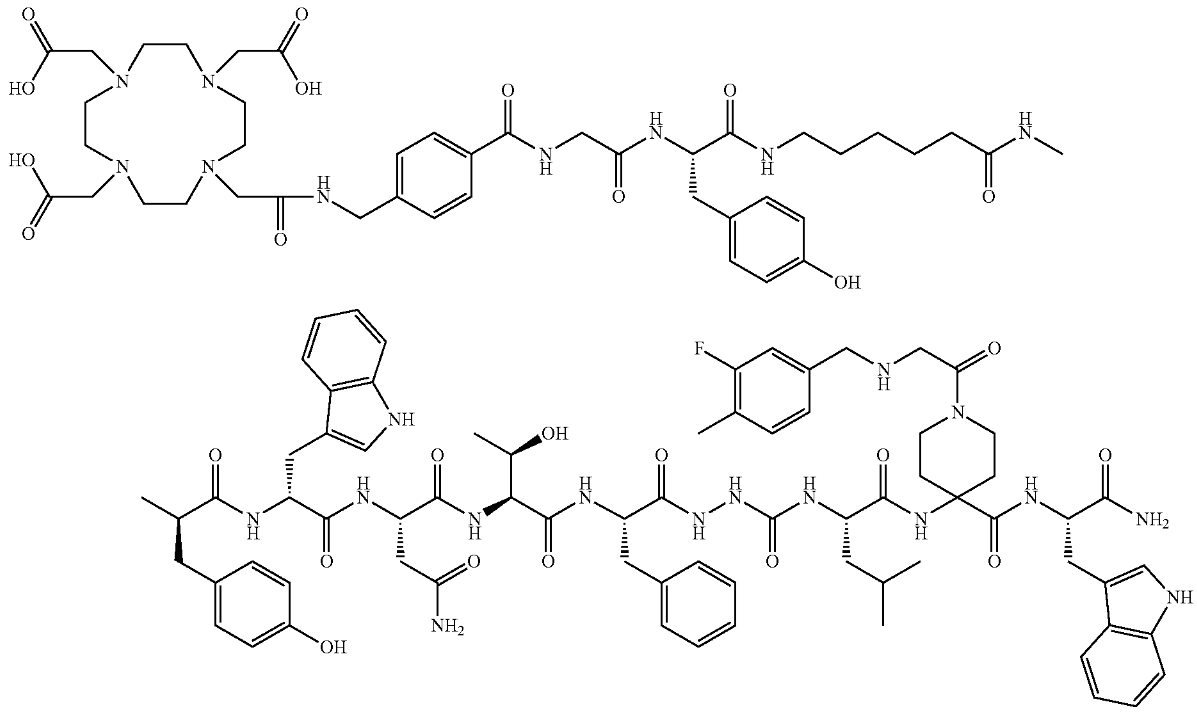
MS: Calc'd 2243.06, found $[M+2H]^{2+}$: 2244.0.
Example 82: Compound 151 (SEQ ID NO: 532)
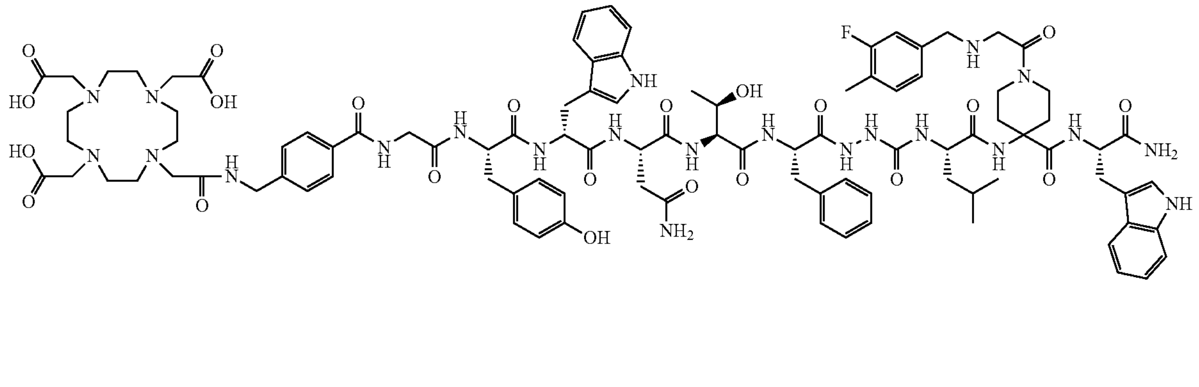 [SMILES: Cc1ccc(CNCC(=O)N2CCC(NC(=O)[C@H](CC(C)C)NC(=O)NNC(=O)[C@H](Cc3ccccc3)NC(=O)[C@@H](NC(=O)[C@H](CC(N)=O)NC(=O)[C@@H](Cc3c[nH]c4ccccc34)NC(=O)[C@H](Cc3ccc(O)cc3)NC(=O)CNC(=O)c3ccc(CNC(=O)CN4CCN(CC(=O)O)CCN(CC(=O)O)CCN(CC(=O)O)CC4)cc3)[C@@H](C)O)(C(=O)N[C@@H](Cc3c[nH]c4ccccc34)C(N)=O)CC2)cc1F]
MS: Calc'd 1833.86, found $[M+2H]^{2+}$: 1834.8.

Example 83: Compound 156 (SEQ ID NO: 537)
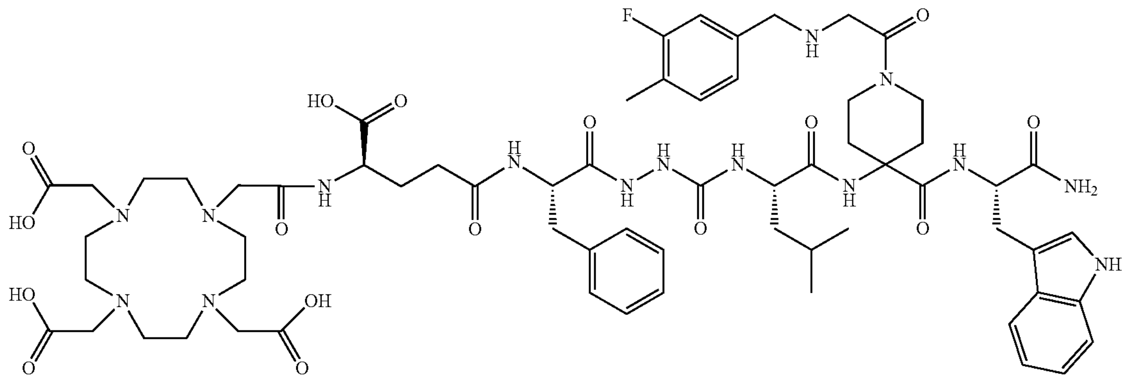 [SMILES: Cc1ccc(CNCC(=O)N2CCC(NC(=O)[C@H](CC(C)C)NC(=O)NNC(=O)[C@H](Cc3ccccc3)NC(=O)CC[C@@H](NC(=O)CN3CCN(CC(=O)O)CCN(CC(=O)O)CCN(CC(=O)O)CC3)C(=O)O)(C(=O)N[C@@H](Cc3c[nH]c4ccccc34)C(N)=O)CC2)cc1F]
MS: Calc'd 1341.65, found $[M+3H]^{3+}$: 448.6.
Example 158: Compound 158 (SEQ ID NO: 539)
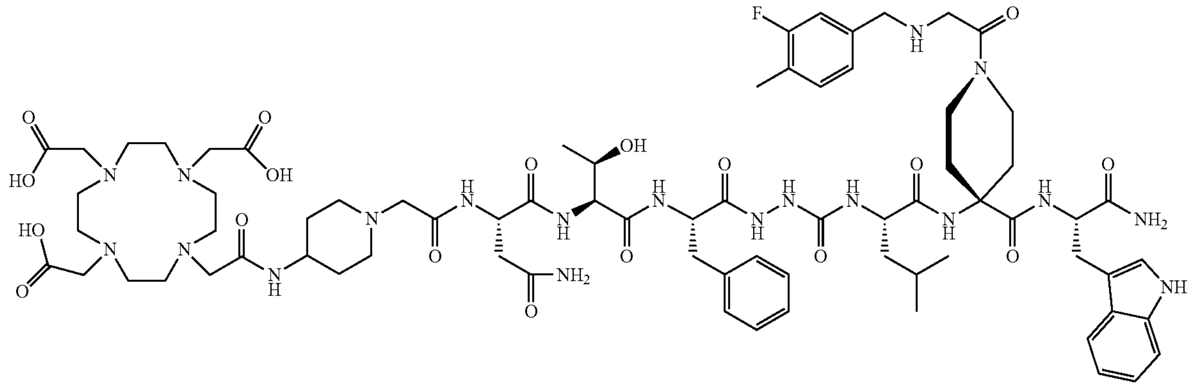
MS: Calc'd 1567.79, found $[M+2H]^{2+}$: 1569.0.
Example 84: Compound 159 (SEQ ID NO: 540)
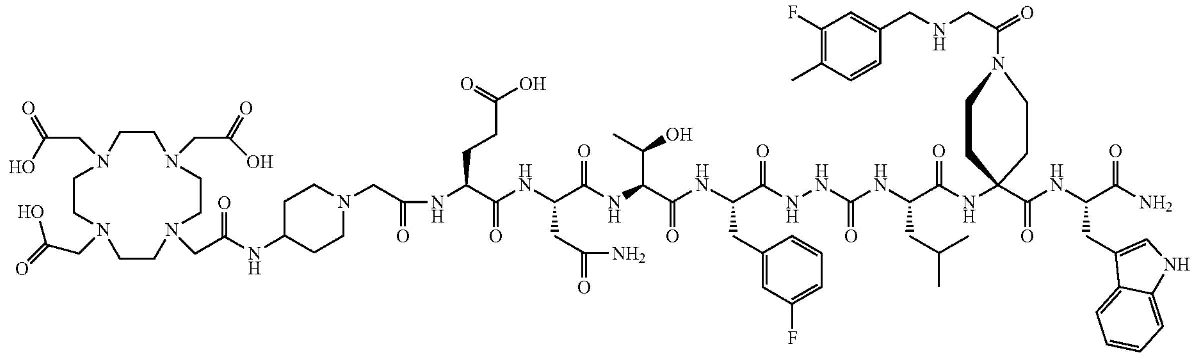
MS: Calc'd 1714.83, found $[M+2H]^{2+}$: 858.9.

Example 85: Compound 160 (SEQ ID NO: 541)
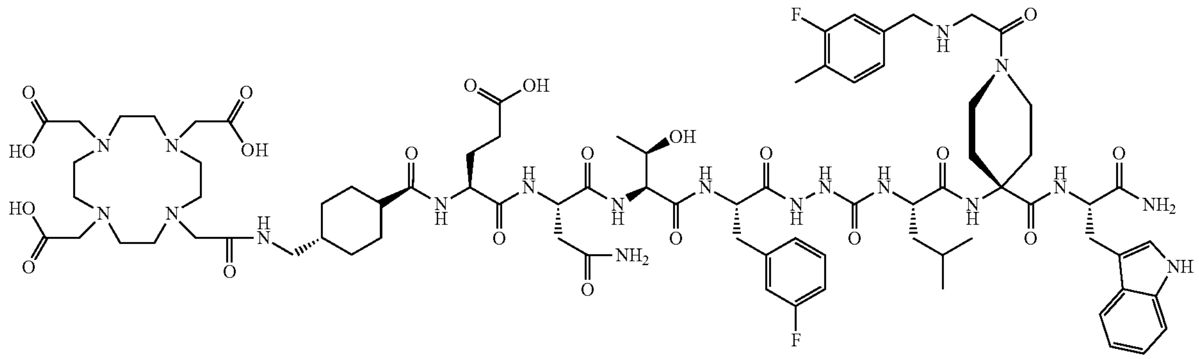
MS: Calc'd 1713.83 found $[M+3H]^{3+}$: 572.75.
Example 86: Compound 161 (SEQ ID NO: 542)
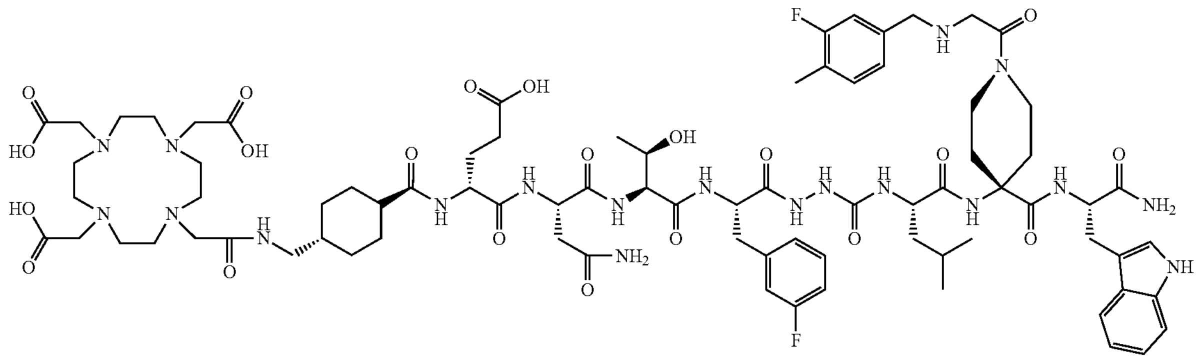
MS: Calc'd 1713.83, found $[M+2H]^{2+}$: 858.5.
Example 87: Compound 164 (SEQ ID NO: 545)
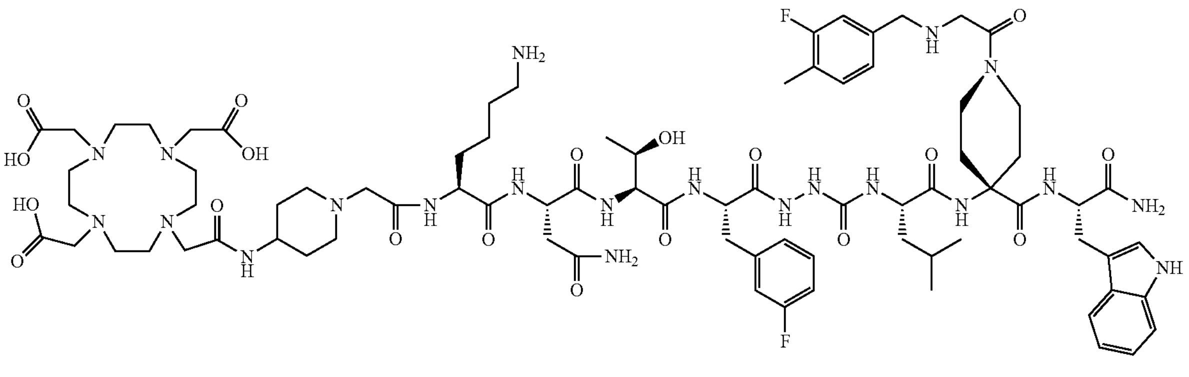
MS: Calc'd 1713.88, found $[M+4H]^{4+}$: 429.8.

Example 88: Compound 165 (SEQ ID NO: 546)
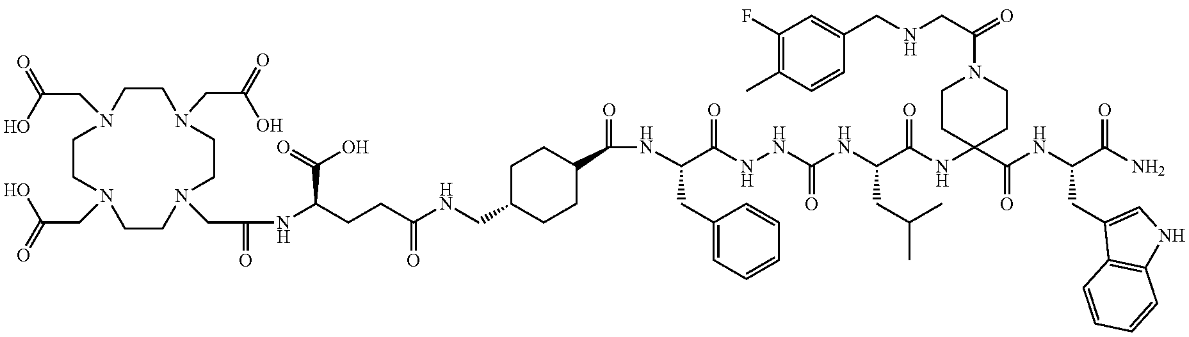
MS: Calc'd 1480.75, found $[M+3H]^{3+}$: 494.9.
Example 89: Compound 166 (SEQ ID NO: 547)
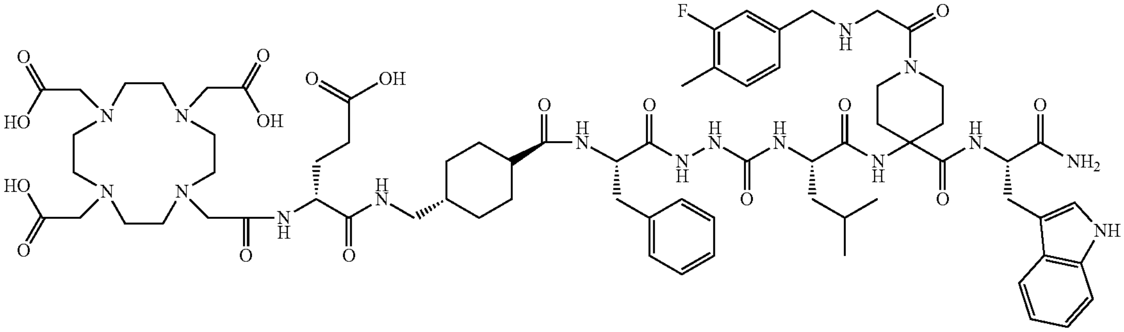
MS: Calc'd 1480.75, found $[M+2H]^{2+}$: 741.8.
Example 90: Compound 167 (SEQ ID NOS 844 and 548)
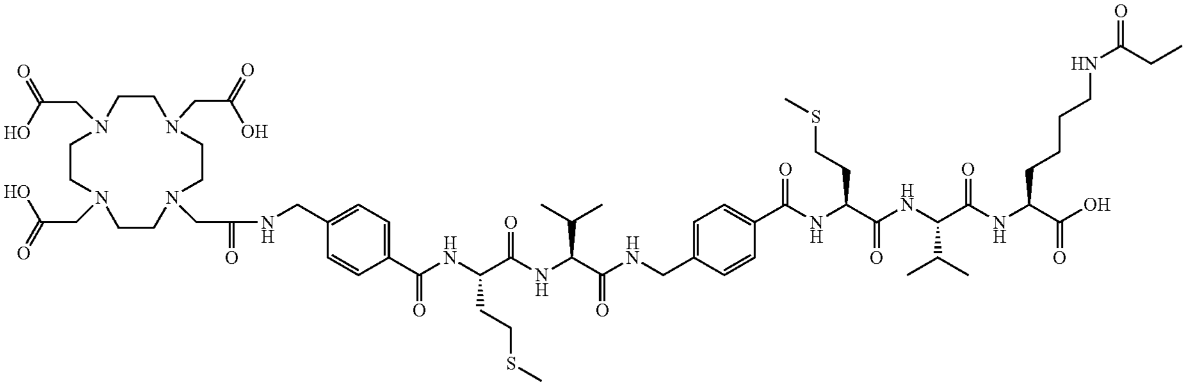

-continued
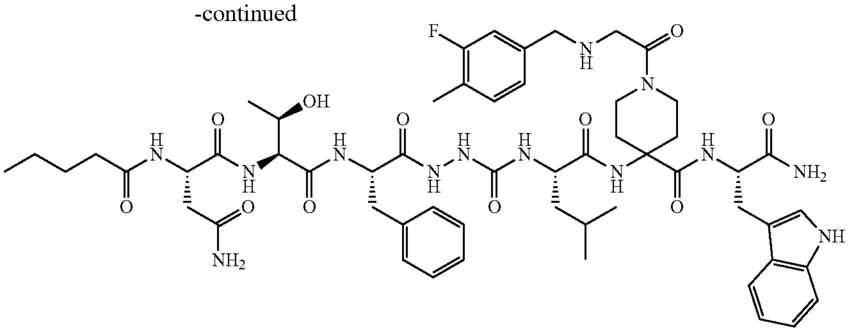
MS: Calc'd 2410.17, found $[M+3H]^{3+}$: 805.0.
Example 91: Compound 168 (SEQ ID NO: 549)
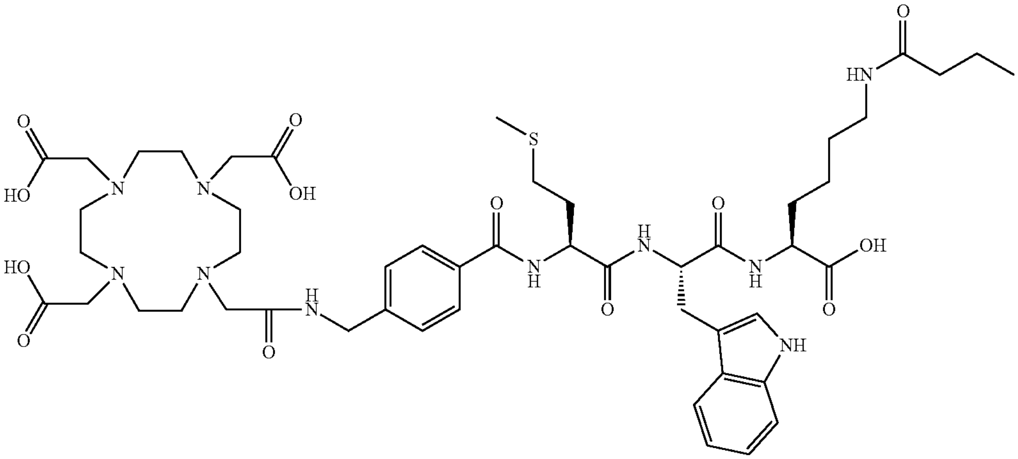
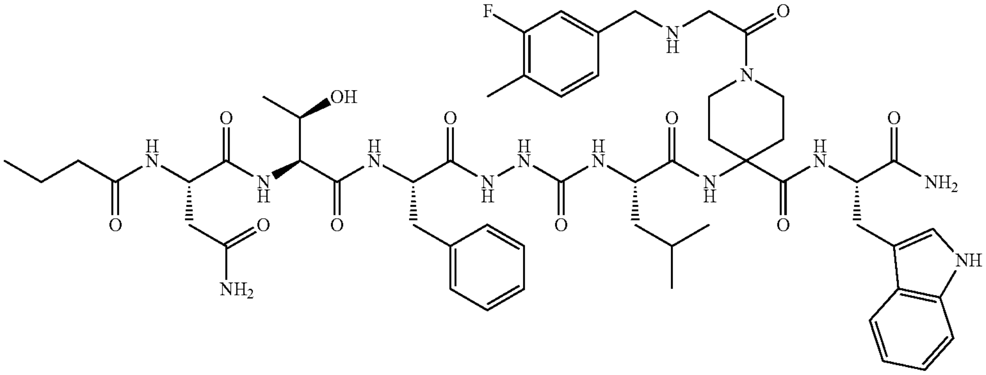
MS: Calc'd 2134.01, found $[M+3H]^{3+}$: 712.95.

Example 92. Compound 169 (SEQ ID NO: 550)
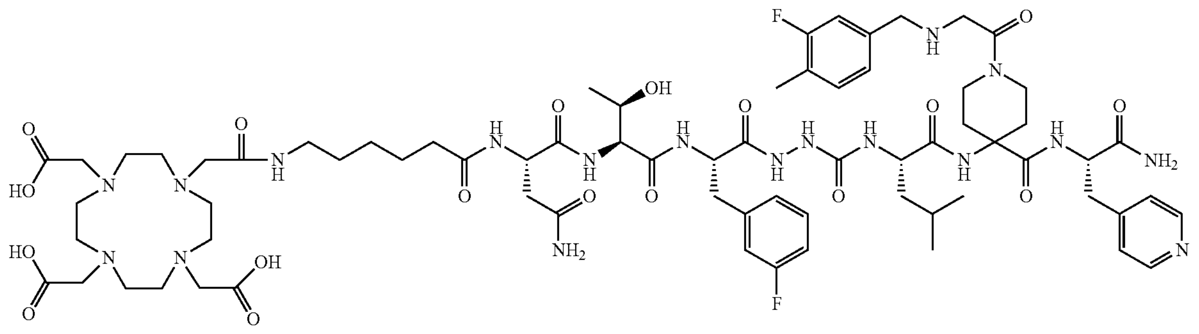 [SMILES: Cc1ccc(CNCC(=O)N2CCC(NC(=O)[C@H](CC(C)C)NC(=O)NNC(=O)[C@H](Cc3cccc(F)c3)NC(=O)[C@@H](NC(=O)[C@H](CC(N)=O)NC(=O)CCCCCNC(=O)CN3CCN(CC(=O)O)CCN(CC(=O)O)CCN(CC(=O)O)CC3)[C@@H](C)O)(C(=O)N[C@@H](Cc3ccncc3)C(N)=O)CC2)cc1F]
MS: Calc'd 1520.76, found $[M+2H]^{2+}$: 761.85.
Example 93: Compound 170 (SEQ ID NO: 551)
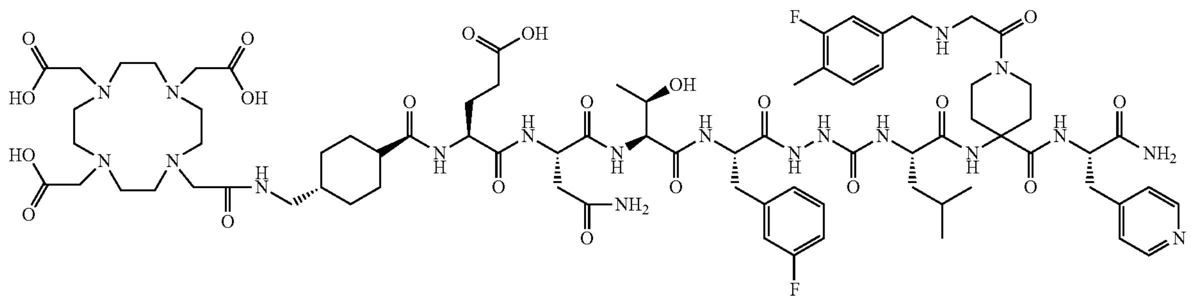
MS: Calc'd 1675.82, found $[M+2H]^{2+}$: 839.45.
Example 94: Compound 171 (SEQ ID NO: 552)
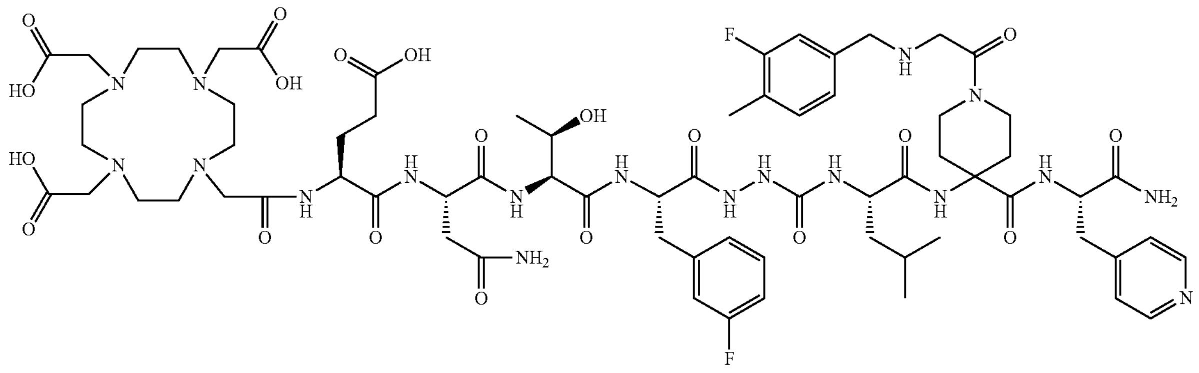 [SMILES: Cc1ccc(CNCC(=O)N2CCC(NC(=O)[C@H](CC(C)C)NC(=O)NNC(=O)[C@H](Cc3cccc(F)c3)NC(=O)[C@@H](NC(=O)[C@H](CC(N)=O)NC(=O)[C@H](CCC(=O)O)NC(=O)CN3CCN(CC(=O)O)CCN(CC(=O)O)CCN(CC(=O)O)CC3)[C@@H](C)O)(C(=O)N[C@@H](Cc3ccncc3)C(N)=O)CC2)cc1F]
MS: Calc'd 1536.72, found $[M+2H]^{2+}$: 769.8.

Example 95: Compound 176 (SEQ ID NO: 555)
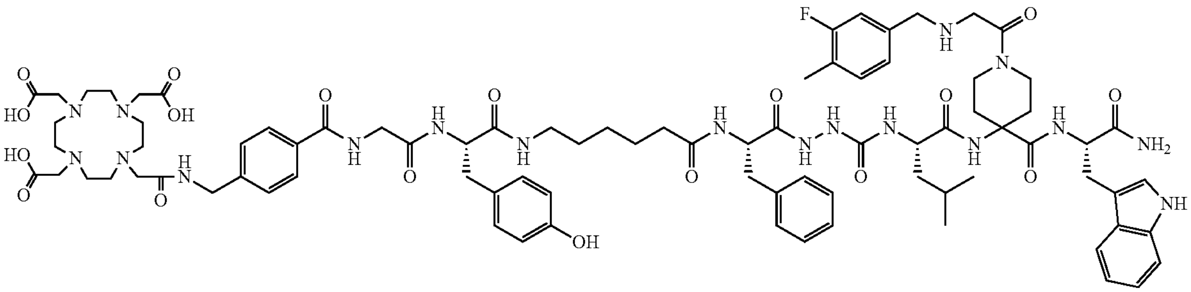 [SMILES: Cc1ccc(CNCC(=O)N2CCC(NC(=O)[C@H](CC(C)C)NC(=O)NNC(=O)[C@H](Cc3ccccc3)NC(=O)CCCCCNC(=O)[C@H](Cc3ccc(O)cc3)NC(=O)CNC(=O)c3ccc(CNC(=O)CN4CCN(CC(=O)O)CCN(CC(=O)O)CCN(CC(=O)O)CC4)cc3)(C(=O)N[C@@H](Cc3c[nH]c4ccccc34)C(N)=O)CC2)cc1F]
MS: Calc'd 1678.83, found $[M+H]^+$: 1679.9.
Example 96: Compound 181 (SEQ ID NO: 560)
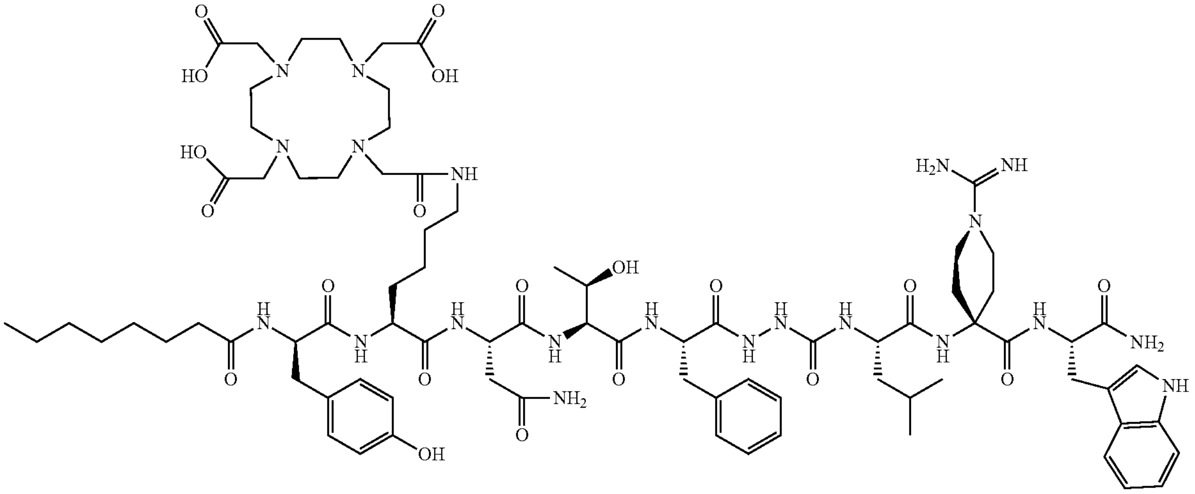
MS: Calc'd 1707.91, found $[M+2H]^{2+}$: 855.4.
Example 97: Compound 182 (SEQ ID NO: 561)
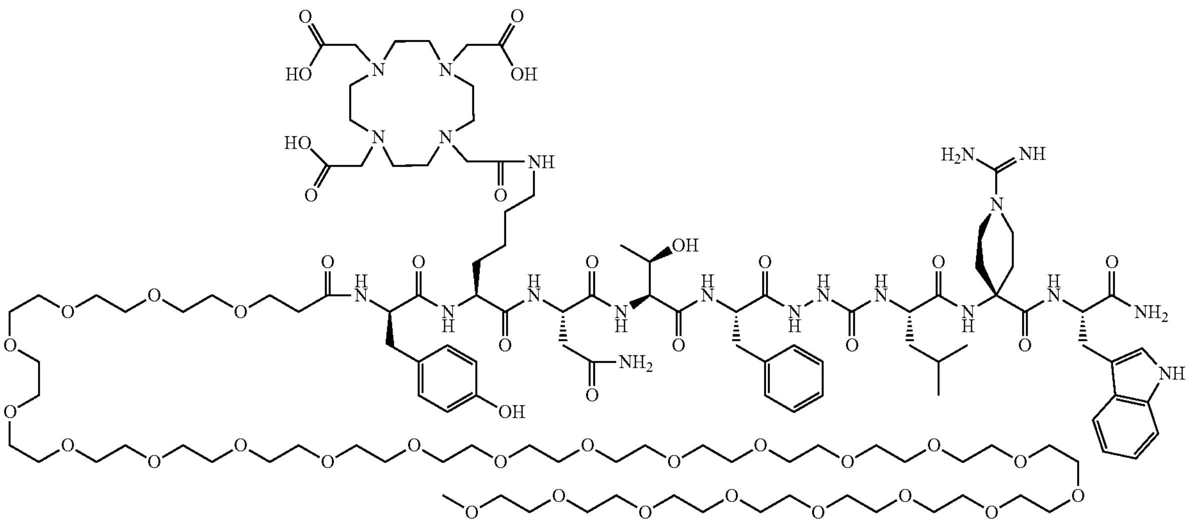
MS: Calc'd 2724.47, found $[M+3H]^{2+}$: 909.7.

Example 98: Compound 183 (SEQ ID NO: 562)
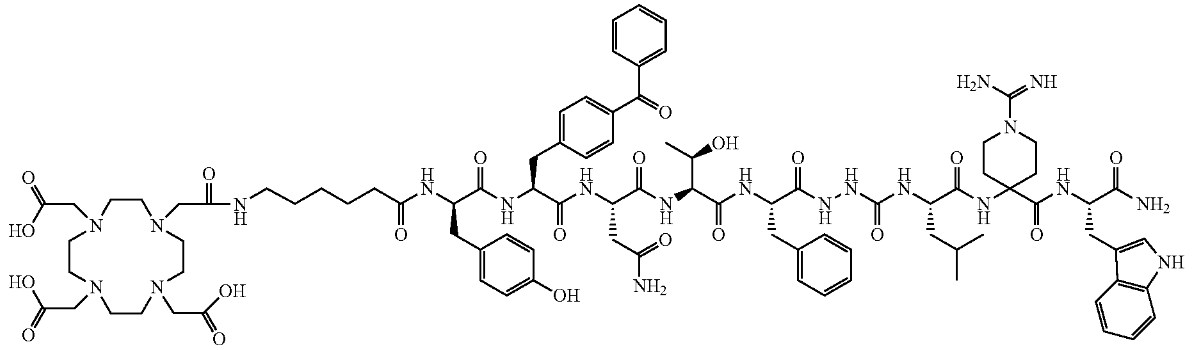 [SMILES: CC(C)C[C@H](NC(=O)NNC(=O)[C@H](Cc1ccccc1)NC(=O)[C@@H](NC(=O)[C@H](CC(N)=O)NC(=O)[C@H](Cc1ccc(C(=O)c2ccccc2)cc1)NC(=O)[C@@H](Cc1ccc(O)cc1)NC(=O)CCCCCNC(=O)CN1CCN(CC(=O)O)CCN(CC(=O)O)CCN(CC(=O)O)CC1)[C@@H](C)O)C(=O)NC1(C(=O)N[C@@H](Cc2c[nH]c3ccccc23)C(N)=O)CCN(C(=N)N)CC1]
MS: Calc'd 1817.89, found $[M+2H]^{2+}$: 910.55.
Example 99: Compound 184 (SEQ ID NO: 563)
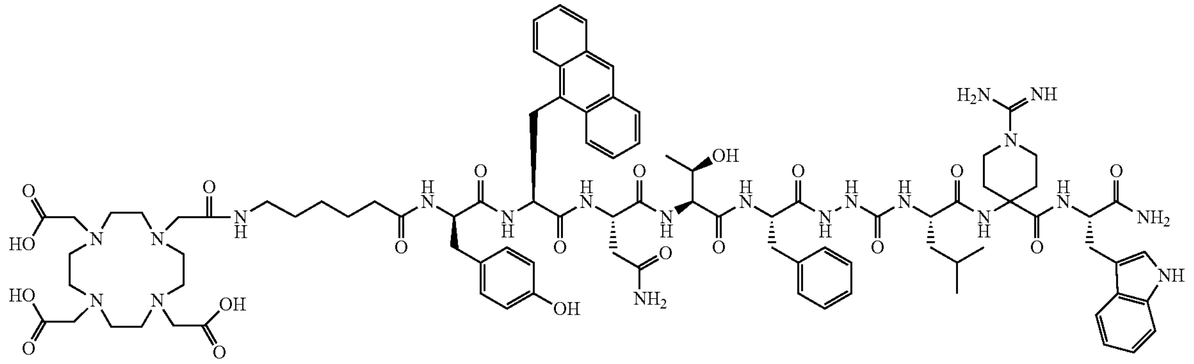 [SMILES: CC(C)C[C@H](NC(=O)NNC(=O)[C@H](Cc1ccccc1)NC(=O)[C@@H](NC(=O)[C@H](CC(N)=O)NC(=O)[C@H](Cc1c2ccccc2cc2ccccc12)NC(=O)[C@@H](Cc1ccc(O)cc1)NC(=O)CCCCCNC(=O)CN1CCN(CC(=O)O)CCN(CC(=O)O)CCN(CC(=O)O)CC1)[C@@H](C)O)C(=O)NC1(C(=O)N[C@@H](Cc2c[nH]c3ccccc23)C(N)=O)CCN(C(=N)N)CC1]
MS: Calc'd 1813.89 found $[M+3H]^{3+}$: 606.05.
Example 100: Compound 185 (SEQ ID NO: 564)
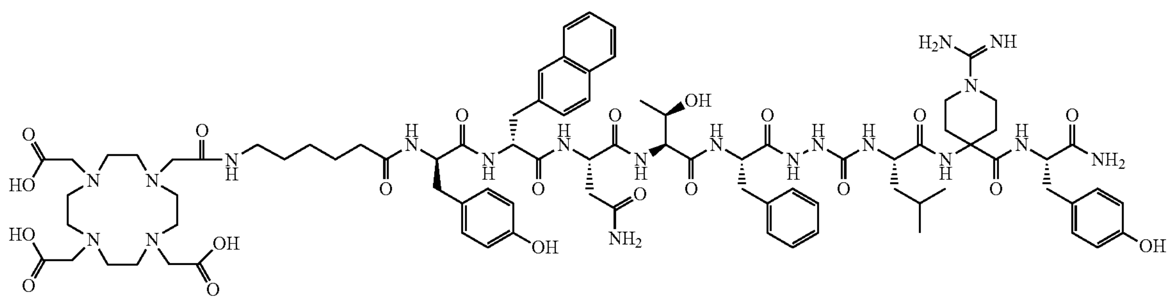 [SMILES: CC(C)C[C@H](NC(=O)NNC(=O)[C@H](Cc1ccccc1)NC(=O)[C@@H](NC(=O)[C@H](CC(N)=O)NC(=O)[C@@H](Cc1ccc2ccccc2c1)NC(=O)[C@@H](Cc1ccc(O)cc1)NC(=O)CCCCCNC(=O)CN1CCN(CC(=O)O)CCN(CC(=O)O)CCN(CC(=O)O)CC1)[C@@H](C)O)C(=O)NC1(C(=O)N[C@@H](Cc2ccc(O)cc2)C(N)=O)CCN(C(=N)N)CC1]
MS: Calc'd 1740.86, found $[M+3H]^{3+}$: 581.75.

Example 101: Compound 186 (SEQ ID NO: 565)
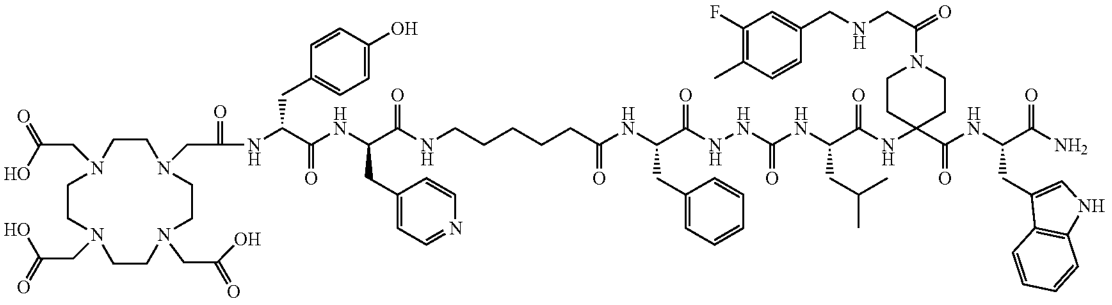 [SMILES: Cc1ccc(CNCC(=O)N2CCC(NC(=O)[C@H](CC(C)C)NC(=O)NNC(=O)[C@H](Cc3ccccc3)NC(=O)CCCCCNC(=O)[C@@H](Cc3ccncc3)NC(=O)[C@@H](Cc3ccc(O)cc3)NC(=O)CN3CCN(CC(=O)O)CCN(CC(=O)O)CCN(CC(=O)O)CC3)(C(=O)N[C@@H](Cc3c[nH]c4ccccc34)C(N)=O)CC2)cc1F]
MS: Calc'd 1636.82, found $[M+3H]^{3+}$: 546.95.
Example 102: Compound 187 (SEQ ID NO: 566)
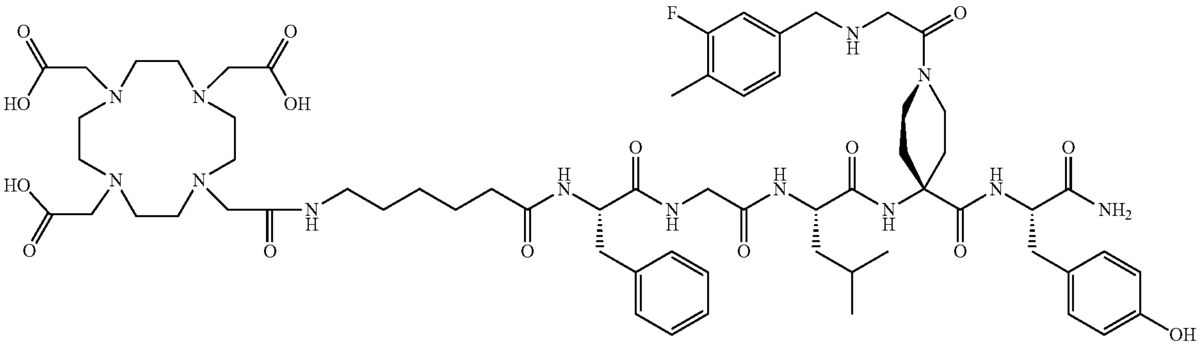
MS: Calc'd 1301.68, found $[M+2H]^{2+}$: 652.2.
Example 103: Compound 188 (SEQ ID NO: 567)
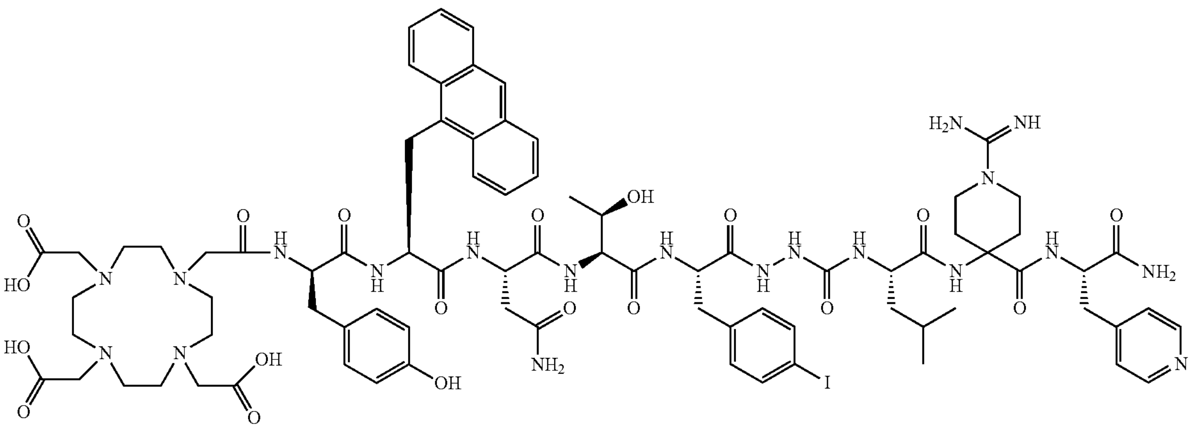 [SMILES: CC(C)C[C@H](NC(=O)NNC(=O)[C@H](Cc1ccc(I)cc1)NC(=O)[C@@H](NC(=O)[C@H](CC(N)=O)NC(=O)[C@H](Cc1c2ccccc2cc2ccccc12)NC(=O)[C@@H](Cc1ccc(O)cc1)NC(=O)CN1CCN(CC(=O)O)CCN(CC(=O)O)CCN(CC(=O)O)CC1)[C@@H](C)O)C(=O)NC1(C(=O)N[C@@H](Cc2ccncc2)C(N)=O)CCN(C(=N)N)CC1]
MS: Calc'd 1788.69, found $[M+3H]^{3+}$: 597.65.

Example 104: Compound 189 (SEQ ID NO: 568)
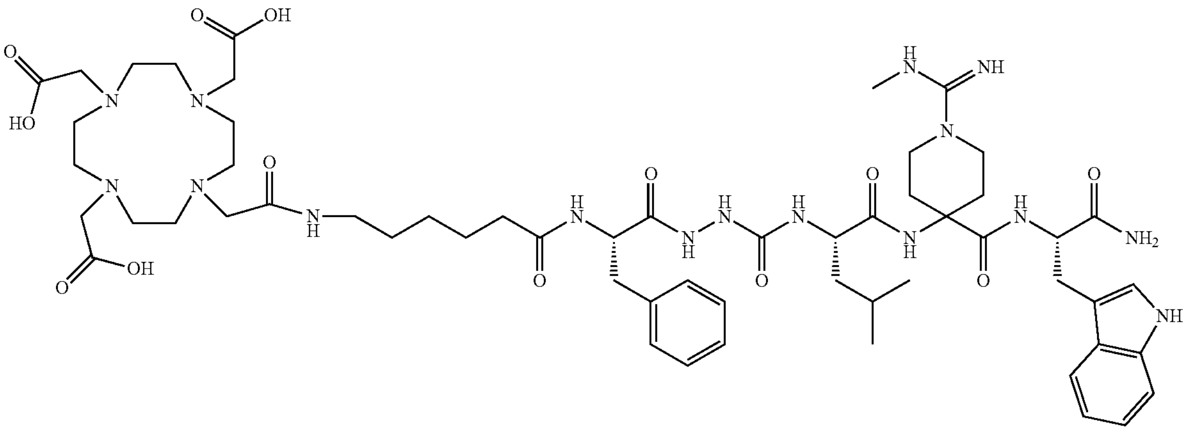 [SMILES: CNC(=N)N1CCC(NC(=O)[C@H](CC(C)C)NC(=O)NNC(=O)[C@H](Cc2ccccc2)NC(=O)CCCCCNC(=O)CN2CCN(CC(=O)O)CCN(CC(=O)O)CCN(CC(=O)O)CC2)(C(=O)N[C@@H](Cc2c[nH]c3ccccc23)C(N)=O)CC1]
MS: Calc'd 1202.66, found $[M+2H]^{2+}$: 602.2.
Example 105: Compound 192 (SEQ ID NO: 571)
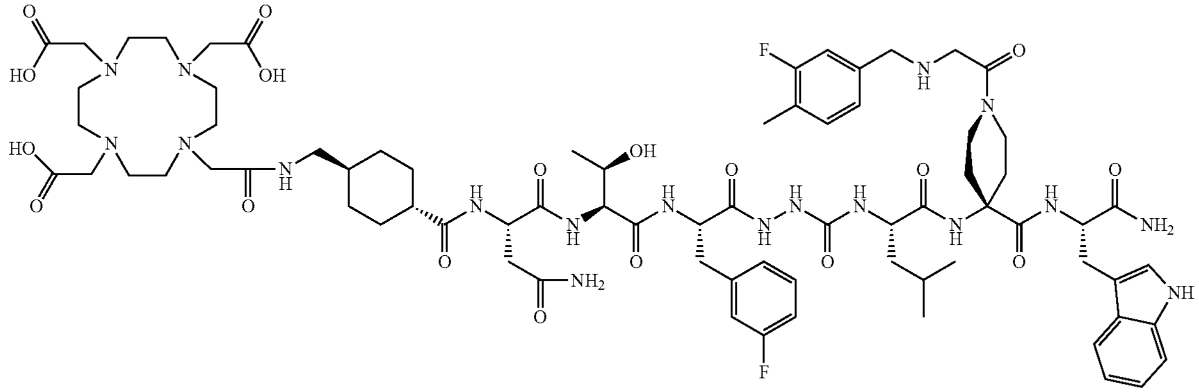
MS: Calc'd 1584.79, found $[M+2H]^{2+}$: 793.9.
Example 106: Compound 193 (SEQ ID NO: 572)
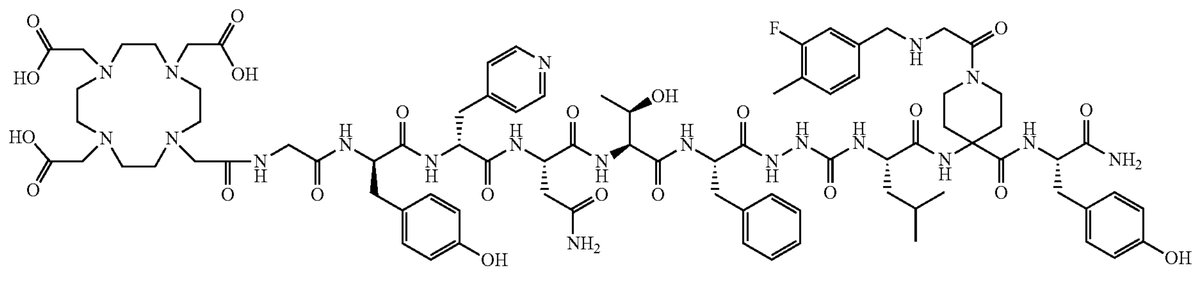 [SMILES: Cc1ccc(CNCC(=O)N2CCC(NC(=O)[C@H](CC(C)C)NC(=O)NNC(=O)[C@H](Cc3ccccc3)NC(=O)[C@@H](NC(=O)[C@H](CC(N)=O)NC(=O)[C@@H](Cc3ccncc3)NC(=O)[C@@H](Cc3ccc(O)cc3)NC(=O)CNC(=O)CN3CCN(CC(=O)O)CCN(CC(=O)O)CCN(CC(=O)O)CC3)[C@@H](C)O)(C(=O)N[C@@H](Cc3ccc(O)cc3)C(N)=O)CC2)cc1F]
MS: Calc'd 1772.83, found $[M+2H]^{2+}$: 887.7.

Compound 193-In (SEQ ID NO: 573)
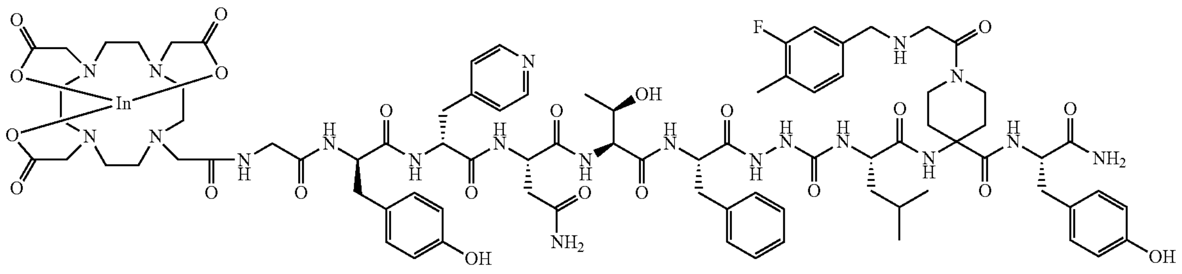
MS: Calc'd 1854.71, found $[M+2H]^{2+}$: 943.35.
Example 107. Compound 195 (SEQ ID NO: 575)
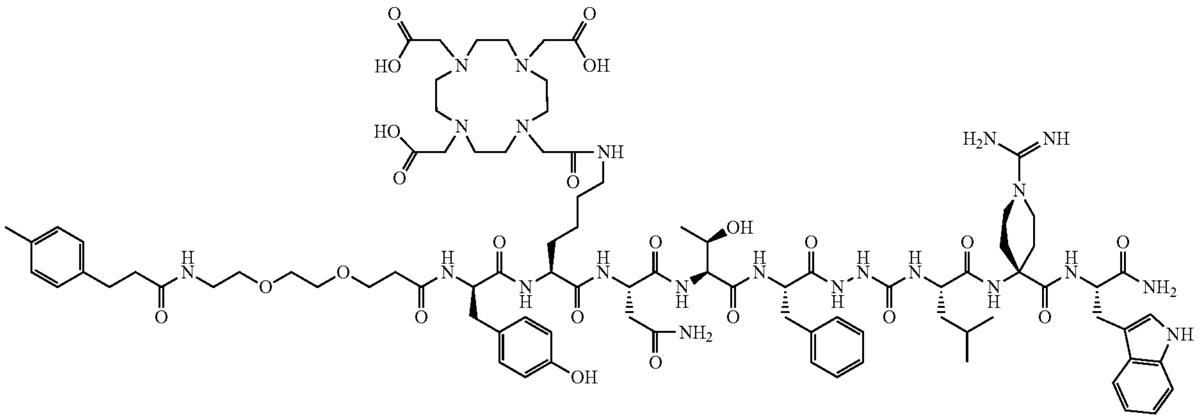
MS: Calc'd 1886.97, found $[M+3H]^{3+}$: 630.4.
Example 108: Compound 196 (SEQ ID NO: 576)
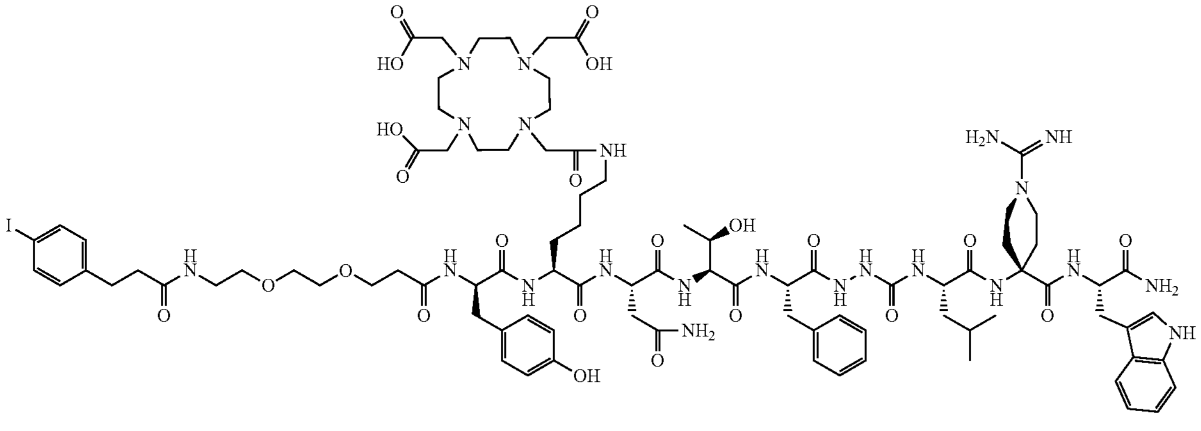
MS: Calc'd 1998.85 found $[M+2H]^{2+}$—1000.65.

Compound 196-In (SEQ ID NO: 577)
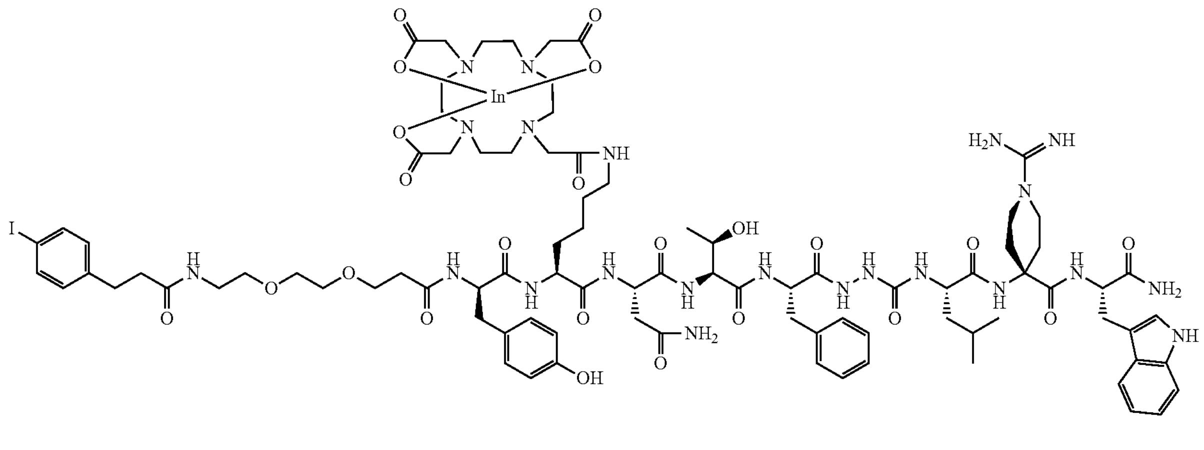
MS: Calc'd 2110.73, found $[M+2H]^{2+}$: 1056.85.
Example 109: Compound 197 (SEQ ID NO: 578)
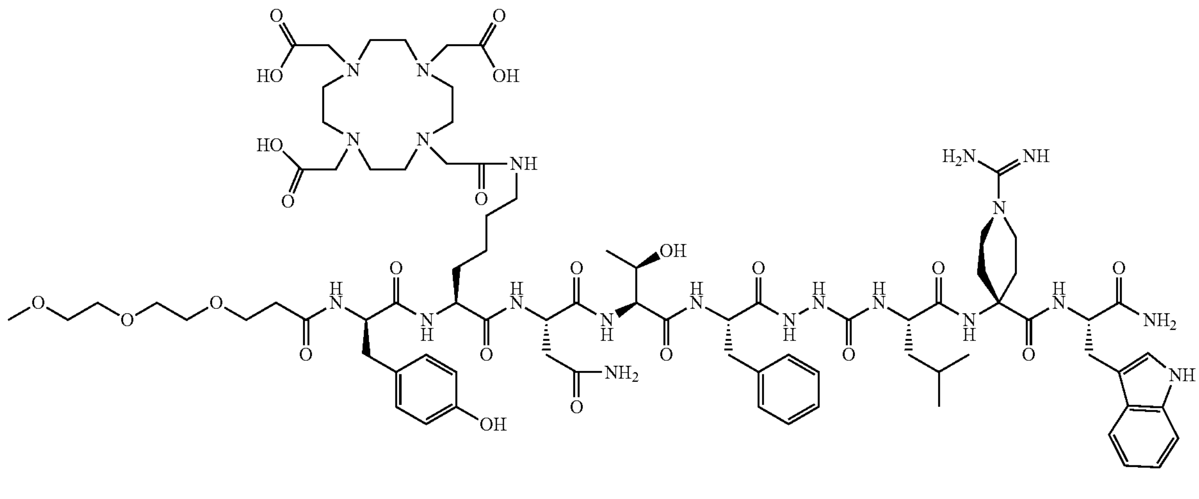
MS: Calc'd 1755.89, found $[M+3H]^{3+}$: 586.7.
Example 110: Compound 198 (SEQ ID NO: 579)
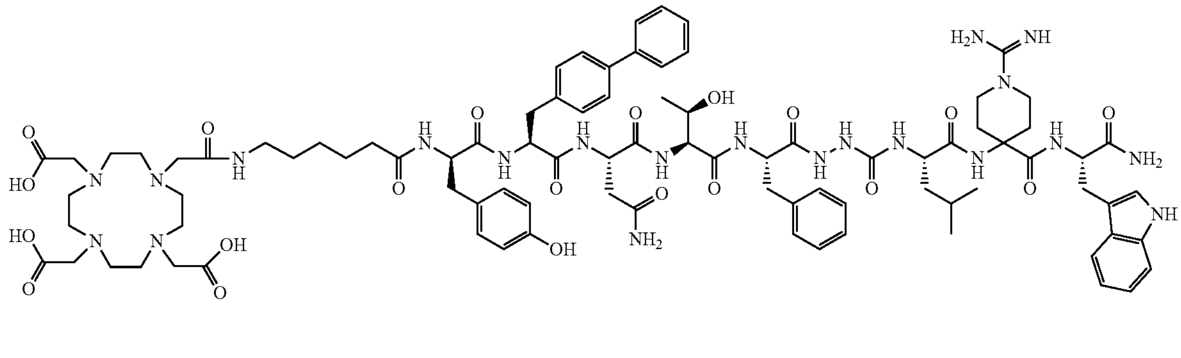 [SMILES: CC(C)C[C@H](NC(=O)NNC(=O)[C@H](Cc1ccccc1)NC(=O)[C@@H](NC(=O)[C@H](CC(N)=O)NC(=O)[C@H](Cc1ccc(-c2ccccc2)cc1)NC(=O)[C@@H](Cc1ccc(O)cc1)NC(=O)CCCCCNC(=O)CN1CCN(CC(=O)O)CCN(CC(=O)O)CCN(CC(=O)O)CC1)[C@@H](C)O)C(=O)NC1(C(=O)N[C@@H](Cc2c[nH]c3ccccc23)C(N)=O)CCN(C(=N)N)CC1]
MS: Calc'd 1789.89, found $[M+2H]^{2+}$: 896.5.

Example 111: Compound 199 (SEQ ID NO: 580)
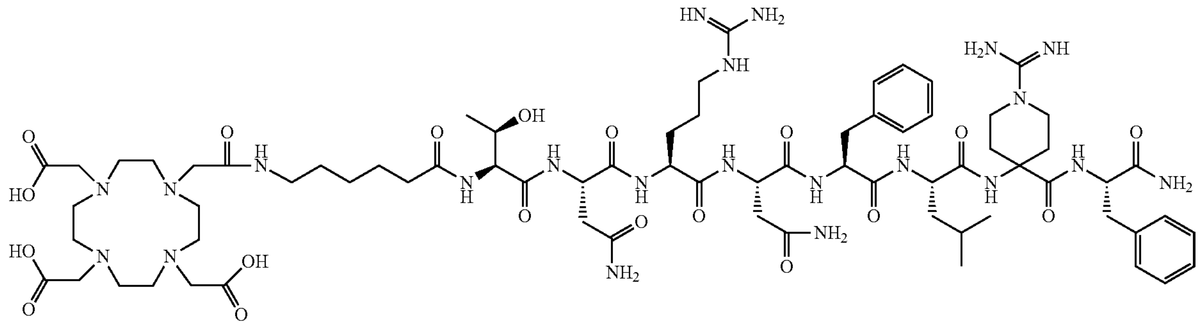 [SMILES: CC(C)C[C@H](NC(=O)[C@H](Cc1ccccc1)NC(=O)[C@H](CC(N)=O)NC(=O)[C@H](CCCNC(=N)N)NC(=O)[C@H](CC(N)=O)NC(=O)[C@@H](NC(=O)CCCCCNC(=O)CN1CCN(CC(=O)O)CCN(CC(=O)O)CCN(CC(=O)O)CC1)[C@@H](C)O)C(=O)NC1(C(=O)N[C@@H](Cc2ccccc2)C(N)=O)CCN(C(=N)N)CC1]
MS: Calc'd 1576.85, found $[M+3H]^{3+}$: 527.0.
Example 112: Compound 201 (SEQ ID NO: 581)
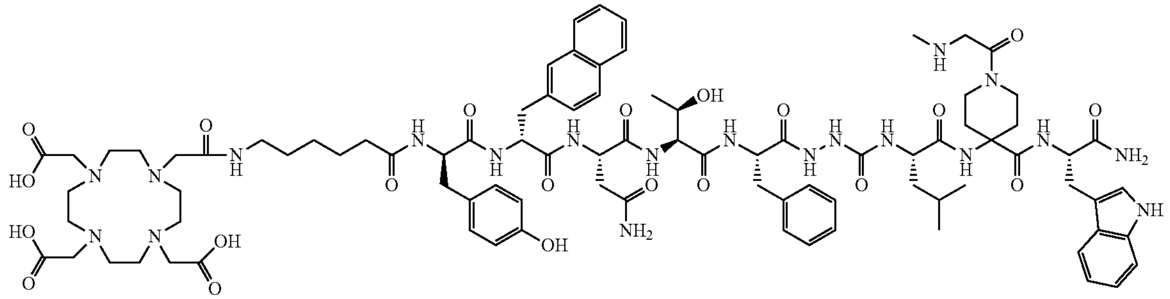 [SMILES: CNCC(=O)N1CCC(NC(=O)[C@H](CC(C)C)NC(=O)NNC(=O)[C@H](Cc2ccccc2)NC(=O)[C@@H](NC(=O)[C@H](CC(N)=O)NC(=O)[C@@H](Cc2ccc3ccccc3c2)NC(=O)[C@@H](Cc2ccc(O)cc2)NC(=O)CCCCCNC(=O)CN2CCN(CC(=O)O)CCN(CC(=O)O)CCN(CC(=O)O)CC2)[C@@H](C)O)(C(=O)N[C@@H](Cc2c[nH]c3ccccc23)C(N)=O)CC1]
MS: Calc'd 1792.89, found $[M+3H]^{3+}$: 599.1.
Compound 201-In (SEQ ID NO: 582)
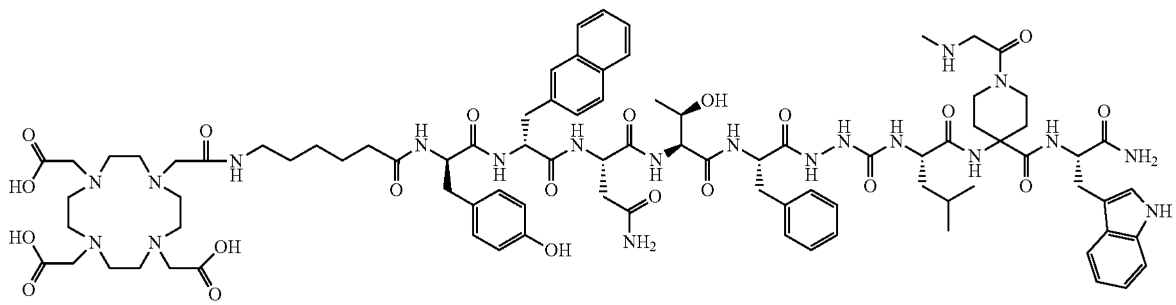 [SMILES: CNCC(=O)N1CCC(NC(=O)[C@H](CC(C)C)NC(=O)NNC(=O)[C@H](Cc2ccccc2)NC(=O)[C@@H](NC(=O)[C@H](CC(N)=O)NC(=O)[C@@H](Cc2ccc3ccccc3c2)NC(=O)[C@@H](Cc2ccc(O)cc2)NC(=O)CCCCCNC(=O)CN2CCN(CC(=O)O)CCN(CC(=O)O)CCN(CC(=O)O)CC2)[C@@H](C)O)(C(=O)N[C@@H](Cc2c[nH]c3ccccc23)C(N)=O)CC1]
MS: Calc'd 1904.77, found $[M+2H]^{2+}$: 953.87.

Example 113: Compound 202 (SEQ ID NO: 583)
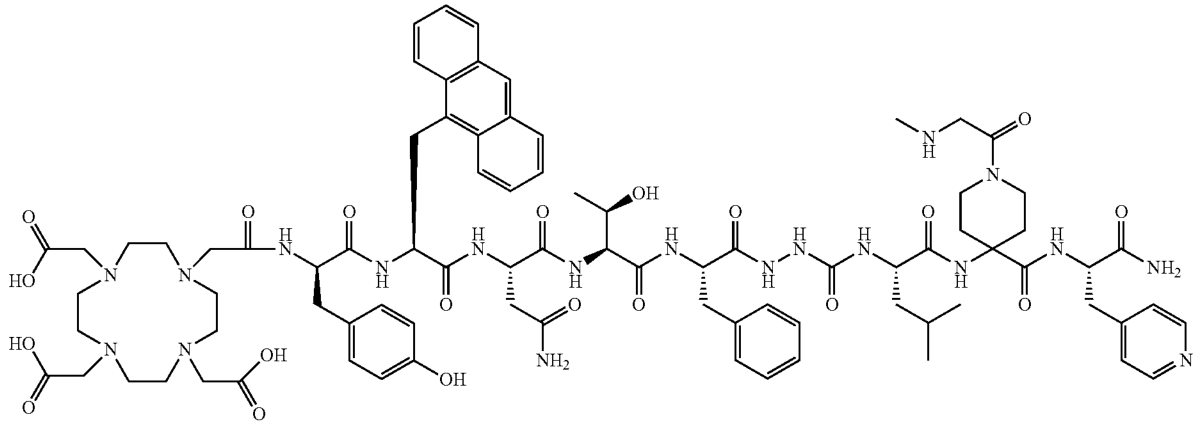 [SMILES: CNCC(=O)N1CCC(NC(=O)[C@H](CC(C)C)NC(=O)NNC(=O)[C@H](Cc2ccccc2)NC(=O)[C@@H](NC(=O)[C@H](CC(N)=O)NC(=O)[C@H](Cc2c3ccccc3cc3ccccc23)NC(=O)[C@@H](Cc2ccc(O)cc2)NC(=O)CN2CCN(CC(=O)O)CCN(CC(=O)O)CCN(CC(=O)O)CC2)[C@@H](C)O)(C(=O)N[C@@H](Cc2ccncc2)C(N)=O)CC1]
MS: Calc'd 1691.81, found $[M+3H]^{3+}$: 565.35.
Example 114: Compound 203 (SEQ ID NO: 584)
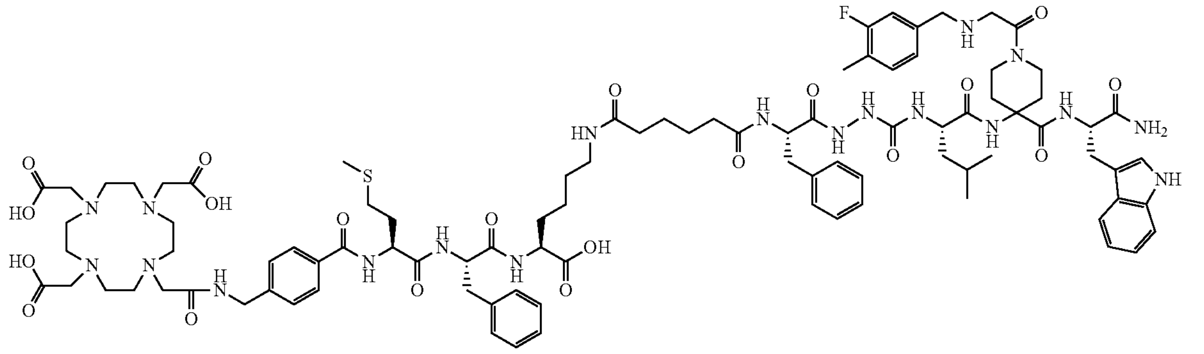 [SMILES: CSCC[C@H](NC(=O)c1ccc(CNC(=O)CN2CCN(CC(=O)O)CCN(CC(=O)O)CCN(CC(=O)O)CC2)cc1)C(=O)N[C@@H](Cc1ccccc1)C(=O)N[C@@H](CCCCNC(=O)CCCCC(=O)N[C@@H](Cc1ccccc1)C(=O)NNC(=O)N[C@@H](CC(C)C)C(=O)NC1(C(=O)N[C@@H](Cc2c[nH]c3ccccc23)C(N)=O)CCN(C(=O)CNCc2ccc(C)c(F)c2)CC1)C(=O)O]
MS: Calc'd 1879.91, found $[M+H]^{+}$: 1881.0.
Example 115: Compound 204
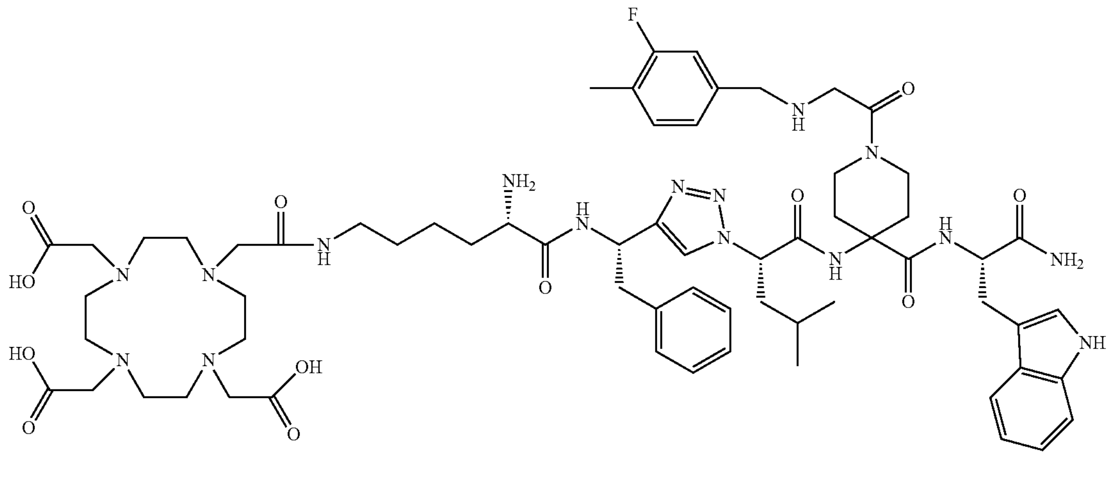 [SMILES: Cc1ccc(CNCC(=O)N2CCC(NC(=O)[C@H](CC(C)C)n3cc([C@H](Cc4ccccc4)NC(=O)[C@@H](N)CCCCNC(=O)CN4CCN(CC(=O)O)CCN(CC(=O)O)CCN(CC(=O)O)CC4)nn3)(C(=O)N[C@@H](Cc3c[nH]c4ccccc34)C(N)=O)CC2)cc1F]
MS: Calc'd 1306.70, found $[M+2H]^{2+}$: 654.8.

Example 116: Compound 205 (SEQ ID NO: 586)
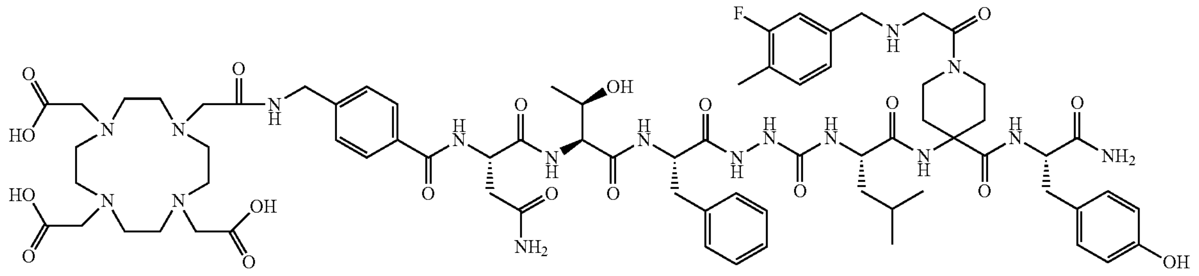 [SMILES: Cc1ccc(CNCC(=O)N2CCC(NC(=O)[C@H](CC(C)C)NC(=O)NNC(=O)[C@H](Cc3ccccc3)NC(=O)[C@@H](NC(=O)[C@H](CC(N)=O)NC(=O)c3ccc(CNC(=O)CN4CCN(CC(=O)O)CCN(CC(=O)O)CCN(CC(=O)O)CC4)cc3)[C@@H](C)O)(C(=O)N[C@@H](Cc3ccc(O)cc3)C(N)=O)CC2)cc1F]
MS: Calc'd 1537.74, found $[M+2H]^{2+}$: 770.3.
Example 117: Compound 206 (SEQ ID NO: 587)
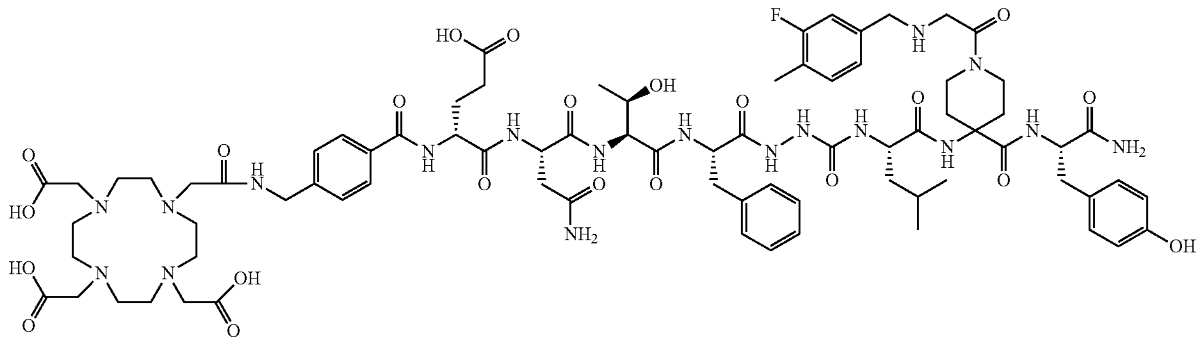 [SMILES: Cc1ccc(CNCC(=O)N2CCC(NC(=O)[C@H](CC(C)C)NC(=O)NNC(=O)[C@H](Cc3ccccc3)NC(=O)[C@@H](NC(=O)[C@H](CC(N)=O)NC(=O)[C@@H](CCC(=O)O)NC(=O)c3ccc(CNC(=O)CN4CCN(CC(=O)O)CCN(CC(=O)O)CCN(CC(=O)O)CC4)cc3)[C@@H](C)O)(C(=O)N[C@@H](Cc3ccc(O)cc3)C(N)=O)CC2)cc1F]
MS: Calc'd 1666.78, found $[M+2H]^{2+}$: 835.0.
Example 118: Compound 213 (SEQ ID NO: 594)
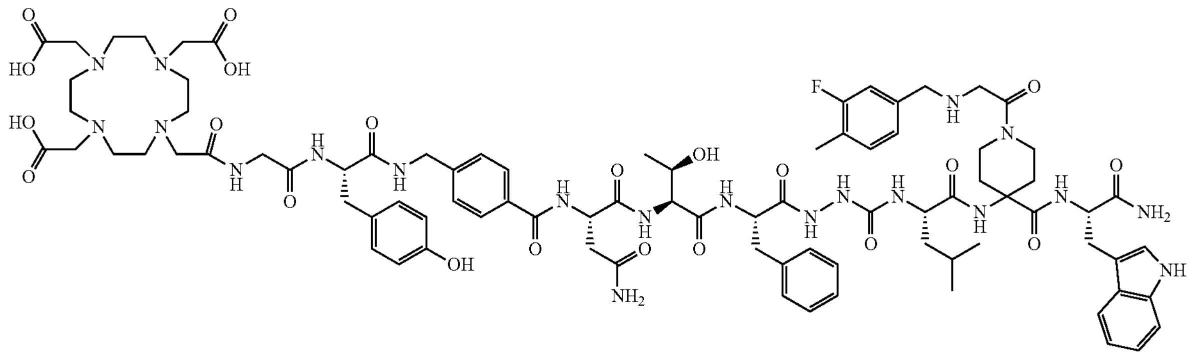 [SMILES: Cc1ccc(CNCC(=O)N2CCC(NC(=O)[C@H](CC(C)C)NC(=O)NNC(=O)[C@H](Cc3ccccc3)NC(=O)[C@@H](NC(=O)[C@H](CC(N)=O)NC(=O)c3ccc(CNC(=O)[C@H](Cc4ccc(O)cc4)NC(=O)CNC(=O)CN4CCN(CC(=O)O)CCN(CC(=O)O)CCN(CC(=O)O)CC4)cc3)[C@@H](C)O)(C(=O)N[C@@H](Cc3c[nH]c4ccccc34)C(N)=O)CC2)cc1F]
MS: Calc'd 1780.84, found [M+H]: $^{+}$1781.7.

Example 119: Compound 214
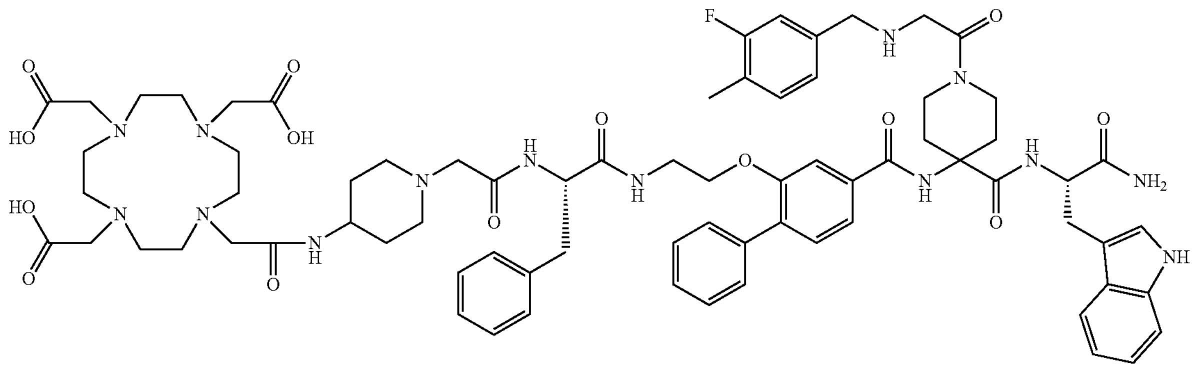 [SMILES: Cc1ccc(CNCC(=O)N2CCC(NC(=O)c3ccc(-c4ccccc4)c(OCCNC(=O)[C@H](Cc4ccccc4)NC(=O)CN4CCC(NC(=O)CN5CCN(CC(=O)O)CCN(CC(=O)O)CCN(CC(=O)O)CC5)CC4)c3)(C(=O)N[C@@H](Cc3c[nH]c4ccccc34)C(N)=O)CC2)cc1F]
MS: Calc'd 1420.70, found $[M+H]^+$: 1421.9.
Example 120: Compound 215
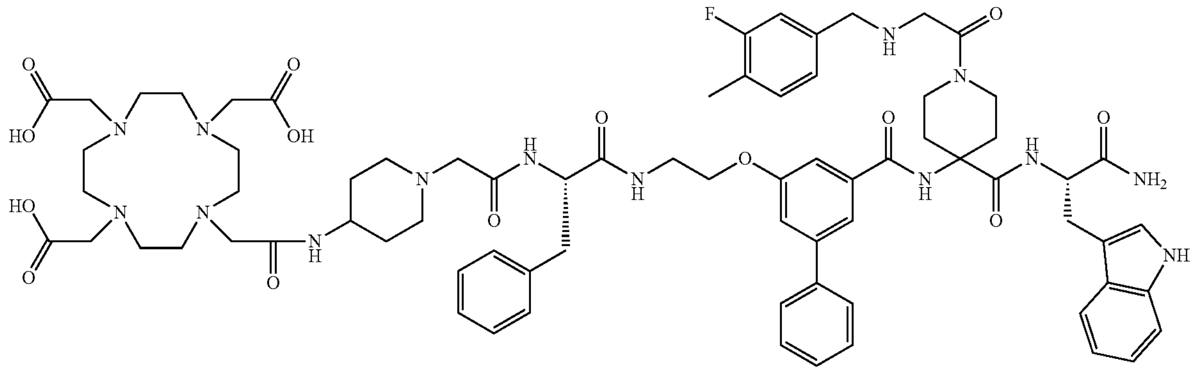 [SMILES: Cc1ccc(CNCC(=O)N2CCC(NC(=O)c3cc(OCCNC(=O)[C@H](Cc4ccccc4)NC(=O)CN4CCC(NC(=O)CN5CCN(CC(=O)O)CCN(CC(=O)O)CCN(CC(=O)O)CC5)CC4)cc(-c4ccccc4)c3)(C(=O)N[C@@H](Cc3c[nH]c4ccccc34)C(N)=O)CC2)cc1F]
MS: Calc'd 1420.70, found $[M+H]^+$: 1421.9.
Example 121: Compound 216
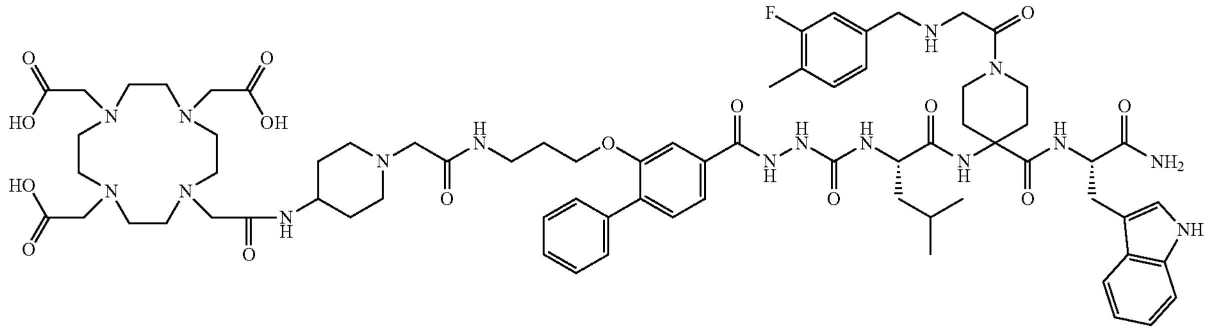 [SMILES: Cc1ccc(CNCC(=O)N2CCC(NC(=O)[C@H](CC(C)C)NC(=O)NNC(=O)c3ccc(-c4ccccc4)c(OCCCNC(=O)CN4CCC(NC(=O)CN5CCN(CC(=O)O)CCN(CC(=O)O)CCN(CC(=O)O)CC5)CC4)c3)(C(=O)N[C@@H](Cc3c[nH]c4ccccc34)C(N)=O)CC2)cc1F]
MS: Calc'd 1458.75, found $[M+H]^+$: 1460.1.

Example 122: Compound 217
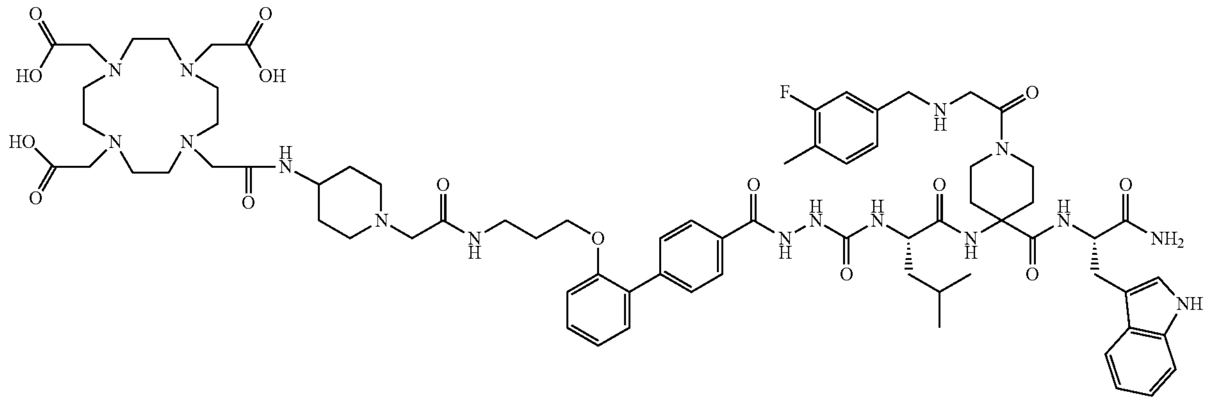 [SMILES: Cc1ccc(CNCC(=O)N2CCC(NC(=O)[C@H](CC(C)C)NC(=O)NNC(=O)c3ccc(-c4ccccc4OCCCNC(=O)CN4CCC(NC(=O)CN5CCN(CC(=O)O)CCN(CC(=O)O)CCN(CC(=O)O)CC5)CC4)cc3)(C(=O)N[C@@H](Cc3c[nH]c4ccccc34)C(N)=O)CC2)cc1F]
MS: Calc'd 1458.75, found $[M+H]^+$: 1459.9.
Example 123: Compound 218 (SEQ ID NO: 599)
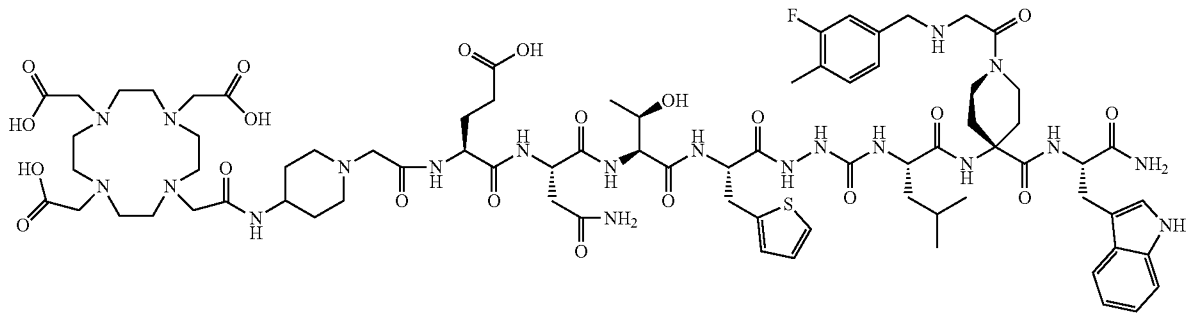
MS: Calc'd 1702.79, found $[M+3H]^{3+}$: 568.95.
Example 124: Compound 221 (SEQ ID NO: 602)
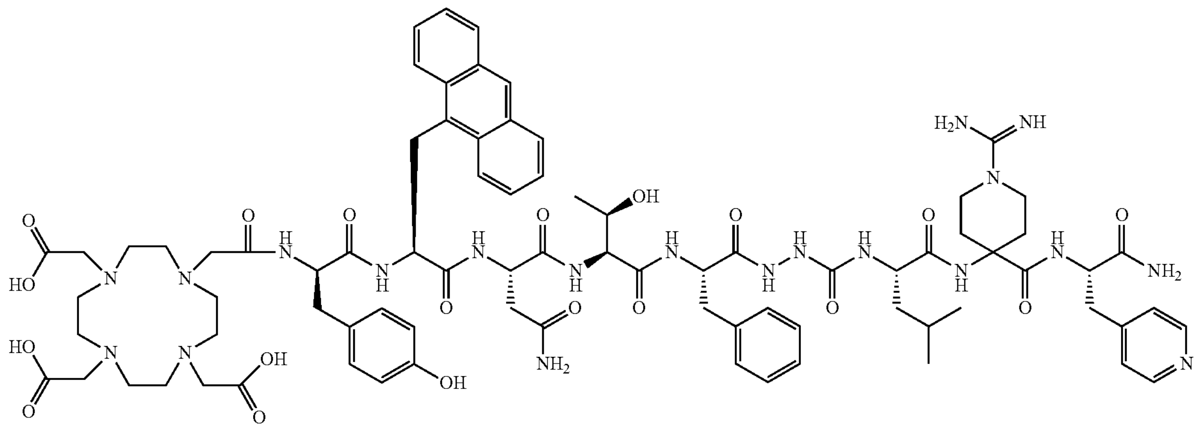
MS: Calc'd 1662.79, found $[M+3H]^{3+}$: 555.7.

Example 125: Compound 222 (SEQ ID NO: 603)
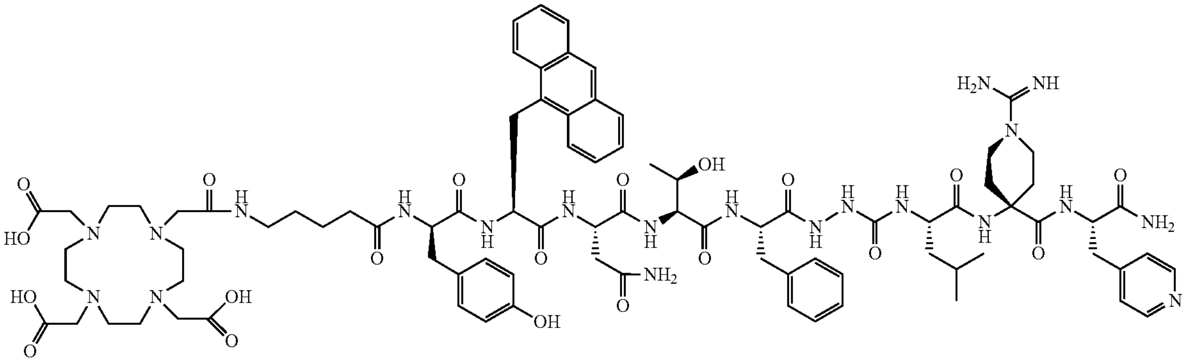
MS: Calc'd 1761.86, found $[M+3H]^{3+}$: 588.7.
Example 126: Compound 226 (SEQ ID NO: 607)
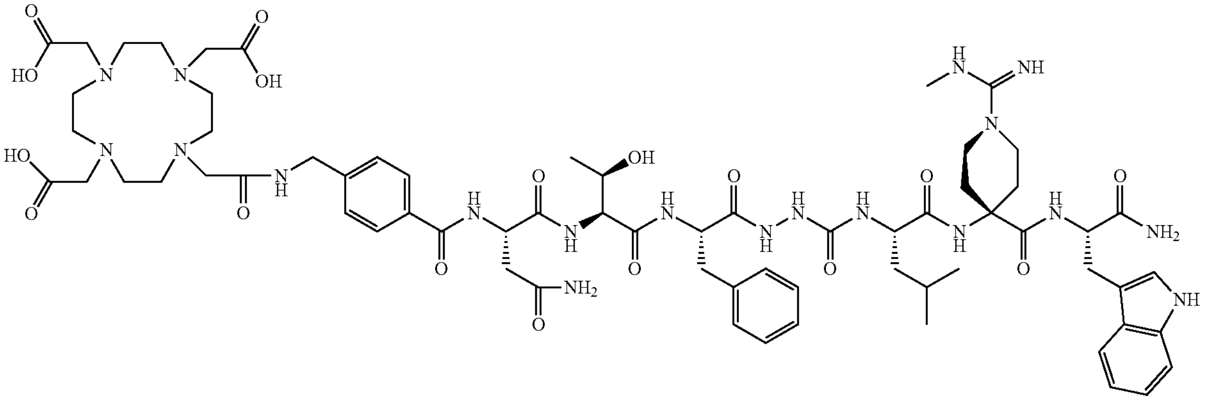
MS: Calc'd 1437.72, found $[M+2H]^{2+}$: 720.2.
Example 128: Compound 230 (SEQ ID NO: 611)
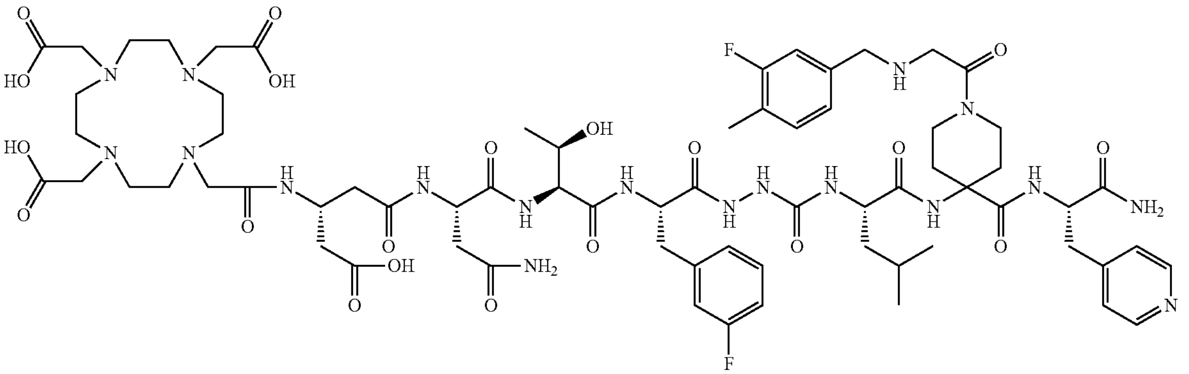 [SMILES: Cc1ccc(CNCC(=O)N2CCC(NC(=O)[C@H](CC(C)C)NC(=O)NNC(=O)[C@H](Cc3cccc(F)c3)NC(=O)[C@@H](NC(=O)[C@H](CC(N)=O)NC(=O)C[C@H](CC(=O)O)NC(=O)CN3CCN(CC(=O)O)CCN(CC(=O)O)CCN(CC(=O)O)CC3)[C@@H](C)O)(C(=O)N[C@@H](Cc3ccncc3)C(N)=O)CC2)cc1F]
MS: Calc'd 1536.72, found $[M+3H]^{3+}$: 513.65.

Example 129: Compound 231 (SEQ ID NO: 612)
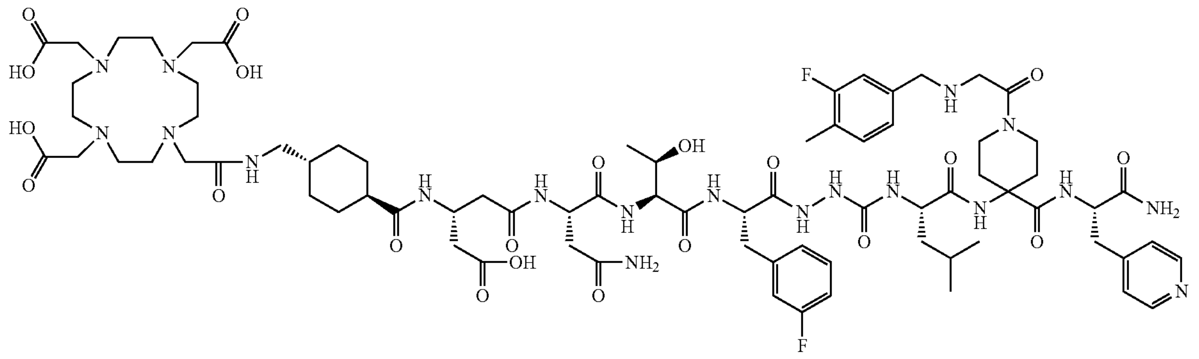 [SMILES: Cc1ccc(CNCC(=O)N2CCC(NC(=O)[C@H](CC(C)C)NC(=O)NNC(=O)[C@H](Cc3cccc(F)c3)NC(=O)[C@@H](NC(=O)[C@H](CC(N)=O)NC(=O)C[C@H](CC(=O)O)NC(=O)[C@H]3CC[C@H](CNC(=O)CN4CCN(CC(=O)O)CCN(CC(=O)O)CCN(CC(=O)O)CC4)CC3)[C@@H](C)O)(C(=O)N[C@@H](Cc3ccncc3)C(N)=O)CC2)cc1F]
MS: Calc'd 1675.82, found $[M+3H]^{3+}$: 560.05.
Example 130: Compound 232 (SEQ ID NO: 613)
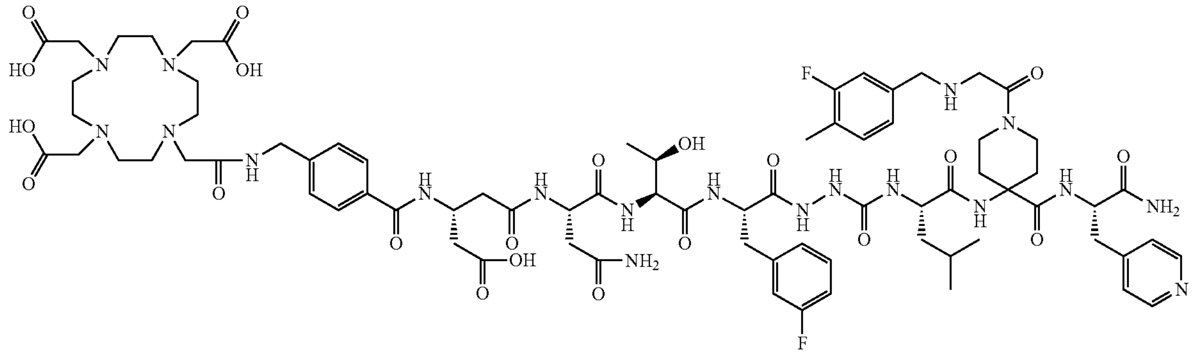 [SMILES: Cc1ccc(CNCC(=O)N2CCC(NC(=O)[C@H](CC(C)C)NC(=O)NNC(=O)[C@H](Cc3cccc(F)c3)NC(=O)[C@@H](NC(=O)[C@H](CC(N)=O)NC(=O)C[C@H](CC(=O)O)NC(=O)c3ccc(CNC(=O)CN4CCN(CC(=O)O)CCN(CC(=O)O)CCN(CC(=O)O)CC4)cc3)[C@@H](C)O)(C(=O)N[C@@H](Cc3ccncc3)C(N)=O)CC2)cc1F]
MS: Calc'd 1669.77, found $[M+3H]^{3+}$: 558.05.
Example 131: Compound 233 (SEQ ID NO: 614)
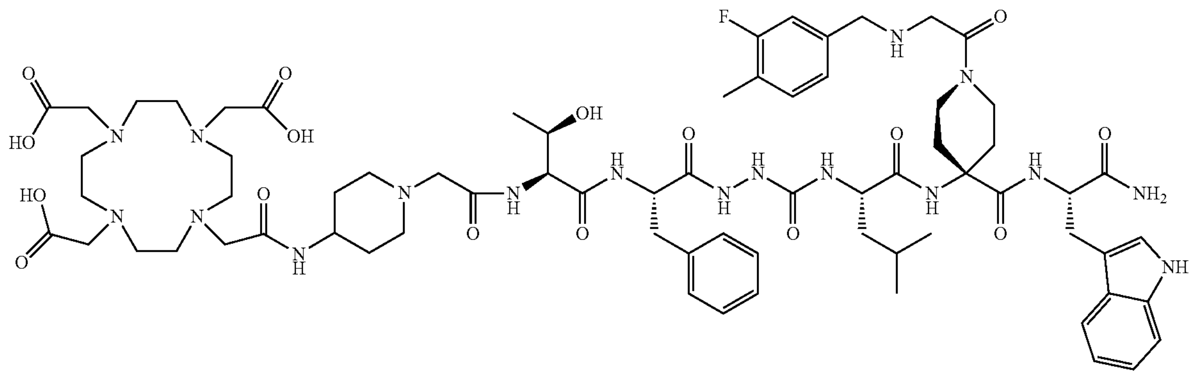
MS: Calc'd 1453.75, found $[M+H]^{3+}$: 1454.9.

Example 132: Compound 234 (SEQ ID NO: 615)
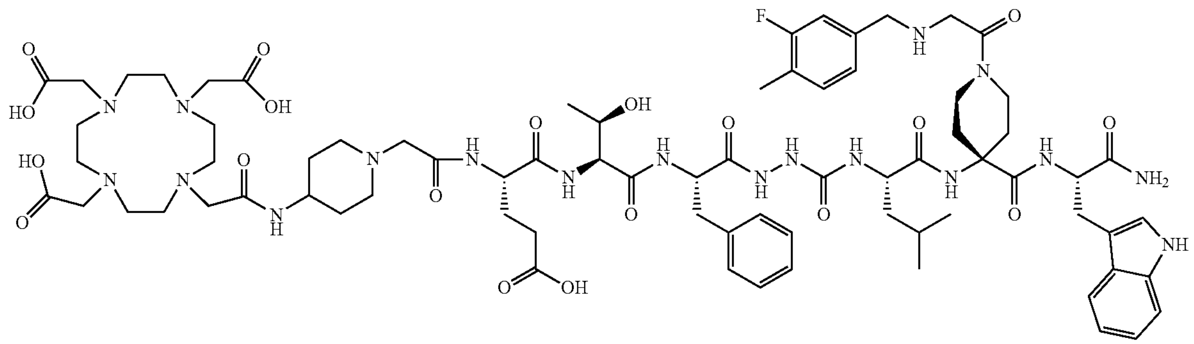
MS: Calc'd 1582.79, found $[M+H]^+$: 1583.9.
Example 133: Compound 235 (SEQ ID NO: 616)
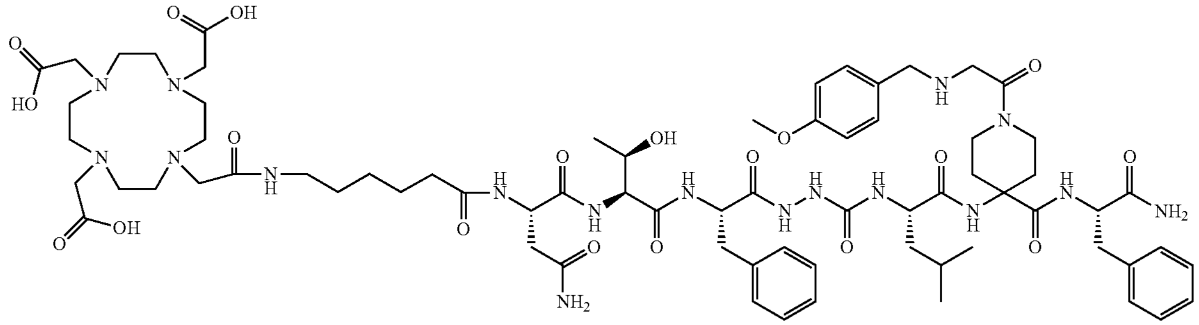 [SMILES: COc1ccc(CNCC(=O)N2CCC(NC(=O)[C@H](CC(C)C)NC(=O)NNC(=O)[C@H](Cc3ccccc3)NC(=O)[C@@H](NC(=O)[C@H](CC(N)=O)NC(=O)CCCCCNC(=O)CN3CCN(CC(=O)O)CCN(CC(=O)O)CCN(CC(=O)O)CC3)[C@@H](C)O)(C(=O)N[C@@H](Cc3ccccc3)C(N)=O)CC2)cc1]
MS: Calc'd 1499.78, found $[M+H]^+$: 1501.1.
Example 134: Compound 236 (SEQ ID NO: 617)
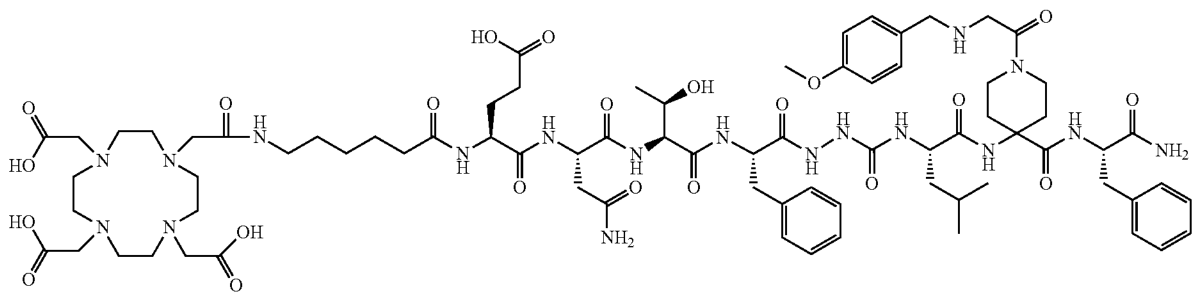 [SMILES: COc1ccc(CNCC(=O)N2CCC(NC(=O)[C@H](CC(C)C)NC(=O)NNC(=O)[C@H](Cc3ccccc3)NC(=O)[C@@H](NC(=O)[C@H](CC(N)=O)NC(=O)[C@H](CCC(=O)O)NC(=O)CCCCCNC(=O)CN3CCN(CC(=O)O)CCN(CC(=O)O)CCN(CC(=O)O)CC3)[C@@H](C)O)(C(=O)N[C@@H](Cc3ccccc3)C(N)=O)CC2)cc1]
MS: Calc'd 1628.82, found $[M+H]^+$: 1630.2.

Example 135: Compound 237 (SEQ ID NO: 618)
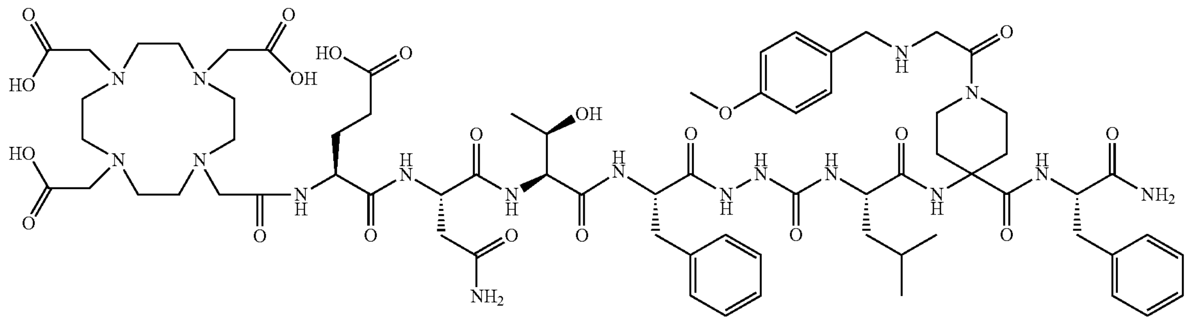 [SMILES: COc1ccc(CNCC(=O)N2CCC(NC(=O)[C@H](CC(C)C)NC(=O)NNC(=O)[C@H](Cc3ccccc3)NC(=O)[C@@H](NC(=O)[C@H](CC(N)=O)NC(=O)[C@H](CCC(=O)O)NC(=O)CN3CCN(CC(=O)O)CCN(CC(=O)O)CCN(CC(=O)O)CC3)[C@@H](C)O)(C(=O)N[C@@H](Cc3ccccc3)C(N)=O)CC2)cc1]
MS: Calc'd 1515.74, found $[M+H]^+$: 1517.1.
Example 136: Compound 238 (SEQ ID NO: 619)
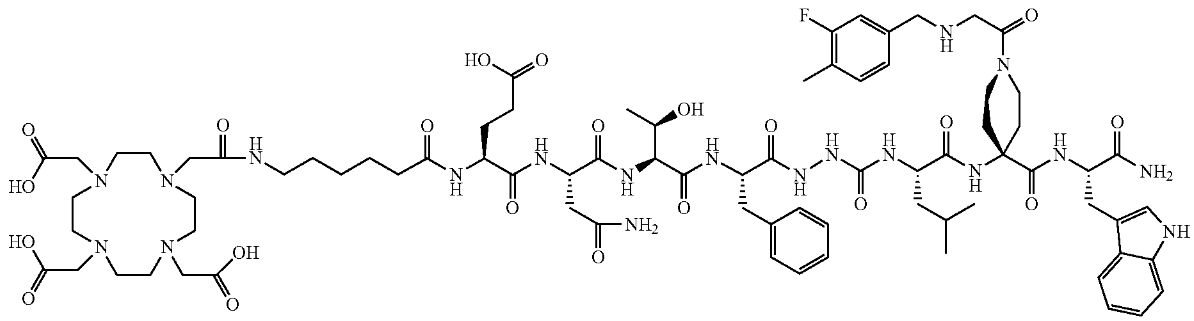
MS: Calc'd 1669.83, found $[M+H]^+$: 1670.9.
Example 137: Compound 239 (SEQ ID NO: 620)
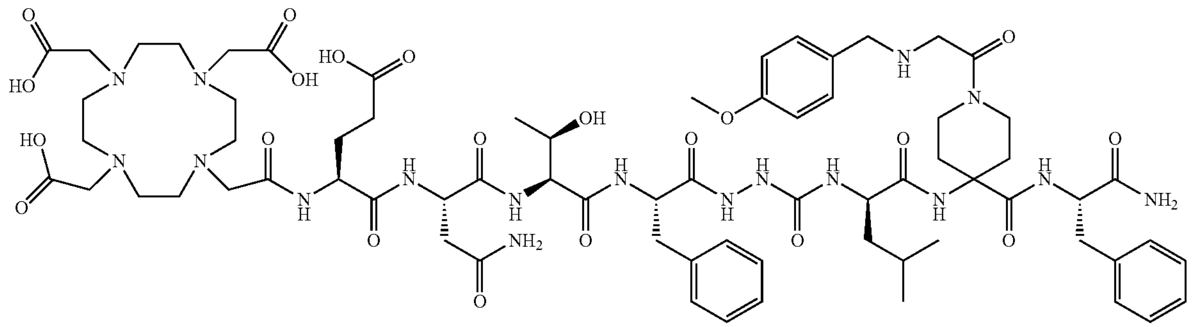 [SMILES: COc1ccc(CNCC(=O)N2CCC(NC(=O)[C@@H](CC(C)C)NC(=O)NNC(=O)[C@H](Cc3ccccc3)NC(=O)[C@@H](NC(=O)[C@H](CC(N)=O)NC(=O)[C@H](CCC(=O)O)NC(=O)CN3CCN(CC(=O)O)CCN(CC(=O)O)CCN(CC(=O)O)CC3)[C@@H](C)O)(C(=O)N[C@@H](Cc3ccccc3)C(N)=O)CC2)cc1]
MS: Calc'd 1515.74, found $[M+H]^+$: 1517.2.

Example 138: Compound 240 (SEQ ID NO: 621)
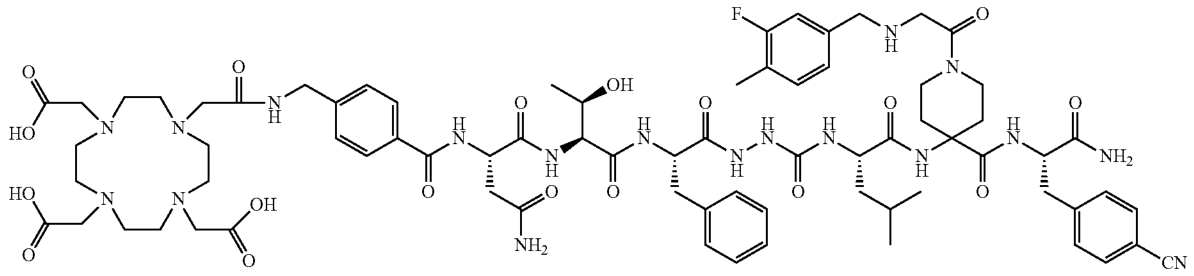 [SMILES: Cc1ccc(CNCC(=O)N2CCC(NC(=O)[C@H](CC(C)C)NC(=O)NNC(=O)[C@H](Cc3ccccc3)NC(=O)[C@@H](NC(=O)[C@H](CC(N)=O)NC(=O)c3ccc(CNC(=O)CN4CCN(CC(=O)O)CCN(CC(=O)O)CCN(CC(=O)O)CC4)cc3)[C@@H](C)O)(C(=O)N[C@@H](Cc3ccc(C#N)cc3)C(N)=O)CC2)cc1F]
MS: Calc'd 1546.74, found $[M+2H]^{2+}$: 774.9.
Example 139: Compound 241 (SEQ ID NO: 622)
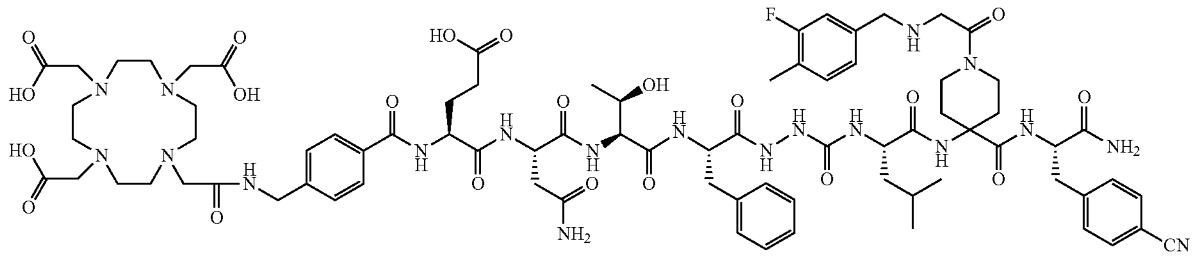 [SMILES: Cc1ccc(CNCC(=O)N2CCC(NC(=O)[C@H](CC(C)C)NC(=O)NNC(=O)[C@H](Cc3ccccc3)NC(=O)[C@@H](NC(=O)[C@H](CC(N)=O)NC(=O)[C@H](CCC(=O)O)NC(=O)c3ccc(CNC(=O)CN4CCN(CC(=O)O)CCN(CC(=O)O)CCN(CC(=O)O)CC4)cc3)[C@@H](C)O)(C(=O)N[C@@H](Cc3ccc(C#N)cc3)C(N)=O)CC2)cc1F]
MS: Calc'd 1675.78, found $[M+3H]^{3+}$: 560.0.
Example 140: Compound 242 (SEQ ID NO: 623)
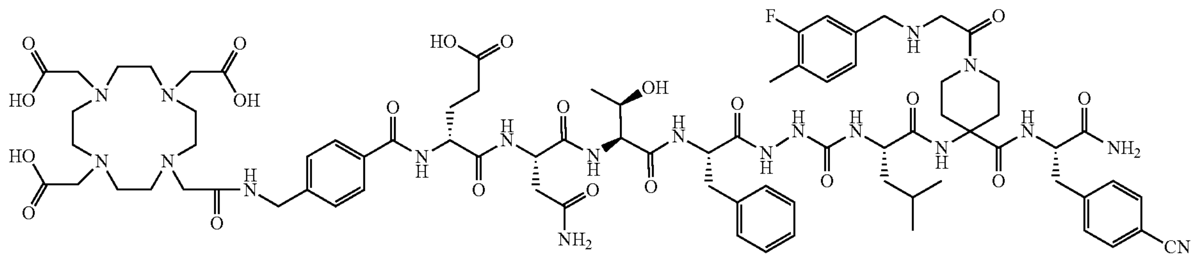 [SMILES: Cc1ccc(CNCC(=O)N2CCC(NC(=O)[C@H](CC(C)C)NC(=O)NNC(=O)[C@H](Cc3ccccc3)NC(=O)[C@@H](NC(=O)[C@H](CC(N)=O)NC(=O)[C@@H](CCC(=O)O)NC(=O)c3ccc(CNC(=O)CN4CCN(CC(=O)O)CCN(CC(=O)O)CCN(CC(=O)O)CC4)cc3)[C@@H](C)O)(C(=O)N[C@@H](Cc3ccc(C#N)cc3)C(N)=O)CC2)cc1F]
MS: Calc'd 1675.78, found $[M+3H]^{3+}$: 560.0.
Example 141: Compound 244 (SEQ ID NO: 625)
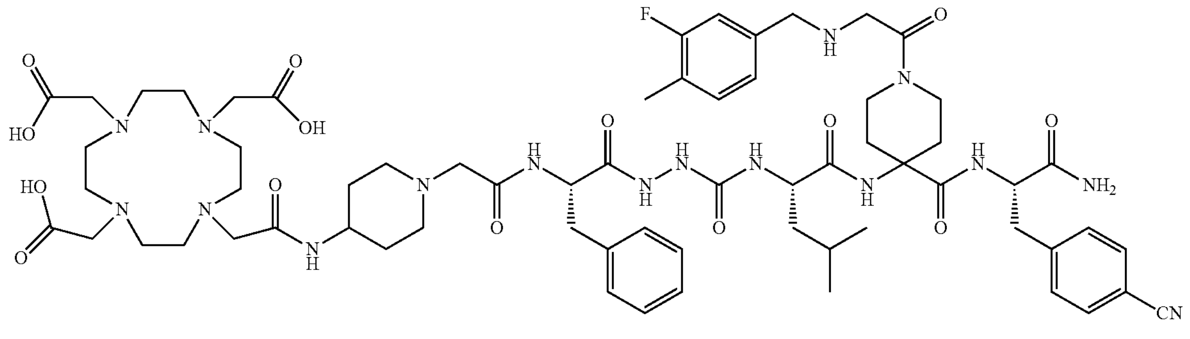 [SMILES: Cc1ccc(CNCC(=O)N2CCC(NC(=O)[C@H](CC(C)C)NC(=O)NNC(=O)[C@H](Cc3ccccc3)NC(=O)CN3CCC(NC(=O)CN4CCN(CC(=O)O)CCN(CC(=O)O)CCN(CC(=O)O)CC4)CC3)(C(=O)N[C@@H](Cc3ccc(C#N)cc3)C(N)=O)CC2)cc1F]
MS: Calc'd 1338.69, found $[M+H]^{+}$: 1339.9.

Example 142: Compound 245 (SEQ ID NO: 626)
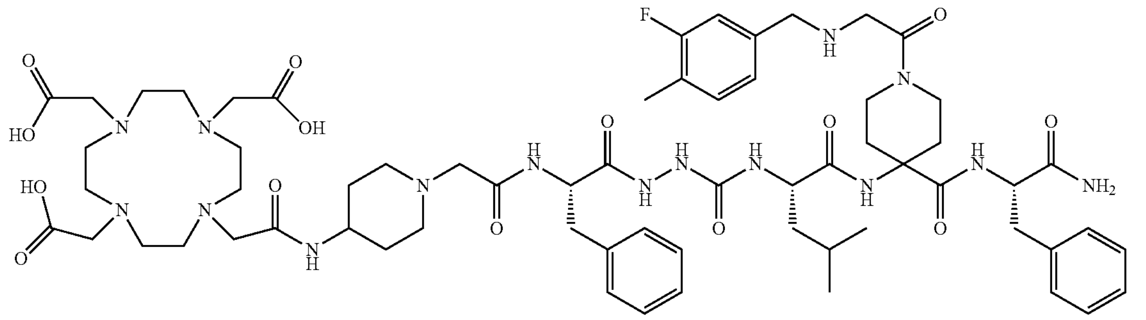 [SMILES: Cc1ccc(CNCC(=O)N2CCC(NC(=O)[C@H](CC(C)C)NC(=O)NNC(=O)[C@H](Cc3ccccc3)NC(=O)CN3CCC(NC(=O)CN4CCN(CC(=O)O)CCN(CC(=O)O)CCN(CC(=O)O)CC4)CC3)(C(=O)N[C@@H](Cc3ccccc3)C(N)=O)CC2)cc1F]
MS: Calc'd 1313.69, found $[M+H]^+$: 1314.9.
Example 143: Compound 246
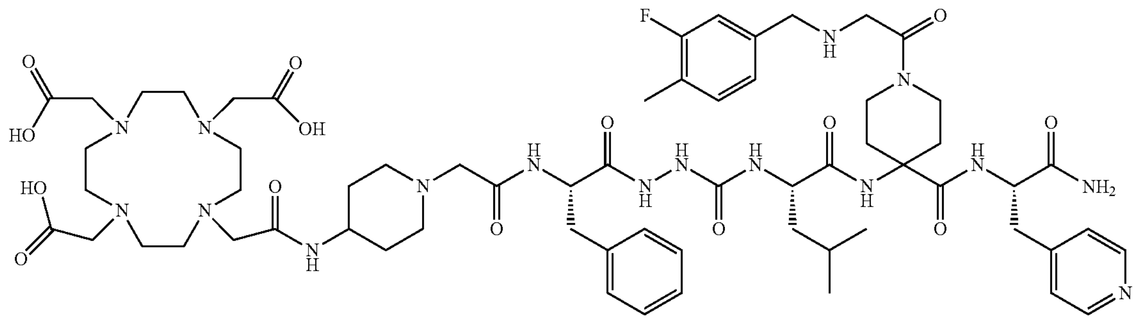 [SMILES: Cc1ccc(CNCC(=O)N2CCC(NC(=O)[C@H](CC(C)C)NC(=O)NNC(=O)[C@H](Cc3ccccc3)NC(=O)CN3CCC(NC(=O)CN4CCN(CC(=O)O)CCN(CC(=O)O)CCN(CC(=O)O)CC4)CC3)(C(=O)N[C@@H](Cc3ccncc3)C(N)=O)CC2)cc1F]
MS: Calc'd 1314.69, found $[M+H]^+$: 1315.8.
Example 144: Compound 247 (SEQ ID NO: 628)
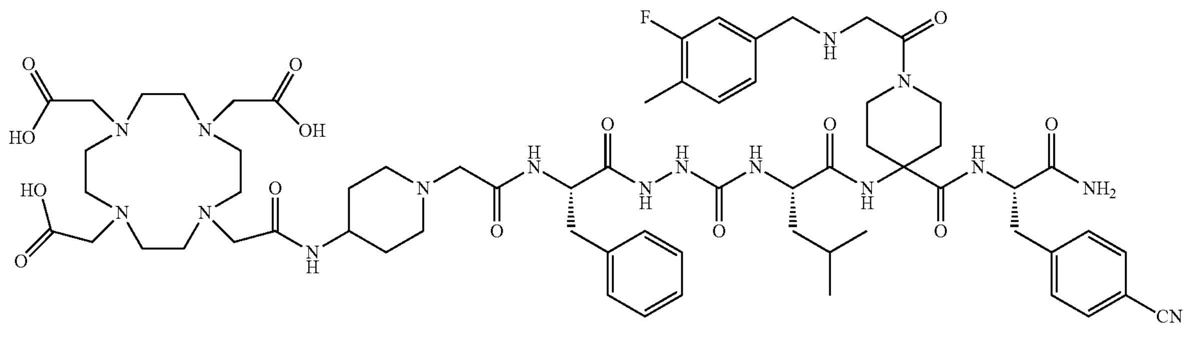 [SMILES: Cc1ccc(CNCC(=O)N2CCC(NC(=O)[C@H](CC(C)C)NC(=O)NNC(=O)[C@H](Cc3ccccc3)NC(=O)CN3CCC(NC(=O)CN4CCN(CC(=O)O)CCN(CC(=O)O)CCN(CC(=O)O)CC4)CC3)(C(=O)N[C@@H](Cc3ccc(C#N)cc3)C(N)=O)CC2)cc1F]
MS: Calc'd 1329.69, found $[M+H]^+$: 1330.7.

Example 145: Compound 248 (SEQ ID NO: 629)
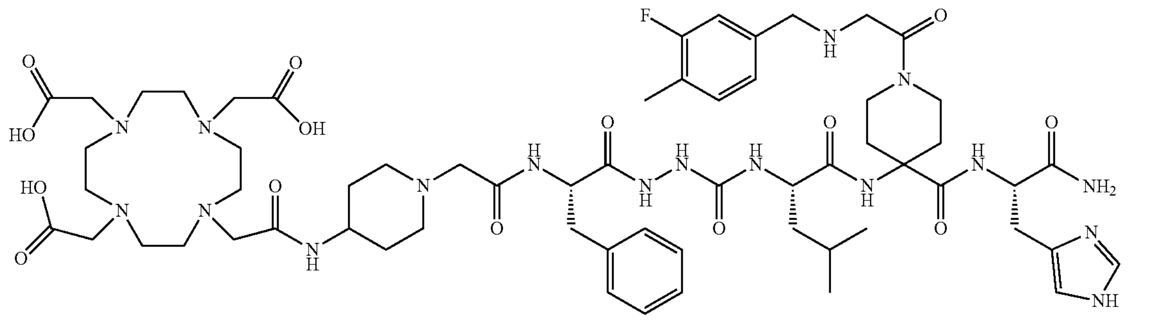 [SMILES: Cc1ccc(CNCC(=O)N2CCC(NC(=O)[C@H](CC(C)C)NC(=O)NNC(=O)[C@H](Cc3ccccc3)NC(=O)CN3CCC(NC(=O)CN4CCN(CC(=O)O)CCN(CC(=O)O)CCN(CC(=O)O)CC4)CC3)(C(=O)N[C@@H](Cc3c[nH]cn3)C(N)=O)CC2)cc1F]
MS: Calc'd 1303.68, found $[M+H]^+$: 1304.8.
Example 146: Compound 249 (SEQ ID NO: 630)
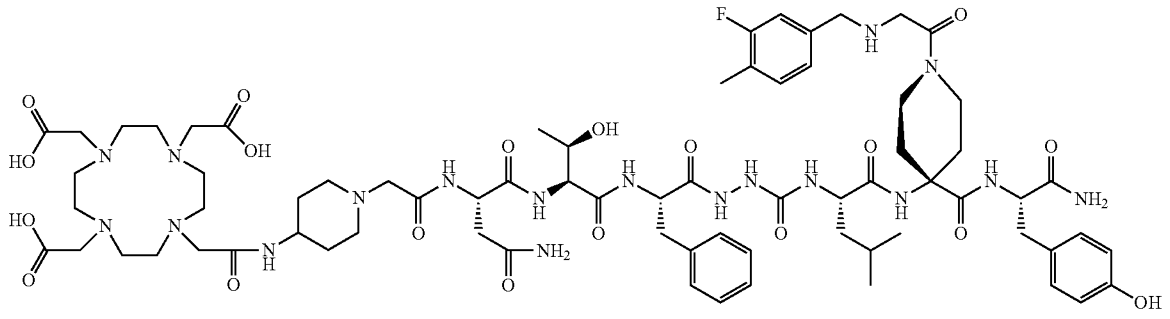
MS: Calc'd 1544.78, found $[M+H]^+$: 1546.0.
Example 147: Compound 250 (SEQ ID NO: 631)
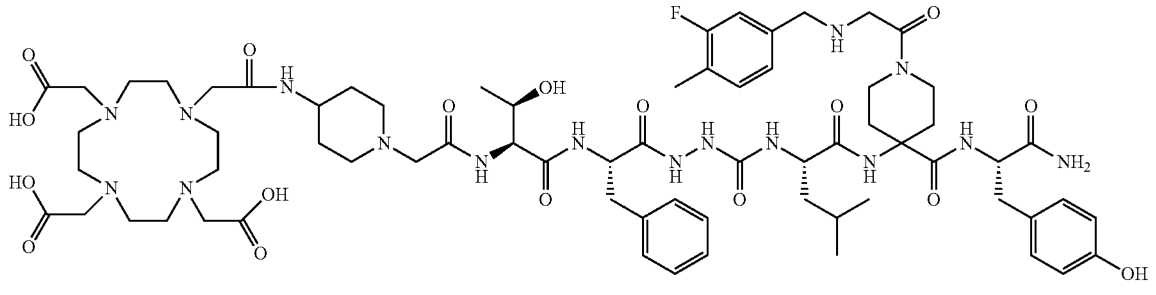 [SMILES: Cc1ccc(CNCC(=O)N2CCC(NC(=O)[C@H](CC(C)C)NC(=O)NNC(=O)[C@H](Cc3ccccc3)NC(=O)[C@@H](NC(=O)CN3CCC(NC(=O)CN4CCN(CC(=O)O)CCN(CC(=O)O)CCN(CC(=O)O)CC4)CC3)[C@@H](C)O)(C(=O)N[C@@H](Cc3ccc(O)cc3)C(N)=O)CC2)cc1F]
MS: Calc'd 1430.74, found $[M+H]^+$: 1431.9.

Example 148: Compound 251 (SEQ ID NO: 632)
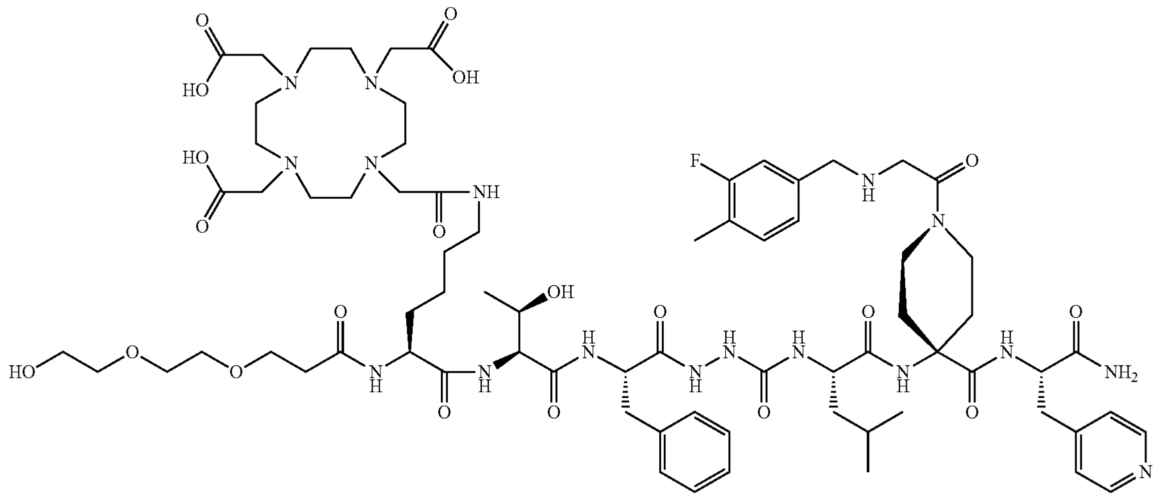
MS: Calc'd 1563.81, found $[M+2H]^{2+}$: 783.45.
Example 149: Compound 252 (SEQ ID NO: 633)
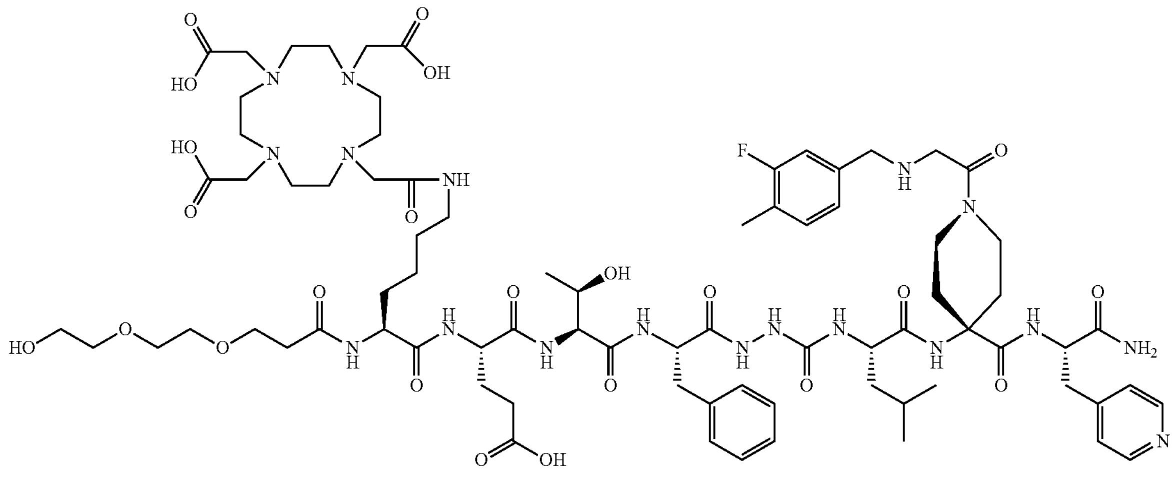
MS: Calc'd 1692.85, found $[M+2H]^{2+}$: 847.95.

Example 150: Compound 253 (SEQ ID NO: 634)
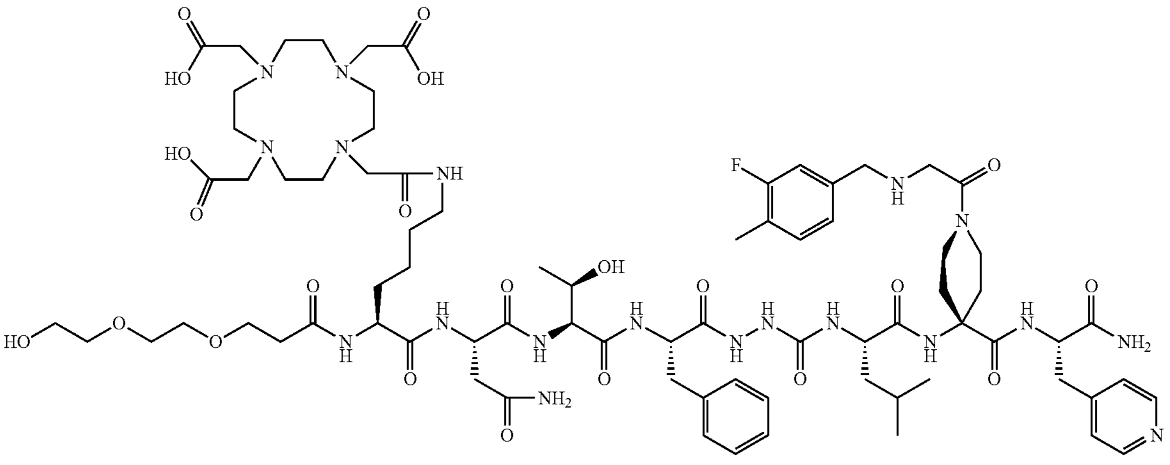
MS: Calc'd 1677.85, found $[M+2H]^{2+}$: 840.5.
Example 151: Compound 254 (SEQ ID NO: 635)
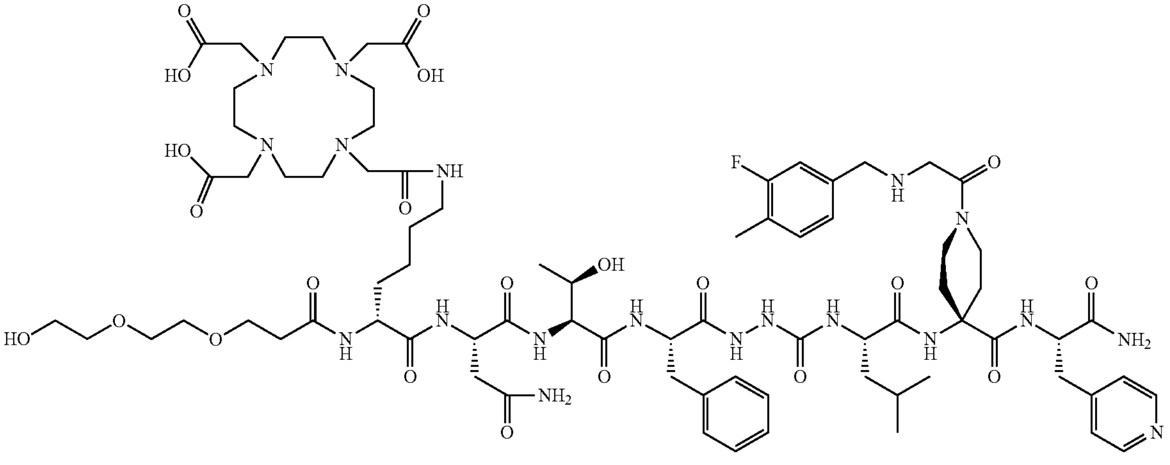
MS: Calc'd 1677.85, found $[M+2H]^{2+}$: 840.45.

Example 152: Compound 255 (SEQ ID NO: 636)
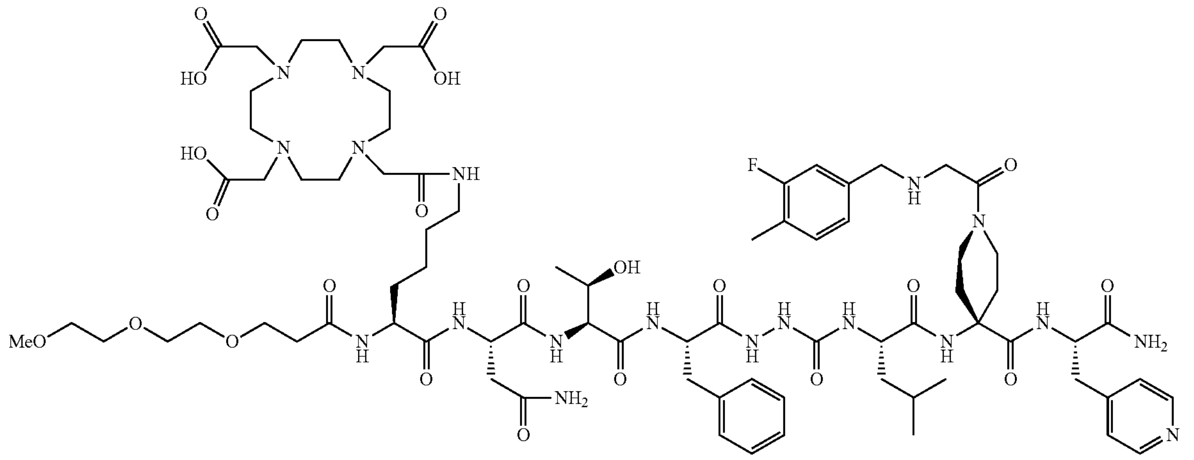
MS: Calc'd 1691.87, found $[M+2H]^{2+}$: 847.4.
Example 153: Compound 256 (SEQ ID NO: 637)
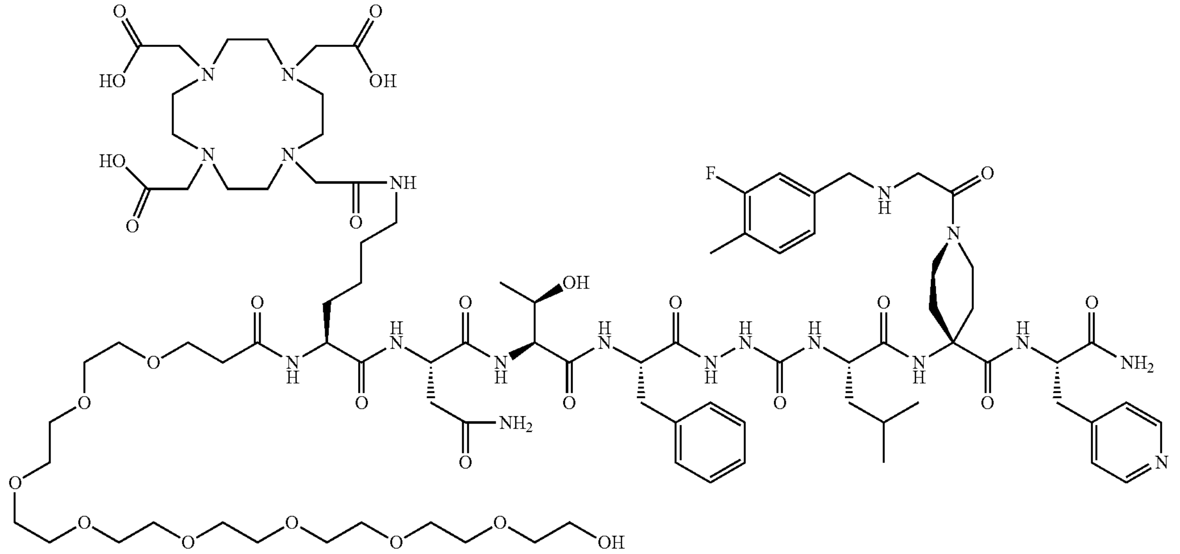
MS: Calc'd 1942.01, found $[M+2H]^{2+}$: 972.55.

Example 154: Compound 258 (SEQ ID NO: 639)
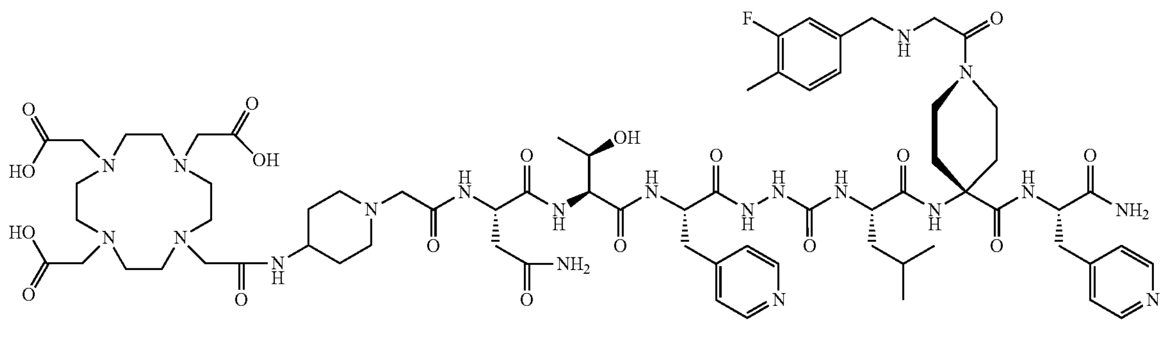
MS: Calc'd 1530.77, found $[M+2H]^{2+}$: 766.85.
Example 155: Compound 259 (SEQ ID NO: 640)
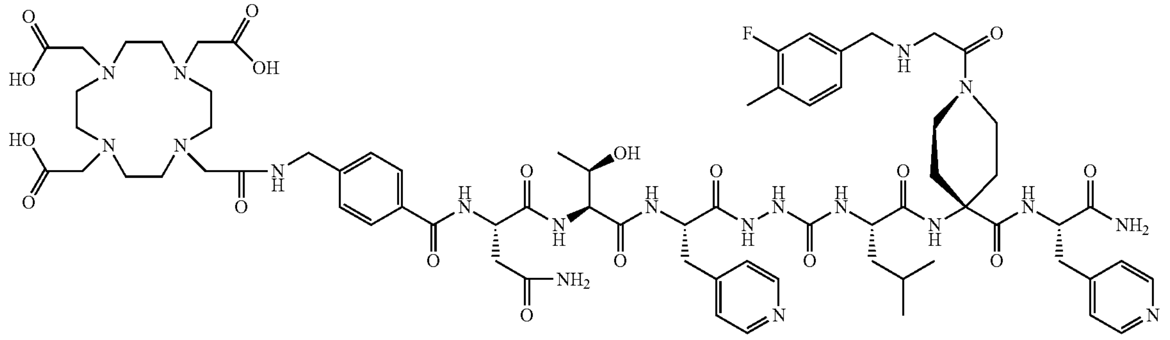
MS: Calc'd 1523.73, found $[M+3H]^{3+}$: 509.25.
Example 156: Compound 260 (SEQ ID NO: 641)
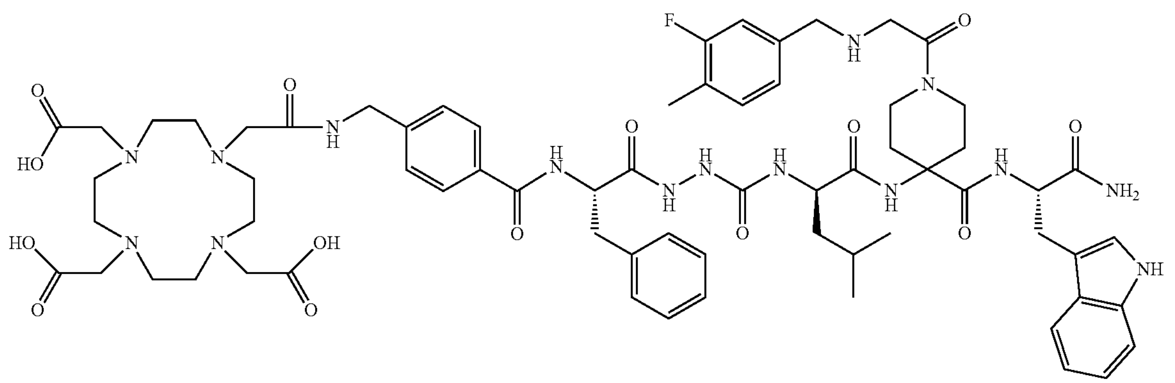 [SMILES: Cc1ccc(CNCC(=O)N2CCC(NC(=O)[C@@H](CC(C)C)NC(=O)NNC(=O)[C@H](Cc3ccccc3)NC(=O)c3ccc(CNC(=O)CN4CCN(CC(=O)O)CCN(CC(=O)O)CCN(CC(=O)O)CC4)cc3)(C(=O)N[C@@H](Cc3c[nH]c4ccccc34)C(N)=O)CC2)cc1F]
MS: Calc'd 1354.66, found $[M+3H]^{3+}$: 674.3.

Example 157: Compound 261
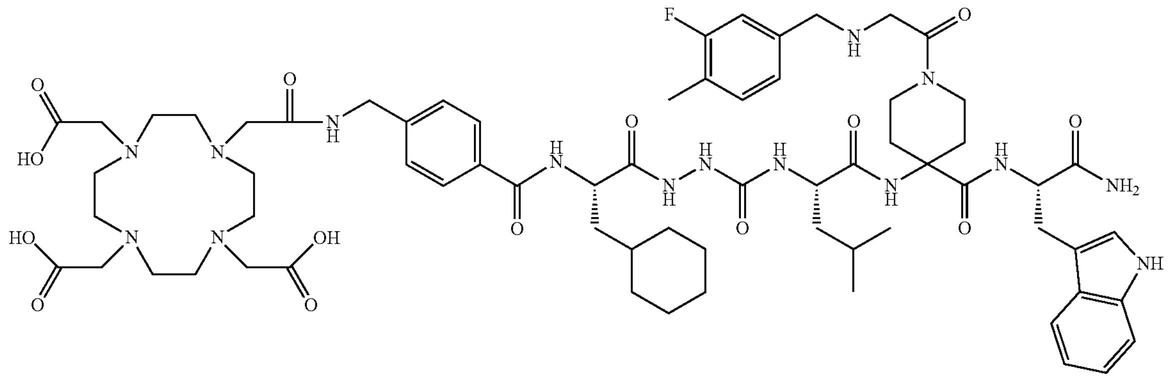 [SMILES: Cc1ccc(CNCC(=O)N2CCC(NC(=O)[C@H](CC(C)C)NC(=O)NNC(=O)[C@H](CC3CCCCC3)NC(=O)c3ccc(CNC(=O)CN4CCN(CC(=O)O)CCN(CC(=O)O)CCN(CC(=O)O)CC4)cc3)(C(=O)N[C@@H](Cc3c[nH]c4ccccc34)C(N)=O)CC2)cc1F]
MS: Calc'd 1351.71, found $[M+2H]^{2+}$: 677.2.
Example 159: Compound 264 (SEQ ID NO: 645)
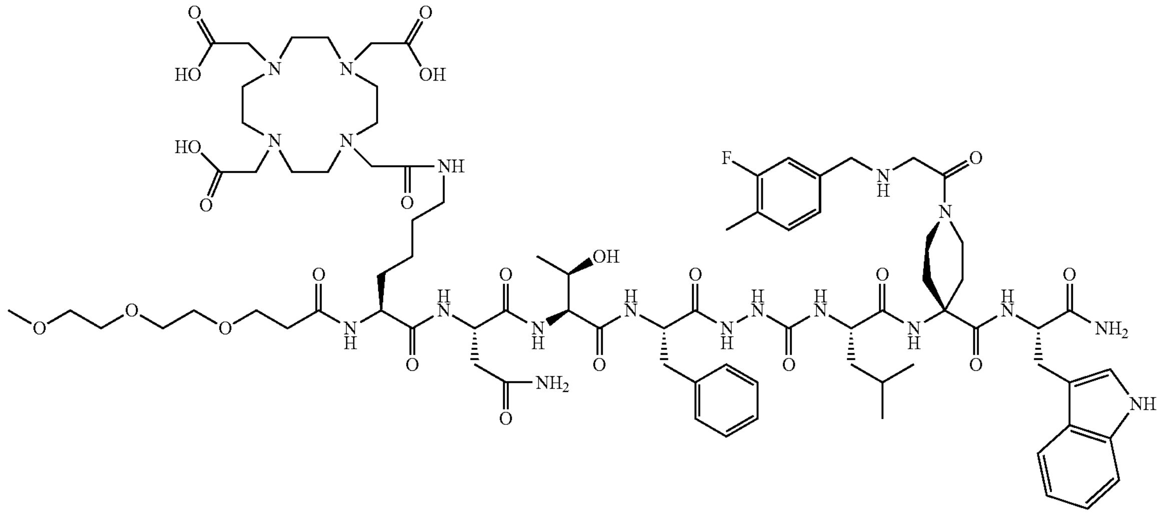
MS: Calc'd 1592.83, found $[M+2H]^{2+}$: 797.9.
Example 161: Compound 266 (SEQ ID NO: 647)
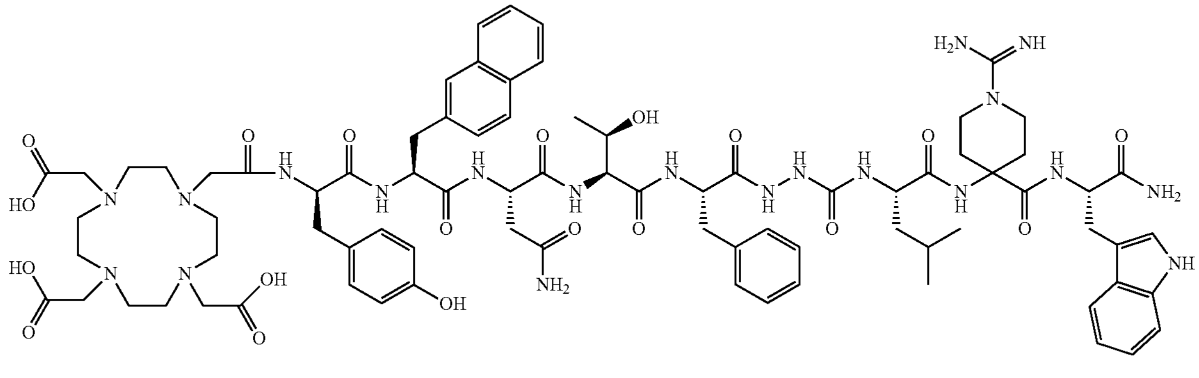 [SMILES: CC(C)C[C@H](NC(=O)NNC(=O)[C@H](Cc1ccccc1)NC(=O)[C@@H](NC(=O)[C@H](CC(N)=O)NC(=O)[C@H](Cc1ccc2ccccc2c1)NC(=O)[C@@H](Cc1ccc(O)cc1)NC(=O)CN1CCN(CC(=O)O)CCN(CC(=O)O)CCN(CC(=O)O)CC1)[C@@H](C)O)C(=O)NC1(C(=O)N[C@@H](Cc2c[nH]c3ccccc23)C(N)=O)CCN(C(=N)N)CC1]
MS: Calc'd 1650.79, found $[M+2H]^{2+}$: 826.95.

Example 162: Compound 269 (SEQ ID NO: 650)
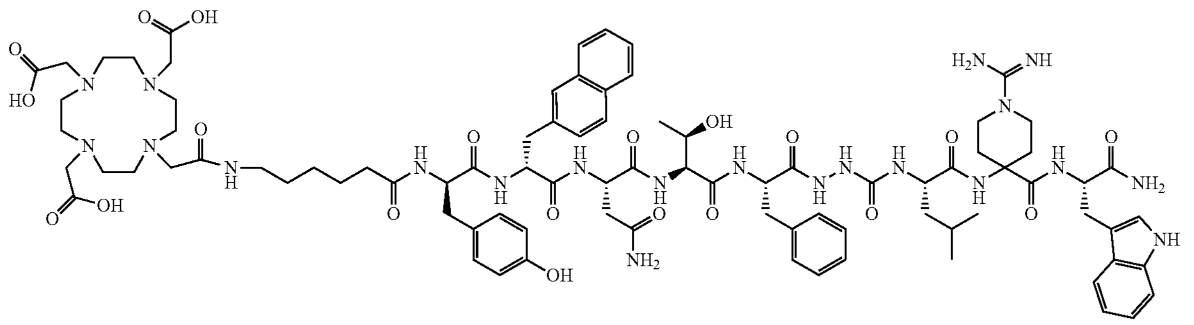 [SMILES: CC(C)C[C@H](NC(=O)NNC(=O)[C@H](Cc1ccccc1)NC(=O)[C@@H](NC(=O)[C@H](CC(N)=O)NC(=O)[C@@H](Cc1ccc2ccccc2c1)NC(=O)[C@@H](Cc1ccc(O)cc1)NC(=O)CCCCCNC(=O)CN1CCN(CC(=O)O)CCN(CC(=O)O)CCN(CC(=O)O)CC1)[C@@H](C)O)C(=O)NC1(C(=O)N[C@@H](Cc2c[nH]c3ccccc23)C(N)=O)CCN(C(=N)N)CC1]
MS: Calc'd 1763.88, found $[M+2H]^{2+}$: 883.5.
Example 163. Compound 270 (SEQ ID NO: 652)
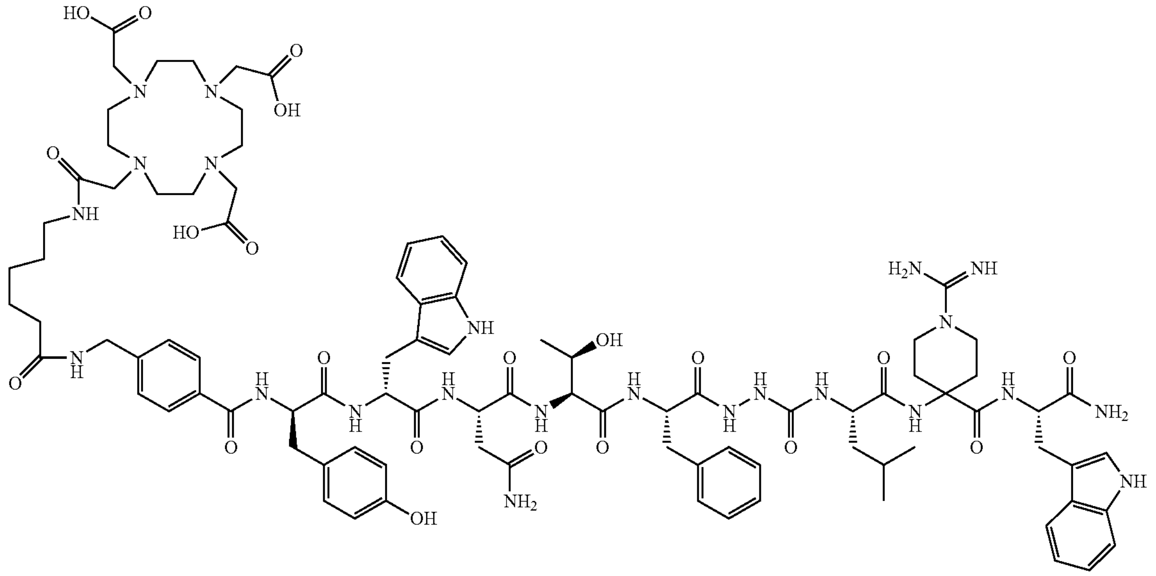 [SMILES: CC(C)C[C@H](NC(=O)NNC(=O)[C@H](Cc1ccccc1)NC(=O)[C@@H](NC(=O)[C@H](CC(N)=O)NC(=O)[C@@H](Cc1c[nH]c2ccccc12)NC(=O)[C@@H](Cc1ccc(O)cc1)NC(=O)c1ccc(CNC(=O)CCCCCNC(=O)CN2CCN(CC(=O)O)CCN(CC(=O)O)CCN(CC(=O)O)CC2)cc1)[C@@H](C)O)C(=O)NC1(C(=O)N[C@@H](Cc2c[nH]c3ccccc23)C(N)=O)CCN(C(=N)N)CC1]
MS: Calc'd 1585.93, found $[M+3H]^{3+}$: 630.15.
Example 164. Compound 271 (SEQ ID NO: 653)
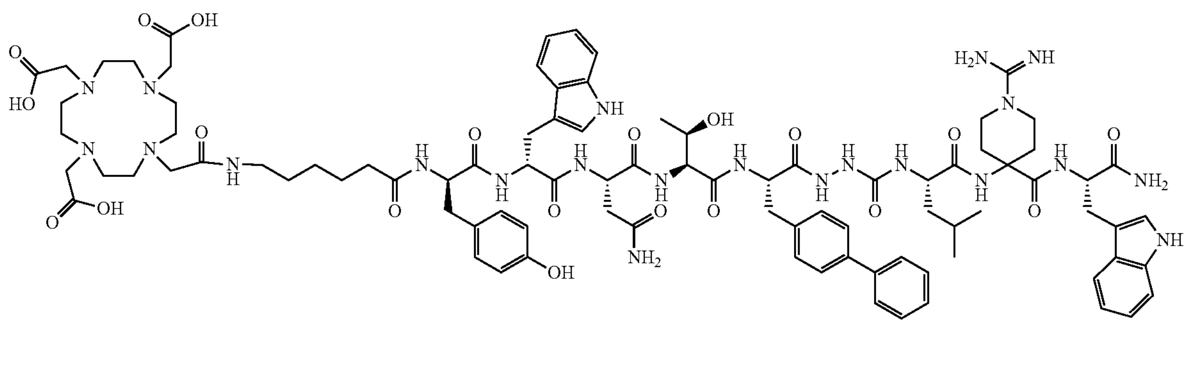 [SMILES: CC(C)C[C@H](NC(=O)NNC(=O)[C@H](Cc1ccc(-c2ccccc2)cc1)NC(=O)[C@@H](NC(=O)[C@H](CC(N)=O)NC(=O)[C@@H](Cc1c[nH]c2ccccc12)NC(=O)[C@@H](Cc1ccc(O)cc1)NC(=O)CCCCCNC(=O)CN1CCN(CC(=O)O)CCN(CC(=O)O)CCN(CC(=O)O)CC1)[C@@H](C)O)C(=O)NC1(C(=O)N[C@@H](Cc2c[nH]c3ccccc23)C(N)=O)CCN(C(=N)N)CC1]
MS: Calc'd 1828.90, found $[M+3H]^{3+}$: 611.05.

Example 165: Compound 272 (SEQ ID NO: 654)
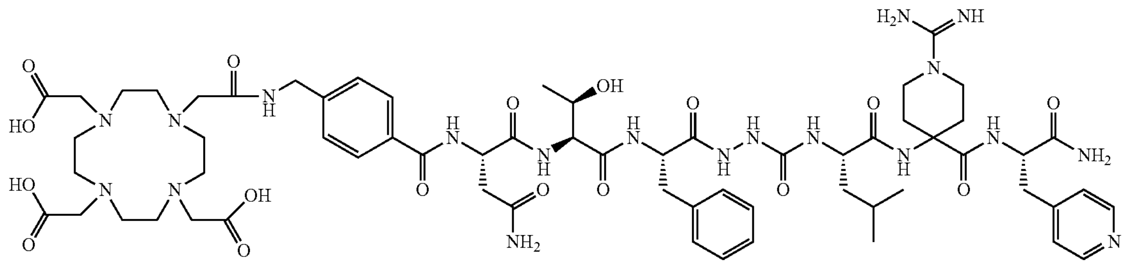 [SMILES: CC(C)C[C@H](NC(=O)NNC(=O)[C@H](Cc1ccccc1)NC(=O)[C@@H](NC(=O)[C@H](CC(N)=O)NC(=O)c1ccc(CNC(=O)CN2CCN(CC(=O)O)CCN(CC(=O)O)CCN(CC(=O)O)CC2)cc1)[C@@H](C)O)C(=O)NC1(C(=O)N[C@@H](Cc2ccncc2)C(N)=O)CCN(C(=N)N)CC1]
MS: Calc'd 1385.68, found $[M+3H]^{3+}$: 463.2.
Example 166: Compound 273 (SEQ ID NO: 655)
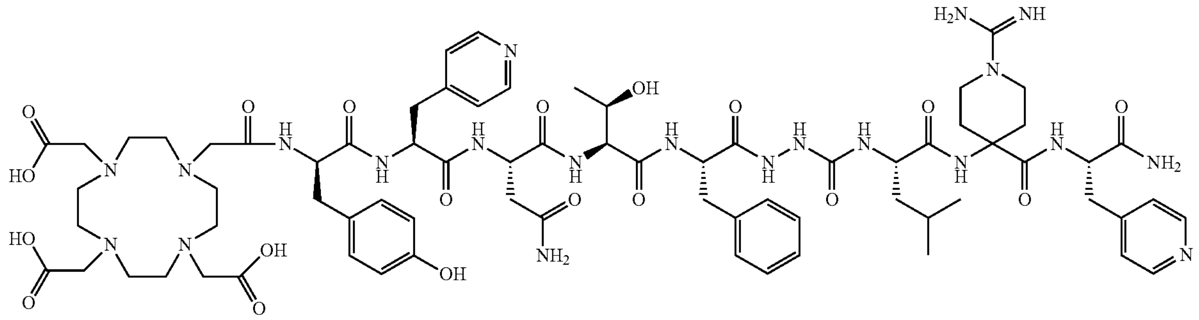 [SMILES: CC(C)C[C@H](NC(=O)NNC(=O)[C@H](Cc1ccccc1)NC(=O)[C@@H](NC(=O)[C@H](CC(N)=O)NC(=O)[C@H](Cc1ccncc1)NC(=O)[C@@H](Cc1ccc(O)cc1)NC(=O)CN1CCN(CC(=O)O)CCN(CC(=O)O)CCN(CC(=O)O)CC1)[C@@H](C)O)C(=O)NC1(C(=O)N[C@@H](Cc2ccncc2)C(N)=O)CCN(C(=N)N)CC1]
MS: Calc'd 1563.76, found $[M+3H]^{3+}$: 522.6.
Example 167: Compound 275 (SEQ ID NO: 657)
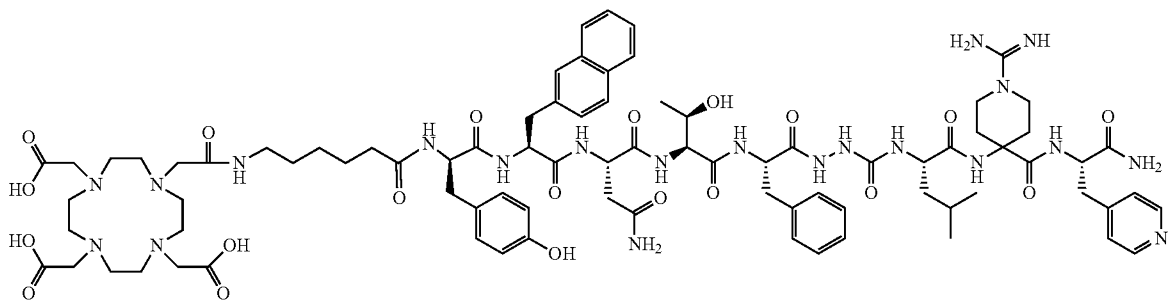 [SMILES: CC(C)C[C@H](NC(=O)NNC(=O)[C@H](Cc1ccccc1)NC(=O)[C@@H](NC(=O)[C@H](CC(N)=O)NC(=O)[C@H](Cc1ccc2ccccc2c1)NC(=O)[C@@H](Cc1ccc(O)cc1)NC(=O)CCCCCNC(=O)CN1CCN(CC(=O)O)CCN(CC(=O)O)CCN(CC(=O)O)CC1)[C@@H](C)O)C(=O)NC1(C(=O)N[C@@H](Cc2ccncc2)C(N)=O)CCN(C(=N)N)CC1]
MS: Calc'd 1725.86, found $[M+3H]^{3+}$: 576.65.

Example 168: Compound 276 (SEQ ID NO: 658)
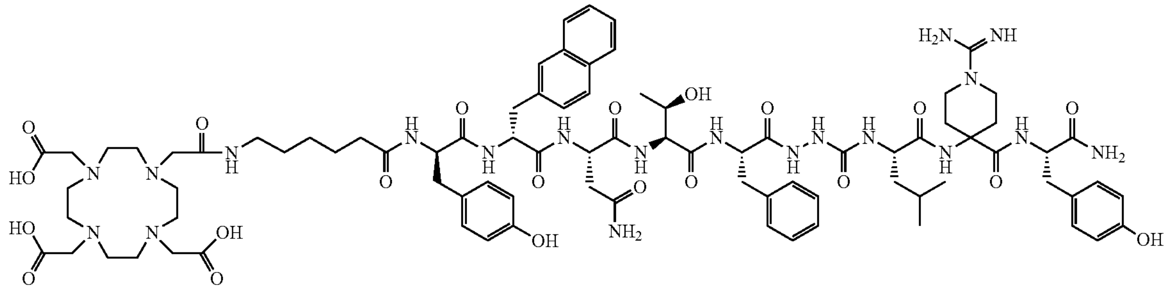 [SMILES: CC(C)C[C@H](NC(=O)NNC(=O)[C@H](Cc1ccccc1)NC(=O)[C@@H](NC(=O)[C@H](CC(N)=O)NC(=O)[C@@H](Cc1ccc2ccccc2c1)NC(=O)[C@@H](Cc1ccc(O)cc1)NC(=O)CCCCCNC(=O)CN1CCN(CC(=O)O)CCN(CC(=O)O)CCN(CC(=O)O)CC1)[C@@H](C)O)C(=O)NC1(C(=O)N[C@@H](Cc2ccc(O)cc2)C(N)=O)CCN(C(=N)N)CC1]
MS: Calc'd 1740.86, found $[M+2H]^{2+}$: 872.0.
Example 169: Compound 276 (SEQ ID NO: 659)
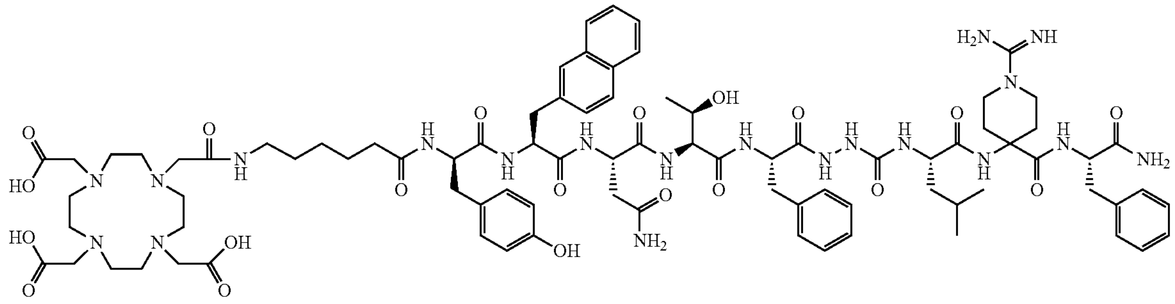 [SMILES: CC(C)C[C@H](NC(=O)NNC(=O)[C@H](Cc1ccccc1)NC(=O)[C@@H](NC(=O)[C@H](CC(N)=O)NC(=O)[C@H](Cc1ccc2ccccc2c1)NC(=O)[C@@H](Cc1ccc(O)cc1)NC(=O)CCCCCNC(=O)CN1CCN(CC(=O)O)CCN(CC(=O)O)CCN(CC(=O)O)CC1)[C@@H](C)O)C(=O)NC1(C(=O)N[C@@H](Cc2ccccc2)C(N)=O)CCN(C(=N)N)CC1]
MS: Calc'd 1724.87, found $[M+2H]^{2+}$: 863.95.
Example 170: Compound 278 (SEQ ID NO: 660)
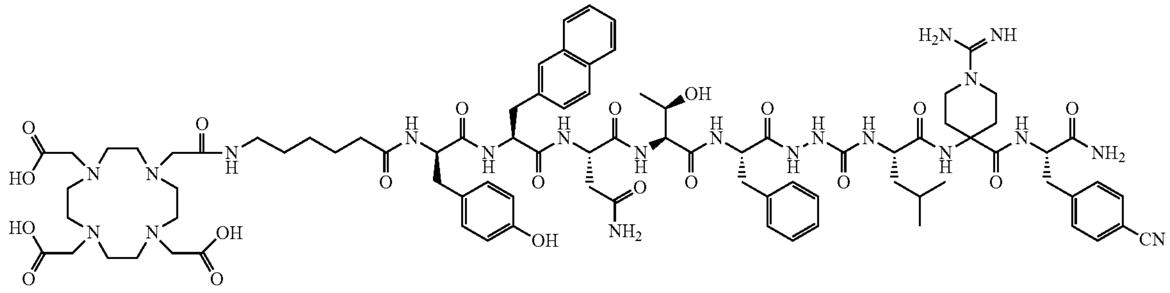 [SMILES: CC(C)C[C@H](NC(=O)NNC(=O)[C@H](Cc1ccccc1)NC(=O)[C@@H](NC(=O)[C@H](CC(N)=O)NC(=O)[C@H](Cc1ccc2ccccc2c1)NC(=O)[C@@H](Cc1ccc(O)cc1)NC(=O)CCCCCNC(=O)CN1CCN(CC(=O)O)CCN(CC(=O)O)CCN(CC(=O)O)CC1)[C@@H](C)O)C(=O)NC1(C(=O)N[C@@H](Cc2ccc(C#N)cc2)C(N)=O)CCN(C(=N)N)CC1]
MS: Calc'd 1749.86, found $[M+3H]^{3+}$: 584.7.

Example 171: Compound 279 (SEQ ID NO: 661)
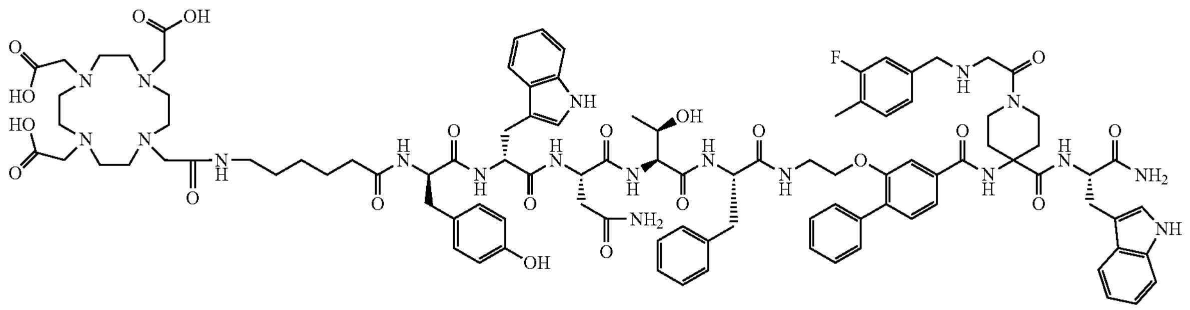 [SMILES: Cc1ccc(CNCC(=O)N2CCC(NC(=O)c3ccc(-c4ccccc4)c(OCCNC(=O)[C@H](Cc4ccccc4)NC(=O)[C@@H](NC(=O)[C@H](CC(N)=O)NC(=O)[C@@H](Cc4c[nH]c5ccccc45)NC(=O)[C@@H](Cc4ccc(O)cc4)NC(=O)CCCCCNC(=O)CN4CCN(CC(=O)O)CCN(CC(=O)O)CCN(CC(=O)O)CC4)[C@@H](C)O)c3)(C(=O)N[C@@H](Cc3c[nH]c4ccccc34)C(N)=O)CC2)cc1F]
MS: Calc'd 1957.92, found $[M+H]^+$: 1959.1.
Example 172: Compound 280
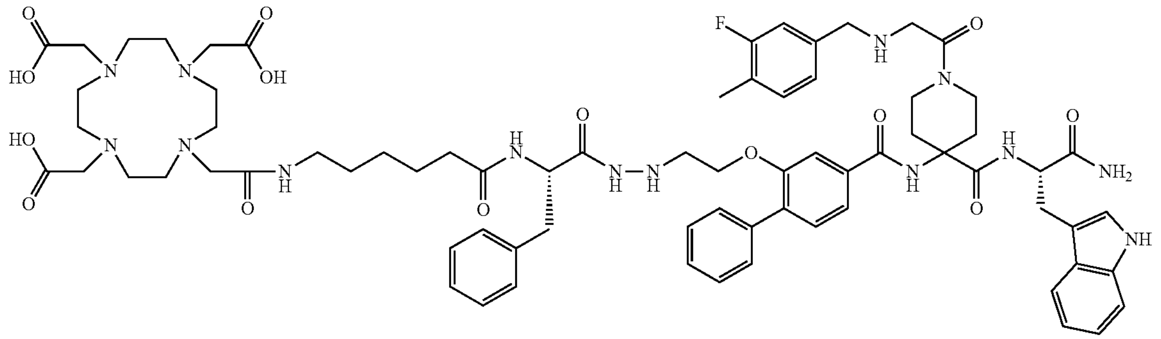 [SMILES: Cc1ccc(CNCC(=O)N2CCC(NC(=O)c3ccc(-c4ccccc4)c(OCCNNC(=O)[C@H](Cc4ccccc4)NC(=O)CCCCCNC(=O)CN4CCN(CC(=O)O)CCN(CC(=O)O)CCN(CC(=O)O)CC4)c3)(C(=O)N[C@@H](Cc3c[nH]c4ccccc34)C(N)=O)CC2)cc1F]
MS: Calc'd 1408.69, found $[M+H]^+$: 1409.5.
Example 173: Compound 281 (SEQ ID NO: 663)
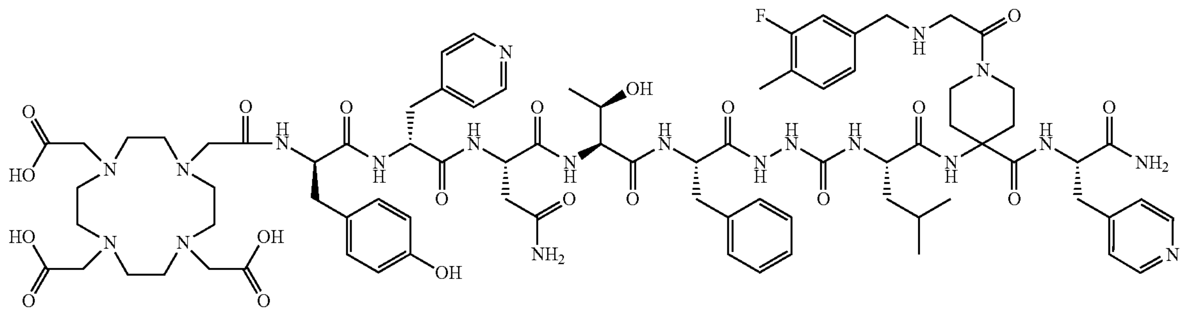 [SMILES: Cc1ccc(CNCC(=O)N2CCC(NC(=O)[C@H](CC(C)C)NC(=O)NNC(=O)[C@H](Cc3ccccc3)NC(=O)[C@@H](NC(=O)[C@H](CC(N)=O)NC(=O)[C@@H](Cc3ccncc3)NC(=O)[C@@H](Cc3ccc(O)cc3)NC(=O)CN3CCN(CC(=O)O)CCN(CC(=O)O)CCN(CC(=O)O)CC3)[C@@H](C)O)(C(=O)N[C@@H](Cc3ccncc3)C(N)=O)CC2)cc1F]
MS: Calc'd 1700.81, found $[M+3H]^{3+}$: 568.3.

Example 174: Compound 282
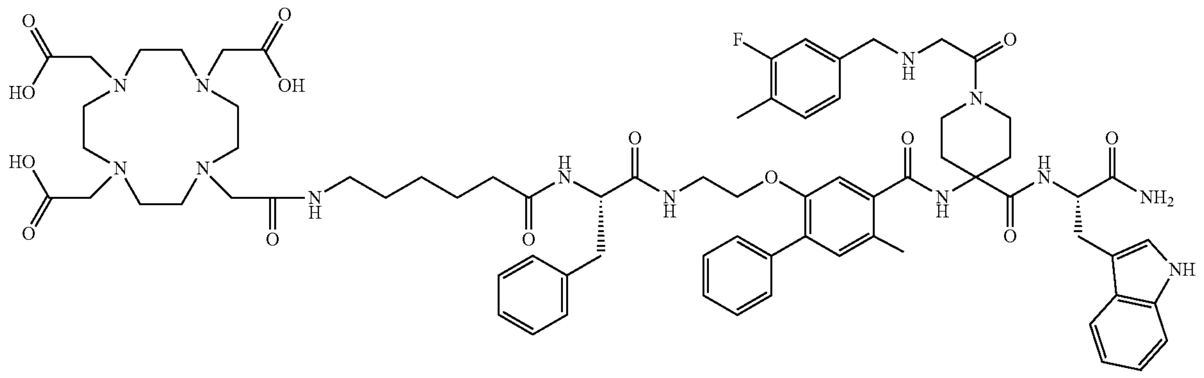 [SMILES: Cc1ccc(CNCC(=O)N2CCC(NC(=O)c3cc(OCCNC(=O)[C@H](Cc4ccccc4)NC(=O)CCCCCNC(=O)CN4CCN(CC(=O)O)CCN(CC(=O)O)CCN(CC(=O)O)CC4)c(-c4ccccc4)cc3C)(C(=O)N[C@@H](Cc3c[nH]c4ccccc34)C(N)=O)CC2)cc1F]
MS: Calc'd 1407.70, found $[M+H]^+$: 1408.8.
Example 175: Compound 283
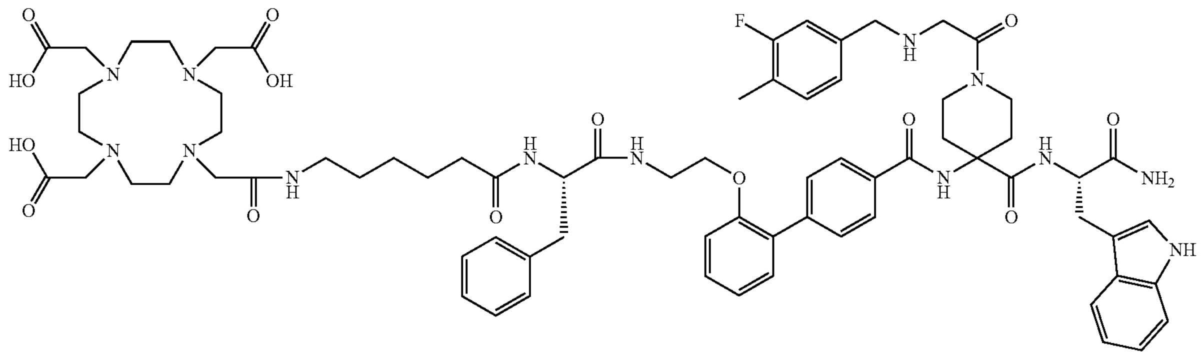 [SMILES: Cc1ccc(CNCC(=O)N2CCC(NC(=O)c3ccc(-c4ccccc4OCCNC(=O)[C@H](Cc4ccccc4)NC(=O)CCCCCNC(=O)CN4CCN(CC(=O)O)CCN(CC(=O)O)CCN(CC(=O)O)CC4)cc3)(C(=O)N[C@@H](Cc3c[nH]c4ccccc34)C(N)=O)CC2)cc1F]
MS: Calc'd 1393.69, found $[M+H]^+$: 1394.8.
Example 176: Compound 284
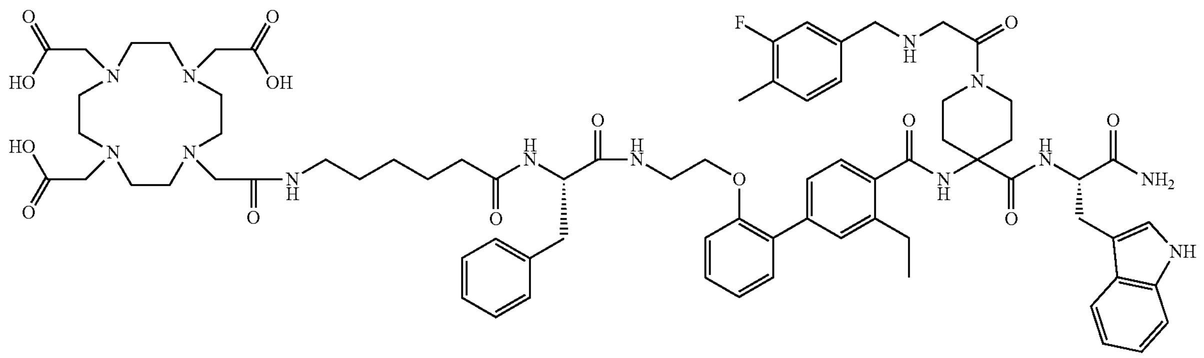 [SMILES: CCc1cc(-c2ccccc2OCCNC(=O)[C@H](Cc2ccccc2)NC(=O)CCCCCNC(=O)CN2CCN(CC(=O)O)CCN(CC(=O)O)CCN(CC(=O)O)CC2)ccc1C(=O)NC1(C(=O)N[C@@H](Cc2c[nH]c3ccccc23)C(N)=O)CCN(C(=O)CNCc2ccc(C)c(F)c2)CC1]
MS: Calc'd 1421.72, found $[M+H]^+$: 1422.8.

Example 177: Compound 285 (SEQ ID NO: 667)
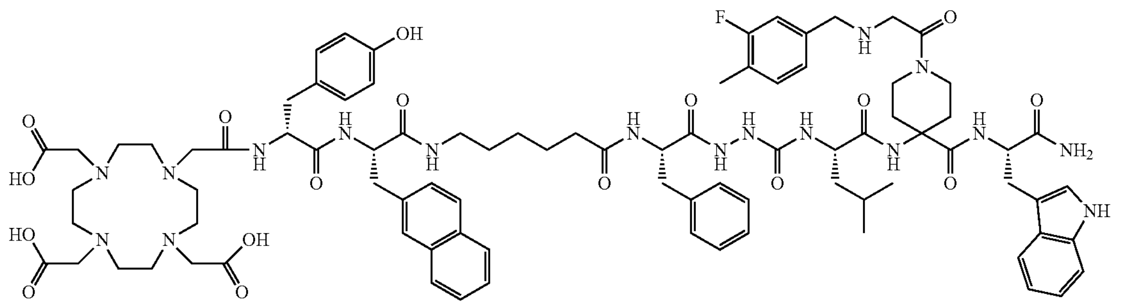 [SMILES: Cc1ccc(CNCC(=O)N2CCC(NC(=O)[C@H](CC(C)C)NC(=O)NNC(=O)[C@H](Cc3ccccc3)NC(=O)CCCCCNC(=O)[C@H](Cc3ccc4ccccc4c3)NC(=O)[C@@H](Cc3ccc(O)cc3)NC(=O)CN3CCN(CC(=O)O)CCN(CC(=O)O)CCN(CC(=O)O)CC3)(C(=O)N[C@@H](Cc3c[nH]c4ccccc34)C(N)=O)CC2)cc1F]
MS: Calc'd 1685.84, found $[M+3H]^{3+}$: 563.35.
Example 178: Compound 286 (SEQ ID NO: 668)
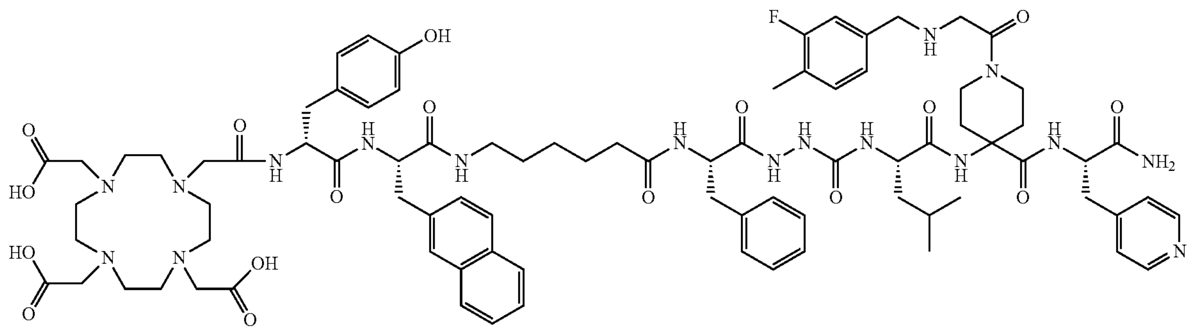 [SMILES: Cc1ccc(CNCC(=O)N2CCC(NC(=O)[C@H](CC(C)C)NC(=O)NNC(=O)[C@H](Cc3ccccc3)NC(=O)CCCCCNC(=O)[C@H](Cc3ccc4ccccc4c3)NC(=O)[C@@H](Cc3ccc(O)cc3)NC(=O)CN3CCN(CC(=O)O)CCN(CC(=O)O)CCN(CC(=O)O)CC3)(C(=O)N[C@@H](Cc3ccncc3)C(N)=O)CC2)cc1F]
MS: Calc'd 1647.83, found $[M+3H]^{3+}$: 550.7.
Example 179: Compound 287 (SEQ ID NO: 669)
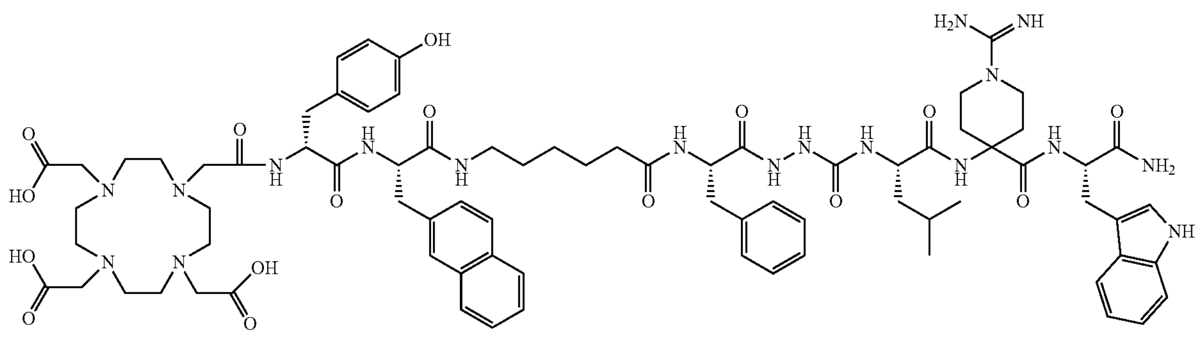 [SMILES: CC(C)C[C@H](NC(=O)NNC(=O)[C@H](Cc1ccccc1)NC(=O)CCCCCNC(=O)[C@H](Cc1ccc2ccccc2c1)NC(=O)[C@@H](Cc1ccc(O)cc1)NC(=O)CN1CCN(CC(=O)O)CCN(CC(=O)O)CCN(CC(=O)O)CC1)C(=O)NC1(C(=O)N[C@@H](Cc2c[nH]c3ccccc23)C(N)=O)CCN(C(=N)N)CC1]
MS: Calc'd 1548.79, found $[M+2H]^{2+}$: 775.9.

Example 180: Compound 288 (SEQ ID NO: 670)
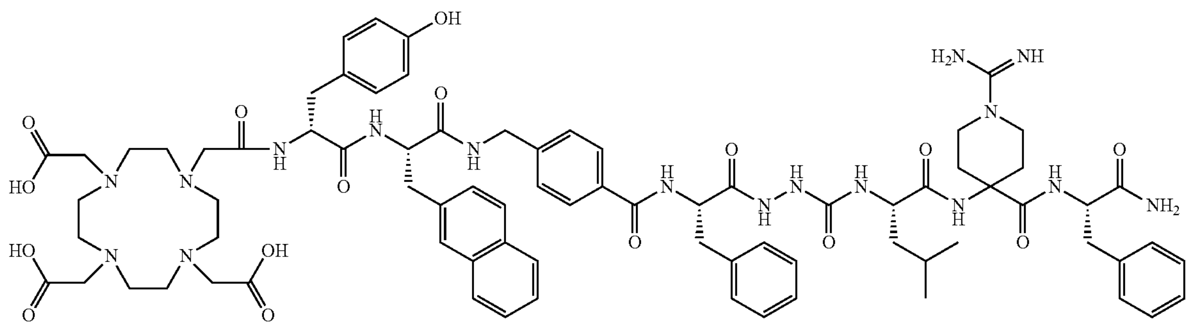 [SMILES: CC(C)C[C@H](NC(=O)NNC(=O)[C@H](Cc1ccccc1)NC(=O)c1ccc(CNC(=O)[C@H](Cc2ccc3ccccc3c2)NC(=O)[C@@H](Cc2ccc(O)cc2)NC(=O)CN2CCN(CC(=O)O)CCN(CC(=O)O)CCN(CC(=O)O)CC2)cc1)C(=O)NC1(C(=O)N[C@@H](Cc2ccccc2)C(N)=O)CCN(C(=N)N)CC1]
MS: Calc'd 1529.75, found $[M+3H]^{3+}$: 511.35.
Example 181. Compound 289 (SEQ ID NO: 671)
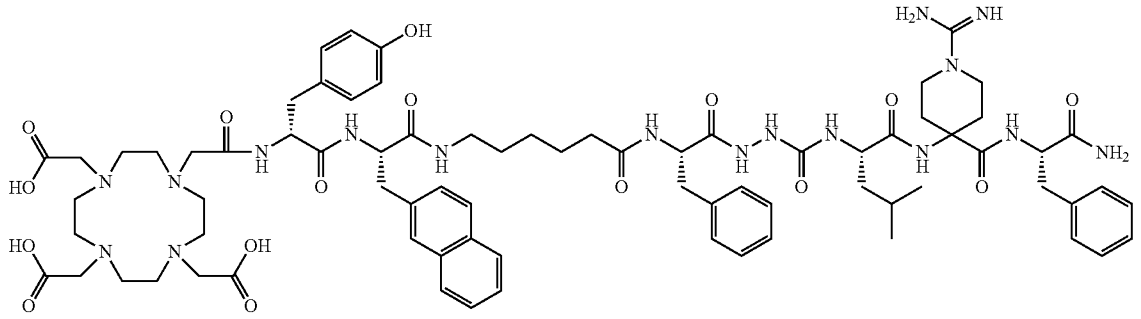 [SMILES: CC(C)C[C@H](NC(=O)NNC(=O)[C@H](Cc1ccccc1)NC(=O)CCCCCNC(=O)[C@H](Cc1ccc2ccccc2c1)NC(=O)[C@@H](Cc1ccc(O)cc1)NC(=O)CN1CCN(CC(=O)O)CCN(CC(=O)O)CCN(CC(=O)O)CC1)C(=O)NC1(C(=O)N[C@@H](Cc2ccccc2)C(N)=O)CCN(C(=N)N)CC1]
MS: Calc'd 1509.78, found $[M+3H]^{3+}$: 504.65.
Example 182: Compound 290 (SEQ ID NO: 672)
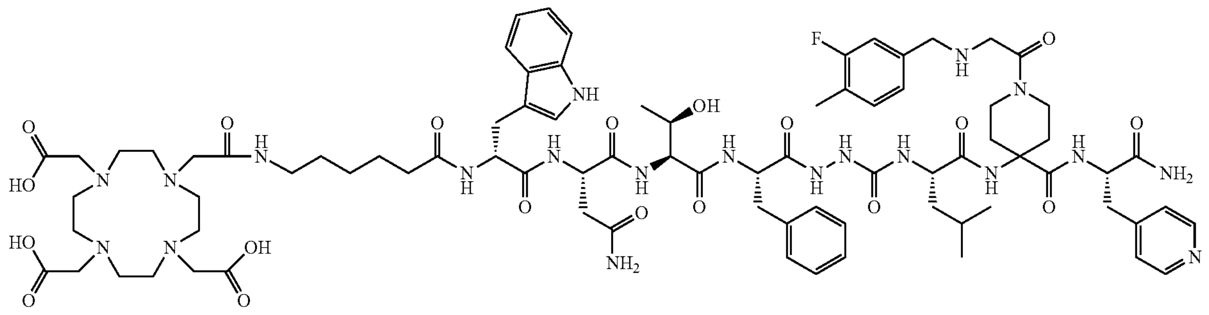 [SMILES: Cc1ccc(CNCC(=O)N2CCC(NC(=O)[C@H](CC(C)C)NC(=O)NNC(=O)[C@H](Cc3ccccc3)NC(=O)[C@@H](NC(=O)[C@H](CC(N)=O)NC(=O)[C@@H](Cc3c[nH]c4ccccc34)NC(=O)CCCCCNC(=O)CN3CCN(CC(=O)O)CCN(CC(=O)O)CCN(CC(=O)O)CC3)[C@@H](C)O)(C(=O)N[C@@H](Cc3ccncc3)C(N)=O)CC2)cc1F]
MS: Calc'd 1688.85, found $[M+2H]^{2+}$: 845.6.

Example 183: Compound 291 (SEQ ID NO: 673)
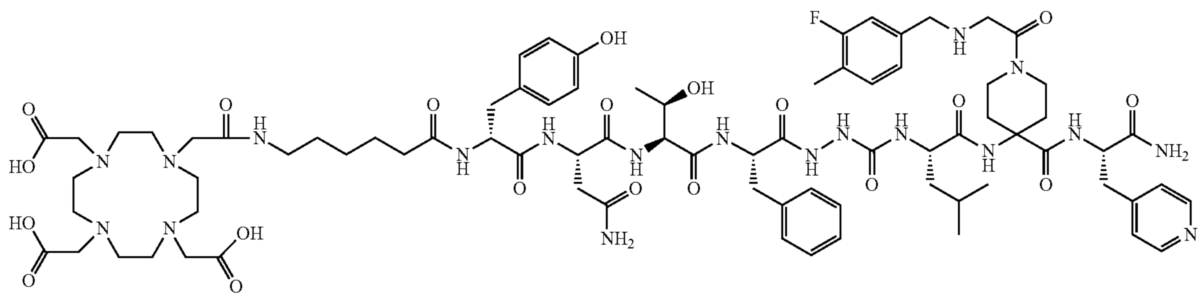 [SMILES: Cc1ccc(CNCC(=O)N2CCC(NC(=O)[C@H](CC(C)C)NC(=O)NNC(=O)[C@H](Cc3ccccc3)NC(=O)[C@@H](NC(=O)[C@H](CC(N)=O)NC(=O)[C@@H](Cc3ccc(O)cc3)NC(=O)CCCCCNC(=O)CN3CCN(CC(=O)O)CCN(CC(=O)O)CCN(CC(=O)O)CC3)[C@@H](C)O)(C(=O)N[C@@H](Cc3ccncc3)C(N)=O)CC2)cc1F]
MS: Calc'd 1665.83, found $[M+2H]^{2+}$: 556.7.
Example 184: Compound 292 (SEQ ID NO: 674)
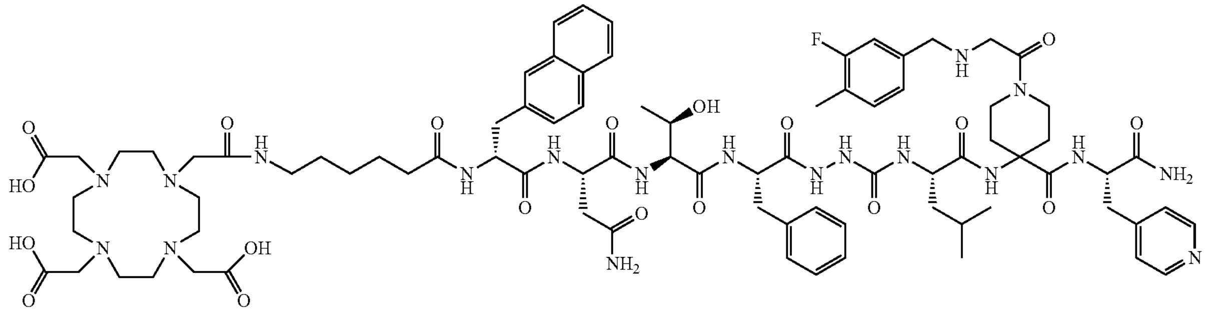 [SMILES: Cc1ccc(CNCC(=O)N2CCC(NC(=O)[C@H](CC(C)C)NC(=O)NNC(=O)[C@H](Cc3ccccc3)NC(=O)[C@@H](NC(=O)[C@H](CC(N)=O)NC(=O)[C@@H](Cc3ccc4ccccc4c3)NC(=O)CCCCCNC(=O)CN3CCN(CC(=O)O)CCN(CC(=O)O)CCN(CC(=O)O)CC3)[C@@H](C)O)(C(=O)N[C@@H](Cc3ccncc3)C(N)=O)CC2)cc1F]
MS: Calc'd 1699.85, found $[M+2H]^{2+}$: 851.15.
Example 185. Compound 293 (SEQ ID NO: 675)
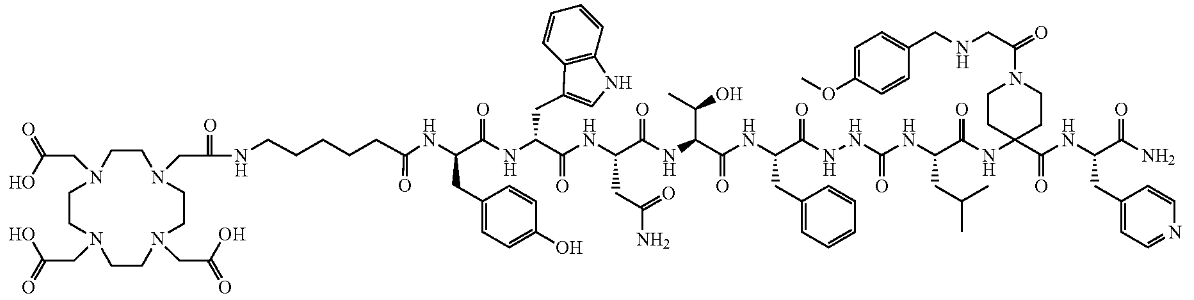 [SMILES: COc1ccc(CNCC(=O)N2CCC(NC(=O)[C@H](CC(C)C)NC(=O)NNC(=O)[C@H](Cc3ccccc3)NC(=O)[C@@H](NC(=O)[C@H](CC(N)=O)NC(=O)[C@@H](Cc3c[nH]c4ccccc34)NC(=O)[C@@H](Cc3ccc(O)cc3)NC(=O)CCCCCNC(=O)CN3CCN(CC(=O)O)CCN(CC(=O)O)CCN(CC(=O)O)CC3)[C@@H](C)O)(C(=O)N[C@@H](Cc3ccncc3)C(N)=O)CC2)cc1]
MS: Calc'd 1849.92, found $[M+H]^{+}$:1850.9.

Example 186: Compound 294 (SEQ ID NO: 676)
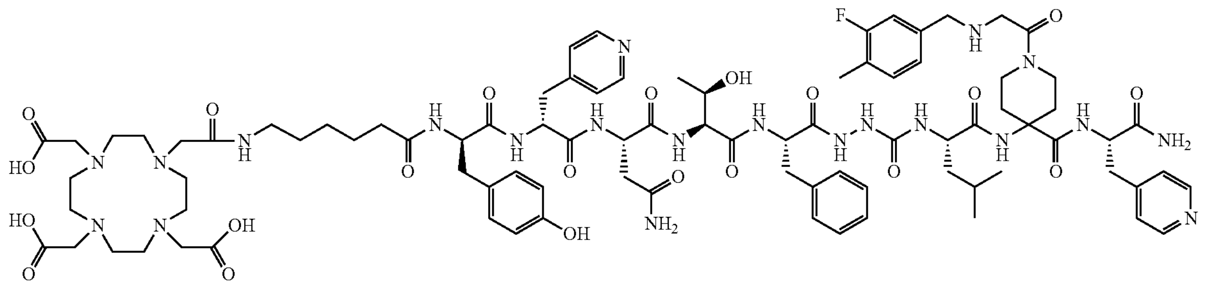 [SMILES: Cc1ccc(CNCC(=O)N2CCC(NC(=O)[C@H](CC(C)C)NC(=O)NNC(=O)[C@H](Cc3ccccc3)NC(=O)[C@@H](NC(=O)[C@H](CC(N)=O)NC(=O)[C@@H](Cc3ccncc3)NC(=O)[C@@H](Cc3ccc(O)cc3)NC(=O)CCCCCNC(=O)CN3CCN(CC(=O)O)CCN(CC(=O)O)CCN(CC(=O)O)CC3)[C@@H](C)O)(C(=O)N[C@@H](Cc3ccncc3)C(N)=O)CC2)cc1F]
MS: Calc'd 1813.90, found $[M+2H]^{2+}$: 908.5.
Example 187: Compound 295 (SEQ ID NO: 67)
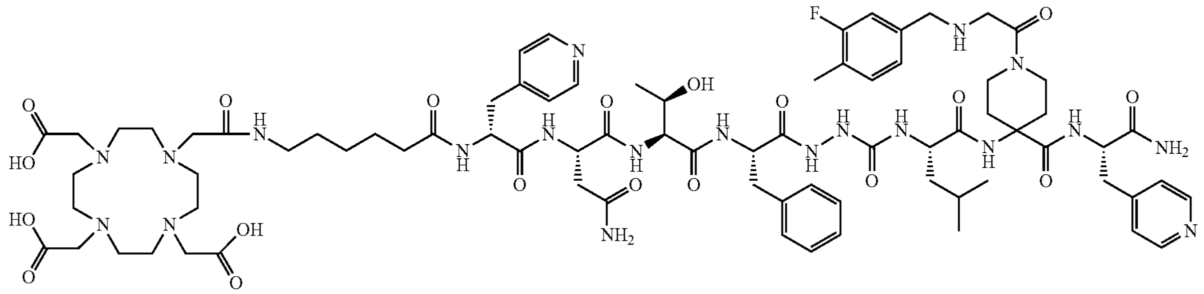 [SMILES: Cc1ccc(CNCC(=O)N2CCC(NC(=O)[C@H](CC(C)C)NC(=O)NNC(=O)[C@H](Cc3ccccc3)NC(=O)[C@@H](NC(=O)[C@H](CC(N)=O)NC(=O)[C@@H](Cc3ccncc3)NC(=O)CCCCCNC(=O)CN3CCN(CC(=O)O)CCN(CC(=O)O)CCN(CC(=O)O)CC3)[C@@H](C)O)(C(=O)N[C@@H](Cc3ccncc3)C(N)=O)CC2)cc1F]
MS: Calc'd 1650.83, found $[M+4H]^{4+}$: 414.05.
Example 188: Compound 296 (SEQ ID NO: 678)
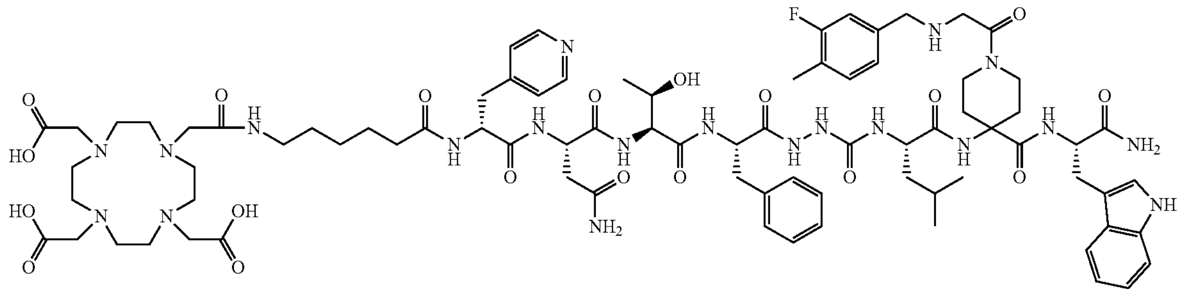 [SMILES: Cc1ccc(CNCC(=O)N2CCC(NC(=O)[C@H](CC(C)C)NC(=O)NNC(=O)[C@H](Cc3ccccc3)NC(=O)[C@@H](NC(=O)[C@H](CC(N)=O)NC(=O)[C@@H](Cc3ccncc3)NC(=O)CCCCCNC(=O)CN3CCN(CC(=O)O)CCN(CC(=O)O)CCN(CC(=O)O)CC3)[C@@H](C)O)(C(=O)N[C@@H](Cc3c[nH]c4ccccc34)C(N)=O)CC2)cc1F]
MS: Calc'd 1688.85, found $[M+2H]^{2+}$: 845.95.

Example 189: Compound 297
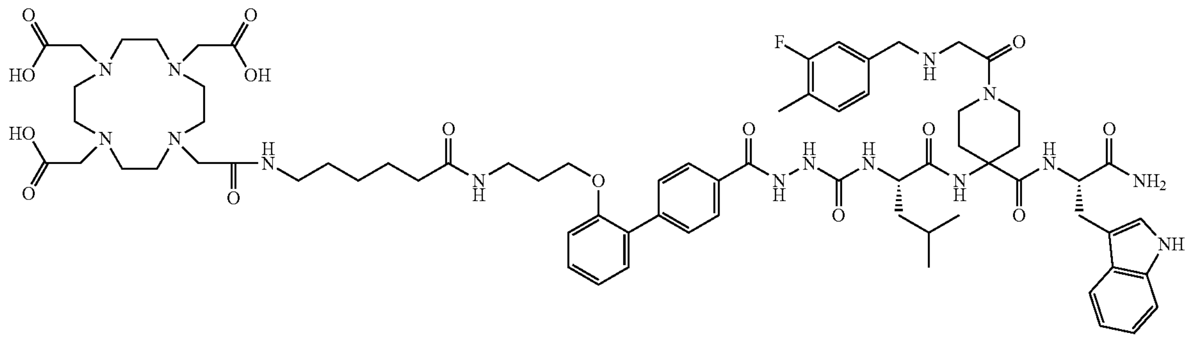 [SMILES: Cc1ccc(CNCC(=O)N2CCC(NC(=O)[C@H](CC(C)C)NC(=O)NNC(=O)c3ccc(-c4ccccc4OCCCNC(=O)CCCCCNC(=O)CN4CCN(CC(=O)O)CCN(CC(=O)O)CCN(CC(=O)O)CC4)cc3)(C(=O)N[C@@H](Cc3c[nH]c4ccccc34)C(N)=O)CC2)cc1F]
MS: Calc'd 1431.74, found $[M+H]^+$: 1432.9.
Example 190: Compound 298
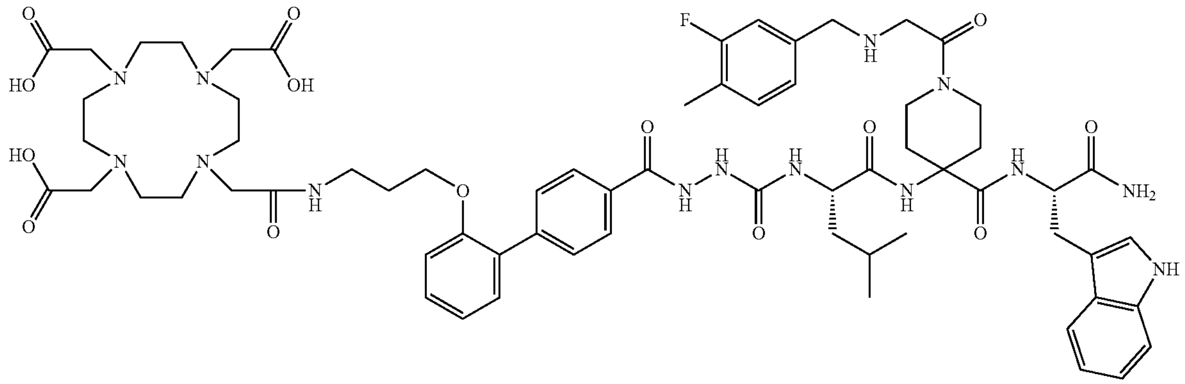 [SMILES: Cc1ccc(CNCC(=O)N2CCC(NC(=O)[C@H](CC(C)C)NC(=O)NNC(=O)c3ccc(-c4ccccc4OCCCNC(=O)CN4CCN(CC(=O)O)CCN(CC(=O)O)CCN(CC(=O)O)CC4)cc3)(C(=O)N[C@@H](Cc3c[nH]c4ccccc34)C(N)=O)CC2)cc1F]
MS: Calc'd 1318.65, found $[M+H]^+$: 1319.6.
Example 191: Compound 299 (SEQ ID NO: 681)
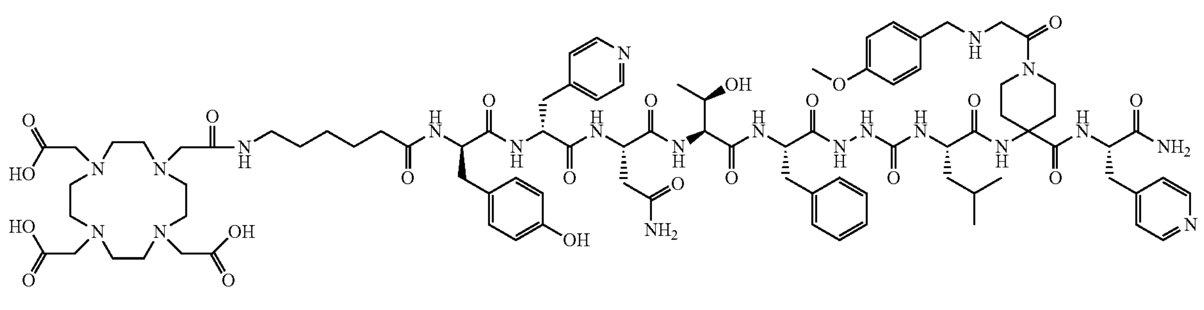 [SMILES: COc1ccc(CNCC(=O)N2CCC(NC(=O)[C@H](CC(C)C)NC(=O)NNC(=O)[C@H](Cc3ccccc3)NC(=O)[C@@H](NC(=O)[C@H](CC(N)=O)NC(=O)[C@@H](Cc3ccncc3)NC(=O)[C@@H](Cc3ccc(O)cc3)NC(=O)CCCCCNC(=O)CN3CCN(CC(=O)O)CCN(CC(=O)O)CCN(CC(=O)O)CC3)[C@@H](C)O)(C(=O)N[C@@H](Cc3ccncc3)C(N)=O)CC2)cc1]
MS: Calc'd 1811.90, found $[M+H]^+$: 1812.9.

Example 192: Compound 300 (SEQ ID NO: 682)
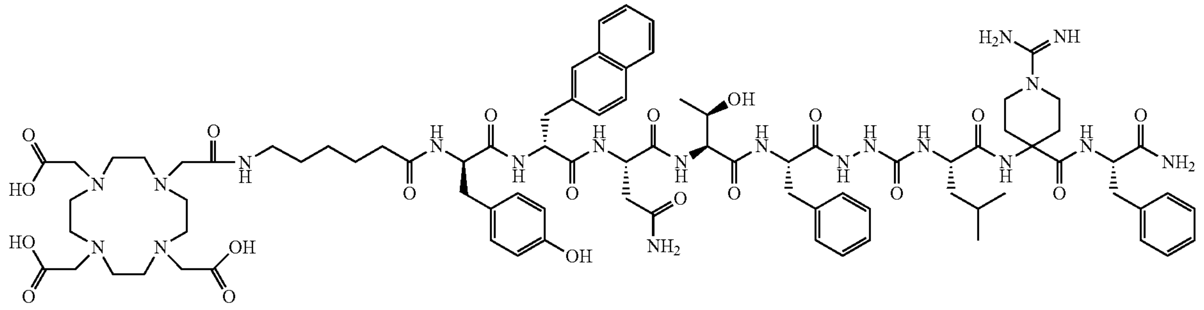 [SMILES: CC(C)C[C@H](NC(=O)NNC(=O)[C@H](Cc1ccccc1)NC(=O)[C@@H](NC(=O)[C@H](CC(N)=O)NC(=O)[C@@H](Cc1ccc2ccccc2c1)NC(=O)[C@@H](Cc1ccc(O)cc1)NC(=O)CCCCCNC(=O)CN1CCN(CC(=O)O)CCN(CC(=O)O)CCN(CC(=O)O)CC1)[C@@H](C)O)C(=O)NC1(C(=O)N[C@@H](Cc2ccccc2)C(N)=O)CCN(C(=N)N)CC1]
MS: Calc'd 1724.87, found $[M+3H]^{3+}$: 576.4.
Example 193: Compound 301 (SEQ ID NO: 683)
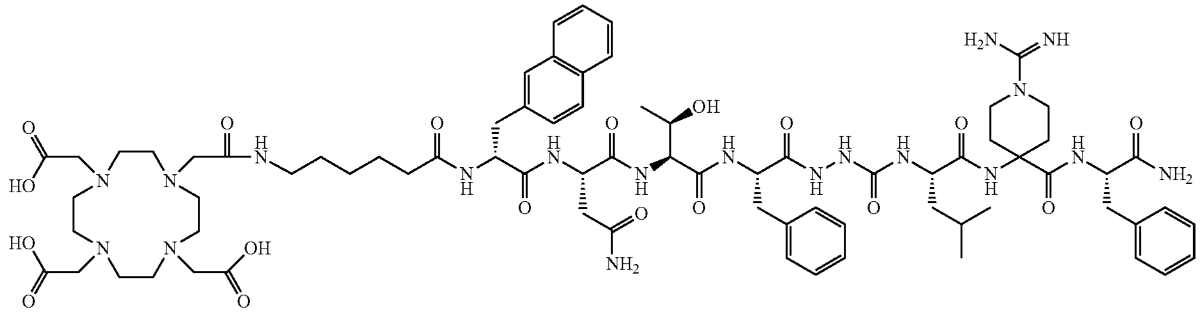 [SMILES: CC(C)C[C@H](NC(=O)NNC(=O)[C@H](Cc1ccccc1)NC(=O)[C@@H](NC(=O)[C@H](CC(N)=O)NC(=O)[C@@H](Cc1ccc2ccccc2c1)NC(=O)CCCCCNC(=O)CN1CCN(CC(=O)O)CCN(CC(=O)O)CCN(CC(=O)O)CC1)[C@@H](C)O)C(=O)NC1(C(=O)N[C@@H](Cc2ccccc2)C(N)=O)CCN(C(=N)N)CC1]
MS: Calc'd 1561.80, found $[M+3H]^{3+}$: 522.0.
Example 194: Compound 302 (SEQ ID NO: 684)
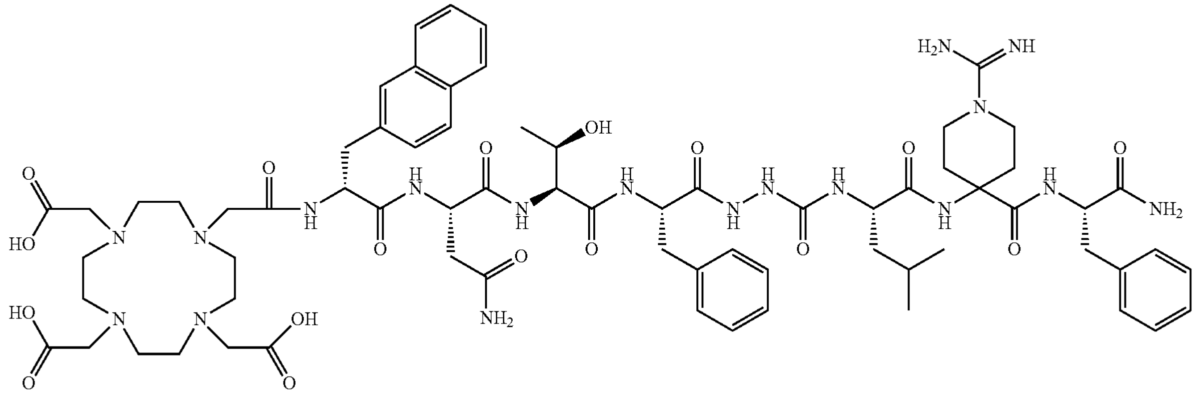 [SMILES: CC(C)C[C@H](NC(=O)NNC(=O)[C@H](Cc1ccccc1)NC(=O)[C@@H](NC(=O)[C@H](CC(N)=O)NC(=O)[C@@H](Cc1ccc2ccccc2c1)NC(=O)CN1CCN(CC(=O)O)CCN(CC(=O)O)CCN(CC(=O)O)CC1)[C@@H](C)O)C(=O)NC1(C(=O)N[C@@H](Cc2ccccc2)C(N)=O)CCN(C(=N)N)CC1]
MS: Calc'd 1448.72, found $[M+3H]^{3+}$: 484.3.

Example 195: Compound 304 (SEQ ID NO: 686)
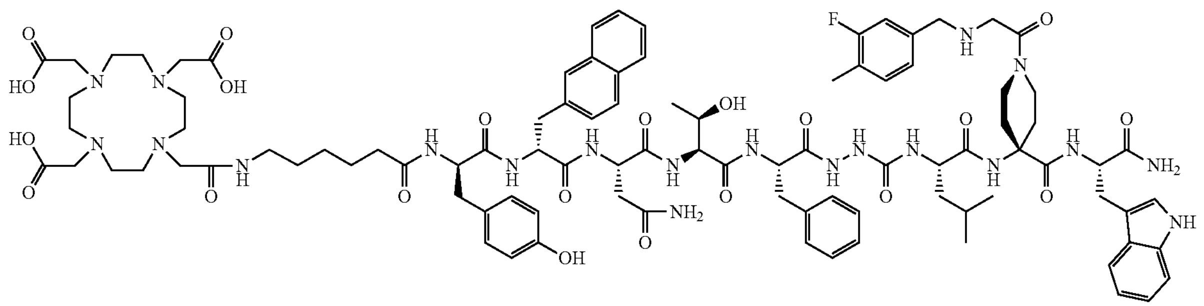
MS: Calc'd 1900.93, found $[M+2H]^{2+}$: 952.1.
Example 196: Compound 305 (SEQ ID NO: 687)
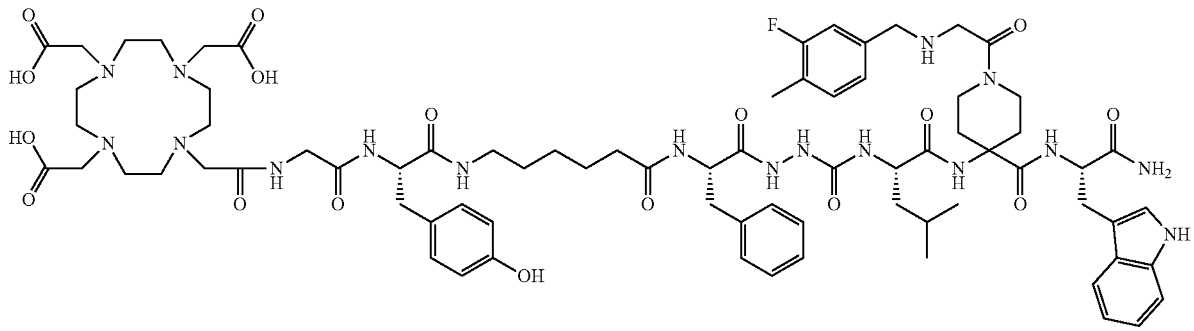 [SMILES: Cc1ccc(CNCC(=O)N2CCC(NC(=O)[C@H](CC(C)C)NC(=O)NNC(=O)[C@H](Cc3ccccc3)NC(=O)CCCCCNC(=O)[C@H](Cc3ccc(O)cc3)NC(=O)CNC(=O)CN3CCN(CC(=O)O)CCN(CC(=O)O)CCN(CC(=O)O)CC3)(C(=O)N[C@@H](Cc3c[nH]c4ccccc34)C(N)=O)CC2)cc1F]
MS: Calc'd 1545.78, found $[M+2H]^{2+}$: 774.4.
Example 197 Compound 306 (SEQ ID NO: 688)
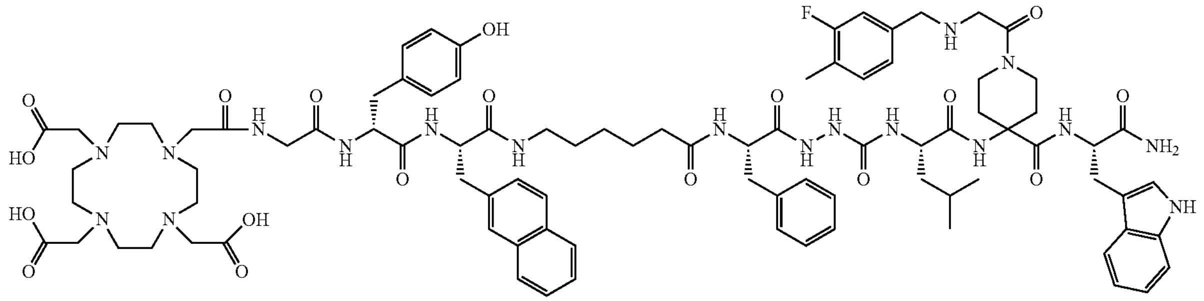 [SMILES: Cc1ccc(CNCC(=O)N2CCC(NC(=O)[C@H](CC(C)C)NC(=O)NNC(=O)[C@H](Cc3ccccc3)NC(=O)CCCCCNC(=O)[C@H](Cc3ccc4ccccc4c3)NC(=O)[C@@H](Cc3ccc(O)cc3)NC(=O)CNC(=O)CN3CCN(CC(=O)O)CCN(CC(=O)O)CCN(CC(=O)O)CC3)(C(=O)N[C@@H](Cc3c[nH]c4ccccc34)C(N)=O)CC2)cc1F]
MS: Calc'd 1742.86, found $[M+2H]^{2+}$: 873.0.

Example 198. Compound 307 (SEQ ID NO: 689)
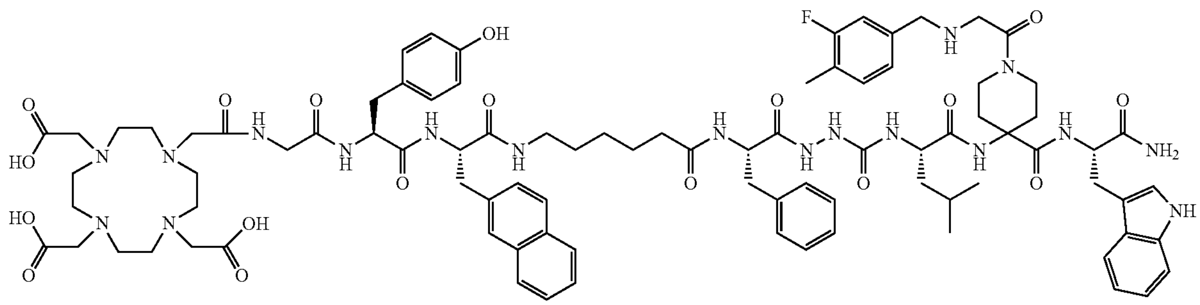 [SMILES: Cc1ccc(CNCC(=O)N2CCC(NC(=O)[C@H](CC(C)C)NC(=O)NNC(=O)[C@H](Cc3ccccc3)NC(=O)CCCCCNC(=O)[C@H](Cc3ccc4ccccc4c3)NC(=O)[C@H](Cc3ccc(O)cc3)NC(=O)CNC(=O)CN3CCN(CC(=O)O)CCN(CC(=O)O)CCN(CC(=O)O)CC3)(C(=O)N[C@@H](Cc3c[nH]c4ccccc34)C(N)=O)CC2)cc1F]
MS: Calc'd 1742.86, found $[M+3H]^{3+}$: 582.4.
Example 199: Compound 308 (SEQ ID NO: 690)
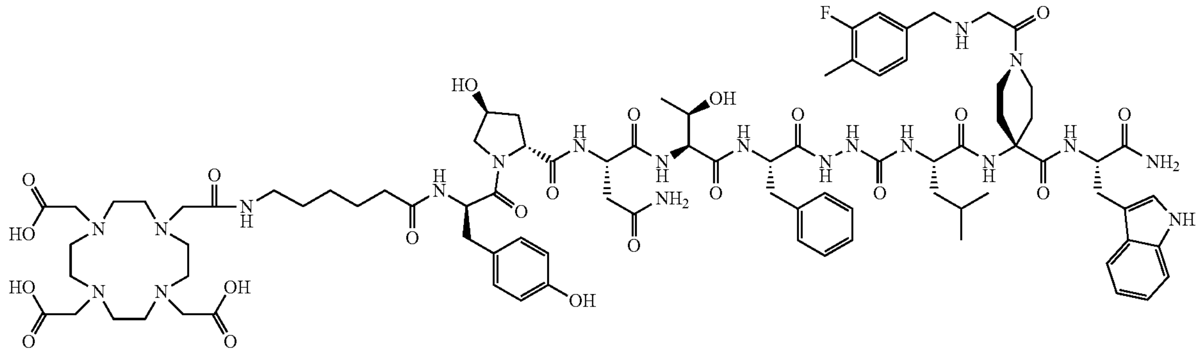
MS: Calc'd 1816.89, found $[M+2H]^{2+}$: 910.15.
Example 200: Compound 309 (SEQ ID NO: 691)
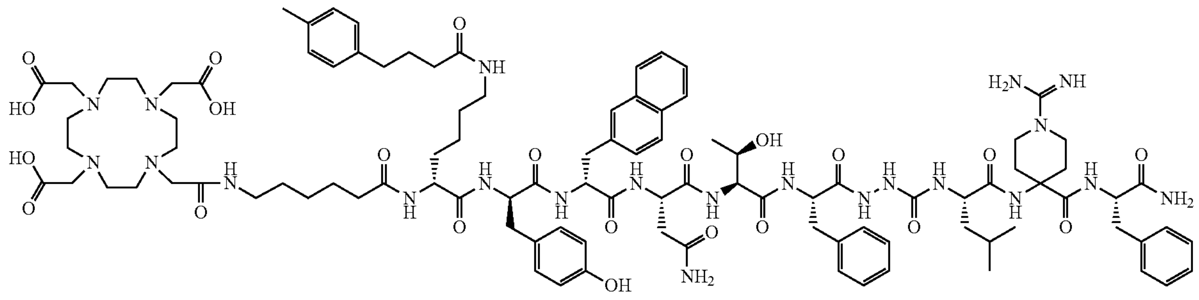 [SMILES: Cc1ccc(CCCC(=O)NCCCC[C@@H](NC(=O)CCCCCNC(=O)CN2CCN(CC(=O)O)CCN(CC(=O)O)CCN(CC(=O)O)CC2)C(=O)N[C@H](Cc2ccc(O)cc2)C(=O)N[C@H](Cc2ccc3ccccc3c2)C(=O)N[C@@H](CC(N)=O)C(=O)N[C@H](C(=O)N[C@@H](Cc2ccccc2)C(=O)NNC(=O)N[C@@H](CC(C)C)C(=O)NC2(C(=O)N[C@@H](Cc3ccccc3)C(N)=O)CCN(C(=N)N)CC2)[C@@H](C)O)cc1]
MS: Calc'd 2013.05, found $[M+2H]^{2+}$: 1008.15.

Example 201: Compound 310 (SEQ ID NO: 692)
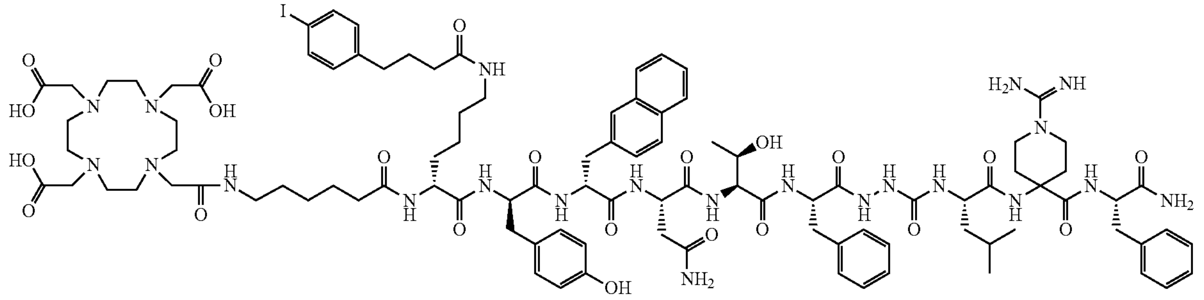 [SMILES: CC(C)C[C@H](NC(=O)NNC(=O)[C@H](Cc1ccccc1)NC(=O)[C@@H](NC(=O)[C@H](CC(N)=O)NC(=O)[C@@H](Cc1ccc2ccccc2c1)NC(=O)[C@@H](Cc1ccc(O)cc1)NC(=O)[C@@H](CCCCNC(=O)CCCc1ccc(I)cc1)NC(=O)CCCCCNC(=O)CN1CCN(CC(=O)O)CCN(CC(=O)O)CCN(CC(=O)O)CC1)[C@@H](C)O)C(=O)NC1(C(=O)N[C@@H](Cc2ccccc2)C(N)=O)CCN(C(=N)N)CC1]
MS: Calc'd 2124.93, found $[M+2H]^{2+}$: 1064.1.
Example 202: Compound 311 (SEQ ID NO: 693)
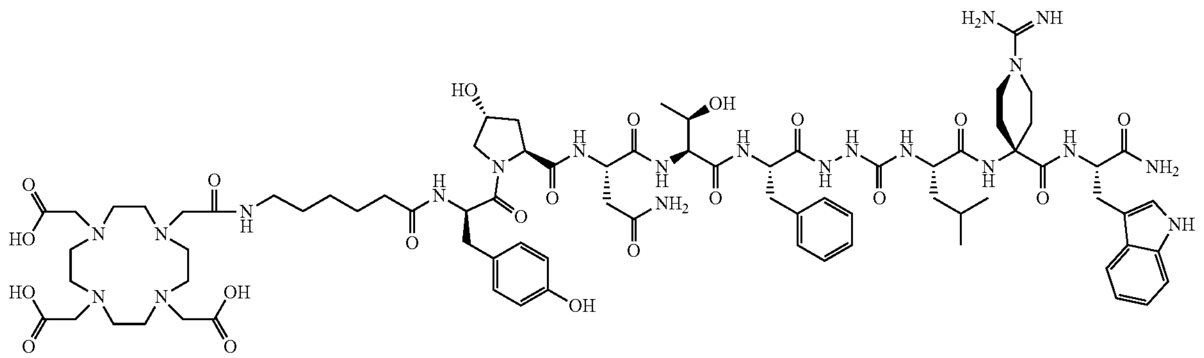
MS: Calc'd 1679.84, found $[M+3H]^{3+}$: 561.35.
Example 203: Compound 312 (SEQ ID NO: 694)
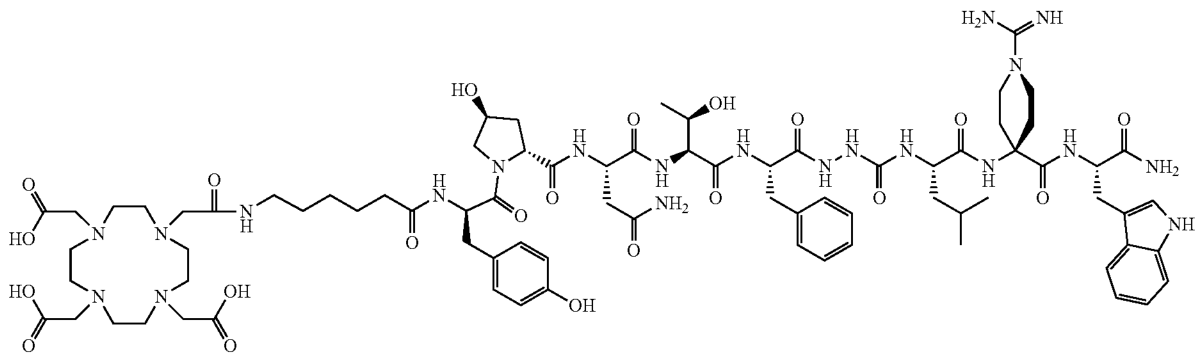
MS: Calc'd 1679.84, found $[M+3H]^{3+}$: 561.4.

Example 204: Compound 313 (SEQ ID NO: 695)
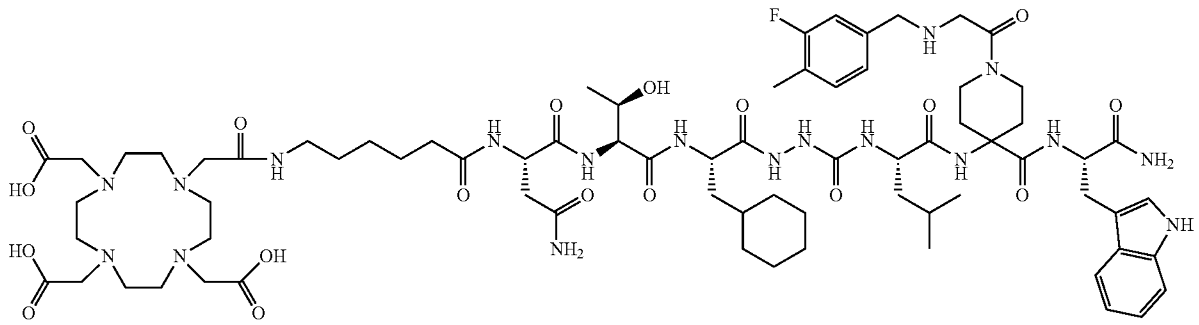 [SMILES: Cc1ccc(CNCC(=O)N2CCC(NC(=O)[C@H](CC(C)C)NC(=O)NNC(=O)[C@H](CC3CCCCC3)NC(=O)[C@@H](NC(=O)[C@H](CC(N)=O)NC(=O)CCCCCNC(=O)CN3CCN(CC(=O)O)CCN(CC(=O)O)CCN(CC(=O)O)CC3)[C@@H](C)O)(C(=O)N[C@@H](Cc3c[nH]c4ccccc34)C(N)=O)CC2)cc1F]
MS: Calc'd 1546.83, found $[M+3H]^{3+}$: 517.0.
Example 205: Compound 314 (SEQ ID NO: 696)
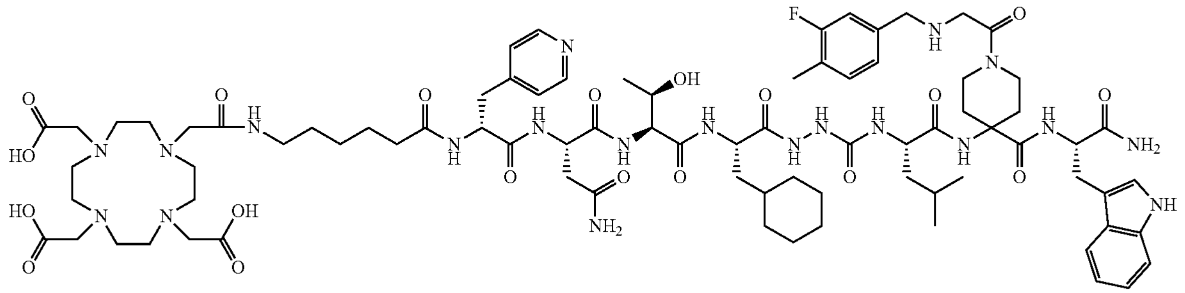 [SMILES: Cc1ccc(CNCC(=O)N2CCC(NC(=O)[C@H](CC(C)C)NC(=O)NNC(=O)[C@H](CC3CCCCC3)NC(=O)[C@@H](NC(=O)[C@H](CC(N)=O)NC(=O)[C@@H](Cc3ccncc3)NC(=O)CCCCCNC(=O)CN3CCN(CC(=O)O)CCN(CC(=O)O)CCN(CC(=O)O)CC3)[C@@H](C)O)(C(=O)N[C@@H](Cc3c[nH]c4ccccc34)C(N)=O)CC2)cc1F]
MS: Calc'd 1694.89, found $[M+2H]^{2+}$: 848.75.
Example 206: Compound 315 (SEQ ID NO: 697)
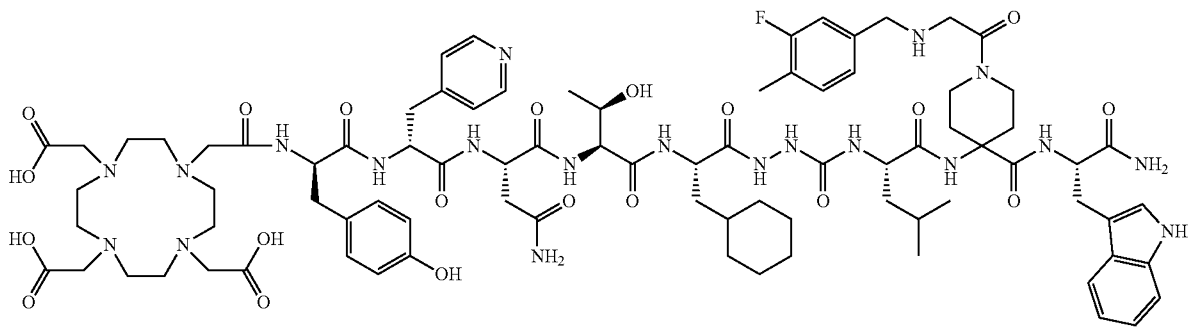
MS: Calc'd 1744.87, found $[M+3H]^{3+}$: 583.05.

Example 207: Compound 316 (SEQ ID NO: 698)
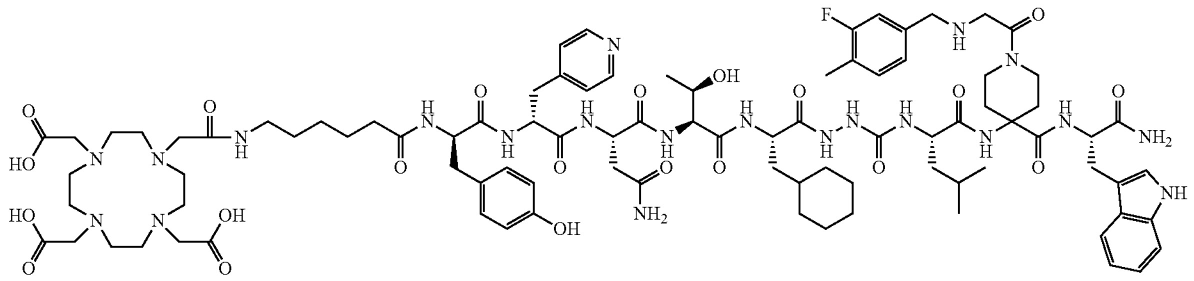 [SMILES: Cc1ccc(CNCC(=O)N2CCC(NC(=O)[C@H](CC(C)C)NC(=O)NNC(=O)[C@H](CC3CCCCC3)NC(=O)[C@@H](NC(=O)[C@H](CC(N)=O)NC(=O)[C@@H](Cc3ccncc3)NC(=O)[C@@H](Cc3ccc(O)cc3)NC(=O)CCCCCNC(=O)CN3CCN(CC(=O)O)CCN(CC(=O)O)CCN(CC(=O)O)CC3)[C@@H](C)O)(C(=O)N[C@@H](Cc3c[nH]c4ccccc34)C(N)=O)CC2)cc1F]
MS: Calc'd 1857.96, found $[M+3H]^{+}$: 620.75.
Example 208: Compound 317 (SEQ ID NO: 699)
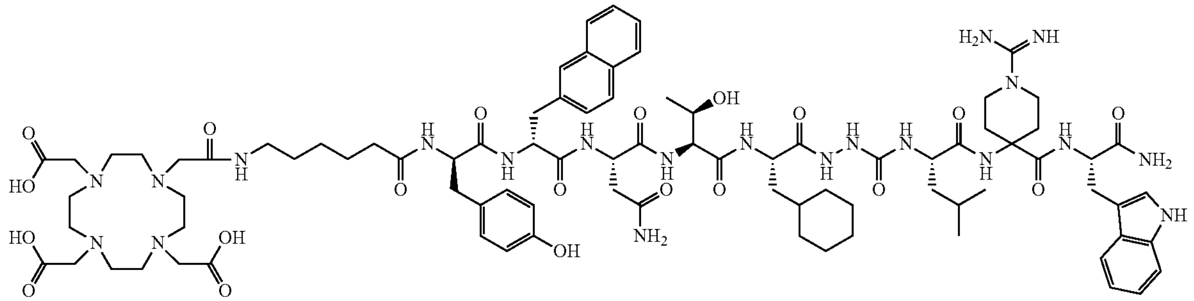 [SMILES: CC(C)C[C@H](NC(=O)NNC(=O)[C@H](CC1CCCCC1)NC(=O)[C@@H](NC(=O)[C@H](CC(N)=O)NC(=O)[C@@H](Cc1ccc2ccccc2c1)NC(=O)[C@@H](Cc1ccc(O)cc1)NC(=O)CCCCCNC(=O)CN1CCN(CC(=O)O)CCN(CC(=O)O)CCN(CC(=O)O)CC1)[C@@H](C)O)C(=O)NC1(C(=O)N[C@@H](Cc2c[nH]c3ccccc23)C(N)=O)CCN(C(=N)N)CC1]
MS: Calc'd 1769.93 found $[M+2H]^{2+}$: 886.5.
Example 209: Compound 318 (SEQ ID NO: 700)
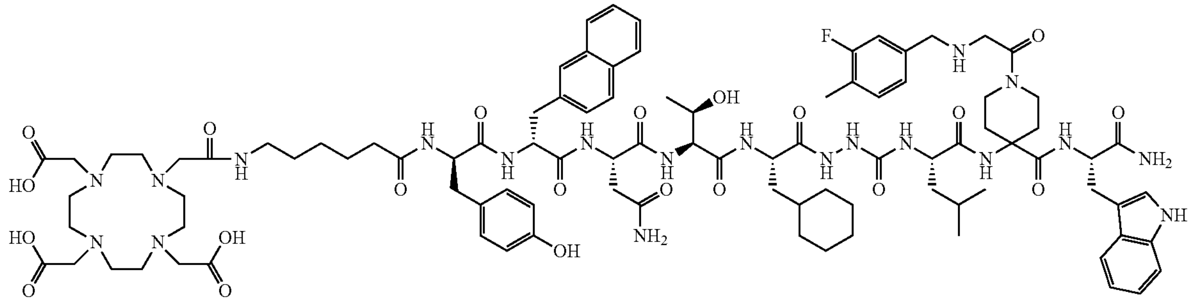 [SMILES: Cc1ccc(CNCC(=O)N2CCC(NC(=O)[C@H](CC(C)C)NC(=O)NNC(=O)[C@H](CC3CCCCC3)NC(=O)[C@@H](NC(=O)[C@H](CC(N)=O)NC(=O)[C@@H](Cc3ccc4ccccc4c3)NC(=O)[C@@H](Cc3ccc(O)cc3)NC(=O)CCCCCNC(=O)CN3CCN(CC(=O)O)CCN(CC(=O)O)CCN(CC(=O)O)CC3)[C@@H](C)O)(C(=O)N[C@@H](Cc3c[nH]c4ccccc34)C(N)=O)CC2)cc1F]
MS: Calc'd 1906.97, found $[M+3H]^{3+}$: 637.1.

Example 210: Compound 319 (SEQ ID NO: 701)
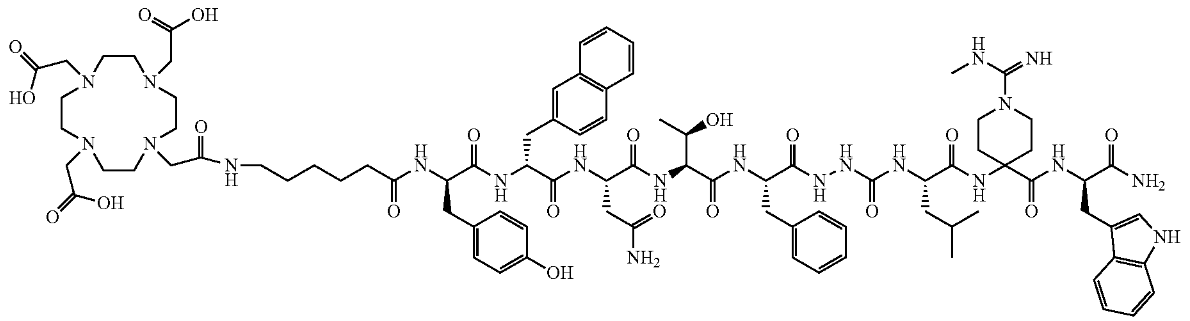 [SMILES: CNC(=N)N1CCC(NC(=O)[C@H](CC(C)C)NC(=O)NNC(=O)[C@H](Cc2ccccc2)NC(=O)[C@@H](NC(=O)[C@H](CC(N)=O)NC(=O)[C@@H](Cc2ccc3ccccc3c2)NC(=O)[C@@H](Cc2ccc(O)cc2)NC(=O)CCCCCNC(=O)CN2CCN(CC(=O)O)CCN(CC(=O)O)CCN(CC(=O)O)CC2)[C@@H](C)O)(C(=O)N[C@H](Cc2c[nH]c3ccccc23)C(N)=O)CC1]
MS: Calc'd 1777.89, found $[M+2H]^{2+}$: 594.1.
Example 211: Compound 320 (SEQ ID NO: 702)
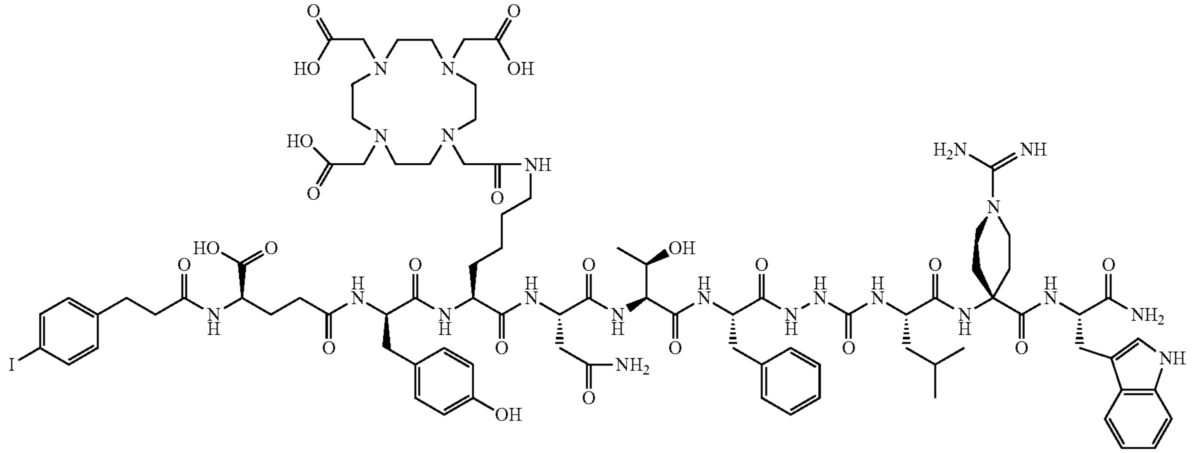
MS: Calc'd 1968.80, found $[M+3H]^{3+}$: 657.7.
Example 212: Compound 321 (SEQ ID NO: 703)
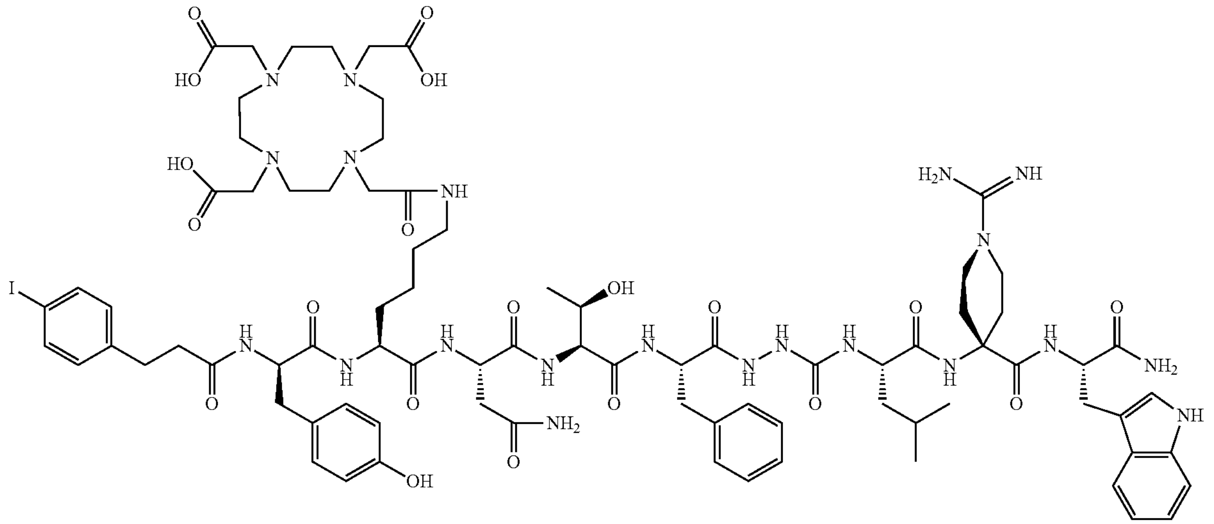
MS: Calc'd 1839.86, found $[M+3H]^{3+}$: 614.65.

Example 213: Compound 322 (SEQ ID NO: 704)
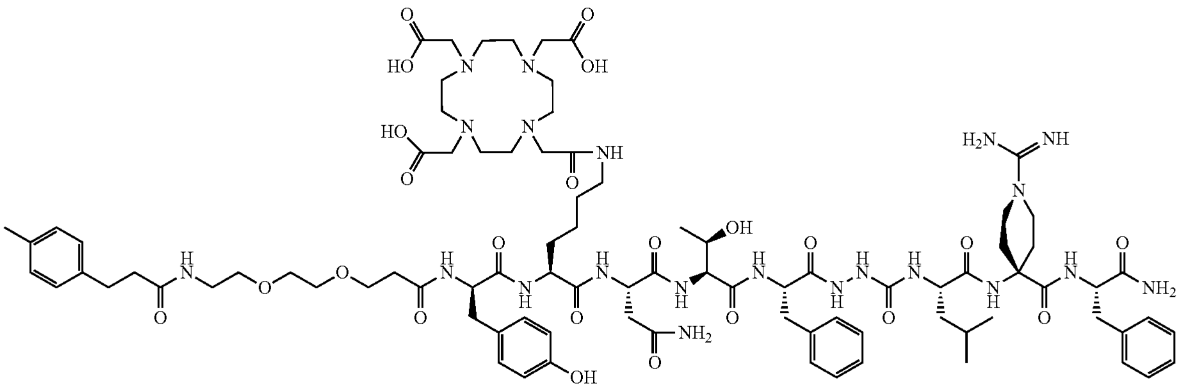
MS: Calc'd 1847.96, found $[M+2H]^{2+}$: 925.5.
Example 214: Compound 323 (SEQ ID NO: 705)
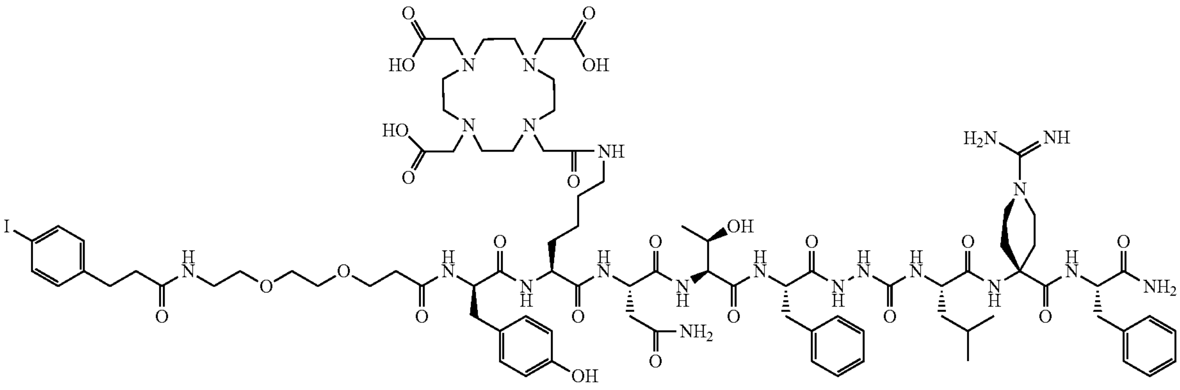
MS: Calc'd 1959.84, found $[M+2H]^{2+}$: 981.4.
Example 215: Compound 324 (SEQ ID NO: 706)
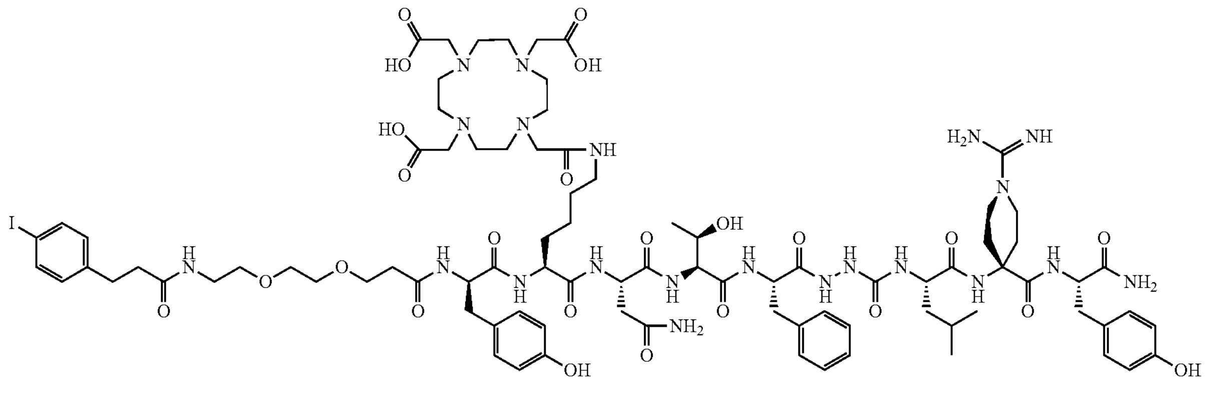
MS: Calc'd 1975.83, found $[M+3H]^{3+}$: 660.05.

Example 216: Compound 325 (SEQ ID NO: 707)
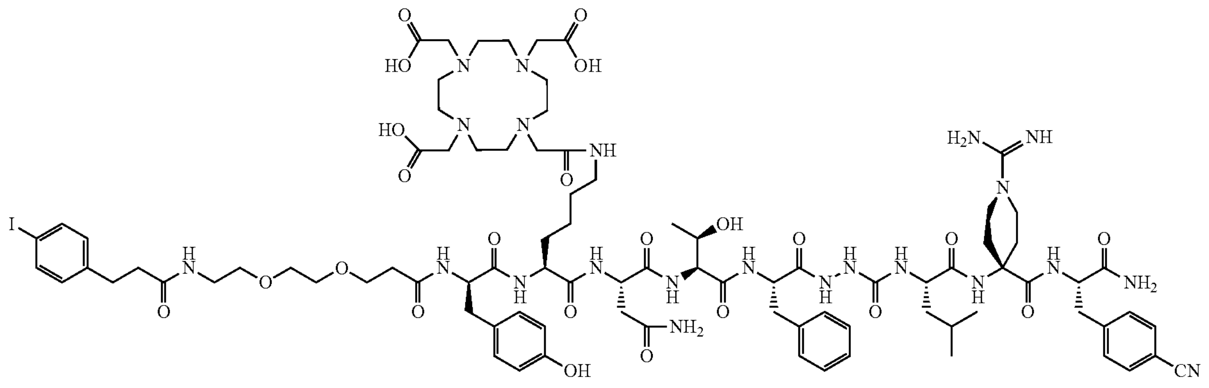
MS: Calc'd 1984.83, found $[M+2H]^{2+}$: 663.05.
Example 217: Compound 326 (SEQ ID NO: 708)
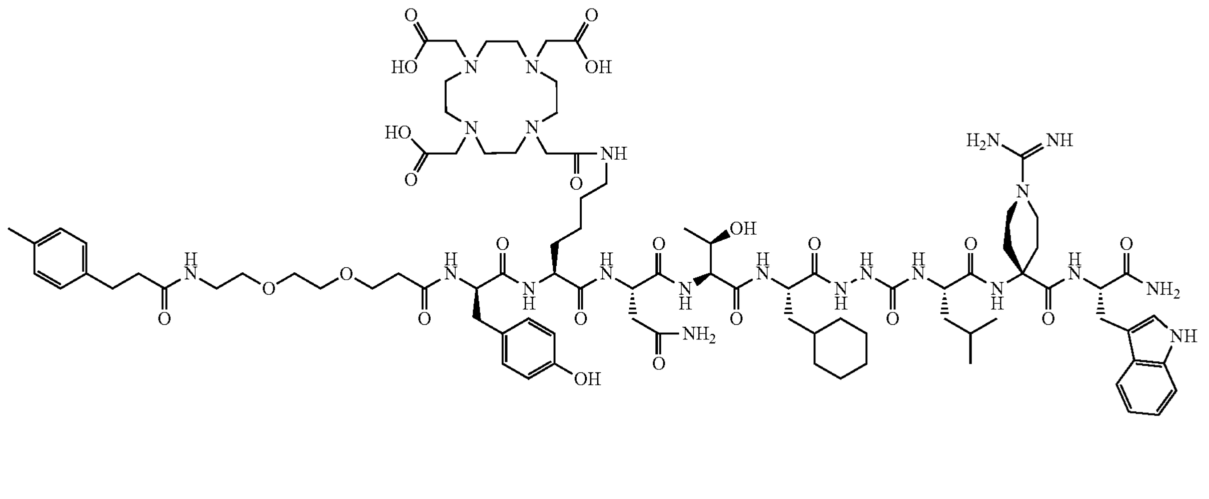
MS: Calc'd 1893.01, found $[M+2H]^{2+}$: 948.05.

Example 218: Compound 327 (SEQ ID NO: 709)
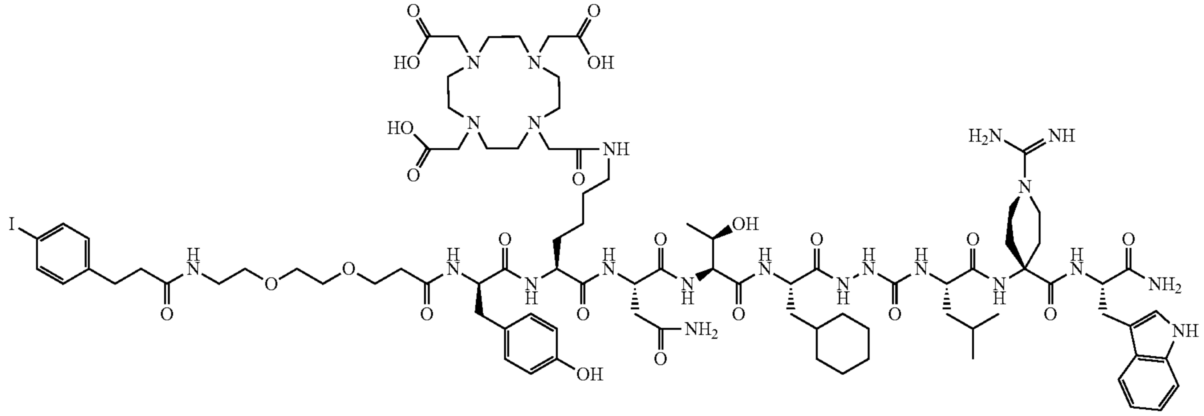
MS: Calc'd 2004.90, found $[M+2H]^{2+}$: 1004.0.
Example 219. Compound 328 (SEQ ID NO: 710)
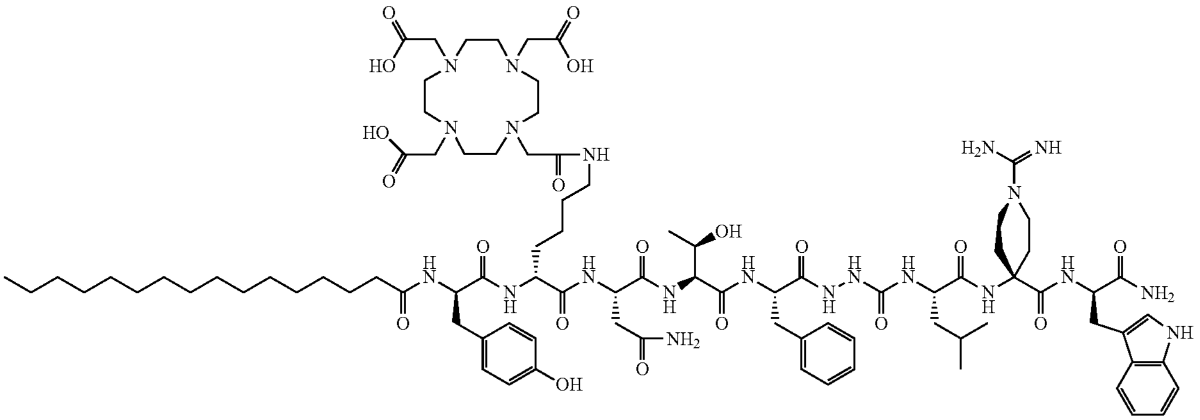
MS: Calc'd 1820.03, found $[M+2H]^{2+}$: 911.5.

Example 220: Compound 329 (SEQ ID NO: 711)
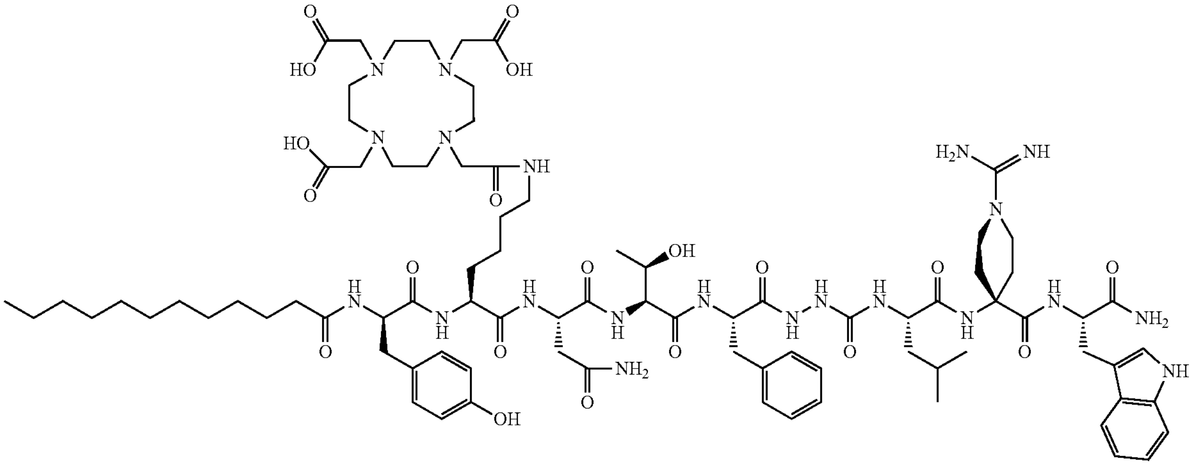
MS: Calc'd 1763.97, found $[M+2H]^{2+}$: 883.45.
Example 221: Compound 330 (SEQ ID NO: 712)
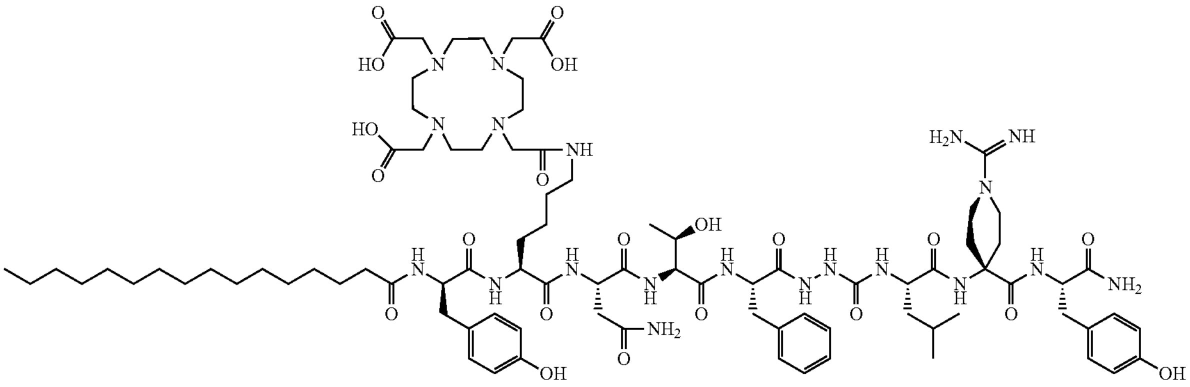
MS: Calc'd 1797.02. found $[M+2H]^{2+}$: 900.0.
Example 222: Compound 331 (SEQ ID NO: 713)
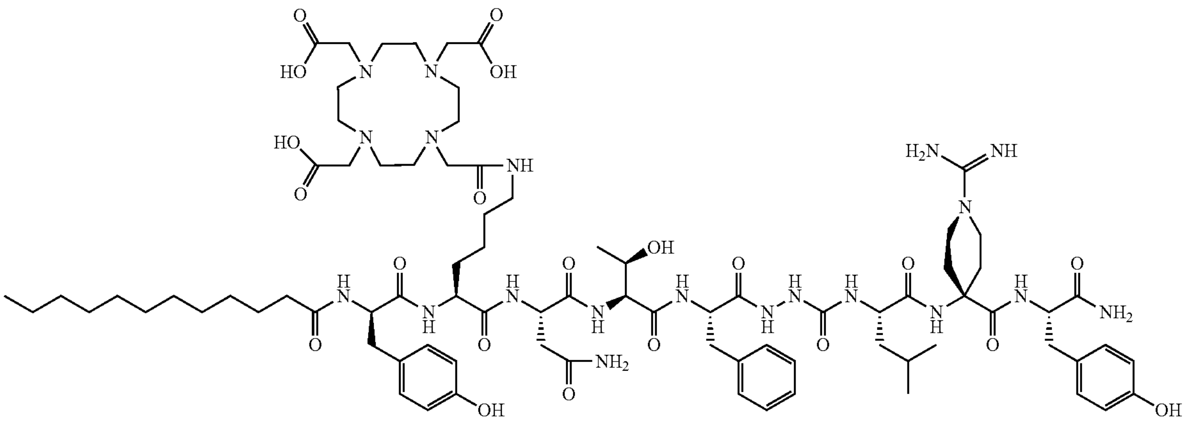
MS: Calc'd 1740.96, found $[M+2H]^{2+}$: 872.0.

Example 223: Compound 332 (SEQ ID NO: 714)
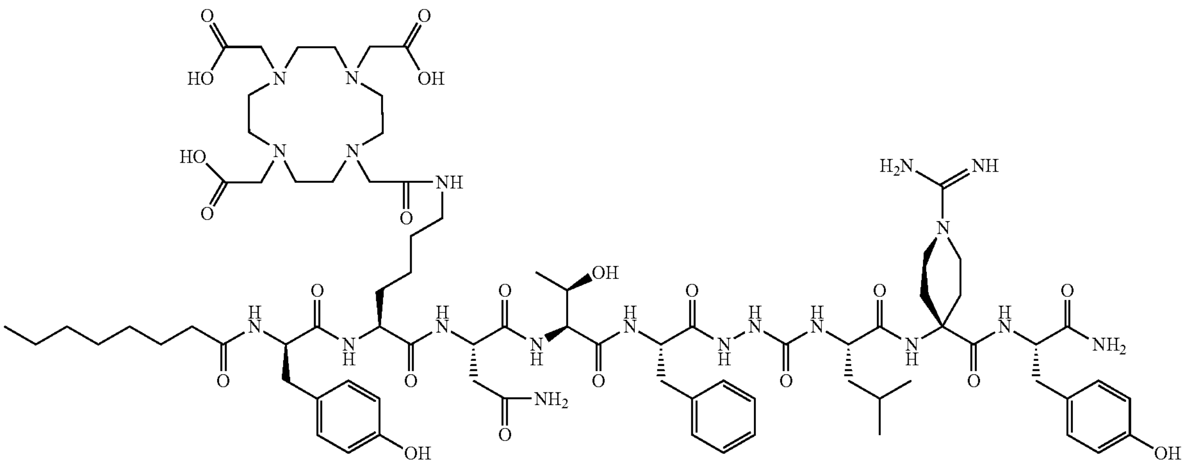
The synthesis of compound 332 was described in Procedure H.
MS: Calc'd 1684.89, found $[M+2H]^{2+}$: 843.95.
Example 224: Compound 333 (SEQ ID NO: 715)
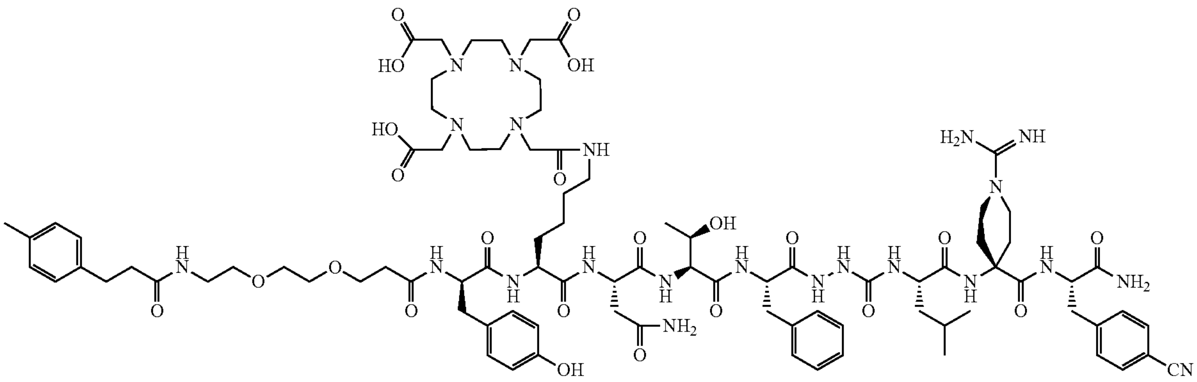
MS: Calc'd 1872.95, found $[M+3H]^{3+}$: 625.8.

Example 225: Compound 334 (SEQ ID NO: 716)
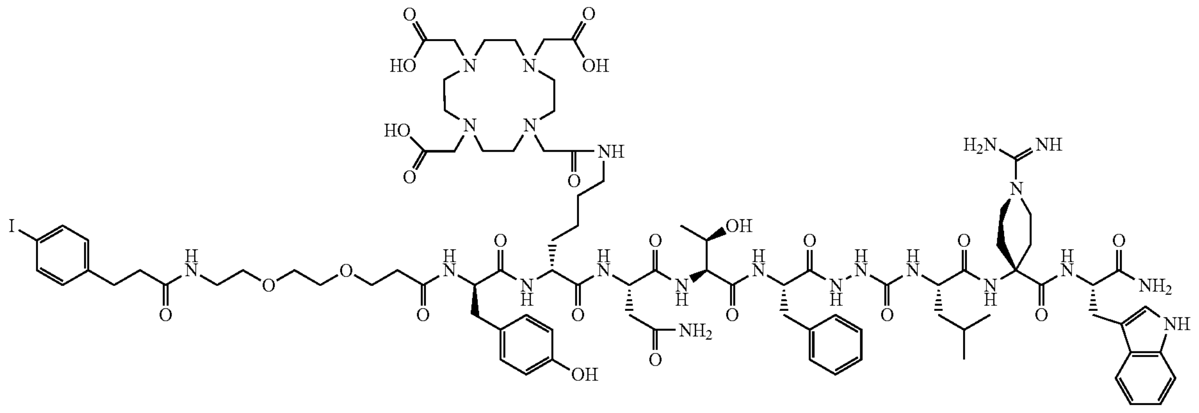
MS: Calc'd 1998.85, found $[M+2H]^{2+}$: 1000.65.
Example 226: Compound 335 (SEQ ID NO: 717)
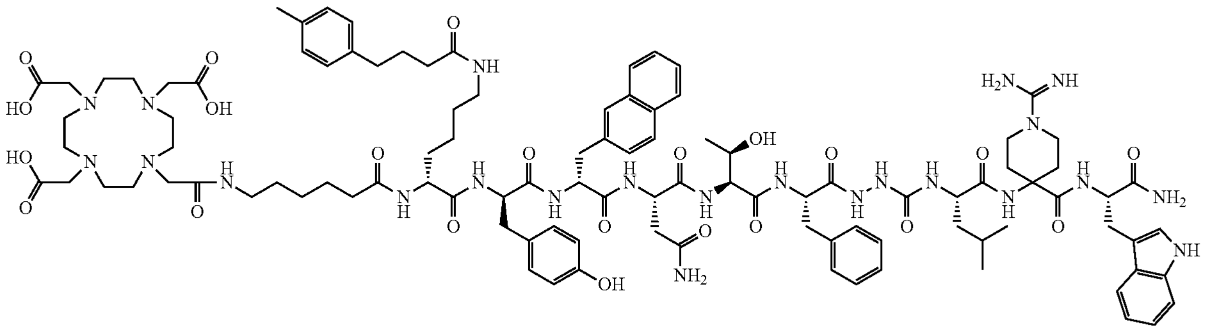 [SMILES: Cc1ccc(CCCC(=O)NCCCC[C@@H](NC(=O)CCCCCNC(=O)CN2CCN(CC(=O)O)CCN(CC(=O)O)CCN(CC(=O)O)CC2)C(=O)N[C@H](Cc2ccc(O)cc2)C(=O)N[C@H](Cc2ccc3ccccc3c2)C(=O)N[C@@H](CC(N)=O)C(=O)N[C@H](C(=O)N[C@@H](Cc2ccccc2)C(=O)NNC(=O)N[C@@H](CC(C)C)C(=O)NC2(C(=O)N[C@@H](Cc3c[nH]c4ccccc34)C(N)=O)CCN(C(=N)N)CC2)[C@@H](C)O)cc1]
MS: Calc'd 2052.06, found $[M+3H]^{3+}$: 685.45.
Example 227: Compound 336 (SEQ ID NO: 718)
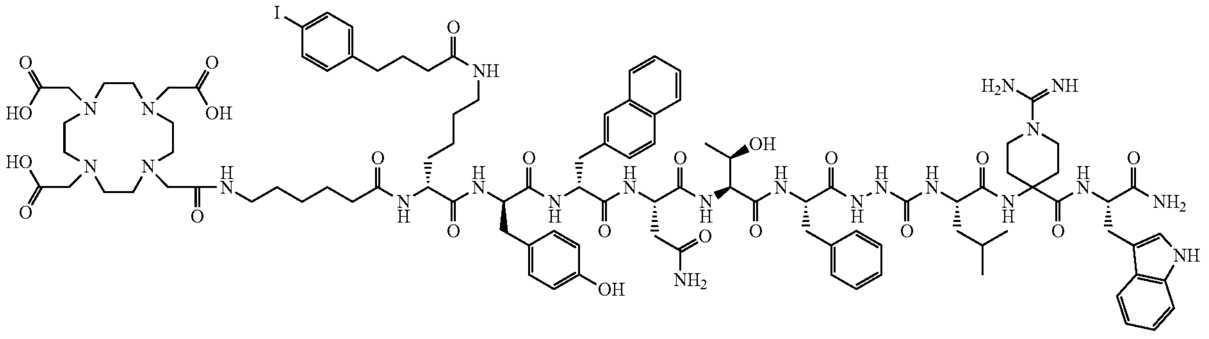 [SMILES: CC(C)C[C@H](NC(=O)NNC(=O)[C@H](Cc1ccccc1)NC(=O)[C@@H](NC(=O)[C@H](CC(N)=O)NC(=O)[C@@H](Cc1ccc2ccccc2c1)NC(=O)[C@@H](Cc1ccc(O)cc1)NC(=O)[C@@H](CCCCNC(=O)CCCc1ccc(I)cc1)NC(=O)CCCCCNC(=O)CN1CCN(CC(=O)O)CCN(CC(=O)O)CCN(CC(=O)O)CC1)[C@@H](C)O)C(=O)NC1(C(=O)N[C@@H](Cc2c[nH]c3ccccc23)C(N)=O)CCN(C(=N)N)CC1]
MS: Calc'd 2163.94, found $[M+3H]^{3+}$: 722.75.

Example 228: Compound 337 (SEQ ID NO: 719)
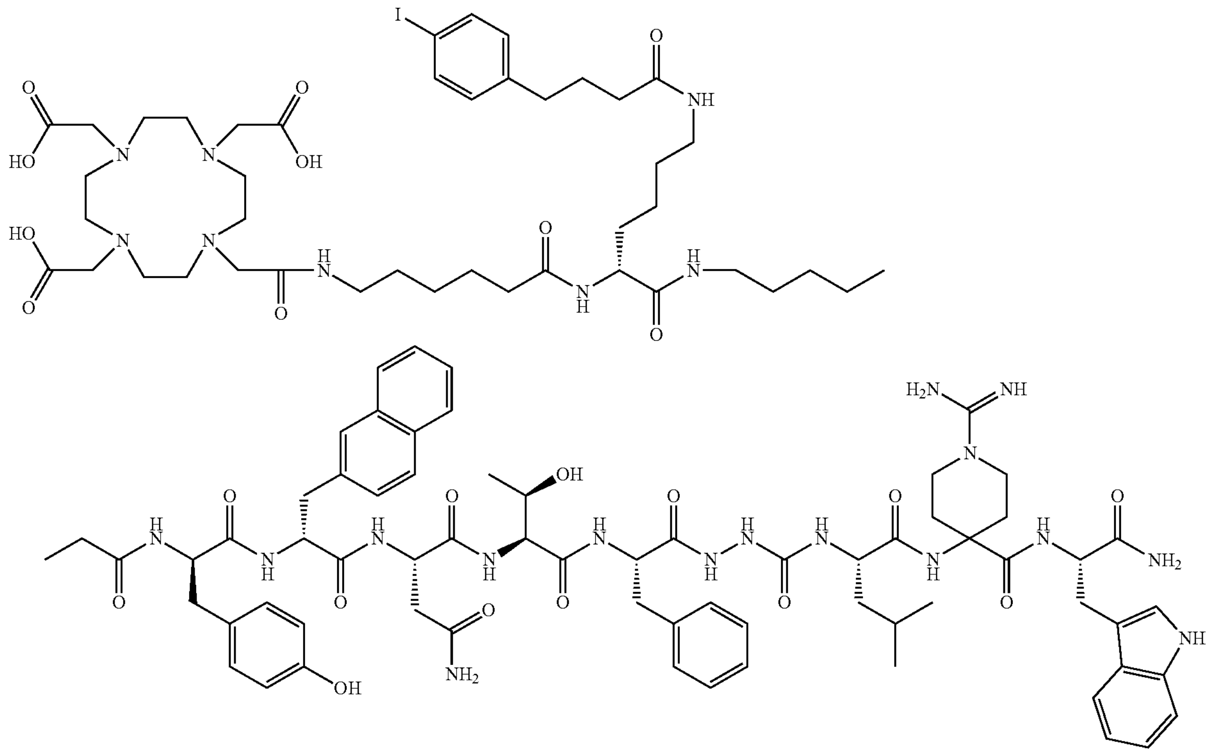
MS: Calc'd 2277.03 found $[M+3H]^{3+}$: 760.45.
Example 229: Compound 338 (SEQ ID NO: 720)
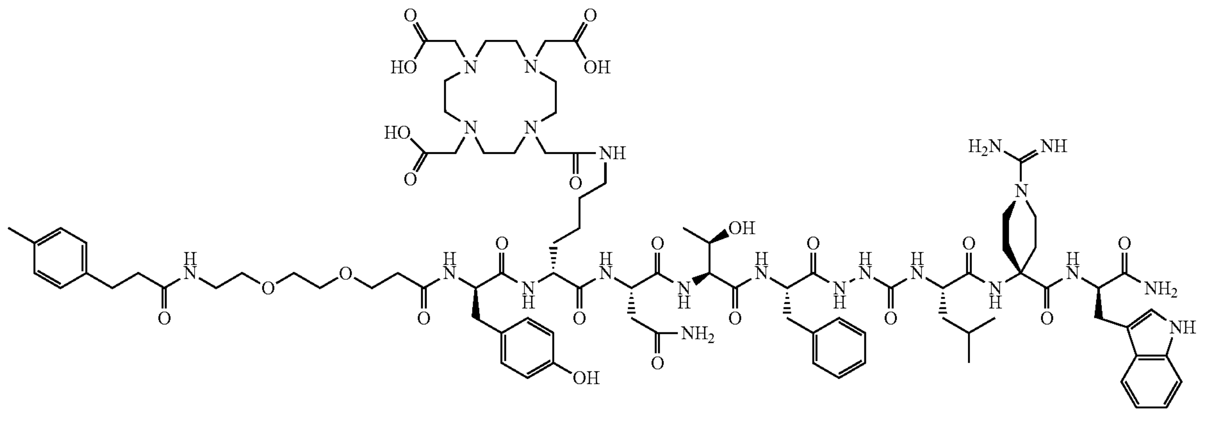
MS: Calc'd 1886.97, found $[M+2H]^{2+}$: 944.75.

Example 230: Compound 339 (SEQ ID NO: 721)
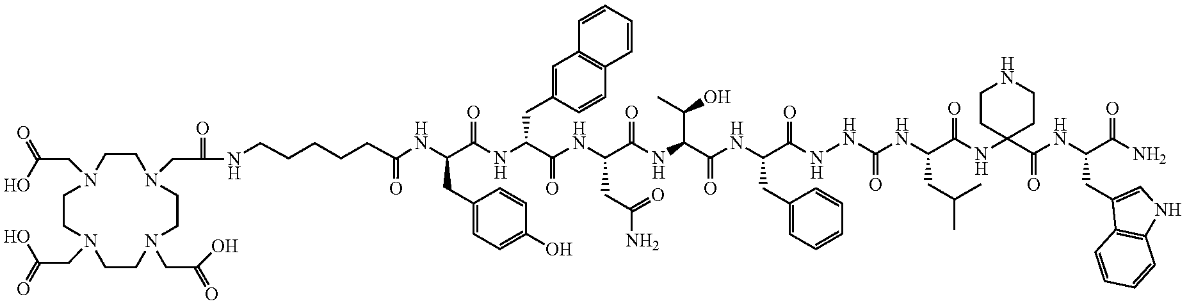 [SMILES: CC(C)C[C@H](NC(=O)NNC(=O)[C@H](Cc1ccccc1)NC(=O)[C@@H](NC(=O)[C@H](CC(N)=O)NC(=O)[C@@H](Cc1ccc2ccccc2c1)NC(=O)[C@@H](Cc1ccc(O)cc1)NC(=O)CCCCCNC(=O)CN1CCN(CC(=O)O)CCN(CC(=O)O)CCN(CC(=O)O)CC1)[C@@H](C)O)C(=O)NC1(C(=O)N[C@@H](Cc2c[nH]c3ccccc23)C(N)=O)CCNCC1]
MS: Calc'd 1721.85, found $[M+3H]^{3+}$: 575.35.
Example 231: Compound 345 (SEQ ID NO: 727)
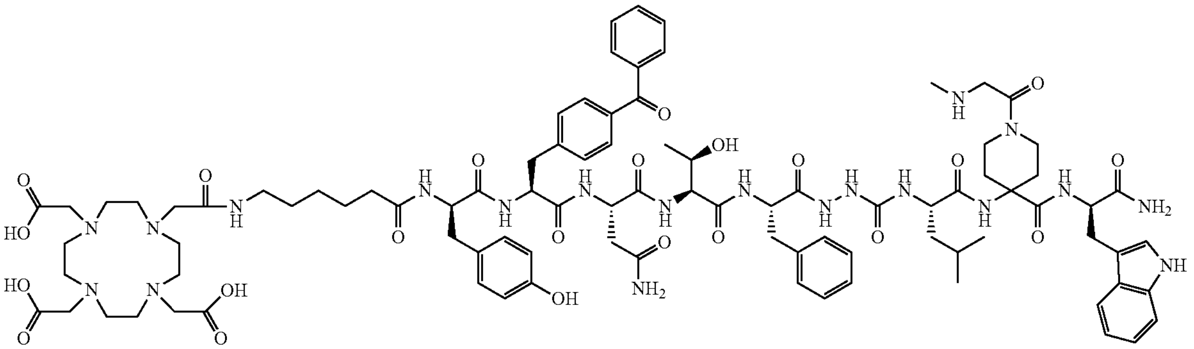 [SMILES: CNCC(=O)N1CCC(NC(=O)[C@H](CC(C)C)NC(=O)NNC(=O)[C@H](Cc2ccccc2)NC(=O)[C@@H](NC(=O)[C@H](CC(N)=O)NC(=O)[C@H](Cc2ccc(C(=O)c3ccccc3)cc2)NC(=O)[C@@H](Cc2ccc(O)cc2)NC(=O)CCCCCNC(=O)CN2CCN(CC(=O)O)CCN(CC(=O)O)CCN(CC(=O)O)CC2)[C@@H](C)O)(C(=O)N[C@H](Cc2c[nH]c3ccccc23)C(N)=O)CC1]
MS: Calc'd 1846.90, found $[M+2H]^{2+}$: 924.9.
Example 232: Compound 346 (SEQ ID NO: 728)
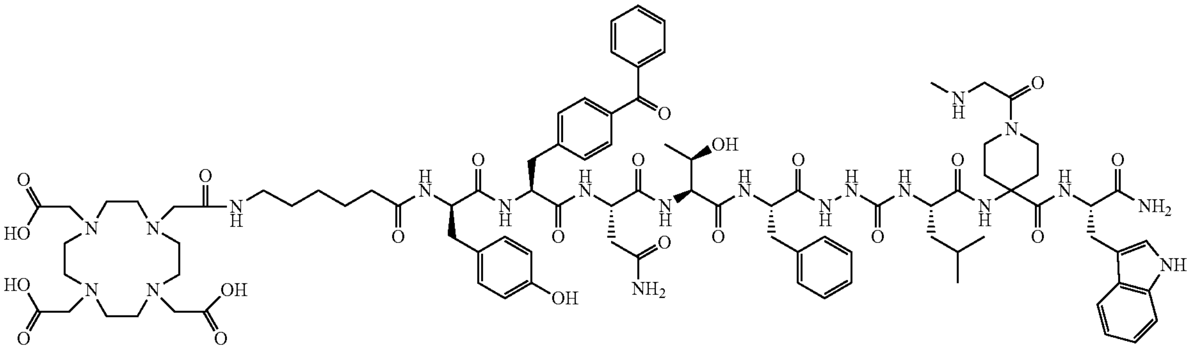 [SMILES: CNCC(=O)N1CCC(NC(=O)[C@H](CC(C)C)NC(=O)NNC(=O)[C@H](Cc2ccccc2)NC(=O)[C@@H](NC(=O)[C@H](CC(N)=O)NC(=O)[C@H](Cc2ccc(C(=O)c3ccccc3)cc2)NC(=O)[C@@H](Cc2ccc(O)cc2)NC(=O)CCCCCNC(=O)CN2CCN(CC(=O)O)CCN(CC(=O)O)CCN(CC(=O)O)CC2)[C@@H](C)O)(C(=O)N[C@@H](Cc2c[nH]c3ccccc23)C(N)=O)CC1]
MS: Calc'd 1846.90, found $[M+3H]^{3+}$: 617.0.

Example 233: Compound 353 (SEQ ID NO: 735)
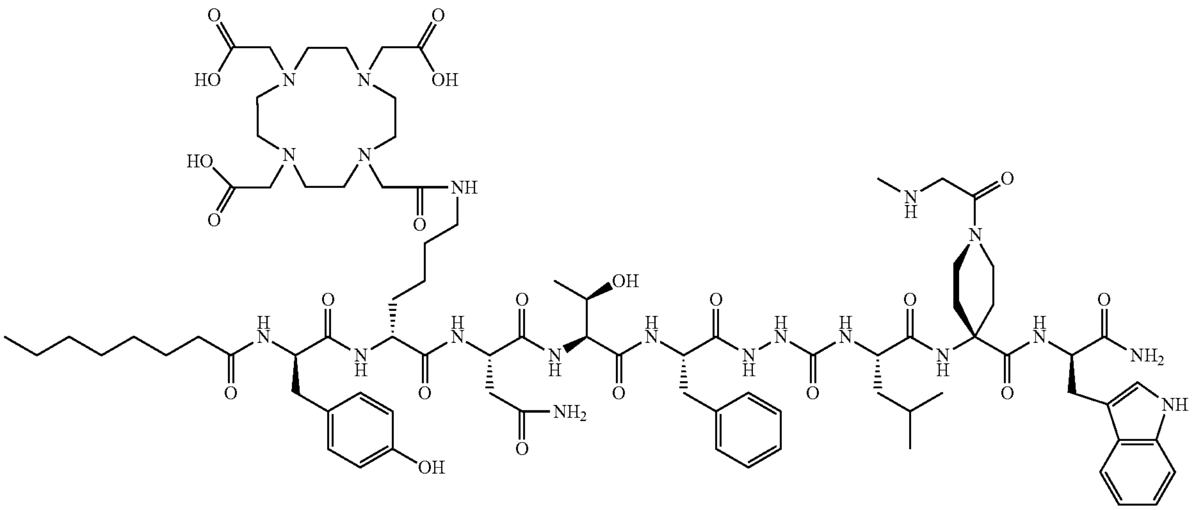
MS: Calc'd 1736.92, found $[M+2H]^{2+}$: 869.9.
Example 234: Compound 354 (SEQ ID NO: 736)
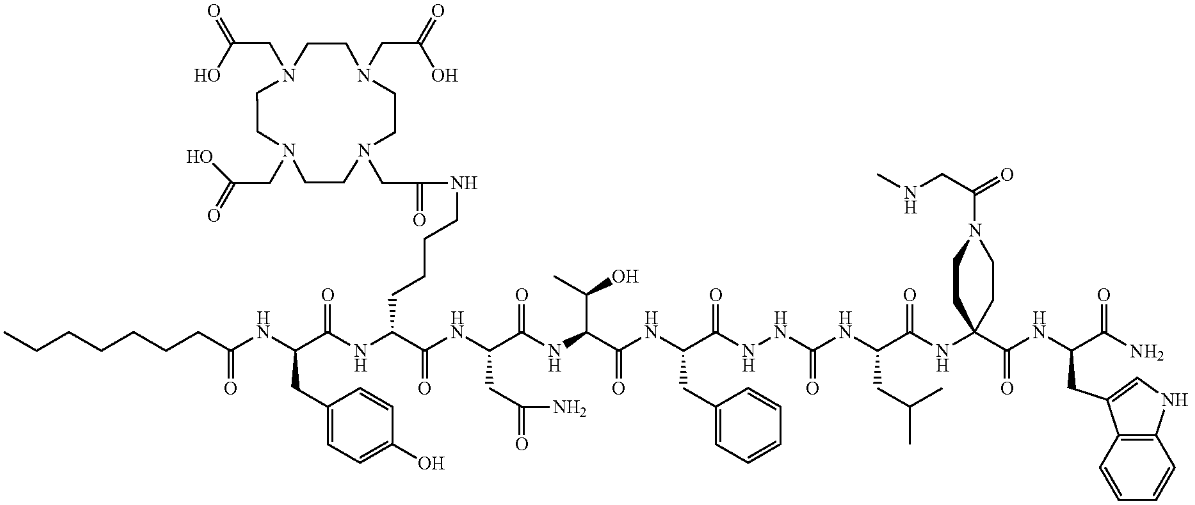
MS: Calc'd 1737.91, found $[M+2H]^{2+}$: 869.9.

Example 235: Compound 355 (SEQ ID NO: 737)
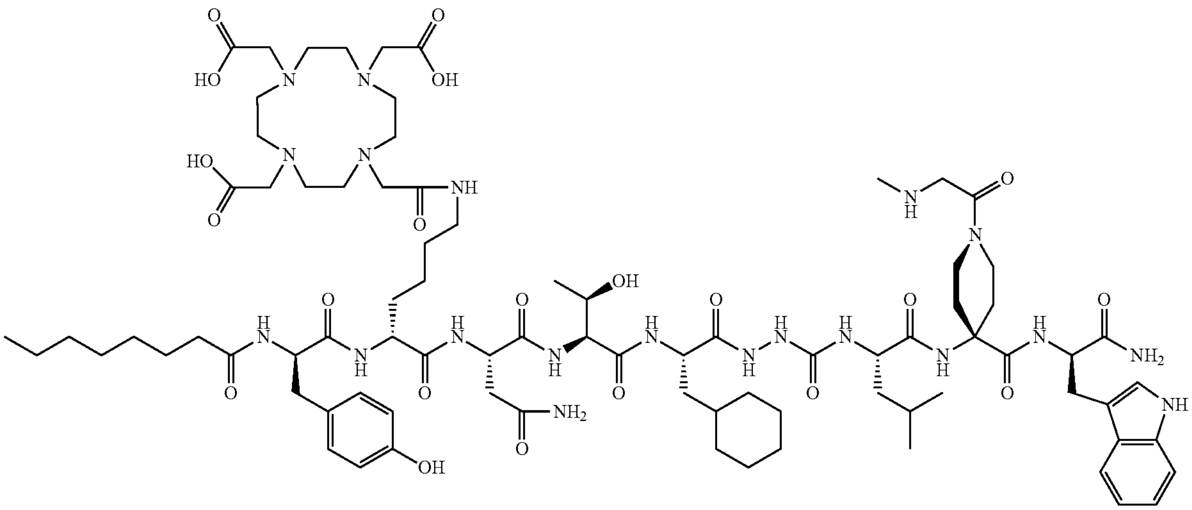
MS: Calc'd 1742.97, found $[M+2H]^{2+}$: 872.9.
Example 236: Compound 356 (SEQ ID NO: 738)
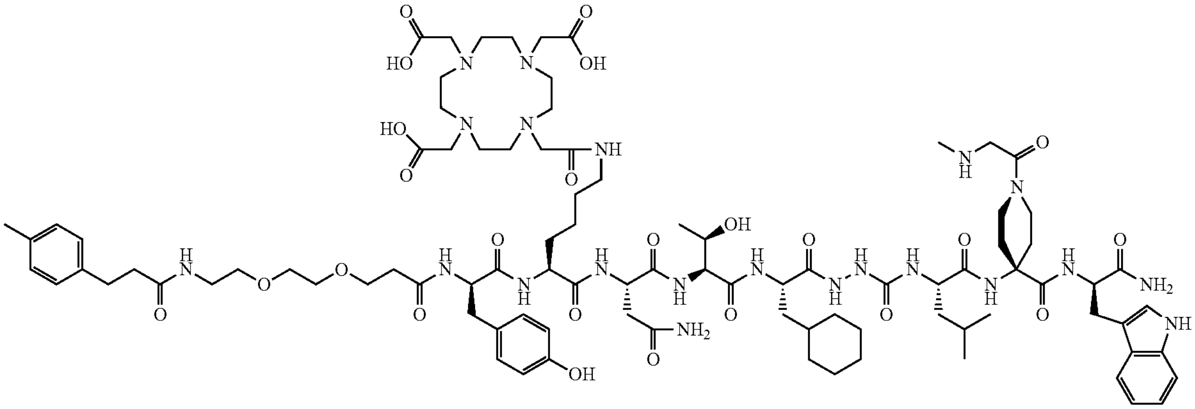
MS: Calc'd 1922.03, found $[M+2H]^{2+}$: 962.6.

Example 237: Compound 357 (SEQ ID NO: 739)
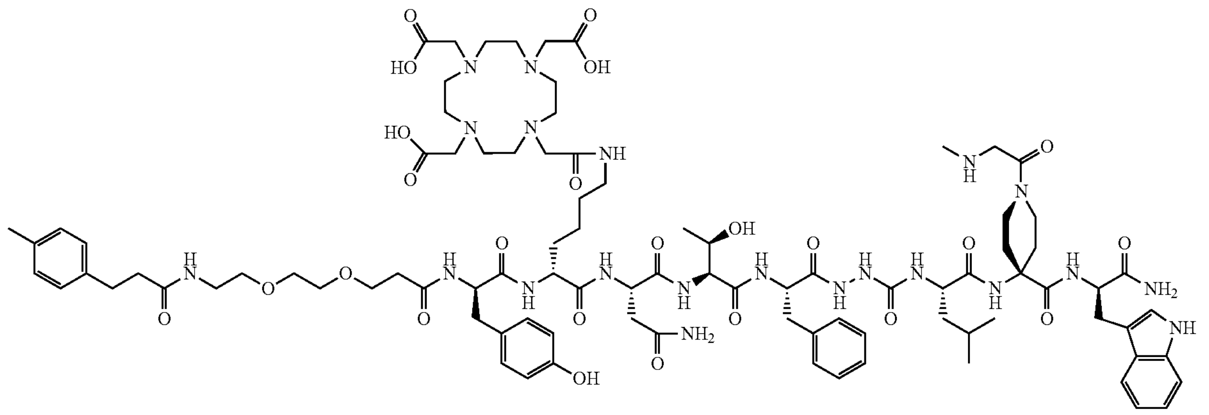
MS: Calc'd 1915.98 found $[M+2H]^{2+}$: 959.4.
Example 238: Compound 358 (SEQ ID NO: 740)
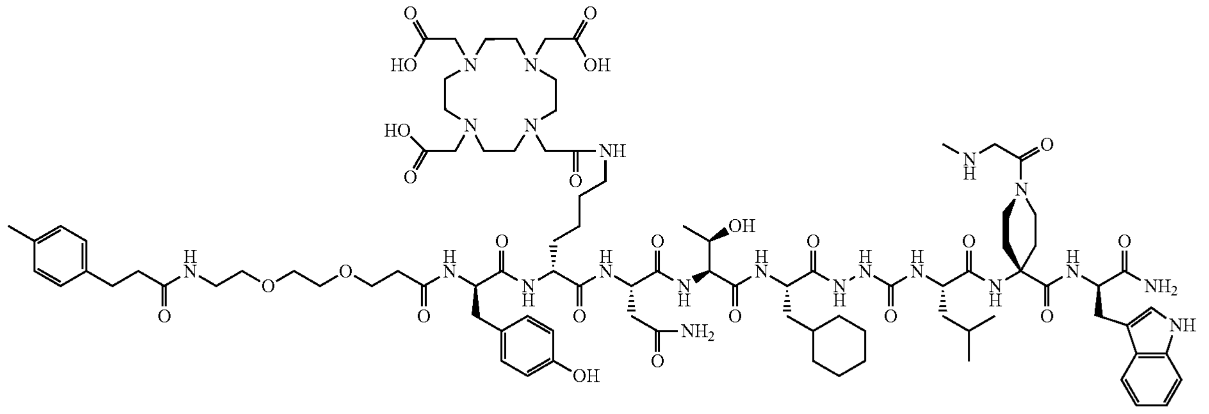
MS: Calc'd 1922.03, found $[M+2H]^{2+}$: 962.5.
Example 239: Compound 359 (SEQ ID NO: 741)
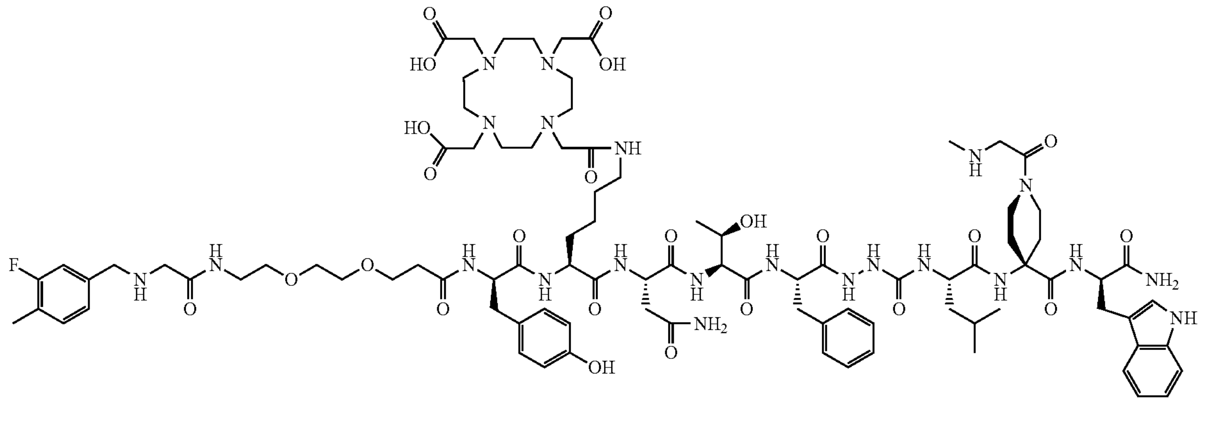
MS: Calc'd 1948.99, found $[M+2H]^{2+}$: 976.0.

Example 240: Compound 360 (SEQ ID NO: 742)
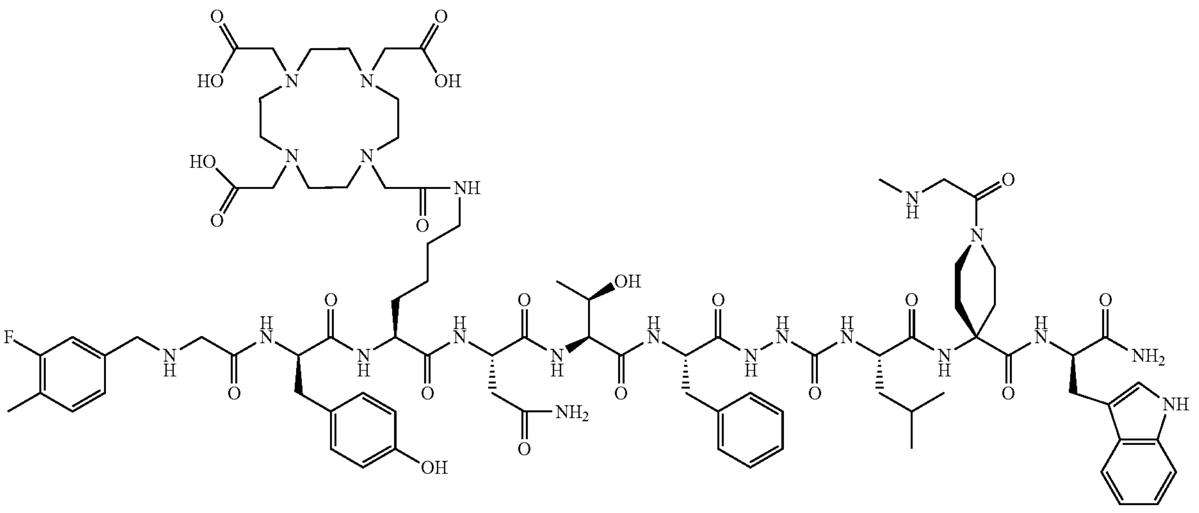
MS: Calc'd 1789.90, found $[M+2H]^{2+}$: 896.4.
Example 241: Compound 363 (SEQ ID NO: 745)
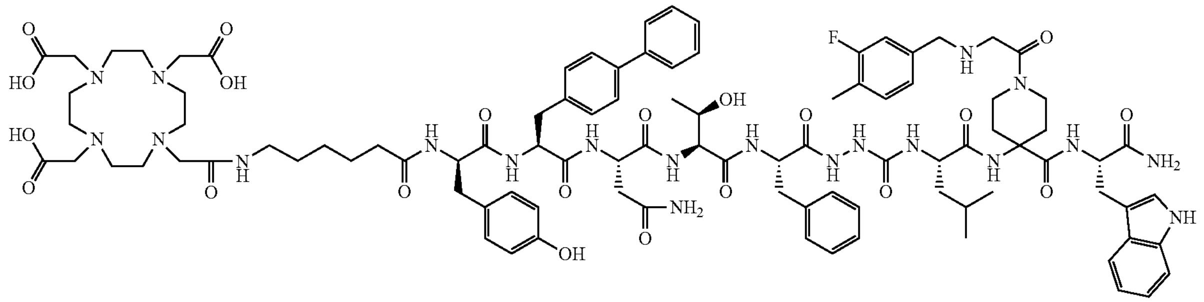 [SMILES: Cc1ccc(CNCC(=O)N2CCC(NC(=O)[C@H](CC(C)C)NC(=O)NNC(=O)[C@H](Cc3ccccc3)NC(=O)[C@@H](NC(=O)[C@H](CC(N)=O)NC(=O)[C@H](Cc3ccc(-c4ccccc4)cc3)NC(=O)[C@@H](Cc3ccc(O)cc3)NC(=O)CCCCCNC(=O)CN3CCN(CC(=O)O)CCN(CC(=O)O)CCN(CC(=O)O)CC3)[C@@H](C)O)(C(=O)N[C@@H](Cc3c[nH]c4ccccc34)C(N)=O)CC2)cc1F]
MS: Calc'd 1926.95, found $[M+2H]^{2+}$: 964.95.
Example 242: Compound 364 (SEQ ID NO: 746)
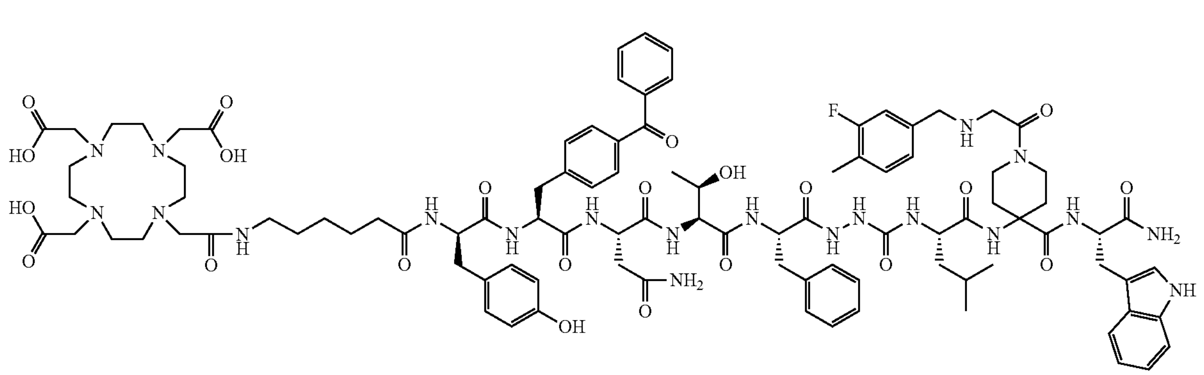 [SMILES: Cc1ccc(CNCC(=O)N2CCC(NC(=O)[C@H](CC(C)C)NC(=O)NNC(=O)[C@H](Cc3ccccc3)NC(=O)[C@@H](NC(=O)[C@H](CC(N)=O)NC(=O)[C@H](Cc3ccc(C(=O)c4ccccc4)cc3)NC(=O)[C@@H](Cc3ccc(O)cc3)NC(=O)CCCCCNC(=O)CN3CCN(CC(=O)O)CCN(CC(=O)O)CCN(CC(=O)O)CC3)[C@@H](C)O)(C(=O)N[C@@H](Cc3c[nH]c4ccccc34)C(N)=O)CC2)cc1F]
MS: Calc'd 1954.94, found $[M+2H]^{2+}$: 979.95.

Example 243: Compound 365 (SEQ ID NO: 741)
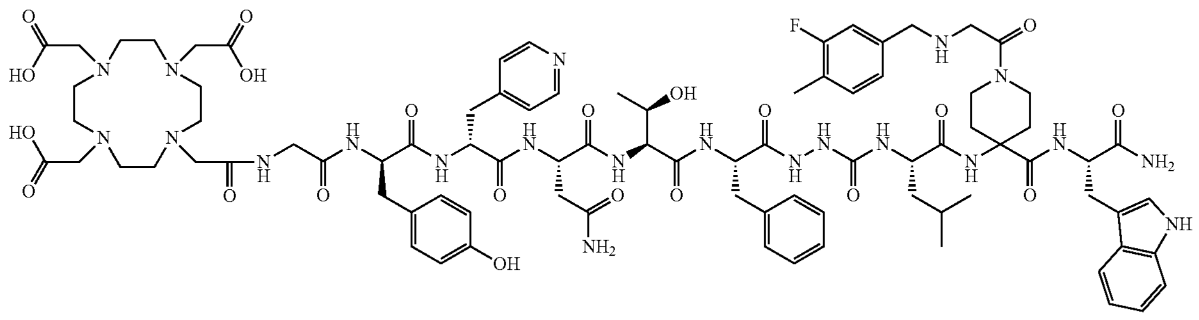 [SMILES: Cc1ccc(CNCC(=O)N2CCC(NC(=O)[C@H](CC(C)C)NC(=O)NNC(=O)[C@H](Cc3ccccc3)NC(=O)[C@@H](NC(=O)[C@H](CC(N)=O)NC(=O)[C@@H](Cc3ccncc3)NC(=O)[C@@H](Cc3ccc(O)cc3)NC(=O)CNC(=O)CN3CCN(CC(=O)O)CCN(CC(=O)O)CCN(CC(=O)O)CC3)[C@@H](C)O)(C(=O)N[C@@H](Cc3c[nH]c4ccccc34)C(N)=O)CC2)cc1F]
MS: Calc'd 1795.85, found $[M+3H]^{3+}$: 600.0.
Example 244: Compound 366 (SEQ ID NO: 748)
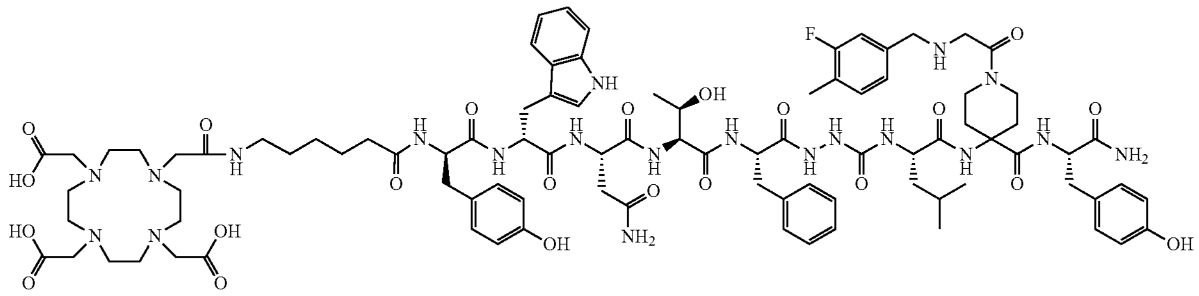
MS: Calc'd 1866.91, found $[M+2H]^{2+}$: 935.0.
Example 245: Compound 367 (SEQ ID NO: 749)
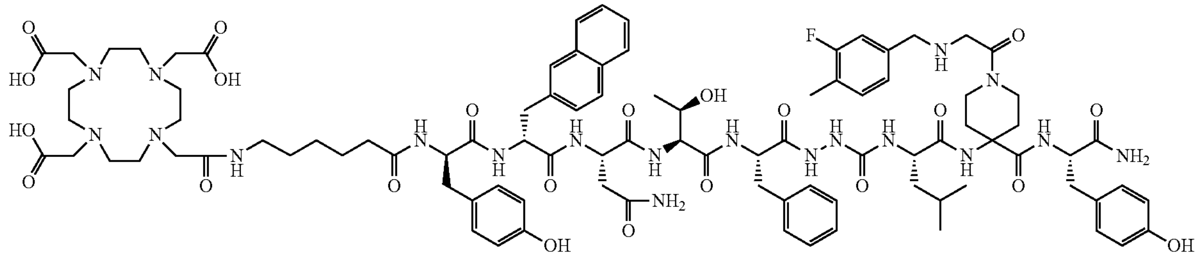 [SMILES: Cc1ccc(CNCC(=O)N2CCC(NC(=O)[C@H](CC(C)C)NC(=O)NNC(=O)[C@H](Cc3ccccc3)NC(=O)[C@@H](NC(=O)[C@H](CC(N)=O)NC(=O)[C@@H](Cc3ccc4ccccc4c3)NC(=O)[C@@H](Cc3ccc(O)cc3)NC(=O)CCCCCNC(=O)CN3CCN(CC(=O)O)CCN(CC(=O)O)CCN(CC(=O)O)CC3)[C@@H](C)O)(C(=O)N[C@@H](Cc3ccc(O)cc3)C(N)=O)CC2)cc1F]
MS: Calc'd 1877.92, found $[M+2H]^{2+}$: 940.4.

Example 246: Compound 368 (SEQ ID NO: 750)
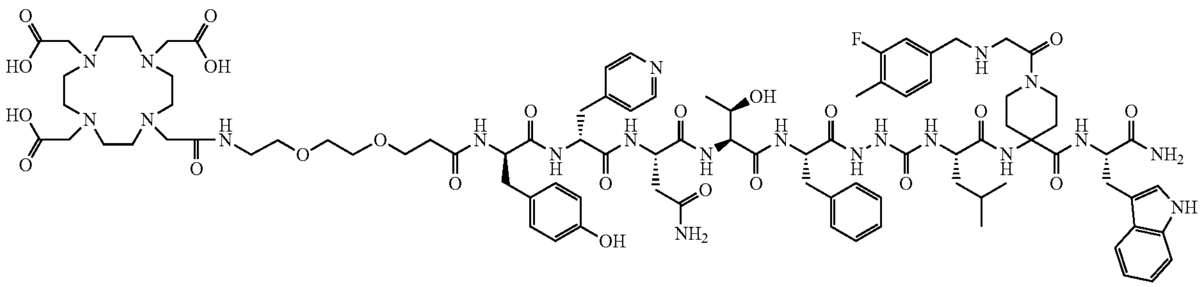 [SMILES: Cc1ccc(CNCC(=O)N2CCC(NC(=O)[C@H](CC(C)C)NC(=O)NNC(=O)[C@H](Cc3ccccc3)NC(=O)[C@@H](NC(=O)[C@H](CC(N)=O)NC(=O)[C@@H](Cc3ccncc3)NC(=O)[C@@H](Cc3ccc(O)cc3)NC(=O)CCOCCOCCNC(=O)CN3CCN(CC(=O)O)CCN(CC(=O)O)CCN(CC(=O)O)CC3)[C@@H](C)O)(C(=O)N[C@@H](Cc3c[nH]c4ccccc34)C(N)=O)CC2)cc1F]
MS: Calc'd 1897.92, found $[M+3H]^{3+}$: 634.05.
Example 247: Compound 370 (SEQ ID NO: 752)
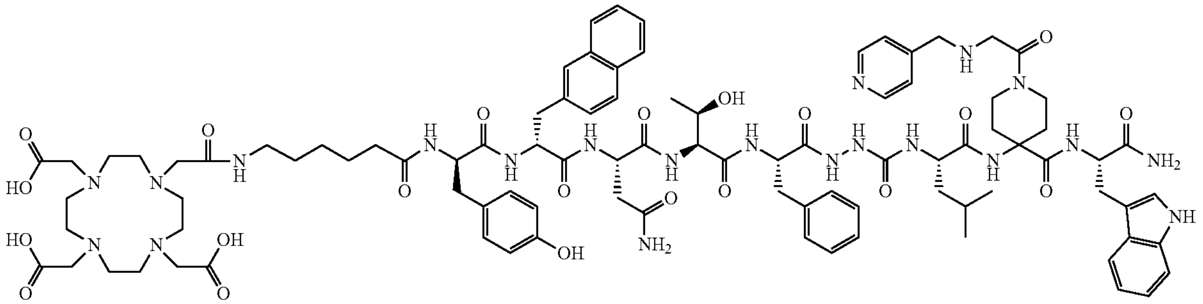 [SMILES: CC(C)C[C@H](NC(=O)NNC(=O)[C@H](Cc1ccccc1)NC(=O)[C@@H](NC(=O)[C@H](CC(N)=O)NC(=O)[C@@H](Cc1ccc2ccccc2c1)NC(=O)[C@@H](Cc1ccc(O)cc1)NC(=O)CCCCCNC(=O)CN1CCN(CC(=O)O)CCN(CC(=O)O)CCN(CC(=O)O)CC1)[C@@H](C)O)C(=O)NC1(C(=O)N[C@@H](Cc2c[nH]c3ccccc23)C(N)=O)CCN(C(=O)CNCc2ccncc2)CC1]
MS: Calc'd 1869.92, found $[M+2H]^{2+}$: 936.45.
Example 248: Compound 371 (SEQ ID NO: 753)
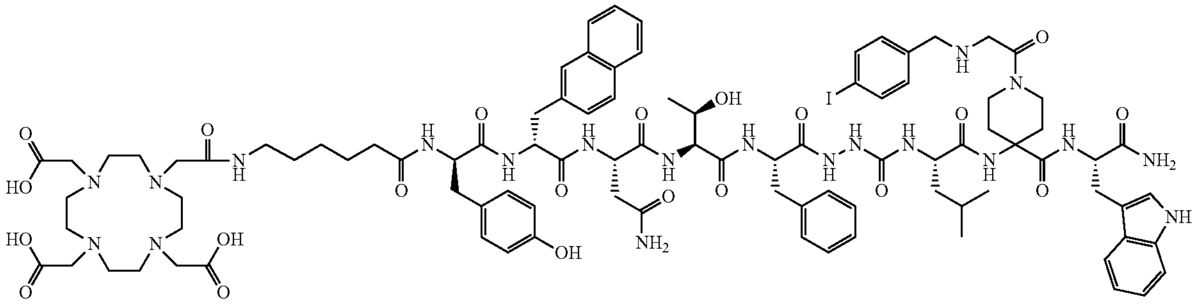 [SMILES: CC(C)C[C@H](NC(=O)NNC(=O)[C@H](Cc1ccccc1)NC(=O)[C@@H](NC(=O)[C@H](CC(N)=O)NC(=O)[C@@H](Cc1ccc2ccccc2c1)NC(=O)[C@@H](Cc1ccc(O)cc1)NC(=O)CCCCCNC(=O)CN1CCN(CC(=O)O)CCN(CC(=O)O)CCN(CC(=O)O)CC1)[C@@H](C)O)C(=O)NC1(C(=O)N[C@@H](Cc2c[nH]c3ccccc23)C(N)=O)CCN(C(=O)CNCc2ccc(I)cc2)CC1]
MS: Calc'd 1994.82, found $[M+3H]^{3+}$: 666.3.

Example 249: Compound 373 (SEQ ID NO: 755)
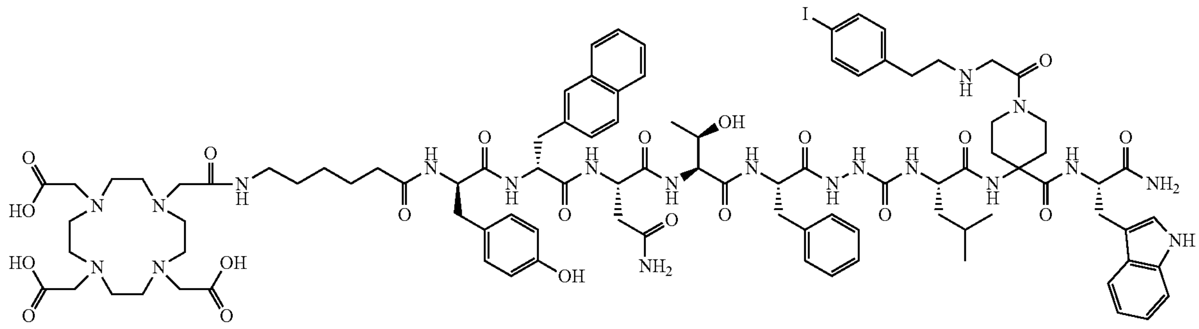 [SMILES: CC(C)C[C@H](NC(=O)NNC(=O)[C@H](Cc1ccccc1)NC(=O)[C@@H](NC(=O)[C@H](CC(N)=O)NC(=O)[C@@H](Cc1ccc2ccccc2c1)NC(=O)[C@@H](Cc1ccc(O)cc1)NC(=O)CCCCCNC(=O)CN1CCN(CC(=O)O)CCN(CC(=O)O)CCN(CC(=O)O)CC1)[C@@H](C)O)C(=O)NC1(C(=O)N[C@@H](Cc2c[nH]c3ccccc23)C(N)=O)CCN(C(=O)CNCCc2ccc(I)cc2)CC1]
MS: Calc'd 2008.83, found $[M+3H]^{3+}$: 670.95.
Example 250: Compound 374 (SEQ ID NO: 756)
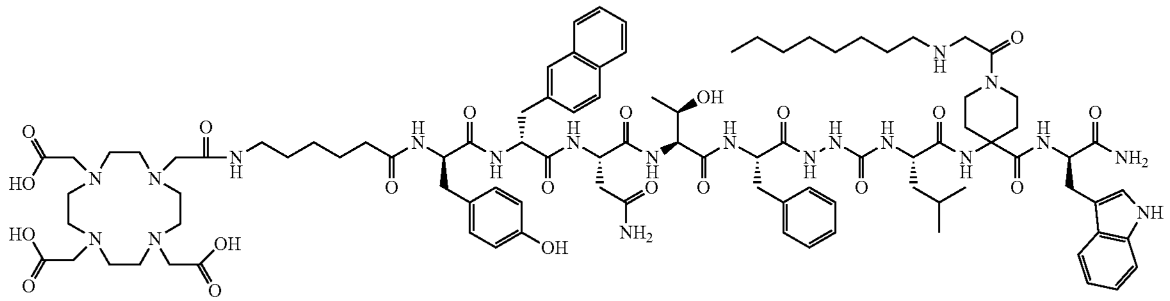 [SMILES: CCCCCCCCNCC(=O)N1CCC(NC(=O)[C@H](CC(C)C)NC(=O)NNC(=O)[C@H](Cc2ccccc2)NC(=O)[C@@H](NC(=O)[C@H](CC(N)=O)NC(=O)[C@@H](Cc2ccc3ccccc3c2)NC(=O)[C@@H](Cc2ccc(O)cc2)NC(=O)CCCCCNC(=O)CN2CCN(CC(=O)O)CCN(CC(=O)O)CCN(CC(=O)O)CC2)[C@@H](C)O)(C(=O)N[C@H](Cc2c[nH]c3ccccc23)C(N)=O)CC1]
MS: Calc'd 1891.00, found $[M+3H]^{3+}$: 631.7.
Example 251: Compound 375 (SEQ ID NO: 757)
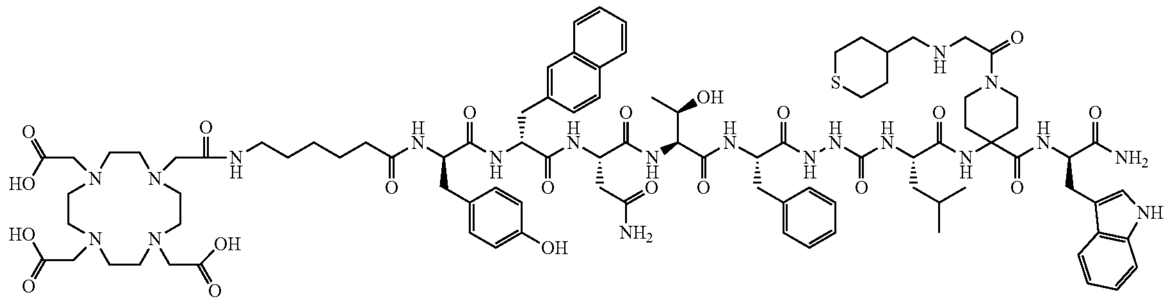 [SMILES: CC(C)C[C@H](NC(=O)NNC(=O)[C@H](Cc1ccccc1)NC(=O)[C@@H](NC(=O)[C@H](CC(N)=O)NC(=O)[C@@H](Cc1ccc2ccccc2c1)NC(=O)[C@@H](Cc1ccc(O)cc1)NC(=O)CCCCCNC(=O)CN1CCN(CC(=O)O)CCN(CC(=O)O)CCN(CC(=O)O)CC1)[C@@H](C)O)C(=O)NC1(C(=O)N[C@H](Cc2c[nH]c3ccccc23)C(N)=O)CCN(C(=O)CNCC2CCSCC2)CC1]
MS: Calc'd 1892.93, found $[M+3H]^{3+}$: 632.4.

Example 252: Compound 376 (SEQ ID NO: 758)
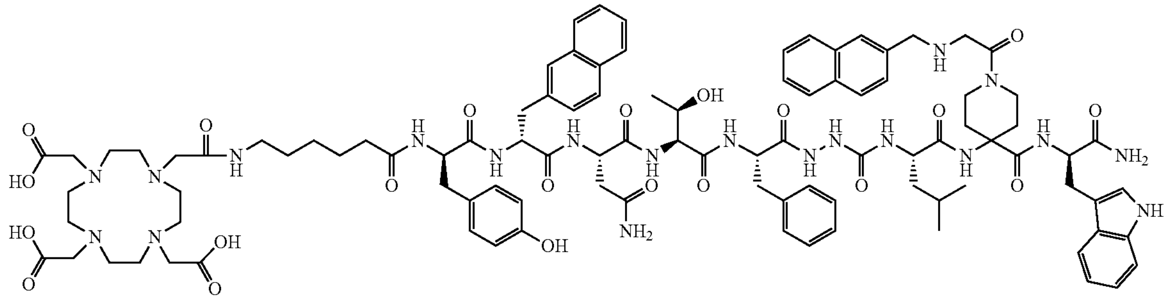 [SMILES: CC(C)C[C@H](NC(=O)NNC(=O)[C@H](Cc1ccccc1)NC(=O)[C@@H](NC(=O)[C@H](CC(N)=O)NC(=O)[C@@H](Cc1ccc2ccccc2c1)NC(=O)[C@@H](Cc1ccc(O)cc1)NC(=O)CCCCCNC(=O)CN1CCN(CC(=O)O)CCN(CC(=O)O)CCN(CC(=O)O)CC1)[C@@H](C)O)C(=O)NC1(C(=O)N[C@H](Cc2c[nH]c3ccccc23)C(N)=O)CCN(C(=O)CNCc2ccc3ccccc3c2)CC1]
MS: Calc'd 1918.94, found $[M+3H]^{3+}$: 641.05.
Example 253: Compound 378 (SEQ ID NO: 759)
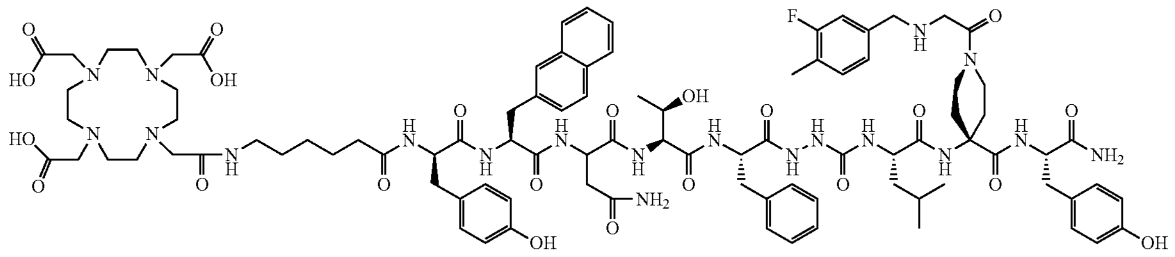
MS: Calc'd 1877.92 found $[M+3H]^{3+}$: 627.35.
Example 254. Compound 379 (SEQ ID NO: 760)
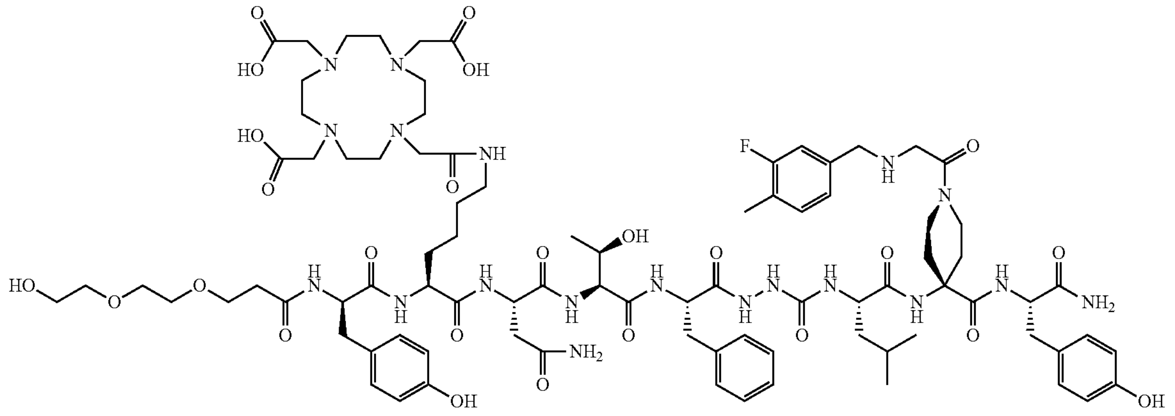
MS: Calc'd 1878.93, found $[M+3H]^{3+}$: 627.65.

Example 255. Compound 380 (SEQ ID NO: 761)
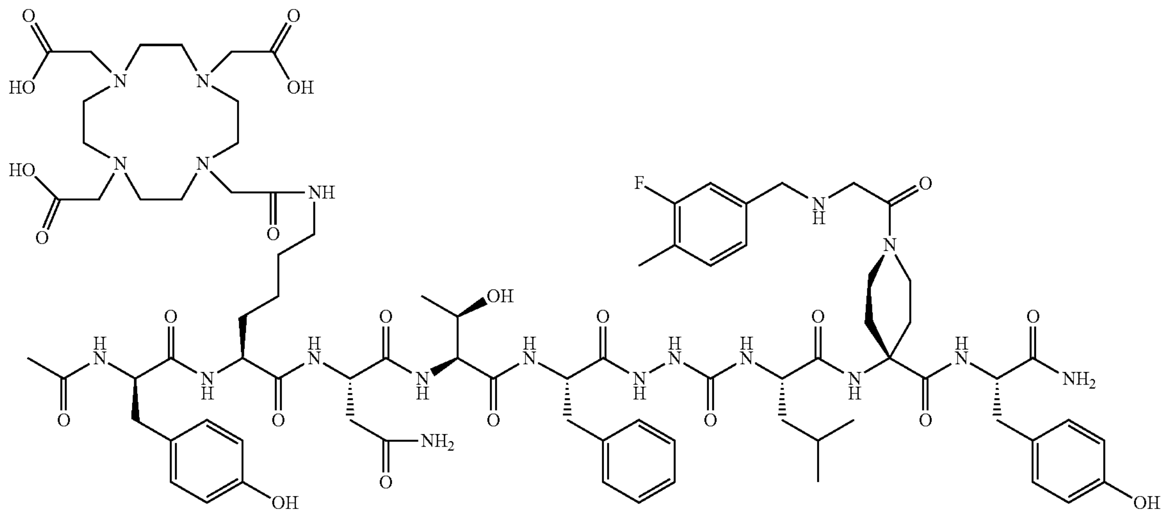
MS: Calc'd 1760.87, found $[M+3H]^{3+}$: 588.3.
Example 256: Compound 381 (SEQ ID NO: 762)
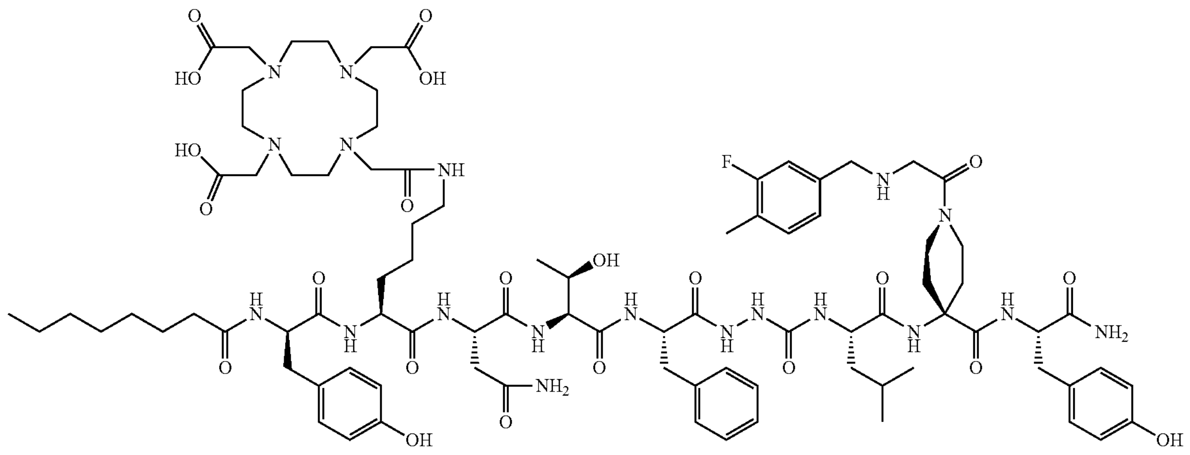
MS: Calc'd 1844.96, found $[M+3H]^{3+}$: 616.4.

Example 25 Compound 382 (SEQ ID NO: 763)
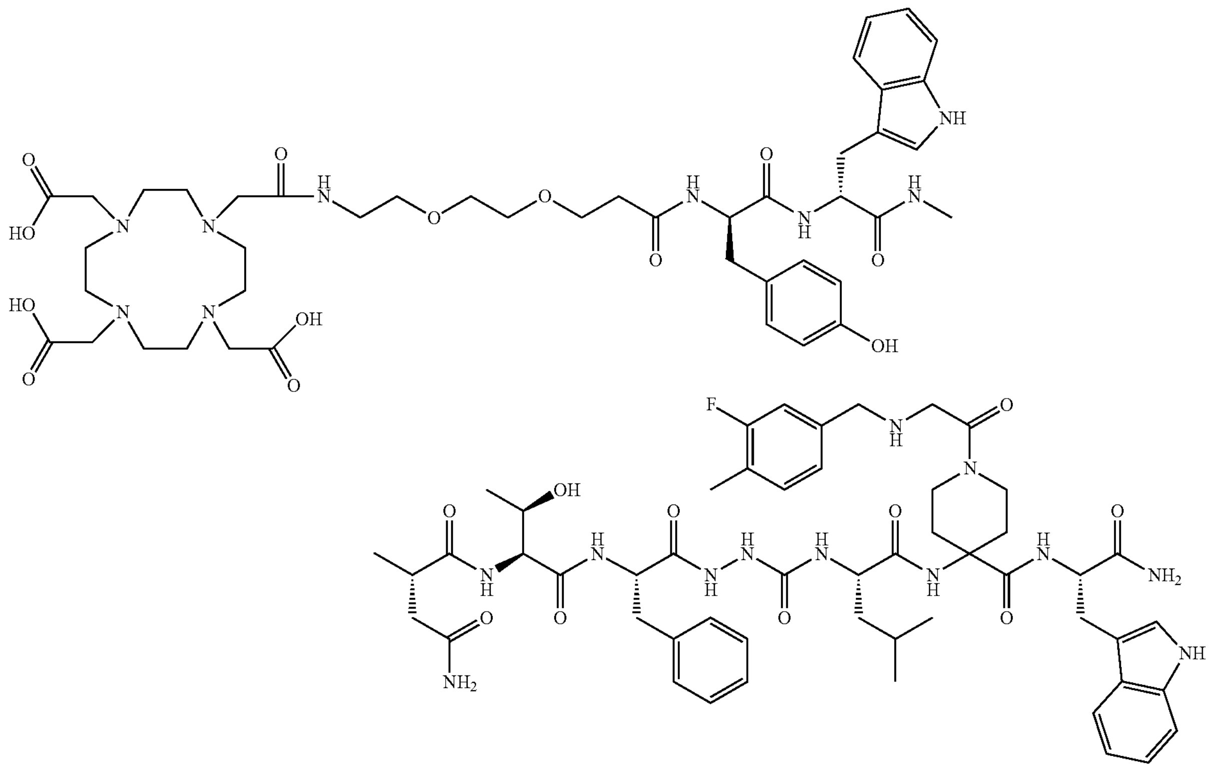
MS: Calc'd 1935.93, found $[M+3H]^{3+}$: 646.7.
Example 258: Compound 383 (SEQ ID NO: 764)
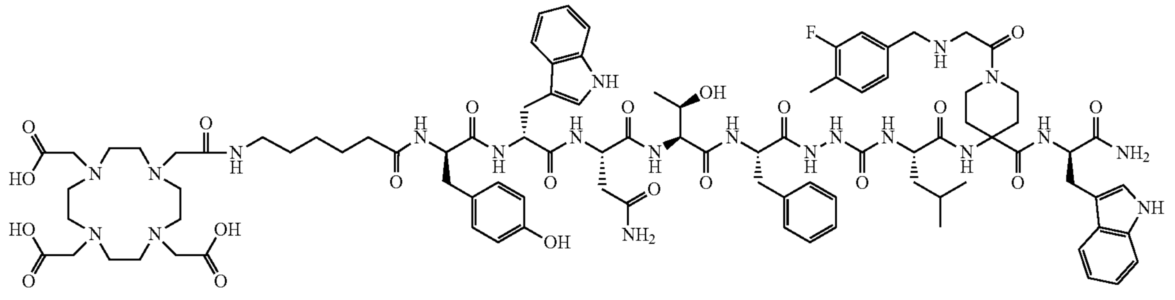 [SMILES: Cc1ccc(CNCC(=O)N2CCC(NC(=O)[C@H](CC(C)C)NC(=O)NNC(=O)[C@H](Cc3ccccc3)NC(=O)[C@@H](NC(=O)[C@H](CC(N)=O)NC(=O)[C@@H](Cc3c[nH]c4ccccc34)NC(=O)[C@@H](Cc3ccc(O)cc3)NC(=O)CCCCCNC(=O)CN3CCN(CC(=O)O)CCN(CC(=O)O)CCN(CC(=O)O)CC3)[C@@H](C)O)(C(=O)N[C@H](Cc3c[nH]c4ccccc34)C(N)=O)CC2)cc1F]
MS: Calc'd 1889.93, found $[M+3H]^{3+}$: 631.4.

Example 259: Compound 384 (SEQ ID NO: 765)
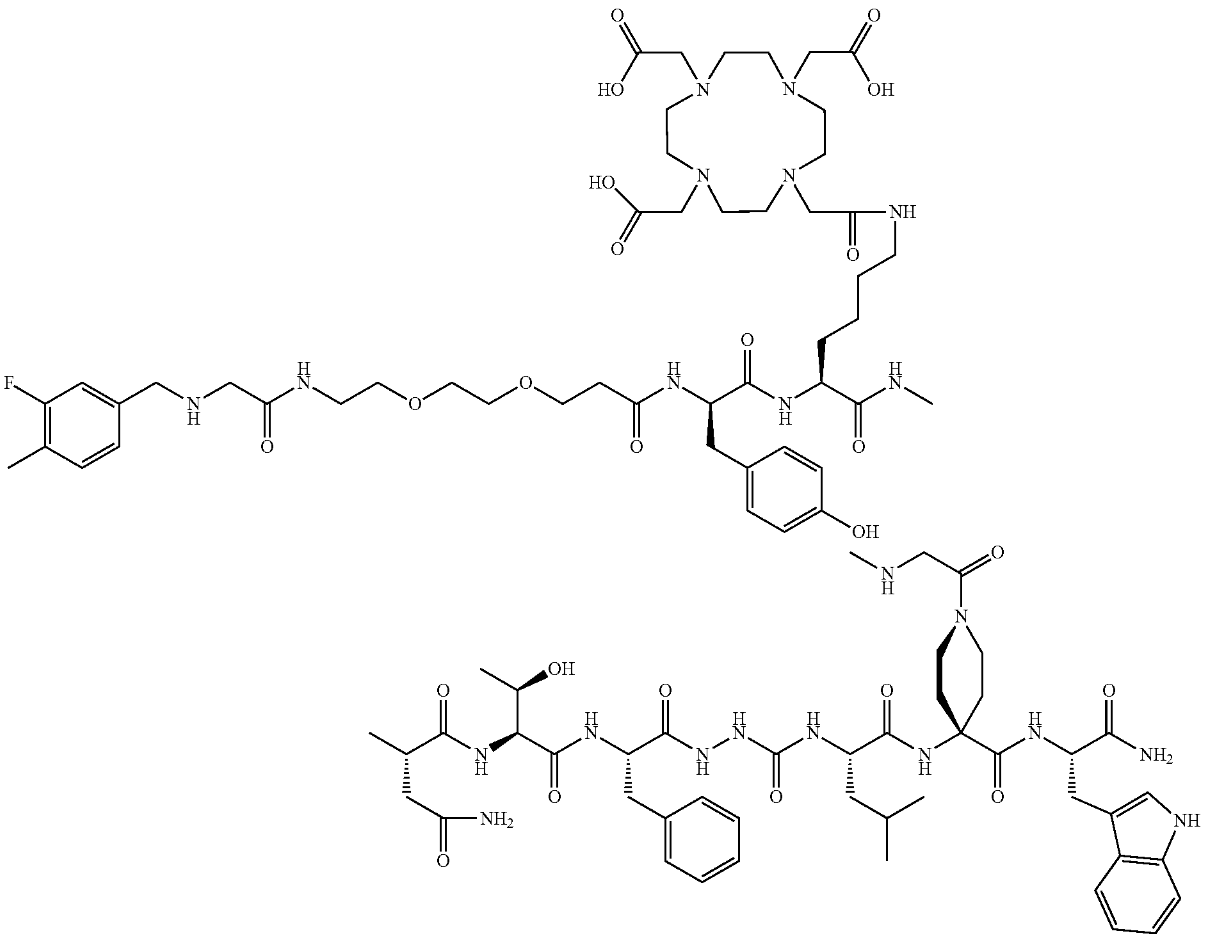
MS: Calc'd 17489.98, found $[M+3H]^{3+}$: 651.1.
Example 260: Compound 386 (SEQ ID NO: 767)
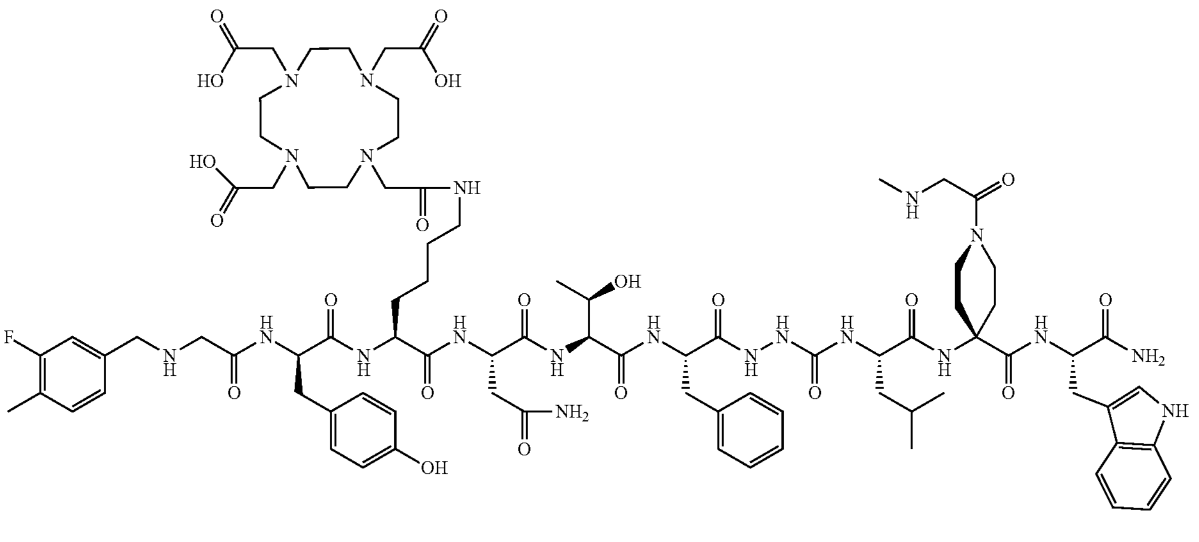
MS: Calc'd 1789.98, found $[M+3H]^{3+}$: 598.1.

Example 261: Compound 387 (SEQ ID NO: 768)
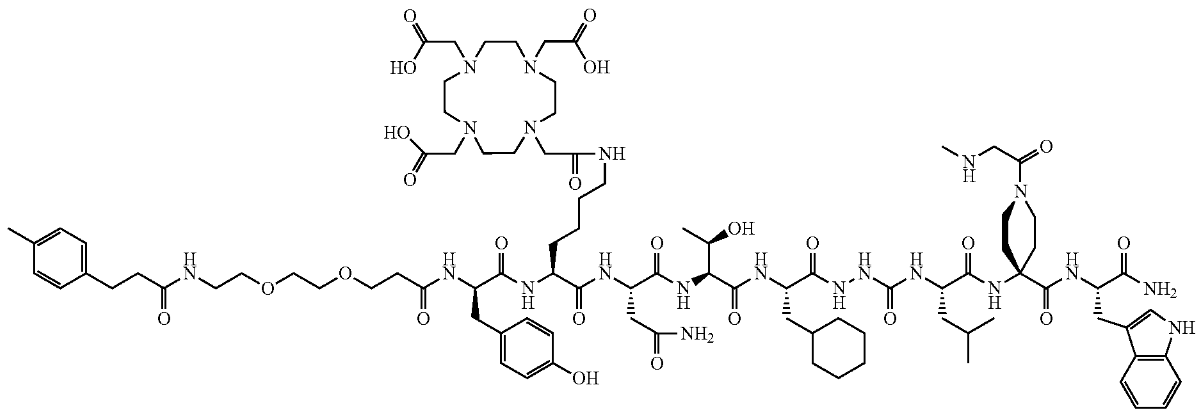
MS: Calc'd 1922.03, found $[M+2H]^{3+}$: 962.6.
Example 262: Compound 388 (SEQ ID NO: 769)
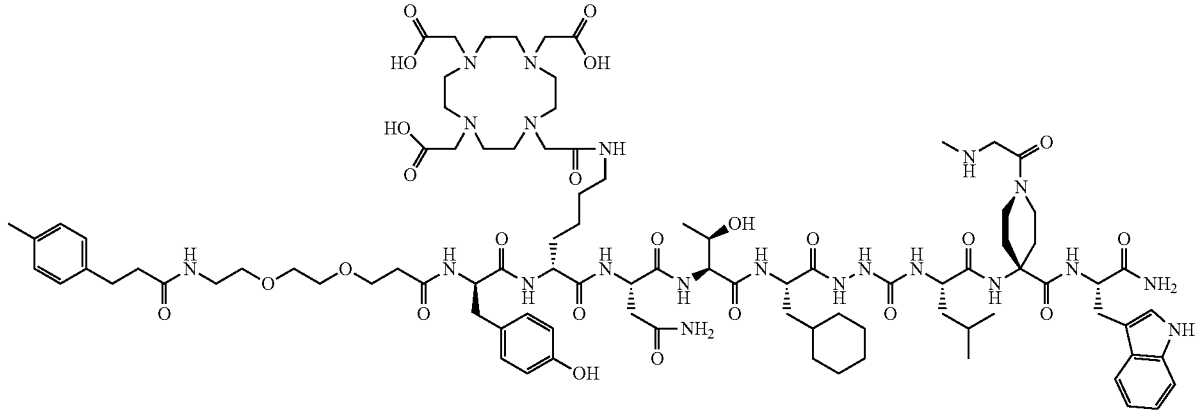
MS: Calc'd 1922.03, found $[M+2H]^{2+}$: 962.5.
Example 263: Compound 389 (SEQ ID NO: 770)
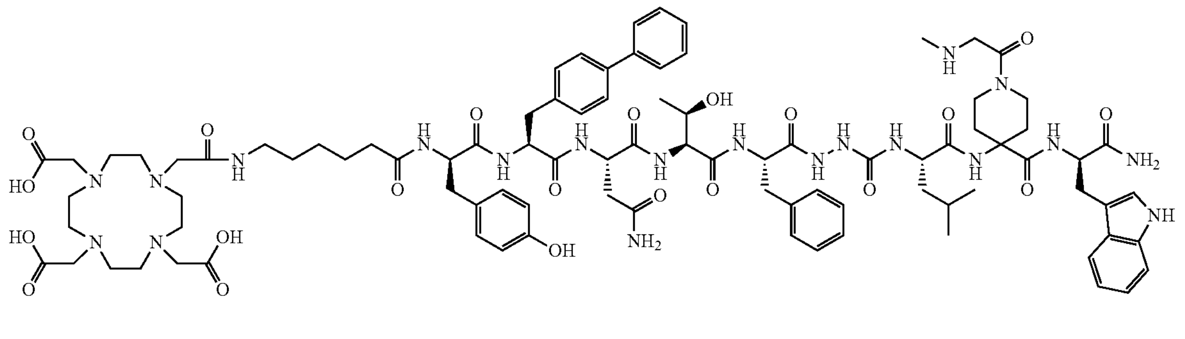 [SMILES: CNCC(=O)N1CCC(NC(=O)[C@H](CC(C)C)NC(=O)NNC(=O)[C@H](Cc2ccccc2)NC(=O)[C@@H](NC(=O)[C@H](CC(N)=O)NC(=O)[C@H](Cc2ccc(-c3ccccc3)cc2)NC(=O)[C@@H](Cc2ccc(O)cc2)NC(=O)CCCCCNC(=O)CN2CCN(CC(=O)O)CCN(CC(=O)O)CCN(CC(=O)O)CC2)[C@@H](C)O)(C(=O)N[C@H](Cc2c[nH]c3ccccc23)C(N)=O)CC1]
MS: Calc'd 1818.9, found $[M+3H]^{3+}$: 607.6.

Example 264: Compound 390 (SEQ ID NO: 802)
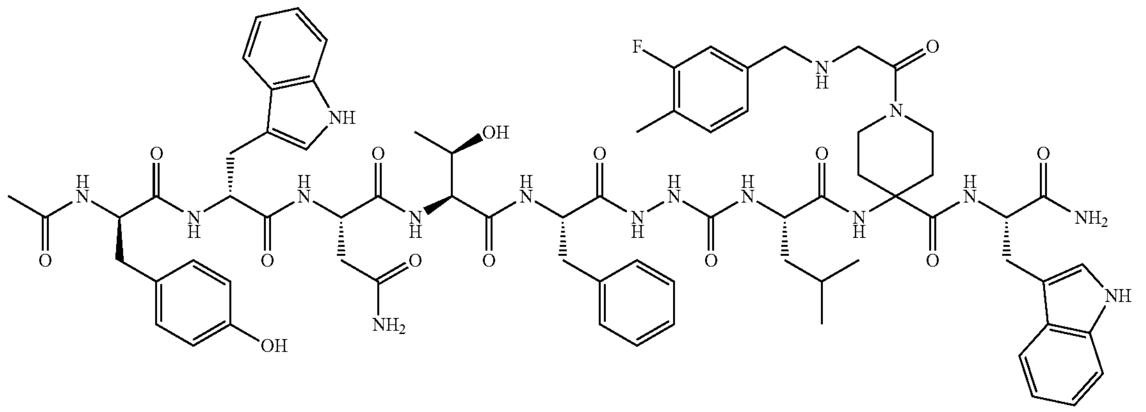 [SMILES: CC(=O)N[C@H](Cc1ccc(O)cc1)C(=O)N[C@H](Cc1c[nH]c2ccccc12)C(=O)N[C@@H](CC(N)=O)C(=O)N[C@H](C(=O)N[C@@H](Cc1ccccc1)C(=O)NNC(=O)N[C@@H](CC(C)C)C(=O)NC1(C(=O)N[C@@H](Cc2c[nH]c3ccccc23)C(N)=O)CCN(C(=O)CNCc2ccc(C)c(F)c2)CC1)[C@@H](C)O]
MS: Calc'd 1432.67, found $[M+2H]^{2+}$: 717.75.
Example 265: Compound 391 (SEQ ID NO: 803)
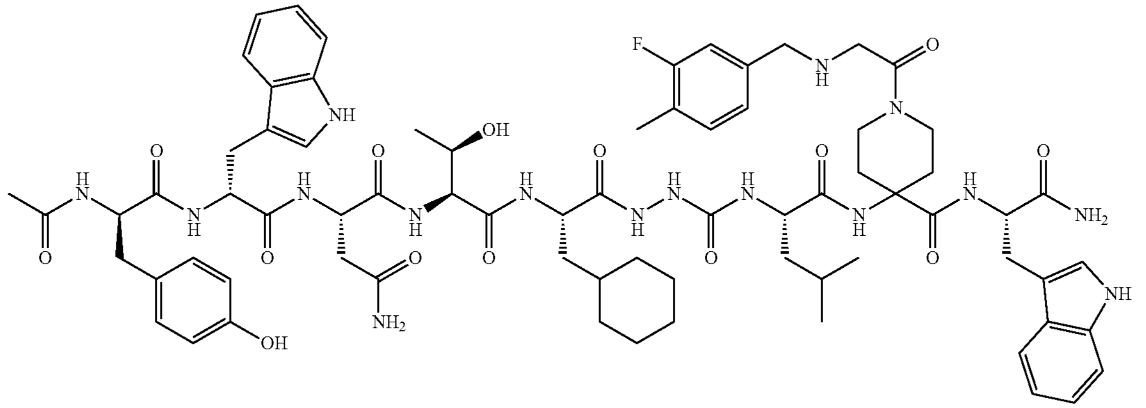 [SMILES: CC(=O)N[C@H](Cc1ccc(O)cc1)C(=O)N[C@H](Cc1c[nH]c2ccccc12)C(=O)N[C@@H](CC(N)=O)C(=O)N[C@H](C(=O)N[C@@H](CC1CCCCC1)C(=O)NNC(=O)N[C@@H](CC(C)C)C(=O)NC1(C(=O)N[C@@H](Cc2c[nH]c3ccccc23)C(N)=O)CCN(C(=O)CNCc2ccc(C)c(F)c2)CC1)[C@@H](C)O]
MS: Calc'd 1438.72, found $[M+2H]^{2+}$: 720.8.
Example 266: Compound 392 (SEQ ID NO: 804)
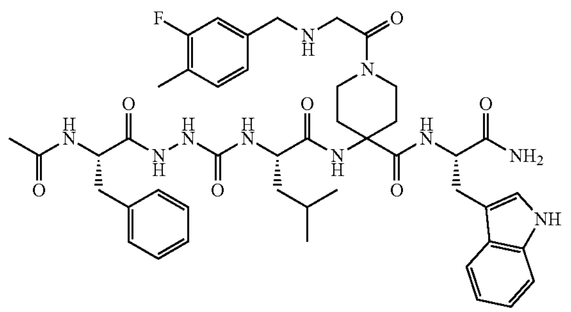 [SMILES: CC(=O)N[C@@H](Cc1ccccc1)C(=O)NNC(=O)N[C@@H](CC(C)C)C(=O)NC1(C(=O)N[C@@H](Cc2c[nH]c3ccccc23)C(N)=O)CCN(C(=O)CNCc2ccc(C)c(F)c2)CC1]
MS: Calc'd 868.44, found $[M+H]^{+}$: 869.55.

Example 267: Compound 393 (SEQ ID NO: 805)
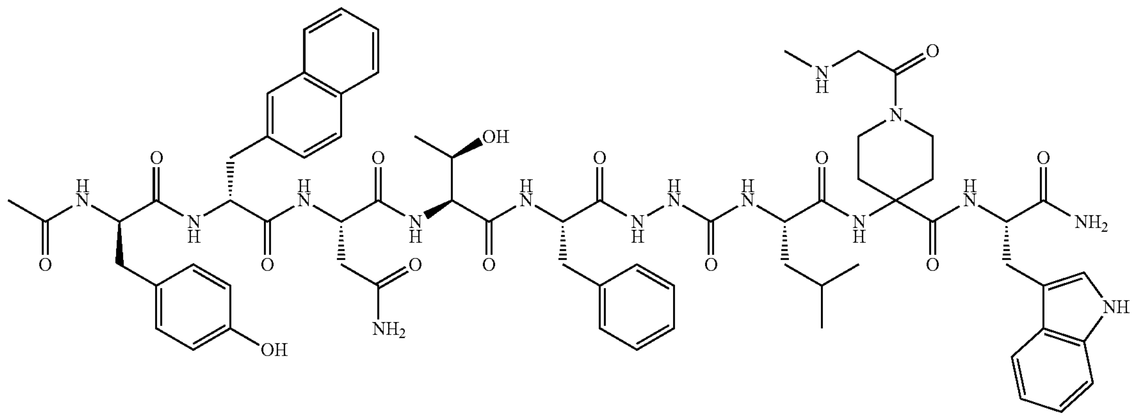 [SMILES: CNCC(=O)N1CCC(NC(=O)[C@H](CC(C)C)NC(=O)NNC(=O)[C@H](Cc2ccccc2)NC(=O)[C@@H](NC(=O)[C@H](CC(N)=O)NC(=O)[C@@H](Cc2ccc3ccccc3c2)NC(=O)[C@@H](Cc2ccc(O)cc2)NC(C)=O)[C@@H](C)O)(C(=O)N[C@@H](Cc2c[nH]c3ccccc23)C(N)=O)CC1]
MS: Calc'd 1335.64, found $[M+2H]^{2+}$: 669.2.
Example 268: Compound 394 (SEQ ID NO: 806)
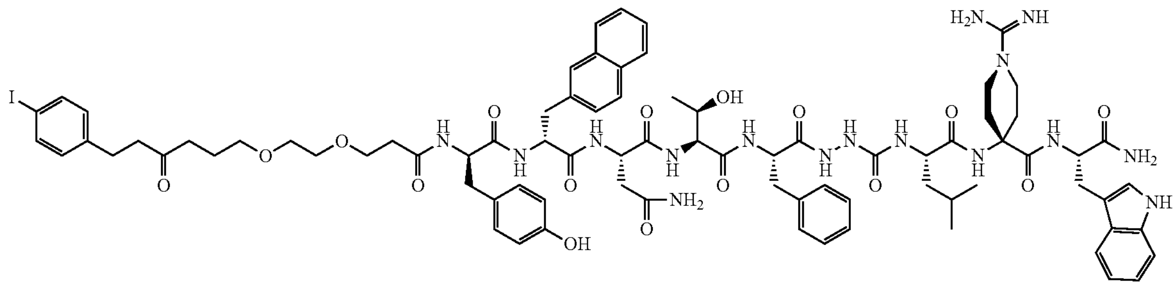
MS: Calc'd 1681.66, found $[M+2H]^{2+}$: 842.3.
Example 269: Compound 395 (SEQ ID NO 807)
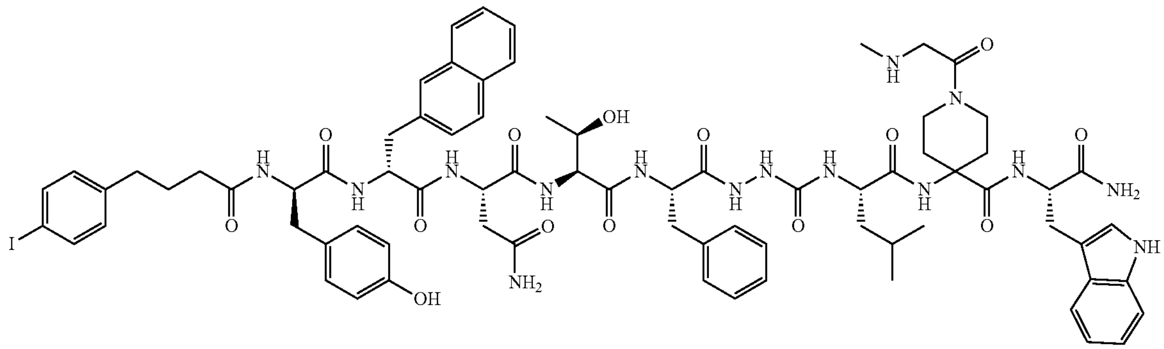 [SMILES: CNCC(=O)N1CCC(NC(=O)[C@H](CC(C)C)NC(=O)NNC(=O)[C@H](Cc2ccccc2)NC(=O)[C@@H](NC(=O)[C@H](CC(N)=O)NC(=O)[C@@H](Cc2ccc3ccccc3c2)NC(=O)[C@@H](Cc2ccc(O)cc2)NC(=O)CCCc2ccc(I)cc2)[C@@H](C)O)(C(=O)N[C@@H](Cc2c[nH]c3ccccc23)C(N)=O)CC1]
MS: Calc'd 1565.60, found $[M+2H]^{2+}$: 784.25.

Example 270: Compound 396 (SEQ ID NO: 808)
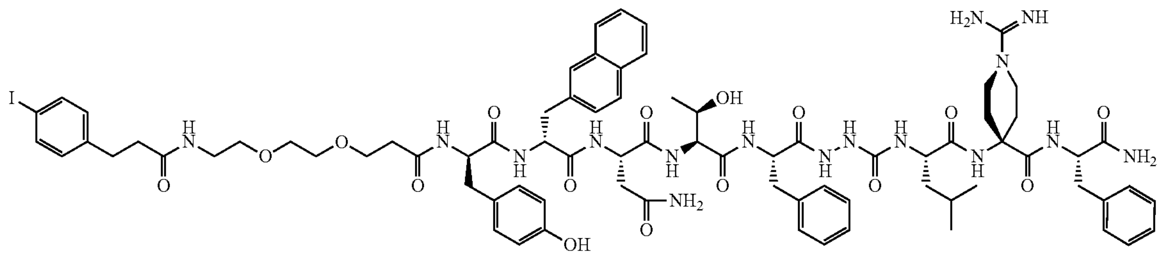
MS: Calc'd 1642.65, found $[M+2H]^{2+}$: 822.75.
Example 271. Compound 397 (SEQ ID NO: 809)
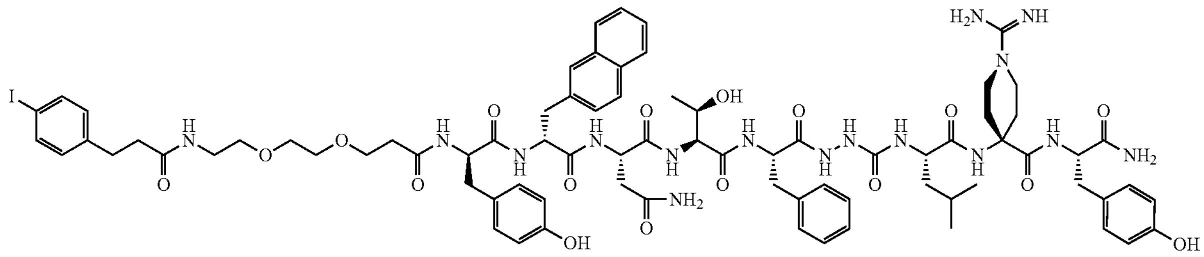
MS: Calc'd 1655.64, found $[M+2H]^{2+}$: 830.8.
Example 272: Compound 398 (SEQ ID NO: 810)
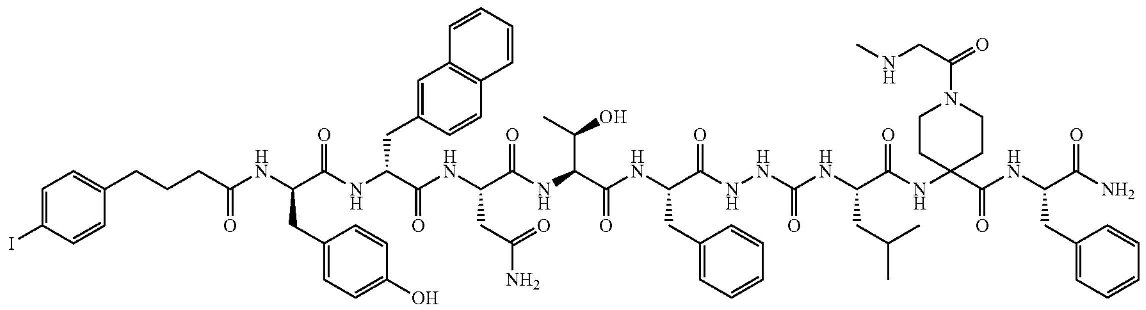 [SMILES: CNCC(=O)N1CCC(NC(=O)[C@H](CC(C)C)NC(=O)NNC(=O)[C@H](Cc2ccccc2)NC(=O)[C@@H](NC(=O)[C@H](CC(N)=O)NC(=O)[C@@H](Cc2ccc3ccccc3c2)NC(=O)[C@@H](Cc2ccc(O)cc2)NC(=O)CCCc2ccc(I)cc2)[C@@H](C)O)(C(=O)N[C@@H](Cc2ccccc2)C(N)=O)CC1]
MS: Calc'd 1526.59, found $[M+2H]^{2+}$: 764.7.

Example 273- Compound 399 (SEQ ID NO: 811)
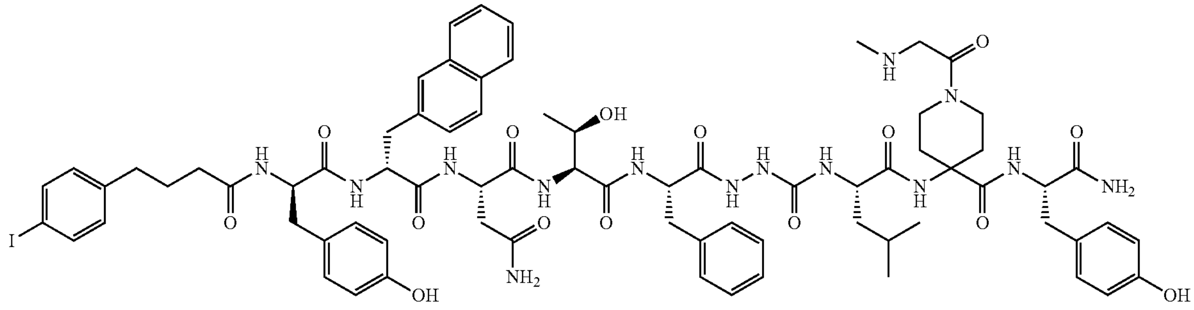 [SMILES: CNCC(=O)N1CCC(NC(=O)[C@H](CC(C)C)NC(=O)NNC(=O)[C@H](Cc2ccccc2)NC(=O)[C@@H](NC(=O)[C@H](CC(N)=O)NC(=O)[C@@H](Cc2ccc3ccccc3c2)NC(=O)[C@@H](Cc2ccc(O)cc2)NC(=O)CCCc2ccc(I)cc2)[C@@H](C)O)(C(=O)N[C@@H](Cc2ccc(O)cc2)C(N)=O)CC1]
MS: Calc'd 1542.58, found $[M+2H]^{2+}$: 772.75.
Example 274. Compound 400 (SEQ ID NO: 812)
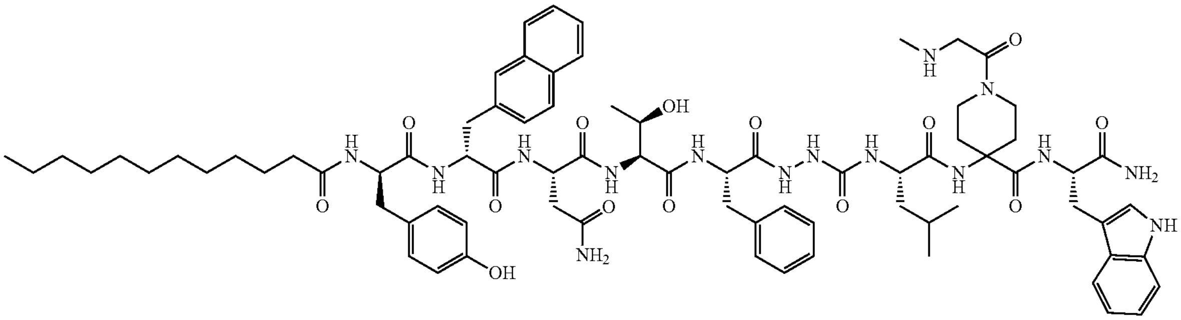 [SMILES: CCCCCCCCCCCC(=O)N[C@H](Cc1ccc(O)cc1)C(=O)N[C@H](Cc1ccc2ccccc2c1)C(=O)N[C@@H](CC(N)=O)C(=O)N[C@H](C(=O)N[C@@H](Cc1ccccc1)C(=O)NNC(=O)N[C@@H](CC(C)C)C(=O)NC1(C(=O)N[C@@H](Cc2c[nH]c3ccccc23)C(N)=O)CCN(C(=O)CNC)CC1)[C@@H](C)O]
MS: Calc'd 1475.80, found $[M+2H]^{2+}$: 739.35.
Example 275. Compound 401 (SEQ ID NO: 813)
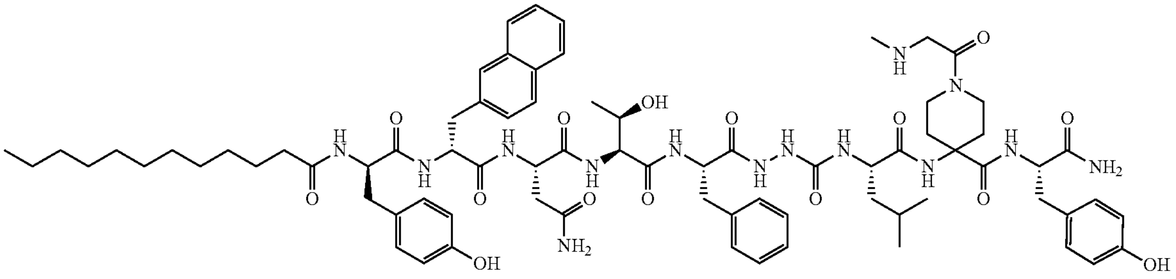 [SMILES: CCCCCCCCCCCC(=O)N[C@H](Cc1ccc(O)cc1)C(=O)N[C@H](Cc1ccc2ccccc2c1)C(=O)N[C@@H](CC(N)=O)C(=O)N[C@H](C(=O)N[C@@H](Cc1ccccc1)C(=O)NNC(=O)N[C@@H](CC(C)C)C(=O)NC1(C(=O)N[C@@H](Cc2ccc(O)cc2)C(N)=O)CCN(C(=O)CNC)CC1)[C@@H](C)O]
MS: Calc'd 1452.78, found $[M+2H]^{2+}$: 727.85.

Example 276: Compound 402 (SEQ ID NO: 814)
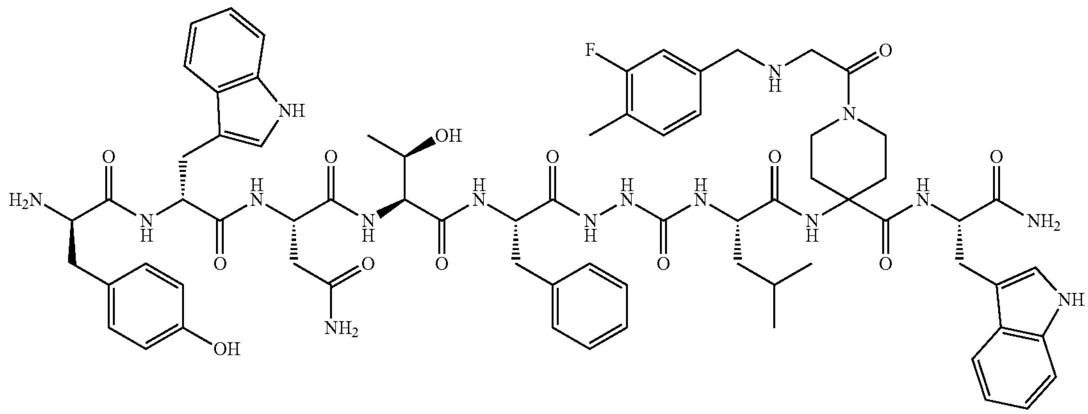 [SMILES: Cc1ccc(CNCC(=O)N2CCC(NC(=O)[C@H](CC(C)C)NC(=O)NNC(=O)[C@H](Cc3ccccc3)NC(=O)[C@@H](NC(=O)[C@H](CC(N)=O)NC(=O)[C@@H](Cc3c[nH]c4ccccc34)NC(=O)[C@H](N)Cc3ccc(O)cc3)[C@@H](C)O)(C(=O)N[C@@H](Cc3c[nH]c4ccccc34)C(N)=O)CC2)cc1F]
MS: Calc'd 1390.66, found $[M+2H]^{2+}$: 696.7.
Example 277: Compound 403 (SEQ ID NO: 815)
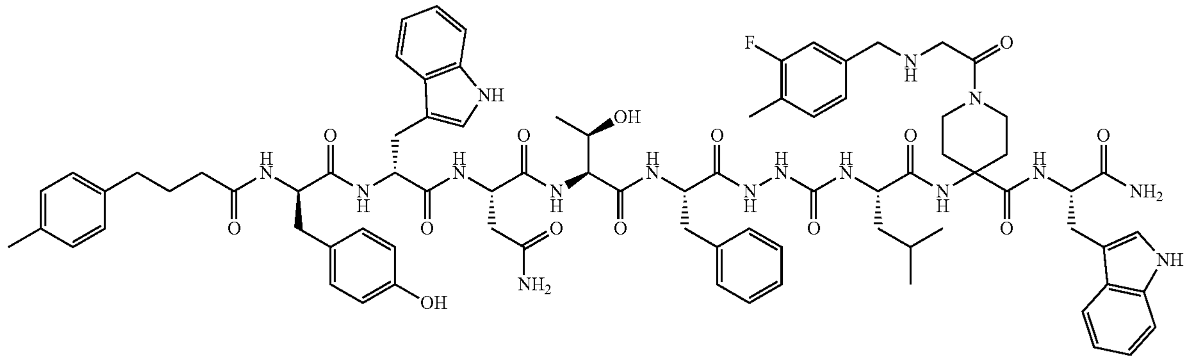 [SMILES: Cc1ccc(CCCC(=O)N[C@H](Cc2ccc(O)cc2)C(=O)N[C@H](Cc2c[nH]c3ccccc23)C(=O)N[C@@H](CC(N)=O)C(=O)N[C@H](C(=O)N[C@@H](Cc2ccccc2)C(=O)NNC(=O)N[C@@H](CC(C)C)C(=O)NC2(C(=O)N[C@@H](Cc3c[nH]c4ccccc34)C(N)=O)CCN(C(=O)CNCc3ccc(C)c(F)c3)CC2)[C@@H](C)O)cc1]
MS: Calc'd 1550.75, found $[M+2H]^{2+}$: 776.85
Example 288: Compound 404 (SEQ ID NO: 816)
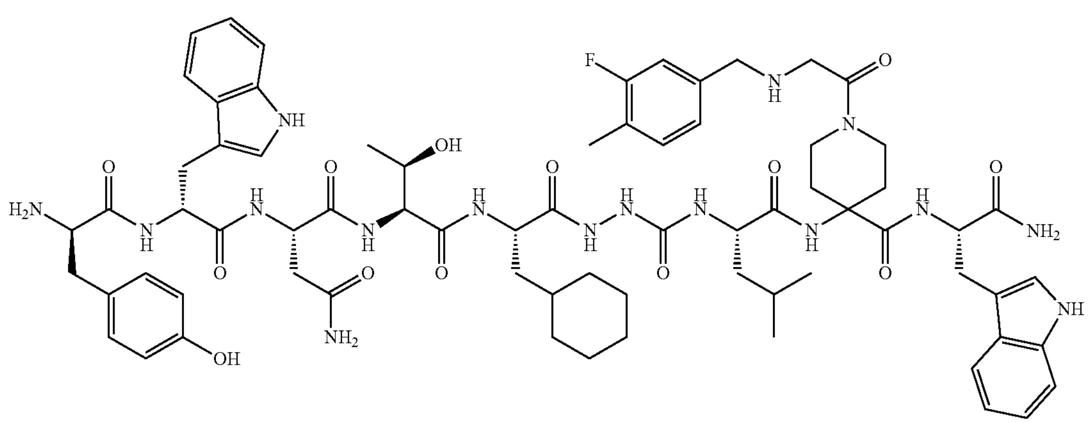 [SMILES: Cc1ccc(CNCC(=O)N2CCC(NC(=O)[C@H](CC(C)C)NC(=O)NNC(=O)[C@H](CC3CCCCC3)NC(=O)[C@@H](NC(=O)[C@H](CC(N)=O)NC(=O)[C@@H](Cc3c[nH]c4ccccc34)NC(=O)[C@H](N)Cc3ccc(O)cc3)[C@@H](C)O)(C(=O)N[C@@H](Cc3c[nH]c4ccccc34)C(N)=O)CC2)cc1F]
MS: Calc'd 1396.71, found $[M+2H]^{2+}$: 699.7.

Example 289: Compound 405 (SEQ ID NO: 817)
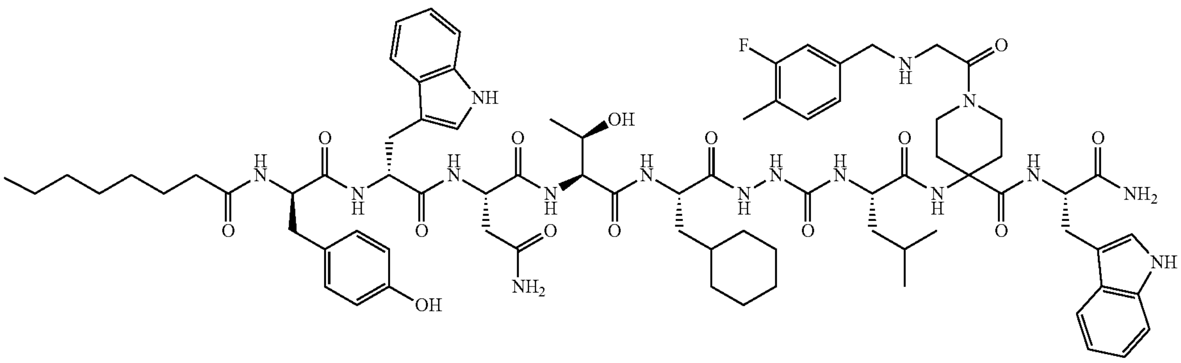 [SMILES: CCCCCCCC(=O)N[C@H](Cc1ccc(O)cc1)C(=O)N[C@H](Cc1c[nH]c2ccccc12)C(=O)N[C@@H](CC(N)=O)C(=O)N[C@H](C(=O)N[C@@H](CC1CCCCC1)C(=O)NNC(=O)N[C@@H](CC(C)C)C(=O)NC1(C(=O)N[C@@H](Cc2c[nH]c3ccccc23)C(N)=O)CCN(C(=O)CNCc2ccc(C)c(F)c2)CC1)[C@@H](C)O]
MS: Calc'd 1522.81 found $[M+2H]^{2+}$: 762.85.
Example 290: Compound 406 (SEQ ID NO: 818)
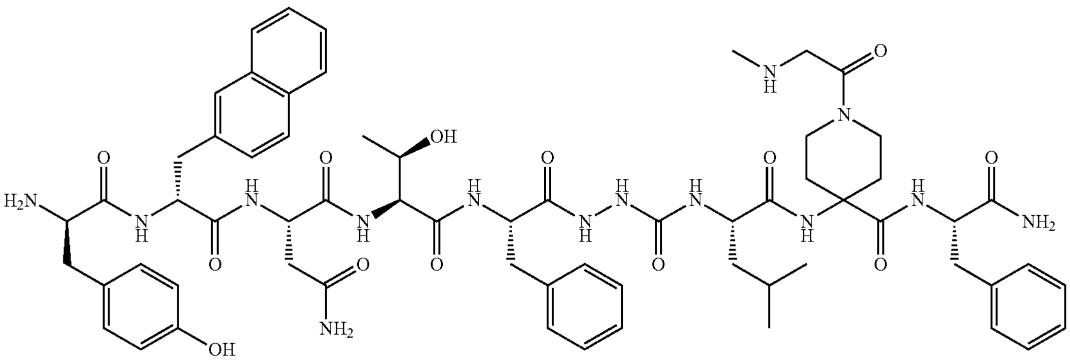 [SMILES: CNCC(=O)N1CCC(NC(=O)[C@H](CC(C)C)NC(=O)NNC(=O)[C@H](Cc2ccccc2)NC(=O)[C@@H](NC(=O)[C@H](CC(N)=O)NC(=O)[C@@H](Cc2ccc3ccccc3c2)NC(=O)[C@H](N)Cc2ccc(O)cc2)[C@@H](C)O)(C(=O)N[C@@H](Cc2ccccc2)C(N)=O)CC1]
MS: Calc'd 1254.62, found $[M+2H]^{3+}$: 628.75.
Example 291: Compound 407 (SEQ ID NO: 819)
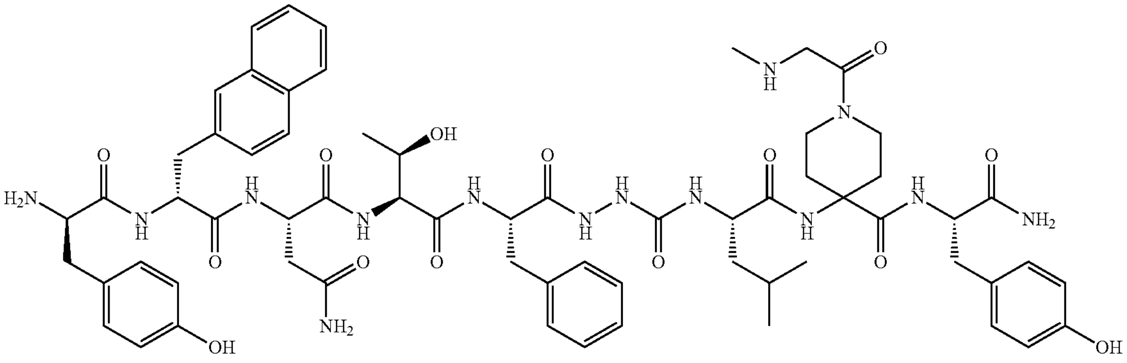 [SMILES: CNCC(=O)N1CCC(NC(=O)[C@H](CC(C)C)NC(=O)NNC(=O)[C@H](Cc2ccccc2)NC(=O)[C@@H](NC(=O)[C@H](CC(N)=O)NC(=O)[C@@H](Cc2ccc3ccccc3c2)NC(=O)[C@H](N)Cc2ccc(O)cc2)[C@@H](C)O)(C(=O)N[C@@H](Cc2ccc(O)cc2)C(N)=O)CC1]
MS: Calc'd 1270.61, found $[M+2H]^{2+}$: 626.7.

Example 292: Compound 408 (SEQ ID NO: 820)
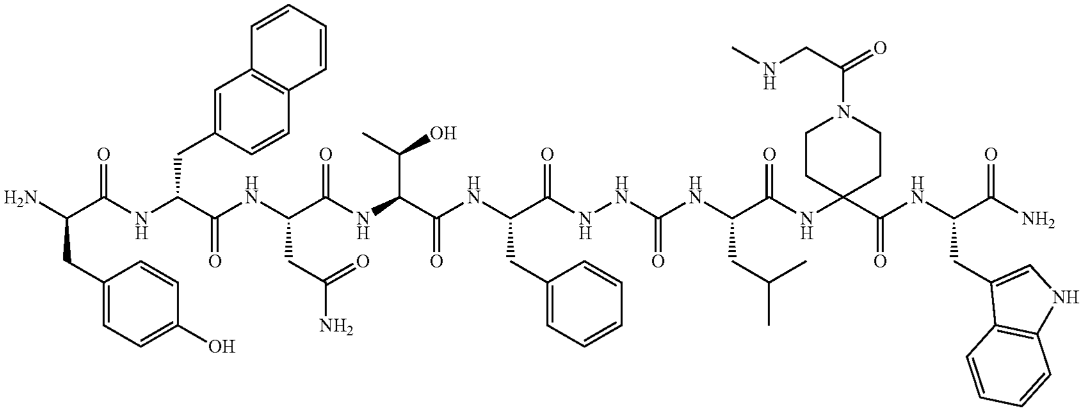 [SMILES: CNCC(=O)N1CCC(NC(=O)[C@H](CC(C)C)NC(=O)NNC(=O)[C@H](Cc2ccccc2)NC(=O)[C@@H](NC(=O)[C@H](CC(N)=O)NC(=O)[C@@H](Cc2ccc3ccccc3c2)NC(=O)[C@H](N)Cc2ccc(O)cc2)[C@@H](C)O)(C(=O)N[C@@H](Cc2c[nH]c3ccccc23)C(N)=O)CC1]
MS: Calc'd 1293.63, found $[M+2H]^{2+}$: 648.2.
Example 293: Compound 409 (SEQ ID NO: 821)
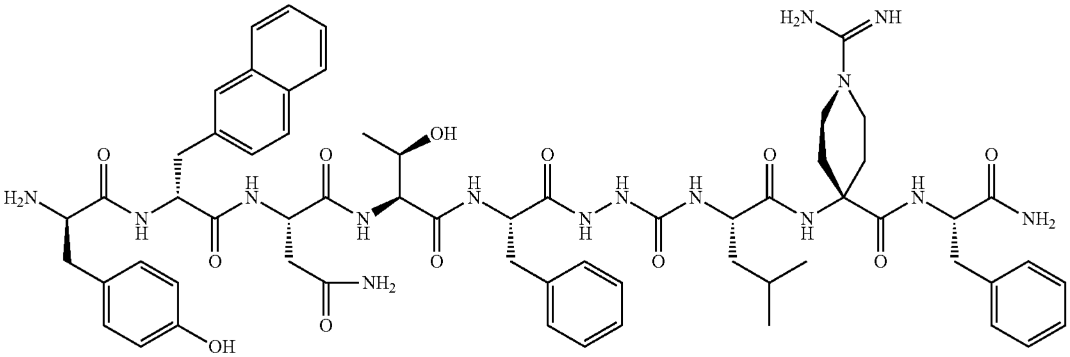
MS: Calc'd 1225.60, found $[M+2H]^{2+}$: 614.25
Example 294: Compound 410 (SEQ ID NO: 822)
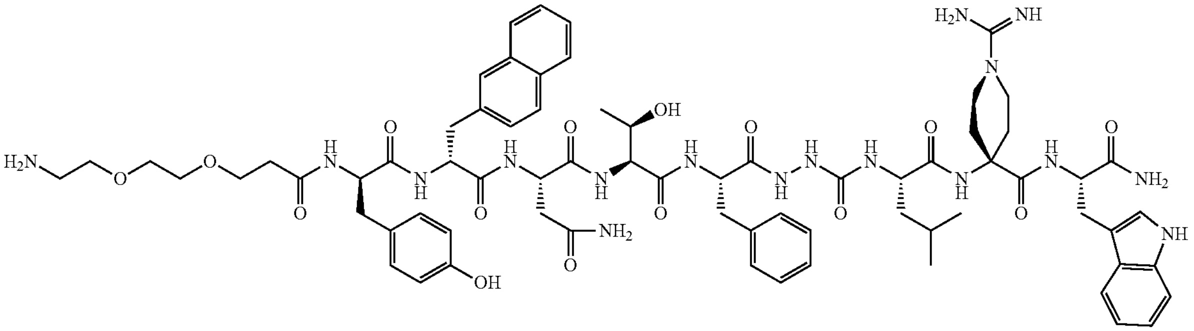
MS: Calc'd 1423.70, found $[M+2H]^{2+}$: 713.35.

Example 295: Compound 411 (SEQ ID NO: 823)

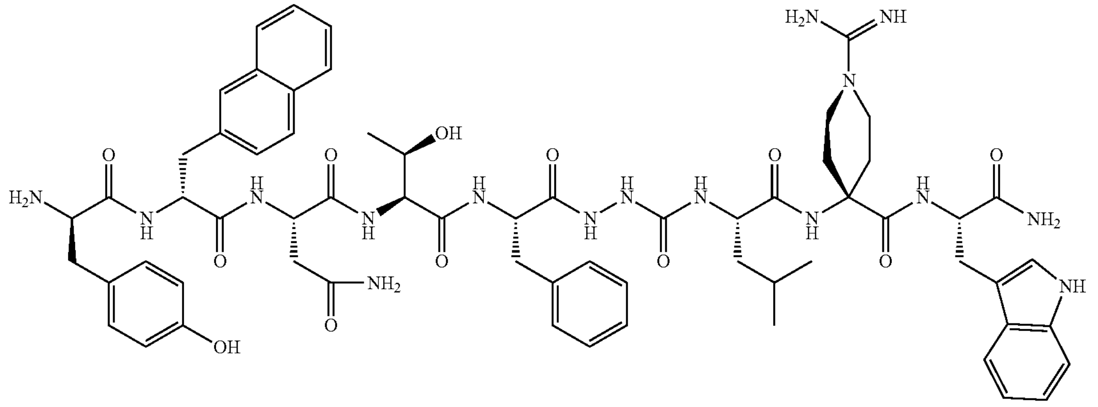

MS: Calc'd 1264.61, found $[M+2H]^{2+}$: 633.8.

Example A-1: Parenteral Pharmaceutical Composition

To prepare a parenteral pharmaceutical composition suitable for administration by injection (subcutaneous, intravenous), 0.001-500 mg of a compound Formula (I), or a pharmaceutically acceptable salt or solvate thereof, is dissolved in sterile water and then mixed with 10 mL of 0.9% sterile saline. A suitable buffer is optionally added as well as optional acid or base to adjust the pH. The mixture is incorporated into a dosage unit form suitable for administration by injection.

BIOLOGY EXAMPLES

Example B-1: Human KISS1R Binding Assay

Membrane Preparation

Crude membrane fractions are prepared from Flp-In T-Rex 293 (Thermo Fisher) cell line expressing the human kisspeptin receptor. The cells are grown to 85-100% confluence on standard tissue culture dishes in Dulbecco's Modified Eagles Medium (DMEM) (Corning) supplemented with 10% FBS (Gemini), 1% penicillin-streptomycin-glutamine (Gibco), 500 μg/mL hygromycin, and 15 μg/mL blasticidin. 48 hrs prior to preparing membranes 10 μg/ml of tetracycline is added to the culture media to induce receptor expression. To prepare membranes, cells are scraped and collected in 1×Dulbecco's phosphate buffered saline (Corning) and then pelleted at 1000 RPMs. The cell pellet is reconstituted in membrane preparation buffer (20 mM HEPES, 6 mM $MgCl_2$ and 1 mM EGTA, protease inhibitor tablets (Pierce), pH 7.4) and placed in a cell disruption vessel (Parr Instrument company) at 1000 PSI for 30 min on ice. The pressurized contents are then released and spun down at 1000 RPMs and the supernatant is collected and further centrifuged at 15,000 RPMs to pellet the membranes. The membrane pellet is resuspended in membrane preparation buffer, snap frozen and stored at −80° C. for later use.

Human Kisspeptin Binding Assay Protocol:

The human kisspeptin membrane binding assay utilizes the following components: radiolabel $[^{125}I]$-metastin (45-54) (human) (PerkinElmer), crude Flp-In T-Rex 293 kisspeptin membranes, and competing small molecule and peptide ligands. The assay is initiated by combining in assay buffer (50 mM TrisHCl, 5 mM $MgCl_2$, 2 mM EGTA, 10 mM $CaCl_2$, 0.1% BSA, p-17.4) a dose response of competing ligand (final concentrations are typically 0-10,000 nM), 5-10 μg of Flp-in T-Rex 293 kisspeptin membranes, and 0.2 n M $[^{125}I]$-metastin (45-54) in a 96-well assay plate and allowed to incubate 90 minutes at room temperature. Assay contents are then filtered through unifilter CF/C: microplates (PerkinElmer) pre-soaked with 0.5% BSA and washed with 9×400 μL of cold wash buffer (10 mM -HEPES, 500 mM NaCl, 0.1% Tween-20, pH7.4). Assay plates are read using a Microbeta$^2$ (PerkinElmer) and Ki values for compounds are determined using a GraphPad Prism 9.3 non-linear regression analysis.

Illustrative biological activity of compounds is demonstrated in Table G. The metal complexes in Table G comprise nonradioactive gallium, indium, and lutetium.

TABLE G

Representative Binding Activity

| Compound | hKiSSR Binding Ki (90 min, nM) |
|---|---|
| 1 | A |
| 1-In | A |
| 1-Lu | A |
| 1-Ga | A |
| 2 | A |
| 2-In | A |
| 3 | C |
| 5 | B |
| 6 | A |
| 6-In | A |
| 7 | B |
| 8 | A |
| 9 | A |
| 10 | A |
| 11 | A |
| 12 | B |
| 13 | B |
| 14 | B |
| 15 | C |
| 16 | C |
| 17 | A |
| 18 | B |
| 19 | B |
| 20 | A |
| 21 | B |

TABLE G-continued

Representative Binding Activity

| Compound | hKiSSR Binding Ki (90 min, nM) |
|---|---|
| 22 | A |
| 23 | A |
| 24 | A |
| 25 | A |
| 26 | A |
| 27 | A |
| 28 | A |
| 29 | A |
| 30 | A |
| 31 | A |
| 32 | A |
| 33 | A |
| 34 | A |
| 35 | A |
| 36 | A |
| 37 | A |
| 38 | C |
| 39 | C |
| 49 | C |
| 50 | A |
| 51 | A |
| 55 | A |
| 57 | A |
| 58 | A |
| 64 | A |
| 91 | A |
| 104 | A |
| 105 | A |
| 105-In | A |
| 106 | A |
| 107 | A |
| 108 | A |
| 109 | A |
| 110 | A |
| 113 | A |
| 114 | A |
| 115 | A |
| 116 | A |
| 117 | A |
| 118 | A |
| 118-Lu | A |
| 119 | A |
| 120 | A |
| 121 | B |
| 123 | C |
| 130 | A |
| 131 | A |
| 132 | A |
| 133 | A |
| 134 | B |
| 135 | C |
| 136 | C |
| 137 | A |
| 138 | B |
| 139 | B |
| 140 | A |
| 141 | B |
| 142 | A |
| 146 | A |
| 147 | C |
| 148 | B |
| 149 | A |
| 151 | A |
| 156 | A |
| 158 | A |
| 159 | A |
| 160 | A |
| 161 | A |
| 164 | A |
| 165 | A |
| 166 | A |
| 167 | A |
| 168 | A |
| 169 | A |

TABLE G-continued

Representative Binding Activity

| Compound | hKiSSR Binding Ki (90 min, nM) |
|---|---|
| 170 | A |
| 171 | B |
| 176 | A |
| 181 | A |
| 182 | A |
| 183 | A |
| 184 | A |
| 185 | A |
| 186 | A |
| 187 | A |
| 188 | B |
| 189 | C |
| 192 | A |
| 193 | A |
| 193-In | A |
| 195 | A |
| 196 | A |
| 196-In | A |
| 197 | A |
| 198 | A |
| 199 | C |
| 201 | A |
| 201-In | A |
| 202 | B |
| 203 | A |
| 204 | C |
| 205 | A |
| 206 | A |
| 213 | A |
| 214 | A |
| 215 | C |
| 216 | A |
| 217 | A |
| 218 | A |
| 221 | A |
| 222 | A |
| 226 | B |
| 230 | B |
| 231 | B |
| 232 | A |
| 233 | A |
| 234 | A |
| 235 | A |
| 236 | A |
| 237 | A |
| 238 | A |
| 239 | C |
| 240 | A |
| 241 | A |
| 242 | A |
| 244 | A |
| 245 | A |
| 246 | B |
| 247 | A |
| 248 | C |
| 249 | A |
| 250 | A |
| 251 | C |
| 252 | C |
| 253 | A |
| 254 | A |
| 255 | A |
| 256 | A |
| 258 | C |
| 259 | B |
| 260 | B |
| 261 | A |
| 264 | A |
| 266 | A |
| 269 | A |
| 270 | A |
| 271 | B |
| 272 | A |
| 273 | B |

TABLE G-continued

| Representative Binding Activity | |
|---|---|
| Compound | hKiSSR Binding Ki (90 min, nM) |
| 275 | A |
| 276 | A |
| 277 | A |
| 278 | A |
| 279 | A |
| 280 | C |
| 281 | A |
| 282 | C |
| 283 | B |
| 284 | B |
| 285 | A |
| 286 | A |
| 287 | B |
| 288 | A |
| 289 | A |
| 290 | A |
| 291 | A |
| 292 | A |
| 293 | A |
| 294 | A |
| 295 | A |
| 296 | A |
| 297 | A |
| 298 | A |
| 299 | A |
| 300 | A |
| 301 | A |
| 302 | A |
| 304 | A |
| 305 | A |
| 306 | A |
| 307 | A |
| 308 | A |
| 309 | A |
| 310 | A |
| 311 | A |
| 312 | B |
| 313 | A |
| 314 | A |
| 315 | A |
| 316 | A |
| 317 | A |
| 318 | A |
| 319 | C |
| 320 | A |
| 321 | A |
| 322 | A |
| 323 | A |
| 324 | A |
| 325 | A |
| 326 | A |
| 327 | A |
| 328 | A |
| 329 | A |
| 330 | A |
| 331 | A |
| 332 | A |
| 333 | A |
| 334 | A |
| 335 | A |
| 336 | A |
| 337 | A |
| 338 | A |
| 339 | A |
| 345 | A |
| 346 | A |
| 353 | A |
| 354 | A |
| 355 | A |
| 356 | A |
| 357 | A |
| 358 | A |
| 359 | A |
| 360 | A |

TABLE G-continued

| Representative Binding Activity | |
|---|---|
| Compound | hKiSSR Binding Ki (90 min, nM) |
| 363 | A |
| 364 | A |
| 365 | A |
| 366 | A |
| 367 | A |
| 368 | A |
| 370 | C |
| 371 | A |
| 373 | B |
| 374 | A |
| 375 | C |
| 376 | B |
| 378 | A |
| 379 | A |
| 380 | A |
| 381 | A |
| 382 | A |
| 383 | A |
| 384 | A |
| 386 | A |
| 387 | A |
| 388 | A |
| 389 | A |
| 390 | A |
| 391 | A |
| 392 | A. |
| 393 | A |
| 394 | A |
| 395 | A |
| 396 | A |
| 397 | A |
| 398 | A |
| 399 | A |
| 400 | A |
| 401 | A |
| 402 | A |
| 403 | A |
| 404 | A |
| 405 | A |
| 406 | A |
| 407 | A |
| 408 | A |
| 409 | A |
| 410 | A |
| 411 | A |

*A is < 10 nM; B is 10-100 nM; C is > 100 nM

Example B-2: Biodistribution of $^{111}$In[In] Complex of Compound 1 in Mouse Tumor Model

TABLE H

| Study outline | | | | |
|---|---|---|---|---|
| Treatment | N value | Dose (MBq/Mouse) | Dose (nmol/mouse) | Time (h) |
| 111In[In]-Compound 1 | 4 | 5-7 | 1 | 0.5 |
| 111In[In]-Compound 1 | 4 | 5-7 | 1 | 2 |
| 111In[In]-Compound 1 | 4 | 5-7 | 1 | 5 |
| 111In[In]-Compound 1 | 4 | 5-7 | 1 | 24 |
| 111In[In]-Compound 1 | 4 | 5-7 | 1 | 72 |
| 111In[In]-Compound 1 + Cold-Compound 1 | 4 | 5-70 | 1 + 100 nm | 2 h |

*Treatment schedule is Q1Dx1(IV)

Study Details : 24 h prior to the start of the biodistribution Compound 1 (CMPD 1) was radiolabeled.

Prior to initiation of the biodistribution study, female Swiss nude mice were subcutaneously inoculated with 10×10$^6$ human cancer cells.

When tumors were between 150-300 mm$^3$, animals were randomized and received a single IV injection of 200 μL into the caudal vein via a catheter with 5-7 MBq of $^{111}$In[In] Compound 1 (1 nmol) per animal. For the competition study arm, 1 nmol of $^{111}$In[In]-Compound 1 was co-injected with 100 nmol of unlabeled Compound 1.

After drug administration, animals were euthanized at timepoints (0.5 h, 2 h, 5 h, 24 h and 72 h) and organs (blood, heart, muscle, lungs, intestines, spleen, bone, brain, tail, carcass, kidneys, liver and tumor) were collected, weighed, and ÿ radioactivity assessed in each organ/tissue. Activity was quantitated and expressed as % ID/g (Percentage of Initial Dose/gram of tissue).

Example B-3: Biodistribution of $^{111}$In[In] Complex of Compound 6 in Mouse Tumor Model

TABLE I

| Study outline | | | | |
|---|---|---|---|---|
| Treatment | N value | Dose MBq/Mouse) | Dose (nmol/mouse) | Time (h) |
| $^{111}$In[In]-Compound 6 | 3 | 5-7 | 1 | 0.75 |
| $^{111}$In[In]-Compound 6 | 3 | 5-7 | 1 | 2 |
| $^{111}$In[In]-Compound 6 | 3 | 5-7 | 1 | 5 |
| $^{111}$In[In]-Compound 6 | 3 | 5-7 | 1 | 24 |
| $^{111}$In[In]-Compound 6 | 3 | 5-7 | 1 | 44 |
| $^{111}$In[In]-Compound 6 + Cold-Compound 6 | 3 | 5-70 | 1 + 100 nm | 2 h |

*Treatment schedule is Q1Dx1(IV)

Study Details: 24 h prior to the start of the biodistribution Compound 6 was radiolabeled as described Prior to initiation of the biodistribution study, female Swiss nude mice were subcutaneously inoculated with 10×10$^6$ human cancer cells.

When tumors were between 150-300 mm$^3$, animals were randomized and received a single IV injection of 200 μL into the caudal vein via a catheter with 5-7 MBq of $^{111}$In[In] Compound 6 (1 nmol) per animal. For the competition study arm, 1 nmol of $^{111}$In[In]-Compound 6 was co injected with 100 nmol of unlabeled Compound-6.

After drug administration, animals were euthanized at timepoints (0.75 h, 2 h, 5 h, 24 h and 44 h) and organs (blood, carcass, gut, kidneys, liver, lungs, muscle, spleen, tail, and tumor) were collected, weighed, and 9, radioactivity assessed in each organ/tissue. Activity was quantitated and expressed as % ID/g (Percentage of Initial Dose/grain of tissue).

Example B-4: Biodistribution of $^{111}$In[In] Complex of Compound 105 in Mouse Tumor Model

TABLE J

| Study outline | | | | |
|---|---|---|---|---|
| Treatment | N value | Dose (MBq/Mouse) | Dose (nmol/mouse) | Time (h) |
| $^{111}$In[In]-Compound 105 | 4 | 5-7 | 1 | 0.5 |
| $^{111}$In[In]-Compound 105 | 4 | 5-7 | 1 | 2 |
| $^{111}$In[In]-Compound 105 | 4 | 5-7 | 1 | 5 |

TABLE J-continued

| Study outline | | | | |
|---|---|---|---|---|
| Treatment | N value | Dose (MBq/Mouse) | Dose (nmol/mouse) | Time (h) |
| $^{111}$In[In]-Compound 105 | 4 | 5-7 | 1 | 24 |
| $^{111}$In[In]-Compound 105 | 4 | 5-7 | 1 | 44 |
| $^{111}$In[In]-Compound 105 + Cold-Compound 105 | 4 | 5-70 | 1 +100 nm | 2 h |

*Treatment schedule is Q1Dx1(IV)

Study Details: 24 h prior to the start of the biodistribution Compound 105 was radiolabeled Prior to initiation of the biodistribution study, female Swiss nude mice were subcutaneously inoculated with 10×10$^6$ human cancer cells.

When tumors were between 150-300 mm$^3$, animals were randomized and received a single IV injection of 200 μL into the caudal vein via a catheter with 5-7 MBq of $^{111}$In[In] Compound 105 (1 nmol) per animal. For the competition study arm, 1 nmol of $^{111}$In[In]-Compound 105 was co injected with 100 nmol of unlabeled Compound 105.

After drug administration, animals were euthanized at timepoints (0.5 h, 2 b, 5 h, 24 h and 44 h) and organs (Blood, Carcass, Gut, Heart, Kidneys, Liver, Lungs, Muscle Spleen Tail, and Tumor) were collected, weighed, and ÿ radioactivity assessed in each organ/tissue. Activity was quantitated and expressed as % ID/g (Percentage of Initial Dose/gram of tissue).

Example B-5: Safety and Dosimetry Study in Patients with Breast Cancer and Healthy Volunteers A non-limiting example of a phase 1 safety and dosimetry study of $^{68}$Ga-complex of a compound of Formula (I) in patients with breast, kidney cancer and non-small cell lung cancer is described below.

This is an open-label, first-in-human, Phase 1 study of $^{68}$Ga-complex of a compound of Formula (I) designed to characterize its safety and biodistribution in patients diagnosed with breast cancer, clear cell renal cell carcinoma or non-small cell lung cancer. In some embodiments, a $^{68}$Ga-complex of a compound of Formula (I) is used to localize KISS1R-expressing lesions and identify breast cancer, clear cell renal cell carcinoma or non-small cell lung cancer patients with KISS1R-expressing tumors who may benefit from treatment with KISS1R-targeting therapeutic agents, such as $^{177}$Lu-complex of a compound of Formula (I). In healthy humans, KISS1R is found primarily in the hypothalamus, pituitary and placenta, and plays a role in regulating puberty and fertility. KISS1R is highly expressed in breast cancer, clear cell renal cell carcinoma and non-small cell lung cancer.

This study will enroll approximately 30 evaluable subjects in total. Patients with locally recurrent or metastatic breast cancer, with metastatic clear cell renal carcinoma, with locally advanced or metastatic non-small cell lung cancer are eligible to participate if they meet all inclusion criteria and none of the exclusion criteria.

Study Populations: Patients with locally recurrent or metastatic breast cancer, or with metastatic clear cell renal cell carcinoma or with locally advanced metastatic non-small cell lung cancer.

Primary Objectives: To describe the safety of $^{68}$Ga-complex of a compound of Formula (I).

Secondary Objectives: To describe the biodistribution of $^{68}$Ga-complex of a compound of Formula (I), to compare Formula (I) positron emission tomography/computed tomography (PET/CT) scans to standard of care anatomic imaging in detecting tumor lesions.

Primary Endpoints: Incidence of adverse events (AE) characterized overall and by type, frequency, seriousness, relationship to the study drug, timing, and severity, graded according to the National Cancer Institute (NCI) Common Terminology Criteria for Adverse Events (CTCAE), Version 5.0.

Secondary Endpoints: Maximum standard uptake value ($SUV_{max}$) of each tumor and $SUV_{mean}$ of organs. Ratio of the tumor SUV over reference region SUV. Number and location of tumors identified by a $^{68}$Ga-complex of a compound of Formula (I) PET/CT, and concordance rate between $^{68}$Ga-complex of a compound of Formula (I) PET/CT and standard of care images.

Study Design: This study will enroll up to approximately 30 evaluable patients. Patients who receive study drug and complete all scheduled imaging procedures are considered evaluable.

There are three patient cohorts in the study: Cohort 1: patients locoregionally recurrent or metastatic breast cancer; Cohort 2: patients with metastatic clear cell renal cell carcinoma; Cohort 3. patients with locally advanced or metastatic non-small cell lung cancer. Patients are enrolled into the three cohorts in parallel. Each cohort will enroll ten evaluable patients. All patients will be evaluated for eligibility prior to enrollment (56-day screening period).

Each eligible patient enrolled will receive a single intravenous injection of a $^{68}$Ga-complex of a compound of Formula (H) on Day 1 of the study at a dose of approximately 5 mCi (185 MBq). Initial patients (approximately 6) will be imaged with a dynamic PET scan in addition to a static whole-body PET/CT scan to establish optimal imaging time for subsequent patients who will undergo a single time-point PET/CT scan following injection of a $^{68}$Ga-complex of a compound of Formula (I).

All patients must meet all the inclusion eligibility criteria and none of the exclusion eligibility criteria, as appropriate and provided below.

Inclusion Criteria: Locally recurrent or metastatic breast cancer (Cohort 1 patients); metastatic clear cell renal cell carcinoma (Cohort 2 patients); locally advanced or metastatic non -small cell lung cancer (Cohort 3 patients). Male or non-pregnant, non-lactating female subjects age ≥18 years. Subjects who are sexually active must agree to use adequate method(s) of effective contraception during their participation in the study. Eastern Cooperative Oncology Group (ECOG) Performance Status 2. Adequate hepatic function as defined by a) serum alanine aminotransaminase (ALT)/aspartate aminotransaminase (AST) ≤0.3×upper limit of normal (ULN) or ≤5×ULN if liver metastases are present or received prior mitotane therapy, and b) serum bilirubin–total ≤1.5×ULN (unless due to Gilbert's syndrome or hemolysis in which case total ≤3.0×ULN). Adequate renal function as measured by creatinine clearance calculated by the Cockcroft-Gault formula (≥60 mL/minute). Able to understand and willing to sign written informed consent.

Exclusion Criteria: Administered a radionuclide within a period of time corresponding to less than 10 physical half-lives of the radionuclide prior to study Day 1. Radiotherapy ≤14 days prior to study Day 1. Major surgery ≤21 days prior to study Day 1 or has not recovered from adverse effects of such procedure. History of cerebrovascular accident within 6 months or that resulted in ongoing neurologic instability. History of other previous or concurrent cancer that would interfere with the determination of safety. Any other condition that in the opinion of the Investigator would place the subject at an unacceptable risk or cause the subject to be unlikely to fully participate or comply with study procedures.

Study Drug, Dose, and Mode of Administration

Study Drug: The study drug is a $^{68}$Ga-complex of a compound of Formula (I). In some embodiments, the $^{68}$Ga-complex is a $^{68}$Ga-complex of a compound of Formula (I). In some embodiments, the $^{68}$Ga-complex is a $^{68}$Ga-complex of Compound 1. In some embodiments, the $^{68}$Ga-complex is a $^{68}$Ga-complex of Compound 6. In some embodiments, the $^{68}$Ga-complex is a $^{68}$Ga-complex of Compound 105. In some embodiments, the $^{68}$Ga-complex is a $^{68}$Ga-complex of Compound 118. In some embodiments, the $^{68}$Ga-complex is a $^{68}$Ga-complex of Compound 193. In some embodiments, the $^{68}$Ga-complex is a $^{68}$Ga-complex of Compound 196. In some embodiments, the $^{68}$Ga-complex is a $^{68}$Ga-complex of Compound 269. In some embodiments, the $^{68}$Ga-complex is a $^{68}$Ga-complex of Compound 332. In some embodiments, the $^{68}$Ga-complex is a $^{68}$Ga-complex of Compound 366.

Dose: 5.0 mCi (±20%); Total carrier mass of the compound of Formula (I): not more than (NMT) 90 μg/dose.

Mode of administration: Intravenous

Duration of Participation: A 56-day screening window will be utilized where the subject will undergo study assessments to deem the subject eligible for the study. Once confirmed, subjects will receive the study drug, $^{68}$Ga-complex of a compound of Formula (I), and PET/CT imaging on Day 1. The subjects will have a safety evaluation on Day 2 (+2 days).

Study Duration: The start of the study will be the date on which the first subject provides informed consent. The end of the study will be when the database is locked The examples and embodiments described herein are for illustrative purposes only and various modifications or changes suggested to persons skilled in the art are to be included within the purview of this application and scope of the appended claims. Other embodiments are set forth in the following claims, along with the full scope of equivalents to which such claims are entitled.

SEQUENCE LISTING

```
Sequence total quantity: 847
SEQ ID NO: 1          moltype = AA  length = 4
FEATURE               Location/Qualifiers
source                1..4
                      mol_type = protein
                      organism = synthetic construct
SITE                  1
                      note = D-Tyrosine
SITE                  2
```

```
                        note = D-Tryptophan
SEQUENCE: 1
YWNT                                                                    4

SEQ ID NO: 2            moltype = AA  length = 5
FEATURE                 Location/Qualifiers
source                  1..5
                        mol_type = protein
                        organism = synthetic construct
SITE                    1
                        note = D-Tyrosine
SITE                    2
                        note = D-Asparagine
SITE                    3
                        note = D-Arginine
SEQUENCE: 2
YNRNT                                                                   5

SEQ ID NO: 3            moltype = AA  length = 4
FEATURE                 Location/Qualifiers
source                  1..4
                        mol_type = protein
                        organism = synthetic construct
SITE                    1
                        note = D-Tyrosine
SEQUENCE: 3
YRNT                                                                    4

SEQ ID NO: 4            moltype = AA  length = 4
FEATURE                 Location/Qualifiers
source                  1..4
                        mol_type = protein
                        organism = synthetic construct
SITE                    1
                        note = D-Tyrosine
SEQUENCE: 4
YKNT                                                                    4

SEQ ID NO: 5            moltype =   length =
SEQUENCE: 5
000

SEQ ID NO: 6            moltype =   length =
SEQUENCE: 6
000

SEQ ID NO: 7            moltype = AA  length = 4
FEATURE                 Location/Qualifiers
source                  1..4
                        mol_type = protein
                        organism = synthetic construct
SITE                    1
                        note = D-Tyrosine
SEQUENCE: 7
YENT                                                                    4

SEQ ID NO: 8            moltype = AA  length = 4
FEATURE                 Location/Qualifiers
source                  1..4
                        mol_type = protein
                        organism = synthetic construct
SITE                    1
                        note = D-Tyrosine
SITE                    2
                        note = D-Alanine
SEQUENCE: 8
YANT                                                                    4

SEQ ID NO: 9            moltype = AA  length = 4
FEATURE                 Location/Qualifiers
source                  1..4
                        mol_type = protein
                        organism = synthetic construct
SITE                    1
                        note = D-Tyrosine
SEQUENCE: 9
YWNA                                                                    4

SEQ ID NO: 10           moltype = AA  length = 4
```

-continued

```
FEATURE                Location/Qualifiers
source                 1..4
                       mol_type = protein
                       organism = synthetic construct
SITE                   1
                       note = D-Tyrosine
SEQUENCE: 10
YWNT                                                                      4

SEQ ID NO: 11          moltype = AA  length = 5
FEATURE                Location/Qualifiers
source                 1..5
                       mol_type = protein
                       organism = synthetic construct
SITE                   1
                       note = D-Tyrosine
SITE                   3
                       note = D-Tryptophan
SEQUENCE: 11
YNWNT                                                                     5

SEQ ID NO: 12          moltype = AA  length = 5
FEATURE                Location/Qualifiers
source                 1..5
                       mol_type = protein
                       organism = synthetic construct
SITE                   1
                       note = D-Tyrosine
SITE                   2
                       note = D-Histidine
SITE                   3
                       note = D-Tryptophan
SEQUENCE: 12
YHWNT                                                                     5

SEQ ID NO: 13          moltype = AA  length = 5
FEATURE                Location/Qualifiers
source                 1..5
                       mol_type = protein
                       organism = synthetic construct
SITE                   1
                       note = D-Alanine
SEQUENCE: 13
ANWNG                                                                     5

SEQ ID NO: 14          moltype = AA  length = 4
FEATURE                Location/Qualifiers
source                 1..4
                       mol_type = protein
                       organism = synthetic construct
SITE                   1
                       note = D-Tryptophan
SEQUENCE: 14
WNTF                                                                      4

SEQ ID NO: 15          moltype = AA  length = 5
FEATURE                Location/Qualifiers
source                 1..5
                       mol_type = protein
                       organism = synthetic construct
SITE                   1
                       note = D-Alanine
SEQUENCE: 15
ANWNS                                                                     5

SEQ ID NO: 16          moltype = AA  length = 4
FEATURE                Location/Qualifiers
source                 1..4
                       mol_type = protein
                       organism = synthetic construct
SITE                   1
                       note = D-Tyrosine
SITE                   2
                       note = Azaglycine
SEQUENCE: 16
YGNT                                                                      4

SEQ ID NO: 17          moltype = AA  length = 5
FEATURE                Location/Qualifiers
```

```
source                  1..5
                        mol_type = protein
                        organism = synthetic construct
SITE                    1
                        note = D-Asparagine
SITE                    2
                        note = D-Asparagine
SITE                    3
                        note = D-Asparagine
SITE                    4
                        note = D-Asparagine
SITE                    5
                        note = D-Asparagine
SEQUENCE: 17
NNNNN                                                                5

SEQ ID NO: 18           moltype = AA  length = 5
FEATURE                 Location/Qualifiers
source                  1..5
                        mol_type = protein
                        organism = synthetic construct
SITE                    1
                        note = D-Asparagine
SITE                    2
                        note = D-Asparagine
SITE                    3
                        note = D-Glutamic Acid
SITE                    4
                        note = D-Glutamic Acid
SITE                    5
                        note = D-Asparagine
SEQUENCE: 18
NNEEN                                                                5

SEQ ID NO: 19           moltype = AA  length = 5
FEATURE                 Location/Qualifiers
source                  1..5
                        mol_type = protein
                        organism = synthetic construct
SITE                    1
                        note = D-Asparagine
SITE                    2
                        note = D-Asparagine
SITE                    3
                        note = D-Lysine
SITE                    4
                        note = D-Glutamic Acid
SITE                    5
                        note = D-Asparagine
SEQUENCE: 19
NNKEN                                                                5

SEQ ID NO: 20           moltype = AA  length = 4
FEATURE                 Location/Qualifiers
source                  1..4
                        mol_type = protein
                        organism = synthetic construct
SITE                    1
                        note = D-Tyrosine
SEQUENCE: 20
YPNT                                                                 4

SEQ ID NO: 21           moltype = AA  length = 4
FEATURE                 Location/Qualifiers
source                  1..4
                        mol_type = protein
                        organism = synthetic construct
SITE                    1
                        note = 2-(2-(2-hydroxyethoxy)ethoxy)acetic acid coupled to
                         N-terminus of D-Tyrosine
SITE                    2
                        note = Lysine bound to an optional linker and chelating
                         moiety or a radionuclide complex
SEQUENCE: 21
YKNT                                                                 4

SEQ ID NO: 22           moltype = AA  length = 7
FEATURE                 Location/Qualifiers
source                  1..7
```

```
                        mol_type = protein
                        organism = synthetic construct
SITE                    1
                        note = palmitic acid coupled to N-terminus of Glutamic Acid
SITE                    2
                        note = Lysine bound to an optional linker and chelating
                         moiety or a radionuclide complex
SEQUENCE: 22
EKYNWNS                                                             7

SEQ ID NO: 23           moltype = AA  length = 7
FEATURE                 Location/Qualifiers
source                  1..7
                        mol_type = protein
                        organism = synthetic construct
SITE                    1
                        note = Acetyl coupled to N-terminus of Glutamic Acid
SITE                    2
                        note = Lysine bound to an optional linker and chelating
                         moiety or a radionuclide complex
SITE                    3
                        note = D-Alanine
SEQUENCE: 23
EKANWNG                                                             7

SEQ ID NO: 24           moltype = AA  length = 4
FEATURE                 Location/Qualifiers
source                  1..4
                        mol_type = protein
                        organism = synthetic construct
SITE                    1
                        note = Sarcosine
SITE                    2
                        note = Sarcosine
SITE                    3
                        note = Sarcosine
SITE                    4
                        note = Sarcosine
SEQUENCE: 24
GGGG                                                                4

SEQ ID NO: 25           moltype = AA  length = 5
FEATURE                 Location/Qualifiers
source                  1..5
                        mol_type = protein
                        organism = synthetic construct
SITE                    1
                        note = Sarcosine
SITE                    2
                        note = Sarcosine
SITE                    3
                        note = Sarcosine
SITE                    4
                        note = Sarcosine
SITE                    5
                        note = Sarcosine
SEQUENCE: 25
GGGGG                                                               5

SEQ ID NO: 26           moltype = AA  length = 5
FEATURE                 Location/Qualifiers
source                  1..5
                        mol_type = protein
                        organism = synthetic construct
SITE                    1
                        note = D-Alanine
SITE                    2
                        note = D-Alanine
SITE                    3
                        note = D-Alanine
SITE                    4
                        note = D-Alanine
SITE                    5
                        note = D-Alanine
SEQUENCE: 26
AAAAA                                                               5

SEQ ID NO: 27           moltype =   length =
SEQUENCE: 27
```

```
000

SEQ ID NO: 28          moltype = AA  length = 4
FEATURE                Location/Qualifiers
source                 1..4
                       mol_type = protein
                       organism = synthetic construct
SEQUENCE: 28
KWNT                                                                4

SEQ ID NO: 29          moltype = AA  length = 4
FEATURE                Location/Qualifiers
source                 1..4
                       mol_type = protein
                       organism = synthetic construct
SITE                   1
                       note = 4-iodophenylalanine
SEQUENCE: 29
FWNT                                                                4

SEQ ID NO: 30          moltype = AA  length = 4
FEATURE                Location/Qualifiers
source                 1..4
                       mol_type = protein
                       organism = synthetic construct
SITE                   1
                       note = D-4-iodophenylalanine
SITE                   2
                       note = D-Tryptophan
SEQUENCE: 30
FWNT                                                                4

SEQ ID NO: 31          moltype =   length =
SEQUENCE: 31
000

SEQ ID NO: 32          moltype = AA  length = 4
FEATURE                Location/Qualifiers
source                 1..4
                       mol_type = protein
                       organism = synthetic construct
SITE                   2
                       note = Azaglycine
SEQUENCE: 32
YGNT                                                                4

SEQ ID NO: 33          moltype =   length =
SEQUENCE: 33
000

SEQ ID NO: 34          moltype =   length =
SEQUENCE: 34
000

SEQ ID NO: 35          moltype =   length =
SEQUENCE: 35
000

SEQ ID NO: 36          moltype =   length =
SEQUENCE: 36
000

SEQ ID NO: 37          moltype =   length =
SEQUENCE: 37
000

SEQ ID NO: 38          moltype = AA  length = 4
FEATURE                Location/Qualifiers
source                 1..4
                       mol_type = protein
                       organism = synthetic construct
SITE                   1
                       note = D-Tyrosine
SITE                   2
                       note =
                        Lysine(1,4,7,10-tetraazacyclododecane-1,4,7,10-tetraacetic
                        acid)
SEQUENCE: 38
YKNT                                                                4
```

```
SEQ ID NO: 39           moltype = AA  length = 4
FEATURE                 Location/Qualifiers
source                  1..4
                        mol_type = protein
                        organism = synthetic construct
SITE                    2
                        note =
                         D-Lysine(1,4,7,10-tetraazacyclododecane-1,4,7,10-tetraaceti
                         c acid)
SEQUENCE: 39
YKNT                                                                        4

SEQ ID NO: 40           moltype = AA  length = 4
FEATURE                 Location/Qualifiers
source                  1..4
                        mol_type = protein
                        organism = synthetic construct
SITE                    1
                        note = D-Tyrosine
SITE                    2
                        note =
                         D-Lysine(1,4,7,10-tetraazacyclododecane-1,4,7,10-tetraaceti
                         c acid)
SEQUENCE: 40
YKNT                                                                        4

SEQ ID NO: 41           moltype =   length =
SEQUENCE: 41
000

SEQ ID NO: 42           moltype =   length =
SEQUENCE: 42
000

SEQ ID NO: 43           moltype =   length =
SEQUENCE: 43
000

SEQ ID NO: 44           moltype =   length =
SEQUENCE: 44
000

SEQ ID NO: 45           moltype = AA  length = 4
FEATURE                 Location/Qualifiers
source                  1..4
                        mol_type = protein
                        organism = synthetic construct
SITE                    1
                        note = D-Tyrosine
SITE                    2
                        note = 4-iodophenylalanine
SEQUENCE: 45
YFNT                                                                        4

SEQ ID NO: 46           moltype = AA  length = 4
FEATURE                 Location/Qualifiers
source                  1..4
                        mol_type = protein
                        organism = synthetic construct
SEQUENCE: 46
YPNT                                                                        4

SEQ ID NO: 47           moltype = AA  length = 4
FEATURE                 Location/Qualifiers
source                  1..4
                        mol_type = protein
                        organism = synthetic construct
SITE                    1
                        note = D-Tyrosine
SITE                    2
                        note = D-Tryptophan
SEQUENCE: 47
YWNA                                                                        4

SEQ ID NO: 48           moltype = AA  length = 5
FEATURE                 Location/Qualifiers
source                  1..5
                        mol_type = protein
```

```
                        organism = synthetic construct
SITE                    1
                        note = gamma-D-Glutamic Acid
SITE                    2
                        note = D-Tyrosine
SITE                    3
                        note =
                         Lysine(1,4,7,10-tetraazacyclododecane-1,4,7,10-tetraacetic
                         acid)
SEQUENCE: 48
EYKNT                                                                       5

SEQ ID NO: 49           moltype = AA  length = 5
FEATURE                 Location/Qualifiers
source                  1..5
                        mol_type = protein
                        organism = synthetic construct
SITE                    2
                        note = D-Tyrosine
SITE                    3
                        note = 3-(2-naphthyl)alanine
SEQUENCE: 49
GYXNT                                                                       5

SEQ ID NO: 50           moltype = AA  length = 5
FEATURE                 Location/Qualifiers
source                  1..5
                        mol_type = protein
                        organism = synthetic construct
SITE                    3
                        note = D-Tryptophan
SEQUENCE: 50
GYWNT                                                                       5

SEQ ID NO: 51           moltype = AA  length = 5
FEATURE                 Location/Qualifiers
source                  1..5
                        mol_type = protein
                        organism = synthetic construct
SEQUENCE: 51
YNWNS                                                                       5

SEQ ID NO: 52           moltype = AA  length = 5
FEATURE                 Location/Qualifiers
source                  1..5
                        mol_type = protein
                        organism = synthetic construct
SITE                    5
                        note = 3-fluorophenylalanine
SEQUENCE: 52
YENTF                                                                       5

SEQ ID NO: 53           moltype = AA  length = 5
FEATURE                 Location/Qualifiers
source                  1..5
                        mol_type = protein
                        organism = synthetic construct
SITE                    2
                        note = D-Tryptophan
SITE                    5
                        note = 3-fluorophenylalanine
SEQUENCE: 53
YWNTF                                                                       5

SEQ ID NO: 54           moltype = AA  length = 5
FEATURE                 Location/Qualifiers
source                  1..5
                        mol_type = protein
                        organism = synthetic construct
SITE                    1
                        note = D-Tyrosine
SITE                    2
                        note = D-Tryptophan
SITE                    5
                        note = 3-fluorophenylalanine
SEQUENCE: 54
YWNTF                                                                       5

SEQ ID NO: 55           moltype = AA  length = 9
```

-continued

```
FEATURE                Location/Qualifiers
source                 1..9
                       mol_type = protein
                       organism = synthetic construct
SITE                   1
                       note = D-Tyrosine
SITE                   2
                       note = D-Tryptophan
SITE                   6
                       note = Azaglycine
SITE                   8
                       note =
                        4-amino-1-((3-fluoro-4-methylbenzyl)glycyl)piperidine-4-car
                        boxamide
SITE                   9
                       note = Amidated Tryptophan
SEQUENCE: 55
YWNTFGLXW                                                          9

SEQ ID NO: 56          moltype = AA  length = 5
FEATURE                Location/Qualifiers
source                 1..5
                       mol_type = protein
                       organism = synthetic construct
SITE                   2
                       note = Azaglycine
SITE                   4
                       note =
                        4-amino-1-((3-fluoro-4-methylbenzyl)glycyl)piperidine-4-car
                        boxamide
SITE                   5
                       note = Amidated Tryptophan
SEQUENCE: 56
FGLXW                                                              5

SEQ ID NO: 57          moltype = AA  length = 5
FEATURE                Location/Qualifiers
source                 1..5
                       mol_type = protein
                       organism = synthetic construct
SITE                   4
                       note = 4-amino-1-carbamimidoylpiperidine-4-carboxylic acid
SITE                   5
                       note = Amidated Tryptophan
SEQUENCE: 57
FGLXW                                                              5

SEQ ID NO: 58          moltype = AA  length = 5
FEATURE                Location/Qualifiers
source                 1..5
                       mol_type = protein
                       organism = synthetic construct
SITE                   1
                       note = alpha-Me-Phenylalanine
SITE                   2
                       note = Azaglycine
SITE                   4
                       note =
                        4-amino-1-((3-fluoro-4-methylbenzyl)glycyl)piperidine-4-car
                        boxamide
SITE                   5
                       note = Amidated Tryptophan
SEQUENCE: 58
FGLXW                                                              5

SEQ ID NO: 59          moltype = AA  length = 5
FEATURE                Location/Qualifiers
source                 1..5
                       mol_type = protein
                       organism = synthetic construct
SITE                   2
                       note = Azaglycine
SITE                   4
                       note = 4-amino-1-carbamimidoylpiperidine-4-carboxylic acid
SITE                   5
                       note = Amidated Tryptophan
SEQUENCE: 59
FGLXW                                                              5
```

```
SEQ ID NO: 60           moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-Tryptophan
SITE                    6
                        note = Azaglycine
SITE                    8
                        note = 4-amino-1-carbamimidoylpiperidine-4-carboxylic acid
SITE                    9
                        note = Amidated Tryptophan
SEQUENCE: 60
YWNTFGLXW                                                                    9

SEQ ID NO: 61           moltype = AA  length = 5
FEATURE                 Location/Qualifiers
source                  1..5
                        mol_type = protein
                        organism = synthetic construct
SITE                    2
                        note = Azaglycine
SITE                    4
                        note =
                         4-amino-1-(4-(p-tolyl)butanoyl)piperidine-4-carboxylic acid
SITE                    5
                        note = Amidated Tryptophan
SEQUENCE: 61
FGLXW                                                                        5

SEQ ID NO: 62           moltype =   length =
SEQUENCE: 62
000

SEQ ID NO: 63           moltype = AA  length = 5
FEATURE                 Location/Qualifiers
source                  1..5
                        mol_type = protein
                        organism = synthetic construct
SITE                    4
                        note =
                         4-amino-1-((3-fluoro-4-methylbenzyl)glycyl)piperidine-4-car
                         boxamide
SITE                    5
                        note = Amidated Phenylalanine
SEQUENCE: 63
FGLXF                                                                        5

SEQ ID NO: 64           moltype = AA  length = 5
FEATURE                 Location/Qualifiers
source                  1..5
                        mol_type = protein
                        organism = synthetic construct
SITE                    2
                        note = Sarcosine
SITE                    4
                        note =
                         4-amino-1-((3-fluoro-4-methylbenzyl)glycyl)piperidine-4-car
                         boxamide
SITE                    5
                        note = Amidated Tryptophan
SEQUENCE: 64
FGLXW                                                                        5

SEQ ID NO: 65           moltype = AA  length = 10
FEATURE                 Location/Qualifiers
source                  1..10
                        mol_type = protein
                        organism = synthetic construct
SITE                    1
                        note = D-Asparagine
SITE                    2
                        note = D-Asparagine
SITE                    3
                        note = D-Glutamic Acid
SITE                    4
```

```
                        note = D-Glutamic Acid
SITE                    5
                        note = D-Asparagine
SITE                    7
                        note = Azaglycine
SITE                    9
                        note =
                         4-amino-1-((3-fluoro-4-methylbenzyl)glycyl)piperidine-4-car
                         boxamide
SITE                    10
                        note = Amidated Tryptophan
SEQUENCE: 65
NNEENFGLXW                                                                    10

SEQ ID NO: 66           moltype = AA  length = 10
FEATURE                 Location/Qualifiers
source                  1..10
                        mol_type = protein
                        organism = synthetic construct
SITE                    1
                        note = D-Asparagine
SITE                    2
                        note = D-Asparagine
SITE                    3
                        note = D-Lysine
SITE                    4
                        note = D-Glutamic Acid
SITE                    5
                        note = D-Asparagine
SITE                    7
                        note = Azaglycine
SITE                    9
                        note =
                         4-amino-1-((3-fluoro-4-methylbenzyl)glycyl)piperidine-4-car
                         boxamide
SITE                    10
                        note = Amidated Tryptophan
SEQUENCE: 66
NNKENFGLXW                                                                    10

SEQ ID NO: 67           moltype = AA  length = 7
FEATURE                 Location/Qualifiers
source                  1..7
                        mol_type = protein
                        organism = synthetic construct
SITE                    1
                        note = D-Asparagine
SITE                    2
                        note = D-Asparagine
SITE                    4
                        note = Azaglycine
SITE                    6
                        note =
                         4-amino-1-((3-fluoro-4-methylbenzyl)glycyl)piperidine-4-car
                         boxamide
SITE                    7
                        note = Amidated Tryptophan
SEQUENCE: 67
NNFGLXW                                                                       7

SEQ ID NO: 68           moltype = AA  length = 7
FEATURE                 Location/Qualifiers
source                  1..7
                        mol_type = protein
                        organism = synthetic construct
SITE                    1
                        note = D-Lysine
SITE                    2
                        note = D-Asparagine
SITE                    4
                        note = Azaglycine
SITE                    6
                        note =
                         4-amino-1-((3-fluoro-4-methylbenzyl)glycyl)piperidine-4-car
                         boxamide
SITE                    7
                        note = Amidated Tryptophan
SEQUENCE: 68
KNFGLXW                                                                       7
```

```
SEQ ID NO: 69            moltype = AA  length = 9
FEATURE                  Location/Qualifiers
source                   1..9
                         mol_type = protein
                         organism = synthetic construct
SITE                     1
                         note = D-Tyrosine
SITE                     2
                         note = hydroxyproline
SITE                     6
                         note = Azaglycine
SITE                     8
                         note =
                          4-amino-1-((3-fluoro-4-methylbenzyl)glycyl)piperidine-4-car
                          boxamide
SITE                     9
                         note = Amidated Tryptophan
SEQUENCE: 69
YXNTFGLXW                                                          9

SEQ ID NO: 70            moltype = AA  length = 6
FEATURE                  Location/Qualifiers
source                   1..6
                         mol_type = protein
                         organism = synthetic construct
SITE                     1
                         note = D-Asparagine
SITE                     3
                         note = Azaglycine
SITE                     5
                         note =
                          4-amino-1-((3-fluoro-4-methylbenzyl)glycyl)piperidine-4-car
                          boxamide
SITE                     6
                         note = Amidated Tryptophan
SEQUENCE: 70
NFGLXW                                                             6

SEQ ID NO: 71            moltype = AA  length = 9
FEATURE                  Location/Qualifiers
source                   1..9
                         mol_type = protein
                         organism = synthetic construct
SITE                     1
                         note = D-Tyrosine
SITE                     2
                         note = D-3-(4-pyridyl)alanine
SITE                     6
                         note = Azaglycine
SITE                     8
                         note =
                          4-amino-1-((3-fluoro-4-methylbenzyl)glycyl)piperidine-4-car
                          boxamide
SITE                     9
                         note = Amidated Tryptophan
SEQUENCE: 71
YXNTFGLXW                                                          9

SEQ ID NO: 72            moltype = AA  length = 9
FEATURE                  Location/Qualifiers
source                   1..9
                         mol_type = protein
                         organism = synthetic construct
SITE                     1
                         note = D-Tyrosine
SITE                     5
                         note = 3-Fluorophenylalanine
SITE                     6
                         note = Azaglycine
SITE                     8
                         note =
                          4-amino-1-((3-fluoro-4-methylbenzyl)glycyl)piperidine-4-car
                          boxamide
SITE                     9
                         note = Amidated Tryptophan
SEQUENCE: 72
YENTFGLXW                                                          9
```

-continued

```
SEQ ID NO: 73           moltype = AA  length = 7
FEATURE                 Location/Qualifiers
source                  1..7
                        mol_type = protein
                        organism = synthetic construct
SITE                    4
                        note = Azaglycine
SITE                    6
                        note =
                         4-amino-1-((3-fluoro-4-methylbenzyl)glycyl)piperidine-4-car
                         boxamide
SITE                    7
                        note = Amidated Tryptophan
SEQUENCE: 73
NTFGLXW                                                                   7

SEQ ID NO: 74           moltype = AA  length = 9
FEATURE                 Location/Qualifiers
source                  1..9
                        mol_type = protein
                        organism = synthetic construct
SITE                    1
                        note = D-Tyrosine
SITE                    5
                        note = 3-Fluorophenylalanine
SITE                    6
                        note = Azaglycine
SITE                    8
                        note =
                         4-amino-1-((3-fluoro-4-methylbenzyl)glycyl)piperidine-4-car
                         boxamide
SITE                    9
                        note = Amidated Tryptophan
SEQUENCE: 74
YKNTFGLXW                                                                 9

SEQ ID NO: 75           moltype = AA  length = 9
FEATURE                 Location/Qualifiers
source                  1..9
                        mol_type = protein
                        organism = synthetic construct
SITE                    1
                        note = D-Tyrosine
SITE                    2
                        note = 3-(4-pyridyl)alanine
SITE                    5
                        note = 3-Fluorophenylalanine
SITE                    6
                        note = Azaglycine
SITE                    8
                        note =
                         4-amino-1-((3-fluoro-4-methylbenzyl)glycyl)piperidine-4-car
                         boxamide
SITE                    9
                        note = Amidated Tryptophan
SEQUENCE: 75
YXNTFGLXW                                                                 9

SEQ ID NO: 76           moltype = AA  length = 8
FEATURE                 Location/Qualifiers
source                  1..8
                        mol_type = protein
                        organism = synthetic construct
SITE                    1
                        note = D-Tyrosine
SITE                    5
                        note = Azaglycine
SITE                    7
                        note =
                         4-amino-1-((3-fluoro-4-methylbenzyl)glycyl)piperidine-4-car
                         boxamide
SITE                    8
                        note = Amidated Tryptophan
SEQUENCE: 76
YNTFGLXW                                                                  8

SEQ ID NO: 77           moltype = AA  length = 10
FEATURE                 Location/Qualifiers
source                  1..10
```

```
                        mol_type = protein
                        organism = synthetic construct
SITE                    1
                        note = D-Tyrosine
SITE                    2
                        note = D-Histidine
SITE                    3
                        note = D-Tryptophan
SITE                    7
                        note = Azaglycine
SITE                    9
                        note =
                         4-amino-1-((3-fluoro-4-methylbenzyl)glycyl)piperidine-4-car
                         boxamide
SITE                    10
                        note = Amidated Tryptophan
SEQUENCE: 77
YHWNTFGLXW                                                  10

SEQ ID NO: 78           moltype = AA  length = 9
FEATURE                 Location/Qualifiers
source                  1..9
                        mol_type = protein
                        organism = synthetic construct
SITE                    1
                        note = D-Tyrosine
SITE                    5
                        note = 3-Fluorophenylalanine
SITE                    6
                        note = Azaglycine
SITE                    8
                        note =
                         4-amino-1-((3-fluoro-4-methylbenzyl)glycyl)piperidine-4-car
                         boxamide
SITE                    9
                        note = Amidated Tryptophan
SEQUENCE: 78
YWNTFGLXW                                                   9

SEQ ID NO: 79           moltype = AA  length = 9
FEATURE                 Location/Qualifiers
source                  1..9
                        mol_type = protein
                        organism = synthetic construct
SITE                    1
                        note = D-Tyrosine
SITE                    5
                        note = 3-Fluorophenylalanine
SITE                    6
                        note = Azaglycine
SITE                    8
                        note =
                         4-amino-1-((3-fluoro-4-methylbenzyl)glycyl)piperidine-4-car
                         boxamide
SITE                    9
                        note = Amidated Tryptophan
SEQUENCE: 79
YENTFGLXW                                                   9

SEQ ID NO: 80           moltype = AA  length = 5
FEATURE                 Location/Qualifiers
source                  1..5
                        mol_type = protein
                        organism = synthetic construct
SITE                    2
                        note = Azaglycine
SITE                    3
                        note = D-Leucine
SITE                    4
                        note =
                         4-amino-1-((3-fluoro-4-methylbenzyl)glycyl)piperidine-4-car
                         boxamide
SITE                    5
                        note = Amidated Tryptophan
SEQUENCE: 80
FGLXW                                                       5

SEQ ID NO: 81           moltype = AA  length = 5
FEATURE                 Location/Qualifiers
```

```
source                  1..5
                        mol_type = protein
                        organism = synthetic construct
SITE                    3
                        note = D-Leucine
SITE                    4
                        note = 4-amino-1-carbamimidoylpiperidine-4-carboxylic acid
SITE                    5
                        note = Amidated Tryptophan
SEQUENCE: 81
FGLXW                                                                       5

SEQ ID NO: 82           moltype = AA  length = 5
FEATURE                 Location/Qualifiers
source                  1..5
                        mol_type = protein
                        organism = synthetic construct
SITE                    2
                        note = Sarcosine
SITE                    3
                        note = Methyl-leucine
SITE                    4
                        note =
                         4-amino-1-((3-fluoro-4-methylbenzyl)glycyl)piperidine-4-car
                         boxamide
SITE                    5
                        note = Amidated Tryptophan
SEQUENCE: 82
FGLXW                                                                       5

SEQ ID NO: 83           moltype = AA  length = 5
FEATURE                 Location/Qualifiers
source                  1..5
                        mol_type = protein
                        organism = synthetic construct
SITE                    2
                        note = Azaglycine
SITE                    4
                        note =
                         4-amino-1-((3-fluoro-4-methylbenzyl)glycyl)piperidine-4-car
                         boxamide
SITE                    5
                        note = Amidated Methyl-tryptophan
SEQUENCE: 83
FGLXW                                                                       5

SEQ ID NO: 84           moltype =   length =
SEQUENCE: 84
000

SEQ ID NO: 85           moltype =   length =
SEQUENCE: 85
000

SEQ ID NO: 86           moltype =   length =
SEQUENCE: 86
000

SEQ ID NO: 87           moltype = AA  length = 5
FEATURE                 Location/Qualifiers
source                  1..5
                        mol_type = protein
                        organism = synthetic construct
SITE                    3
                        note = Methyl-leucine
SITE                    4
                        note =
                         4-amino-1-((3-fluoro-4-methylbenzyl)glycyl)piperidine-4-car
                         boxamide
SITE                    5
                        note = Amidated Tryptophan
SEQUENCE: 87
FGLXW                                                                       5

SEQ ID NO: 88           moltype =   length =
SEQUENCE: 88
000

SEQ ID NO: 89           moltype = AA  length = 5
```

-continued

```
FEATURE                 Location/Qualifiers
source                  1..5
                        mol_type = protein
                        organism = synthetic construct
SITE                    2
                        note = Azaglycine
SITE                    4
                        note =
                         4-amino-1-((3-fluoro-4-methylbenzyl)glycyl)piperidine-4-car
                         boxamide
SITE                    5
                        note = Amidated Phenylalanine
SEQUENCE: 89
FGLXF                                                                       5

SEQ ID NO: 90           moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-Tryptophan
SITE                    6
                        note = Azaglycine
SITE                    8
                        note =
                         4-amino-1-((3-fluoro-4-methylbenzyl)glycyl)piperidine-4-car
                         boxamide
SITE                    9
                        note = Amidated Phenylalanine
SEQUENCE: 90
YWNTFGLXF                                                                   9

SEQ ID NO: 91           moltype = AA  length = 9
FEATURE                 Location/Qualifiers
source                  1..9
                        mol_type = protein
                        organism = synthetic construct
SITE                    1
                        note = D-Tyrosine
SITE                    2
                        note = 3-(2-Naphthyl)alanine or
SITE                    6
                        note = Azaglycine
SITE                    8
                        note =
                         4-amino-1-((3-fluoro-4-methylbenzyl)glycyl)piperidine-4-car
                         boxamide
SITE                    9
                        note = Amidated Tryptophan
SEQUENCE: 91
YXNTFGLXW                                                                   9

SEQ ID NO: 92           moltype = AA  length = 9
FEATURE                 Location/Qualifiers
source                  1..9
                        mol_type = protein
                        organism = synthetic construct
SITE                    1
                        note = D-Tyrosine
SITE                    6
                        note = Azaglycine
SITE                    8
                        note =
                         4-amino-1-((3-fluoro-4-methylbenzyl)glycyl)piperidine-4-car
                         boxamide
SITE                    9
                        note = Amidated Tryptophan
SEQUENCE: 92
YRNTFGLXW                                                                   9

SEQ ID NO: 93           moltype = AA  length = 10
FEATURE                 Location/Qualifiers
source                  1..10
                        mol_type = protein
                        organism = synthetic construct
SITE                    1
```

```
                         note = D-Tyrosine
SITE                     2
                         note = D-Asparagine
SITE                     3
                         note = D-Arginine
SITE                     7
                         note = Azaglycine
SITE                     9
                         note =
                          4-amino-1-((3-fluoro-4-methylbenzyl)glycyl)piperidine-4-car
                          boxamide
SITE                     10
                         note = Amidated Tryptophan
SEQUENCE: 93
YNRNTFGLXW                                                    10

SEQ ID NO: 94            moltype = AA  length = 7
FEATURE                  Location/Qualifiers
source                   1..7
                         mol_type = protein
                         organism = synthetic construct
SITE                     1
                         note = D-Glutamic Acid
SITE                     2
                         note = D-Asparagine
SITE                     4
                         note = Azaglycine
SITE                     6
                         note =
                          4-amino-1-((3-fluoro-4-methylbenzyl)glycyl)piperidine-4-car
                          boxamide
SITE                     7
                         note = Amidated Tryptophan
SEQUENCE: 94
ENFGLXW                                                       7

SEQ ID NO: 95            moltype = AA  length = 9
FEATURE                  Location/Qualifiers
source                   1..9
                         mol_type = protein
                         organism = synthetic construct
SITE                     1
                         note = D-Tyrosine
SITE                     2
                         note = D-Alanine
SITE                     6
                         note = Azaglycine
SITE                     8
                         note =
                          4-amino-1-((3-fluoro-4-methylbenzyl)glycyl)piperidine-4-car
                          boxamide
SITE                     9
                         note = Amidated Tryptophan
SEQUENCE: 95
YANTFGLXW                                                     9

SEQ ID NO: 96            moltype = AA  length = 9
FEATURE                  Location/Qualifiers
source                   1..9
                         mol_type = protein
                         organism = synthetic construct
SITE                     1
                         note = D-Tyrosine
SITE                     2
                         note = Lysine bound to an optional linker and chelating
                          moiety or a radionuclide complex
SITE                     5
                         note = 3-Fluorophenylalanine
SITE                     6
                         note = Azaglycine
SITE                     8
                         note =
                          4-amino-1-((3-fluoro-4-methylbenzyl)glycyl)piperidine-4-car
                          boxamide
SITE                     9
                         note = Amidated Tryptophan
SEQUENCE: 96
YKNTFGLXW                                                     9
```

-continued

```
SEQ ID NO: 97           moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-Tryptophan
SITE                    6
                        note = Azaglycine
SITE                    8
                        note =
                         4-amino-1-(4-(3-fluoro-4-methylphenyl)butanoyl)piperidine-4
                         -carboxylic acid
SITE                    9
                        note = Amidated Tryptophan
SEQUENCE: 97
YWNTFGLXW                                                                 9

SEQ ID NO: 98           moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-Tryptophan
SITE                    6
                        note = Azaglycine
SITE                    8
                        note =
                         4-amino-1-(4-(p-tolyl)butanoyl)piperidine-4-carboxylic acid
SITE                    9
                        note = Amidated Tryptophan
SEQUENCE: 98
YWNTFGLXW                                                                 9

SEQ ID NO: 99           moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-Tryptophan
SITE                    6
                        note = Azaglycine
SITE                    8
                        note = 4-amino-1-(2-(p-tolyl)acetyl)piperidine-4-carboxylic
                         acid
SITE                    9
                        note = Amidated Tryptophan
SEQUENCE: 99
YWNTFGLXW                                                                 9

SEQ ID NO: 100          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-Tryptophan
SITE                    6
                        note = Azaglycine
SITE                    8
                        note =
                         4-amino-1-(2-(4-iodophenyl)acetyl)piperidine-4-carboxylic
                         acid
SITE                    9
                        note = Amidated Tryptophan
SEQUENCE: 100
YWNTFGLXW                                                                 9

SEQ ID NO: 101          moltype = AA  length = 9
```

-continued

```
FEATURE                Location/Qualifiers
source                 1..9
                       mol_type = protein
                       organism = synthetic construct
SITE                   1
                       note = D-Tyrosine
SITE                   2
                       note = D-Tryptophan
SITE                   6
                       note = Azaglycine
SITE                   8
                       note =
                        4-amino-1-((4-aminobenzyl)glycyl)piperidine-4-carboxylic
                        acid
SITE                   9
                       note = Amidated Tryptophan
SEQUENCE: 101
YWNTFGLXW                                                                    9

SEQ ID NO: 102         moltype = AA  length = 9
FEATURE                Location/Qualifiers
source                 1..9
                       mol_type = protein
                       organism = synthetic construct
SITE                   1
                       note = D-Tyrosine
SITE                   2
                       note = D-Tryptophan
SITE                   6
                       note = Azaglycine
SITE                   8
                       note =
                        4-amino-1-(2-amino-2-(3-fluoro-4-methylphenyl)acetyl)piperi
                        dine-4-carboxylic acid
SITE                   9
                       note = Amidated Tryptophan
SEQUENCE: 102
YWNTFGLXW                                                                    9

SEQ ID NO: 103         moltype = AA  length = 9
FEATURE                Location/Qualifiers
source                 1..9
                       mol_type = protein
                       organism = synthetic construct
SITE                   1
                       note = D-Tyrosine
SITE                   2
                       note = D-Tryptophan
SITE                   6
                       note = Azaglycine
SITE                   8
                       note =
                        4-amino-1-(N-(2-aminoethyl)-N-methylglycyl)piperidine-4-car
                        boxylic acid
SITE                   9
                       note = Amidated Tryptophan
SEQUENCE: 103
YWNTFGLXW                                                                    9

SEQ ID NO: 104         moltype = AA  length = 9
FEATURE                Location/Qualifiers
source                 1..9
                       mol_type = protein
                       organism = synthetic construct
SITE                   1
                       note = D-Tyrosine
SITE                   2
                       note = D-Tryptophan
SITE                   6
                       note = Azaglycine
SITE                   8
                       note =
                        4-amino-1-((4-cyclopropylbenzyl)glycyl)piperidine-4-carboxy
                        lic acid
SITE                   9
                       note = Amidated Tryptophan
SEQUENCE: 104
YWNTFGLXW                                                                    9
```

-continued

```
SEQ ID NO: 105          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-Tryptophan
SITE                    6
                        note = Azaglycine
SITE                    8
                        note =
                         4-amino-1-((4-ethylbenzyl)glycyl)piperidine-4-carboxylic
                         acid
SITE                    9
                        note = Amidated Tryptophan
SEQUENCE: 105
YWNTFGLXW                                                                   9

SEQ ID NO: 106          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-Tryptophan
SITE                    6
                        note = Azaglycine
SITE                    8
                        note =
                         4-amino-1-((4-hydroxybenzyl)glycyl)piperidine-4-carboxylic
                         acid
SITE                    9
                        note = Amidated Tryptophan
SEQUENCE: 106
YWNTFGLXW                                                                   9

SEQ ID NO: 107          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-Tryptophan
SITE                    6
                        note = Azaglycine
SITE                    8
                        note =
                         4-amino-1-((3,5-difluoro-4-hydroxybenzyl)glycyl)piperidine-
                         4-carboxylic acid
SITE                    9
                        note = Amidated Tryptophan
SEQUENCE: 107
YWNTFGLXW                                                                   9

SEQ ID NO: 108          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-Tryptophan
SITE                    6
                        note = Azaglycine
SITE                    8
                        note =
                         (R)-4-amino-1-((R)-(1-(3-fluoro-4-methylphenyl)ethyl)glycyl
                         )piperidine-4-carboxylic acid
SITE                    9
                        note = Amidated Tryptophan
SEQUENCE: 108
YWNTFGLXW                                                                   9
```

```
SEQ ID NO: 109          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-Tryptophan
SITE                    6
                        note = Azaglycine
SITE                    8
                        note =
                         4-amino-1-((3,4-dimethylbenzyl)glycyl)piperidine-4-carboxyl
                         ic acid
SITE                    9
                        note = Amidated Tryptophan
SEQUENCE: 109
YWNTFGLXW                                                                  9

SEQ ID NO: 110          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-Tryptophan
SITE                    6
                        note = Azaglycine
SITE                    8
                        note =
                         4-amino-1-((4-chloro-3-fluorobenzyl)glycyl)piperidine-4-car
                         boxylic acid
SITE                    9
                        note = Amidated Tryptophan
SEQUENCE: 110
YWNTFGLXW                                                                  9

SEQ ID NO: 111          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-Tryptophan
SITE                    6
                        note = Azaglycine
SITE                    8
                        note =
                         4-amino-1-((4-carboxybenzyl)glycyl)piperidine-4-carboxylic
                         acid
SITE                    9
                        note = Amidated Tryptophan
SEQUENCE: 111
YWNTFGLXW                                                                  9

SEQ ID NO: 112          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-Tryptophan
SITE                    6
                        note = Azaglycine
SITE                    8
                        note =
                         4-amino-1-((4-carboxy-2,3-difluorobenzyl)glycyl)piperidine-
                         4-carboxylic acid
SITE                    9
                        note = Amidated Tryptophan
SEQUENCE: 112
```

-continued

```
YWNTFGLXW                                                          9

SEQ ID NO: 113          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-Tryptophan
SITE                    6
                        note = Azaglycine
SITE                    8
                        note =
                         4-amino-1-((3-fluoro-4-methoxybenzyl)glycyl)piperidine-4-ca
                         rboxylic acid
SITE                    9
                        note = Amidated Tryptophan
SEQUENCE: 113
YWNTFGLXW                                                          9

SEQ ID NO: 114          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-Tryptophan
SITE                    6
                        note = Azaglycine
SITE                    8
                        note =
                         4-amino-1-((3-chloro-4-methylbenzyl)glycyl)piperidine-4-car
                         boxylic acid
SITE                    9
                        note = Amidated Tryptophan
SEQUENCE: 114
YWNTFGLXW                                                          9

SEQ ID NO: 115          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-Tryptophan
SITE                    6
                        note = Azaglycine
SITE                    8
                        note =
                         4-amino-1-((3,4,5-trifluorobenzyl)glycyl)piperidine-4-carbo
                         xylic acid
SITE                    9
                        note = Amidated Tryptophan
SEQUENCE: 115
YWNTFGLXW                                                          9

SEQ ID NO: 116          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-Tryptophan
SITE                    6
                        note = Azaglycine
SITE                    8
                        note =
                         4-amino-1-((4-(methylamino)benzyl)glycyl)piperidine-4-carbo
                         xylic acid
SITE                    9
                        note = Amidated Tryptophan
```

-continued

```
SEQUENCE: 116
YWNTFGLXW                                                           9

SEQ ID NO: 117          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-Tryptophan
SITE                    6
                        note = Azaglycine
SITE                    8
                        note =
                         (Z)-4-amino-1-(N'-((3-fluoro-4-methylbenzyl)carbamoyl)carba
                         mimidoyl)piperidine-4-carboxylic acid
SITE                    9
                        note = Amidated Tryptophan
SEQUENCE: 117
YWNTFGLXW                                                           9

SEQ ID NO: 118          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-Tryptophan
SITE                    6
                        note = Azaglycine
SITE                    8
                        note =
                         4-amino-1-((3-fluoro-4-methylbenzyl)glycyl)piperidine-4-car
                         boxylic acid
SITE                    9
                        note = Amidated Tryptophan
SEQUENCE: 118
YWNTFGLXW                                                           9

SEQ ID NO: 119          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-Tryptophan
SITE                    6
                        note = Azaglycine
SITE                    8
                        note =
                         4-amino-1-(N-methylcarbamimidoyl)piperidine-4-carboxylic
                         acid
SITE                    9
                        note = Amidated Tryptophan
SEQUENCE: 119
YWNTFGLXW                                                           9

SEQ ID NO: 120          moltype = AA  length = 5
FEATURE                 Location/Qualifiers
source                  1..5
                        mol_type = protein
                        organism = synthetic construct
SITE                    4
                        note =
                         4-amino-1-(N-methylcarbamimidoyl)piperidine-4-carboxylic
                         acid
SITE                    5
                        note = Amidated Tryptophan
SEQUENCE: 120
FGLXW                                                               5

SEQ ID NO: 121          moltype = AA  length = 7
FEATURE                 Location/Qualifiers
```

```
source                  1..7
                        mol_type = protein
                        organism = synthetic construct
SITE                    1
                        note = D-Tyrosine
SITE                    2
                        note = hydroxyproline
SITE                    5
                        note =
                         (S)-2-(4-((S)-1-amino-2-phenylethyl)-1H-1,2,3-triazol-1-yl)
                         -4-methylpentanoic acid
SITE                    6
                        note =
                         4-amino-1-((3-fluoro-4-methylbenzyl)glycyl)piperidine-4-car
                         boxamide
SITE                    7
                        note = Amidated Tryptophan
SEQUENCE: 121
YXNTXXW                                                                      7

SEQ ID NO: 122          moltype = AA  length = 7
FEATURE                 Location/Qualifiers
source                  1..7
                        mol_type = protein
                        organism = synthetic construct
SITE                    1
                        note = D-Asparagine
SITE                    4
                        note = Azaglycine
SITE                    6
                        note =
                         4-amino-1-((3-fluoro-4-methylbenzyl)glycyl)piperidine-4-car
                         boxamide
SITE                    7
                        note = Amidated Tryptophan
SEQUENCE: 122
NGFGLXW                                                                      7

SEQ ID NO: 123          moltype = AA  length = 7
FEATURE                 Location/Qualifiers
source                  1..7
                        mol_type = protein
                        organism = synthetic construct
SITE                    4
                        note = Azaglycine
SITE                    6
                        note =
                         4-amino-1-((3-fluoro-4-methylbenzyl)glycyl)piperidine-4-car
                         boxamide
SITE                    7
                        note = Amidated Tryptophan
SEQUENCE: 123
NGFGLXW                                                                      7

SEQ ID NO: 124          moltype = AA  length = 7
FEATURE                 Location/Qualifiers
source                  1..7
                        mol_type = protein
                        organism = synthetic construct
SITE                    1
                        note = D-Asparagine
SITE                    4
                        note = Azaglycine
SITE                    6
                        note =
                         4-amino-1-((3-fluoro-4-methylbenzyl)glycyl)piperidine-4-car
                         boxamide
SITE                    7
                        note = Amidated Tryptophan
SEQUENCE: 124
NTFGLXW                                                                      7

SEQ ID NO: 125          moltype = AA  length = 8
FEATURE                 Location/Qualifiers
source                  1..8
                        mol_type = protein
                        organism = synthetic construct
SITE                    1
                        note = D-Tryptophan
```

```
SITE                    5
                        note = Azaglycine
SITE                    7
                        note =
                         4-amino-1-((3-fluoro-4-methylbenzyl)glycyl)piperidine-4-car
                         boxamide
SITE                    8
                        note = Amidated Tryptophan
SEQUENCE: 125
WNTFGLXW                                                    8

SEQ ID NO: 126          moltype = AA  length = 6
FEATURE                 Location/Qualifiers
source                  1..6
                        mol_type = protein
                        organism = synthetic construct
SITE                    3
                        note = Azaglycine
SITE                    5
                        note =
                         4-amino-1-((3-fluoro-4-methylbenzyl)glycyl)piperidine-4-car
                         boxamide
SITE                    6
                        note = Amidated Tryptophan
SEQUENCE: 126
WFGLXW                                                      6

SEQ ID NO: 127          moltype = AA  length = 6
FEATURE                 Location/Qualifiers
source                  1..6
                        mol_type = protein
                        organism = synthetic construct
SITE                    1
                        note = (S)-2-amino-3-(pyridin-2-yl)propanoic acid
SITE                    3
                        note = Azaglycine
SITE                    5
                        note =
                         4-amino-1-((3-fluoro-4-methylbenzyl)glycyl)piperidine-4-car
                         boxamide
SITE                    6
                        note = Amidated Tryptophan
SEQUENCE: 127
XFGLXW                                                      6

SEQ ID NO: 128          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-Tryptophan
SITE                    6
                        note = Azaglycine
SITE                    8
                        note =
                         4-amino-1-((3-fluoro-4-methylbenzyl)glycyl)piperidine-4-car
                         boxamide
SITE                    9
                        note = Amidated 4-cyano phenylalanine
SEQUENCE: 128
YWNTFGLXF                                                   9

SEQ ID NO: 129          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-Tryptophan
SITE                    6
                        note = Azaglycine
SITE                    8
                        note =
                         4-amino-1-((3-fluoro-4-methylbenzyl)glycyl)piperidine-4-car
```

```
                       boxamide
SITE                   9
                       note = Amidated 3-(4-pyridyl)alanine
SEQUENCE: 129
YWNTFGLXX                                                     9

SEQ ID NO: 130         moltype = AA  length = 10
FEATURE                Location/Qualifiers
source                 1..10
                       mol_type = protein
                       organism = synthetic construct
SITE                   1
                       note = D-Tyrosine
SITE                   3
                       note = D-Tryptophan
SITE                   7
                       note = Azaglycine
SITE                   9
                       note =
                        4-amino-1-((3-fluoro-4-methylbenzyl)glycyl)piperidine-4-car
                        boxamide
SITE                   10
                       note = Amidated 3-(4-pyridyl)alanine
SEQUENCE: 130
YNWNTFGLXX                                                    10

SEQ ID NO: 131         moltype = AA  length = 10
FEATURE                Location/Qualifiers
source                 1..10
                       mol_type = protein
                       organism = synthetic construct
SITE                   1
                       note = D-Tyrosine
SITE                   2
                       note = D-Histidine
SITE                   3
                       note = D-Tryptophan
SITE                   7
                       note = Azaglycine
SITE                   9
                       note =
                        4-amino-1-((3-fluoro-4-methylbenzyl)glycyl)piperidine-4-car
                        boxamide
SITE                   10
                       note = Amidated 3-(4-pyridyl)alanine
SEQUENCE: 131
YHWNTFGLXX                                                    10

SEQ ID NO: 132         moltype = AA  length = 9
FEATURE                Location/Qualifiers
source                 1..9
                       mol_type = protein
                       organism = synthetic construct
SITE                   1
                       note = D-Tyrosine
SITE                   2
                       note = Azaglycine
SITE                   6
                       note = Azaglycine
SITE                   8
                       note =
                        4-amino-1-((3-fluoro-4-methylbenzyl)glycyl)piperidine-4-car
                        boxamide
SITE                   9
                       note = Amidated Tryptophan
SEQUENCE: 132
YGNTFGLXW                                                     9

SEQ ID NO: 133         moltype = AA  length = 9
FEATURE                Location/Qualifiers
source                 1..9
                       mol_type = protein
                       organism = synthetic construct
SITE                   1
                       note = D-Tyrosine
SITE                   2
                       note = D-Tryptophan
SITE                   6
                       note = Azaglycine
```

-continued

```
SITE                    8
                        note =
                         4-amino-1-((3-fluoro-4-methylbenzyl)glycyl)piperidine-4-car
                         boxamide
SITE                    9
                        note = Amidated Phenylalanine
SEQUENCE: 133
YWNAFGLXF                                                                   9

SEQ ID NO: 134          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-Tryptophan
SITE                    6
                        note = Azaglycine
SITE                    8
                        note =
                         4-amino-1-((3-fluoro-4-methylbenzyl)glycyl)piperidine-4-car
                         boxamide
SITE                    9
                        note = Amidated Leucine
SEQUENCE: 134
YWNAFGLXL                                                                   9

SEQ ID NO: 135          moltype =   length =
SEQUENCE: 135
000

SEQ ID NO: 136          moltype =   length =
SEQUENCE: 136
000

SEQ ID NO: 137          moltype =   length =
SEQUENCE: 137
000

SEQ ID NO: 138          moltype =   length =
SEQUENCE: 138
000

SEQ ID NO: 139          moltype =   length =
SEQUENCE: 139
000

SEQ ID NO: 140          moltype =   length =
SEQUENCE: 140
000

SEQ ID NO: 141          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-Tryptophan
SITE                    6
                        note = Azaglycine
SITE                    8
                        note =
                         4-amino-1-((4-methoxybenzyl)glycyl)piperidine-4-carboxylic
                         acid
SITE                    9
                        note = Amidated Phenylalanine
SEQUENCE: 141
YWNTFGLXF                                                                   9

SEQ ID NO: 142          moltype =   length =
SEQUENCE: 142
000

SEQ ID NO: 143          moltype =   length =
SEQUENCE: 143
```

-continued

```
000

SEQ ID NO: 144          moltype =   length =
SEQUENCE: 144
000

SEQ ID NO: 145          moltype =   length =
SEQUENCE: 145
000

SEQ ID NO: 146          moltype = AA  length = 10
FEATURE                 Location/Qualifiers
source                  1..10
                        mol_type = protein
                        organism = synthetic construct
SITE                    3
                        note = D-Tryptophan
SITE                    7
                        note = Azaglycine
SITE                    9
                        note =
                         4-amino-1-((3-fluoro-4-methylbenzyl)glycyl)piperidine-4-car
                         boxamide
SITE                    10
                        note = Amidated Tryptophan
SEQUENCE: 146
GYWNTFGLXW                                                                  10

SEQ ID NO: 147          moltype = AA  length = 7
FEATURE                 Location/Qualifiers
source                  1..7
                        mol_type = protein
                        organism = synthetic construct
SITE                    3
                        note = 3-Fluorophenylalanine
SITE                    4
                        note = Azaglycine
SITE                    6
                        note =
                         4-amino-1-((3-fluoro-4-methylbenzyl)glycyl)piperidine-4-car
                         boxamide
SITE                    7
                        note = Amidated Tryptophan
SEQUENCE: 147
NTFGLXW                                                                     7

SEQ ID NO: 148          moltype = AA  length = 8
FEATURE                 Location/Qualifiers
source                  1..8
                        mol_type = protein
                        organism = synthetic construct
SITE                    4
                        note = 3-Fluorophenylalanine
SITE                    5
                        note = Azaglycine
SITE                    7
                        note =
                         4-amino-1-((3-fluoro-4-methylbenzyl)glycyl)piperidine-4-car
                         boxamide
SITE                    8
                        note = Amidated Tryptophan
SEQUENCE: 148
ENTFGLXW                                                                    8

SEQ ID NO: 149          moltype = AA  length = 8
FEATURE                 Location/Qualifiers
source                  1..8
                        mol_type = protein
                        organism = synthetic construct
SITE                    1
                        note = D-Glutamic Acid
SITE                    4
                        note = 3-Fluorophenylalanine
SITE                    5
                        note = Azaglycine
SITE                    7
                        note =
                         4-amino-1-((3-fluoro-4-methylbenzyl)glycyl)piperidine-4-car
                         boxamide
```

```
SITE                    8
                        note = Amidated Tryptophan
SEQUENCE: 149
ENTFGLXW                                                                     8

SEQ ID NO: 150          moltype = AA  length = 8
FEATURE                 Location/Qualifiers
source                  1..8
                        mol_type = protein
                        organism = synthetic construct
SITE                    4
                        note = 3-Fluorophenylalanine
SITE                    5
                        note = Azaglycine
SITE                    7
                        note =
                         4-amino-1-((3-fluoro-4-methylbenzyl)glycyl)piperidine-4-car
                         boxamide
SITE                    8
                        note = Amidated Tryptophan
SEQUENCE: 150
KNTFGLXW                                                                     8

SEQ ID NO: 151          moltype = AA  length = 7
FEATURE                 Location/Qualifiers
source                  1..7
                        mol_type = protein
                        organism = synthetic construct
SITE                    3
                        note = 3-Fluorophenylalanine
SITE                    4
                        note = Azaglycine
SITE                    6
                        note =
                         4-amino-1-((3-fluoro-4-methylbenzyl)glycyl)piperidine-4-car
                         boxamide
SITE                    7
                        note = Amidated 3-(4-pyridyl)alanine
SEQUENCE: 151
NTFGLXX                                                                      7

SEQ ID NO: 152          moltype = AA  length = 8
FEATURE                 Location/Qualifiers
source                  1..8
                        mol_type = protein
                        organism = synthetic construct
SITE                    4
                        note = 3-Fluorophenylalanine
SITE                    5
                        note = Azaglycine
SITE                    7
                        note =
                         4-amino-1-((3-fluoro-4-methylbenzyl)glycyl)piperidine-4-car
                         boxamide
SITE                    8
                        note = Amidated 3-(4-pyridyl)alanine
SEQUENCE: 152
ENTFGLXX                                                                     8

SEQ ID NO: 153          moltype = AA  length = 5
FEATURE                 Location/Qualifiers
source                  1..5
                        mol_type = protein
                        organism = synthetic construct
SITE                    2
                        note = Azaglycine
SITE                    4
                        note =
                         4-amino-1-((3-fluoro-4-methylbenzyl)glycyl)piperidine-4-car
                         boxamide
SITE                    5
                        note = Amidated Tyrosine
SEQUENCE: 153
FGLXY                                                                        5

SEQ ID NO: 154          moltype = AA  length = 9
FEATURE                 Location/Qualifiers
source                  1..9
                        mol_type = protein
```

```
                        organism = synthetic construct
SITE                    1
                        note = D-Tyrosine
SITE                    2
                        note = D-Tryptophan
SITE                    6
                        note = Azaglycine
SITE                    7
                        note = (S)-2-aminopentanoic acid
SITE                    8
                        note =
                         4-amino-1-((3-fluoro-4-methylbenzyl)glycyl)piperidine-4-car
                         boxamide
SITE                    9
                        note = Amidated 3-(4-pyridyl)alanine
SEQUENCE: 154
YWNTFGXXX                                                                  9

SEQ ID NO: 155          moltype = AA  length = 9
FEATURE                 Location/Qualifiers
source                  1..9
                        mol_type = protein
                        organism = synthetic construct
SITE                    2
                        note = D-Tryptophan
SITE                    6
                        note = Azaglycine
SITE                    8
                        note = 4-amino-1-R1-piperidine-4-carboxylic acid
SITE                    9
                        note = Amidated Tryptophan
SEQUENCE: 155
YWNTFGLXW                                                                  9

SEQ ID NO: 156          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-Tryptophan
SITE                    6
                        note = Azaglycine
SITE                    8
                        note = 4-amino-1-R1-piperidine-4-carboxylic acid
SITE                    9
                        note = Amidated Tryptophan
SEQUENCE: 156
YWNTFGLXW                                                                  9

SEQ ID NO: 157          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-Tryptophan
SITE                    5
                        note = 3-Fluorophenylalanine
SITE                    6
                        note = Azaglycine
SITE                    8
                        note = 4-amino-1-R1-piperidine-4-carboxylic acid
SITE                    9
                        note = Amidated Tryptophan
SEQUENCE: 157
YWNTFGLXW                                                                  9

SEQ ID NO: 158          moltype = AA  length = 9
FEATURE                 Location/Qualifiers
source                  1..9
                        mol_type = protein
                        organism = synthetic construct
SITE                    2
                        note = D-Tryptophan
```

```
SITE                    5
                        note = 3-Fluorophenylalanine
SITE                    6
                        note = Azaglycine
SITE                    8
                        note = 4-amino-1-R1-piperidine-4-carboxylic acid
SITE                    9
                        note = Amidated Tryptophan
SEQUENCE: 158
YWNTFGLXW                                                                9

SEQ ID NO: 159          moltype = AA  length = 5
FEATURE                 Location/Qualifiers
source                  1..5
                        mol_type = protein
                        organism = synthetic construct
SITE                    2
                        note = Azaglycine
SITE                    4
                        note = 4-amino-1-R1-piperidine-4-carboxylic acid
SITE                    5
                        note = Amidated Tryptophan
SEQUENCE: 159
FGLXW                                                                    5

SEQ ID NO: 160          moltype = AA  length = 5
FEATURE                 Location/Qualifiers
source                  1..5
                        mol_type = protein
                        organism = synthetic construct
SITE                    2
                        note = Azaglycine
SITE                    3
                        note = D-Leucine
SITE                    4
                        note = 4-amino-1-R1-piperidine-4-carboxylic acid
SITE                    5
                        note = Amidated Tryptophan
SEQUENCE: 160
FGLXW                                                                    5

SEQ ID NO: 161          moltype = AA  length = 5
FEATURE                 Location/Qualifiers
source                  1..5
                        mol_type = protein
                        organism = synthetic construct
SITE                    2
                        note = Azaglycine
SITE                    4
                        note = 4-amino-1-R1-piperidine-4-carboxylic acid
SITE                    5
                        note = Me-Trp-NH2
SEQUENCE: 161
FGLXW                                                                    5

SEQ ID NO: 162          moltype = AA  length = 5
FEATURE                 Location/Qualifiers
source                  1..5
                        mol_type = protein
                        organism = synthetic construct
SITE                    4
                        note = 4-amino-1-R1-piperidine-4-carboxylic acid
SITE                    5
                        note = Amidated Tryptophan
SEQUENCE: 162
FGLXW                                                                    5

SEQ ID NO: 163          moltype = AA  length = 5
FEATURE                 Location/Qualifiers
source                  1..5
                        mol_type = protein
                        organism = synthetic construct
SITE                    3
                        note = Methyl-leucine
SITE                    4
                        note = 4-amino-1-R1-piperidine-4-carboxylic acid
SITE                    5
                        note = Amidated Tryptophan
SEQUENCE: 163
```

```
FGLXW                                                     5

SEQ ID NO: 164          moltype = AA  length = 5
FEATURE                 Location/Qualifiers
source                  1..5
                        mol_type = protein
                        organism = synthetic construct
SITE                    1
                        note = alpha-Me-Phenylalanine
SITE                    2
                        note = Azaglycine
SITE                    4
                        note = 4-amino-1-R1-piperidine-4-carboxylic acid
SITE                    5
                        note = Amidated Tryptophan
SEQUENCE: 164
FGLXW                                                     5

SEQ ID NO: 165          moltype = AA  length = 5
FEATURE                 Location/Qualifiers
source                  1..5
                        mol_type = protein
                        organism = synthetic construct
SITE                    2
                        note = Sarcosine
SITE                    4
                        note = 4-amino-1-R1-piperidine-4-carboxylic acid
SITE                    5
                        note = Amidated Tryptophan
SEQUENCE: 165
FGLXW                                                     5

SEQ ID NO: 166          moltype = AA  length = 5
FEATURE                 Location/Qualifiers
source                  1..5
                        mol_type = protein
                        organism = synthetic construct
SITE                    2
                        note = Sarcosine
SITE                    3
                        note = Methyl-leucine
SITE                    4
                        note = 4-amino-1-R1-piperidine-4-carboxylic acid
SITE                    5
                        note = Amidated Tryptophan
SEQUENCE: 166
FGLXW                                                     5

SEQ ID NO: 167          moltype = AA  length = 10
FEATURE                 Location/Qualifiers
source                  1..10
                        mol_type = protein
                        organism = synthetic construct
SITE                    7
                        note = Azaglycine
SITE                    9
                        note = 4-amino-1-R1-piperidine-4-carboxylic acid
SITE                    10
                        note = Amidated Tryptophan
SEQUENCE: 167
AAAAAFGLXW                                                10

SEQ ID NO: 168          moltype = AA  length = 10
FEATURE                 Location/Qualifiers
source                  1..10
                        mol_type = protein
                        organism = synthetic construct
SITE                    7
                        note = Azaglycine
SITE                    9
                        note = 4-amino-1-R1-piperidine-4-carboxylic acid
SITE                    10
                        note = Amidated Tryptophan
SEQUENCE: 168
NNNNNFGLXW                                                10

SEQ ID NO: 169          moltype = AA  length = 10
FEATURE                 Location/Qualifiers
source                  1..10
```

```
                        mol_type = protein
                        organism = synthetic construct
SITE                    7
                        note = Azaglycine
SITE                    9
                        note = 4-amino-1-R1-piperidine-4-carboxylic acid
SITE                    10
                        note = Amidated Tryptophan
SEQUENCE: 169
NNEENFGLXW                                                       10

SEQ ID NO: 170          moltype = AA  length = 10
FEATURE                 Location/Qualifiers
source                  1..10
                        mol_type = protein
                        organism = synthetic construct
SITE                    7
                        note = Azaglycine
SITE                    9
                        note = 4-amino-1-R1-piperidine-4-carboxylic acid
SITE                    10
                        note = Amidated Tryptophan
SEQUENCE: 170
NNKENFGLXW                                                       10

SEQ ID NO: 171          moltype = AA  length = 7
FEATURE                 Location/Qualifiers
source                  1..7
                        mol_type = protein
                        organism = synthetic construct
SITE                    1
                        note = Sarcosine
SITE                    2
                        note = Sarcosine
SITE                    4
                        note = Azaglycine
SITE                    6
                        note = 4-amino-1-R1-piperidine-4-carboxylic acid
SITE                    7
                        note = Amidated Tryptophan
SEQUENCE: 171
GGFGLXW                                                          7

SEQ ID NO: 172          moltype = AA  length = 7
FEATURE                 Location/Qualifiers
source                  1..7
                        mol_type = protein
                        organism = synthetic construct
SITE                    4
                        note = Azaglycine
SITE                    6
                        note = 4-amino-1-R1-piperidine-4-carboxylic acid
SITE                    7
                        note = Amidated Tryptophan
SEQUENCE: 172
NNFGLXW                                                          7

SEQ ID NO: 173          moltype = AA  length = 7
FEATURE                 Location/Qualifiers
source                  1..7
                        mol_type = protein
                        organism = synthetic construct
SITE                    4
                        note = Azaglycine
SITE                    6
                        note = 4-amino-1-R1-piperidine-4-carboxylic acid
SITE                    7
                        note = Amidated Tryptophan
SEQUENCE: 173
KNFGLXW                                                          7

SEQ ID NO: 174          moltype = AA  length = 8
FEATURE                 Location/Qualifiers
source                  1..8
                        mol_type = protein
                        organism = synthetic construct
SITE                    4
                        note = 3-Fluorophenylalanine
SITE                    5
```

-continued

```
                     note = Azaglycine
SITE                 7
                     note = 4-amino-1-R1-piperidine-4-carboxylic acid
SITE                 8
                     note = Amidated Tryptophan
SEQUENCE: 174
KNTFGLXW                                                     8

SEQ ID NO: 175       moltype = AA  length = 9
FEATURE              Location/Qualifiers
source               1..9
                     mol_type = protein
                     organism = synthetic construct
SITE                 6
                     note = Azaglycine
SITE                 8
                     note = 4-amino-1-R1-piperidine-4-carboxylic acid
SITE                 9
                     note = Amidated Tryptophan
SEQUENCE: 175
YPNTFGLXW                                                    9

SEQ ID NO: 176       moltype = AA  length = 6
FEATURE              Location/Qualifiers
source               1..6
                     mol_type = protein
                     organism = synthetic construct
SITE                 3
                     note = Azaglycine
SITE                 5
                     note = 4-amino-1-R1-piperidine-4-carboxylic acid
SITE                 6
                     note = Amidated Tryptophan
SEQUENCE: 176
NFGLXW                                                       6

SEQ ID NO: 177       moltype = AA  length = 9
FEATURE              Location/Qualifiers
source               1..9
                     mol_type = protein
                     organism = synthetic construct
SITE                 2
                     note = 3-(4-pyridyl)alanine
SITE                 6
                     note = Azaglycine
SITE                 8
                     note = 4-amino-1-R1-piperidine-4-carboxylic acid
SITE                 9
                     note = Amidated Tryptophan
SEQUENCE: 177
YXNTFGLXW                                                    9

SEQ ID NO: 178       moltype = AA  length = 9
FEATURE              Location/Qualifiers
source               1..9
                     mol_type = protein
                     organism = synthetic construct
SITE                 1
                     note = D-Tyrosine
SITE                 2
                     note = 3-(4-pyridyl)alanine
SITE                 6
                     note = Azaglycine
SITE                 8
                     note = 4-amino-1-R1-piperidine-4-carboxylic acid
SITE                 9
                     note = Amidated Tryptophan
SEQUENCE: 178
YXNTFGLXW                                                    9

SEQ ID NO: 179       moltype = AA  length = 9
FEATURE              Location/Qualifiers
source               1..9
                     mol_type = protein
                     organism = synthetic construct
SITE                 1
                     note = D-Tyrosine
SITE                 2
                     note = D-3-(4-pyridyl)alanine
```

-continued

```
SITE                    6
                        note = Azaglycine
SITE                    8
                        note = 4-amino-1-R1-piperidine-4-carboxylic acid
SITE                    9
                        note = Amidated Tryptophan
SEQUENCE: 179
YXNTFGLXW                                                                    9

SEQ ID NO: 180          moltype = AA  length = 8
FEATURE                 Location/Qualifiers
source                  1..8
                        mol_type = protein
                        organism = synthetic construct
SITE                    1
                        note = D-3-(4-pyridyl)alanine
SITE                    5
                        note = Azaglycine
SITE                    7
                        note = 4-amino-1-R1-piperidine-4-carboxylic acid
SITE                    8
                        note = Amidated Tryptophan
SEQUENCE: 180
XNTFGLXW                                                                     8

SEQ ID NO: 181          moltype = AA  length = 9
FEATURE                 Location/Qualifiers
source                  1..9
                        mol_type = protein
                        organism = synthetic construct
SITE                    1
                        note = D-Tyrosine
SITE                    5
                        note = 3-Fluorophenylalanine
SITE                    6
                        note = Azaglycine
SITE                    8
                        note = 4-amino-1-R1-piperidine-4-carboxylic acid
SITE                    9
                        note = Amidated Tryptophan
SEQUENCE: 181
YENTFGLXW                                                                    9

SEQ ID NO: 182          moltype = AA  length = 9
FEATURE                 Location/Qualifiers
source                  1..9
                        mol_type = protein
                        organism = synthetic construct
SITE                    5
                        note = 3-Fluorophenylalanine
SITE                    6
                        note = Azaglycine
SITE                    8
                        note = 4-amino-1-R1-piperidine-4-carboxylic acid
SITE                    9
                        note = Amidated Tryptophan
SEQUENCE: 182
YENTFGLXW                                                                    9

SEQ ID NO: 183          moltype = AA  length = 7
FEATURE                 Location/Qualifiers
source                  1..7
                        mol_type = protein
                        organism = synthetic construct
SITE                    1
                        note = D-Asparagine
SITE                    4
                        note = Azaglycine
SITE                    6
                        note = 4-amino-1-R1-piperidine-4-carboxylic acid
SITE                    7
                        note = Amidated Tryptophan
SEQUENCE: 183
NTFGLXW                                                                      7

SEQ ID NO: 184          moltype = AA  length = 7
FEATURE                 Location/Qualifiers
source                  1..7
                        mol_type = protein
```

```
                        organism = synthetic construct
SITE                    4
                        note = Azaglycine
SITE                    6
                        note = 4-amino-1-R1-piperidine-4-carboxylic acid
SITE                    7
                        note = Amidated Tryptophan
SEQUENCE: 184
NTFGLXW                                                                     7

SEQ ID NO: 185          moltype = AA  length = 7
FEATURE                 Location/Qualifiers
source                  1..7
                        mol_type = protein
                        organism = synthetic construct
SITE                    3
                        note = 3-Fluorophenylalanine
SITE                    4
                        note = Azaglycine
SITE                    6
                        note = 4-amino-1-R1-piperidine-4-carboxylic acid
SITE                    7
                        note = Amidated Tryptophan
SEQUENCE: 185
NTFGLXW                                                                     7

SEQ ID NO: 186          moltype = AA  length = 9
FEATURE                 Location/Qualifiers
source                  1..9
                        mol_type = protein
                        organism = synthetic construct
SITE                    5
                        note = 3-Fluorophenylalanine
SITE                    6
                        note = Azaglycine
SITE                    8
                        note = 4-amino-1-R1-piperidine-4-carboxylic acid
SITE                    9
                        note = Amidated Tryptophan
SEQUENCE: 186
YKNTFGLXW                                                                   9

SEQ ID NO: 187          moltype = AA  length = 8
FEATURE                 Location/Qualifiers
source                  1..8
                        mol_type = protein
                        organism = synthetic construct
SITE                    1
                        note = D-Tryptophan
SITE                    4
                        note = 3-Fluorophenylalanine
SITE                    5
                        note = Azaglycine
SITE                    7
                        note = 4-amino-1-R1-piperidine-4-carboxylic acid
SITE                    8
                        note = Amidated Tryptophan
SEQUENCE: 187
WNTFGLXW                                                                    8

SEQ ID NO: 188          moltype = AA  length = 8
FEATURE                 Location/Qualifiers
source                  1..8
                        mol_type = protein
                        organism = synthetic construct
SITE                    5
                        note = Azaglycine
SITE                    7
                        note = 4-amino-1-R1-piperidine-4-carboxylic acid
SITE                    8
                        note = Amidated Tryptophan
SEQUENCE: 188
WNTFGLXW                                                                    8

SEQ ID NO: 189          moltype = AA  length = 10
FEATURE                 Location/Qualifiers
source                  1..10
                        mol_type = protein
                        organism = synthetic construct
```

```
SITE                    7
                        note = Azaglycine
SITE                    9
                        note = 4-amino-1-R1-piperidine-4-carboxylic acid
SITE                    10
                        note = Amidated Tryptophan
SEQUENCE: 189
YHWNTFGLXW                                                  10

SEQ ID NO: 190          moltype = AA  length = 10
FEATURE                 Location/Qualifiers
source                  1..10
                        mol_type = protein
                        organism = synthetic construct
SITE                    1
                        note = D-Tyrosine
SITE                    7
                        note = Azaglycine
SITE                    9
                        note = 4-amino-1-R1-piperidine-4-carboxylic acid
SITE                    10
                        note = Amidated Tryptophan
SEQUENCE: 190
YHWNTFGLXW                                                  10

SEQ ID NO: 191          moltype = AA  length = 9
FEATURE                 Location/Qualifiers
source                  1..9
                        mol_type = protein
                        organism = synthetic construct
SITE                    1
                        note = Sarcosine
SITE                    2
                        note = Sarcosine
SITE                    3
                        note = Sarcosine
SITE                    4
                        note = Sarcosine
SITE                    8
                        note = 4-amino-1-R1-piperidine-4-carboxylic acid
SITE                    9
                        note = Amidated Tryptophan
SEQUENCE: 191
GGGGFGLXW                                                   9

SEQ ID NO: 192          moltype = AA  length = 5
FEATURE                 Location/Qualifiers
source                  1..5
                        mol_type = protein
                        organism = synthetic construct
SITE                    2
                        note = Azaglycine
SITE                    4
                        note = 4-amino-1-R1-piperidine-4-carboxylic acid
SITE                    5
                        note = Amidated Tryptophan
SEQUENCE: 192
YGLXW                                                       5

SEQ ID NO: 193          moltype =   length =
SEQUENCE: 193
000

SEQ ID NO: 194          moltype = AA  length = 8
FEATURE                 Location/Qualifiers
source                  1..8
                        mol_type = protein
                        organism = synthetic construct
SITE                    1
                        note = Sarcosine
SITE                    2
                        note = Sarcosine
SITE                    3
                        note = Sarcosine
SITE                    4
                        note = Sarcosine
SITE                    5
                        note = Sarcosine
SITE                    7
```

```
                        note = 4-amino-1-R1-piperidine-4-carboxylic acid
SITE                    8
                        note = Amidated Tryptophan
SEQUENCE: 194
GGGGGFXW                                                                   8

SEQ ID NO: 195          moltype = AA  length = 8
FEATURE                 Location/Qualifiers
source                  1..8
                        mol_type = protein
                        organism = synthetic construct
SITE                    1
                        note = Sarcosine
SITE                    2
                        note = Sarcosine
SITE                    3
                        note = Sarcosine
SITE                    4
                        note = Sarcosine
SITE                    5
                        note = Sarcosine
SITE                    6
                        note = phenylglycine
SITE                    7
                        note = 4-amino-1-R1-piperidine-4-carboxylic acid
SITE                    8
                        note = Amidated Tryptophan
SEQUENCE: 195
GGGGGGXW                                                                   8

SEQ ID NO: 196          moltype =   length =
SEQUENCE: 196
000

SEQ ID NO: 197          moltype = AA  length = 5
FEATURE                 Location/Qualifiers
source                  1..5
                        mol_type = protein
                        organism = synthetic construct
SITE                    2
                        note = Azaglycine
SITE                    4
                        note = 4-amino-1-R1-piperidine-4-carboxylic acid
SITE                    5
                        note = Amidated Phenylalanine
SEQUENCE: 197
FGLXF                                                                      5

SEQ ID NO: 198          moltype = AA  length = 9
FEATURE                 Location/Qualifiers
source                  1..9
                        mol_type = protein
                        organism = synthetic construct
SITE                    2
                        note = D-Tryptophan
SITE                    5
                        note = 3-Fluorophenylalanine
SITE                    6
                        note = Azaglycine
SITE                    8
                        note = 4-amino-1-R1-piperidine-4-carboxylic acid
SITE                    9
                        note = Amidated Phenylalanine
SEQUENCE: 198
YWNTFGLXF                                                                  9

SEQ ID NO: 199          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-Tryptophan
SITE                    6
                        note = Azaglycine
SITE                    8
                        note = 4-amino-1-R1-piperidine-4-carboxylic acid
```

```
SITE                    9
                        note = Amidated Phenylalanine
SEQUENCE: 199
YWNTFGLXF                                                                 9

SEQ ID NO: 200          moltype = AA  length = 9
FEATURE                 Location/Qualifiers
source                  1..9
                        mol_type = protein
                        organism = synthetic construct
SITE                    6
                        note = Azaglycine
SITE                    8
                        note = 4-amino-1-R1-piperidine-4-carboxylic acid
SITE                    9
                        note = Amidated 4-cyano phenylalanine
SEQUENCE: 200
YWNTFGLXF                                                                 9

SEQ ID NO: 201          moltype = AA  length = 8
FEATURE                 Location/Qualifiers
source                  1..8
                        mol_type = protein
                        organism = synthetic construct
SITE                    5
                        note = Azaglycine
SITE                    7
                        note = 4-amino-1-R1-piperidine-4-carboxylic acid
SITE                    8
                        note = Amidated Phenylalanine
SEQUENCE: 201
ENTFGLXF                                                                  8

SEQ ID NO: 202          moltype = AA  length = 8
FEATURE                 Location/Qualifiers
source                  1..8
                        mol_type = protein
                        organism = synthetic construct
SITE                    5
                        note = Azaglycine
SITE                    7
                        note = 4-amino-1-R1-piperidine-4-carboxylic acid
SITE                    8
                        note = Amidated 4-cyano phenylalanine
SEQUENCE: 202
ENTFGLXF                                                                  8

SEQ ID NO: 203          moltype = AA  length = 8
FEATURE                 Location/Qualifiers
source                  1..8
                        mol_type = protein
                        organism = synthetic construct
SITE                    1
                        note = D-Glutamic Acid
SITE                    5
                        note = Azaglycine
SITE                    7
                        note = 4-amino-1-R1-piperidine-4-carboxylic acid
SITE                    8
                        note = Amidated 4-cyano phenylalanine
SEQUENCE: 203
ENTFGLXF                                                                  8

SEQ ID NO: 204          moltype = AA  length = 7
FEATURE                 Location/Qualifiers
source                  1..7
                        mol_type = protein
                        organism = synthetic construct
SITE                    4
                        note = Azaglycine
SITE                    6
                        note = 4-amino-1-R1-piperidine-4-carboxylic acid
SITE                    7
                        note = Amidated Phenylalanine
SEQUENCE: 204
NTFGLXF                                                                   7

SEQ ID NO: 205          moltype = AA  length = 7
FEATURE                 Location/Qualifiers
```

```
source                  1..7
                        mol_type = protein
                        organism = synthetic construct
SITE                    4
                        note = Azaglycine
SITE                    6
                        note = 4-amino-1-R1-piperidine-4-carboxylic acid
SITE                    7
                        note = Amidated 4-cyano phenylalanine
SEQUENCE: 205
NTFGLXF                                                              7

SEQ ID NO: 206          moltype = AA  length = 5
FEATURE                 Location/Qualifiers
source                  1..5
                        mol_type = protein
                        organism = synthetic construct
SITE                    2
                        note = Azaglycine
SITE                    4
                        note = 4-amino-1-R1-piperidine-4-carboxylic acid
SITE                    5
                        note = Amidated 4-cyano phenylalanine
SEQUENCE: 206
FGLXF                                                                5

SEQ ID NO: 207          moltype = AA  length = 9
FEATURE                 Location/Qualifiers
source                  1..9
                        mol_type = protein
                        organism = synthetic construct
SITE                    1
                        note = D-Tyrosine
SITE                    6
                        note = Azaglycine
SITE                    8
                        note = 4-amino-1-R1-piperidine-4-carboxylic acid
SITE                    9
                        note = Amidated Phenylalanine
SEQUENCE: 207
YWNAFGLXF                                                            9

SEQ ID NO: 208          moltype = AA  length = 9
FEATURE                 Location/Qualifiers
source                  1..9
                        mol_type = protein
                        organism = synthetic construct
SITE                    2
                        note = D-3-(2-naphthyl)-alanine
SITE                    6
                        note = Azaglycine
SITE                    8
                        note = 4-amino-1-R1-piperidine-4-carboxylic acid
SITE                    9
                        note = Amidated Phenylalanine
SEQUENCE: 208
YXNTFGLXF                                                            9

SEQ ID NO: 209          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-3-(2-naphthyl)-alanine
SITE                    6
                        note = Azaglycine
SITE                    8
                        note = 4-amino-1-R1-piperidine-4-carboxylic acid
SITE                    9
                        note = Amidated Phenylalanine
SEQUENCE: 209
YXNTFGLXF                                                            9

SEQ ID NO: 210          moltype = AA  length = 9
FEATURE                 Location/Qualifiers
source                  1..9
```

```
                       mol_type = protein
                       organism = synthetic construct
SITE                   1
                       note = D-Tyrosine
SITE                   2
                       note = D-3-(2-naphthyl)-alanine
SITE                   6
                       note = Azaglycine
SITE                   8
                       note = 4-amino-1-R1-piperidine-4-carboxylic acid
SITE                   9
                       note = Amidated Phenylalanine
SEQUENCE: 210
YXNTFGLXF                                                   9

SEQ ID NO: 211         moltype = AA  length = 8
FEATURE                Location/Qualifiers
source                 1..8
                       mol_type = protein
                       organism = synthetic construct
SITE                   1
                       note = 3-(2-naphthyl)alanine
SITE                   5
                       note = Azaglycine
SITE                   7
                       note = 4-amino-1-R1-piperidine-4-carboxylic acid
SITE                   8
                       note = Amidated Phenylalanine
SEQUENCE: 211
XNTFGLXF                                                    8

SEQ ID NO: 212         moltype = AA  length = 9
FEATURE                Location/Qualifiers
source                 1..9
                       mol_type = protein
                       organism = synthetic construct
SITE                   1
                       note = D-Tyrosine
SITE                   2
                       note = 3-(2-naphthyl)alanine
SITE                   6
                       note = Azaglycine
SITE                   8
                       note = 4-amino-1-R1-piperidine-4-carboxylic acid
SITE                   9
                       note = Amidated 4-cyano phenylalanine
SEQUENCE: 212
YXNTFGLXF                                                   9

SEQ ID NO: 213         moltype = AA  length = 8
FEATURE                Location/Qualifiers
source                 1..8
                       mol_type = protein
                       organism = synthetic construct
SITE                   7
                       note = 4-amino-1-R1-piperidine-4-carboxylic acid
SITE                   8
                       note = Amidated Phenylalanine
SEQUENCE: 213
TNRNFLXF                                                    8

SEQ ID NO: 214         moltype = AA  length = 9
FEATURE                Location/Qualifiers
source                 1..9
                       mol_type = protein
                       organism = synthetic construct
SITE                   1
                       note = D-Tyrosine
SITE                   2
                       note = 3-(2-naphthyl)alanine
SITE                   6
                       note = Azaglycine
SITE                   8
                       note = 4-amino-1-R1-piperidine-4-carboxylic acid
SITE                   9
                       note = Amidated Tryptophan
SEQUENCE: 214
YXNTFGLXW                                                   9
```

-continued

```
SEQ ID NO: 215          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-3-(2-naphthyl)-alanine
SITE                    6
                        note = Azaglycine
SITE                    8
                        note = 4-amino-1-R1-piperidine-4-carboxylic acid
SITE                    9
                        note = Amidated Tryptophan
SEQUENCE: 215
YXNTFGLXW                                                             9

SEQ ID NO: 216          moltype = AA  length = 9
FEATURE                 Location/Qualifiers
source                  1..9
                        mol_type = protein
                        organism = synthetic construct
SITE                    1
                        note = D-Tyrosine
SITE                    6
                        note = Azaglycine
SITE                    8
                        note = 4-amino-1-R1-piperidine-4-carboxylic acid
SITE                    9
                        note = Amidated Tryptophan
SEQUENCE: 216
YRNTFGLXW                                                             9

SEQ ID NO: 217          moltype = AA  length = 10
FEATURE                 Location/Qualifiers
source                  1..10
                        mol_type = protein
                        organism = synthetic construct
SITE                    1
                        note = D-Tyrosine
SITE                    7
                        note = Azaglycine
SITE                    9
                        note = 4-amino-1-R1-piperidine-4-carboxylic acid
SITE                    10
                        note = Amidated Tryptophan
SEQUENCE: 217
YNRNTFGLXW                                                            10

SEQ ID NO: 218          moltype = AA  length = 10
FEATURE                 Location/Qualifiers
source                  1..10
                        mol_type = protein
                        organism = synthetic construct
SITE                    1
                        note = Sarcosine
SITE                    2
                        note = Sarcosine
SITE                    3
                        note = Sarcosine
SITE                    4
                        note = Sarcosine
SITE                    5
                        note = Sarcosine
SITE                    7
                        note = Azaglycine
SITE                    9
                        note = 4-amino-1-R1-piperidine-4-carboxylic acid
SITE                    10
                        note = Amidated Tryptophan
SEQUENCE: 218
GGGGGFGLXW                                                            10

SEQ ID NO: 219          moltype = AA  length = 7
FEATURE                 Location/Qualifiers
source                  1..7
                        mol_type = protein
                        organism = synthetic construct
```

```
SITE                    4
                        note = Azaglycine
SITE                    6
                        note = 4-amino-1-R1-piperidine-4-carboxylic acid
SITE                    7
                        note = Amidated Tryptophan
SEQUENCE: 219
ENFGLXW                                                                     7

SEQ ID NO: 220          moltype = AA  length = 8
FEATURE                 Location/Qualifiers
source                  1..8
                        mol_type = protein
                        organism = synthetic construct
SITE                    5
                        note = Azaglycine
SITE                    7
                        note = 4-amino-1-R1-piperidine-4-carboxylic acid
SITE                    8
                        note = Amidated Tryptophan
SEQUENCE: 220
ENTFGLXW                                                                    8

SEQ ID NO: 221          moltype = AA  length = 8
FEATURE                 Location/Qualifiers
source                  1..8
                        mol_type = protein
                        organism = synthetic construct
SITE                    4
                        note = 3-Fluorophenylalanine
SITE                    5
                        note = Azaglycine
SITE                    7
                        note = 4-amino-1-R1-piperidine-4-carboxylic acid
SITE                    8
                        note = Amidated Tryptophan
SEQUENCE: 221
ENTFGLXW                                                                    8

SEQ ID NO: 222          moltype = AA  length = 8
FEATURE                 Location/Qualifiers
source                  1..8
                        mol_type = protein
                        organism = synthetic construct
SITE                    1
                        note = D-Glutamic Acid
SITE                    4
                        note = 3-Fluorophenylalanine
SITE                    5
                        note = Azaglycine
SITE                    7
                        note = 4-amino-1-R1-piperidine-4-carboxylic acid
SITE                    8
                        note = Amidated Tryptophan
SEQUENCE: 222
ENTFGLXW                                                                    8

SEQ ID NO: 223          moltype = AA  length = 9
FEATURE                 Location/Qualifiers
source                  1..9
                        mol_type = protein
                        organism = synthetic construct
SITE                    1
                        note = D-Tyrosine
SITE                    6
                        note = Azaglycine
SITE                    8
                        note = 4-amino-1-R1-piperidine-4-carboxylic acid
SITE                    9
                        note = Amidated Tryptophan
SEQUENCE: 223
YANTFGLXW                                                                   9

SEQ ID NO: 224          moltype = AA  length = 9
FEATURE                 Location/Qualifiers
source                  1..9
                        mol_type = protein
                        organism = synthetic construct
SITE                    1
```

```
                        note = D-Tyrosine
SITE                    6
                        note = Azaglycine
SITE                    8
                        note = 4-amino-1-R1-piperidine-4-carboxylic acid
SITE                    9
                        note = Amidated Tryptophan
SEQUENCE: 224
YPNTFGLXW                                                   9

SEQ ID NO: 225          moltype = AA  length = 7
FEATURE                 Location/Qualifiers
source                  1..7
                        mol_type = protein
                        organism = synthetic construct
SITE                    1
                        note = D-Asparagine
SITE                    4
                        note = Azaglycine
SITE                    6
                        note = 4-amino-1-R1-piperidine-4-carboxylic acid
SITE                    7
                        note = Amidated Tryptophan
SEQUENCE: 225
NGFGLXW                                                     7

SEQ ID NO: 226          moltype = AA  length = 7
FEATURE                 Location/Qualifiers
source                  1..7
                        mol_type = protein
                        organism = synthetic construct
SITE                    4
                        note = Azaglycine
SITE                    6
                        note = 4-amino-1-R1-piperidine-4-carboxylic acid
SITE                    7
                        note = Amidated Tryptophan
SEQUENCE: 226
NGFGLXW                                                     7

SEQ ID NO: 227          moltype = AA  length = 6
FEATURE                 Location/Qualifiers
source                  1..6
                        mol_type = protein
                        organism = synthetic construct
SITE                    3
                        note = Azaglycine
SITE                    5
                        note = 4-amino-1-R1-piperidine-4-carboxylic acid
SITE                    6
                        note = Amidated Tryptophan
SEQUENCE: 227
WFGLXW                                                      6

SEQ ID NO: 228          moltype = AA  length = 6
FEATURE                 Location/Qualifiers
source                  1..6
                        mol_type = protein
                        organism = synthetic construct
SITE                    1
                        note = 2-Pal
SITE                    3
                        note = Azaglycine
SITE                    5
                        note = 4-amino-1-R1-piperidine-4-carboxylic acid
SITE                    6
                        note = Amidated Tryptophan
SEQUENCE: 228
XFGLXW                                                      6

SEQ ID NO: 229          moltype = AA  length = 9
FEATURE                 Location/Qualifiers
source                  1..9
                        mol_type = protein
                        organism = synthetic construct
SITE                    2
                        note = Azaglycine
SITE                    6
                        note = Azaglycine
```

-continued

```
SITE                    8
                        note = 4-amino-1-R1-piperidine-4-carboxylic acid
SITE                    9
                        note = Amidated Tryptophan
SEQUENCE: 229
YGNTFGLXW                                                   9

SEQ ID NO: 230          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-Tryptophan
SITE                    6
                        note = Azaglycine
SITE                    8
                        note = 4-amino-1-R1-piperidine-4-carboxylic acid
SITE                    9
                        note = Amidated Leucine
SEQUENCE: 230
YWNAFGLXL                                                   9

SEQ ID NO: 231          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-Tryptophan
SITE                    6
                        note = Azaglycine
SITE                    8
                        note = 4-amino-1-R1-piperidine-4-carboxylic acid
SITE                    9
                        note = Amidated 3-(4-pyridyl)alanine
SEQUENCE: 231
YWNTFGLXX                                                   9

SEQ ID NO: 232          moltype = AA  length = 10
FEATURE                 Location/Qualifiers
source                  1..10
                        mol_type = protein
                        organism = synthetic construct
SITE                    1
                        note = D-Tyrosine
SITE                    3
                        note = D-Tryptophan
SITE                    7
                        note = Azaglycine
SITE                    9
                        note = 4-amino-1-R1-piperidine-4-carboxylic acid
SITE                    10
                        note = Amidated 3-(4-pyridyl)alanine
SEQUENCE: 232
YNWNTFGLXX                                                  10

SEQ ID NO: 233          moltype = AA  length = 10
FEATURE                 Location/Qualifiers
source                  1..10
                        mol_type = protein
                        organism = synthetic construct
SITE                    1
                        note = D-Tyrosine
SITE                    3
                        note = D-Tryptophan
SITE                    7
                        note = Azaglycine
SITE                    9
                        note = 4-amino-1-R1-piperidine-4-carboxylic acid
SITE                    10
                        note = Amidated 3-(4-pyridyl)alanine
SEQUENCE: 233
YHWNTFGLXX                                                  10
```

```
SEQ ID NO: 234          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = 4-iodophenylalanine
SITE                    5
                        note = 4-iodophenylalanine
SITE                    6
                        note = Azaglycine
SITE                    8
                        note = 4-amino-1-R1-piperidine-4-carboxylic acid
SITE                    9
                        note = Amidated 3-(4-pyridyl)alanine
SEQUENCE: 234
YFNTFGLXX                                                                9

SEQ ID NO: 235          moltype = AA  length = 10
FEATURE                 Location/Qualifiers
source                  1..10
                        mol_type = protein
                        organism = synthetic construct
SITE                    1
                        note = D-Tyrosine
SITE                    3
                        note = D-Tryptophan
SITE                    7
                        note = Azaglycine
SITE                    9
                        note = 4-amino-1-R1-piperidine-4-carboxylic acid
SITE                    10
                        note = Amidated 3-(4-pyridyl)alanine
SEQUENCE: 235
YNWNTFGLXX                                                               10

SEQ ID NO: 236          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = (S)-2-amino-3-(anthracen-9-yl)propanoic acid
SITE                    6
                        note = Azaglycine
SITE                    7
                        note = Norleucine
SITE                    8
                        note = 4-amino-1-R1-piperidine-4-carboxylic acid
SITE                    9
                        note = Amidated 3-(4-pyridyl)alanine
SEQUENCE: 236
YXNTFGXXX                                                                9

SEQ ID NO: 237          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = (S)-2-amino-3-(anthracen-9-yl)propanoic acid
SITE                    6
                        note = Azaglycine
SITE                    8
                        note = 4-amino-1-R1-piperidine-4-carboxylic acid
SITE                    9
                        note = Amidated 3-(4-pyridyl)alanine
SEQUENCE: 237
YXNTFGLXX                                                                9

SEQ ID NO: 238          moltype = AA  length = 8
FEATURE                 Location/Qualifiers
source                  1..8
```

```
                         mol_type = protein
                         organism = synthetic construct
SITE                     1
                         note = D-Tyrosine
SITE                     5
                         note = Azaglycine
SITE                     7
                         note = 4-amino-1-R1-piperidine-4-carboxylic acid
SITE                     8
                         note = Amidated 3-(4-pyridyl)alanine
SEQUENCE: 238
YNTFGLXX                                                    8

SEQ ID NO: 239           moltype = AA  length = 8
FEATURE                  Location/Qualifiers
source                   1..8
                         mol_type = protein
                         organism = synthetic construct
SITE                     1
                         note = 3-(9-anthryl)-alanine
SITE                     5
                         note = Azaglycine
SITE                     7
                         note = 4-amino-1-R1-piperidine-4-carboxylic acid
SITE                     8
                         note = Amidated 3-(4-pyridyl)alanine
SEQUENCE: 239
XNTFGLXX                                                    8

SEQ ID NO: 240           moltype = AA  length = 9
FEATURE                  Location/Qualifiers
source                   1..9
                         mol_type = protein
                         organism = synthetic construct
SITE                     1
                         note = D-Tyrosine
SITE                     2
                         note = 3-(9-anthryl)-alanine
SITE                     5
                         note = 4-iodophenylalanine
SITE                     6
                         note = Azaglycine
SITE                     8
                         note = 4-amino-1-R1-piperidine-4-carboxylic acid
SITE                     9
                         note = Amidated 3-(4-pyridyl)alanine
SEQUENCE: 240
YXNTFGLXX                                                   9

SEQ ID NO: 241           moltype = AA  length = 7
FEATURE                  Location/Qualifiers
source                   1..7
                         mol_type = protein
                         organism = synthetic construct
SITE                     4
                         note = Azaglycine
SITE                     6
                         note = 4-amino-1-R1-piperidine-4-carboxylic acid
SITE                     7
                         note = Amidated 3-(4-pyridyl)alanine
SEQUENCE: 241
NTFGLXX                                                     7

SEQ ID NO: 242           moltype = AA  length = 7
FEATURE                  Location/Qualifiers
source                   1..7
                         mol_type = protein
                         organism = synthetic construct
SITE                     3
                         note = 3-Fluorophenylalanine
SITE                     4
                         note = Azaglycine
SITE                     6
                         note = 4-amino-1-R1-piperidine-4-carboxylic acid
SITE                     7
                         note = Amidated 3-(4-pyridyl)alanine
SEQUENCE: 242
NTFGLXX                                                     7
```

-continued

```
SEQ ID NO: 243          moltype = AA  length = 8
FEATURE                 Location/Qualifiers
source                  1..8
                        mol_type = protein
                        organism = synthetic construct
SITE                    4
                        note = 3-Fluorophenylalanine
SITE                    5
                        note = Azaglycine
SITE                    7
                        note = 4-amino-1-R1-piperidine-4-carboxylic acid
SITE                    8
                        note = Amidated 3-(4-pyridyl)alanine
SEQUENCE: 243
ENTFGLXX                                                      8

SEQ ID NO: 244          moltype = AA  length = 9
FEATURE                 Location/Qualifiers
source                  1..9
                        mol_type = protein
                        organism = synthetic construct
SITE                    6
                        note = Azaglycine
SITE                    7
                        note = Nva
SITE                    8
                        note = 4-amino-1-R1-piperidine-4-carboxylic acid
SITE                    9
                        note = Amidated 3-(4-pyridyl)alanine
SEQUENCE: 244
YWNTFGXXX                                                     9

SEQ ID NO: 245          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-Tryptophan
SITE                    6
                        note = Azaglycine
SITE                    7
                        note = Nva
SITE                    8
                        note = 4-amino-1-R1-piperidine-4-carboxylic acid
SITE                    9
                        note = Amidated 3-(4-pyridyl)alanine
SEQUENCE: 245
YWNTFGXXX                                                     9

SEQ ID NO: 246          moltype = AA  length = 9
FEATURE                 Location/Qualifiers
source                  1..9
                        mol_type = protein
                        organism = synthetic construct
SITE                    2
                        note = 3-(2-naphthyl)alanine
SITE                    6
                        note = Azaglycine
SITE                    8
                        note = 4-amino-1-R1-piperidine-4-carboxylic acid
SITE                    9
                        note = Amidated 3-(4-pyridyl)alanine
SEQUENCE: 246
YXNTFGLXX                                                     9

SEQ ID NO: 247          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = 3-(2-naphthyl)alanine
SITE                    6
                        note = Azaglycine
```

```
SITE                  8
                      note = 4-amino-1-R1-piperidine-4-carboxylic acid
SITE                  9
                      note = Amidated 3-(4-pyridyl)alanine
SEQUENCE: 247
YXNTFGLXX                                                                    9

SEQ ID NO: 248        moltype = AA  length = 8
FEATURE               Location/Qualifiers
source                1..8
                      mol_type = protein
                      organism = synthetic construct
SITE                  1
                      note = 3-(2-naphthyl)alanine
SITE                  5
                      note = Azaglycine
SITE                  7
                      note = 4-amino-1-R1-piperidine-4-carboxylic acid
SITE                  8
                      note = Amidated 3-(4-pyridyl)alanine
SEQUENCE: 248
XNTFGLXX                                                                     8

SEQ ID NO: 249        moltype = AA  length = 9
FEATURE               Location/Qualifiers
source                1..9
                      mol_type = protein
                      organism = synthetic construct
SITE                  1
                      note = D-Tyrosine
SITE                  2
                      note = 3-(4-pyridyl)alanine
SITE                  6
                      note = Azaglycine
SITE                  8
                      note = 4-amino-1-R1-piperidine-4-carboxylic acid
SITE                  9
                      note = Amidated 3-(4-pyridyl)alanine
SEQUENCE: 249
YXNTFGLXX                                                                    9

SEQ ID NO: 250        moltype = AA  length = 9
FEATURE               Location/Qualifiers
source                1..9
                      mol_type = protein
                      organism = synthetic construct
SITE                  1
                      note = D-Tyrosine
SITE                  2
                      note = D-3-(4-pyridyl)alanine
SITE                  6
                      note = Azaglycine
SITE                  8
                      note = 4-amino-1-R1-piperidine-4-carboxylic acid
SITE                  9
                      note = Amidated 3-(4-pyridyl)alanine
SEQUENCE: 250
YXNTFGLXX                                                                    9

SEQ ID NO: 251        moltype = AA  length = 8
FEATURE               Location/Qualifiers
source                1..8
                      mol_type = protein
                      organism = synthetic construct
SITE                  1
                      note = D-3-(4-pyridyl)alanine
SITE                  5
                      note = Azaglycine
SITE                  7
                      note = 4-amino-1-R1-piperidine-4-carboxylic acid
SITE                  8
                      note = Amidated 3-(4-pyridyl)alanine
SEQUENCE: 251
XNTFGLXX                                                                     8

SEQ ID NO: 252        moltype = AA  length = 8
FEATURE               Location/Qualifiers
source                1..8
                      mol_type = protein
```

```
                        organism = synthetic construct
SITE                    1
                        note = bGlu
SITE                    4
                        note = 3-Fluorophenylalanine
SITE                    5
                        note = Azaglycine
SITE                    7
                        note = 4-amino-1-R1-piperidine-4-carboxylic acid
SITE                    8
                        note = Amidated 3-(4-pyridyl)alanine
SEQUENCE: 252
ENTFGLXX                                                                    8

SEQ ID NO: 253          moltype = AA  length = 7
FEATURE                 Location/Qualifiers
source                  1..7
                        mol_type = protein
                        organism = synthetic construct
SITE                    3
                        note = 3-(4-pyridyl)alanine
SITE                    4
                        note = Azaglycine
SITE                    6
                        note = 4-amino-1-R1-piperidine-4-carboxylic acid
SITE                    7
                        note = Amidated 3-(4-pyridyl)alanine
SEQUENCE: 253
NTXGLXX                                                                     7

SEQ ID NO: 254          moltype =   length =
SEQUENCE: 254
000

SEQ ID NO: 255          moltype =   length =
SEQUENCE: 255
000

SEQ ID NO: 256          moltype =   length =
SEQUENCE: 256
000

SEQ ID NO: 257          moltype = AA  length = 10
FEATURE                 Location/Qualifiers
source                  1..10
                        mol_type = protein
                        organism = synthetic construct
SITE                    3
                        note = D-Tryptophan
SITE                    7
                        note = Azaglycine
SITE                    9
                        note = 4-amino-1-R1-piperidine-4-carboxylic acid
SITE                    10
                        note = Amidated Tryptophan
SEQUENCE: 257
GYWNTFGLXW                                                                  10

SEQ ID NO: 258          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = 4-benzoylphenylalanine
SITE                    6
                        note = Azaglycine
SITE                    8
                        note = 4-amino-1-R1-piperidine-4-carboxylic acid
SITE                    9
                        note = Amidated Tryptophan
SEQUENCE: 258
YXNTFGLXW                                                                   9

SEQ ID NO: 259          moltype = AA  length = 9
FEATURE                 Location/Qualifiers
source                  1..9
```

```
                        mol_type = protein
                        organism = synthetic construct
SITE                    1
                        note = D-Tyrosine
SITE                    2
                        note = 3-(9-anthryl)-alanine
SITE                    6
                        note = Azaglycine
SITE                    8
                        note = 4-amino-1-R1-piperidine-4-carboxylic acid
SITE                    9
                        note = Amidated Tryptophan
SEQUENCE: 259
YXNTFGLXW                                                9

SEQ ID NO: 260          moltype =   length =
SEQUENCE: 260
000

SEQ ID NO: 261          moltype = AA  length = 5
FEATURE                 Location/Qualifiers
source                  1..5
                        mol_type = protein
                        organism = synthetic construct
SITE                    4
                        note = 4-amino-1-R1-piperidine-4-carboxylic acid
SITE                    5
                        note = Amidated Tyrosine
SEQUENCE: 261
FGLXY                                                    5

SEQ ID NO: 262          moltype = AA  length = 5
FEATURE                 Location/Qualifiers
source                  1..5
                        mol_type = protein
                        organism = synthetic construct
SITE                    2
                        note = Azaglycine
SITE                    4
                        note = 4-amino-1-R1-piperidine-4-carboxylic acid
SITE                    5
                        note = Amidated Tyrosine
SEQUENCE: 262
FGLXY                                                    5

SEQ ID NO: 263          moltype = AA  length = 6
FEATURE                 Location/Qualifiers
source                  1..6
                        mol_type = protein
                        organism = synthetic construct
SITE                    3
                        note = Azaglycine
SITE                    5
                        note = 4-amino-1-R1-piperidine-4-carboxylic acid
SITE                    6
                        note = Amidated Tyrosine
SEQUENCE: 263
TFGLXY                                                   6

SEQ ID NO: 264          moltype = AA  length = 7
FEATURE                 Location/Qualifiers
source                  1..7
                        mol_type = protein
                        organism = synthetic construct
SITE                    4
                        note = Azaglycine
SITE                    6
                        note = 4-amino-1-R1-piperidine-4-carboxylic acid
SITE                    7
                        note = Amidated Tyrosine
SEQUENCE: 264
NTFGLXY                                                  7

SEQ ID NO: 265          moltype = AA  length = 8
FEATURE                 Location/Qualifiers
source                  1..8
                        mol_type = protein
                        organism = synthetic construct
SITE                    1
```

```
                        note = D-Glutamic Acid
SITE                    5
                        note = Azaglycine
SITE                    7
                        note = 4-amino-1-R1-piperidine-4-carboxylic acid
SITE                    8
                        note = Amidated Tyrosine
SEQUENCE: 265
ENTFGLXY                                                                     8

SEQ ID NO: 266          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = 3-(2-naphthyl)alanine
SITE                    6
                        note = Azaglycine
SITE                    8
                        note = 4-amino-1-R1-piperidine-4-carboxylic acid
SITE                    9
                        note = Amidated Tyrosine
SEQUENCE: 266
YXNTFGLXY                                                                    9

SEQ ID NO: 267          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-3-(2-naphthyl)-alanine
SITE                    6
                        note = Azaglycine
SITE                    8
                        note = 4-amino-1-R1-piperidine-4-carboxylic acid
SITE                    9
                        note = Amidated Tyrosine
SEQUENCE: 267
YXNTFGLXY                                                                    9

SEQ ID NO: 268          moltype = AA  length = 10
FEATURE                 Location/Qualifiers
source                  1..10
                        mol_type = protein
                        organism = synthetic construct
SITE                    2
                        note = D-Tyrosine
SITE                    3
                        note = D-3-(4-pyridyl)alanine
SITE                    7
                        note = Azaglycine
SITE                    9
                        note = 4-amino-1-R1-piperidine-4-carboxylic acid
SITE                    10
                        note = Amidated Tyrosine
SEQUENCE: 268
GYXNTFGLXY                                                                   10

SEQ ID NO: 269          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-Tryptophan
SITE                    6
                        note = Azaglycine
SITE                    8
                        note = 4-amino-1-R1-piperidine-4-carboxylic acid
SITE                    9
                        note = Amidated Tyrosine
```

```
SEQUENCE: 269
YWNTFGLXY                                                     9

SEQ ID NO: 270          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = Bip
SITE                    6
                        note = Azaglycine
SITE                    8
                        note = 4-amino-1-R1-piperidine-4-carboxylic acid
SITE                    9
                        note = Amidated Tryptophan
SEQUENCE: 270
YXNTFGLXW                                                     9

SEQ ID NO: 271          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = Bip
SITE                    6
                        note = Azaglycine
SITE                    8
                        note = 4-amino-1-R1-piperidine-4-carboxylic acid
SITE                    9
                        note = Amidated D-Tryptophan
SEQUENCE: 271
YXNTFGLXW                                                     9

SEQ ID NO: 272          moltype = AA  length = 8
FEATURE                 Location/Qualifiers
source                  1..8
                        mol_type = protein
                        organism = synthetic construct
SITE                    4
                        note = beta-(2-thienyl)-Ala
SITE                    5
                        note = Azaglycine
SITE                    7
                        note = 4-amino-1-R1-piperidine-4-carboxylic acid
SITE                    8
                        note = Amidated Tryptophan
SEQUENCE: 272
ENTAGLXW                                                      8

SEQ ID NO: 273          moltype = AA  length = 9
FEATURE                 Location/Qualifiers
source                  1..9
                        mol_type = protein
                        organism = synthetic construct
SITE                    1
                        note = 4-iodophenylalanine
SITE                    6
                        note = Azaglycine
SITE                    8
                        note = 4-amino-1-R1-piperidine-4-carboxylic acid
SITE                    9
                        note = Amidated Tryptophan
SEQUENCE: 273
FWNTFGLXW                                                     9

SEQ ID NO: 274          moltype = AA  length = 9
FEATURE                 Location/Qualifiers
source                  1..9
                        mol_type = protein
                        organism = synthetic construct
SITE                    6
                        note = Azaglycine
SITE                    8
```

```
                        note = 4-amino-1-R1-piperidine-4-carboxylic acid
SITE                    9
                        note = Amidated Tryptophan
SEQUENCE: 274
KWNTFGLXW                                                     9

SEQ ID NO: 275          moltype = AA  length = 6
FEATURE                 Location/Qualifiers
source                  1..6
                        mol_type = protein
                        organism = synthetic construct
SITE                    3
                        note = Azaglycine
SITE                    5
                        note = 4-amino-1-R1-piperidine-4-carboxylic acid
SITE                    6
                        note = Amidated Tryptophan
SEQUENCE: 275
TFGLXW                                                        6

SEQ ID NO: 276          moltype = AA  length = 7
FEATURE                 Location/Qualifiers
source                  1..7
                        mol_type = protein
                        organism = synthetic construct
SITE                    4
                        note = Azaglycine
SITE                    6
                        note = 4-amino-1-R1-piperidine-4-carboxylic acid
SITE                    7
                        note = Amidated Tryptophan
SEQUENCE: 276
ETFGLXW                                                       7

SEQ ID NO: 277          moltype = AA  length = 5
FEATURE                 Location/Qualifiers
source                  1..5
                        mol_type = protein
                        organism = synthetic construct
SITE                    2
                        note = Azaglycine
SITE                    4
                        note = 4-amino-1-R1-piperidine-4-carboxylic acid
SITE                    5
                        note = Amidated Histidine
SEQUENCE: 277
FGLXH                                                         5

SEQ ID NO: 278          moltype = AA  length = 7
FEATURE                 Location/Qualifiers
source                  1..7
                        mol_type = protein
                        organism = synthetic construct
SITE                    4
                        note = Azaglycine
SITE                    6
                        note = 4-amino-1-R1-piperidine-4-carboxylic acid
SITE                    7
                        note = Tyr(3-NO2)-NH2
SEQUENCE: 278
NTFGLXY                                                       7

SEQ ID NO: 279          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-Tryptophan
SITE                    5
                        note = biphenylalanine
SITE                    6
                        note = Azaglycine
SITE                    8
                        note = 4-amino-1-R1-piperidine-4-carboxylic acid
SITE                    9
                        note = Amidated Tryptophan
```

```
SEQUENCE: 279
YWNTXGLXW                                                    9

SEQ ID NO: 280          moltype = AA  length = 8
FEATURE                 Location/Qualifiers
source                  1..8
                        mol_type = protein
                        organism = synthetic construct
SITE                    1
                        note = 3-(2-(2-hydroxyethoxy)ethoxy)propanoic acid D-Lysine
                         bound to an optional linker and chelating moiety or a
                         radionuclide complex
SITE                    5
                        note = Azaglycine
SITE                    7
                        note = 4-amino-1-R1-piperidine-4-carboxylic acid
SITE                    8
                        note = Amidated 3-(4-pyridyl)alanine
SEQUENCE: 280
KNTFGLXX                                                     8

SEQ ID NO: 281          moltype = AA  length = 9
FEATURE                 Location/Qualifiers
source                  1..9
                        mol_type = protein
                        organism = synthetic construct
SITE                    2
                        note = hydroxyproline
SITE                    6
                        note = Azaglycine
SITE                    8
                        note = 4-amino-1-R1-piperidine-4-carboxylic acid
SITE                    9
                        note = Amidated Tryptophan
SEQUENCE: 281
YXNTFGLXW                                                    9

SEQ ID NO: 282          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = hydroxyproline
SITE                    6
                        note = Azaglycine
SITE                    8
                        note = 4-amino-1-R1-piperidine-4-carboxylic acid
SITE                    9
                        note = Amidated Tryptophan
SEQUENCE: 282
YXNTFGLXW                                                    9

SEQ ID NO: 283          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-hydroxyproline
SITE                    6
                        note = Azaglycine
SITE                    8
                        note = 4-amino-1-R1-piperidine-4-carboxylic acid
SITE                    9
                        note = Amidated Tryptophan
SEQUENCE: 283
YXNTFGLXW                                                    9

SEQ ID NO: 284          moltype =   length =
SEQUENCE: 284
000

SEQ ID NO: 285          moltype = AA  length = 7
FEATURE                 Location/Qualifiers
```

```
source                  1..7
                        mol_type = protein
                        organism = synthetic construct
SITE                    3
                        note = cyclohexylalanine
SITE                    4
                        note = Azaglycine
SITE                    6
                        note = 4-amino-1-R1-piperidine-4-carboxylic acid
SITE                    7
                        note = Amidated Tryptophan
SEQUENCE: 285
NTXGLXW                                                                    7

SEQ ID NO: 286          moltype = AA  length = 8
FEATURE                 Location/Qualifiers
source                  1..8
                        mol_type = protein
                        organism = synthetic construct
SITE                    1
                        note = D-3-(4-pyridyl)alanine
SITE                    4
                        note = cyclohexylalanine
SITE                    5
                        note = Azaglycine
SITE                    7
                        note = 4-amino-1-R1-piperidine-4-carboxylic acid
SITE                    8
                        note = Amidated Tryptophan
SEQUENCE: 286
XNTXGLXW                                                                   8

SEQ ID NO: 287          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-3-(4-pyridyl)alanine
SITE                    5
                        note = cyclohexylalanine
SITE                    6
                        note = Azaglycine
SITE                    8
                        note = 4-amino-1-R1-piperidine-4-carboxylic acid
SITE                    9
                        note = Amidated Tryptophan
SEQUENCE: 287
YXNTXGLXW                                                                  9

SEQ ID NO: 288          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-3-(2-naphthyl)-alanine
SITE                    5
                        note = cyclohexylalanine
SITE                    6
                        note = Azaglycine
SITE                    8
                        note = 4-amino-1-R1-piperidine-4-carboxylic acid
SITE                    9
                        note = Amidated Tryptophan
SEQUENCE: 288
YXNTXGLXW                                                                  9

SEQ ID NO: 289          moltype =   length =
SEQUENCE: 289
000

SEQ ID NO: 290          moltype = AA  length = 7
FEATURE                 Location/Qualifiers
source                  1..7
```

```
                        mol_type = protein
                        organism = synthetic construct
SITE                    1
                        note = D-Tyrosine
SITE                    5
                        note =
                         (S)-2-(4-((S)-1-amino-2-phenylethyl)-1H-1,2,3-triazol-1-yl)
                         -4-methylpentanoic acid
SITE                    6
                        note = 4-amino-1-R1-piperidine-4-carboxylic acid
SITE                    7
                        note = Amidated Tryptophan
SEQUENCE: 290
YPNTXXW                                                      7

SEQ ID NO: 291          moltype =   length =
SEQUENCE: 291
000

SEQ ID NO: 292          moltype =   length =
SEQUENCE: 292
000

SEQ ID NO: 293          moltype =   length =
SEQUENCE: 293
000

SEQ ID NO: 294          moltype =   length =
SEQUENCE: 294
000

SEQ ID NO: 295          moltype =   length =
SEQUENCE: 295
000

SEQ ID NO: 296          moltype =   length =
SEQUENCE: 296
000

SEQ ID NO: 297          moltype =   length =
SEQUENCE: 297
000

SEQ ID NO: 298          moltype =   length =
SEQUENCE: 298
000

SEQ ID NO: 299          moltype =   length =
SEQUENCE: 299
000

SEQ ID NO: 300          moltype =   length =
SEQUENCE: 300
000

SEQ ID NO: 301          moltype =   length =
SEQUENCE: 301
000

SEQ ID NO: 302          moltype = AA  length = 8
FEATURE                 Location/Qualifiers
source                  1..8
                        mol_type = protein
                        organism = synthetic construct
SITE                    1
                        note = D-Tyrosine
SITE                    2
                        note = D-Tryptophan
SITE                    6
                        note = 2-(2-aminoethoxy)-[1,1'-biphenyl]-4-carboxylic acid
SITE                    7
                        note = 4-amino-1-R1-piperidine-4-carboxylic acid
SITE                    8
                        note = Amidated Tryptophan
SEQUENCE: 302
YWNTFXXW                                                     8

SEQ ID NO: 303          moltype =   length =
SEQUENCE: 303
```

```
000

SEQ ID NO: 304          moltype =   length =
SEQUENCE: 304
000

SEQ ID NO: 305          moltype =   length =
SEQUENCE: 305
000

SEQ ID NO: 306          moltype = AA  length = 9
FEATURE                 Location/Qualifiers
source                  1..9
                        mol_type = protein
                        organism = synthetic construct
SITE                    1
                        note = Lysine bound to an optional linker and chelating
                         moiety or a radionuclide complex
SITE                    6
                        note = Azaglycine
SITE                    8
                        note = 4-amino-1-R1-piperidine-4-carboxylic acid
SITE                    9
                        note = Amidated Tryptophan
SEQUENCE: 306
KWNTFGLXW                                                                  9

SEQ ID NO: 307          moltype = AA  length = 8
FEATURE                 Location/Qualifiers
source                  1..8
                        mol_type = protein
                        organism = synthetic construct
SITE                    1
                        note = (3-(2-(2-methoxyethoxy)ethoxy)propanoyl)-L-Lysine
                         bound to an optional linker and chelating moiety or a
                         radionuclide complex
SITE                    5
                        note = Azaglycine
SITE                    7
                        note = 4-amino-1-R1-piperidine-4-carboxylic acid
SITE                    8
                        note = Amidated Tryptophan
SEQUENCE: 307
KNTFGLXW                                                                   8

SEQ ID NO: 308          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = Lysine bound to an optional linker and chelating
                         moiety or a radionuclide complex
SITE                    5
                        note = 3-Fluorophenylalanine
SITE                    6
                        note = Azaglycine
SITE                    8
                        note = 4-amino-1-R1-piperidine-4-carboxylic acid
SITE                    9
                        note = Amidated Tryptophan
SEQUENCE: 308
YKNTFGLXW                                                                  9

SEQ ID NO: 309          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = Lysine bound to an optional linker and chelating
                         moiety or a radionuclide complex
SITE                    6
                        note = Azaglycine
SITE                    8
```

-continued

```
                         note = 4-amino-1-R1-piperidine-4-carboxylic acid
SITE                     9
                         note = Amidated Tryptophan
SEQUENCE: 309
YKNTFGLXW                                                                9

SEQ ID NO: 310           moltype = AA  length = 9
FEATURE                  Location/Qualifiers
source                   1..9
                         mol_type = protein
                         organism = synthetic construct
SITE                     1
                         note = Ac-D-Tyrosine
SITE                     2
                         note = Lysine bound to an optional linker and chelating
                          moiety or a radionuclide complex
SITE                     6
                         note = Azaglycine
SITE                     8
                         note = 4-amino-1-R1-piperidine-4-carboxylic acid
SITE                     9
                         note = Amidated Tryptophan
SEQUENCE: 310
YKNTFGLXW                                                                9

SEQ ID NO: 311           moltype = AA  length = 9
FEATURE                  Location/Qualifiers
source                   1..9
                         mol_type = protein
                         organism = synthetic construct
SITE                     1
                         note = octanoic acid-D-Tyrosine
SITE                     2
                         note = Lysine bound to an optional linker and chelating
                          moiety or a radionuclide complex
SITE                     6
                         note = Azaglycine
SITE                     8
                         note = 4-amino-1-R1-piperidine-4-carboxylic acid
SITE                     9
                         note = Amidated Tryptophan
SEQUENCE: 311
YKNTFGLXW                                                                9

SEQ ID NO: 312           moltype = AA  length = 9
FEATURE                  Location/Qualifiers
source                   1..9
                         mol_type = protein
                         organism = synthetic construct
SITE                     1
                         note = dodecanoic acid acid-D-Tyrosine
SITE                     2
                         note = Lysine bound to an optional linker and chelating
                          moiety or a radionuclide complex
SITE                     6
                         note = Azaglycine
SITE                     8
                         note = 4-amino-1-R1-piperidine-4-carboxylic acid
SITE                     9
                         note = Amidated Tryptophan
SEQUENCE: 312
YKNTFGLXW                                                                9

SEQ ID NO: 313           moltype = AA  length = 9
FEATURE                  Location/Qualifiers
source                   1..9
                         mol_type = protein
                         organism = synthetic construct
SITE                     1
                         note = palmitic acid-D-Tyrosine
SITE                     2
                         note = Lysine bound to an optional linker and chelating
                          moiety or a radionuclide complex
SITE                     6
                         note = Azaglycine
SITE                     8
                         note = 4-amino-1-R1-piperidine-4-carboxylic acid
SITE                     9
                         note = Amidated Tryptophan
```

```
SEQUENCE: 313
YKNTFGLXW                                                        9

SEQ ID NO: 314          moltype = AA  length = 9
FEATURE                 Location/Qualifiers
source                  1..9
                        mol_type = protein
                        organism = synthetic construct
SITE                    1
                        note = 3-(4-iodophenyl)propanoic acid-D-Tyrosine
SITE                    2
                        note = Lysine bound to an optional linker and chelating
                         moiety or a radionuclide complex
SITE                    6
                        note = Azaglycine
SITE                    8
                        note = 4-amino-1-R1-piperidine-4-carboxylic acid
SITE                    9
                        note = Amidated Tryptophan
SEQUENCE: 314
YKNTFGLXW                                                        9

SEQ ID NO: 315          moltype = AA  length = 10
FEATURE                 Location/Qualifiers
source                  1..10
                        mol_type = protein
                        organism = synthetic construct
SITE                    1
                        note = (3-fluoro-4-methylbenzyl)glycine
SITE                    2
                        note = D-Tyrosine
SITE                    3
                        note = Lysine bound to an optional linker and chelating
                         moiety or a radionuclide complex
SITE                    7
                        note = Azaglycine
SITE                    9
                        note = 4-amino-1-R1-piperidine-4-carboxylic acid
SITE                    10
                        note = Amidated Tryptophan
SEQUENCE: 315
GYKNTFGLXW                                                       10

SEQ ID NO: 316          moltype = AA  length = 9
FEATURE                 Location/Qualifiers
source                  1..9
                        mol_type = protein
                        organism = synthetic construct
SITE                    1
                        note = 3-(2-(2-hydroxyethoxy)ethoxy)propanoic
                         acid-D-Tyrosine
SITE                    2
                        note = Lysine bound to an optional linker and chelating
                         moiety or a radionuclide complex
SITE                    6
                        note = Azaglycine
SITE                    8
                        note = 4-amino-1-R1-piperidine-4-carboxylic acid
SITE                    9
                        note = Amidated Tryptophan
SEQUENCE: 316
YKNTFGLXW                                                        9

SEQ ID NO: 317          moltype = AA  length = 9
FEATURE                 Location/Qualifiers
source                  1..9
                        mol_type = protein
                        organism = synthetic construct
SITE                    1
                        note = 3-(2-(2-methoxyethoxy)ethoxy)propanoic
                         acid-D-Tyrosine
SITE                    2
                        note = Lysine bound to an optional linker and chelating
                         moiety or a radionuclide complex
SITE                    6
                        note = Azaglycine
SITE                    8
                        note = 4-amino-1-R1-piperidine-4-carboxylic acid
SITE                    9
```

```
                        note = Amidated Tryptophan
SEQUENCE: 317
YKNTFGLXW                                                            9

SEQ ID NO: 318          moltype = AA  length = 9
FEATURE                 Location/Qualifiers
source                  1..9
                        mol_type = protein
                        organism = synthetic construct
SITE                    1
                        note =
                         3-(2-(2-(3-(p-tolyl)propanamido)ethoxy)ethoxy)propanoic
                         acid-D-Tyrosine
SITE                    2
                        note = Lysine bound to an optional linker and chelating
                         moiety or a radionuclide complex
SITE                    6
                        note = Azaglycine
SITE                    8
                        note = 4-amino-1-R1-piperidine-4-carboxylic acid
SITE                    9
                        note = Amidated Tryptophan
SEQUENCE: 318
YKNTFGLXW                                                            9

SEQ ID NO: 319          moltype = AA  length = 9
FEATURE                 Location/Qualifiers
source                  1..9
                        mol_type = protein
                        organism = synthetic construct
SITE                    1
                        note =
                         3-(2-(2-(3-(4-iodophenyl)propanamido)ethoxy)ethoxy)propanoi
                         c acid-D-Tyrosine
SITE                    2
                        note = Lysine bound to an optional linker and chelating
                         moiety or a radionuclide complex
SITE                    6
                        note = Azaglycine
SITE                    8
                        note = 4-amino-1-R1-piperidine-4-carboxylic acid
SITE                    9
                        note = Amidated Tryptophan
SEQUENCE: 319
YKNTFGLXW                                                            9

SEQ ID NO: 320          moltype = AA  length = 9
FEATURE                 Location/Qualifiers
source                  1..9
                        mol_type = protein
                        organism = synthetic construct
SITE                    1
                        note =
                         1-(3-fluoro-4-methylphenyl)-4-oxo-8,11-dioxa-2,5-diazatetra
                         decan-14-oic acid-D-Tyrosine
SITE                    2
                        note = Lysine bound to an optional linker and chelating
                         moiety or a radionuclide complex
SITE                    6
                        note = Azaglycine
SITE                    8
                        note = 4-amino-1-R1-piperidine-4-carboxylic acid
SITE                    9
                        note = Amidated Tryptophan
SEQUENCE: 320
YKNTFGLXW                                                            9

SEQ ID NO: 321          moltype = AA  length = 10
FEATURE                 Location/Qualifiers
source                  1..10
                        mol_type = protein
                        organism = synthetic construct
SITE                    1
                        note = 3-(p-tolyl)propanoyl)-L-glutamic acid
SITE                    2
                        note = D-Tyrosine
SITE                    3
                        note = Lysine bound to an optional linker and chelating
                         moiety or a radionuclide complex
```

-continued

```
SITE                    7
                        note = Azaglycine
SITE                    9
                        note = 4-amino-1-R1-piperidine-4-carboxylic acid
SITE                    10
                        note = Amidated Tryptophan
SEQUENCE: 321
XYKNTFGLXW                                                                  10

SEQ ID NO: 322          moltype = AA  length = 9
FEATURE                 Location/Qualifiers
source                  1..9
                        mol_type = protein
                        organism = synthetic construct
SITE                    1
                        note =
                         2,5,8,11,14,17,20,23,26,29,32,35,38,41,44,47,50,53,56,59,62
                         ,65,68,71,74-pentacosaoxaheptaheptacontan-77-oic
                         acid-D-Tyrosine
SITE                    2
                        note = Lysine bound to an optional linker and chelating
                         moiety or a radionuclide complex
SITE                    6
                        note = Azaglycine
SITE                    8
                        note = 4-amino-1-R1-piperidine-4-carboxylic acid
SITE                    9
                        note = Amidated Tryptophan
SEQUENCE: 322
YKNTFGLXW                                                                   9

SEQ ID NO: 323          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-Lysine bound to an optional linker and chelating
                         moiety or a radionuclide complex
SITE                    6
                        note = Azaglycine
SITE                    8
                        note = 4-amino-1-R1-piperidine-4-carboxylic acid
SITE                    9
                        note = Amidated Tryptophan
SEQUENCE: 323
YKNTFGLXW                                                                   9

SEQ ID NO: 324          moltype = AA  length = 9
FEATURE                 Location/Qualifiers
source                  1..9
                        mol_type = protein
                        organism = synthetic construct
SITE                    1
                        note = Octanoic acid-D-Tyrosine
SITE                    2
                        note = D-Lysine bound to an optional linker and chelating
                         moiety or a radionuclide complex
SITE                    6
                        note = Azaglycine
SITE                    8
                        note = 4-amino-1-R1-piperidine-4-carboxylic acid
SITE                    9
                        note = Amidated Tryptophan
SEQUENCE: 324
YKNTFGLXW                                                                   9

SEQ ID NO: 325          moltype = AA  length = 9
FEATURE                 Location/Qualifiers
source                  1..9
                        mol_type = protein
                        organism = synthetic construct
SITE                    1
                        note =
                         3-(2-(2-(3-(4-iodophenyl)propanamido)ethoxy)ethoxy)propanoi
                         c acid-D-Tyrosine
SITE                    2
```

```
                         note = D-Lysine bound to an optional linker and chelating
                          moiety or a radionuclide complex
SITE                     6
                         note = Azaglycine
SITE                     8
                         note = 4-amino-1-R1-piperidine-4-carboxylic acid
SITE                     9
                         note = Amidated Tryptophan
SEQUENCE: 325
YKNTFGLXW                                                                    9

SEQ ID NO: 326           moltype = AA  length = 9
FEATURE                  Location/Qualifiers
source                   1..9
                         mol_type = protein
                         organism = synthetic construct
SITE                     1
                         note =
                          3-(2-(2-(3-(p-tolyl)propanamido)ethoxy)ethoxy)propanoic
                          acid-D-Tyrosine
SITE                     2
                         note = D-Lysine bound to an optional linker and chelating
                          moiety or a radionuclide complex
SITE                     6
                         note = Azaglycine
SITE                     8
                         note = 4-amino-1-R1-piperidine-4-carboxylic acid
SITE                     9
                         note = Amidated Tryptophan
SEQUENCE: 326
YKNTFGLXW                                                                    9

SEQ ID NO: 327           moltype = AA  length = 10
FEATURE                  Location/Qualifiers
source                   1..10
                         mol_type = protein
                         organism = synthetic construct
SITE                     1
                         note = 3-fluoro-4-methylbenzyl)glycine
SITE                     2
                         note = D-Tyrosine
SITE                     3
                         note = D-Lysine bound to an optional linker and chelating
                          moiety or a radionuclide complex
SITE                     7
                         note = Azaglycine
SITE                     9
                         note = 4-amino-1-R1-piperidine-4-carboxylic acid
SITE                     10
                         note = Amidated Tryptophan
SEQUENCE: 327
GYKNTFGLXW                                                                   10

SEQ ID NO: 328           moltype = AA  length = 9
FEATURE                  Location/Qualifiers
source                   1..9
                         mol_type = protein
                         organism = synthetic construct
SITE                     1
                         note =
                          1-(3-fluoro-4-methylphenyl)-4-oxo-8,11-dioxa-2,5-diazatetra
                          decan-14-oic acid-D-Tyrosine
SITE                     2
                         note = D-Lysine bound to an optional linker and chelating
                          moiety or a radionuclide complex
SITE                     6
                         note = Azaglycine
SITE                     8
                         note = 4-amino-1-R1-piperidine-4-carboxylic acid
SITE                     9
                         note = Amidated Tryptophan
SEQUENCE: 328
YKNTFGLXW                                                                    9

SEQ ID NO: 329           moltype = AA  length = 10
FEATURE                  Location/Qualifiers
source                   1..10
                         mol_type = protein
                         organism = synthetic construct
```

```
SITE                    1
                        note = gamma-D-Glutamic Acid
SITE                    2
                        note = D-Tyrosine
SITE                    3
                        note = Lysine bound to an optional linker and chelating
                         moiety or a radionuclide complex
SITE                    7
                        note = Azaglycine
SITE                    9
                        note = 4-amino-1-R1-piperidine-4-carboxylic acid
SITE                    10
                        note = Amidated Tryptophan
SEQUENCE: 329
EYKNTFGLXW                                                       10

SEQ ID NO: 330          moltype = AA  length = 10
FEATURE                 Location/Qualifiers
source                  1..10
                        mol_type = protein
                        organism = synthetic construct
SITE                    1
                        note = 3-(4-iodophenyl)propanoic acid Gamma-D-Glutamic acid
SITE                    2
                        note = D-Tyrosine
SITE                    3
                        note = Lysine bound to an optional linker and chelating
                         moiety or a radionuclide complex
SITE                    7
                        note = Azaglycine
SITE                    9
                        note = 4-amino-1-R1-piperidine-4-carboxylic acid
SITE                    10
                        note = Amidated Tryptophan
SEQUENCE: 330
EYKNTFGLXW                                                       10

SEQ ID NO: 331          moltype = AA  length = 7
FEATURE                 Location/Qualifiers
source                  1..7
                        mol_type = protein
                        organism = synthetic construct
SITE                    1
                        note = Lysine bound to an optional linker and chelating
                         moiety or a radionuclide complex
SITE                    4
                        note = Azaglycine
SITE                    6
                        note = 4-amino-1-R1-piperidine-4-carboxylic acid
SITE                    7
                        note = Amidated 3-(4-pyridyl)alanine
SEQUENCE: 331
KTFGLXX                                                          7

SEQ ID NO: 332          moltype = AA  length = 7
FEATURE                 Location/Qualifiers
source                  1..7
                        mol_type = protein
                        organism = synthetic construct
SITE                    1
                        note = 3-(2-(2-hydroxyethoxy)ethoxy)propanoic acid Lysine
                         bound to an optional linker and chelating moiety or a
                         radionuclide complex
SITE                    4
                        note = Azaglycine
SITE                    6
                        note = 4-amino-1-R1-piperidine-4-carboxylic acid
SITE                    7
                        note = Amidated 3-(4-pyridyl)alanine
SEQUENCE: 332
KTFGLXX                                                          7

SEQ ID NO: 333          moltype = AA  length = 7
FEATURE                 Location/Qualifiers
source                  1..7
                        mol_type = protein
                        organism = synthetic construct
SITE                    1
                        note = D-Lysine bound to an optional linker and chelating
```

```
                        moiety or a radionuclide complex
SITE                   4
                       note = Azaglycine
SITE                   6
                       note = 4-amino-1-R1-piperidine-4-carboxylic acid
SITE                   7
                       note = Amidated 3-(4-pyridyl)alanine
SEQUENCE: 333
KTFGLXX                                                                    7

SEQ ID NO: 334         moltype = AA  length = 7
FEATURE                Location/Qualifiers
source                 1..7
                       mol_type = protein
                       organism = synthetic construct
SITE                   1
                       note = 3-(2-(2-hydroxyethoxy)ethoxy)propanoic acid D-Lysine
                        bound to an optional linker and chelating moiety or a
                        radionuclide complex
SITE                   4
                       note = Azaglycine
SITE                   6
                       note = 4-amino-1-R1-piperidine-4-carboxylic acid
SITE                   7
                       note = Amidated 3-(4-pyridyl)alanine
SEQUENCE: 334
KTFGLXX                                                                    7

SEQ ID NO: 335         moltype = AA  length = 8
FEATURE                Location/Qualifiers
source                 1..8
                       mol_type = protein
                       organism = synthetic construct
SITE                   1
                       note = Lysine bound to an optional linker and chelating
                        moiety or a radionuclide complex
SITE                   5
                       note = Azaglycine
SITE                   7
                       note = 4-amino-1-R1-piperidine-4-carboxylic acid
SITE                   8
                       note = Amidated 3-(4-pyridyl)alanine
SEQUENCE: 335
KNTFGLXX                                                                   8

SEQ ID NO: 336         moltype = AA  length = 8
FEATURE                Location/Qualifiers
source                 1..8
                       mol_type = protein
                       organism = synthetic construct
SITE                   1
                       note = Octanoic acid Lysine bound to an optional linker and
                        chelating moiety or a radionuclide complex
SITE                   5
                       note = Azaglycine
SITE                   7
                       note = 4-amino-1-R1-piperidine-4-carboxylic acid
SITE                   8
                       note = Amidated 3-(4-pyridyl)alanine
SEQUENCE: 336
KNTFGLXX                                                                   8

SEQ ID NO: 337         moltype = AA  length = 8
FEATURE                Location/Qualifiers
source                 1..8
                       mol_type = protein
                       organism = synthetic construct
SITE                   1
                       note = 3-(2-(2-hydroxyethoxy)ethoxy)propanoic acid Lysine
                        bound to an optional linker and chelating moiety or a
                        radionuclide complex
SITE                   5
                       note = Azaglycine
SITE                   7
                       note = 4-amino-1-R1-piperidine-4-carboxylic acid
SITE                   8
                       note = Amidated 3-(4-pyridyl)alanine
SEQUENCE: 337
KNTFGLXX                                                                   8
```

```
SEQ ID NO: 338          moltype = AA  length = 8
FEATURE                 Location/Qualifiers
source                  1..8
                        mol_type = protein
                        organism = synthetic construct
SITE                    1
                        note = 3-(2-(2-methoxyethoxy)ethoxy)propanoic acid Lysine
                         bound to an optional linker and chelating moiety or a
                         radionuclide complex
SITE                    5
                        note = Azaglycine
SITE                    7
                        note = 4-amino-1-R1-piperidine-4-carboxylic acid
SITE                    8
                        note = Amidated 3-(4-pyridyl)alanine
SEQUENCE: 338
KNTFGLXX                                                                   8

SEQ ID NO: 339          moltype = AA  length = 8
FEATURE                 Location/Qualifiers
source                  1..8
                        mol_type = protein
                        organism = synthetic construct
SITE                    1
                        note =
                         3-(2-(2-(3-(p-tolyl)propanamido)ethoxy)ethoxy)propanoic
                         acid Lysine bound to an optional linker and chelating
                         moiety or a radionuclide complex
SITE                    5
                        note = Azaglycine
SITE                    7
                        note = 4-amino-1-R1-piperidine-4-carboxylic acid
SITE                    8
                        note = Amidated 3-(4-pyridyl)alanine
SEQUENCE: 339
KNTFGLXX                                                                   8

SEQ ID NO: 340          moltype = AA  length = 8
FEATURE                 Location/Qualifiers
source                  1..8
                        mol_type = protein
                        organism = synthetic construct
SITE                    1
                        note =
                         3-(2-(2-(3-(4-iodophenyl)propanamido)ethoxy)ethoxy)propanoi
                         c acid Lysine bound to an optional linker and chelating
                         moiety or a radionuclide complex
SITE                    5
                        note = Azaglycine
SITE                    7
                        note = 4-amino-1-R1-piperidine-4-carboxylic acid
SITE                    8
                        note = Amidated 3-(4-pyridyl)alanine
SEQUENCE: 340
KNTFGLXX                                                                   8

SEQ ID NO: 341          moltype = AA  length = 8
FEATURE                 Location/Qualifiers
source                  1..8
                        mol_type = protein
                        organism = synthetic construct
SITE                    1
                        note =
                         1-hydroxy-3,6,9,12,15,18,21,24-octaoxaheptacosan-27-oic
                         acid-Lysine bound to an optional linker and chelating
                         moiety or a radionuclide complex
SITE                    5
                        note = Azaglycine
SITE                    7
                        note = 4-amino-1-R1-piperidine-4-carboxylic acid
SITE                    8
                        note = Amidated 3-(4-pyridyl)alanine
SEQUENCE: 341
KNTFGLXX                                                                   8

SEQ ID NO: 342          moltype = AA  length = 8
FEATURE                 Location/Qualifiers
source                  1..8
```

```
                        mol_type = protein
                        organism = synthetic construct
SITE                    1
                        note =
                         2,5,8,11,14,17,20,23,26,29,32,35,38,41,44,47,50,53,56,59,62
                         ,65,68,71,74-pentacosaoxaheptaheptacontan-77-oic acid
                         Lysine bound to an optional linker and chelating moiety or
                         a radionuclide complex
SITE                    5
                        note = Azaglycine
SITE                    7
                        note = 4-amino-1-R1-piperidine-4-carboxylic acid
SITE                    8
                        note = Amidated 3-(4-pyridyl)alanine
SEQUENCE: 342
KNTFGLXX                                                                     8

SEQ ID NO: 343          moltype = AA  length = 8
FEATURE                 Location/Qualifiers
source                  1..8
                        mol_type = protein
                        organism = synthetic construct
SITE                    1
                        note = Lysine bound to an optional linker and chelating
                         moiety or a radionuclide complex
SITE                    5
                        note = Azaglycine
SITE                    7
                        note = 4-amino-1-R1-piperidine-4-carboxylic acid
SITE                    8
                        note = Amidated 3-(4-pyridyl)alanine
SEQUENCE: 343
KETFGLXX                                                                     8

SEQ ID NO: 344          moltype = AA  length = 8
FEATURE                 Location/Qualifiers
source                  1..8
                        mol_type = protein
                        organism = synthetic construct
SITE                    1
                        note = 3-(2-(2-hydroxyethoxy)ethoxy)propanoic acid-Lysine
                         bound to an optional linker and chelating moiety or a
                         radionuclide complex
SITE                    5
                        note = Azaglycine
SITE                    7
                        note = 4-amino-1-R1-piperidine-4-carboxylic acid
SITE                    8
                        note = Amidated 3-(4-pyridyl)alanine
SEQUENCE: 344
KETFGLXX                                                                     8

SEQ ID NO: 345          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = Lysine bound to an optional linker and chelating
                         moiety or a radionuclide complex
SITE                    6
                        note = Azaglycine
SITE                    8
                        note = 4-amino-1-R1-piperidine-4-carboxylic acid
SITE                    9
                        note = Amidated Phenylalanine
SEQUENCE: 345
YKNTFGLXF                                                                    9

SEQ ID NO: 346          moltype = AA  length = 9
FEATURE                 Location/Qualifiers
source                  1..9
                        mol_type = protein
                        organism = synthetic construct
SITE                    1
                        note =
                         3-(2-(2-(3-(p-tolyl)propanamido)ethoxy)ethoxy)propanoic
```

-continued

```
                          acid-D-Tyrosine
SITE                      2
                          note = Lysine bound to an optional linker and chelating
                           moiety or a radionuclide complex
SITE                      6
                          note = Azaglycine
SITE                      8
                          note = 4-amino-1-R1-piperidine-4-carboxylic acid
SITE                      9
                          note = Amidated Phenylalanine
SEQUENCE: 346
YKNTFGLXF                                                                    9

SEQ ID NO: 347            moltype = AA  length = 9
FEATURE                   Location/Qualifiers
source                    1..9
                          mol_type = protein
                          organism = synthetic construct
SITE                      1
                          note =
                           3-(2-(2-(3-(4-iodophenyl)propanamido)ethoxy)ethoxy)propanoi
                           c acid-D-Tyrosine
SITE                      2
                          note = Lysine bound to an optional linker and chelating
                           moiety or a radionuclide complex
SITE                      6
                          note = Azaglycine
SITE                      8
                          note = 4-amino-1-R1-piperidine-4-carboxylic acid
SITE                      9
                          note = Amidated Phenylalanine
SEQUENCE: 347
YKNTFGLXF                                                                    9

SEQ ID NO: 348            moltype = AA  length = 9
FEATURE                   Location/Qualifiers
source                    1..9
                          mol_type = protein
                          organism = synthetic construct
SITE                      1
                          note = D-Tyrosine
SITE                      2
                          note = Lysine bound to an optional linker and chelating
                           moiety or a radionuclide complex
SITE                      6
                          note = Azaglycine
SITE                      8
                          note = 4-amino-1-R1-piperidine-4-carboxylic acid
SITE                      9
                          note = Amidated Tyrosine
SEQUENCE: 348
YKNTFGLXY                                                                    9

SEQ ID NO: 349            moltype = AA  length = 9
FEATURE                   Location/Qualifiers
source                    1..9
                          mol_type = protein
                          organism = synthetic construct
SITE                      1
                          note = palmitic acid-D-Tyrosine
SITE                      2
                          note = Lysine bound to an optional linker and chelating
                           moiety or a radionuclide complex
SITE                      6
                          note = Azaglycine
SITE                      8
                          note = 4-amino-1-R1-piperidine-4-carboxylic acid
SITE                      9
                          note = Amidated Tyrosine
SEQUENCE: 349
YKNTFGLXY                                                                    9

SEQ ID NO: 350            moltype = AA  length = 9
FEATURE                   Location/Qualifiers
source                    1..9
                          mol_type = protein
                          organism = synthetic construct
SITE                      1
                          note = dodecanoic acid-D-Tyrosine
```

```
SITE                    2
                        note = Lysine bound to an optional linker and chelating
                         moiety or a radionuclide complex
SITE                    6
                        note = Azaglycine
SITE                    8
                        note = 4-amino-1-R1-piperidine-4-carboxylic acid
SITE                    9
                        note = Amidated Tyrosine
SEQUENCE: 350
YKNTFGLXY                                                   9

SEQ ID NO: 351          moltype = AA  length = 9
FEATURE                 Location/Qualifiers
source                  1..9
                        mol_type = protein
                        organism = synthetic construct
SITE                    1
                        note = dodecanoic acid-D-Tyrosine
SITE                    2
                        note = D-Lysine bound to an optional linker and chelating
                         moiety or a radionuclide complex
SITE                    6
                        note = Azaglycine
SITE                    8
                        note = 4-amino-1-R1-piperidine-4-carboxylic acid
SITE                    9
                        note = Amidated Tyrosine
SEQUENCE: 351
YKNTFGLXY                                                   9

SEQ ID NO: 352          moltype = AA  length = 9
FEATURE                 Location/Qualifiers
source                  1..9
                        mol_type = protein
                        organism = synthetic construct
SITE                    1
                        note = dodecanoic acid-D-Tyrosine
SITE                    2
                        note = Lysine bound to an optional linker and chelating
                         moiety or a radionuclide complex
SITE                    6
                        note = Azaglycine
SITE                    8
                        note = 4-amino-1-R1-piperidine-4-carboxylic acid
SITE                    9
                        note = Amidated Tyrosine
SEQUENCE: 352
YKNTFGLXY                                                   9

SEQ ID NO: 353          moltype = AA  length = 9
FEATURE                 Location/Qualifiers
source                  1..9
                        mol_type = protein
                        organism = synthetic construct
SITE                    1
                        note =
                         3-(2-(2-(3-(4-iodophenyl)propanamido)ethoxy)ethoxy)propanoi
                         c acid-D-Tyrosine
SITE                    2
                        note = Lysine bound to an optional linker and chelating
                         moiety or a radionuclide complex
SITE                    6
                        note = Azaglycine
SITE                    8
                        note = 4-amino-1-R1-piperidine-4-carboxylic acid
SITE                    9
                        note = Amidated Tyrosine
SEQUENCE: 353
YKNTFGLXY                                                   9

SEQ ID NO: 354          moltype = AA  length = 9
FEATURE                 Location/Qualifiers
source                  1..9
                        mol_type = protein
                        organism = synthetic construct
SITE                    1
                        note = D-Tyrosine
SITE                    2
```

```
                        note = Lysine bound to an optional linker and chelating
                         moiety or a radionuclide complex
SITE                    6
                        note = Azaglycine
SITE                    8
                        note = 4-amino-1-R1-piperidine-4-carboxylic acid
SITE                    9
                        note = Amidated 4-cyano phenylalanine
SEQUENCE: 354
YKNTFGLXF                                                                   9

SEQ ID NO: 355          moltype = AA  length = 9
FEATURE                 Location/Qualifiers
source                  1..9
                        mol_type = protein
                        organism = synthetic construct
SITE                    1
                        note =
                         3-(2-(2-(3-(4-iodophenyl)propanamido)ethoxy)ethoxy)propanoi
                         c acid-D-Tyrosine
SITE                    2
                        note = Lysine bound to an optional linker and chelating
                         moiety or a radionuclide complex
SITE                    6
                        note = Azaglycine
SITE                    8
                        note = 4-amino-1-R1-piperidine-4-carboxylic acid
SITE                    9
                        note = Amidated 4-cyano phenylalanine
SEQUENCE: 355
YKNTFGLXF                                                                   9

SEQ ID NO: 356          moltype = AA  length = 9
FEATURE                 Location/Qualifiers
source                  1..9
                        mol_type = protein
                        organism = synthetic construct
SITE                    1
                        note =
                         3-(2-(2-(3-(p-tolyl)propanamido)ethoxy)ethoxy)propanoic
                         acid-D-Tyrosine
SITE                    2
                        note = Lysine bound to an optional linker and chelating
                         moiety or a radionuclide complex
SITE                    6
                        note = Azaglycine
SITE                    8
                        note = 4-amino-1-R1-piperidine-4-carboxylic acid
SITE                    9
                        note = Amidated 4-cyano phenylalanine
SEQUENCE: 356
YKNTFGLXF                                                                   9

SEQ ID NO: 357          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = Lysine bound to an optional linker and chelating
                         moiety or a radionuclide complex
SITE                    5
                        note = cyclohexylalanine
SITE                    6
                        note = Azaglycine
SITE                    8
                        note = 4-amino-1-R1-piperidine-4-carboxylic acid
SITE                    9
                        note = Amidated Tryptophan
SEQUENCE: 357
YKNTXGLXW                                                                   9

SEQ ID NO: 358          moltype = AA  length = 9
FEATURE                 Location/Qualifiers
source                  1..9
                        mol_type = protein
                        organism = synthetic construct
```

```
SITE                    1
                        note =
                         3-(2-(2-(3-(p-tolyl)propanamido)ethoxy)ethoxy)propanoic
                         acid-D-Tyrosine
SITE                    2
                        note = Lysine bound to an optional linker and chelating
                         moiety or a radionuclide complex
SITE                    5
                        note = cyclohexylalanine
SITE                    6
                        note = Azaglycine
SITE                    8
                        note = 4-amino-1-R1-piperidine-4-carboxylic acid
SITE                    9
                        note = Amidated Tryptophan
SEQUENCE: 358
YKNTXGLXW                                                                    9

SEQ ID NO: 359          moltype = AA  length = 9
FEATURE                 Location/Qualifiers
source                  1..9
                        mol_type = protein
                        organism = synthetic construct
SITE                    1
                        note =
                         3-(2-(2-(3-(4-iodophenyl)propanamido)ethoxy)ethoxy)propanoi
                         c acid-D-Tyrosine
SITE                    2
                        note = Lysine bound to an optional linker and chelating
                         moiety or a radionuclide complex
SITE                    5
                        note = cyclohexylalanine
SITE                    6
                        note = Azaglycine
SITE                    8
                        note = 4-amino-1-R1-piperidine-4-carboxylic acid
SITE                    9
                        note = Amidated Tryptophan
SEQUENCE: 359
YKNTXGLXW                                                                    9

SEQ ID NO: 360          moltype = AA  length = 9
FEATURE                 Location/Qualifiers
source                  1..9
                        mol_type = protein
                        organism = synthetic construct
SITE                    1
                        note = octanoic acid-D-Tyrosine
SITE                    2
                        note = Lysine bound to an optional linker and chelating
                         moiety or a radionuclide complex
SITE                    5
                        note = cyclohexylalanine
SITE                    6
                        note = Azaglycine
SITE                    8
                        note = 4-amino-1-R1-piperidine-4-carboxylic acid
SITE                    9
                        note = Amidated Tryptophan
SEQUENCE: 360
YKNTXGLXW                                                                    9

SEQ ID NO: 361          moltype = AA  length = 9
FEATURE                 Location/Qualifiers
source                  1..9
                        mol_type = protein
                        organism = synthetic construct
SITE                    1
                        note =
                         3-(2-(2-(3-(p-tolyl)propanamido)ethoxy)ethoxy)propanoic
                         acid-D-Tyrosine
SITE                    2
                        note = D-Lysine bound to an optional linker and chelating
                         moiety or a radionuclide complex
SITE                    5
                        note = cyclohexylalanine
SITE                    6
                        note = Azaglycine
SITE                    8
```

```
                         note = 4-amino-1-R1-piperidine-4-carboxylic acid
SITE                     9
                         note = Amidated Tryptophan
SEQUENCE: 361
YKNTXGLXW                                                                   9

SEQ ID NO: 362           moltype =   length =
SEQUENCE: 362
000

SEQ ID NO: 363           moltype = AA  length = 7
FEATURE                  Location/Qualifiers
source                   1..7
                         mol_type = protein
                         organism = synthetic construct
SITE                     1
                         note = D-Asparagine
SITE                     2
                         note = D-Asparagine
SITE                     4
                         note = Azaglycine
SITE                     6
                         note =
                          4-amino-1-((3-fluoro-4-methylbenzyl)glycyl)piperidine-4-car
                          boxamide
SITE                     7
                         note = Amidated Tryptophan
SEQUENCE: 363
NNFGLXW                                                                     7

SEQ ID NO: 364           moltype = AA  length = 7
FEATURE                  Location/Qualifiers
source                   1..7
                         mol_type = protein
                         organism = synthetic construct
SITE                     1
                         note = D-Lysine
SITE                     2
                         note = D-Asparagine
SITE                     4
                         note = Azaglycine
SITE                     6
                         note =
                          4-amino-1-((3-fluoro-4-methylbenzyl)glycyl)piperidine-4-car
                          boxamide
SITE                     7
                         note = Amidated Tryptophan
SEQUENCE: 364
KNFGLXW                                                                     7

SEQ ID NO: 365           moltype = AA  length = 6
FEATURE                  Location/Qualifiers
source                   1..6
                         mol_type = protein
                         organism = synthetic construct
SITE                     1
                         note = D-Asparagine
SITE                     3
                         note = Azaglycine
SITE                     5
                         note =
                          4-amino-1-((3-fluoro-4-methylbenzyl)glycyl)piperidine-4-car
                          boxamide
SITE                     6
                         note = Amidated Tryptophan
SEQUENCE: 365
NFGLXW                                                                      6

SEQ ID NO: 366           moltype = AA  length = 10
FEATURE                  Location/Qualifiers
source                   1..10
                         mol_type = protein
                         organism = synthetic construct
SITE                     1
                         note = D-Tyrosine
SITE                     2
                         note = D-Histidine
SITE                     3
                         note = D-Tryptophan
```

-continued

```
SITE                    7
                        note = Azaglycine
SITE                    9
                        note =
                         4-amino-1-((3-fluoro-4-methylbenzyl)glycyl)piperidine-4-car
                         boxamide
SITE                    10
                        note = Amidated Tryptophan
SEQUENCE: 366
YHWNTFGLXW                                                                  10

SEQ ID NO: 367          moltype = AA  length = 9
FEATURE                 Location/Qualifiers
source                  1..9
                        mol_type = protein
                        organism = synthetic construct
SITE                    1
                        note = D-Tyrosine
SITE                    5
                        note = 3-Fluorophenylalanine
SITE                    6
                        note = Azaglycine
SITE                    8
                        note = 4-amino-1-R1-piperidine-4-carboxylic acid
SITE                    9
                        note = Amidated Tryptophan
SEQUENCE: 367
YWNTFGLXW                                                                   9

SEQ ID NO: 368          moltype = AA  length = 7
FEATURE                 Location/Qualifiers
source                  1..7
                        mol_type = protein
                        organism = synthetic construct
SITE                    1
                        note = D-Glutamic Acid
SITE                    2
                        note = D-Asparagine
SITE                    4
                        note = Azaglycine
SITE                    6
                        note = 4-amino-1-R1-piperidine-4-carboxylic acid
SITE                    7
                        note = Amidated Tryptophan
SEQUENCE: 368
ENFGLXW                                                                     7

SEQ ID NO: 369          moltype = AA  length = 8
FEATURE                 Location/Qualifiers
source                  1..8
                        mol_type = protein
                        organism = synthetic construct
SITE                    1
                        note = D-Tryptophan
SITE                    5
                        note = Azaglycine
SITE                    7
                        note = 4-amino-1-R1-piperidine-4-carboxylic acid
SITE                    8
                        note = Amidated Tryptophan
SEQUENCE: 369
WNTFGLXW                                                                    8

SEQ ID NO: 370          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = Azaglycine
SITE                    6
                        note = Azaglycine
SITE                    8
                        note = 4-amino-1-R1-piperidine-4-carboxylic acid
SITE                    9
                        note = Amidated Tryptophan
SEQUENCE: 370
```

```
YGNTFGLXW                                                        9

SEQ ID NO: 371          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-Tryptophan
SITE                    6
                        note = Azaglycine
SITE                    8
                        note = 4-amino-1-R1-piperidine-4-carboxylic acid
SITE                    9
                        note = Amidated Phenylalanine
SEQUENCE: 371
YWNAFGLXF                                                        9

SEQ ID NO: 372          moltype = AA  length = 9
FEATURE                 Location/Qualifiers
source                  1..9
                        mol_type = protein
                        organism = synthetic construct
SITE                    1
                        note = D-4-iodophenylalanine
SITE                    2
                        note = D-Tryptophan
SITE                    6
                        note = Azaglycine
SITE                    8
                        note = 4-amino-1-R1-piperidine-4-carboxylic acid
SITE                    9
                        note = Amidated Tryptophan
SEQUENCE: 372
FWNTFGLXW                                                        9

SEQ ID NO: 373          moltype = AA  length = 8
FEATURE                 Location/Qualifiers
source                  1..8
                        mol_type = protein
                        organism = synthetic construct
SITE                    1
                        note = D-beta-glutamic acid
SITE                    4
                        note = 3-Fluorophenylalanine
SITE                    5
                        note = Azaglycine
SITE                    7
                        note = 4-amino-1-R1-piperidine-4-carboxylic acid
SITE                    8
                        note = Amidated 3-(4-pyridyl)alanine
SEQUENCE: 373
ENTFGLXX                                                         8

SEQ ID NO: 374          moltype = AA  length = 8
FEATURE                 Location/Qualifiers
source                  1..8
                        mol_type = protein
                        organism = synthetic construct
SITE                    1
                        note = D-3-(2-naphthyl)-alanine
SITE                    5
                        note = Azaglycine
SITE                    7
                        note = 4-amino-1-R1-piperidine-4-carboxylic acid
SITE                    8
                        note = Amidated Phenylalanine
SEQUENCE: 374
XNTFGLXF                                                         8

SEQ ID NO: 375          moltype = AA  length = 9
FEATURE                 Location/Qualifiers
source                  1..9
                        mol_type = protein
                        organism = synthetic construct
SITE                    1
                        note = D-Tyrosine
```

-continued

```
SITE                    2
                        note = D-3-(2-Naphthyl)alanine
SITE                    6
                        note = Azaglycine
SITE                    8
                        note = 4-amino-1-R1-piperidine-4-carboxylic acid
SITE                    9
                        note = Amidated Tryptophan
SEQUENCE: 375
YXNTFGLXW                                                                   9

SEQ ID NO: 376          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = 4-benzoylphenylalanine
SITE                    6
                        note = Azaglycine
SITE                    8
                        note = 4-amino-1-R1-piperidine-4-carboxylic acid
SITE                    9
                        note = Amidated D-Tryptophan
SEQUENCE: 376
YXNTFGLXW                                                                   9

SEQ ID NO: 377          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-Lysine bound to an optional linker and chelating
                         moiety or a radionuclide complex
SITE                    6
                        note = Azaglycine
SITE                    8
                        note = 4-amino-1-R1-piperidine-4-carboxylic acid
SITE                    9
                        note = Amidated D-Tryptophan
SEQUENCE: 377
YKNTFGLXW                                                                   9

SEQ ID NO: 378          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-Lysine bound to an optional linker and chelating
                         moiety or a radionuclide complex
SITE                    6
                        note = cyclohexylalanine
SITE                    8
                        note = Azaglycine
SITE                    9
                        note = Amidated D-Tryptophan
SEQUENCE: 378
YKNTXGLXW                                                                   9

SEQ ID NO: 379          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = Lysine bound to an optional linker and chelating
                         moiety or a radionuclide complex
SITE                    5
                        note = cyclohexylalanine
```

```
SITE                   6
                       note = Azaglycine
SITE                   8
                       note = 4-amino-1-R1-piperidine-4-carboxylic acid
SITE                   9
                       note = Amidated Tryptophan
SEQUENCE: 379
YKNTXGLXW                                                   9

SEQ ID NO: 380         moltype = AA  length = 9
FEATURE                Location/Qualifiers
source                 1..9
                       mol_type = protein
                       organism = synthetic construct
SITE                   1
                       note = D-Tyrosine
SITE                   2
                       note = D-Lysine bound to an optional linker and chelating
                        moiety or a radionuclide complex
SITE                   5
                       note = cyclohexylalanine
SITE                   6
                       note = Azaglycine
SITE                   8
                       note = 4-amino-1-R1-piperidine-4-carboxylic acid
SITE                   9
                       note = Amidated Tryptophan
SEQUENCE: 380
YKNTXGLXW                                                   9

SEQ ID NO: 381         moltype = AA  length = 9
FEATURE                Location/Qualifiers
source                 1..9
                       mol_type = protein
                       organism = synthetic construct
SITE                   1
                       note = D-Tyrosine
SITE                   2
                       note = Lysine bound to an optional linker and chelating
                        moiety or a radionuclide complex
SITE                   6
                       note = Azaglycine
SITE                   8
                       note = 4-amino-1-R1-piperidine-4-carboxylic acid
SITE                   9
                       note = Amidated D-Tryptophan
SEQUENCE: 381
YKNTFGLXW                                                   9

SEQ ID NO: 382         moltype = AA  length = 9
FEATURE                Location/Qualifiers
source                 1..9
                       mol_type = protein
                       organism = synthetic construct
SITE                   1
                       note = D-Tyrosine
SITE                   2
                       note = D-Tryptophan
SITE                   6
                       note = Azaglycine
SITE                   8
                       note = 4-amino-1-R1-piperidine-4-carboxylic acid
SITE                   9
                       note = Amidated D-Tryptophan
SEQUENCE: 382
YWNTFGLXW                                                   9

SEQ ID NO: 383         moltype = AA  length = 8
FEATURE                Location/Qualifiers
source                 1..8
                       mol_type = protein
                       organism = synthetic construct
SITE                   5
                       note = Azaglycine
SITE                   6
                       note = D-Leucine
SITE                   7
                       note = 4-amino-1-R1-piperidine-4-carboxylic acid
SITE                   8
```

```
                        note = Amidated Phenylalanine
SEQUENCE: 383
ENTFGLXF                                                                    8

SEQ ID NO: 384          moltype = AA  length = 8
FEATURE                 Location/Qualifiers
source                  1..8
                        mol_type = protein
                        organism = synthetic construct
SITE                    1
                        note = D-Lysine bound to an optional linker and chelating
                         moiety or a radionuclide complex
SITE                    5
                        note = Azaglycine
SITE                    7
                        note = 4-amino-1-R1-piperidine-4-carboxylic acid
SITE                    8
                        note = Amidated 3-(4-pyridyl)alanine
SEQUENCE: 384
KNTFGLXX                                                                    8

SEQ ID NO: 385          moltype = AA  length = 8
FEATURE                 Location/Qualifiers
source                  1..8
                        mol_type = protein
                        organism = synthetic construct
SITE                    1
                        note =
                         1-hydroxy-3,6,9,12,15,18,21,24-octaoxaheptacosan-27-oic
                         acid-Lysine bound to an optional linker and chelating
                         moiety or a radionuclide complex
SITE                    5
                        note = Azaglycine
SITE                    7
                        note = 4-amino-1-R1-piperidine-4-carboxylic acid
SITE                    8
                        note = Amidated 3-(4-pyridyl)alanine
SEQUENCE: 385
KNTFGLXX                                                                    8

SEQ ID NO: 386          moltype = AA  length = 6
FEATURE                 Location/Qualifiers
source                  1..6
                        mol_type = protein
                        organism = synthetic construct
SITE                    1
                        note = DOTA-bAla
SITE                    2
                        note = Sarcosine
SITE                    3
                        note = Sarcosine
SITE                    4
                        note = Sarcosine
SITE                    5
                        note = Sarcosine
SITE                    6
                        note = Sarcosine
SEQUENCE: 386
AGGGGG                                                                      6

SEQ ID NO: 387          moltype = AA  length = 5
FEATURE                 Location/Qualifiers
source                  1..5
                        mol_type = protein
                        organism = synthetic construct
SITE                    1
                        note = DOTA-D-Ala
SITE                    2
                        note = D-Alanine
SITE                    3
                        note = D-Alanine
SITE                    4
                        note = D-Alanine
SITE                    5
                        note = D-Alanine
SEQUENCE: 387
AAAAA                                                                       5

SEQ ID NO: 388          moltype = AA  length = 6
```

```
FEATURE                 Location/Qualifiers
source                  1..6
                        mol_type = protein
                        organism = synthetic construct
SITE                    1
                        note = DOTA-Beta-Alanine
SITE                    2
                        note = D-Asparagine
SITE                    3
                        note = D-Asparagine
SITE                    4
                        note = D-Asparagine
SITE                    5
                        note = D-Asparagine
SITE                    6
                        note = D-Asparagine
SEQUENCE: 388
ANNNNN                                                                       6

SEQ ID NO: 389          moltype = AA  length = 6
FEATURE                 Location/Qualifiers
source                  1..6
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-Beta-Alanine
SITE                    2
                        note = D-Asparagine
SITE                    3
                        note = D-Asparagine
SITE                    4
                        note = D-Glutamic Acid
SITE                    5
                        note = D-Glutamic Acid
SITE                    6
                        note = D-Asparagine
SEQUENCE: 389
ANNEEN                                                                       6

SEQ ID NO: 390          moltype = AA  length = 6
FEATURE                 Location/Qualifiers
source                  1..6
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-Beta-Alanine
SITE                    2
                        note = D-Asparagine
SITE                    3
                        note = D-Asparagine
SITE                    4
                        note = D-Lysine
SITE                    5
                        note = D-Glutamic Acid
SITE                    6
                        note = D-Asparagine
SEQUENCE: 390
ANNKEN                                                                       6

SEQ ID NO: 391          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-Tryptophan
SITE                    7
                        note = Azaglycine
SITE                    9
```

```
                        note =
                         4-amino-1-((3-fluoro-4-methylbenzyl)glycyl)piperidine-4-car
                         boxamide
SITE                    10
                        note = Amidated Tryptophan
SEQUENCE: 391
XYWNTFGLXW                                                                   10

SEQ ID NO: 392          moltype = AA  length = 10
FEATURE                 Location/Qualifiers
source                  1..10
                        mol_type = protein
                        organism = synthetic construct
SITE                    1
                        note = indium(III)
                         2,2',2''-(10-(2-((5-carboxypentyl)amino)-2-oxoethyl)-1,4,7,
                         10-tetraazacyclododecane-1,4,7-triyl)triacetate
SITE                    2
                        note = D-Tyrosine
SITE                    3
                        note = D-Tryptophan
SITE                    7
                        note = Azaglycine
SITE                    9
                        note =
                         4-amino-1-((3-fluoro-4-methylbenzyl)glycyl)piperidine-4-car
                         boxamide
SITE                    10
                        note = Amidated Tryptophan
SEQUENCE: 392
XYWNTFGLXW                                                                   10

SEQ ID NO: 393          moltype = AA  length = 10
FEATURE                 Location/Qualifiers
source                  1..10
                        mol_type = protein
                        organism = synthetic construct
SITE                    1
                        note = Lutetium (III)
                         2,2',2''-(10-(2-((5-carboxypentyl)amino)-2-oxoethyl)-1,4,7,
                         10-tetraazacyclododecane-1,4,7-triyl)triacetate
SITE                    2
                        note = D-Tyrosine
SITE                    3
                        note = D-Tryptophan
SITE                    7
                        note = Azaglycine
SITE                    9
                        note =
                         4-amino-1-((3-fluoro-4-methylbenzyl)glycyl)piperidine-4-car
                         boxamide
SITE                    10
                        note = Amidated Tryptophan
SEQUENCE: 393
XYWNTFGLXW                                                                   10

SEQ ID NO: 394          moltype = AA  length = 10
FEATURE                 Location/Qualifiers
source                  1..10
                        mol_type = protein
                        organism = synthetic construct
SITE                    1
                        note = gallium(III)
                         2,2',2''-(10-(2-((5-carboxypentyl)amino)-2-oxoethyl)-1,4,7,
                         10-tetraazacyclododecane-1,4,7-triyl)triacetate
SITE                    2
                        note = D-Tyrosine
SITE                    3
                        note = D-Tryptophan
SITE                    7
                        note = Azaglycine
SITE                    9
                        note =
                         4-amino-1-((3-fluoro-4-methylbenzyl)glycyl)piperidine-4-car
                         boxamide
SITE                    10
                        note = Amidated Tryptophan
SEQUENCE: 394
XYWNTFGLXW                                                                   10
```

```
SEQ ID NO: 395          moltype = AA  length = 6
FEATURE                 Location/Qualifiers
source                  1..6
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    3
                        note = Azaglycine
SITE                    5
                        note =
                         4-amino-1-((3-fluoro-4-methylbenzyl)glycyl)piperidine-4-car
                         boxamide
SITE                    6
                        note = Amidated Tryptophan
SEQUENCE: 395
XFGLXW                                                                  6

SEQ ID NO: 396          moltype = AA  length = 6
FEATURE                 Location/Qualifiers
source                  1..6
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    5
                        note = 4-amino-1-carbamimidoylpiperidine-4-carboxylic acid
SITE                    6
                        note = Amidated Tryptophan
SEQUENCE: 396
XFGLXW                                                                  6

SEQ ID NO: 397          moltype = AA  length = 6
FEATURE                 Location/Qualifiers
source                  1..6
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = alpha-Me-Phenylalanine
SITE                    3
                        note = Azaglycine
SITE                    5
                        note =
                         4-amino-1-((3-fluoro-4-methylbenzyl)glycyl)piperidine-4-car
                         boxamide
SITE                    6
                        note = Amidated Tryptophan
SEQUENCE: 397
XFGLXW                                                                  6

SEQ ID NO: 398          moltype = AA  length = 6
FEATURE                 Location/Qualifiers
source                  1..6
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    3
                        note = Azaglycine
SITE                    5
                        note = 4-amino-1-carbamimidoylpiperidine-4-carboxylic acid
SITE                    6
                        note = Amidated Tryptophan
SEQUENCE: 398
XFGLXW                                                                  6

SEQ ID NO: 399          moltype = AA  length = 10
FEATURE                 Location/Qualifiers
```

```
source              1..10
                    mol_type = protein
                    organism = synthetic construct
SITE                1
                    note =
                     2,2',2'',2'''-(1,4,7,10-tetraazacyclododecane-1,4,7,10-tetr
                     ayl)tetraacetic acid 6-aminohexanoic acid
SITE                2
                    note = D-Tyrosine
SITE                3
                    note = D-Tryptophan
SITE                7
                    note = Azaglycine
SITE                9
                    note = 4-amino-1-carbamimidoylpiperidine-4-carboxylic acid
SITE                10
                    note = Amidated Tryptophan
SEQUENCE: 399
XYWNTFGLXW                                                         10

SEQ ID NO: 400      moltype = AA  length = 6
FEATURE             Location/Qualifiers
source              1..6
                    mol_type = protein
                    organism = synthetic construct
SITE                1
                    note =
                     2,2',2'',2'''-(1,4,7,10-tetraazacyclododecane-1,4,7,10-tetr
                     ayl)tetraacetic acid 6-aminohexanoic acid
SITE                3
                    note = Azaglycine
SITE                5
                    note =
                     4-amino-1-(4-(p-tolyl)butanoyl)piperidine-4-carboxylic acid
SITE                6
                    note = Amidated Tryptophan
SEQUENCE: 400
XFGLXW                                                             6

SEQ ID NO: 401      moltype =   length =
SEQUENCE: 401
000

SEQ ID NO: 402      moltype =   length =
SEQUENCE: 402
000

SEQ ID NO: 403      moltype = AA  length = 6
FEATURE             Location/Qualifiers
source              1..6
                    mol_type = protein
                    organism = synthetic construct
SITE                1
                    note =
                     2,2',2'',2'''-(1,4,7,10-tetraazacyclododecane-1,4,7,10-tetr
                     ayl)tetraacetic acid 6-aminohexanoic acid
SITE                5
                    note =
                     4-amino-1-((3-fluoro-4-methylbenzyl)glycyl)piperidine-4-car
                     boxamide
SITE                6
                    note = Amidated Tryptophan
SEQUENCE: 403
XFGLXW                                                             6

SEQ ID NO: 404      moltype = AA  length = 6
FEATURE             Location/Qualifiers
source              1..6
                    mol_type = protein
                    organism = synthetic construct
SITE                1
                    note =
                     2,2',2'',2'''-(1,4,7,10-tetraazacyclododecane-1,4,7,10-tetr
                     ayl)tetraacetic acid 6-aminohexanoic acid
SITE                5
                    note =
                     4-amino-1-((3-fluoro-4-methylbenzyl)glycyl)piperidine-4-car
                     boxamide
SITE                6
```

```
                         note = Amidated Tyrosine
SEQUENCE: 404
XFGLXY                                                                      6

SEQ ID NO: 405           moltype = AA  length = 6
FEATURE                  Location/Qualifiers
source                   1..6
                         mol_type = protein
                         organism = synthetic construct
SITE                     1
                         note =
                          2,2',2'',2'''-(1,4,7,10-tetraazacyclododecane-1,4,7,10-tetr
                          ayl)tetraacetic acid 6-aminohexanoic acid
SITE                     3
                         note = Sarcosine
SITE                     5
                         note =
                          4-amino-1-((3-fluoro-4-methylbenzyl)glycyl)piperidine-4-car
                          boxamide
SITE                     6
                         note = Amidated Tryptophan
SEQUENCE: 405
XFGLXW                                                                      6

SEQ ID NO: 406           moltype = AA  length = 11
FEATURE                  Location/Qualifiers
source                   1..11
                         mol_type = protein
                         organism = synthetic construct
SITE                     1
                         note =
                          2,2',2'',2'''-(1,4,7,10-tetraazacyclododecane-1,4,7,10-tetr
                          ayl)tetraacetic acid 6-aminohexanoic acid
SITE                     2
                         note = D-Alanine
SITE                     3
                         note = D-Alanine
SITE                     4
                         note = D-Alanine
SITE                     5
                         note = D-Alanine
SITE                     6
                         note = D-Alanine
SITE                     8
                         note = Azaglycine
SITE                     10
                         note =
                          4-amino-1-((3-fluoro-4-methylbenzyl)glycyl)piperidine-4-car
                          boxamide
SITE                     11
                         note = Amidated Tryptophan
SEQUENCE: 406
XAAAAAFGLX W                                                                11

SEQ ID NO: 407           moltype = AA  length = 11
FEATURE                  Location/Qualifiers
source                   1..11
                         mol_type = protein
                         organism = synthetic construct
SITE                     1
                         note = DOTA-beta-Alanine
SITE                     2
                         note = D-Asparagine
SITE                     3
                         note = D-Asparagine
SITE                     4
                         note = D-Asparagine
SITE                     5
                         note = D-Asparagine
SITE                     6
                         note = D-Asparagine
SITE                     8
                         note = Azaglycine
SITE                     10
                         note =
                          4-amino-1-((3-fluoro-4-methylbenzyl)glycyl)piperidine-4-car
                          boxamide
SITE                     11
                         note = Amidated Tryptophan
```

```
SEQUENCE: 407
ANNNNNFGLX W                                                    11

SEQ ID NO: 408          moltype = AA  length = 11
FEATURE                 Location/Qualifiers
source                  1..11
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-beta-Alanine
SITE                    2
                        note = D-Asparagine
SITE                    3
                        note = D-Asparagine
SITE                    4
                        note = D-Glutamic Acid
SITE                    5
                        note = D-Glutamic Acid
SITE                    6
                        note = D-Asparagine
SITE                    8
                        note = Azaglycine
SITE                    10
                        note =
                         4-amino-1-((3-fluoro-4-methylbenzyl)glycyl)piperidine-4-car
                         boxamide
SITE                    11
                        note = Amidated Tryptophan
SEQUENCE: 408
ANNEENFGLX W                                                    11

SEQ ID NO: 409          moltype = AA  length = 11
FEATURE                 Location/Qualifiers
source                  1..11
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-beta-Alanine
SITE                    2
                        note = D-Asparagine
SITE                    3
                        note = D-Asparagine
SITE                    4
                        note = D-Lysine
SITE                    5
                        note = D-Glutamic Acid
SITE                    6
                        note = D-Asparagine
SITE                    8
                        note = Azaglycine
SITE                    10
                        note =
                         4-amino-1-((3-fluoro-4-methylbenzyl)glycyl)piperidine-4-car
                         boxamide
SITE                    11
                        note = Amidated Tryptophan
SEQUENCE: 409
ANNKENFGLX W                                                    11

SEQ ID NO: 410          moltype = AA  length = 7
FEATURE                 Location/Qualifiers
source                  1..7
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-Sarcosine
SITE                    2
                        note = Sarcosine
SITE                    4
                        note = Azaglycine
SITE                    6
                        note =
                         4-amino-1-((3-fluoro-4-methylbenzyl)glycyl)piperidine-4-car
```

```
                        boxamide
SITE                    7
                        note = Amidated Tryptophan
SEQUENCE: 410
GGFGLXW                                                                     7

SEQ ID NO: 411          moltype = AA  length = 7
FEATURE                 Location/Qualifiers
source                  1..7
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-D-Asparagine
SITE                    2
                        note = D-Asparagine
SITE                    4
                        note = Azaglycine
SITE                    6
                        note =
                         4-amino-1-((3-fluoro-4-methylbenzyl)glycyl)piperidine-4-car
                         boxamide
SITE                    7
                        note = Amidated Tryptophan
SEQUENCE: 411
NNFGLXW                                                                     7

SEQ ID NO: 412          moltype = AA  length = 7
FEATURE                 Location/Qualifiers
source                  1..7
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-D-Lys
SITE                    2
                        note = D-Asparagine
SITE                    4
                        note = Azaglycine
SITE                    6
                        note =
                         4-amino-1-((3-fluoro-4-methylbenzyl)glycyl)piperidine-4-car
                         boxamide
SITE                    7
                        note = Amidated Tryptophan
SEQUENCE: 412
KNFGLXW                                                                     7

SEQ ID NO: 413          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    7
                        note = Azaglycine
SITE                    9
                        note =
                         4-amino-1-((3-fluoro-4-methylbenzyl)glycyl)piperidine-4-car
                         boxamide
SITE                    10
                        note = Amidated Tryptophan
SEQUENCE: 413
XYPNTFGLXW                                                                  10

SEQ ID NO: 414          moltype = AA  length = 6
FEATURE                 Location/Qualifiers
source                  1..6
                        mol_type = protein
                        organism = synthetic construct
SITE                    1
                        note =
```

```
                         2,2',2'',2'''-(1,4,7,10-tetraazacyclododecane-1,4,7,10-tetr
                         ayl)tetraacetic acid-D-Asn
SITE                    3
                        note = Azaglycine
SITE                    5
                        note =
                         4-amino-1-((3-fluoro-4-methylbenzyl)glycyl)piperidine-4-car
                         boxamide
SITE                    6
                        note = Amidated Tryptophan
SEQUENCE: 414
NFGLXW                                                                            6

SEQ ID NO: 415          moltype = AA  length = 7
FEATURE                 Location/Qualifiers
source                  1..7
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    3
                        note = NHCH2-Phenylalanine-C(=O)-
SITE                    3
                        note = Azaglycine
SITE                    5
                        note =
                         4-amino-1-((3-fluoro-4-methylbenzyl)glycyl)piperidine-4-car
                         boxamide
SITE                    6
                        note = Amidated Tryptophan
SEQUENCE: 415
XFFGLXW                                                                           7

SEQ ID NO: 416          moltype = AA  length = 9
FEATURE                 Location/Qualifiers
source                  1..9
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-D-Tyrosine
SITE                    2
                        note = D-3-(4-pyridyl)alanine
SITE                    6
                        note = Azaglycine
SITE                    8
                        note =
                         4-amino-1-((3-fluoro-4-methylbenzyl)glycyl)piperidine-4-car
                         boxamide
SITE                    9
                        note = Amidated Tryptophan
SEQUENCE: 416
YXNTFGLXW                                                                         9

SEQ ID NO: 417          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-2-(4-aminopiperidin-1-yl)acetic acid
SITE                    2
                        note = D-Tyrosine
SITE                    6
                        note = 3-fluorophenylalanine
SITE                    7
                        note = Azaglycine
SITE                    9
                        note =
                         4-amino-1-((3-fluoro-4-methylbenzyl)glycyl)piperidine-4-car
                         boxamide
SITE                    10
                        note = Amidated Tryptophan
SEQUENCE: 417
```

```
XYENTFGLXW                                                          10

SEQ ID NO: 418          moltype = AA  length = 6
FEATURE                 Location/Qualifiers
source                  1..6
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-NHCH2-Chx-C(=O)-
SITE                    3
                        note = Azaglycine
SITE                    5
                        note =
                         4-amino-1-((3-fluoro-4-methylbenzyl)glycyl)piperidine-4-car
                         boxamide
SITE                    6
                        note = Amidated Tryptophan
SEQUENCE: 418
XFGLXW                                                              6

SEQ ID NO: 419          moltype = AA  length = 8
FEATURE                 Location/Qualifiers
source                  1..8
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    5
                        note = Azaglycine
SITE                    7
                        note =
                         4-amino-1-((3-fluoro-4-methylbenzyl)glycyl)piperidine-4-car
                         boxamide
SITE                    8
                        note = Amidated Tryptophan
SEQUENCE: 419
XNTFGLXW                                                            8

SEQ ID NO: 420          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    6
                        note = 3-fluorophenylalanine
SITE                    7
                        note = Azaglycine
SITE                    9
                        note =
                         4-amino-1-((3-fluoro-4-methylbenzyl)glycyl)piperidine-4-car
                         boxamide
SITE                    10
                        note = Amidated Tryptophan
SEQUENCE: 420
XYKNTFGLXW                                                          10

SEQ ID NO: 421          moltype = AA  length = 6
FEATURE                 Location/Qualifiers
source                  1..6
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-APM
SITE                    3
                        note = Azaglycine
SITE                    5
                        note =
```

```
                          4-amino-1-((3-fluoro-4-methylbenzyl)glycyl)piperidine-4-car
                          boxamide
SITE                      6
                          note = Amidated Tryptophan
SEQUENCE: 421
XFGLXW                                                                      6

SEQ ID NO: 422            moltype = AA  length = 10
FEATURE                   Location/Qualifiers
source                    1..10
                          mol_type = protein
                          organism = synthetic construct
SITE                      1
                          note =
                          2,2',2'',2'''-(1,4,7,10-tetraazacyclododecane-1,4,7,10-tetr
                          ayl)tetraacetic acid-2-(4-aminopiperidin-1-yl)acetic acid
SITE                      2
                          note = D-Tyrosine
SITE                      3
                          note = D-3-(4-pyridyl)alanine
SITE                      7
                          note = Azaglycine
SITE                      9
                          note =
                          4-amino-1-((3-fluoro-4-methylbenzyl)glycyl)piperidine-4-car
                          boxamide
SITE                      10
                          note = Amidated Tryptophan
SEQUENCE: 422
XYXNTFGLXW                                                                  10

SEQ ID NO: 423            moltype = AA  length = 9
FEATURE                   Location/Qualifiers
source                    1..9
                          mol_type = protein
                          organism = synthetic construct
SITE                      1
                          note =
                          2,2',2'',2'''-(1,4,7,10-tetraazacyclododecane-1,4,7,10-tetr
                          ayl)tetraacetic acid 6-aminohexanoic acid
SITE                      2
                          note = D-Tryptophan
SITE                      6
                          note = Azaglycine
SITE                      8
                          note =
                          4-amino-1-((3-fluoro-4-methylbenzyl)glycyl)piperidine-4-car
                          boxamide
SITE                      9
                          note = Amidated Tryptophan
SEQUENCE: 423
XWNTFGLXW                                                                   9

SEQ ID NO: 424            moltype = AA  length = 10
FEATURE                   Location/Qualifiers
source                    1..10
                          mol_type = protein
                          organism = synthetic construct
SITE                      1
                          note =
                          2,2',2'',2'''-(1,4,7,10-tetraazacyclododecane-1,4,7,10-tetr
                          ayl)tetraacetic acid 6-aminohexanoic acid
SITE                      2
                          note = D-Tyrosine
SITE                      3
                          note = D-3-(4-pyridyl)alanine
SITE                      7
                          note = Azaglycine
SITE                      9
                          note =
                          4-amino-1-((3-fluoro-4-methylbenzyl)glycyl)piperidine-4-car
                          boxamide
SITE                      10
                          note = Amidated Tryptophan
SEQUENCE: 424
XYXNTFGLXW                                                                  10

SEQ ID NO: 425            moltype = AA  length = 11
FEATURE                   Location/Qualifiers
```

-continued

```
source                  1..11
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-Histidine
SITE                    4
                        note = D-Tryptophan
SITE                    8
                        note = Azaglycine
SITE                    10
                        note =
                         4-amino-1-((3-fluoro-4-methylbenzyl)glycyl)piperidine-4-car
                         boxamide
SITE                    11
                        note = Amidated Tryptophan
SEQUENCE: 425
XYHWNTFGLX W                                                                  11

SEQ ID NO: 426          moltype = AA  length = 11
FEATURE                 Location/Qualifiers
source                  1..11
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-APM
SITE                    2
                        note = D-Tyrosine
SITE                    3
                        note = D-Histidine
SITE                    4
                        note = D-Tryptophan
SITE                    8
                        note = Azaglycine
SITE                    10
                        note =
                         4-amino-1-((3-fluoro-4-methylbenzyl)glycyl)piperidine-4-car
                         boxamide
SITE                    11
                        note = Amidated Tryptophan
SEQUENCE: 426
XYHWNTFGLX W                                                                  11

SEQ ID NO: 427          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-APM
SITE                    2
                        note = D-Tyrosine
SITE                    3
                        note = D-Tryptophan
SITE                    6
                        note = 3-fluorophenylalanine
SITE                    7
                        note = Azaglycine
SITE                    9
                        note =
                         4-amino-1-((3-fluoro-4-methylbenzyl)glycyl)piperidine-4-car
                         boxamide
SITE                    10
                        note = Amidated Tryptophan
SEQUENCE: 427
XYWNTFGLXW                                                                    10

SEQ ID NO: 428          moltype = AA  length = 10
FEATURE                 Location/Qualifiers
source                  1..10
```

```
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    6
                        note = 3-fluorophenylalanine
SITE                    7
                        note = Azaglycine
SITE                    9
                        note =
                         4-amino-1-((3-fluoro-4-methylbenzyl)glycyl)piperidine-4-car
                         boxamide
SITE                    10
                        note = Amidated Tryptophan
SEQUENCE: 428
XYWNTFGLXW                                                    10

SEQ ID NO: 429          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    6
                        note = 3-fluorophenylalanine
SITE                    7
                        note = Azaglycine
SITE                    9
                        note =
                         4-amino-1-((3-fluoro-4-methylbenzyl)glycyl)piperidine-4-car
                         boxamide
SITE                    10
                        note = Amidated Tryptophan
SEQUENCE: 429
XYENTFGLXW                                                    10

SEQ ID NO: 430          moltype = AA  length = 6
FEATURE                 Location/Qualifiers
source                  1..6
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-Lys
SITE                    3
                        note = Azaglycine
SITE                    5
                        note =
                         4-amino-1-((3-fluoro-4-methylbenzyl)glycyl)piperidine-4-car
                         boxamide
SITE                    6
                        note = Amidated Tryptophan
SEQUENCE: 430
KFGLXW                                                        6

SEQ ID NO: 431          moltype = AA  length = 7
FEATURE                 Location/Qualifiers
source                  1..7
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = NHCH2-Chx-C(=O)
SITE                    4
                        note = Azaglycine
SITE                    6
```

```
                        note =
                         4-amino-1-((3-fluoro-4-methylbenzyl)glycyl)piperidine-4-car
                         boxamide
SITE                    7
                        note = Amidated Tryptophan
SEQUENCE: 431
XXFGLXW                                                                     7

SEQ ID NO: 432          moltype =   length =
SEQUENCE: 432
000

SEQ ID NO: 433          moltype = AA  length = 6
FEATURE                 Location/Qualifiers
source                  1..6
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    3
                        note = Azaglycine
SITE                    4
                        note = D-Leucine
SITE                    5
                        note =
                         4-amino-1-((3-fluoro-4-methylbenzyl)glycyl)piperidine-4-car
                         boxamide
SITE                    6
                        note = Amidated Tryptophan
SEQUENCE: 433
XFGLXW                                                                      6

SEQ ID NO: 434          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = Sarcosine
SITE                    3
                        note = Sarcosine
SITE                    4
                        note = Sarcosine
SITE                    5
                        note = Sarcosine
SITE                    9
                        note = 4-amino-1-carbamimidoylpiperidine-4-carboxylic acid
SITE                    10
                        note = Amidated Tryptophan
SEQUENCE: 434
XGGGGFGLXW                                                                  10

SEQ ID NO: 435          moltype = AA  length = 6
FEATURE                 Location/Qualifiers
source                  1..6
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    3
                        note = Sarcosine
SITE                    4
                        note = Methyl-leucine
SITE                    5
                        note =
                         4-amino-1-((3-fluoro-4-methylbenzyl)glycyl)piperidine-4-car
                         boxamide
SITE                    6
                        note = Amidated Tryptophan
SEQUENCE: 435
XFGLXW                                                                      6
```

```
SEQ ID NO: 436          moltype = AA  length = 6
FEATURE                 Location/Qualifiers
source                  1..6
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    3
                        note = Azaglycine
SITE                    5
                        note =
                         4-amino-1-((3-fluoro-4-methylbenzyl)glycyl)piperidine-4-car
                         boxamide
SITE                    6
                        note = Me-Trp-NH2
SEQUENCE: 436
XFGLXW                                                                    6

SEQ ID NO: 437          moltype =   length =
SEQUENCE: 437
000

SEQ ID NO: 438          moltype =   length =
SEQUENCE: 438
000

SEQ ID NO: 439          moltype = AA  length = 9
FEATURE                 Location/Qualifiers
source                  1..9
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-Beta-Alanine
SITE                    2
                        note = Sarcosine
SITE                    3
                        note = Sarcosine
SITE                    4
                        note = Sarcosine
SITE                    5
                        note = Sarcosine
SITE                    6
                        note = Sarcosine
SITE                    8
                        note =
                         4-amino-1-((3-fluoro-4-methylbenzyl)glycyl)piperidine-4-car
                         boxamide
SITE                    9
                        note = Amidated Tryptophan
SEQUENCE: 439
AGGGGGFXW                                                                 9

SEQ ID NO: 440          moltype = AA  length = 9
FEATURE                 Location/Qualifiers
source                  1..9
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-Beta-Alanine
SITE                    2
                        note = Sarcosine
SITE                    3
                        note = Sarcosine
SITE                    4
                        note = Sarcosine
SITE                    5
                        note = Sarcosine
SITE                    6
                        note = Sarcosine
SITE                    7
                        note = phenylglycine
SITE                    8
```

```
                        note =
                         4-amino-1-((3-fluoro-4-methylbenzyl)glycyl)piperidine-4-car
                         boxamide
SITE                    9
                        note = Amidated Tryptophan
SEQUENCE: 440
AGGGGGGXW                                                   9

SEQ ID NO: 441          moltype = AA  length = 5
FEATURE                 Location/Qualifiers
source                  1..5
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-Phe
SITE                    2
                        note = Azaglycine
SITE                    4
                        note =
                         4-amino-1-((3-fluoro-4-methylbenzyl)glycyl)piperidine-4-car
                         boxamide
SITE                    5
                        note = Amidated Tryptophan
SEQUENCE: 441
FGLXW                                                       5

SEQ ID NO: 442          moltype = AA  length = 6
FEATURE                 Location/Qualifiers
source                  1..6
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-ABA
SITE                    3
                        note = Azaglycine
SITE                    5
                        note =
                         4-amino-1-((3-fluoro-4-methylbenzyl)glycyl)piperidine-4-car
                         boxamide
SITE                    6
                        note = Amidated Tryptophan
SEQUENCE: 442
XFGLXW                                                      6

SEQ ID NO: 443          moltype =   length =
SEQUENCE: 443
000

SEQ ID NO: 444          moltype = AA  length = 6
FEATURE                 Location/Qualifiers
source                  1..6
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-ABA
SITE                    3
                        note = Sarcosine
SITE                    4
                        note = Methyl-leucine
SITE                    5
                        note =
                         4-amino-1-((3-fluoro-4-methylbenzyl)glycyl)piperidine-4-car
                         boxamide
SITE                    6
                        note = Amidated Tryptophan
SEQUENCE: 444
XFGLXW                                                      6

SEQ ID NO: 445          moltype = AA  length = 6
FEATURE                 Location/Qualifiers
source                  1..6
                        mol_type = protein
                        organism = synthetic construct
```

```
SITE                    1
                        note =
                         2,2',2'',2'''-(1,4,7,10-tetraazacyclododecane-1,4,7,10-tetr
                         ayl)tetraacetic acid-ABA
SITE                    4
                        note = N-Me-Leu
SITE                    5
                        note =
                         4-amino-1-((3-fluoro-4-methylbenzyl)glycyl)piperidine-4-car
                         boxamide
SITE                    6
                        note = Amidated Tryptophan
SEQUENCE: 445
XFGLXW                                                                      6

SEQ ID NO: 446          moltype =   length =
SEQUENCE: 446
000

SEQ ID NO: 447          moltype = AA  length = 6
FEATURE                 Location/Qualifiers
source                  1..6
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    3
                        note = Azaglycine
SITE                    5
                        note =
                         4-amino-1-((3-fluoro-4-methylbenzyl)glycyl)piperidine-4-car
                         boxamide
SITE                    6
                        note = Amidated Phenylalanine
SEQUENCE: 447
XFGLXF                                                                      6

SEQ ID NO: 448          moltype = AA  length = 9
FEATURE                 Location/Qualifiers
source                  1..9
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-NH-glycol D-Tyrosine
SITE                    2
                        note = D-Tryptophan
SITE                    6
                        note = Azaglycine
SITE                    8
                        note =
                         4-amino-1-((3-fluoro-4-methylbenzyl)glycyl)piperidine-4-car
                         boxamide
SITE                    9
                        note = Amidated Phenylalanine
SEQUENCE: 448
YWNTFGLXF                                                                   9

SEQ ID NO: 449          moltype = AA  length = 9
FEATURE                 Location/Qualifiers
source                  1..9
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-NH-glycol-D-Tyrosine
SITE                    2
                        note = D-Tryptophan
SITE                    6
                        note = Azaglycine
SITE                    8
                        note =
                         4-amino-1-((3-fluoro-4-methylbenzyl)glycyl)piperidine-4-car
                         boxamide
SITE                    9
```

| | |
|---|---|
| | note = Amidated Tryptophan |
| SEQUENCE: 449 | |
| YWNTFGLXW | 9 |
| SEQ ID NO: 450 | moltype = AA length = 9 |
| FEATURE | Location/Qualifiers |
| source | 1..9 |
| | mol_type = protein |
| | organism = synthetic construct |
| SITE | 1 |
| | note = 2,2',2'',2'''-(1,4,7,10-tetraazacyclododecane-1,4,7,10-tetr ayl)tetraacetic acid-NH-glycol D-Tyrosine |
| SITE | 2 |
| | note = 3-(2-Naphthyl)alanine or |
| SITE | 6 |
| | note = Azaglycine |
| SITE | 8 |
| | note = 4-amino-1-((3-fluoro-4-methylbenzyl)glycyl)piperidine-4-car boxamide |
| SITE | 9 |
| | note = Amidated Tryptophan |
| SEQUENCE: 450 | |
| YXNTFGLXW | 9 |
| SEQ ID NO: 451 | moltype = AA length = 9 |
| FEATURE | Location/Qualifiers |
| source | 1..9 |
| | mol_type = protein |
| | organism = synthetic construct |
| SITE | 1 |
| | note = 2,2',2'',2'''-(1,4,7,10-tetraazacyclododecane-1,4,7,10-tetr ayl)tetraacetic acid-NH-glycol D-Tyrosine |
| SITE | 6 |
| | note = Azaglycine |
| SITE | 8 |
| | note = 4-amino-1-((3-fluoro-4-methylbenzyl)glycyl)piperidine-4-car boxamide |
| SITE | 9 |
| | note = Amidated Tryptophan |
| SEQUENCE: 451 | |
| YRNTFGLXW | 9 |
| SEQ ID NO: 452 | moltype = AA length = 10 |
| FEATURE | Location/Qualifiers |
| source | 1..10 |
| | mol_type = protein |
| | organism = synthetic construct |
| SITE | 1 |
| | note = 2,2',2'',2'''-(1,4,7,10-tetraazacyclododecane-1,4,7,10-tetr ayl)tetraacetic acid-NH-glycol D-Tyrosine |
| SITE | 2 |
| | note = D-Asparagine |
| SITE | 3 |
| | note = D-Arginine |
| SITE | 7 |
| | note = Azaglycine |
| SITE | 9 |
| | note = 4-amino-1-((3-fluoro-4-methylbenzyl)glycyl)piperidine-4-car boxamide |
| SITE | 10 |
| | note = Amidated Tryptophan |
| SEQUENCE: 452 | |
| YNRNTFGLXW | 10 |
| SEQ ID NO: 453 | moltype = AA length = 11 |
| FEATURE | Location/Qualifiers |
| source | 1..11 |
| | mol_type = protein |
| | organism = synthetic construct |
| SITE | 1 |
| | note = 2,2',2'',2'''-(1,4,7,10-tetraazacyclododecane-1,4,7,10-tetr ayl)tetraacetic acid-beta-Alanine |

-continued

```
SITE                    2
                        note = Sarcosine
SITE                    3
                        note = Sarcosine
SITE                    4
                        note = Sarcosine
SITE                    5
                        note = Sarcosine
SITE                    6
                        note = Sarcosine
SITE                    8
                        note = Azaglycine
SITE                    10
                        note =
                         4-amino-1-((3-fluoro-4-methylbenzyl)glycyl)piperidine-4-car
                         boxamide
SITE                    11
                        note = Amidated Tryptophan
SEQUENCE: 453
AGGGGGFGLX W                                                        11

SEQ ID NO: 454          moltype = AA  length = 7
FEATURE                 Location/Qualifiers
source                  1..7
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-D-Glu
SITE                    2
                        note = D-Asparagine
SITE                    4
                        note = Azaglycine
SITE                    6
                        note =
                         4-amino-1-((3-fluoro-4-methylbenzyl)glycyl)piperidine-4-car
                         boxamide
SITE                    7
                        note = Amidated Tryptophan
SEQUENCE: 454
ENFGLXW                                                             7

SEQ ID NO: 455          moltype = AA  length = 9
FEATURE                 Location/Qualifiers
source                  1..9
                        mol_type = protein
                        organism = synthetic construct
SITE                    1
                        note =
                         2,2',2''-(10-(2-((2-(carboxymethoxy)ethyl)amino)-2-oxoethyl
                         )-1,4,7,10-tetraazacyclododecane-1,4,7-triyl)triacetic
                         acid coupled to N-term of D-Tyrosine
SITE                    2
                        note = D-Alanine
SITE                    6
                        note = Azaglycine
SITE                    8
                        note =
                         4-amino-1-((3-fluoro-4-methylbenzyl)glycyl)piperidine-4-car
                         boxamide
SITE                    9
                        note = Amidated Tryptophan
SEQUENCE: 455
YANTFGLXW                                                           9

SEQ ID NO: 456          moltype = AA  length = 9
FEATURE                 Location/Qualifiers
source                  1..9
                        mol_type = protein
                        organism = synthetic construct
SITE                    1
                        note = HO-PEG3-C(=O)-D-Tyrosine
SITE                    2
                        note =
                         Lysine(1,4,7,10-tetraazacyclododecane-1,4,7,10-tetraacetic
                         acid)
SITE                    5
                        note = 3-fluorophenylalanine
```

```
SITE                    6
                        note = Azaglycine
SITE                    8
                        note =
                         4-amino-1-((3-fluoro-4-methylbenzyl)glycyl)piperidine-4-car
                         boxamide
SITE                    9
                        note = Amidated Tryptophan
SEQUENCE: 456
YKNTFGLXW                                                                  9

SEQ ID NO: 457          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-Tryptophan
SITE                    7
                        note = Azaglycine
SITE                    9
                        note =
                         4-amino-1-(4-(3-fluoro-4-methylphenyl)butanoyl)piperidine-4
                         -carboxylic acid
SITE                    10
                        note = Amidated Tryptophan
SEQUENCE: 457
XYWNTFGLXW                                                                 10

SEQ ID NO: 458          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-Tryptophan
SITE                    7
                        note = Azaglycine
SITE                    9
                        note =
                         4-amino-1-(4-(p-tolyl)butanoyl)piperidine-4-carboxylic acid
SITE                    10
                        note = Amidated Tryptophan
SEQUENCE: 458
XYWNTFGLXW                                                                 10

SEQ ID NO: 459          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-Tryptophan
SITE                    7
                        note = Azaglycine
SITE                    9
                        note = 4-amino-1-(2-(p-tolyl)acetyl)piperidine-4-carboxylic
                         acid
SITE                    10
                        note = Amidated Tryptophan
SEQUENCE: 459
```

```
XYWNTFGLXW                                                            10

SEQ ID NO: 460          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-Tryptophan
SITE                    7
                        note = Azaglycine
SITE                    9
                        note =
                         4-amino-1-(2-(4-iodophenyl)acetyl)piperidine-4-carboxylic
                         acid
SITE                    10
                        note = Amidated Tryptophan
SEQUENCE: 460
XYWNTFGLXW                                                            10

SEQ ID NO: 461          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-Tryptophan
SITE                    7
                        note = Azaglycine
SITE                    9
                        note =
                         4-amino-1-((4-aminobenzyl)glycyl)piperidine-4-carboxylic
                         acid
SITE                    10
                        note = Amidated Tryptophan
SEQUENCE: 461
XYWNTFGLXW                                                            10

SEQ ID NO: 462          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-Tryptophan
SITE                    7
                        note = Azaglycine
SITE                    9
                        note =
                         4-amino-1-(2-amino-2-(3-fluoro-4-methylphenyl)acetyl)piperi
                         dine-4-carboxylic acid
SITE                    10
                        note = Amidated Tryptophan
SEQUENCE: 462
XYWNTFGLXW                                                            10

SEQ ID NO: 463          moltype = AA  length = 10
FEATURE                 Location/Qualifiers
source                  1..10
                        mol_type = protein
                        organism = synthetic construct
```

```
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-Tryptophan
SITE                    7
                        note = Azaglycine
SITE                    9
                        note =
                         4-amino-1-(N-(2-aminoethyl)-N-methylglycyl)piperidine-4-car
                         boxylic acid
SITE                    10
                        note = Amidated Tryptophan
SEQUENCE: 463
XYWNTFGLXW                                                                    10

SEQ ID NO: 464          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-Tryptophan
SITE                    7
                        note = Azaglycine
SITE                    9
                        note =
                         4-amino-1-((4-cyclopropylbenzyl)glycyl)piperidine-4-carboxy
                         lic acid
SITE                    10
                        note = Amidated Tryptophan
SEQUENCE: 464
XYWNTFGLXW                                                                    10

SEQ ID NO: 465          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-Tryptophan
SITE                    7
                        note = Azaglycine
SITE                    9
                        note =
                         4-amino-1-((4-ethylbenzyl)glycyl)piperidine-4-carboxylic
                         acid
SITE                    10
                        note = Amidated Tryptophan
SEQUENCE: 465
XYWNTFGLXW                                                                    10

SEQ ID NO: 466          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
```

```
                     note = D-Tryptophan
SITE                 7
                     note = Azaglycine
SITE                 9
                     note =
                      4-amino-1-((4-hydroxybenzyl)glycyl)piperidine-4-carboxylic
                      acid
SITE                 10
                     note = Amidated Tryptophan
SEQUENCE: 466
XYWNTFGLXW                                                              10

SEQ ID NO: 467       moltype = AA  length = 10
FEATURE              Location/Qualifiers
source               1..10
                     mol_type = protein
                     organism = synthetic construct
SITE                 1
                     note =
                      2,2',2'',2'''-(1,4,7,10-tetraazacyclododecane-1,4,7,10-tetr
                      ayl)tetraacetic acid 6-aminohexanoic acid
SITE                 2
                     note = D-Tyrosine
SITE                 3
                     note = D-Tryptophan
SITE                 7
                     note = Azaglycine
SITE                 9
                     note =
                      4-amino-1-((3,5-difluoro-4-methylbenzyl)glycyl)piperidine-4
                      -carboxylic acid
SITE                 10
                     note = Amidated Tryptophan
SEQUENCE: 467
XYWNTFGLXW                                                              10

SEQ ID NO: 468       moltype = AA  length = 10
FEATURE              Location/Qualifiers
source               1..10
                     mol_type = protein
                     organism = synthetic construct
SITE                 1
                     note =
                      2,2',2'',2'''-(1,4,7,10-tetraazacyclododecane-1,4,7,10-tetr
                      ayl)tetraacetic acid 6-aminohexanoic acid
SITE                 2
                     note = D-Tyrosine
SITE                 3
                     note = D-Tryptophan
SITE                 7
                     note = Azaglycine
SITE                 9
                     note =
                      (R)-4-amino-1-((R)-(1-(3-fluoro-4-methylphenyl)ethyl)glycyl
                      )piperidine-4-carboxylic acid
SITE                 10
                     note = Amidated Tryptophan
SEQUENCE: 468
XYWNTFGLXW                                                              10

SEQ ID NO: 469       moltype = AA  length = 10
FEATURE              Location/Qualifiers
source               1..10
                     mol_type = protein
                     organism = synthetic construct
SITE                 1
                     note =
                      2,2',2'',2'''-(1,4,7,10-tetraazacyclododecane-1,4,7,10-tetr
                      ayl)tetraacetic acid 6-aminohexanoic acid
SITE                 2
                     note = D-Tyrosine
SITE                 3
                     note = D-Tryptophan
SITE                 7
                     note = Azaglycine
SITE                 9
                     note =
                      4-amino-1-((3,4-dimethylbenzyl)glycyl)piperidine-4-carboxyl
                      ic acid
```

```
SITE                    10
                        note = Amidated Tryptophan
SEQUENCE: 469
XYWNTFGLXW                                                                  10

SEQ ID NO: 470          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-Tryptophan
SITE                    7
                        note = Azaglycine
SITE                    9
                        note =
                         4-amino-1-((4-chloro-3-fluorobenzyl)glycyl)piperidine-4-car
                         boxylic acid
SITE                    10
                        note = Amidated Tryptophan
SEQUENCE: 470
XYWNTFGLXW                                                                  10

SEQ ID NO: 471          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-Tryptophan
SITE                    7
                        note = Azaglycine
SITE                    9
                        note =
                         4-amino-1-((4-carboxybenzyl)glycyl)piperidine-4-carboxylic
                         acid
SITE                    10
                        note = Amidated Tryptophan
SEQUENCE: 471
XYWNTFGLXW                                                                  10

SEQ ID NO: 472          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-Tryptophan
SITE                    7
                        note = Azaglycine
SITE                    9
                        note =
                         4-amino-1-((2,3-difluoro-4-methylbenzyl)glycyl)piperidine-4
                         -carboxylic acid
SITE                    10
                        note = Amidated Tryptophan
SEQUENCE: 472
XYWNTFGLXW                                                                  10

SEQ ID NO: 473          moltype = AA  length = 10
FEATURE                 Location/Qualifiers
```

-continued

```
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-Tryptophan
SITE                    7
                        note = Azaglycine
SITE                    9
                        note =
                         4-amino-1-((3-fluoro-4-methoxybenzyl)glycyl)piperidine-4-ca
                         rboxylic acid
SITE                    10
                        note = Amidated Tryptophan
SEQUENCE: 473
XYWNTFGLXW                                                                  10

SEQ ID NO: 474          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-Tryptophan
SITE                    7
                        note = Azaglycine
SITE                    9
                        note =
                         4-amino-1-((3-chloro-4-methylbenzyl)glycyl)piperidine-4-car
                         boxylic acid
SITE                    10
                        note = Amidated Tryptophan
SEQUENCE: 474
XYWNTFGLXW                                                                  10

SEQ ID NO: 475          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-Tryptophan
SITE                    7
                        note = Azaglycine
SITE                    9
                        note =
                         4-amino-1-((3,4,5-trifluorobenzyl)glycyl)piperidine-4-carbo
                         xylic acid
SITE                    10
                        note = Amidated Tryptophan
SEQUENCE: 475
XYWNTFGLXW                                                                  10

SEQ ID NO: 476          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
```

```
SITE                    2
                        note = D-Tyrosine
SITE                    3
                        note = D-Tryptophan
SITE                    7
                        note = Azaglycine
SITE                    9
                        note =
                         4-amino-1-((4-(methylamino)benzyl)glycyl)piperidine-4-carbo
                         xylic acid
SITE                    10
                        note = Amidated Tryptophan
SEQUENCE: 476
XYWNTFGLXW                                                                  10

SEQ ID NO: 477          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-Tryptophan
SITE                    7
                        note = Azaglycine
SITE                    9
                        note =
                         (Z)-4-amino-1-(N'-((3-fluoro-4-methylbenzyl)carbamoyl)carba
                         mimidoyl)piperidine-4-carboxylic acid
SITE                    10
                        note = Amidated Tryptophan
SEQUENCE: 477
XYWNTFGLXW                                                                  10

SEQ ID NO: 478          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-Tryptophan
SITE                    7
                        note = Azaglycine
SITE                    9
                        note =
                         4-amino-1-((3-fluoro-4-methylbenzyl)glycyl)piperidine-4-car
                         boxylic acid
SITE                    10
                        note = Amidated Tryptophan
SEQUENCE: 478
XYWNTFGLXW                                                                  10

SEQ ID NO: 479          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-Tryptophan
SITE                    7
                        note = Azaglycine
SITE                    9
```

```
                        note = 4-amino-1-carbamimidoylpiperidine-4-carboxylic
                         acid(Me)
SITE                    10
                        note = Amidated Tryptophan
SEQUENCE: 479
XYWNTFGLXW                                                              10

SEQ ID NO: 480          moltype = AA  length = 6
FEATURE                 Location/Qualifiers
source                  1..6
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    5
                        note = 4-amino-1-carbamimidoylpiperidine-4-carboxylic
                         acid(Me)
SITE                    6
                        note = Amidated Tryptophan
SEQUENCE: 480
XFGLXW                                                                  6

SEQ ID NO: 481          moltype = AA  length = 9
FEATURE                 Location/Qualifiers
source                  1..9
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-NH-glycol-D-Tyrosine
SITE                    6
                        note = Azaglycine
SITE                    8
                        note =
                         4-amino-1-((3-fluoro-4-methylbenzyl)glycyl)piperidine-4-car
                         boxamide
SITE                    9
                        note = Amidated Tryptophan
SEQUENCE: 481
YPNTFGLXW                                                               9

SEQ ID NO: 482          moltype = AA  length = 8
FEATURE                 Location/Qualifiers
source                  1..8
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    6
                        note =
                         (S)-2-(4-((S)-1-amino-2-phenylethyl)-1H-1,2,3-triazol-1-yl)
                         -4-methylpentanoic acid
SITE                    7
                        note =
                         4-amino-1-((3-fluoro-4-methylbenzyl)glycyl)piperidine-4-car
                         boxamide
SITE                    8
                        note = Amidated Tryptophan
SEQUENCE: 482
XYPNTXXW                                                                8

SEQ ID NO: 483          moltype = AA  length = 7
FEATURE                 Location/Qualifiers
source                  1..7
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-D-Asn
SITE                    4
                        note = Azaglycine
```

```
SITE                    6
                        note =
                         4-amino-1-((3-fluoro-4-methylbenzyl)glycyl)piperidine-4-car
                         boxamide
SITE                    7
                        note = Amidated Tryptophan
SEQUENCE: 483
NGFGLXW                                                                      7

SEQ ID NO: 484          moltype = AA  length = 7
FEATURE                 Location/Qualifiers
source                  1..7
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-Asn
SITE                    4
                        note = Azaglycine
SITE                    6
                        note =
                         4-amino-1-((3-fluoro-4-methylbenzyl)glycyl)piperidine-4-car
                         boxamide
SITE                    7
                        note = Amidated Tryptophan
SEQUENCE: 484
NGFGLXW                                                                      7

SEQ ID NO: 485          moltype = AA  length = 7
FEATURE                 Location/Qualifiers
source                  1..7
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-D-Asn
SITE                    4
                        note = Azaglycine
SITE                    6
                        note =
                         4-amino-1-((3-fluoro-4-methylbenzyl)glycyl)piperidine-4-car
                         boxamide
SITE                    7
                        note = Amidated Tryptophan
SEQUENCE: 485
NTFGLXW                                                                      7

SEQ ID NO: 486          moltype = AA  length = 8
FEATURE                 Location/Qualifiers
source                  1..8
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    5
                        note = Azaglycine
SITE                    7
                        note =
                         4-amino-1-((3-fluoro-4-methylbenzyl)glycyl)piperidine-4-car
                         boxamide
SITE                    8
                        note = Amidated Tryptophan
SEQUENCE: 486
XNTFGLXW                                                                     8

SEQ ID NO: 487          moltype = AA  length = 7
FEATURE                 Location/Qualifiers
source                  1..7
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-Asn
SITE                    4
```

```
                        note = Azaglycine
SITE                    6
                        note =
                         4-amino-1-((3-fluoro-4-methylbenzyl)glycyl)piperidine-4-car
                         boxamide
SITE                    7
                        note = Amidated Tryptophan
SEQUENCE: 487
NTFGLXW                                                                     7

SEQ ID NO: 488          moltype = AA  length = 8
FEATURE                 Location/Qualifiers
source                  1..8
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-D-Trp
SITE                    5
                        note = Azaglycine
SITE                    7
                        note =
                         4-amino-1-((3-fluoro-4-methylbenzyl)glycyl)piperidine-4-car
                         boxamide
SITE                    8
                        note = Amidated Tryptophan
SEQUENCE: 488
WNTFGLXW                                                                    8

SEQ ID NO: 489          moltype = AA  length = 7
FEATURE                 Location/Qualifiers
source                  1..7
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    4
                        note = Azaglycine
SITE                    6
                        note =
                         4-amino-1-((3-fluoro-4-methylbenzyl)glycyl)piperidine-4-car
                         boxamide
SITE                    7
                        note = Amidated Tryptophan
SEQUENCE: 489
XWFGLXW                                                                     7

SEQ ID NO: 490          moltype = AA  length = 7
FEATURE                 Location/Qualifiers
source                  1..7
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = 2-Pal
SITE                    4
                        note = Azaglycine
SITE                    6
                        note =
                         4-amino-1-((3-fluoro-4-methylbenzyl)glycyl)piperidine-4-car
                         boxamide
SITE                    7
                        note = Amidated Tryptophan
SEQUENCE: 490
XXFGLXW                                                                     7

SEQ ID NO: 491          moltype = AA  length = 10
FEATURE                 Location/Qualifiers
source                  1..10
                        mol_type = protein
                        organism = synthetic construct
SITE                    1
                        note =
```

```
                     2,2',2'',2'''-(1,4,7,10-tetraazacyclododecane-1,4,7,10-tetr
                     ayl)tetraacetic acid 6-aminohexanoic acid
SITE                 2
                     note = D-Tyrosine
SITE                 3
                     note = D-Tryptophan
SITE                 7
                     note = Azaglycine
SITE                 9
                     note =
                     4-amino-1-((3-fluoro-4-methylbenzyl)glycyl)piperidine-4-car
                     boxamide
SITE                 10
                     note = Amidated 4-cyano phenylalanine
SEQUENCE: 491
XYWNTFGLXF                                                          10

SEQ ID NO: 492       moltype = AA  length = 10
FEATURE              Location/Qualifiers
source               1..10
                     mol_type = protein
                     organism = synthetic construct
SITE                 1
                     note =
                     2,2',2'',2'''-(1,4,7,10-tetraazacyclododecane-1,4,7,10-tetr
                     ayl)tetraacetic acid 6-aminohexanoic acid
SITE                 2
                     note = D-Tyrosine
SITE                 3
                     note = D-Tryptophan
SITE                 7
                     note = Azaglycine
SITE                 9
                     note =
                     4-amino-1-((3-fluoro-4-methylbenzyl)glycyl)piperidine-4-car
                     boxamide
SITE                 10
                     note = Amidated 3-(4-pyridyl)alanine
SEQUENCE: 492
XYWNTFGLXX                                                          10

SEQ ID NO: 493       moltype = AA  length = 10
FEATURE              Location/Qualifiers
source               1..10
                     mol_type = protein
                     organism = synthetic construct
SITE                 1
                     note = indium(III)
                     2,2',2''-(10-(2-((5-carboxypentyl)amino)-2-oxoethyl)-1,4,7,
                     10-tetraazacyclododecane-1,4,7-triyl)triacetate
SITE                 2
                     note = D-Tyrosine
SITE                 3
                     note = D-Tryptophan
SITE                 7
                     note = Azaglycine
SITE                 9
                     note =
                     4-amino-1-((3-fluoro-4-methylbenzyl)glycyl)piperidine-4-car
                     boxamide
SITE                 10
                     note = Amidated 3-(4-pyridyl)alanine
SEQUENCE: 493
XYWNTFGLXX                                                          10

SEQ ID NO: 494       moltype = AA  length = 11
FEATURE              Location/Qualifiers
source               1..11
                     mol_type = protein
                     organism = synthetic construct
SITE                 1
                     note =
                     2,2',2'',2'''-(1,4,7,10-tetraazacyclododecane-1,4,7,10-tetr
                     ayl)tetraacetic acid 6-aminohexanoic acid
SITE                 2
                     note = D-Tyrosine
SITE                 4
                     note = D-Tryptophan
SITE                 8
```

```
                      note = Azaglycine
SITE                  10
                      note =
                       4-amino-1-((3-fluoro-4-methylbenzyl)glycyl)piperidine-4-car
                       boxamide
SITE                  11
                      note = Amidated 3-(4-pyridyl)alanine
SEQUENCE: 494
XYNWNTFGLX X                                                           11

SEQ ID NO: 495        moltype = AA  length = 11
FEATURE               Location/Qualifiers
source                1..11
                      mol_type = protein
                      organism = synthetic construct
SITE                  1
                      note =
                       2,2',2'',2'''-(1,4,7,10-tetraazacyclododecane-1,4,7,10-tetr
                       ayl)tetraacetic acid 6-aminohexanoic acid
SITE                  2
                      note = D-Tyrosine
SITE                  3
                      note = D-Histidine
SITE                  4
                      note = D-Tryptophan
SITE                  8
                      note = Azaglycine
SITE                  10
                      note =
                       4-amino-1-((3-fluoro-4-methylbenzyl)glycyl)piperidine-4-car
                       boxamide
SITE                  11
                      note = Amidated 3-(4-pyridyl)alanine
SEQUENCE: 495
XYHWNTFGLX X                                                           11

SEQ ID NO: 496        moltype = AA  length = 10
FEATURE               Location/Qualifiers
source                1..10
                      mol_type = protein
                      organism = synthetic construct
SITE                  1
                      note =
                       2,2',2'',2'''-(1,4,7,10-tetraazacyclododecane-1,4,7,10-tetr
                       ayl)tetraacetic acid 6-aminohexanoic acid
SITE                  2
                      note = D-Tyrosine
SITE                  3
                      note = Azaglycine
SITE                  7
                      note = Azaglycine
SITE                  9
                      note =
                       4-amino-1-((3-fluoro-4-methylbenzyl)glycyl)piperidine-4-car
                       boxamide
SITE                  10
                      note = Amidated Tryptophan
SEQUENCE: 496
XYGNTFGLXW                                                             10

SEQ ID NO: 497        moltype = AA  length = 6
FEATURE               Location/Qualifiers
source                1..6
                      mol_type = protein
                      organism = synthetic construct
SITE                  1
                      note =
                       2,2',2'',2'''-(1,4,7,10-tetraazacyclododecane-1,4,7,10-tetr
                       ayl)tetraacetic acid-AMBA
SITE                  3
                      note = Azaglycine
SITE                  5
                      note =
                       4-amino-1-((3-fluoro-4-methylbenzyl)glycyl)piperidine-4-car
                       boxamide
SITE                  6
                      note = Amidated Tryptophan
SEQUENCE: 497
XFGLXW                                                                 6
```

```
SEQ ID NO: 498          moltype = AA  length = 7
FEATURE                 Location/Qualifiers
source                  1..7
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-AMBA
SITE                    2
                        note = (1r,4r)-4-(aminomethyl)cyclohexane-1-carboxylic acid
SITE                    4
                        note = Azaglycine
SITE                    6
                        note =
                         4-amino-1-((3-fluoro-4-methylbenzyl)glycyl)piperidine-4-car
                         boxamide
SITE                    7
                        note = Amidated Tryptophan
SEQUENCE: 498
XXFGLXW                                                                     7

SEQ ID NO: 499          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-Tryptophan
SITE                    7
                        note = Azaglycine
SITE                    9
                        note =
                         4-amino-1-((3-fluoro-4-methylbenzyl)glycyl)piperidine-4-car
                         boxamide
SITE                    10
                        note = Amidated Phenylalanine
SEQUENCE: 499
XYWNAFGLXF                                                                  10

SEQ ID NO: 500          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-Tryptophan
SITE                    7
                        note = Azaglycine
SITE                    9
                        note =
                         4-amino-1-((3-fluoro-4-methylbenzyl)glycyl)piperidine-4-car
                         boxamide
SITE                    10
                        note = Amidated Leucine
SEQUENCE: 500
XYWNAFGLXL                                                                  10

SEQ ID NO: 501          moltype = AA  length = 13
FEATURE                 Location/Qualifiers
source                  1..13
                        mol_type = protein
                        organism = synthetic construct
SITE                    1
                        note =
                         2,2',2'',2'''-(1,4,7,10-tetraazacyclododecane-1,4,7,10-tetr
```

```
                        ayl)tetraacetic acid-D-CsA
SITE                    2
                        note = D-CsA
SITE                    3
                        note = D-CsA
SITE                    4
                        note = Ahx
SITE                    5
                        note = D-Tyrosine
SITE                    6
                        note = D-Tryptophan
SITE                    10
                        note = Azaglycine
SITE                    12
                        note =
                         4-amino-1-((3-fluoro-4-methylbenzyl)glycyl)piperidine-4-car
                         boxamide
SITE                    13
                        note = Amidated Tryptophan
SEQUENCE: 501
XXXXYWNTFG LXW                                                   13

SEQ ID NO: 502          moltype = AA  length = 11
FEATURE                 Location/Qualifiers
source                  1..11
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-D-CsA
SITE                    2
                        note = Ahx
SITE                    3
                        note = D-Tyrosine
SITE                    4
                        note = D-Tryptophan
SITE                    8
                        note = Azaglycine
SITE                    10
                        note =
                         4-amino-1-((3-fluoro-4-methylbenzyl)glycyl)piperidine-4-car
                         boxamide
SITE                    11
                        note = Amidated Tryptophan
SEQUENCE: 502
XXYWNTFGLX W                                                     11

SEQ ID NO: 503          moltype = AA  length = 7
FEATURE                 Location/Qualifiers
source                  1..7
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-D-CsA
SITE                    2
                        note = Ahx
SITE                    4
                        note = Azaglycine
SITE                    6
                        note =
                         4-amino-1-((3-fluoro-4-methylbenzyl)glycyl)piperidine-4-car
                         boxamide
SITE                    7
                        note = Amidated Tryptophan
SEQUENCE: 503
XXFGLXW                                                          7

SEQ ID NO: 504          moltype = AA  length = 9
FEATURE                 Location/Qualifiers
source                  1..9
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-AMBA-Met-Val-Lyse-ada-D-Tyrosine
```

```
SITE                   2
                       note = D-Tryptophan
SITE                   6
                       note = Azaglycine
SITE                   8
                       note =
                        4-amino-1-((3-fluoro-4-methylbenzyl)glycyl)piperidine-4-car
                        boxamide
SITE                   9
                       note = Amidated Tryptophan
SEQUENCE: 504
YWNTFGLXW                                                    9

SEQ ID NO: 505         moltype = AA  length = 10
FEATURE                Location/Qualifiers
source                 1..10
                       mol_type = protein
                       organism = synthetic construct
SITE                   1
                       note =
                        2,2',2'',2'''-(1,4,7,10-tetraazacyclododecane-1,4,7,10-tetr
                        ayl)tetraacetic acid 6-aminohexanoic acid
SITE                   2
                       note = D-Tyrosine
SITE                   3
                       note = 3-(2-Naphthyl)alanine or
SITE                   7
                       note = Azaglycine
SITE                   9
                       note =
                        4-amino-1-((3-fluoro-4-methylbenzyl)glycyl)piperidine-4-car
                        boxamide
SITE                   10
                       note = Amidated Tryptophan
SEQUENCE: 505
XYXNTFGLXW                                                   10

SEQ ID NO: 506         moltype = AA  length = 11
FEATURE                Location/Qualifiers
source                 1..11
                       mol_type = protein
                       organism = synthetic construct
SITE                   1
                       note = (C16-gGlu)
SITE                   2
                       note = (DOTA-PEG4)-eLys
SITE                   3
                       note = D-Tyrosine
SITE                   4
                       note = D-Tryptophan
SITE                   8
                       note = Azaglycine
SITE                   10
                       note =
                        4-amino-1-((3-fluoro-4-methylbenzyl)glycyl)piperidine-4-car
                        boxamide
SITE                   11
                       note = Amidated Tryptophan
SEQUENCE: 506
XKYWNTFGLX W                                                 11

SEQ ID NO: 507         moltype = AA  length = 12
FEATURE                Location/Qualifiers
source                 1..12
                       mol_type = protein
                       organism = synthetic construct
SITE                   1
                       note =
                        2,2',2'',2'''-(1,4,7,10-tetraazacyclododecane-1,4,7,10-tetr
                        ayl)tetraacetic acid-D-CsA
SITE                   2
                       note = D-CsA
SITE                   3
                       note = Ahx
SITE                   4
                       note = D-Tyrosine
SITE                   5
                       note = D-Tryptophan
SITE                   9
```

```
                        note = Azaglycine
SITE                    11
                        note =
                         4-amino-1-((3-fluoro-4-methylbenzyl)glycyl)piperidine-4-car
                         boxamide
SITE                    12
                        note = Amidated Tryptophan
SEQUENCE: 507
XXXYWNTFGL XW                                                               12

SEQ ID NO: 508          moltype = AA  length = 9
FEATURE                 Location/Qualifiers
source                  1..9
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-D-Tyrosine
SITE                    2
                        note = 4-iodophenylalanine
SITE                    5
                        note = 4-iodophenylalanine
SITE                    6
                        note = Azaglycine
SITE                    8
                        note = 4-amino-1-carbamimidoylpiperidine-4-carboxylic acid
SITE                    9
                        note = Amidated 3-(4-pyridyl)alanine
SEQUENCE: 508
YFNTFGLXX                                                                   9

SEQ ID NO: 509          moltype = AA  length = 8
FEATURE                 Location/Qualifiers
source                  1..8
                        mol_type = protein
                        organism = synthetic construct
SITE                    1
                        note = CH3-(Peg)25-C(=O)-Lys(DOTA)
SITE                    5
                        note = Azaglycine
SITE                    7
                        note = 4-amino-1-carbamimidoylpiperidine-4-carboxylic acid
SITE                    8
                        note = Amidated 3-(4-pyridyl)alanine
SEQUENCE: 509
KNTFGLXX                                                                    8

SEQ ID NO: 510          moltype = AA  length = 9
FEATURE                 Location/Qualifiers
source                  1..9
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-D-Tyrosine
SITE                    2
                        note = 3-(9-anthryl)-alanine
SITE                    6
                        note = Azaglycine
SITE                    7
                        note = Norleucine
SITE                    8
                        note = 4-amino-1-carbamimidoylpiperidine-4-carboxylic acid
SITE                    9
                        note = Amidated 3-(4-pyridyl)alanine
SEQUENCE: 510
YXNTFGXXX                                                                   9

SEQ ID NO: 511          moltype = AA  length = 8
FEATURE                 Location/Qualifiers
source                  1..8
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-D-CsA
```

```
SITE                    2
                        note = D-CsA
SITE                    3
                        note = 6-aminohexanoic acid
SITE                    5
                        note = Azaglycine
SITE                    7
                        note =
                         4-amino-1-((3-fluoro-4-methylbenzyl)glycyl)piperidine-4-car
                         boxamide
SITE                    8
                        note = Amidated Tryptophan
SEQUENCE: 511
XXXFGLXW                                                                    8

SEQ ID NO: 512          moltype = AA  length = 9
FEATURE                 Location/Qualifiers
source                  1..9
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-D-CsA
SITE                    2
                        note = D-CsA
SITE                    3
                        note = D-CsA
SITE                    4
                        note = 6-aminohexanoic acid
SITE                    6
                        note = Azaglycine
SITE                    8
                        note =
                         4-amino-1-((3-fluoro-4-methylbenzyl)glycyl)piperidine-4-car
                         boxamide
SITE                    9
                        note = Amidated Tryptophan
SEQUENCE: 512
XXXXFGLXW                                                                   9

SEQ ID NO: 513          moltype = AA  length = 6
FEATURE                 Location/Qualifiers
source                  1..6
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-AMBA-Met-Val-Lyse-Ada
SITE                    3
                        note = Azaglycine
SITE                    5
                        note =
                         4-amino-1-((3-fluoro-4-methylbenzyl)glycyl)piperidine-4-car
                         boxamide
SITE                    6
                        note = Amidated Tryptophan
SEQUENCE: 513
XFGLXW                                                                      6

SEQ ID NO: 514          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-Met-Val-Lyse-Ada
SITE                    2
                        note = D-Tyrosine
SITE                    3
                        note = D-Tryptophan
SITE                    7
                        note = Azaglycine
SITE                    9
                        note =
                         4-amino-1-((3-fluoro-4-methylbenzyl)glycyl)piperidine-4-car
```

```
                         boxamide
SITE                     10
                         note = Amidated Tryptophan
SEQUENCE: 514
XYWNTFGLXW                                                    10

SEQ ID NO: 515           moltype =   length =
SEQUENCE: 515
000

SEQ ID NO: 516           moltype =   length =
SEQUENCE: 516
000

SEQ ID NO: 517           moltype =   length =
SEQUENCE: 517
000

SEQ ID NO: 518           moltype =   length =
SEQUENCE: 518
000

SEQ ID NO: 519           moltype =   length =
SEQUENCE: 519
000

SEQ ID NO: 520           moltype =   length =
SEQUENCE: 520
000

SEQ ID NO: 521           moltype = AA  length = 10
FEATURE                  Location/Qualifiers
source                   1..10
                         mol_type = protein
                         organism = synthetic construct
SITE                     1
                         note =
                          2,2',2'',2'''-(1,4,7,10-tetraazacyclododecane-1,4,7,10-tetr
                          ayl)tetraacetic acid 6-aminohexanoic acid
SITE                     2
                         note = D-Tyrosine
SITE                     3
                         note = D-Tryptophan
SITE                     7
                         note = Azaglycine
SITE                     9
                         note =
                          4-amino-1-((4-methoxybenzyl)glycyl)piperidine-4-carboxylic
                          acid
SITE                     10
                         note = Amidated Phenylalanine
SEQUENCE: 521
XYWNTFGLXF                                                    10

SEQ ID NO: 522           moltype =   length =
SEQUENCE: 522
000

SEQ ID NO: 523           moltype =   length =
SEQUENCE: 523
000

SEQ ID NO: 524           moltype = AA  length = 6
FEATURE                  Location/Qualifiers
source                   1..6
                         mol_type = protein
                         organism = synthetic construct
SITE                     1
                         note =
                          2,2',2'',2'''-(1,4,7,10-tetraazacyclododecane-1,4,7,10-tetr
                          ayl)tetraacetic
                          acid-bAla-Met-Val-Lys-C(=O)-6-aminohexanoic acid
SITE                     3
                         note = Azaglycine
SITE                     5
                         note =
                          4-amino-1-((3-fluoro-4-methylbenzyl)glycyl)piperidine-4-car
                          boxamide
SITE                     6
```

```
                         note = Amidated Tryptophan
SEQUENCE: 524
XFGLXW                                                                      6

SEQ ID NO: 525           moltype = AA  length = 9
FEATURE                  Location/Qualifiers
source                   1..9
                         mol_type = protein
                         organism = synthetic construct
SITE                     1
                         note =
                          2,2',2'',2'''-(1,4,7,10-tetraazacyclododecane-1,4,7,10-tetr
                          ayl)tetraacetic acid--Met-Val-Lys-C(=O)-6-aminohexanoic
                          acid
SITE                     2
                         note = D-Tryptophan
SITE                     6
                         note = Azaglycine
SITE                     8
                         note =
                          4-amino-1-((3-fluoro-4-methylbenzyl)glycyl)piperidine-4-car
                          boxamide
SITE                     9
                         note = Amidated Tryptophan
SEQUENCE: 525
XWNTFGLXW                                                                   9

SEQ ID NO: 526           moltype = AA  length = 8
FEATURE                  Location/Qualifiers
source                   1..8
                         mol_type = protein
                         organism = synthetic construct
SITE                     1
                         note =
                          2,2',2'',2'''-(1,4,7,10-tetraazacyclododecane-1,4,7,10-tetr
                          ayl)tetraacetic acid--Met-Val-Lys-C(=O)-6-aminohexanoic
                          acid
SITE                     5
                         note = Azaglycine
SITE                     7
                         note =
                          4-amino-1-((3-fluoro-4-methylbenzyl)glycyl)piperidine-4-car
                          boxamide
SITE                     8
                         note = Amidated Tryptophan
SEQUENCE: 526
XNTFGLXW                                                                    8

SEQ ID NO: 527           moltype = AA  length = 8
FEATURE                  Location/Qualifiers
source                   1..8
                         mol_type = protein
                         organism = synthetic construct
SITE                     1
                         note =
                          2,2',2'',2'''-(1,4,7,10-tetraazacyclododecane-1,4,7,10-tetr
                          ayl)tetraacetic acid-D-CsA
SITE                     2
                         note = D-CsA
SITE                     3
                         note = 4-(aminomethyl)benzoic acid
SITE                     5
                         note = Azaglycine
SITE                     7
                         note =
                          4-amino-1-((3-fluoro-4-methylbenzyl)glycyl)piperidine-4-car
                          boxamide
SITE                     8
                         note = Amidated Tryptophan
SEQUENCE: 527
XXXFGLXW                                                                    8

SEQ ID NO: 528           moltype =   length =
SEQUENCE: 528
000

SEQ ID NO: 529           moltype =   length =
SEQUENCE: 529
000
```

```
SEQ ID NO: 530          moltype = AA  length = 13
FEATURE                 Location/Qualifiers
source                  1..13
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-4-(aminomethyl)benzoic acid
SITE                    4
                        note = 6-aminohexanoic acid
SITE                    5
                        note = D-Tyrosine
SITE                    6
                        note = D-Tryptophan
SITE                    10
                        note = Azaglycine
SITE                    12
                        note =
                         4-amino-1-((3-fluoro-4-methylbenzyl)glycyl)piperidine-4-car
                         boxamide
SITE                    13
                        note = Amidated Tryptophan
SEQUENCE: 530
XGYXYWNTFG LXW                                                    13

SEQ ID NO: 531          moltype = AA  length = 11
FEATURE                 Location/Qualifiers
source                  1..11
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-4-(aminomethyl)benzoic acid
SITE                    4
                        note = D-Tryptophan
SITE                    8
                        note = Azaglycine
SITE                    10
                        note =
                         4-amino-1-((3-fluoro-4-methylbenzyl)glycyl)piperidine-4-car
                         boxamide
SITE                    11
                        note = Amidated Tryptophan
SEQUENCE: 531
XGYWNTFGLX W                                                      11

SEQ ID NO: 532          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-Glycine
SITE                    3
                        note = D-Tryptophan
SITE                    7
                        note = Azaglycine
SITE                    9
                        note =
                         4-amino-1-((3-fluoro-4-methylbenzyl)glycyl)piperidine-4-car
                         boxamide
SITE                    10
                        note = Amidated Tryptophan
SEQUENCE: 532
GYWNTFGLXW                                                        10

SEQ ID NO: 533          moltype = AA  length = 9
FEATURE                 Location/Qualifiers
source                  1..9
                        mol_type = protein
                        organism = synthetic construct
SITE                    1
                        note =
                         2,2',2'',2'''-(1,4,7,10-tetraazacyclododecane-1,4,7,10-tetr
```

```
                        ayl)tetraacetic acid-4-(aminomethyl)benzoic acid
SITE                    2
                        note = D-Tyrosine
SITE                    3
                        note = D-Tryptophan
SITE                    6
                        note = Azaglycine
SITE                    8
                        note =
                         4-amino-1-((3-fluoro-4-methylbenzyl)glycyl)piperidine-4-car
                         boxamide
SITE                    9
                        note = Amidated Tryptophan
SEQUENCE: 533
YWNTFGLXW                                                    9

SEQ ID NO: 534          moltype = AA  length = 6
FEATURE                 Location/Qualifiers
source                  1..6
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-4-(aminomethyl)benzoic acid
SITE                    3
                        note = Azaglycine
SITE                    5
                        note =
                         4-amino-1-((3-fluoro-4-methylbenzyl)glycyl)piperidine-4-car
                         boxamide
SITE                    6
                        note = Amidated Tryptophan
SEQUENCE: 534
XFGLXW                                                       6

SEQ ID NO: 535          moltype = AA  length = 8
FEATURE                 Location/Qualifiers
source                  1..8
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-4-(aminomethyl)benzoic acid
SITE                    4
                        note = 3-fluorophenylalanine
SITE                    5
                        note = Azaglycine
SITE                    7
                        note =
                         4-amino-1-((3-fluoro-4-methylbenzyl)glycyl)piperidine-4-car
                         boxamide
SITE                    8
                        note = Amidated Tryptophan
SEQUENCE: 535
XNTFGLXW                                                     8

SEQ ID NO: 536          moltype = AA  length = 6
FEATURE                 Location/Qualifiers
source                  1..6
                        mol_type = protein
                        organism = synthetic construct
SITE                    1
                        note =
                         2,2',2''-(10-(2-(4-(3-carboxypropanamido)piperidin-1-yl)-2-
                         oxoethyl)-1,4,7,10-tetraazacyclododecane-1,4,7-triyl)triace
                         tic acid-Phenylalanine
SITE                    3
                        note = Azaglycine
SITE                    5
                        note =
                         4-amino-1-((3-fluoro-4-methylbenzyl)glycyl)piperidine-4-car
                         boxamide
SITE                    6
                        note = Amidated Tryptophan
SEQUENCE: 536
XFGLXW                                                       6
```

```
SEQ ID NO: 537          moltype = AA  length = 6
FEATURE                 Location/Qualifiers
source                  1..6
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-gamma-D-Glutamic acid
SITE                    3
                        note = Azaglycine
SITE                    5
                        note =
                         4-amino-1-((3-fluoro-4-methylbenzyl)glycyl)piperidine-4-car
                         boxamide
SITE                    6
                        note = Amidated Tryptophan
SEQUENCE: 537
EFGLXW                                                                      6

SEQ ID NO: 538          moltype = AA  length = 5
FEATURE                 Location/Qualifiers
source                  1..5
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic
                         acid-2,2',2''-(10-(2-(4-carboxypiperidin-1-yl)-2-oxoethyl)-
                         1,4,7,10-tetraazacyclododecane-1,4,7-triyl)triacetic
                         acid-Phenylalanine
SITE                    2
                        note = Azaglycine
SITE                    4
                        note =
                         4-amino-1-((3-fluoro-4-methylbenzyl)glycyl)piperidine-4-car
                         boxamide
SITE                    5
                        note = Amidated Tryptophan
SEQUENCE: 538
FGLXW                                                                       5

SEQ ID NO: 539          moltype = AA  length = 8
FEATURE                 Location/Qualifiers
source                  1..8
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-APM
SITE                    5
                        note = Azaglycine
SITE                    7
                        note =
                         4-amino-1-((3-fluoro-4-methylbenzyl)glycyl)piperidine-4-car
                         boxamide
SITE                    8
                        note = Amidated Tryptophan
SEQUENCE: 539
XNTFGLXW                                                                    8

SEQ ID NO: 540          moltype = AA  length = 9
FEATURE                 Location/Qualifiers
source                  1..9
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-APM
SITE                    5
                        note = 3-fluorophenylalanine
SITE                    6
                        note = Azaglycine
SITE                    8
                        note =
                         4-amino-1-((3-fluoro-4-methylbenzyl)glycyl)piperidine-4-car
```

```
                         boxamide
SITE                    9
                        note = Amidated Tryptophan
SEQUENCE: 540
XENTFGLXW                                                                  9

SEQ ID NO: 541          moltype = AA  length = 9
FEATURE                 Location/Qualifiers
source                  1..9
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic
                         acid-(1r,4r)-4-(aminomethyl)cyclohexane-1-carboxylic acid
SITE                    5
                        note = 3-fluorophenylalanine
SITE                    6
                        note = Azaglycine
SITE                    8
                        note =
                         4-amino-1-((3-fluoro-4-methylbenzyl)glycyl)piperidine-4-car
                         boxamide
SITE                    9
                        note = Amidated Tryptophan
SEQUENCE: 541
XENTFGLXW                                                                  9

SEQ ID NO: 542          moltype = AA  length = 9
FEATURE                 Location/Qualifiers
source                  1..9
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic
                         acid-(1r,4r)-4-(aminomethyl)cyclohexane-1-carboxylic acid
SITE                    2
                        note = D-Glutamic Acid
SITE                    5
                        note = 3-fluorophenylalanine
SITE                    6
                        note = Azaglycine
SITE                    8
                        note =
                         4-amino-1-((3-fluoro-4-methylbenzyl)glycyl)piperidine-4-car
                         boxamide
SITE                    9
                        note = Amidated Tryptophan
SEQUENCE: 542
XENTFGLXW                                                                  9

SEQ ID NO: 543          moltype = AA  length = 5
FEATURE                 Location/Qualifiers
source                  1..5
                        mol_type = protein
                        organism = synthetic construct
SITE                    1
                        note =  2,2',2''-(10-(2-(4-(3-carboxy-N-(2-(2-(2-carboxyetho
                         xy)ethoxy)ethyl)propanamido)piperidin-1-yl)-2-oxoethyl)-1,4
                         ,7,10-tetraazacyclododecane-1,4,7-triyl)triacetic
                         acid-Phenylalanine
SITE                    2
                        note = Azaglycine
SITE                    4
                        note =
                         4-amino-1-((3-fluoro-4-methylbenzyl)glycyl)piperidine-4-car
                         boxamide
SITE                    5
                        note = Amidated Tryptophan
SEQUENCE: 543
FGLXW                                                                      5

SEQ ID NO: 544          moltype = AA  length = 5
FEATURE                 Location/Qualifiers
source                  1..5
                        mol_type = protein
```

```
                        organism = synthetic construct
SITE                    1
                        note =  2,2',2''-(10-(2-(4-(3-carboxy-N-(2-(2-(2-carboxyetho
                         xy)ethoxy)ethyl)propanamido)piperidin-1-yl)-2-oxoethyl)-1,4
                         ,7,10-tetraazacyclododecane-1,4,7-triyl)triacetic
                         acid-Phenylalanine
SITE                    2
                        note = Azaglycine
SITE                    4
                        note =
                         4-amino-1-((3-fluoro-4-methylbenzyl)glycyl)piperidine-4-car
                         boxamide
SITE                    5
                        note = Amidated Tryptophan
SEQUENCE: 544
FGLXW                                                                5

SEQ ID NO: 545          moltype = AA  length = 9
FEATURE                 Location/Qualifiers
source                  1..9
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-2-(4-aminopiperidin-1-yl)acetic acid
SITE                    5
                        note = 3-fluorophenylalanine
SITE                    6
                        note = Azaglycine
SITE                    8
                        note =
                         4-amino-1-((3-fluoro-4-methylbenzyl)glycyl)piperidine-4-car
                         boxamide
SITE                    9
                        note = Amidated Tryptophan
SEQUENCE: 545
XKNTFGLXW                                                            9

SEQ ID NO: 546          moltype = AA  length = 7
FEATURE                 Location/Qualifiers
source                  1..7
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-gamma-D-Glutamic Acid
SITE                    2
                        note = (1r,4r)-4-(aminomethyl)cyclohexane-1-carboxylic acid
SITE                    4
                        note = Azaglycine
SITE                    6
                        note =
                         4-amino-1-((3-fluoro-4-methylbenzyl)glycyl)piperidine-4-car
                         boxamide
SITE                    7
                        note = Amidated Tryptophan
SEQUENCE: 546
XXFGLXW                                                              7

SEQ ID NO: 547          moltype = AA  length = 7
FEATURE                 Location/Qualifiers
source                  1..7
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-D-Glutamic Acid
SITE                    2
                        note = (1r,4r)-4-(aminomethyl)cyclohexane-1-carboxylic acid
SITE                    4
                        note = Azaglycine
SITE                    6
                        note =
                         4-amino-1-((3-fluoro-4-methylbenzyl)glycyl)piperidine-4-car
                         boxamide
SITE                    7
```

```
                        note = Amidated Tryptophan
SEQUENCE: 547
XXFGLXW                                                         7

SEQ ID NO: 548          moltype = AA  length = 7
FEATURE                 Location/Qualifiers
source                  1..7
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-4-(aminomethyl)benzoic
                         acid-M-V-4-(aminomethyl)benzoic
                         acid-Met-Val-Lyse-Ada-Asparagine
SITE                    4
                        note = Azaglycine
SITE                    6
                        note =
                         4-amino-1-((3-fluoro-4-methylbenzyl)glycyl)piperidine-4-car
                         boxamide
SITE                    7
                        note = Amidated Tryptophan
SEQUENCE: 548
NTFGLXW                                                         7

SEQ ID NO: 549          moltype = AA  length = 7
FEATURE                 Location/Qualifiers
source                  1..7
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-4-(aminomethyl)benzoic
                         acid-Met-Trp-Lyse-Ada-Asn
SITE                    4
                        note = Azaglycine
SITE                    6
                        note =
                         4-amino-1-((3-fluoro-4-methylbenzyl)glycyl)piperidine-4-car
                         boxamide
SITE                    7
                        note = Amidated Tryptophan
SEQUENCE: 549
NTFGLXW                                                         7

SEQ ID NO: 550          moltype = AA  length = 8
FEATURE                 Location/Qualifiers
source                  1..8
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    4
                        note = 3-fluorophenylalanine
SITE                    5
                        note = Azaglycine
SITE                    7
                        note =
                         4-amino-1-((3-fluoro-4-methylbenzyl)glycyl)piperidine-4-car
                         boxamide
SITE                    8
                        note = Amidated 3-(4-pyridyl)alanine
SEQUENCE: 550
XNTFGLXX                                                        8

SEQ ID NO: 551          moltype = AA  length = 8
FEATURE                 Location/Qualifiers
source                  1..8
                        mol_type = protein
                        organism = synthetic construct
SITE                    1
                        note =
                         2,2',2''-(10-(2-((((1s,4s)-4-carboxycyclohexyl)methyl)amino
                         )-2-oxoethyl)-1,4,7,10-tetraazacyclododecane-1,4,7-triyl)tr
                         iacetic acid coupled-Glu
```

```
SITE                    4
                        note = 3-fluorophenylalanine
SITE                    5
                        note = Azaglycine
SITE                    7
                        note =
                         4-amino-1-((3-fluoro-4-methylbenzyl)glycyl)piperidine-4-car
                         boxamide
SITE                    8
                        note = Amidated 3-(4-pyridyl)alanine
SEQUENCE: 551
ENTFGLXX                                                                  8

SEQ ID NO: 552          moltype = AA  length = 8
FEATURE                 Location/Qualifiers
source                  1..8
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-Glu
SITE                    4
                        note = 3-fluorophenylalanine
SITE                    5
                        note = Azaglycine
SITE                    7
                        note =
                         4-amino-1-((3-fluoro-4-methylbenzyl)glycyl)piperidine-4-car
                         boxamide
SITE                    8
                        note = Amidated 3-(4-pyridyl)alanine
SEQUENCE: 552
ENTFGLXX                                                                  8

SEQ ID NO: 553          moltype = AA  length = 9
FEATURE                 Location/Qualifiers
source                  1..9
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-8-aminoquinoline-4-carboxylic acid
SITE                    5
                        note = 3-fluorophenylalanine
SITE                    6
                        note = Azaglycine
SITE                    8
                        note =
                         4-amino-1-((3-fluoro-4-methylbenzyl)glycyl)piperidine-4-car
                         boxamide
SITE                    9
                        note = Amidated Tryptophan
SEQUENCE: 553
XENTFGLXW                                                                 9

SEQ ID NO: 554          moltype = AA  length = 6
FEATURE                 Location/Qualifiers
source                  1..6
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    3
                        note = Azaglycine
SITE                    5
                        note =
                         4-amino-1-((3-fluoro-4-methylbenzyl)glycyl)piperidine-4-car
                         boxamide
SITE                    6
                        note = Amidated Tyrosine
SEQUENCE: 554
XFGLXY                                                                    6

SEQ ID NO: 555          moltype = AA  length = 9
FEATURE                 Location/Qualifiers
```

```
source                1..9
                      mol_type = protein
                      organism = synthetic construct
SITE                  1
                      note =
                       2,2',2'',2'''-(1,4,7,10-tetraazacyclododecane-1,4,7,10-tetr
                       ayl)tetraacetic acid-4-(aminomethyl)benzoic acid
SITE                  4
                      note = 6-aminohexanoic acid
SITE                  6
                      note = Azaglycine
SITE                  8
                      note =
                       4-amino-1-((3-fluoro-4-methylbenzyl)glycyl)piperidine-4-car
                       boxamide
SITE                  9
                      note = Amidated Tryptophan
SEQUENCE: 555
XGYXFGLXW                                                    9

SEQ ID NO: 556        moltype = AA  length = 6
FEATURE               Location/Qualifiers
source                1..6
                      mol_type = protein
                      organism = synthetic construct
SITE                  1
                      note =
                       2,2',2'',2'''-(1,4,7,10-tetraazacyclododecane-1,4,7,10-tetr
                       ayl)tetraacetic acid-4-(aminomethyl)benzoic
                       acid-Met-Phe-Lyse-C(=O)-6-aminohexanoic acid
SITE                  3
                      note = Azaglycine
SITE                  5
                      note =
                       4-amino-1-((3-fluoro-4-methylbenzyl)glycyl)piperidine-4-car
                       boxamide
SITE                  6
                      note = Amidated Tryptophan
SEQUENCE: 556
XFGLXW                                                       6

SEQ ID NO: 557        moltype = AA  length = 6
FEATURE               Location/Qualifiers
source                1..6
                      mol_type = protein
                      organism = synthetic construct
SITE                  1
                      note =
                       2,2',2'',2'''-(1,4,7,10-tetraazacyclododecane-1,4,7,10-tetr
                       ayl)tetraacetic acid-4-(aminomethyl)benzoic
                       acid-Met-Trp-Lyse-C(=O)-6-aminohexanoic acid
SITE                  3
                      note = Azaglycine
SITE                  5
                      note =
                       4-amino-1-((3-fluoro-4-methylbenzyl)glycyl)piperidine-4-car
                       boxamide
SITE                  6
                      note = Amidated Tryptophan
SEQUENCE: 557
XFGLXW                                                       6

SEQ ID NO: 558        moltype = AA  length = 10
FEATURE               Location/Qualifiers
source                1..10
                      mol_type = protein
                      organism = synthetic construct
SITE                  1
                      note =
                       2,2',2'',2'''-(1,4,7,10-tetraazacyclododecane-1,4,7,10-tetr
                       ayl)tetraacetic acid 6-aminohexanoic acid
SITE                  2
                      note = D-Tyrosine
SITE                  3
                      note = D-Tryptophan
SITE                  7
                      note = Azaglycine
SITE                  8
                      note = norvaline
```

```
SITE                    9
                        note =
                         4-amino-1-((3-fluoro-4-methylbenzyl)glycyl)piperidine-4-car
                         boxamide
SITE                    10
                        note = Amidated 3-(4-pyridyl)alanine
SEQUENCE: 558
XYWNTFGXXX                                                                    10

SEQ ID NO: 559          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-4-(aminomethyl)benzoic acid
SITE                    2
                        note = D-Tyrosine
SITE                    3
                        note = 3-(2-Naphthyl)alanine
SITE                    7
                        note = Azaglycine
SITE                    9
                        note =
                         4-amino-1-((3-fluoro-4-methylbenzyl)glycyl)piperidine-4-car
                         boxamide
SITE                    10
                        note = Amidated 3-(4-pyridyl)alanine
SEQUENCE: 559
XYXNTFGLXX                                                                    10

SEQ ID NO: 560          moltype = AA  length = 9
FEATURE                 Location/Qualifiers
source                  1..9
                        mol_type = protein
                        organism = synthetic construct
SITE                    1
                        note = C7H15-C(=O)-D-Tyrosine
SITE                    2
                        note =
                         Lysine(1,4,7,10-tetraazacyclododecane-1,4,7,10-tetraacetic
                         acid)
SITE                    6
                        note = Azaglycine
SITE                    8
                        note =
                         4-amino-1-((3-fluoro-4-methylbenzyl)glycyl)piperidine-4-car
                         boxamide
SITE                    9
                        note = Amidated Tryptophan
SEQUENCE: 560
YKNTFGLXW                                                                     9

SEQ ID NO: 561          moltype = AA  length = 9
FEATURE                 Location/Qualifiers
source                  1..9
                        mol_type = protein
                        organism = synthetic construct
SITE                    1
                        note = Me-PEG25-C(=O)-D-Tyrosine
SITE                    2
                        note =
                         Lysine(1,4,7,10-tetraazacyclododecane-1,4,7,10-tetraacetic
                         acid)
SITE                    6
                        note = Azaglycine
SITE                    8
                        note = 4-amino-1-carbamimidoylpiperidine-4-carboxylic acid
SITE                    9
                        note = Amidated Tryptophan
SEQUENCE: 561
YKNTFGLXW                                                                     9

SEQ ID NO: 562          moltype = AA  length = 10
FEATURE                 Location/Qualifiers
source                  1..10
                        mol_type = protein
```

```
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = 4-benzoylphenylalanine
SITE                    7
                        note = Azaglycine
SITE                    9
                        note = 4-amino-1-carbamimidoylpiperidine-4-carboxylic acid
SITE                    10
                        note = Amidated Tryptophan
SEQUENCE: 562
XYXNTFGLXW                                                                   10

SEQ ID NO: 563          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = 3-(9-anthryl)-alanine
SITE                    7
                        note = Azaglycine
SITE                    9
                        note = 4-amino-1-carbamimidoylpiperidine-4-carboxylic acid
SITE                    10
                        note = Amidated Tryptophan
SEQUENCE: 563
XYXNTFGLXW                                                                   10

SEQ ID NO: 564          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-2Nal
SITE                    7
                        note = Azaglycine
SITE                    9
                        note = 4-amino-1-carbamimidoylpiperidine-4-carboxylic acid
SITE                    10
                        note = Amidated Tyrosine
SEQUENCE: 564
XYXNTFGLXY                                                                   10

SEQ ID NO: 565          moltype = AA  length = 8
FEATURE                 Location/Qualifiers
source                  1..8
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-D-Tyrosine
SITE                    2
                        note = D-3-(4-pyridyl)alanine
SITE                    3
                        note = 6-aminohexanoic acid
SITE                    5
                        note = Azaglycine
SITE                    7
                        note =
```

```
                        4-amino-1-((3-fluoro-4-methylbenzyl)glycyl)piperidine-4-car
                        boxamide
SITE                    8
                        note = Amidated Tryptophan
SEQUENCE: 565
YXXFGLXW                                                                 8

SEQ ID NO: 566          moltype = AA  length = 8
FEATURE                 Location/Qualifiers
source                  1..8
                        mol_type = protein
                        organism = synthetic construct
SITE                    1
                        note =
                        2,2',2'',2'''-(1,4,7,10-tetraazacyclododecane-1,4,7,10-tetr
                        ayl)tetraacetic acid-D-Tyrosine
SITE                    2
                        note = D-3-(4-pyridyl)alanine
SITE                    3
                        note = 6-aminohexanoic acid
SITE                    5
                        note = Azaglycine
SITE                    7
                        note =
                        4-amino-1-((3-fluoro-4-methylbenzyl)glycyl)piperidine-4-car
                        boxamide
SITE                    8
                        note = Amidated Tryptophan
SEQUENCE: 566
YXXFGLXW                                                                 8

SEQ ID NO: 567          moltype = AA  length = 11
FEATURE                 Location/Qualifiers
source                  1..11
                        mol_type = protein
                        organism = synthetic construct
SITE                    1
                        note =
                        2,2',2'',2'''-(1,4,7,10-tetraazacyclododecane-1,4,7,10-tetr
                        ayl)tetraacetic acid-D-Tyrosine
SITE                    2
                        note = 3-(9-anthryl)-alanine
SITE                    5
                        note = 4-iodophenylalanine
SITE                    6
                        note = Azaglycine
SITE                    8
                        note = 4-amino-1-carbamimidoylpiperidine-4-carboxylic acid
SITE                    9
                        note = Amidated 3-(4-pyridyl)alanine
SEQUENCE: 567
YXYXNTFGLX X                                                             11

SEQ ID NO: 568          moltype = AA  length = 6
FEATURE                 Location/Qualifiers
source                  1..6
                        mol_type = protein
                        organism = synthetic construct
SITE                    1
                        note =
                        2,2',2'',2'''-(1,4,7,10-tetraazacyclododecane-1,4,7,10-tetr
                        ayl)tetraacetic acid 6-aminohexanoic acid
SITE                    3
                        note = Azaglycine
SITE                    5
                        note =
                        4-amino-1-(N-methylcarbamimidoyl)piperidine-4-carboxylic
                        acid
SITE                    6
                        note = Amidated Tryptophan
SEQUENCE: 568
XFGLXW                                                                   6

SEQ ID NO: 569          moltype = AA  length = 8
FEATURE                 Location/Qualifiers
source                  1..8
                        mol_type = protein
                        organism = synthetic construct
SITE                    1
```

-continued

```
                        note =
                         3-(2-(2-(3-(p-tolyl)propanamido)ethoxy)ethoxy)propanoic
                         acid coupled to N-term of
                         (S)-2,2',2''-(10-(2-((5-amino-5-carboxypentyl)amino)-2-oxoe
                         thyl)-1,4,7,10-tetraazacyclododecane-1,4,7-triyl)triacetic
                         acid
SITE                    5
                        note = Azaglycine
SITE                    7
                        note = 4-amino-1-carbamimidoylpiperidine-4-carboxylic acid
SITE                    8
                        note = Amidated 3-(4-pyridyl)alanine
SEQUENCE: 569
KNTFGLXX                                                                     8

SEQ ID NO: 570          moltype = AA  length = 8
FEATURE                 Location/Qualifiers
source                  1..8
                        mol_type = protein
                        organism = synthetic construct
SITE                    1
                        note =
                         3-(2-(2-(3-(4-iodophenyl)propanamido)ethoxy)ethoxy)propanoi
                         c acid coupled to N-term of
                         (S)-2,2',2''-(10-(2-((5-amino-5-carboxypentyl)amino)-2-oxoe
                         thyl)-1,4,7,10-tetraazacyclododecane-1,4,7-triyl)triacetic
                         acid
SITE                    5
                        note = Azaglycine
SITE                    7
                        note = 4-amino-1-carbamimidoylpiperidine-4-carboxylic acid
SITE                    8
                        note = Amidated 3-(4-pyridyl)alanine
SEQUENCE: 570
KNTFGLXX                                                                     8

SEQ ID NO: 571          moltype = AA  length = 6
FEATURE                 Location/Qualifiers
source                  1..6
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic
                         acid-(1r,4r)-4-(aminomethyl)cyclohexane-1-carboxylic acid
SITE                    3
                        note = Azaglycine
SITE                    5
                        note =
                         4-amino-1-((3-fluoro-4-methylbenzyl)glycyl)piperidine-4-car
                         boxamide
SITE                    6
                        note = Amidated Tryptophan
SEQUENCE: 571
XFGLXW                                                                       6

SEQ ID NO: 572          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-Glycine
SITE                    2
                        note = D-Tyrosine
SITE                    3
                        note = D-3-(4-pyridyl)alanine
SITE                    7
                        note = Azaglycine
SITE                    9
                        note =
                         4-amino-1-((3-fluoro-4-methylbenzyl)glycyl)piperidine-4-car
                         boxamide
SITE                    10
                        note = Amidated Tyrosine
SEQUENCE: 572
```

```
GYXNTFGLXY                                                  10

SEQ ID NO: 573          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-In-Glycine
SITE                    2
                        note = D-Tyrosine
SITE                    3
                        note = D-3-(4-pyridyl)alanine
SITE                    7
                        note = Azaglycine
SITE                    9
                        note =
                         4-amino-1-((3-fluoro-4-methylbenzyl)glycyl)piperidine-4-car
                         boxamide
SITE                    10
                        note = Amidated Tyrosine
SEQUENCE: 573
GYXNTFGLXY                                                  10

SEQ ID NO: 574          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = 3-(9-anthryl)-alanine
SITE                    7
                        note = Azaglycine
SITE                    9
                        note = 4-amino-1-carbamimidoylpiperidine-4-carboxylic acid
SITE                    10
                        note = Amidated 3-(4-pyridyl)alanine
SEQUENCE: 574
XYXNTFGLXX                                                  10

SEQ ID NO: 575          moltype = AA  length = 9
FEATURE                 Location/Qualifiers
source                  1..9
                        mol_type = protein
                        organism = synthetic construct
SITE                    1
                        note =
                         3-(2-(2-(3-(p-tolyl)propanamido)ethoxy)ethoxy)propanoic
                         acid-D-Tyrosine
SITE                    2
                        note =
                         Lysine(1,4,7,10-tetraazacyclododecane-1,4,7,10-tetraacetic
                         acid)
SITE                    6
                        note = Azaglycine
SITE                    8
                        note = 4-amino-1-carbamimidoylpiperidine-4-carboxylic acid
SITE                    9
                        note = Amidated Tryptophan
SEQUENCE: 575
YKNTFGLXW                                                   9

SEQ ID NO: 576          moltype = AA  length = 9
FEATURE                 Location/Qualifiers
source                  1..9
                        mol_type = protein
                        organism = synthetic construct
SITE                    1
                        note =
                         3-(2-(2-(3-(4-iodophenyl)propanamido)ethoxy)ethoxy)propanoi
                         c acid-D-Tyrosine
```

```
SITE                    2
                        note =
                         Lysine(1,4,7,10-tetraazacyclododecane-1,4,7,10-tetraacetic
                         acid)
SITE                    6
                        note = Azaglycine
SITE                    8
                        note = 4-amino-1-carbamimidoylpiperidine-4-carboxylic acid
SITE                    9
                        note = Amidated Tryptophan
SEQUENCE: 576
YKNTFGLXW                                                                    9

SEQ ID NO: 577          moltype = AA  length = 9
FEATURE                 Location/Qualifiers
source                  1..9
                        mol_type = protein
                        organism = synthetic construct
SITE                    1
                        note =
                         3-(2-(2-(3-(4-iodophenyl)propanamido)ethoxy)ethoxy)propanoi
                         c acid coupled-D-Tyrosine
SITE                    2
                        note = Indium(III)
                         (S)-2,2',2''-(10-(2-((5-amino-5-carboxypentyl)amino)-2-oxoe
                         thyl)-1,4,7,10-tetraazacyclododecane-1,4,7-triyl)triacetate
SITE                    6
                        note = Azaglycine
SITE                    8
                        note = 4-amino-1-carbamimidoylpiperidine-4-carboxylic acid
SITE                    9
                        note = Amidated Tryptophan
SEQUENCE: 577
YKNTFGLXW                                                                    9

SEQ ID NO: 578          moltype = AA  length = 9
FEATURE                 Location/Qualifiers
source                  1..9
                        mol_type = protein
                        organism = synthetic construct
SITE                    1
                        note = 3-(2-(2-methoxyethoxy)ethoxy)propanoic
                         acid-D-Tyrosine
SITE                    2
                        note =
                         Lysine(1,4,7,10-tetraazacyclododecane-1,4,7,10-tetraacetic
                         acid)
SITE                    6
                        note = Azaglycine
SITE                    8
                        note = 4-amino-1-carbamimidoylpiperidine-4-carboxylic acid
SITE                    9
                        note = Amidated Tryptophan
SEQUENCE: 578
YKNTFGLXW                                                                    9

SEQ ID NO: 579          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = biphenylalanine
SITE                    7
                        note = Azaglycine
SITE                    9
                        note = 4-amino-1-carbamimidoylpiperidine-4-carboxylic acid
SITE                    10
                        note = Amidated Tryptophan
SEQUENCE: 579
XYXNTFGLXW                                                                   10

SEQ ID NO: 580          moltype = AA  length = 9
```

```
FEATURE                 Location/Qualifiers
source                  1..9
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    8
                        note = 4-amino-1-carbamimidoylpiperidine-4-carboxylic acid
SITE                    9
                        note = Amidated Phenylalanine
SEQUENCE: 580
XTNRNFLXF                                                                  9

SEQ ID NO: 581          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-2Nal
SITE                    7
                        note = Azaglycine
SITE                    9
                        note = Piperidine-2-carboxylic acid(MeGly)
SITE                    10
                        note = Amidated Tryptophan
SEQUENCE: 581
XYXNTFGLXW                                                                 10

SEQ ID NO: 582          moltype = AA  length = 10
FEATURE                 Location/Qualifiers
source                  1..10
                        mol_type = protein
                        organism = synthetic construct
SITE                    1
                        note = indium(III)
                         2,2',2''-(10-(2-((5-carboxypentyl)amino)-2-oxoethyl)-1,4,7,
                         10-tetraazacyclododecane-1,4,7-triyl)triacetate
SITE                    2
                        note = D-Tyrosine
SITE                    3
                        note = D-3-(2-Naphthyl)alanine
SITE                    7
                        note = Azaglycine
SITE                    9
                        note = Piperidine-2-carboxylic acid(MeGly)
SITE                    10
                        note = Amidated Tryptophan
SEQUENCE: 582
XYXNTFGLXW                                                                 10

SEQ ID NO: 583          moltype = AA  length = 9
FEATURE                 Location/Qualifiers
source                  1..9
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-D-Tyrosine
SITE                    2
                        note = 3-(9-anthryl)-alanine
SITE                    6
                        note = Azaglycine
SITE                    8
                        note = Piperidine-2-carboxylic acid(MeGly)
SITE                    9
                        note = Amidated 3-(4-pyridyl)alanine
SEQUENCE: 583
YXNTFGLXX                                                                  9
```

```
SEQ ID NO: 584          moltype = AA  length = 5
FEATURE                 Location/Qualifiers
source                  1..5
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-4-(aminomethyl)benzoic
                         acid-Met-Phe-Lyse-Ada-phenylalanine
SITE                    2
                        note = Azaglycine
SITE                    4
                        note =
                         4-amino-1-((3-fluoro-4-methylbenzyl)glycyl)Piperidine-2-car
                         boxylic acideridine-4-carboxamide
SITE                    5
                        note = Amidated Tryptophan
SEQUENCE: 584
FGLXW                                                                       5

SEQ ID NO: 585          moltype =   length =
SEQUENCE: 585
000

SEQ ID NO: 586          moltype = AA  length = 8
FEATURE                 Location/Qualifiers
source                  1..8
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-4-(aminomethyl)benzoic acid
SITE                    5
                        note = Azaglycine
SITE                    7
                        note =
                         4-amino-1-((3-fluoro-4-methylbenzyl)glycyl)Piperidine-2-car
                         boxylic acideridine-4-carboxamide
SITE                    8
                        note = Amidated Tyrosine
SEQUENCE: 586
XNTFGLXY                                                                    8

SEQ ID NO: 587          moltype = AA  length = 9
FEATURE                 Location/Qualifiers
source                  1..9
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-4-(aminomethyl)benzoic acid
SITE                    2
                        note = D-Glutamic Acid
SITE                    6
                        note = Azaglycine
SITE                    8
                        note =
                         4-amino-1-((3-fluoro-4-methylbenzyl)glycyl)Piperidine-2-car
                         boxylic acideridine-4-carboxamide
SITE                    9
                        note = Amidated Tyrosine
SEQUENCE: 587
XENTFGLXY                                                                   9

SEQ ID NO: 588          moltype = AA  length = 8
FEATURE                 Location/Qualifiers
source                  1..8
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    5
                        note = Azaglycine
SITE                    7
```

```
                    note =
                     4-amino-1-((3-fluoro-4-methylbenzyl)glycyl)Piperidine-2-car
                     boxylic acideridine-4-carboxamide
SITE                8
                    note = Amidated 4-cyano phenylalanine
SEQUENCE: 588
XNTFGLXF                                                    8

SEQ ID NO: 589      moltype = AA  length = 9
FEATURE             Location/Qualifiers
source              1..9
                    mol_type = protein
                    organism = synthetic construct
SITE                1
                    note =
                     2,2',2'',2'''-(1,4,7,10-tetraazacyclododecane-1,4,7,10-tetr
                     ayl)tetraacetic acid 6-aminohexanoic acid
SITE                6
                    note = Azaglycine
SITE                8
                    note =
                     4-amino-1-((3-fluoro-4-methylbenzyl)glycyl)Piperidine-2-car
                     boxylic acideridine-4-carboxamide
SITE                9
                    note = Amidated 4-cyano phenylalanine
SEQUENCE: 589
XENTFGLXF                                                   9

SEQ ID NO: 590      moltype = AA  length = 9
FEATURE             Location/Qualifiers
source              1..9
                    mol_type = protein
                    organism = synthetic construct
SITE                1
                    note =
                     2,2',2'',2'''-(1,4,7,10-tetraazacyclododecane-1,4,7,10-tetr
                     ayl)tetraacetic acid 6-aminohexanoic acid
SITE                2
                    note = D-Glutamic Acid
SITE                6
                    note = Azaglycine
SITE                8
                    note =
                     4-amino-1-((3-fluoro-4-methylbenzyl)glycyl)Piperidine-2-car
                     boxylic acideridine-4-carboxamide
SITE                9
                    note = Amidated 4-cyano phenylalanine
SEQUENCE: 590
XENTFGLXF                                                   9

SEQ ID NO: 591      moltype = AA  length = 7
FEATURE             Location/Qualifiers
source              1..7
                    mol_type = protein
                    organism = synthetic construct
SITE                1
                    note =
                     2,2',2''-(10-(2-(((S)-1-((((1s,4R)-4-carboxycyclohexyl)meth
                     yl)amino)-1,5-dioxo-5-(((2S,3R,4R,5R)-2,3,4,5,6-pentahydrox
                     yhexyl)amino)pentan-2-yl)amino)-2-oxoethyl)-1,4,7,10-tetraa
                     zacyclododecane-1,4,7-triyl)triacetic acid-Asn
SITE                4
                    note = Azaglycine
SITE                6
                    note =
                     4-amino-1-((3-fluoro-4-methylbenzyl)glycyl)Piperidine-2-car
                     boxylic acideridine-4-carboxamide
SITE                7
                    note = Amidated Tryptophan
SEQUENCE: 591
NTFGLXW                                                     7

SEQ ID NO: 592      moltype = AA  length = 6
FEATURE             Location/Qualifiers
source              1..6
                    mol_type = protein
                    organism = synthetic construct
SITE                1
                    note =
```

```
                        2,2',2'',2'''-(1,4,7,10-tetraazacyclododecane-1,4,7,10-tetr
                        ayl)tetraacetic acid 6-aminohexanoic acid
SITE                    2
                        note = AzaPhenylalanine
SITE                    3
                        note = Azaglycine
SITE                    5
                        note =
                        4-amino-1-((3-fluoro-4-methylbenzyl)glycyl)Piperidine-2-car
                        boxylic acideridine-4-carboxamide
SITE                    6
                        note = Amidated Tyrosine
SEQUENCE: 592
XFGLXY                                                                      6

SEQ ID NO: 593          moltype = AA  length = 7
FEATURE                 Location/Qualifiers
source                  1..7
                        mol_type = protein
                        organism = synthetic construct
SITE                    1
                        note =
                        2,2',2''-(10-(2-((((2S,3R,4R,5R,6S)-6-((((1s,4R)-4-carboxyc
                        yclohexyl)methyl)carbamoyl)-3,4,5-trihydroxytetrahydro-2H-p
                        yran-2-yl)methyl)amino)-2-oxoethyl)-1,4,7,10-tetraazacyclod
                        odecane-1,4,7-triyl)triacetic acid coupled to N-term of
                        Asparagine
SITE                    4
                        note = Azaglycine
SITE                    6
                        note =
                        4-amino-1-((3-fluoro-4-methylbenzyl)glycyl)Piperidine-2-car
                        boxylic acideridine-4-carboxamide
SITE                    7
                        note = Amidated Tryptophan
SEQUENCE: 593
NTFGLXW                                                                     7

SEQ ID NO: 594          moltype = AA  length = 10
FEATURE                 Location/Qualifiers
source                  1..10
                        mol_type = protein
                        organism = synthetic construct
SITE                    1
                        note =
                        2,2',2'',2'''-(1,4,7,10-tetraazacyclododecane-1,4,7,10-tetr
                        ayl)tetraacetic acid-Glycine
SITE                    3
                        note = 4-(aminomethyl)benzoic acid
SITE                    7
                        note = Azaglycine
SITE                    9
                        note =
                        4-amino-1-((3-fluoro-4-methylbenzyl)glycyl)Piperidine-2-car
                        boxylic acideridine-4-carboxamide
SITE                    10
                        note = Amidated Tryptophan
SEQUENCE: 594
GYXNTFGLXW                                                                  10

SEQ ID NO: 595          moltype =   length =
SEQUENCE: 595
000

SEQ ID NO: 596          moltype =   length =
SEQUENCE: 596
000

SEQ ID NO: 597          moltype =   length =
SEQUENCE: 597
000

SEQ ID NO: 598          moltype =   length =
SEQUENCE: 598
000

SEQ ID NO: 599          moltype = AA  length = 9
FEATURE                 Location/Qualifiers
source                  1..9
```

```
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-APM
SITE                    5
                        note = beta-(2-thienyl)-Alanine
SITE                    6
                        note = Azaglycine
SITE                    8
                        note =
                         4-amino-1-((3-fluoro-4-methylbenzyl)glycyl)Piperidine-2-car
                         boxylic acideridine-4-carboxamide
SITE                    9
                        note = Amidated Tryptophan
SEQUENCE: 599
XENTAGLXW                                                                    9

SEQ ID NO: 600          moltype = AA  length = 9
FEATURE                 Location/Qualifiers
source                  1..9
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-APM
SITE                    2
                        note = O-(dihydroxy(oxo)-l6-phosphaneyl)-L-serine
SITE                    5
                        note = 3-Fluorophenylalanine
SITE                    6
                        note = Azaglycine
SITE                    8
                        note =
                         4-amino-1-((3-fluoro-4-methylbenzyl)glycyl)Piperidine-2-car
                         boxylic acideridine-4-carboxamide
SITE                    9
                        note = Amidated Tryptophan
SEQUENCE: 600
XSNTFGLXW                                                                    9

SEQ ID NO: 601          moltype = AA  length = 9
FEATURE                 Location/Qualifiers
source                  1..9
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-APM
SITE                    2
                        note = (S)-2-amino-4-(2H-tetrazol-5-yl)butanoic acid
SITE                    5
                        note = 3-Fluorophenylalanine
SITE                    6
                        note = Azaglycine
SITE                    8
                        note =
                         4-amino-1-((3-fluoro-4-methylbenzyl)glycyl)Piperidine-2-car
                         boxylic acideridine-4-carboxamide
SITE                    9
                        note = Amidated Tryptophan
SEQUENCE: 601
XXNTFGLXW                                                                    9

SEQ ID NO: 602          moltype = AA  length = 9
FEATURE                 Location/Qualifiers
source                  1..9
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-D-Tyrosine
SITE                    2
                        note = 3-(9-anthryl)-alanine
SITE                    6
```

```
                         note = Azaglycine
SITE                     8
                         note = 4-amino-1-carbamimidoylPiperidine-2-carboxylic
                          acideridine-4-carboxylic acid
SITE                     9
                         note = Amidated 3-(4-pyridyl)alanine
SEQUENCE: 602
YXNTFGLXX                                                    9

SEQ ID NO: 603           moltype = AA  length = 10
FEATURE                  Location/Qualifiers
source                   1..10
                         mol_type = protein
                         organism = synthetic construct
SITE                     1
                         note =
                          2,2',2'',2'''-(1,4,7,10-tetraazacyclododecane-1,4,7,10-tetr
                          ayl)tetraacetic acid 6-aminohexanoic acid
SITE                     2
                         note = D-Tyrosine
SITE                     3
                         note = 3-(9-anthryl)-alanine
SITE                     7
                         note = Azaglycine
SITE                     9
                         note = 4-amino-1-carbamimidoylPiperidine-2-carboxylic
                          acideridine-4-carboxylic acid
SITE                     10
                         note = Amidated 3-(4-pyridyl)alanine
SEQUENCE: 603
XYXNTFGLXX                                                   10

SEQ ID NO: 604           moltype =   length =
SEQUENCE: 604
000

SEQ ID NO: 605           moltype = AA  length = 9
FEATURE                  Location/Qualifiers
source                   1..9
                         mol_type = protein
                         organism = synthetic construct
SITE                     1
                         note =
                          2,2',2'',2'''-(1,4,7,10-tetraazacyclododecane-1,4,7,10-tetr
                          ayl)tetraacetic acid-4-(aminomethyl)benzoic acid
SITE                     2
                         note = 3-(9-anthryl)-alanine
SITE                     6
                         note = Azaglycine
SITE                     8
                         note =
                          4-amino-1-((3-fluoro-4-methylbenzyl)glycyl)Piperidine-2-car
                          boxylic acideridine-4-carboxamide
SITE                     9
                         note = Amidated Tryptophan
SEQUENCE: 605
XXNTFGLXW                                                    9

SEQ ID NO: 606           moltype = AA  length = 8
FEATURE                  Location/Qualifiers
source                   1..8
                         mol_type = protein
                         organism = synthetic construct
SITE                     1
                         note = CH3-(Peg)3-C(=O)-Lys(DOTA)
SITE                     5
                         note = Azaglycine
SITE                     7
                         note = 4-amino-1-carbamimidoylPiperidine-2-carboxylic
                          acideridine-4-carboxylic acid
SITE                     8
                         note = Amidated 3-(4-pyridyl)alanine
SEQUENCE: 606
KNTFGLXX                                                     8

SEQ ID NO: 607           moltype = AA  length = 8
FEATURE                  Location/Qualifiers
source                   1..8
                         mol_type = protein
```

```
                        organism = synthetic construct
SITE                    1
                        note =
                         C7H15-C(=O)-Lyssine(2,2',2'',2'''-(1,4,7,10-tetraazacyclodo
                         decane-1,4,7,10-tetrayl)tetraacetic acid)
SITE                    5
                        note = Azaglycine
SITE                    7
                        note = 4-amino-1-carbamimidoylPiperidine-2-carboxylic
                         acideridine-4-carboxylic acid
SITE                    8
                        note = Amidated 3-(4-pyridyl)alanine
SEQUENCE: 607
KNTFGLXX                                                                     8

SEQ ID NO: 608          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-4-iodophenylalanine
SITE                    3
                        note = D-Tryptophan
SITE                    7
                        note = Azaglycine
SITE                    9
                        note =
                         4-amino-1-(N-methylcarbamimidoyl)Piperidine-2-carboxylic
                         acideridine-4-carboxylic acid
SITE                    10
                        note = Amidated Tryptophan
SEQUENCE: 608
XFWNTFGLXW                                                                   10

SEQ ID NO: 609          moltype =   length =
SEQUENCE: 609
000

SEQ ID NO: 610          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-4-(aminomethyl)benzoic acid
SITE                    7
                        note = Azaglycine
SITE                    9
                        note =
                         4-amino-1-(N-methylcarbamimidoyl)Piperidine-2-carboxylic
                         acideridine-4-carboxylic acid
SITE                    10
                        note = Amidated Tryptophan
SEQUENCE: 610
XKWNTFGLXW                                                                   10

SEQ ID NO: 611          moltype = AA  length = 8
FEATURE                 Location/Qualifiers
source                  1..8
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-D-bGlu
SITE                    4
                        note = 3-fluorophenylalanine
SITE                    5
                        note = Azaglycine
SITE                    7
                        note =
                         4-amino-1-((3-fluoro-4-methylbenzyl)glycyl)Piperidine-2-car
```

```
                     boxylic acideridine-4-carboxamide
SITE                8
                    note = Amidated 3-(4-pyridyl)alanine
SEQUENCE: 611
ENTFGLXX                                                          8

SEQ ID NO: 612      moltype = AA  length = 9
FEATURE             Location/Qualifiers
source              1..9
                    mol_type = protein
                    organism = synthetic construct
SITE                1
                    note =
                     2,2',2'',2'''-(1,4,7,10-tetraazacyclododecane-1,4,7,10-tetr
                     ayl)tetraacetic
                     acid-(1r,4r)-4-(aminomethyl)cyclohexane-1-carboxylic acid
SITE                2
                    note = D-3-aminopentanedioic acid
SITE                5
                    note = 3-fluorophenylalanine
SITE                6
                    note = Azaglycine
SITE                8
                    note =
                     4-amino-1-((3-fluoro-4-methylbenzyl)glycyl)Piperidine-2-car
                     boxylic acideridine-4-carboxamide
SITE                9
                    note = Amidated 3-(4-pyridyl)alanine
SEQUENCE: 612
XENTFGLXX                                                         9

SEQ ID NO: 613      moltype = AA  length = 9
FEATURE             Location/Qualifiers
source              1..9
                    mol_type = protein
                    organism = synthetic construct
SITE                1
                    note =
                     2,2',2'',2'''-(1,4,7,10-tetraazacyclododecane-1,4,7,10-tetr
                     ayl)tetraacetic acid-4-(aminomethyl)benzoic acid
SITE                2
                    note = D-3-aminopentanedioic acid
SITE                5
                    note = 3-fluorophenylalanine
SITE                6
                    note = Azaglycine
SITE                8
                    note =
                     4-amino-1-((3-fluoro-4-methylbenzyl)glycyl)Piperidine-2-car
                     boxylic acideridine-4-carboxamide
SITE                9
                    note = Amidated 3-(4-pyridyl)alanine
SEQUENCE: 613
XENTFGLXX                                                         9

SEQ ID NO: 614      moltype = AA  length = 7
FEATURE             Location/Qualifiers
source              1..7
                    mol_type = protein
                    organism = synthetic construct
SITE                1
                    note =
                     2,2',2'',2'''-(1,4,7,10-tetraazacyclododecane-1,4,7,10-tetr
                     ayl)tetraacetic acid-APM
SITE                4
                    note = Azaglycine
SITE                6
                    note =
                     4-amino-1-((3-fluoro-4-methylbenzyl)glycyl)Piperidine-2-car
                     boxylic acideridine-4-carboxamide
SITE                7
                    note = Amidated Tryptophan
SEQUENCE: 614
XTFGLXW                                                           7

SEQ ID NO: 615      moltype = AA  length = 8
FEATURE             Location/Qualifiers
source              1..8
                    mol_type = protein
```

```
                        organism = synthetic construct
SITE                    1
                        note =
                         2,2',2'',2'''-(1,4,7,10-tetraazacyclododecane-1,4,7,10-tetr
                         ayl)tetraacetic acid-APM
SITE                    5
                        note = Azaglycine
SITE                    7
                        note =
                         4-amino-1-((3-fluoro-4-methylbenzyl)glycyl)Piperidine-2-car
                         boxylic acideridine-4-carboxamide
SITE                    8
                        note = Amidated Tryptophan
SEQUENCE: 615
XETFGLXW                                                                  8

SEQ ID NO: 616          moltype = AA  length = 8
FEATURE                 Location/Qualifiers
source                  1..8
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    5
                        note = Azaglycine
SITE                    7
                        note =
                         4-amino-1-((3-fluoro-4-methylbenzyl)glycyl)piperidine-4-car
                         boxamide(4-OMe)
SITE                    8
                        note = Amidated Phenylalanine
SEQUENCE: 616
XNTFGLXF                                                                  8

SEQ ID NO: 617          moltype = AA  length = 9
FEATURE                 Location/Qualifiers
source                  1..9
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    6
                        note = Azaglycine
SITE                    8
                        note = Apc(4-OMe)
SITE                    9
                        note = Amidated Phenylalanine
SEQUENCE: 617
XENTFGLXF                                                                 9

SEQ ID NO: 618          moltype = AA  length = 8
FEATURE                 Location/Qualifiers
source                  1..8
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-Glu
SITE                    5
                        note = Azaglycine
SITE                    7
                        note = Apc(4-OMe)
SITE                    8
                        note = Amidated Phenylalanine
SEQUENCE: 618
ENTFGLXF                                                                  8

SEQ ID NO: 619          moltype = AA  length = 9
FEATURE                 Location/Qualifiers
source                  1..9
                        mol_type = protein
                        organism = synthetic construct
SITE                    1
                        note =
```

```
                        2,2',2'',2'''-(1,4,7,10-tetraazacyclododecane-1,4,7,10-tetr
                        ayl)tetraacetic acid 6-aminohexanoic acid
SITE                    6
                        note = Azaglycine
SITE                    8
                        note =
                        4-amino-1-((3-fluoro-4-methylbenzyl)glycyl)Piperidine-2-car
                        boxylic acideridine-4-carboxamide
SITE                    9
                        note = Amidated Tryptophan
SEQUENCE: 619
XENTFGLXW                                                                    9

SEQ ID NO: 620          moltype = AA  length = 9
FEATURE                 Location/Qualifiers
source                  1..9
                        mol_type = protein
                        organism = synthetic construct
SITE                    1
                        note =
                        2,2',2'',2'''-(1,4,7,10-tetraazacyclododecane-1,4,7,10-tetr
                        ayl)tetraacetic acid-Glu
SITE                    5
                        note = Azaglycine
SITE                    6
                        note = D-Leucine
SITE                    7
                        note = Apc(4-OMe)
SITE                    8
                        note = Amidated Phenylalanine
SEQUENCE: 620
XENTFGLXF                                                                    9

SEQ ID NO: 621          moltype = AA  length = 8
FEATURE                 Location/Qualifiers
source                  1..8
                        mol_type = protein
                        organism = synthetic construct
SITE                    1
                        note =
                        2,2',2'',2'''-(1,4,7,10-tetraazacyclododecane-1,4,7,10-tetr
                        ayl)tetraacetic acid-4-(aminomethyl)benzoic acid
SITE                    5
                        note =
                        2,2',2'',2'''-(1,4,7,10-tetraazacyclododecane-1,4,7,10-tetr
                        ayl)tetraacetic acid-4-(aminomethyl)benzoic acid
SITE                    7
                        note =
                        4-amino-1-((3-fluoro-4-methylbenzyl)glycyl)Piperidine-2-car
                        boxylic acideridine-4-carboxamide
SITE                    8
                        note = Amidated 4-cyano phenylalanine
SEQUENCE: 621
XNTFGLXF                                                                     8

SEQ ID NO: 622          moltype = AA  length = 9
FEATURE                 Location/Qualifiers
source                  1..9
                        mol_type = protein
                        organism = synthetic construct
SITE                    1
                        note =
                        2,2',2'',2'''-(1,4,7,10-tetraazacyclododecane-1,4,7,10-tetr
                        ayl)tetraacetic acid-4-(aminomethyl)benzoic acid
SITE                    6
                        note = Azaglycine
SITE                    8
                        note =
                        4-amino-1-((3-fluoro-4-methylbenzyl)glycyl)Piperidine-2-car
                        boxylic acideridine-4-carboxamide
SITE                    9
                        note = Amidated 4-cyano phenylalanine
SEQUENCE: 622
XENTFGLXF                                                                    9

SEQ ID NO: 623          moltype = AA  length = 9
FEATURE                 Location/Qualifiers
source                  1..9
                        mol_type = protein
```

```
                         organism = synthetic construct
SITE                     1
                         note =
                          2,2',2'',2'''-(1,4,7,10-tetraazacyclododecane-1,4,7,10-tetr
                          ayl)tetraacetic acid-4-(aminomethyl)benzoic acid
SITE                     2
                         note = D-Glutamic Acid
SITE                     6
                         note = Azaglycine
SITE                     8
                         note =
                          4-amino-1-((3-fluoro-4-methylbenzyl)glycyl)Piperidine-2-car
                          boxylic acideridine-4-carboxamide
SITE                     9
                         note = Amidated 4-cyano phenylalanine
SEQUENCE: 623
XENTFGLXF                                                                     9

SEQ ID NO: 624           moltype = AA  length = 8
FEATURE                  Location/Qualifiers
source                   1..8
                         mol_type = protein
                         organism = synthetic construct
SITE                     1
                         note =
                          2,2',2'',2'''-(1,4,7,10-tetraazacyclododecane-1,4,7,10-tetr
                          ayl)tetraacetic acid-4-oxo-4-(Piperidine-2-carboxylic
                          acideridin-4-ylamino)butanoic acid
SITE                     5
                         note = Azaglycine
SITE                     7
                         note =
                          4-amino-1-((3-fluoro-4-methylbenzyl)glycyl)Piperidine-2-car
                          boxylic acideridine-4-carboxamide
SITE                     8
                         note = Amidated Tryptophan
SEQUENCE: 624
XNTFGLXW                                                                      8

SEQ ID NO: 625           moltype = AA  length = 6
FEATURE                  Location/Qualifiers
source                   1..6
                         mol_type = protein
                         organism = synthetic construct
SITE                     1
                         note =
                          2,2',2'',2'''-(1,4,7,10-tetraazacyclododecane-1,4,7,10-tetr
                          ayl)tetraacetic acid-APM
SITE                     3
                         note = Azaglycine
SITE                     5
                         note =
                          4-amino-1-((3-fluoro-4-methylbenzyl)glycyl)Piperidine-2-car
                          boxylic acideridine-4-carboxamide
SITE                     6
                         note = Amidated 4-cyano phenylalanine
SEQUENCE: 625
XFGLXF                                                                        6

SEQ ID NO: 626           moltype = AA  length = 6
FEATURE                  Location/Qualifiers
source                   1..6
                         mol_type = protein
                         organism = synthetic construct
SITE                     1
                         note =
                          2,2',2'',2'''-(1,4,7,10-tetraazacyclododecane-1,4,7,10-tetr
                          ayl)tetraacetic acid-APM
SITE                     3
                         note = Azaglycine
SITE                     5
                         note =
                          4-amino-1-((3-fluoro-4-methylbenzyl)glycyl)Piperidine-2-car
                          boxylic acideridine-4-carboxamide
SITE                     6
                         note = Amidated Phenylalanine
SEQUENCE: 626
XFGLXF                                                                        6
```

```
SEQ ID NO: 627          moltype =   length =
SEQUENCE: 627
000

SEQ ID NO: 628          moltype = AA  length = 6
FEATURE                 Location/Qualifiers
source                  1..6
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-APM
SITE                    3
                        note = Azaglycine
SITE                    5
                        note =
                         4-amino-1-((3-fluoro-4-methylbenzyl)glycyl)Piperidine-2-car
                         boxylic acideridine-4-carboxamide
SITE                    6
                        note = Amidated Tyrosine
SEQUENCE: 628
XFGLXY                                                                      6

SEQ ID NO: 629          moltype = AA  length = 6
FEATURE                 Location/Qualifiers
source                  1..6
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-APM
SITE                    3
                        note = Azaglycine
SITE                    5
                        note =
                         4-amino-1-((3-fluoro-4-methylbenzyl)glycyl)Piperidine-2-car
                         boxylic acideridine-4-carboxamide
SITE                    6
                        note = Amidated Histidine
SEQUENCE: 629
XFGLXH                                                                      6

SEQ ID NO: 630          moltype = AA  length = 8
FEATURE                 Location/Qualifiers
source                  1..8
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-APM
SITE                    5
                        note = Azaglycine
SITE                    7
                        note =
                         4-amino-1-((3-fluoro-4-methylbenzyl)glycyl)Piperidine-2-car
                         boxylic acideridine-4-carboxamide
SITE                    8
                        note = Amidated Tyrosine
SEQUENCE: 630
XNTFGLXY                                                                    8

SEQ ID NO: 631          moltype = AA  length = 7
FEATURE                 Location/Qualifiers
source                  1..7
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-APM
SITE                    4
                        note = Azaglycine
SITE                    6
                        note =
                         4-amino-1-((3-fluoro-4-methylbenzyl)glycyl)Piperidine-2-car
                         boxylic acideridine-4-carboxamide
```

```
SITE                    7
                        note = Amidated Tyrosine
SEQUENCE: 631
XTFGLXY                                                                    7

SEQ ID NO: 632          moltype = AA  length = 7
FEATURE                 Location/Qualifiers
source                  1..7
                        mol_type = protein
                        organism = synthetic construct
SITE                    1
                        note = 3-(2-(2-hydroxyethoxy)ethoxy)propanoic
                         acid-Lys-(DOTA)
SITE                    4
                        note = Azaglycine
SITE                    6
                        note =
                         4-amino-1-((3-fluoro-4-methylbenzyl)glycyl)Piperidine-2-car
                         boxylic acideridine-4-carboxamide
SITE                    7
                        note = Amidated 3-(4-pyridyl)alanine
SEQUENCE: 632
KTFGLXX                                                                    7

SEQ ID NO: 633          moltype = AA  length = 8
FEATURE                 Location/Qualifiers
source                  1..8
                        mol_type = protein
                        organism = synthetic construct
SITE                    1
                        note = 3-(2-(2-hydroxyethoxy)ethoxy)propanoic acid-Lys(DOTA)
SITE                    5
                        note = Azaglycine
SITE                    7
                        note =
                         4-amino-1-((3-fluoro-4-methylbenzyl)glycyl)Piperidine-2-car
                         boxylic acideridine-4-carboxamide
SITE                    8
                        note = Amidated 3-(4-pyridyl)alanine
SEQUENCE: 633
KETFGLXX                                                                   8

SEQ ID NO: 634          moltype = AA  length = 8
FEATURE                 Location/Qualifiers
source                  1..8
                        mol_type = protein
                        organism = synthetic construct
SITE                    1
                        note = 3-(2-(2-hydroxyethoxy)ethoxy)propanoic acid-Lys(DOTA)
SITE                    5
                        note = Azaglycine
SITE                    7
                        note =
                         4-amino-1-((3-fluoro-4-methylbenzyl)glycyl)Piperidine-2-car
                         boxylic acideridine-4-carboxamide
SITE                    8
                        note = Amidated 3-(4-pyridyl)alanine
SEQUENCE: 634
KNTFGLXX                                                                   8

SEQ ID NO: 635          moltype = AA  length = 8
FEATURE                 Location/Qualifiers
source                  1..8
                        mol_type = protein
                        organism = synthetic construct
SITE                    1
                        note = 3-(2-(2-hydroxyethoxy)ethoxy)propanoic
                         acid-D-Lys(DOTA)
SITE                    5
                        note = Azaglycine
SITE                    7
                        note =
                         4-amino-1-((3-fluoro-4-methylbenzyl)glycyl)Piperidine-2-car
                         boxylic acideridine-4-carboxamide
SITE                    8
                        note = Amidated 3-(4-pyridyl)alanine
SEQUENCE: 635
KNTFGLXX                                                                   8
```

```
SEQ ID NO: 636          moltype = AA  length = 8
FEATURE                 Location/Qualifiers
source                  1..8
                        mol_type = protein
                        organism = synthetic construct
SITE                    1
                        note = 3-(2-(2-methoxyethoxy)ethoxy)propanoic acid-Lys(DOTA)
SITE                    5
                        note = Azaglycine
SITE                    7
                        note =
                         4-amino-1-((3-fluoro-4-methylbenzyl)glycyl)Piperidine-2-car
                         boxylic acideridine-4-carboxamide
SITE                    8
                        note = Amidated 3-(4-pyridyl)alanine
SEQUENCE: 636
KNTFGLXX                                                                   8

SEQ ID NO: 637          moltype = AA  length = 8
FEATURE                 Location/Qualifiers
source                  1..8
                        mol_type = protein
                        organism = synthetic construct
SITE                    1
                        note =
                         1-hydroxy-3,6,9,12,15,18,21,24-octaoxaheptacosan-27-oic
                         acid-Lys(DOTA)
SITE                    5
                        note = Azaglycine
SITE                    7
                        note =
                         4-amino-1-((3-fluoro-4-methylbenzyl)glycyl)Piperidine-2-car
                         boxylic acideridine-4-carboxamide
SITE                    8
                        note = Amidated 3-(4-pyridyl)alanine
SEQUENCE: 637
KNTFGLXX                                                                   8

SEQ ID NO: 638          moltype = AA  length = 8
FEATURE                 Location/Qualifiers
source                  1..8
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-APM
SITE                    5
                        note = Azaglycine
SITE                    7
                        note =
                         4-amino-1-((3-fluoro-4-methylbenzyl)glycyl)Piperidine-2-car
                         boxylic acideridine-4-carboxamide
SITE                    8
                        note = Tyr(3-NO2)-NH2
SEQUENCE: 638
XNTFGLXY                                                                   8

SEQ ID NO: 639          moltype = AA  length = 8
FEATURE                 Location/Qualifiers
source                  1..8
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-APM
SITE                    4
                        note = 3-(4-pyridyl)alanine
SITE                    5
                        note = Azaglycine
SITE                    7
                        note =
                         4-amino-1-((3-fluoro-4-methylbenzyl)glycyl)Piperidine-2-car
                         boxylic acideridine-4-carboxamide
SITE                    8
                        note = Amidated 3-(4-pyridyl)alanine
SEQUENCE: 639
XNTXGLXX                                                                   8
```

```
SEQ ID NO: 640          moltype = AA  length = 8
FEATURE                 Location/Qualifiers
source                  1..8
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-4-(aminomethyl)benzoic acid
SITE                    4
                        note = 3-(4-pyridyl)alanine
SITE                    5
                        note = Azaglycine
SITE                    7
                        note =
                         4-amino-1-((3-fluoro-4-methylbenzyl)glycyl)Piperidine-2-car
                         boxylic acideridine-4-carboxamide
SITE                    8
                        note = Amidated 3-(4-pyridyl)alanine
SEQUENCE: 640
XNTXGLXX                                                                    8

SEQ ID NO: 641          moltype = AA  length = 6
FEATURE                 Location/Qualifiers
source                  1..6
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-4-(aminomethyl)benzoic acid
SITE                    3
                        note = Azaglycine
SITE                    4
                        note = D-Leucine
SITE                    5
                        note =
                         4-amino-1-((3-fluoro-4-methylbenzyl)glycyl)Piperidine-2-car
                         boxylic acideridine-4-carboxamide
SITE                    6
                        note = Amidated Tryptophan
SEQUENCE: 641
XFGLXW                                                                      6

SEQ ID NO: 642          moltype =   length =
SEQUENCE: 642
000

SEQ ID NO: 643          moltype = AA  length = 8
FEATURE                 Location/Qualifiers
source                  1..8
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-8-aminoquinoline-3-carboxylic acid
SITE                    5
                        note = Azaglycine
SITE                    7
                        note = 4-amino-1-carbamimidoylPiperidine-2-carboxylic
                         acideridine-4-carboxylic acid
SITE                    8
                        note = Amidated Tryptophan
SEQUENCE: 643
XNTFGLXW                                                                    8

SEQ ID NO: 644          moltype =   length =
SEQUENCE: 644
000

SEQ ID NO: 645          moltype = AA  length = 8
FEATURE                 Location/Qualifiers
source                  1..8
                        mol_type = protein
                        organism = synthetic construct
SITE                    1
                        note = 3-(2-(2-methoxyethoxy)ethoxy)propanoic acid-Lys(DOTA)
```

```
SITE                    5
                        note = Azaglycine
SITE                    7
                        note = 4-amino-1-carbamimidoylPiperidine-2-carboxylic
                         acideridine-4-carboxylic acid
SITE                    8
                        note = Amidated Tryptophan
SEQUENCE: 645
KNTFGLXW                                                                    8

SEQ ID NO: 646          moltype =   length =
SEQUENCE: 646
000

SEQ ID NO: 647          moltype = AA  length = 9
FEATURE                 Location/Qualifiers
source                  1..9
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-D-Tyrosine
SITE                    2
                        note = 3-(2-Naphthyl)alanine or
SITE                    6
                        note = Azaglycine
SITE                    8
                        note = 4-amino-1-carbamimidoylPiperidine-2-carboxylic
                         acideridine-4-carboxylic acid
SITE                    9
                        note = Amidated Tryptophan
SEQUENCE: 647
YXNTFGLXW                                                                   9

SEQ ID NO: 648          moltype = AA  length = 6
FEATURE                 Location/Qualifiers
source                  1..6
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-4-(aminomethyl)benzoic acid
SITE                    3
                        note = Azaglycine
SITE                    5
                        note =
                         4-amino-1-((3-fluoro-4-methylbenzyl)glycyl)Piperidine-2-car
                         boxylic acideridine-4-carboxamide
SITE                    6
                        note = Amidated Tryptophan
SEQUENCE: 648
XYGLXW                                                                      6

SEQ ID NO: 649          moltype =   length =
SEQUENCE: 649
000

SEQ ID NO: 650          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-3-(2-Naphthyl)alanine
SITE                    7
                        note = Azaglycine
SITE                    9
                        note = 4-amino-1-carbamimidoylPiperidine-2-carboxylic
                         acideridine-4-carboxylic acid
SITE                    10
                        note = Amidated Tryptophan
```

```
SEQUENCE: 650
XYXNTFGLXW                                                          10

SEQ ID NO: 651          moltype = AA  length = 10
FEATURE                 Location/Qualifiers
source                  1..10
                        mol_type = protein
                        organism = synthetic construct
SITE                    1
                        note = indium(III)
                         2,2',2''-(10-(2-((5-carboxypentyl)amino)-2-oxoethyl)-1,4,7,
                         10-tetraazacyclododecane-1,4,7-triyl)triacetate
SITE                    2
                        note = D-Tyrosine
SITE                    3
                        note = D-3-(2-Naphthyl)alanine
SITE                    7
                        note = Azaglycine
SITE                    9
                        note = 4-amino-1-carbamimidoylPiperidine-2-carboxylic
                         acideridine-4-carboxylic acid
SITE                    10
                        note = Amidated Tryptophan
SEQUENCE: 651
XYXNTFGLXW                                                          10

SEQ ID NO: 652          moltype = AA  length = 11
FEATURE                 Location/Qualifiers
source                  1..11
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = 4-(aminomethyl)benzoic acid
SITE                    3
                        note = D-Tyrosine
SITE                    4
                        note = D-Tryptophan
SITE                    8
                        note = Azaglycine
SITE                    10
                        note = 4-amino-1-carbamimidoylPiperidine-2-carboxylic
                         acideridine-4-carboxylic acid
SITE                    11
                        note = Amidated Tryptophan
SEQUENCE: 652
XXYWNTFGLX W                                                        11

SEQ ID NO: 653          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-Tryptophan
SITE                    6
                        note = biphenylalanine
SITE                    7
                        note = Azaglycine
SITE                    9
                        note = 4-amino-1-carbamimidoylPiperidine-2-carboxylic
                         acideridine-4-carboxylic acid
SITE                    10
                        note = Amidated Tryptophan
SEQUENCE: 653
XYWNTXGLXW                                                          10

SEQ ID NO: 654          moltype = AA  length = 8
FEATURE                 Location/Qualifiers
source                  1..8
```

```
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-4-(aminomethyl)benzoic acid
SITE                    5
                        note = Azaglycine
SITE                    7
                        note = 4-amino-1-carbamimidoylPiperidine-2-carboxylic
                         acideridine-4-carboxylic acid
SITE                    8
                        note = Amidated 3-(4-pyridyl)alanine
SEQUENCE: 654
XNTFGLXX                                                    8

SEQ ID NO: 655          moltype = AA  length = 9
FEATURE                 Location/Qualifiers
source                  1..9
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-D-Tyrosine
SITE                    2
                        note = 3-(4-pyridyl)alanine
SITE                    6
                        note = Azaglycine
SITE                    8
                        note = 4-amino-1-carbamimidoylPiperidine-2-carboxylic
                         acideridine-4-carboxylic acid
SITE                    9
                        note = Amidated 3-(4-pyridyl)alanine
SEQUENCE: 655
YXNTFGLXX                                                   9

SEQ ID NO: 656          moltype =   length =
SEQUENCE: 656
000

SEQ ID NO: 657          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = 3-(2-Naphthyl)alanine or
SITE                    7
                        note = Azaglycine
SITE                    9
                        note = 4-amino-1-carbamimidoylPiperidine-2-carboxylic
                         acideridine-4-carboxylic acid
SITE                    10
                        note = Amidated 3-(4-pyridyl)alanine
SEQUENCE: 657
XYXNTFGLXX                                                  10

SEQ ID NO: 658          moltype = AA  length = 10
FEATURE                 Location/Qualifiers
source                  1..10
                        mol_type = protein
                        organism = synthetic construct
SITE                    1
                        note = (DOTA)-6-aminohexanoic acid
SITE                    2
                        note = D-Tyrosine
SITE                    3
                        note = 3-(2-Naphthyl)alanine or
SITE                    7
                        note = Azaglycine
SITE                    9
                        note = 4-amino-1-carbamimidoylPiperidine-2-carboxylic
```

```
                         acideridine-4-carboxylic acid
SITE                    10
                        note = Amidated Tyrosine
SEQUENCE: 658
XYXNTFGLXY                                                       10

SEQ ID NO: 659          moltype = AA  length = 10
FEATURE                 Location/Qualifiers
source                  1..10
                        mol_type = protein
                        organism = synthetic construct
SITE                    1
                        note = (DOTA)-6-aminohexanoic acid
SITE                    2
                        note = D-Tyrosine
SITE                    3
                        note = 3-(2-Naphthyl)alanine or
SITE                    7
                        note = Azaglycine
SITE                    9
                        note = 4-amino-1-carbamimidoylPiperidine-2-carboxylic
                         acideridine-4-carboxylic acid
SITE                    10
                        note = Amidated Phenylalanine
SEQUENCE: 659
XYXNTFGLXF                                                       10

SEQ ID NO: 660          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = 3-(2-Naphthyl)alanine or
SITE                    7
                        note = Azaglycine
SITE                    9
                        note = 4-amino-1-carbamimidoylPiperidine-2-carboxylic
                         acideridine-4-carboxylic acid
SITE                    10
                        note = Amidated 4-cyano phenylalanine
SEQUENCE: 660
XYXNTFGLXF                                                       10

SEQ ID NO: 661          moltype = AA  length = 9
FEATURE                 Location/Qualifiers
source                  1..9
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-Tryptophan
SITE                    7
                        note = 2-(2-aminoethoxy)-[1,1'-biphenyl]-4-carboxylic acid
SITE                    8
                        note =
                         4-amino-1-((3-fluoro-4-methylbenzyl)glycyl)Piperidine-2-car
                         boxylic acideridine-4-carboxamide
SITE                    9
                        note = Amidated Tryptophan
SEQUENCE: 661
XYWNTFXXW                                                        9

SEQ ID NO: 662          moltype =   length =
SEQUENCE: 662
000

SEQ ID NO: 663          moltype = AA  length = 9
```

```
FEATURE                 Location/Qualifiers
source                  1..9
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-D-Tyrosine
SITE                    2
                        note = D-3-(4-pyridyl)alanine
SITE                    6
                        note = Azaglycine
SITE                    8
                        note =
                         4-amino-1-((3-fluoro-4-methylbenzyl)glycyl)Piperidine-2-car
                         boxylic acideridine-4-carboxamide
SITE                    9
                        note = Amidated 3-(4-pyridyl)alanine
SEQUENCE: 663
YXNTFGLXX                                                                     9

SEQ ID NO: 664          moltype =   length =
SEQUENCE: 664
000

SEQ ID NO: 665          moltype =   length =
SEQUENCE: 665
000

SEQ ID NO: 666          moltype =   length =
SEQUENCE: 666
000

SEQ ID NO: 667          moltype = AA  length = 8
FEATURE                 Location/Qualifiers
source                  1..8
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-D-Tyrosine
SITE                    2
                        note = 3-(2-Naphthyl)alanine or
SITE                    3
                        note = 6-aminohexanoic acid
SITE                    5
                        note = Azaglycine
SITE                    7
                        note =
                         4-amino-1-((3-fluoro-4-methylbenzyl)glycyl)Piperidine-2-car
                         boxylic acideridine-4-carboxamide
SITE                    8
                        note = Amidated Tryptophan
SEQUENCE: 667
YXXFGLXW                                                                      8

SEQ ID NO: 668          moltype = AA  length = 8
FEATURE                 Location/Qualifiers
source                  1..8
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-D-Tyrosine
SITE                    2
                        note = 3-(2-Naphthyl)alanine or
SITE                    3
                        note = 6-aminohexanoic acid
SITE                    5
                        note = Azaglycine
SITE                    7
                        note =
                         4-amino-1-((3-fluoro-4-methylbenzyl)glycyl)Piperidine-2-car
                         boxylic acideridine-4-carboxamide
SITE                    8
                        note = Amidated 3-(4-pyridyl)alanine
SEQUENCE: 668
```

```
YXXFGLXX                                                          8

SEQ ID NO: 669          moltype = AA  length = 8
FEATURE                 Location/Qualifiers
source                  1..8
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-D-Tyrosine
SITE                    2
                        note = 3-(2-Naphthyl)alanine or
SITE                    3
                        note = ahx
SITE                    5
                        note = Azaglycine
SITE                    7
                        note = 4-amino-1-carbamimidoylPiperidine-2-carboxylic
                         acideridine-4-carboxylic acid
SITE                    8
                        note = Amidated Tryptophan
SEQUENCE: 669
YXXFGLXW                                                          8

SEQ ID NO: 670          moltype = AA  length = 8
FEATURE                 Location/Qualifiers
source                  1..8
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-D-Tyrosine
SITE                    2
                        note = 3-(2-Naphthyl)alanine or
SITE                    3
                        note = 4-(aminomethyl)benzoic acid
SITE                    5
                        note = Azaglycine
SITE                    7
                        note = 4-amino-1-carbamimidoylPiperidine-2-carboxylic
                         acideridine-4-carboxylic acid
SITE                    8
                        note = Amidated Phenylalanine
SEQUENCE: 670
YXXFGLXF                                                          8

SEQ ID NO: 671          moltype = AA  length = 8
FEATURE                 Location/Qualifiers
source                  1..8
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-D-Tyrosine
SITE                    2
                        note = 3-(2-Naphthyl)alanine or
SITE                    3
                        note = 6-aminohexanoic acid
SITE                    5
                        note = Azaglycine
SITE                    7
                        note = 4-amino-1-carbamimidoylPiperidine-2-carboxylic
                         acideridine-4-carboxylic acid
SITE                    8
                        note = Amidated Phenylalanine
SEQUENCE: 671
YXXFGLXF                                                          8

SEQ ID NO: 672          moltype = AA  length = 9
FEATURE                 Location/Qualifiers
source                  1..9
                        mol_type = protein
                        organism = synthetic construct
SITE                    1
                        note =
                         2,2',2'',2'''-(1,4,7,10-tetraazacyclododecane-1,4,7,10-tetr
```

```
                        ayl)tetraacetic acid 6-aminohexanoic acid
SITE                    2
                        note = D-Tryptophan
SITE                    6
                        note = Azaglycine
SITE                    8
                        note =
                         4-amino-1-((3-fluoro-4-methylbenzyl)glycyl)Piperidine-2-car
                         boxylic acideridine-4-carboxamide
SITE                    9
                        note = Amidated 3-(4-pyridyl)alanine
SEQUENCE: 672
XWNTFGLXX                                                                  9

SEQ ID NO: 673          moltype = AA  length = 9
FEATURE                 Location/Qualifiers
source                  1..9
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    6
                        note = Azaglycine
SITE                    8
                        note =
                         4-amino-1-((3-fluoro-4-methylbenzyl)glycyl)Piperidine-2-car
                         boxylic acideridine-4-carboxamide
SITE                    9
                        note = Amidated 3-(4-pyridyl)alanine
SEQUENCE: 673
XYNTFGLXX                                                                  9

SEQ ID NO: 674          moltype = AA  length = 9
FEATURE                 Location/Qualifiers
source                  1..9
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-3-(2-Naphthyl)alanine
SITE                    6
                        note = Azaglycine
SITE                    8
                        note =
                         4-amino-1-((3-fluoro-4-methylbenzyl)glycyl)Piperidine-2-car
                         boxylic acideridine-4-carboxamide
SITE                    9
                        note = Amidated 3-(4-pyridyl)alanine
SEQUENCE: 674
XXNTFGLXX                                                                  9

SEQ ID NO: 675          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-Tryptophan
SITE                    7
                        note = Azaglycine
SITE                    9
                        note = Apc(OMe)
SITE                    10
                        note = Amidated 3-(4-pyridyl)alanine
SEQUENCE: 675
XYWNTFGLXX                                                                 10
```

```
SEQ ID NO: 676          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-3-(4-pyridyl)alanine
SITE                    7
                        note = Azaglycine
SITE                    9
                        note =
                         4-amino-1-((3-fluoro-4-methylbenzyl)glycyl)Piperidine-2-car
                         boxylic acideridine-4-carboxamide
SITE                    10
                        note = Amidated 3-(4-pyridyl)alanine
SEQUENCE: 676
XYXNTFGLXX                                                            10

SEQ ID NO: 677          moltype = AA  length = 9
FEATURE                 Location/Qualifiers
source                  1..9
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-3-(4-pyridyl)alanine
SITE                    6
                        note = Azaglycine
SITE                    8
                        note =
                         4-amino-1-((3-fluoro-4-methylbenzyl)glycyl)Piperidine-2-car
                         boxylic acideridine-4-carboxamide
SITE                    9
                        note = Amidated 3-(4-pyridyl)alanine
SEQUENCE: 677
XXNTFGLXX                                                             9

SEQ ID NO: 678          moltype = AA  length = 9
FEATURE                 Location/Qualifiers
source                  1..9
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-3-(4-pyridyl)alanine
SITE                    6
                        note = Azaglycine
SITE                    8
                        note =
                         4-amino-1-((3-fluoro-4-methylbenzyl)glycyl)Piperidine-2-car
                         boxylic acideridine-4-carboxamide
SITE                    9
                        note = Amidated Tryptophan
SEQUENCE: 678
XXNTFGLXW                                                             9

SEQ ID NO: 679          moltype =   length =
SEQUENCE: 679
000

SEQ ID NO: 680          moltype =   length =
SEQUENCE: 680
000

SEQ ID NO: 681          moltype = AA  length = 10
FEATURE                 Location/Qualifiers
```

-continued

| | |
|---|---|
| source | 1..10 |
| | mol_type = protein |
| | organism = synthetic construct |
| SITE | 1 |
| | note = |
| | 2,2',2'',2'''-(1,4,7,10-tetraazacyclododecane-1,4,7,10-tetr ayl)tetraacetic acid 6-aminohexanoic acid |
| SITE | 2 |
| | note = D-Tyrosine |
| SITE | 3 |
| | note = D-3-(4-pyridyl)alanine |
| SITE | 7 |
| | note = Azaglycine |
| SITE | 9 |
| | note = Apc(OMe) |
| SITE | 10 |
| | note = Amidated 3-(4-pyridyl)alanine |
| SEQUENCE: 681 | |
| XYXNTFGLXX | 10 |
| | |
| SEQ ID NO: 682 | moltype = AA length = 10 |
| FEATURE | Location/Qualifiers |
| source | 1..10 |
| | mol_type = protein |
| | organism = synthetic construct |
| SITE | 1 |
| | note = |
| | 2,2',2'',2'''-(1,4,7,10-tetraazacyclododecane-1,4,7,10-tetr ayl)tetraacetic acid 6-aminohexanoic acid |
| SITE | 2 |
| | note = D-Tyrosine |
| SITE | 3 |
| | note = D-3-(2-Naphthyl)alanine |
| SITE | 7 |
| | note = Azaglycine |
| SITE | 9 |
| | note = 4-amino-1-carbamimidoylPiperidine-2-carboxylic acideridine-4-carboxylic acid |
| SITE | 10 |
| | note = Amidated Phenylalanine |
| SEQUENCE: 682 | |
| XYXNTFGLXF | 10 |
| | |
| SEQ ID NO: 683 | moltype = AA length = 9 |
| FEATURE | Location/Qualifiers |
| source | 1..9 |
| | mol_type = protein |
| | organism = synthetic construct |
| SITE | 1 |
| | note = |
| | 2,2',2'',2'''-(1,4,7,10-tetraazacyclododecane-1,4,7,10-tetr ayl)tetraacetic acid 6-aminohexanoic acid |
| SITE | 2 |
| | note = D-3-(2-Naphthyl)alanine |
| SITE | 6 |
| | note = Azaglycine |
| SITE | 8 |
| | note = 4-amino-1-carbamimidoylPiperidine-2-carboxylic acideridine-4-carboxylic acid |
| SITE | 9 |
| | note = Amidated Phenylalanine |
| SEQUENCE: 683 | |
| XXNTFGLXF | 9 |
| | |
| SEQ ID NO: 684 | moltype = AA length = 8 |
| FEATURE | Location/Qualifiers |
| source | 1..8 |
| | mol_type = protein |
| | organism = synthetic construct |
| SITE | 1 |
| | note = |
| | 2,2',2'',2'''-(1,4,7,10-tetraazacyclododecane-1,4,7,10-tetr ayl)tetraacetic acid-D-3-(2-Naphthyl)alanine |
| SITE | 5 |
| | note = Azaglycine |
| SITE | 7 |
| | note = 4-amino-1-carbamimidoylPiperidine-2-carboxylic acideridine-4-carboxylic acid |
| SITE | 8 |

```
                        note = Amidated Phenylalanine
SEQUENCE: 684
XNTFGLXF                                                        8

SEQ ID NO: 685          moltype =   length =
SEQUENCE: 685
000

SEQ ID NO: 686          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-3-(2-Naphthyl)alanine
SITE                    7
                        note = Azaglycine
SITE                    9
                        note =
                         4-amino-1-((3-fluoro-4-methylbenzyl)glycyl)Piperidine-2-car
                         boxylic acideridine-4-carboxamide
SITE                    10
                        note = Amidated Tryptophan
SEQUENCE: 686
XYXNTFGLXW                                                      10

SEQ ID NO: 687          moltype = AA  length = 8
FEATURE                 Location/Qualifiers
source                  1..8
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-Glycine
SITE                    3
                        note = 6-aminohexanoic acid
SITE                    5
                        note = Azaglycine
SITE                    7
                        note =
                         4-amino-1-((3-fluoro-4-methylbenzyl)glycyl)Piperidine-2-car
                         boxylic acideridine-4-carboxamide
SITE                    8
                        note = Amidated Tryptophan
SEQUENCE: 687
GYXFGLXW                                                        8

SEQ ID NO: 688          moltype = AA  length = 9
FEATURE                 Location/Qualifiers
source                  1..9
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-Glycine
SITE                    2
                        note = D-Tyrosine
SITE                    3
                        note = 3-(2-Naphthyl)alanine or
SITE                    4
                        note = 6-aminohexanoic acid
SITE                    6
                        note = Azaglycine
SITE                    8
                        note =
                         4-amino-1-((3-fluoro-4-methylbenzyl)glycyl)Piperidine-2-car
                         boxylic acideridine-4-carboxamide
SITE                    9
                        note = Amidated Tryptophan
SEQUENCE: 688
GYXXFGLXW                                                       9
```

```
SEQ ID NO: 689          moltype = AA  length = 9
FEATURE                 Location/Qualifiers
source                  1..9
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-Glycine
SITE                    3
                        note = 3-(2-Naphthyl)alanine or
SITE                    4
                        note = 6-aminohexanoic acid
SITE                    6
                        note = Azaglycine
SITE                    8
                        note =
                         4-amino-1-((3-fluoro-4-methylbenzyl)glycyl)Piperidine-2-car
                         boxylic acideridine-4-carboxamide
SITE                    9
                        note = Amidated Tryptophan
SEQUENCE: 689
GYXXFGLXW                                                                9

SEQ ID NO: 690          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-hydroxyproline
SITE                    7
                        note = Azaglycine
SITE                    9
                        note =
                         4-amino-1-((3-fluoro-4-methylbenzyl)glycyl)Piperidine-2-car
                         boxylic acideridine-4-carboxamide
SITE                    10
                        note = Amidated Tryptophan
SEQUENCE: 690
XYXNTFGLXW                                                               10

SEQ ID NO: 691          moltype = AA  length = 11
FEATURE                 Location/Qualifiers
source                  1..11
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = N6-(4-(p-tolyl)butanoyl)-D-lysine
SITE                    3
                        note = D-Tyrosine
SITE                    4
                        note = D-3-(2-Naphthyl)alanine
SITE                    8
                        note = Azaglycine
SITE                    10
                        note = 4-amino-1-carbamimidoylPiperidine-2-carboxylic
                         acideridine-4-carboxylic acid
SITE                    11
                        note = Amidated Phenylalanine
SEQUENCE: 691
XXYXNTFGLX F                                                             11

SEQ ID NO: 692          moltype = AA  length = 11
FEATURE                 Location/Qualifiers
source                  1..11
                        mol_type = protein
                        organism = synthetic construct
```

```
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = N6-(4-(4-iodophenyl)butanoyl)-D-lysine
SITE                    3
                        note = D-Tyrosine
SITE                    4
                        note = D-3-(2-Naphthyl)alanine
SITE                    8
                        note = Azaglycine
SITE                    10
                        note = 4-amino-1-carbamimidoylPiperidine-2-carboxylic
                         acideridine-4-carboxylic acid
SITE                    11
                        note = Amidated Phenylalanine
SEQUENCE: 692
XXYXNTFGLX F                                                    11

SEQ ID NO: 693          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = hydroxyproline
SITE                    7
                        note = Azaglycine
SITE                    9
                        note = 4-amino-1-carbamimidoylPiperidine-2-carboxylic
                         acideridine-4-carboxylic acid
SITE                    10
                        note = Amidated Tryptophan
SEQUENCE: 693
XYXNTFGLXW                                                      10

SEQ ID NO: 694          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-hydroxyproline
SITE                    7
                        note = Azaglycine
SITE                    9
                        note = 4-amino-1-carbamimidoylPiperidine-2-carboxylic
                         acideridine-4-carboxylic acid
SITE                    10
                        note = Amidated Tryptophan
SEQUENCE: 694
XYXNTFGLXW                                                      10

SEQ ID NO: 695          moltype = AA  length = 8
FEATURE                 Location/Qualifiers
source                  1..8
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    4
                        note = cyclohexylalanine
SITE                    5
                        note = Azaglycine
```

```
SITE                    7
                        note =
                         4-amino-1-((3-fluoro-4-methylbenzyl)glycyl)Piperidine-2-car
                         boxylic acideridine-4-carboxamide
SITE                    8
                        note = Amidated Tryptophan
SEQUENCE: 695
XNTXGLXW                                                                    8

SEQ ID NO: 696          moltype = AA  length = 9
FEATURE                 Location/Qualifiers
source                  1..9
                        mol_type = protein
                        organism = synthetic construct
SITE                    1
                        note =
                         (2,2',2'',2'''-(1,4,7,10-tetraazacyclododecane-1,4,7,10-tet
                         rayl)tetraacetic acid)-6-aminohexanoic acid
SITE                    2
                        note = D-3-(4-pyridyl)alanine
SITE                    5
                        note = cyclohexylalanine
SITE                    6
                        note = Azaglycine
SITE                    8
                        note =
                         4-amino-1-((3-fluoro-4-methylbenzyl)glycyl)Piperidine-2-car
                         boxylic acideridine-4-carboxamide
SITE                    9
                        note = Amidated Tryptophan
SEQUENCE: 696
XXNTXGLXW                                                                   9

SEQ ID NO: 697          moltype = AA  length = 9
FEATURE                 Location/Qualifiers
source                  1..9
                        mol_type = protein
                        organism = synthetic construct
SITE                    1
                        note =
                         (2,2',2'',2'''-(1,4,7,10-tetraazacyclododecane-1,4,7,10-tet
                         rayl)tetraacetic acid)-D-Tyrosine
SITE                    2
                        note = D-3-(4-pyridyl)alanine
SITE                    5
                        note = cyclohexylalanine
SITE                    6
                        note = Azaglycine
SITE                    8
                        note =
                         4-amino-1-((3-fluoro-4-methylbenzyl)glycyl)Piperidine-2-car
                         boxylic acideridine-4-carboxamide
SITE                    9
                        note = Amidated Tryptophan
SEQUENCE: 697
YXNTXGLXW                                                                   9

SEQ ID NO: 698          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-3-(4-pyridyl)alanine
SITE                    6
                        note = cyclohexylalanine
SITE                    7
                        note = Azaglycine
SITE                    9
                        note =
                         4-amino-1-((3-fluoro-4-methylbenzyl)glycyl)Piperidine-2-car
                         boxylic acideridine-4-carboxamide
SITE                    10
```

```
                         note = Amidated Tryptophan
SEQUENCE: 698
XYXNTXGLXW                                                          10

SEQ ID NO: 699           moltype = AA  length = 10
FEATURE                  Location/Qualifiers
source                   1..10
                         mol_type = protein
                         organism = synthetic construct
SITE                     1
                         note = (DOTA)-6-aminohexanoic acid
SITE                     2
                         note = D-Tyrosine
SITE                     3
                         note = D-3-(2-Naphthyl)alanine
SITE                     6
                         note = cyclohexylalanine
SITE                     7
                         note = Azaglycine
SITE                     9
                         note = 4-amino-1-carbamimidoylPiperidine-2-carboxylic
                          acideridine-4-carboxylic acid
SITE                     10
                         note = Amidated Tryptophan
SEQUENCE: 699
XYXNTXGLXW                                                          10

SEQ ID NO: 700           moltype = AA  length = 9
FEATURE                  Location/Qualifiers
source                   1..9
                         mol_type = protein
                         organism = synthetic construct
SITE                     1
                         note = (DOTA)-D-Tyrosine
SITE                     2
                         note = D-3-(2-Naphthyl)alanine
SITE                     5
                         note = cyclohexylalanine
SITE                     6
                         note = Azaglycine
SITE                     8
                         note =
                          4-amino-1-((3-fluoro-4-methylbenzyl)glycyl)Piperidine-2-car
                          boxylic acideridine-4-carboxamide
SITE                     9
                         note = Amidated Tryptophan
SEQUENCE: 700
YXNTXGLXW                                                           9

SEQ ID NO: 701           moltype = AA  length = 10
FEATURE                  Location/Qualifiers
source                   1..10
                         mol_type = protein
                         organism = synthetic construct
SITE                     1
                         note = (DOTA)-6-aminohexanoic acid
SITE                     2
                         note = D-Tyrosine
SITE                     3
                         note = D-3-(2-Naphthyl)alanine
SITE                     7
                         note = Azaglycine
SITE                     9
                         note =
                          4-amino-1-(N-methylcarbamimidoyl)Piperidine-2-carboxylic
                          acideridine-4-carboxylic acid
SITE                     10
                         note = Amidated D-Tryptophan
SEQUENCE: 701
XYXNTFGLXW                                                          10

SEQ ID NO: 702           moltype = AA  length = 10
FEATURE                  Location/Qualifiers
source                   1..10
                         mol_type = protein
                         organism = synthetic construct
SITE                     1
                         note = 3-(4-iodophenyl)propanoic acid-gamma-D-Glu
SITE                     2
```

```
                        note = D-Tyrosine
SITE                    3
                        note =
                         Lysine(1,4,7,10-tetraazacyclododecane-1,4,7,10-tetraacetic
                         acid)
SITE                    7
                        note = Azaglycine
SITE                    9
                        note = 4-amino-1-carbamimidoylPiperidine-2-carboxylic
                         acideridine-4-carboxylic acid
SITE                    10
                        note = Amidated Tryptophan
SEQUENCE: 702
EYKNTFGLXW                                                                    10

SEQ ID NO: 703          moltype = AA  length = 9
FEATURE                 Location/Qualifiers
source                  1..9
                        mol_type = protein
                        organism = synthetic construct
SITE                    1
                        note = 3-(4-iodophenyl)propanoic acid-D-Tyrosine
SITE                    2
                        note =
                         Lysine(1,4,7,10-tetraazacyclododecane-1,4,7,10-tetraacetic
                         acid)
SITE                    6
                        note = Azaglycine
SITE                    8
                        note = 4-amino-1-carbamimidoylPiperidine-2-carboxylic
                         acideridine-4-carboxylic acid
SITE                    9
                        note = Amidated Tryptophan
SEQUENCE: 703
YKNTFGLXW                                                                     9

SEQ ID NO: 704          moltype = AA  length = 9
FEATURE                 Location/Qualifiers
source                  1..9
                        mol_type = protein
                        organism = synthetic construct
SITE                    1
                        note =
                         3-(2-(2-(3-(p-tolyl)propanamido)ethoxy)ethoxy)propanoic
                         acid-D-Tyrosine
SITE                    2
                        note =
                         Lysine(1,4,7,10-tetraazacyclododecane-1,4,7,10-tetraacetic
                         acid)
SITE                    6
                        note = Azaglycine
SITE                    8
                        note = 4-amino-1-carbamimidoylPiperidine-2-carboxylic
                         acideridine-4-carboxylic acid
SITE                    9
                        note = Amidated Phenylalanine
SEQUENCE: 704
YKNTFGLXF                                                                     9

SEQ ID NO: 705          moltype = AA  length = 9
FEATURE                 Location/Qualifiers
source                  1..9
                        mol_type = protein
                        organism = synthetic construct
SITE                    1
                        note =
                         3-(2-(2-(3-(4-iodophenyl)propanamido)ethoxy)ethoxy)propanoi
                         c-D-Tyrosine
SITE                    2
                        note =
                         Lysine(1,4,7,10-tetraazacyclododecane-1,4,7,10-tetraacetic
                         acid)
SITE                    6
                        note = Azaglycine
SITE                    8
                        note = 4-amino-1-carbamimidoylPiperidine-2-carboxylic
                         acideridine-4-carboxylic acid
SITE                    9
                        note = Amidated Phenylalanine
```

-continued

```
SEQUENCE: 705
YKNTFGLXF                                                        9

SEQ ID NO: 706          moltype = AA  length = 9
FEATURE                 Location/Qualifiers
source                  1..9
                        mol_type = protein
                        organism = synthetic construct
SITE                    1
                        note =
                         3-(2-(2-(3-(4-iodophenyl)propanamido)ethoxy)ethoxy)propanoi
                         c acid-D-Tyrosine
SITE                    2
                        note =
                         Lysine(1,4,7,10-tetraazacyclododecane-1,4,7,10-tetraacetic
                         acid)
SITE                    6
                        note = Azaglycine
SITE                    8
                        note = 4-amino-1-carbamimidoylPiperidine-2-carboxylic
                         acideridine-4-carboxylic acid
SITE                    9
                        note = Amidated Tyrosine
SEQUENCE: 706
YKNTFGLXY                                                        9

SEQ ID NO: 707          moltype = AA  length = 9
FEATURE                 Location/Qualifiers
source                  1..9
                        mol_type = protein
                        organism = synthetic construct
SITE                    1
                        note =
                         3-(2-(2-(3-(4-iodophenyl)propanamido)ethoxy)ethoxy)propanoi
                         c acid-D-Tyrosine
SITE                    2
                        note =
                         Lysine(1,4,7,10-tetraazacyclododecane-1,4,7,10-tetraacetic
                         acid)
SITE                    6
                        note = Azaglycine
SITE                    8
                        note = 4-amino-1-carbamimidoylPiperidine-2-carboxylic
                         acideridine-4-carboxylic acid
SITE                    9
                        note = Amidated 4-cyano phenylalanine
SEQUENCE: 707
YKNTFGLXF                                                        9

SEQ ID NO: 708          moltype = AA  length = 9
FEATURE                 Location/Qualifiers
source                  1..9
                        mol_type = protein
                        organism = synthetic construct
SITE                    1
                        note =
                         3-(2-(2-(3-(p-tolyl)propanamido)ethoxy)ethoxy)propanoic
                         acid-D-Tyrosine
SITE                    2
                        note =
                         Lysine(1,4,7,10-tetraazacyclododecane-1,4,7,10-tetraacetic
                         acid)
SITE                    5
                        note = cyclohexylalanine
SITE                    6
                        note = Azaglycine
SITE                    8
                        note = 4-amino-1-carbamimidoylPiperidine-2-carboxylic
                         acideridine-4-carboxylic acid
SITE                    9
                        note = Amidated Tryptophan
SEQUENCE: 708
YKNTXGLXW                                                        9

SEQ ID NO: 709          moltype = AA  length = 9
FEATURE                 Location/Qualifiers
source                  1..9
                        mol_type = protein
                        organism = synthetic construct
```

```
SITE                    1
                        note =
                         3-(2-(2-(3-(4-iodophenyl)propanamido)ethoxy)ethoxy)propanoi
                         c acid-D-Tyrosine
SITE                    2
                        note =
                         Lysine(1,4,7,10-tetraazacyclododecane-1,4,7,10-tetraacetic
                         acid)
SITE                    5
                        note = cyclohexylalanine
SITE                    6
                        note = Azaglycine
SITE                    8
                        note = 4-amino-1-carbamimidoylPiperidine-2-carboxylic
                         acideridine-4-carboxylic acid
SITE                    9
                        note = Amidated Tryptophan
SEQUENCE: 709
YKNTXGLXW                                                                   9

SEQ ID NO: 710          moltype = AA  length = 9
FEATURE                 Location/Qualifiers
source                  1..9
                        mol_type = protein
                        organism = synthetic construct
SITE                    1
                        note = palmitic acid-D-Tyrosine
SITE                    2
                        note =
                         Lysine(1,4,7,10-tetraazacyclododecane-1,4,7,10-tetraacetic
                         acid)
SITE                    6
                        note = Azaglycine
SITE                    8
                        note = 4-amino-1-carbamimidoylPiperidine-2-carboxylic
                         acideridine-4-carboxylic acid
SITE                    9
                        note = Amidated Tryptophan
SEQUENCE: 710
YKNTFGLXW                                                                   9

SEQ ID NO: 711          moltype = AA  length = 9
FEATURE                 Location/Qualifiers
source                  1..9
                        mol_type = protein
                        organism = synthetic construct
SITE                    1
                        note = dodecanoic acid-D-Tyrosine
SITE                    2
                        note =
                         Lysine(1,4,7,10-tetraazacyclododecane-1,4,7,10-tetraacetic
                         acid)
SITE                    6
                        note = Azaglycine
SITE                    8
                        note = 4-amino-1-carbamimidoylPiperidine-2-carboxylic
                         acideridine-4-carboxylic acid
SITE                    9
                        note = Amidated Tryptophan
SEQUENCE: 711
YKNTFGLXW                                                                   9

SEQ ID NO: 712          moltype = AA  length = 9
FEATURE                 Location/Qualifiers
source                  1..9
                        mol_type = protein
                        organism = synthetic construct
SITE                    1
                        note = palmitic acid-D-Tyrosine
SITE                    2
                        note =
                         Lysine(1,4,7,10-tetraazacyclododecane-1,4,7,10-tetraacetic
                         acid)
SITE                    6
                        note = Azaglycine
SITE                    8
                        note = 4-amino-1-carbamimidoylPiperidine-2-carboxylic
                         acideridine-4-carboxylic acid
SITE                    9
```

-continued

```
                        note = Amidated Tyrosine
SEQUENCE: 712
YKNTFGLXY                                                                   9

SEQ ID NO: 713          moltype = AA  length = 9
FEATURE                 Location/Qualifiers
source                  1..9
                        mol_type = protein
                        organism = synthetic construct
SITE                    1
                        note = dodecanoic acid-D-Tyrosine
SITE                    2
                        note =
                         Lysine(1,4,7,10-tetraazacyclododecane-1,4,7,10-tetraacetic
                         acid)
SITE                    6
                        note = Azaglycine
SITE                    8
                        note = 4-amino-1-carbamimidoylPiperidine-2-carboxylic
                         acideridine-4-carboxylic acid
SITE                    9
                        note = Amidated Tyrosine
SEQUENCE: 713
YKNTFGLXY                                                                   9

SEQ ID NO: 714          moltype = AA  length = 9
FEATURE                 Location/Qualifiers
source                  1..9
                        mol_type = protein
                        organism = synthetic construct
SITE                    1
                        note = octanoic acid-D-Tyrosine
SITE                    2
                        note =
                         Lysine(1,4,7,10-tetraazacyclododecane-1,4,7,10-tetraacetic
                         acid)
SITE                    6
                        note = Azaglycine
SITE                    8
                        note = 4-amino-1-carbamimidoylPiperidine-2-carboxylic
                         acideridine-4-carboxylic acid
SITE                    9
                        note = Amidated Tyrosine
SEQUENCE: 714
YKNTFGLXY                                                                   9

SEQ ID NO: 715          moltype = AA  length = 9
FEATURE                 Location/Qualifiers
source                  1..9
                        mol_type = protein
                        organism = synthetic construct
SITE                    1
                        note =
                         3-(2-(2-(3-(p-tolyl)propanamido)ethoxy)ethoxy)propanoic
                         acid-D-Tyrosine
SITE                    2
                        note =
                         Lysine(1,4,7,10-tetraazacyclododecane-1,4,7,10-tetraacetic
                         acid)
SITE                    6
                        note = Azaglycine
SITE                    8
                        note = 4-amino-1-carbamimidoylPiperidine-2-carboxylic
                         acideridine-4-carboxylic acid
SITE                    9
                        note = Amidated 4-cyano phenylalanine
SEQUENCE: 715
YKNTFGLXF                                                                   9

SEQ ID NO: 716          moltype = AA  length = 9
FEATURE                 Location/Qualifiers
source                  1..9
                        mol_type = protein
                        organism = synthetic construct
SITE                    1
                        note =
                         3-(2-(2-(3-(4-iodophenyl)propanamido)ethoxy)ethoxy)propanoi
                         c acid-D-Tyrosine
SITE                    2
```

```
                         note =
                          D-Lysine(1,4,7,10-tetraazacyclododecane-1,4,7,10-tetraaceti
                          c acid)
SITE                     6
                         note = Azaglycine
SITE                     8
                         note = 4-amino-1-carbamimidoylPiperidine-2-carboxylic
                          acideridine-4-carboxylic acid
SITE                     9
                         note = Amidated Tryptophan
SEQUENCE: 716
YKNTFGLXW                                                   9

SEQ ID NO: 717           moltype = AA  length = 11
FEATURE                  Location/Qualifiers
source                   1..11
                         mol_type = protein
                         organism = synthetic construct
SITE                     1
                         note =
                          2,2',2'',2'''-(1,4,7,10-tetraazacyclododecane-1,4,7,10-tetr
                          ayl)tetraacetic acid 6-aminohexanoic acid
SITE                     2
                         note = N6-(4-(p-tolyl)butanoyl)-D-lysine
SITE                     3
                         note = D-Tyrosine
SITE                     4
                         note = D-3-(2-Naphthyl)alanine
SITE                     8
                         note = Azaglycine
SITE                     10
                         note = 4-amino-1-carbamimidoylPiperidine-2-carboxylic
                          acideridine-4-carboxylic acid
SITE                     11
                         note = Amidated Tryptophan
SEQUENCE: 717
XKYXNTFGLX W                                                11

SEQ ID NO: 718           moltype = AA  length = 11
FEATURE                  Location/Qualifiers
source                   1..11
                         mol_type = protein
                         organism = synthetic construct
SITE                     1
                         note =
                          2,2',2'',2'''-(1,4,7,10-tetraazacyclododecane-1,4,7,10-tetr
                          ayl)tetraacetic acid 6-aminohexanoic acid
SITE                     2
                         note = N6-(4-(4-iodophenyl)butanoyl)-D-lysine
SITE                     3
                         note = D-Tyrosine
SITE                     4
                         note = D-2-Nal
SITE                     8
                         note = Azaglycine
SITE                     10
                         note = 4-amino-1-carbamimidoylPiperidine-2-carboxylic
                          acideridine-4-carboxylic acid
SITE                     11
                         note = Amidated Tryptophan
SEQUENCE: 718
XKYXNTFGLX W                                                11

SEQ ID NO: 719           moltype = AA  length = 12
FEATURE                  Location/Qualifiers
source                   1..12
                         mol_type = protein
                         organism = synthetic construct
SITE                     1
                         note =
                          2,2',2'',2'''-(1,4,7,10-tetraazacyclododecane-1,4,7,10-tetr
                          ayl)tetraacetic acid 6-aminohexanoic acid
SITE                     2
                         note = N6-(4-(4-iodophenyl)butanoyl)-D-lysine
SITE                     3
                         note = ahx
SITE                     4
                         note = D-Tyrosine
SITE                     5
```

```
                         note = D-3-(2-Naphthyl)alanine
SITE                     9
                         note = Azaglycine
SITE                     11
                         note = 4-amino-1-carbamimidoylPiperidine-2-carboxylic
                          acideridine-4-carboxylic acid
SITE                     12
                         note = Amidated Tryptophan
SEQUENCE: 719
XKXYXNTFGL XW                                                    12

SEQ ID NO: 720           moltype = AA  length = 9
FEATURE                  Location/Qualifiers
source                   1..9
                         mol_type = protein
                         organism = synthetic construct
SITE                     1
                         note =
                          3-(2-(2-(3-(p-tolyl)propanamido)ethoxy)ethoxy)propanoic
                          acid-D-Tyrosine
SITE                     2
                         note =
                          D-Lysine(1,4,7,10-tetraazacyclododecane-1,4,7,10-tetraaceti
                          c acid)
SITE                     6
                         note = Azaglycine
SITE                     8
                         note = 4-amino-1-carbamimidoylPiperidine-2-carboxylic
                          acideridine-4-carboxylic acid
SITE                     9
                         note = Amidated Tryptophan
SEQUENCE: 720
YKNTFGLXW                                                        9

SEQ ID NO: 721           moltype = AA  length = 10
FEATURE                  Location/Qualifiers
source                   1..10
                         mol_type = protein
                         organism = synthetic construct
SITE                     1
                         note =
                          2,2',2'',2'''-(1,4,7,10-tetraazacyclododecane-1,4,7,10-tetr
                          ayl)tetraacetic acid 6-aminohexanoic acid
SITE                     2
                         note = D-Tyrosine
SITE                     3
                         note = D-3-(2-Naphthyl)alanine
SITE                     7
                         note = Azaglycine
SITE                     9
                         note = Piperidine-2-carboxylic acid
SITE                     10
                         note = Amidated D-Tryptophan
SEQUENCE: 721
XYXNTFGLXW                                                       10

SEQ ID NO: 722           moltype = AA  length = 10
FEATURE                  Location/Qualifiers
source                   1..10
                         mol_type = protein
                         organism = synthetic construct
SITE                     1
                         note =
                          2,2',2'',2'''-(1,4,7,10-tetraazacyclododecane-1,4,7,10-tetr
                          ayl)tetraacetic acid 6-aminohexanoic acid
SITE                     2
                         note = D-Tyrosine
SITE                     3
                         note = D-3-(2-Naphthyl)alanine
SITE                     7
                         note = Azaglycine
SITE                     9
                         note = 4-amino-1-(methyl-D-alanyl)Piperidine-2-carboxylic
                          acideridine-4-carboxylic acid
SITE                     10
                         note = Amidated Tryptophan
SEQUENCE: 722
XYXNTFGLXW                                                       10
```

```
SEQ ID NO: 723          moltype = AA  length = 9
FEATURE                 Location/Qualifiers
source                  1..9
                        mol_type = protein
                        organism = synthetic construct
SITE                    1
                        note =
                         1-(3-fluoro-4-methylphenyl)-4-oxo-8,11-dioxa-2,5-diazatetra
                         decan-14-oic acid-D-Tyrosine
SITE                    2
                        note =
                         Lysine(1,4,7,10-tetraazacyclododecane-1,4,7,10-tetraacetic
                         acid)
SITE                    6
                        note = Azaglycine
SITE                    8
                        note = 4-amino-1-carbamimidoylPiperidine-2-carboxylic
                         acideridine-4-carboxylic acid
SITE                    9
                        note = Amidated Tryptophan
SEQUENCE: 723
YKNTFGLXW                                                                   9

SEQ ID NO: 724          moltype = AA  length = 10
FEATURE                 Location/Qualifiers
source                  1..10
                        mol_type = protein
                        organism = synthetic construct
SITE                    1
                        note = (3-fluoro-4-methylbenzyl)glycine
SITE                    2
                        note = D-Tyrosine
SITE                    3
                        note =
                         Lysine(1,4,7,10-tetraazacyclododecane-1,4,7,10-tetraacetic
                         acid)
SITE                    7
                        note = Azaglycine
SITE                    9
                        note = 4-amino-1-carbamimidoylPiperidine-2-carboxylic
                         acideridine-4-carboxylic acid
SITE                    10
                        note = Amidated Tryptophan
SEQUENCE: 724
GYKNTFGLXW                                                                  10

SEQ ID NO: 725          moltype = AA  length = 10
FEATURE                 Location/Qualifiers
source                  1..10
                        mol_type = protein
                        organism = synthetic construct
SITE                    1
                        note = (3-fluoro-4-methylbenzyl)glycine
SITE                    2
                        note = D-Tyrosine
SITE                    3
                        note =
                         D-Lysine(1,4,7,10-tetraazacyclododecane-1,4,7,10-tetraaceti
                         c acid)
SITE                    7
                        note = Azaglycine
SITE                    9
                        note = 4-amino-1-carbamimidoylPiperidine-2-carboxylic
                         acideridine-4-carboxylic acid
SITE                    10
                        note = Amidated Tryptophan
SEQUENCE: 725
GYKNTFGLXW                                                                  10

SEQ ID NO: 726          moltype = AA  length = 9
FEATURE                 Location/Qualifiers
source                  1..9
                        mol_type = protein
                        organism = synthetic construct
SITE                    1
                        note =
                         1-(3-fluoro-4-methylphenyl)-4-oxo-8,11-dioxa-2,5-diazatetra
                         decan-14-oic acid-D-Tyrosine
SITE                    2
```

```
                         note =
                          D-Lysine(1,4,7,10-tetraazacyclododecane-1,4,7,10-tetraaceti
                          c acid)
SITE                     6
                         note = Azaglycine
SITE                     8
                         note = 4-amino-1-carbamimidoylPiperidine-2-carboxylic
                          acideridine-4-carboxylic acid
SITE                     9
                         note = Amidated Tryptophan
SEQUENCE: 726
YKNTFGLXW                                                                    9

SEQ ID NO: 727           moltype = AA  length = 10
FEATURE                  Location/Qualifiers
source                   1..10
                         mol_type = protein
                         organism = synthetic construct
SITE                     1
                         note =
                          2,2',2'',2'''-(1,4,7,10-tetraazacyclododecane-1,4,7,10-tetr
                          ayl)tetraacetic acid 6-aminohexanoic acid
SITE                     2
                         note = D-Tyrosine
SITE                     3
                         note = 4-benzoylphenylalanine
SITE                     7
                         note = Azaglycine
SITE                     9
                         note = 4-amino-1-carbamimidoylpiperidine-4-carboxylic
                          acid(Sarcosine)
SITE                     10
                         note = Amidated D-Tryptophan
SEQUENCE: 727
XYXNTFGLXW                                                                   10

SEQ ID NO: 728           moltype = AA  length = 10
FEATURE                  Location/Qualifiers
source                   1..10
                         mol_type = protein
                         organism = synthetic construct
SITE                     1
                         note =
                          2,2',2'',2'''-(1,4,7,10-tetraazacyclododecane-1,4,7,10-tetr
                          ayl)tetraacetic acid 6-aminohexanoic acid
SITE                     2
                         note = D-Tyrosine
SITE                     3
                         note = 4-benzoylphenylalanine
SITE                     7
                         note = Azaglycine
SITE                     9
                         note = 4-amino-1-carbamimidoylpiperidine-4-carboxylic
                          acid(Sarcosine)
SITE                     10
                         note = Amidated Tryptophan
SEQUENCE: 728
XYXNTFGLXW                                                                   10

SEQ ID NO: 729           moltype = AA  length = 10
FEATURE                  Location/Qualifiers
source                   1..10
                         mol_type = protein
                         organism = synthetic construct
SITE                     1
                         note =
                          2,2',2'',2'''-(1,4,7,10-tetraazacyclododecane-1,4,7,10-tetr
                          ayl)tetraacetic acid 6-aminohexanoic acid
SITE                     2
                         note = D-Tyrosine
SITE                     3
                         note = biphenylalanine
SITE                     7
                         note = Azaglycine
SITE                     9
                         note = 4-amino-1-carbamimidoylpiperidine-4-carboxylic
                          acid(Sarcosine)
SITE                     10
                         note = Amidated Tryptophan
```

```
SEQUENCE: 729
XYXNTFGLXW                                                  10

SEQ ID NO: 730          moltype = AA  length = 9
FEATURE                 Location/Qualifiers
source                  1..9
                        mol_type = protein
                        organism = synthetic construct
SITE                    1
                        note = dodecanoic acid-D-Tyrosine
SITE                    2
                        note =
                         D-Lysine(1,4,7,10-tetraazacyclododecane-1,4,7,10-tetraaceti
                         c acid)
SITE                    6
                        note = Azaglycine
SITE                    8
                        note = 4-amino-1-carbamimidoylPiperidine-2-carboxylic
                         acideridine-4-carboxylic acid
SITE                    9
                        note = Amidated Tyrosine
SEQUENCE: 730
YKNTFGLXY                                                   9

SEQ ID NO: 731          moltype = AA  length = 10
FEATURE                 Location/Qualifiers
source                  1..10
                        mol_type = protein
                        organism = synthetic construct
SITE                    1
                        note = (3-(4-(15-methyl)phenyl)propanoyl)-D-glutamic acid
SITE                    2
                        note = D-Tyrosine
SITE                    3
                        note =
                         Lysine(1,4,7,10-tetraazacyclododecane-1,4,7,10-tetraacetic
                         acid)
SITE                    7
                        note = Azaglycine
SITE                    9
                        note = 4-amino-1-carbamimidoylPiperidine-2-carboxylic
                         acideridine-4-carboxylic acid
SITE                    10
                        note = Amidated Tryptophan
SEQUENCE: 731
EYKNTFGLXW                                                  10

SEQ ID NO: 732          moltype = AA  length = 9
FEATURE                 Location/Qualifiers
source                  1..9
                        mol_type = protein
                        organism = synthetic construct
SITE                    1
                        note = octanoic acid-D-Tyrosine
SITE                    2
                        note =
                         D-Lysine(1,4,7,10-tetraazacyclododecane-1,4,7,10-tetraaceti
                         c acid)
SITE                    6
                        note = Azaglycine
SITE                    8
                        note = 4-amino-1-carbamimidoylPiperidine-2-carboxylic
                         acideridine-4-carboxylic acid
SITE                    9
                        note = Amidated Tryptophan
SEQUENCE: 732
YKNTFGLXW                                                   9

SEQ ID NO: 733          moltype = AA  length = 9
FEATURE                 Location/Qualifiers
source                  1..9
                        mol_type = protein
                        organism = synthetic construct
SITE                    1
                        note = octanoic acid-D-Tyrosine
SITE                    2
                        note =
                         D-Lysine(1,4,7,10-tetraazacyclododecane-1,4,7,10-tetraaceti
                         c acid)
```

-continued

```
SITE                    5
                        note = cyclohexylalanine
SITE                    6
                        note = Azaglycine
SITE                    8
                        note = 4-amino-1-carbamimidoylPiperidine-2-carboxylic
                         acideridine-4-carboxylic acid
SITE                    9
                        note = Amidated Tryptophan
SEQUENCE: 733
YKNTXGLXW                                                                    9

SEQ ID NO: 734          moltype = AA  length = 9
FEATURE                 Location/Qualifiers
source                  1..9
                        mol_type = protein
                        organism = synthetic construct
SITE                    1
                        note =
                         3-(2-(2-(3-(p-tolyl)propanamido)ethoxy)ethoxy)propanoic
                         acid-D-Tyrosine
SITE                    2
                        note =
                         D-Lysine(1,4,7,10-tetraazacyclododecane-1,4,7,10-tetraaceti
                         c acid)
SITE                    5
                        note = cyclohexylalanine
SITE                    6
                        note = Azaglycine
SITE                    8
                        note = 4-amino-1-carbamimidoylPiperidine-2-carboxylic
                         acideridine-4-carboxylic acid
SITE                    9
                        note = Amidated Tryptophan
SEQUENCE: 734
YKNTXGLXW                                                                    9

SEQ ID NO: 735          moltype = AA  length = 9
FEATURE                 Location/Qualifiers
source                  1..9
                        mol_type = protein
                        organism = synthetic construct
SITE                    1
                        note = octanoic acid-D-Tyrosine
SITE                    2
                        note =
                         D-Lysine(1,4,7,10-tetraazacyclododecane-1,4,7,10-tetraaceti
                         c acid)
SITE                    6
                        note = Azaglycine
SITE                    8
                        note = 4-amino-1-carbamimidoylpiperidine-4-carboxylic
                         acid(Sarcosine)
SITE                    9
                        note = Amidated D-Tryptophan
SEQUENCE: 735
YKNTFGLXW                                                                    9

SEQ ID NO: 736          moltype = AA  length = 9
FEATURE                 Location/Qualifiers
source                  1..9
                        mol_type = protein
                        organism = synthetic construct
SITE                    1
                        note = octanoic acid-D-Tyrosine
SITE                    2
                        note =
                         D-Lysine(1,4,7,10-tetraazacyclododecane-1,4,7,10-tetraaceti
                         c acid)
SITE                    6
                        note = Azaglycine
SITE                    8
                        note = 4-amino-1-carbamimidoylpiperidine-4-carboxylic
                         acid(Sarcosine)
SITE                    9
                        note = Amidated Tryptophan
SEQUENCE: 736
YKNTFGLXW                                                                    9
```

```
SEQ ID NO: 737          moltype = AA  length = 9
FEATURE                 Location/Qualifiers
source                  1..9
                        mol_type = protein
                        organism = synthetic construct
SITE                    1
                        note = octanoic acid-D-Tyrosine
SITE                    2
                        note =
                         D-Lysine(1,4,7,10-tetraazacyclododecane-1,4,7,10-tetraaceti
                         c acid)
SITE                    5
                        note = cyclohexylalanine
SITE                    6
                        note = Azaglycine
SITE                    8
                        note = 4-amino-1-carbamimidoylpiperidine-4-carboxylic
                         acid(Sarcosine)
SITE                    9
                        note = Amidated D-Tryptophan
SEQUENCE: 737
YKNTXGLXW                                                                   9

SEQ ID NO: 738          moltype = AA  length = 9
FEATURE                 Location/Qualifiers
source                  1..9
                        mol_type = protein
                        organism = synthetic construct
SITE                    1
                        note =
                         3-(2-(2-(3-(p-tolyl)propanamido)ethoxy)ethoxy)propanoic
                         acid-D-Tyrosine
SITE                    2
                        note =
                         Lysine(1,4,7,10-tetraazacyclododecane-1,4,7,10-tetraacetic
                         acid)
SITE                    5
                        note = cyclohexylalanine
SITE                    6
                        note = Azaglycine
SITE                    8
                        note = 4-amino-1-carbamimidoylpiperidine-4-carboxylic
                         acid(Sarcosine)
SITE                    9
                        note = Amidated D-Tryptophan
SEQUENCE: 738
YKNTXGLXW                                                                   9

SEQ ID NO: 739          moltype = AA  length = 9
FEATURE                 Location/Qualifiers
source                  1..9
                        mol_type = protein
                        organism = synthetic construct
SITE                    1
                        note =
                         3-(2-(2-(3-(p-tolyl)propanamido)ethoxy)ethoxy)propanoic
                         acid-D-Tyrosine
SITE                    2
                        note =
                         Lysine(1,4,7,10-tetraazacyclododecane-1,4,7,10-tetraacetic
                         acid)
SITE                    5
                        note = cyclohexylalanine
SITE                    6
                        note = Azaglycine
SITE                    8
                        note = 4-amino-1-carbamimidoylpiperidine-4-carboxylic
                         acid(Sarcosine)
SITE                    9
                        note = Amidated Tryptophan
SEQUENCE: 739
YKNTXGLXW                                                                   9

SEQ ID NO: 740          moltype = AA  length = 9
FEATURE                 Location/Qualifiers
source                  1..9
                        mol_type = protein
                        organism = synthetic construct
SITE                    1
```

```
                        note =
                         3-(2-(2-(3-(p-tolyl)propanamido)ethoxy)ethoxy)propanoic
                         acid-D-Tyrosine
SITE                    2
                        note =
                         D-Lysine(1,4,7,10-tetraazacyclododecane-1,4,7,10-tetraaceti
                         c acid)
SITE                    5
                        note = cyclohexylalanine
SITE                    6
                        note = Azaglycine
SITE                    8
                        note = 4-amino-1-carbamimidoylpiperidine-4-carboxylic
                         acid(Sarcosine)
SITE                    9
                        note = Amidated D-Tryptophan
SEQUENCE: 740
YKNTXGLXW                                                         9

SEQ ID NO: 741          moltype = AA  length = 9
FEATURE                 Location/Qualifiers
source                  1..9
                        mol_type = protein
                        organism = synthetic construct
SITE                    1
                        note =
                         1-(3-fluoro-4-methylphenyl)-4-oxo-8,11-dioxa-2,5-diazatetra
                         decan-14-oic acid-D-Tyrosine
SITE                    2
                        note =
                         Lysine(1,4,7,10-tetraazacyclododecane-1,4,7,10-tetraacetic
                         acid)
SITE                    6
                        note = Azaglycine
SITE                    8
                        note = 4-amino-1-carbamimidoylpiperidine-4-carboxylic
                         acid(Sarcosine)
SITE                    9
                        note = Amidated D-Tryptophan
SEQUENCE: 741
YKNTFGLXW                                                         9

SEQ ID NO: 742          moltype = AA  length = 10
FEATURE                 Location/Qualifiers
source                  1..10
                        mol_type = protein
                        organism = synthetic construct
SITE                    1
                        note = (3-fluoro-4-methylbenzyl)glycine
SITE                    2
                        note = D-Tyrosine
SITE                    3
                        note =
                         Lysine(1,4,7,10-tetraazacyclododecane-1,4,7,10-tetraacetic
                         acid)
SITE                    7
                        note = Azaglycine
SITE                    9
                        note = 4-amino-1-carbamimidoylpiperidine-4-carboxylic
                         acid(Sarcosine)
SITE                    10
                        note = Amidated D-Tryptophan
SEQUENCE: 742
GYKNTFGLXW                                                        10

SEQ ID NO: 743          moltype = AA  length = 9
FEATURE                 Location/Qualifiers
source                  1..9
                        mol_type = protein
                        organism = synthetic construct
SITE                    1
                        note =
                         1-(3-fluoro-4-methylphenyl)-4-oxo-8,11-dioxa-2,5-diazatetra
                         decan-14-oic acid-D-Tyrosine
SITE                    2
                        note =
                         D-Lysine(1,4,7,10-tetraazacyclododecane-1,4,7,10-tetraaceti
                         c acid)
SITE                    6
```

-continued

```
                        note = Azaglycine
SITE                    8
                        note = 4-amino-1-carbamimidoylpiperidine-4-carboxylic
                         acid(Sarcosine)
SITE                    9
                        note = Amidated Tryptophan
SEQUENCE: 743
YKNTFGLXW                                                             9

SEQ ID NO: 744          moltype = AA  length = 9
FEATURE                 Location/Qualifiers
source                  1..9
                        mol_type = protein
                        organism = synthetic construct
SITE                    1
                        note = (3-fluoro-4-methylbenzyl)glycine
SITE                    2
                        note = D-Tyrosine
SITE                    2
                        note =
                         D-Lysine(1,4,7,10-tetraazacyclododecane-1,4,7,10-tetraaceti
                         c acid)
SITE                    6
                        note = Azaglycine
SITE                    8
                        note = 4-amino-1-carbamimidoylpiperidine-4-carboxylic
                         acid(Sarcosine)
SITE                    9
                        note = Amidated Tryptophan
SEQUENCE: 744
YKNTFGLXW                                                             9

SEQ ID NO: 745          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = biphenylalanine
SITE                    7
                        note = Azaglycine
SITE                    9
                        note =
                         4-amino-1-((3-fluoro-4-methylbenzyl)glycyl)Piperidine-2-car
                         boxylic acideridine-4-carboxamide
SITE                    10
                        note = Amidated Tryptophan
SEQUENCE: 745
XYXNTFGLXW                                                            10

SEQ ID NO: 746          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = 4-benzoylphenylalanine
SITE                    7
                        note = Azaglycine
SITE                    9
                        note =
                         4-amino-1-((3-fluoro-4-methylbenzyl)glycyl)Piperidine-2-car
                         boxylic acideridine-4-carboxamide
SITE                    10
                        note = Amidated Tryptophan
SEQUENCE: 746
XYXNTFGLXW                                                            10
```

```
SEQ ID NO: 747          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-Gly
SITE                    2
                        note = D-Tyrosine
SITE                    3
                        note = D-3-(2-Naphthyl)alanine
SITE                    7
                        note = Azaglycine
SITE                    9
                        note =
                         4-amino-1-((3-fluoro-4-methylbenzyl)glycyl)Piperidine-2-car
                         boxylic acideridine-4-carboxamide
SITE                    10
                        note = Amidated Tryptophan
SEQUENCE: 747
GYXNTFGLXW                                                        10

SEQ ID NO: 748          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-Tryptophan
SITE                    7
                        note = Azaglycine
SITE                    9
                        note =
                         4-amino-1-((3-fluoro-4-methylbenzyl)glycyl)Piperidine-2-car
                         boxylic acideridine-4-carboxamide
SITE                    10
                        note = Amidated Tyrosine
SEQUENCE: 748
XYWNTFGLXY                                                        10

SEQ ID NO: 749          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-3-(2-Naphthyl)alanine
SITE                    7
                        note = Azaglycine
SITE                    9
                        note =
                         4-amino-1-((3-fluoro-4-methylbenzyl)glycyl)Piperidine-2-car
                         boxylic acideridine-4-carboxamide
SITE                    10
                        note = Amidated Tyrosine
SEQUENCE: 749
XYXNTFGLXY                                                        10

SEQ ID NO: 750          moltype = AA  length = 9
FEATURE                 Location/Qualifiers
source                  1..9
                        mol_type = protein
                        organism = synthetic construct
SITE                    1
```

```
                        note =
                         2,2',2''-(10-(2-((2-(2-(2-carboxyethoxy)ethoxy)ethyl)amino)
                         -2-oxoethyl)-1,4,7,10-tetraazacyclododecane-1,4,7-triyl)tri
                         acetic acid-D-Tyrosine
SITE                    2
                        note = D-3-(4-pyridyl)alanine
SITE                    6
                        note = Azaglycine
SITE                    8
                        note =
                         4-amino-1-((3-fluoro-4-methylbenzyl)glycyl)Piperidine-2-car
                         boxylic acideridine-4-carboxamide
SITE                    9
                        note = Amidated Tryptophan
SEQUENCE: 750
YXNTFGLXW                                                        9

SEQ ID NO: 751          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-3-(2-Naphthyl)alanine
SITE                    7
                        note = Azaglycine
SITE                    9
                        note = 4-amino-1-(((1-methylPiperidine-2-carboxylic
                         acideridin-4-yl)methyl)glycyl)Piperidine-2-carboxylic
                         acideridine-4-carboxylic acid
SITE                    10
                        note = Amidated Tryptophan
SEQUENCE: 751
XYXNTFGLXW                                                       10

SEQ ID NO: 752          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-3-(2-Naphthyl)alanine
SITE                    7
                        note = Azaglycine
SITE                    9
                        note =
                         4-amino-1-((pyridin-4-ylmethyl)glycyl)Piperidine-2-carboxyl
                         ic acideridine-4-carboxylic acid
SITE                    10
                        note = Amidated D-Tryptophan
SEQUENCE: 752
XYXNTFGLXW                                                       10

SEQ ID NO: 753          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-3-(2-Naphthyl)alanine
SITE                    7
```

```
                        note = Azaglycine
SITE                    9
                        note =
                         4-amino-1-((4-iodobenzyl)glycyl)Piperidine-2-carboxylic
                         acideridine-4-carboxylic acid
SITE                    10
                        note = Amidated D-Tryptophan
SEQUENCE: 753
XYXNTFGLXW                                                                  10

SEQ ID NO: 754          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-3-(2-Naphthyl)alanine
SITE                    7
                        note = Azaglycine
SITE                    9
                        note =
                         1-(((1H-pyrrol-2-yl)methyl)glycyl)-4-aminoPiperidine-2-carb
                         oxylic acideridine-4-carboxylic acid
SITE                    10
                        note = Amidated Tryptophan
SEQUENCE: 754
XYXNTFGLXW                                                                  10

SEQ ID NO: 755          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-3-(2-Naphthyl)alanine
SITE                    7
                        note = Azaglycine
SITE                    9
                        note =
                         4-amino-1-((4-iodophenethyl)glycyl)Piperidine-2-carboxylic
                         acideridine-4-carboxylic acid
SITE                    10
                        note = Amidated D-Tryptophan
SEQUENCE: 755
XYXNTFGLXW                                                                  10

SEQ ID NO: 756          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-3-(2-Naphthyl)alanine
SITE                    7
                        note = Azaglycine
SITE                    9
                        note = 4-amino-1-(octylglycyl)Piperidine-2-carboxylic
                         acideridine-4-carboxylic acid
SITE                    10
                        note = Amidated D-Tryptophan
SEQUENCE: 756
```

```
XYXNTFGLXW                                                        10

SEQ ID NO: 757          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-3-(2-Naphthyl)alanine
SITE                    7
                        note = Azaglycine
SITE                    9
                        note =
                         4-amino-1-(((tetrahydro-2H-thiopyran-4-yl)methyl)glycyl)Pip
                         eridine-2-carboxylic acideridine-4-carboxylic acid
SITE                    10
                        note = Amidated D-Tryptophan
SEQUENCE: 757
XYXNTFGLXW                                                        10

SEQ ID NO: 758          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = D-3-(2-Naphthyl)alanine
SITE                    7
                        note = Azaglycine
SITE                    9
                        note =
                         4-amino-1-((naphthalen-2-ylmethyl)glycyl)Piperidine-2-carbo
                         xylic acideridine-4-carboxylic acid
SITE                    10
                        note = Amidated D-Tryptophan
SEQUENCE: 758
XYXNTFGLXW                                                        10

SEQ ID NO: 759          moltype = AA  length = 10
FEATURE                 Location/Qualifiers
source                  1..10
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tyrosine
SITE                    3
                        note = 3-(2-Naphthyl)alanine or
SITE                    7
                        note = Azaglycine
SITE                    9
                        note =
                         4-amino-1-((3-fluoro-4-methylbenzyl)glycyl)Piperidine-2-car
                         boxylic acideridine-4-carboxamide
SITE                    10
                        note = Amidated Tyrosine
SEQUENCE: 759
XYXNTFGLXY                                                        10

SEQ ID NO: 760          moltype = AA  length = 9
FEATURE                 Location/Qualifiers
source                  1..9
                        mol_type = protein
                        organism = synthetic construct
```

```
SITE                    1
                        note = 3-(2-(2-hydroxyethoxy)ethoxy)propanoic
                         acid-D-Tyrosine
SITE                    2
                        note =
                         Lysine(1,4,7,10-tetraazacyclododecane-1,4,7,10-tetraacetic
                         acid)
SITE                    6
                        note = Azaglycine
SITE                    8
                        note =
                         4-amino-1-((3-fluoro-4-methylbenzyl)glycyl)Piperidine-2-car
                         boxylic acideridine-4-carboxamide
SITE                    9
                        note = Amidated Tryptophan
SEQUENCE: 760
YKNTFGLXW                                                                   9

SEQ ID NO: 761          moltype = AA  length = 9
FEATURE                 Location/Qualifiers
source                  1..9
                        mol_type = protein
                        organism = synthetic construct
SITE                    1
                        note = Acetyl-D-Tyrosine
SITE                    2
                        note =
                         Lysine(1,4,7,10-tetraazacyclododecane-1,4,7,10-tetraacetic
                         acid)
SITE                    6
                        note = Azaglycine
SITE                    8
                        note =
                         4-amino-1-((3-fluoro-4-methylbenzyl)glycyl)Piperidine-2-car
                         boxylic acideridine-4-carboxamide
SITE                    9
                        note = Amidated Tryptophan
SEQUENCE: 761
YKNTFGLXW                                                                   9

SEQ ID NO: 762          moltype = AA  length = 9
FEATURE                 Location/Qualifiers
source                  1..9
                        mol_type = protein
                        organism = synthetic construct
SITE                    1
                        note = octanoic acid-D-Tyrosine
SITE                    2
                        note =
                         Lysine(1,4,7,10-tetraazacyclododecane-1,4,7,10-tetraacetic
                         acid)
SITE                    6
                        note = Azaglycine
SITE                    8
                        note =
                         4-amino-1-((3-fluoro-4-methylbenzyl)glycyl)Piperidine-2-car
                         boxylic acideridine-4-carboxamide
SITE                    9
                        note = Amidated Tryptophan
SEQUENCE: 762
YKNTFGLXW                                                                   9

SEQ ID NO: 763          moltype = AA  length = 9
FEATURE                 Location/Qualifiers
source                  1..9
                        mol_type = protein
                        organism = synthetic construct
SITE                    1
                        note =
                         2,2',2''-(10-(2-((2-(2-(2-carboxyethoxy)ethoxy)ethyl)amino)
                         -2-oxoethyl)-1,4,7,10-tetraazacyclododecane-1,4,7-triyl)tri
                         acetic acid-D-Tyrosine
SITE                    2
                        note = D-Tryptophan
SITE                    6
                        note = Azaglycine
SITE                    8
                        note =
                         4-amino-1-((3-fluoro-4-methylbenzyl)glycyl)Piperidine-2-car
```

```
                        boxylic acideridine-4-carboxamide
SITE                   9
                       note = Amidated Tryptophan
SEQUENCE: 763
YWNTFGLXW                                                          9

SEQ ID NO: 764         moltype = AA  length = 10
FEATURE                Location/Qualifiers
source                 1..10
                       mol_type = protein
                       organism = synthetic construct
SITE                   1
                       note =
                        2,2',2'',2'''-(1,4,7,10-tetraazacyclododecane-1,4,7,10-tetr
                        ayl)tetraacetic acid 6-aminohexanoic acid
SITE                   2
                       note = D-Tyrosine
SITE                   3
                       note = D-Tryptophan
SITE                   7
                       note = Azaglycine
SITE                   9
                       note =
                        4-amino-1-((3-fluoro-4-methylbenzyl)glycyl)Piperidine-2-car
                        boxylic acideridine-4-carboxamide
SITE                   10
                       note = Amidated D-Tryptophan
SEQUENCE: 764
XYWNTFGLXW                                                         10

SEQ ID NO: 765         moltype = AA  length = 9
FEATURE                Location/Qualifiers
source                 1..9
                       mol_type = protein
                       organism = synthetic construct
SITE                   1
                       note =
                        1-(3-fluoro-4-methylphenyl)-4-oxo-8,11-dioxa-2,5-diazatetra
                        decan-14-oic acid-D-Tyrosine
SITE                   2
                       note =
                        Lysine(1,4,7,10-tetraazacyclododecane-1,4,7,10-tetraacetic
                        acid)
SITE                   6
                       note = Azaglycine
SITE                   8
                       note = 4-amino-1-carbamimidoylpiperidine-4-carboxylic
                        acid(Sarcosine)
SITE                   9
                       note = Amidated Tryptophan
SEQUENCE: 765
YKNTFGLXW                                                          9

SEQ ID NO: 766         moltype = AA  length = 10
FEATURE                Location/Qualifiers
source                 1..10
                       mol_type = protein
                       organism = synthetic construct
SITE                   1
                       note =
                        2,2',2'',2'''-(1,4,7,10-tetraazacyclododecane-1,4,7,10-tetr
                        ayl)tetraacetic acid 6-aminohexanoic acid
SITE                   2
                       note = D-Tyrosine
SITE                   3
                       note = D-3-(2-Naphthyl)alanine
SITE                   7
                       note = Azaglycine
SITE                   9
                       note = 4-amino-1-(octylglycyl)Piperidine-2-carboxylic
                        acideridine-4-carboxylic acid
SITE                   10
                       note = Amidated Tryptophan
SEQUENCE: 766
XYXNTFGLXW                                                         10

SEQ ID NO: 767         moltype = AA  length = 9
FEATURE                Location/Qualifiers
source                 1..9
```

-continued

```
                         mol_type = protein
                         organism = synthetic construct
SITE                     1
                         note = (3-fluoro-4-methylbenzyl)glycine
SITE                     2
                         note = D-Tyrosine
SITE                     3
                         note =
                          Lysine(1,4,7,10-tetraazacyclododecane-1,4,7,10-tetraacetic
                          acid)
SITE                     6
                         note = Azaglycine
SITE                     8
                         note = 4-amino-1-carbamimidoylpiperidine-4-carboxylic
                          acid(Sarcosine)
SITE                     9
                         note = Amidated Tryptophan
SEQUENCE: 767
YKNTFGLXW                                                                    9

SEQ ID NO: 768           moltype = AA  length = 9
FEATURE                  Location/Qualifiers
source                   1..9
                         mol_type = protein
                         organism = synthetic construct
SITE                     1
                         note =
                          3-(2-(2-(3-(p-tolyl)propanamido)ethoxy)ethoxy)propanoic
                          acid-D-Tyrosine
SITE                     2
                         note =
                          Lysine(1,4,7,10-tetraazacyclododecane-1,4,7,10-tetraacetic
                          acid)
SITE                     5
                         note = cyclohexylalanine
SITE                     6
                         note = Azaglycine
SITE                     8
                         note = 4-amino-1-carbamimidoylpiperidine-4-carboxylic
                          acid(Sarcosine)
SITE                     9
                         note = Amidated Tryptophan
SEQUENCE: 768
YKNTXGLXW                                                                    9

SEQ ID NO: 769           moltype = AA  length = 9
FEATURE                  Location/Qualifiers
source                   1..9
                         mol_type = protein
                         organism = synthetic construct
SITE                     1
                         note =
                          3-(2-(2-(3-(p-tolyl)propanamido)ethoxy)ethoxy)propanoic
                          acid-D-Tyrosine
SITE                     2
                         note =
                          D-Lysine(1,4,7,10-tetraazacyclododecane-1,4,7,10-tetraaceti
                          c acid)
SITE                     5
                         note = cyclohexylalanine
SITE                     6
                         note = Azaglycine
SITE                     8
                         note = 4-amino-1-carbamimidoylpiperidine-4-carboxylic
                          acid(Sarcosine)
SITE                     9
                         note = Amidated Tryptophan
SEQUENCE: 769
YKNTXGLXW                                                                    9

SEQ ID NO: 770           moltype = AA  length = 10
FEATURE                  Location/Qualifiers
source                   1..10
                         mol_type = protein
                         organism = synthetic construct
SITE                     1
                         note =
                          2,2',2'',2'''-(1,4,7,10-tetraazacyclododecane-1,4,7,10-tetr
                          ayl)tetraacetic acid 6-aminohexanoic acid
```

```
SITE                    2
                        note = D-Tyrosine
SITE                    3
                        note = biphenylalanine
SITE                    7
                        note = Azaglycine
SITE                    9
                        note = 4-amino-1-carbamimidoylpiperidine-4-carboxylic
                         acid(Sarcosine)
SITE                    10
                        note = Amidated D-Tryptophan
SEQUENCE: 770
XYXNTFGLXW                                                                  10

SEQ ID NO: 771          moltype = AA  length = 6
FEATURE                 Location/Qualifiers
source                  1..6
                        mol_type = protein
                        organism = synthetic construct
SITE                    1
                        note = indium(III)
                         2,2',2''-(10-(2-((5-carboxypentyl)amino)-2-oxoethyl)-1,4,7,
                         10-tetraazacyclododecane-1,4,7-triyl)triacetate
SITE                    3
                        note = Azaglycine
SITE                    5
                        note =
                         4-amino-1-((3-fluoro-4-methylbenzyl)glycyl)Piperidine-2-car
                         boxylic acideridine-4-carboxamide
SITE                    6
                        note = Amidated Tryptophan
SEQUENCE: 771
XFGLXW                                                                      6

SEQ ID NO: 772          moltype = AA  length = 10
FEATURE                 Location/Qualifiers
source                  1..10
                        mol_type = protein
                        organism = synthetic construct
SITE                    1
                        note = indium(III)
                         2,2',2''-(10-(2-((5-carboxypentyl)amino)-2-oxoethyl)-1,4,7,
                         10-tetraazacyclododecane-1,4,7-triyl)triacetate
SITE                    2
                        note = D-Tyrosine
SITE                    3
                        note = D-Tryptophan
SITE                    7
                        note = Azaglycine
SITE                    9
                        note = 4-amino-1-carbamimidoylPiperidine-2-carboxylic
                         acideridine-4-carboxylic acid
SITE                    10
                        note = Amidated Tryptophan
SEQUENCE: 772
XYWNTFGLXW                                                                  10

SEQ ID NO: 773          moltype =   length =
SEQUENCE: 773
000

SEQ ID NO: 774          moltype = AA  length = 5
FEATURE                 Location/Qualifiers
source                  1..5
                        mol_type = protein
                        organism = synthetic construct
SITE                    1
                        note = 3-Fluorophenylalanine
SITE                    2
                        note = Azaglycine
SITE                    4
                        note = 4-amino-1-R1-Piperidine-2-carboxylic
                         acideridine-4-carboxylic acid
SITE                    5
                        note = Amidated 4-cyano phenylalanine
SEQUENCE: 774
FGLXF                                                                       5

SEQ ID NO: 775          moltype = AA  length = 5
```

-continued

```
FEATURE                 Location/Qualifiers
source                  1..5
                        mol_type = protein
                        organism = synthetic construct
SITE                    1
                        note = 3-Fluorophenylalanine
SITE                    2
                        note = Azaglycine
SITE                    4
                        note = 4-amino-1-R1-Piperidine-2-carboxylic
                         acideridine-4-carboxylic acid
SITE                    5
                        note = Amidated Tryptophan
SEQUENCE: 775
FGLXW                                                                    5

SEQ ID NO: 776          moltype =   length =
SEQUENCE: 776
000

SEQ ID NO: 777          moltype =   length =
SEQUENCE: 777
000

SEQ ID NO: 778          moltype =   length =
SEQUENCE: 778
000

SEQ ID NO: 779          moltype =   length =
SEQUENCE: 779
000

SEQ ID NO: 780          moltype =   length =
SEQUENCE: 780
000

SEQ ID NO: 781          moltype =   length =
SEQUENCE: 781
000

SEQ ID NO: 782          moltype =   length =
SEQUENCE: 782
000

SEQ ID NO: 783          moltype =   length =
SEQUENCE: 783
000

SEQ ID NO: 784          moltype =   length =
SEQUENCE: 784
000

SEQ ID NO: 785          moltype =   length =
SEQUENCE: 785
000

SEQ ID NO: 786          moltype = AA  length = 5
FEATURE                 Location/Qualifiers
source                  1..5
                        mol_type = protein
                        organism = synthetic construct
SITE                    2
                        note = Azaglycine
SITE                    4
                        note = 4-amino-1-R1-Piperidine-2-carboxylic
                         acideridine-4-carboxylic acid
SITE                    5
                        note = Amidated Leucine
SEQUENCE: 786
FGLXL                                                                    5

SEQ ID NO: 787          moltype =   length =
SEQUENCE: 787
000

SEQ ID NO: 788          moltype =   length =
SEQUENCE: 788
000
```

```
SEQ ID NO: 789          moltype =   length =
SEQUENCE: 789
000

SEQ ID NO: 790          moltype = AA  length = 5
FEATURE                 Location/Qualifiers
source                  1..5
                        mol_type = protein
                        organism = synthetic construct
SITE                    1
                        note = AzaPhe
SITE                    2
                        note = Azaglycine
SITE                    4
                        note =
                         4-amino-1-((3-fluoro-4-methylbenzyl)glycyl)Piperidine-2-car
                         boxylic acideridine-4-carboxamide
SITE                    5
                        note = Amidated Tyrosine
SEQUENCE: 790
FGLXY                                                                       5

SEQ ID NO: 791          moltype =   length =
SEQUENCE: 791
000

SEQ ID NO: 792          moltype = AA  length = 5
FEATURE                 Location/Qualifiers
source                  1..5
                        mol_type = protein
                        organism = synthetic construct
SITE                    1
                        note = beta-(2-thienyl)-Ala
SITE                    2
                        note = Azaglycine
SITE                    4
                        note = 4-amino-1-R1-Piperidine-2-carboxylic
                         acideridine-4-carboxylic acid
SITE                    5
                        note = Amidated Tryptophan
SEQUENCE: 792
AGLXW                                                                       5

SEQ ID NO: 793          moltype = AA  length = 5
FEATURE                 Location/Qualifiers
source                  1..5
                        mol_type = protein
                        organism = synthetic construct
SITE                    2
                        note = Azaglycine
SITE                    4
                        note = 4-amino-1-R1-Piperidine-2-carboxylic
                         acideridine-4-carboxylic acid
SITE                    5
                        note = Trp(3-NO2)-OH-NH2
SEQUENCE: 793
AGLXW                                                                       5

SEQ ID NO: 794          moltype =   length =
SEQUENCE: 794
000

SEQ ID NO: 795          moltype =   length =
SEQUENCE: 795
000

SEQ ID NO: 796          moltype = AA  length = 7
FEATURE                 Location/Qualifiers
source                  1..7
                        mol_type = protein
                        organism = synthetic construct
SITE                    1
                        note = 4-(aminomethyl)benzoic acid
SITE                    4
                        note = 4-(aminomethyl)benzoic acid
SITE                    7
                        note = N6-(5-carboxypentanoyl)-L-lysine
SEQUENCE: 796
XMVXMVX                                                                     7
```

```
SEQ ID NO: 797          moltype = AA  length = 6
FEATURE                 Location/Qualifiers
source                  1..6
                        mol_type = protein
                        organism = synthetic construct
SITE                    1
                        note = 6-(DOTA-amino)hexanoic acid
SITE                    2
                        note = Sarcosine
SITE                    3
                        note = Sarcosine
SITE                    4
                        note = Sarcosine
SITE                    5
                        note = Sarcosine
SITE                    6
                        note = Sarcosine
SEQUENCE: 797
XGGGGG                                                      6

SEQ ID NO: 798          moltype = AA  length = 6
FEATURE                 Location/Qualifiers
source                  1..6
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = Sarcosine
SITE                    3
                        note = Sarcosine
SITE                    4
                        note = Sarcosine
SITE                    5
                        note = Sarcosine
SEQUENCE: 798
XGGGGG                                                      6

SEQ ID NO: 799          moltype = AA  length = 7
FEATURE                 Location/Qualifiers
source                  1..7
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid coupled to N-term of
                         4-(aminomethyl)benzoic acid (4-(aminomethyl)benzoic acid)
SITE                    4
                        note = 4-(aminomethyl)benzoic acid
SITE                    7
                        note = N6-(5-carboxypentanoyl)-L-lysine
SEQUENCE: 799
XMVXMVX                                                     7

SEQ ID NO: 800          moltype = AA  length = 8
FEATURE                 Location/Qualifiers
source                  1..8
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    5
                        note = Azaglycine
SITE                    7
                        note = 1-amino-4-guanidinocyclohexane-1-carboxylic acid
SITE                    8
                        note = Amidated Tryptophan
SEQUENCE: 800
XNTFGLXW                                                    8

SEQ ID NO: 801          moltype = AA  length = 10
FEATURE                 Location/Qualifiers
source                  1..10
```

```
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid 6-aminohexanoic acid
SITE                    2
                        note = D-Tryptophan
SITE                    6
                        note = Azaglycine
SITE                    8
                        note = 1-amino-4-guanidinocyclohexane-1-carboxylic acid
SITE                    9
                        note = Amidated Tryptophan
SEQUENCE: 801
XYWNTFGLXW                                                                   10

SEQ ID NO: 802          moltype = AA  length = 9
FEATURE                 Location/Qualifiers
source                  1..9
                        mol_type = protein
                        organism = synthetic construct
SITE                    1
                        note = Acetyl-D-Tyrosine
SITE                    2
                        note = D-Tryptophan
SITE                    6
                        note = Azaglycine
SITE                    8
                        note =
                         4-amino-1-((3-fluoro-4-methylbenzyl)glycyl)Piperidine-2-car
                         boxylic acideridine-4-carboxamide
SITE                    9
                        note = Amidated Tryptophan
SEQUENCE: 802
YWNTFGLXW                                                                    9

SEQ ID NO: 803          moltype = AA  length = 9
FEATURE                 Location/Qualifiers
source                  1..9
                        mol_type = protein
                        organism = synthetic construct
SITE                    1
                        note = Acetyl-D-Tyrosine
SITE                    2
                        note = D-Tryptophan
SITE                    5
                        note = cyclohexylalanine
SITE                    6
                        note = Azaglycine
SITE                    8
                        note =
                         4-amino-1-((3-fluoro-4-methylbenzyl)glycyl)Piperidine-2-car
                         boxylic acideridine-4-carboxamide
SITE                    9
                        note = Amidated Tryptophan
SEQUENCE: 803
YWNTXGLXW                                                                    9

SEQ ID NO: 804          moltype = AA  length = 5
FEATURE                 Location/Qualifiers
source                  1..5
                        mol_type = protein
                        organism = synthetic construct
SITE                    1
                        note = Acetyl-Phe
SITE                    2
                        note = Azaglycine
SITE                    4
                        note =
                         4-amino-1-((3-fluoro-4-methylbenzyl)glycyl)Piperidine-2-car
                         boxylic acideridine-4-carboxamide
SITE                    5
                        note = Amidated Tryptophan
SEQUENCE: 804
FGLXW                                                                        5

SEQ ID NO: 805          moltype = AA  length = 9
FEATURE                 Location/Qualifiers
```

```
source                  1..9
                        mol_type = protein
                        organism = synthetic construct
SITE                    1
                        note = Acetyl-D-Tyrosine
SITE                    2
                        note = D-3-(2-naphthyl)-alanine
SITE                    6
                        note = Azaglycine
SITE                    8
                        note = 4-amino-1-carbamimidoylpiperidine-4-carboxylic
                         acid(Sarcosine)
SITE                    9
                        note = Amidated Tryptophan
SEQUENCE: 805
YXNTFGLXW                                                                    9

SEQ ID NO: 806          moltype = AA  length = 9
FEATURE                 Location/Qualifiers
source                  1..9
                        mol_type = protein
                        organism = synthetic construct
SITE                    1
                        note =
                         3-(2-(2-(3-(4-iodophenyl)propanamido)ethoxy)ethoxy)propanoi
                         c acid coupled to N-term of D-Tyrosine
SITE                    2
                        note = D-3-(2-naphthyl)-alanine
SITE                    6
                        note = Azaglycine
SITE                    8
                        note = 4-amino-1-carbamimidoylPiperidine-2-carboxylic
                         acideridine-4-carboxylic acid
SITE                    9
                        note = Amidated Tryptophan
SEQUENCE: 806
YXNTFGLXW                                                                    9

SEQ ID NO: 807          moltype = AA  length = 9
FEATURE                 Location/Qualifiers
source                  1..9
                        mol_type = protein
                        organism = synthetic construct
SITE                    1
                        note = 4-(4-iodophenyl)butanoic acid coupled to N-term of
                         D-Tyrosine
SITE                    2
                        note = D-3-(2-naphthyl)-alanine
SITE                    6
                        note = Azaglycine
SITE                    8
                        note = 4-amino-1-carbamimidoylpiperidine-4-carboxylic
                         acid(Sarcosine)
SITE                    9
                        note = Amidated Tryptophan
SEQUENCE: 807
YXNTFGLXW                                                                    9

SEQ ID NO: 808          moltype = AA  length = 9
FEATURE                 Location/Qualifiers
source                  1..9
                        mol_type = protein
                        organism = synthetic construct
SITE                    1
                        note =
                         3-(2-(2-(3-(4-iodophenyl)propanamido)ethoxy)ethoxy)propanoi
                         c acid coupled to N-term of D-Tyrosine
SITE                    2
                        note = D-3-(2-naphthyl)-alanine
SITE                    6
                        note = Azaglycine
SITE                    8
                        note = 4-amino-1-carbamimidoylpiperidine-4-carboxylic
                         acid(Sarcosine)
SITE                    9
                        note = Amidated Tryptophan
SEQUENCE: 808
YXNTFGLXF                                                                    9
```

```
SEQ ID NO: 809          moltype = AA  length = 9
FEATURE                 Location/Qualifiers
source                  1..9
                        mol_type = protein
                        organism = synthetic construct
SITE                    1
                        note =
                         3-(2-(2-(3-(4-iodophenyl)propanamido)ethoxy)ethoxy)propanoi
                         c acid coupled to N-term of D-Tyrosine
SITE                    2
                        note = D-3-(2-naphthyl)-alanine
SITE                    6
                        note = Azaglycine
SITE                    8
                        note = 4-amino-1-carbamimidoylPiperidine-2-carboxylic
                         acideridine-4-carboxylic acid
SITE                    9
                        note = Amidated Phenylalanine
SEQUENCE: 809
YXNTFGLXY                                                                    9

SEQ ID NO: 810          moltype = AA  length = 9
FEATURE                 Location/Qualifiers
source                  1..9
                        mol_type = protein
                        organism = synthetic construct
SITE                    1
                        note = 4-(4-iodophenyl)butanoic acid coupled to N-term of
                         D-Tyrosine
SITE                    2
                        note = D-3-(2-naphthyl)-alanine
SITE                    6
                        note = Azaglycine
SITE                    8
                        note = 4-amino-1-carbamimidoylpiperidine-4-carboxylic
                         acid(Sarcosine)
SITE                    9
                        note = Amidated Phenylalanine
SEQUENCE: 810
YXNTFGLXF                                                                    9

SEQ ID NO: 811          moltype = AA  length = 9
FEATURE                 Location/Qualifiers
source                  1..9
                        mol_type = protein
                        organism = synthetic construct
SITE                    1
                        note = 4-(4-iodophenyl)butanoic acid coupled to N-term of
                         D-Tyrosine
SITE                    2
                        note = D-3-(2-naphthyl)-alanine
SITE                    6
                        note = Azaglycine
SITE                    8
                        note = 4-amino-1-carbamimidoylpiperidine-4-carboxylic
                         acid(Sarcosine)
SITE                    9
                        note = Amidated Tyrosine
SEQUENCE: 811
YXNTFGLXY                                                                    9

SEQ ID NO: 812          moltype = AA  length = 9
FEATURE                 Location/Qualifiers
source                  1..9
                        mol_type = protein
                        organism = synthetic construct
SITE                    1
                        note = dodecanoic acid coupled to N-term of D-Tyrosine
SITE                    2
                        note = D-3-(2-naphthyl)-alanine
SITE                    6
                        note = Azaglycine
SITE                    8
                        note = 4-amino-1-carbamimidoylpiperidine-4-carboxylic
                         acid(Sarcosine)
SITE                    9
                        note = Amidated Tyrosine
SEQUENCE: 812
YXNTFGLXW                                                                    9
```

```
SEQ ID NO: 813          moltype = AA  length = 9
FEATURE                 Location/Qualifiers
source                  1..9
                        mol_type = protein
                        organism = synthetic construct
SITE                    1
                        note = dodecanoic acid coupled to N-term of D-Tyrosine
SITE                    2
                        note = D-3-(2-naphthyl)-alanine
SITE                    6
                        note = Azaglycine
SITE                    8
                        note = 4-amino-1-carbamimidoylpiperidine-4-carboxylic
                         acid(Sarcosine)
SITE                    9
                        note = Amidated Tyrosine
SEQUENCE: 813
YXNTFGLXY                                                                  9

SEQ ID NO: 814          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-Tryptophan
SITE                    6
                        note = Azaglycine
SITE                    8
                        note =
                         4-amino-1-((3-fluoro-4-methylbenzyl)glycyl)Piperidine-2-car
                         boxylic acideridine-4-carboxamide
SITE                    9
                        note = Amidated Tryptophan
SEQUENCE: 814
YWNTFGLXW                                                                  9

SEQ ID NO: 815          moltype = AA  length = 9
FEATURE                 Location/Qualifiers
source                  1..9
                        mol_type = protein
                        organism = synthetic construct
SITE                    1
                        note = 4-(p-tolyl)butanoic acid coupled to N-term of
                         D-Tyrosine
SITE                    2
                        note = D-Tryptophan
SITE                    6
                        note = Azaglycine
SITE                    8
                        note =
                         4-amino-1-((3-fluoro-4-methylbenzyl)glycyl)Piperidine-2-car
                         boxylic acideridine-4-carboxamide
SITE                    9
                        note = Amidated Tryptophan
SEQUENCE: 815
YWNTFGLXW                                                                  9

SEQ ID NO: 816          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-Tryptophan
SITE                    5
                        note = cyclohexylalanine
SITE                    6
                        note = Azaglycine
SITE                    8
                        note =
                         4-amino-1-((3-fluoro-4-methylbenzyl)glycyl)Piperidine-2-car
                         boxylic acideridine-4-carboxamide
SITE                    9
```

```
                        note = Amidated Tryptophan
SEQUENCE: 816
YWNTXGLXW                                                       9

SEQ ID NO: 817          moltype = AA  length = 9
FEATURE                 Location/Qualifiers
source                  1..9
                        mol_type = protein
                        organism = synthetic construct
SITE                    1
                        note = Octanoic acid coupled to N-term of D-Tyrosine
SITE                    2
                        note = D-Tryptophan
SITE                    5
                        note = cyclohexylalanine
SITE                    6
                        note = Azaglycine
SITE                    8
                        note =
                         4-amino-1-((3-fluoro-4-methylbenzyl)glycyl)Piperidine-2-car
                         boxylic acideridine-4-carboxamide
SITE                    9
                        note = Amidated Tryptophan
SEQUENCE: 817
YWNTXGLXW                                                       9

SEQ ID NO: 818          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-3-(2-naphthyl)-alanine
SITE                    6
                        note = Azaglycine
SITE                    8
                        note = 4-amino-1-carbamimidoylpiperidine-4-carboxylic
                         acid(Sarcosine)
SITE                    9
                        note = Amidated Phenylalanine
SEQUENCE: 818
YXNTFGLXF                                                       9

SEQ ID NO: 819          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-3-(2-naphthyl)-alanine
SITE                    6
                        note = Azaglycine
SITE                    8
                        note = 4-amino-1-carbamimidoylpiperidine-4-carboxylic
                         acid(Sarcosine)
SITE                    9
                        note = Amidated Tyrosine
SEQUENCE: 819
YXNTFGLXY                                                       9

SEQ ID NO: 820          moltype = AA  length = 9
FEATURE                 Location/Qualifiers
source                  1..9
                        mol_type = protein
                        organism = synthetic construct
SITE                    1
                        note = D-Tyrosine
SITE                    2
                        note = D-3-(2-naphthyl)-alanine
SITE                    6
                        note = Azaglycine
SITE                    8
                        note = 4-amino-1-carbamimidoylpiperidine-4-carboxylic
                         acid(Sarcosine)
SITE                    9
```

```
                         note = Amidated Tryptophan
SEQUENCE: 820
YXNTFGLXW                                                                   9

SEQ ID NO: 821           moltype = AA  length = 9
FEATURE                  Location/Qualifiers
source                   1..9
                         mol_type = protein
                         organism = synthetic construct
SITE                     1
                         note = D-Tyrosine
SITE                     2
                         note = D-3-(2-naphthyl)-alanine
SITE                     6
                         note = Azaglycine
SITE                     8
                         note = 4-amino-1-carbamimidoylPiperidine-2-carboxylic
                          acideridine-4-carboxylic acid
SITE                     9
                         note = Amidated Phenylalanine
SEQUENCE: 821
YXNTFGLXF                                                                   9

SEQ ID NO: 822           moltype = AA  length = 9
FEATURE                  Location/Qualifiers
source                   1..9
                         mol_type = protein
                         organism = synthetic construct
SITE                     1
                         note = 3-(2-(2-aminoethoxy)ethoxy)propanoic acid coupled to
                          N-term of D-Tyrosine
SITE                     2
                         note = D-3-(2-naphthyl)-alanine
SITE                     6
                         note = Azaglycine
SITE                     8
                         note = 4-amino-1-carbamimidoylPiperidine-2-carboxylic
                          acideridine-4-carboxylic acid
SITE                     9
                         note = Amidated Tryptophan
SEQUENCE: 822
YXNTFGLXW                                                                   9

SEQ ID NO: 823           moltype = AA  length = 9
FEATURE                  Location/Qualifiers
source                   1..9
                         mol_type = protein
                         organism = synthetic construct
SITE                     1
                         note = D-Tyrosine
SITE                     2
                         note = D-3-(2-naphthyl)-alanine
SITE                     6
                         note = Azaglycine
SITE                     8
                         note = 4-amino-1-carbamimidoylPiperidine-2-carboxylic
                          acideridine-4-carboxylic acid
SITE                     9
                         note = Amidated Tryptophan
SEQUENCE: 823
YXNTFGLXW                                                                   9

SEQ ID NO: 824           moltype = AA  length = 9
FEATURE                  Location/Qualifiers
source                   1..9
                         mol_type = protein
                         organism = synthetic construct
SITE                     1
                         note =
                          (R)-3-(4-(tert-butoxy)phenyl)-2-(6-(2-(4,7,10-tris(2-(tert-
                          butoxy)-2-oxoethyl)-1,4,7,10-tetraazacyclododecan-1-yl)acet
                          amido)hexanamido)propanoic acid
SITE                     2
                         note = 1-(tert-butoxycarbonyl)-D-tryptophan
SITE                     3
                         note = N4-trityl-L-asparagine
SITE                     4
                         note = O-(tert-butyl)-L-threonine
SITE                     6
```

```
                        note = Azaglycine
SITE                    8
                        note =
                         4-amino-1-(N-(tert-butoxycarbonyl)-N-(3-fluoro-4-methylbenz
                         yl)glycyl)Piperidine-2-carboxylic acideridine-4-carboxylic
                         acid
SITE                    9
                        note = 1-(tert-butoxycarbonyl)-L-tryptophan
SEQUENCE: 824
XWDTFGLXW                                                            9

SEQ ID NO: 825          moltype = AA  length = 9
FEATURE                 Location/Qualifiers
source                  1..9
                        mol_type = protein
                        organism = synthetic construct
SITE                    1
                        note = (R)-3-(4-(tert-butoxy)phenyl)-2-octanamidopropanoic
                         acid
SITE                    2
                        note =
                         N6-(1-(4,4-dimethyl-2,6-dioxocyclohexylidene)ethyl)-L-lysin
                         e
SITE                    3
                        note = N4-trityl-L-asparagine
SITE                    4
                        note = O-(tert-butyl)-L-threonine
SITE                    6
                        note = Azaglycine
SITE                    3
                        note = N4-trityl-L-asparagine
SITE                    4
                        note = O-(tert-butyl)-L-threonine
SITE                    8
                        note =
                         4-amino-1-(tert-butoxycarbonyl)Piperidine-2-carboxylic
                         acideridine-4-carboxylic acid
SITE                    9
                        note = (S)-2-amino-3-(4-(tert-butoxy)phenyl)propanoic acid
SEQUENCE: 825
XKDTFGLXX                                                            9

SEQ ID NO: 826          moltype = AA  length = 9
FEATURE                 Location/Qualifiers
source                  1..9
                        mol_type = protein
                        organism = synthetic construct
SITE                    1
                        note = (R)-3-(4-(tert-butoxy)phenyl)-2-octanamidopropanoic
                         acid
SITE                    2
                        note =
                         (S)-2,2',2''-(10-(2-((5-amino-5-carboxypentyl)amino)-2-oxoe
                         thyl)-1,4,7,10-tetraazacyclododecane-1,4,7-triyl)triacetic
                         acid
SITE                    3
                        note = N4-trityl-L-asparagine
SITE                    4
                        note = O-(tert-butyl)-L-threonine
SITE                    6
                        note = Azaglycine
SITE                    8
                        note =
                         4-amino-1-(tert-butoxycarbonyl)Piperidine-2-carboxylic
                         acideridine-4-carboxylic acid
SITE                    9
                        note = (S)-2-amino-3-(4-(tert-butoxy)phenyl)propanoic acid
SEQUENCE: 826
XXDTFGLXX                                                            9

SEQ ID NO: 827          moltype = AA  length = 9
FEATURE                 Location/Qualifiers
source                  1..9
                        mol_type = protein
                        organism = synthetic construct
SITE                    1
                        note = D-Tyrosine
SITE                    2
                        note =
```

```
                        (S)-2,2',2''-(10-(2-((5-amino-5-carboxypentyl)amino)-2-oxoe
                        thyl)-1,4,7,10-tetraazacyclododecane-1,4,7-triyl)triacetic
                        acid
SITE                    6
                        note = Azaglycine
SITE                    8
                        note = 4-aminoPiperidine-2-carboxylic
                        acideridine-4-carboxylic acid
SITE                    9
                        note = Amidated Tyrosine
SEQUENCE: 827
YXNTFGLXY                                                    9

SEQ ID NO: 828          moltype = AA  length = 10
FEATURE                 Location/Qualifiers
source                  1..10
                        mol_type = protein
                        organism = synthetic construct
SEQUENCE: 828
YNWNSFGLRF                                                   10

SEQ ID NO: 829          moltype = AA  length = 4
FEATURE                 Location/Qualifiers
source                  1..4
                        mol_type = protein
                        organism = synthetic construct
SITE                    2
                        note = D-Lysine
SEQUENCE: 829
YKNT                                                         4

SEQ ID NO: 830          moltype = AA  length = 4
FEATURE                 Location/Qualifiers
source                  1..4
                        mol_type = protein
                        organism = synthetic construct
SITE                    1
                        note = D-Tyrosine
SITE                    2
                        note = D-Lysine
SEQUENCE: 830
YKNT                                                         4

SEQ ID NO: 831          moltype = AA  length = 6
FEATURE                 Location/Qualifiers
source                  1..6
                        mol_type = protein
                        organism = synthetic construct
SITE                    1
                        note = Sarcosine
SITE                    2
                        note = Sarcosine
SITE                    3
                        note = Sarcosine
SITE                    4
                        note = Sarcosine
SITE                    5
                        note = Sarcosine
SITE                    6
                        note = Sarcosine
SEQUENCE: 831
GGGGGG                                                       6

SEQ ID NO: 832          moltype = AA  length = 4
FEATURE                 Location/Qualifiers
source                  1..4
                        mol_type = protein
                        organism = synthetic construct
SEQUENCE: 832
GFGG                                                         4

SEQ ID NO: 833          moltype = AA  length = 6
FEATURE                 Location/Qualifiers
source                  1..6
                        mol_type = protein
                        organism = synthetic construct
VARIANT                 2..6
                        note = Residues may be deleted
SEQUENCE: 833
```

```
GGGGGG                                                      6

SEQ ID NO: 834          moltype = AA  length = 6
FEATURE                 Location/Qualifiers
source                  1..6
                        mol_type = protein
                        organism = synthetic construct
SITE                    1..6
                        note = beta-Alanine
VARIANT                 2..6
                        note = Residues may be deleted
SEQUENCE: 834
AAAAAA                                                      6

SEQ ID NO: 835          moltype = AA  length = 6
FEATURE                 Location/Qualifiers
source                  1..6
                        mol_type = protein
                        organism = synthetic construct
VARIANT                 2..6
                        note = Residues may be deleted
SEQUENCE: 835
AAAAAA                                                      6

SEQ ID NO: 836          moltype = AA  length = 6
FEATURE                 Location/Qualifiers
source                  1..6
                        mol_type = protein
                        organism = synthetic construct
VARIANT                 2..6
                        note = Residues may be deleted
SEQUENCE: 836
EEEEEE                                                      6

SEQ ID NO: 837          moltype = AA  length = 6
FEATURE                 Location/Qualifiers
source                  1..6
                        mol_type = protein
                        organism = synthetic construct
SITE                    1..6
                        note = Sarcosine
VARIANT                 2..6
                        note = Residues may be deleted
SEQUENCE: 837
GGGGGG                                                      6

SEQ ID NO: 838          moltype = AA  length = 6
FEATURE                 Location/Qualifiers
source                  1..6
                        mol_type = protein
                        organism = synthetic construct
VARIANT                 2..6
                        note = Residues may be deleted
SEQUENCE: 838
NNNNNN                                                      6

SEQ ID NO: 839          moltype = AA  length = 7
FEATURE                 Location/Qualifiers
source                  1..7
                        mol_type = protein
                        organism = synthetic construct
SITE                    1
                        note = beta-Alanine
VARIANT                 2..7
                        note = Residues may be deleted
SEQUENCE: 839
AGGGGGG                                                     7

SEQ ID NO: 840          moltype = AA  length = 7
FEATURE                 Location/Qualifiers
source                  1..7
                        mol_type = protein
                        organism = synthetic construct
SITE                    1
                        note = beta-Alanine
SITE                    2..7
                        note = Sarcosine
VARIANT                 2..7
                        note = Residues may be deleted
```

```
SEQUENCE: 840
AGGGGGG                                                                    7

SEQ ID NO: 841          moltype = AA  length = 7
FEATURE                 Location/Qualifiers
source                  1..7
                        mol_type = protein
                        organism = synthetic construct
SITE                    1
                        note = beta-Alanine
VARIANT                 2..7
                        note = Residues may be deleted
SEQUENCE: 841
AEEEEEE                                                                    7

SEQ ID NO: 842          moltype = AA  length = 7
FEATURE                 Location/Qualifiers
source                  1..7
                        mol_type = protein
                        organism = synthetic construct
SITE                    1
                        note = beta-Alanine
VARIANT                 2..7
                        note = Residues may be deleted
SEQUENCE: 842
ANNNNNN                                                                    7

SEQ ID NO: 843          moltype = AA  length = 7
FEATURE                 Location/Qualifiers
source                  1..7
                        mol_type = protein
                        organism = synthetic construct
VARIANT                 2..6
                        note = Residues may be deleted
SITE                    7
                        note = beta-Alanine
SEQUENCE: 843
EEEEEEX                                                                    7

SEQ ID NO: 844          moltype = AA  length = 7
FEATURE                 Location/Qualifiers
source                  1..7
                        mol_type = protein
                        organism = synthetic construct
SITE                    1
                        note =
                         2,2',2'',2'''-(1,4,7,10-tetraazacyclododecane-1,4,7,10-tetr
                         ayl)tetraacetic acid-4-(aminomethyl)benzoic acid
SITE                    4
                        note = 4-(aminomethyl)benzoic acid
SITE                    7
                        note = N6-(5-carboxypentanoyl)-L-lysine
SEQUENCE: 844
XMVXMVX                                                                    7

SEQ ID NO: 845          moltype = AA  length = 4
FEATURE                 Location/Qualifiers
source                  1..4
                        mol_type = protein
                        organism = synthetic construct
SITE                    1
                        note = 2-(2-(2-hydroxyethoxy)ethoxy)acetic acid coupled to
                         N-terminus of D-Tyrosine
SITE                    2
                        note =
                         Lysine(2,2',2'',2'''-(1,4,7,10-tetraazacyclododecane-1,4,7,
                         10-tetrayl)tetraacetic acid)
SEQUENCE: 845
YKNT                                                                       4

SEQ ID NO: 846          moltype = AA  length = 7
FEATURE                 Location/Qualifiers
source                  1..7
                        mol_type = protein
                        organism = synthetic construct
SITE                    1
                        note = palmitic acid coupled to N-terminus of Glutamic Acid
SITE                    2
                        note =
```

-continued

| | |
|---|---|
| | Lysine(2,2',2'',2'''-(1,4,7,10-tetraazacyclododecane-1,4,7, 10-tetrayl)tetraacetic acid) |
| SEQUENCE: 846 | |
| EKYNWNS | 7 |
| SEQ ID NO: 847 | moltype = AA length = 7 |
| FEATURE | Location/Qualifiers |
| source | 1..7 |
| | mol_type = protein |
| | organism = synthetic construct |
| SITE | 1 |
| | note = Acetyl coupled to N-terminus of Glutamic Acid |
| SITE | 2 |
| | note = Lysine(2,2',2'',2'''-(1,4,7,10-tetraazacyclododecane-1,4,7, 10-tetrayl)tetraacetic acid) |
| SITE | 3 |
| | note = D-Alanine |
| SEQUENCE: 847 | |
| EKANWNG | 7 |

What is claimed is:

1. A compound of Formula (I), or a pharmaceutically acceptable salt thereof:

Formula (I)

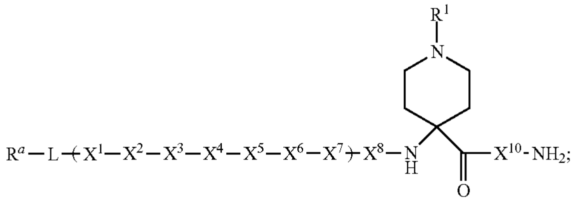

wherein:

$R^a$ is a chelating moiety for a radionuclide or a radionuclide complex thereof;

L is an optional linker that is attached to any one of $X^1$, $X^2$, $X^3$, $X^4$, $X^5$, $X^6$, or $X^7$; or L is attached to $X^8$ if $X^1$, $X^2$, $X^3$, $X^4$, $X^5$, $X^6$, and $X^7$ are absent; and $R^1$ is H,

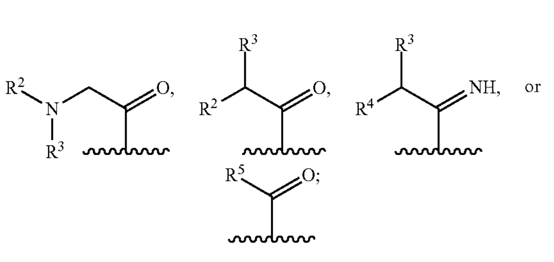

$R^2$ is $C_1$-$C_8$ alkyl, substituted or unsubstituted heteroalkyl, —$(CHR^6)_n$-heterocycloalkyl, —$(CHR^6)_n$-aryl, —$(CHR^6)_n$-heteroaryl, —C(═O)—$(CHR^6)_n$-aryl, or —C(═O)NH—$(CHR^6)_n$-aryl; wherein $C_1$-$C_8$ alkyl is optionally substituted with $R^7$, and wherein the heterocycloalkyl, aryl, or heteroaryl are each independently optionally substituted with $R^7$, $R^8$, $R^9$, $R^{10}$, and $R^{11}$;

$R^3$ is H or $C_1$-$C_4$ alkyl;

$R^4$ is H, $C_1$-$C_4$ alkyl, or $R^2$;

$R^5$ is substituted or unsubstituted alkyl, substituted or unsubstituted heteroalkyl, or —$(CHR^6)_n$-aryl; wherein aryl is optionally substituted with $R^7$, $R^8$, $R^9$, $R^{10}$, and $R^{11}$;

each $R^6$ is independently H, F, —$CH_3$, —$NH_2$, or —OH;

$R^7$, $R^8$, $R^9$, $R^{10}$, and $R^{11}$ are each independently selected from H, F, Cl, Br, I, —OH, —O—$C_1$—$C_4$ alkyl, —$NH_2$, —$NHC_1$-$C_4$ alkyl, —N($C_1$-$C_4$ alkyl)$_2$, —CN, —$CO_2$H, —$CO_2C_1$-$C_4$ alkyl, —$C_1$-$C_6$ alkyl, —$C_1$-$C_6$ fluroroalkyl or —$C_3$-$C_6$ cycloalkyl;

n is 0, 1, 2, 3, 4, 5, or 6;

$X^1$ is absent, tyrosine (Tyr), glycine (Gly), sarcosine (Sar), alanine (Ala), aspartic acid (Asp), lysine (Lys), phenylalanine (Phe), 3-(3-pyridyl)alanine (3-Pal), threonine (Thr), methionine (Met), 4-iodophenylalanine (Phe(4-I)), N6-(4-(p-tolyl)butanoyl)-lysine, N6-(4-(4-iodophenyl)butanoyl)-lysine, or γ-glutamic acid (γ-Glu));

$X^2$ is absent, asparagine (Asn), glutamine (Gln), aspartic acid (Asp), glutamic acid (Glu), serine (Ser), histidine (His), alanine (Ala), sarcosine (Sar), tyrosine (Tyr), proline (Pro), hydroxyproline (Hyp), azetidine-2-carboxylic acid (Aze), 2,3,4,5-tetrahydroisoquinoline-3-carboxylic acid (Tic), phenylalanine (Phe), 3-(2-pyridyl)alanine (2-Pal), 3-(3-pyridyl)alanine (3-Pal), or 3-(4-pyridyl)alanine (4-Pal);

$X^3$ is absent, tryptophan (Trp), serine (Ser), leucine (Leu), isoleucine (Ile), phenylalanine (Phe), 4-iodophenylalanine (Phe(4-I)), 3-(2-pyridyl)alanine (2-Pal), 3-(3-pyridyl)alanine (3-Pal), 3-(4-pyridyl)alanine (4-Pal), 2-amino-3-(naphthalen-2-yl)propanoic acid (H-2-NAL-OH), lysine (Lys), asparagine (Asn), glutamine (Gln), aspartic acid (Asp), glutamic acid (Glu), arginine (Arg), methyl arginine (Arg(Me)), norarginine (AGBA), methyl norarginine (AGBA(Me)), homoarginine (Harg), methyl homoarginine (Harg(Me)), citrulline (Cit), methyl citrulline (Cit(Me)), canavanine, methyl-canavanine, glycine (Gly), alanine (Ala), sarcosine (Sar), tyrosine (Tyr), cyclohexylalanine (Cha), 3-(1-naphthyl)alanine (α-Nal), 3-(2-naphthyl)alanine (β-Nal), threonine (Thr), proline (Pro), hydroxyproline (Hyp), tetrahydroisoquinoline-3-carboxylic acid (Tic), O-phospho-serine (SOP), 2-amino-4-(2H-tetrazol-5-yl) butanoic acid, β-glutamic acid, 8-aminoquinoline-3-carboxylic acid, biphenylalanine (Bip), 4-benzoylphenylalanine (Bpa), or 3-(9-anthryl)-alanine (H-Ala(9-Anth)-OH or AAP);

$X^4$ is absent, asparagine (Asn), glutamine (Gln), aspartic acid (Asp), glutamic acid (Glu), tryptophan (Trp), glycine (Gly), tyrosine (Tyr), alanine (Ala), sarcosine (Sar), or arginine (Arg);

$X^5$ is absent, serine (Ser), threonine (Thr), lysine (Lys), asparagine (Asn), glutamine (Gln), aspartic acid (Asp), glutamic acid (Glu), glycine (Gly), alanine (Ala), or sarcosine (Sar);

$X^6$ is absent, phenylalanine (Phe), alpha-methylphenylalanine (α-Me-Phe), N-methylphenylalanine (N-Me-Phe), 2-fluorophenylalanine (2-F-Phe), 3-fluorophenylalanine (3-F-Phe), 4-fluorophenylalanine (4-F-Phe), 4-iodophenylalanine (Phe(4-I)), 2-amino-2-indancarboxylic acid (Aic), biphenylalanine (Bip), (β-(2-thienyl)-Ala), tryptophan (Trp), 2-aminotetralin-2-carboxylic acid (Atc), 3-(2-thienyl)-alanine, 3-(4-pyridyl) alanine (4-Pal), cyclohexylalanine (Cha), or tyrosine (Tyr);

$X^7$ is absent, glycine (Gly), aza-glycine (aza-Gly), alanine (Ala), N-methylglycine (Sar), or 1-aminocyclopropane-1-carboxylic acid (ACC);

$X^8$ is leucine (Leu), norvaline (Nva), valine (Val), isoleucine (Ile), homoalanine (Hala), tryptophan (Trp), phenylalanine (Phe), or phenylglycine (Phg);

or —$X^7$—$X^8$— is

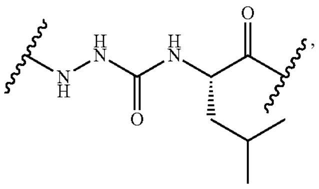

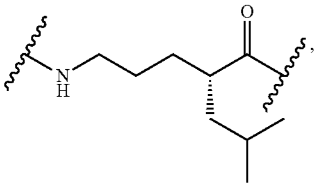

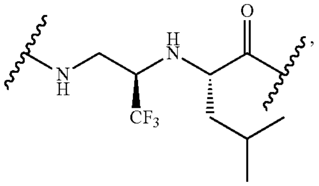

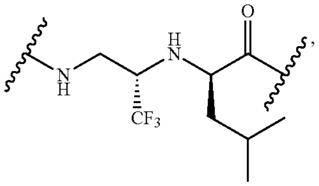

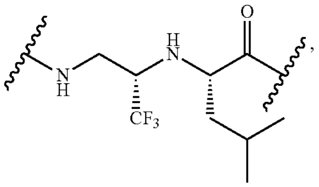

-continued

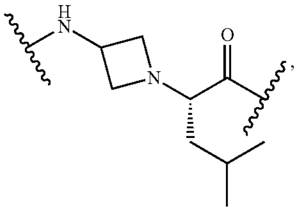

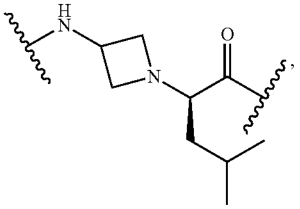

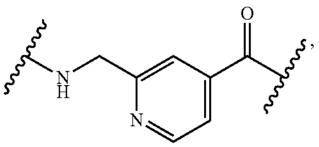

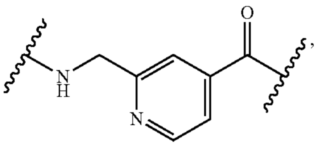

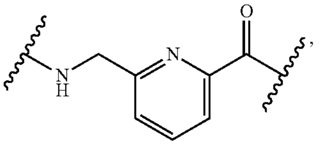

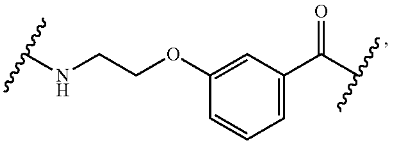

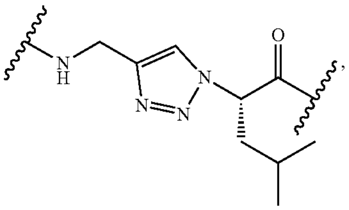

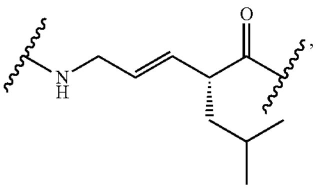

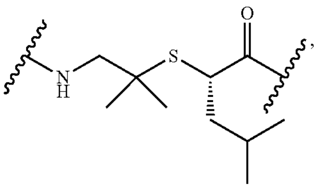

-continued
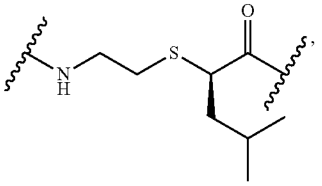
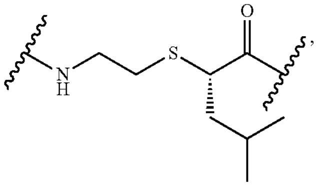
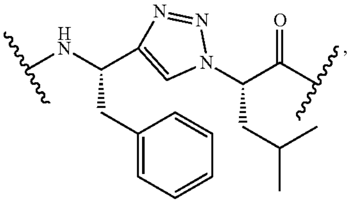
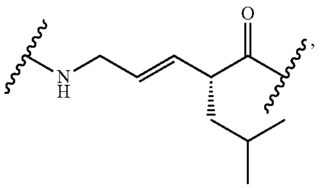
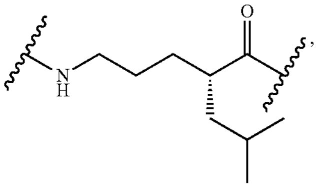
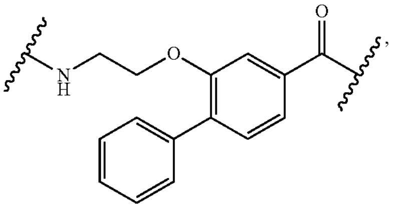
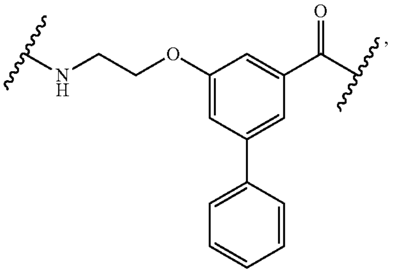
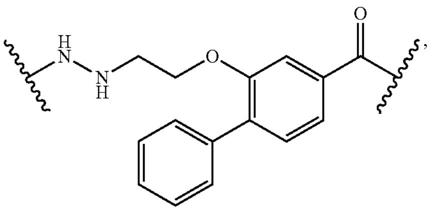
-continued
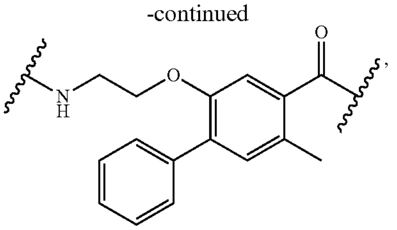
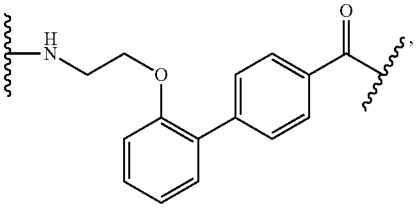
or
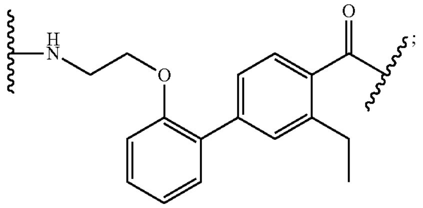
or —$X^6$—$X^7$—$X^8$— is
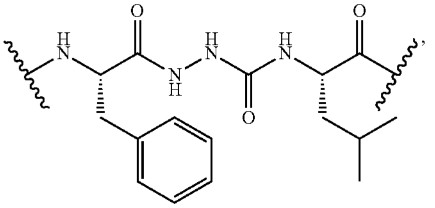
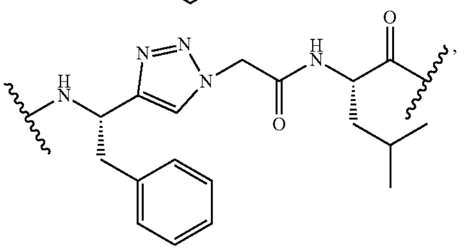
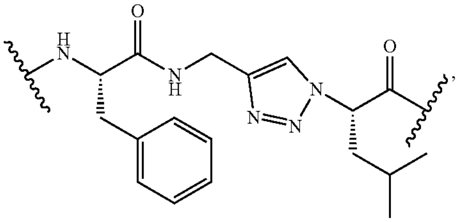
or
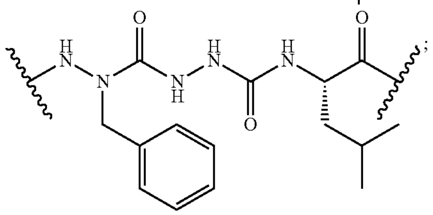
$X^{10}$ is tryptophan (Trp), 1-methyltryptophan (1MT), tyrosine (Tyr), phenylalanine (Phe), 4-cyano phenylalanine (Phe(4-CN)), 3-(4-pyridyl)alanine (4-Pal), leucine (Leu), phenylglycine (Phg), cyclohexylalanine (Cha), 3-(1-naphthyl)alanine (α-Nal), 3-(2-naphthyl)-alanine (β-Nal), histidine (His), or 3-nitro-tyrosine (Tyr(3-$NO_2$)), wherein the N-terminal amino acid or the compound of Formula (I) is optionally substituted with —C(═O)—$C_1$-$C_{20}$ alkyl, —C(═O)—$(CH_2CH_2O)_y$—$CH_2CH_2$—$R^{15}$, $C_1$-$C_{20}$ alkyl, N-hexadecanoyl-Glu, $C_4$-$C_{20}$ polyethylene glycol, —$R^{16}$, —C(═O)—$(CH_2CH_2O)_x$—$CH_3$, —C(═O)—$(CH_2CH_2O)_x$—H, —C(═O)—$CH_2CH_2CH(COOH)$—$R^{15}$, —C(═O)—$(CH_2)_2R^{19}$, or —C(═O)$CH_2NHCH_2R^{19}$;

$R^{15}$ is selected from —$OR^{16}$, —$N(R^{16})_2$, —C(═O)$OR^{16}$, or —C(═O)$N(R^{16})_2$;

each $R^{16}$ is independently H, —$C_1$-$C_6$ alkyl, —C(═O)—$(CH_2)_vR^{19}$, or —C(═O)$CH_2NHCH_2R^{19}$;

$R^9$ is 4-iodophenylene, 4-methylphenylene, or 3-fluoro-4-methylphenylene;

y is 0, 1, 2, 3, 4, 5, 6, 7, 8, 9, or 10;

x is an integer from 1 and 25; and v is 1, 2, 3, or 4;

wherein any free —NH— of a peptide bond is optionally independently substituted with —$CH_3$ or —$CH_2CH_3$; and wherein any alpha position of an amino acid is optionally independently substituted with —$CH_3$ or —$CH_2CH_3$.

2. The compound of claim 1, or a pharmaceutically acceptable salt thereof, wherein:

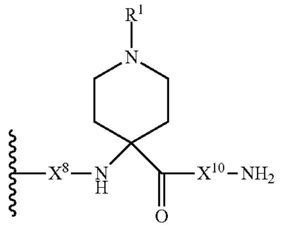 is

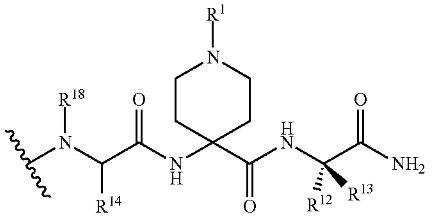

wherein, $R^{18}$ is H or —$CH_3$;

$R^{12}$ is

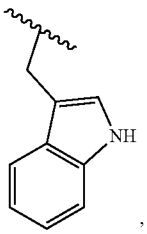,
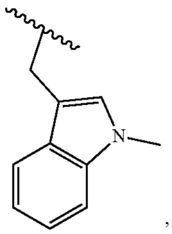,
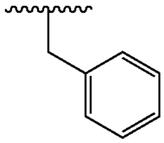,
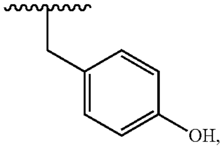,
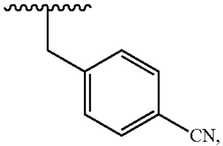,

-continued

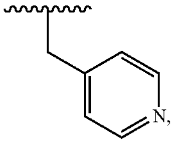 or 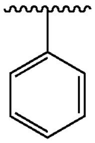;

$R^{13}$ is H or —$CH_3$; and $R^{14}$ is

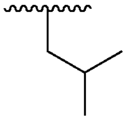,
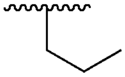,
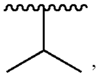,
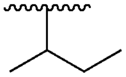,
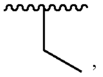,
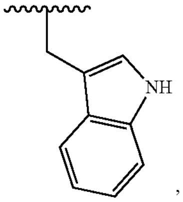,
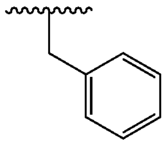, or
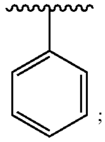;

3. The compound of claim 1, or a pharmaceutically acceptable salt thereof, wherein:

$X^6$ is 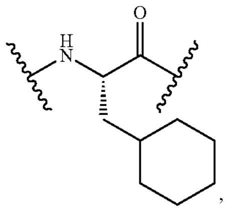,
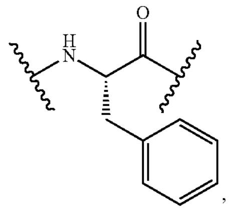,
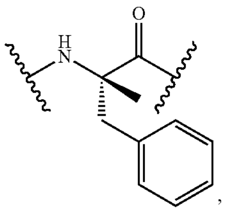,
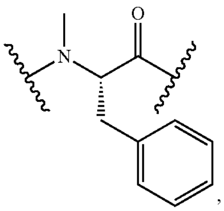,
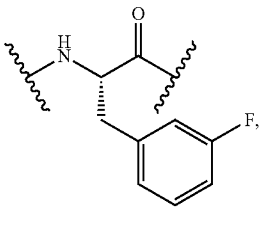,

-continued
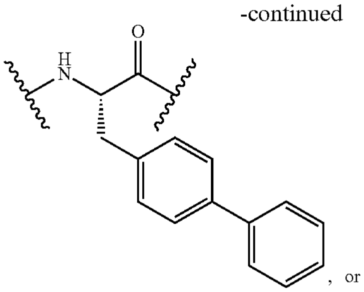
, or
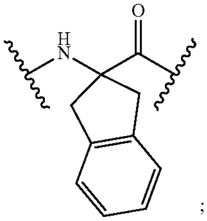
;
$X^7$ is
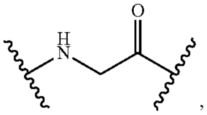
,
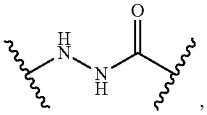
,
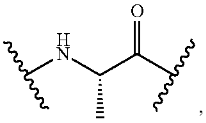
,
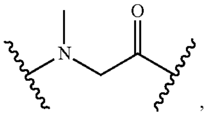
, or
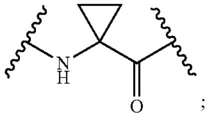
; and $X^8$ is
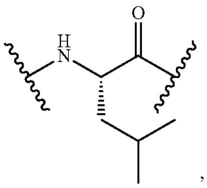
,
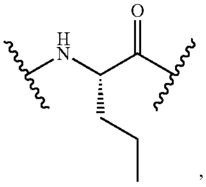
,
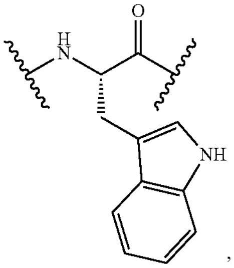
,
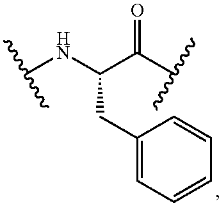
, or
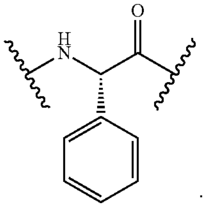
.
4. The compound of claim 1, or a pharmaceutically acceptable salt thereof, wherein:
$X^6$ is
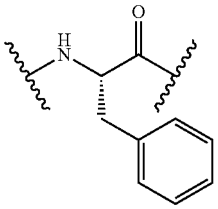
,
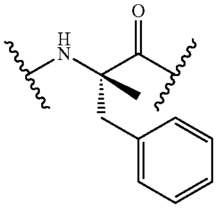
,
-continued
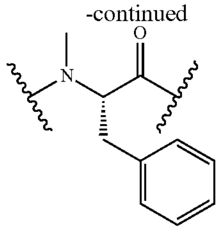
, or
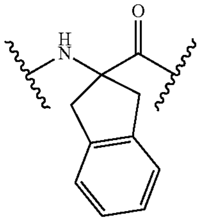
; and
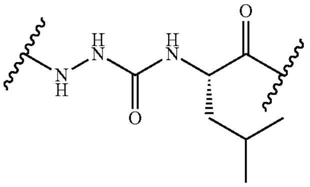
,
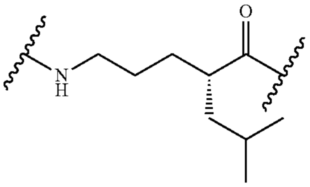
,
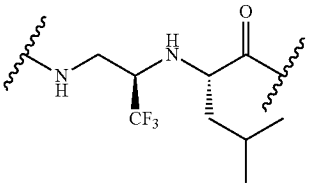
,
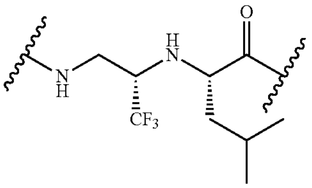
,
$X^7$-$X^8$-is
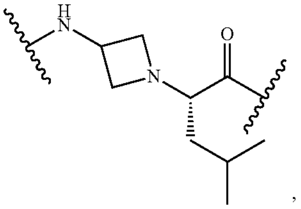
,
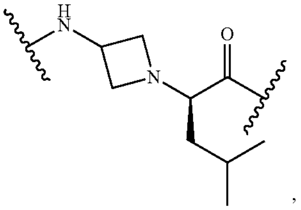
,
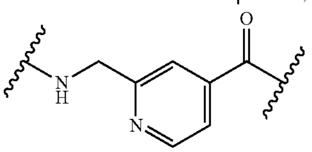
, -continued
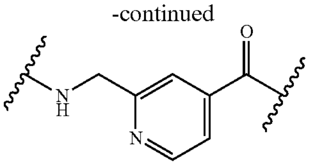
,
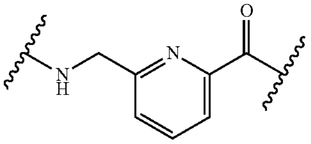
,
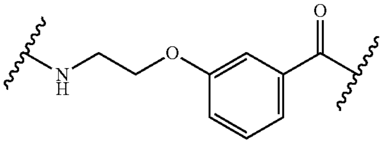
,
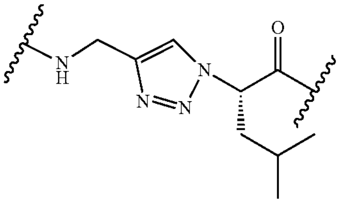
,
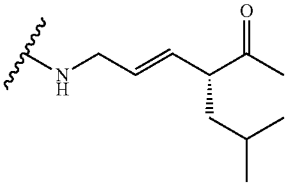
,
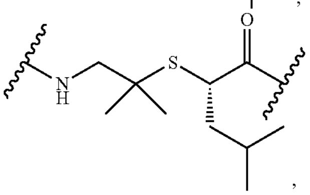
,
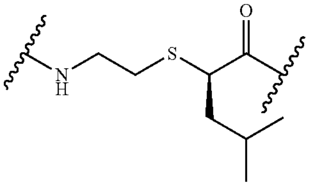
, or
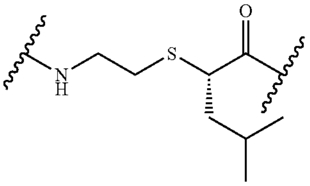
.
5. The compound of claim 1, or a pharmaceutically acceptable salt thereof, wherein:
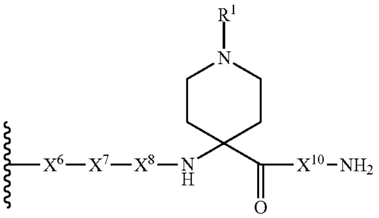
is
-continued
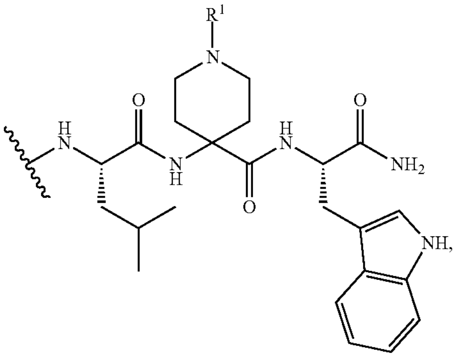
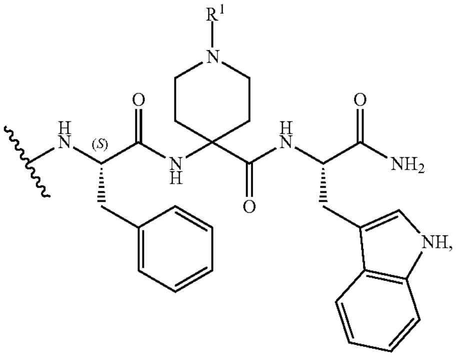
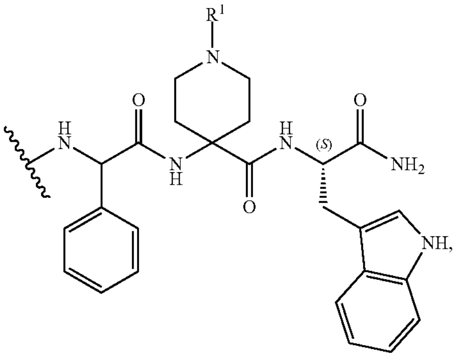
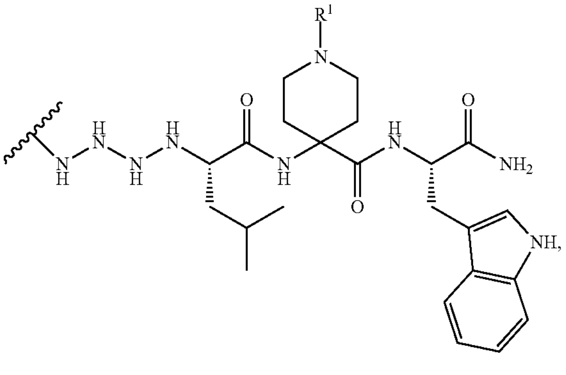

-continued
(SEQ ID NO: 159)
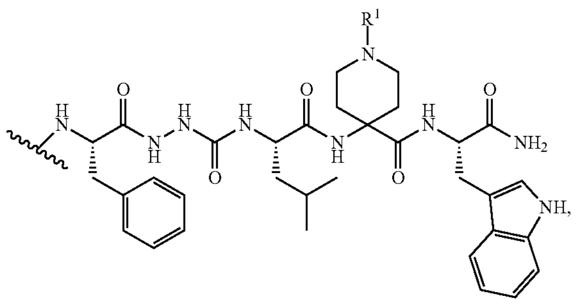
(SEQ ID NO: 162)
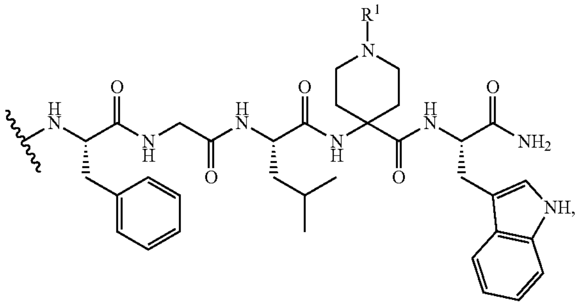
(SEQ ID NO: 164)
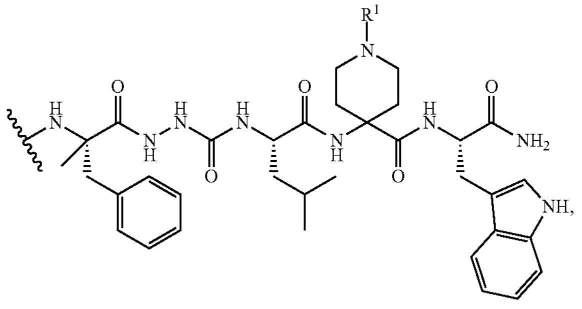
(SEQ ID NO: 161)
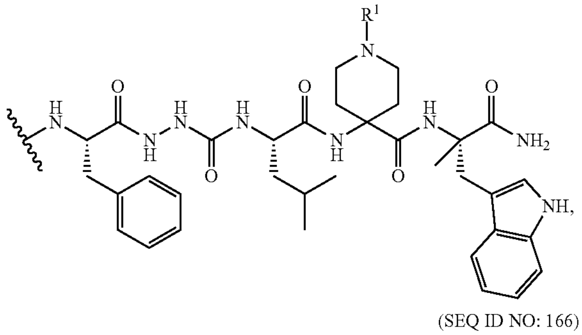
(SEQ ID NO: 166)
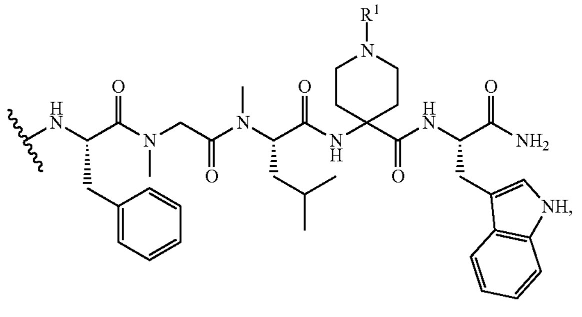
-continued
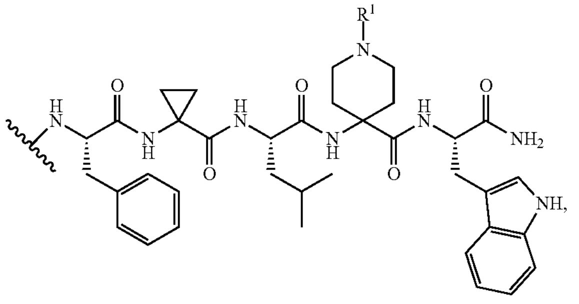
(SEQ ID NO: 163)
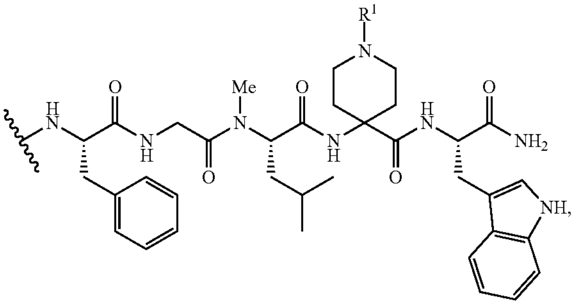
(SEQ ID NO: 165)
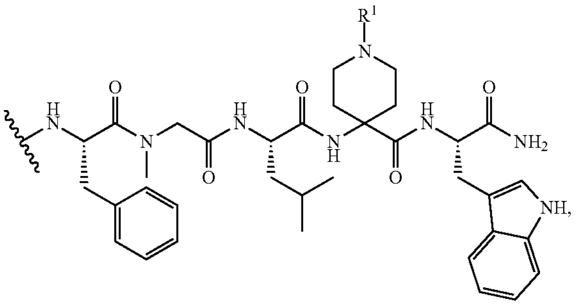
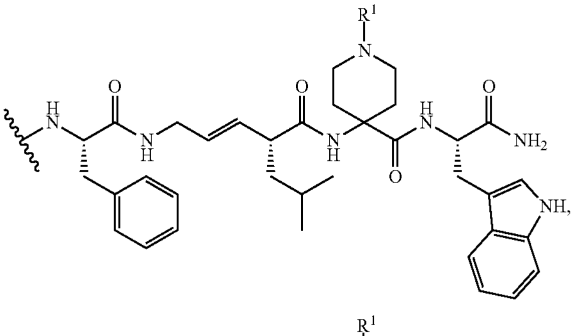
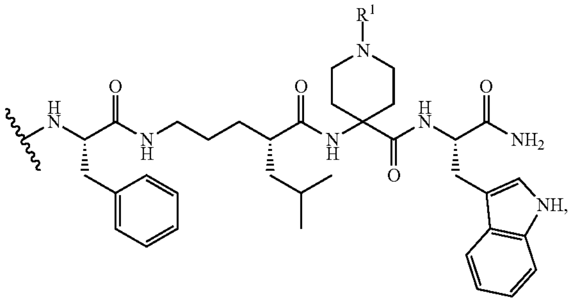

-continued
(SEQ ID NO: 160)
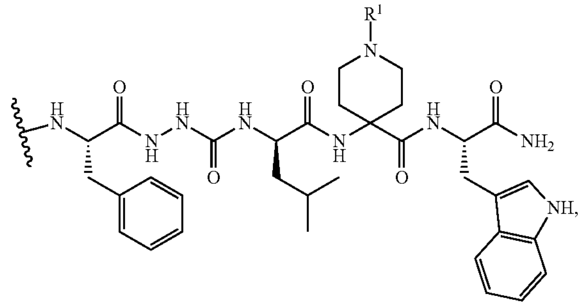
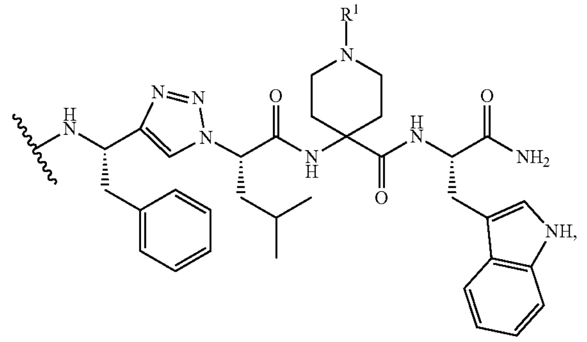
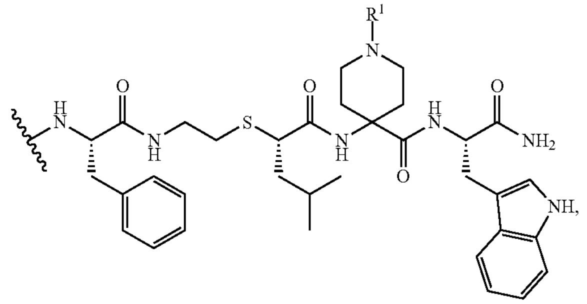
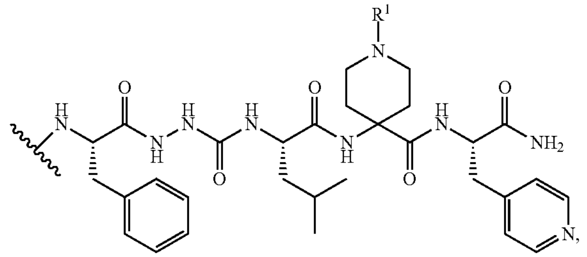
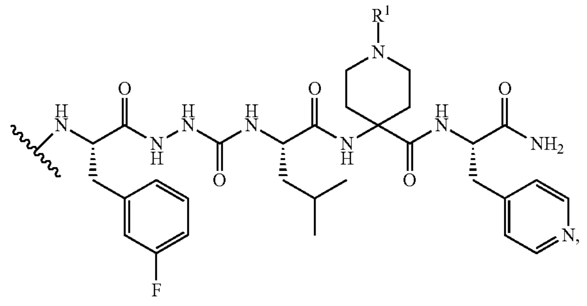
-continued
(SEQ ID NO: 197)
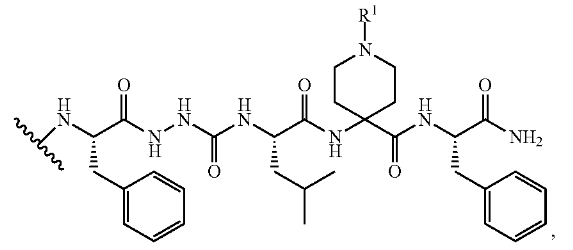
(SEQ ID NO: 774)
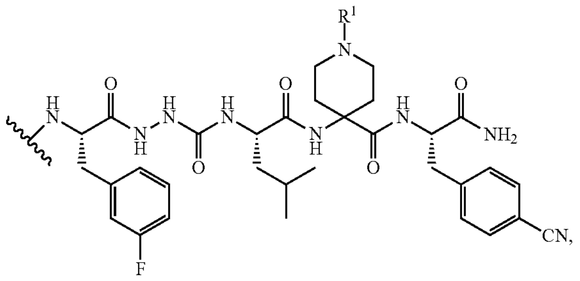
(SEQ ID NO. 775)
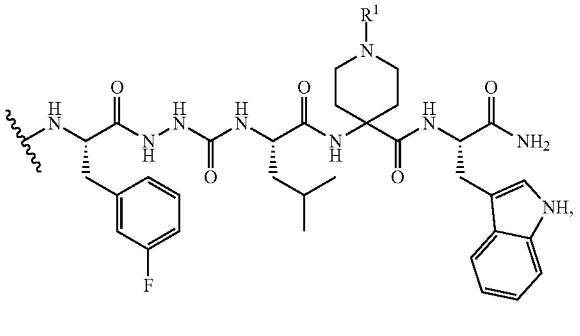
(SEQ ID NO: 160)
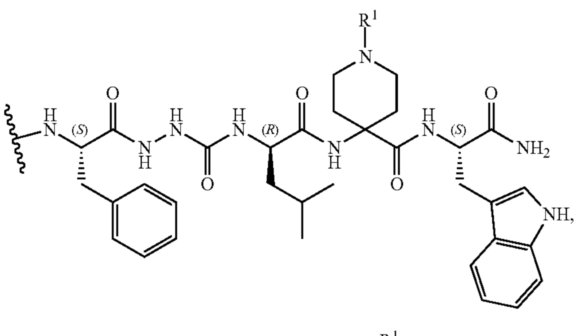
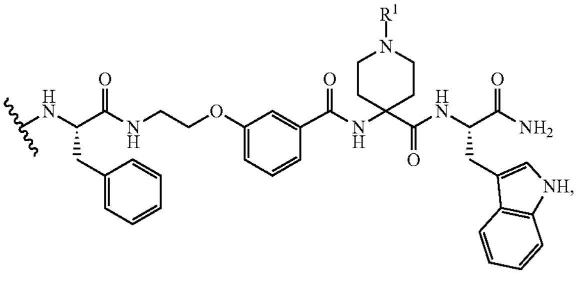

-continued
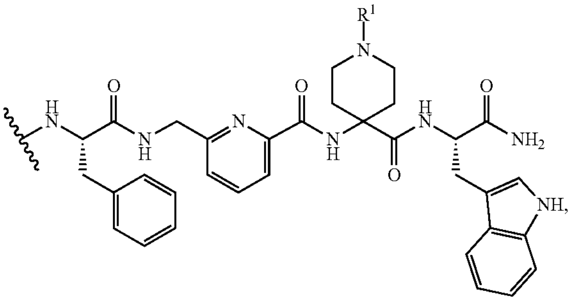
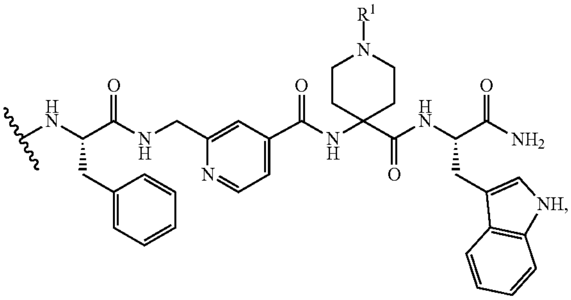
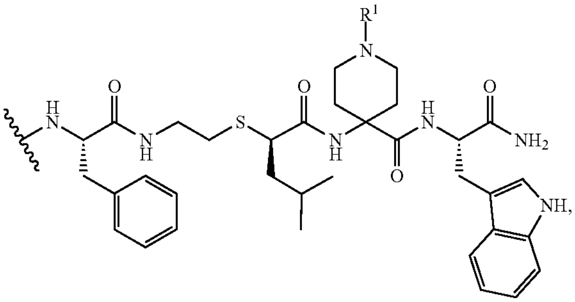
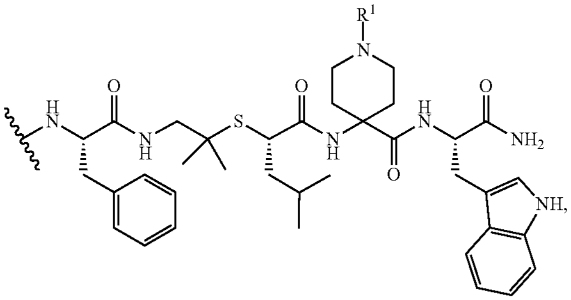
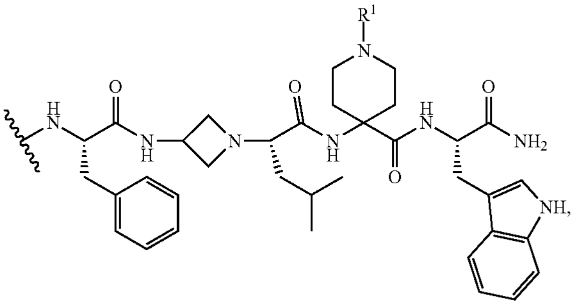
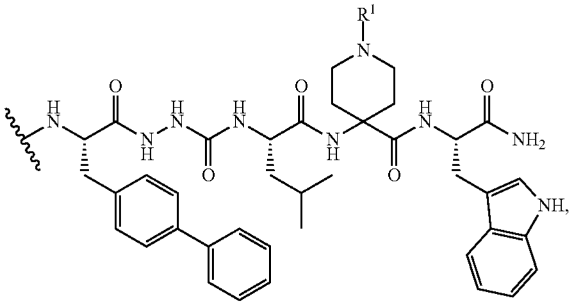
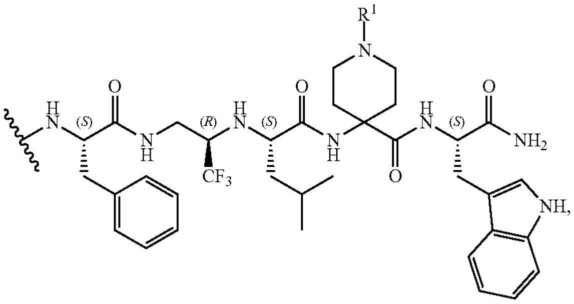
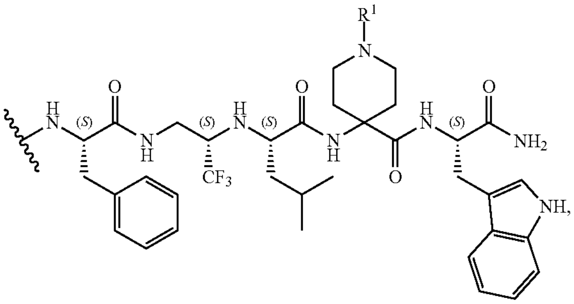
(SEQ ID NO: 206)
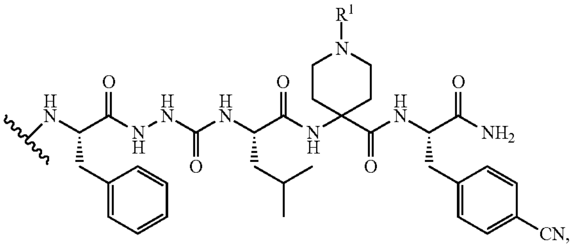
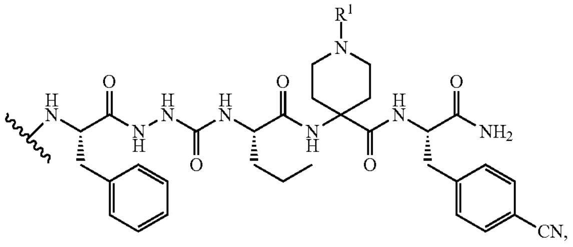
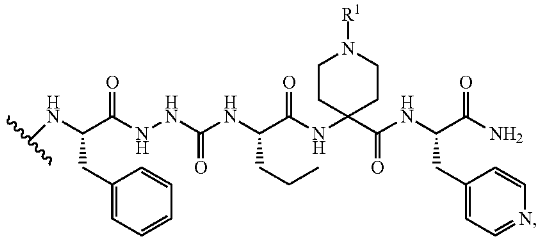
or -continued

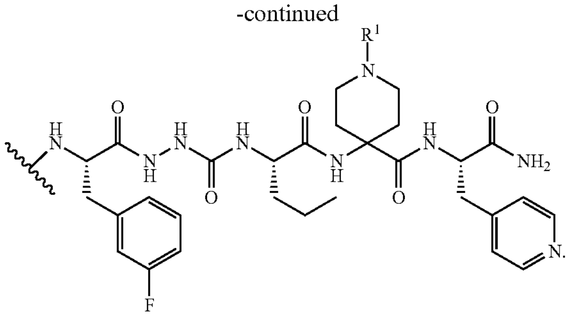

6. The compound of claim 1, or a pharmaceutically acceptable salt thereof, wherein: $X^{10}$ is tryptophan (Trp), 1-methyltryptophan (1MT), tyrosine (Tyr), phenylalanine (Phe), 4-cyano phenylalanine (Phe(4-CN)), 3-(4-pyridyl) alanine (4-Pal), or leucine (Leu).

7. The compound of claim 1, or a pharmaceutically acceptable salt thereof, wherein $R^1$ is H,

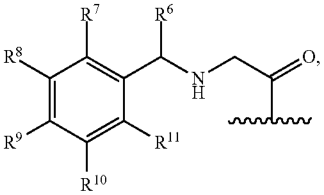

or

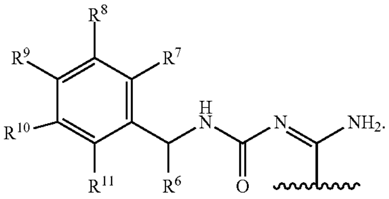

8. The compound of claim 1, or a pharmaceutically acceptable salt thereof, wherein:

$R^2$ is

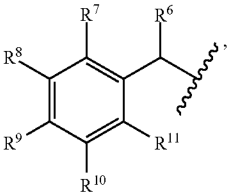

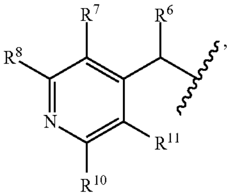

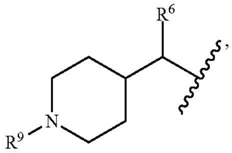

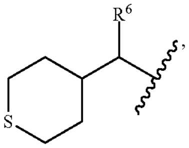

or

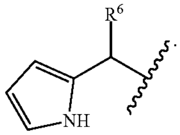

9. The compound of claim 1, or a pharmaceutically acceptable salt thereof, wherein:

$R^7$, $R^8$, $R^9$, $R^{10}$, and $R^{11}$ are independently selected from H, F, Cl, Br, I, —OH, —$OCH_3$, —$OCH_2CH_3$, —$NH_2$, —$NHCH_3$, —$N(CH_3)_2$, —CN, —$CO_2H$, —$CO_2CH_3$, —$CO_2CH_2CH_3$, —$CH_3$, —$CH_2CH_3$, —$CH(CH_3)_2$, —$(CH_3)_3$, —$CF_3$, —$CH_2F$, —$CH_2F$, or cyclopropyl.

10. The compound of claim 1, or a pharmaceutically acceptable salt thereof, wherein:

$R^1$ is

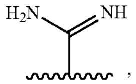

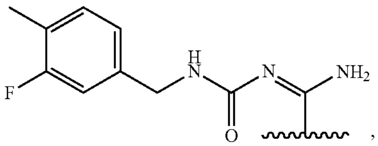

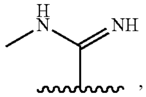

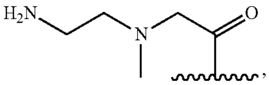

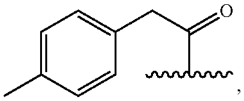

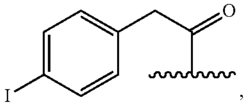

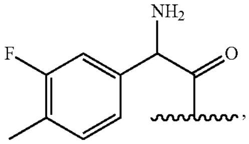

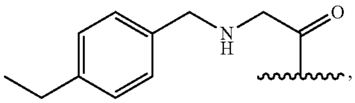

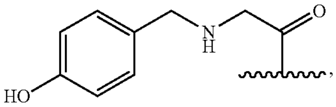

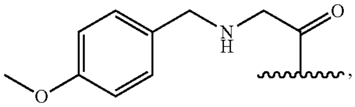

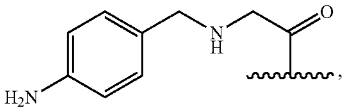

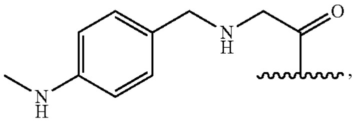

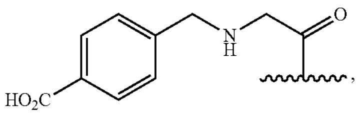

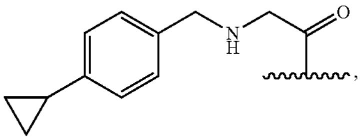

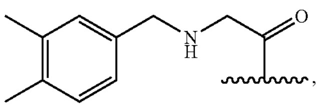

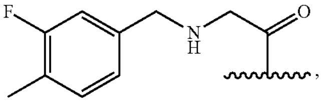

-continued

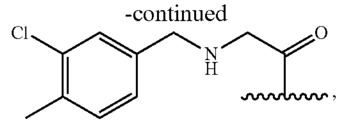

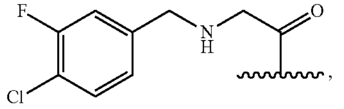

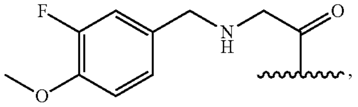

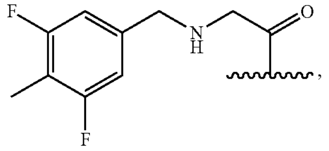

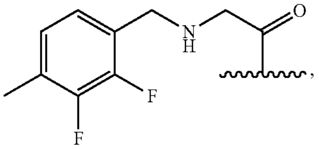

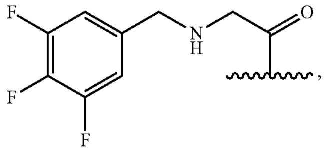

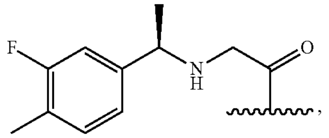

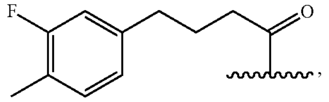

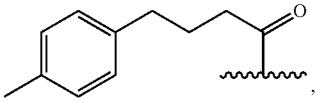 , 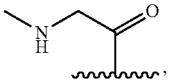

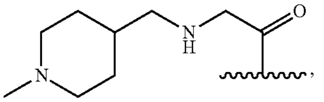

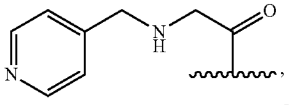

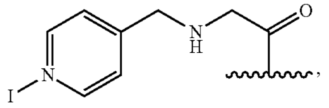

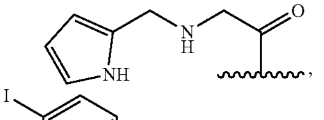

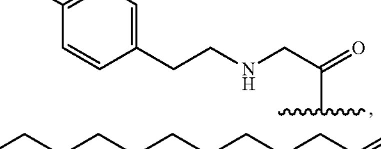

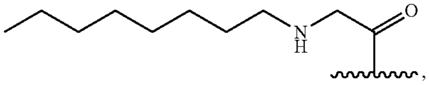

-continued

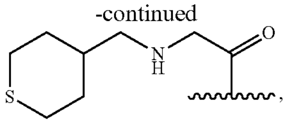

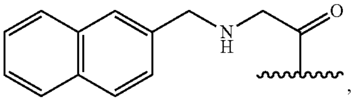 , or 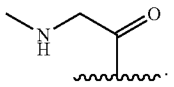

11. The compound of claim 1, or a pharmaceutically acceptable salt thereof, wherein:

$R^1$ is

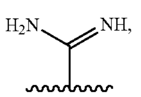 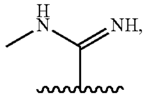

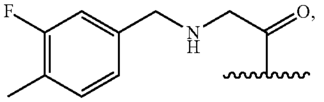 or

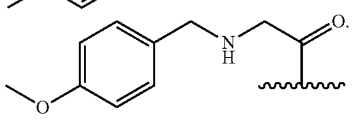

12. The compound of claim 1, or a pharmaceutically acceptable salt thereof, wherein:

$X^1$ is absent, Tyr, Asp, Lys, 3-Pal, Sar, or Phe;

$X^2$ is absent, Asn, Gln, Asp, Glu, Ser, His, Ala, Sar, Pro, Hyp, Aze, Tic, Phe, or 4-Pal;

$X^3$ is Trp, Ser, Ile, Phe, 4-Pal, Lys, Asn, Gln, Asp, Glu, Arg, Arg(Me), Gly, Ala, Sar, Tyr, Cha, β-Nal, Hyp, Thr, Bip, Bpa, or AAP;

$X^4$ is Asn, Gln, Asp, Glu, Trp, Gly, Ala, or Sar; and $X^5$ is absent, Thr, Ser, Gly, or Ala.

13. The compound of claim 1, or a pharmaceutically acceptable salt thereof, wherein:

$X^1$ is tyrosine (Tyr), glycine (Gly), or 3-(3-pyridyl)alanine (3-Pal));

$X^2$ is absent, asparagine (Asn), glutamine (Gln), serine (Ser), D-histidine (His), tyrosine (Tyr), or phenylalanine (Phe);

$X^3$ is tryptophan (Trp), isoleucine (Ile), 3-(4-pyridyl) alanine (4-Pal), 2-amino-3-(naphthalen-2-yl)propanoic acid (H-2-NAL-OH), lysine (Lys), aspartic acid (Asp), glutamic acid (Glu), glycine (Gly), alanine (Ala), cyclohexylalanine (Cha), (Hyp), biphenylalanine (Bip); 4-benzoylphenylalanine (Bpa), or 3-(9-anthryl)-alanine (AAP);

$X^4$ is asparagine (Asn), or glutamine (Gln); and $X^5$ is serine (Ser), threonine (Thr), glycine (Gly), or alanine (Ala).

14. The compound of claim 1, or a pharmaceutically acceptable salt thereof, wherein

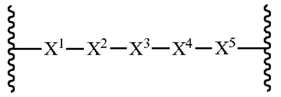

is absent, (SEQ ID NO: 1)
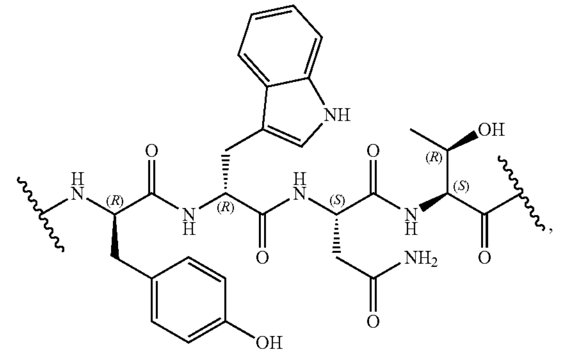
(SEQ ID NO: 2)
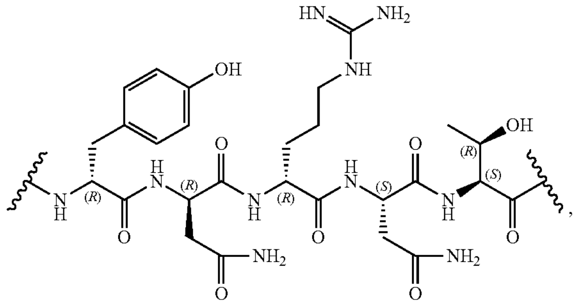
(SEQ ID NO: 3)
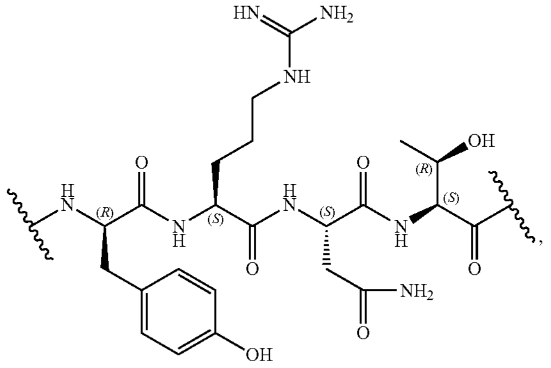
(SEQ ID NO: 4)
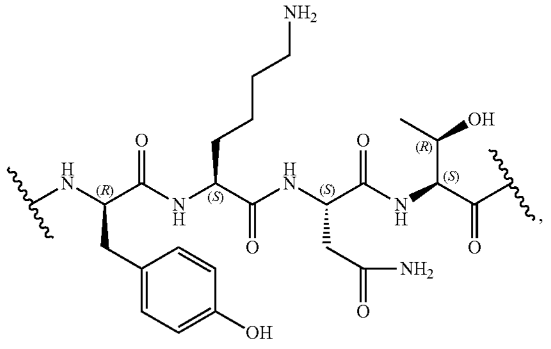
-continued
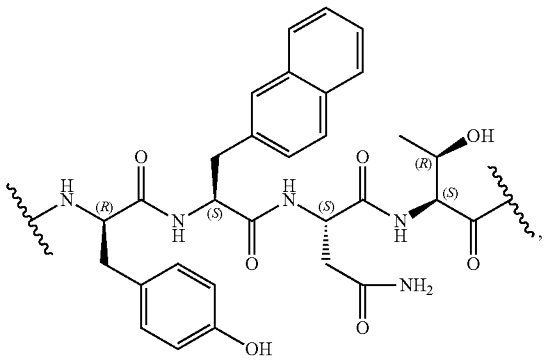
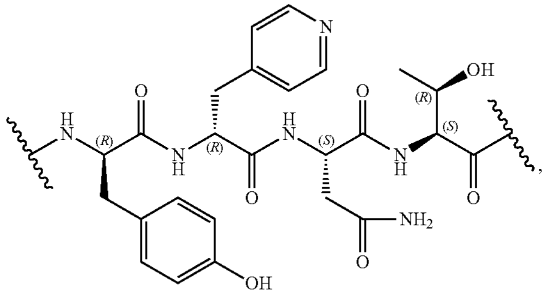
(SEQ ID NO: 7)
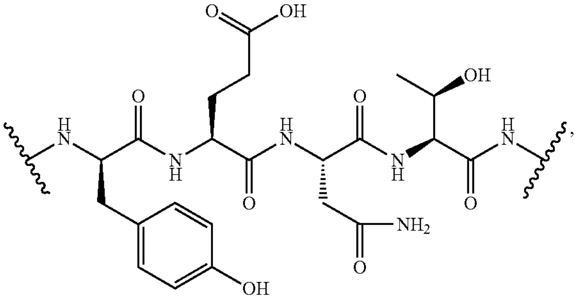
(SEQ ID NO: 8)
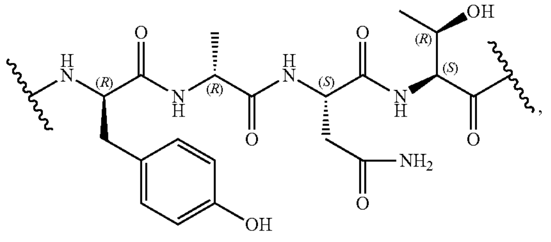
(SEQ ID NO: 9)
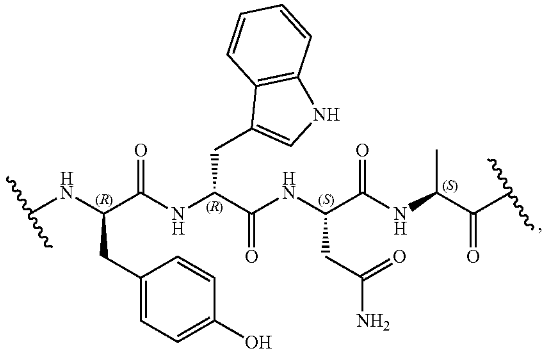

-continued
(SEQ ID NO: 10)
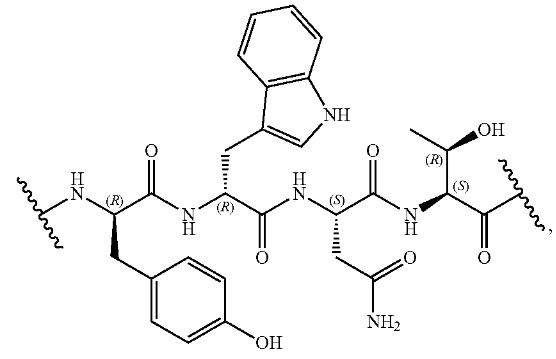
,
(SEQ ID NO: 11)
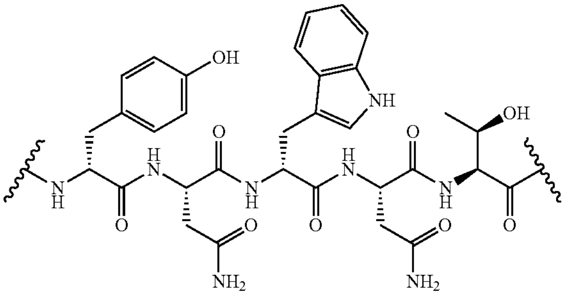
,
(SEQ ID NO: 12)
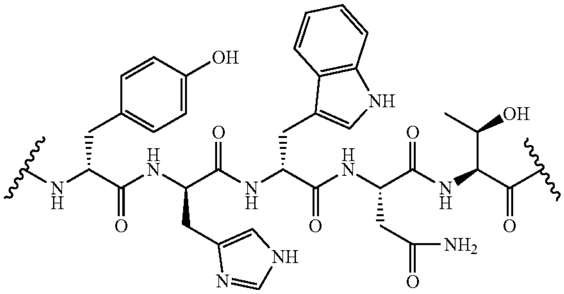
,
(SEQ ID NO: 13)
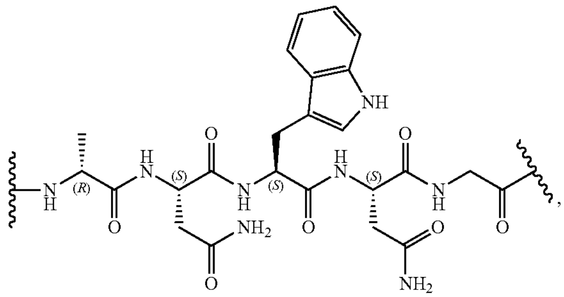
,
-continued
(SEQ ID NO: 14)
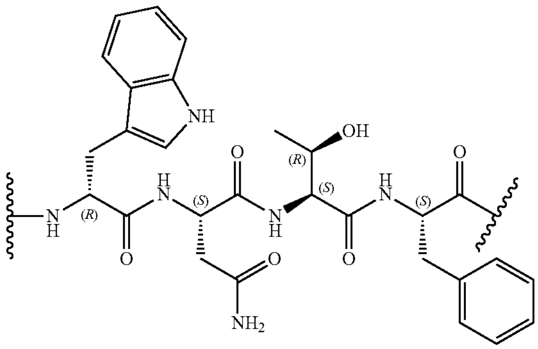
,
(SEQ ID NO: 15)
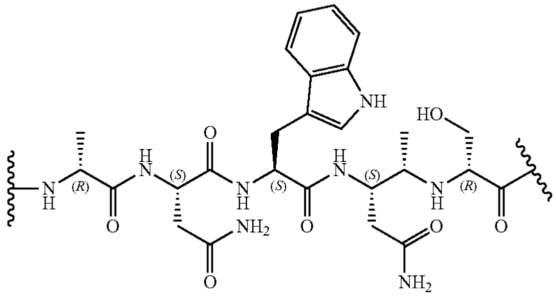
,
(SEQ ID NO: 16)
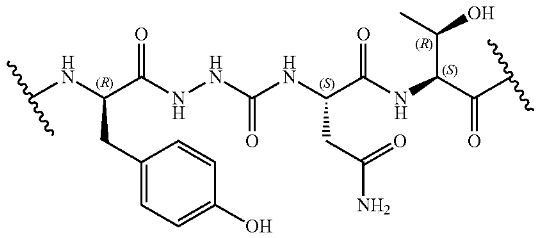
,
(SEQ ID NO: 17)
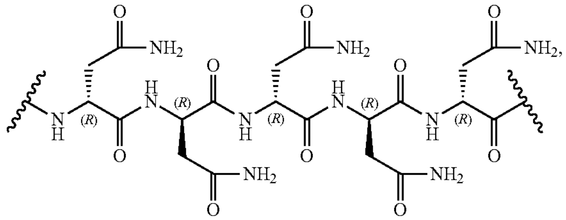
(SEQ ID NO: 18)
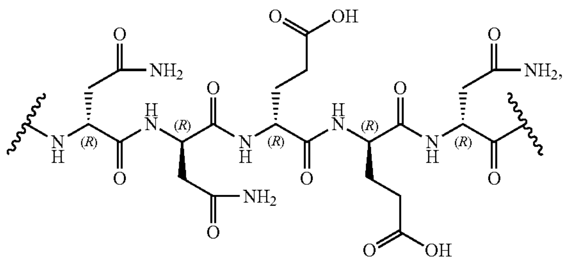

-continued
(SEQ ID NO: 19)
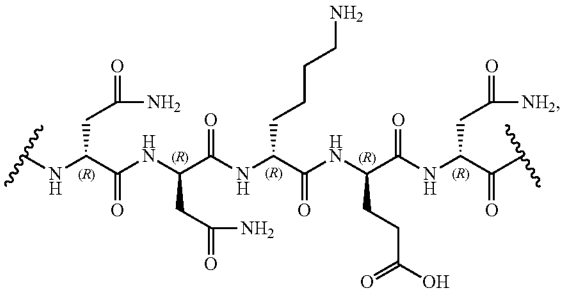
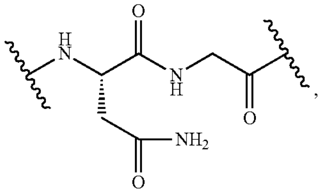
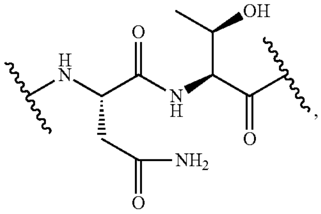
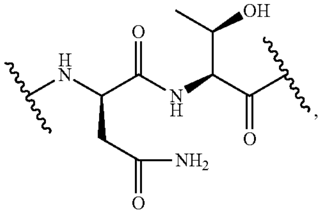
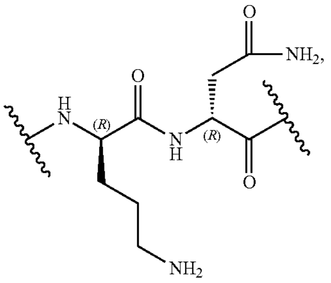
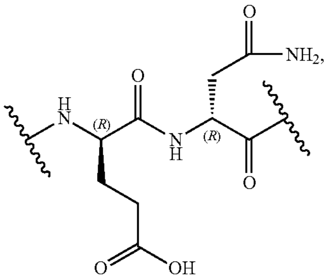
-continued
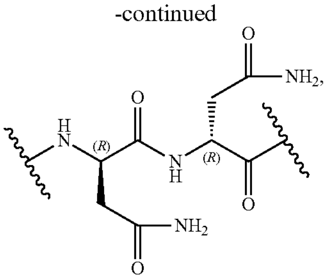
(SEQ ID NO: 20)
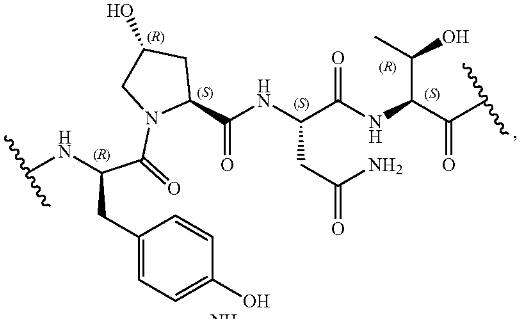
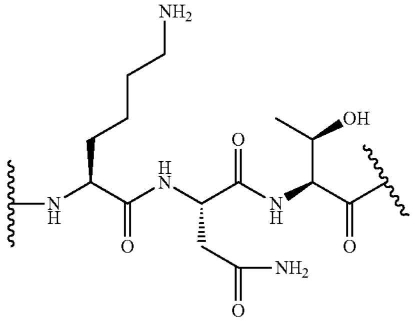
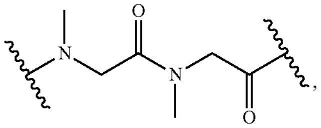
(SEQ ID NO: 24)
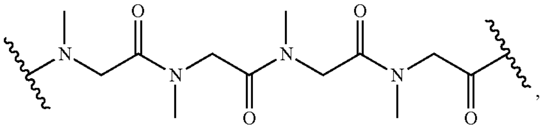
(SEQ ID NO: 25)
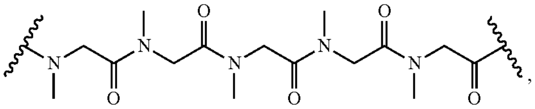
or
(SEQ ID NO: 26)
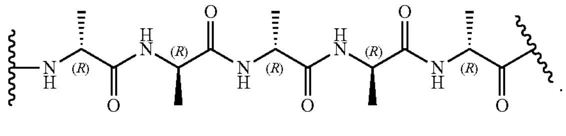
15. The compound of claim 1, or a pharmaceutically acceptable salt thereof, wherein:

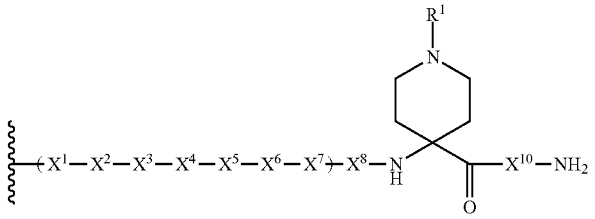
is
(SEQ ID NO: 55)
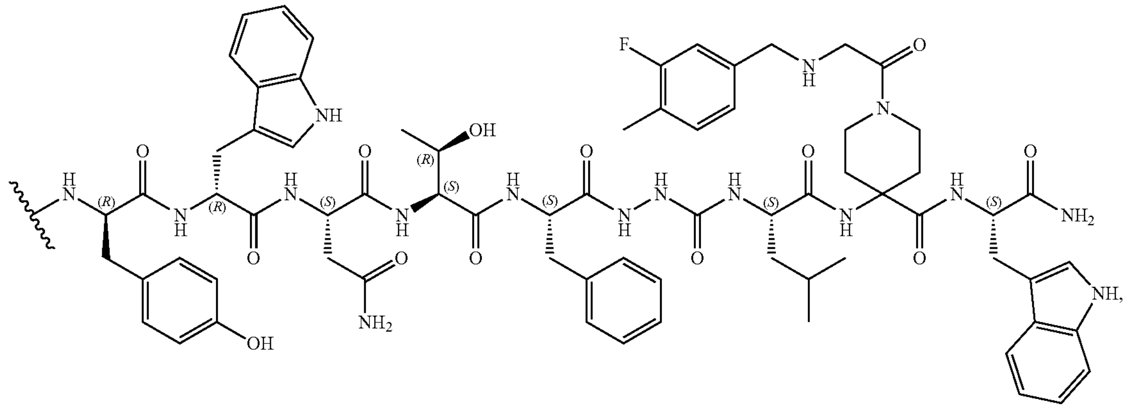
(SEQ ID NO: 56)
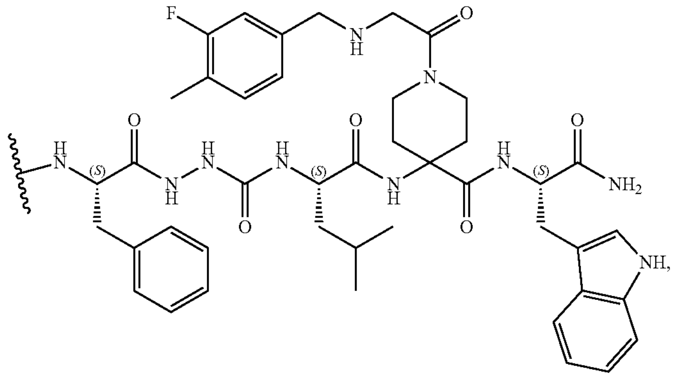
(SEQ ID NO: 57)
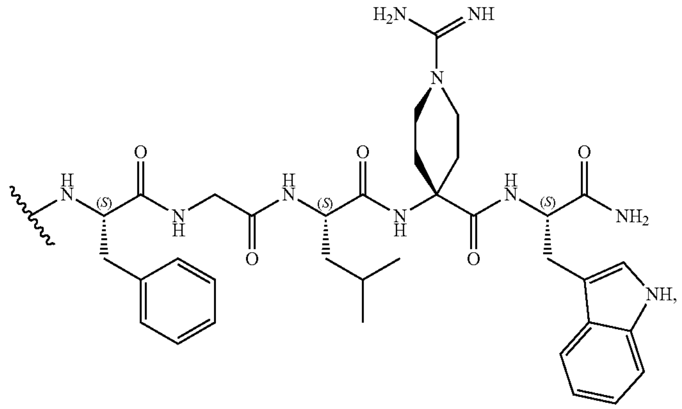

-continued
(SEQ ID NO: 58)
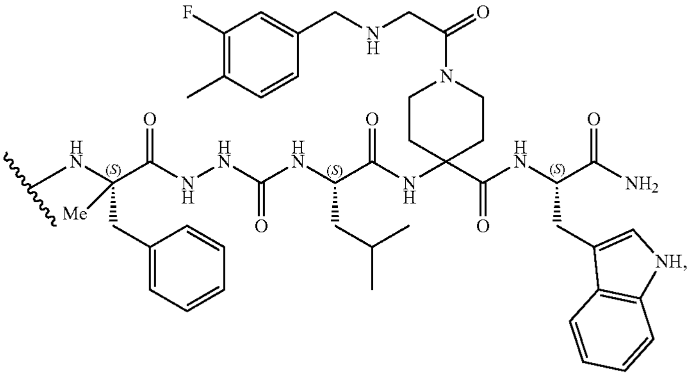
(SEQ ID NO: 59)
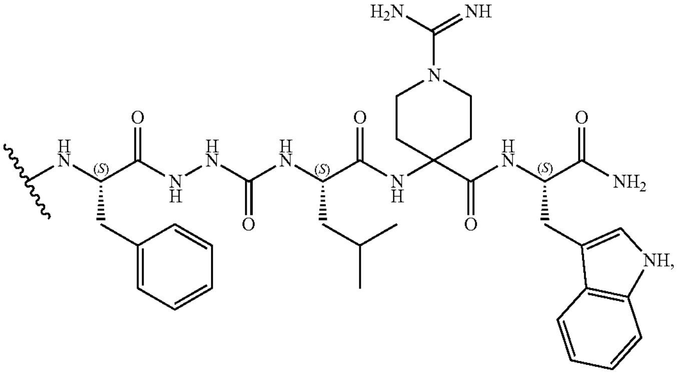
(SEQ ID NO: 60)
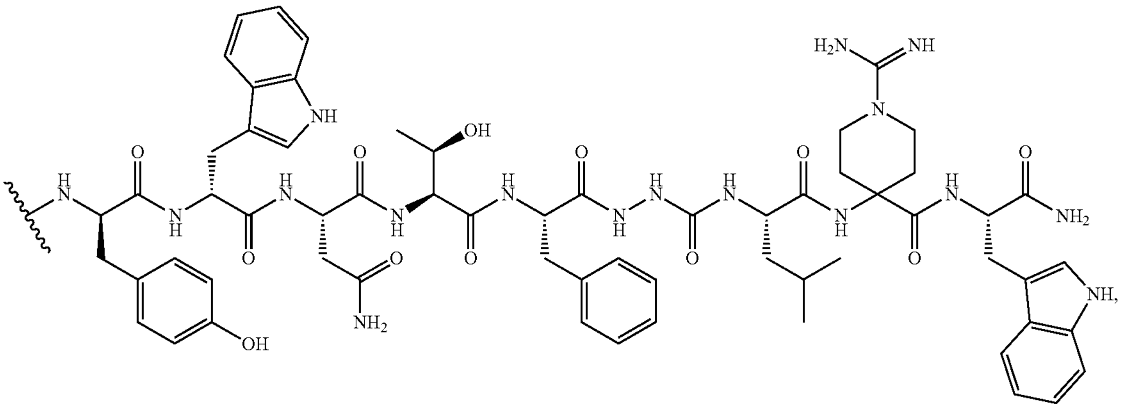
(SEQ ID NO: 61)
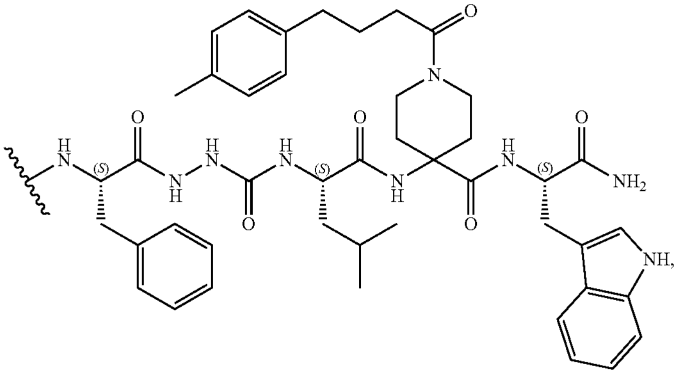

-continued
(SEQ ID NO: 63)
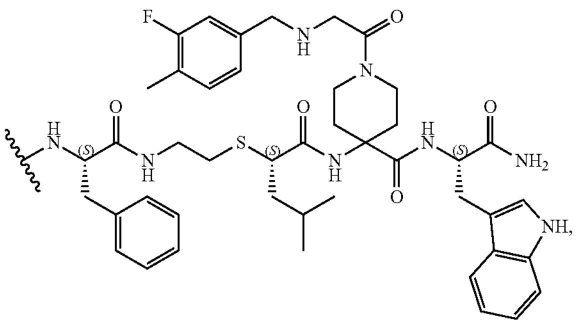
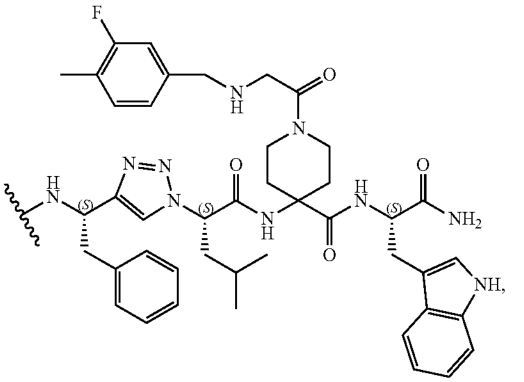
(SEQ ID NO: 64)
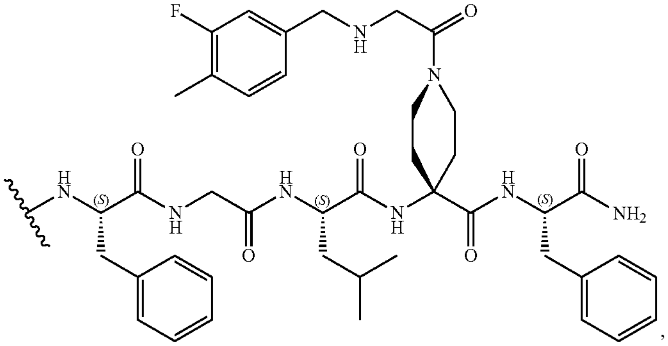
(SEQ ID NO: 65)
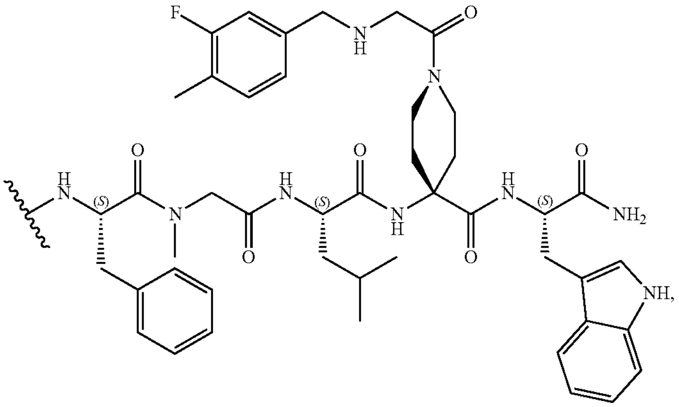
(SEQ ID NO: 65)
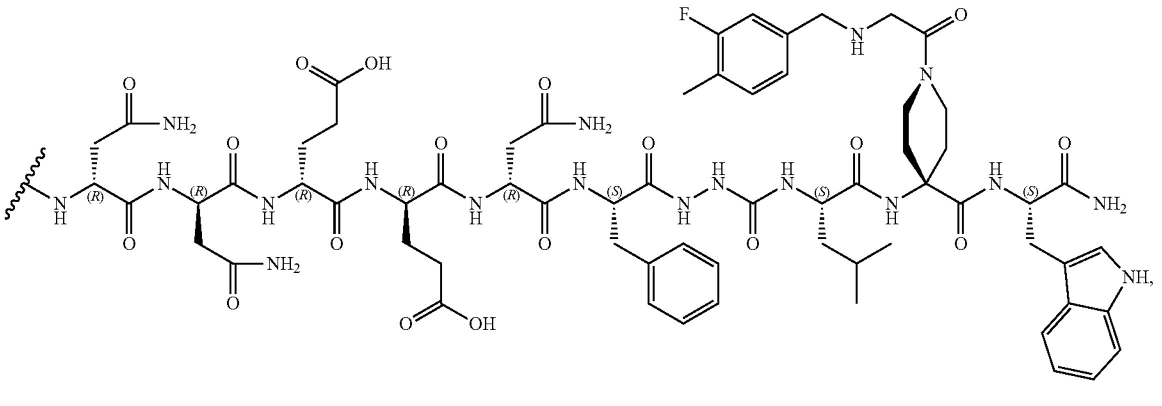

-continued
(SEQ ID NO: 66)
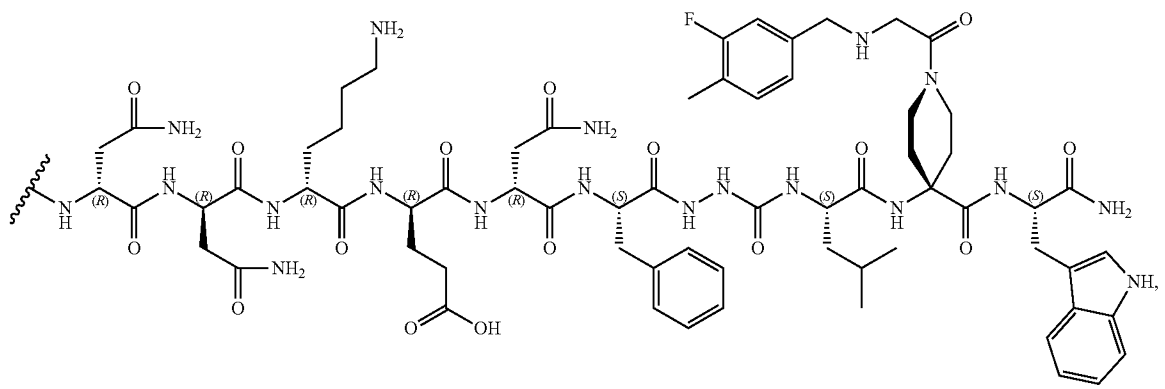
(SEQ ID NO: 67)
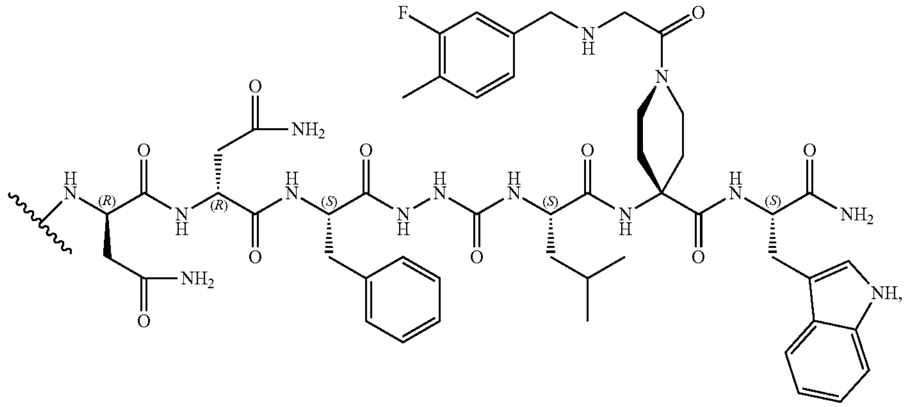
(SEQ ID NO: 68)
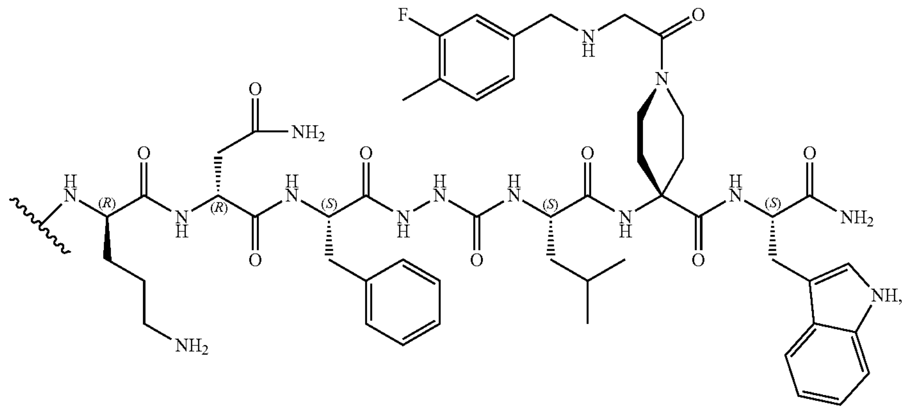
(SEQ ID NO: 69)
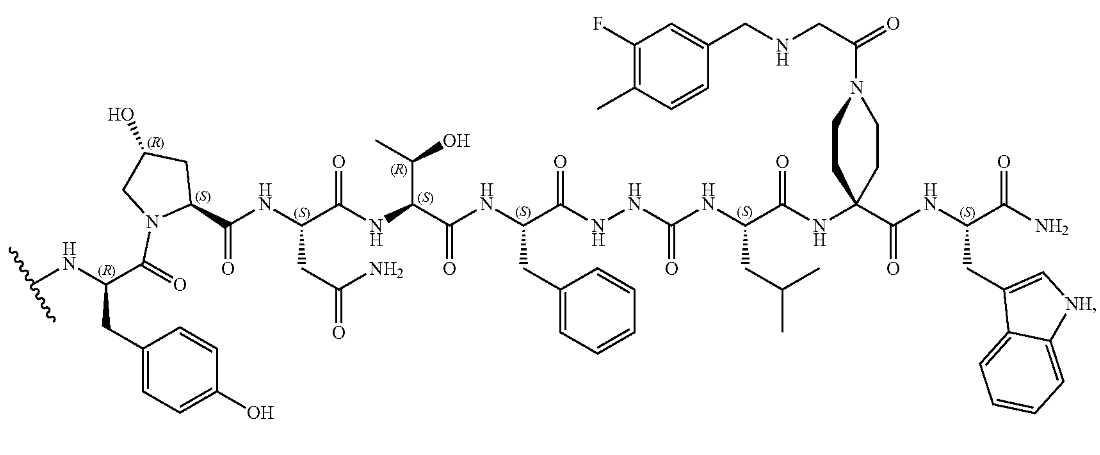

-continued
(SEQ ID NO: 70)
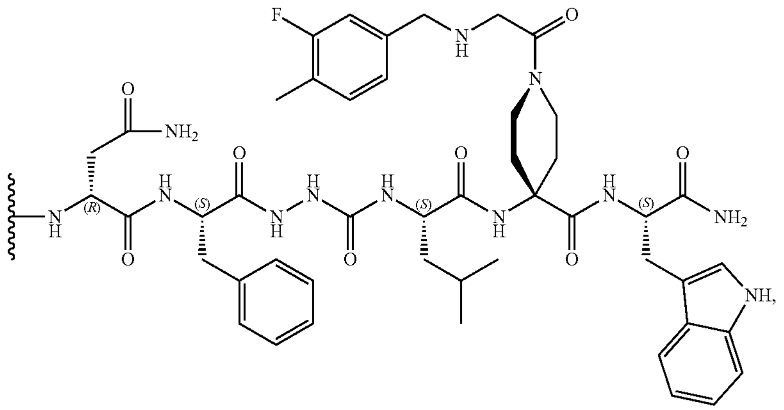
(SEQ ID NO: 71)
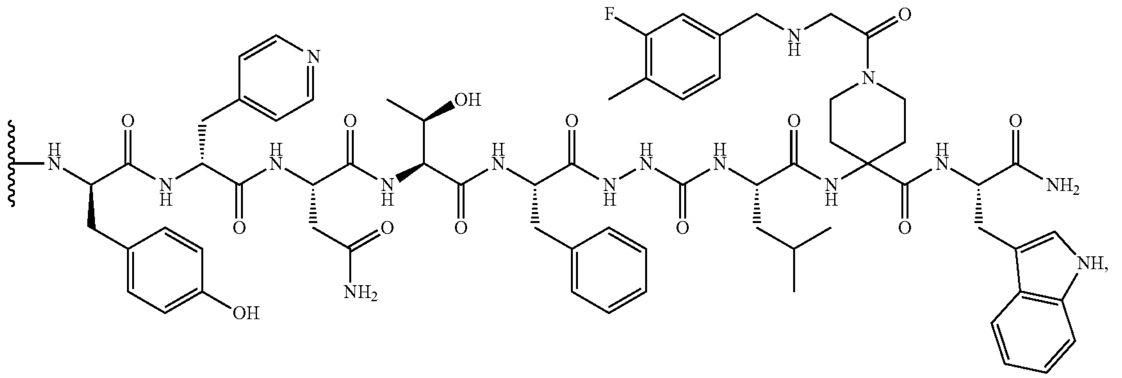
(SEQ ID NO: 72)
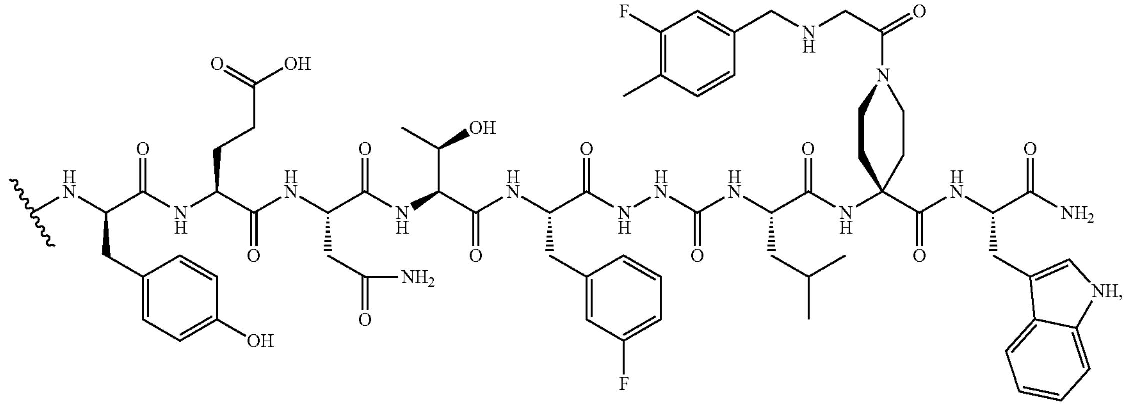
(SEQ ID NO: 73)
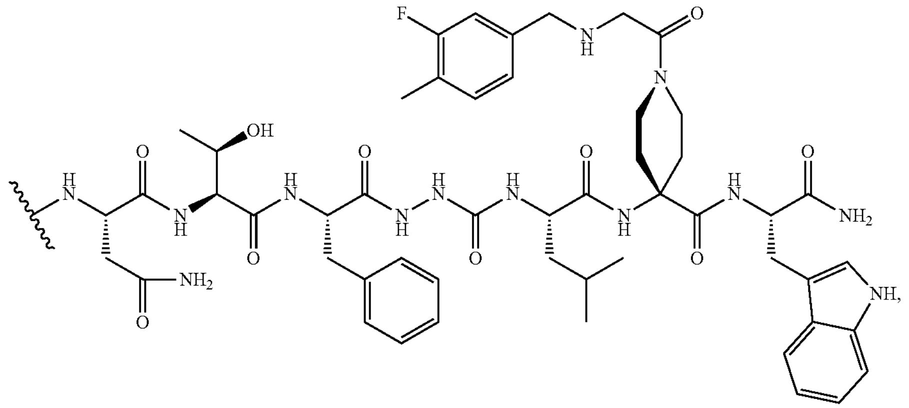

-continued
(SEQ ID NO: 74)
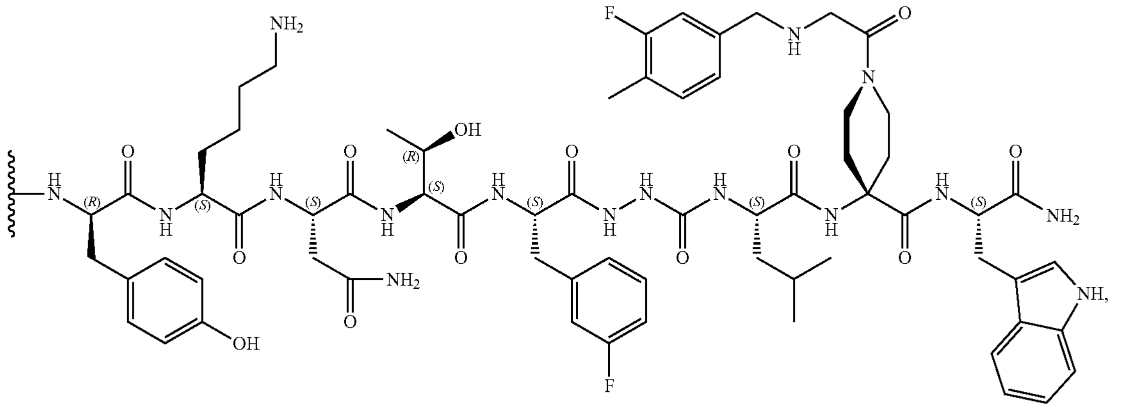
(SEQ ID NO: 75)
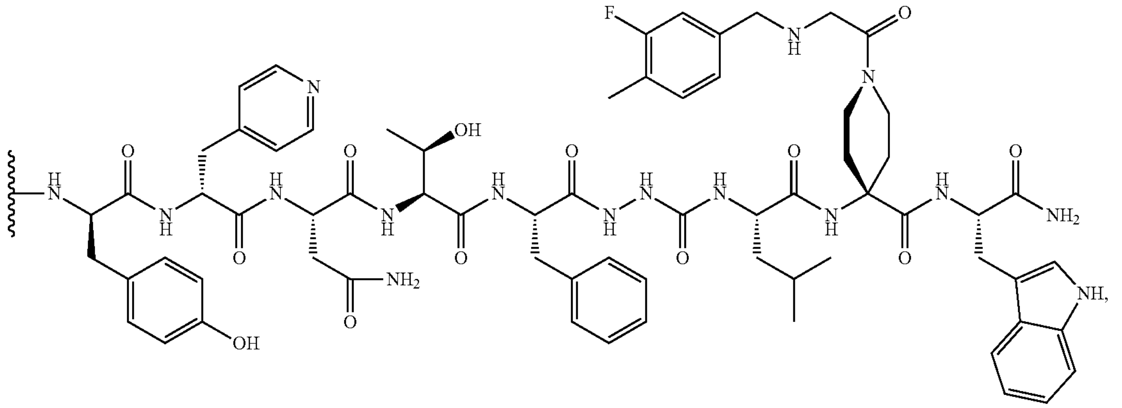
(SEQ ID NO: 76)
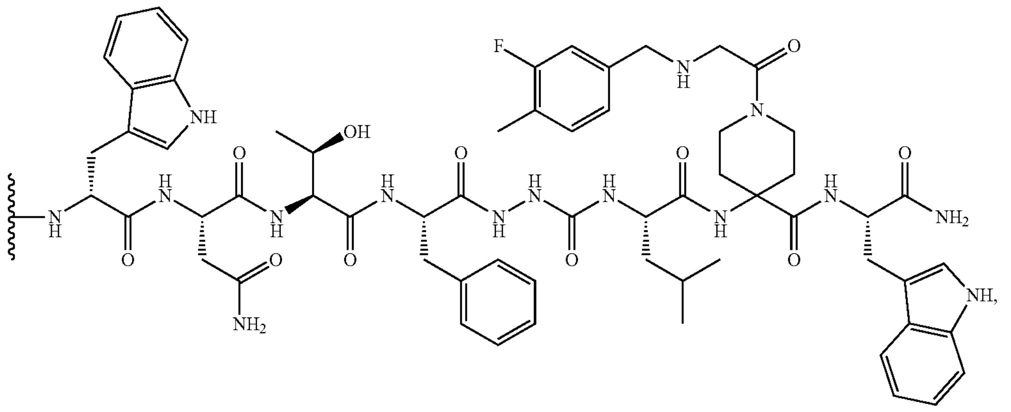

-continued
(SEQ ID NO: 77)
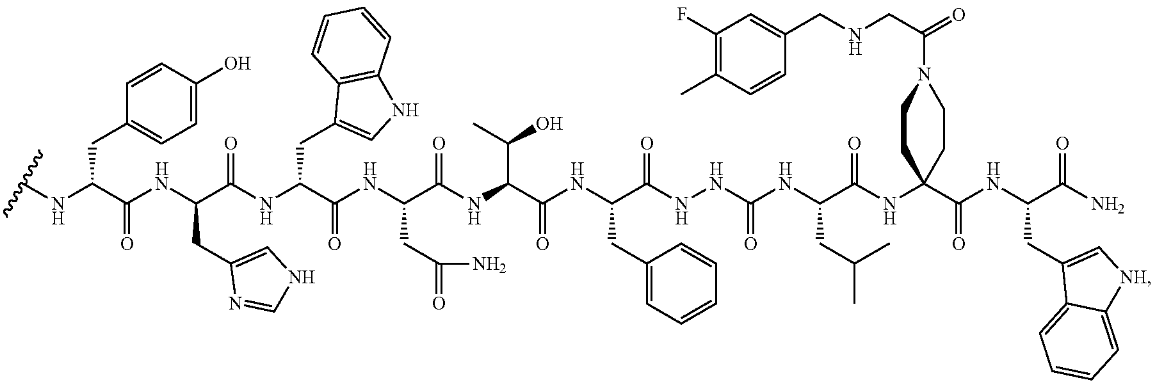
(SEQ ID NO: 78)
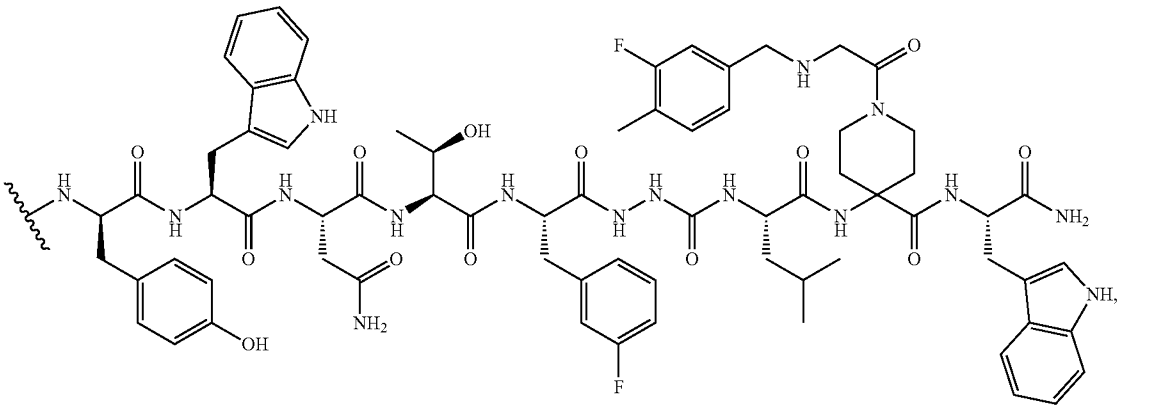
(SEQ ID NO: 79)
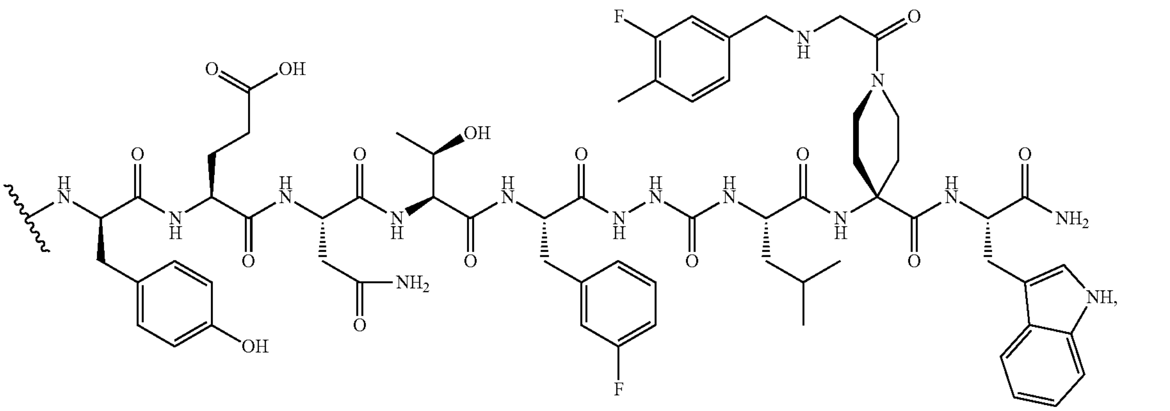

-continued
(SEQ ID NO: 80)
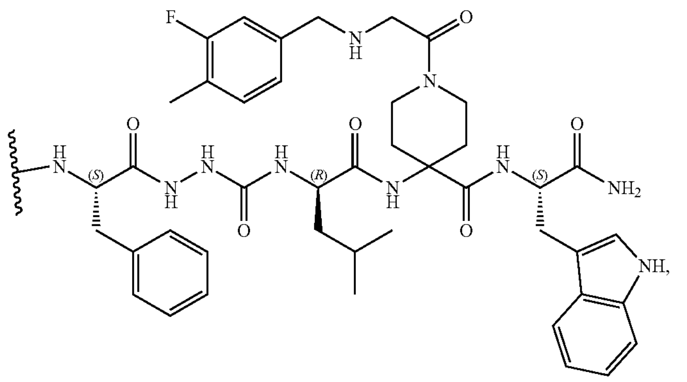
(SEQ ID NO: 81)
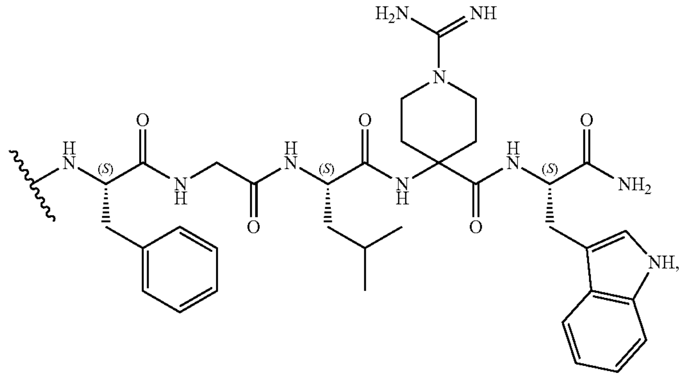
(SEQ ID NO: 82)
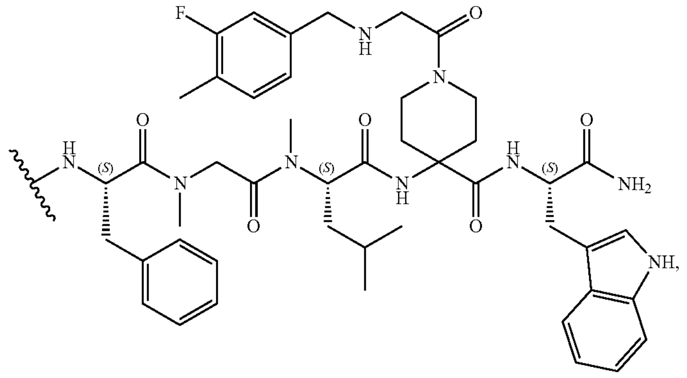
(SEQ ID NO: 83)
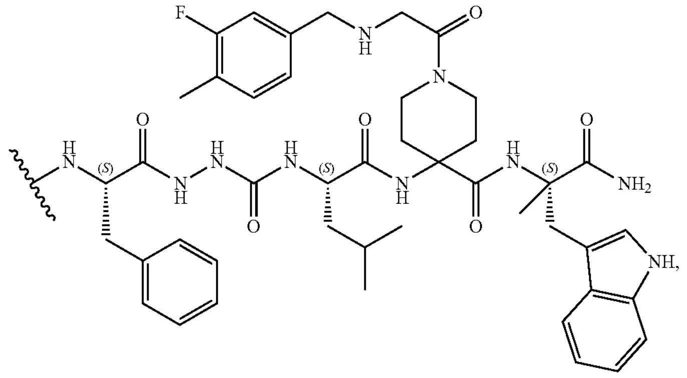

-continued
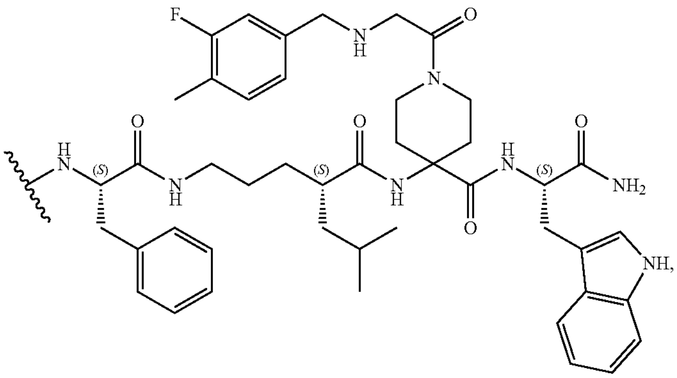
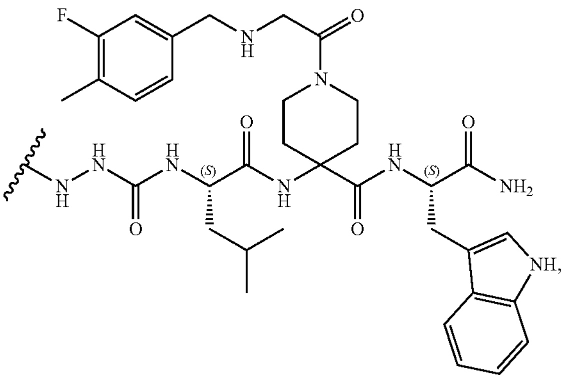
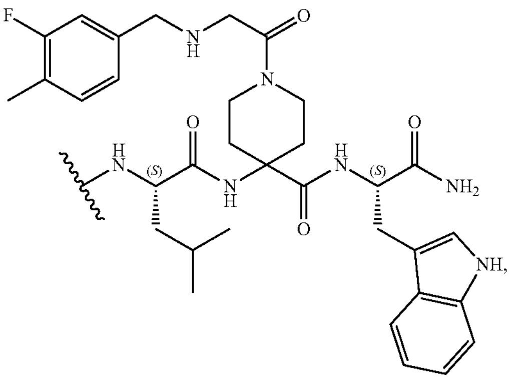
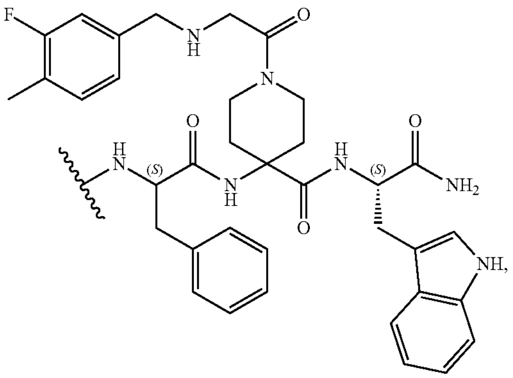
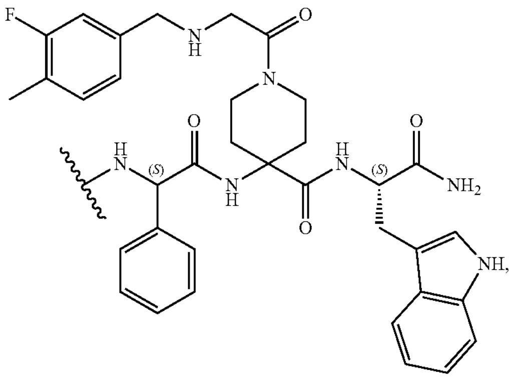
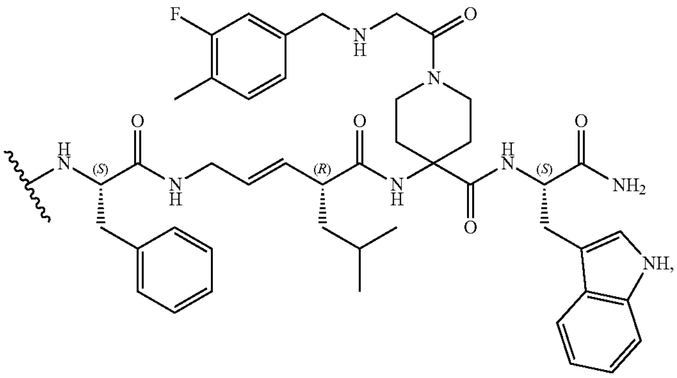

-continued
(SEQ ID NO: 87)
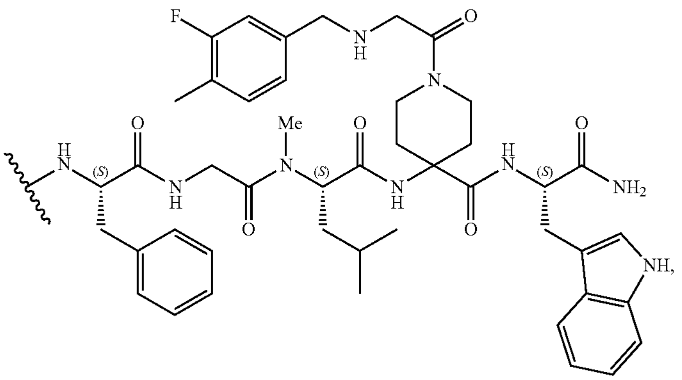
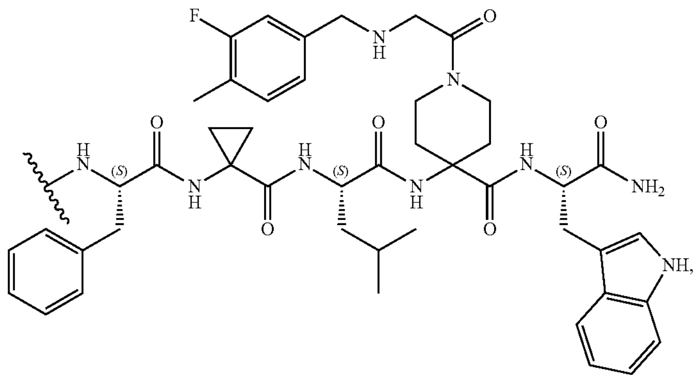
(SEQ ID NO: 89)
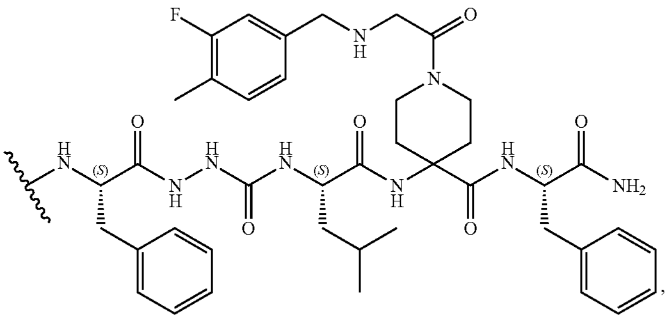
(SEQ ID NO: 90)
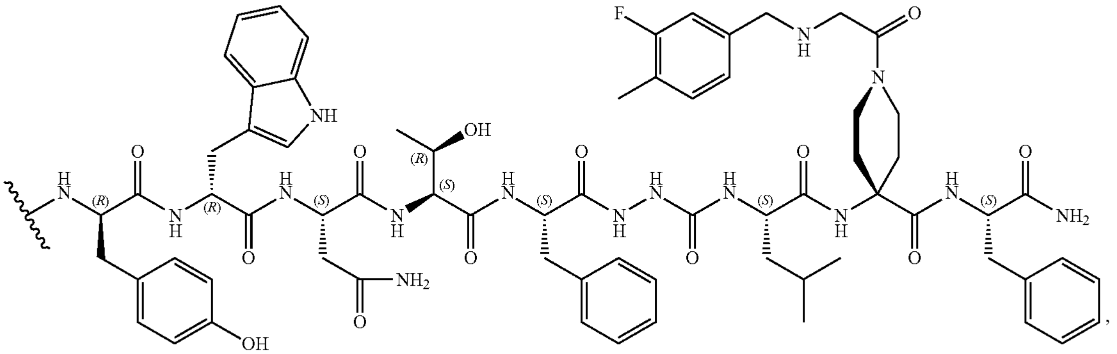

-continued
(SEQ ID NO: 91)
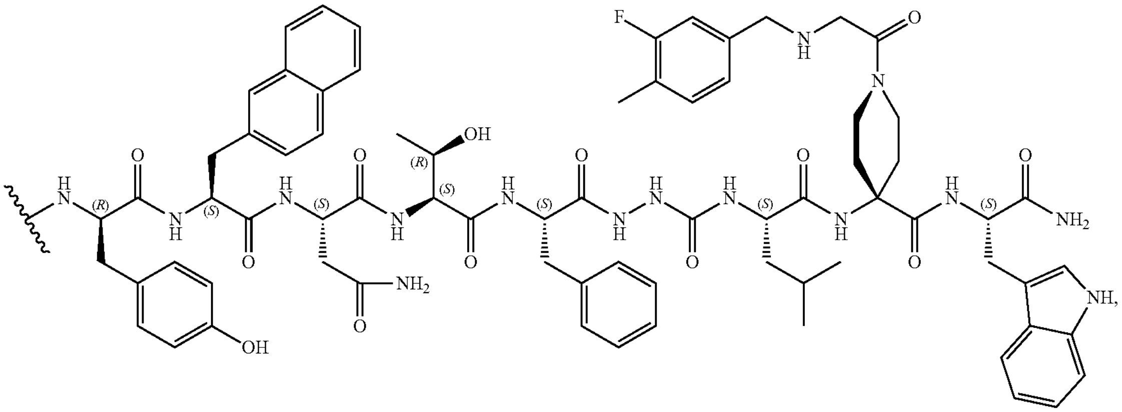
(SEQ ID NO: 92)
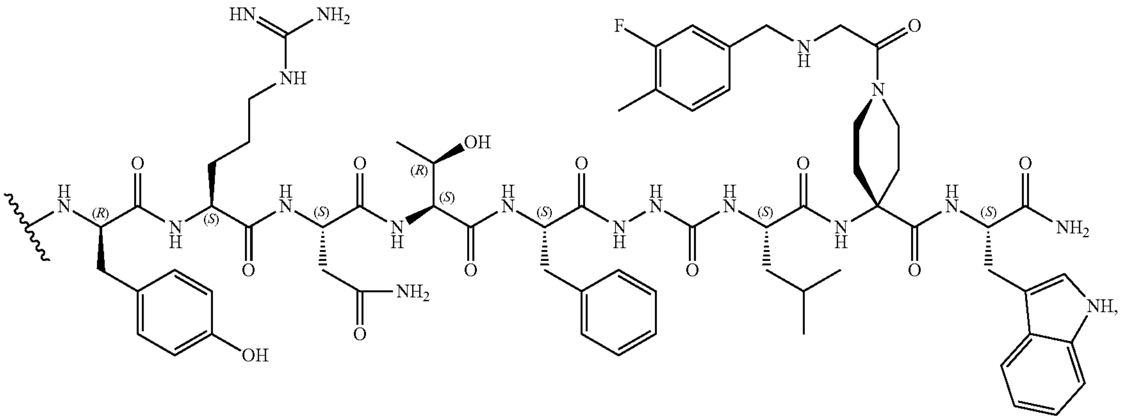
(SEQ ID NO: 93)
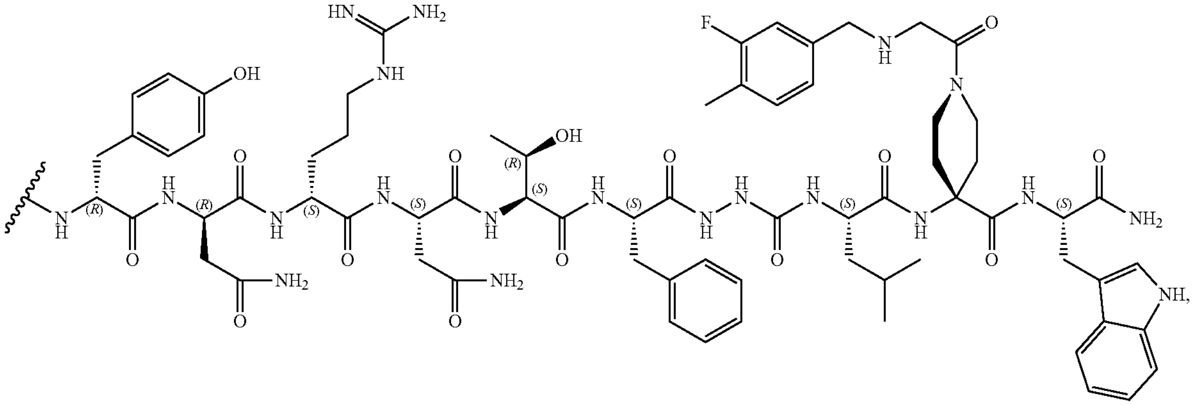

-continued
(SEQ ID NO: 94)
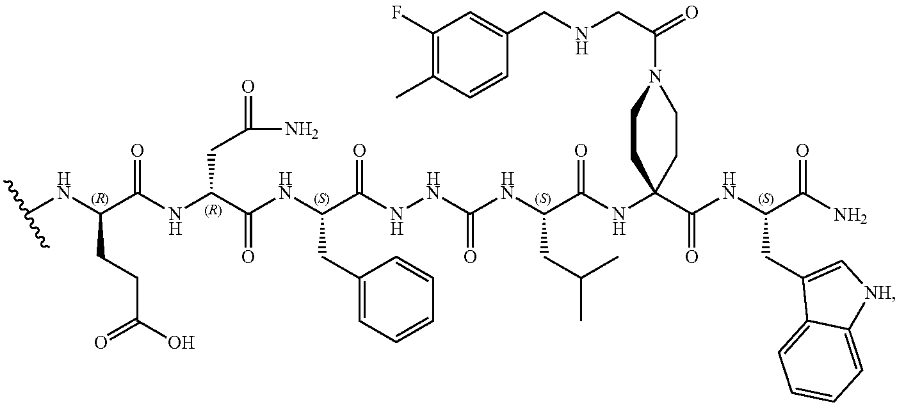
(SEQ ID NO: 95)
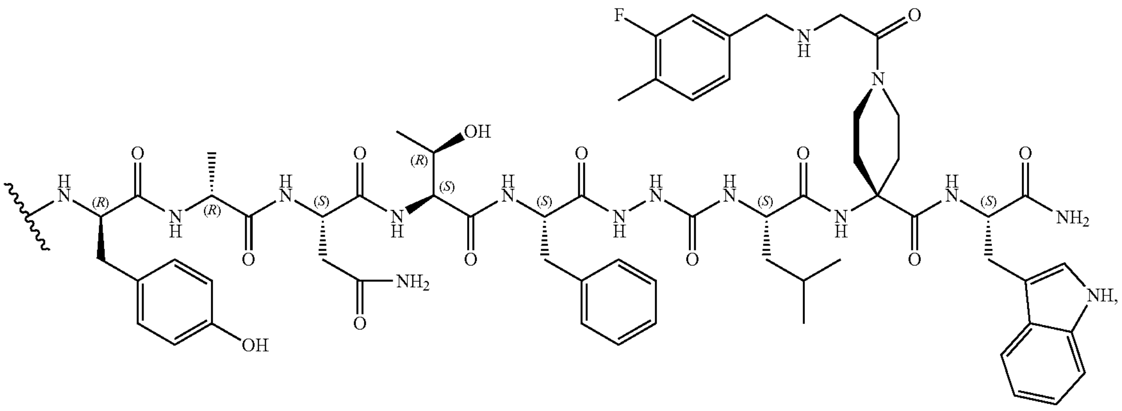
(SEQ ID NO: 96)
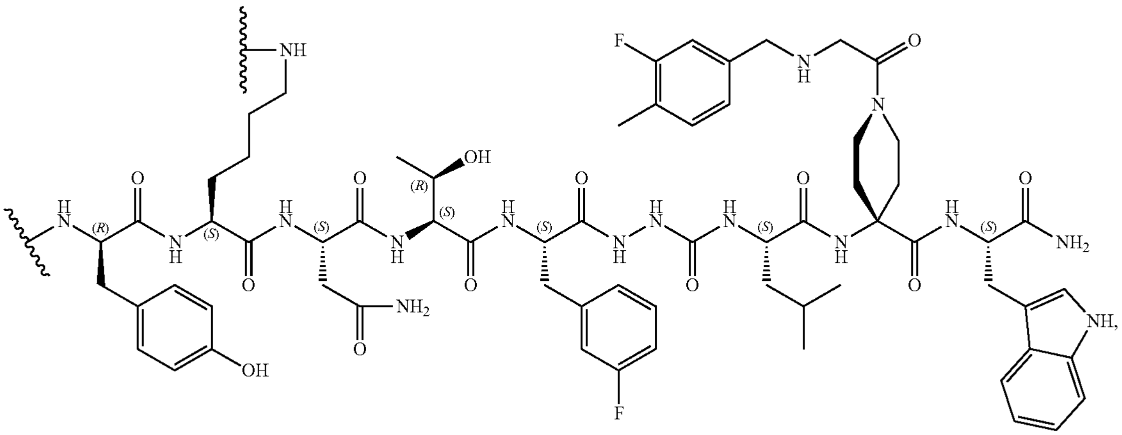

-continued
(SEQ ID NO: 97)
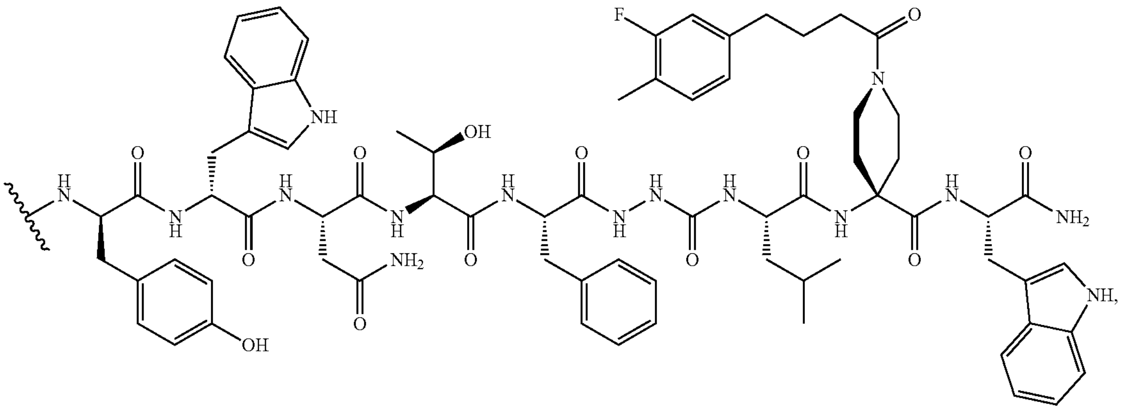
(SEQ ID NO: 98)
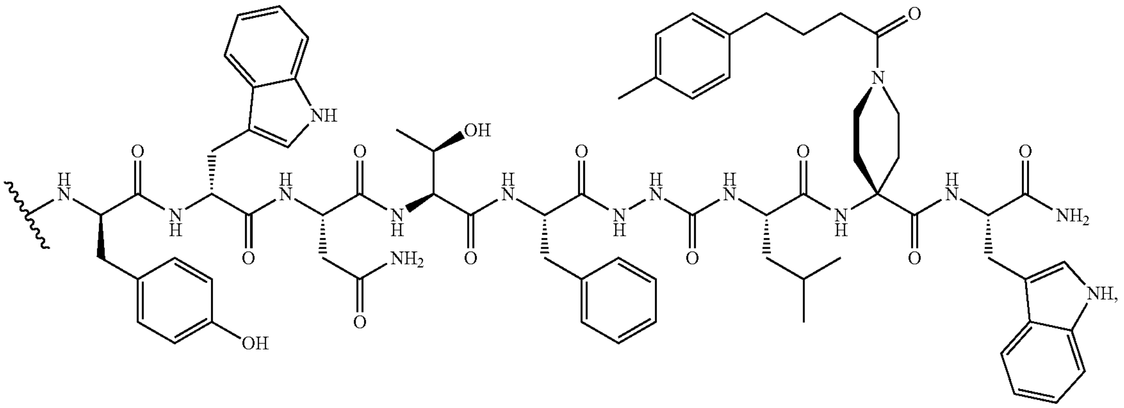
(SEQ ID NO: 99)
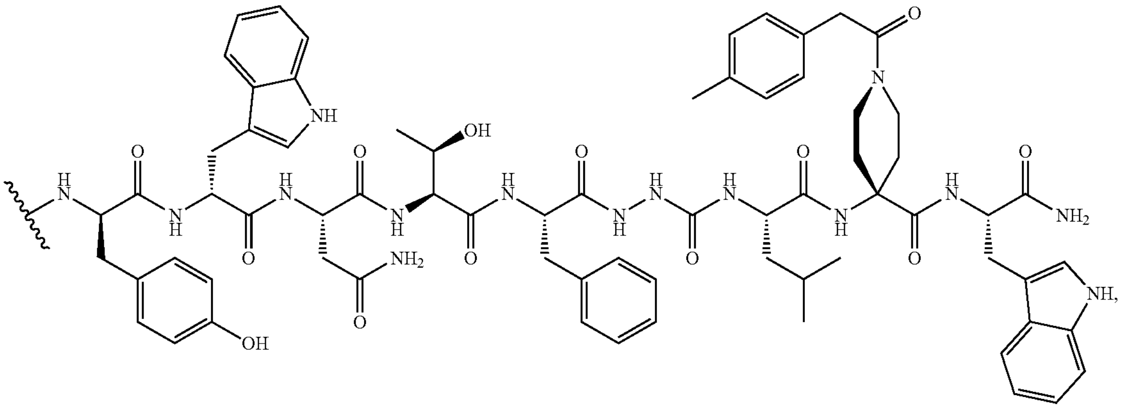

-continued
(SEQ ID NO: 100)
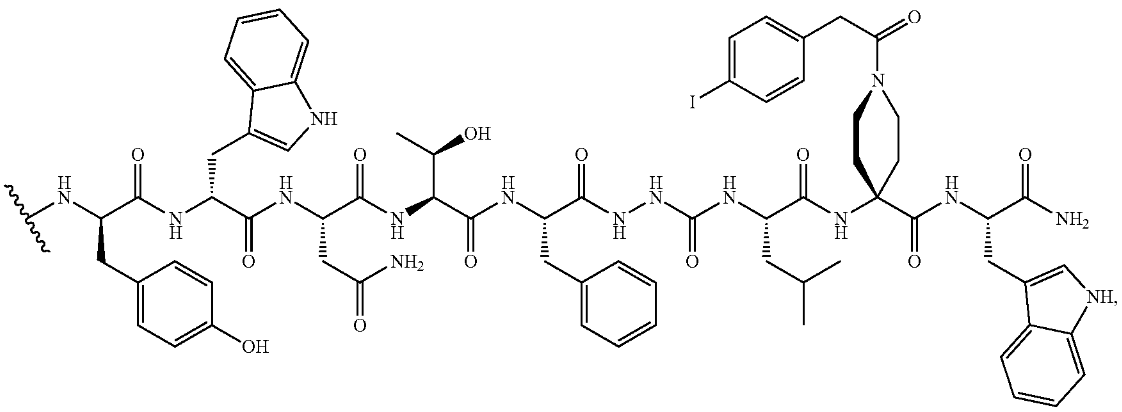
(SEQ ID NO: 101)
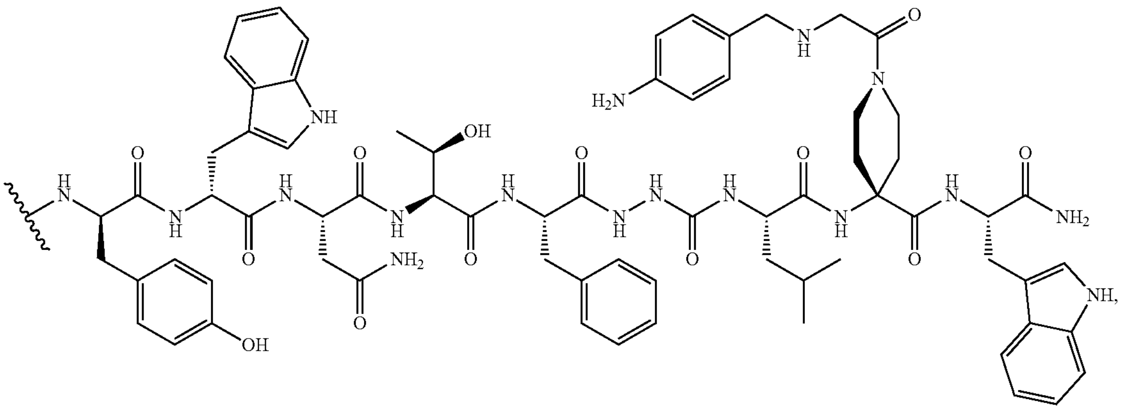
(SEQ ID NO: 102)
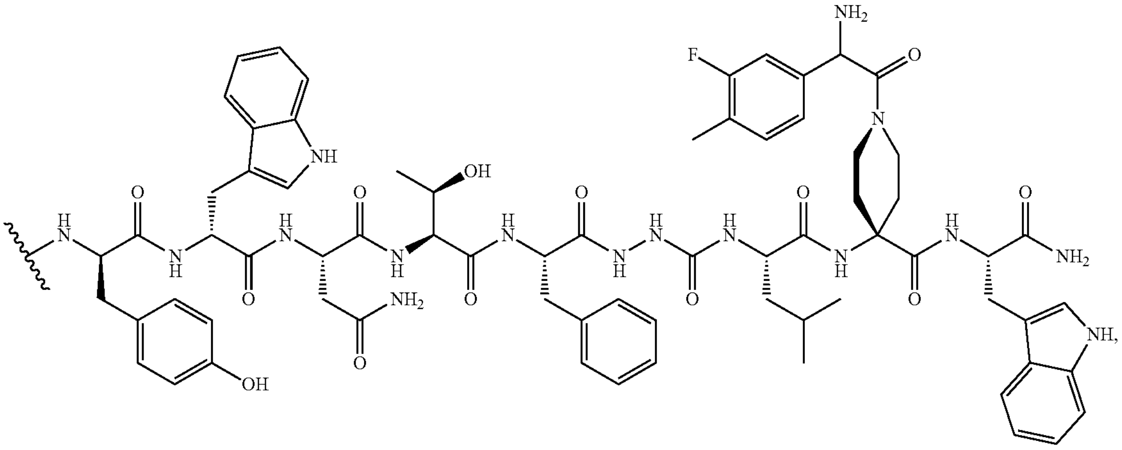

-continued
(SEQ ID NO: 103)
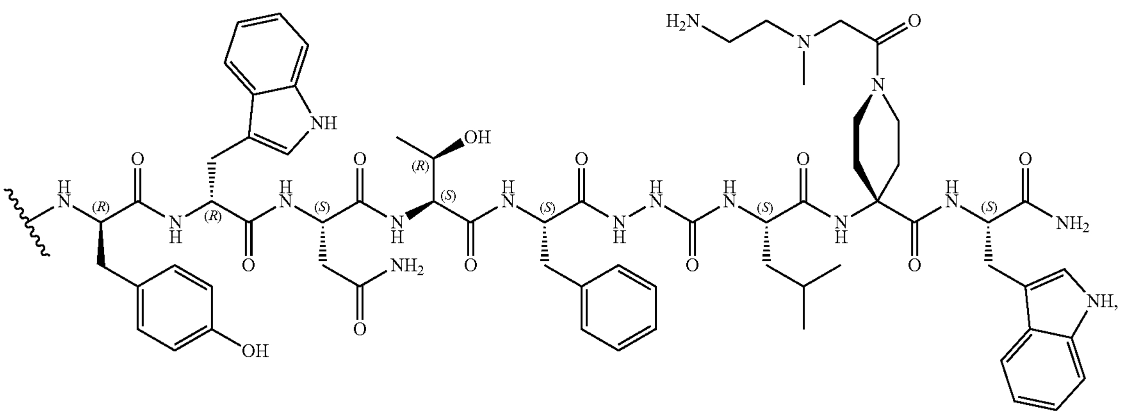
(SEQ ID NO: 104)
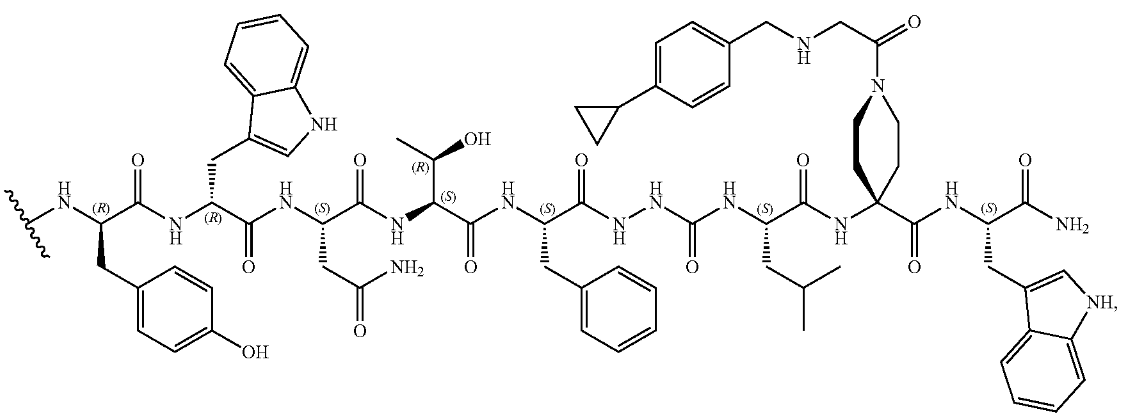
(SEQ ID NO: 105)
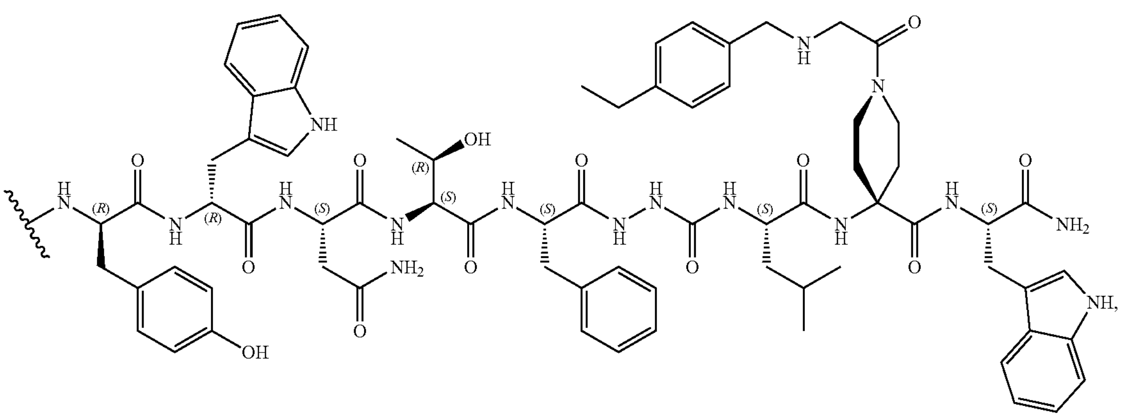

-continued
(SEQ ID NO: 106)
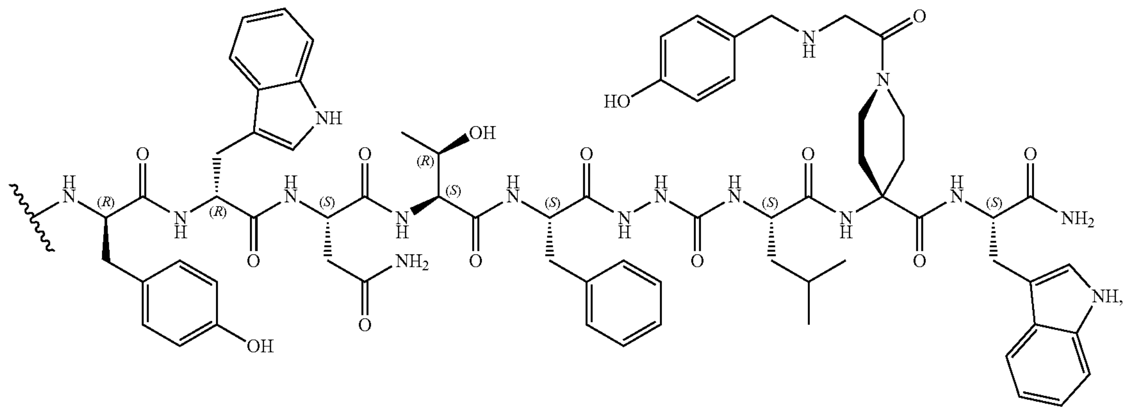
(SEQ ID NO: 107)
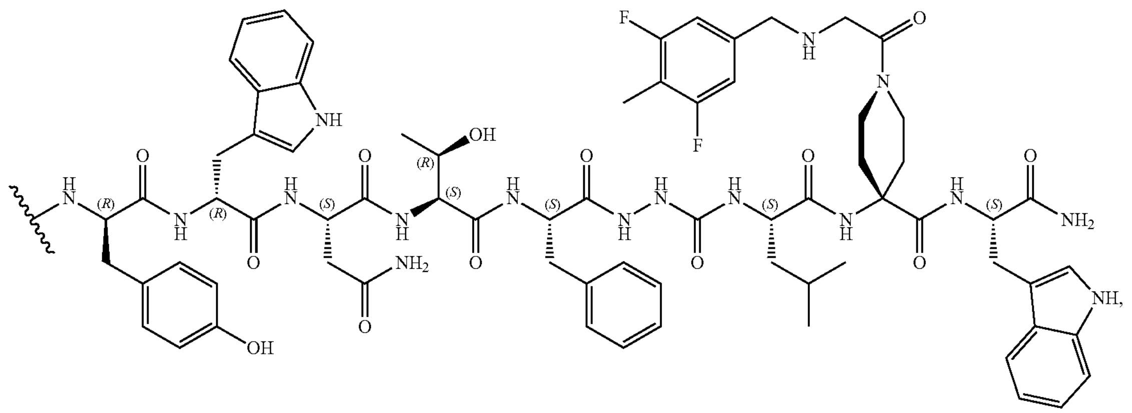
(SEQ ID NO: 108)
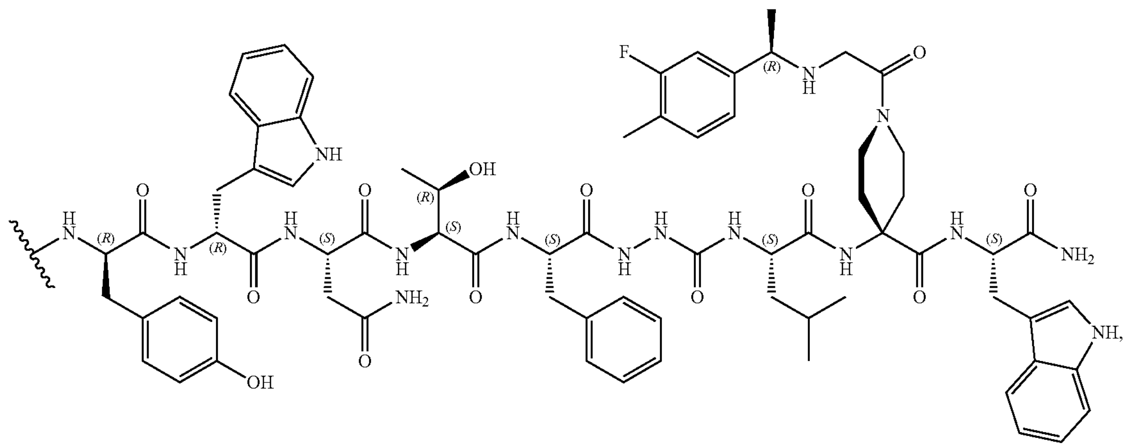

-continued
(SEQ ID NO: 109)
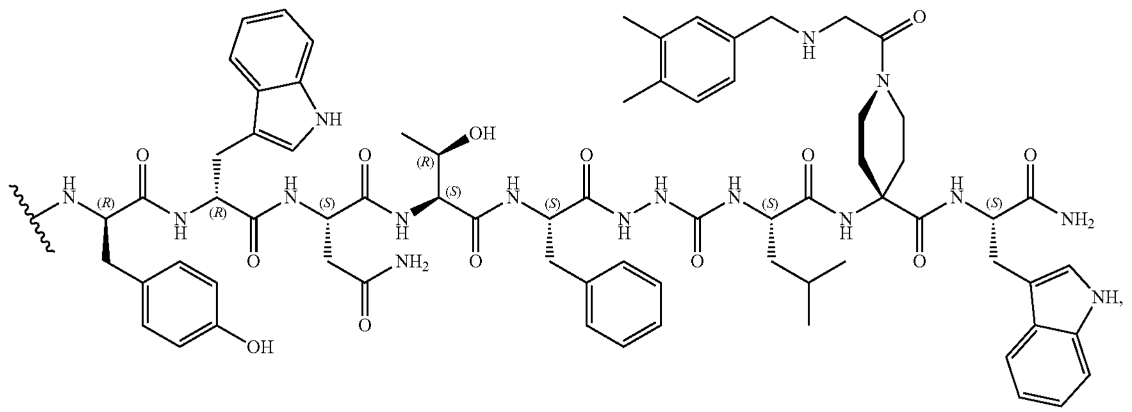
(SEQ ID NO: 110)
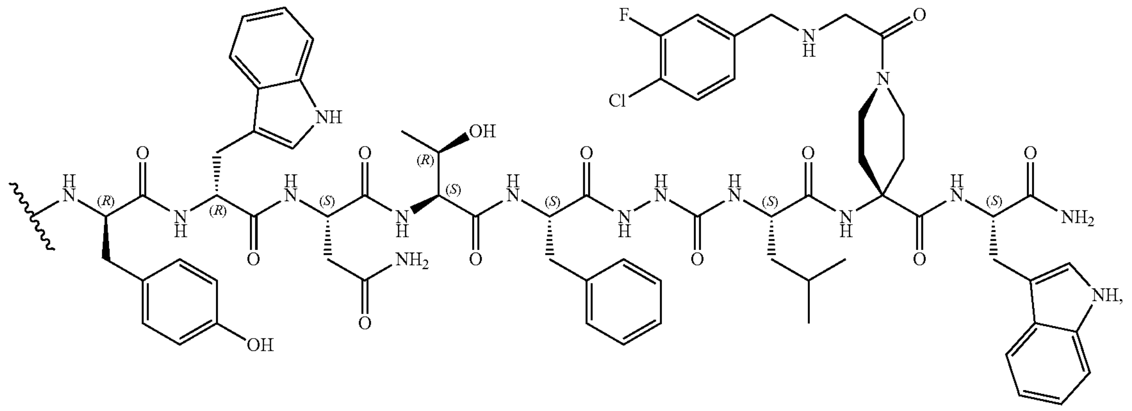
(SEQ ID NO: 111)
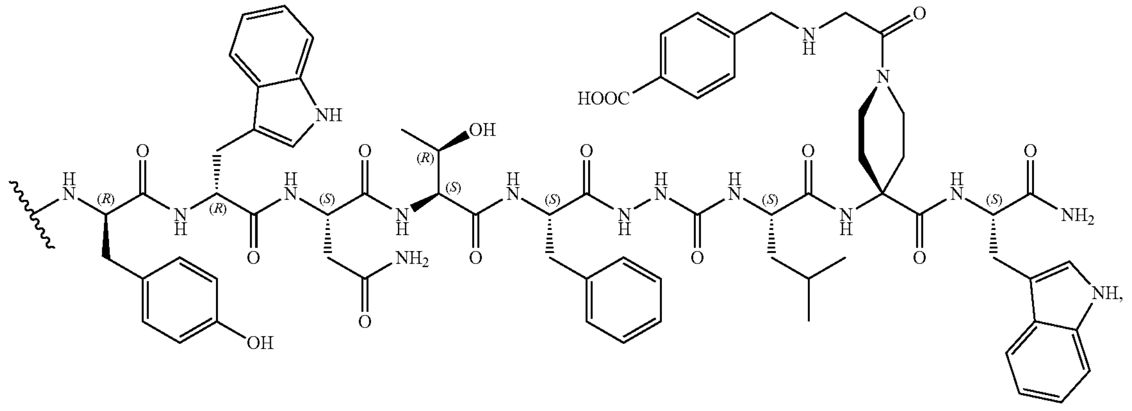

(SEQ ID NO: 112)
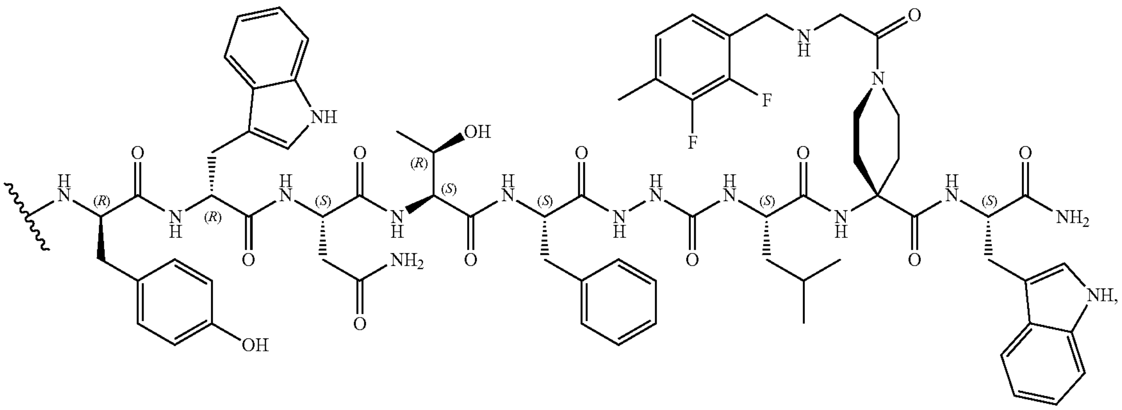
(SEQ ID NO: 113)
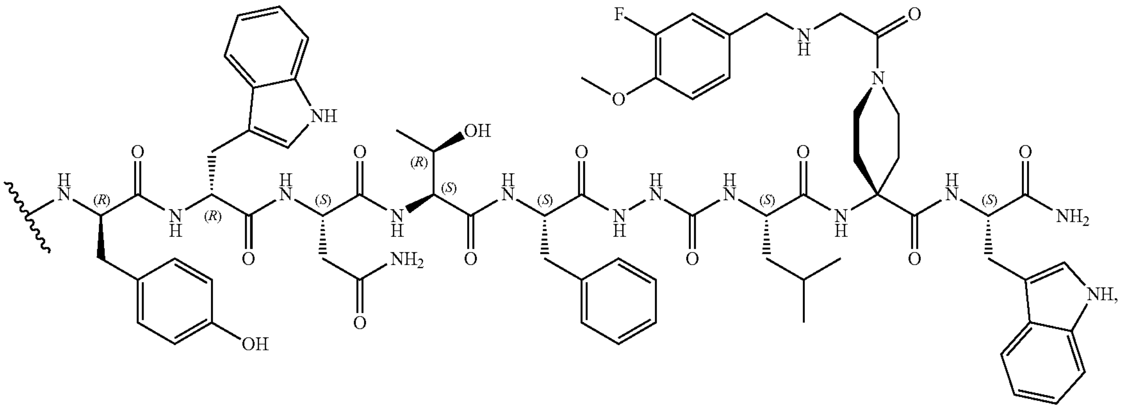
(SEQ ID NO: 114)
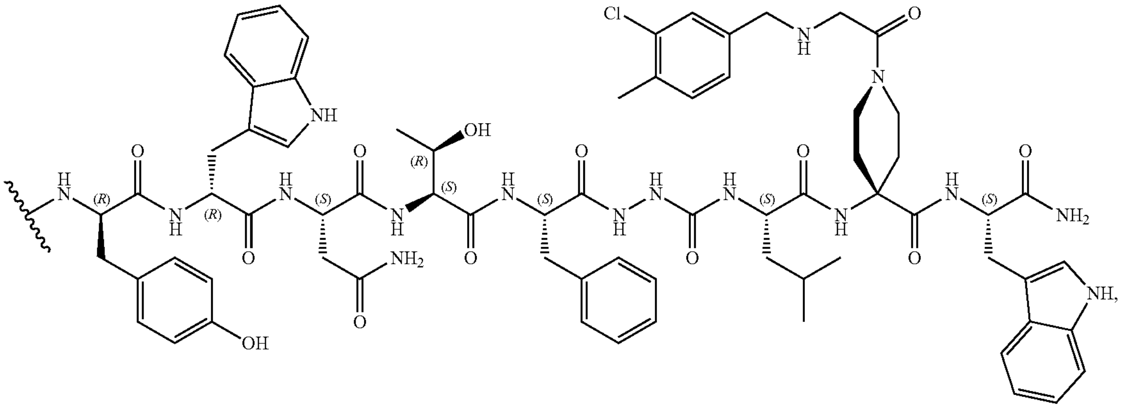

-continued
(SEQ ID NO: 115)
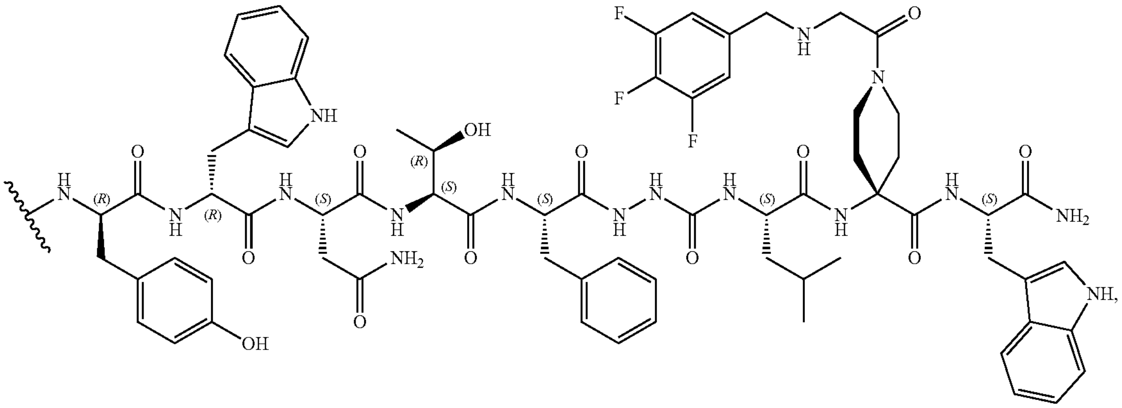
(SEQ ID NO: 116)
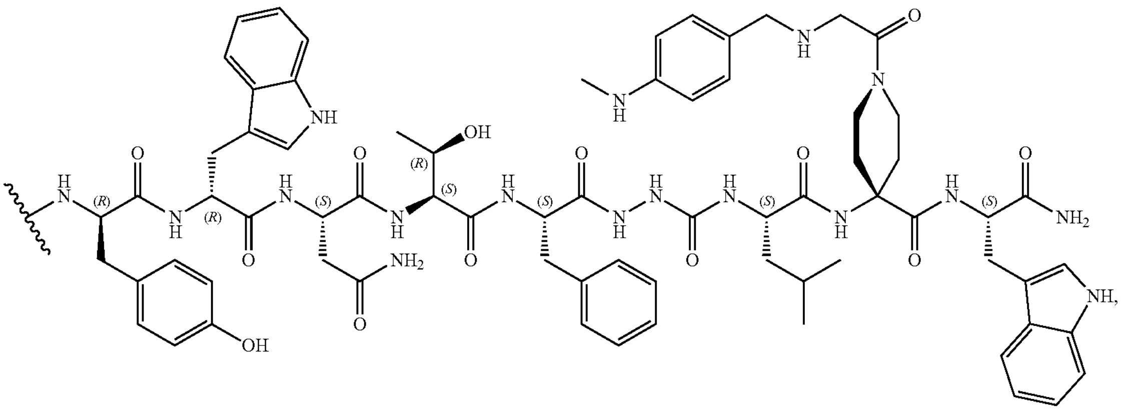
(SEQ ID NO: 117)
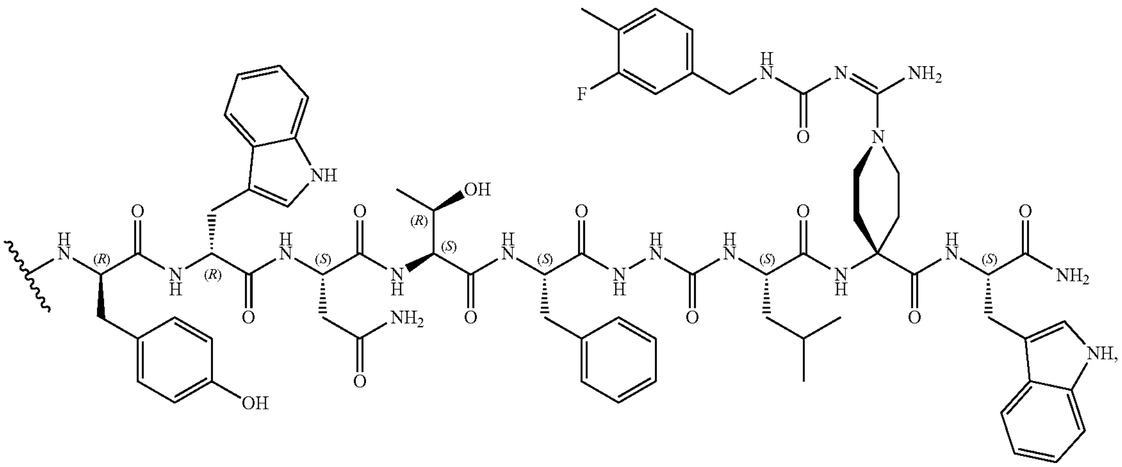

-continued
(SEQ ID NO: 118)
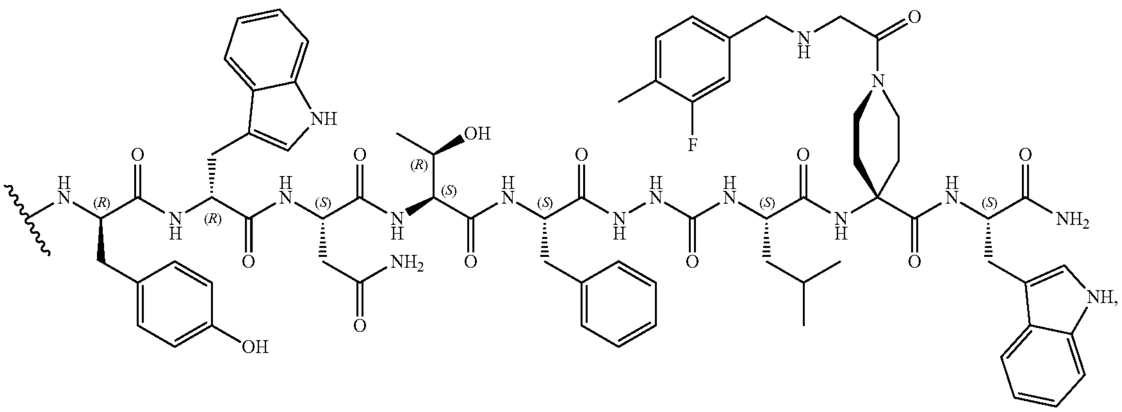
(SEQ ID NO: 120)
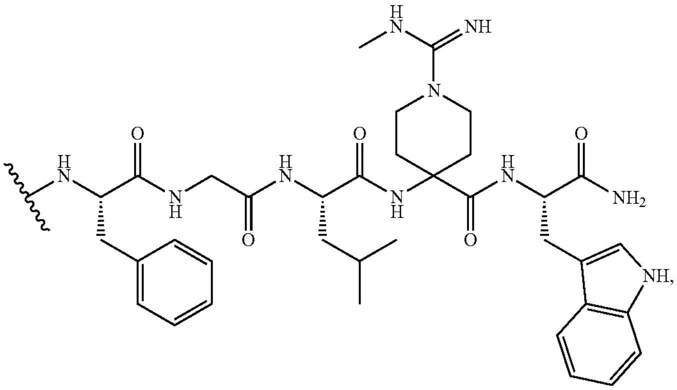
(SEQ ID NO: 119)
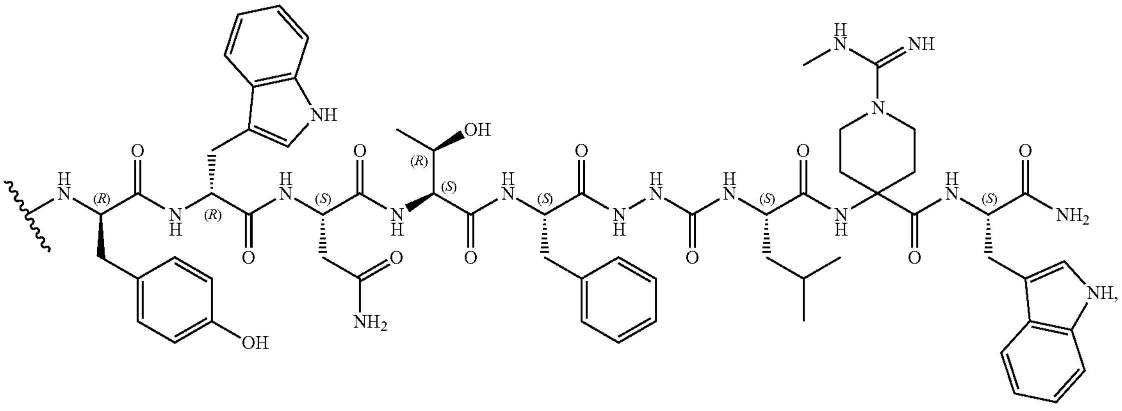

-continued
(SEQ ID NO: 121)
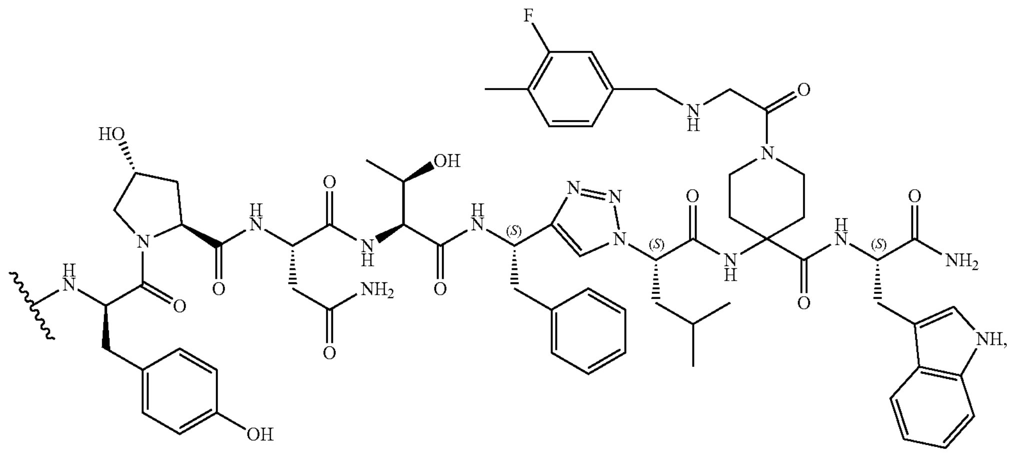
(SEQ ID NO: 122)
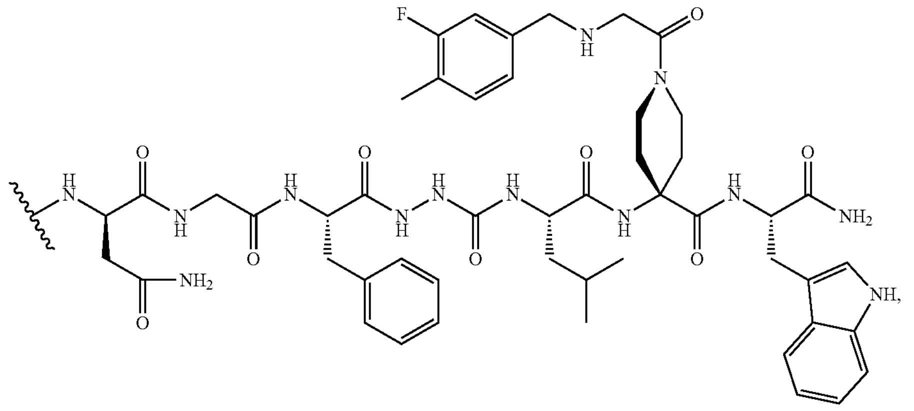
(SEQ ID NO: 123)
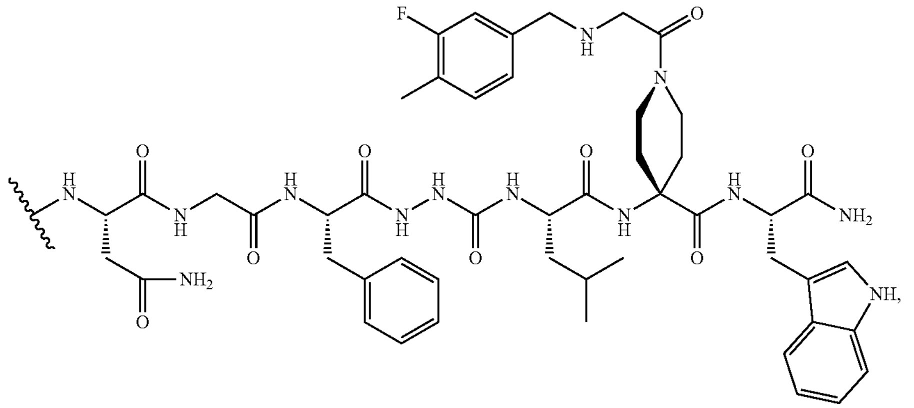

-continued
(SEQ ID NO: 124)
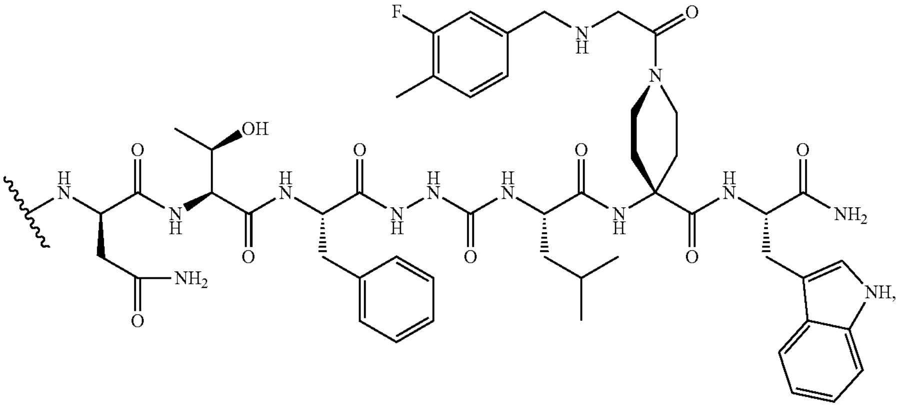
(SEQ ID NO: 127)
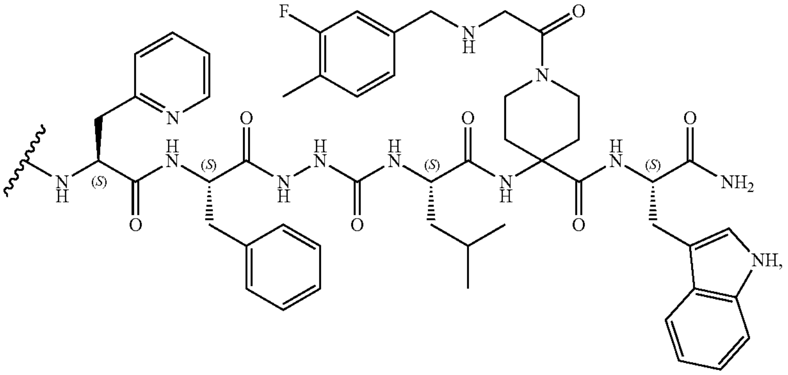
(SEQ ID NO: 125)
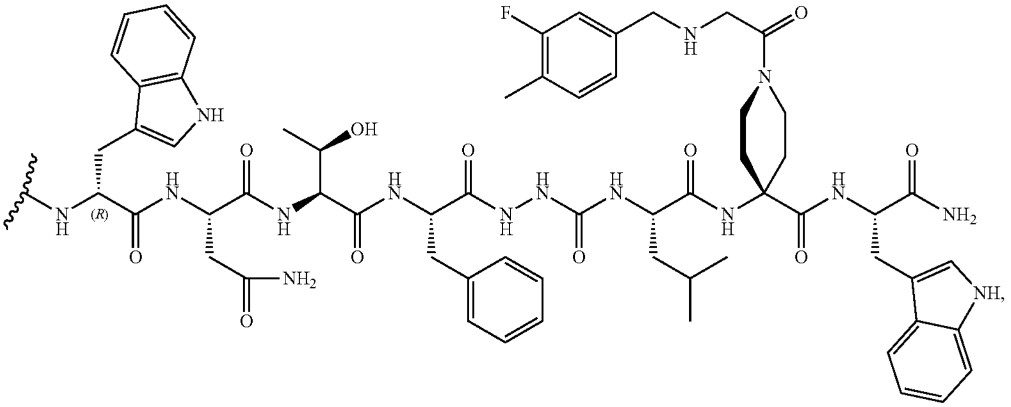
(SEQ ID NO: 126)
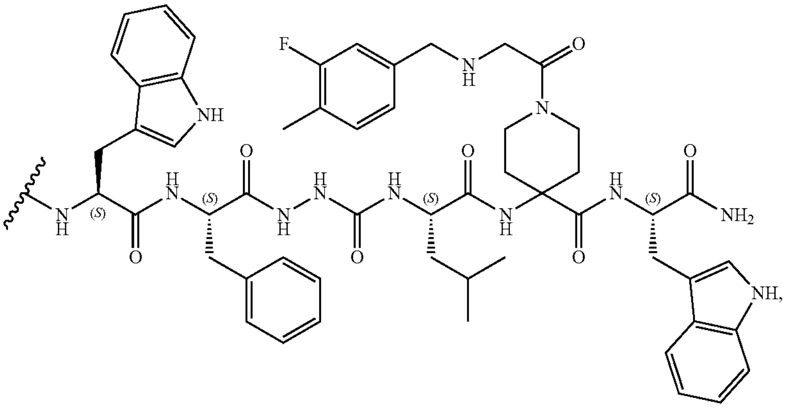

-continued
(SEQ ID NO: 128)
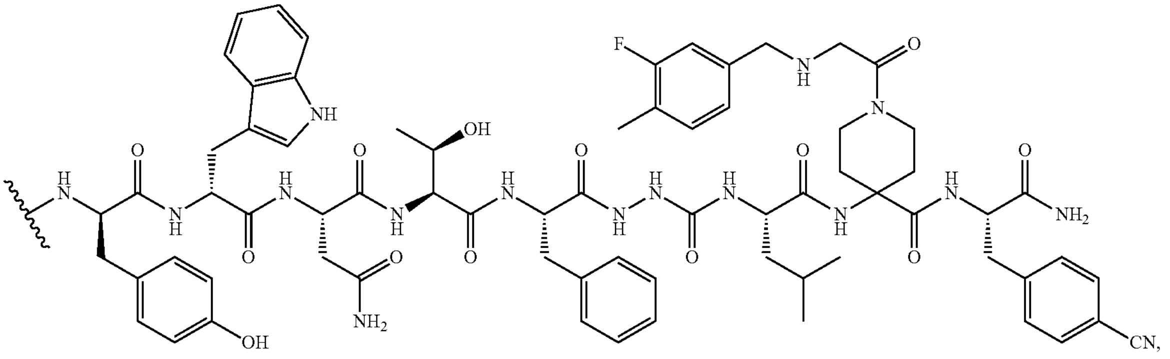
(SEQ ID NO: 129)
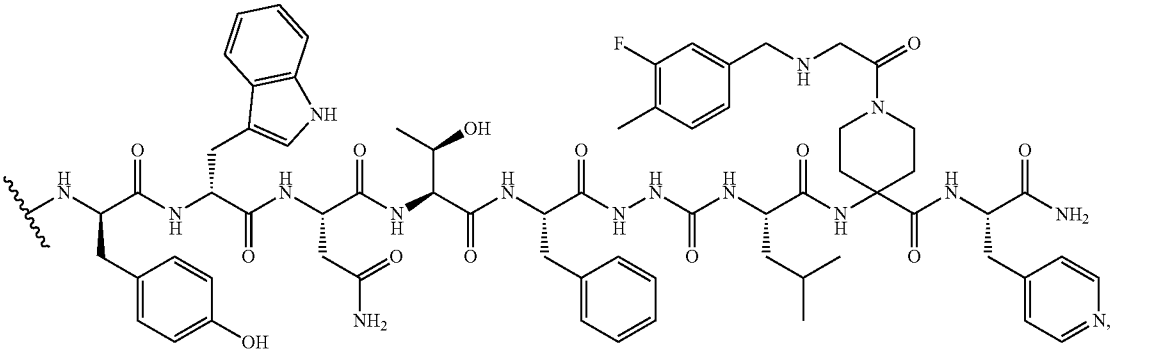
(SEQ ID NO: 130)
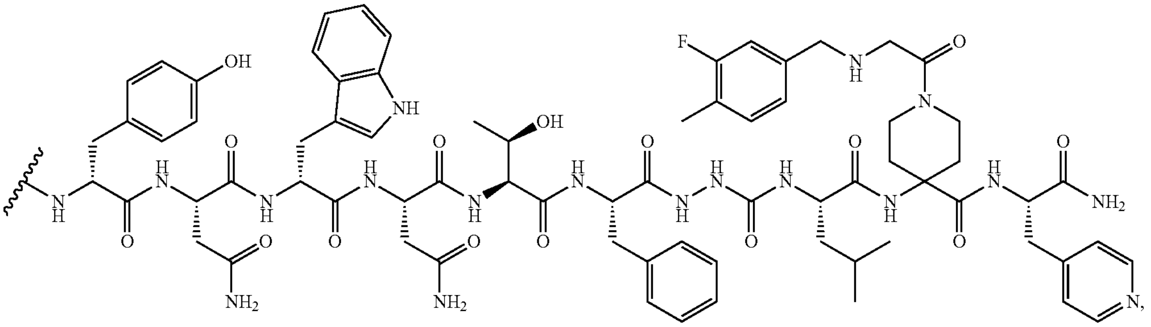
(SEQ ID NO: 131)
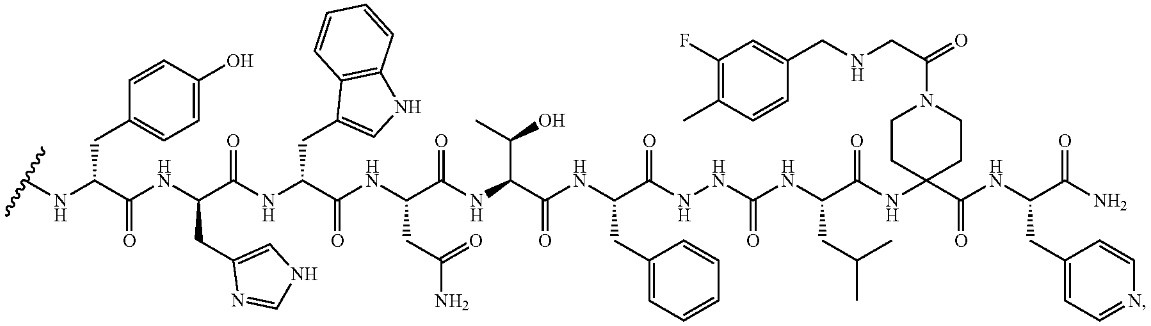

-continued
(SEQ ID NO: 132)
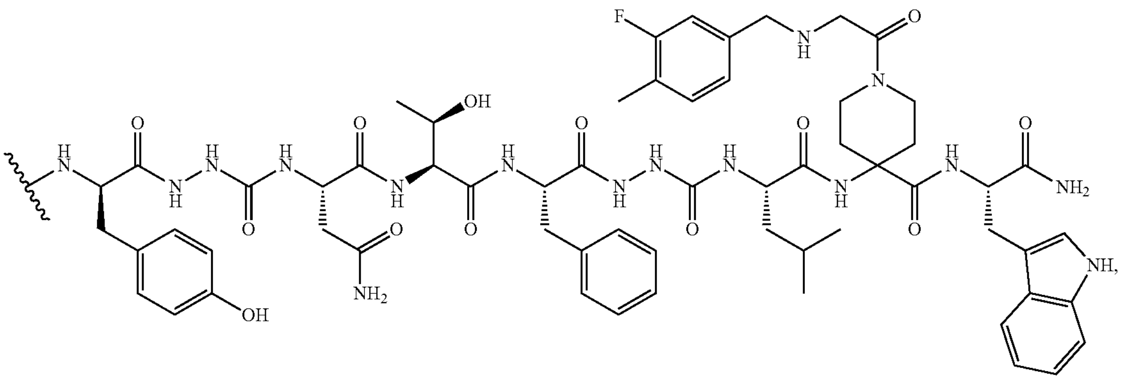
(SEQ ID NO: 133)
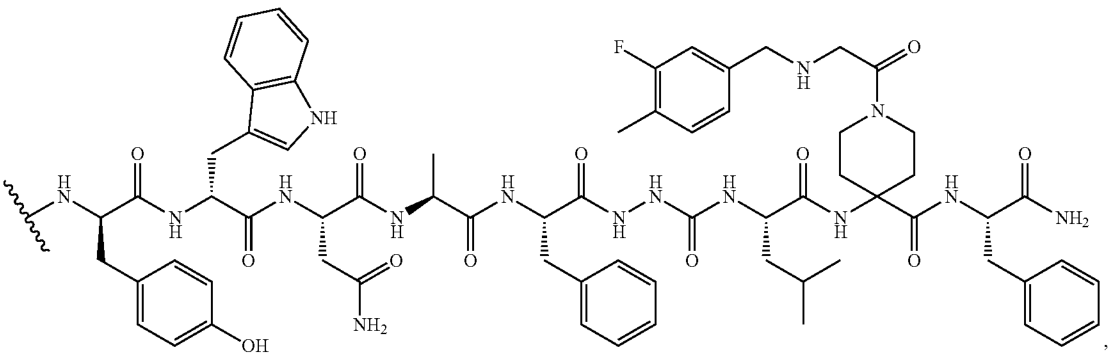
,
(SEQ ID NO: 134)
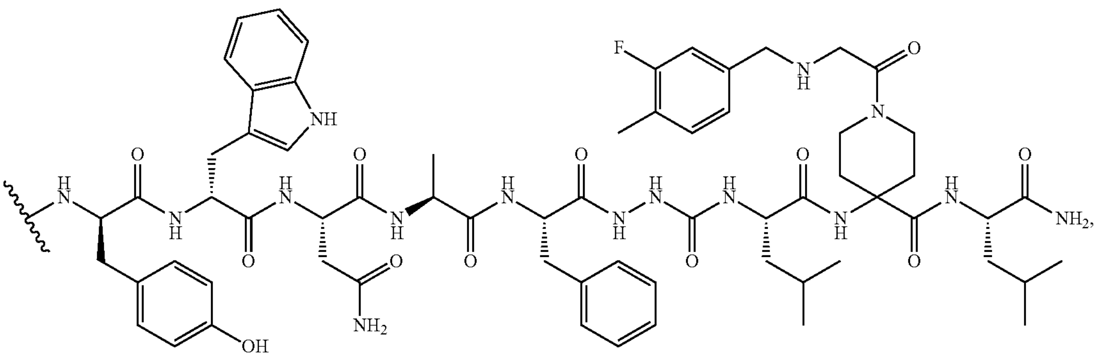
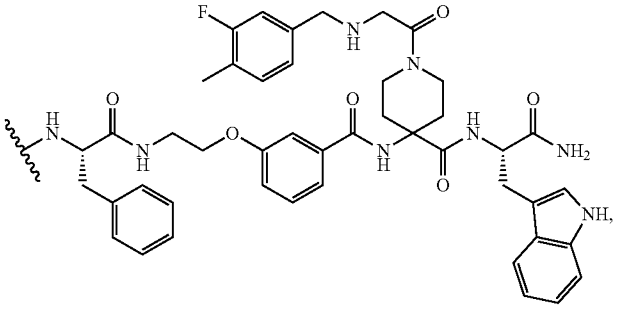
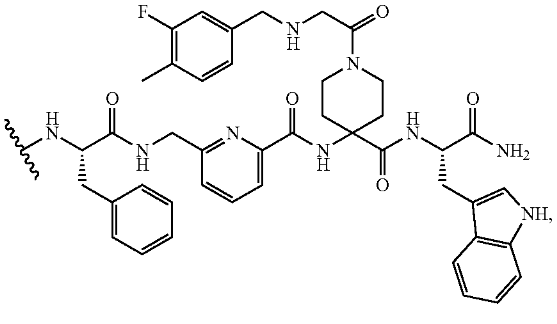

-continued
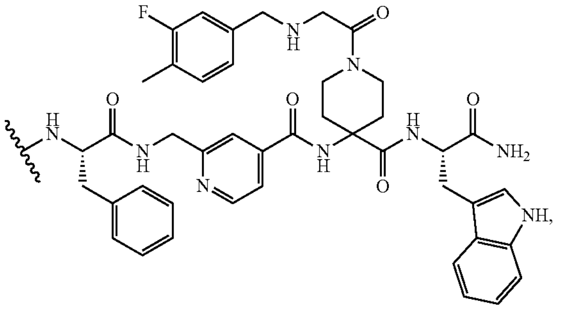
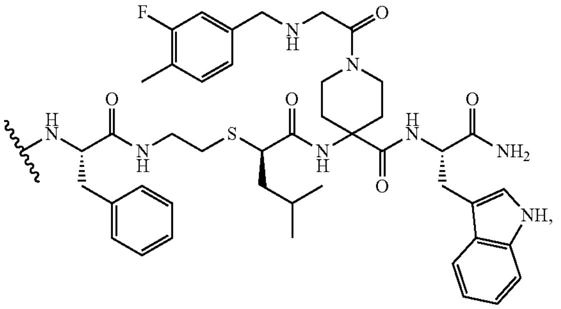
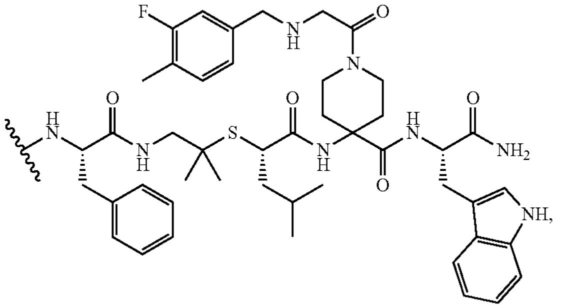
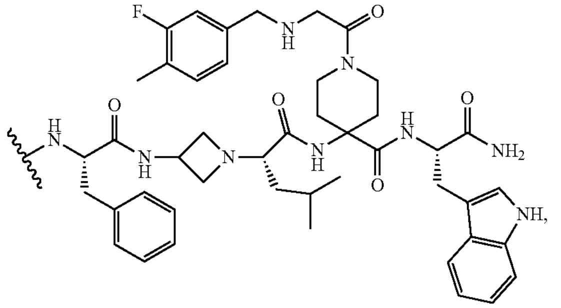
(SEQ ID NO: 141)
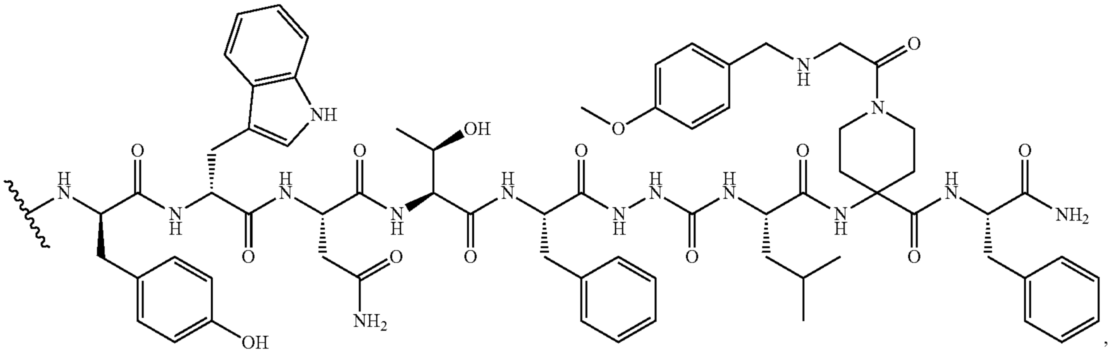
,
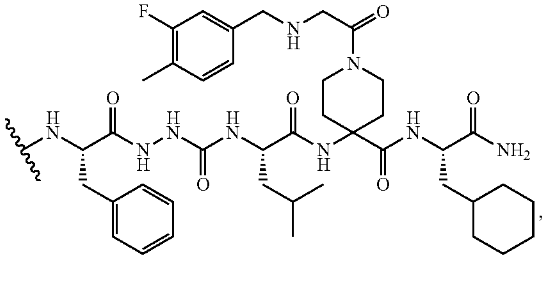
,
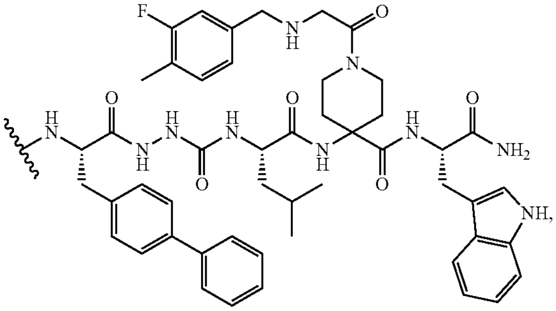
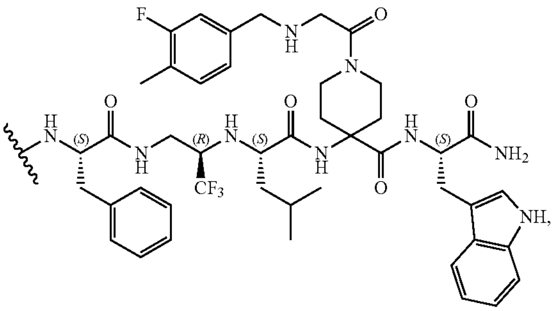
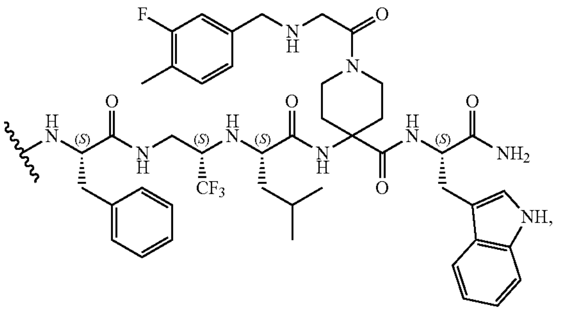

-continued
(SEQ ID NO: 146)
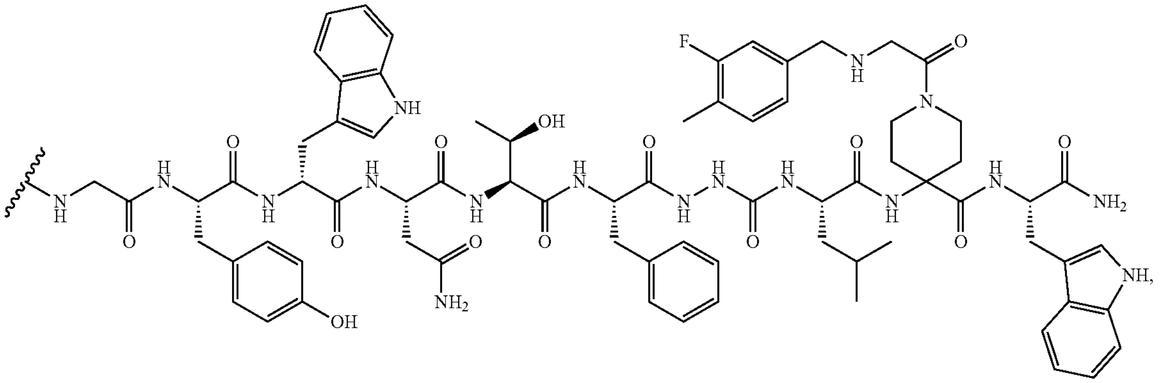
(SEQ ID NO: 147)
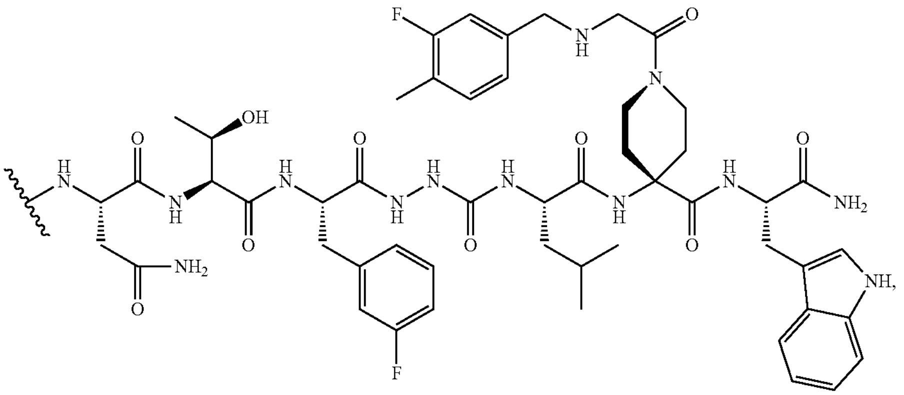
(SEQ ID NO: 148)
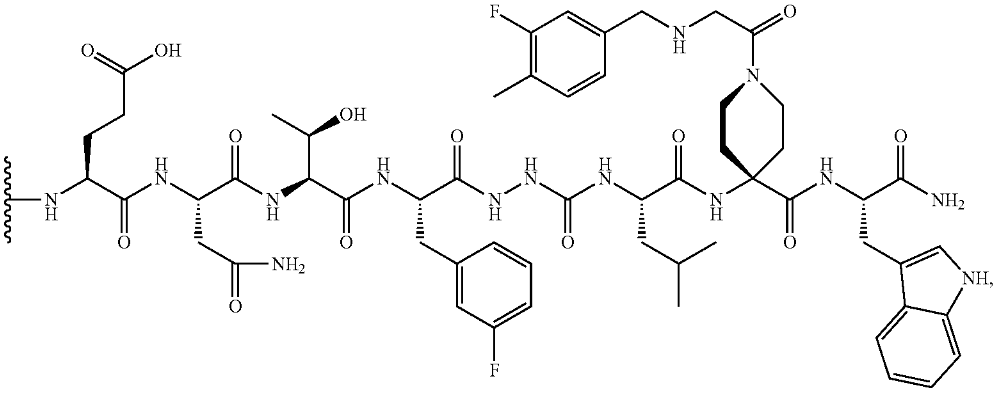

-continued
(SEQ ID NO: 149)
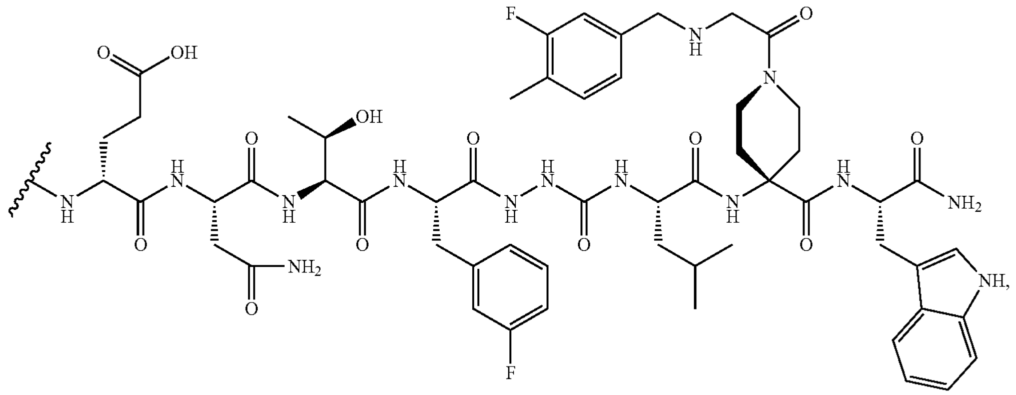
(SEQ ID NO: 150)
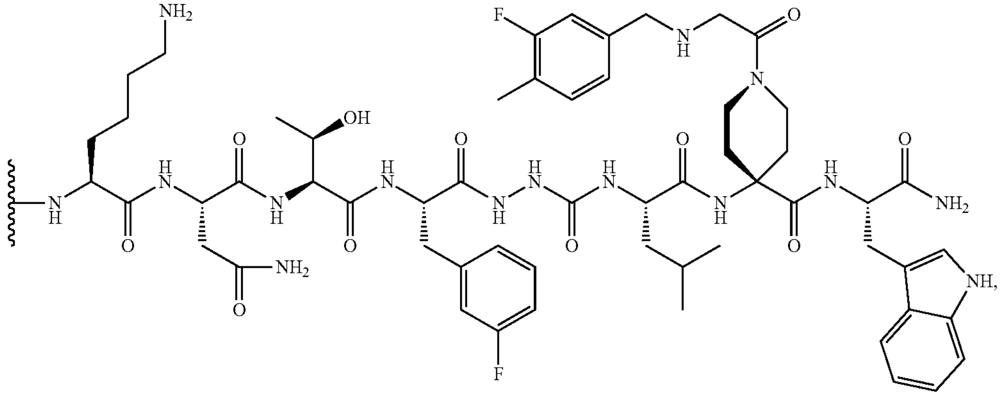
(SEQ ID NO: 151)
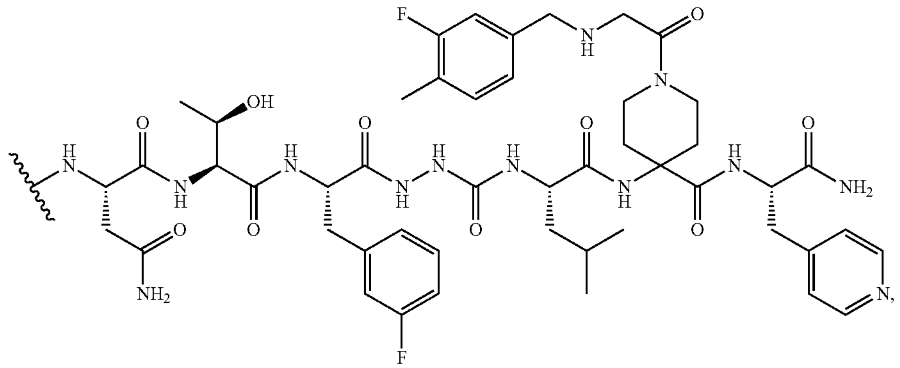
(SEQ ID NO: 152)
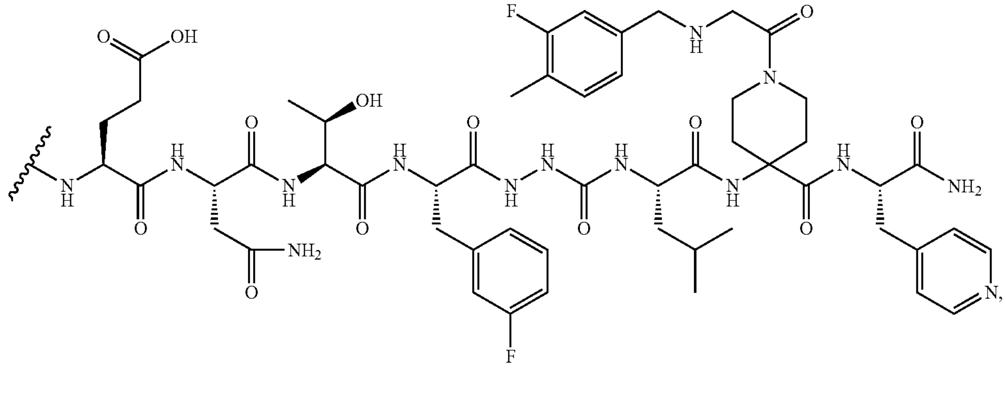

-continued (SEQ ID NO: 153)

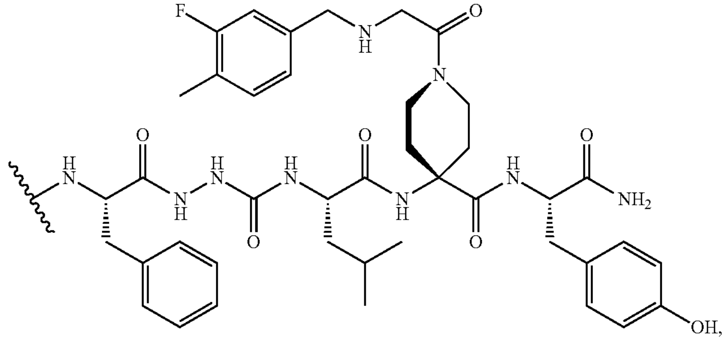

or (SEQ ID NO: 154)

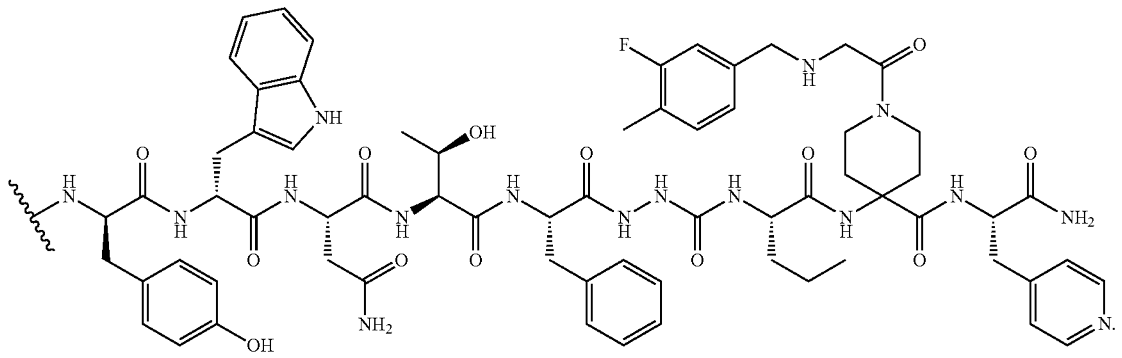

16. The compound of claim 1, or a pharmaceutically acceptable salt thereof, wherein $R^a$ is a chelating moiety independently selected from the group consisting of:

1,4,7,10-tetraazacyclododecane-1,4,7,10-tetraacetic acid (DOTA);

2,2',2"-(10-(2-amino-2-oxoethyl)-1,4,7,10-tetraazacyclododecane-1,4,7-triyl)triacetic acid (PSC);

1,4,7,10-tetraazacyclododecane-1,4,7-triacetic acid (DO3A);

1,4,7,10-tetraazacyclododecane-1,7-diacetic acid (DO2A);

α,α',α",α'"-tetramethyl-1,4,7,10-tetraazacyclododecane-1,4,7,10-tetraacetic acid (DOTMA);

1,4,7,10-tetrakis(carbamoylmethyl)-1,4,7,10-tetraazacyclododecane (DOTAM);

1,4,7,10-tetraazacyclododecane-1,4,7,10-tetrapropionic acid (DOTPA);

2,2',2"-(10-(2-amino-2-oxoethyl)-1,4,7,10-tetraazacyclododecane-1,4,7-triyl)triacetic acid;

benzyl-1,4,7,10-tetraazacyclododecane-1,4,7,10-tetraacetic acid (Bn-DOTA);

p-hydroxy-benzyl-1,4,7,10-tetraazacyclododecane-1,4,7,10-tetraacetic acid (p-OH-Bn-DOTA);

6,6'-((pyridine-2,6-diylbis(methylene))bis((carboxymethyl)azanediyl))bis(methylene))dipicolinic acid ($H_4$pypa);

$H_4$pypa-benzyl;

6,6',6",6'"-(((pyridine-2,6-diylbis(methylene))bis(azanetriyl))tetrakis(methylene)-tetrapicolinic acid ($H_4$py4pa);

$H_4$py4pa-benzyl;

2,2',2"-1,4,7-triazacyclononane-1,4,7-triyl)triacetic acid (NOTA);

6,6'-((1,4,10,13-tetraoxa-7,16-diazacyclooctadecane-7,16-diyl)bis(methylene))dipicolinic acid (macropa);

2,2',2",2'"-(1,10-dioxa-4,7,13,16-tetraazacyclooctadecane-4,7,13,16-tetrayl)tetraacetic acid (crown);

6,6'-((ethane-1,2-diylbis((carboxymethyl)azanediyl))bis(methylene))dipicolinic acid ($H_4$octapa);

$H_4$octapa-benzyl; and 3,6,9,12-tetrakis(carboxymethyl)-3,6,9,12-tetraazatetradecanedioic acid (TTHA);

or a radionuclide complex thereof.

17. The compound of claim 1, or a pharmaceutically acceptable salt thereof, wherein $R^a$ is

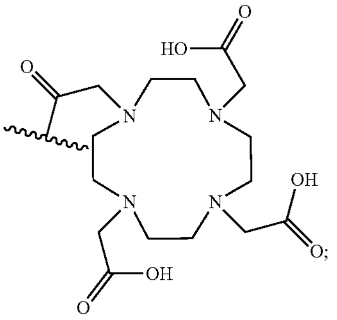 [SMILES: *C(=O)CN1CCN(CC(=O)O)CCN(CC(=O)O)CCN(CC(=O)O)CC1]

or a radionuclide complex thereof.

18. The compound of claim 1, or a pharmaceutically acceptable salt thereof, wherein:

L- is absent, *-$L^1$-, —$NR^{17}$-$L^1$- *—$NR^{17}$-$L^5$-$L^1$, *—$NR^{17}$-$L^5$-C(═O)-$L^1$, *—$NR^{17}$-$L^5$-$NR^{17}$—C(═O)-$L^1$-, *-$L^5$-C(═O)-$L^1$-, *-$L^5$-$L^1$-, *—$NR^{17}$-$L^5$-$NR^{17}$-$L^1$-, *—$NR^{17}$-$L^5$-C(═O)$NR^{17}$-$L^1$-, *-$(L^3)_w$-, *—$NR^{17}$-$L^5$-C(═O)-$L^3$-$NR^{17}$-$L^5$-C(═O)—, or *-$(L^3)_w$-$NR^{17}$-$L^5$-C(═O)-$L^1$-;

wherein * denotes the attachment point to $R^a$;

$L^5$ is substituted or unsubstituted $C_1$-$C_6$ alkylene;

or $L^5$ and $R^{17}$ are taken together with the N atom to which they are attached to form N-heterocyclyl;

$R^{17}$ is selected from hydrogen, $C_1$-$C_6$ alkyl, $C_1$-$C_6$ alkyl-$CO_2H$, —$(CH_2CH_2O)_z$—$CH_2CH_2$—$CO_2H$;

$L^1$ is absent or -$L^2$-, -$L^2$-$(^3)_w$-, -$(L^3)_w$-$L^2$-, or -$L^2$-$(L^3)_w$;

each $L^2$ is independently absent, —$C_0$-$C_6$ alkylene-(substituted or unsubstituted aryl)-$C_0$-$C_6$ alkylene-C(═O)—, —$C_0$-$C_6$ alkylene-(substituted or unsubstituted arylene)-$C_0$-$C_6$alkylene-OC(═O)—, —$C_0$-$C_0$alkylene-(substituted or unsubstituted cyclohexylene)-$C_0$-$C_6$alkylene-C(═O)—, —$C_0$-$C_6$ alkylene-(substituted or unsubstituted heterocycloalkylene)-$C_0$-$C_6$ alkylene-C(═O)—, —$C_0$-$C_6$ alkylene-(substituted or unsubstituted heteroarylene)-$C_0$-$C_6$ alkylene-C(═O)—, —$C_0$-$C_6$ alkylene-(substituted or unsubstituted heteroarylene)-$C_0$-$C_6$ alkylene-OC(═O)—, —$C_4$-$C_{20}$ polyethylene glycol, —$C_4$-$C_{20}$ polyethylene glycol-C(═O)—, substituted or unsubstituted —$C_1$-$C_{20}$ alkylene, substituted or unsubstituted —$C_1$-$C_{20}$ alkylene-C(═O)—, substituted or unsubstituted 2 to 20 membered heteroalkylene, —$(CH_2CH_2O)_z$—$CH_2$—, —$(CH_2CH_2O)_z$—$CH_2CH_2$—, —$(CH_2CH_2O)_z$—$CH_2$—C(═O)—, or —$(CH_2CH_2O)_z$—$CH_2CH_2$—C(═O)—;

each z, is independently 1, 2, 3, 4, 5, or 6;

each $L^3$ is independently selected from natural or unnatural amino acids, wherein any free amine of an amino acid or peptide bond is optionally independently substituted with $L^4$, and wherein when two or more amino acids are present then the N atom of the amide linking the amino acids is optionally substituted with —$CH_3$;

each $L^4$ is independently selected from —C(═O)—$C_1$-$C_6$ alkylene-C(═O)—, —C(═O)—NH—$C_1$-$C_6$ alkylene-C(═O)—, and —C(═O)—$C_1$-$C_6$ alkylene-(substituted or unsubstituted triazolylene)-$C_1$-$C_6$alkylene-C(═O)—; wherein if $L^4$ is present then: $L^4$ is attached to the any one of $X^1$, $X^2$, $X^3$, $X^4$, $X^5$, $X^6$, or $X^7$, or $L^4$ is attached to $X^8$ if $X^1$, $X^2$, $X^3$, $X^4$, $X^5$, $X^6$, and $X^7$ are absent; and each w is independently 1, 2, 3, 4, 5, or 6.

19. The compound of claim 18, or a pharmaceutically acceptable salt thereof, wherein:

-L- is absent, *—$NR^{17}$—, *—$NR^{17}$-$L^5$, *—$NR^5$-$L^5$-C(═O)—, *—$NR^{17}$—$C_0$-$C_6$alkylene-(substituted or unsubstituted phenylene)-$C_0$-$C_6$alkylene-C(═O)—, *—$NR^{17}$—$C_0$-$C_6$alkylene-(substituted or unsubstituted cyclohexylene)-$C_0$-$C_6$ alkylene-C(═O)—, *—$NR^{17}$—$C_0$-$C_6$ alkylene-(substituted or unsubstituted heterocycloalkylene)-$C_0$-$C_6$ alkylene-C(═O)—, *—$NR^{17}$—$C_0$-$C_6$ alkylene-(substituted or unsubstituted heteroarylene)-$C_0$-$C_6$ alkylene-C(═O)—, *—$NR^{17}$-substituted or unsubstituted $C_1$-$C_{20}$ alkylene-C(═O), *—$NR^{17}$—$(CH_2CH_2O)$—$CH_2$—C(═O)—, *—$NR^{17}$—$(CH_2CH_2O)_z$—$CH_2CH_2$—C(═O)—, *—$R^{17}$-$L^5$-C(═O)-$(L^3)_w$-, *—$NR^5$-$L^5$-C(═O)$NR^{17}$—$C_0$-$C_6$ alkylene-(substituted or unsubstituted phenylene)-$C_0$-$C_6$ alkylene-C(═O)—, *—NR-$L^5$-C(═O)$NR^{17}$—$C_0$—C-$_6$ alkylene-(substituted or unsubstituted cyclohexylene)-$C_0$-$C_6$ alkylene-C(═O)—, *—$NR^5$-$L^5$-C(═O)$NR^{17}$—$C_0$-$C_6$ alkylene-(substituted or unsubstituted heterocycloalkylene)-$C_0$-$C_6$alkylene-C(═O)—, or *—$NR^5$-$L^5$-C(═O)$NR^{17}$—$C_0$-$C_6$ alkylene-(substituted or unsubstituted heteroarylene)-$C_0$-$C_6$ alkylene-C(═O)—; and z is 1, 2, 3, 4, 5, or 6;

wherein * denotes the attachment point to $R^a$.

20. The compound of claim 18, or a pharmaceutically acceptable salt thereof, wherein:

-$(L^3)_w$- is sarcosine, sarcosine-sarcosine, sarcosine-sarcosine-sarcosine, sarcosine-sarcosine-sarcosine-sarcosine (SEQ ID NO: 24), sarcosine-sarcosine-sarcosine-sarcosine-sarcosine (SEQ ID NO: 25), sarcosine-sarcosine-sarcosine-sarcosine-sarcosine-sarcosine (SEQ ID NO: 831), valine-citrulline, valine-alanine, methionine-valine-lysine, glycine-phenylalanine-glycine-glycine (SEQ ID NO: 832), tyrosine-arginine-valine, arginine-valine, 3-sulfo-alanine, 3-sulfo-alanine-3-sulfo-alanine, 3-sulfo-alanine-3-sulfo-alanine-3-sulfo-alanine, glycine-glutamate, glycine-glutamate-glycine, glycine-glutamate-glutamate, methionine-tryptophan-lysine, methionine-phenylalanine-lysine, methionine-valine, methionine-valine-lysine, or phenylalanine-lysine, wherein the free amine of lysine is optionally substituted with $L^4$;

$L^4$ is —C(═O)—$(CH_2)_3$—C(═O)—, —C(═O)—$(CH_2)_4$—C(═O)—, —C(═O)—$(CH_2)_5$—C(═O)—, —C(═O)—$(CH_2)_6$—C(═O)—, —C(═O)NH—$(CH_2)_3$—C(═O)—, —C(═O)NH—$(CH_2)_4$—C(═O)—, —C(═O)NH—$(CH_2)_5$—C(═O)—, —C(═O)NH—$(CH_2)_6$—C(═O)—, —C(═O)—$(CH_2)_2$-(triazolylene)-$(CH_2)_1$—C(═O)— or —C(═O)—$(CH_2)_2$-(triazolylene)-$(CH_2)_2$—C(═O)—; wherein if $L^4$ is present then: $L^4$ is attached to the any one of $X^1$, $X^2$, $X^3$, $X^4$, $X^5$, $X^6$, or $X^7$, or $L^4$ is attached to $X^8$ if $X^1$, $X^2$, $X^3$, $X^4$, $X^5$, $X^6$, and $X^7$ are absent.

21. The compound of claim 1, or a pharmaceutically acceptable salt thereof, wherein: -L- is: absent,

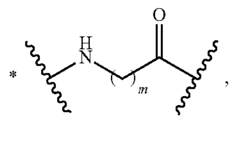
,
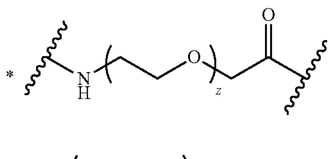
, (SEQ ID NO: 833)

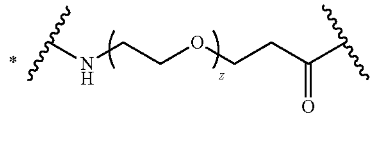
,
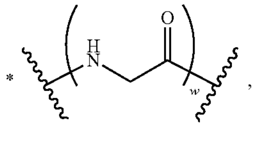
,

-continued
(SEQ ID NO: 834)
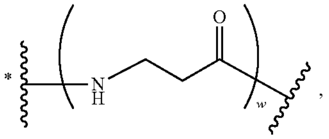
(SEQ ID NO: 835
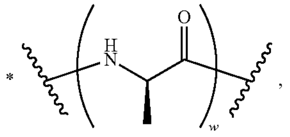
(SEQ ID NO: 836)
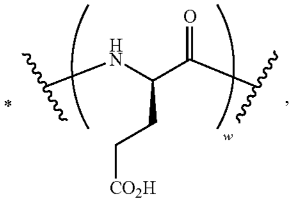
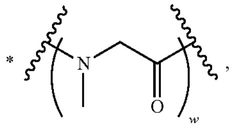
(SEQ ID NO: 838)
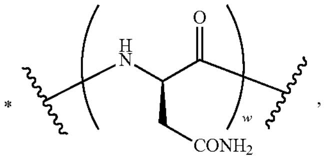
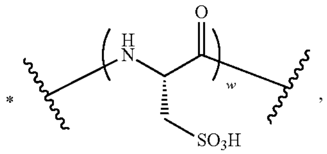
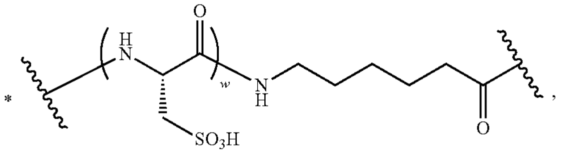
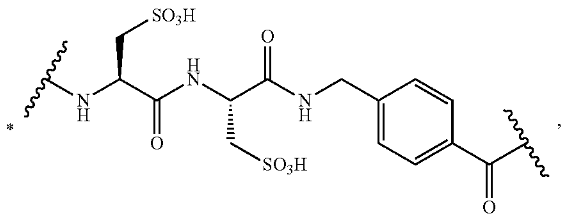
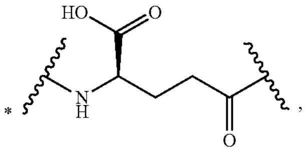
(SEQ ID NO: 839)
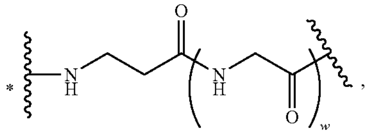
(SEQ ID NO: 840)
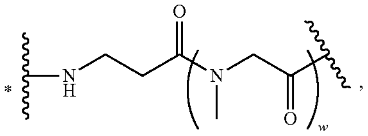
(SEQ ID NO: 841)
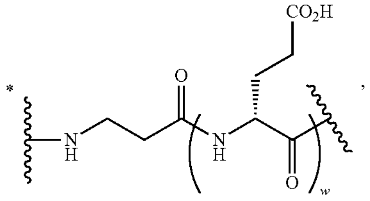
(SEQ ID NO: 842)
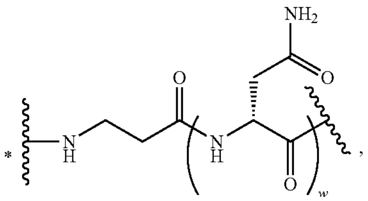
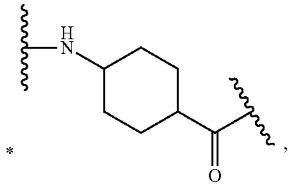
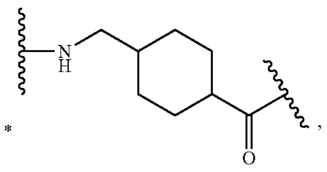
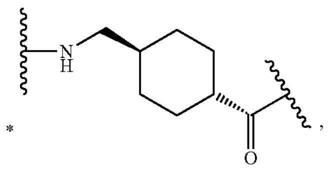

-continued
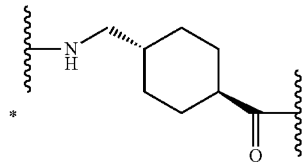,
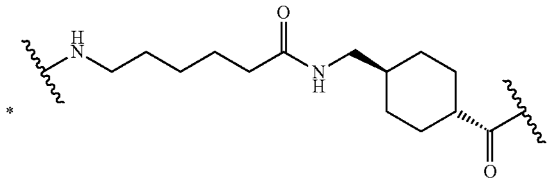,
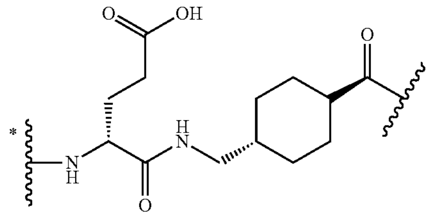,
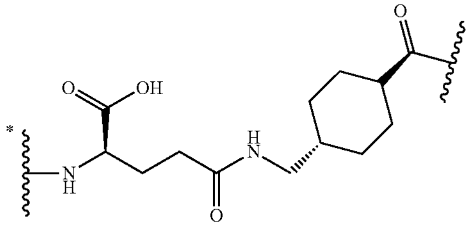,
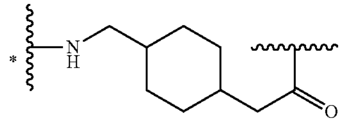,
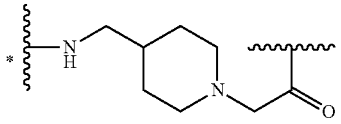,
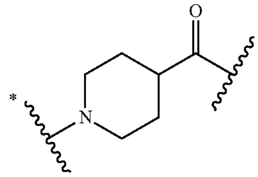,
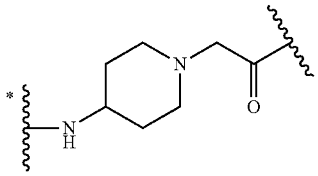,
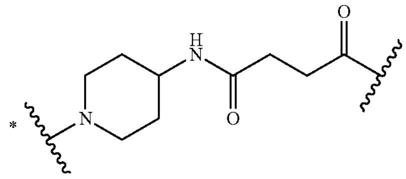,
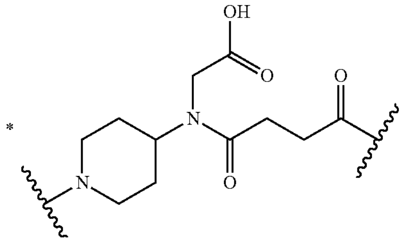,
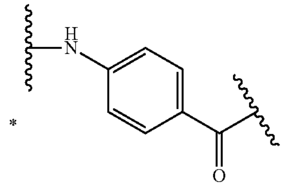,
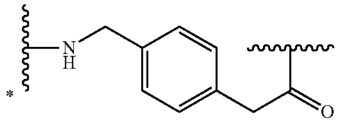,
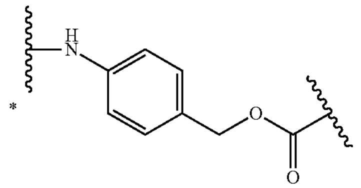,
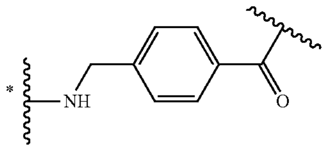,
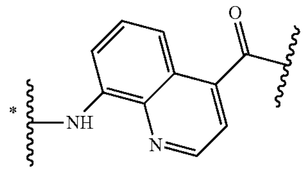,
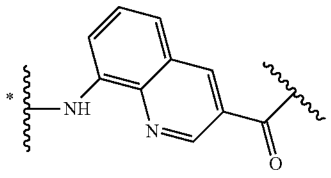, -continued
* 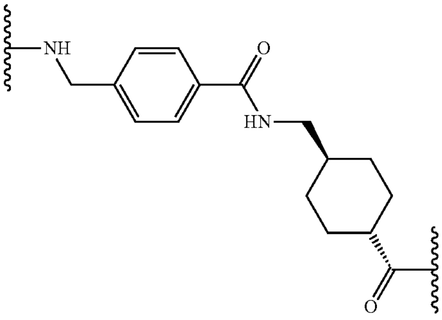 ,
* 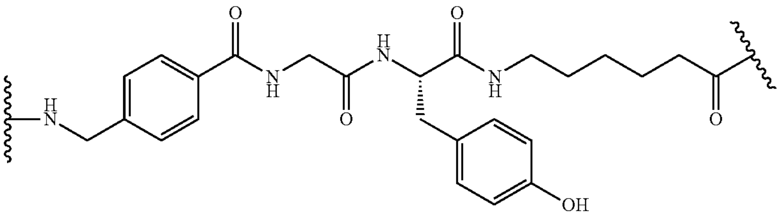 ,
* 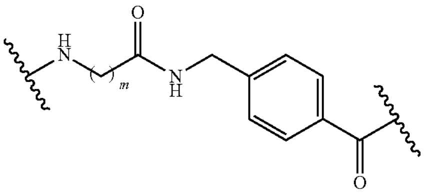 , * 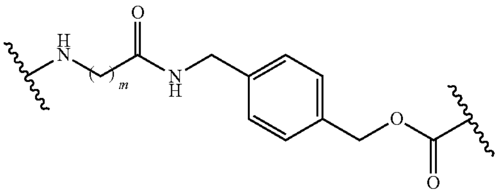 ,
* 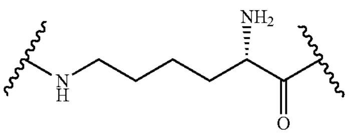 , * 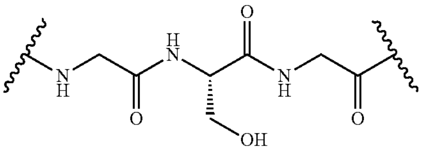 ,
* 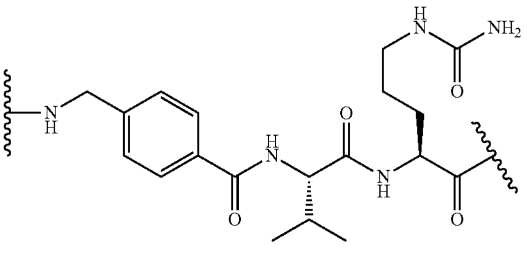 , * 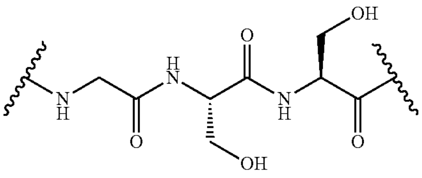 ,
* 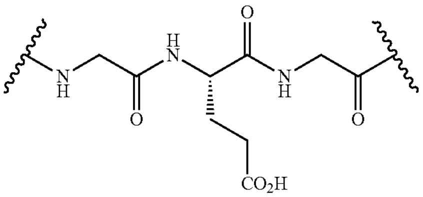 , * 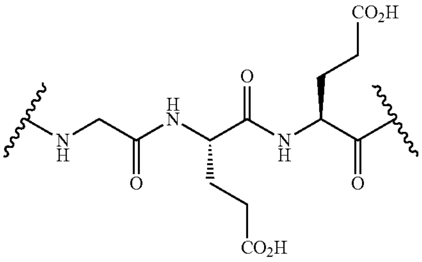 , -continued
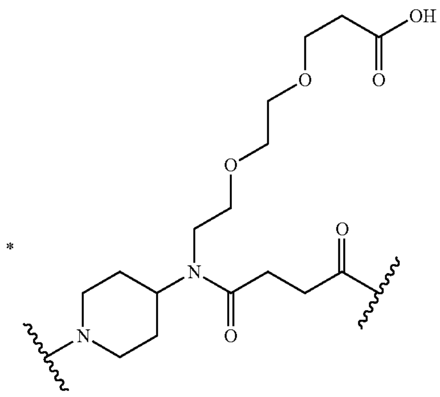
,
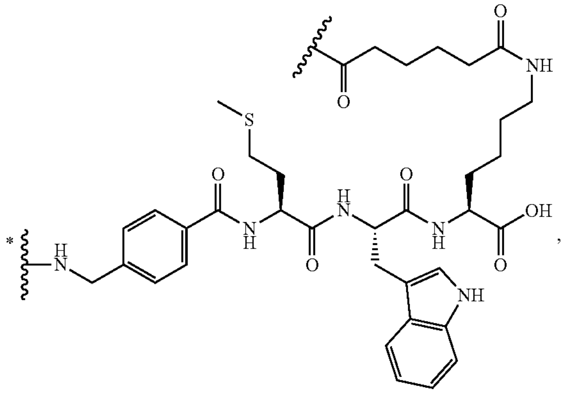
,
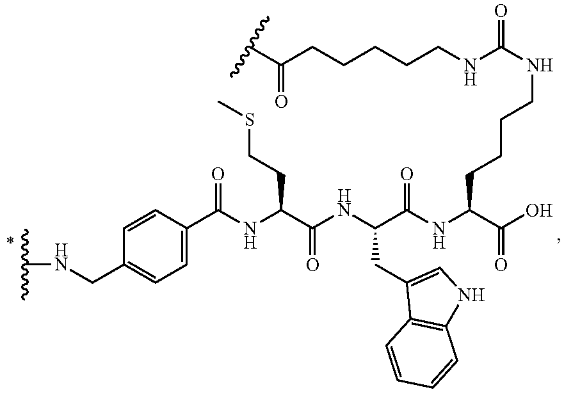
,
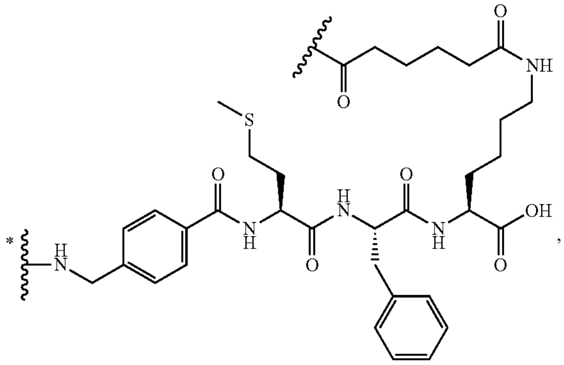
,
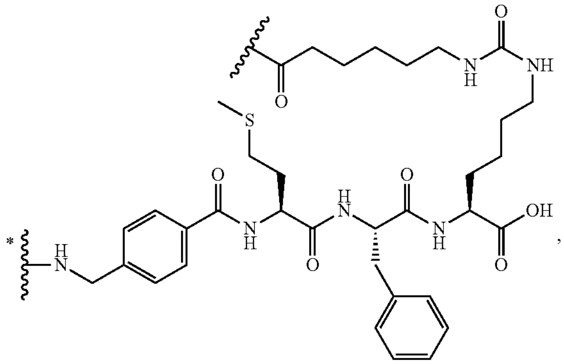
,
(SEQ ID NO: 796)
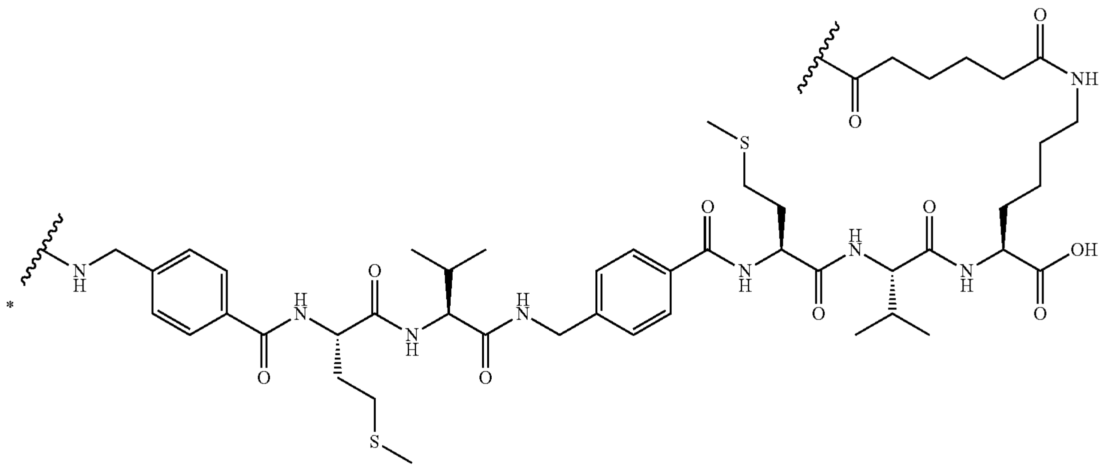
, -continued
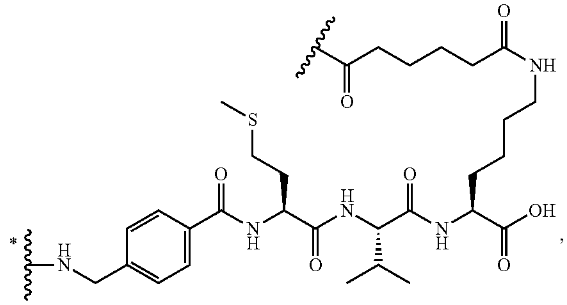
,
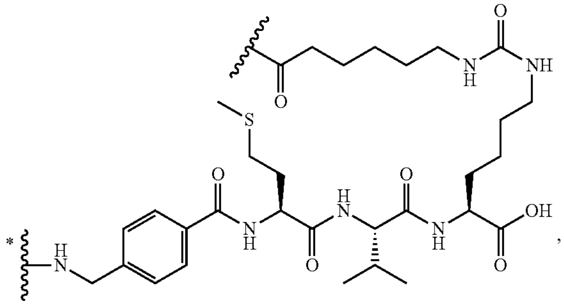
,
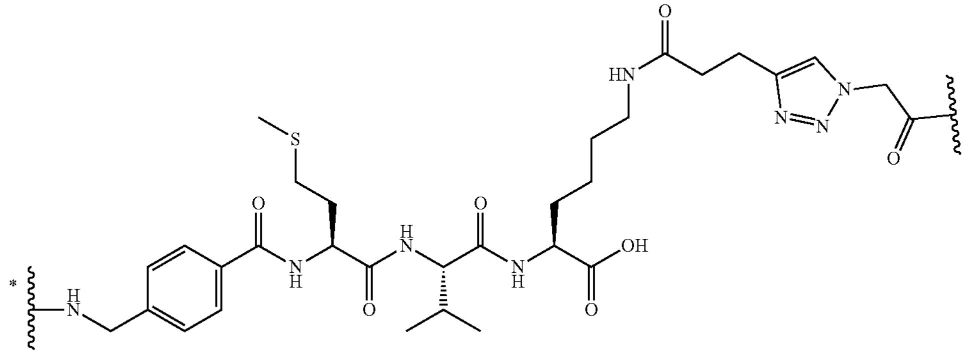
,
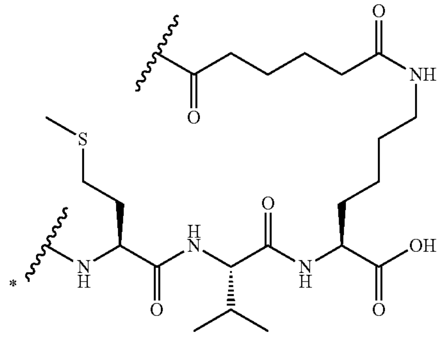
,
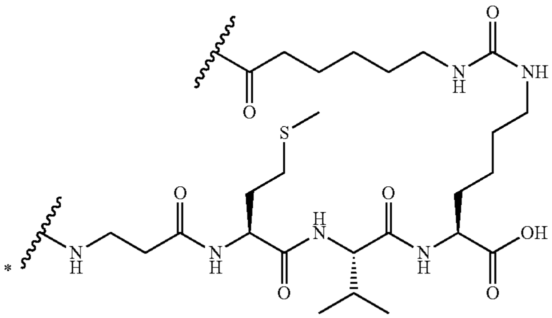
,
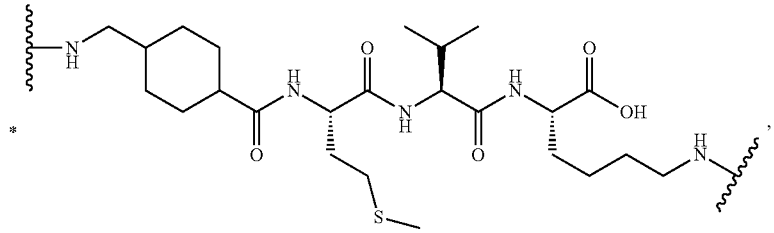
,
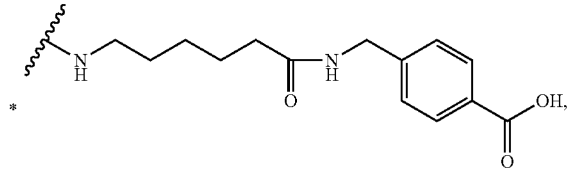
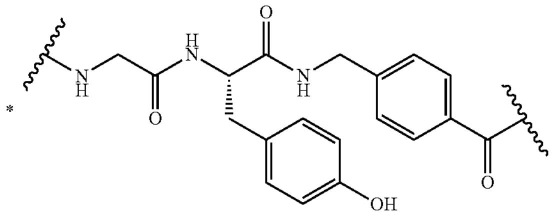
, -continued
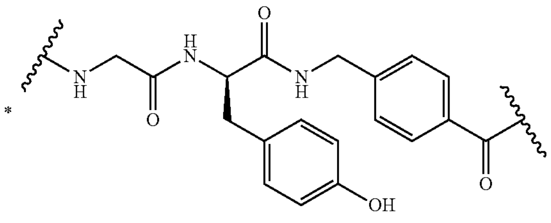,
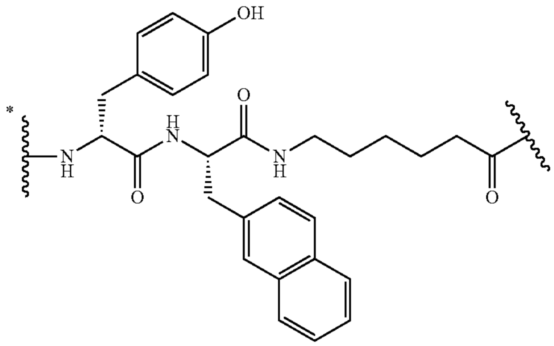,
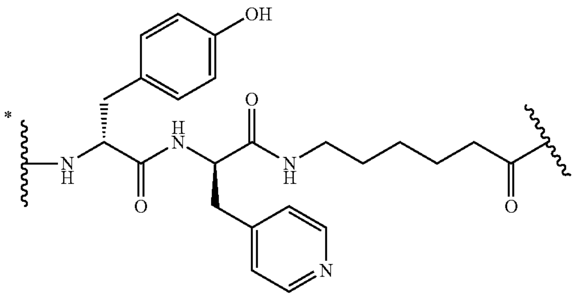,
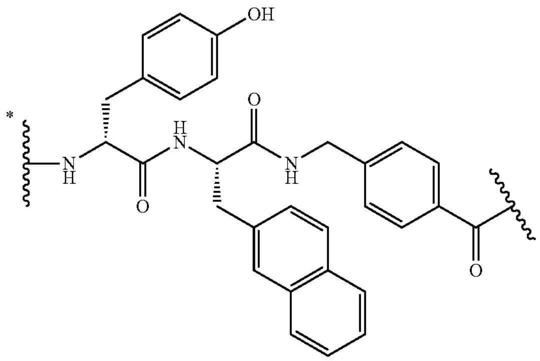,
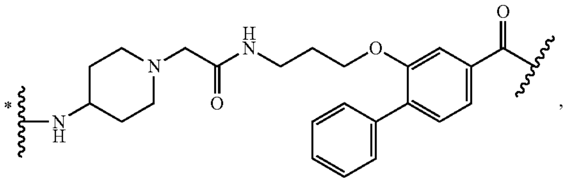,
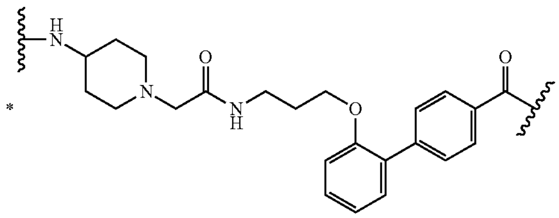,
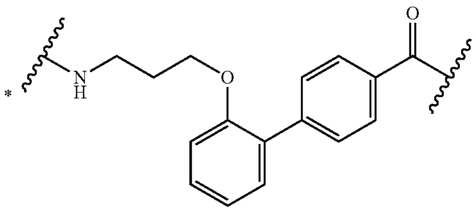,
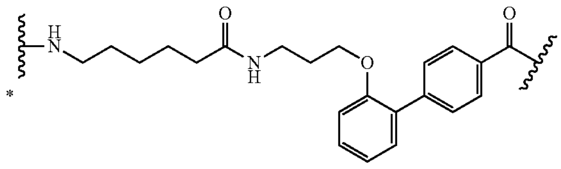,
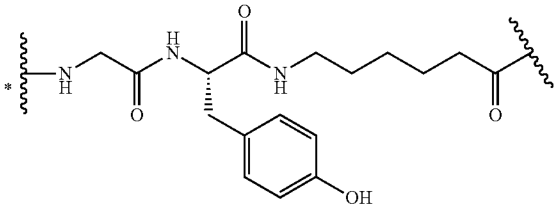,
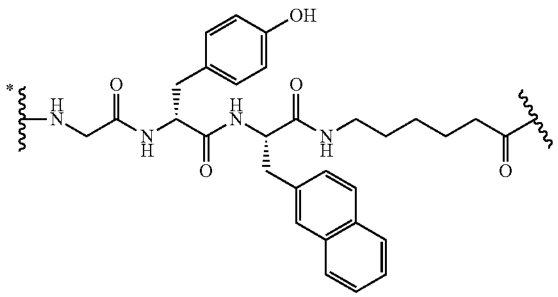,
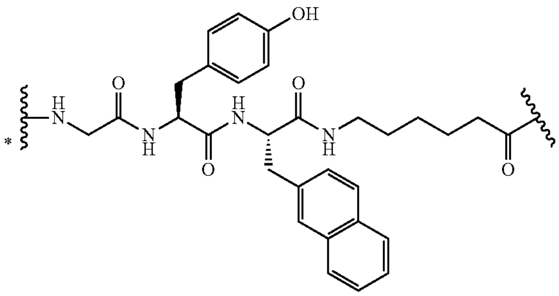,
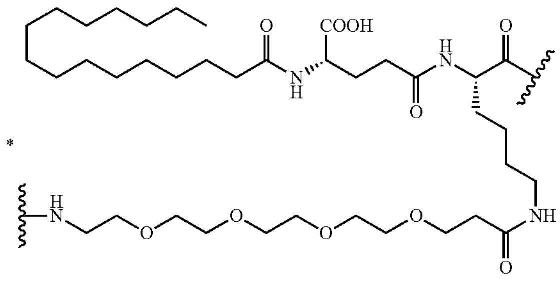, -continued
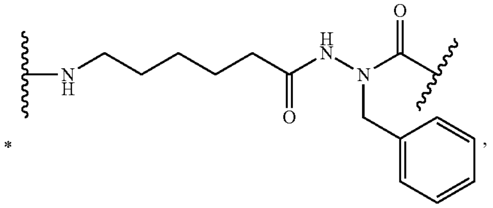
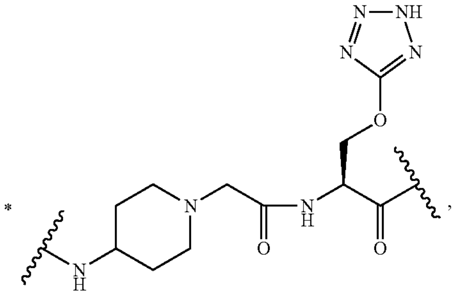
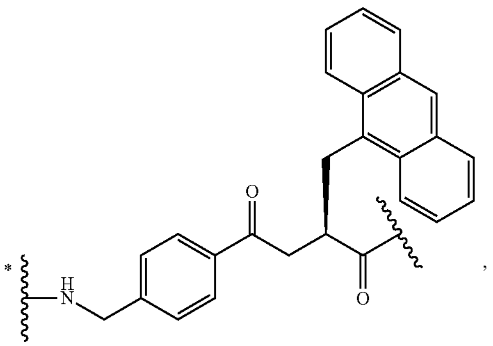
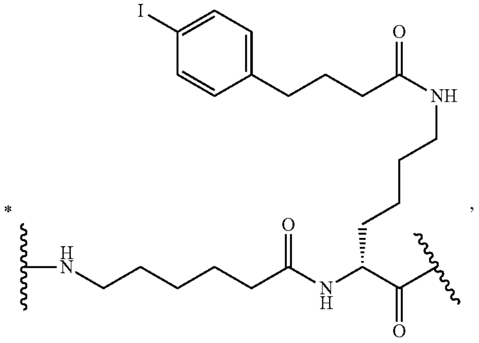
, or
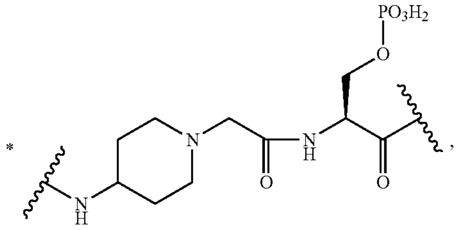
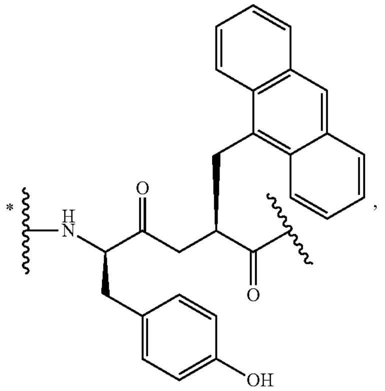
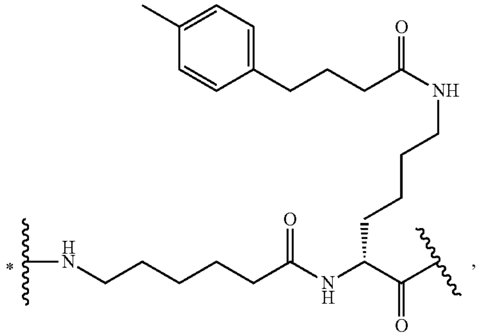
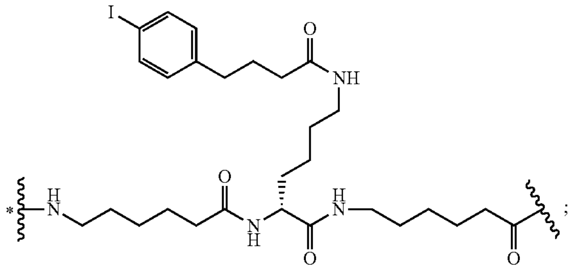
m is 1, 2, 3, 4, 5, or 6;
z is 1, 2, 3, 4, 5, or 6;
w is 1, 2, 3, 4, 5, or 6;
wherein * denotes the attachment point to $R^a$.
22. The compound of claim 1, or a pharmaceutically acceptable salt thereof, wherein -L- is:
absent,
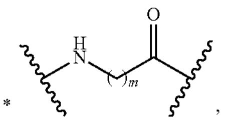
-continued
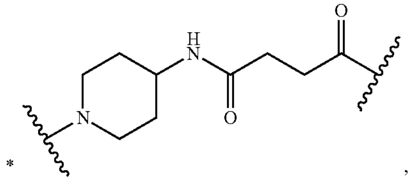

-continued
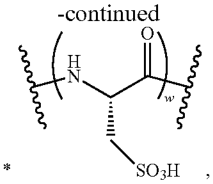
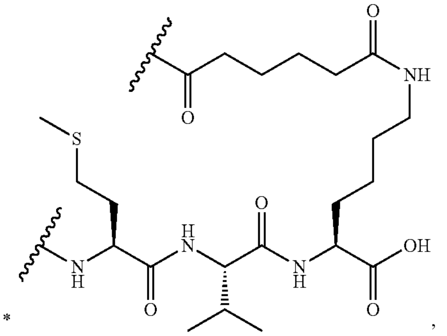
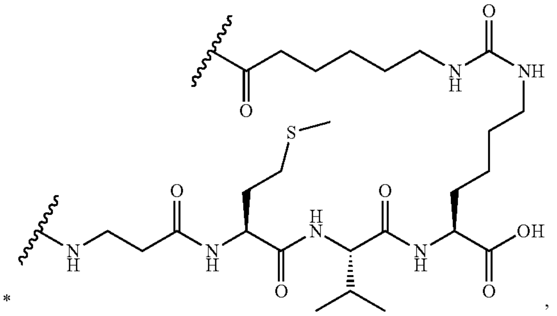
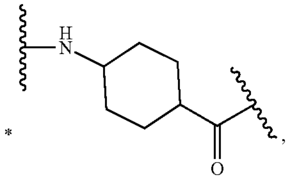
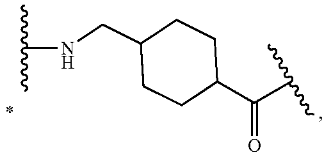
-continued
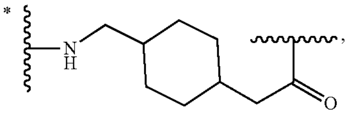
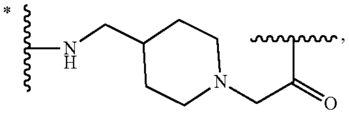
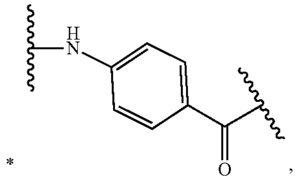
, or
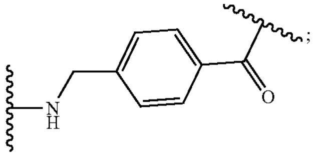
wherein * denotes the attachment point to $R^a$; and
m is 1, 2, 3, 4, 5, or 6.
23. The compound of claim 1, or a pharmaceutically acceptable salt thereof, wherein: -L- is: absent,
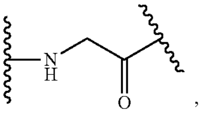
, or
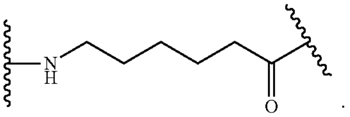
24. The compound of claim 1, or a pharmaceutically acceptable salt thereof, wherein $R^a$-L- is:
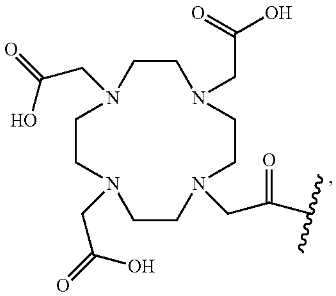
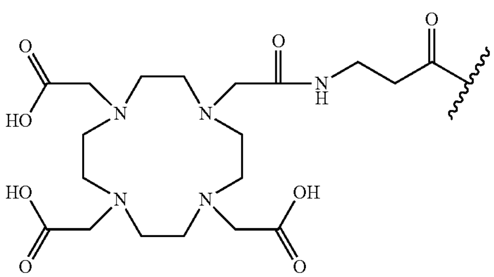
, -continued
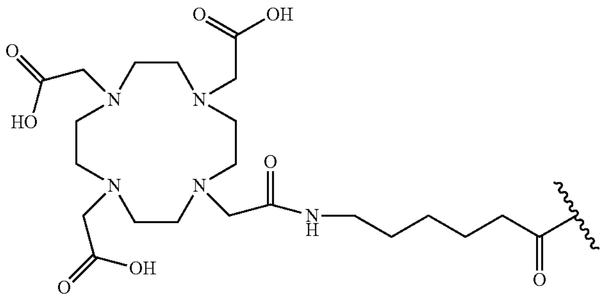,
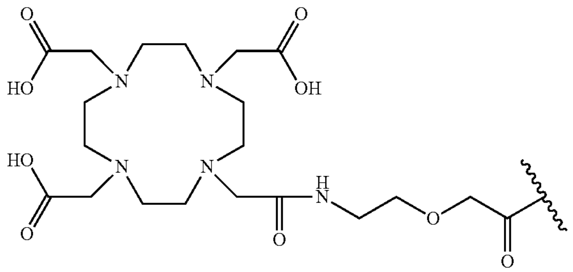,
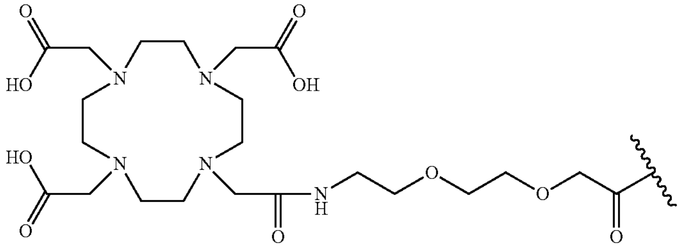,
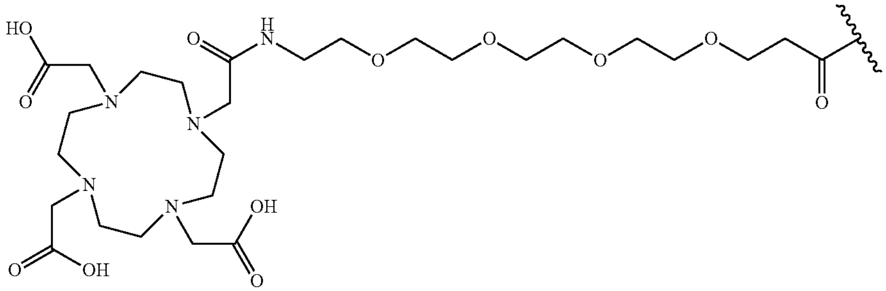,
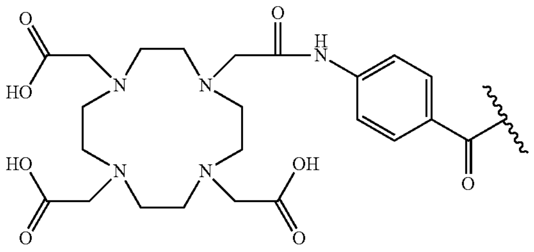,
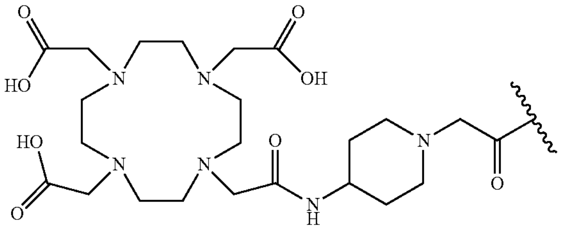,
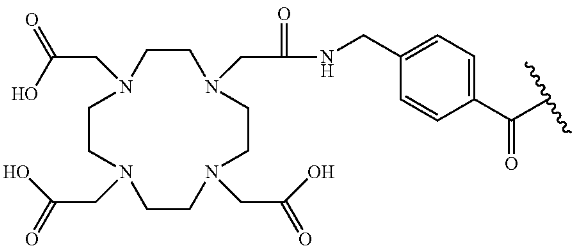,
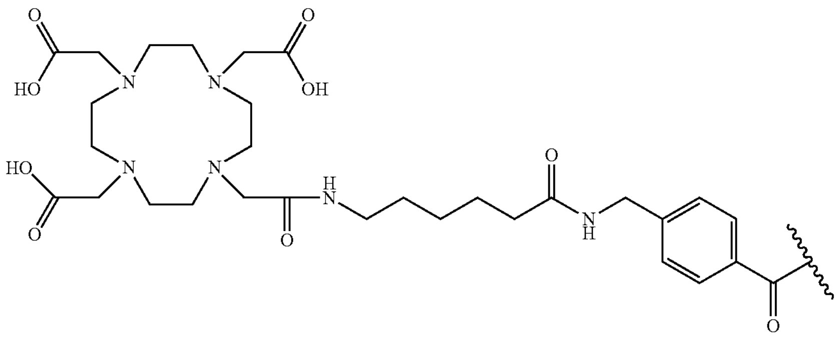, -continued
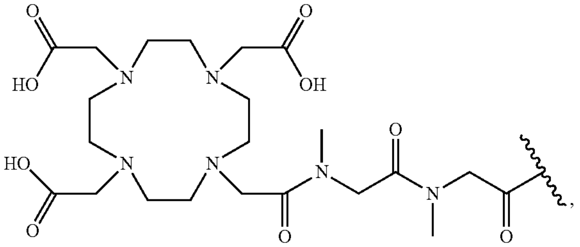
(SEQ ID NO: 798)
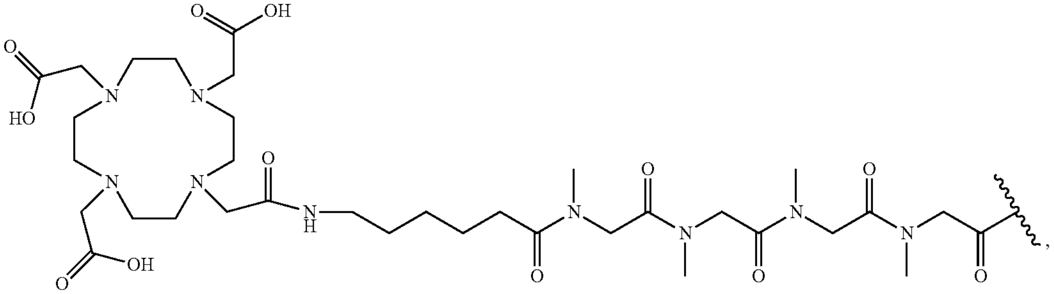
(SEQ ID NO: 386)
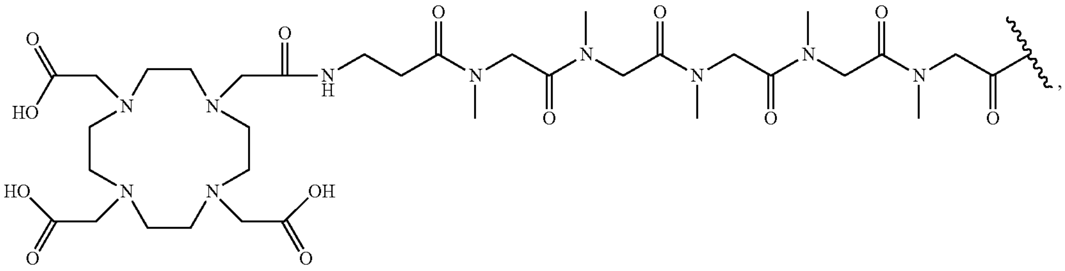
(SEQ ID NO: 387)
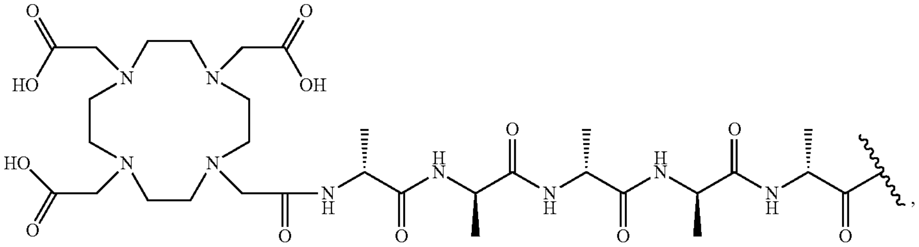
(SEQ ID NO: 388)
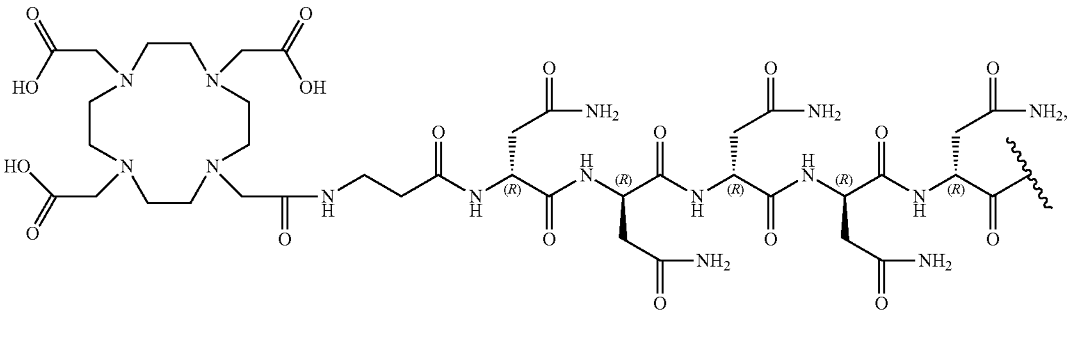

-continued
(SEQ ID NO: 389)
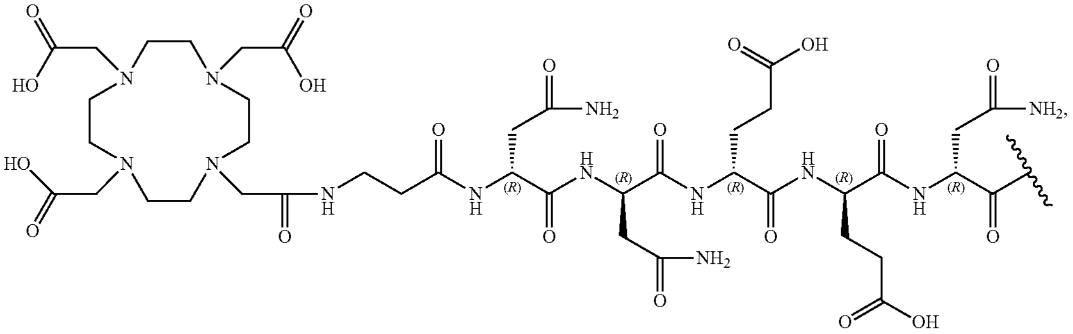
(SEQ ID NO: 390)
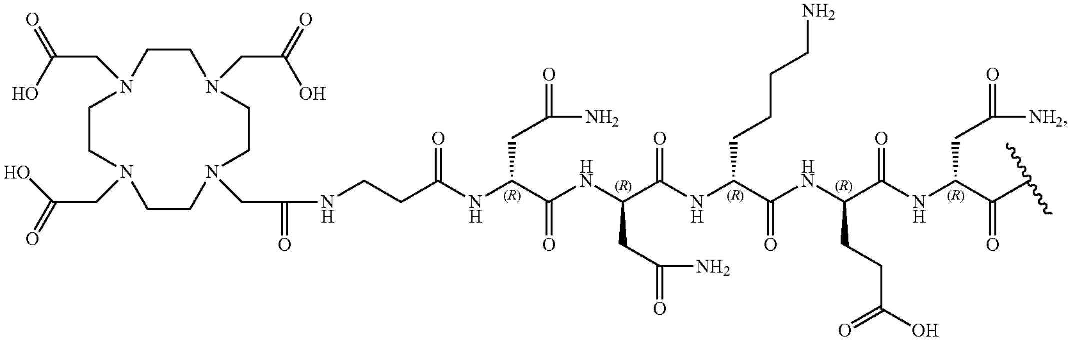
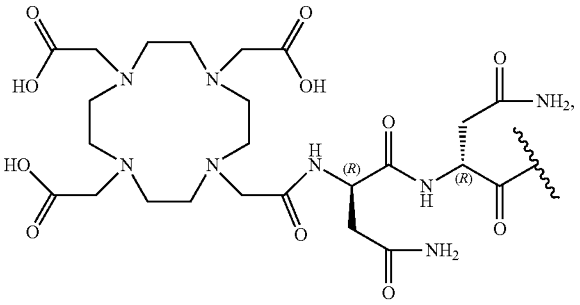
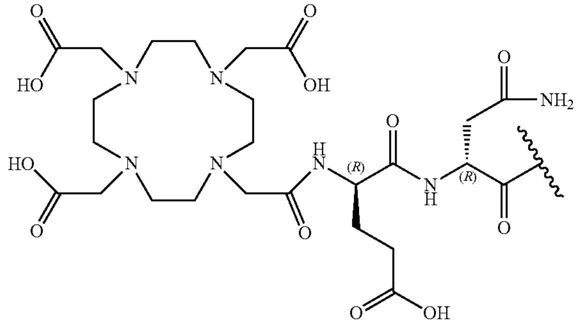
,
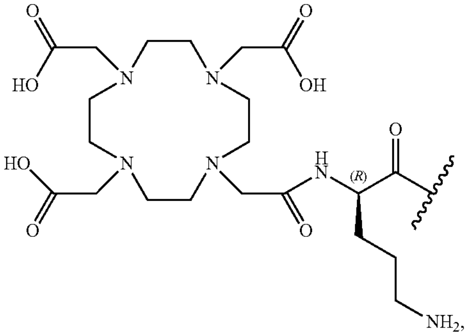
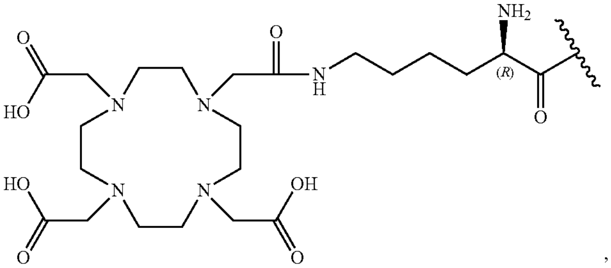
,
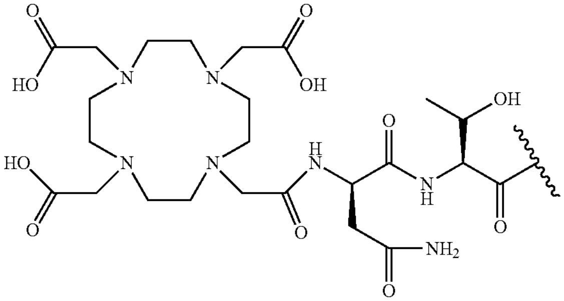
,
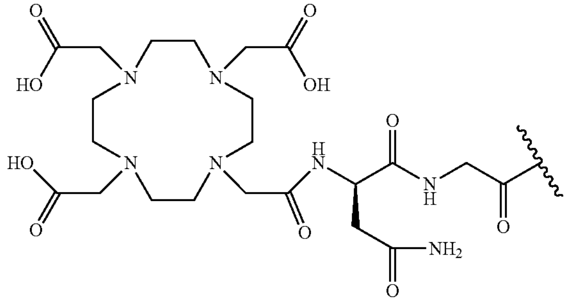
, -continued
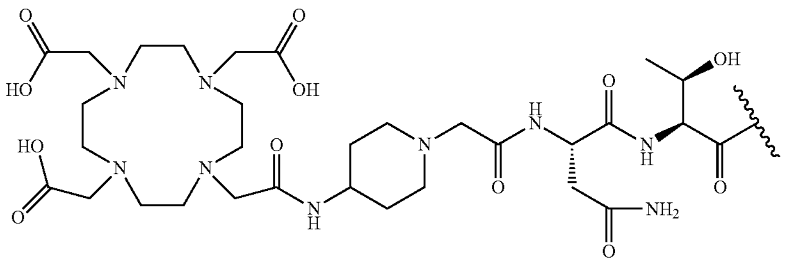
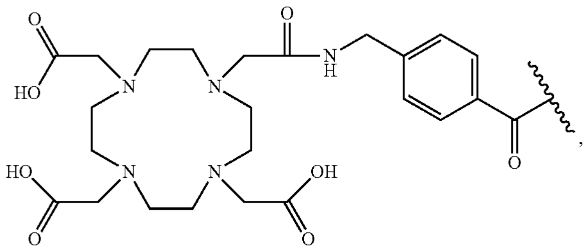
,
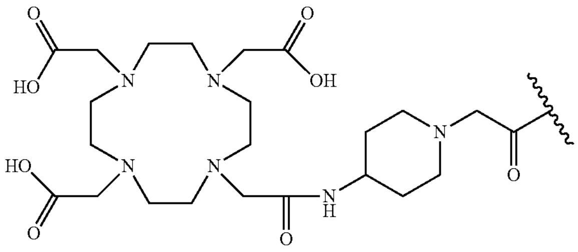
,
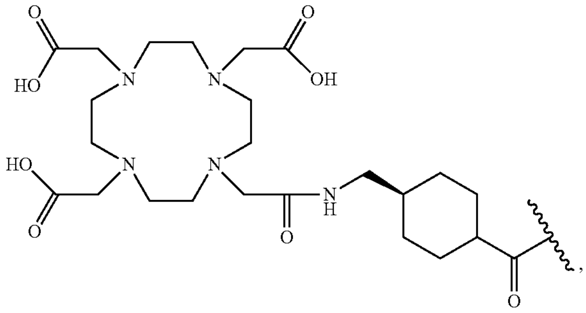
,
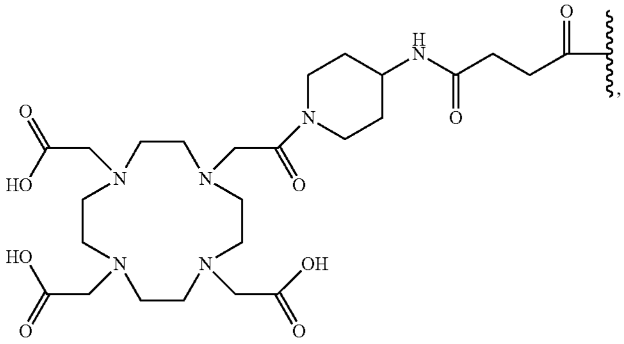
,
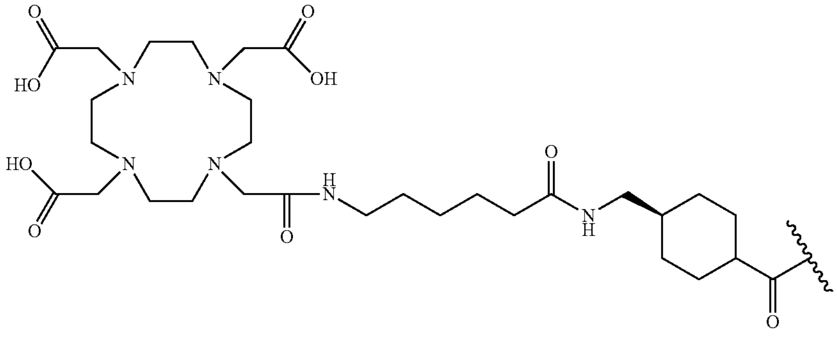
, -continued
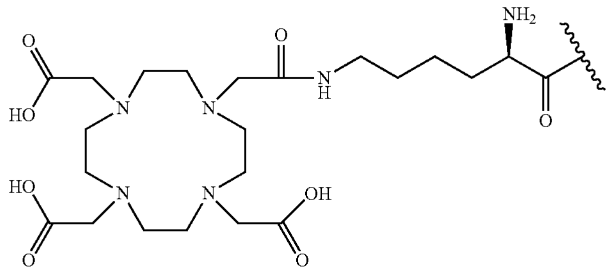
,
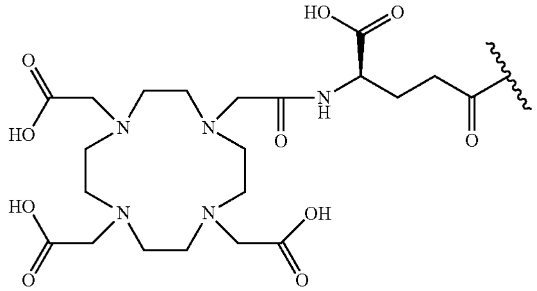
,
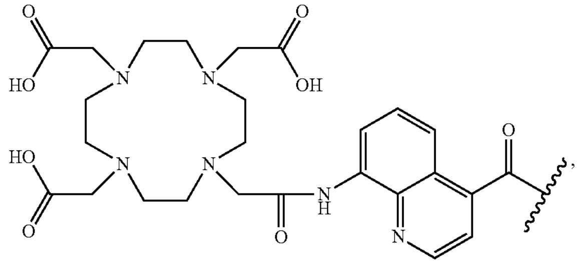
,
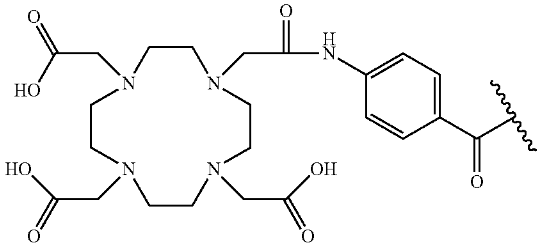
,
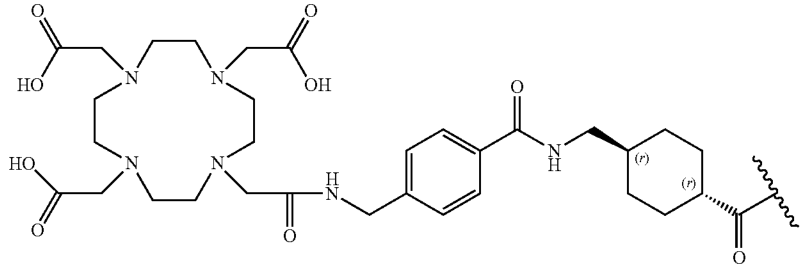
,
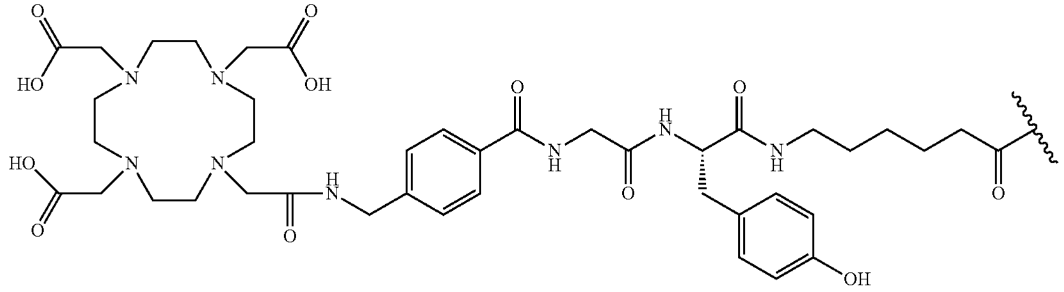
,
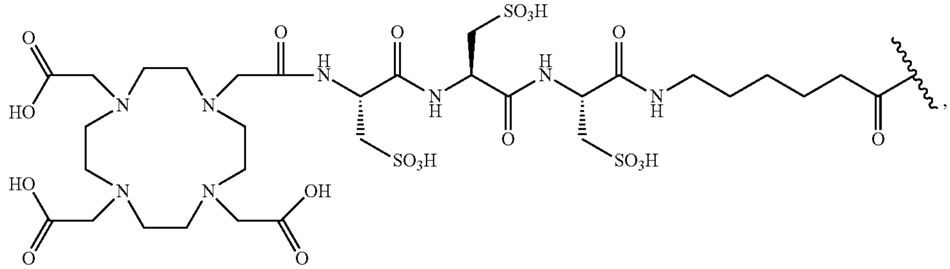
,
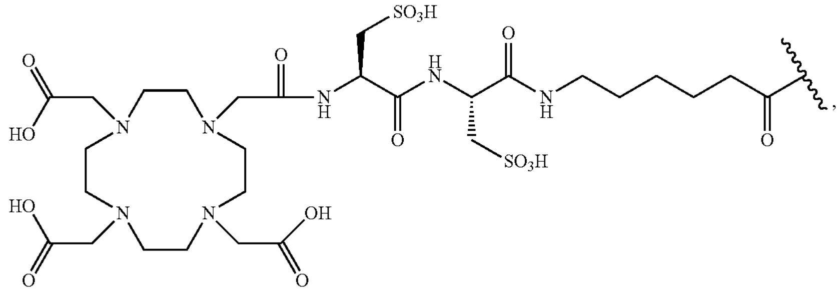
, -continued
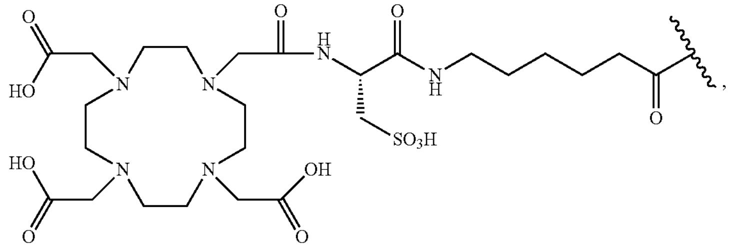
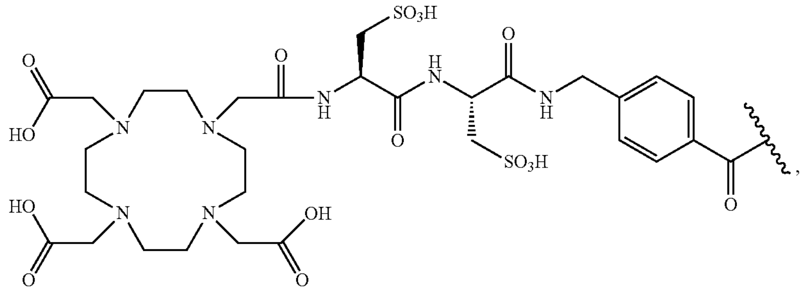
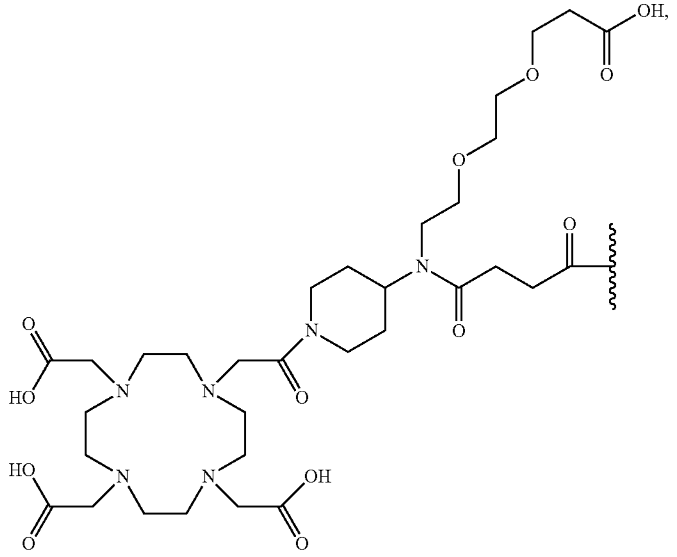
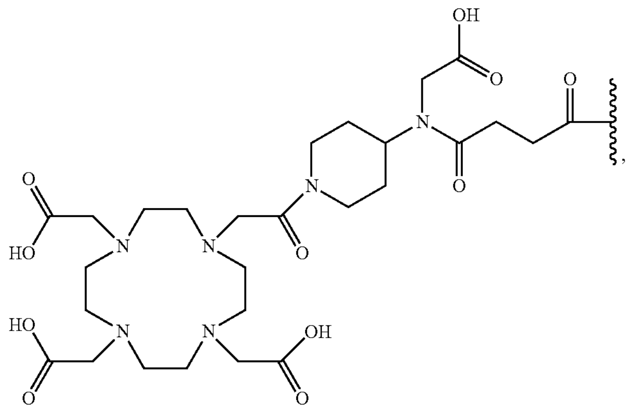

-continued
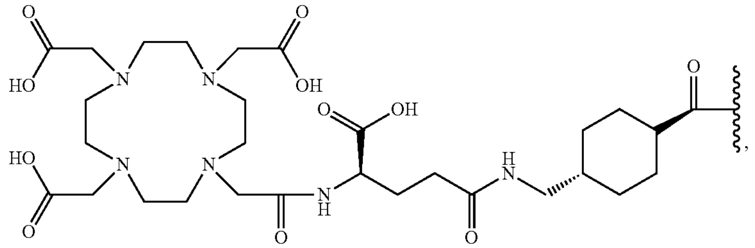
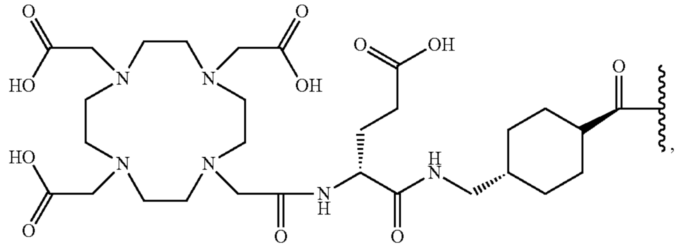
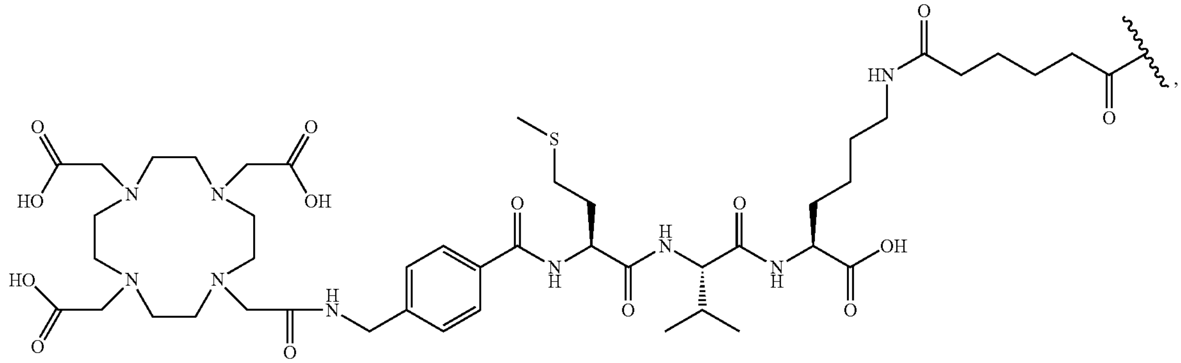
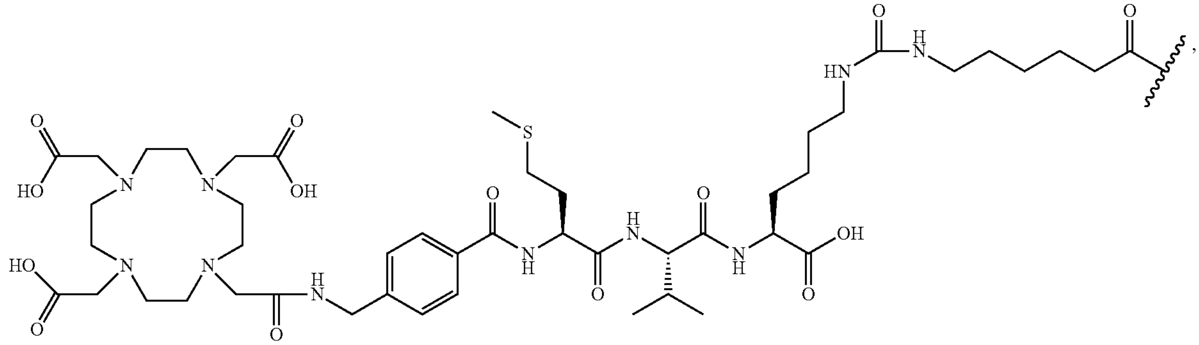
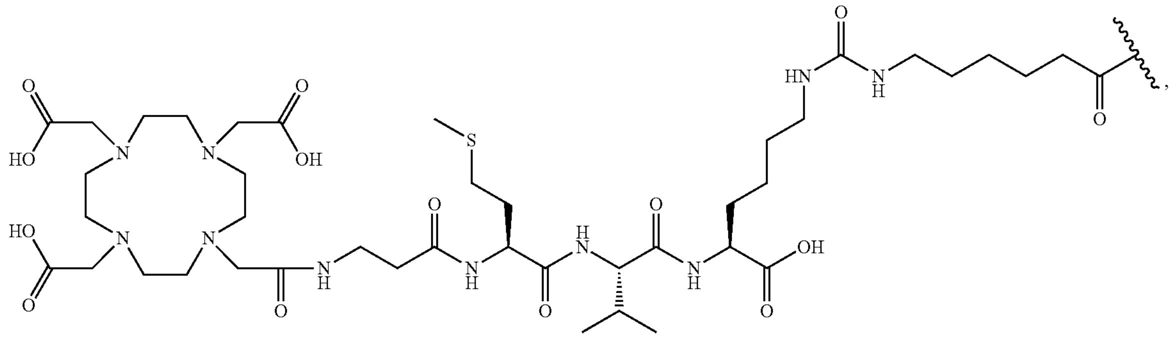

-continued
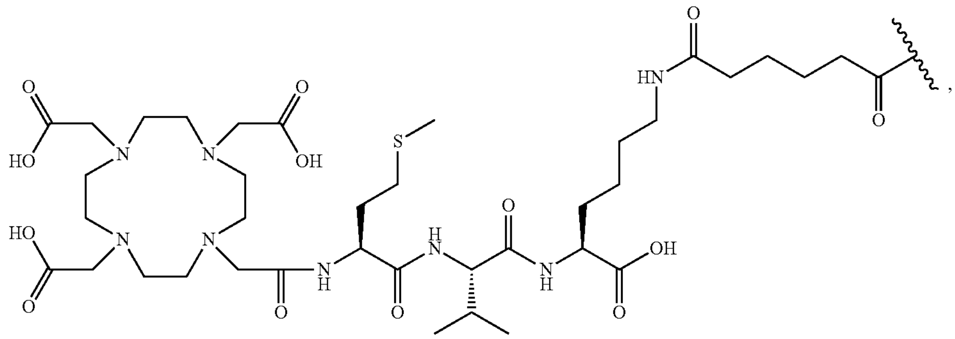,
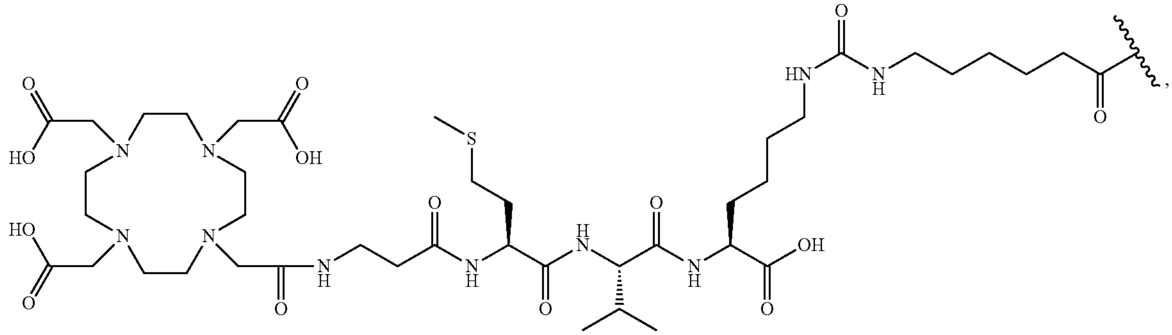,
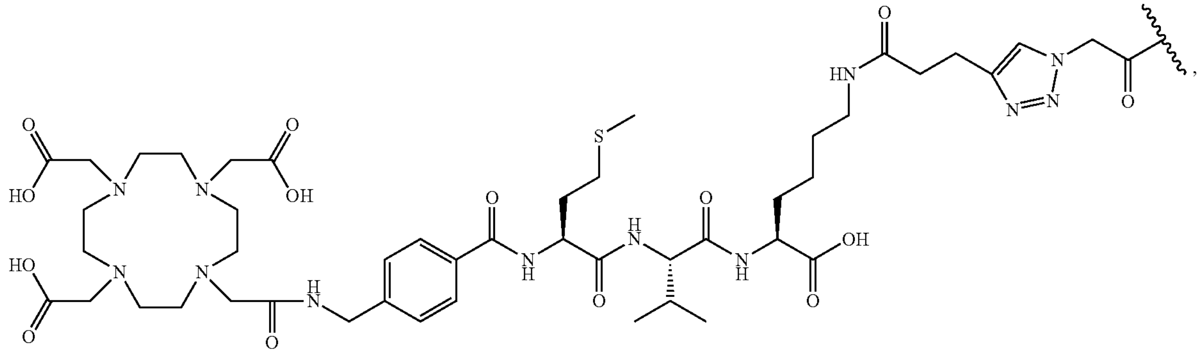,
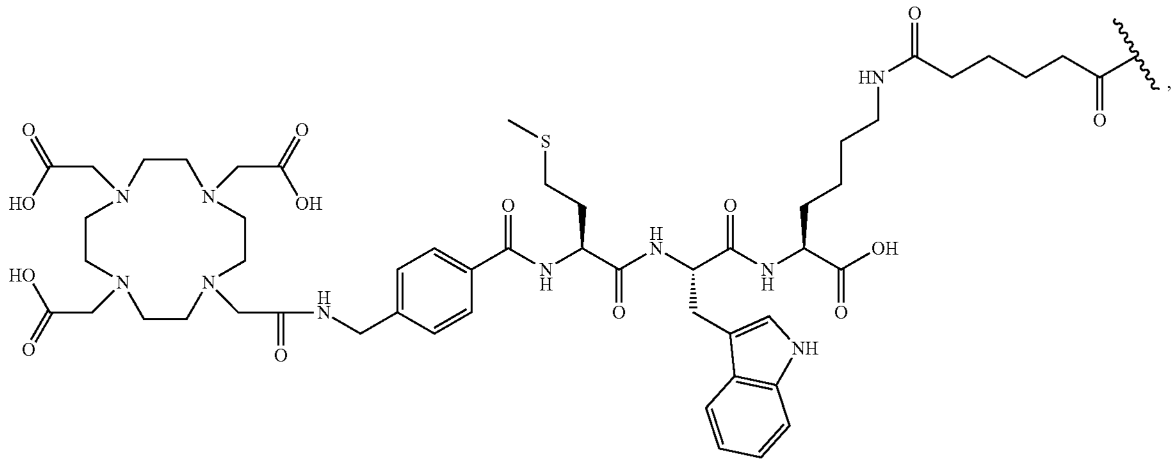,

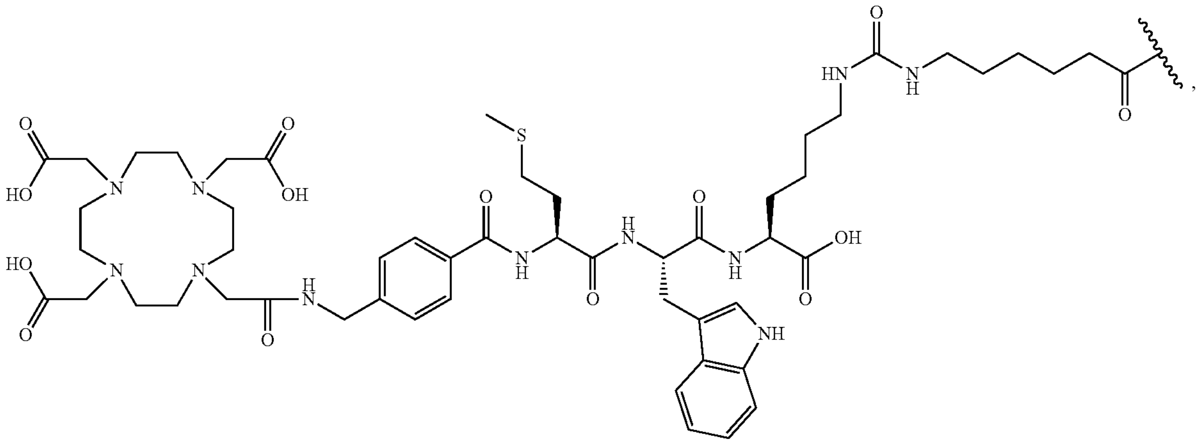

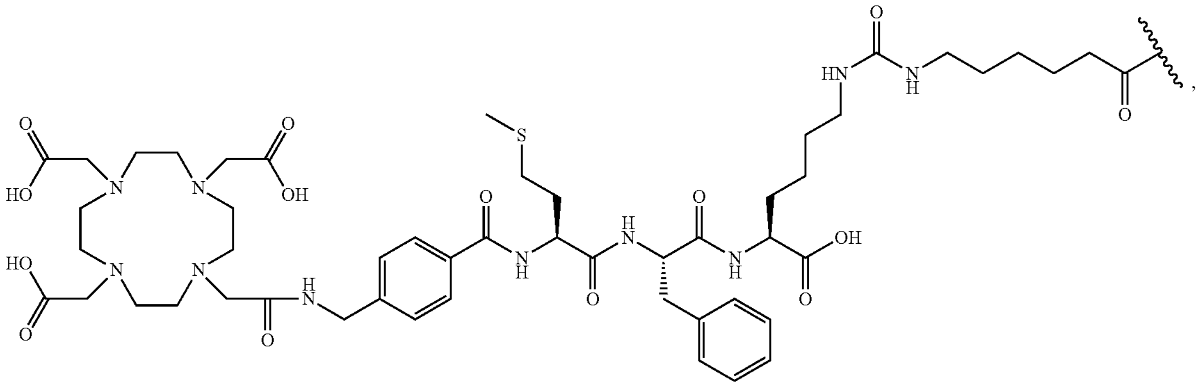

(SEQ ID NO: 799)

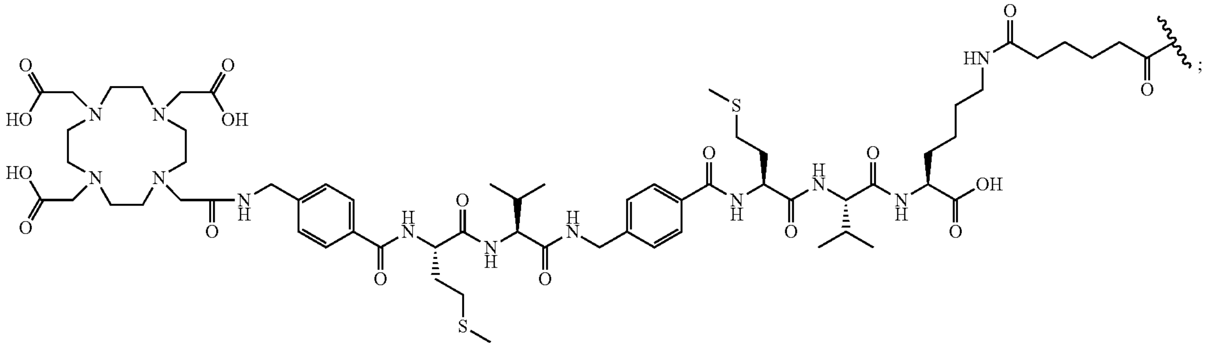

or a radionuclide complex thereof.

25. The compound of claim 1, or a pharmaceutically acceptable salt thereof, wherein the compound of Formula (I) has the chemical structure corresponding to one of the following SEQ ID numbers, or a pharmaceutically acceptable salt thereof:

(SEQ ID NO: 391), (SEQ ID NO: 392), (SEQ ID NO: 393), (SEQ ID NO: 394), (SEQ ID NO: 395), (SEQ ID NO: 771), (SEQ ID NO: 396), (SEQ ID NO: 397), (SEQ ID NO: 398), (SEQ ID NO: 399), (SEQ ID NO: 772), (SEQ ID NO: 400),

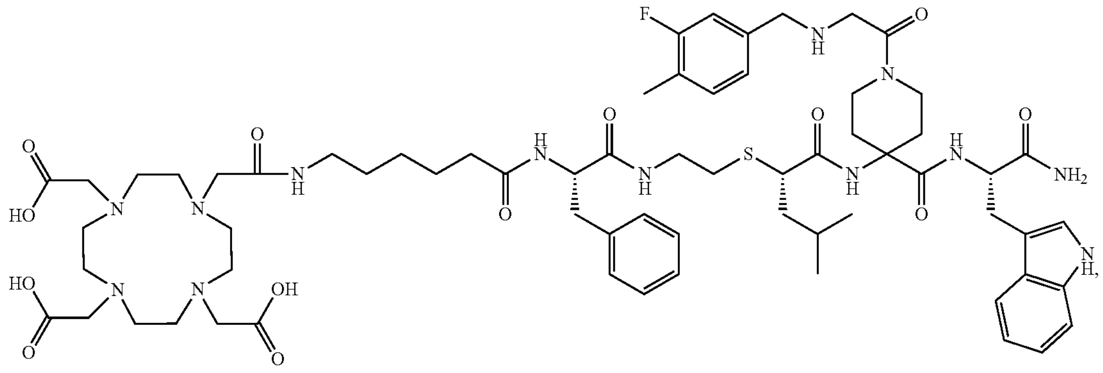
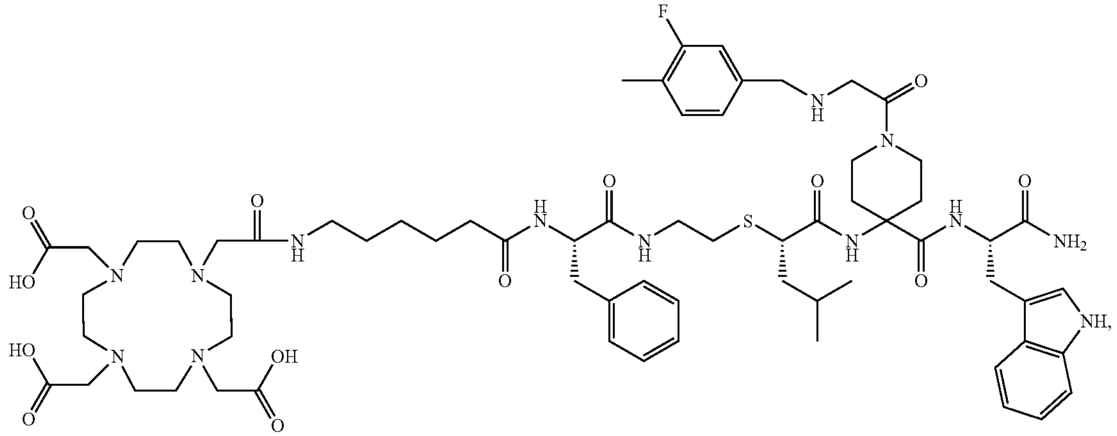
(SEQ ID NO: 403), (SEQ ID NO: 404), (SEQ ID NO: 405), (SEQ ID NO: 406), (SEQ ID NO: 407), (SEQ ID NO: 408), (SEQ ID NO: 409), (SEQ ID NO: 410 (SEQ ID NO: 411), (SEQ ID NO: 412), (SEQ ID NO: 413), (SEQ ID NO: 414), (SEQ ID NO: 415), (SEQ ID NO: 416), (SEQ ID NO: 417), (SEQ ID NO: 418), (SEQ ID NO: 419), (SEQ ID NO: 420), (SEQ ID NO: 421), (SEQ ID NO: 422), (SEQ ID NO: 423), (SEQ ID NO: 424 (SEQ ID NO: 425), (SEQ ID NO: 426), (SEQ ID NO: 427), (SEQ ID NO: 428), (SEQ ID NO: 429), (SEQ ID NO: 430), (SEQ ID NO: 431),
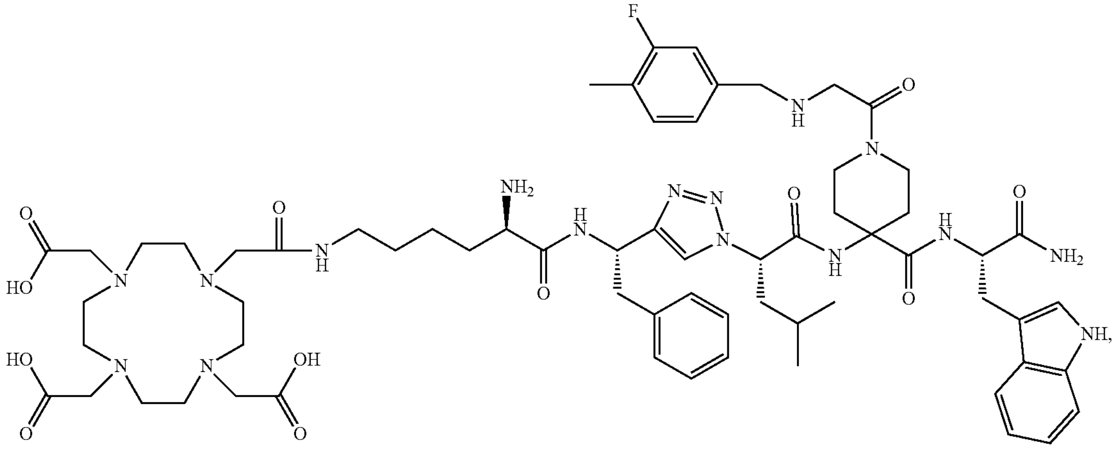 [SMILES: Cc1ccc(CNCC(=O)N2CCC(NC(=O)[C@H](CC(C)C)n3cc([C@H](Cc4ccccc4)NC(=O)[C@H](N)CCCCNC(=O)CN4CCN(CC(=O)O)CCN(CC(=O)O)CCN(CC(=O)O)CC4)nn3)(C(=O)N[C@@H](Cc3c[nH]c4ccccc34)C(N)=O)CC2)cc1F]

(SEQ ID NO: 433), (SEQ ID NO: 434), (SEQ ID NO: 435), (SEQ ID NO: 436),
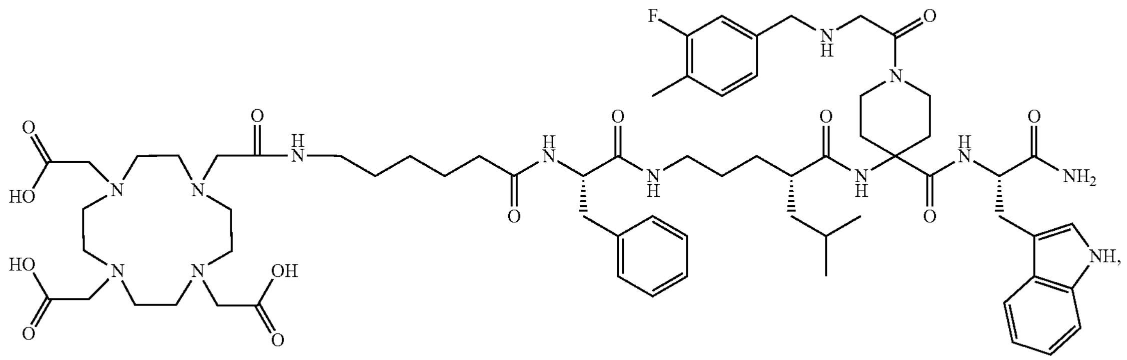
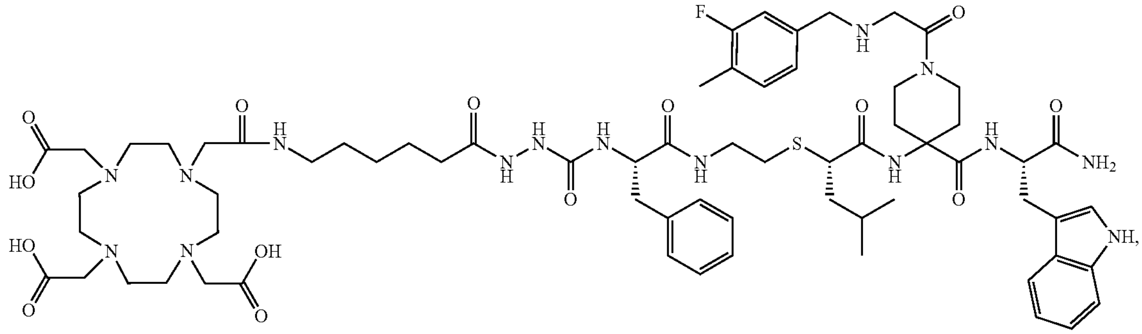
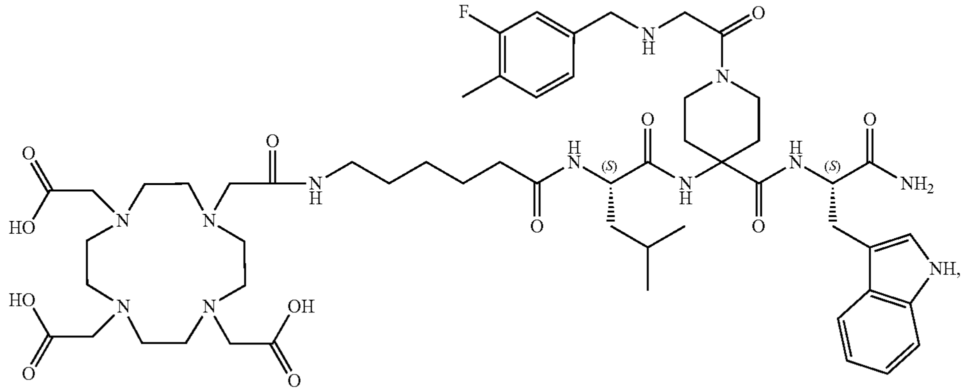
(SEQ ID NO: 439), (SEQ ID NO. 440), (SEQ ID NO: 441), (SEQ ID NO: 442),
(SEQ ID NO: 444)
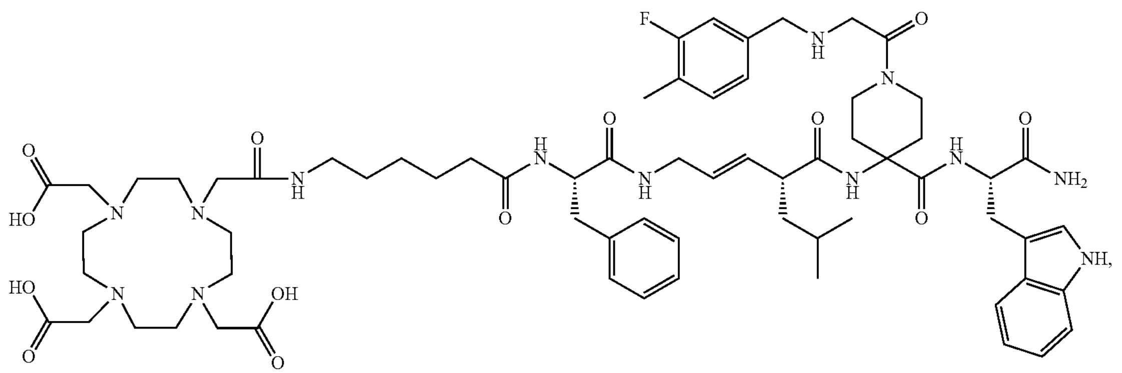

-continued (SEQ ID NO: 445)

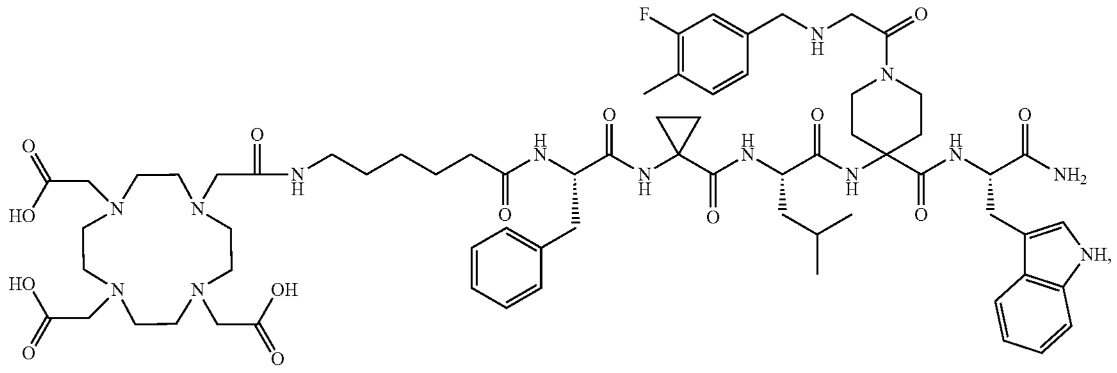

(SEQ ID NO: 447), (SEQ ID NO: 448), (SEQ ID NO: 449), (SEQ ID NO: 450), (SEQ ID NO: 451), (SEQ ID NO: 452), (SEQ ID NO: 453), (SEQ ID NO: 454), (SEQ ID NO: 455), (SEQ ID NO: 456), (SEQ ID NO: 457), (SEQ ID NO: 458), (SEQ ID NO: 459), (SEQ ID NO: 460), (SEQ ID NO: 461), (SEQ ID NO: 462), (SEQ ID NO: 463), (SEQ ID NO: 464), (SEQ ID NO: 465), (SEQ ID NO: 466), (SEQ ID NO: 467), (SEQ ID NO: 468), (SEQ ID NO: 469 (SEQ ID NO: 470), (SEQ ID NO: 471), (SEQ ID NO: 472), (SEQ ID NO: 473), (SEQ ID NO: 474), (SEQ ID NO: 475), (SEQ ID NO: 476), (SEQ ID NO: 477), (SEQ ID NO: 478), (SEQ ID NO: 479), (SEQ ID NO: 480), (SEQ ID NO: 481), (SEQ ID NO: 482), (SEQ ID NO: 483), (SEQ ID NO: 484), (SEQ ID NO: 485), (SEQ ID NO: 486), (SEQ ID NO: 487), (SEQ ID NO: 488), (SEQ ID NO: 489), (SEQ ID NO: 490), (SEQ ID NO: 491), (SEQ ID NO: 492), (SEQ ID NO: 493), (SEQ ID NO: 494), (SEQ ID NO: 495), (SEQ ID NO: 496), (SEQ ID NO: 497), (SEQ ID NO: 498), (SEQ ID NO: 499), (SEQ ID NO: 500), (SEQ ID NO: 501), (SEQ ID NO: 502), (SEQ ID NO: 503), (SEQ ID N): 504), (SEQ ID NO: 505),

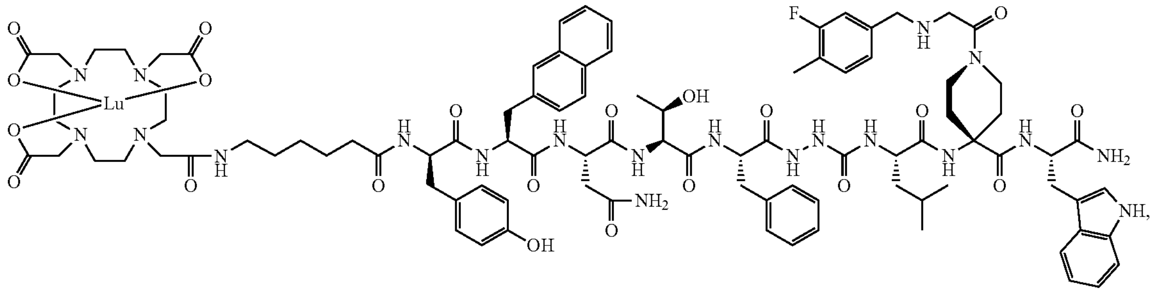

(SEQ ID NO: 506), (SEQ ID NO: 507), (SEQ ID NO: 508 (SEQ ID NO: 509), (SEQ ID NO: 510), (SEQ ID NO: 511), (SEQ ID NO: 512), (SEQ ID NO: 513), (SEQ ID NO: 514),

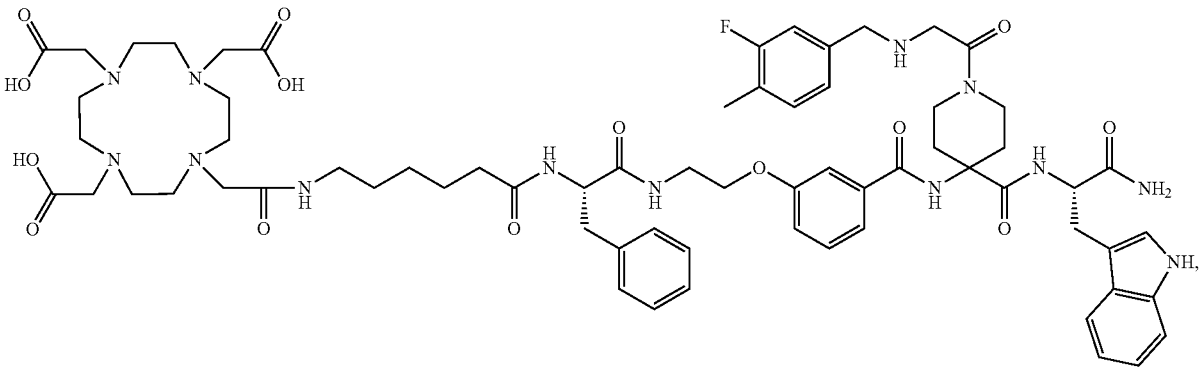

-continued
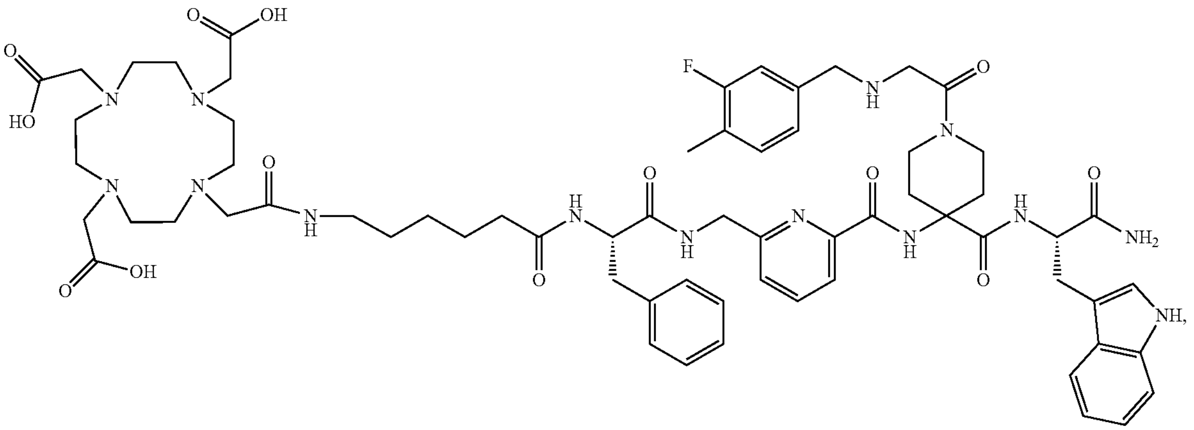
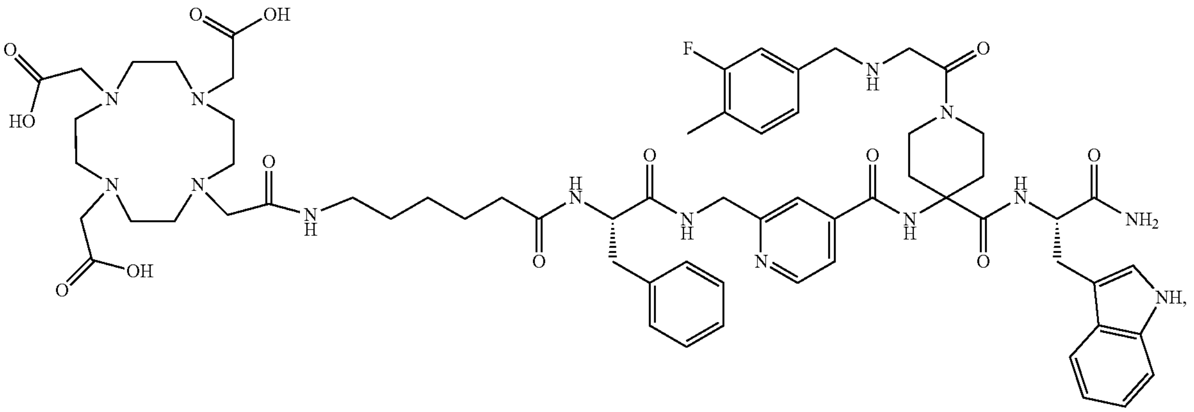
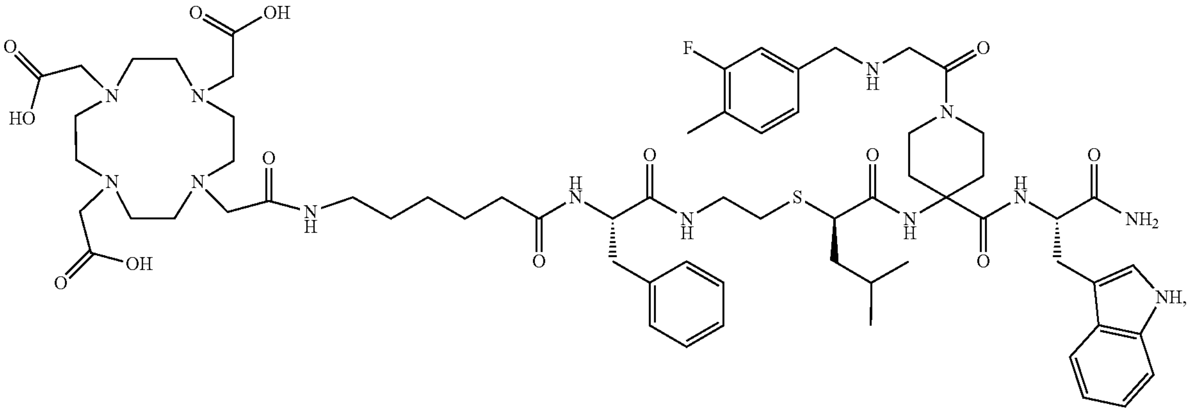
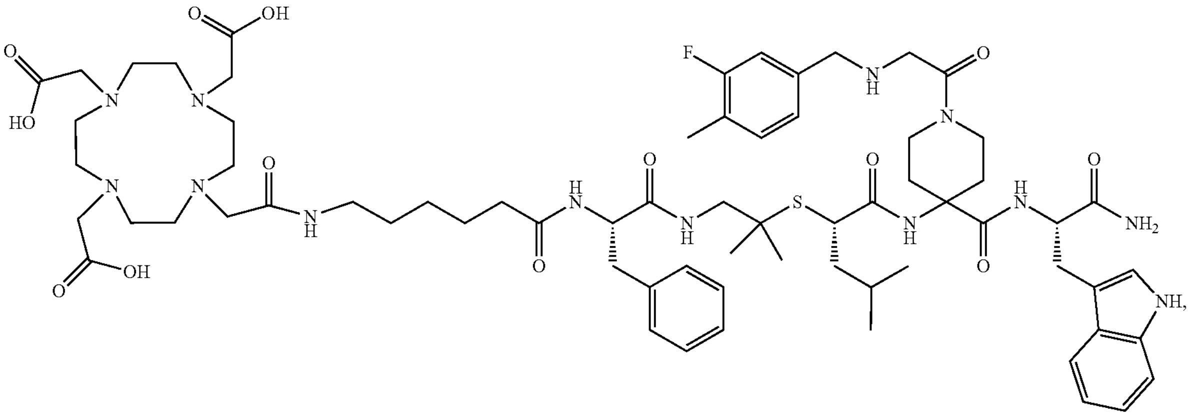

-continued
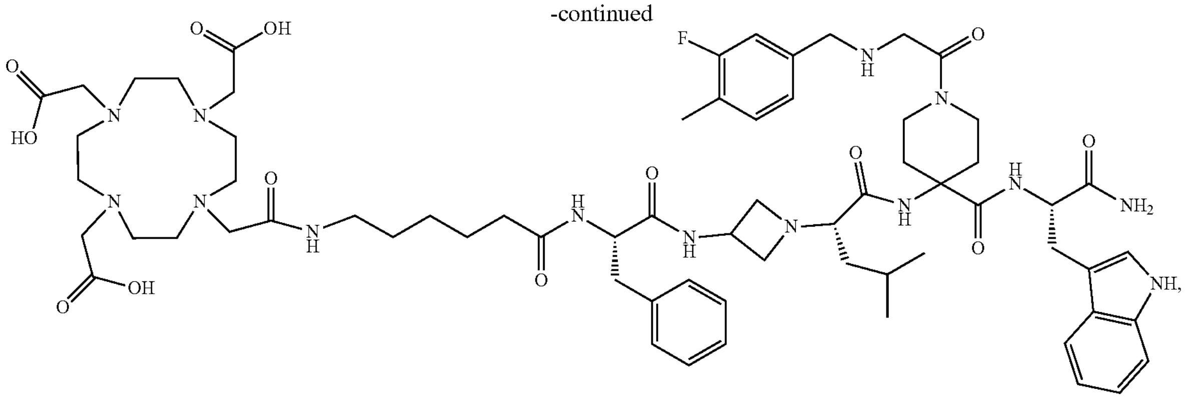
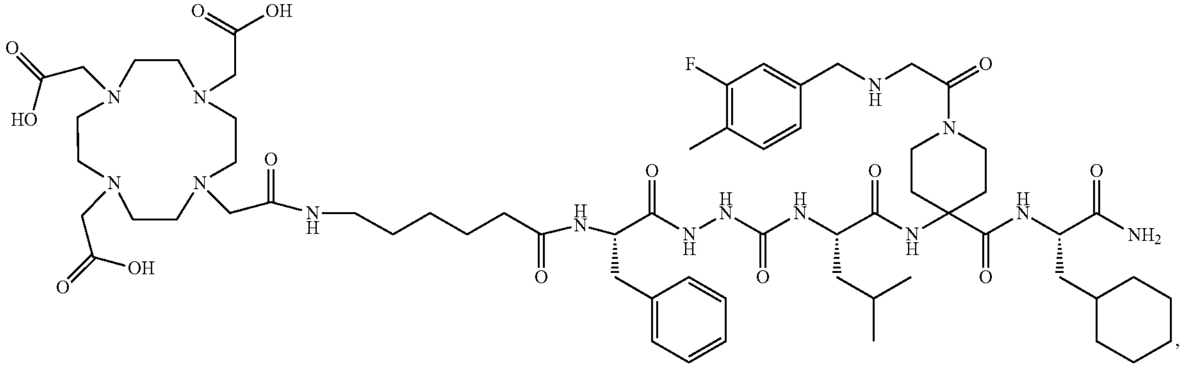
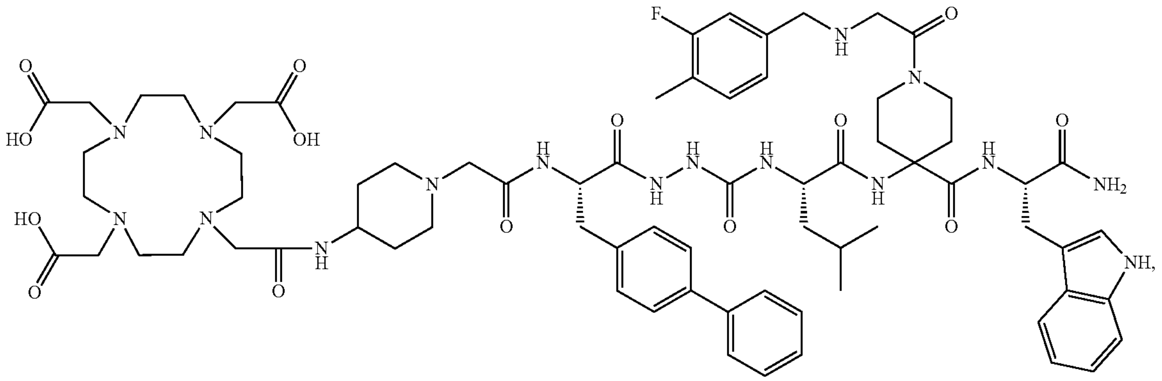 [SMILES: Cc1ccc(CNCC(=O)N2CCC(NC(=O)[C@H](CC(C)C)NC(=O)NNC(=O)[C@H](Cc3ccc(-c4ccccc4)cc3)NC(=O)CN3CCC(NC(=O)CN4CCN(CC(=O)O)CCN(CC(=O)O)CCN(CC(=O)O)CC4)CC3)(C(=O)N[C@@H](Cc3c[nH]c4ccccc34)C(N)=O)CC2)cc1F]
(SEQ ID NO: 524), (SEQ ID NO: 525), (SEQ ID NO: 526), (SEQ ID NO: 527),
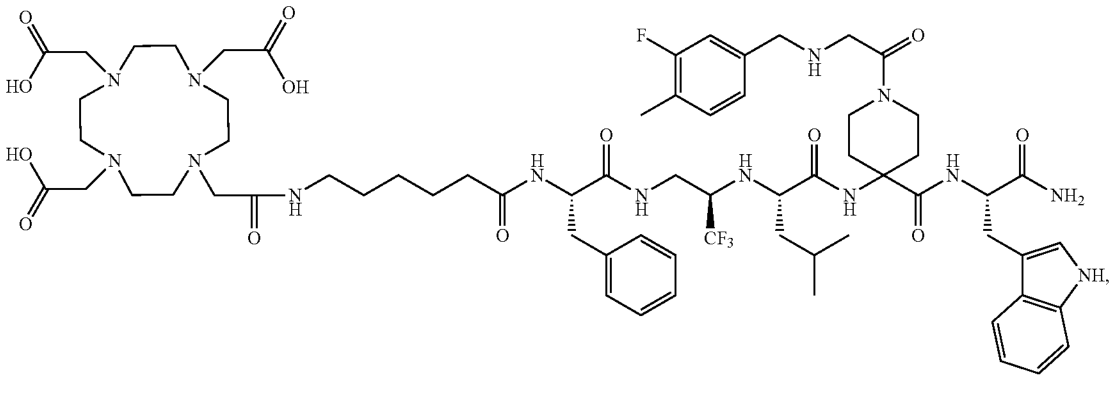

-continued

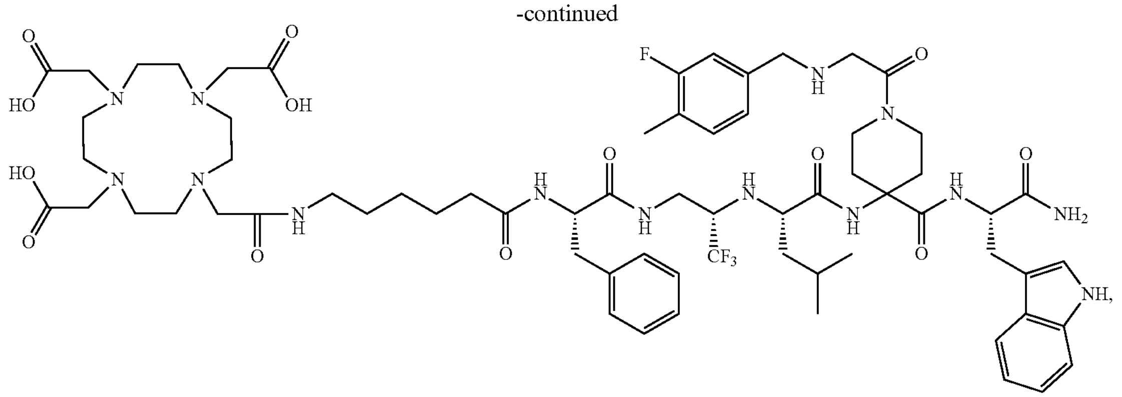

(SEQ ID NO: 530), (SEQ ID NO: 531), (SEQ ID NO: 532), (SEQ ID NO: 533), (SEQ ID NO: 534), (SEQ ID NO: 535), (SEQ ID NO: 536), (SEQ ID NO: 537), (SEQ ID NO: 538), (SEQ ID NO: 539), (SEQ ID NO: 540), (SEQ ID NO: 541), (SEQ ID NO: 542), (SEQ ID NO: 543), (SEQ ID NO: 544), (SEQ ID NO: 545), (SEQ ID NO: 546), (SEQ ID NO: 547), (SEQ ID NO: 548), (SEQ ID NO: 549), (SEQ ID NO: 550), (SEQ ID NO: 551), (SEQ ID NO: 552), (SEQ ID NO: 553), (SEQ ID NO: 554), (SEQ ID NO: 555), (SEQ ID NO: 556), (SEQ ID NO: 557), (SEQ ID NO: 558), (SEQ ID NO: 559), (SEQ ID NO: 560), (SEQ ID NO: 561), (SEQ ID NO: 562), (SEQ ID NO: 563), (SEQ ID NO: 564), (SEQ ID NO: 565), (SEQ ID NO: 566), (SEQ ID NO: 567), (SEQ ID NO: 568), (SEQ ID NO: 569), (SEQ ID NO: 570), (SEQ ID NO: 571), (SEQ ID NO: 572), (SEQ ID NO: 573), (SEQ ID NO: 574), (SEQ ID NO: 575), (SEQ ID NO: 576), (SEQ ID NO: 577), (SEQ ID NO: 578), (SEQ ID NO: 579), (SEQ ID NO: 580), (SEQ ID NO: 581 (SEQ ID NO: 582), (SEQ ID NO: 583), (SEQ ID NO: 584),

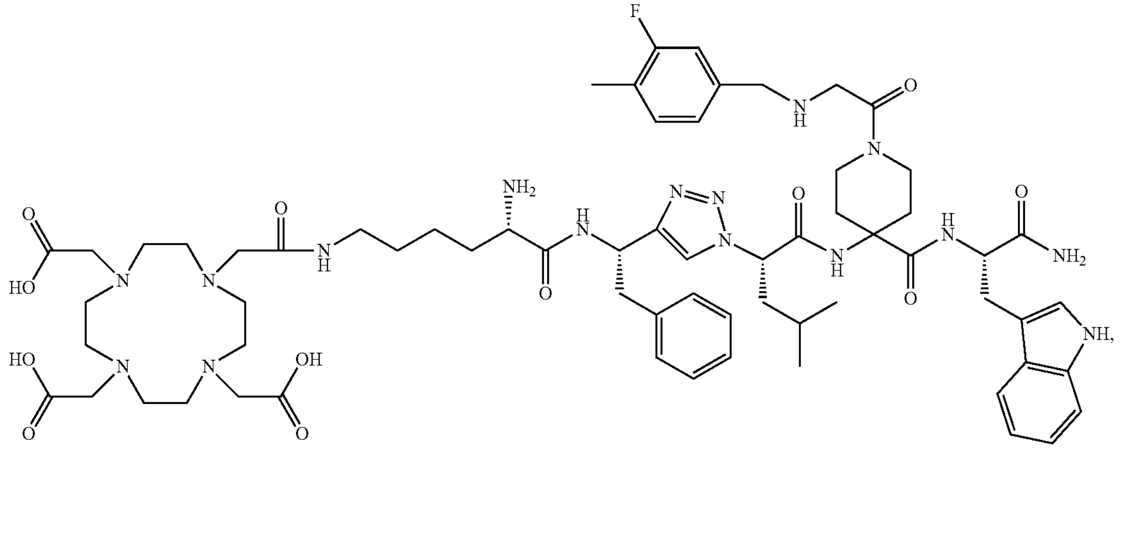 [SMILES: Cc1ccc(CNCC(=O)N2CCC(NC(=O)[C@H](CC(C)C)n3cc([C@H](Cc4ccccc4)NC(=O)[C@@H](N)CCCCNC(=O)CN4CCN(CC(=O)O)CCN(CC(=O)O)CCN(CC(=O)O)CC4)nn3)(C(=O)N[C@@H](Cc3c[nH]c4ccccc34)C(N)=O)CC2)cc1F]

(SEQ ID NO: 586) (SEQ ID NO: 587), (SEQ ID NO: 588), (SEQ ID NO: 589), (SEQ ID NO: 590),

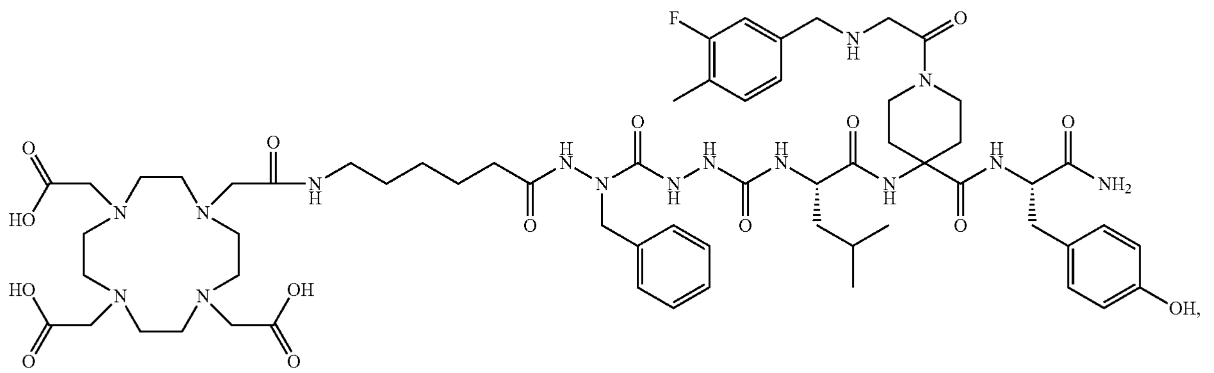
(SEQ ID NO: 594)
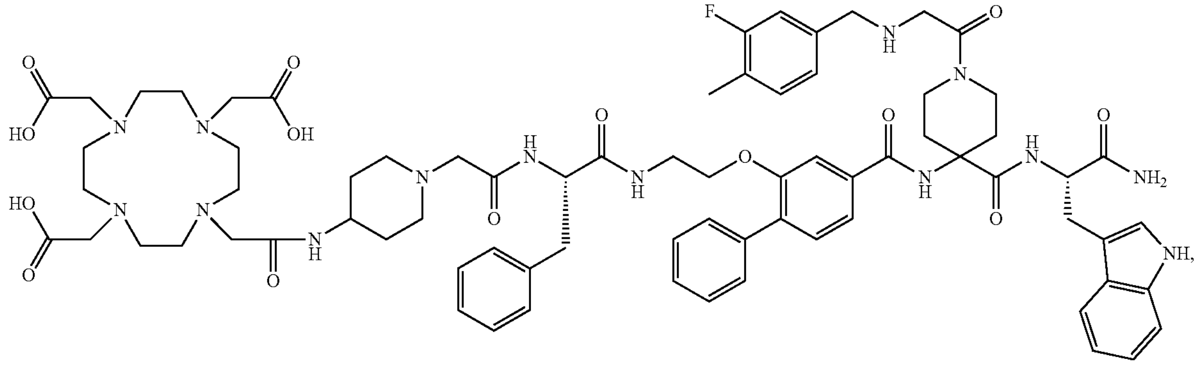
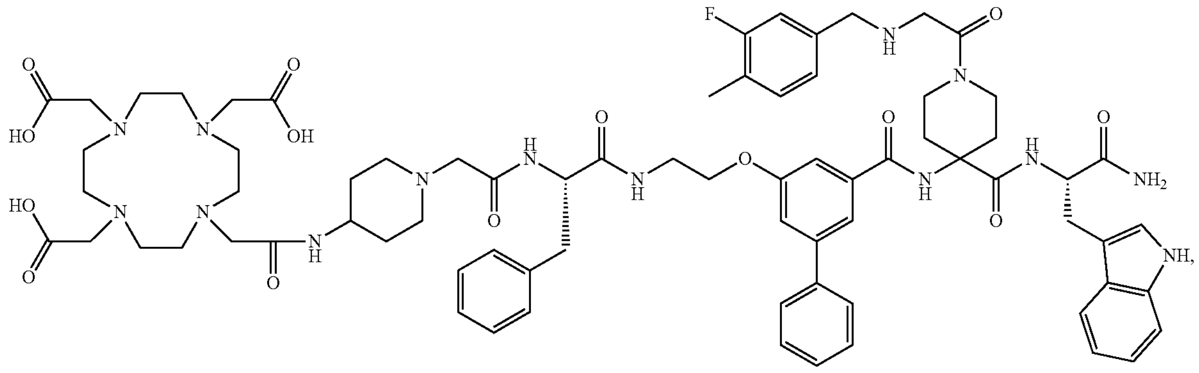
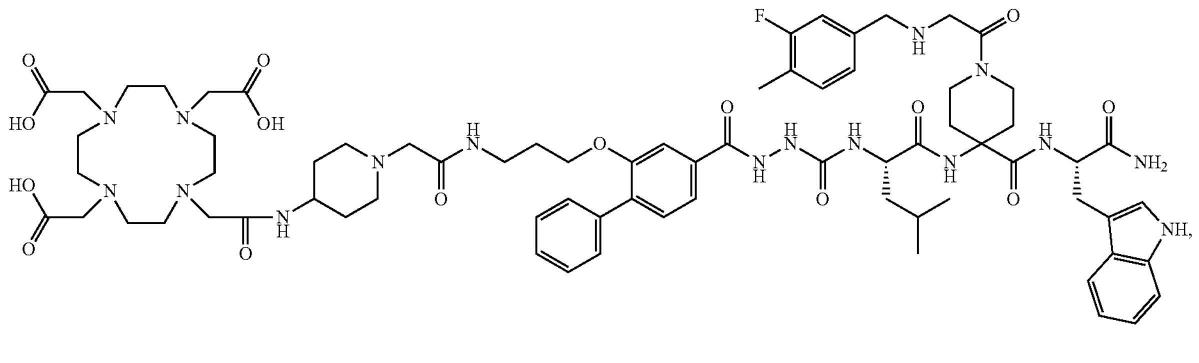

-continued
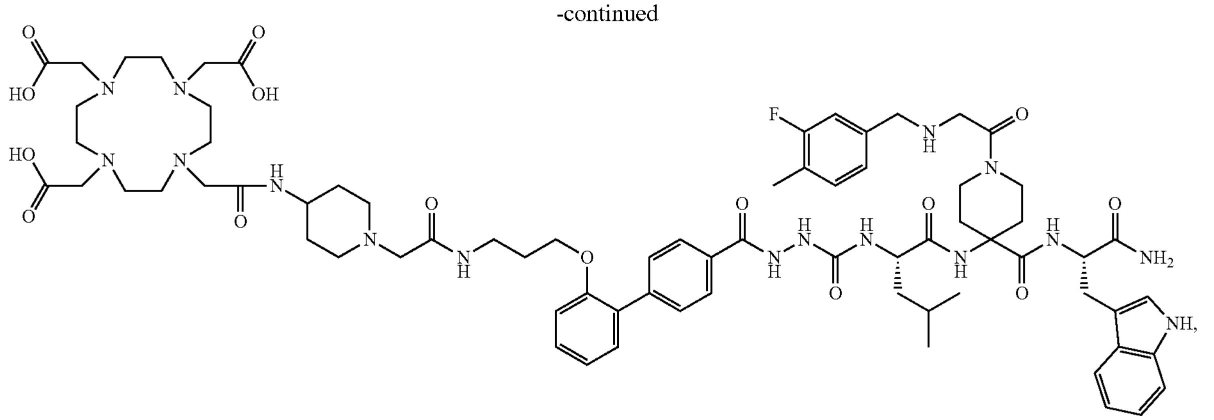
(SEQ ID NO: 599), (SEQ ID NO: 600), (SEQ ID NO: 601), (SEQ ID NO: 602), (SEQ ID NO: 603), (SEQ ID NO: 605), (SEQ ID NO: 606), (SEQ ID NO: 607), (SEQ ID NO: 608), (SEQ ID NO: 610), (SEQ ID NO: 611), (SEQ ID NO: 612), (SEQ ID NO: 613), (SEQ ID NO: 614), (SEQ ID NO: 615), (SEQ ID NO: 616), (SEQ ID NO: 617), (SEQ ID NO: 618); (SEQ ID NO: 619), (SEQ ID NO: 6201) (SEQ ID NO: 621), (SEQ ID NO: 622), (SEQ ID NO: 623); (SEQ ID NO: 624), (SEQ ID NO: 625), (SEQ ID NO.: 626),
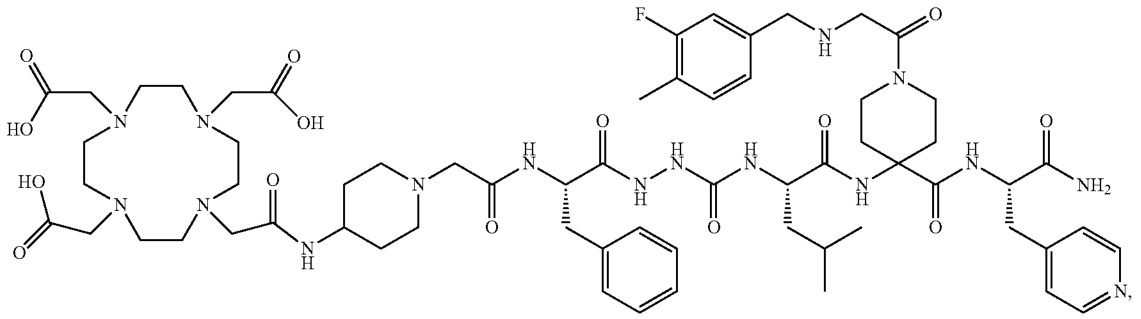 [SMILES: Cc1ccc(CNCC(=O)N2CCC(NC(=O)[C@H](CC(C)C)NC(=O)NNC(=O)[C@H](Cc3ccccc3)NC(=O)CN3CCC(NC(=O)CN4CCN(CC(=O)O)CCN(CC(=O)O)CCN(CC(=O)O)CC4)CC3)(C(=O)N[C@@H](Cc3ccncc3)C(N)=O)CC2)cc1F]
(SEQ ID NO: 628), (SEQ ID NO: 629), (SEQ ID NO: 630), (SEQ ID NO: 631), (SEQ ID NO: 632), (SEQ ID NO: 633), (SEQ ID NO: 634), (SEQ ID NO: 635), (SEQ ID NO: 636), (SEQ ID NO: 637), (SEQ ID NO: 638), (SEQ ID NO: 639), (SEQ ID NO: 640), (SEQ ID NO: 641),
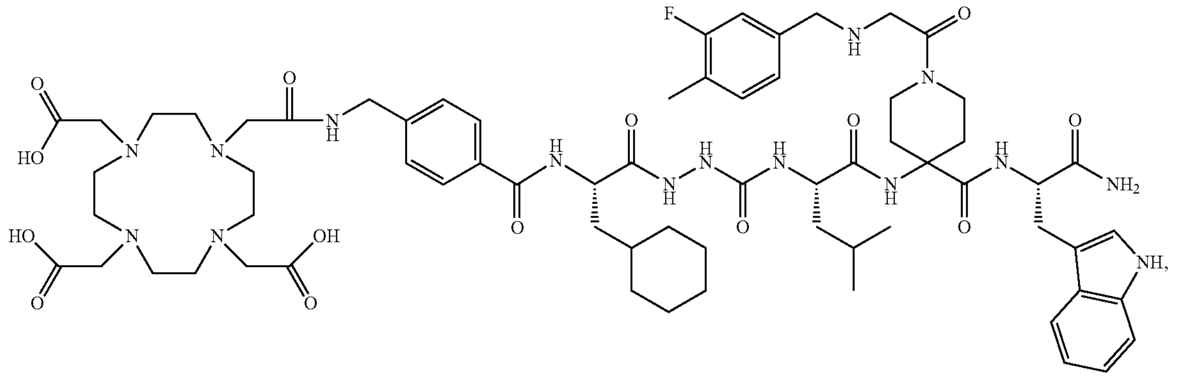 [SMILES: Cc1ccc(CNCC(=O)N2CCC(NC(=O)[C@H](CC(C)C)NC(=O)NNC(=O)[C@H](CC3CCCCC3)NC(=O)c3ccc(CNC(=O)CN4CCN(CC(=O)O)CCN(CC(=O)O)CCN(CC(=O)O)CC4)cc3)(C(=O)N[C@@H](Cc3c[nH]c4ccccc34)C(N)=O)CC2)cc1F]

(SEQ ID NO: 643), (SEQ ID NO: 645), (SEQ ID NO: 647), (SEQ ID NO: 648),
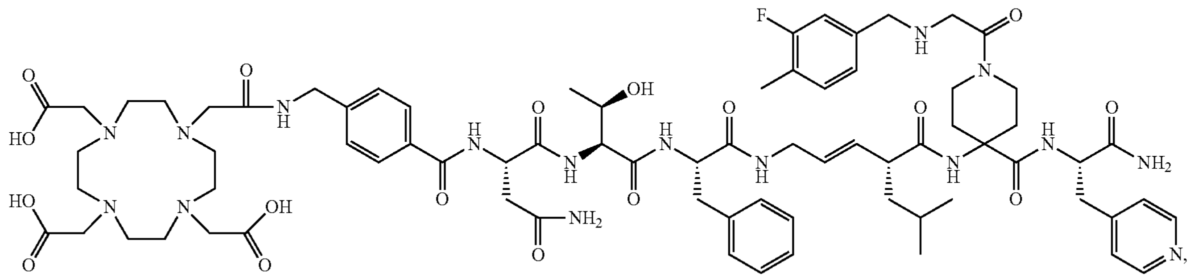 [SMILES: Cc1ccc(CNCC(=O)N2CCC(NC(=O)[C@@H](/C=C/CNC(=O)[C@H](Cc3ccccc3)NC(=O)[C@@H](NC(=O)[C@H](CC(N)=O)NC(=O)c3ccc(CNC(=O)CN4CCN(CC(=O)O)CCN(CC(=O)O)CCN(CC(=O)O)CC4)cc3)[C@@H](C)O)CC(C)C)(C(=O)N[C@@H](Cc3ccncc3)C(N)=O)CC2)cc1F]
(SEQ ID NO: 650), (SEQ ID NO: 651), (SEQ ID NO: 652), (SEQ ID NO: 653), (SEQ ID NO: 654), (SEQ ID NO: 655),
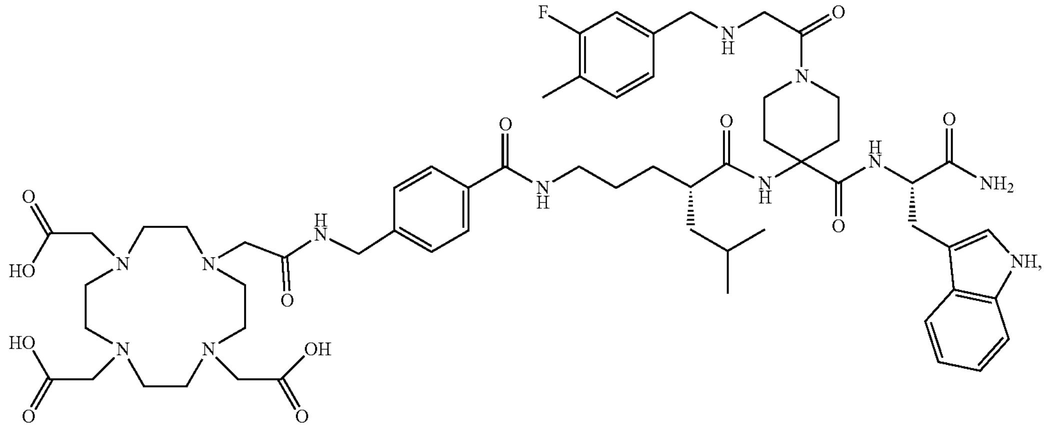 [SMILES: Cc1ccc(CNCC(=O)N2CCC(NC(=O)[C@@H](CCCNC(=O)c3ccc(CNC(=O)CN4CCN(CC(=O)O)CCN(CC(=O)O)CCN(CC(=O)O)CC4)cc3)CC(C)C)(C(=O)N[C@@H](Cc3c[nH]c4ccccc34)C(N)=O)CC2)cc1F]
(SEQ ID NO: 657), (SEQ ID NO: 658), (SEQ ID NO: 659), (SEQ ID NO: 660), (SEQ ID NO: 661),
(SEQ ID NO: 663)
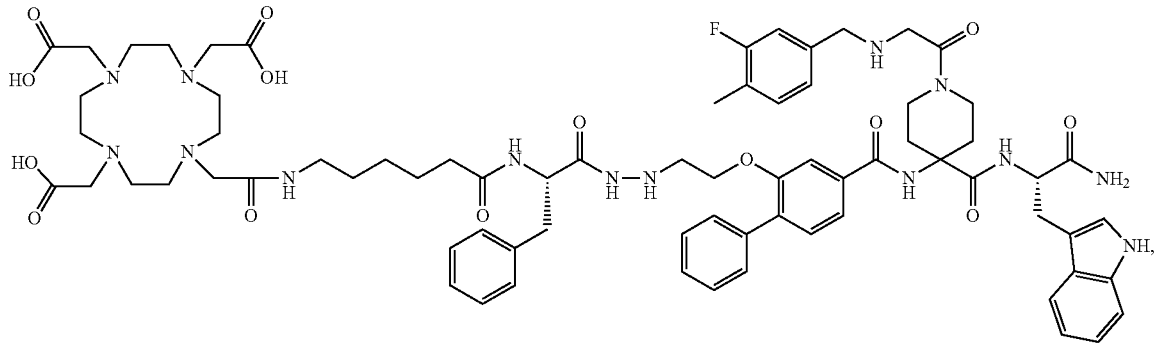

-continued
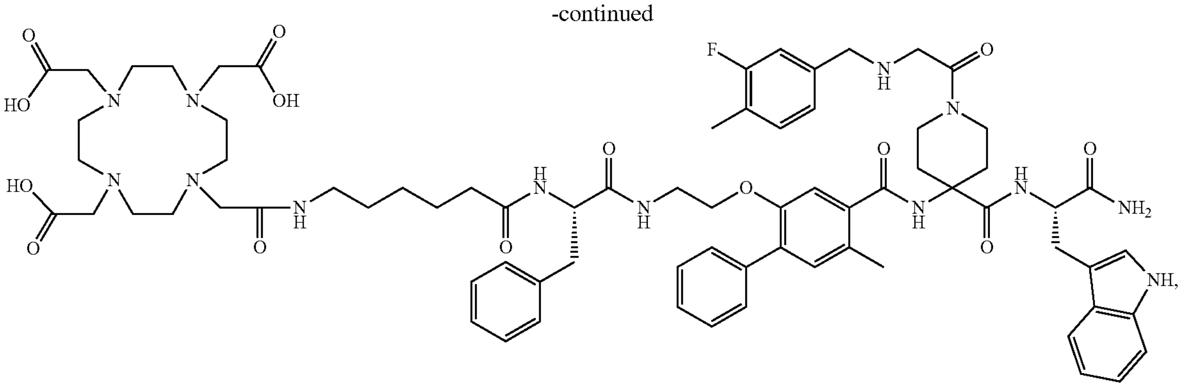
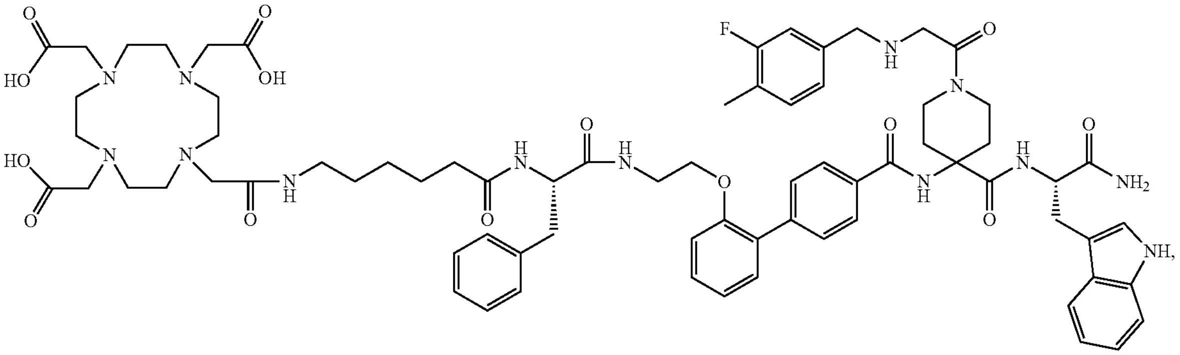
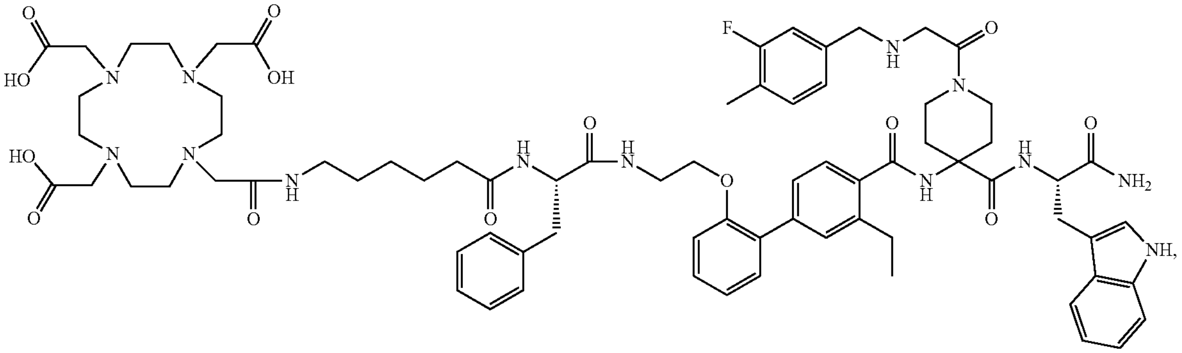
(SEQ ID NO: 667), (SEQ ID NO: 668), (SEQ ID NO. 669), (SEQ ID NO: 670), (SEQ ID NO: 671), (SEQ ID NO. 672), (SEQ ID NO: 673), (SEQ ID NO: 674), (SEQ ID NO: 675), (SEQ ID NO: 676), (SEQ ID NO: 677), (SEQ ID NO: 678),
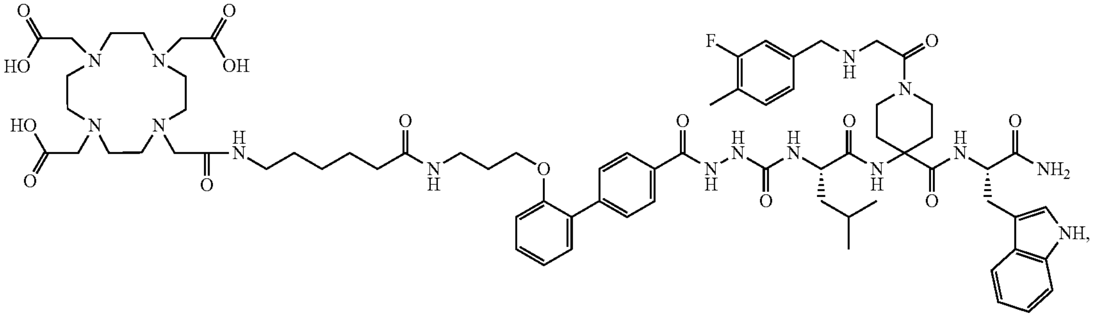

-continued

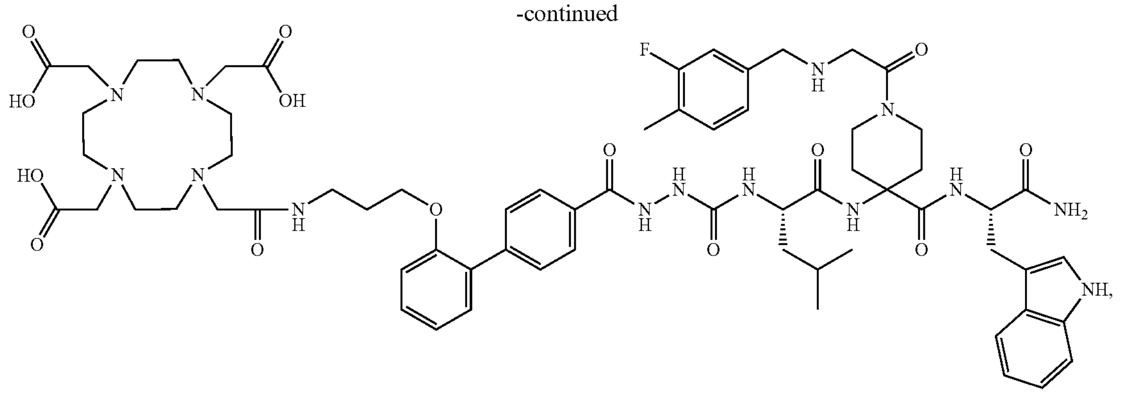

(SEQ ID NO: 681), (SEQ ID NO: 682), (SEQ ID NO: 683), (SEQ ID NO: 684), (SEQ ID NO: 686), (SEQ ID NO: 687), (SEQ ID NO: 688), (SEQ ID NO: 689), (SEQ ID NO: 690), (SEQ ID NO: 691), (SEQ ID NO: 692), (SEQ ID NO: 693), (SEQ ID NO: 694), (SEQ ID NO: 695), (SEQ ID NO: 696), (SEQ ID NO: 697), (SEQ ID NO: 698), (SEQ ID NO: 699), (SEQ ID NO: 700), (SEQ ID NO: 701), (SEQ ID NO: 702), (SEQ ID NO: 703), (SEQ ID NO: 704), (SEQ ID NO: 705), (SEQ ID NO: 706), (SEQ ID NO: 707), (SEQ ID NO: 708), (SEQ ID NO: 709), (SEQ ID NO: 710), (SEQ ID NO: 711), (SEQ ID NO: 712), (SEQ ID NO: 713), (SEQ ID NO: 714), (SEQ ID NO: 715), (SEQ ID NO: 716), (SEQ ID NO: 717), (SEQ ID NO: 718), (SEQ ID NO: 719), (SEQ ID NO: 720), (SEQ ID NO: 721), (SEQ ID NO: 722), (SEQ ID NO: 723), (SEQ ID NO: 724), (SEQ ID NO: 725), (SEQ ID NO: 726), (SEQ ID NO: 727), (SEQ ID NO: 728), (SEQ ID NO: 729), (SEQ ID NO: 730), (SEQ ID NO: 731), (SEQ ID NO: 732), (SEQ ID NO: 733), (SEQ ID NO: 734), (SEQ ID NO: 735), (SEQ ID NO: 736), (SEQ ID NO: 737), (SEQ ID NO: 738), (SEQ ID NO: 739), (SEQ ID NO: 740), (SEQ ID NO: 741), (SEQ ID NO: 742), (SEQ ID NO: 743), (SEQ ID NO: 744), (SEQ ID NO: 745), (SEQ ID NO: 746), (SEQ ID NO: 747), (SEQ ID NO: 748), (SEQ ID NO: 749), (SEQ ID NO: 750), (SEQ ID NO: 751), (SEQ ID NO: 752), (SEQ ID NO: 753), (SEQ ID NO: 754), (SEQ ID NO: 755), (SEQ ID NO: 756), (SEQ ID NO: 757), (SEQ ID NO: 758), (SEQ ID NO: 759), (SEQ ID NO: 760), (SEQ ID NO: 761), (SEQ ID NO: 762), (SEQ ID NO: 763), (SEQ ID NO: 764), (SEQ ID NO: 765), (SEQ ID NO: 766), (SEQ ID NO: 767), (SEQ ID NO: 768), (SEQ ID NO: 769), or (SEQ ID NO: 770), or a radionuclide complex thereof;

wherein the radionuclide of the radionuclide complex is an Auger electron-emitting radionuclide, α-emitting radionuclide, β-emitting radionuclide, or γ-emitting radionuclide.

26. The compound of claim 1, or a pharmaceutically acceptable salt thereof, wherein: the compound is a radionuclide complex and the radionuclide of the radionuclide complex is 111-indium ($^{111}$In), 67-gallium ($^{67}$Ga), 68-gallium ($^{68}$Ga), 69-gallium ($^{69}$Ga), 71-gallium (71Ga), 225-actinium ($^{225}$Ac), 175-lutetium ($^{175}$Lu), 177-lutetium ($^{177}$Lu), 204-lead ($^{204}$Pb), 206-lead ($^{206}$Pb), 207-lead ($^{207}$Pb), 208-lead ($^{208}$Pb), 212-lead ($^{212}$Pb), 63-copper ($^{63}$Cu), 64-copper ($^{64}$Cu), 65-copper ($^{65}$Cu), or 67-copper ($^{67}$Cu).

27. The compound of claim 1, or a pharmaceutically acceptable salt thereof, wherein: the compound is a radionuclide complex and the radionuclide of the radionuclide complex is 64-copper ($^{64}$Cu), 67-copper ($^{67}$Cu), 90-yttrium ($^{90}$Y), 111-indium ($^{111}$In), 67-gallium ($^{67}$Ga), 68-gallium ($^{68}$Ga), 225-actinium ($^{225}$Ac), or 177-lutetium ($^{177}$Lu) or 212-lead ($^{212}$Pb).

28. A pharmaceutical composition comprising a compound of claim 1, or a pharmaceutically acceptable salt thereof, and at least one pharmaceutically acceptable excipient.

29. A method for the treatment of cancer comprising administering to a mammal with cancer an effective amount of a compound of claim 1, or a pharmaceutically acceptable salt thereof; wherein the compound is a radionuclide complex and the radionuclide of the radionuclide complex is:

an α-emitting radionuclide that is 225-actinium ($^{225}$Ac), 213-bismuth ($^{213}$Bi), 223-radium ($^{223}$Ra), or 212-lead ($^{212}$Pb); or a β-emitting radionuclide that is 90-yttrium ($^{90}$Y), 177-lutetium ($^{177}$Lu), 64-copper ($^{64}$Cu), 67-copper ($^{67}$Cu), or 153-samarium ($^{153}$Sm);

wherein the cancer is glioma, thyroid cancer, lung cancer, colorectal cancer, stomach cancer, liver cancer, pancreatic cancer, renal cancer, prostate cancer, testis cancer, breast cancer, cervical cancer, endometrial cancer, ovarian cancer, or melanoma.

30. A method of killing tumors in a mammal that overexpress Kisspeptin receptor (KISS1R) comprising administering to the mammal with tumors a compound of claim 1, or a pharmaceutically acceptable salt thereof, wherein the compound is a radionuclide complex and the radionuclide of the radionuclide complex is:

an α-emitting radionuclide that is 225-actinium ($^{225}$Ac), 213-bismuth ($^{213}$Bi), 223-radium ($^{223}$Ra), or 212-lead ($^{212}$Pb); or a β-emitting radionuclide that is 90-yttrium ($^{90}$Y), 177-lutetium ($^{177}$Lu), 64-copper ($^{64}$Cu), 67-copper ($^{67}$Cu), or 153-samarium ($^{153}$Sm);

wherein the tumor is glioma, thyroid cancer, lung cancer, colorectal cancer, stomach cancer, liver cancer, pancreatic cancer, renal cancer, prostate cancer, testis cancer, breast cancer, cervical cancer, endometrial cancer, ovarian cancer, or melanoma.

* * * * *